US012441703B2

(12) United States Patent
Thomson et al.

(10) Patent No.: US 12,441,703 B2
(45) Date of Patent: Oct. 14, 2025

(54) CARBOXAMIDES AS MODULATORS OF SODIUM CHANNELS

(71) Applicant: VERTEX PHARMACEUTICALS INCORPORATED, Boston, MA (US)

(72) Inventors: Stephen Andrew Thomson, Del Mar, CA (US); Nadia Ahmad, Didcot (GB); Corey Anderson, Brighton, MA (US); Vijayalaksmi Arumugam, San Marcos, CA (US); Iuliana Luci Asgian, San Diego, CA (US); Joanne Louise Camp, Didcot (GB); Lev Tyler Dewey Fanning, San Marcos, CA (US); Sara Sabina Hadida Ruah, La Jolia, CA (US); Dennis Hurley, San Marcos, CA (US); Yvonne Schmidt, San Diego, CA (US); David Shaw, Oxford (GB); Urvi Patel, San Diego, CA (US); Lidio Marx Carvalho Meireles, San Marcos, CA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 1092 days.

(21) Appl. No.: 17/421,944

(22) PCT Filed: Jan. 9, 2020

(86) PCT No.: PCT/US2020/012994
§ 371 (c)(1),
(2) Date: Jul. 9, 2021

(87) PCT Pub. No.: WO2020/146682
PCT Pub. Date: Jul. 16, 2020

(65) Prior Publication Data

US 2023/0062053 A1 Mar. 2, 2023

Related U.S. Application Data

(60) Provisional application No. 62/790,897, filed on Jan. 10, 2019, provisional application No. 62/791,011, filed on Jan. 10, 2019.

(51) Int. Cl.

| | |
|---|---|
| ***C07D 401/12*** | (2006.01) |
| ***A61P 3/12*** | (2006.01) |
| ***C07D 213/56*** | (2006.01) |
| ***C07D 213/89*** | (2006.01) |
| ***C07D 239/36*** | (2006.01) |
| ***C07D 405/12*** | (2006.01) |

(52) U.S. Cl.
CPC .............. *C07D 401/12* (2013.01); *A61P 3/12* (2018.01); *C07D 213/56* (2013.01); *C07D 213/89* (2013.01); *C07D 239/36* (2013.01); *C07D 405/12* (2013.01)

(58) Field of Classification Search
CPC ... C07D 213/81; C07D 213/56; C07D 213/89
See application file for complete search history.

(56) References Cited

U.S. PATENT DOCUMENTS

| | | | |
|---|---|---|---|
| 2,511,231 | A | 6/1950 | Weissberger et al. |
| 2,657,134 | A | 10/1953 | Graham et al. |
| 2,688,617 | A | 9/1954 | Hein et al. |
| 2,694,718 | A | 11/1954 | Salminen et al. |
| 2,710,802 | A | 6/1955 | Parmerter et al. |
| 2,710,803 | A | 6/1955 | Salminen et al. |
| 2,721,798 | A | 10/1955 | Loria et al. |
| 2,725,292 | A | 11/1955 | Graham et al. |
| 2,772,163 | A | 11/1956 | Tong |
| 4,146,637 | A | 3/1979 | Metz et al. |
| 4,218,765 | A | 8/1980 | Kinkade |
| 4,639,273 | A | 1/1987 | Gilmore et al. |
| 5,258,407 | A | 11/1993 | Washburn et al. |
| 5,304,121 | A | 4/1994 | Sahatjian |
| 5,310,760 | A | 5/1994 | Washburn et al. |
| 5,312,960 | A | 5/1994 | Kramer et al. |
| 5,532,235 | A | 7/1996 | Albright et al. |
| 5,536,718 | A | 7/1996 | Albright et al. |
| 5,886,026 | A | 3/1999 | Hunter et al. |
| 6,099,562 | A | 8/2000 | Ding et al. |
| 6,211,242 | B1 | 4/2001 | Setoi et al. |
| 6,235,680 | B1 | 5/2001 | Ziemer et al. |
| 6,531,291 | B1 | 3/2003 | Kabbash et al. |
| 6,699,994 | B1 | 3/2004 | Babu et al. |

(Continued)

FOREIGN PATENT DOCUMENTS

| | | |
|---|---|---|
| BE | 854683 | 11/1977 |
| CA | 1091247 | 12/1980 |

(Continued)

OTHER PUBLICATIONS

Akopian, A.N., L. Sivilotti, and J.N. Wood, A tetrodotoxin-resistant voltage-gated sodium channel expressed by sensory neurons. *Nature*, 1996. 379(6562): p. 257-62.

(Continued)

*Primary Examiner* — Alicia L Otton

(74) *Attorney, Agent, or Firm* — Steve M. Sturlis; Joshua E. Ney

(57) ABSTRACT

Compounds, and pharmaceutically acceptable salts thereof, useful as inhibitors of sodium channels are provided. Also provided are pharmaceutical compositions comprising the compounds or pharmaceutically acceptable salts and methods of using the compounds, pharmaceutically acceptable salts, and pharmaceutical compositions in the treatment of various disorders, including pain.

23 Claims, No Drawings

(56) References Cited

U.S. PATENT DOCUMENTS

| | | | |
|---|---|---|---|
| 6,936,719 | B2 | 8/2005 | Babu et al. |
| 7,056,910 | B2 | 6/2006 | Koshio et al. |
| 7,374,749 | B2 | 5/2008 | Haase et al. |
| 7,863,280 | B2 | 1/2011 | Paukert et al. |
| 8,389,734 | B2 | 3/2013 | Chen et al. |
| 8,466,188 | B2 | 6/2013 | Chafeev et al. |
| 8,481,479 | B1 | 7/2013 | Mousa |
| 8,519,137 | B2 | 8/2013 | Joshi et al. |
| 8,779,197 | B2 | 7/2014 | Chen et al. |
| 8,841,483 | B2 | 9/2014 | Joshi et al. |
| 8,865,771 | B2 | 10/2014 | Chen et al. |
| 8,883,840 | B2 | 11/2014 | Chafeev et al. |
| 9,051,270 | B2 | 6/2015 | Hadida-Ruah et al. |
| 9,108,903 | B2 | 8/2015 | Hadida-Ruah et al. |
| 9,139,529 | B2 | 9/2015 | Hadida-Ruah et al. |
| 9,163,042 | B2 | 10/2015 | Anderson et al. |
| 9,169,246 | B2 | 10/2015 | Benazet et al. |
| 9,393,235 | B2 | 7/2016 | Hadida-Ruah et al. |
| 9,421,196 | B2 | 8/2016 | Hadida-Ruah et al. |
| 9,464,102 | B2 | 10/2016 | Anderson et al. |
| 9,758,483 | B2 | 9/2017 | Hadida-Ruah et al. |
| 9,783,501 | B2 | 10/2017 | Hadida-Ruah et al. |
| 9,828,397 | B2 | 11/2017 | Anderson et al. |
| 9,951,065 | B2 | 4/2018 | Bartlett et al. |
| 10,087,143 | B2 | 10/2018 | Hadida-Ruah et al. |
| 10,253,054 | B2 | 4/2019 | Anderson et al. |
| 10,647,661 | B2 | 5/2020 | Ahmad et al. |
| 10,738,009 | B2 | 8/2020 | Hadida Ruah et al. |
| 10,787,472 | B2 | 9/2020 | Anderson et al. |
| 11,203,571 | B2 | 12/2021 | Hadida-Ruah et al. |
| 2002/0002183 | A1 | 1/2002 | Zhu et al. |
| 2002/0032238 | A1 | 3/2002 | Priepke et al. |
| 2002/0173656 | A1 | 11/2002 | Peyman et al. |
| 2003/0225158 | A1 | 12/2003 | Auerbach et al. |
| 2004/0058903 | A1 | 3/2004 | Takasugi et al. |
| 2004/0132745 | A1 | 7/2004 | Bertinato et al. |
| 2004/0186148 | A1 | 9/2004 | Shankar et al. |
| 2005/0038035 | A1 | 2/2005 | Takasugi et al. |
| 2005/0207972 | A1 | 9/2005 | Friebe et al. |
| 2007/0237840 | A1 | 10/2007 | Chern et al. |
| 2007/0238733 | A1 | 10/2007 | Joshi et al. |
| 2008/0192127 | A1 | 8/2008 | Sakal et al. |
| 2008/0312235 | A1 | 12/2008 | Lane et al. |
| 2009/0012091 | A1 | 1/2009 | Yu |
| 2009/0029994 | A1 | 1/2009 | Nakamura et al. |
| 2009/0048306 | A1 | 2/2009 | Bagal et al. |
| 2009/0074884 | A1 | 3/2009 | Chesney et al. |
| 2009/0099233 | A1 | 4/2009 | Joshi et al. |
| 2009/0118333 | A1 | 5/2009 | Chen et al. |
| 2009/0118338 | A1 | 5/2009 | Chen et al. |
| 2009/0163545 | A1 | 6/2009 | Goldfarb |
| 2009/0326020 | A1 | 12/2009 | Miller et al. |
| 2010/0009970 | A1 | 1/2010 | Johansen et al. |
| 2010/0075948 | A1 | 3/2010 | Ding et al. |
| 2010/0152190 | A1 | 6/2010 | Bartkovitz et al. |
| 2011/0046370 | A1 | 2/2011 | Sim et al. |
| 2011/0178089 | A1 | 7/2011 | Bissantz et al. |
| 2011/0257196 | A1 | 10/2011 | Lu et al. |
| 2011/0306607 | A1 | 12/2011 | Hadida-Ruah et al. |
| 2012/0196869 | A1 | 8/2012 | Hadida Ruah et al. |
| 2012/0220605 | A1 | 8/2012 | Pajouhesh et al. |
| 2012/0245136 | A1 | 9/2012 | Hadida-Ruah et al. |
| 2012/0264749 | A1 | 10/2012 | Hadida-Ruah et al. |
| 2013/0150339 | A1 | 6/2013 | Boezio et al. |
| 2013/0231370 | A1 | 9/2013 | Chen et al. |
| 2013/0274243 | A1 | 10/2013 | Bagal et al. |
| 2013/0295187 | A1 | 11/2013 | Mousa |
| 2013/0303535 | A1 | 11/2013 | Tsuboi et al. |
| 2014/0094457 | A1 | 4/2014 | Gardner et al. |
| 2014/0187533 | A1 | 7/2014 | Pajouhesh et al. |
| 2014/0200215 | A1 | 7/2014 | Buckman et al. |
| 2014/0213616 | A1 | 7/2014 | Hadida-Ruah et al. |
| 2014/0221435 | A1 | 8/2014 | Hadida-Ruah et al. |
| 2014/0228371 | A1 | 8/2014 | Hadida-Ruah et al. |
| 2014/0296313 | A1 | 10/2014 | Bagal et al. |
| 2015/0005304 | A1 | 1/2015 | Hadida-Ruah et al. |
| 2015/0166589 | A1 | 6/2015 | Anderson et al. |
| 2015/0246028 | A1 | 9/2015 | Hadida-Ruah et al. |
| 2015/0328196 | A1 | 11/2015 | Hadida-Ruah et al. |
| 2015/0336945 | A1 | 11/2015 | Hadida-Ruah et al. |
| 2016/0009743 | A1 | 1/2016 | Anderson et al. |
| 2016/0152561 | A1 | 6/2016 | Hadida-Ruah et al. |
| 2016/0376295 | A1 | 12/2016 | Anderson et al. |
| 2017/0037009 | A1 | 2/2017 | Hadida-Ruah et al. |
| 2018/0016235 | A1 | 1/2018 | Hadida-Ruah et al. |
| 2018/0044361 | A1 | 2/2018 | Anderson et al. |
| 2019/0005521 | A1 | 1/2019 | Nobe |
| 2019/0016671 | A1 | 1/2019 | Ahmad et al. |
| 2019/0248745 | A1 | 8/2019 | Hadida Ruah et al. |
| 2019/0276483 | A1 | 9/2019 | Anderson et al. |
| 2019/0343817 | A1 | 11/2019 | Agarwal et al. |
| 2021/0047271 | A1 | 2/2021 | Hadida Ruah et al. |
| 2021/0052610 | A1 | 2/2021 | Agarwal et al. |
| 2021/0094906 | A1 | 4/2021 | Ahmad et al. |
| 2021/0155643 | A1 | 5/2021 | Jiang et al. |
| 2021/0198241 | A1 | 7/2021 | Durrant |
| 2022/0110923 | A1 | 4/2022 | Thomson |

FOREIGN PATENT DOCUMENTS

| | | |
|---|---|---|
| CA | 2109195 | 2/1993 |
| CA | 2512582 | 7/2004 |
| CA | 2851462 | 7/2004 |
| CN | 101838264 | 9/2010 |
| CN | 103012397 | 4/2013 |
| CN | 103961348 | 8/2014 |
| CN | 106317027 | 1/2017 |
| DE | 2623228 | 12/1977 |
| DE | 4023008 | 1/1991 |
| DE | 4019307 | 12/1991 |
| DE | 19523640 | 1/1997 |
| DE | 102004009238 | 9/2005 |
| DE | 102004050196 | 4/2006 |
| EP | 407217 | 1/1991 |
| EP | 569912 | 11/1993 |
| EP | 1217000 | 6/2002 |
| EP | 2573073 | 3/2013 |
| EP | 2606726 | 6/2013 |
| EP | 2997966 | 3/2016 |
| FR | 2628864 | 9/1989 |
| GB | 1555723 | 11/1979 |
| IT | 1349739 | 12/2008 |
| JP | 63-182182 | 7/1988 |
| JP | 05313169 | 11/1993 |
| JP | 10-191842 | 7/1998 |
| JP | 10-213820 | 8/1998 |
| JP | 2003342175 | 12/2003 |
| JP | 2004043456 | 2/2004 |
| JP | 2004175739 | 6/2004 |
| JP | 2004315395 | 11/2004 |
| JP | 2008106017 | 5/2008 |
| JP | 2009108152 | 5/2009 |
| JP | 2009149754 | 7/2009 |
| JP | 2009209090 | 9/2009 |
| JP | 2009242540 | 10/2009 |
| JP | 2010001284 | 1/2010 |
| JP | 2010059131 | 3/2010 |
| JP | 2010066630 | 3/2010 |
| JP | 2010126651 | 6/2010 |
| JP | 2011006360 | 1/2011 |
| JP | 2011162678 | 8/2011 |
| JP | 2011207765 | 10/2011 |
| JP | 2014232188 | 12/2014 |
| WO | WO 1993016684 | 9/1993 |
| WO | WO 1995029152 | 11/1995 |
| WO | WO 1995032943 | 12/1995 |
| WO | WO 1996022282 | 7/1996 |
| WO | WO 1997001542 | 1/1997 |
| WO | WO 1997045016 | 12/1997 |
| WO | WO 1997049707 | 12/1997 |
| WO | WO 1998047879 | 10/1998 |
| WO | WO 1999047529 | 9/1999 |
| WO | WO 1999055663 | 11/1999 |
| WO | WO 1999065874 | 12/1999 |

(56) References Cited

FOREIGN PATENT DOCUMENTS

| | | |
|---|---|---|
| WO | WO 2000024707 | 5/2000 |
| WO | WO 2000064876 | 11/2000 |
| WO | WO 2001007028 | 2/2001 |
| WO | WO 2001019788 | 3/2001 |
| WO | WO 2001043732 | 6/2001 |
| WO | WO 2001056989 | 8/2001 |
| WO | WO 2001064642 | 9/2001 |
| WO | WO 2001064643 | 9/2001 |
| WO | WO 2001066098 | 9/2001 |
| WO | WO 2001070671 | 9/2001 |
| WO | WO 2001080894 | 11/2001 |
| WO | WO 2002004403 | 1/2002 |
| WO | WO 2002028835 | 4/2002 |
| WO | WO 2002034711 | 5/2002 |
| WO | WO 2002042273 | 5/2002 |
| WO | WO 2002046159 | 6/2002 |
| WO | WO 2002051397 | 7/2002 |
| WO | WO 2002054077 | 7/2002 |
| WO | WO 2002070483 | 9/2002 |
| WO | WO 2002090347 | 11/2002 |
| WO | WO 2002098839 | 12/2002 |
| WO | WO 2002101007 | 12/2002 |
| WO | WO 2003003008 | 1/2003 |
| WO | WO 2003003009 | 1/2003 |
| WO | WO 2003004020 | 1/2003 |
| WO | WO 2003007955 | 1/2003 |
| WO | WO 2003013516 | 2/2003 |
| WO | WO 2003018536 | 3/2003 |
| WO | WO 2003045921 | 6/2003 |
| WO | WO 2003055477 | 7/2003 |
| WO | WO 2003057205 | 7/2003 |
| WO | WO 2003062221 | 7/2003 |
| WO | WO 2003072532 | 9/2003 |
| WO | WO 2003075907 | 9/2003 |
| WO | WO 2004000820 | 12/2003 |
| WO | WO 2004014844 | 2/2004 |
| WO | WO 2004018428 | 3/2004 |
| WO | WO 2004052837 | 6/2004 |
| WO | WO 2004056777 | 7/2004 |
| WO | WO 2004062601 | 7/2004 |
| WO | WO 2005000309 | 1/2005 |
| WO | WO 2005023761 | 3/2005 |
| WO | WO 2005033079 | 4/2005 |
| WO | WO 2005040135 | 5/2005 |
| WO | WO 2005073165 | 8/2005 |
| WO | WO 2005085202 | 9/2005 |
| WO | WO 2006007864 | 1/2006 |
| WO | WO 2006011050 | 2/2006 |
| WO | WO 2006058905 | 6/2006 |
| WO | WO 2006067445 | 6/2006 |
| WO | WO 2006068199 | 6/2006 |
| WO | WO 2006137376 | 12/2006 |
| WO | WO 2007008627 | 1/2007 |
| WO | WO 2007013332 | 2/2007 |
| WO | WO 2007030567 | 3/2007 |
| WO | WO 2007052843 | 5/2007 |
| WO | WO 2007056143 | 5/2007 |
| WO | WO 2007071632 | 6/2007 |
| WO | WO 2007088996 | 8/2007 |
| WO | WO 2008044767 | 4/2008 |
| WO | WO 2008073670 | 6/2008 |
| WO | WO 2008074997 | 6/2008 |
| WO | WO 2008104994 | 9/2008 |
| WO | WO 2008135826 | 11/2008 |
| WO | WO 2008140810 | 11/2008 |
| WO | WO 2009000413 | 12/2008 |
| WO | WO 2009047105 | 4/2009 |
| WO | WO 2009047151 | 4/2009 |
| WO | WO 2009049180 | 4/2009 |
| WO | WO 2009049181 | 4/2009 |
| WO | WO 2009049183 | 4/2009 |
| WO | WO 2009070533 | 6/2009 |
| WO | WO 2010027746 | 3/2010 |
| WO | WO 2010031713 | 3/2010 |
| WO | WO 2010048149 | 4/2010 |
| WO | WO 2010133312 | 11/2010 |
| WO | WO 2010133748 | 11/2010 |
| WO | WO 2010138901 | 12/2010 |
| WO | WO 2011026240 | 3/2011 |
| WO | WO 2011032169 | 3/2011 |
| WO | WO 2011109059 | 9/2011 |
| WO | WO 2011133729 | 10/2011 |
| WO | WO 2011139765 | 11/2011 |
| WO | WO 2011140425 | 11/2011 |
| WO | WO 2012016133 | 2/2012 |
| WO | WO 2012026931 | 3/2012 |
| WO | WO 2012027392 | 3/2012 |
| WO | WO 2012106499 | 3/2012 |
| WO | WO 2012080729 | 6/2012 |
| WO | WO 2012112743 | 8/2012 |
| WO | WO 2012116440 | 9/2012 |
| WO | WO 2012125613 | 9/2012 |
| WO | WO 2012129562 | 9/2012 |
| WO | WO 2012166951 | 12/2012 |
| WO | WO 2012177668 | 12/2012 |
| WO | WO 2013003112 | 1/2013 |
| WO | WO 2013045400 | 4/2013 |
| WO | WO 2013061205 | 5/2013 |
| WO | WO 2013072502 | 5/2013 |
| WO | WO 2013092350 | 6/2013 |
| WO | WO 2013096060 | 6/2013 |
| WO | WO 2013109521 | 7/2013 |
| WO | WO 2013114250 | 8/2013 |
| WO | WO 2013131018 | 9/2013 |
| WO | WO 2014041125 | 3/2014 |
| WO | WO 2014055634 | 4/2014 |
| WO | WO 2014120808 | 8/2014 |
| WO | WO 2014120815 | 8/2014 |
| WO | WO 2014120820 | 8/2014 |
| WO | WO 2014134127 | 9/2014 |
| WO | WO 2014149207 | 9/2014 |
| WO | WO 2014157267 | 10/2014 |
| WO | WO 2014192681 | 12/2014 |
| WO | WO 2014204831 | 12/2014 |
| WO | WO 2015003816 | 1/2015 |
| WO | WO 2015010065 | 1/2015 |
| WO | WO 2015011284 | 1/2015 |
| WO | WO 2015014900 | 2/2015 |
| WO | WO 2015030898 | 3/2015 |
| WO | WO 2015046827 | 4/2015 |
| WO | WO 2015085238 | 6/2015 |
| WO | WO 2015089361 | 6/2015 |
| WO | WO 2015196072 | 12/2015 |
| WO | WO 2016022626 | 1/2016 |
| WO | WO 2016040449 | 3/2016 |
| WO | WO 2017040982 | 3/2017 |
| WO | WO 2017062751 | 4/2017 |
| WO | WO 2017066705 | 4/2017 |
| WO | WO 2017161028 | 9/2017 |
| WO | WO 2018060110 | 4/2018 |
| WO | WO 2018064119 | 4/2018 |
| WO | WO 2018161033 | 9/2018 |
| WO | WO 2018195439 | 10/2018 |
| WO | WO 2018202681 | 11/2018 |
| WO | WO 2019014352 | 1/2019 |
| WO | WO 2019018119 | 1/2019 |
| WO | WO 2019036657 | 2/2019 |
| WO | WO 2019150220 | 8/2019 |
| WO | WO 2019206925 | 10/2019 |
| WO | WO 2019207081 | 10/2019 |
| WO | WO 2019241787 | 12/2019 |
| WO | WO 2020051207 | 3/2020 |
| WO | WO 2020081572 | 4/2020 |
| WO | WO 2020123675 | 6/2020 |
| WO | WO 2020139748 | 7/2020 |
| WO | WO 2020146612 | 7/2020 |
| WO | WO 2020146682 | 7/2020 |
| WO | WO 2020152079 | 7/2020 |
| WO | WO 2020159576 | 8/2020 |
| WO | WO 2020176763 | 9/2020 |
| WO | WO 2020190774 | 9/2020 |
| WO | WO 2020198712 | 10/2020 |
| WO | WO 2020219867 | 10/2020 |

(56) References Cited

FOREIGN PATENT DOCUMENTS

| | | |
|---|---|---|
| WO | WO 2020221677 | 11/2020 |
| WO | WO 2020251974 | 12/2020 |
| ZA | 9704663 | 12/1997 |

OTHER PUBLICATIONS

Balasegaram, T. et al., "Structure-Activity Relations. Part 9. The Biological Activity and Mode of Action of Substituted 2-Phenoxy-N'phenyl-pyridine-3-carboxamides," J. Chem. Research (S), (1991), pp. 234.

Berge, S.M., et al. describe pharmaceutically acceptable salts in detail in *J. Pharmaceutical Sciences*, 1977, 66, 1-19.

Black, J.A., et al., Multiple sodium channel isoforms and mitogen-activated protein kinases are present in painful human neuromas. *Ann. Neurol.*, 2008. 64(6): p. 644-53.

Blair, N.T. and B.P. Bean, Roles of tetrodotoxin (TTX)-sensitive Na+ current, TTX-resistant $Na^+$ current, and $Ca^{2+}$ current in the action potentials of nociceptive sensory neurons. *J. Neurosci.*, 2002. 22(23): p. 10277-90.

Bolton et al., "Discovery of nonbenzamidine factor VIIa inhibitors using a biaryl acid scaffold," Bioorganic & Medicinal Chemistry Letters, vol. 23, Iss. 18, (Sep. 15, 2013), pp. 5239-5243.

Catterall, W. A., Goldin, A. L., and Waxman, S. G., International Union of Pharmacology. XLVII. Nomenclature and structure-function relationships of voltage-gated sodium channels. *Pharmacol. Rev.* 57 (4), p. 397 (2005).

Chahine, M., Chatelier, A., Babich, O., and Krupp, J. J., Voltage-gated sodium channels in neurological disorders. *CNS Neurol. Disord. Drug Targets* 7 (2), p. 144-58 (2008).

Cheney et al., "Discovery of Novel P1 Groups for Coagulation Factor VIIa Inhibition Using Fragment-Based Screening," J. med. Chem., (2015), 58, 6, pp. 2799-2808.

Choi, J.S. and S.G. Waxman, Physiological interactions between $Na_V1.7$ and $Na_V1.8$ sodium channels: a computer simulation study. *J. Neurophysiol.* 106(6): p. 3173-84.

Coward, K., et al., Immunolocalization of SNS/PN3 and NaN/SNS2 sodium channels in human pain states. *Pain*, 2000. 85(1-2): p. 41-50.

Deak HL, et al., "N-(3-(Phenylcarbamoyl)arylpyrimidine)-5-carboxamides as potent and selective inhibitors of Lck: Structure, synthesis and SAR." Bioorg. Med. Chem. Lett., (Feb. 1, 2008); 18(3); pp. 1172-1176.

Dieleman, J.P., et al., Incidence rates and treatment of neuropathic pain conditions in the general population. *Pain*, 2008. 137(3): p. 681-8.

Dong, X.W., et al., Small interfering RNA-mediated selective knockdown of $Na_{(V)}1.8$ tetrodotoxin-resistant sodium channel reverses mechanical allodynia in neuropathic rats. *Neuroscience*, 2007. 146(2): p. 812-21.

England, S., Voltage-gated sodium channels: the search for subtype-selective analgesics. *Expert Opin. Investig. Drugs* 17 (12), p. 1849-64 (2008).

Harbeson, S.L., and Tung, *Deuterium In Drug Discovery and Development*, Ann. Rep. Med. Chem. 2011, 46, 403-417.

Huang, H.L., et al., Proteomic profiling of neuromas reveals alterations in protein composition and local protein synthesis in hyper-excitable nerves. *Mol. Pain*, 2008. 4: p. 33.

Jarvis, M.F., et al., A-803467, a potent and selective $Na_V1.8$ sodium channel blocker, attenuates neuropathic and inflammatory pain in the rat. *Proc. Natl. Acad. Sci.* U S A, 2007. 104(20): p. 8520-5.

Joshi, S.K., et al., Involvement of the TTX-resistant sodium channel Nav1.8 in inflammatory and neuropathic, but not post-operative, pain states. *Pain*, 2006. 123(1-2): pp. 75-82.

Kassah, E.A. et al., "Synthesis and behavior of a static benzoxazinone derivative towards nitrogen and sulphur nucleophieles," Egyptian Journal of Chemistry, 44, (2001); pp. 169-180.

Krafte, D. S. and Bannon, A. W., Sodium channels and nociception: recent concepts and therapeutic opportunities. *Curr. Opin. Pharmacol.* 8 (1), p. 50-56 (2008).

Lai, J., et al., Inhibition of neuropathic pain by decreased expression of the tetrodotoxin-resistant sodium channel, $Na_V1.8$. *Pain*, 2002. 95(1-2): p. 143-52.

Lambeng et al., "Arylsulfonamides as a new class of cannabinoid $CB_1$ receptor ligands: Identification of a lead and initial SAR studies," Bioorganic & Medicinal Chemistry Letters, vol. 17, Iss. 1, (Jan. 1, 2007), pp. 272-277.

Li, J., et al., "Discovery of potent and orally active MTP inhibitors as potential anti-obesity agents," Bioorganic & Medicinal Chemistry Letters, vol. 16, Iss. 11, 16 (Jun. 2006), pp. 3039-3042.

Liew et al., "SVM Model for Virtual Screening of Lck Inhibitors," J. Chem. Inf. Model. (2009), 44, 4, pp. 877-885.

List of Registry Compounds from CAS STN® Registry Database, with dates of entry in database.

Mehta et al., "Synthesis, characterization and antimicrobial activity of 1, 3, 4,-oxadiazoles derivatives of benzimidazoles," Chem. Sci. Rev. & Lett., 2014, 3(11), pp. 522-528.

Mehta et al., "Synthesis, characterization and antimicrobial evaluation of some novel benzenesulfonylhydrazone derivatives of benzimidazole," Der ChemicaSinica, 2015, 6(2): pp. 29-34.

Micronized amino-substituted hydroxyphenylbenzophenone derivatives IP.com Journal (Feb. 24, 2006) IP134143D.

Miura et al., "Design, synthesis and biological activity of selective and orally available TF/FVIIa complex inhibitors containing non-amidine P1 ligands," Bioorg. Med. Chem. (Jan. 1, 2007); 15(1): pp. 160-173.

Miura et la., "Potent and selective TF/FVIIa inhibitors containing a neutral P1 ligand," Bioorg. Med. Chem. (Dec. 1, 2006); 14(23): pp. 7688-7705.

Naruto et al., "Synthesis of yokonoside and its related compounds," Yakugaku Zassh (Aug. 1976); 96(8): pp. 945-951.

Nielsen et la., "2-(4-Methoxyphenoxy)-5-nitro-N-(4-sulfamoylphenyl)benzamide activates Kir6.2/SUR1 KATP channels," Bioorg. Med. Chem. Lett. (Dec. 6, 2004); 14(23): pp. 5727-5730.

Preparation of amino substituted hydroxyl phenyl benzophenone derivatives and their uses as UV filters in sunscreen formulations, IP.com Journal (Aug. 4, 2003) IP 18721D.

Qiu, F., et al., Increased expression of tetrodotoxin-resistant sodium channels $Na_V1.8$ and $Na_V1.9$ within dorsal root ganglia in a rat model of bone cancer pain. *Neurosci. Lett.*, 512(2): p. 61-6).

Renganathan, M., T.R. Cummins, and S.G. Waxman, Contribution of $Na_{(V)}1.8$ sodium channels to action potential electrogenesis in DRG neurons. *J. Neurophysiol.*, 2001. 86(2): p. 629-40.

Roza, C., et al., The tetrodotoxin-resistant $Na^+$ channel $Na_V1.8$ is essential for the expression of spontaneous activity in damaged sensory axons of mice. *J. Physiol.*, 2003. 550(Pt 3): p. 921-6.

Ruangsri, S., et al., Relationship of axonal voltage-gated sodium channel 1.8 ($Na_V1.8$) mRNA accumulation to sciatic nerve injury-induced painful neuropathy in rats. *J. Biol. Chem.* 286(46): p. 39836-47).

Rush, A.M. and T.R. Cummins, *Painful Research: Identification of a Small-Molecule Inhibitor that Selectively Targets $Na_V1.8$ Sodium Channels*. Mol. Interv., 2007. 7(4): p. 192-5).

Rush, A.M., et al., A single sodium channel mutation produces hyper- or hypoexcitability in different types of neurons. *Proc. Natl. Acad. Sci. USA*, 2006. 103(21): p. 8245-50).

Shirley, V.S., & Lederer, C.M., Isotopes Project, Nuclear Science Division, Lawrence Berkeley Laboratory, Table of Nuclides (Jan. 1980).

Soderpalm, B., Anticonvulsants: aspects of their mechanisms of action. *Eur. J. Pain* 6 Suppl. A, p. 3-9 (2002).

Strickland, I.T., et al., Changes in the expression of NaV1.7, $Na_V1.8$ and $Na_V1.9$ in a distinct population of dorsal root ganglia innervating the rat knee joint in a model of chronic inflammatory joint pain. *Eur. J. Pain*, 2008. 12(5): p. 564-72.

Sun, W., et al., Reduced conduction failure of the main axon of polymodal nociceptive C-fibers contributes to painful diabetic neuropathy in rats. *Brain*, 135(Pt 2): p. 359-75.

(56) References Cited

OTHER PUBLICATIONS

Use of amino hydroxy benzophenone derivatives for protecting human hair and skin, IP.com Journal (Aug. 10, 2006) IP 138915D.

Use of aminohydroxybenzophenone derivatives in sunscreen preparations, IP.com Journal (Aug. 24, 2006) IP139425D.

Vertex Announces Treatment with the NaV1.8 Inhibitor VX-150 Showed Significant Relief of Acute Pain in Phase 2 Study (Feb. 14, 2018).

Wang et al., "Kinetics of extractable residue, bound residue and mineralization of a novel herbicide, ZJ0273, in aerobic soils," Chemosphere, vol. 76, Iss. 8, (Aug. 2009), pp. 1036-1040.

Wang et al., "Studies on the anoxic dissipation and metabolism of pyribambenz propyl (ZJ0273) in soils using position-specific radiolabeling," Science of the Total Environment 472, (2014), pp. 582-589.

Wang et al., "Transformation of 14C-pyrimidynyloxybenzoic herbicide ZJ0273 in aerobic soils," Science of The Total Environment, vol. 408, Iss. 10, (Apr. 15, 2010); pp. 2239-2244.

Wang, G. K., Mitchell, J., and Wang, S. Y., Block of persistent late $Na^+$ currents by antifepressant sertraline and paroxetine. *J. Membr. Biol*. 222 (2), p. 79-90 (2008).

Written Opinion of the International Searching Authority and International Search Report for PCT/US2018/041649 dated Oct. 17, 2018.

Yiangou, Y., et al., SNS/PN3 and SNS2/NaN sodium channel-like immunoreactivity in human adult and neonate injured sensory nerves. *FEBS Lett*., 2000. 467(2-3): p. 249-52.

Yue et al., "The metabolism of a novel herbicide ZJ0273 in oilseed rape and crickweed," Pesticide Biochemistry and Physiology, vol. 104, Iss.3, (Sep. 2012), pp. 44-49.

CARBOXAMIDES AS MODULATORS OF SODIUM CHANNELS

CROSS-REFERENCE TO RELATED APPLICATIONS

This application is a National Stage application of International Application No., PCT/US2020/012994 filed on Jan. 9, 2020, which claims the benefit of priority of U.S. Provisional Application Ser. No. 62/790,897, filed on Jan. 10, 2019 and U.S. Provisional Application Ser. No. 62/791,011, filed on Jan. 10, 2019, each of which are incorporated by reference herein in their entirety.

BACKGROUND

Pain is a protective mechanism that allows healthy animals to avoid tissue damage and to prevent further damage to injured tissue. Nonetheless there are many conditions where pain persists beyond its usefulness, or where patients would benefit from inhibition of pain. Neuropathic pain is a form of chronic pain caused by an injury to the sensory nerves (Dieleman, J. P., et al., Incidence rates and treatment of neuropathic pain conditions in the general population. *Pain,* 2008. 137(3): p. 681-8). Neuropathic pain can be divided into two categories, pain caused by generalized metabolic damage to the nerve and pain caused by a discrete nerve injury. The metabolic neuropathies include post-herpetic neuropathy, diabetic neuropathy, and drug-induced neuropathy. Discrete nerve injury indications include post amputation pain, post-surgical nerve injury pain, and nerve entrapment injuries like neuropathic back pain.

Voltage-gated sodium channels ($Na_V$s) are involved in pain signaling. $Na_V$s are biological mediators of electrical signaling as they mediate the rapid upstroke of the action potential of many excitable cell types (e.g. neurons, skeletal myocytes, cardiac myocytes). The evidence for the role of these channels in normal physiology, the pathological states arising from mutations in sodium channel genes, preclinical work in animal models, and the clinical pharmacology of known sodium channel modulating agents all point to the central role of $Na_V$s in pain sensation (Rush, A. M. and T. R. Cummins, *Painful Research: Identification of a Small-Molecule Inhibitor that Selectively Targets $Na_V$1.8 Sodium Channels*. Mol. Interv., 2007. 7(4): p. 192-5); England, S., Voltage-gated sodium channels: the search for subtype-selective analgesics. *Expert Opin. Investig. Drugs* 17 (12), p. 1849-64 (2008); Krafte, D. S. and Bannon, A. W., Sodium channels and nociception: recent concepts and therapeutic opportunities. *Curr. Opin. Pharmacol.* 8 (1), p. 50-56 (2008)). $Na_V$s mediate the rapid upstroke of the action potential of many excitable cell types (e.g. neurons, skeletal myocytes, cardiac myocytes), and thus are involved in the initiation of signaling in those cells (Hille, Bertil, *Ion Channels of Excitable Membranes*, Third ed. (Sinauer Associates, Inc., Sunderland, MA, 2001)). Because of the role $Na_V$s play in the initiation and propagation of neuronal signals, antagonists that reduce $Na_V$ currents can prevent or reduce neural signaling and $Na_V$ channels have been considered likely targets to reduce pain in conditions where hyper-excitability is observed (Chahine, M., Chatelier, A., Babich, O., and Krupp, J. J., Voltage-gated sodium channels in neurological disorders. *CNS Neurol. Disord. Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anticonvulsants: aspects of their mechanisms of action. *Eur. J. Pain* 6 Suppl. A, p. 3-9 (2002); Wang, G. K., Mitchell, J., and Wang, S. Y., Block of persistent late $Na^+$ currents by antidepressant sertraline and paroxetine. *J. Membr. Biol.* 222 (2), p. 79-90 (2008)).

The $Na_V$s form a subfamily of the voltage-gated ion channel super-family and comprises 9 isoforms, designated $Na_V$1.1-$Na_V$1.9. The tissue localizations of the nine isoforms vary. $Na_V$1.4 is the primary sodium channel of skeletal muscle, and $Na_V$1.5 is primary sodium channel of cardiac myocytes. $Na_V$s 1.7, 1.8 and 1.9 are primarily localized to the peripheral nervous system, while $Na_V$s 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol. Rev.* 57 (4), p. 397 (2005)).

Upon their discovery, $Na_V$1.8 channels were identified as likely targets for analgesia (Akopian, A. N., L. Sivilotti, and J. N. Wood, A tetrodotoxin-resistant voltage-gated sodium channel expressed by sensory neurons. *Nature,* 1996. 379 (6562): p. 257-62). Since then, $Na_V$1.8 has been shown to be a carrier of the sodium current that maintains action potential firing in small dorsal root ganglia (DRG) neurons (Blair, N. T. and B. P. Bean, Roles oftetrodotoxin (TTX)-sensitive $Na^+$ current, TTX-resistant $Na^+$ current, and $Ca^{2+}$ current in the action potentials of nociceptive sensory neurons. *J. Neurosci.,* 2002. 22(23): p. 10277-90). $Na_V$1.8 is involved in spontaneous firing in damaged neurons, like those that drive neuropathic pain (Roza, C., et al., The tetrodotoxin-resistant $Na^+$ channel $Na_V$1.8 is essential for the expression of spontaneous activity in damaged sensory axons of mice. J Physiol., 2003. 550 (Pt 3): p. 921-6; Jarvis, M. F., et al., A-803467, a potent and selective $Na_V$1.8 sodium channel blocker, attenuates neuropathic and inflammatory pain in the rat. *Proc. Natl. Acad. Sci. USA,* 2007. 104(20): p. 8520-5; Joshi, S. K., et al., Involvement of the TTX-resistant sodium channel $Na_V$1.8 in inflammatory and neuropathic, but not post-operative, pain states. *Pain,* 2006. 123(1-2): pp. 75-82; Lai, J., et al., Inhibition of neuropathic pain by decreased expression of the tetrodotoxin-resistant sodium channel, $Na_V$1.8. *Pain,* 2002. 95(1-2): p. 143-52; Dong, X. W., et al., Small interfering RNA-mediated selective knockdown of $Na_V$1.8 tetrodotoxin-resistant sodium channel reverses mechanical allodynia in neuropathic rats. *Neuroscience,* 2007. 146(2): p. 812-21; Huang, H. L., et al., Proteomic profiling of neuromas reveals alterations in protein composition and local protein synthesis in hyper-excitable nerves. *Mol. Pain,* 2008. 4: p. 33; Black, J. A., et al., Multiple sodium channel isoforms and mitogen-activated protein kinases are present in painful human neuromas. *Ann. Neurol.,* 2008. 64(6): p. 644-53; Coward, K., et al., Immunolocalization of SNS/PN3 and NaN/SNS2 sodium channels in human pain states. *Pain,* 2000. 85(1-2): p. 41-50; Yiangou, Y., et al., SNS/PN3 and SNS2/NaN sodium channel-like immunoreactivity in human adult and neonate injured sensory nerves. *FEBS Lett.,* 2000. 467(2-3): p. 249-52; Ruangsri, S., et al., Relationship of axonal voltage-gated sodium channel 1.8 ($Na_V$1.8) mRNA accumulation to sciatic nerve injury-induced painful neuropathy in rats. J Biol. Chem. 286(46): p. 39836-47). The small DRG neurons where $Na_V$1.8 is expressed include the nociceptors involved in pain signaling. $Na_V$1.8 mediates large amplitude action potentials in small neurons of the dorsal root ganglia (Blair, N. T. and B. P. Bean, Roles of tetrodotoxin (TTX)-sensitive $Na^+$ current, TTX-resistant $Na^+$ current, and $Ca^{2+}$ current in the action potentials of nociceptive sensory neurons. J Neurosci., 2002. 22(23): p. 10277-90). $Na_V$1.8 is necessary for rapid repetitive action potentials in nociceptors, and for spontaneous activity of damaged neurons. (Choi, J. S. and S. G. Waxman, Physiological interactions between $Na_V$1.7 and $Na_V$1.8 sodium channels: a computer simulation study. J Neurophysiol. 106(6): p. 3173-84; Renganathan, M., T. R. Cummins, and S. G. Waxman, Contribution of Na(v)1.8 sodium channels to action potential electrogenesis in DRG neurons. *J. Neurophysiol.,* 2001. 86(2): p. 629-40; Roza, C., et al., The tetrodotoxin-resistant $Na^+$ channel $Na_V$1.8 is essential for the expression of spontaneous activity in damaged sensory axons of mice. *J. Physiol.,* 2003. 550 (Pt 3): p. 921-6). In depolarized or damaged DRG neurons, $Na_V$1.8 appears to be a driver of hyper-excitablility (Rush, A. M., et al., A single sodium channel mutation produces hyper- or hypoexcitability in different types of neurons. *Proc. Natl. Acad. Sci. USA,* 2006. 103(21): p. 8245-50). In some animal pain models, $Na_V$1.8 mRNA expression levels have been shown to increase in the DRG (Sun, W., et al., Reduced conduction failure of the main axon of polymodal nociceptive C-fibers contributes to painful diabetic neuropathy in rats. Brain, 135 (Pt 2): p. 359-75; Strickland, I. T., et al., Changes in the expression of $Na_V$1.7, $Na_V$1.8 and $Na_V$1.9 in a distinct population of dorsal root ganglia innervating the rat knee joint in a model of chronic inflammatory joint pain. *Eur. J. Pain,* 2008. 12(5): p. 564-72; Qiu, F., et al., Increased expression of tetrodotoxin-resistant sodium channels $Na_V$1.8 and $Na_V$1.9 within dorsal root ganglia in a rat model of bone cancer pain. Neurosci. Lett., 512(2): p. 61-6).

The primary drawback to some known $Na_V$ inhibitors is their poor therapeutic window, and this is likely a consequence of their lack of isoform selectivity. Since $Na_V$1.8 is primarily restricted to the neurons that sense pain, selective $Na_V$1.8 blockers are unlikely to induce the adverse events common to non-selective $Na_V$ blockers. Accordingly, there remains a need to develop additional $Na_V$ channel modulators, preferably those that are highly potent and selective for $Na_V$1.8.

SUMMARY

In one aspect, the invention relates to a compound described herein, or a pharmaceutically acceptable salt thereof.

In another aspect, the invention relates to a pharmaceutical composition comprising the compound, or a pharmaceutically acceptable salt thereof, and one or more pharmaceutically acceptable carriers or vehicles.

In still another aspect, the invention relates to a method of inhibiting a voltage gated sodium channel in a subject by administering the compound, pharmaceutically acceptable salt, or pharmaceutical composition to the subject.

In yet another aspect, the invention relates to a method of treating or lessening the severity in a subject of a variety of diseases, disorders, or conditions, including, but not limited to, chronic pain, gut pain, neuropathic pain, musculoskeletal pain, acute pain, inflammatory pain, cancer pain, idiopathic pain, postsurgical pain (e.g., bunionectomy pain, herniorrhaphy pain, or abdominoplasty pain), visceral pain, multiple sclerosis, Charcot-Marie-Tooth syndrome, incontinence, pathological cough, and cardiac arrhythmia, by administering the compound, pharmaceutically acceptable salt, or pharmaceutical composition to the subject.

DETAILED DESCRIPTION

In one aspect, the invention relates to a compound of formula (I) or (II)

I

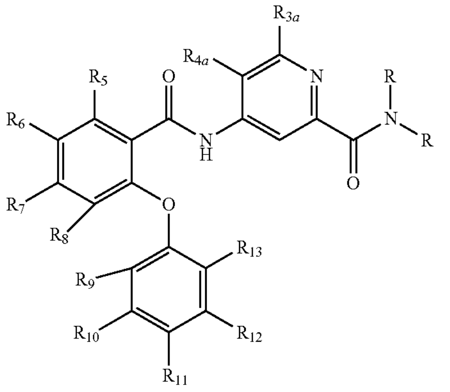

II

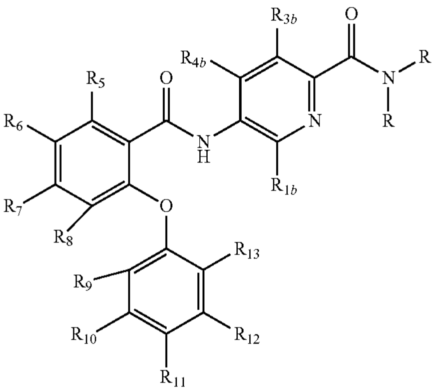

or a pharmaceutically acceptable salt thereof, wherein R, $R_{3a}$, $R_{4a}$, $R_{1b}$, $R_{3b}$, $R_{4b}$, $R_5$, $R_6$, $R_7$, $R_8$, $R_9$, $R_{10}$, $R_{11}$, $R_{12}$, and $R_{13}$ are defined as described herein.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference.

As used herein, the term "compounds of the invention" refers to the compounds of formulas (I) and (II), and all of the embodiments thereof, as described herein, and to the compounds identified in Tables A, B, C, and D.

As described herein, the compounds of the invention comprise multiple variable groups (e.g., R, $R_{3a}$, $R_5$, etc.). As one of ordinary skill in the art will recognize, combinations of groups envisioned by this invention are those combinations that result in the formation of stable or chemically feasible compounds. The term "stable," in this context, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, the term "substituted," refers to a group in which one or more hydrogen radicals has been replaced with a specified substituent. Unless otherwise indicated, a substituted group can have a substituent at any substitutable position of the group, and when more than one position in any given structure can be substituted with more than one substituent selected from a specified group, the substituent can be either the same or different at every position. As one of ordinary skill in the art will recognize, substituted groups envisioned by this invention are those that result in the formation of stable or chemically feasible compounds.

As used herein, the term "halo" means F, Cl, Br or I.

As used herein, the term "alkyl" refers to a straight or branched hydrocarbon chain radical group consisting solely of carbon and hydrogen atoms, containing no unsaturation, and having the specified number of carbon atoms, which is attached to the rest of the molecule by a single bond. For example, a "$C_1$-$C_6$ alkyl" group is an alkyl group having between one and six carbon atoms.

As used herein, the term "haloalkyl" refers to an alkyl group having the specified number of carbon atoms, wherein one or more of the hydrogen atoms of the alkyl group are replaced by halo groups. For example, a "$C_1$-$C_6$ haloalkyl" group is an alkyl group having between one and six carbon atoms, wherein one or more of the hydrogen atoms of the alkyl group are replaced by halo groups.

As used herein, the term "alkoxy" refers to a radical of the formula —$OR_a$ where $R_a$ is an alkyl group having the specified number of carbon atoms. For example, a "$C_1$-$C_6$ alkoxy" group is a radical of the formula —$OR_a$ where $R_a$ is an alkyl group having the between one and six carbon atoms.

As used herein, the term "haloalkoxy" refers to an alkoxy group having the specified number of carbon atoms, wherein one or more of the hydrogen atoms of the of the alkyl group are replaced by halo groups.

As used herein, the term "alkylsulfanyl" refers to a radical of the formula —$SR_a$ where $R_a$ is an alkyl group having the specified number of carbon atoms. For example, a "$C_1$-$C_6$ alkylsulfanyl" group is a radical of the formula —$SR_a$ where $R_a$ is an alkyl group having the between one and six carbon atoms.

As used herein, the term "cycloalkyl" refers to a stable, non-aromatic, mono- or bicyclic (fused, bridged, or spiro) saturated hydrocarbon radical consisting solely of carbon and hydrogen atoms, having the specified number of carbon ring atoms, and which is attached to the rest of the molecule by a single bond.

As used herein, the term "cycloalkenyl" refers to a stable, non-aromatic, mono- or bicyclic (fused, bridged, or spiro) unsaturated hydrocarbon radical consisting solely of carbon and hydrogen atoms, having the specified number of carbon ring atoms and one or more carbon-carbon double bonds in the ring, and which is attached to the rest of the molecule by a single bond.

As used herein, the term "heteroaryl" refers to a stable, aromatic, mono- or bicyclic ring radical having the specified number of ring atoms and comprising one or more heteroatoms individually selected from nitrogen, oxygen and sulfur.

As used herein, the term "heterocyclyl" refers to a stable, non-aromatic, mono- or bicyclic (fused, bridged, or spiro) saturated or unsaturated radical, having the specified number of ring atoms, including one or more ring heteroatoms selected from nitrogen, oxygen and sulfur, and which is attached to the rest of the molecule by a single bond.

As used herein, the term "heterocycloalkyl" refers to a stable, non-aromatic, mono- or bicyclic (fused, bridged, or spiro) saturated radical, having the specified number of ring atoms, including one or more ring heteroatoms selected from nitrogen, oxygen and sulfur, and which is attached to the rest of the molecule by a single bond.

As used herein, the term "heterocycloalkenyl" refers to a stable, non-aromatic, mono- or bicyclic (fused, bridged, or spiro) unsaturated hydrocarbon radical, having the specified number of ring atoms, including one or more ring heteroatoms selected from nitrogen, oxygen and sulfur, and one or more carbon-carbon or carbon-heteroatom double bonds in the ring, and which is attached to the rest of the molecule by a single bond.

As used herein, "*6" and "*7" in the following structure designate the carbon atom in formula (I) or (II) to which $R_6$ and $R_7$, respectively, are attached.

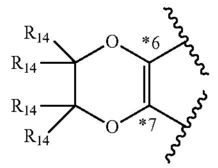

Unless otherwise specified, the compounds of the invention, whether identified by chemical name or chemical structure, include all stereoisomers (e.g., enantiomers and diastereomers), double bond isomers (e.g., (Z) and (E)), conformational isomers, and tautomers, of the compounds identified by the chemical names and chemical structures provided herein. In addition, single stereoisomers, double bond isomers, conformation isomers, and tautomers as well as mixtures of stereoisomers, double bond isomers, conformation isomers, and tautomers are within the scope of the invention.

As used herein, in any chemical structure or formula, a bold or hashed straight bond attached to a stereocenter of a compound, such as in

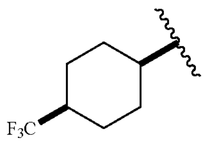

and

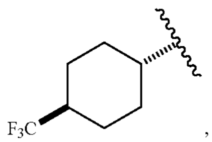

, denotes the relative stereochemistry of the stereocenter, relative to other stereocenter(s) to which bold or hashed straight bonds are attached.

As used herein, the term "compound," when referring to the compounds of the invention, refers to a collection of molecules having identical chemical structures, except that there may be isotopic variation among the constituent atoms of the molecules. The term "compound" includes such a collection of molecules without regard to the purity of a given sample containing the collection of molecules. Thus, the term "compound" includes such a collection of molecules in pure form, in a mixture (e.g., solution, suspension, or colloid) with one or more other substances, or in the form of a hydrate, solvate, or co-crystal.

In the specification and claims, unless otherwise specified, any atom not specifically designated as a particular isotope in any compound of the invention is meant to represent any stable isotope of the specified element. In the Examples, where an atom is not specifically designated as a particular isotope in any compound of the invention, no effort was made to enrich that atom in a particular isotope, and therefore a person of ordinary skill in the art would understand that such atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

As used herein in the specification and claims, "H" refers to hydrogen and includes any stable isotope of hydrogen, namely $^{1}H$ and D. In the Examples, where an atom is designated as "H," no effort was made to enrich that atom in a particular isotope of hydrogen, and therefore a person of ordinary skill in the art would understand that such hydrogen atom likely was present at approximately the natural abundance isotopic composition of hydrogen.

As used herein, "$^{1}H$" refers to protium. Where an atom in a compound of the invention, or a pharmaceutically acceptable salt thereof, is designated as protium, protium is present at the specified position at at least the natural abundance concentration of protium.

As used herein, "D," "d," and "$^{2}H$" refer to deuterium.

In some embodiments, the compounds of the invention, and pharmaceutically acceptable salts thereof, include each constituent atom at approximately the natural abundance isotopic composition of the specified element.

In some embodiments, the compounds of the invention, and pharmaceutically acceptable salts thereof, include one or more atoms having an atomic mass or mass number which differs from the atomic mass or mass number of the most abundant isotope of the specified element ("isotope-labeled" compounds and salts). Examples of stable isotopes which are commercially available and suitable for the invention include without limitation isotopes of hydrogen, carbon, nitrogen, oxygen, and phosphorus, for example $^{2}H$, $^{13}C$, $^{15}N$, $^{18}O$, $^{17}O$, and $^{31}P$, respectively.

The isotope-labeled compounds and salts can be used in a number of beneficial ways, including as medicaments. In some embodiments, the isotope-labeled compounds and salts are deuterium (2H)-labeled. Deuterium ($^{2}H$)-labeled compounds and salts are therapeutically useful with potential therapeutic advantages over the non-$^{2}H$-labeled compounds. In general, deuterium ($^{2}H$)-labeled compounds and salts can have higher metabolic stability as compared to those that are not isotope-labeled owing to the kinetic isotope effect described below. Higher metabolic stability translates directly into an increased in vivo half-life or lower dosages, which under most circumstances would represent a preferred embodiment of the present invention. The isotope-labeled compounds and salts can usually be prepared by carrying out the procedures disclosed in the synthesis schemes, the examples and the related description, replacing a non-isotope-labeled reactant by a readily available isotope-labeled reactant.

The deuterium ($^{2}H$)-labeled compounds and salts can manipulate the rate of oxidative metabolism of the compound by way of the primary kinetic isotope effect. The primary kinetic isotope effect is a change of the rate for a chemical reaction that results from exchange of isotopic nuclei, which in turn is caused by the change in ground state energies of the covalent bonds involved in the reaction. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_H/k_D$=2-7 are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of an isotope (e.g., deuterium) incorporated at a given position of an isotope-labeled compound of the invention, or a pharmaceutically acceptable salt thereof, may be defined by the isotopic enrichment factor. The term "isotopic enrichment factor," as used herein, means the ratio between the abundance of an isotope at a given position in an isotope-labeled compound (or salt) and the natural abundance of the isotope.

Where an atom in a compound of the invention, or a pharmaceutically acceptable salt thereof, is designated as deuterium, such compound (or salt) has an isotopic enrichment factor for such atom of at least 3000 (45% deuterium incorporation). In some embodiments, the isotopic enrichment factor is at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In one aspect, the invention relates to a compound of formula (I) or (II)

I

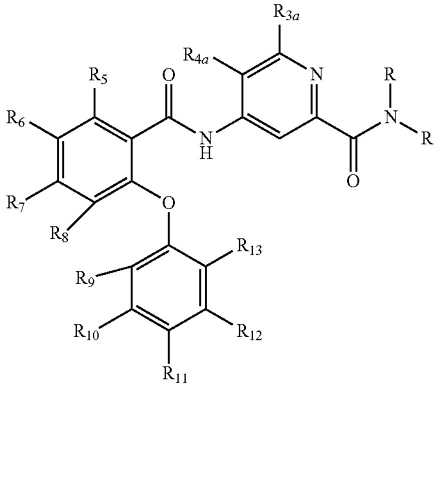

-continued

II

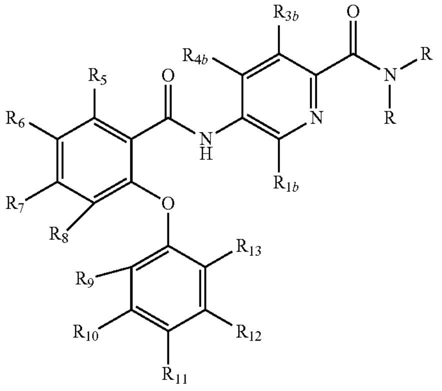

or a pharmaceutically acceptable salt thereof, wherein:

each R is independently H or $C_1$-$C_6$ alkyl;

$R_{3a}$ is H, halo, $C_1$-$C_6$ alkyl, $C_1$-$C_6$ haloalkyl, $C_1$-$C_6$ alkoxy, or $C_1$-$C_6$ haloalkoxy;

$R_{4a}$ is H, halo, $C_1$-$C_6$ alkyl, $C_1$-$C_6$ haloalkyl, $C_1$-$C_6$ alkoxy, or $C_1$-$C_6$ haloalkoxy;

$R_{1b}$ is H, halo, $C_1$-$C_6$ alkyl, $C_1$-$C_6$ haloalkyl, $C_1$-$C_6$ alkoxy, or $C_1$-$C_6$ haloalkoxy;

$R_{3b}$ is H, halo, $C_1$-$C_6$ alkyl, $C_1$-$C_6$ haloalkyl, $C_1$-$C_6$ alkoxy, or $C_1$-$C_6$ haloalkoxy;

$R_{4b}$ is H, halo, $C_1$-$C_6$ alkyl, $C_1$-$C_6$ haloalkyl, $C_1$-$C_6$ alkoxy, or $C_1$-$C_6$ haloalkoxy;

$R_5$, $R_6$, $R_7$, and $R_8$ are defined as follows:

(i) $R_5$, $R_6$, and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is $C_1$-$C_6$ alkyl;

(ii) $R_5$ is W—$(CH_2)_n$—$R_z$, $C_1$-$C_6$ alkylsulfanyl, —O—$(CH_2)_p$—$R_w$, or —O—$(CH_2)_p$—N($C_1$-$C_6$ alkyl)$_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H;

(iii) $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$, —C≡C—$R_x$, or 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H; or (iv) $R_5$ is H, halo, $C_1$-$C_6$ alkyl, $C_1$-$C_6$ haloalkyl, $C_1$-$C_6$ alkoxy, or $C_1$-$C_6$ haloalkoxy; $R_6$ and $R_7$,

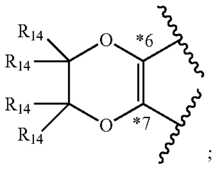

;

together with the carbon atoms to which they are attached, form a ring of formula $R_{14}$; and $R_8$ is H;

$R_9$ is H, halo, $C_1$-$C_6$ alkyl, $C_1$-$C_6$ haloalkyl, $C_1$-$C_6$ alkoxy, or $C_1$-$C_6$ haloalkoxy;

$R_{10}$ is H, halo, $C_1$-$C_6$ alkyl, $C_1$-$C_6$ haloalkyl, $C_1$-$C_6$ alkoxy, or $C_1$-$C_6$ haloalkoxy;

$R_{11}$ is H, halo, $C_1$-$C_6$ alkyl, $C_1$-$C_6$ haloalkyl, $C_1$-$C_6$ alkoxy, or $C_1$-$C_6$ haloalkoxy;

$R_{12}$ is H, halo, $C_1$-$C_6$ alkyl, $C_1$-$C_6$ haloalkyl, $C_1$-$C_6$ alkoxy, or $C_1$-$C_6$ haloalkoxy;

$R_{13}$ is H, halo, $C_1$-$C_6$ alkyl, $C_1$-$C_6$ haloalkyl, $C_1$-$C_6$ alkoxy, or $C_1$-$C_6$ haloalkoxy;

each $R_{14}$ is independently H, halo, $C_1$-$C_4$ alkyl, or $C_1$-$C_4$ haloalkyl;

each W is independently O or a single bond;

$R_x$ is $C_1$-$C_6$ alkyl or 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl;

$R_z$ is 3-6 membered heterocyclyl, 7-8 membered cycloalkyl, or 4-8 membered cycloalkenyl, wherein said 3-6 membered heterocyclyl, 7-8 membered cycloalkyl, or 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring;

n is 0 or 1; and p is 2 or 3.

In some embodiments, the invention relates to a compound of formula (I) or (II), or a pharmaceutically acceptable salt thereof, wherein each R is H. In other embodiments, each R is independently $C_1$-$C_6$ alkyl.

In some embodiments, the invention relates to a compound of formula (I) or (II), or a pharmaceutically acceptable salt thereof, wherein $R_{3a}$ and $R_{4a}$ are each H.

In some embodiments, the invention relates to a compound of formula (I) or (II), or a pharmaceutically acceptable salt thereof, wherein $R_{1b}$, $R_{3b}$, and $R_{4b}$ are each H.

In some embodiments, the invention relates to a compound of formula (I) or (II), or a pharmaceutically acceptable salt thereof, wherein $R_5$, $R_6$, and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is $C_1$-$C_6$ alkyl. In other embodiments, $R_5$ is H; $R_6$ is $C_1$-$C_6$ haloalkyl; $R_7$ is H; and $R_8$ is $C_1$-$C_6$ alkyl. In other embodiments, $R_5$ is H; $R_6$ is $CF_3$; $R_7$ is H; and $R_8$ is $CH_3$.

In some embodiments, the invention relates to a compound of formula (I) or (II), or a pharmaceutically acceptable salt thereof, wherein $R_5$ is W—$(CH_2)_n$—$R_z$, $C_1$-$C_6$ alkylsulfanyl, —O—$(CH_2)_p$—$R_w$, or —O—$(CH_2)_p$—N($C_1$-$C_6$ alkyl)$_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is W—$(CH_2)_n$—$R_z$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is O—$R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; $R_6$ is $C_1$-$C_6$ haloalkyl; $R_7$ is H; and $R_8$ is H. In other embodiments, $R_5$ is O—$R_z$, and $R_z$ is 3-6 membered heterocyclyl; $R_6$ is $C_1$-$C_6$ haloalkyl; $R_7$ is H; and $R_8$ is H. In other embodiments, $R_5$ is O—$R_z$, and $R_z$ is oxetanyl or tetrahydrofuranyl; $R_6$ is $C_1$-$C_6$ haloalkyl; $R_7$ is H; and $R_8$ is H. In other embodiments, $R_5$ is $C_1$-$C_6$ alkylsulfanyl; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is $C_1$-$C_6$ alkylsulfanyl; $R_6$ is $C_1$-$C_6$ haloalkyl; $R_7$ is H; and $R_8$ is H. In other embodiments, $R_5$ is —O—$(CH_2)_p$—$R_w$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is —O—$(CH_2)_p$—$R_w$; $R_6$ is $C_1$-$C_6$ haloalkyl; $R_7$ is H; and $R_8$ is H. In other embodiments, $R_5$ is —O—$(CH_2)_p$—$R_w$, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl; $R_6$ is $C_1$-$C_6$ haloalkyl; $R_7$ is H; and $R_8$ is H. In other embodiments, $R_5$ is —O—$(CH_2)_p$—$R_w$, and $R_w$ is 3-6 membered cycloalkyl; $R_6$ is $C_1$-$C_6$ haloalkyl; $R_7$ is H; and $R_8$ is H. In other embodiments, $R_5$ is —O—$(CH_2)_2$—$R_w$, and $R_w$ is 3-6 membered cycloalkyl; $R_6$ is $C_1$-$C_6$ haloalkyl; $R_7$ is H; and $R_8$ is H. In other embodiments, $R_5$ is —O—$(CH_2)_p$—$N(C_1$-$C_6$ alkyl$)_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is —O—$(CH_2)_p$—$N(CH_3)_2$; $R_6$ is $C_1$-$C_6$ haloalkyl; $R_7$ is H; and $R_8$ is H. In other embodiments, $R_5$ is —O—$(CH_2)_2$—$N(C_1$-$C_6$ alkyl$)_2$; $R_6$ is $C_1$-$C_6$ haloalkyl; $R_7$ is H; and $R_8$ is H. In other embodiments, $R_5$ is

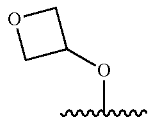
, $SCH_3$,

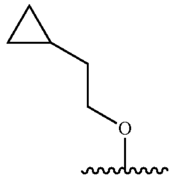
, or $O(CH_2)_2N(CH_3)_2$; $R_6$ is $CF_3$; $R_7$ is H; and $R_8$ is H. In other embodiments, $R_5$ is

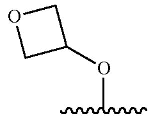
;

$R_6$ is $CF_3$; $R_7$ is H; and $R_8$ is H. In other embodiments, $R_5$ is $SCH_3$; $R_6$ is $CF_3$; $R_7$ is H; and $R_8$ is H. In other embodiments, $R_5$ is

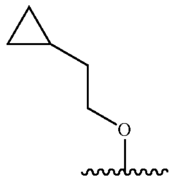
;

$R_6$ is $CF_3$; $R_7$ is H; and $R_8$ is H. In other embodiments, $R_5$ is $O(CH_2)_2N(CH_3)_2$; $R_6$ is $CF_3$; $R_7$ is H; and $R_8$ is H.

In some embodiments, the invention relates to a compound of formula (I) or (II), or a pharmaceutically acceptable salt thereof, wherein $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$, —C≡C—$R_x$, or 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocyclyl, wherein said 5-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocyclyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkyl, wherein said 5-6 membered heterocycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is tetrahydropyran-4-yl or tetrahydrofuran-3-yl, wherein said tetrahydropyran-4-yl or tetrahydrofuran-3-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is tetrahydropyran-4-yl or tetrahydrofuran-3-yl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkenyl, wherein said 5-6 membered heterocycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkenyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl, wherein said 3,4-dihydropyran-5-yl, 3,6-dihydropyran-4-yl, 2,5-dihydrofuran-3-yl, or 2,3-dihydrofuran-4-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 7-8 membered cycloalkyl, wherein said 7-8 membered cycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 7-8 membered cycloalkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered cycloalkenyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is cyclohexen-1-yl or cyclopenten-1-yl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is O—$R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is O—$R_z$, and $R_z$ is $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is O—$R_z$, and $R_z$ is $R_z$ is cyclobutenyl, wherein said cyclobutenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H.

In other embodiments, $R_5$ is H, halo, or $C_1$-$C_6$ alkyl; $R_6$ is H; $R_7$ is W—$(CH_2)_n$—$R_z$; and $R_8$ is H. In other embodiments, $R_5$ is H, halo, or $C_1$-$C_6$ alkyl; $R_6$ is H; $R_7$ is W—$R_z$; and $R_8$ is H. In other embodiments, $R_5$ is H, halo, or $C_1$-$C_6$ alkyl; $R_6$ is H; $R_7$ is $R_z$; and $R_8$ is H. In other embodiments, $R_5$ is H, halo, or $C_1$-$C_6$ alkyl; $R_6$ is H; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered heterocyclyl, wherein said 5-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered heterocyclyl; and $R_8$ is H. In other embodiments, $R_8$ is H, halo, or $C_1$-$C_6$ alkyl; $R_6$ is H; $R_7$ is $R_z$, and $R_z$ is 5-6 membered heterocycloalkyl, wherein said 5-6 membered heterocycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_8$ is H, halo, or $C_1$-$C_6$ alkyl; $R_6$ is H; $R_7$ is $R_z$, and $R_z$ is 5-6 membered heterocycloalkyl; and $R_8$ is H. In other embodiments, $R_8$ is H, halo, or $C_1$-$C_6$ alkyl; $R_6$ is H; $R_7$ is $R_z$, and $R_z$ is tetrahydropyran-4-yl or tetrahydrofuran-3-yl, wherein said tetrahydropyran-4-yl or tetrahydrofuran-3-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_8$ is H, halo, or $C_1$-$C_6$ alkyl; $R_6$ is H; $R_7$ is $R_z$, and $R_z$ is tetrahydropyran-4-yl or tetrahydrofuran-3-yl; and $R_8$ is H. In other embodiments, $R_8$ is H, halo, or $C_1$-$C_6$ alkyl; $R_6$ is H; $R_7$ is $R_z$, and $R_z$ is 5-6 membered heterocycloalkenyl, wherein said 5-6 membered heterocycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_8$ is H, halo, or $C_1$-$C_6$ alkyl; $R_6$ is H; $R_7$ is $R_z$, and $R_z$ is 5-6 membered heterocycloalkenyl; and $R_8$ is H. In other embodiments, $R_8$ is H, halo, or $C_1$-$C_6$ alkyl; $R_6$ is H; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl, wherein said 3,4-dihydropyran-5-yl, 3,6-dihydropyran-4-yl, 2,5-dihydrofuran-3-yl, or 2,3-dihydrofuran-4-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_8$ is H, halo, or $C_1$-$C_6$ alkyl; $R_6$ is H; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl; and $R_8$ is H. In other embodiments, $R_8$ is H, halo, or $C_1$-$C_6$ alkyl; $R_6$ is H; $R_7$ is $R_z$, and $R_z$ is 7-8 membered cycloalkyl, wherein said 7-8 membered cycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_8$ is H, halo, or $C_1$-$C_6$ alkyl; $R_6$ is H; $R_7$ is $R_z$, and $R_z$ is 7-8 membered cycloalkyl; and $R_8$ is H. In other embodiments, $R_8$ is H, halo, or $C_1$-$C_6$ alkyl; $R_6$ is H; $R_7$ is $R_z$, and $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_8$ is H, halo, or $C_1$-$C_6$ alkyl; $R_6$ is H; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered cycloalkenyl; and $R_8$ is H. In other embodiments, $R_5$ is H, halo, or $C_1$-$C_6$ alkyl; $R_6$ is H; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is cyclohexen-1-yl or cyclopenten-1-yl; and $R_8$ is H. In other embodiments, $R_8$ is H, halo, or $C_1$-$C_6$ alkyl; $R_6$ is H; $R_7$ is O—$R_z$; and $R_8$ is H. In other embodiments, $R_5$ is H, halo, or $C_1$-$C_6$ alkyl; $R_6$ is H; $R_7$ is O—$R_z$, and $R_z$ is $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is O—$R_z$, and $R_z$ is $R_z$ is cyclobutenyl, wherein said cyclobutenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H.

In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is $C_1$-$C_6$ alkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is 3-6 membered cycloalkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is cyclopropyl or cyclobutyl; and $R_8$ is H.

In other embodiments, $R_5$ is H, halo, or $C_1$-$C_6$ alkyl; $R_6$ is H; $R_7$ is —C≡C—$R_x$; and $R_8$ is H. In other embodiments, $R_5$ is H, halo, or $C_1$-$C_6$ alkyl; $R_6$ is H; $R_7$ is —C≡C—$R_x$, and $R_x$ is $C_1$-$C_6$ alkyl; and $R_8$ is H. In other embodiments, $R_5$ is H, halo, or $C_1$-$C_6$ alkyl; $R_6$ is H; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_8$ is H. In other embodiments, $R_5$ is H, halo, or $C_1$-$C_6$ alkyl; $R_6$ is H; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_8$ is H. In other embodiments, $R_5$ is H, halo, or $C_1$-$C_6$ alkyl; $R_6$ is H; $R_7$ is —C≡C—$R_x$, and $R_x$ is 3-6 membered cycloalkyl; and $R_8$ is H. In other embodiments, $R_5$ is H, halo, or $C_1$-$C_6$ alkyl; $R_6$ is H; $R_7$ is —C≡C—$R_x$, and $R_x$ is cyclopropyl or cyclobutyl; and $R_8$ is H.

In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is 3-6 membered cycloalkyl, wherein said 3-6 membered cycloalkyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is cyclohexyl, wherein said cyclohexyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is phenyl, wherein said phenyl is substituted with 1-3 substituents selected from a group consisting of $C_1$-$C_6$ alkoxy, CN, and —C(O)$NH_2$; and $R_8$ is H.

In other embodiments, $R_5$ is H, halo, or $C_1$-$C_6$ alkyl; $R_6$ is H; $R_7$ is 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H. In other embodiments, $R_5$ is H, halo, or $C_1$-$C_6$ alkyl; $R_6$ is H; $R_7$ is 3-6 membered cycloalkyl, wherein said 3-6 membered cycloalkyl is substituted with 1-3 substituents selected from a group consisting of $C_1$-$C_6$ alkoxy, CN, and —C(O)$NH_2$; and $R_8$ is H. In other embodiments, $R_8$ is H, halo, or $C_1$-$C_6$ alkyl; $R_6$ is H; $R_7$ is cyclohexyl, wherein said cyclohexyl is substituted with 1-3 substituents selected from a group consisting of $C_1$-$C_6$ alkoxy, CN, and —C(O)$NH_2$; and $R_8$ is H. In other embodiments, $R_8$ is H, halo, or $C_1$-$C_6$ alkyl; $R_6$ is H; $R_7$ is phenyl, wherein said phenyl is substituted with 1-3 substituents selected from a group consisting of $C_1$-$C_6$ alkoxy, CN, and —C(O)$NH_2$; and $R_8$ is H. In other embodiments, $R_5$ is H, F, or $CH_3$; $R_6$ is H; $R_7$ is

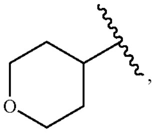, 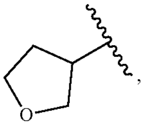, 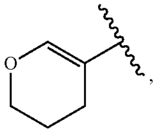,

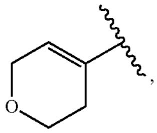, 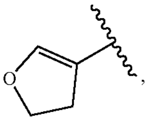, 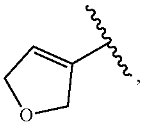,

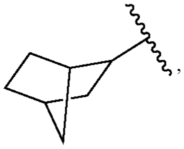, 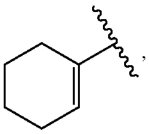, 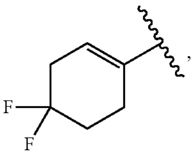,

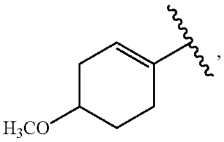, 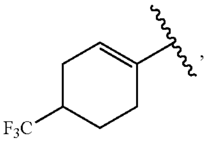,

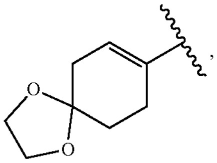, 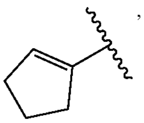,

-continued

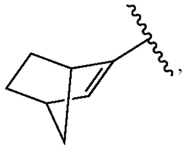, 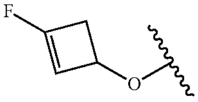,

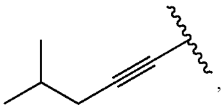, 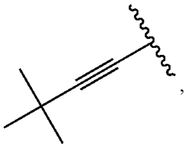,

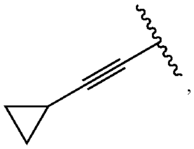, 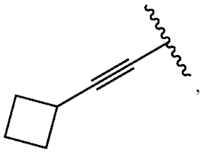,

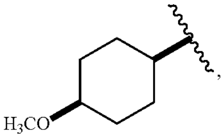, 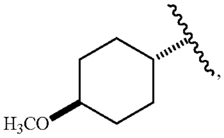,

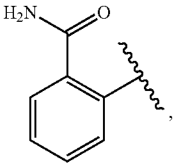, 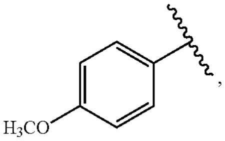,

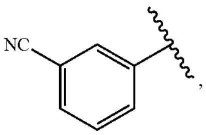, or 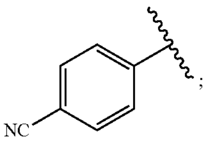;

and $R_8$ is H. In other embodiments, $R_5$ is H, F, or $CH_3$; $R_6$ is H; $R_7$ is

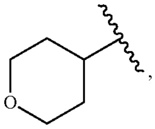, 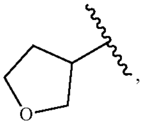, 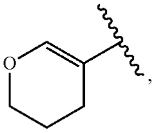,

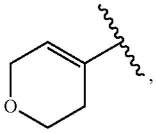, 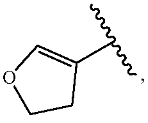, 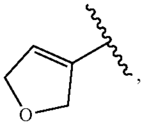,

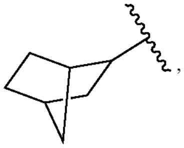, 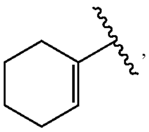, 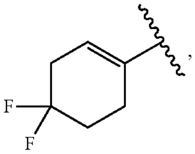,

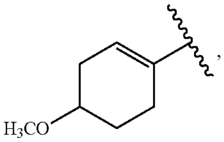, 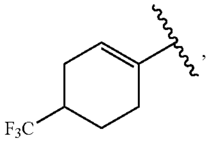,

-continued

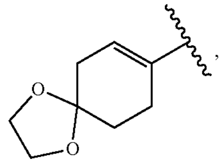,
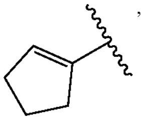,
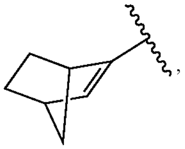, or
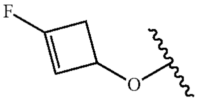;

and $R_8$ is H. In other embodiments, $R_5$ is H, F, or $CH_3$; $R_6$ is H; $R_7$ is

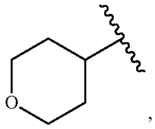,
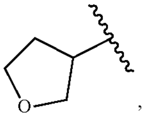,
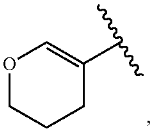,
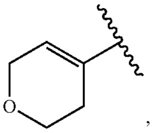,
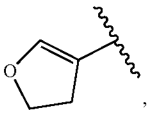, or
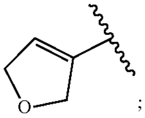;

and $R_8$ is H. In other embodiments, $R_5$ is H, F, or $CH_3$; $R_6$ is H; $R_7$ is

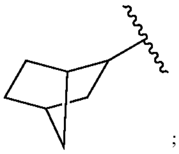 [SMILES: *C1CC2CCC1C2];

and $R_8$ is H. In other embodiments, $R_5$ is H, F, or $CH_3$; $R_6$ is H; $R_7$ is

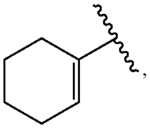,
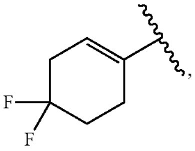,
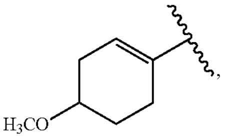,
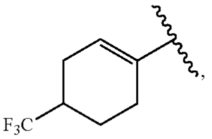,
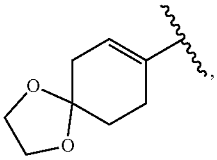,
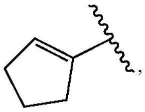, or

-continued

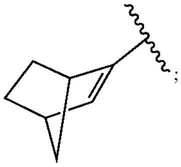;

and $R_8$ is H. In other embodiments, $R_5$ is H, F, or $CH_3$; $R_6$ is H; $R_7$ is

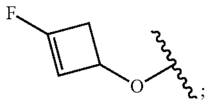 [SMILES: *OC1C=C(F)C1];

and $R_8$ is H. In other embodiments, $R_5$ is H, F, or $CH_3$; $R_6$ is H; $R_7$ is

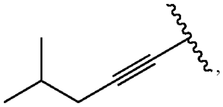,
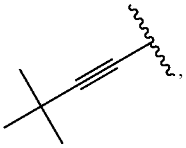,
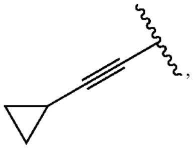, or
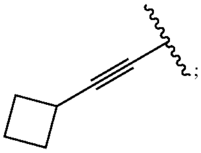;

or and $R_8$ is H. In other embodiments, $R_5$ is H, F, or $CH_3$; $R_6$ is H; $R_7$ is

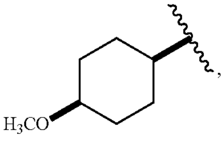,
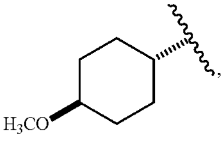,
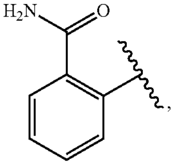,
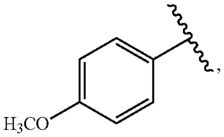,
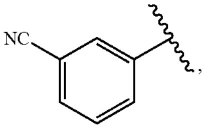, or
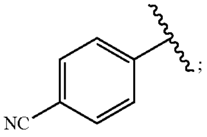;

and $R_8$ is H. In other embodiments, $R_5$ is H, F, or $CH_3$; $R_6$ is H; $R_7$ is

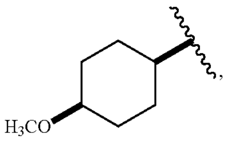

, or

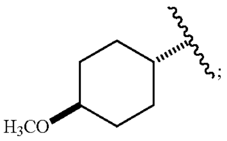

;

and $R_8$ is H. In other embodiments, $R_5$ is H, F, or $CH_3$; $R_6$ is H; $R_7$ is

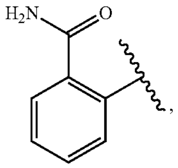

,

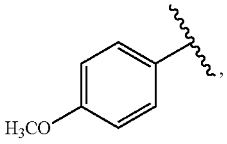

,

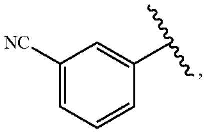

, or

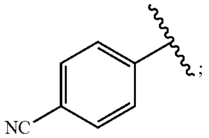

;

and $R_8$ is H.

In some embodiments, the invention relates to a compound of formula (I) or (II), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ haloalkoxy; $R_6$ and $R_7$, together with the carbon atoms to which they are attached, form a ring of formula

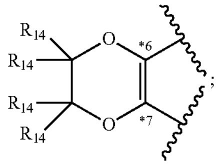

;

and $R_8$ is H. In other embodiments, $R_5$ is H or halo; $R_6$ and $R_7$, together with the carbon atoms to which they are attached, form a ring of formula

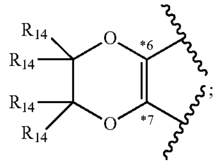

;

and $R_8$ is H. In other embodiments, $R_5$ is H or halo; $R_6$ and $R_7$, together with the carbon atoms to which they are attached, form a ring of formula

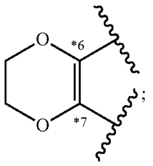 [SMILES: *C1=C(*)OCCO1]

;

and $R_8$ is H. In other embodiments, $R_5$ is H or F; $R_6$ and $R_7$, together with the carbon atoms to which they are attached, form a ring of formula

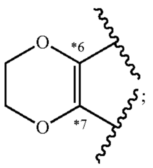 [SMILES: *C1=C(*)OCCO1]

;

and $R_8$ is H.

In some embodiments, the invention relates to a compound of formula (I) or (II), or a pharmaceutically acceptable salt thereof, wherein $R_9$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_9$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_9$ is H, halo, $C_1$-$C_6$ haloalkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ haloalkyl, or $C_1$-$C_6$ haloalkoxy. In other embodiments, $R_9$ is H, halo, $C_1$-$C_6$ alkyl, $C_1$-$C_6$ haloalkyl, or $C_1$-$C_6$ alkoxy. In other embodiments, $R_9$ is $C_1$-$C_6$ alkoxy. In other embodiments, $R_9$ is $OCH_3$, $OC(^1H)_3$, or $OCD_3$. In other embodiments, $R_9$ is $OCH_3$. In other embodiments, $R_9$ is $OC(^1H)_3$. In other embodiments, $R_9$ is $OCD_3$.

In some embodiments, the invention relates to a compound of formula (I) or (II), or a pharmaceutically acceptable salt thereof, wherein $R_{10}$ is H. In other embodiments, $R_{10}$ is halo. In other embodiments, $R_{10}$ is F.

In some embodiments, the invention relates to a compound of formula (I) or (II), or a pharmaceutically acceptable salt thereof, wherein $R_{11}$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_{11}$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_{11}$ is H, halo, $C_1$-$C_6$ haloalkyl, $C_1$-$C_6$ alkoxy, or $C_1$-$C_6$ haloalkoxy. In other embodiments, $R_{11}$ is H, halo, $C_1$-$C_6$ alkyl, $C_1$-$C_6$ alkoxy, or $C_1$-$C_6$ haloalkoxy. In other embodiments, $R_{11}$ is H, halo, $C_1$-$C_6$ alkyl, $C_1$-$C_6$ haloalkyl, or $C_1$-$C_6$ haloalkoxy. In other embodiments, $R_{11}$ is H, halo, $C_1$-$C_6$ alkyl, $C_1$-$C_6$ haloalkyl, or $C_1$-$C_6$ alkoxy. In other embodiments, $R_{11}$ is $C_1$-$C_6$ haloalkoxy. In other embodiments, $R_{11}$ is $OCF_3$.

In some embodiments, the invention relates to a compound of formula (I) or (II), or a pharmaceutically acceptable salt thereof, wherein $R_{12}$ is H.

In some embodiments, the invention relates to a compound of formula (I) or (II), or a pharmaceutically acceptable salt thereof, wherein $R_{13}$ is H.

In some embodiments, the invention relates to a compound of formula (I) or (II), i.e., the compound in non-salt form.

In one aspect, the invention relates to a compound of formula (I)

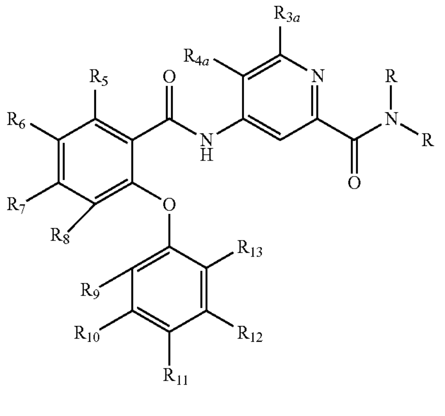

I or a pharmaceutically acceptable salt thereof, wherein:

each R is independently H or $C_1$-$C_6$ alkyl;

$R_{3a}$ is H, halo, $C_1$-$C_6$ alkyl, $C_1$-$C_6$ haloalkyl, $C_1$-$C_6$ alkoxy, or $C_1$-$C_6$ haloalkoxy;

$R_{4a}$ is H, halo, $C_1$-$C_6$ alkyl, $C_1$-$C_6$ haloalkyl, $C_1$-$C_6$ alkoxy, or $C_1$-$C_6$ haloalkoxy;

$R_5$, $R_6$, $R_7$, and $R_8$ are defined as follows:

(i) $R_5$, $R_6$, and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is $C_1$-$C_6$ alkyl;

(ii) $R_5$ is W—$(CH_2)_n$—$R_z$, $C_1$-$C_6$ alkylsulfanyl, —O—$(CH_2)_p$—$R_w$, or —O—$(CH_2)_p$—N($C_1$-$C_6$ alkyl)$_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H;

(iii) $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$, —C≡C—$R_x$, or 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H; or (iv) $R_8$ is H, halo, $C_1$-$C_6$ alkyl, $C_1$-$C_6$ haloalkyl, $C_1$-$C_6$ alkoxy, or $C_1$-$C_6$ haloalkoxy; $R_6$ and $R_7$, together with the carbon atoms to which they are attached, form a ring of formula

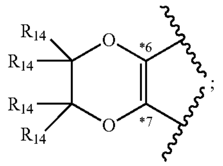

and $R_8$ is H;

$R_9$, $R_{10}$, $R_{11}$, $R_{12}$, and $R_{13}$ are each independently H, halo, $C_1$-$C_6$ alkyl, $C_1$-$C_6$ haloalkyl, $C_1$-$C_6$ alkoxy, or $C_1$-$C_6$ haloalkoxy;

each $R_{14}$ is independently H, halo, $C_1$-$C_4$ alkyl, or $C_1$-$C_4$ haloalkyl;

each W is independently O or a single bond;

$R_x$ is $C_1$-$C_6$ alkyl or 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl;

$R_z$ is 3-6 membered heterocyclyl, 7-8 membered cycloalkyl, or 4-8 membered cycloalkenyl, wherein said 3-6 membered heterocyclyl, 7-8 membered cycloalkyl, or 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring;

n is 0 or 1; and p is 2 or 3.

In some embodiments, the invention relates to a compound of formula (I), or a pharmaceutically acceptable salt thereof, wherein each R is H. In other embodiments, each R is independently $C_1$-$C_6$ alkyl.

In some embodiments, the invention relates to a compound of formula (I), or a pharmaceutically acceptable salt thereof, wherein $R_{3a}$ and $R_{4a}$ are each H.

In some embodiments, the invention relates to a compound of formula (I), or a pharmaceutically acceptable salt thereof, wherein $R_{1b}$, $R_{3b}$, and $R_{4b}$ are each H.

In some embodiments, the invention relates to a compound of formula (I), or a pharmaceutically acceptable salt thereof, wherein $R_5$, $R_6$, and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is $C_1$-$C_6$ alkyl. In other embodiments, $R_5$ is H; $R_6$ is $C_1$-$C_6$ haloalkyl; $R_7$ is H; and $R_8$ is $C_1$-$C_6$ alkyl. In other embodiments, $R_5$ is H; $R_6$ is $CF_3$; $R_7$ is H; and $R_8$ is $CH_3$.

In some embodiments, the invention relates to a compound of formula (I), or a pharmaceutically acceptable salt thereof, wherein $R_5$ is W—$(CH_2)_n$—$R_z$, $C_1$-$C_6$ alkylsulfanyl, —O—$(CH_2)_p$—$R_w$, or —O—$(CH_2)_p$—N($C_1$-$C_6$ alkyl)$_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is W—$(CH_2)_n$—$R_z$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is O—$R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; $R_6$ is $C_1$-$C_6$ haloalkyl; $R_7$ is H; and $R_8$ is H. In other embodiments, $R_5$ is O—$R_z$, and $R_z$ is 3-6 membered heterocyclyl; $R_6$ is $C_1$-$C_6$ haloalkyl; $R_7$ is H; and $R_8$ is H. In other embodiments, $R_5$ is O—$R_z$, and $R_z$ is oxetanyl or tetrahydrofuranyl; $R_6$ is $C_1$-$C_6$ haloalkyl; $R_7$ is H; and $R_8$ is H. In other embodiments, $R_5$ is $C_1$-$C_6$ alkylsulfanyl; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is $C_1$-$C_6$ alkylsulfanyl; $R_6$ is $C_1$-$C_6$ haloalkyl; $R_7$ is H; and $R_8$ is H. In other embodiments, $R_5$ is —O—$(CH_2)_p$—$R_w$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is —O—$(CH_2)_p$—$R_w$; $R_6$ is $C_1$-$C_6$ haloalkyl; $R_7$ is H; and $R_8$ is H. In other embodiments, $R_5$ is —O—$(CH_2)_p$—$R_w$, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl; $R_6$ is $C_1$-$C_6$ haloalkyl; $R_7$ is H; and $R_8$ is H. In other embodiments, $R_5$ is —O—$(CH_2)_p$—$R_w$, and $R_w$ is 3-6 membered cycloalkyl; $R_6$ is $C_1$-$C_6$ haloalkyl; $R_7$ is H; and $R_8$ is H. In other embodiments, $R_5$ is —O—$(CH_2)_2$—$R_w$, and $R_w$ is 3-6 membered cycloalkyl; $R_6$ is $C_1$-$C_6$ haloalkyl; $R_7$ is H; and $R_8$ is H. In other embodiments, $R_5$ is –0-$(CH_2)_p$—N($C_1$-$C_6$ alkyl$)_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_5$ is —O—$(CH_2)_p$—$N(CH_3)_2$; $R_6$ is $C_1$-$C_6$ haloalkyl; $R_7$ is H; and $R_8$ is H. In other embodiments, $R_5$ is —O—$(CH_2)_2$—N($C_1$-$C_6$ alkyl$)_2$; $R_6$ is $C_1$-$C_6$ haloalkyl; $R_7$ is H; and $R_8$ is H. In other embodiments, $R_5$ is

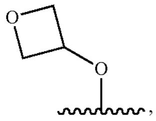 [SMILES: *OC1COC1]

, $SCH_3$,

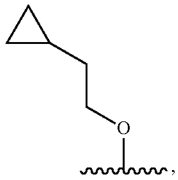 [SMILES: *OCCC1CC1]

, or $O(CH_2)_2N(CH_3)_2$; $R_6$ is $CF_3$; $R_7$ is H; and $R_5$ is H. In other embodiments, $R_5$ is

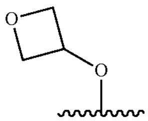

;

$R_6$ is $CF_3$; $R_7$ is H; and $R_8$ is H. In other embodiments, $R_5$ is $SCH_3$; $R_6$ is $CF_3$; $R_7$ is H; and $R_8$ is H. In other embodiments, $R_5$ is

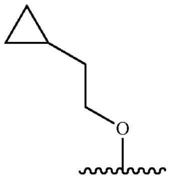

;

$R_6$ is $CF_3$; $R_7$ is H; and $R_8$ is H. In other embodiments, $R_5$ is $O(CH_2)_2N(CH_3)_2$; $R_6$ is $CF_3$; $R_7$ is H; and $R_8$ is H.

In some embodiments, the invention relates to a compound of formula (I), or a pharmaceutically acceptable salt thereof, wherein $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$, —C≡C—$R_x$, or 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocyclyl, wherein said 5-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocyclyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkyl, wherein said 5-6 membered heterocycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is tetrahydropyran-4-yl or tetrahydrofuran-3-yl, wherein said tetrahydropyran-4-yl or tetrahydrofuran-3-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is tetrahydropyran-4-yl or tetrahydrofuran-3-yl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkenyl, wherein said 5-6 membered heterocycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkenyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl, wherein said 3,4-dihydropyran-5-yl, 3,6-dihydropyran-4-yl, 2,5-dihydrofuran-3-yl, or 2,3-dihydrofuran-4-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 7-8 membered cycloalkyl, wherein said 7-8 membered cycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 7-8 membered cycloalkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered cycloalkenyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is cyclohexen-1-yl or cyclopenten-1-yl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is O—$R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is O—$R_z$, and $R_z$ is $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is O—$R_z$, and $R_z$ is $R_z$ is cyclobutenyl, wherein said cyclobutenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H.

In other embodiments, $R_5$ is H, halo, or $C_1$-$C_6$ alkyl; $R_6$ is H; $R_7$ is W—$(CH_2)_n$—$R_z$; and $R_8$ is H. In other embodiments, $R_5$ is H, halo, or $C_1$-$C_6$ alkyl; $R_6$ is H; $R_7$ is W—$R_z$; and $R_8$ is H. In other embodiments, $R_5$ is H, halo, or $C_1$-$C_6$ alkyl; $R_6$ is H; $R_7$ is $R_z$; and $R_8$ is H. In other embodiments, $R_5$ is H, halo, or $C_1$-$C_6$ alkyl; $R_6$ is H; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_8$ is H, halo, or $C_1$-$C_6$ alkyl; $R_6$ is H; $R_7$ is $R_z$, and $R_z$ is 5-6 membered heterocyclyl, wherein said 5-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered heterocyclyl; and $R_8$ is H. In other embodiments, $R_5$ is H, halo, or $C_1$-$C_6$ alkyl; $R_6$ is H; $R_7$ is $R_z$, and $R_z$ is 5-6 membered heterocycloalkyl, wherein said 5-6 membered heterocycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered heterocycloalkyl; and $R_8$ is H. In other embodiments, $R_5$ is H, halo, or $C_1$-$C_6$ alkyl; $R_6$ is H; $R_7$ is $R_z$, and $R_z$ is tetrahydropyran-4-yl or tetrahydrofuran-3-yl, wherein said tetrahydropyran-4-yl or tetrahydrofuran-3-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is tetrahydropyran-4-yl or tetrahydrofuran-3-yl; and $R_8$ is H. In other embodiments, $R_5$ is H, halo, or $C_1$-$C_6$ alkyl; $R_6$ is H; $R_7$ is $R_z$, and $R_z$ is 5-6 membered heterocycloalkenyl, wherein said 5-6 membered heterocycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered heterocycloalkenyl; and $R_8$ is H. In other embodiments, $R_5$ is H, halo, or $C_1$-$C_6$ alkyl; $R_6$ is H; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl, wherein said 3,4-dihydropyran-5-yl, 3,6-dihydropyran-4-yl, 2,5-dihydrofuran-3-yl, or 2,3-dihydrofuran-4-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl; and $R_8$ is H. In other embodiments, $R_5$ is H, halo, or $C_1$-$C_6$ alkyl; $R_6$ is H; $R_7$ is $R_z$, and $R_z$ is 7-8 membered cycloalkyl, wherein said 7-8 membered cycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 7-8 membered cycloalkyl; and $R_8$ is H. In other embodiments, $R_5$ is H, halo, or $C_1$-$C_6$ alkyl; $R_6$ is H; $R_7$ is $R_z$, and $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered cycloalkenyl; and $R_8$ is H. In other embodiments, $R_5$ is H, halo, or $C_1$-$C_6$ alkyl; $R_6$ is H; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_s$ is H. In other embodiments, $R_5$ is H, halo, or $C_1$-$C_6$ alkyl; $R_6$ is H; $R_7$ is $R_z$, and $R_z$ is cyclohexen-1-yl or cyclopenten-1-yl; and $R_8$ is H. In other embodiments, $R_5$ is H, halo, or $C_1$-$C_6$ alkyl; $R_6$ is H; $R_7$ is O—$R_z$; and $R_8$ is H. In other embodiments, $R_5$ is H, halo, or $C_1$-$C_6$ alkyl; $R_6$ is H; $R_7$ is O—$R_z$, and $R_z$ is $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is O—$R_z$, and $R_z$ is $R_z$ is cyclobutenyl, wherein said cyclobutenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H.

In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and R, is $C_1$-$C_6$ alkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and R, is 3-6 membered cycloalkyl, wherein said 3-6 membered cycloalkyl may be unsubstituted or may be substituted with 1-3 substituents selected from a group consisting of halo; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is 3-6 membered cycloalkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is cyclopropyl or cyclobutyl; and $R_8$ is H.

In other embodiments, $R_5$ is H, halo, or $C_1$-$C_6$ alkyl; $R_6$ is H; $R_7$ is —C≡C—$R_x$; and $R_8$ is H. In other embodiments, $R_5$ is H, halo, or $C_1$-$C_6$ alkyl; $R_6$ is H; $R_7$ is —C≡C—$R_x$, and $R_x$ is $C_1$-$C_6$ alkyl; and $R_8$ is H. In other embodiments, $R_5$ is H, halo, or $C_1$-$C_6$ alkyl; $R_6$ is H; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_s$ is H. In other embodiments, $R_5$ is H, halo, or $C_1$-$C_6$ alkyl; $R_6$ is H; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_8$ is H. In other embodiments, $R_5$ is H, halo, or $C_1$-$C_6$ alkyl; $R_6$ is H; $R_7$ is —C≡C—$R_x$, and $R_x$ is 3-6 membered cycloalkyl; and $R_8$ is H. In other embodiments, $R_5$ is H, halo, or $C_1$-$C_6$ alkyl; $R_6$ is H; $R_7$ is —C≡C—$R_x$, and $R_x$ is cyclopropyl or cyclobutyl; and $R_8$ is H.

In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is 3-6 membered cycloalkyl, wherein said 3-6 membered cycloalkyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is cyclohexyl, wherein said cyclohexyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is phenyl, wherein said phenyl is substituted with 1-3 substituents selected from a group consisting of $C_1$-$C_6$ alkoxy, CN, and —C(O)$NH_2$; and $R_8$ is H.

In other embodiments, $R_5$ is H, halo, or $C_1$-$C_6$ alkyl; $R_6$ is H; $R_7$ is 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H. In other embodiments, $R_5$ is H, halo, or $C_1$-$C_6$ alkyl; $R_6$ is H; $R_7$ is 3-6 membered cycloalkyl, wherein said 3-6 membered cycloalkyl is substituted with 1-3 substituents selected from a group consisting of $C_1$-$C_6$ alkoxy, CN, and —C(O)$NH_2$; and $R_8$ is H. In other embodiments, $R_5$ is H, halo, or $C_1$-$C_6$ alkyl; $R_6$ is H; $R_7$ is cyclohexyl, wherein said cyclohexyl is substituted with 1-3 substituents selected from a group consisting of $C_1$-$C_6$ alkoxy, CN, and —C(O)$NH_2$; and $R_8$ is H. In other embodiments, $R_5$ is H, halo, or $C_1$-$C_6$ alkyl; $R_6$ is H; $R_7$ is phenyl, wherein said phenyl is substituted with 1-3 substituents selected from a group consisting of $C_1$-$C_6$ alkoxy, CN, and —C(O)$NH_2$; and $R_8$ is H. In other embodiments, $R_5$ is H, F, or $CH_3$; $R_6$ is H; $R_7$ is

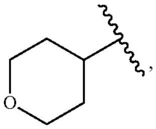, 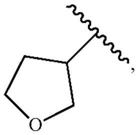, 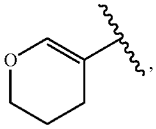,

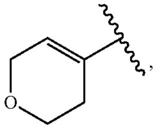, 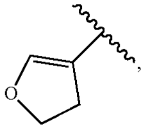, 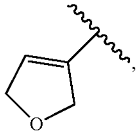,

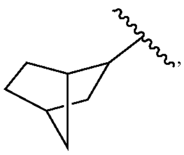, 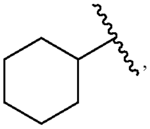, 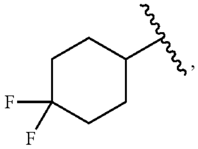,

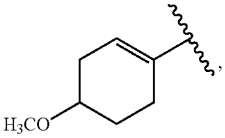, 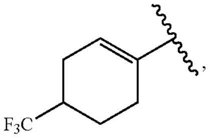,

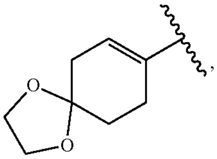, 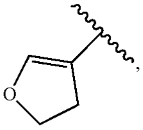, 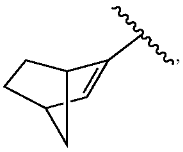,

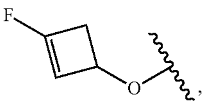, 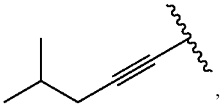,

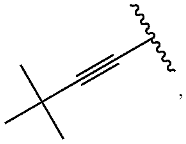, 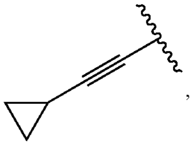,

-continued

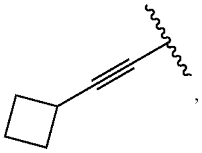, 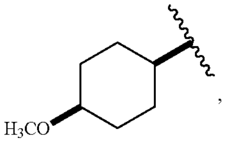,

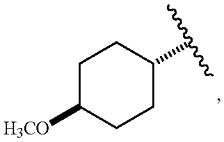, 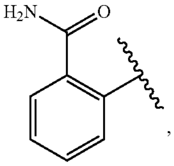,

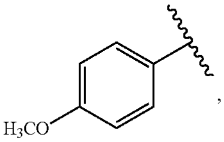, 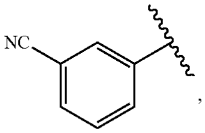, or

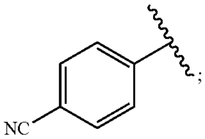;

and $R_8$ is H. In other embodiments, $R_5$ is H, F, or $CH_3$; $R_6$ is H; $R_7$ is

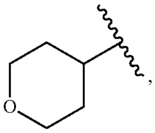, 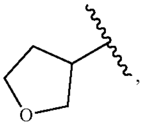, 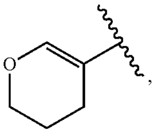,

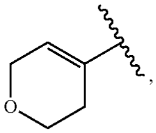, 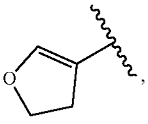, 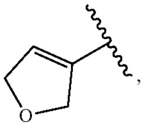,

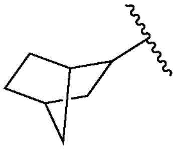, 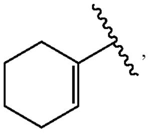, 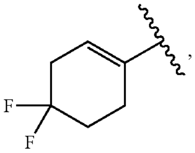,

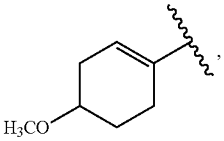, 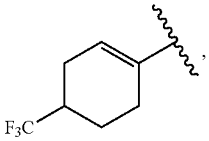,

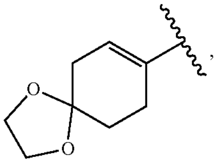, 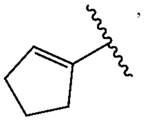,

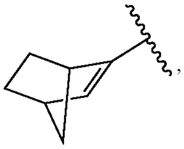, or 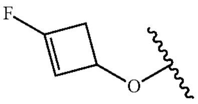;

and $R_8$ is H. In other embodiments, $R_5$ is H, F, or $CH_3$; $R_6$ is H; $R_7$ is

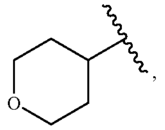,
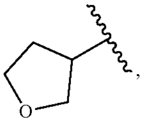,
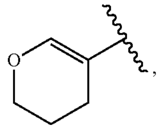,
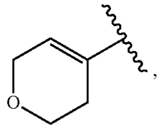,
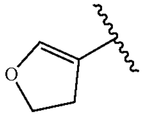, or
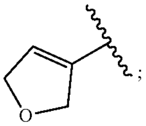;

and $R_8$ is H. In other embodiments, $R_5$ is H, F, or $CH_3$; $R_6$ is H; $R_7$ is

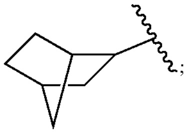 [SMILES: *C1CC2CCC1C2];

and $R_8$ is H. In other embodiments, $R_5$ is H, F, or $CH_3$; $R_6$ is H; $R_7$ is

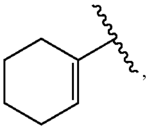,
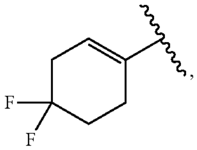,
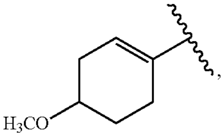,
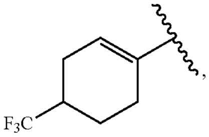,
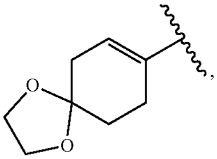,
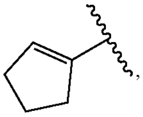, or -continued

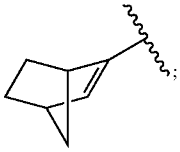;

and $R_8$ is H. In other embodiments, $R_5$ is H, F, or $CH_3$; $R_6$ is H; $R_7$ is

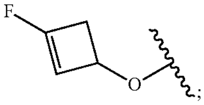 [SMILES: *OC1C=C(F)C1];

and $R_8$ is H. In other embodiments, $R_5$ is H, F, or $CH_3$; $R_6$ is H; $R_7$ is

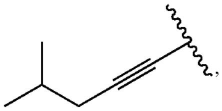,
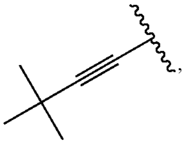,
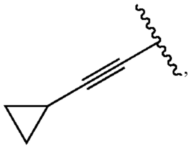, or
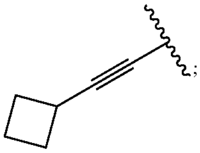;

and $R_8$ is H. In other embodiments, $R_5$ is H, F, or $CH_3$; $R_6$ is H; $R_7$ is

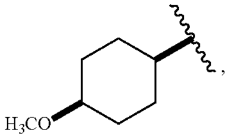,
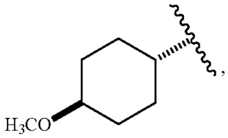,
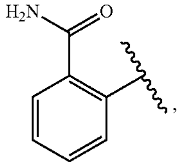,

-continued

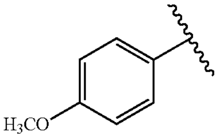,

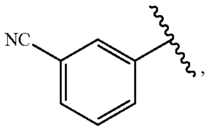, or

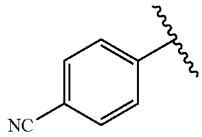;

and $R_8$ is H. In other embodiments, $R_5$ is H, F, or $CH_3$; $R_6$ is H; $R_7$ is

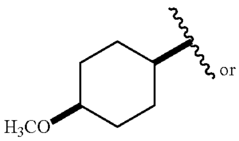 or

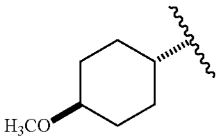;

and $R_8$ is H. In other embodiments, $R_5$ is H, F, or $CH_3$; $R_6$ is H; $R_7$ is

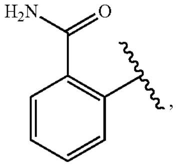,

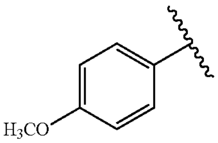,

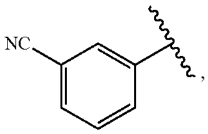, or

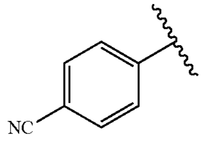;

and $R_8$ is H.

In some embodiments, the invention relates to a compound of formula (I), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ haloalkoxy; $R_6$ and $R_7$, together with the carbon atoms to which they are attached, form a ring of formula

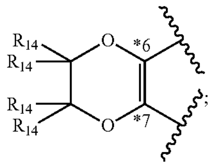;

and $R_8$ is H. In other embodiments, $R_5$ is H or halo; $R_6$ and $R_7$, together with the carbon atoms to which they are attached, form a ring of formula

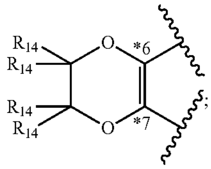;

and $R_8$ is H. In other embodiments, $R_5$ is H or halo; $R_6$ and $R_7$, together with the carbon atoms to which they are attached, form a ring of formula

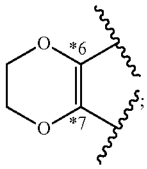 [SMILES: *C1=C(*)OCCO1];

and $R_8$ is H. In other embodiments, $R_s$ is H or F; $R_6$ and $R_7$, together with the carbon atoms to which they are attached, form a ring of formula

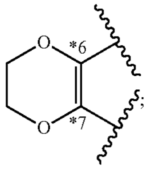 [SMILES: *C1=C(*)OCCO1];

and $R_8$ is H.

In some embodiments, the invention relates to a compound of formula (I), or a pharmaceutically acceptable salt thereof, wherein $R_9$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_9$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_9$ is H, halo, $C_1$-$C_6$ haloalkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ haloalkyl, or $C_1$-$C_6$ haloalkoxy. In other embodiments, $R_9$ is H, halo, $C_1$-$C_6$ alkyl, $C_1$-$C_6$ haloalkyl, or $C_1$-$C_6$ alkoxy. In other embodiments, $R_9$ is $C_1$-$C_6$ alkoxy. In other embodiments, $R_9$ is $OCH_3$, $OC(^1H)_3$, or $OCD_3$. In other embodiments, $R_9$ is $OCH_3$. In other embodiments, $R_9$ is $OC(^1H)_3$. In other embodiments, $R_9$ is $OCD_3$.

In some embodiments, the invention relates to a compound of formula (I), or a pharmaceutically acceptable salt thereof, wherein $R_{10}$ is H. In other embodiments, $R_{10}$ is halo. In other embodiments, $R_{10}$ is F.

In some embodiments, the invention relates to a compound of formula (I), or a pharmaceutically acceptable salt thereof, wherein $R_{11}$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_{11}$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_{11}$ is H, halo, $C_1$-$C_6$ haloalkyl, $C_1$-$C_6$ alkoxy, or $C_1$-$C_6$ haloalkoxy. In other embodiments, $R_{11}$ is H, halo, $C_1$-$C_6$ alkyl, $C_1$-$C_6$ alkoxy, or $C_1$-$C_6$ haloalkoxy. In other embodiments, $R_{11}$ is H, halo, $C_1$-$C_6$ alkyl, $C_1$-$C_6$ haloalkyl, or $C_1$-$C_6$ haloalkoxy. In other embodiments, $R_{11}$ is H, halo, $C_1$-$C_6$ alkyl, $C_1$-$C_6$ haloalkyl, or $C_1$-$C_6$ alkoxy. In other embodiments, $R_{11}$ is $C_1$-$C_6$ haloalkoxy. In other embodiments, $R_{11}$ is $OCF_3$.

In some embodiments, the invention relates to a compound of formula (I), or a pharmaceutically acceptable salt thereof, wherein $R_{12}$ is H.

In some embodiments, the invention relates to a compound of formula (I), or a pharmaceutically acceptable salt thereof, wherein $R_{13}$ is H.

In some embodiments, the invention relates to a compound of formula (I), i.e., the compound in non-salt form.

In one aspect, the invention relates to a compound of formula (II)

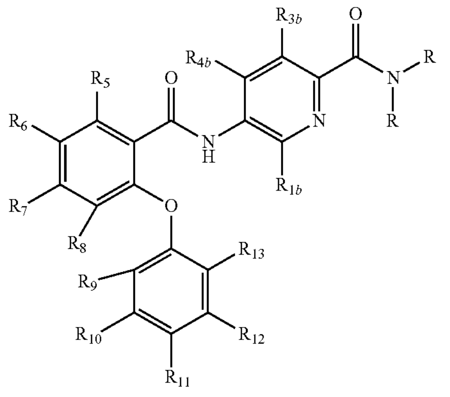

II or a pharmaceutically acceptable salt thereof, wherein:

each R is independently H or $C_1$-$C_6$ alkyl;

$R_{1b}$ is H, halo, $C_1$-$C_6$ alkyl, $C_1$-$C_6$ haloalkyl, $C_1$-$C_6$ alkoxy, or $C_1$-$C_6$ haloalkoxy;

$R_{3b}$ is H, halo, $C_1$-$C_6$ alkyl, $C_1$-$C_6$ haloalkyl, $C_1$-$C_6$ alkoxy, or $C_1$-$C_6$ haloalkoxy;

$R_{4b}$ is H, halo, $C_1$-$C_6$ alkyl, $C_1$-$C_6$ haloalkyl, $C_1$-$C_6$ alkoxy, or $C_1$-$C_6$ haloalkoxy;

$R_5$, $R_6$, $R_7$, and $R_8$ are defined as follows:

(i) $R_5$, $R_6$, and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is $C_1$-$C_6$ alkyl;

(ii) $R_5$ is W—$(CH_2)_n$—$R_z$, $C_1$-$C_6$ alkylsulfanyl, —O—$(CH_2)_p$—$R_w$, or —O—$(CH_2)_p$—N($C_1$-$C_6$ alkyl)$_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H;

(iii) $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$, —C≡C—$R_x$, or 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H; or (iv) $R_5$ is H, halo, $C_1$-$C_6$ alkyl, $C_1$-$C_6$ haloalkyl, $C_1$-$C_6$ alkoxy, or $C_1$-$C_6$ haloalkoxy; $R_6$ and $R_7$, together with the carbon atoms to which they are attached, form a ring of formula

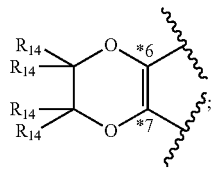

;

and $R_8$ is H;

$R_9$, $R_{10}$, $R_{11}$, $R_{12}$, and $R_{13}$ are each independently H, halo, $C_1$-$C_6$ alkyl, $C_1$-$C_6$ haloalkyl, $C_1$-$C_6$ alkoxy, or $C_1$-$C_6$ haloalkoxy;

each $R_{14}$ is independently H, halo, $C_1$-$C_4$ alkyl, or $C_1$-$C_4$ haloalkyl;

each W is independently O or a single bond;

$R_x$ is $C_1$-$C_6$ alkyl or 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl;

$R_z$ is 3-6 membered heterocyclyl, 7-8 membered cycloalkyl, or 4-8 membered cycloalkenyl, wherein said 3-6 membered heterocyclyl, 7-8 membered cycloalkyl, or 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring;

n is 0 or 1; and p is 2 or 3.

In some embodiments, the invention relates to a compound of formula (II), or a pharmaceutically acceptable salt thereof, wherein each R is H. In other embodiments, each R is independently $C_1$-$C_6$ alkyl.

In some embodiments, the invention relates to a compound of formula (II), or a pharmaceutically acceptable salt thereof, wherein $R_{3a}$ and $R_{4a}$ are each H.

In some embodiments, the invention relates to a compound of formula (II), or a pharmaceutically acceptable salt thereof, wherein $R_{1b}$, $R_{3b}$, and $R_{4b}$ are each H.

In some embodiments, the invention relates to a compound of formula (II), or a pharmaceutically acceptable salt thereof, wherein $R_5$, $R_6$, and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_s$ is $C_1$-$C_6$ alkyl. In other embodiments, $R_s$ is H; $R_6$ is $C_1$-$C_6$ haloalkyl; $R_7$ is H; and $R_s$ is $C_1$-$C_6$ alkyl. In other embodiments, $R_s$ is H; $R_6$ is $CF_3$; $R_7$ is H; and $R_8$ is $CH_3$.

In some embodiments, the invention relates to a compound of formula (II), or a pharmaceutically acceptable salt thereof, wherein $R_5$ is W—$(CH_2)_n$—$R_z$, $C_1$-$C_6$ alkylsulfanyl, —O—$(CH_2)_p$—$R_w$, or —O—$(CH_2)_p$—N($C_1$-$C_6$ alkyl$)_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_s$ is H. In other embodiments, $R_5$ is W—$(CH_2)_n$—$R_z$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_s$ is H. In other embodiments, $R_s$ is O—$R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; $R_6$ is $C_1$-$C_6$ haloalkyl; $R_7$ is H; and $R_8$ is H. In other embodiments, $R_s$ is O—$R_z$, and $R_z$ is 3-6 membered heterocyclyl; $R_6$ is $C_1$-$C_6$ haloalkyl; $R_7$ is H; and $R_8$ is H. In other embodiments, $R_s$ is O—$R_z$, and $R_z$ is oxetanyl or tetrahydrofuranyl; $R_6$ is $C_1$-$C_6$ haloalkyl; $R_7$ is H; and $R_8$ is H. In other embodiments, $R_8$ is $C_1$-$C_6$ alkylsulfanyl; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_s$ is H. In other embodiments, $R_s$ is $C_1$-$C_6$ alkylsulfanyl; $R_6$ is $C_1$-$C_6$ haloalkyl; $R_7$ is H; and $R_s$ is H. In other embodiments, $R_s$ is —O—$(CH_2)_p$—$R_w$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_s$ is H. In other embodiments, $R_s$ is —O—$(CH_2)_p$—$R_w$; $R_6$ is $C_1$-$C_6$ haloalkyl; $R_7$ is H; and $R_8$ is H. In other embodiments, $R_s$ is —O—$(CH_2)_p$—$R_w$, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl; $R_6$ is $C_1$-$C_6$ haloalkyl; $R_7$ is H; and $R_s$ is H. In other embodiments, $R_s$ is —O—$(CH_2)_p$—$R_w$, and $R_w$ is 3-6 membered cycloalkyl; $R_6$ is $C_1$-$C_6$ haloalkyl; $R_7$ is H; and $R_8$ is H. In other embodiments, $R_s$ is —O—$(CH_2)_2$—$R_w$, and $R_w$ is 3-6 membered cycloalkyl; $R_6$ is $C_1$-$C_6$ haloalkyl; $R_7$ is H; and $R_s$ is H. In other embodiments, $R_s$ is —O—$(CH_2)_p$—N($C_1$-$C_6$ alkyl$)_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H. In other embodiments, $R_s$ is —O—$(CH_2)_p$—N$(CH_3)_2$; $R_6$ is $C_1$-$C_6$ haloalkyl; $R_7$ is H; and $R_8$ is H. In other embodiments, $R_s$ is —O—$(CH_2)_2$—N($C_1$-$C_6$ alkyl$)_2$; $R_6$ is $C_1$-$C_6$ haloalkyl; $R_7$ is H; and $R_8$ is H. In other embodiments, $R_5$ is

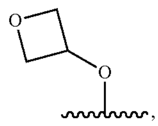 [SMILES: *OC1COC1]
, $SCH_3$,

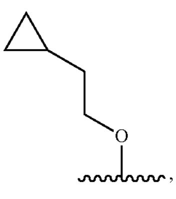 [SMILES: *OCCC1CC1]
, or $O(CH_2)_2N(CH_3)_2$; $R_6$ is $CF_3$; $R_7$ is H; and $R_8$ is H. In other embodiments, $R_5$ is

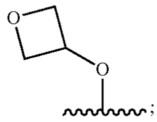 [SMILES: *OC1COC1]
;

$R_6$ is $CF_3$; $R_7$ is H; and $R_8$ is H. In other embodiments, $R_s$ is $SCH_3$; $R_6$ is $CF_3$; $R_7$ is H; and $R_8$ is H. In other embodiments, $R_5$ is

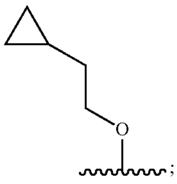 [SMILES: *OCCC1CC1]
;

is $CF_3$; $R_7$ is H; and $R_8$ is H. In other embodiments, $R_5$ is $O(CH_2)_2N(CH_3)_2$; $R_6$ is $CF_3$; $R_7$ is H; and $R_s$ is H.

In some embodiments, the invention relates to a compound of formula (I) or (II), or a pharmaceutically acceptable salt thereof, wherein $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$, —C≡C—$R_x$, or 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocyclyl, wherein said 5-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocyclyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkyl, wherein said 5-6 membered heterocycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is tetrahydropyran-4-yl or tetrahydrofuran-3-yl, wherein said tetrahydropyran-4-yl or tetrahydrofuran-3-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is tetrahydropyran-4-yl or tetrahydrofuran-3-yl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkenyl, wherein said 5-6 membered heterocycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered heterocycloalkenyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl, wherein said 3,4-dihydropyran-5-yl, 3,6-dihydropyran-4-yl, 2,5-dihydrofuran-3-yl, or 2,3-dihydrofuran-4-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 7-8 membered cycloalkyl, wherein said 7-8 membered cycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 7-8 membered cycloalkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is 5-6 membered cycloalkenyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is $R_z$, and $R_z$ is cyclohexen-1-yl or cyclopenten-1-yl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is O—$R_z$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is O—$R_z$, and $R_z$ is $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is O—$R_z$, and $R_z$ is $R_z$ is cyclobutenyl, wherein said cyclobutenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H.

In other embodiments, $R_5$ is H, halo, or $C_1$-$C_6$ alkyl; $R_6$ is H; $R_7$ is W—$(CH_2)_n$—$R_z$; and $R_8$ is H. In other embodiments, $R_5$ is H, halo, or $C_1$-$C_6$ alkyl; $R_6$ is H; $R_7$ is W—$R_z$; and $R_8$ is H. In other embodiments, $R_5$ is H, halo, or $C_1$-$C_6$ alkyl; $R_6$ is H; $R_7$ is $R_z$; and $R_8$ is H. In other embodiments, $R_5$ is H, halo, or $C_1$-$C_6$ alkyl; $R_6$ is H; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 3-6 membered heterocyclyl, wherein said 3-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered heterocyclyl, wherein said 5-6 membered heterocyclyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_8$ is H, halo, or $C_1$-$C_6$ alkyl; $R_6$ is H; $R_7$ is $R_z$, and $R_z$ is 5-6 membered heterocyclyl; and $R_8$ is H. In other embodiments, $R_5$ is H, halo, or $C_1$-$C_6$ alkyl; $R_6$ is H; $R_7$ is $R_z$, and $R_z$ is 5-6 membered heterocycloalkyl, wherein said 5-6 membered heterocycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered heterocycloalkyl; and $R_s$ is H. In other embodiments, $R_5$ is H, halo, or $C_1$-$C_6$ alkyl; $R_6$ is H; $R_7$ is $R_z$, and $R_z$ is tetrahydropyran-4-yl or tetrahydrofuran-3-yl, wherein said tetrahydropyran-4-yl or tetrahydrofuran-3-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is tetrahydropyran-4-yl or tetrahydrofuran-3-yl; and $R_8$ is H. In other embodiments, $R_5$ is H, halo, or $C_1$-$C_6$ alkyl; $R_6$ is H; $R_7$ is $R_z$, and $R_z$ is 5-6 membered heterocycloalkenyl, wherein said 5-6 membered heterocycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_s$ is H. In other embodiments, $R_5$ is H, halo, or $C_1$-$C_6$ alkyl; $R_6$ is H; $R_7$ is $R_z$, and $R_z$ is 5-6 membered heterocycloalkenyl; and $R_8$ is H. In other embodiments, $R_5$ is H, halo, or $C_1$-$C_6$ alkyl; $R_6$ is H; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl, wherein said 3,4-dihydropyran-5-yl, 3,6-dihydropyran-4-yl, 2,5-dihydrofuran-3-yl, or 2,3-dihydrofuran-4-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 3,4-dihydropyran-5-yl, 3,6-dihydropyran-4-yl, 2,5-dihydrofuran-3-yl, or 2,3-dihydrofuran-4-yl; and $R_8$ is H. In other embodiments, $R_5$ is H, halo, or $C_1$-$C_6$ alkyl; $R_6$ is H; $R_7$ is $R_z$, and $R_z$ is 7-8 membered cycloalkyl, wherein said 7-8 membered cycloalkyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 7-8 membered cycloalkyl; and $R_s$ is H. In other embodiments, $R_5$ is H, halo, or $C_1$-$C_6$ alkyl; $R_6$ is H; $R_7$ is $R_z$, and $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_8$ is H. In other embodiments, $R_5$ is H, halo, or $C_1$-$C_6$ alkyl; $R_6$ is H; $R_7$ is $R_z$, and $R_z$ is 5-6 membered cycloalkenyl, wherein said 5-6 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_5$ is H, halo, or $C_1$-$C_6$ alkyl; $R_6$ is H; $R_7$ is $R_z$, and $R_z$ is 5-6 membered cycloalkenyl; and $R_8$ is H. In other embodiments, $R_5$ is H, halo, or $C_1$-$C_6$ alkyl; $R_6$ is H; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring; and $R_s$ is H. In other embodiments, $R_5$ is H, halo, or $C_1$-$C_6$ alkyl; $R_6$ is H; $R_7$ is $R_z$, and $R_z$ is cyclohexen-1-yl or cyclopenten-1-yl, wherein said cyclohexen-1-yl or cyclopenten-1-yl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_s$ is H. In other embodiments, $R_5$ is H, halo, or $C_1$-$C_6$ alkyl; $R_6$ is H; $R_7$ is $R_z$, and $R_z$ is cyclohexen-1-yl or cyclopenten-1-yl; and $R_8$ is H. In other embodiments, $R_s$ is H, halo, or $C_1$-$C_6$ alkyl; $R_6$ is H; $R_7$ is O—$R_z$; and $R_8$ is H. In other embodiments, $R_s$ is H, halo, or $C_1$-$C_6$ alkyl; $R_6$ is H; $R_7$ is O—$R_z$, and $R_z$ is $R_z$ is 4-8 membered cycloalkenyl, wherein said 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H. In other embodiments, $R_s$ is H, halo, or $C_1$-$C_6$ alkyl; $R_6$ is H; $R_7$ is O—$R_z$, and $R_z$ is $R_z$ is cyclobutenyl, wherein said cyclobutenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy; and $R_8$ is H.

In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is $C_1$-$C_6$ alkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and R, is 3-6 membered cycloalkyl, wherein said 3-6 membered cycloalkyl may be unsubstituted or may be substituted with 1-3 substituents selected from a group consisting of halo; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and R, is 3-6 membered cycloalkyl; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is —C≡C—$R_x$, and $R_x$ is cyclopropyl or cyclobutyl; and $R_8$ is H.

In other embodiments, $R_s$ is H, halo, or $C_1$-$C_6$ alkyl; $R_6$ is H; $R_7$ is —C≡C—$R_x$; and $R_8$ is H. In other embodiments, $R_s$ is H, halo, or $C_1$-$C_6$ alkyl; $R_6$ is H; $R_7$ is —C≡C—$R_x$, and $R_x$ is $C_1$-$C_6$ alkyl; and $R_8$ is H. In other embodiments, $R_s$ is H, halo, or $C_1$-$C_6$ alkyl; $R_6$ is H; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_s$ is H. In other embodiments, $R_s$ is H, halo, or $C_1$-$C_6$ alkyl; $R_6$ is H; $R_7$ is —C≡C—$R_x$, and $R_x$ is 3-6 membered cycloalkyl, wherein said 3-6 membered cycloalkyl may be unsubstituted or may be substituted with 1-3 substituents selected from a group consisting of halo; and $R_8$ is H. In other embodiments, $R_s$ is H, halo, or $C_1$-$C_6$ alkyl; $R_6$ is H; $R_7$ is —C≡C—$R_x$, and $R_x$ is 3-6 membered cycloalkyl; and $R_8$ is H. In other embodiments, $R_s$ is H, halo, or $C_1$-$C_6$ alkyl; $R_6$ is H; $R_7$ is —C≡C—$R_x$, and $R_x$ is cyclopropyl or cyclobutyl; and $R_8$ is H.

In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is 3-6 membered cycloalkyl, wherein said 3-6 membered cycloalkyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is cyclohexyl, wherein said cyclohexyl is substituted with 1-3 substituents selected from a group consisting of $C_1$-$C_6$ alkoxy, CN, and —C(O)$NH_2$; and $R_8$ is H. In other embodiments, $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is phenyl, wherein said phenyl is substituted with 1-3 substituents selected from a group consisting of $C_1$-$C_6$ alkoxy, CN, and —C(O)$NH_2$; and $R_8$ is H.

In other embodiments, $R_s$ is H, halo, or $C_1$-$C_6$ alkyl; $R_6$ is H; $R_7$ is 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H. In other embodiments, $R_s$ is H, halo, or $C_1$-$C_6$ alkyl; $R_6$ is H; $R_7$ is 3-6 membered cycloalkyl, wherein said 3-6 membered cycloalkyl is substituted with 1-3 substituents selected from a group consisting of $C_1$-$C_6$ alkoxy, CN, and —C(O)$NH_2$; and $R_8$ is H. In other embodiments, $R_s$ is H, halo, or $C_1$-$C_6$ alkyl; $R_6$ is H; $R_7$ is cyclohexyl, wherein said cyclohexyl is substituted with 1-3 substituents selected from a group consisting of $C_1$-$C_6$ alkoxy, CN, and —C(O)$NH_2$; and $R_8$ is H. In other embodiments, $R_s$ is H, halo, or $C_1$-$C_6$ alkyl; $R_6$ is H; $R_7$ is phenyl, wherein said phenyl is substituted with 1-3 substituents selected from a group consisting of $C_1$-$C_6$ alkoxy, CN, and —C(O)$NH_2$; and $R_8$ is H. In other embodiments, $R_s$ is H, F, or $CH_3$; $R_6$ is H; $R_7$ is

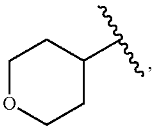,
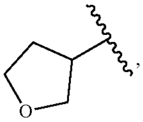,
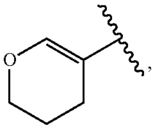,

-continued

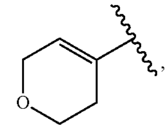,
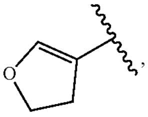,
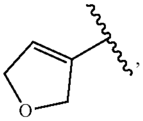,
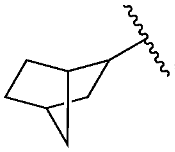,
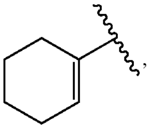,
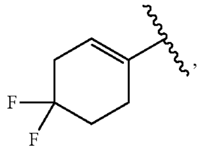,
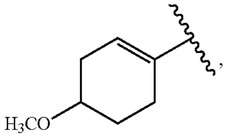,
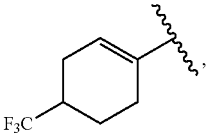,
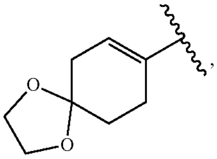,
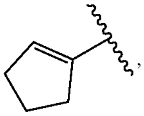,
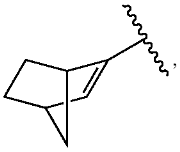,
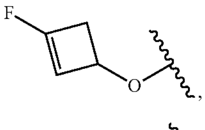,
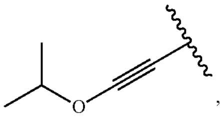,
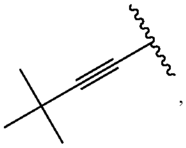,
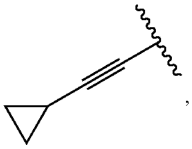,
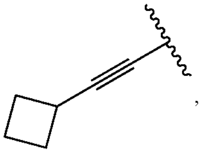,
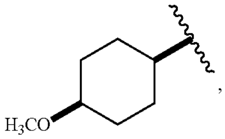,
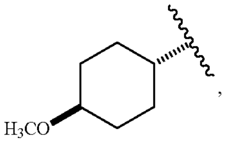,
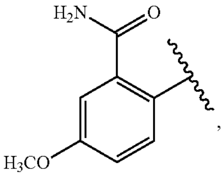,
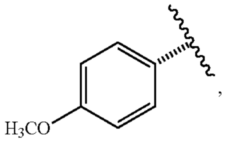,
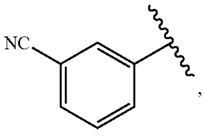, or
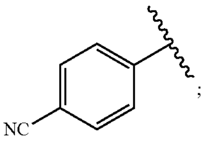;

and $R_8$ is H. In other embodiments, $R_5$ is H, F, or $CH_3$; $R_6$ is H; $R_7$ is

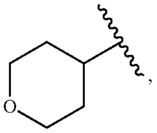, 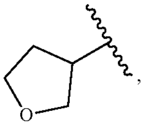, 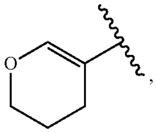, 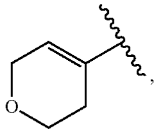, 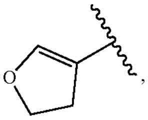, 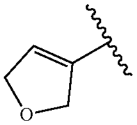, 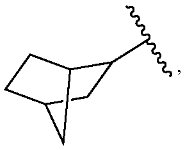, 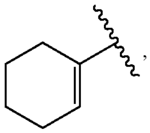, 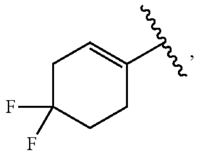, 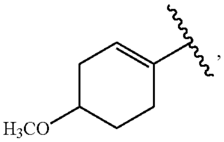, 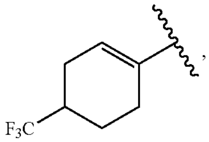, 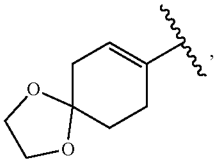, 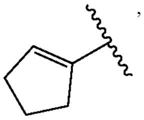, 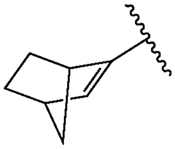, or 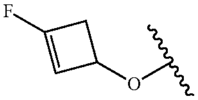;

and $R_8$ is H. In other embodiments, $R_5$ is H, F, or $CH_3$; $R_6$ is H; $R_7$ is

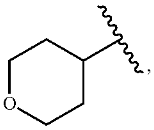, 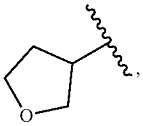, 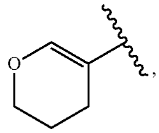, 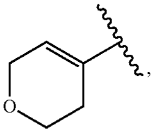, 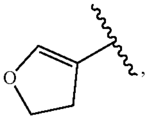, or 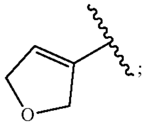;

and $R_8$ is H. In other embodiments, $R_5$ is H, F, or $CH_3$; $R_6$ is H; $R_7$ is

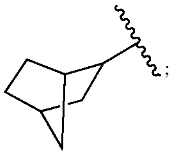 [SMILES: *C1CC2CCC1C2];

and $R_8$ is H. In other embodiments, $R_5$ is H, F, or $CH_3$; $R_6$ is $R_7$ is

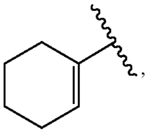, 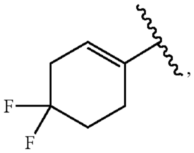, 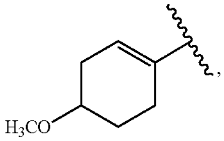, 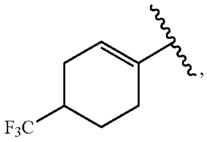, 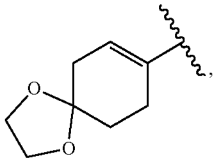, 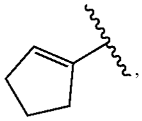, or 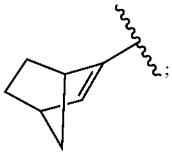;

and $R_8$ is H. In other embodiments, $R_s$ is H, F, or $CH_3$; $R_6$ is H; $R_7$ is

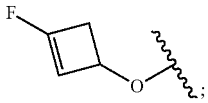 [SMILES: *OC1C=C(F)C1];

and $R_8$ is H. In other embodiments, $R_5$ is H, F, or $CH_3$; $R_6$ is H; $R_7$ is

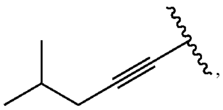, 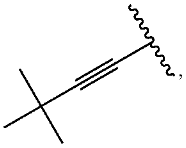, 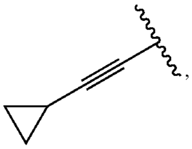, or 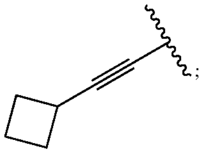;

and $R_8$ is H. In other embodiments, $R_5$ is H, F, or $CH_3$; $R_6$ is H; $R_7$ is

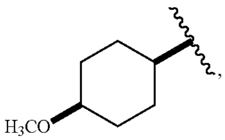, 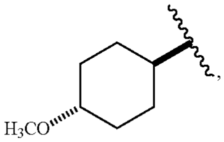, 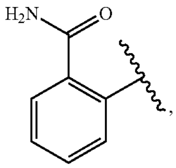, 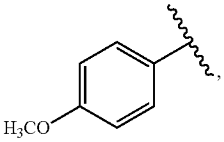,

-continued

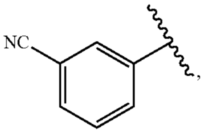

, or

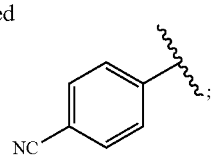

;

and $R_8$ is H. In other embodiments, $R_5$ is H, F, or $CH_3$; $R_6$ is H; $R_7$ is

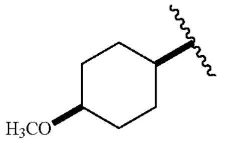

or

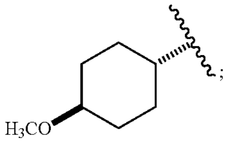

;

and $R_8$ is H. In other embodiments, $R_5$ is H, F, or $CH_3$; $R_6$ is H; $R_7$ is

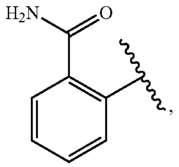

,

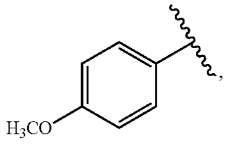

,

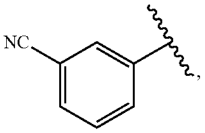

, or

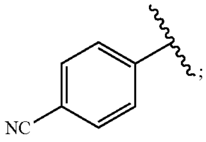

;

and $R_8$ is H.

In some embodiments, the invention relates to a compound of formula (II), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ haloalkoxy; $R_6$ and $R_7$, together with the carbon atoms to which they are attached, form a ring of formula

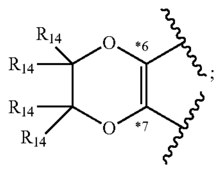

;

and $R_8$ is H. In other embodiments, $R_5$ is H or halo: $R_6$ and $R_7$, together with the carbon atoms to which they are attached, form a ring of formula

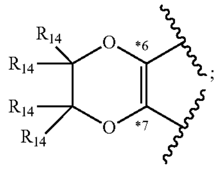

;

and $R_8$ is H. In other embodiments, $R_5$ is H or halo; $R_6$ and $R_7$, together with the carbon atoms to which they are attached, form a ring of formula

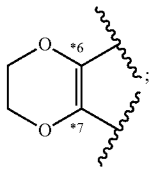 [SMILES: *C1=C(*)OCCO1]

;

and $R_8$ is H. In other embodiments, $R_5$ is H or F; $R_6$ and $R_7$, together with the carbon atoms to which they are attached, form a ring of formula

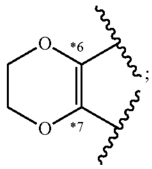 [SMILES: *C1=C(*)OCCO1]

;

and $R_8$ is H.

In some embodiments, the invention relates to a compound of formula (II), or a pharmaceutically acceptable salt thereof, wherein $R_9$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_9$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_9$ is H, halo, $C_1$-$C_6$ haloalkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ haloalkyl, or $C_1$-$C_6$ haloalkoxy. In other embodiments, $R_9$ is H, halo, $C_1$-$C_6$ alkyl, $C_1$-$C_6$ haloalkyl, or $C_1$-$C_6$ alkoxy. In other embodiments, $R_9$ is $C_1$-$C_6$ alkoxy. In other embodiments, $R_9$ is $OCH_3$, $OC(^1H)_3$, or $OCD_3$. In other embodiments, $R_9$ is $OCH_3$. In other embodiments, $R_9$ is $OC(^1H)_3$. In other embodiments, $R_9$ is $OCD_3$.

In some embodiments, the invention relates to a compound of formula (II), or a pharmaceutically acceptable salt thereof, wherein $R_{10}$ is H. In other embodiments, $R_{10}$ is halo. In other embodiments, $R_{10}$ is F.

In some embodiments, the invention relates to a compound of formula (II), or a pharmaceutically acceptable salt thereof, wherein $R_{11}$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_{11}$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_{11}$ is H, halo, $C_1$-$C_6$ haloalkyl, $C_1$-$C_6$ alkoxy, or $C_1$-$C_6$ haloalkoxy. In other embodiments, $R_{11}$ is H, halo, $C_1$-$C_6$ alkyl, $C_1$-$C_6$ alkoxy, or $C_1$-$C_6$ haloalkoxy. In other embodiments, $R_{11}$ is H, halo, $C_1$-$C_6$ alkyl, $C_1$-$C_6$ haloalkyl, or $C_1$-$C_6$ haloalkoxy. In other embodiments, $R_{11}$ is H, halo, $C_1$-$C_6$ alkyl, $C_1$-$C_6$ haloalkyl, or $C_1$-$C_6$ alkoxy. In other embodiments, $R_{11}$ is $C_1$-$C_6$ haloalkoxy. In other embodiments, $R_{11}$ is $OCF_3$.

In some embodiments, the invention relates to a compound of formula (II), or a pharmaceutically acceptable salt thereof, wherein $R_{12}$ is H.

In some embodiments, the invention relates to a compound of formula (II), or a pharmaceutically acceptable salt thereof, wherein $R_{13}$ is H.

In some embodiments, the invention relates to a compound of formula (II), i.e., the compound in non-salt form.

In one aspect, the invention relates to a compound selected from Table A or a pharmaceutically acceptable salt thereof. In other embodiments, the invention relates to a compound selected from Table A, i.e., the compound in non-salt form.

TABLE A

| Compound Numbers and Structures. | |
|---|---|
| 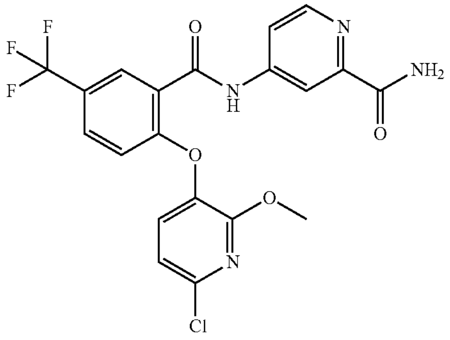 [SMILES: COc1nc(Cl)ccc1Oc1ccc(C(F)(F)F)cc1C(=O)Nc1ccnc(C(N)=O)c1] | 1 |
| 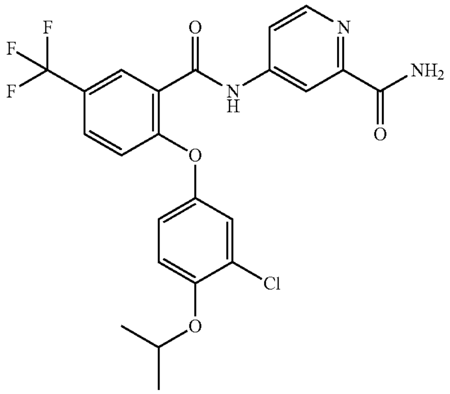 [SMILES: CC(C)Oc1ccc(Oc2ccc(C(F)(F)F)cc2C(=O)Nc2ccnc(C(N)=O)c2)cc1Cl] | 2 |
| 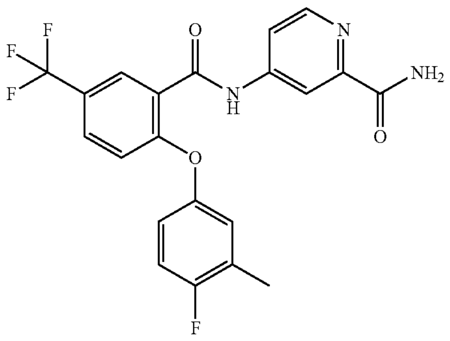 [SMILES: Cc1cc(Oc2ccc(C(F)(F)F)cc2C(=O)Nc2ccnc(C(N)=O)c2)ccc1F] | 3 |

TABLE A-continued

| Compound Numbers and Structures. | |
|---|---|
| 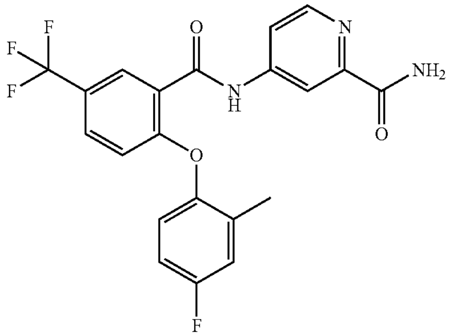 [SMILES: Cc1cc(F)ccc1Oc1ccc(C(F)(F)F)cc1C(=O)Nc1ccnc(C(N)=O)c1] | 4 |
| 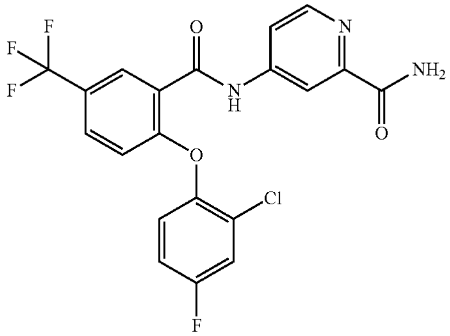 [SMILES: NC(=O)c1cc(NC(=O)c2cc(C(F)(F)F)ccc2Oc2ccc(F)cc2Cl)ccn1] | 5 |
| 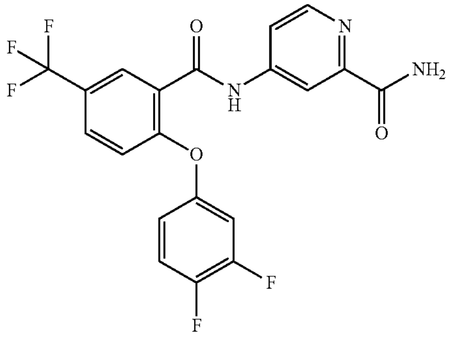 [SMILES: NC(=O)c1cc(NC(=O)c2cc(C(F)(F)F)ccc2Oc2ccc(F)c(F)c2)ccn1] | 6 |
| 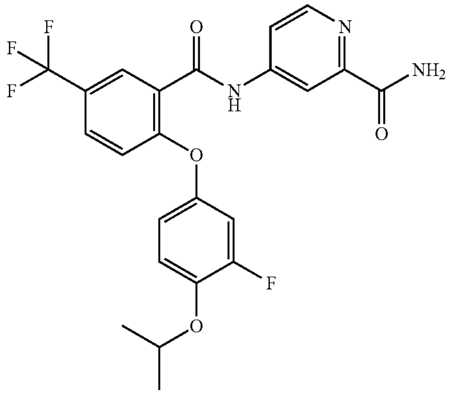 [SMILES: CC(C)Oc1ccc(Oc2ccc(C(F)(F)F)cc2C(=O)Nc2ccnc(C(N)=O)c2)cc1F] | 7 |

TABLE A-continued
| Compound Numbers and Structures. | |
|---|---|
| 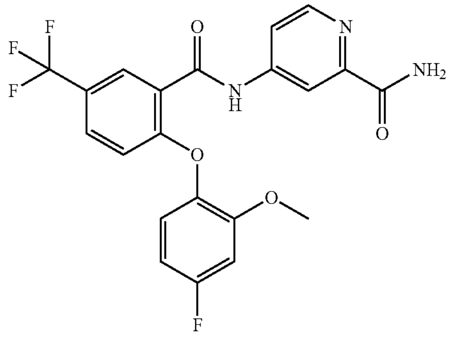 [SMILES: COc1cc(F)ccc1Oc1ccc(C(F)(F)F)cc1C(=O)Nc1ccnc(C(N)=O)c1] | 8 |
| 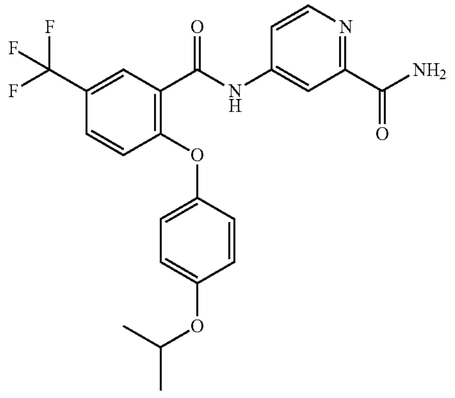 [SMILES: CC(C)Oc1ccc(Oc2ccc(C(F)(F)F)cc2C(=O)Nc2ccnc(C(N)=O)c2)cc1] | 9 |
| 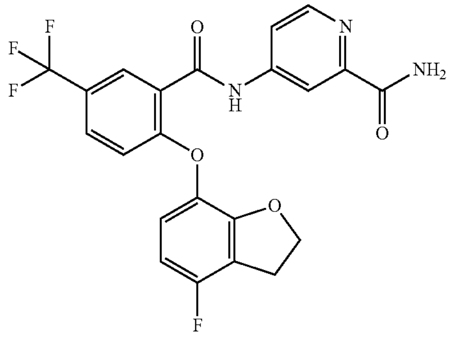 [SMILES: NC(=O)c1cc(NC(=O)c2cc(C(F)(F)F)ccc2Oc2ccc(F)c3c2OCC3)ccn1] | 10 |
| 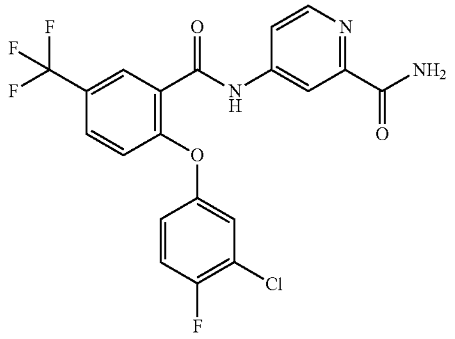 [SMILES: NC(=O)c1cc(NC(=O)c2cc(C(F)(F)F)ccc2Oc2ccc(F)c(Cl)c2)ccn1] | 11 |
TABLE A-continued
| Compound Numbers and Structures. | |
|---|---|
| 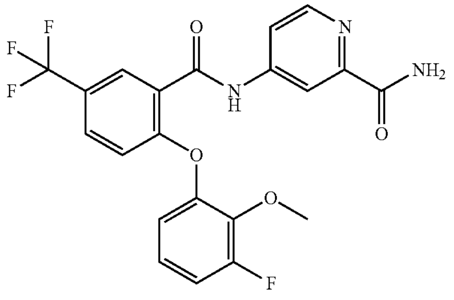 [SMILES: COc1c(F)cccc1Oc1ccc(C(F)(F)F)cc1C(=O)Nc1ccnc(C(N)=O)c1] | 12 |
| 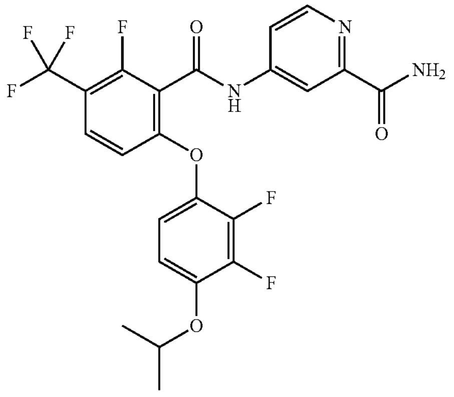 [SMILES: CC(C)Oc1ccc(Oc2ccc(C(F)(F)F)c(F)c2C(=O)Nc2ccnc(C(N)=O)c2)c(F)c1F] | 18 |
| 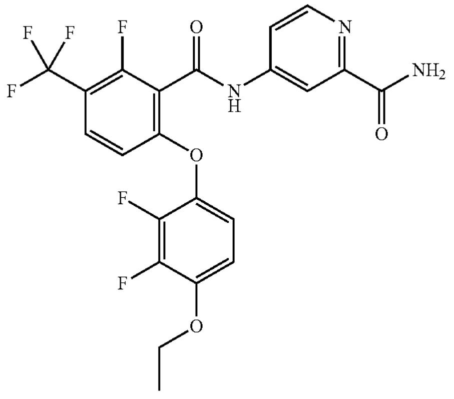 [SMILES: CCOc1ccc(Oc2ccc(C(F)(F)F)c(F)c2C(=O)Nc2ccnc(C(N)=O)c2)c(F)c1F] | 19 |
| 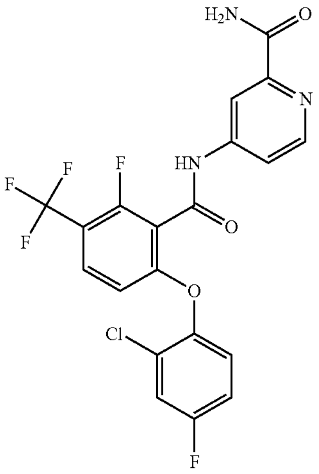 [SMILES: NC(=O)c1cc(NC(=O)c2c(Oc3ccc(F)cc3Cl)ccc(C(F)(F)F)c2F)ccn1] | 20 |

TABLE A-continued
| Compound Numbers and Structures. |
| --- |
| 21 |
| 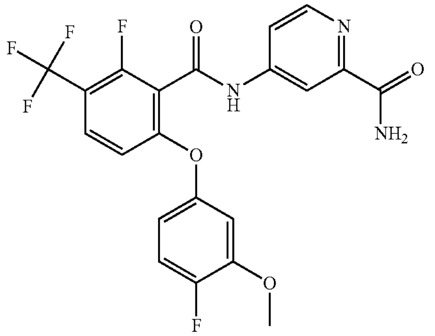 [SMILES: COc1cc(Oc2ccc(C(F)(F)F)c(F)c2C(=O)Nc2ccnc(C(N)=O)c2)ccc1F] |
| 22 |
| 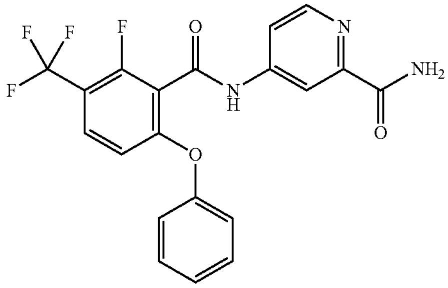 [SMILES: NC(=O)c1cc(NC(=O)c2c(Oc3ccccc3)ccc(C(F)(F)F)c2F)ccn1] |
| 23 |
| 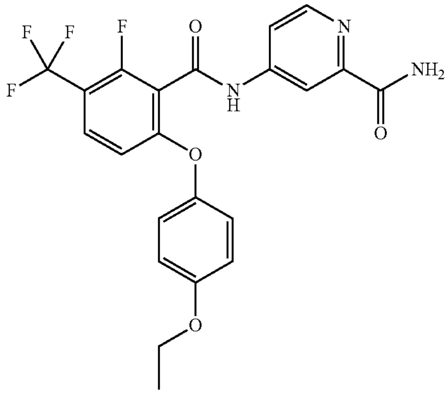 [SMILES: CCOc1ccc(Oc2ccc(C(F)(F)F)c(F)c2C(=O)Nc2ccnc(C(N)=O)c2)cc1] |
| 24 |
| 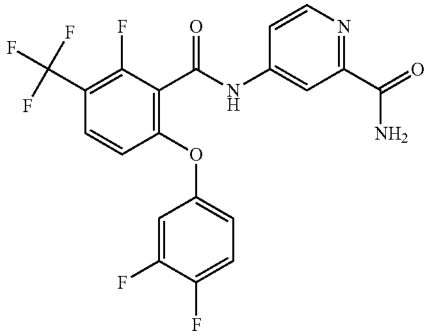 [SMILES: NC(=O)c1cc(NC(=O)c2c(Oc3ccc(F)c(F)c3)ccc(C(F)(F)F)c2F)ccn1] |
TABLE A-continued
| Compound Numbers and Structures. |
| --- |
| 25 |
| 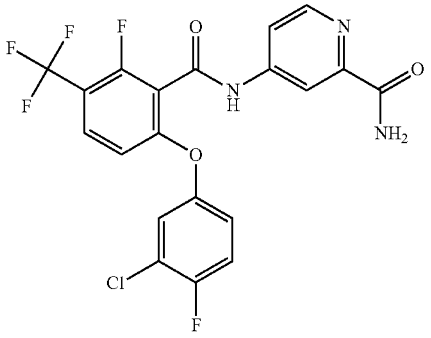 [SMILES: NC(=O)c1cc(NC(=O)c2c(Oc3ccc(F)c(Cl)c3)ccc(C(F)(F)F)c2F)ccn1] |
| 26 |
| 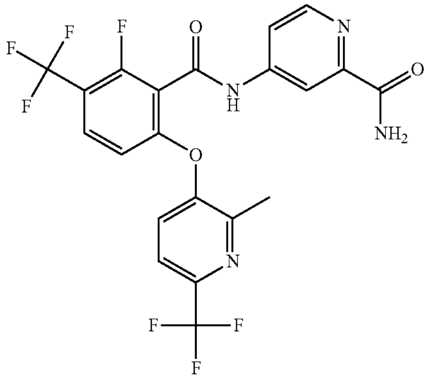 [SMILES: Cc1nc(C(F)(F)F)ccc1Oc1ccc(C(F)(F)F)c(F)c1C(=O)Nc1ccnc(C(N)=O)c1] |
| 27 |
| 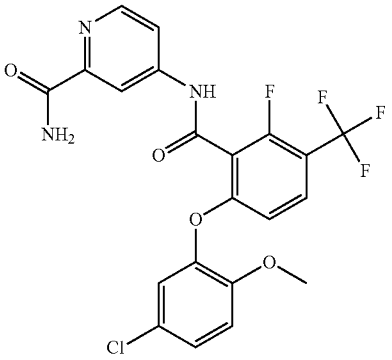 [SMILES: COc1ccc(Cl)cc1Oc1ccc(C(F)(F)F)c(F)c1C(=O)Nc1ccnc(C(N)=O)c1] |
| 28 |
| 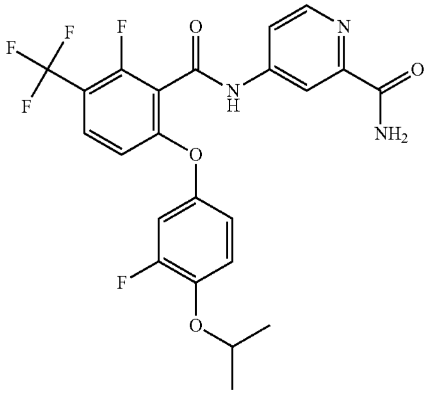 [SMILES: CC(C)Oc1ccc(Oc2ccc(C(F)(F)F)c(F)c2C(=O)Nc2ccnc(C(N)=O)c2)cc1F] |

TABLE A-continued
Compound Numbers and Structures.
29
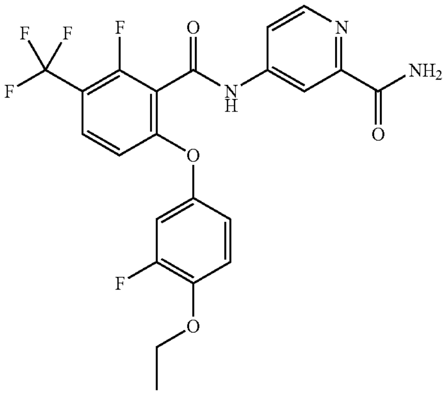 [SMILES: CCOc1ccc(Oc2ccc(C(F)(F)F)c(F)c2C(=O)Nc2ccnc(C(N)=O)c2)cc1F]
30
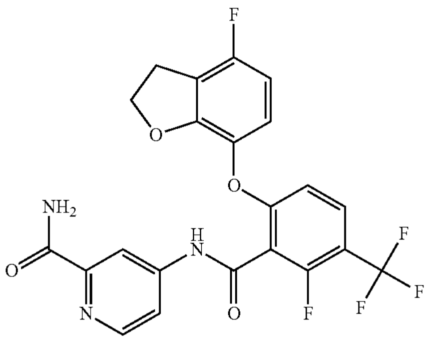 [SMILES: NC(=O)c1cc(NC(=O)c2c(Oc3ccc(F)c4c3OCC4)ccc(C(F)(F)F)c2F)ccn1]
31
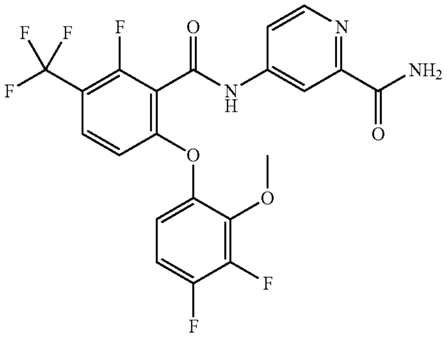 [SMILES: COc1c(Oc2ccc(C(F)(F)F)c(F)c2C(=O)Nc2ccnc(C(N)=O)c2)ccc(F)c1F]
32
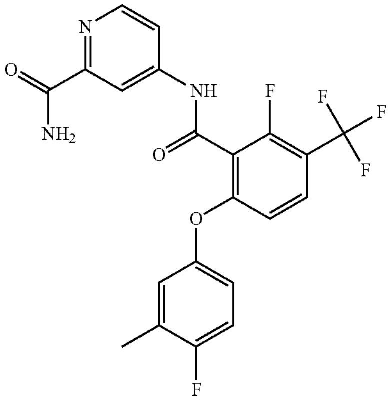 [SMILES: Cc1cc(Oc2ccc(C(F)(F)F)c(F)c2C(=O)Nc2ccnc(C(N)=O)c2)ccc1F]
TABLE A-continued
Compound Numbers and Structures.
33
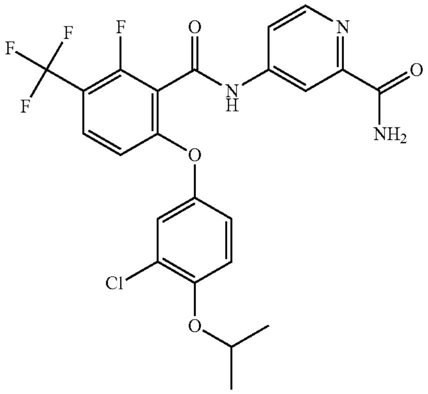 [SMILES: CC(C)Oc1ccc(Oc2ccc(C(F)(F)F)c(F)c2C(=O)Nc2ccnc(C(N)=O)c2)cc1Cl]
34
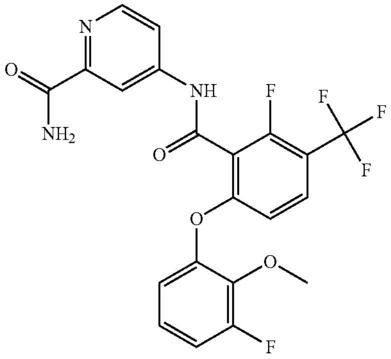 [SMILES: COc1c(F)cccc1Oc1ccc(C(F)(F)F)c(F)c1C(=O)Nc1ccnc(C(N)=O)c1]
35
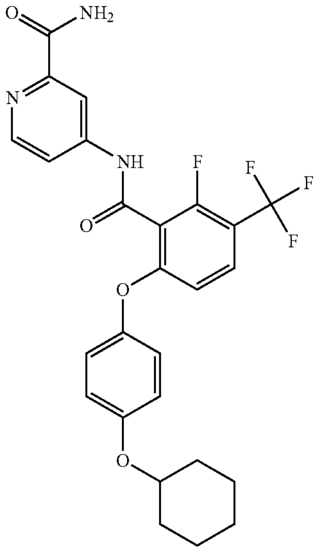 [SMILES: NC(=O)c1cc(NC(=O)c2c(Oc3ccc(OC4CCCCC4)cc3)ccc(C(F)(F)F)c2F)ccn1]

TABLE A-continued
| Compound Numbers and Structures. |
| --- |
36
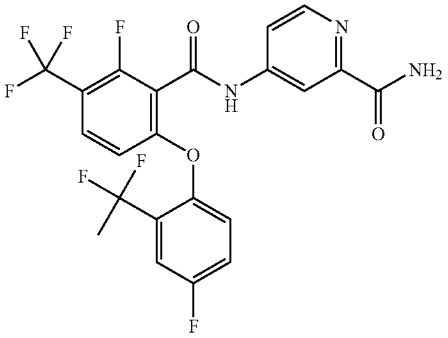 [SMILES: CC(F)(F)c1cc(F)ccc1Oc1ccc(C(F)(F)F)c(F)c1C(=O)Nc1ccnc(C(N)=O)c1]
37
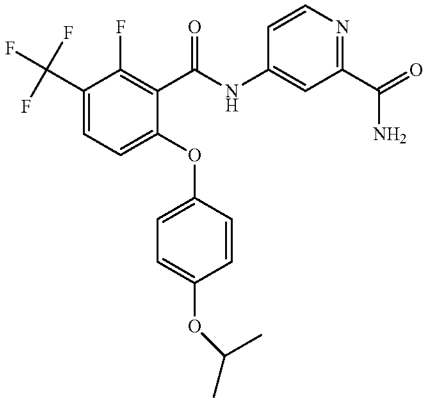 [SMILES: CC(C)Oc1ccc(Oc2ccc(C(F)(F)F)c(F)c2C(=O)Nc2ccnc(C(N)=O)c2)cc1]
38
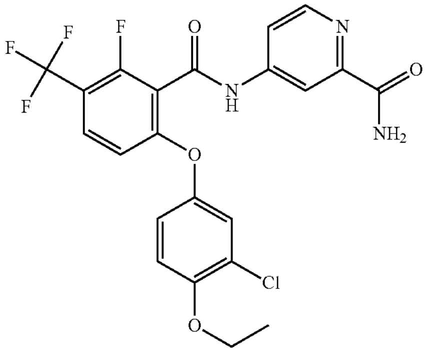 [SMILES: CCOc1ccc(Oc2ccc(C(F)(F)F)c(F)c2C(=O)Nc2ccnc(C(N)=O)c2)cc1Cl]
39
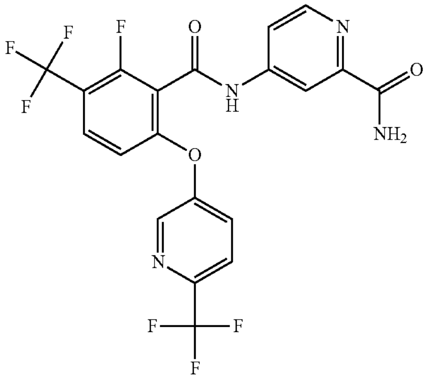 [SMILES: NC(=O)c1cc(NC(=O)c2c(Oc3ccc(C(F)(F)F)nc3)ccc(C(F)(F)F)c2F)ccn1]
TABLE A-continued
| Compound Numbers and Structures. |
| --- |
40
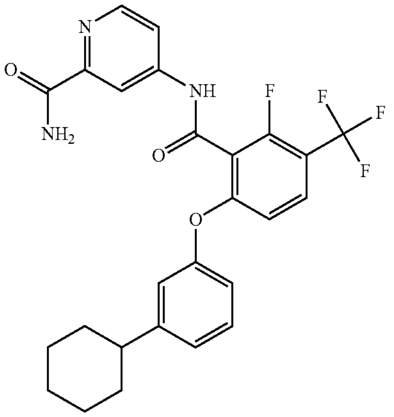 [SMILES: NC(=O)c1cc(NC(=O)c2c(Oc3cccc(C4CCCCC4)c3)ccc(C(F)(F)F)c2F)ccn1]
41
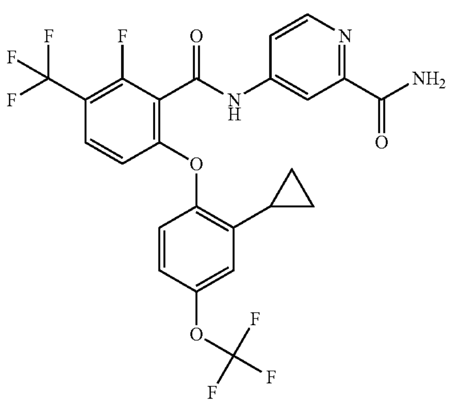 [SMILES: NC(=O)c1cc(NC(=O)c2c(Oc3ccc(OC(F)(F)F)cc3C3CC3)ccc(C(F)(F)F)c2F)ccn1]
42
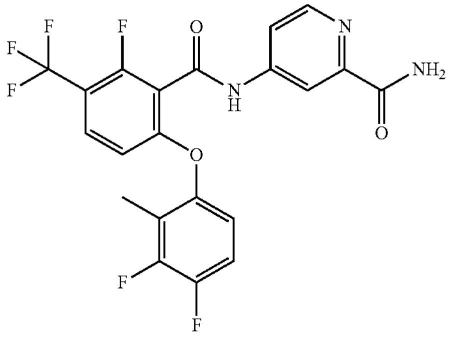 [SMILES: Cc1c(Oc2ccc(C(F)(F)F)c(F)c2C(=O)Nc2ccnc(C(N)=O)c2)ccc(F)c1F]
43
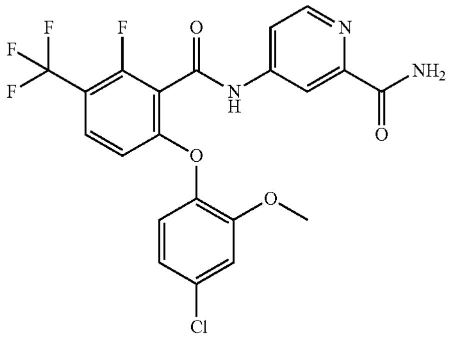 [SMILES: COc1cc(Cl)ccc1Oc1ccc(C(F)(F)F)c(F)c1C(=O)Nc1ccnc(C(N)=O)c1]

TABLE A-continued
| Compound Numbers and Structures. |
| --- |
| 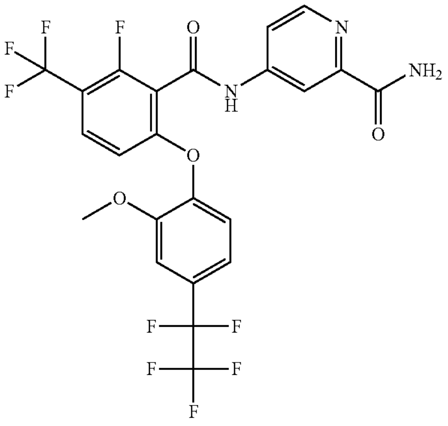 [SMILES: COc1cc(C(F)(F)C(F)(F)F)ccc1Oc1ccc(C(F)(F)F)c(F)c1C(=O)Nc1ccnc(C(N)=O)c1] 44 |
| 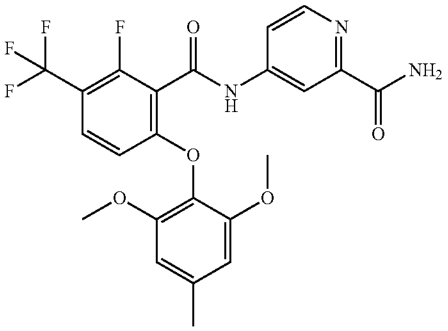 [SMILES: COc1cc(C)cc(OC)c1Oc1ccc(C(F)(F)F)c(F)c1C(=O)Nc1ccnc(C(N)=O)c1] 45 |
| 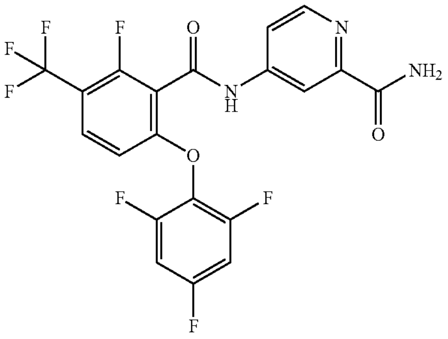 46 |
| 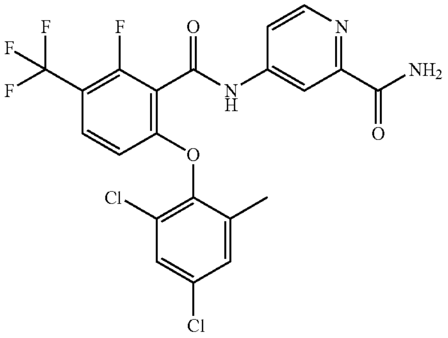 47 |
TABLE A-continued
| Compound Numbers and Structures. |
| --- |
| 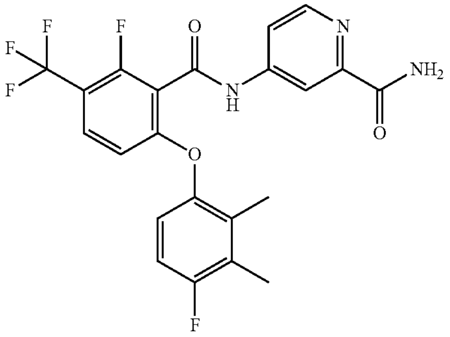 [SMILES: Cc1c(F)ccc(Oc2ccc(C(F)(F)F)c(F)c2C(=O)Nc2ccnc(C(N)=O)c2)c1C] 48 |
| 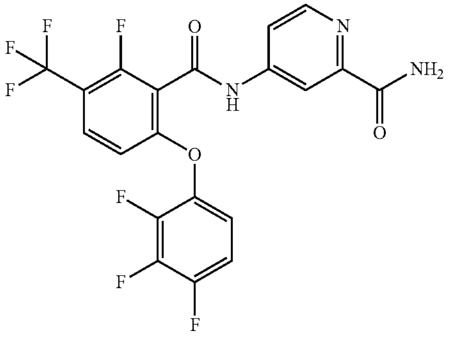 [SMILES: NC(=O)c1cc(NC(=O)c2c(Oc3ccc(F)c(F)c3F)ccc(C(F)(F)F)c2F)ccn1] 49 |
| 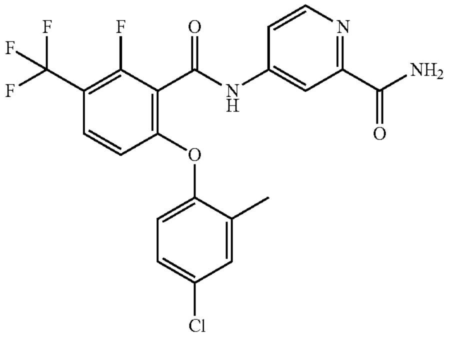 50 |
| 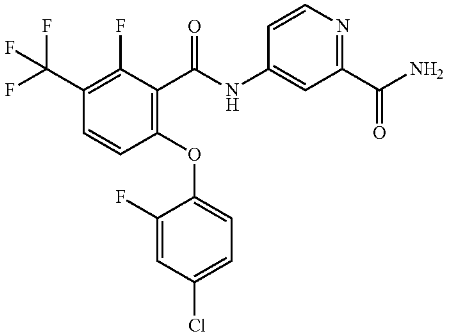 51 |

TABLE A-continued
Compound Numbers and Structures.
52
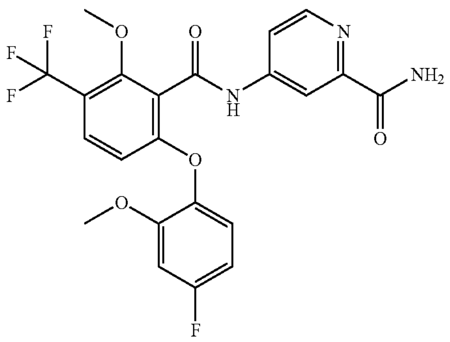 [SMILES: COc1cc(F)ccc1Oc1ccc(C(F)(F)F)c(OC)c1C(=O)Nc1ccnc(C(N)=O)c1]
53
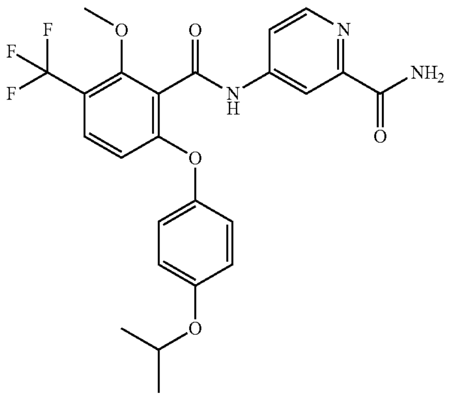 [SMILES: COc1c(C(F)(F)F)ccc(Oc2ccc(OC(C)C)cc2)c1C(=O)Nc1ccnc(C(N)=O)c1]
54
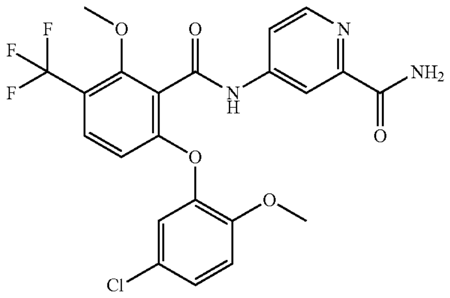 [SMILES: COc1ccc(Cl)cc1Oc1ccc(C(F)(F)F)c(OC)c1C(=O)Nc1ccnc(C(N)=O)c1]
55
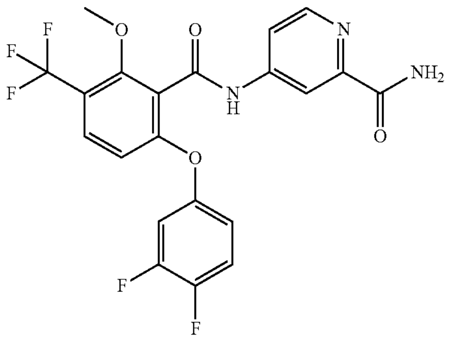 [SMILES: COc1c(C(F)(F)F)ccc(Oc2ccc(F)c(F)c2)c1C(=O)Nc1ccnc(C(N)=O)c1]
TABLE A-continued
Compound Numbers and Structures.
56
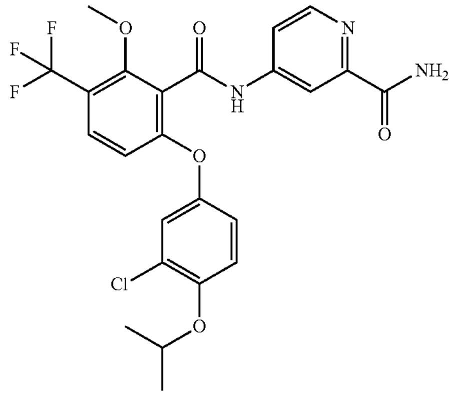
57
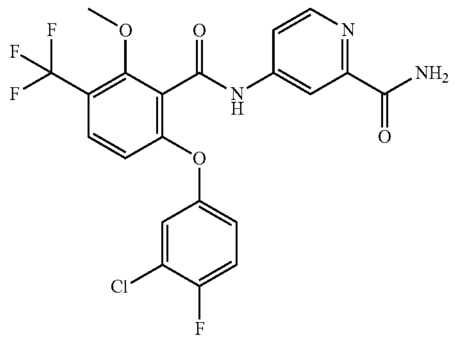 [SMILES: COc1c(C(F)(F)F)ccc(Oc2ccc(F)c(Cl)c2)c1C(=O)Nc1ccnc(C(N)=O)c1]
58
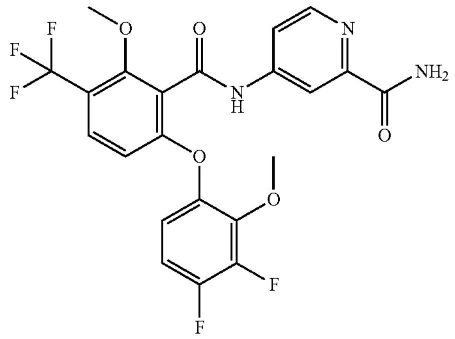 [SMILES: COc1c(Oc2ccc(C(F)(F)F)c(OC)c2C(=O)Nc2ccnc(C(N)=O)c2)ccc(F)c1F]
59
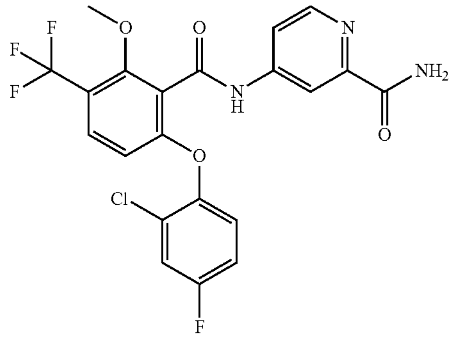 [SMILES: COc1c(C(F)(F)F)ccc(Oc2ccc(F)cc2Cl)c1C(=O)Nc1ccnc(C(N)=O)c1]

TABLE A-continued
| Compound Numbers and Structures. |
| --- |
| 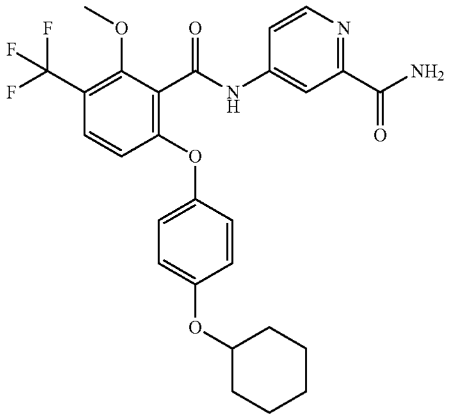 [SMILES: COc1c(C(F)(F)F)ccc(Oc2ccc(OC3CCCCC3)cc2)c1C(=O)Nc1ccnc(C(N)=O)c1] 60 |
| 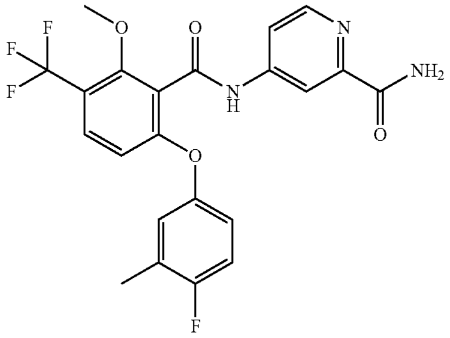 [SMILES: COc1c(C(F)(F)F)ccc(Oc2ccc(F)c(C)c2)c1C(=O)Nc1ccnc(C(N)=O)c1] 61 |
| 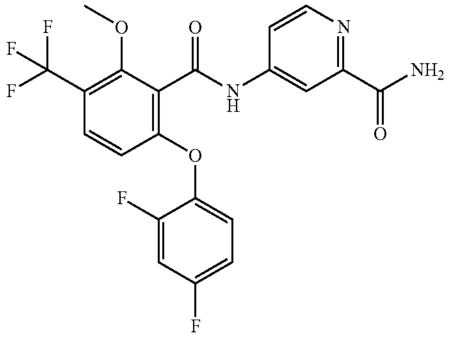 62 |
| 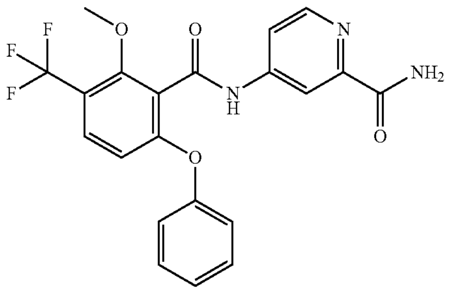 [SMILES: COc1c(C(F)(F)F)ccc(Oc2ccccc2)c1C(=O)Nc1ccnc(C(N)=O)c1] 63 |
TABLE A-continued
| Compound Numbers and Structures. |
| --- |
| 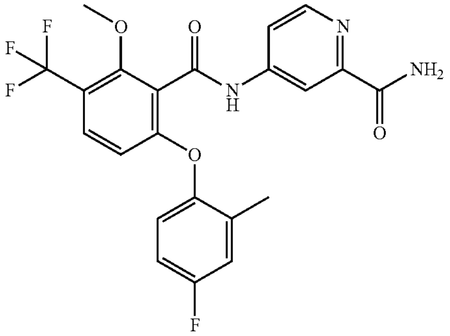 [SMILES: COc1c(C(F)(F)F)ccc(Oc2ccc(F)cc2C)c1C(=O)Nc1ccnc(C(N)=O)c1] 64 |
| 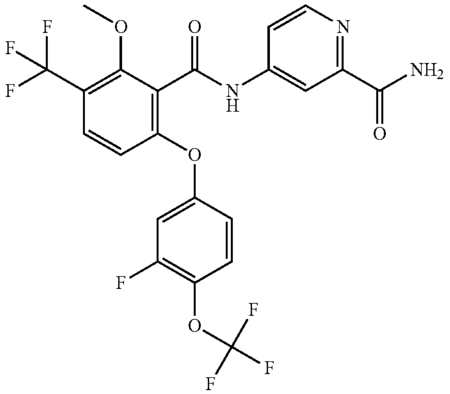 [SMILES: COc1c(C(F)(F)F)ccc(Oc2ccc(OC(F)(F)F)c(F)c2)c1C(=O)Nc1ccnc(C(N)=O)c1] 65 |
| 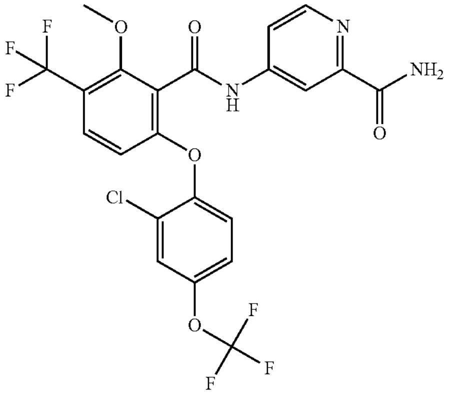 [SMILES: COc1c(C(F)(F)F)ccc(Oc2ccc(OC(F)(F)F)cc2Cl)c1C(=O)Nc1ccnc(C(N)=O)c1] 66 |
| 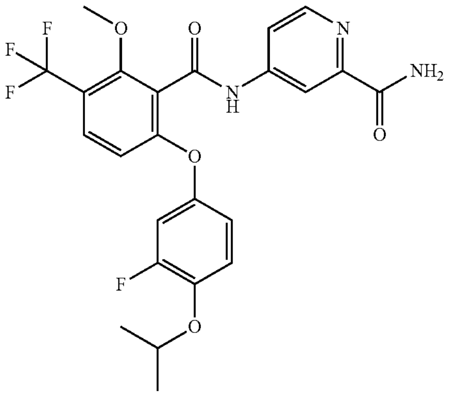 [SMILES: COc1c(C(F)(F)F)ccc(Oc2ccc(OC(C)C)c(F)c2)c1C(=O)Nc1ccnc(C(N)=O)c1] 67 |

TABLE A-continued
| Compound Numbers and Structures. |
| --- |
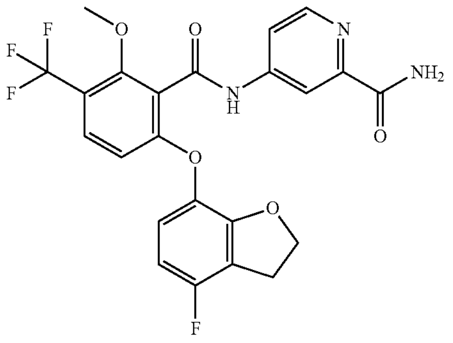 [SMILES: COc1c(C(F)(F)F)ccc(Oc2ccc(F)c3c2OCC3)c1C(=O)Nc1ccnc(C(N)=O)c1]
68
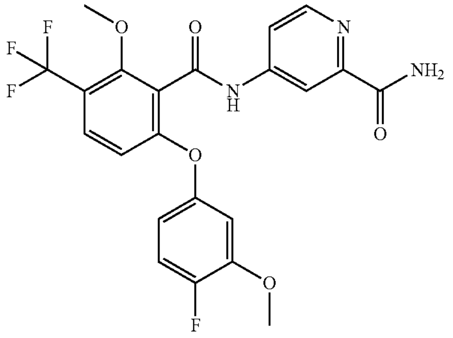 [SMILES: COc1cc(Oc2ccc(C(F)(F)F)c(OC)c2C(=O)Nc2ccnc(C(N)=O)c2)ccc1F]
69
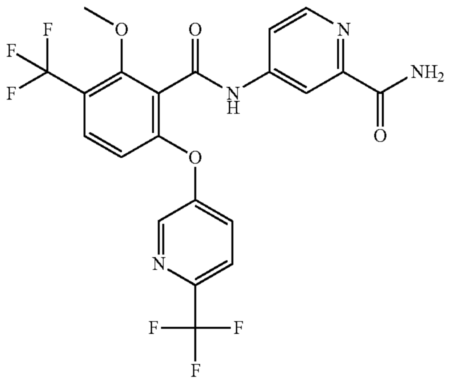 [SMILES: COc1c(C(F)(F)F)ccc(Oc2ccc(C(F)(F)F)nc2)c1C(=O)Nc1ccnc(C(N)=O)c1]
70
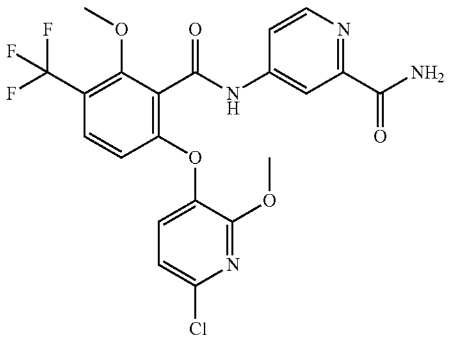 [SMILES: COc1nc(Cl)ccc1Oc1ccc(C(F)(F)F)c(OC)c1C(=O)Nc1ccnc(C(N)=O)c1]
71
TABLE A-continued
| Compound Numbers and Structures. |
| --- |
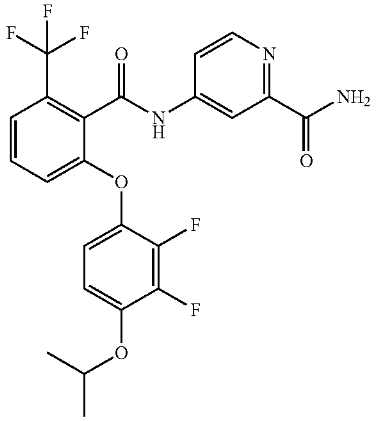 [SMILES: CC(C)Oc1ccc(Oc2cccc(C(F)(F)F)c2C(=O)Nc2ccnc(C(N)=O)c2)c(F)c1F]
72
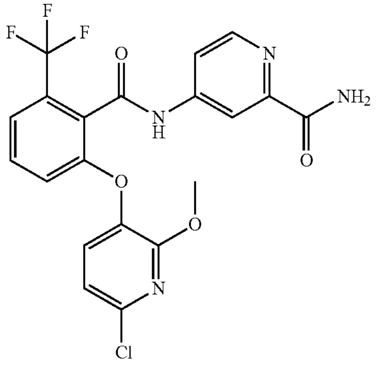 [SMILES: COc1nc(Cl)ccc1Oc1cccc(C(F)(F)F)c1C(=O)Nc1ccnc(C(N)=O)c1]
73
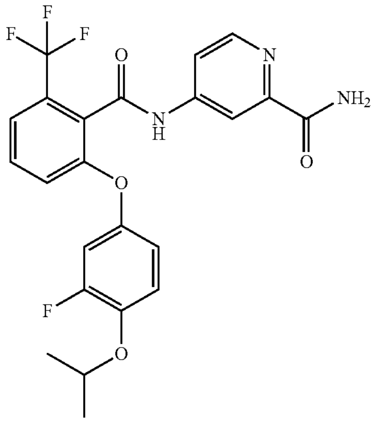 [SMILES: CC(C)Oc1ccc(Oc2cccc(C(F)(F)F)c2C(=O)Nc2ccnc(C(N)=O)c2)cc1F]
74
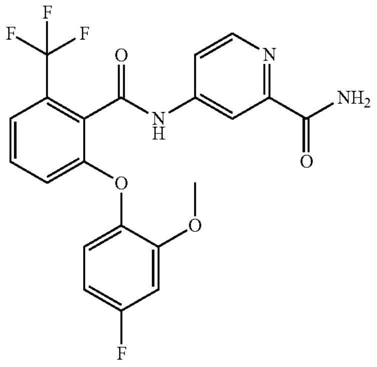 [SMILES: COc1cc(F)ccc1Oc1cccc(C(F)(F)F)c1C(=O)Nc1ccnc(C(N)=O)c1]
75

TABLE A-continued
| Compound Numbers and Structures. |
|---|
| 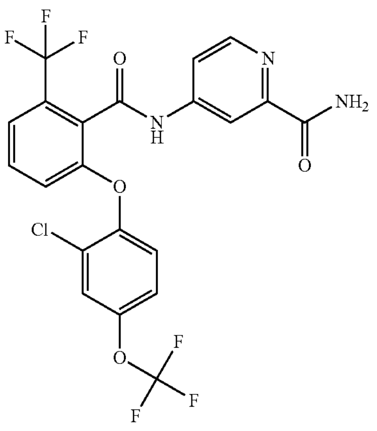 [SMILES: NC(=O)c1cc(NC(=O)c2c(Oc3ccc(OC(F)(F)F)cc3Cl)cccc2C(F)(F)F)ccn1] 76 |
| 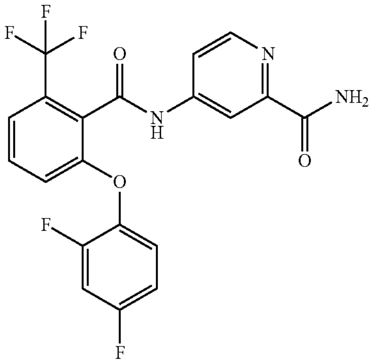 [SMILES: NC(=O)c1cc(NC(=O)c2c(Oc3ccc(F)cc3F)cccc2C(F)(F)F)ccn1] 77 |
| 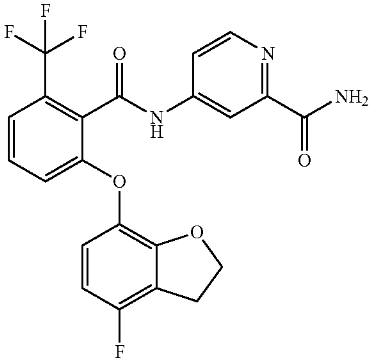 [SMILES: NC(=O)c1cc(NC(=O)c2c(Oc3ccc(F)c4c3OCC4)cccc2C(F)(F)F)ccn1] 78 |
| 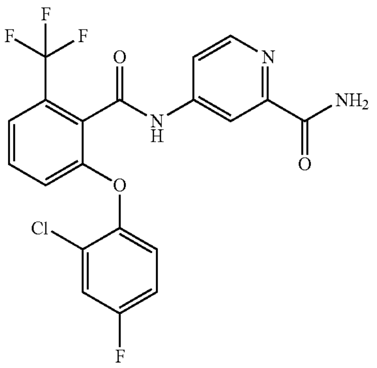 [SMILES: NC(=O)c1cc(NC(=O)c2c(Oc3ccc(F)cc3Cl)cccc2C(F)(F)F)ccn1] 79 |
TABLE A-continued
| Compound Numbers and Structures. |
|---|
| 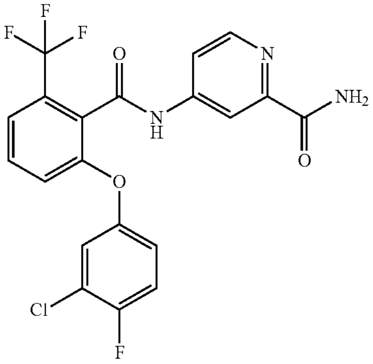 [SMILES: NC(=O)c1cc(NC(=O)c2c(Oc3ccc(F)c(Cl)c3)cccc2C(F)(F)F)ccn1] 80 |
| 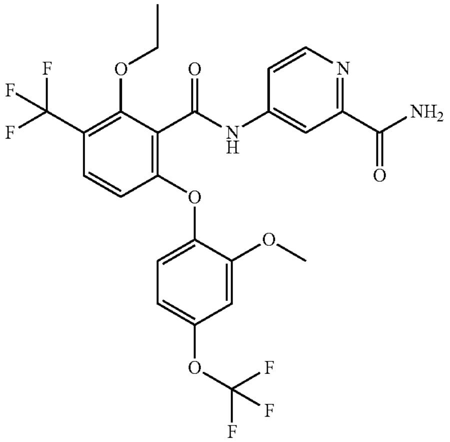 [SMILES: CCOc1c(C(F)(F)F)ccc(Oc2ccc(OC(F)(F)F)cc2OC)c1C(=O)Nc1ccnc(C(N)=O)c1] 83 |
| 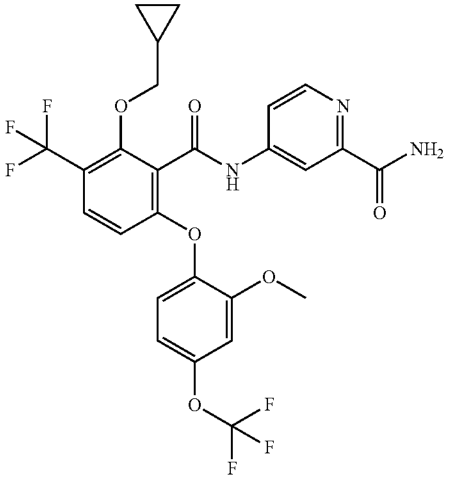 [SMILES: COc1cc(OC(F)(F)F)ccc1Oc1ccc(C(F)(F)F)c(OCC2CC2)c1C(=O)Nc1ccnc(C(N)=O)c1] 84 |

TABLE A-continued
| Compound Numbers and Structures. |
| --- |
85
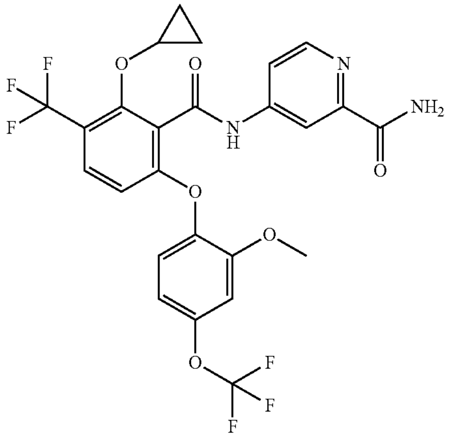 [SMILES: COc1cc(OC(F)(F)F)ccc1Oc1ccc(C(F)(F)F)c(OC2CC2)c1C(=O)Nc1ccnc(C(N)=O)c1]
86
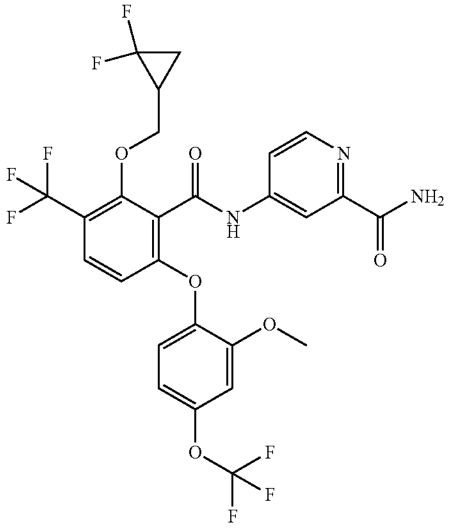 [SMILES: COc1cc(OC(F)(F)F)ccc1Oc1ccc(C(F)(F)F)c(OCC2CC2(F)F)c1C(=O)Nc1ccnc(C(N)=O)c1]
87
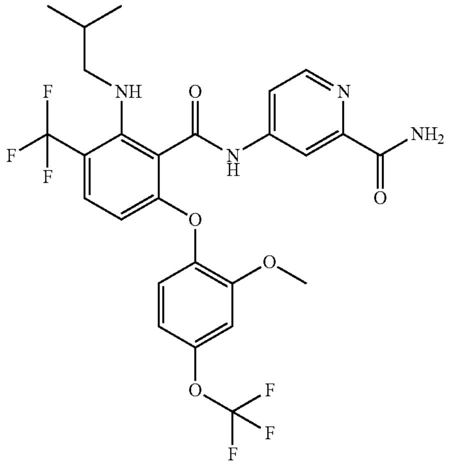 [SMILES: COc1cc(OC(F)(F)F)ccc1Oc1ccc(C(F)(F)F)c(NCC(C)C)c1C(=O)Nc1ccnc(C(N)=O)c1]
TABLE A-continued
| Compound Numbers and Structures. |
| --- |
88
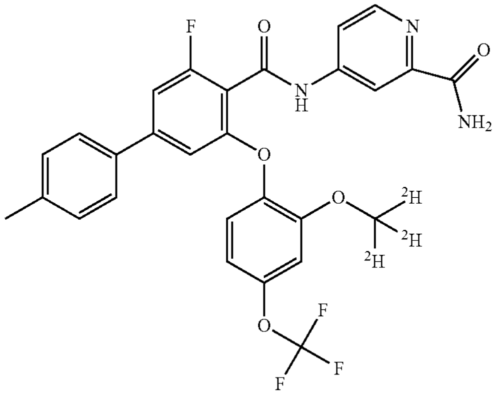 [SMILES: [2H]C([2H])([2H])Oc1cc(OC(F)(F)F)ccc1Oc1cc(-c2ccc(C)cc2)cc(F)c1C(=O)Nc1ccnc(C(N)=O)c1]
89
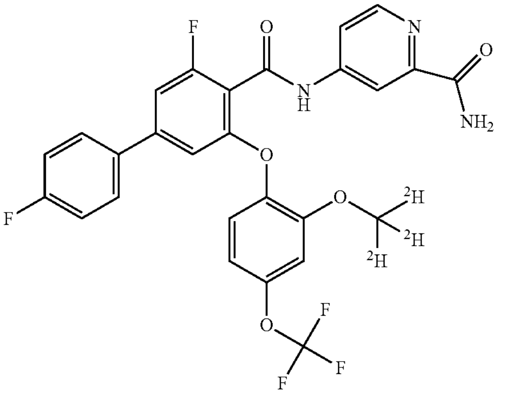 [SMILES: [2H]C([2H])([2H])Oc1cc(OC(F)(F)F)ccc1Oc1cc(-c2ccc(F)cc2)cc(F)c1C(=O)Nc1ccnc(C(N)=O)c1]
90
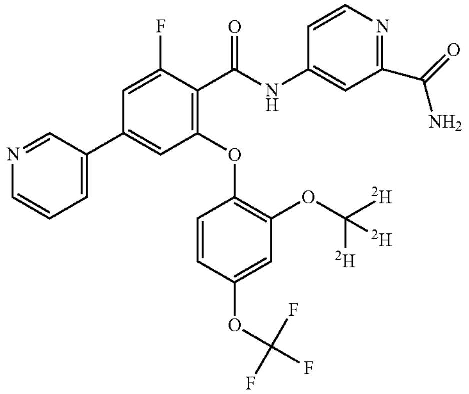 [SMILES: [2H]C([2H])([2H])Oc1cc(OC(F)(F)F)ccc1Oc1cc(-c2cccnc2)cc(F)c1C(=O)Nc1ccnc(C(N)=O)c1]
91
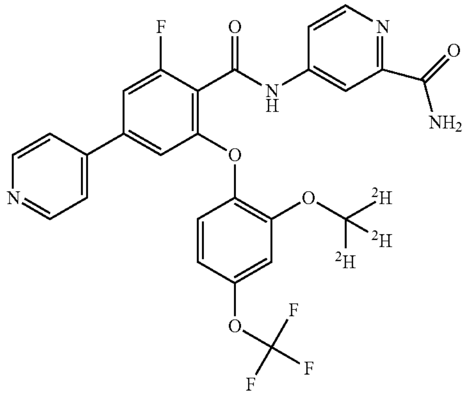 [SMILES: [2H]C([2H])([2H])Oc1cc(OC(F)(F)F)ccc1Oc1cc(-c2ccncc2)cc(F)c1C(=O)Nc1ccnc(C(N)=O)c1]

TABLE A-continued
| Compound Numbers and Structures. |
|---|
| 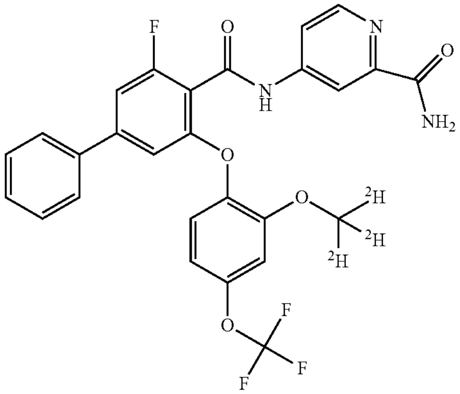 [SMILES: [2H]C([2H])([2H])Oc1cc(OC(F)(F)F)ccc1Oc1cc(-c2ccccc2)cc(F)c1C(=O)Nc1ccnc(C(N)=O)c1] 92 |
| 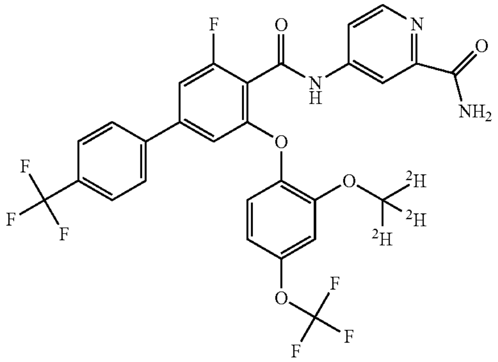 [SMILES: [2H]C([2H])([2H])Oc1cc(OC(F)(F)F)ccc1Oc1cc(-c2ccc(C(F)(F)F)cc2)cc(F)c1C(=O)Nc1ccnc(C(N)=O)c1] 93 |
| 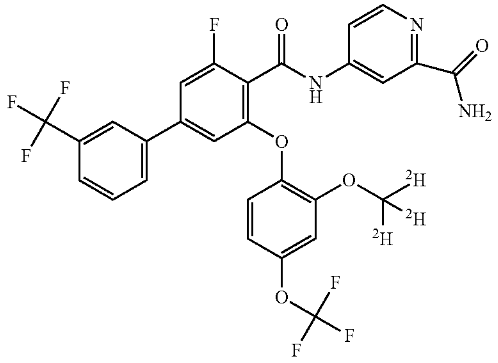 [SMILES: [2H]C([2H])([2H])Oc1cc(OC(F)(F)F)ccc1Oc1cc(-c2cccc(C(F)(F)F)c2)cc(F)c1C(=O)Nc1ccnc(C(N)=O)c1] 94 |
| 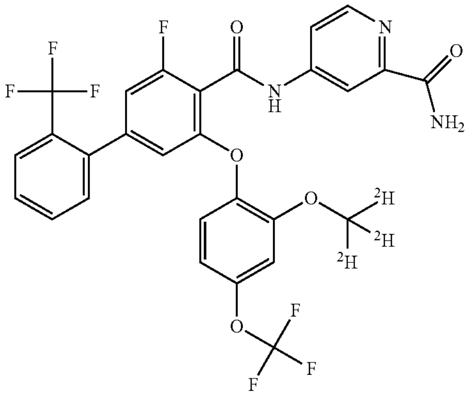 [SMILES: [2H]C([2H])([2H])Oc1cc(OC(F)(F)F)ccc1Oc1cc(-c2ccccc2C(F)(F)F)cc(F)c1C(=O)Nc1ccnc(C(N)=O)c1] 95 |
TABLE A-continued
| Compound Numbers and Structures. |
|---|
| 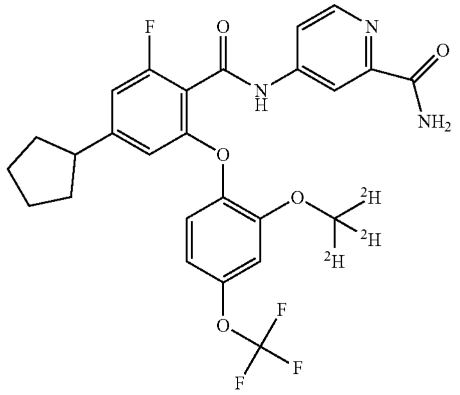 [SMILES: [2H]C([2H])([2H])Oc1cc(OC(F)(F)F)ccc1Oc1cc(C2CCCC2)cc(F)c1C(=O)Nc1ccnc(C(N)=O)c1] 96 |
| 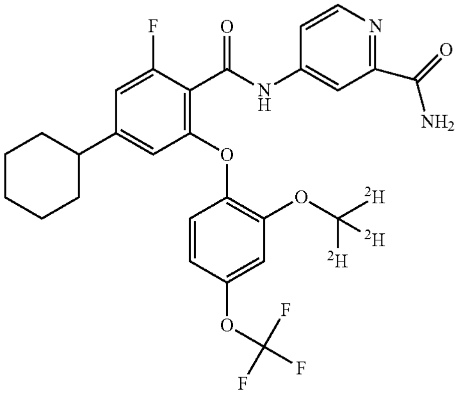 [SMILES: [2H]C([2H])([2H])Oc1cc(OC(F)(F)F)ccc1Oc1cc(C2CCCCC2)cc(F)c1C(=O)Nc1ccnc(C(N)=O)c1] 97 |
| 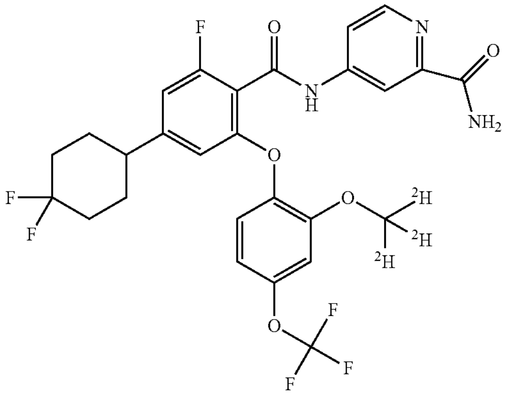 [SMILES: [2H]C([2H])([2H])Oc1cc(OC(F)(F)F)ccc1Oc1cc(C2CCC(F)(F)CC2)cc(F)c1C(=O)Nc1ccnc(C(N)=O)c1] 98 |

TABLE A-continued
| Compound Numbers and Structures. |
| --- |
| 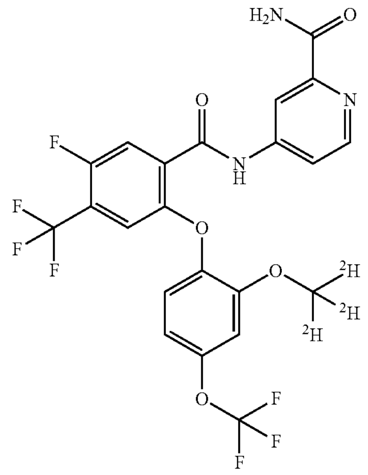 [SMILES: [2H]C([2H])([2H])Oc1cc(OC(F)(F)F)ccc1Oc1cc(C(F)(F)F)c(F)cc1C(=O)Nc1ccnc(C(N)=O)c1] 99 |
| 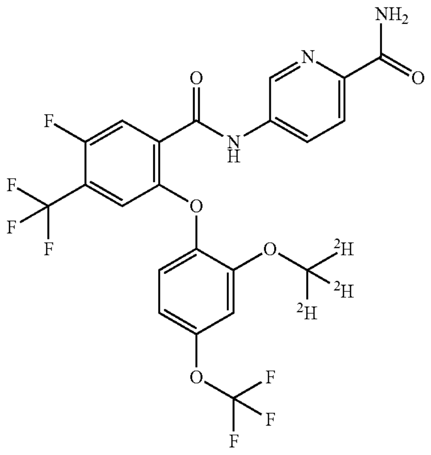 [SMILES: [2H]C([2H])([2H])Oc1cc(OC(F)(F)F)ccc1Oc1cc(C(F)(F)F)c(F)cc1C(=O)Nc1ccc(C(N)=O)nc1] 100 |
| 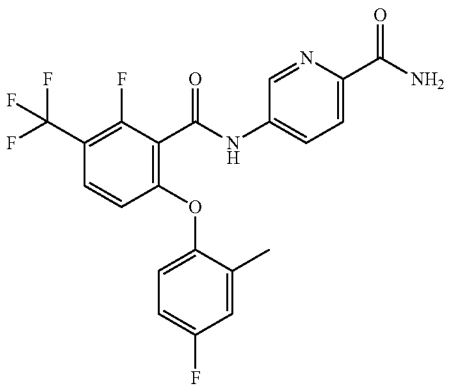 [SMILES: Cc1cc(F)ccc1Oc1ccc(C(F)(F)F)c(F)c1C(=O)Nc1ccc(C(N)=O)nc1] 101 |
TABLE A-continued
| Compound Numbers and Structures. |
| --- |
| 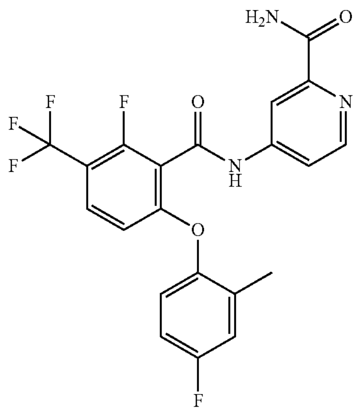 [SMILES: Cc1cc(F)ccc1Oc1ccc(C(F)(F)F)c(F)c1C(=O)Nc1ccnc(C(N)=O)c1] 102 |
| 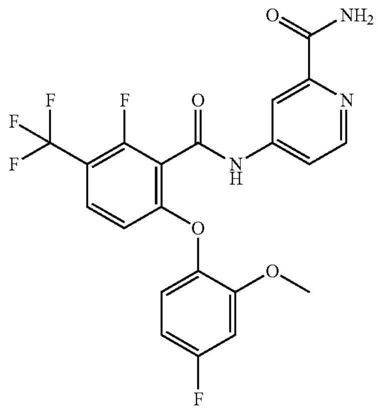 [SMILES: COc1cc(F)ccc1Oc1ccc(C(F)(F)F)c(F)c1C(=O)Nc1ccnc(C(N)=O)c1] 103 |
| 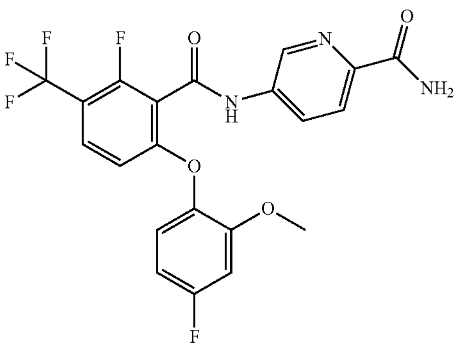 [SMILES: COc1cc(F)ccc1Oc1ccc(C(F)(F)F)c(F)c1C(=O)Nc1ccc(C(N)=O)nc1] 104 |

TABLE A-continued
| Compound Numbers and Structures. |
|---|
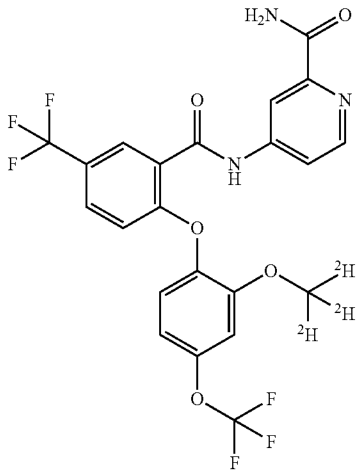 [SMILES: [2H]C([2H])([2H])Oc1cc(OC(F)(F)F)ccc1Oc1ccc(C(F)(F)F)cc1C(=O)Nc1ccnc(C(N)=O)c1]
105
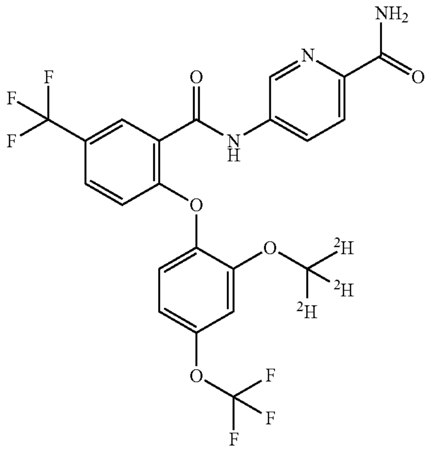 [SMILES: [2H]C([2H])([2H])Oc1cc(OC(F)(F)F)ccc1Oc1ccc(C(F)(F)F)cc1C(=O)Nc1ccc(C(N)=O)nc1]
106
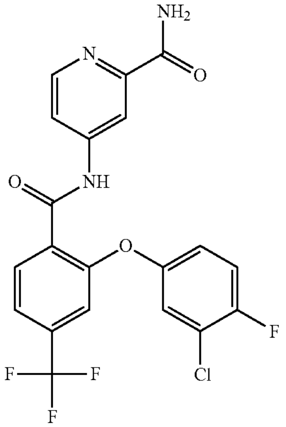 [SMILES: NC(=O)c1cc(NC(=O)c2ccc(C(F)(F)F)cc2Oc2ccc(F)c(Cl)c2)ccn1]
107
TABLE A-continued
| Compound Numbers and Structures. |
|---|
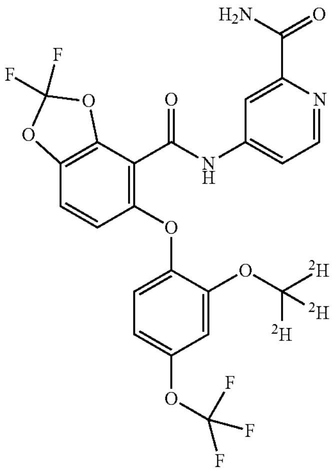 [SMILES: [2H]C([2H])([2H])Oc1cc(OC(F)(F)F)ccc1Oc1ccc2c(c1C(=O)Nc1ccnc(C(N)=O)c1)OC(F)(F)O2]
114
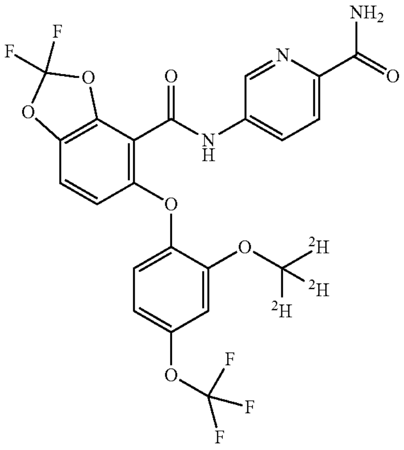 [SMILES: [2H]C([2H])([2H])Oc1cc(OC(F)(F)F)ccc1Oc1ccc2c(c1C(=O)Nc1ccc(C(N)=O)nc1)OC(F)(F)O2]
115
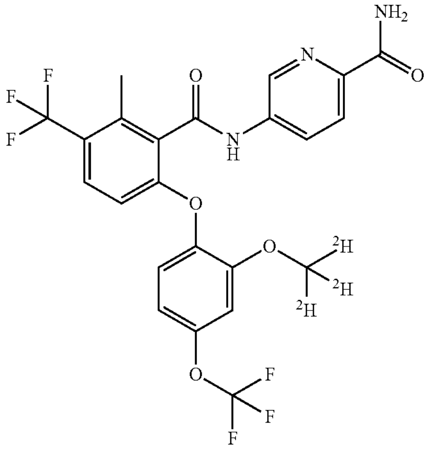 [SMILES: [2H]C([2H])([2H])Oc1cc(OC(F)(F)F)ccc1Oc1ccc(C(F)(F)F)c(C)c1C(=O)Nc1ccc(C(N)=O)nc1]
116

TABLE A-continued
| Compound Numbers and Structures. |
| --- |
| 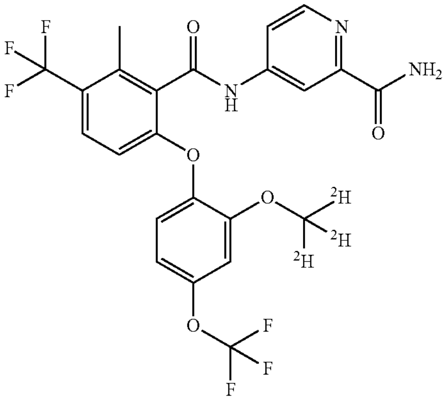 [SMILES: [2H]C([2H])([2H])Oc1cc(OC(F)(F)F)ccc1Oc1ccc(C(F)(F)F)c(C)c1C(=O)Nc1ccnc(C(N)=O)c1] 117 |
| 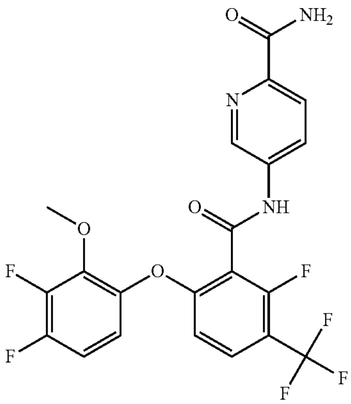 [SMILES: COc1c(Oc2ccc(C(F)(F)F)c(F)c2C(=O)Nc2ccc(C(N)=O)nc2)ccc(F)c1F] 118 |
| 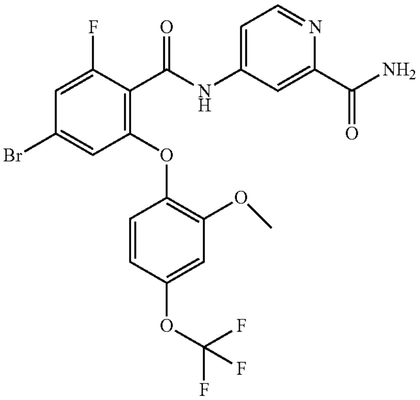 [SMILES: COc1cc(OC(F)(F)F)ccc1Oc1cc(Br)cc(F)c1C(=O)Nc1ccnc(C(N)=O)c1] 119 |
| 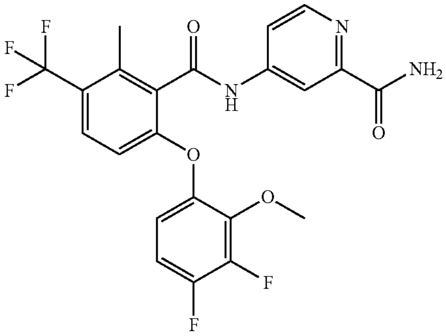 [SMILES: COc1c(Oc2ccc(C(F)(F)F)c(C)c2C(=O)Nc2ccnc(C(N)=O)c2)ccc(F)c1F] 120 |
TABLE A-continued
| Compound Numbers and Structures. |
| --- |
| 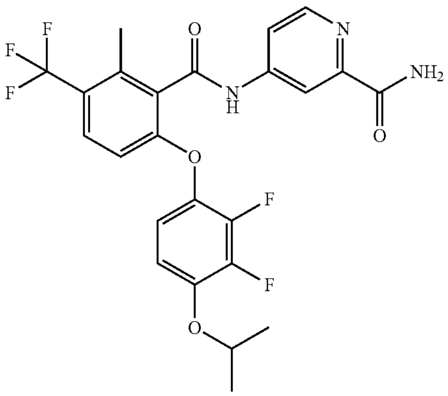 [SMILES: Cc1c(C(F)(F)F)ccc(Oc2ccc(OC(C)C)c(F)c2F)c1C(=O)Nc1ccnc(C(N)=O)c1] 121 |
| 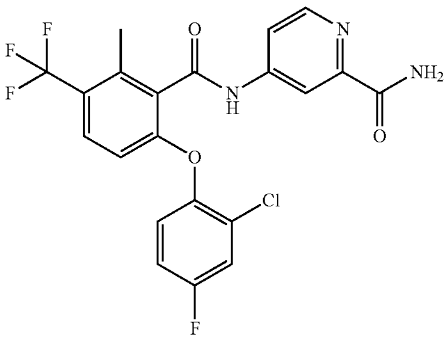 122 |
| 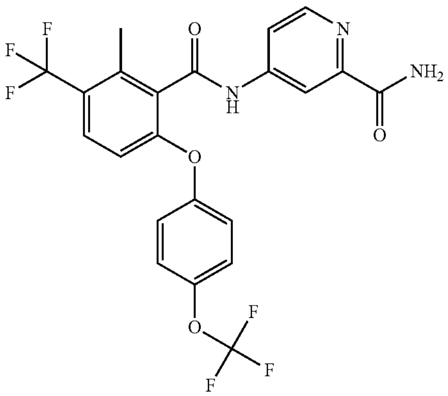 [SMILES: Cc1c(C(F)(F)F)ccc(Oc2ccc(OC(F)(F)F)cc2)c1C(=O)Nc1ccnc(C(N)=O)c1] 123 |
| 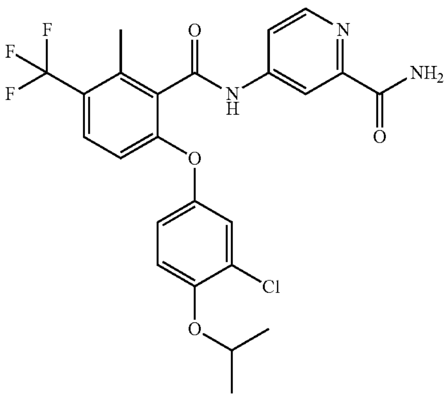 [SMILES: Cc1c(C(F)(F)F)ccc(Oc2ccc(OC(C)C)c(Cl)c2)c1C(=O)Nc1ccnc(C(N)=O)c1] 124 |

TABLE A-continued
| Compound Numbers and Structures. |
|---|
| 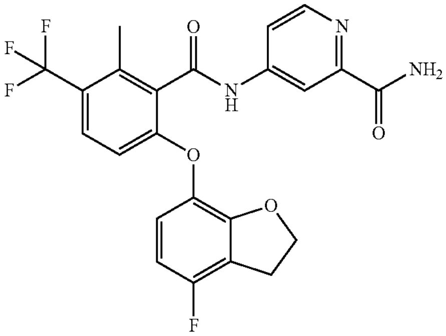 [SMILES: Cc1c(C(F)(F)F)ccc(Oc2ccc(F)c3c2OCC3)c1C(=O)Nc1ccnc(C(N)=O)c1] 125 |
| 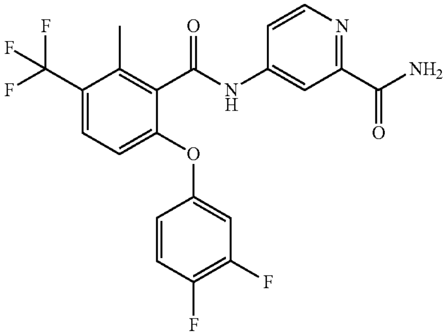 [SMILES: Cc1c(C(F)(F)F)ccc(Oc2ccc(F)c(F)c2)c1C(=O)Nc1ccnc(C(N)=O)c1] 126 |
| 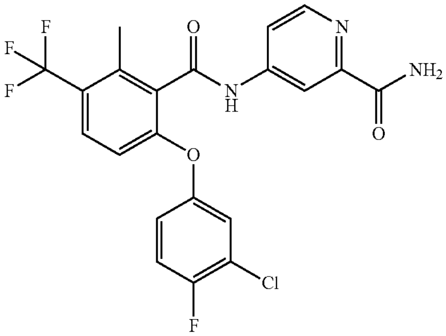 [SMILES: Cc1c(C(F)(F)F)ccc(Oc2ccc(F)c(Cl)c2)c1C(=O)Nc1ccnc(C(N)=O)c1] 127 |
| 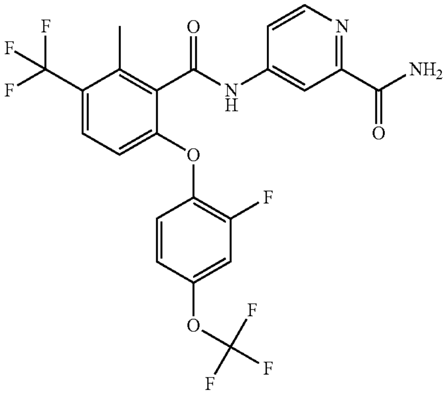 [SMILES: Cc1c(C(F)(F)F)ccc(Oc2ccc(OC(F)(F)F)cc2F)c1C(=O)Nc1ccnc(C(N)=O)c1] 128 |
TABLE A-continued
| Compound Numbers and Structures. |
|---|
| 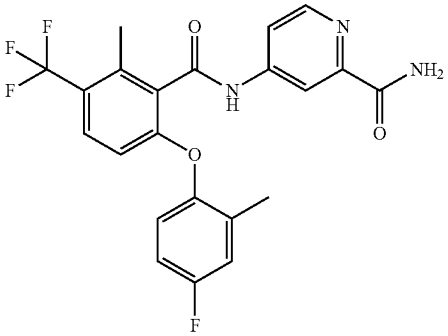 [SMILES: Cc1cc(F)ccc1Oc1ccc(C(F)(F)F)c(C)c1C(=O)Nc1ccnc(C(N)=O)c1] 129 |
| 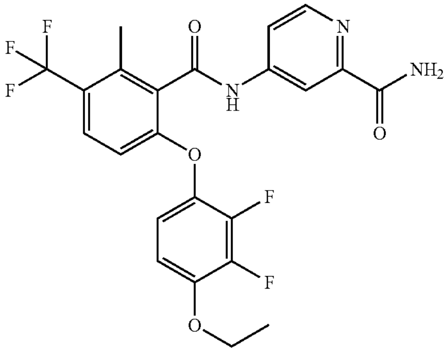 [SMILES: CCOc1ccc(Oc2ccc(C(F)(F)F)c(C)c2C(=O)Nc2ccnc(C(N)=O)c2)c(F)c1F] 130 |
| 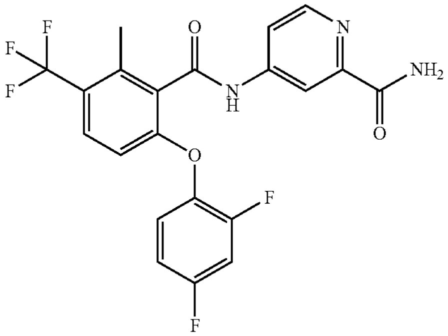 [SMILES: Cc1c(C(F)(F)F)ccc(Oc2ccc(F)cc2F)c1C(=O)Nc1ccnc(C(N)=O)c1] 131 |
| 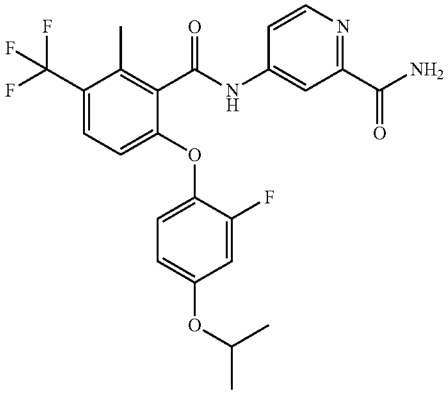 [SMILES: Cc1c(C(F)(F)F)ccc(Oc2ccc(OC(C)C)cc2F)c1C(=O)Nc1ccnc(C(N)=O)c1] 132 |

TABLE A-continued
| Compound Numbers and Structures. |
|---|
| 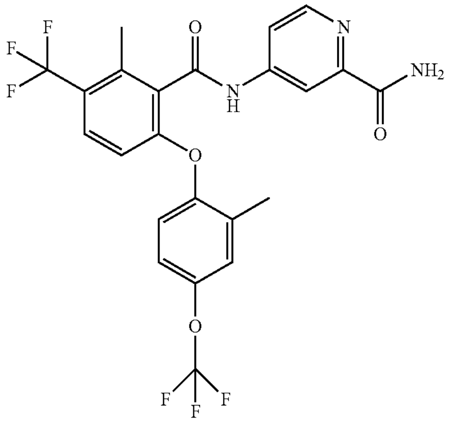 [SMILES: Cc1cc(OC(F)(F)F)ccc1Oc1ccc(C(F)(F)F)c(C)c1C(=O)Nc1ccnc(C(N)=O)c1] 133 |
| 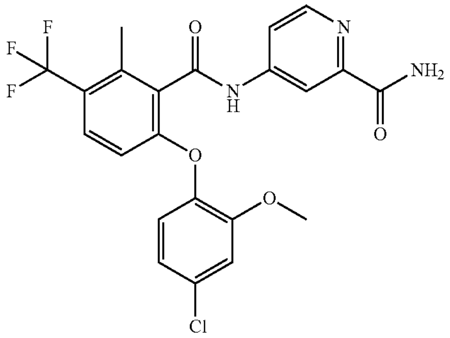 134 |
| 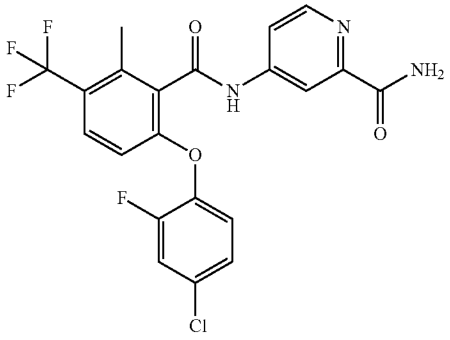 [SMILES: Cc1c(C(F)(F)F)ccc(Oc2ccc(Cl)cc2F)c1C(=O)Nc1ccnc(C(N)=O)c1] 135 |
| 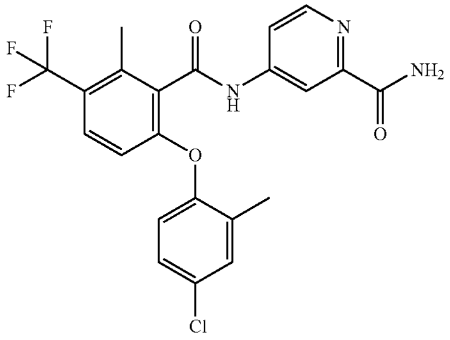 [SMILES: Cc1cc(Cl)ccc1Oc1ccc(C(F)(F)F)c(C)c1C(=O)Nc1ccnc(C(N)=O)c1] 136 |
TABLE A-continued
| Compound Numbers and Structures. |
|---|
| 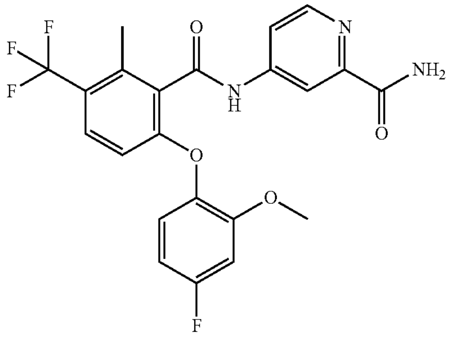 [SMILES: COc1cc(F)ccc1Oc1ccc(C(F)(F)F)c(C)c1C(=O)Nc1ccnc(C(N)=O)c1] 137 |
| 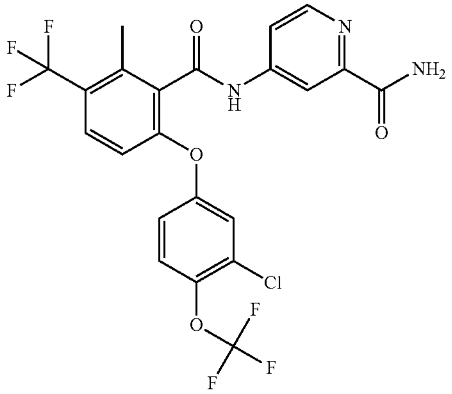 [SMILES: Cc1c(C(F)(F)F)ccc(Oc2ccc(OC(F)(F)F)c(Cl)c2)c1C(=O)Nc1ccnc(C(N)=O)c1] 138 |
| 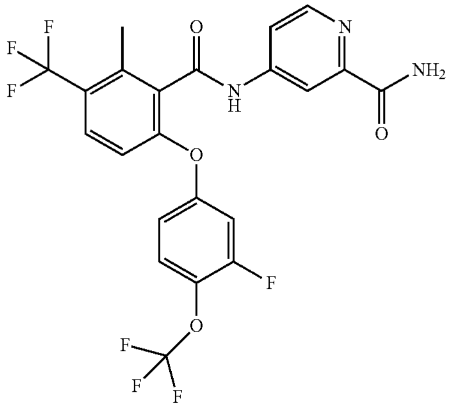 [SMILES: Cc1c(C(F)(F)F)ccc(Oc2ccc(OC(F)(F)F)c(F)c2)c1C(=O)Nc1ccnc(C(N)=O)c1] 139 |
| 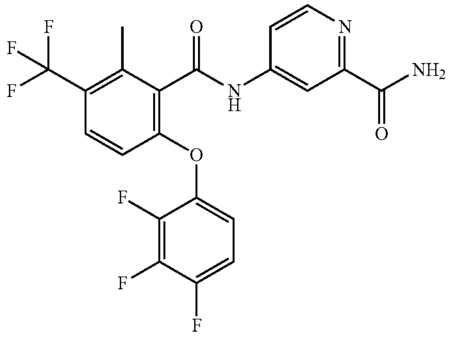 140 |

TABLE A-continued
| Compound Numbers and Structures. |
|---|
| 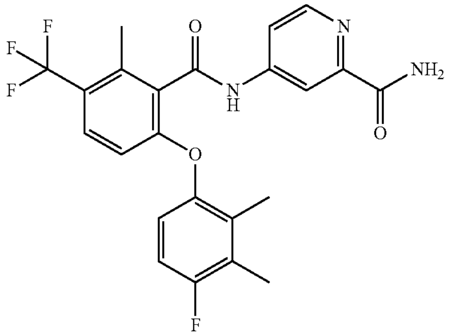 [SMILES: Cc1c(F)ccc(Oc2ccc(C(F)(F)F)c(C)c2C(=O)Nc2ccnc(C(N)=O)c2)c1C] 141 |
| 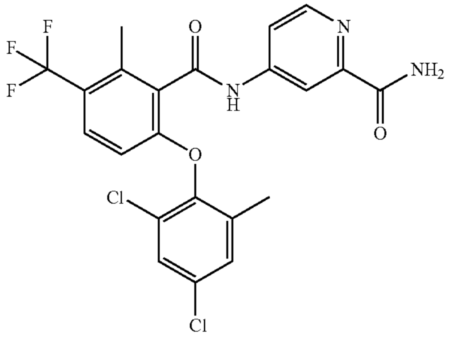 [SMILES: Cc1cc(Cl)cc(Cl)c1Oc1ccc(C(F)(F)F)c(C)c1C(=O)Nc1ccnc(C(N)=O)c1] 142 |
| 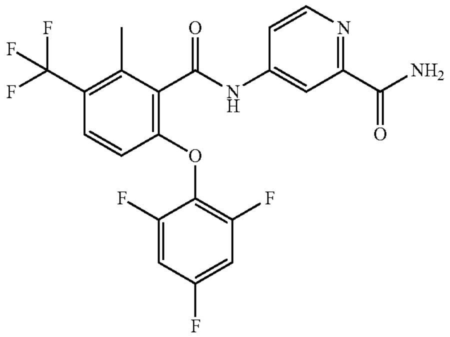 [SMILES: Cc1c(C(F)(F)F)ccc(Oc2c(F)cc(F)cc2F)c1C(=O)Nc1ccnc(C(N)=O)c1] 143 |
| 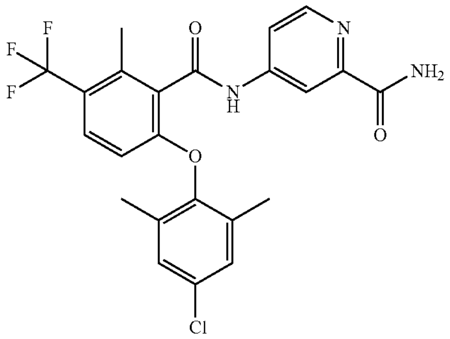 [SMILES: Cc1cc(Cl)cc(C)c1Oc1ccc(C(F)(F)F)c(C)c1C(=O)Nc1ccnc(C(N)=O)c1] 144 |
TABLE A-continued
| Compound Numbers and Structures. |
|---|
| 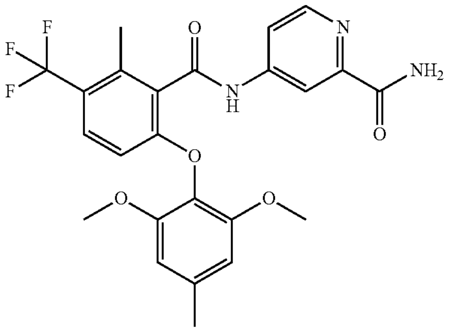 [SMILES: COc1cc(C)cc(OC)c1Oc1ccc(C(F)(F)F)c(C)c1C(=O)Nc1ccnc(C(N)=O)c1] 145 |
| 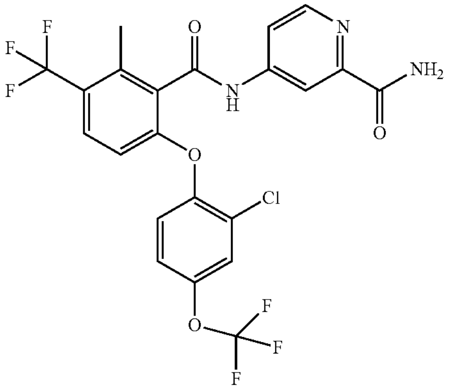 [SMILES: Cc1c(C(F)(F)F)ccc(Oc2ccc(OC(F)(F)F)cc2Cl)c1C(=O)Nc1ccnc(C(N)=O)c1] 146 |
| 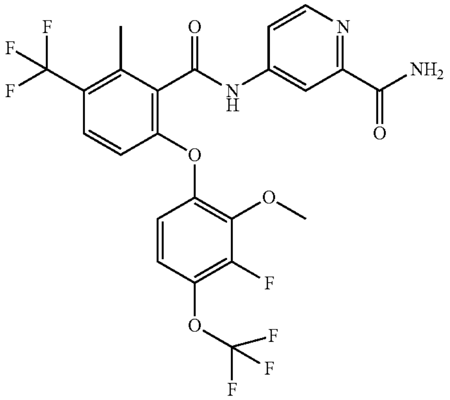 [SMILES: COc1c(Oc2ccc(C(F)(F)F)c(C)c2C(=O)Nc2ccnc(C(N)=O)c2)ccc(OC(F)(F)F)c1F] 147 |
| 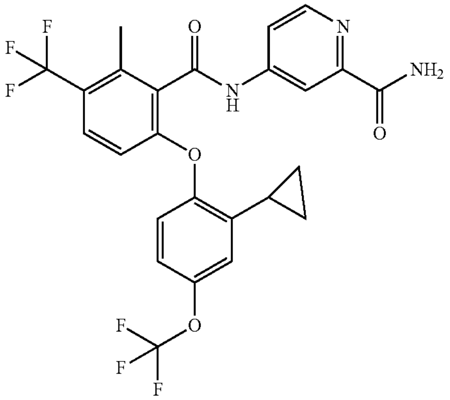 [SMILES: Cc1c(C(F)(F)F)ccc(Oc2ccc(OC(F)(F)F)cc2C2CC2)c1C(=O)Nc1ccnc(C(N)=O)c1] 148 |

TABLE A-continued
Compound Numbers and Structures.
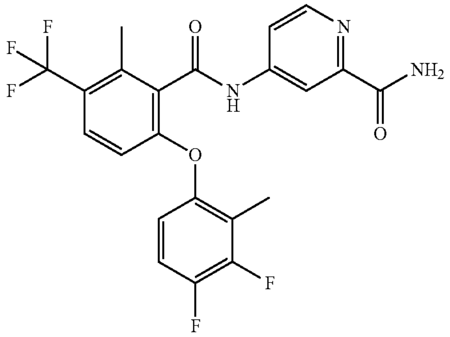 [SMILES: Cc1c(Oc2ccc(C(F)(F)F)c(C)c2C(=O)Nc2ccnc(C(N)=O)c2)ccc(F)c1F]
149
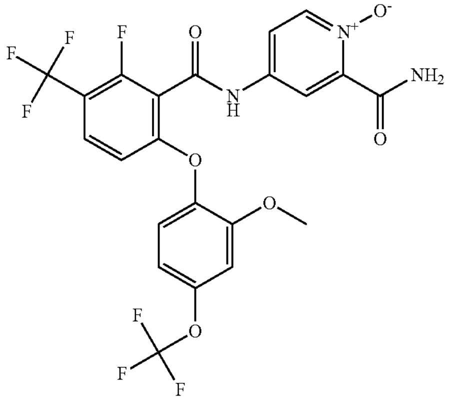 [SMILES: COc1cc(OC(F)(F)F)ccc1Oc1ccc(C(F)(F)F)c(F)c1C(=O)Nc1cc[n+]([O-])c(C(N)=O)c1]
150
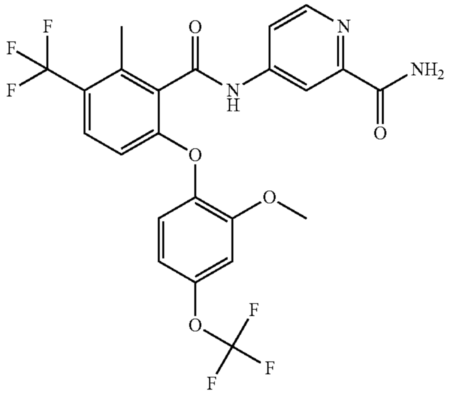 [SMILES: COc1cc(OC(F)(F)F)ccc1Oc1ccc(C(F)(F)F)c(C)c1C(=O)Nc1ccnc(C(N)=O)c1]
151
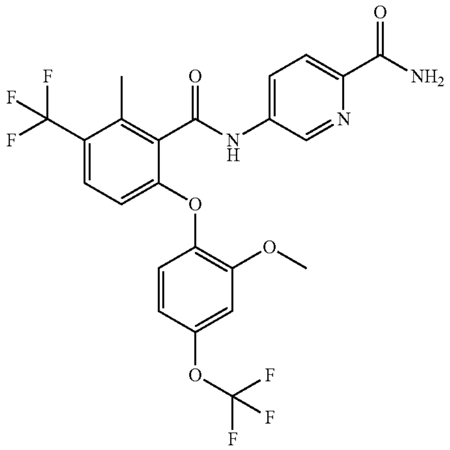 [SMILES: COc1cc(OC(F)(F)F)ccc1Oc1ccc(C(F)(F)F)c(C)c1C(=O)Nc1ccc(C(N)=O)nc1]
152
TABLE A-continued
Compound Numbers and Structures.
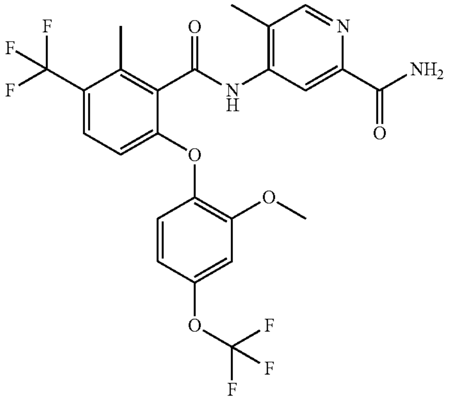 [SMILES: COc1cc(OC(F)(F)F)ccc1Oc1ccc(C(F)(F)F)c(C)c1C(=O)Nc1cc(C(N)=O)ncc1C]
153
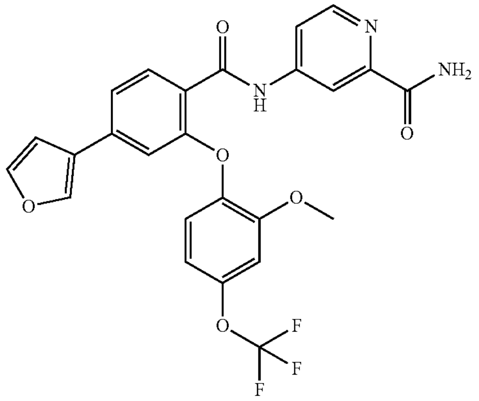 [SMILES: COc1cc(OC(F)(F)F)ccc1Oc1cc(-c2ccoc2)ccc1C(=O)Nc1ccnc(C(N)=O)c1]
154
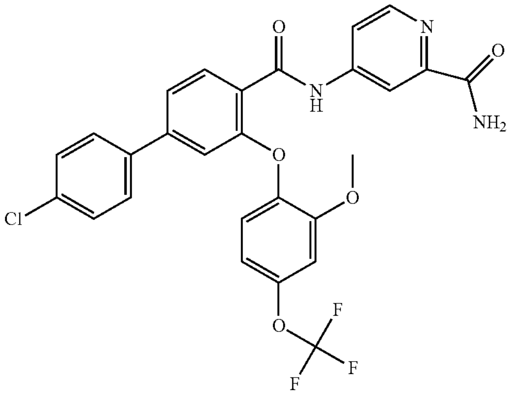 [SMILES: COc1cc(OC(F)(F)F)ccc1Oc1cc(-c2ccc(Cl)cc2)ccc1C(=O)Nc1ccnc(C(N)=O)c1]
155
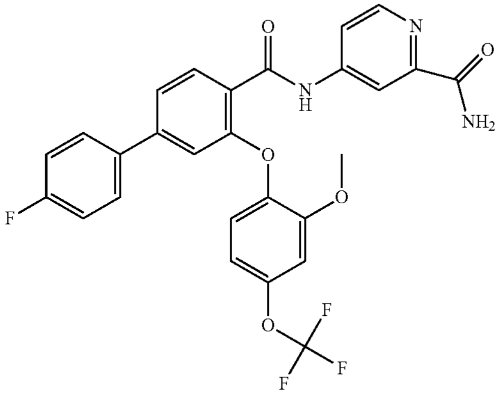 [SMILES: COc1cc(OC(F)(F)F)ccc1Oc1cc(-c2ccc(F)cc2)ccc1C(=O)Nc1ccnc(C(N)=O)c1]
156

TABLE A-continued
Compound Numbers and Structures.
157
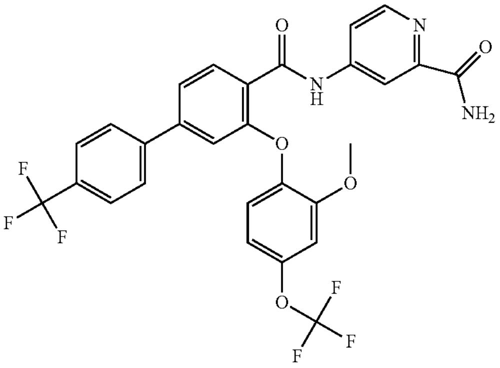 [SMILES: COc1cc(OC(F)(F)F)ccc1Oc1cc(-c2ccc(C(F)(F)F)cc2)ccc1C(=O)Nc1ccnc(C(N)=O)c1]
158-a
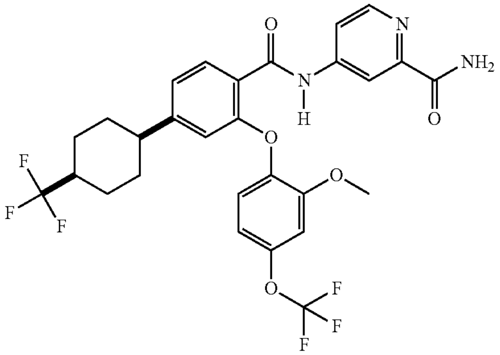
158-b
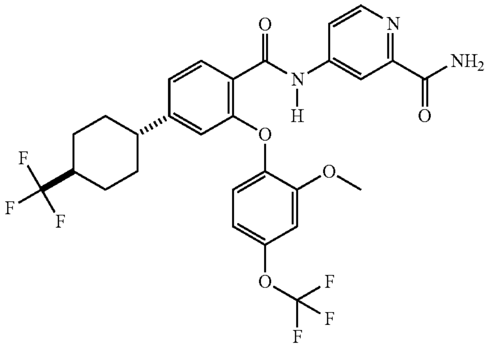
159
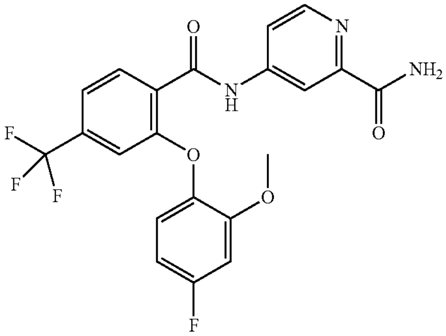 [SMILES: COc1cc(F)ccc1Oc1cc(C(F)(F)F)ccc1C(=O)Nc1ccnc(C(N)=O)c1]
TABLE A-continued
Compound Numbers and Structures.
160
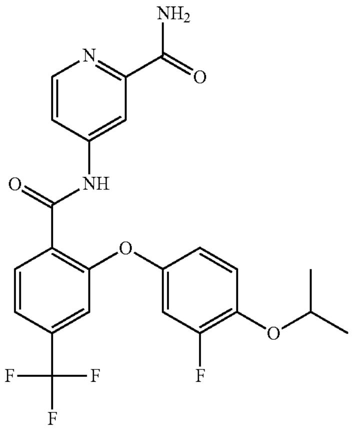 [SMILES: CC(C)Oc1ccc(Oc2cc(C(F)(F)F)ccc2C(=O)Nc2ccnc(C(N)=O)c2)cc1F]
161
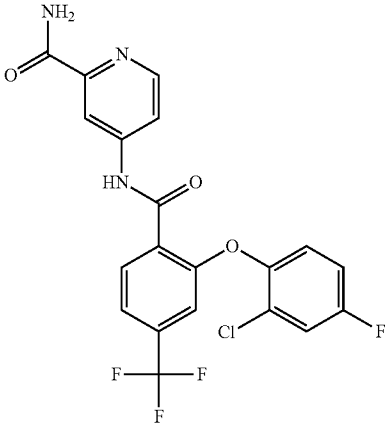 [SMILES: NC(=O)c1cc(NC(=O)c2ccc(C(F)(F)F)cc2Oc2ccc(F)cc2Cl)ccn1]
162
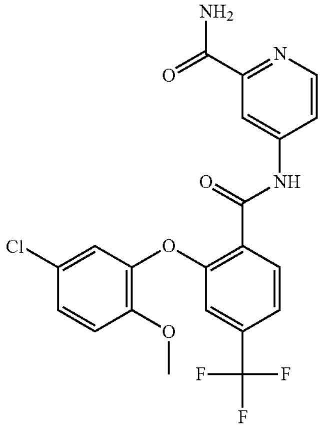 [SMILES: COc1ccc(Cl)cc1Oc1cc(C(F)(F)F)ccc1C(=O)Nc1ccnc(C(N)=O)c1]

TABLE A-continued
Compound Numbers and Structures.
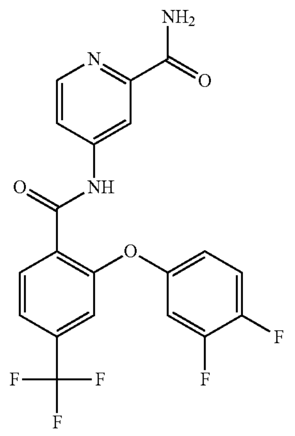 [SMILES: NC(=O)c1cc(NC(=O)c2ccc(C(F)(F)F)cc2Oc2ccc(F)c(F)c2)ccn1]
163
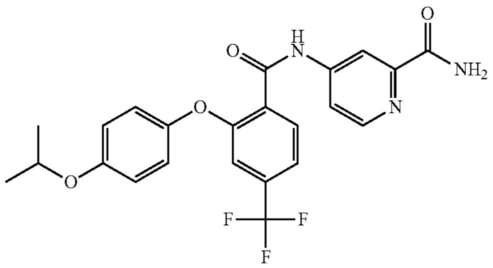 [SMILES: CC(C)Oc1ccc(Oc2cc(C(F)(F)F)ccc2C(=O)Nc2ccnc(C(N)=O)c2)cc1]
164
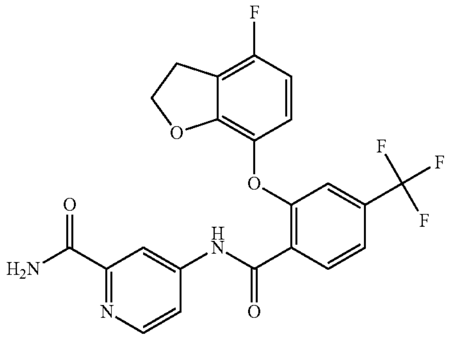 [SMILES: NC(=O)c1cc(NC(=O)c2ccc(C(F)(F)F)cc2Oc2ccc(F)c3c2OCC3)ccn1]
165
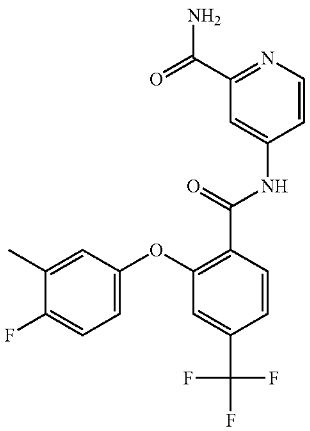 [SMILES: Cc1cc(Oc2cc(C(F)(F)F)ccc2C(=O)Nc2ccnc(C(N)=O)c2)ccc1F]
166
TABLE A-continued
Compound Numbers and Structures.
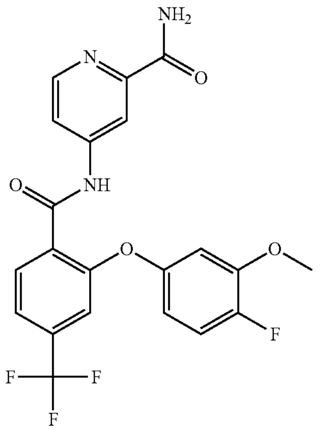 [SMILES: COc1cc(Oc2cc(C(F)(F)F)ccc2C(=O)Nc2ccnc(C(N)=O)c2)ccc1F]
167
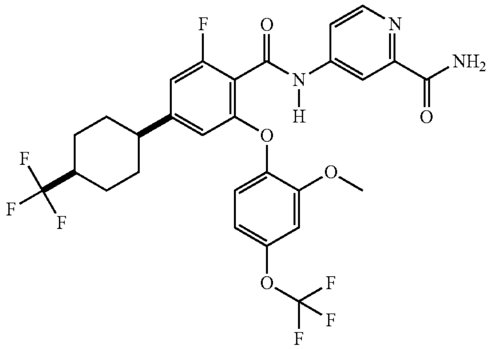
168-a
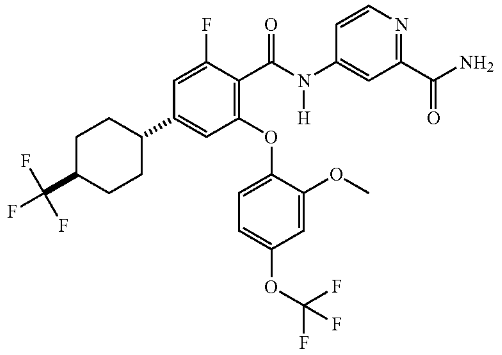
168-b
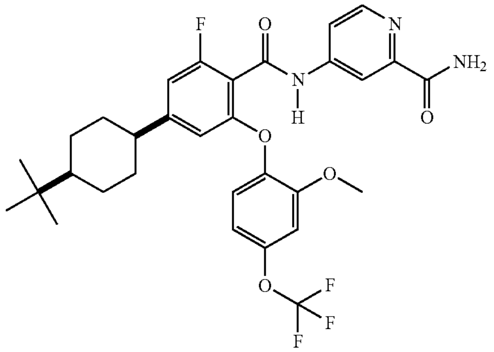
169-a TABLE A-continued
| Compound Numbers and Structures. |
| --- |
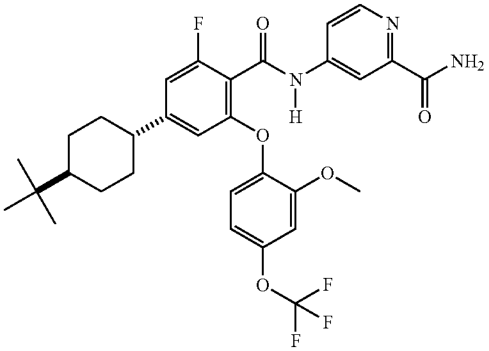
169-b
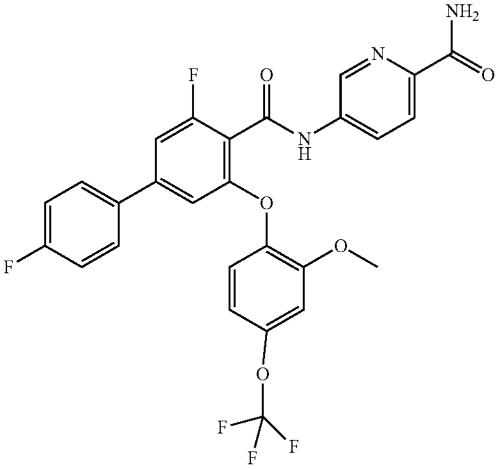 [SMILES: COc1cc(OC(F)(F)F)ccc1Oc1cc(-c2ccc(F)cc2)cc(F)c1C(=O)Nc1ccc(C(N)=O)nc1]
170
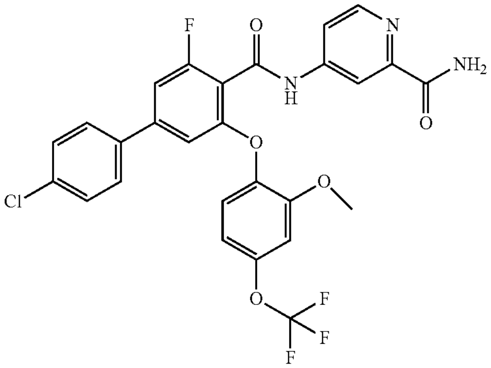 [SMILES: COc1cc(OC(F)(F)F)ccc1Oc1cc(-c2ccc(Cl)cc2)cc(F)c1C(=O)Nc1ccnc(C(N)=O)c1]
171
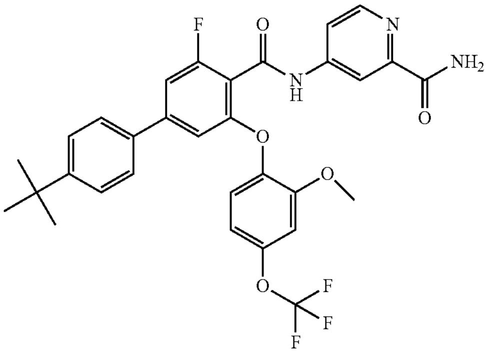 [SMILES: COc1cc(OC(F)(F)F)ccc1Oc1cc(-c2ccc(C(C)(C)C)cc2)cc(F)c1C(=O)Nc1ccnc(C(N)=O)c1]
172
TABLE A-continued
| Compound Numbers and Structures. |
| --- |
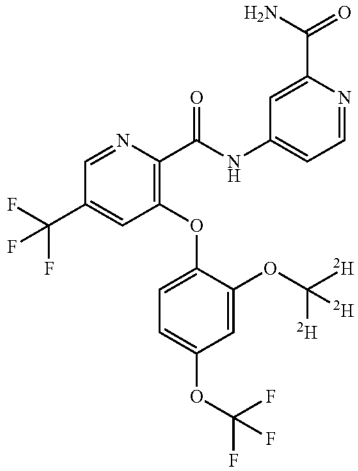 [SMILES: [2H]C([2H])([2H])Oc1cc(OC(F)(F)F)ccc1Oc1cc(C(F)(F)F)cnc1C(=O)Nc1ccnc(C(N)=O)c1]
173
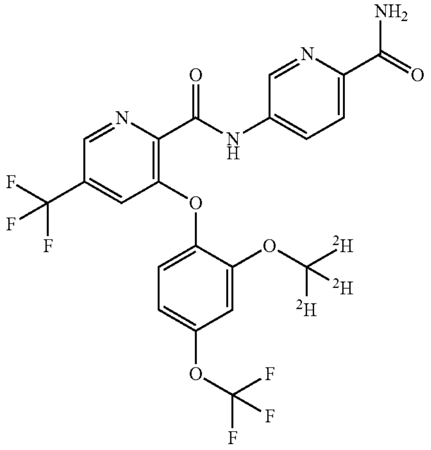 [SMILES: [2H]C([2H])([2H])Oc1cc(OC(F)(F)F)ccc1Oc1cc(C(F)(F)F)cnc1C(=O)Nc1ccc(C(N)=O)nc1]
174
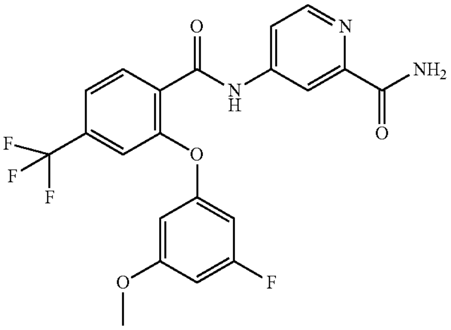 [SMILES: COc1cc(F)cc(Oc2cc(C(F)(F)F)ccc2C(=O)Nc2ccnc(C(N)=O)c2)c1]
175

TABLE A-continued
Compound Numbers and Structures.
176
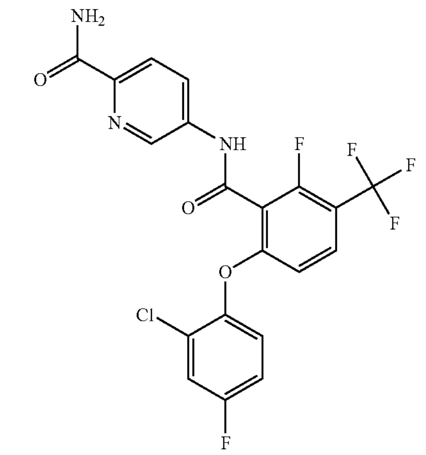
177
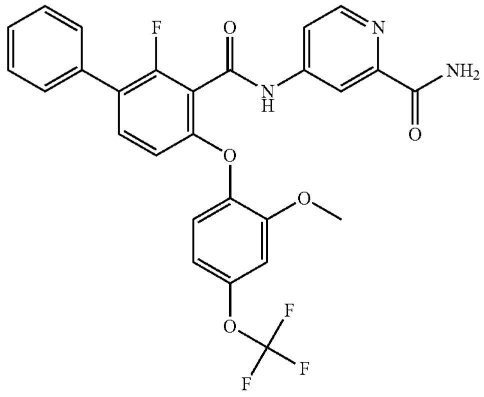 [SMILES: COc1cc(OC(F)(F)F)ccc1Oc1ccc(-c2ccccc2)c(F)c1C(=O)Nc1ccnc(C(N)=O)c1]
178
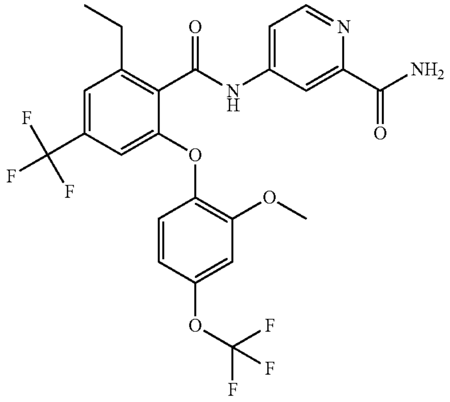 [SMILES: CCc1cc(C(F)(F)F)cc(Oc2ccc(OC(F)(F)F)cc2OC)c1C(=O)Nc1ccnc(C(N)=O)c1]
TABLE A-continued
Compound Numbers and Structures.
179
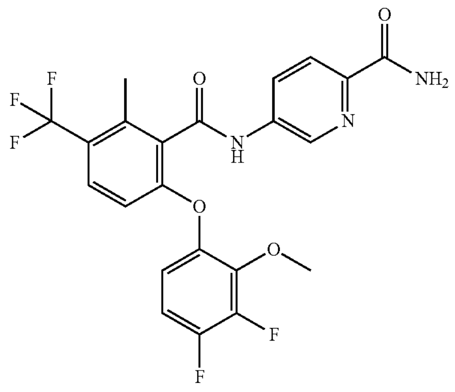 [SMILES: COc1c(Oc2ccc(C(F)(F)F)c(C)c2C(=O)Nc2ccc(C(N)=O)nc2)ccc(F)c1F]
180
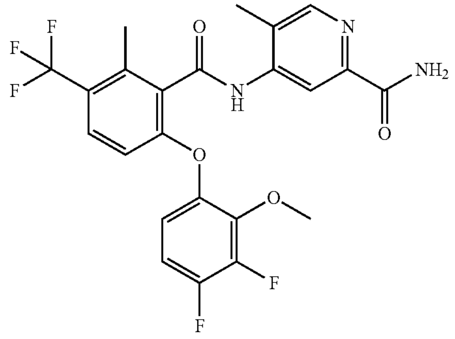 [SMILES: COc1c(Oc2ccc(C(F)(F)F)c(C)c2C(=O)Nc2cc(C(N)=O)ncc2C)ccc(F)c1F]
181
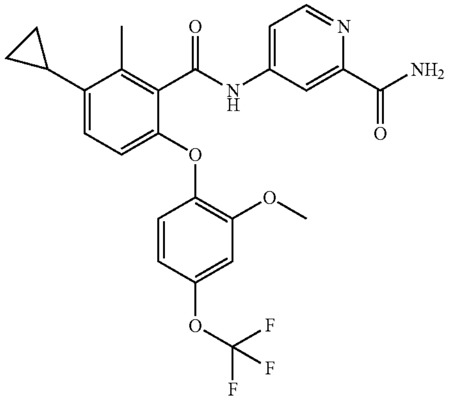 [SMILES: COc1cc(OC(F)(F)F)ccc1Oc1ccc(C2CC2)c(C)c1C(=O)Nc1ccnc(C(N)=O)c1]
182
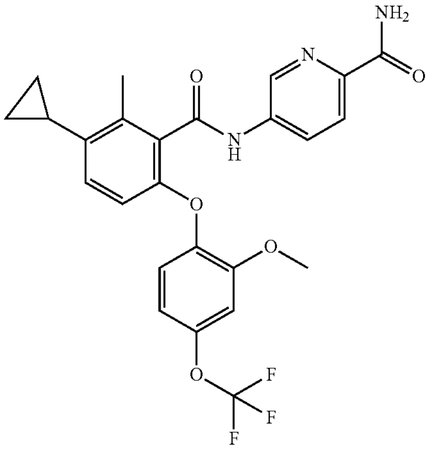 [SMILES: COc1cc(OC(F)(F)F)ccc1Oc1ccc(C2CC2)c(C)c1C(=O)Nc1ccc(C(N)=O)nc1]

TABLE A-continued
Compound Numbers and Structures.
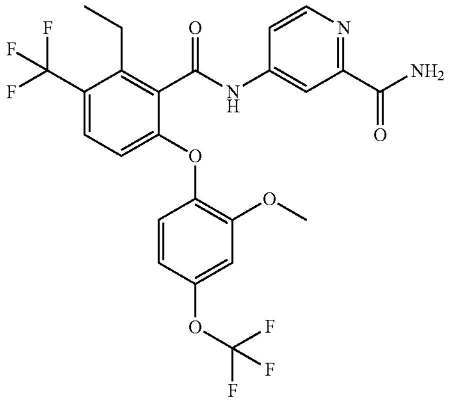 [SMILES: CCc1c(C(F)(F)F)ccc(Oc2ccc(OC(F)(F)F)cc2OC)c1C(=O)Nc1ccnc(C(N)=O)c1]
183
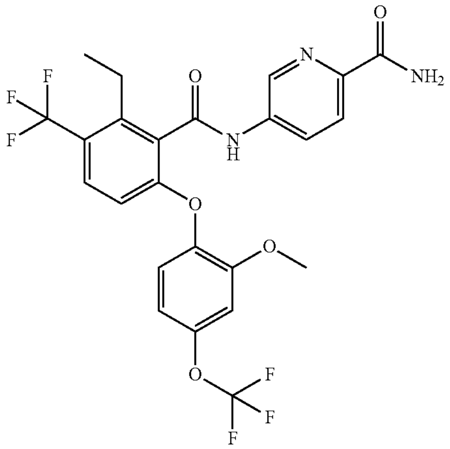 [SMILES: CCc1c(C(F)(F)F)ccc(Oc2ccc(OC(F)(F)F)cc2OC)c1C(=O)Nc1ccc(C(N)=O)nc1]
184
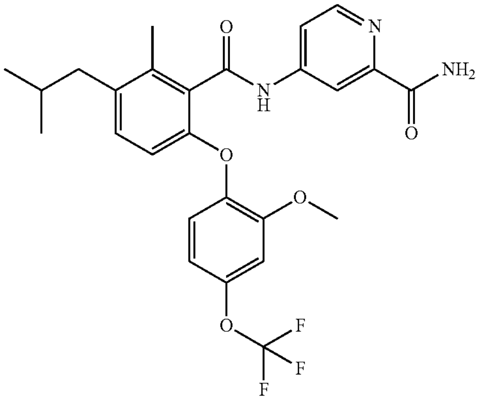 [SMILES: COc1cc(OC(F)(F)F)ccc1Oc1ccc(CC(C)C)c(C)c1C(=O)Nc1ccnc(C(N)=O)c1]
185
TABLE A-continued
Compound Numbers and Structures.
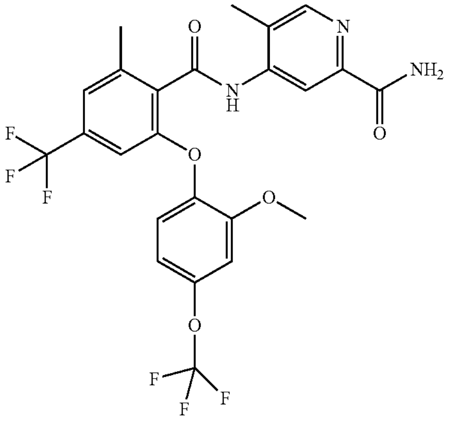 [SMILES: COc1cc(OC(F)(F)F)ccc1Oc1cc(C(F)(F)F)cc(C)c1C(=O)Nc1cc(C(N)=O)ncc1C]
186
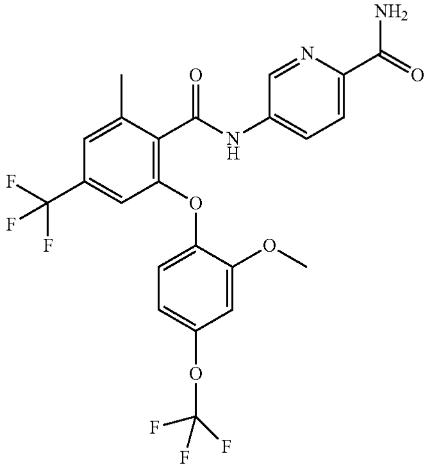 [SMILES: COc1cc(OC(F)(F)F)ccc1Oc1cc(C(F)(F)F)cc(C)c1C(=O)Nc1ccc(C(N)=O)nc1]
187
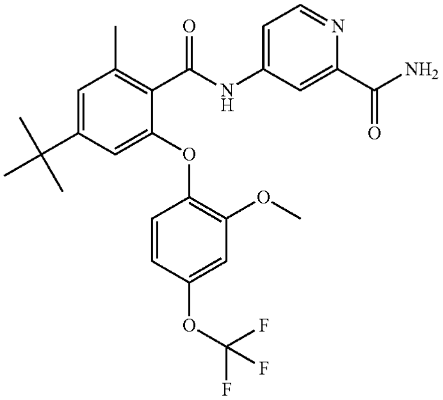 [SMILES: COc1cc(OC(F)(F)F)ccc1Oc1cc(C(C)(C)C)cc(C)c1C(=O)Nc1ccnc(C(N)=O)c1]
188

TABLE A-continued
Compound Numbers and Structures.
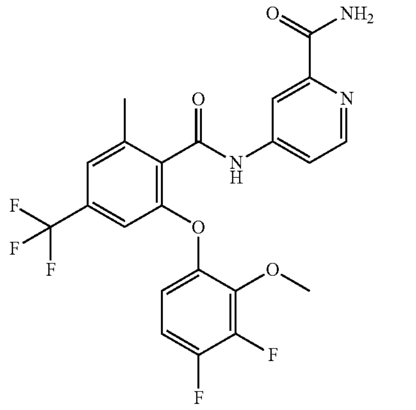 [SMILES: COc1c(Oc2cc(C(F)(F)F)cc(C)c2C(=O)Nc2ccnc(C(N)=O)c2)ccc(F)c1F]
189
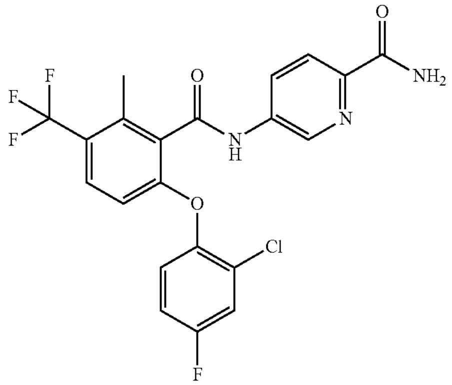 [SMILES: Cc1c(C(F)(F)F)ccc(Oc2ccc(F)cc2Cl)c1C(=O)Nc1ccc(C(N)=O)nc1]
190
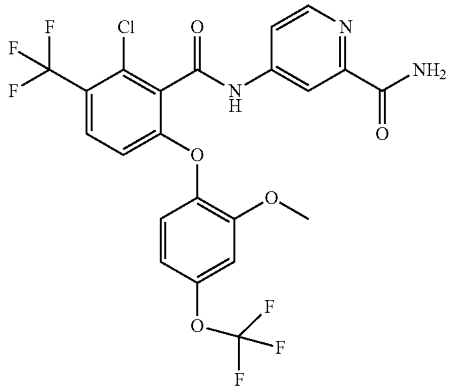 [SMILES: COc1cc(OC(F)(F)F)ccc1Oc1ccc(C(F)(F)F)c(Cl)c1C(=O)Nc1ccnc(C(N)=O)c1]
191
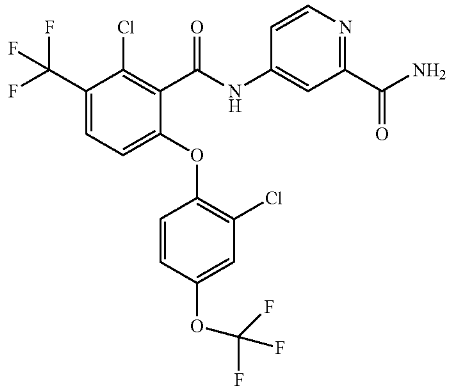 [SMILES: NC(=O)c1cc(NC(=O)c2c(Oc3ccc(OC(F)(F)F)cc3Cl)ccc(C(F)(F)F)c2Cl)ccn1]
192
TABLE A-continued
Compound Numbers and Structures.
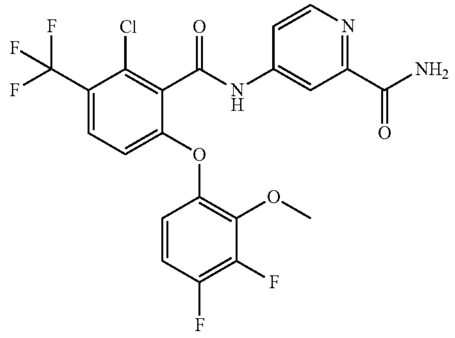 [SMILES: COc1c(Oc2ccc(C(F)(F)F)c(Cl)c2C(=O)Nc2ccnc(C(N)=O)c2)ccc(F)c1F]
193
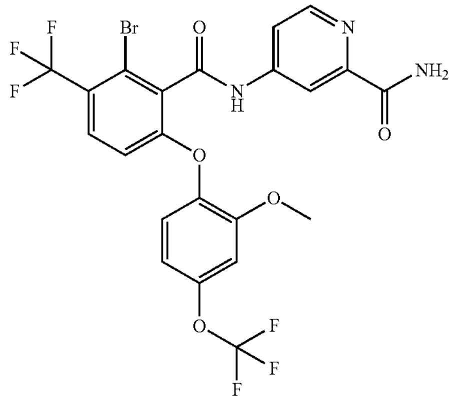 [SMILES: COc1cc(OC(F)(F)F)ccc1Oc1ccc(C(F)(F)F)c(Br)c1C(=O)Nc1ccnc(C(N)=O)c1]
194
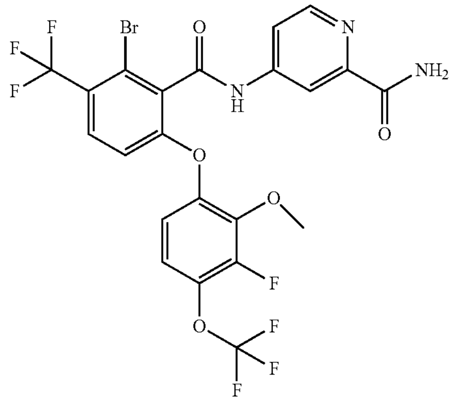 [SMILES: COc1c(Oc2ccc(C(F)(F)F)c(Br)c2C(=O)Nc2ccnc(C(N)=O)c2)ccc(OC(F)(F)F)c1F]
195
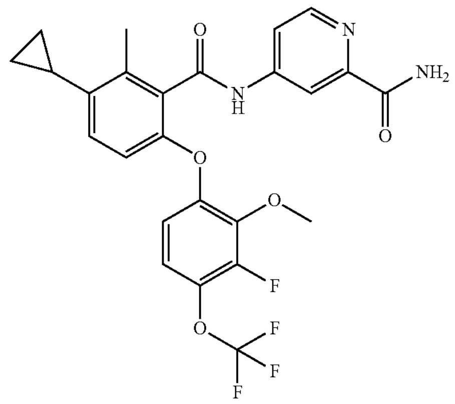 [SMILES: COc1c(Oc2ccc(C3CC3)c(C)c2C(=O)Nc2ccnc(C(N)=O)c2)ccc(OC(F)(F)F)c1F]
196

TABLE A-continued
| Compound Numbers and Structures. |
|---|
| 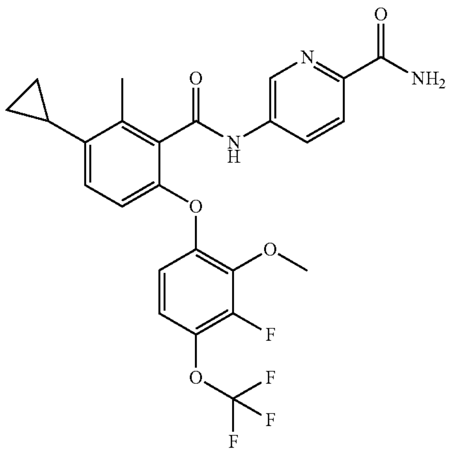 [SMILES: COc1c(Oc2ccc(C3CC3)c(C)c2C(=O)Nc2ccc(C(N)=O)nc2)ccc(OC(F)(F)F)c1F] 197 |
| 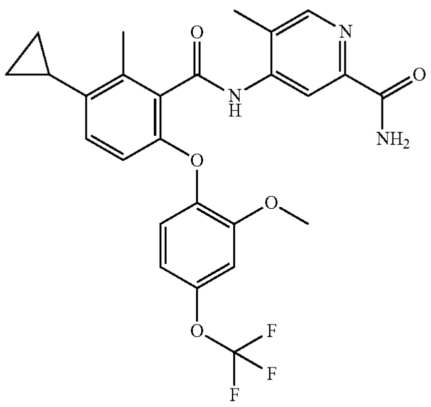 [SMILES: COc1cc(OC(F)(F)F)ccc1Oc1ccc(C2CC2)c(C)c1C(=O)Nc1cc(C(N)=O)ncc1C] 198 |
| 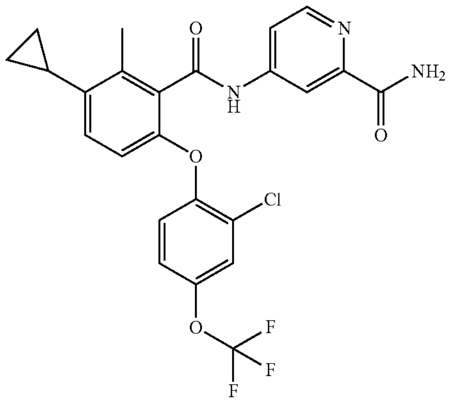 [SMILES: Cc1c(C2CC2)ccc(Oc2ccc(OC(F)(F)F)cc2Cl)c1C(=O)Nc1ccnc(C(N)=O)c1] 199 |
TABLE A-continued
| Compound Numbers and Structures. |
|---|
| 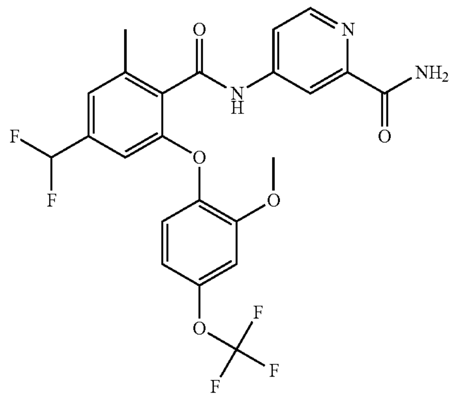 [SMILES: COc1cc(OC(F)(F)F)ccc1Oc1cc(C(F)F)cc(C)c1C(=O)Nc1ccnc(C(N)=O)c1] 200 |
| 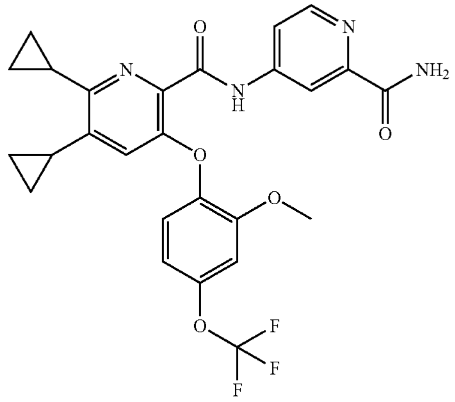 [SMILES: COc1cc(OC(F)(F)F)ccc1Oc1cc(C2CC2)c(C2CC2)nc1C(=O)Nc1ccnc(C(N)=O)c1] 201 |
| 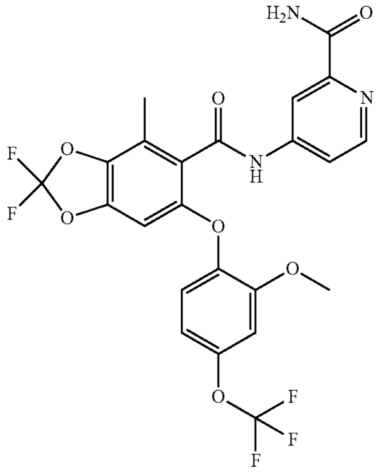 [SMILES: COc1cc(OC(F)(F)F)ccc1Oc1cc2c(c(C)c1C(=O)Nc1ccnc(C(N)=O)c1)OC(F)(F)O2] 202 |

TABLE A-continued
| Compound Numbers and Structures. |
|---|
| 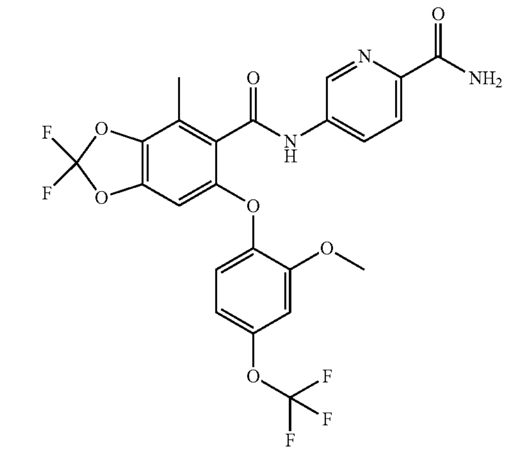 [SMILES: COc1cc(OC(F)(F)F)ccc1Oc1cc2c(c(C)c1C(=O)Nc1ccc(C(N)=O)nc1)OC(F)(F)O2] 203 |
| 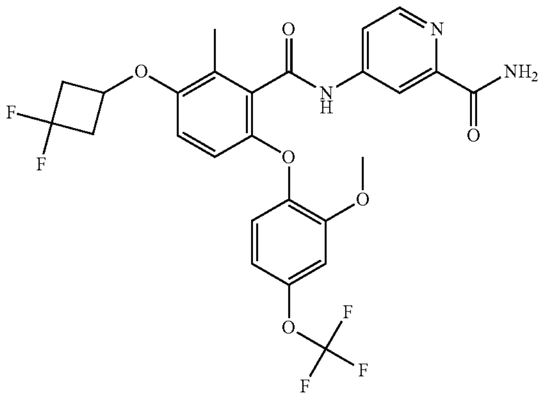 [SMILES: COc1cc(OC(F)(F)F)ccc1Oc1ccc(OC2CC(F)(F)C2)c(C)c1C(=O)Nc1ccnc(C(N)=O)c1] 204 |
| 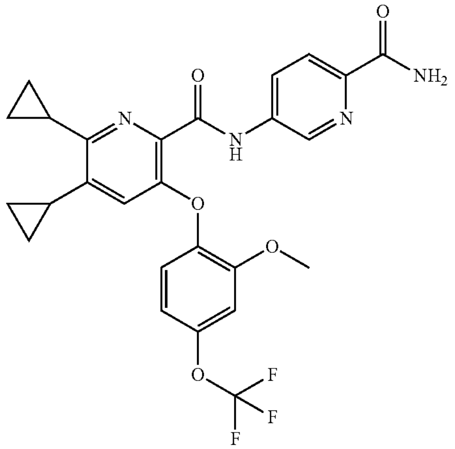 [SMILES: COc1cc(OC(F)(F)F)ccc1Oc1cc(C2CC2)c(C2CC2)nc1C(=O)Nc1ccc(C(N)=O)nc1] 205 |
TABLE A-continued
| Compound Numbers and Structures. |
|---|
| 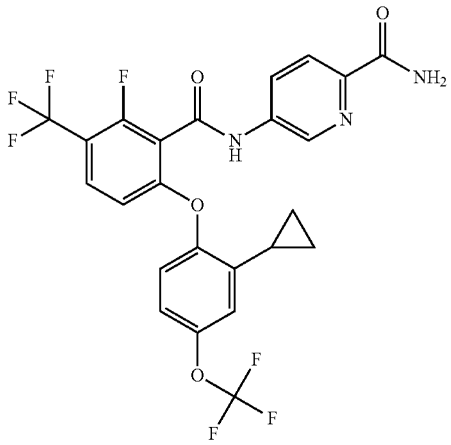 [SMILES: NC(=O)c1ccc(NC(=O)c2c(Oc3ccc(OC(F)(F)F)cc3C3CC3)ccc(C(F)(F)F)c2F)cn1] 206 |
| 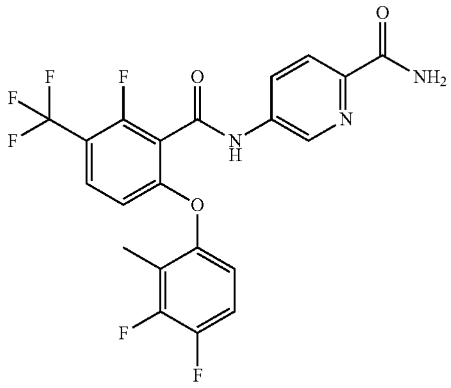 [SMILES: Cc1c(Oc2ccc(C(F)(F)F)c(F)c2C(=O)Nc2ccc(C(N)=O)nc2)ccc(F)c1F] 207 |
| 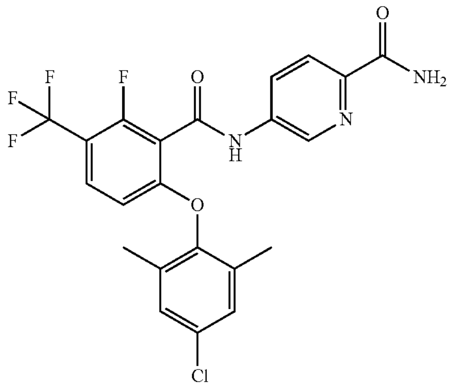 [SMILES: Cc1cc(Cl)cc(C)c1Oc1ccc(C(F)(F)F)c(F)c1C(=O)Nc1ccc(C(N)=O)nc1] 208 |

TABLE A-continued
| Compound Numbers and Structures. |
| --- |
| 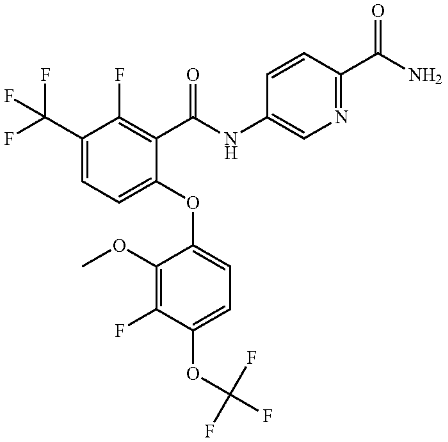 [SMILES: COc1c(Oc2ccc(C(F)(F)F)c(F)c2C(=O)Nc2ccc(C(N)=O)nc2)ccc(OC(F)(F)F)c1F] 209 |
| 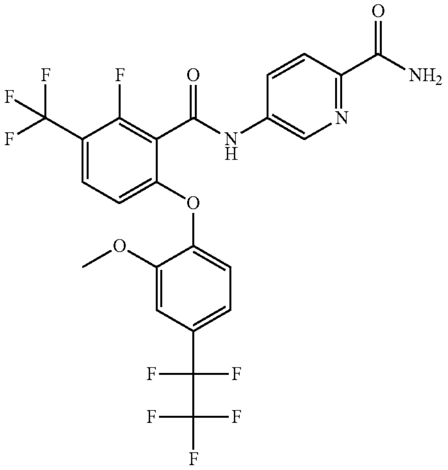 [SMILES: COc1cc(C(F)(F)C(F)(F)F)ccc1Oc1ccc(C(F)(F)F)c(F)c1C(=O)Nc1ccc(C(N)=O)nc1] 210 |
| 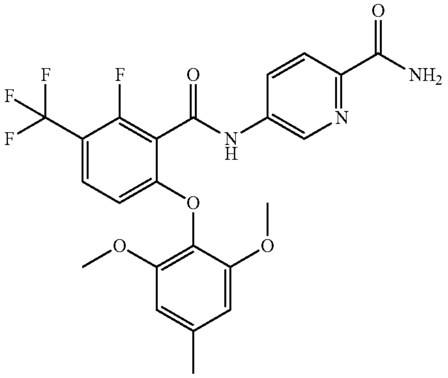 [SMILES: COc1cc(C)cc(OC)c1Oc1ccc(C(F)(F)F)c(F)c1C(=O)Nc1ccc(C(N)=O)nc1] 211 |
TABLE A-continued
| Compound Numbers and Structures. |
| --- |
| 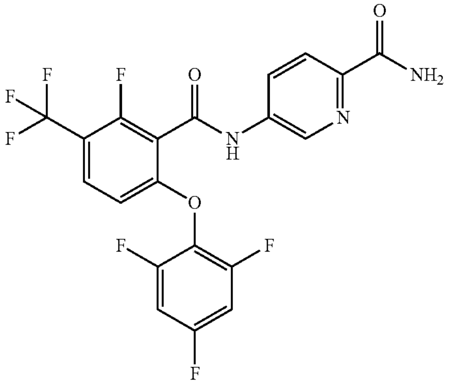 [SMILES: NC(=O)c1ccc(NC(=O)c2c(Oc3c(F)cc(F)cc3F)ccc(C(F)(F)F)c2F)cn1] 212 |
| 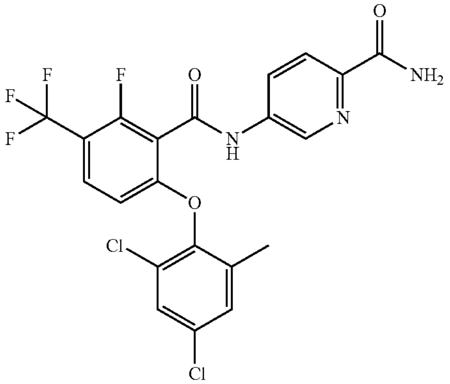 [SMILES: Cc1cc(Cl)cc(Cl)c1Oc1ccc(C(F)(F)F)c(F)c1C(=O)Nc1ccc(C(N)=O)nc1] 213 |
| 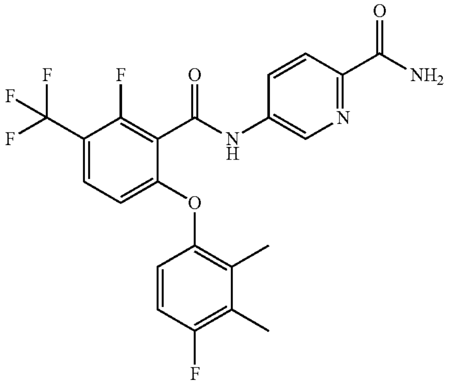 [SMILES: Cc1c(F)ccc(Oc2ccc(C(F)(F)F)c(F)c2C(=O)Nc2ccc(C(N)=O)nc2)c1C] 214 |
| 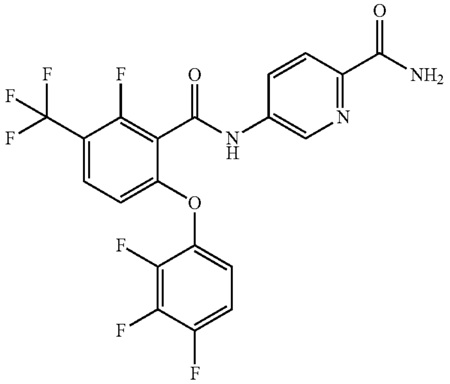 [SMILES: NC(=O)c1ccc(NC(=O)c2c(Oc3ccc(F)c(F)c3F)ccc(C(F)(F)F)c2F)cn1] 215 |

TABLE A-continued
| Compound Numbers and Structures. |
| --- |
216
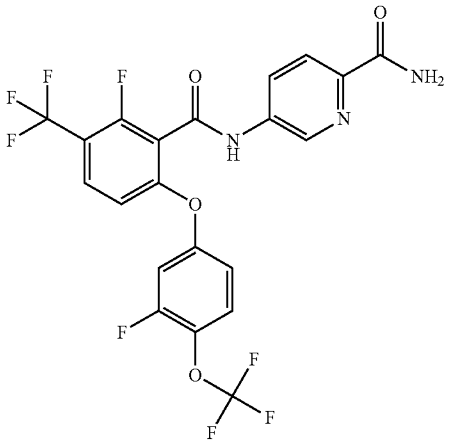 [SMILES: NC(=O)c1ccc(NC(=O)c2c(Oc3ccc(OC(F)(F)F)c(F)c3)ccc(C(F)(F)F)c2F)cn1]
217
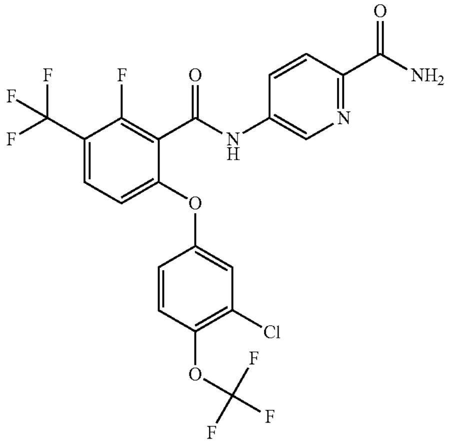 [SMILES: NC(=O)c1ccc(NC(=O)c2c(Oc3ccc(OC(F)(F)F)c(Cl)c3)ccc(C(F)(F)F)c2F)cn1]
218
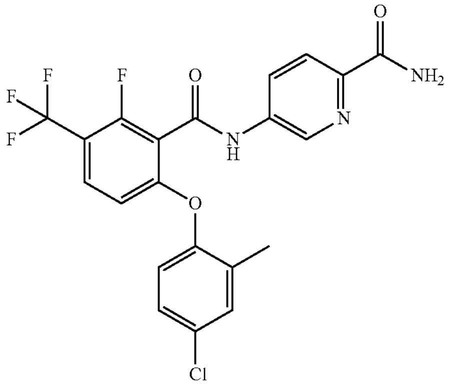 [SMILES: Cc1cc(Cl)ccc1Oc1ccc(C(F)(F)F)c(F)c1C(=O)Nc1ccc(C(N)=O)nc1]
TABLE A-continued
| Compound Numbers and Structures. |
| --- |
219
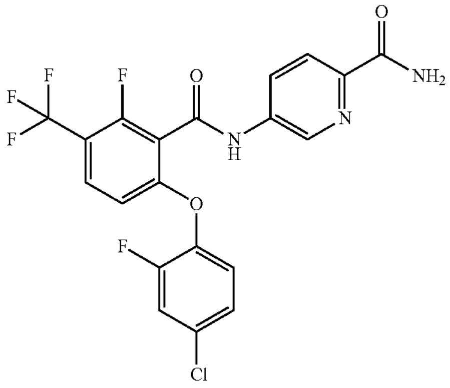 [SMILES: NC(=O)c1ccc(NC(=O)c2c(Oc3ccc(Cl)cc3F)ccc(C(F)(F)F)c2F)cn1]
220
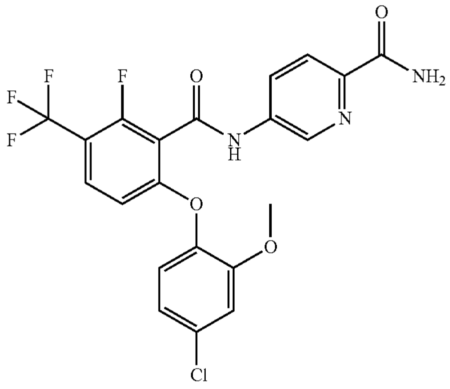 [SMILES: COc1cc(Cl)ccc1Oc1ccc(C(F)(F)F)c(F)c1C(=O)Nc1ccc(C(N)=O)nc1]
221
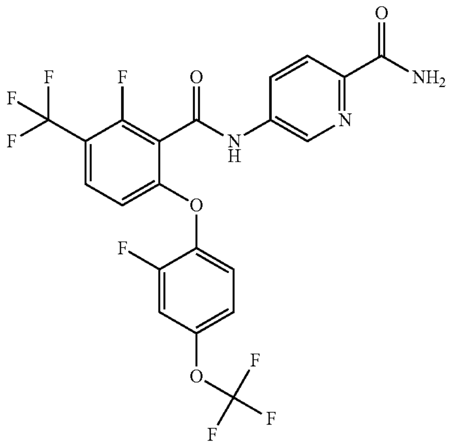 [SMILES: NC(=O)c1ccc(NC(=O)c2c(Oc3ccc(OC(F)(F)F)cc3F)ccc(C(F)(F)F)c2F)cn1]

TABLE A-continued
| Compound Numbers and Structures. |
| --- |
| 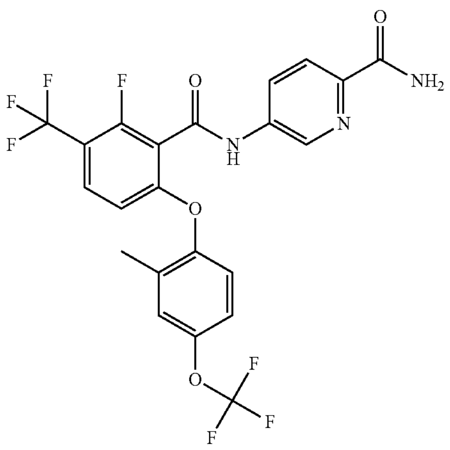 [SMILES: Cc1cc(OC(F)(F)F)ccc1Oc1ccc(C(F)(F)F)c(F)c1C(=O)Nc1ccc(C(N)=O)nc1] 222 |
| 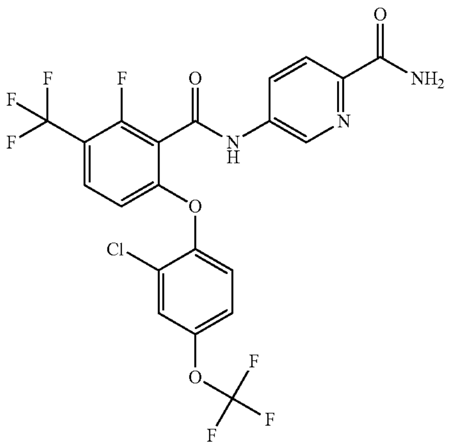 [SMILES: NC(=O)c1ccc(NC(=O)c2c(Oc3ccc(OC(F)(F)F)cc3Cl)ccc(C(F)(F)F)c2F)cn1] 223 |
| 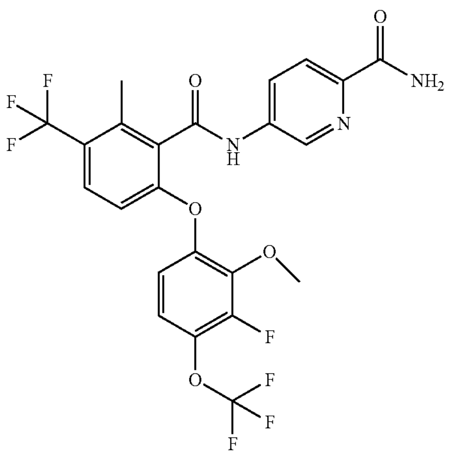 [SMILES: COc1c(Oc2ccc(C(F)(F)F)c(C)c2C(=O)Nc2ccc(C(N)=O)nc2)ccc(OC(F)(F)F)c1F] 224 |
TABLE A-continued
| Compound Numbers and Structures. |
| --- |
| 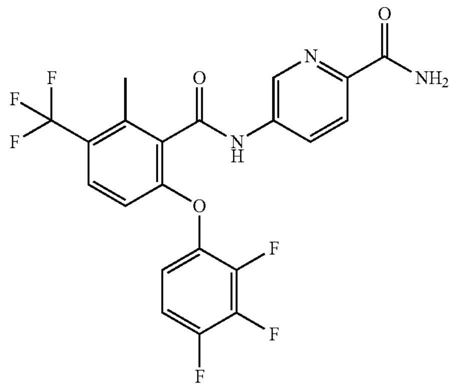 [SMILES: Cc1c(C(F)(F)F)ccc(Oc2ccc(F)c(F)c2F)c1C(=O)Nc1ccc(C(N)=O)nc1] 225 |
| 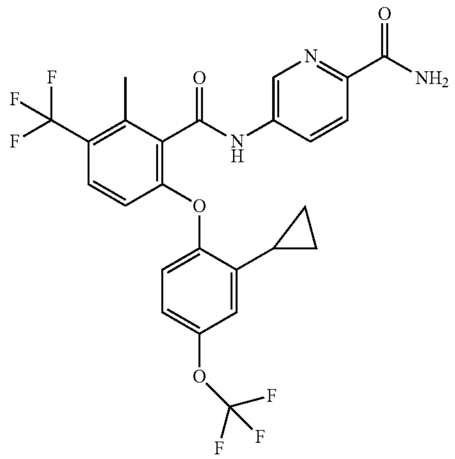 [SMILES: Cc1c(C(F)(F)F)ccc(Oc2ccc(OC(F)(F)F)cc2C2CC2)c1C(=O)Nc1ccc(C(N)=O)nc1] 226 |
| 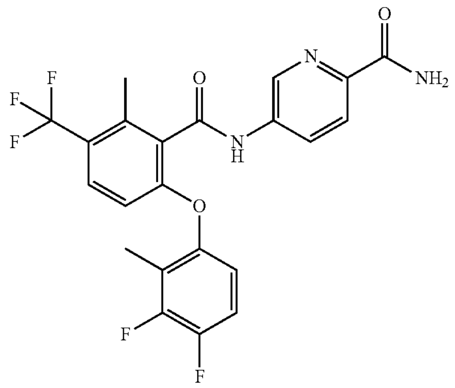 [SMILES: Cc1c(Oc2ccc(C(F)(F)F)c(C)c2C(=O)Nc2ccc(C(N)=O)nc2)ccc(F)c1F] 227 |
| 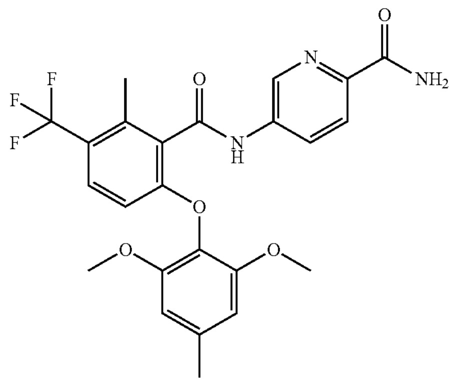 [SMILES: COc1cc(C)cc(OC)c1Oc1ccc(C(F)(F)F)c(C)c1C(=O)Nc1ccc(C(N)=O)nc1] 228 |

TABLE A-continued
| Compound Numbers and Structures. |
| --- |
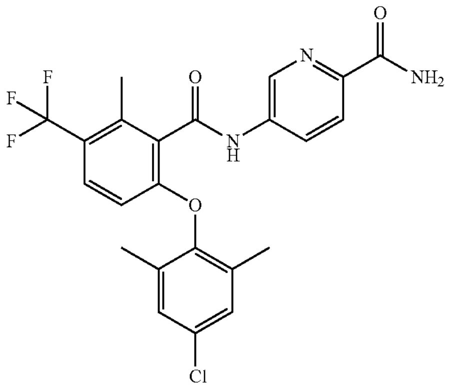 [SMILES: Cc1cc(Cl)cc(C)c1Oc1ccc(C(F)(F)F)c(C)c1C(=O)Nc1ccc(C(N)=O)nc1]
229
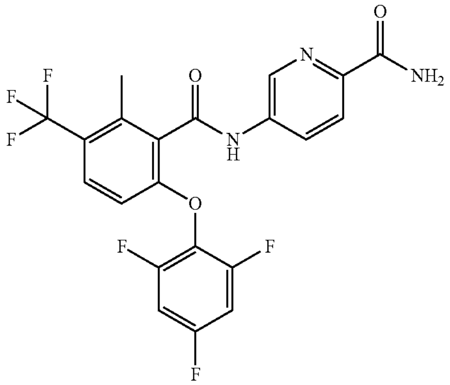 [SMILES: Cc1c(C(F)(F)F)ccc(Oc2c(F)cc(F)cc2F)c1C(=O)Nc1ccc(C(N)=O)nc1]
230
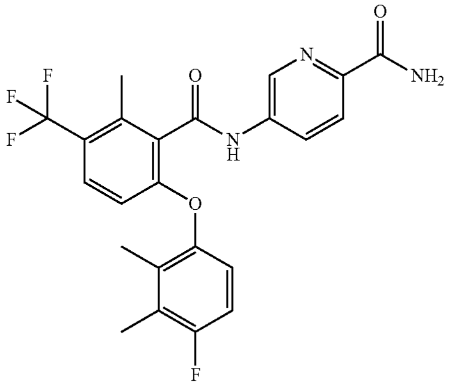 [SMILES: Cc1c(F)ccc(Oc2ccc(C(F)(F)F)c(C)c2C(=O)Nc2ccc(C(N)=O)nc2)c1C]
231
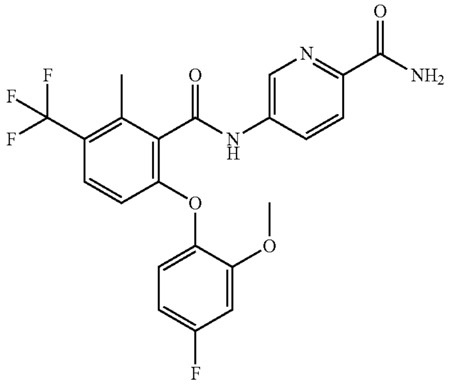 [SMILES: COc1cc(F)ccc1Oc1ccc(C(F)(F)F)c(C)c1C(=O)Nc1ccc(C(N)=O)nc1]
232
TABLE A-continued
| Compound Numbers and Structures. |
| --- |
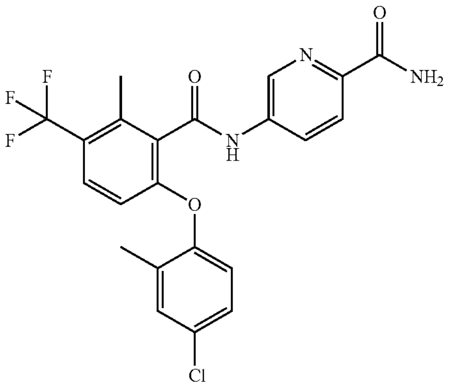 [SMILES: Cc1cc(Cl)ccc1Oc1ccc(C(F)(F)F)c(C)c1C(=O)Nc1ccc(C(N)=O)nc1]
233
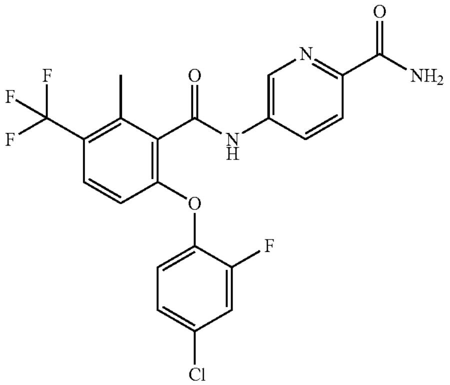 [SMILES: Cc1c(C(F)(F)F)ccc(Oc2ccc(Cl)cc2F)c1C(=O)Nc1ccc(C(N)=O)nc1]
234
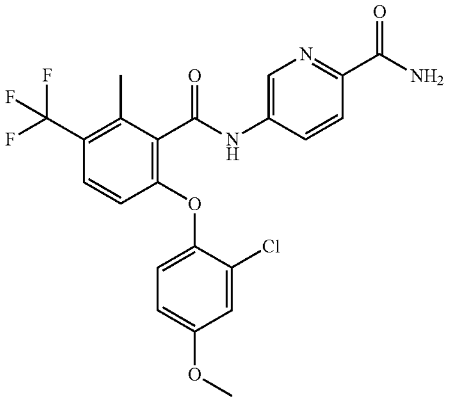 [SMILES: COc1ccc(Oc2ccc(C(F)(F)F)c(C)c2C(=O)Nc2ccc(C(N)=O)nc2)c(Cl)c1]
235

TABLE A-continued
| Compound Numbers and Structures. |
| --- |
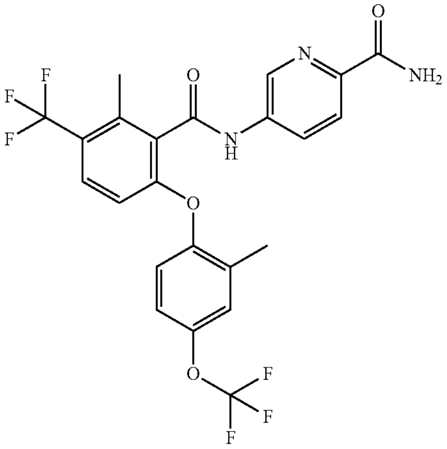 [SMILES: Cc1cc(OC(F)(F)F)ccc1Oc1ccc(C(F)(F)F)c(C)c1C(=O)Nc1ccc(C(N)=O)nc1]
236
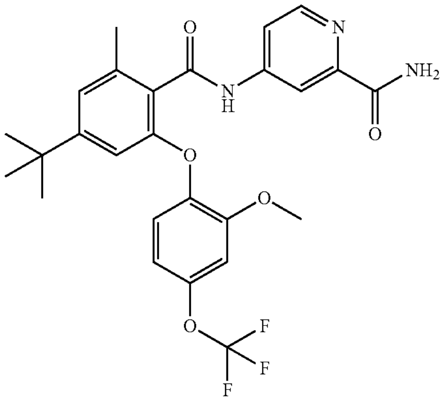 [SMILES: COc1cc(OC(F)(F)F)ccc1Oc1cc(C(C)(C)C)cc(C)c1C(=O)Nc1ccnc(C(N)=O)c1]
237
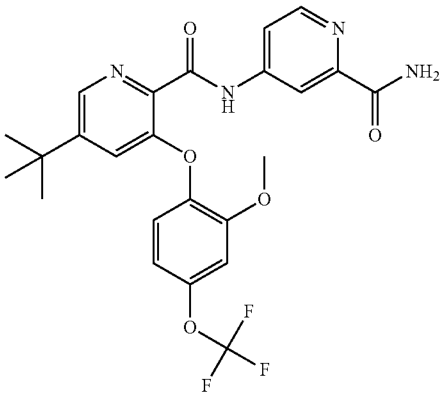 [SMILES: COc1cc(OC(F)(F)F)ccc1Oc1cc(C(C)(C)C)cnc1C(=O)Nc1ccnc(C(N)=O)c1]
238
TABLE A-continued
| Compound Numbers and Structures. |
| --- |
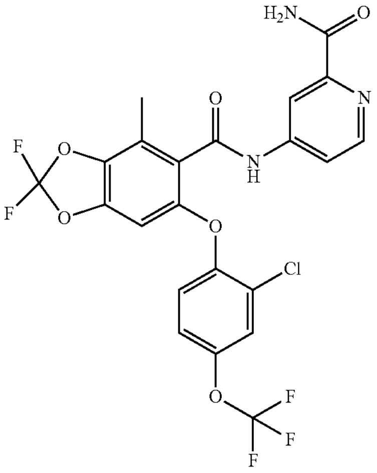 [SMILES: Cc1c2c(cc(Oc3ccc(OC(F)(F)F)cc3Cl)c1C(=O)Nc1ccnc(C(N)=O)c1)OC(F)(F)O2]
239
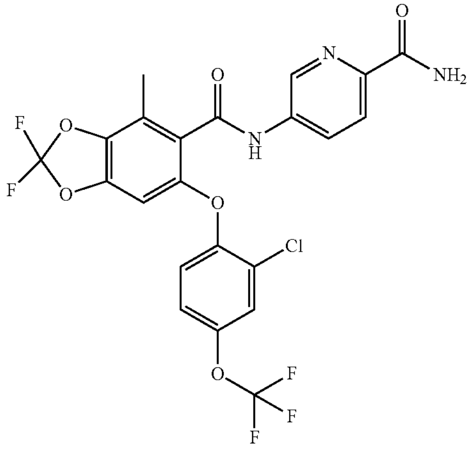 [SMILES: Cc1c2c(cc(Oc3ccc(OC(F)(F)F)cc3Cl)c1C(=O)Nc1ccc(C(N)=O)nc1)OC(F)(F)O2]
240
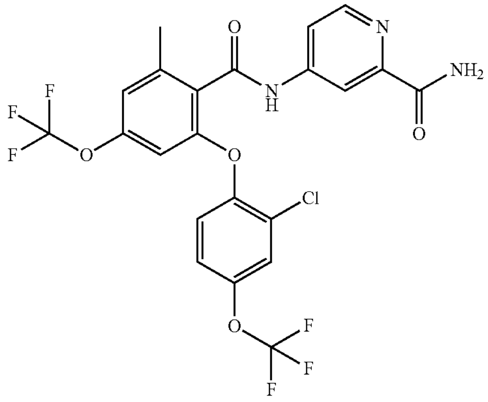 [SMILES: Cc1cc(OC(F)(F)F)cc(Oc2ccc(OC(F)(F)F)cc2Cl)c1C(=O)Nc1ccnc(C(N)=O)c1]
241

TABLE A-continued
| Compound Numbers and Structures. | |
|---|---|
| 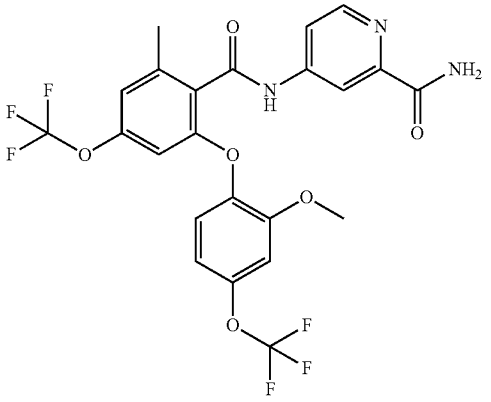 [SMILES: COc1cc(OC(F)(F)F)ccc1Oc1cc(OC(F)(F)F)cc(C)c1C(=O)Nc1ccnc(C(N)=O)c1] | 242 |
| 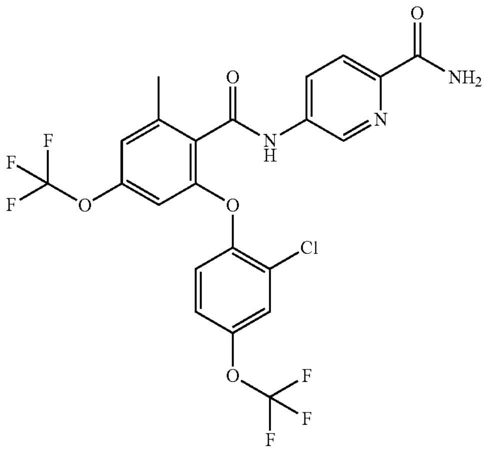 [SMILES: Cc1cc(OC(F)(F)F)cc(Oc2ccc(OC(F)(F)F)cc2Cl)c1C(=O)Nc1ccc(C(N)=O)nc1] | 243 |
| 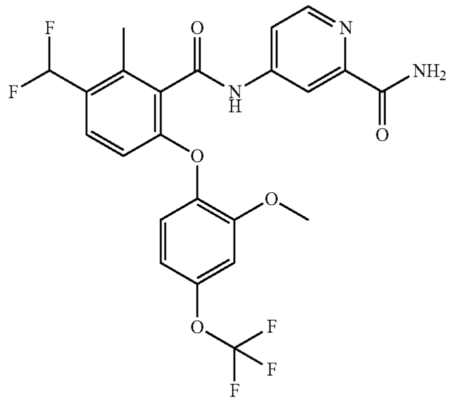 [SMILES: COc1cc(OC(F)(F)F)ccc1Oc1ccc(C(F)F)c(C)c1C(=O)Nc1ccnc(C(N)=O)c1] | 244 |
TABLE A-continued
| Compound Numbers and Structures. | |
|---|---|
| 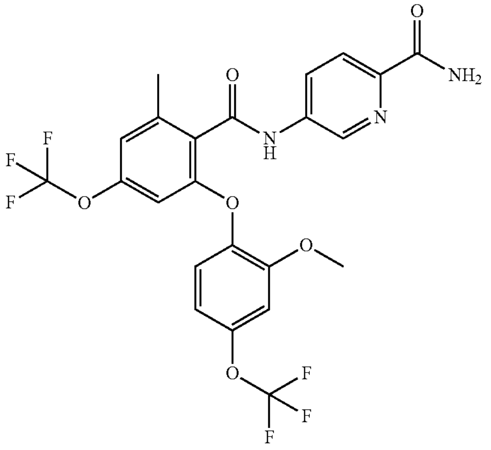 [SMILES: COc1cc(OC(F)(F)F)ccc1Oc1cc(OC(F)(F)F)cc(C)c1C(=O)Nc1ccc(C(N)=O)nc1] | 245 |
| 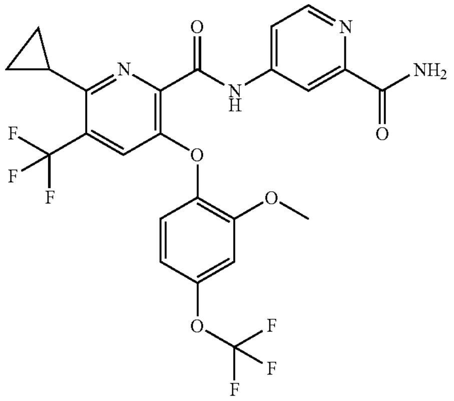 [SMILES: COc1cc(OC(F)(F)F)ccc1Oc1cc(C(F)(F)F)c(C2CC2)nc1C(=O)Nc1ccnc(C(N)=O)c1] | 246 |
| 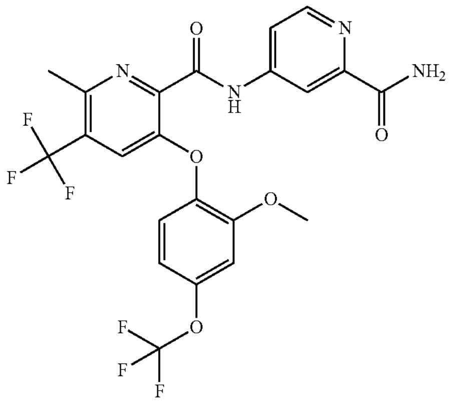 [SMILES: COc1cc(OC(F)(F)F)ccc1Oc1cc(C(F)(F)F)c(C)nc1C(=O)Nc1ccnc(C(N)=O)c1] | 247 |

TABLE A-continued
Compound Numbers and Structures.
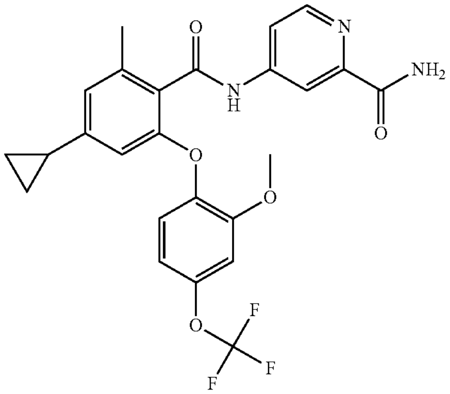 [SMILES: COc1cc(OC(F)(F)F)ccc1Oc1cc(C2CC2)cc(C)c1C(=O)Nc1ccnc(C(N)=O)c1]
248
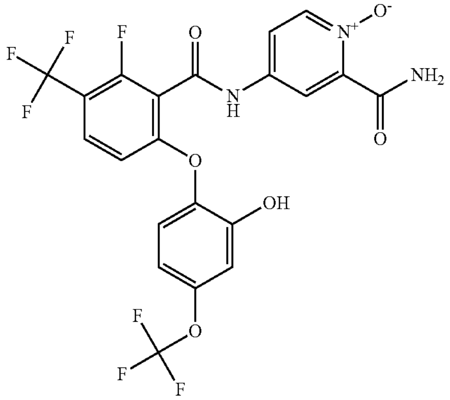 [SMILES: NC(=O)c1cc(NC(=O)c2c(Oc3ccc(OC(F)(F)F)cc3O)ccc(C(F)(F)F)c2F)cc[n+]1[O-]]
249
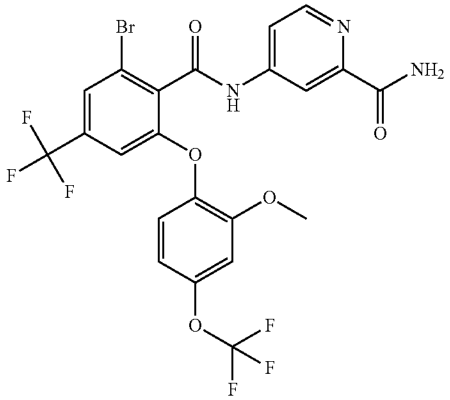 [SMILES: COc1cc(OC(F)(F)F)ccc1Oc1cc(C(F)(F)F)cc(Br)c1C(=O)Nc1ccnc(C(N)=O)c1]
255
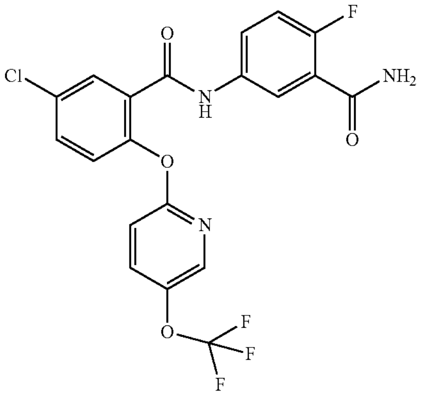 [SMILES: NC(=O)c1cc(NC(=O)c2cc(Cl)ccc2Oc2ccc(OC(F)(F)F)cn2)ccc1F]
256
TABLE A-continued
Compound Numbers and Structures.
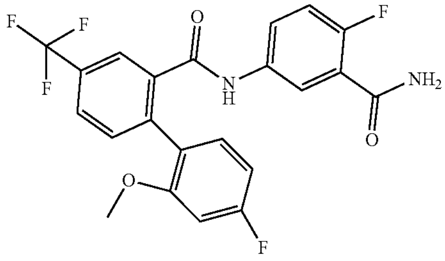 [SMILES: COc1cc(F)ccc1-c1ccc(C(F)(F)F)cc1C(=O)Nc1ccc(F)c(C(N)=O)c1]
253
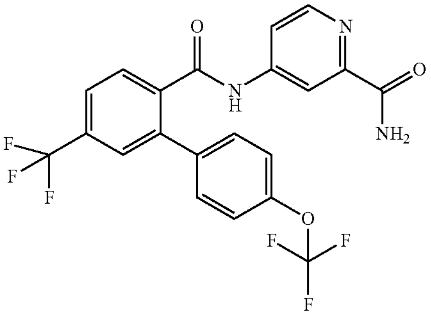 [SMILES: NC(=O)c1cc(NC(=O)c2ccc(C(F)(F)F)cc2-c2ccc(OC(F)(F)F)cc2)ccn1]
254
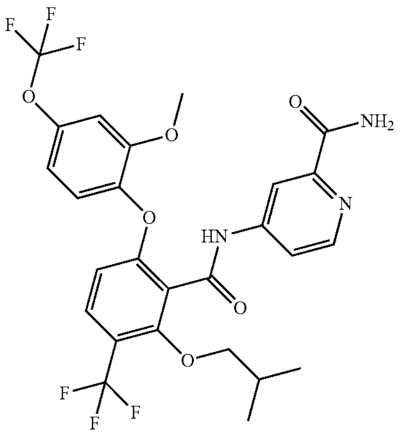 [SMILES: COc1cc(OC(F)(F)F)ccc1Oc1ccc(C(F)(F)F)c(OCC(C)C)c1C(=O)Nc1ccnc(C(N)=O)c1]
82
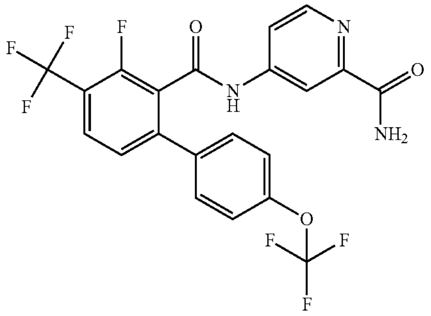 [SMILES: NC(=O)c1cc(NC(=O)c2c(-c3ccc(OC(F)(F)F)cc3)ccc(C(F)(F)F)c2F)ccn1]
250

TABLE A-continued
Compound Numbers and Structures.
252
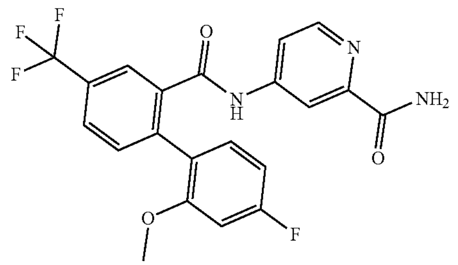 [SMILES: COc1cc(F)ccc1-c1ccc(C(F)(F)F)cc1C(=O)Nc1ccnc(C(N)=O)c1]
81
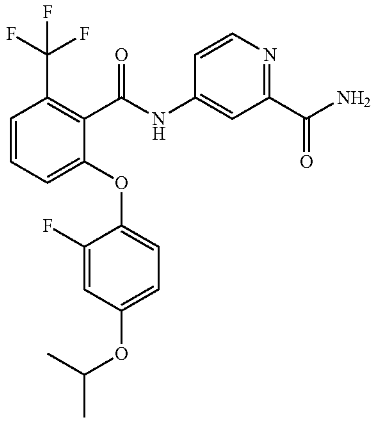 [SMILES: CC(C)Oc1ccc(Oc2cccc(C(F)(F)F)c2C(=O)Nc2ccnc(C(N)=O)c2)c(F)c1]
258
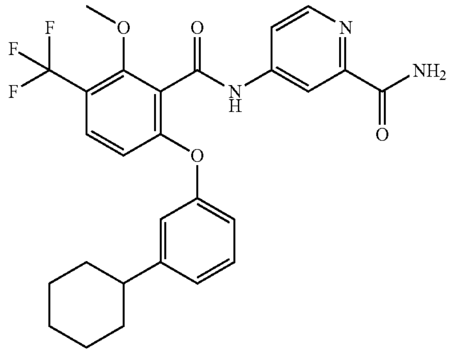 [SMILES: COc1c(C(F)(F)F)ccc(Oc2cccc(C3CCCCC3)c2)c1C(=O)Nc1ccnc(C(N)=O)c1]
108
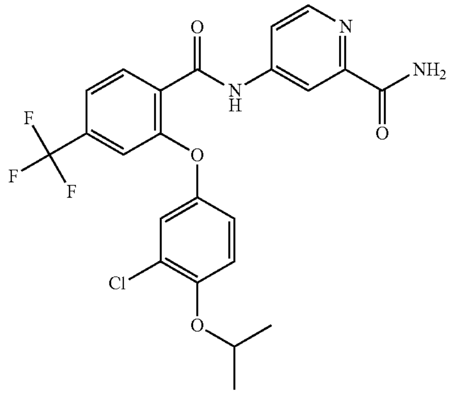 [SMILES: CC(C)Oc1ccc(Oc2cc(C(F)(F)F)ccc2C(=O)Nc2ccnc(C(N)=O)c2)cc1Cl]
TABLE A-continued
Compound Numbers and Structures.
110
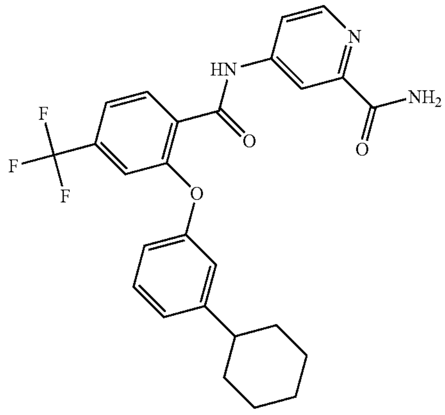 [SMILES: NC(=O)c1cc(NC(=O)c2ccc(C(F)(F)F)cc2Oc2cccc(C3CCCCC3)c2)ccn1]
111
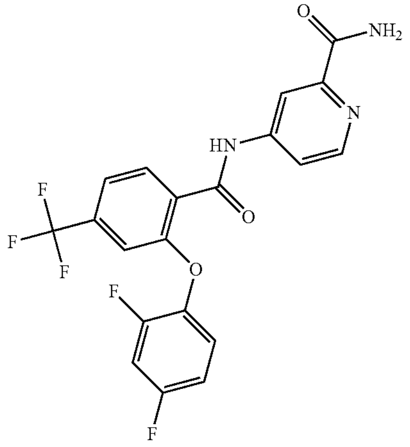 [SMILES: NC(=O)c1cc(NC(=O)c2ccc(C(F)(F)F)cc2Oc2ccc(F)cc2F)ccn1]
251
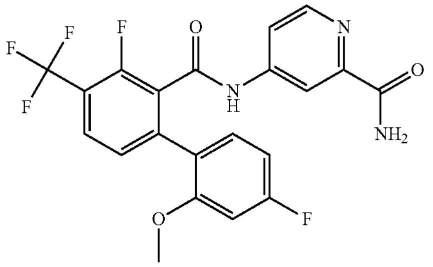 [SMILES: COc1cc(F)ccc1-c1ccc(C(F)(F)F)c(F)c1C(=O)Nc1ccnc(C(N)=O)c1]
112
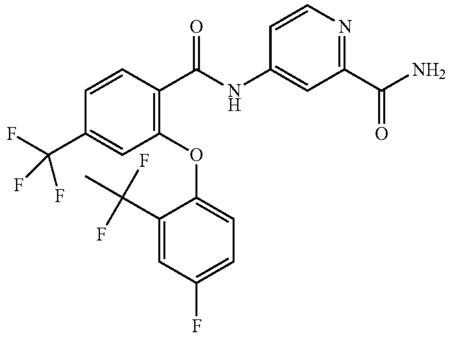 [SMILES: CC(F)(F)c1cc(F)ccc1Oc1cc(C(F)(F)F)ccc1C(=O)Nc1ccnc(C(N)=O)c1]

TABLE A-continued
Compound Numbers and Structures.
13
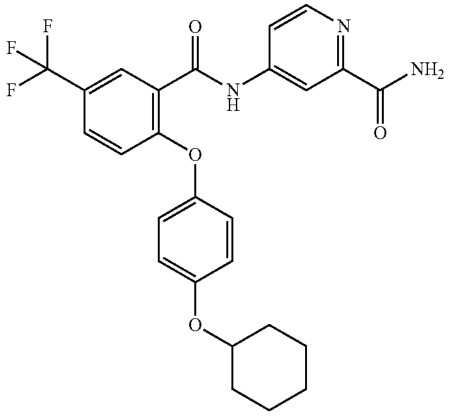 [SMILES: NC(=O)c1cc(NC(=O)c2cc(C(F)(F)F)ccc2Oc2ccc(OC3CCCCC3)cc2)ccn1]
14
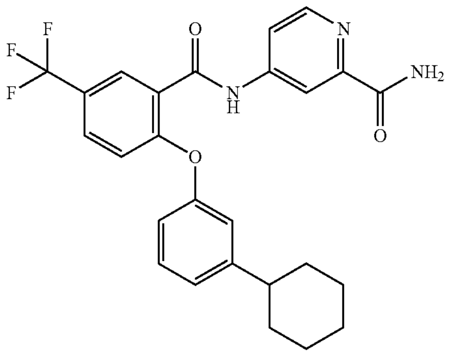 [SMILES: NC(=O)c1cc(NC(=O)c2cc(C(F)(F)F)ccc2Oc2cccc(C3CCCCC3)c2)ccn1]
15
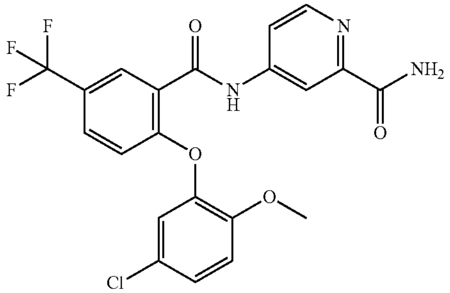 [SMILES: COc1ccc(Cl)cc1Oc1ccc(C(F)(F)F)cc1C(=O)Nc1ccnc(C(N)=O)c1]
16
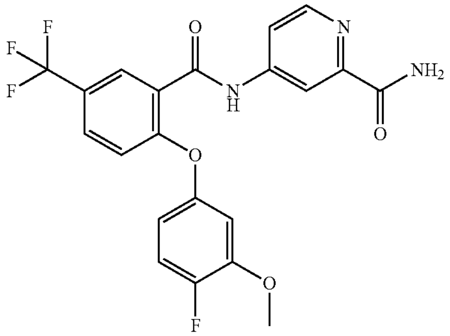 [SMILES: COc1cc(Oc2ccc(C(F)(F)F)cc2C(=O)Nc2ccnc(C(N)=O)c2)ccc1F]
17
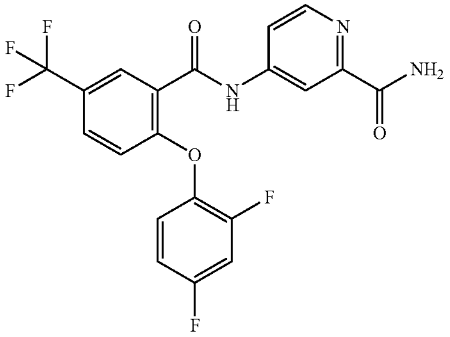
113
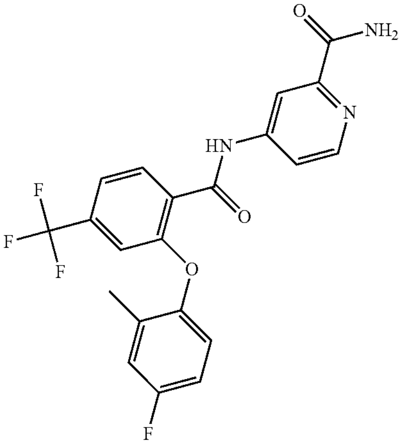 [SMILES: Cc1cc(F)ccc1Oc1cc(C(F)(F)F)ccc1C(=O)Nc1ccnc(C(N)=O)c1]
257
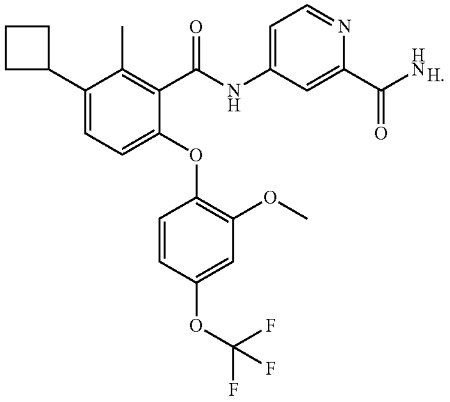
In another aspect, the invention relates to a compound selected from Table B or a pharmaceutically acceptable salt thereof. In other embodiments, the invention relates to a compound selected from Table B, i.e., the compound in non-salt form.

TABLE B
| Compound Numbers and Structures. |
|---|
| 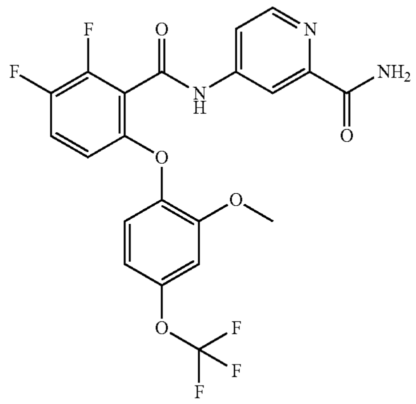 [SMILES: COc1cc(OC(F)(F)F)ccc1Oc1ccc(F)c(F)c1C(=O)Nc1ccnc(C(N)=O)c1] 259 |
| 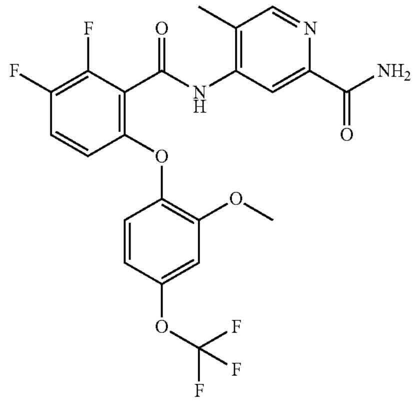 [SMILES: COc1cc(OC(F)(F)F)ccc1Oc1ccc(F)c(F)c1C(=O)Nc1cc(C(N)=O)ncc1C] 260 |
| 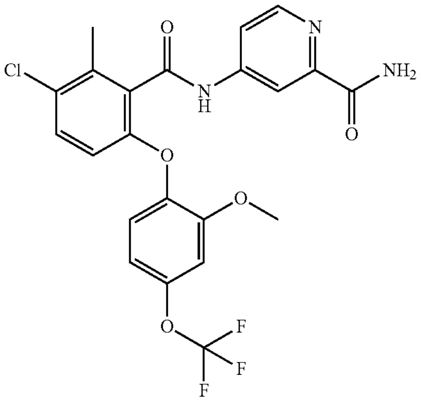 [SMILES: COc1cc(OC(F)(F)F)ccc1Oc1ccc(Cl)c(C)c1C(=O)Nc1ccnc(C(N)=O)c1] 261 |
TABLE B-continued
| Compound Numbers and Structures. |
|---|
| 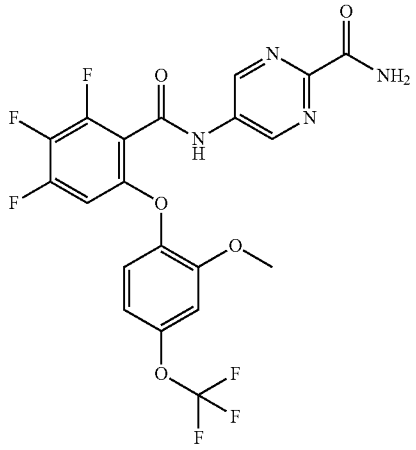 [SMILES: COc1cc(OC(F)(F)F)ccc1Oc1cc(F)c(F)c(F)c1C(=O)Nc1cnc(C(N)=O)nc1] 262 |
| 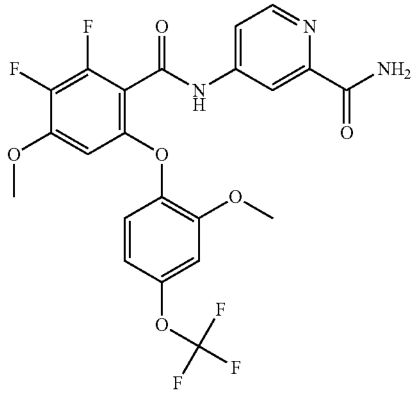 [SMILES: COc1cc(OC(F)(F)F)ccc1Oc1cc(OC)c(F)c(F)c1C(=O)Nc1ccnc(C(N)=O)c1] 263 |
| 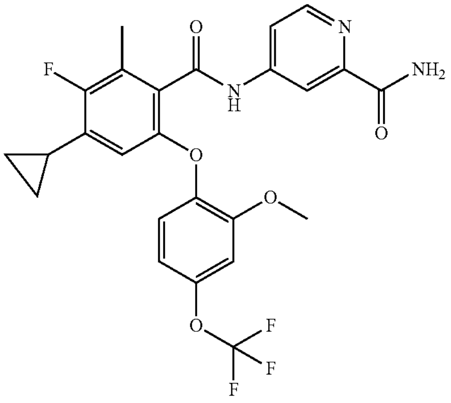 [SMILES: COc1cc(OC(F)(F)F)ccc1Oc1cc(C2CC2)c(F)c(C)c1C(=O)Nc1ccnc(C(N)=O)c1] 264 |

TABLE B-continued
Compound Numbers and Structures.
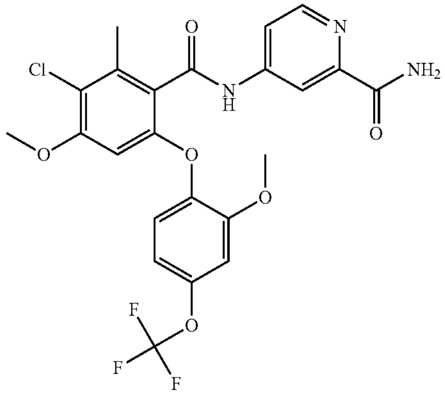 [SMILES: COc1cc(OC(F)(F)F)ccc1Oc1cc(OC)c(Cl)c(C)c1C(=O)Nc1ccnc(C(N)=O)c1]
265
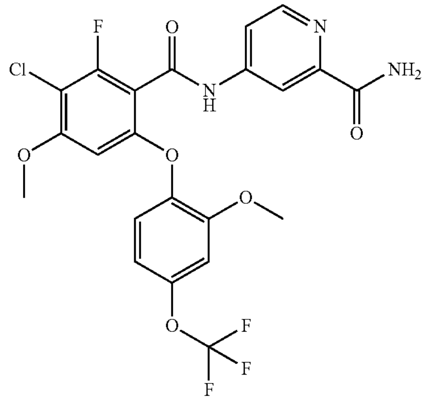 [SMILES: COc1cc(OC(F)(F)F)ccc1Oc1cc(OC)c(Cl)c(F)c1C(=O)Nc1ccnc(C(N)=O)c1]
266
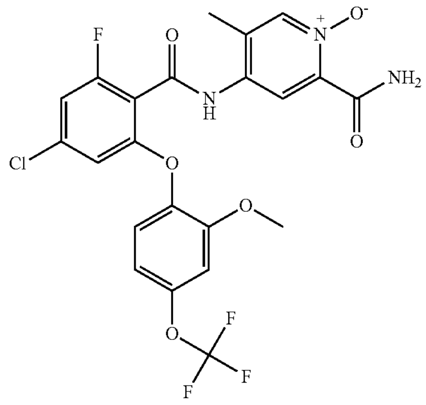
267
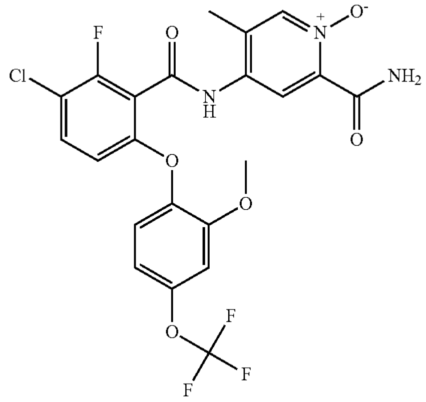
268
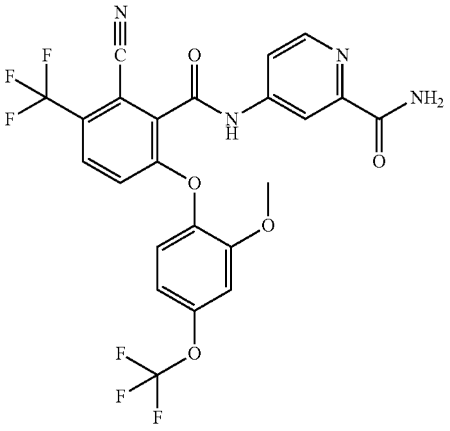 [SMILES: COc1cc(OC(F)(F)F)ccc1Oc1ccc(C(F)(F)F)c(C#N)c1C(=O)Nc1ccnc(C(N)=O)c1]
269
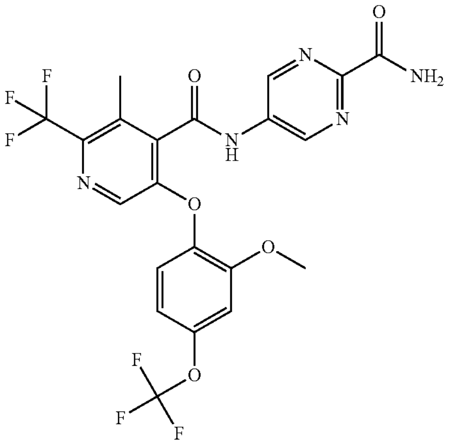 [SMILES: COc1cc(OC(F)(F)F)ccc1Oc1cnc(C(F)(F)F)c(C)c1C(=O)Nc1cnc(C(N)=O)nc1]
270
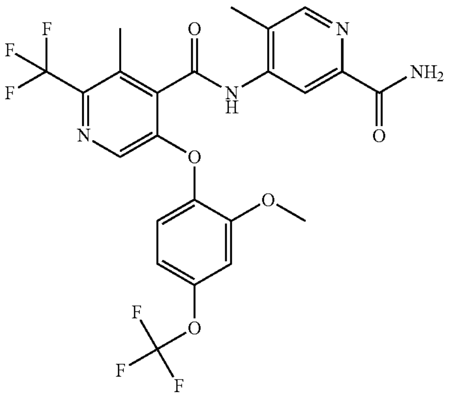 [SMILES: COc1cc(OC(F)(F)F)ccc1Oc1cnc(C(F)(F)F)c(C)c1C(=O)Nc1cc(C(N)=O)ncc1C]
271

TABLE B-continued
| Compound Numbers and Structures. |
|---|
| 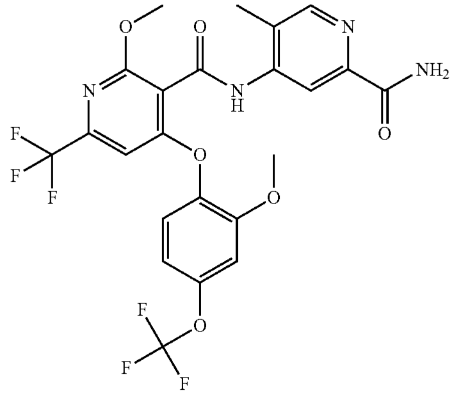 [SMILES: COc1cc(OC(F)(F)F)ccc1Oc1cc(C(F)(F)F)nc(OC)c1C(=O)Nc1cc(C(N)=O)ncc1C] 272 |
| 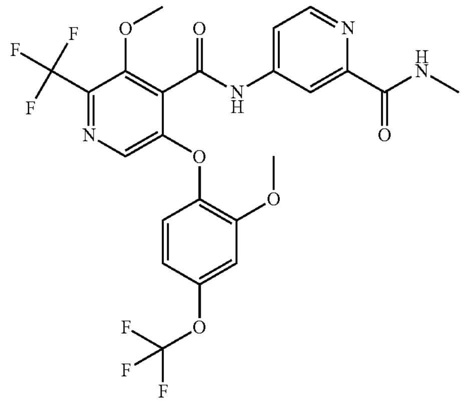 [SMILES: CNC(=O)c1cc(NC(=O)c2c(Oc3ccc(OC(F)(F)F)cc3OC)cnc(C(F)(F)F)c2OC)ccn1] 273 |
| 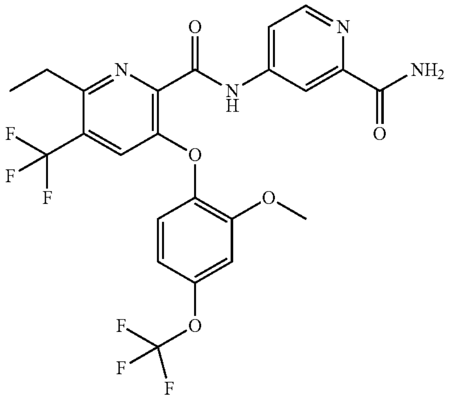 [SMILES: CCc1nc(C(=O)Nc2ccnc(C(N)=O)c2)c(Oc2ccc(OC(F)(F)F)cc2OC)cc1C(F)(F)F] 274 |
| 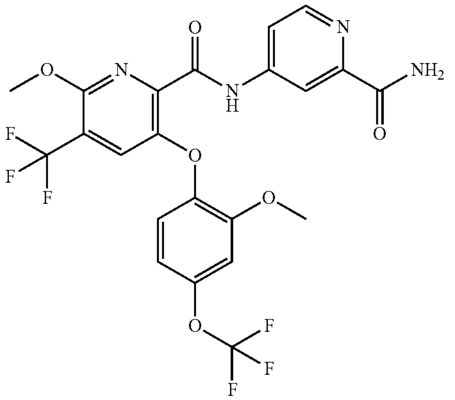 275 |
TABLE B-continued
| Compound Numbers and Structures. |
|---|
| 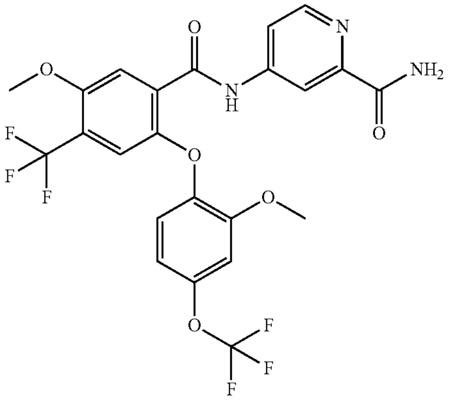 [SMILES: COc1cc(OC(F)(F)F)ccc1Oc1cc(C(F)(F)F)c(OC)cc1C(=O)Nc1ccnc(C(N)=O)c1] 276 |
| 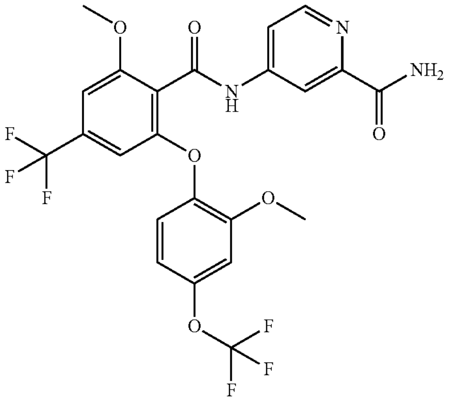 [SMILES: COc1cc(OC(F)(F)F)ccc1Oc1cc(C(F)(F)F)cc(OC)c1C(=O)Nc1ccnc(C(N)=O)c1] 277 |
| 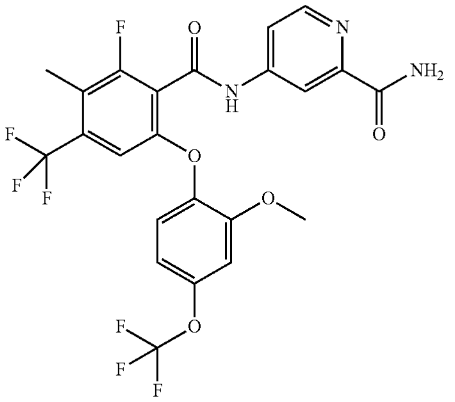 [SMILES: COc1cc(OC(F)(F)F)ccc1Oc1cc(C(F)(F)F)c(C)c(F)c1C(=O)Nc1ccnc(C(N)=O)c1] 278 |

TABLE B-continued
| Compound Numbers and Structures. |
| --- |
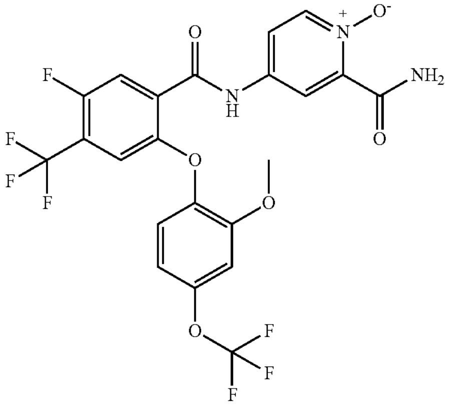
279
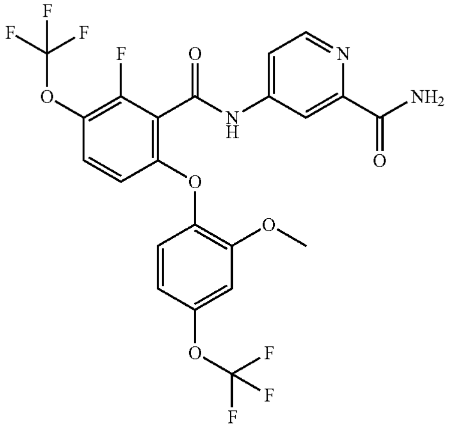 [SMILES: COc1cc(OC(F)(F)F)ccc1Oc1ccc(OC(F)(F)F)c(F)c1C(=O)Nc1ccnc(C(N)=O)c1]
280
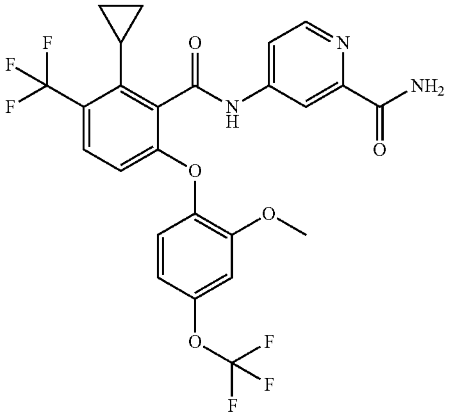 [SMILES: COc1cc(OC(F)(F)F)ccc1Oc1ccc(C(F)(F)F)c(C2CC2)c1C(=O)Nc1ccnc(C(N)=O)c1]
281
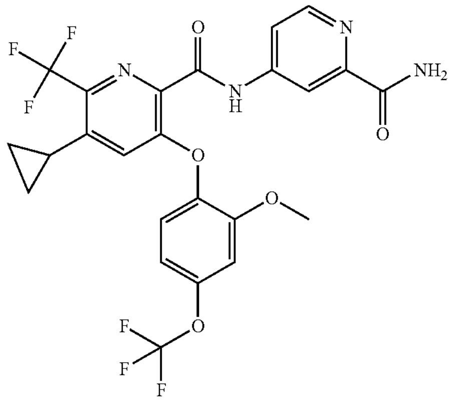 [SMILES: COc1cc(OC(F)(F)F)ccc1Oc1cc(C2CC2)c(C(F)(F)F)nc1C(=O)Nc1ccnc(C(N)=O)c1]
282
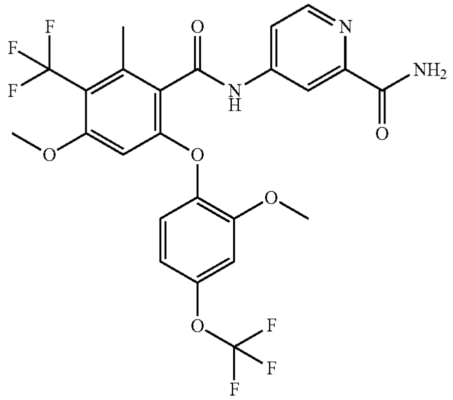 [SMILES: COc1cc(OC(F)(F)F)ccc1Oc1cc(OC)c(C(F)(F)F)c(C)c1C(=O)Nc1ccnc(C(N)=O)c1]
283
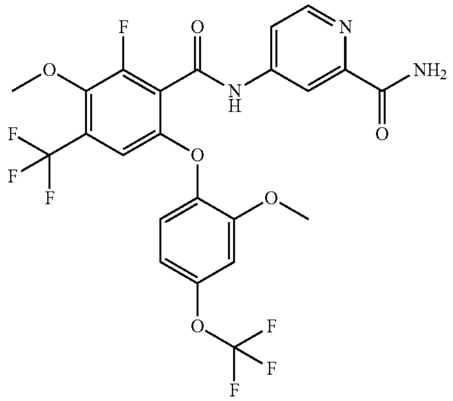 [SMILES: COc1cc(OC(F)(F)F)ccc1Oc1cc(C(F)(F)F)c(OC)c(F)c1C(=O)Nc1ccnc(C(N)=O)c1]
284
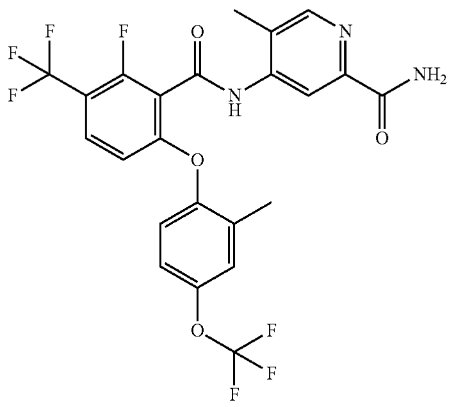 [SMILES: Cc1cnc(C(N)=O)cc1NC(=O)c1c(Oc2ccc(OC(F)(F)F)cc2C)ccc(C(F)(F)F)c1F]
285

TABLE B-continued
| Compound Numbers and Structures. |
|---|
| 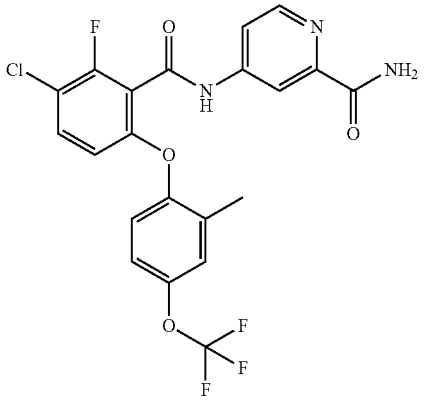 [SMILES: Cc1cc(OC(F)(F)F)ccc1Oc1ccc(Cl)c(F)c1C(=O)Nc1ccnc(C(N)=O)c1] 286 |
| 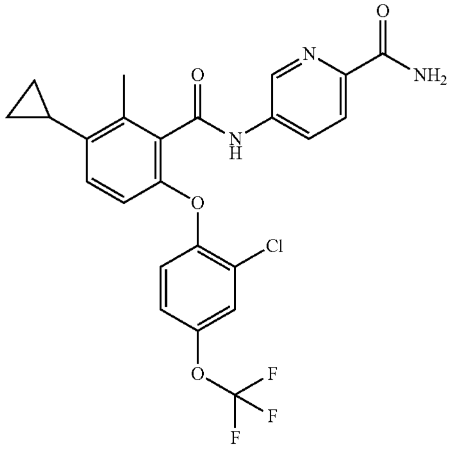 [SMILES: Cc1c(C2CC2)ccc(Oc2ccc(OC(F)(F)F)cc2Cl)c1C(=O)Nc1ccc(C(N)=O)nc1] 287 |
| 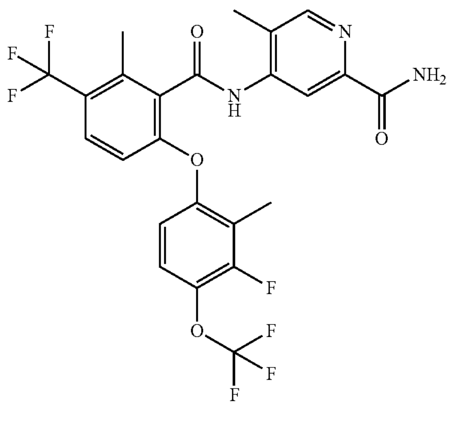 [SMILES: Cc1cnc(C(N)=O)cc1NC(=O)c1c(Oc2ccc(OC(F)(F)F)c(F)c2C)ccc(C(F)(F)F)c1C] 288 |
TABLE B-continued
| Compound Numbers and Structures. |
|---|
| 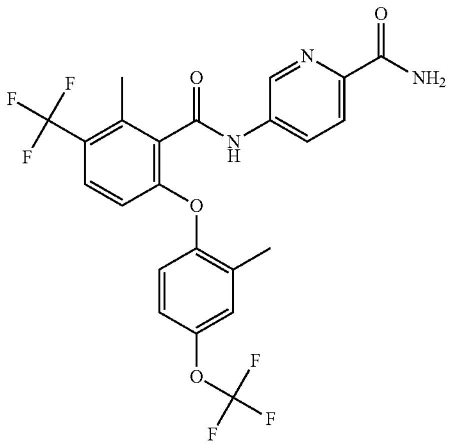 [SMILES: Cc1cc(OC(F)(F)F)ccc1Oc1ccc(C(F)(F)F)c(C)c1C(=O)Nc1ccc(C(N)=O)nc1] 289 |
| 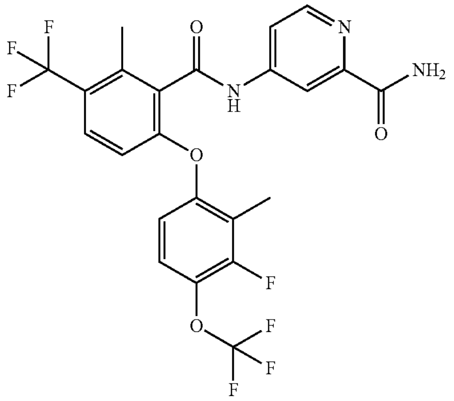 [SMILES: Cc1c(Oc2ccc(C(F)(F)F)c(C)c2C(=O)Nc2ccnc(C(N)=O)c2)ccc(OC(F)(F)F)c1F] 290 |
| 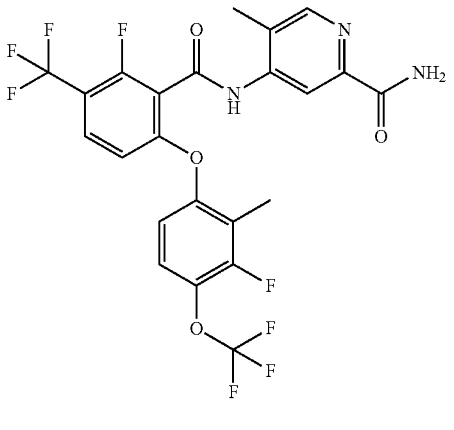 [SMILES: Cc1cnc(C(N)=O)cc1NC(=O)c1c(Oc2ccc(OC(F)(F)F)c(F)c2C)ccc(C(F)(F)F)c1F] 291 |

TABLE B-continued
| Compound Numbers and Structures. |
| --- |
| 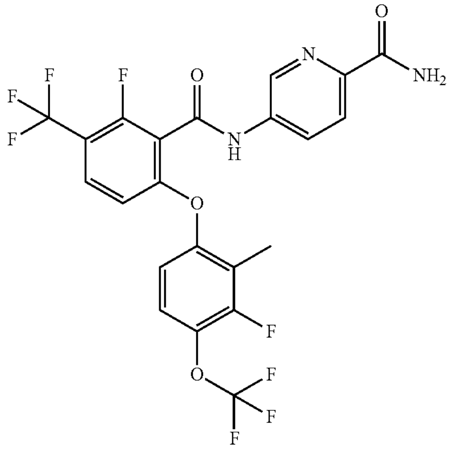 [SMILES: Cc1c(Oc2ccc(C(F)(F)F)c(F)c2C(=O)Nc2ccc(C(N)=O)nc2)ccc(OC(F)(F)F)c1F] 292 |
| 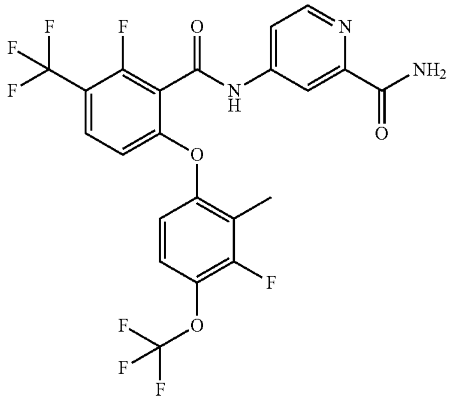 [SMILES: Cc1c(Oc2ccc(C(F)(F)F)c(F)c2C(=O)Nc2ccnc(C(N)=O)c2)ccc(OC(F)(F)F)c1F] 293 |
| 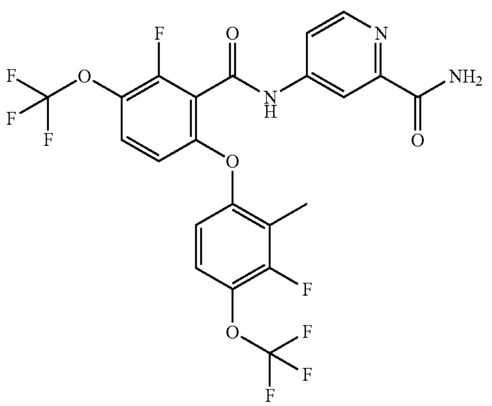 [SMILES: Cc1c(Oc2ccc(OC(F)(F)F)c(F)c2C(=O)Nc2ccnc(C(N)=O)c2)ccc(OC(F)(F)F)c1F] 294 |
TABLE B-continued
| Compound Numbers and Structures. |
| --- |
| 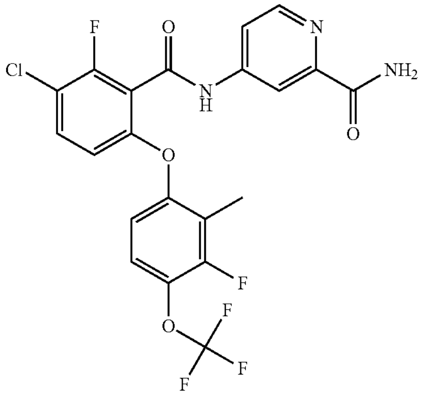 [SMILES: Cc1c(Oc2ccc(Cl)c(F)c2C(=O)Nc2ccnc(C(N)=O)c2)ccc(OC(F)(F)F)c1F] 295 |
| 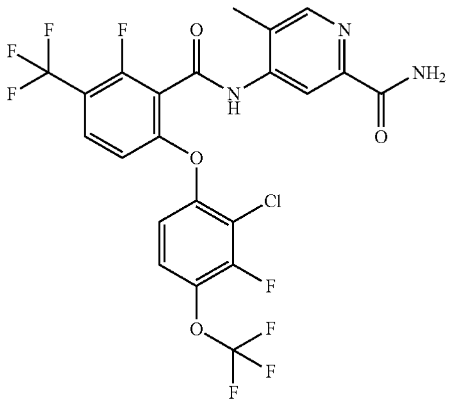 296 |
| 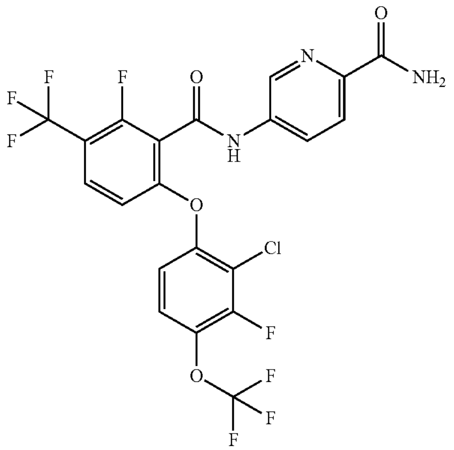 297 |

TABLE B-continued
Compound Numbers and Structures.
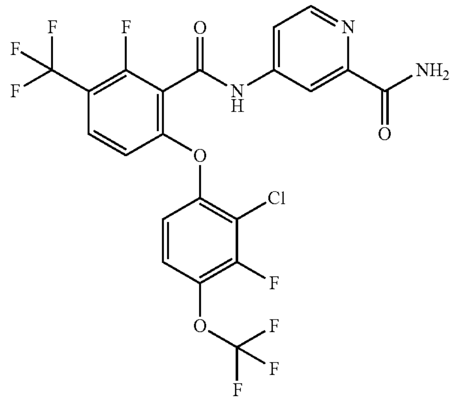 [SMILES: NC(=O)c1cc(NC(=O)c2c(Oc3ccc(OC(F)(F)F)c(F)c3Cl)ccc(C(F)(F)F)c2F)ccn1]
298
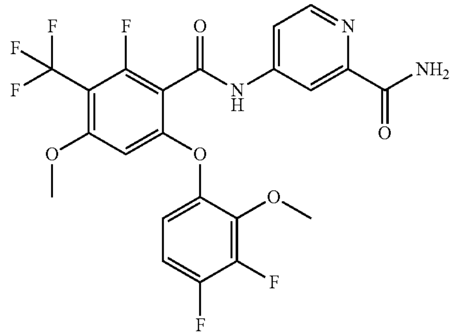 [SMILES: COc1cc(Oc2ccc(F)c(F)c2OC)c(C(=O)Nc2ccnc(C(N)=O)c2)c(F)c1C(F)(F)F]
299
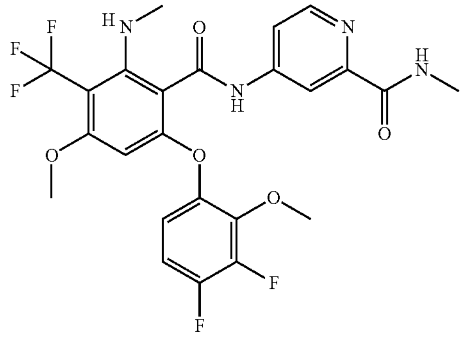
300
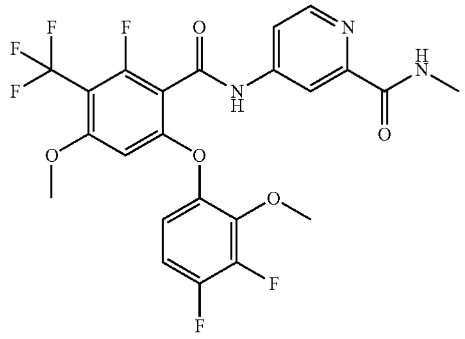 [SMILES: CNC(=O)c1cc(NC(=O)c2c(Oc3ccc(F)c(F)c3OC)cc(OC)c(C(F)(F)F)c2F)ccn1]
301
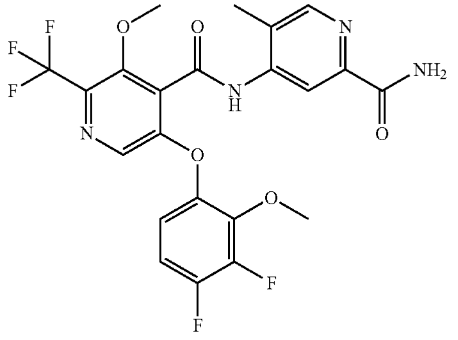 [SMILES: COc1c(Oc2cnc(C(F)(F)F)c(OC)c2C(=O)Nc2cc(C(N)=O)ncc2C)ccc(F)c1F]
302
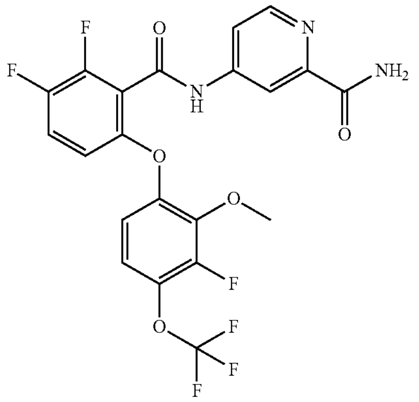 [SMILES: COc1c(Oc2ccc(F)c(F)c2C(=O)Nc2ccnc(C(N)=O)c2)ccc(OC(F)(F)F)c1F]
303
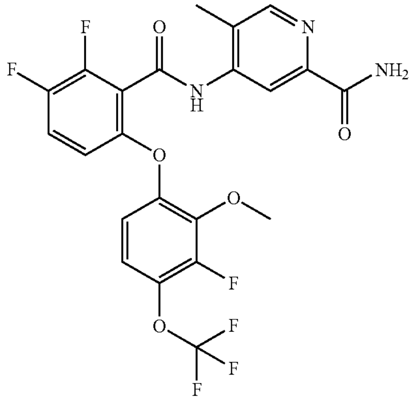 [SMILES: COc1c(Oc2ccc(F)c(F)c2C(=O)Nc2cc(C(N)=O)ncc2C)ccc(OC(F)(F)F)c1F]
304
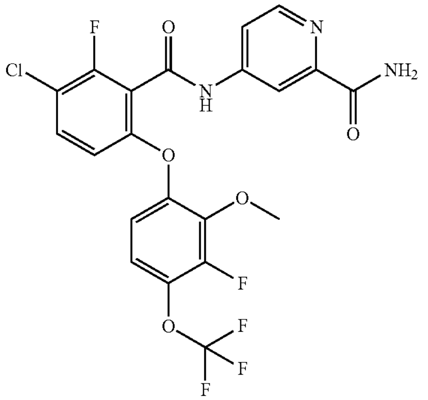 [SMILES: COc1c(Oc2ccc(Cl)c(F)c2C(=O)Nc2ccnc(C(N)=O)c2)ccc(OC(F)(F)F)c1F]
305

TABLE B-continued
| Compound Numbers and Structures. |
| --- |
| 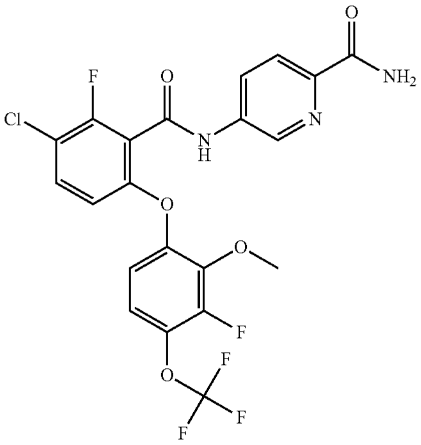 [SMILES: COc1c(Oc2ccc(Cl)c(F)c2C(=O)Nc2ccc(C(N)=O)nc2)ccc(OC(F)(F)F)c1F] 306 |
| 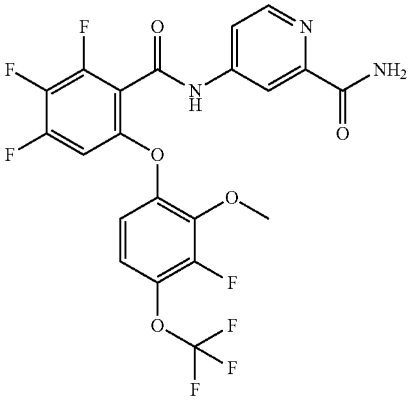 [SMILES: COc1c(Oc2cc(F)c(F)c(F)c2C(=O)Nc2ccnc(C(N)=O)c2)ccc(OC(F)(F)F)c1F] 307 |
| 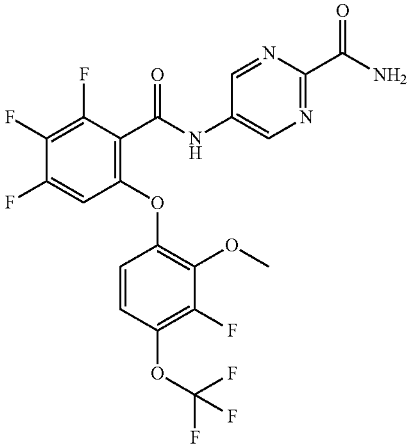 [SMILES: COc1c(Oc2cc(F)c(F)c(F)c2C(=O)Nc2cnc(C(N)=O)nc2)ccc(OC(F)(F)F)c1F] 308 |
TABLE B-continued
| Compound Numbers and Structures. |
| --- |
| 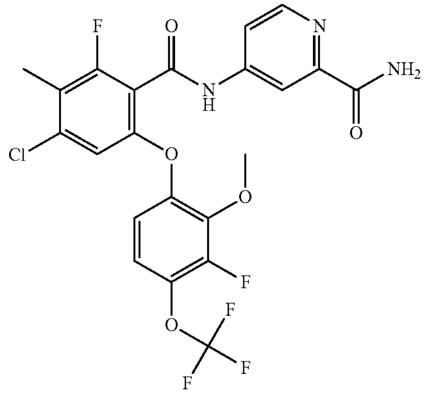 [SMILES: COc1c(Oc2cc(Cl)c(C)c(F)c2C(=O)Nc2ccnc(C(N)=O)c2)ccc(OC(F)(F)F)c1F] 309 |
| 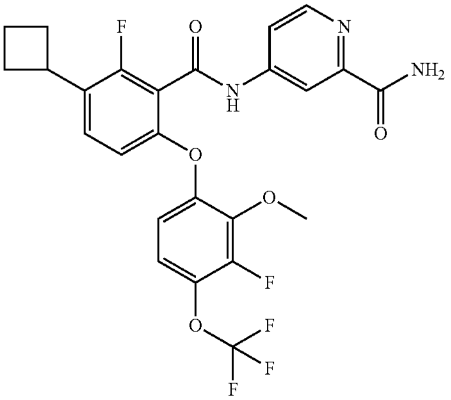 [SMILES: COc1c(Oc2ccc(C3CCC3)c(F)c2C(=O)Nc2ccnc(C(N)=O)c2)ccc(OC(F)(F)F)c1F] 310 |
| 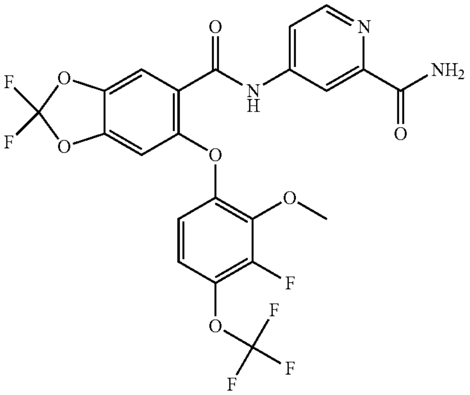 [SMILES: COc1c(Oc2cc3c(cc2C(=O)Nc2ccnc(C(N)=O)c2)OC(F)(F)O3)ccc(OC(F)(F)F)c1F] 311 |
| 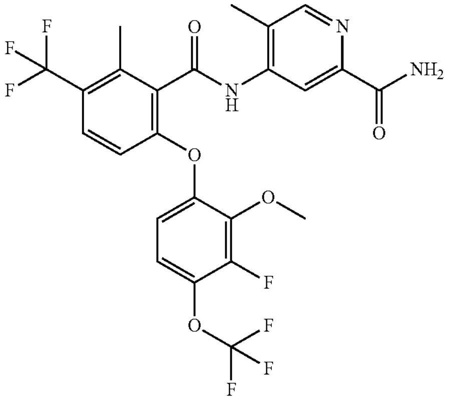 [SMILES: COc1c(Oc2ccc(C(F)(F)F)c(C)c2C(=O)Nc2cc(C(N)=O)ncc2C)ccc(OC(F)(F)F)c1F] 312 |

TABLE B-continued
| Compound Numbers and Structures. |
| --- |
| 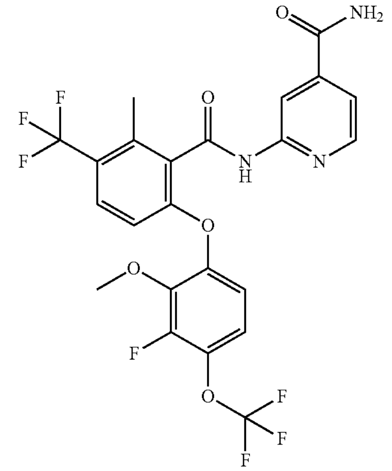 [SMILES: COc1c(Oc2ccc(C(F)(F)F)c(C)c2C(=O)Nc2cc(C(N)=O)ccn2)ccc(OC(F)(F)F)c1F] 313 |
| 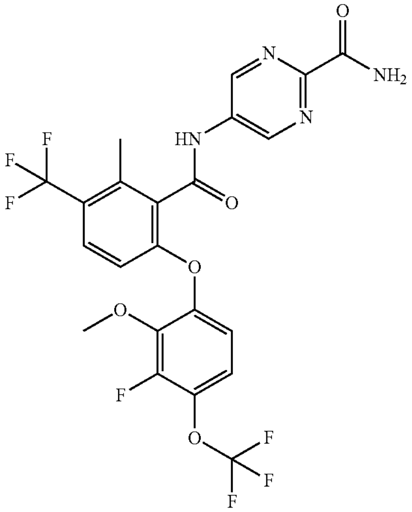 [SMILES: COc1c(Oc2ccc(C(F)(F)F)c(C)c2C(=O)Nc2cnc(C(N)=O)nc2)ccc(OC(F)(F)F)c1F] 314 |
| 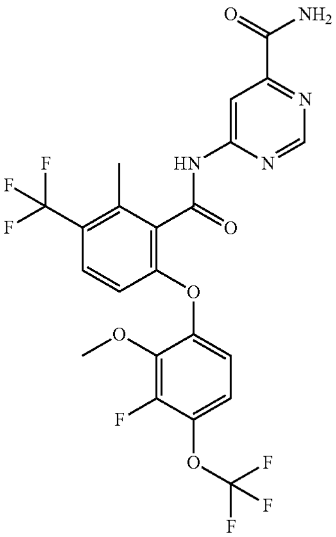 [SMILES: COc1c(Oc2ccc(C(F)(F)F)c(C)c2C(=O)Nc2cc(C(N)=O)ncn2)ccc(OC(F)(F)F)c1F] 315 |
TABLE B-continued
| Compound Numbers and Structures. |
| --- |
| 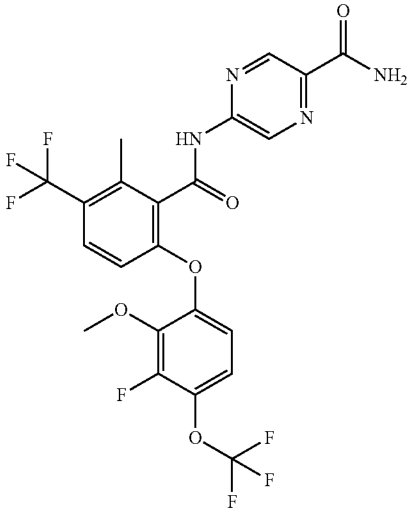 [SMILES: COc1c(Oc2ccc(C(F)(F)F)c(C)c2C(=O)Nc2cnc(C(N)=O)cn2)ccc(OC(F)(F)F)c1F] 316 |
| 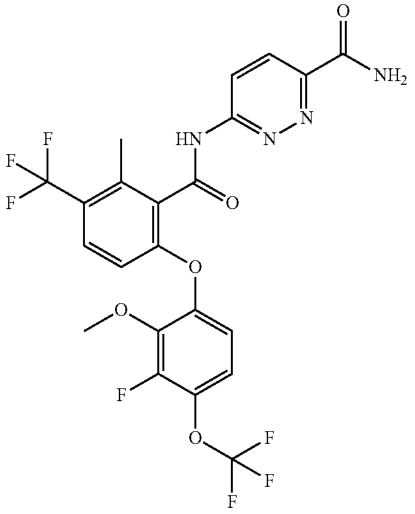 [SMILES: COc1c(Oc2ccc(C(F)(F)F)c(C)c2C(=O)Nc2ccc(C(N)=O)nn2)ccc(OC(F)(F)F)c1F] 317 |
| 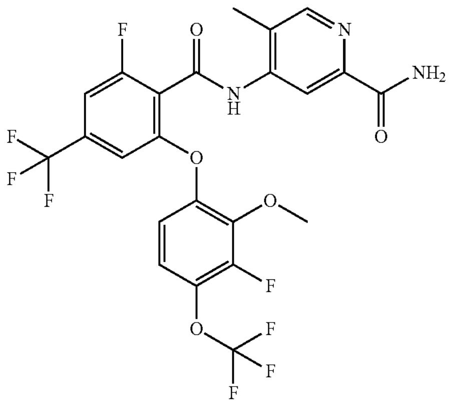 [SMILES: COc1c(Oc2cc(C(F)(F)F)cc(F)c2C(=O)Nc2cc(C(N)=O)ncc2C)ccc(OC(F)(F)F)c1F] 318 |

TABLE B-continued
Compound Numbers and Structures.
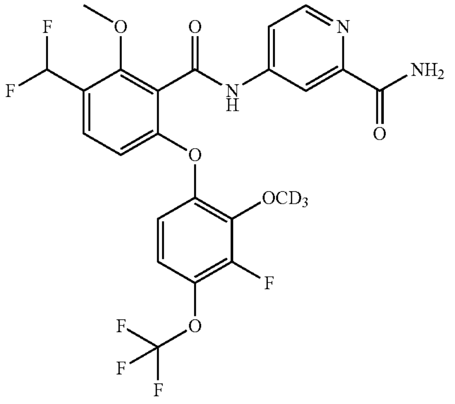
319
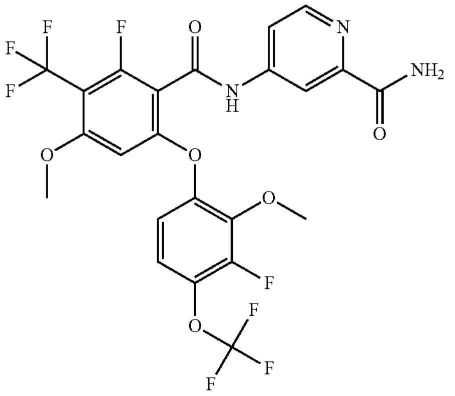 [SMILES: COc1cc(Oc2ccc(OC(F)(F)F)c(F)c2OC)c(C(=O)Nc2ccnc(C(N)=O)c2)c(F)c1C(F)(F)F]
320
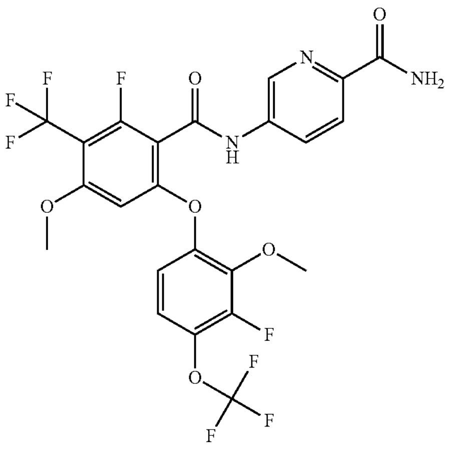 [SMILES: COc1cc(Oc2ccc(OC(F)(F)F)c(F)c2OC)c(C(=O)Nc2ccc(C(N)=O)nc2)c(F)c1C(F)(F)F]
321
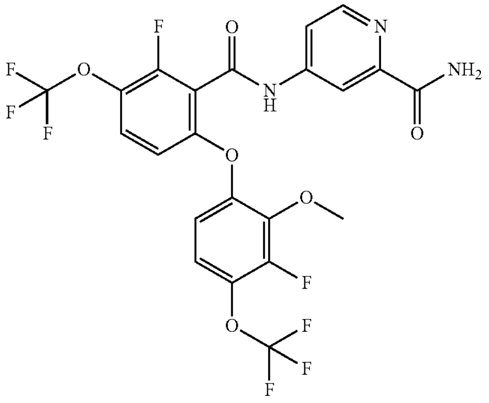 [SMILES: COc1c(Oc2ccc(OC(F)(F)F)c(F)c2C(=O)Nc2ccnc(C(N)=O)c2)ccc(OC(F)(F)F)c1F]
322
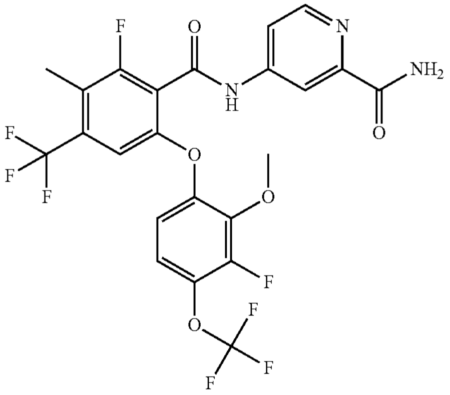 [SMILES: COc1c(Oc2cc(C(F)(F)F)c(C)c(F)c2C(=O)Nc2ccnc(C(N)=O)c2)ccc(OC(F)(F)F)c1F]
323
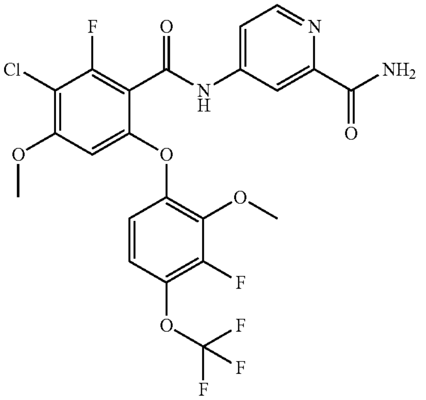 [SMILES: COc1cc(Oc2ccc(OC(F)(F)F)c(F)c2OC)c(C(=O)Nc2ccnc(C(N)=O)c2)c(F)c1Cl]
324
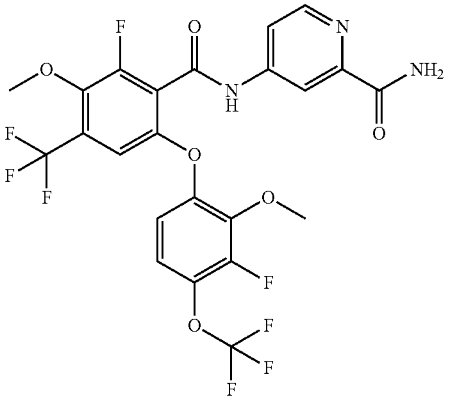 [SMILES: COc1c(Oc2cc(C(F)(F)F)c(OC)c(F)c2C(=O)Nc2ccnc(C(N)=O)c2)ccc(OC(F)(F)F)c1F]
325

TABLE B-continued
| Compound Numbers and Structures. |
|---|
| 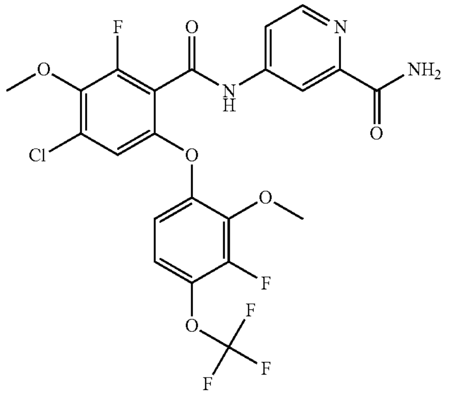 [SMILES: COc1c(Cl)cc(Oc2ccc(OC(F)(F)F)c(F)c2OC)c(C(=O)Nc2ccnc(C(N)=O)c2)c1F] 326 |
| 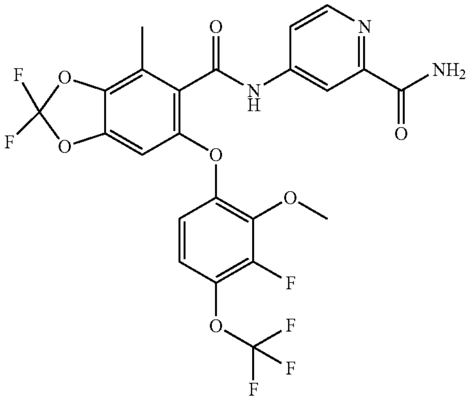 [SMILES: COc1c(Oc2cc3c(c(C)c2C(=O)Nc2ccnc(C(N)=O)c2)OC(F)(F)O3)ccc(OC(F)(F)F)c1F] 327 |
| 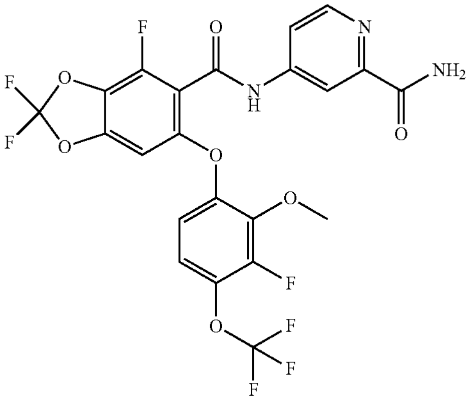 [SMILES: COc1c(Oc2cc3c(c(F)c2C(=O)Nc2ccnc(C(N)=O)c2)OC(F)(F)O3)ccc(OC(F)(F)F)c1F] 328 |
TABLE B-continued
| Compound Numbers and Structures. |
|---|
| 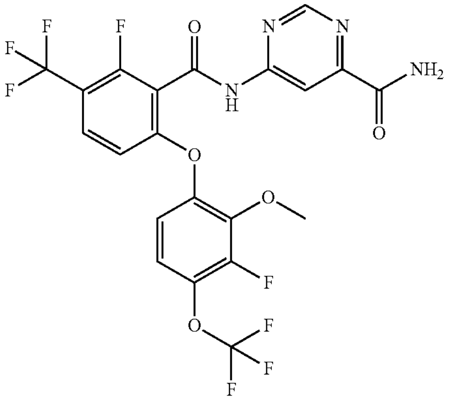 [SMILES: COc1c(Oc2ccc(C(F)(F)F)c(F)c2C(=O)Nc2cc(C(N)=O)ncn2)ccc(OC(F)(F)F)c1F] 329 |
| 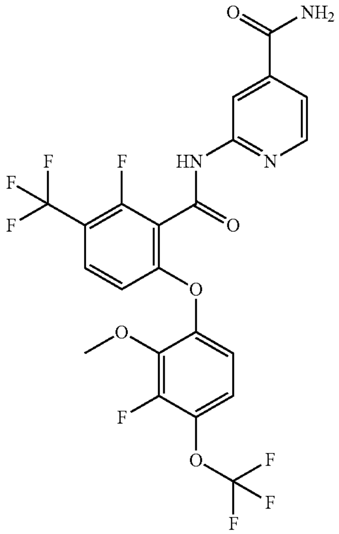 [SMILES: COc1c(Oc2ccc(C(F)(F)F)c(F)c2C(=O)Nc2cc(C(N)=O)ccn2)ccc(OC(F)(F)F)c1F] 330 |
| 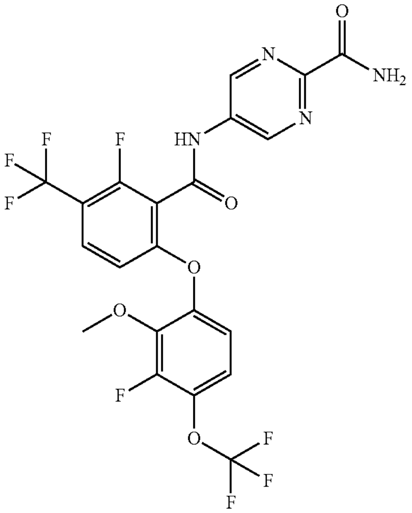 [SMILES: COc1c(Oc2ccc(C(F)(F)F)c(F)c2C(=O)Nc2cnc(C(N)=O)nc2)ccc(OC(F)(F)F)c1F] 331 |

TABLE B-continued
| Compound Numbers and Structures. |
|---|
| 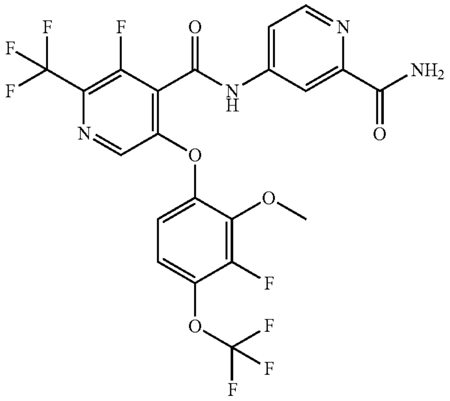 [SMILES: COc1c(Oc2cnc(C(F)(F)F)c(F)c2C(=O)Nc2ccnc(C(N)=O)c2)ccc(OC(F)(F)F)c1F] 332 |
| 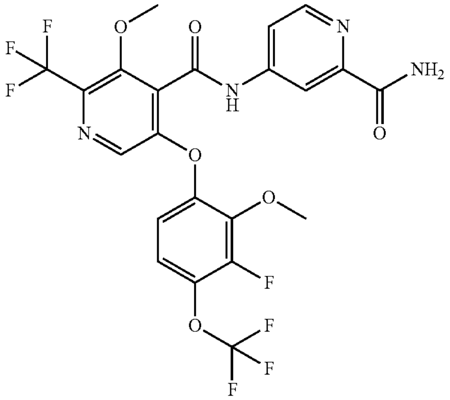 [SMILES: COc1c(Oc2cnc(C(F)(F)F)c(OC)c2C(=O)Nc2ccnc(C(N)=O)c2)ccc(OC(F)(F)F)c1F] 333 |
| 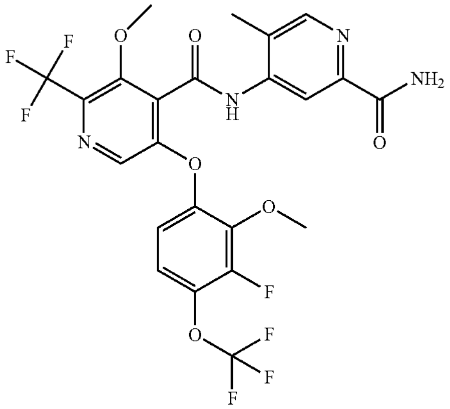 [SMILES: COc1c(Oc2cnc(C(F)(F)F)c(OC)c2C(=O)Nc2cc(C(N)=O)ncc2C)ccc(OC(F)(F)F)c1F] 334 |
TABLE B-continued
| Compound Numbers and Structures. |
|---|
| 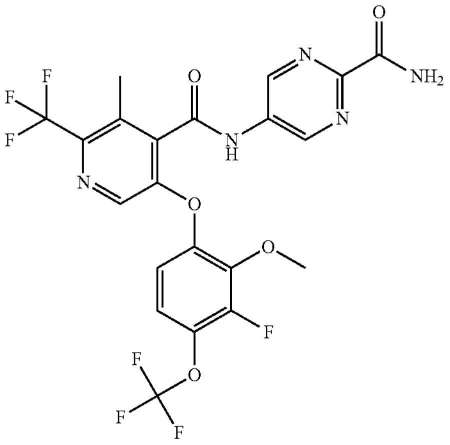 [SMILES: COc1c(Oc2cnc(C(F)(F)F)c(C)c2C(=O)Nc2cnc(C(N)=O)nc2)ccc(OC(F)(F)F)c1F] 335 |
| 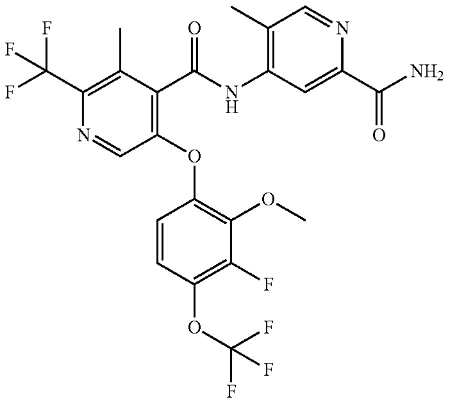 [SMILES: COc1c(Oc2cnc(C(F)(F)F)c(C)c2C(=O)Nc2cc(C(N)=O)ncc2C)ccc(OC(F)(F)F)c1F] 336 |
| 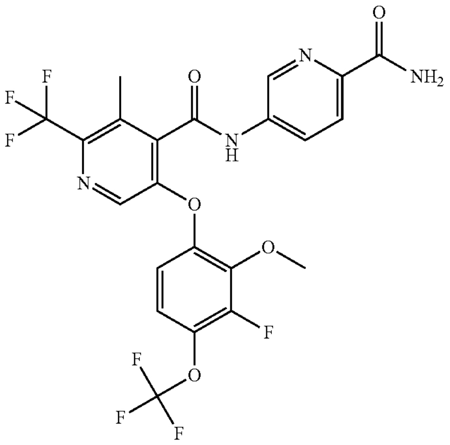 [SMILES: COc1c(Oc2cnc(C(F)(F)F)c(C)c2C(=O)Nc2ccc(C(N)=O)nc2)ccc(OC(F)(F)F)c1F] 337 |

TABLE B-continued
| Compound Numbers and Structures. |
| --- |
| 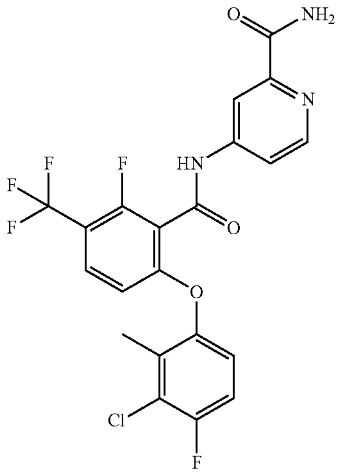 [SMILES: Cc1c(Oc2ccc(C(F)(F)F)c(F)c2C(=O)Nc2ccnc(C(N)=O)c2)ccc(F)c1Cl] 338 |
| 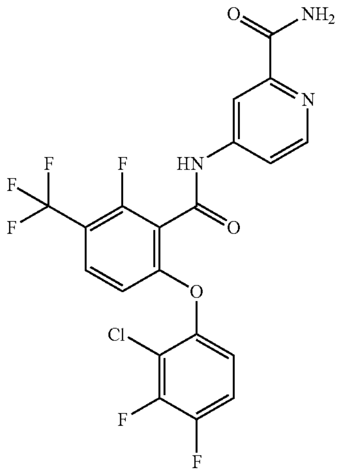 [SMILES: NC(=O)c1cc(NC(=O)c2c(Oc3ccc(F)c(F)c3Cl)ccc(C(F)(F)F)c2F)ccn1] 339 |
| 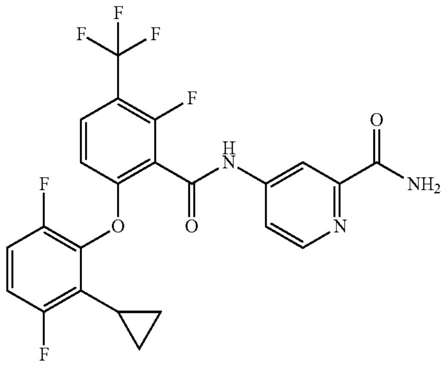 [SMILES: NC(=O)c1cc(NC(=O)c2c(Oc3c(F)ccc(F)c3C3CC3)ccc(C(F)(F)F)c2F)ccn1] 340 |
TABLE B-continued
| Compound Numbers and Structures. |
| --- |
| 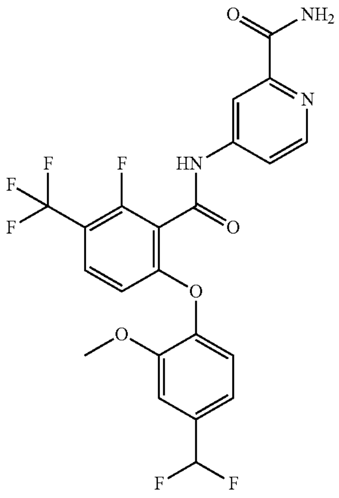 [SMILES: COc1cc(C(F)F)ccc1Oc1ccc(C(F)(F)F)c(F)c1C(=O)Nc1ccnc(C(N)=O)c1] 341 |
| 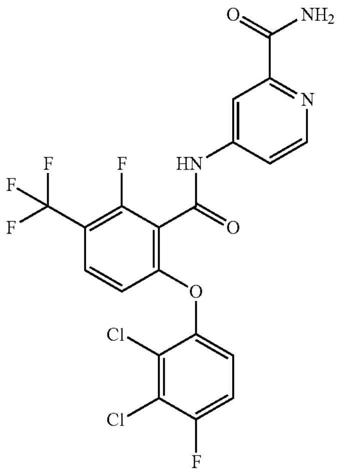 [SMILES: NC(=O)c1cc(NC(=O)c2c(Oc3ccc(F)c(Cl)c3Cl)ccc(C(F)(F)F)c2F)ccn1] 342 |
| 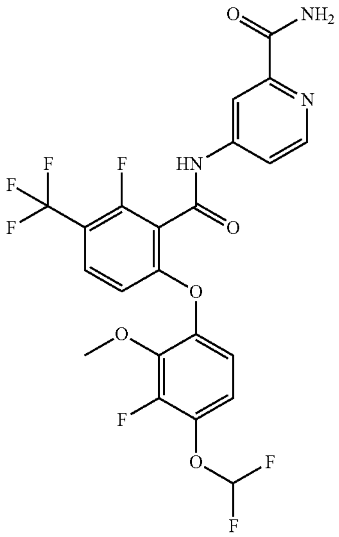 [SMILES: COc1c(Oc2ccc(C(F)(F)F)c(F)c2C(=O)Nc2ccnc(C(N)=O)c2)ccc(OC(F)F)c1F] 343 |

TABLE B-continued
| Compound Numbers and Structures. |
| --- |
| 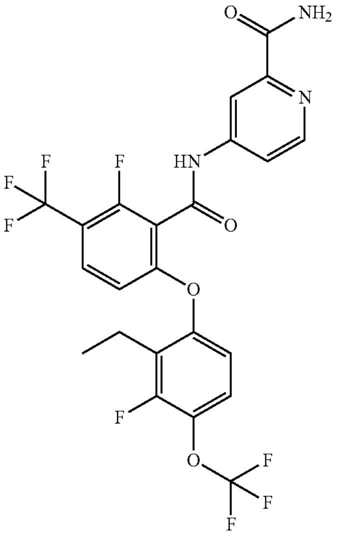 [SMILES: CCc1c(Oc2ccc(C(F)(F)F)c(F)c2C(=O)Nc2ccnc(C(N)=O)c2)ccc(OC(F)(F)F)c1F] 344 |
| 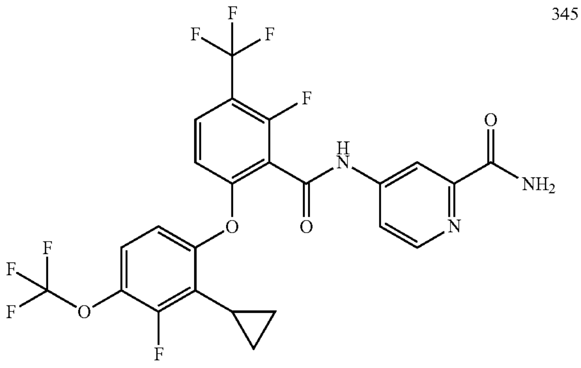 345 |
| 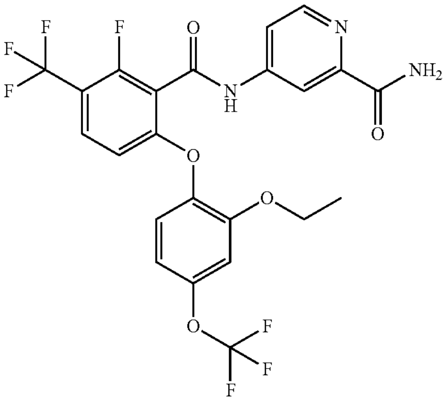 [SMILES: CCOc1cc(OC(F)(F)F)ccc1Oc1ccc(C(F)(F)F)c(F)c1C(=O)Nc1ccnc(C(N)=O)c1] 346 |
TABLE B-continued
| Compound Numbers and Structures. |
| --- |
| 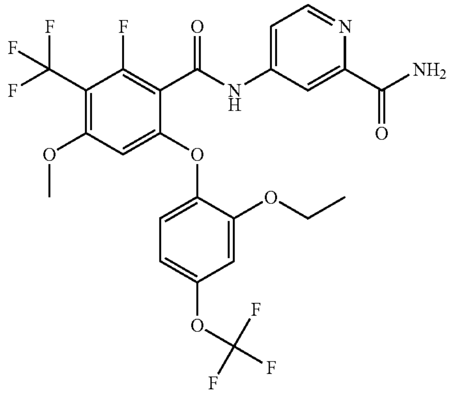 [SMILES: CCOc1cc(OC(F)(F)F)ccc1Oc1cc(OC)c(C(F)(F)F)c(F)c1C(=O)Nc1ccnc(C(N)=O)c1] 347 |
| 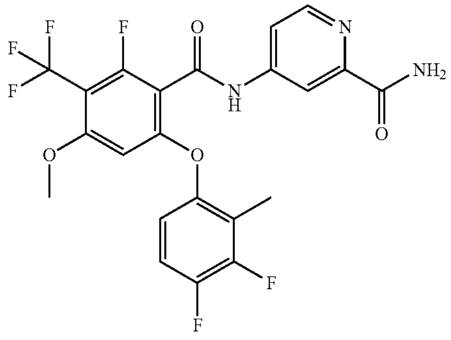 [SMILES: COc1cc(Oc2ccc(F)c(F)c2C)c(C(=O)Nc2ccnc(C(N)=O)c2)c(F)c1C(F)(F)F] 348 |
| 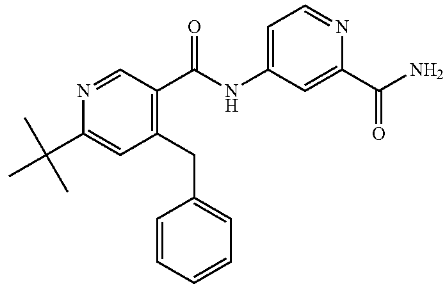 [SMILES: CC(C)(C)c1cc(Cc2ccccc2)c(C(=O)Nc2ccnc(C(N)=O)c2)cn1] 349 |
| 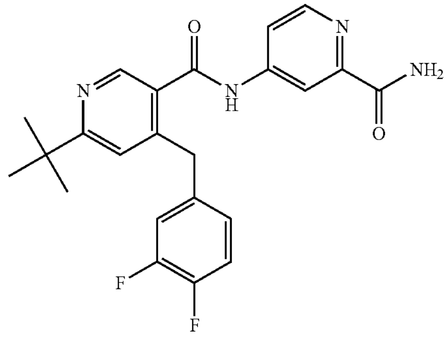 [SMILES: CC(C)(C)c1cc(Cc2ccc(F)c(F)c2)c(C(=O)Nc2ccnc(C(N)=O)c2)cn1] 350 |

TABLE B-continued
| Compound Numbers and Structures. |
| --- |
| 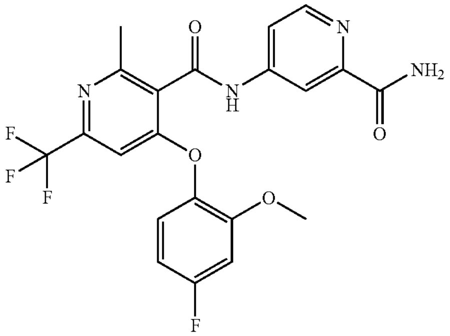 [SMILES: COc1cc(F)ccc1Oc1cc(C(F)(F)F)nc(C)c1C(=O)Nc1ccnc(C(N)=O)c1] 351 |
| 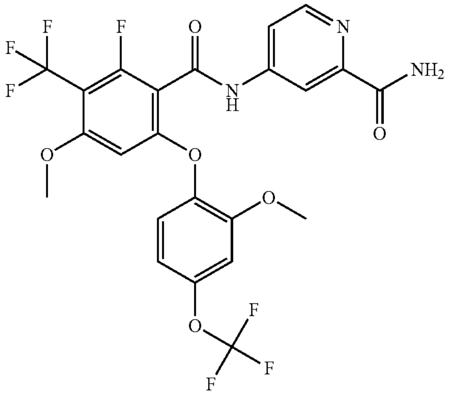 [SMILES: COc1cc(OC(F)(F)F)ccc1Oc1cc(OC)c(C(F)(F)F)c(F)c1C(=O)Nc1ccnc(C(N)=O)c1] 352 |
| 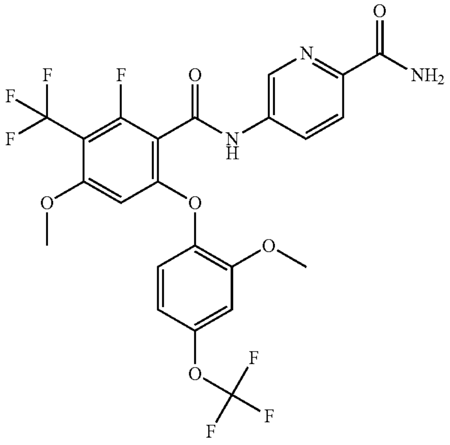 [SMILES: COc1cc(OC(F)(F)F)ccc1Oc1cc(OC)c(C(F)(F)F)c(F)c1C(=O)Nc1ccc(C(N)=O)nc1] 353 |
| 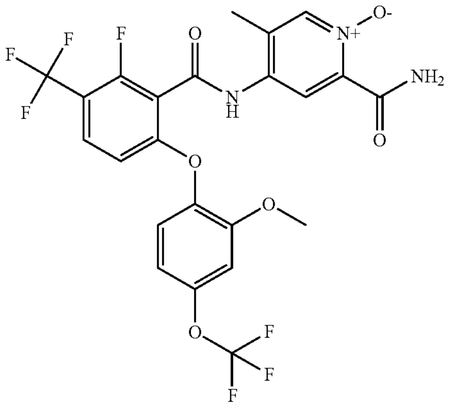 [SMILES: COc1cc(OC(F)(F)F)ccc1Oc1ccc(C(F)(F)F)c(F)c1C(=O)Nc1cc(C(N)=O)[n+]([O-])cc1C] 354 |
TABLE B-continued
| Compound Numbers and Structures. |
| --- |
| 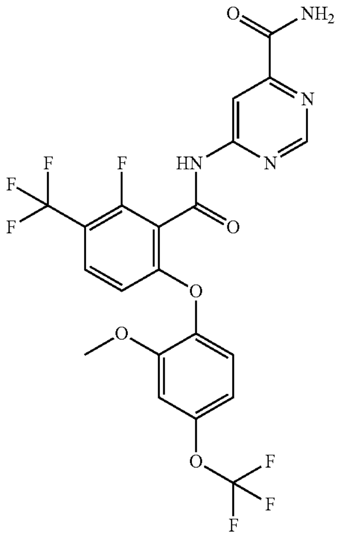 [SMILES: COc1cc(OC(F)(F)F)ccc1Oc1ccc(C(F)(F)F)c(F)c1C(=O)Nc1cc(C(N)=O)ncn1] 355 |
| 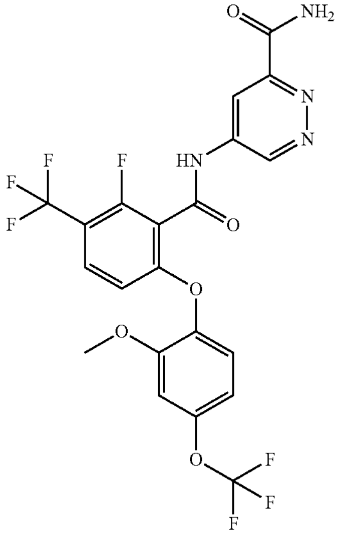 [SMILES: COc1cc(OC(F)(F)F)ccc1Oc1ccc(C(F)(F)F)c(F)c1C(=O)Nc1cnnc(C(N)=O)c1] 356 |
| 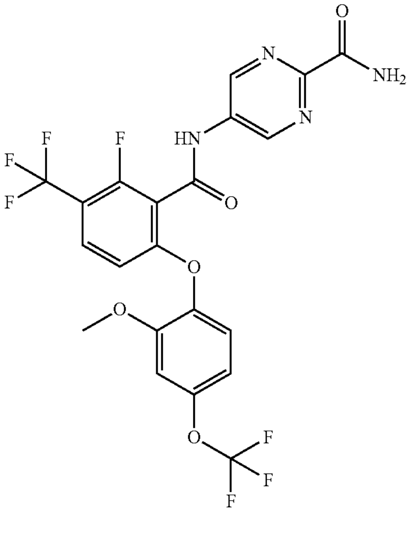 [SMILES: COc1cc(OC(F)(F)F)ccc1Oc1ccc(C(F)(F)F)c(F)c1C(=O)Nc1cnc(C(N)=O)nc1] 357 |

TABLE B-continued
Compound Numbers and Structures.
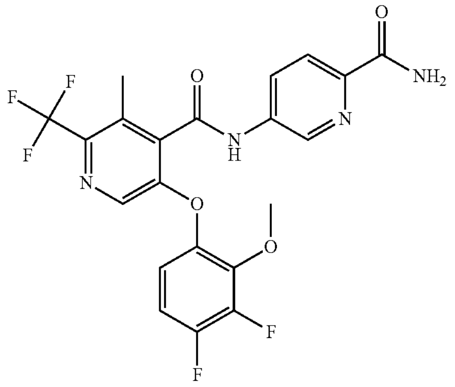 [SMILES: COc1c(Oc2cnc(C(F)(F)F)c(C)c2C(=O)Nc2ccc(C(N)=O)nc2)ccc(F)c1F]
358
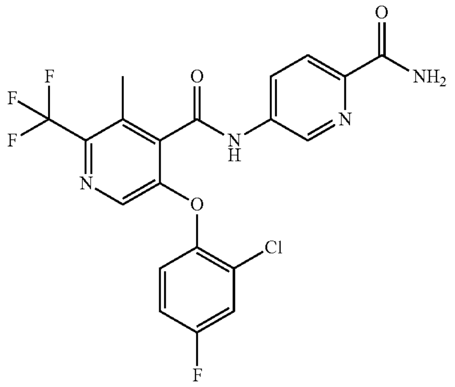 [SMILES: Cc1c(C(F)(F)F)ncc(Oc2ccc(F)cc2Cl)c1C(=O)Nc1ccc(C(N)=O)nc1]
359
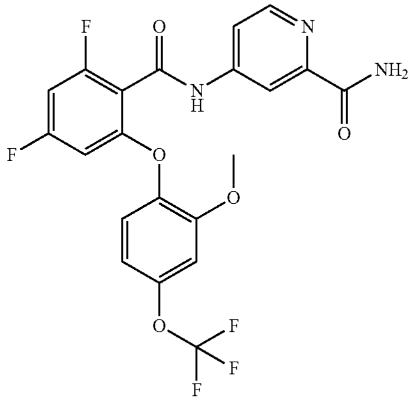 [SMILES: COc1cc(OC(F)(F)F)ccc1Oc1cc(F)cc(F)c1C(=O)Nc1ccnc(C(N)=O)c1]
360
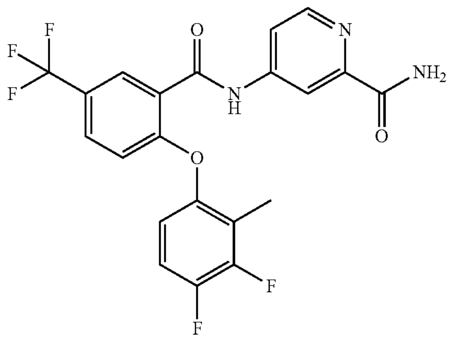 [SMILES: Cc1c(Oc2ccc(C(F)(F)F)cc2C(=O)Nc2ccnc(C(N)=O)c2)ccc(F)c1F]
361
TABLE B-continued
Compound Numbers and Structures.
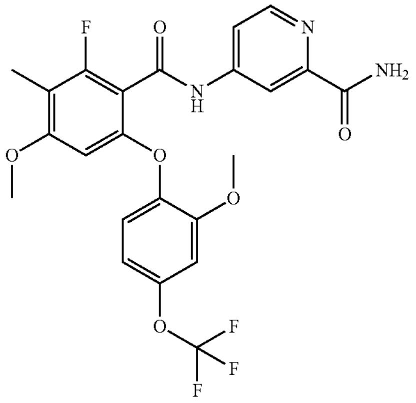 [SMILES: COc1cc(OC(F)(F)F)ccc1Oc1cc(OC)c(C)c(F)c1C(=O)Nc1ccnc(C(N)=O)c1]
362
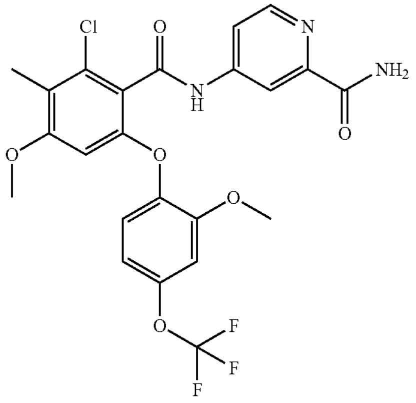 [SMILES: COc1cc(OC(F)(F)F)ccc1Oc1cc(OC)c(C)c(Cl)c1C(=O)Nc1ccnc(C(N)=O)c1]
363
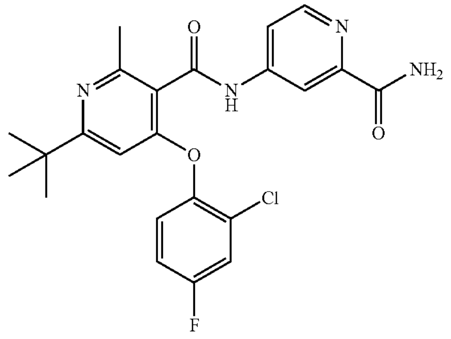 [SMILES: Cc1nc(C(C)(C)C)cc(Oc2ccc(F)cc2Cl)c1C(=O)Nc1ccnc(C(N)=O)c1]
364
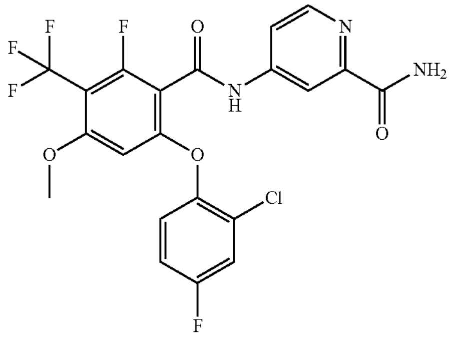 [SMILES: COc1cc(Oc2ccc(F)cc2Cl)c(C(=O)Nc2ccnc(C(N)=O)c2)c(F)c1C(F)(F)F]
365

TABLE B-continued
| Compound Numbers and Structures. |
|---|
| 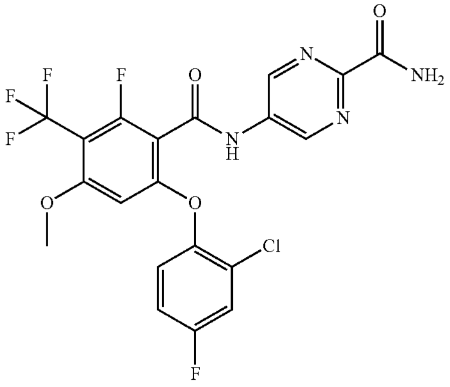 [SMILES: COc1cc(Oc2ccc(F)cc2Cl)c(C(=O)Nc2cnc(C(N)=O)nc2)c(F)c1C(F)(F)F] 366 |
| 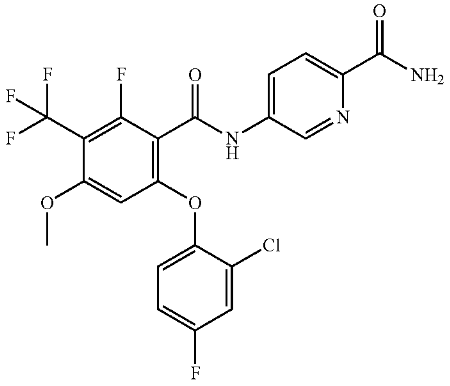 [SMILES: COc1cc(Oc2ccc(F)cc2Cl)c(C(=O)Nc2ccc(C(N)=O)nc2)c(F)c1C(F)(F)F] 367 |
| 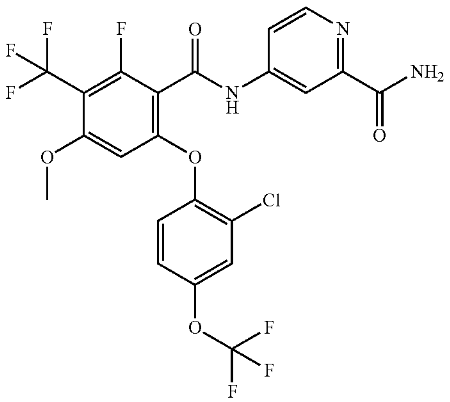 [SMILES: COc1cc(Oc2ccc(OC(F)(F)F)cc2Cl)c(C(=O)Nc2ccnc(C(N)=O)c2)c(F)c1C(F)(F)F] 368 |
TABLE B-continued
| Compound Numbers and Structures. |
|---|
| 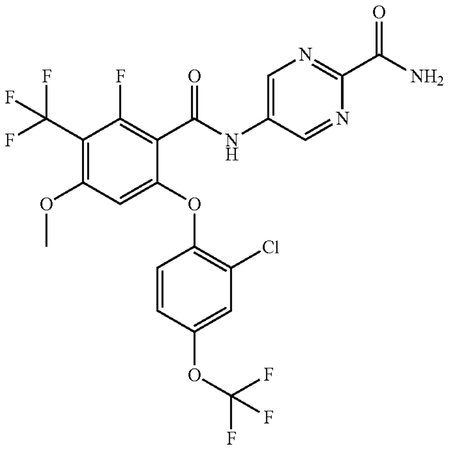 [SMILES: COc1cc(Oc2ccc(OC(F)(F)F)cc2Cl)c(C(=O)Nc2cnc(C(N)=O)nc2)c(F)c1C(F)(F)F] 369 |
| 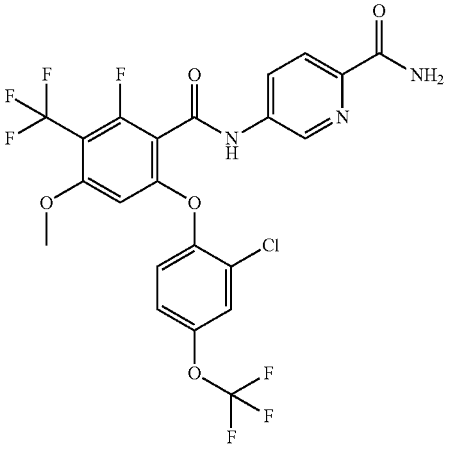 [SMILES: COc1cc(Oc2ccc(OC(F)(F)F)cc2Cl)c(C(=O)Nc2ccc(C(N)=O)nc2)c(F)c1C(F)(F)F] 370 |
| 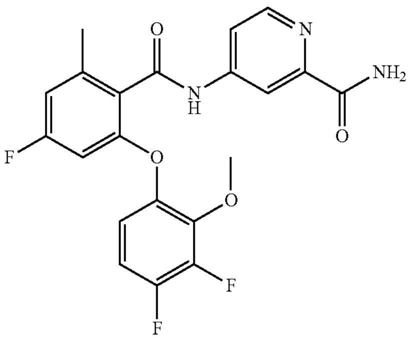 [SMILES: COc1c(Oc2cc(F)cc(C)c2C(=O)Nc2ccnc(C(N)=O)c2)ccc(F)c1F] 371 |
| 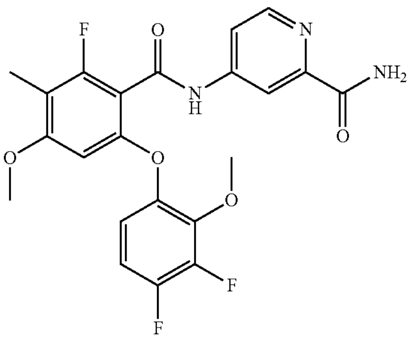 [SMILES: COc1cc(Oc2ccc(F)c(F)c2OC)c(C(=O)Nc2ccnc(C(N)=O)c2)c(F)c1C] 372 |

TABLE B-continued
Compound Numbers and Structures.
373
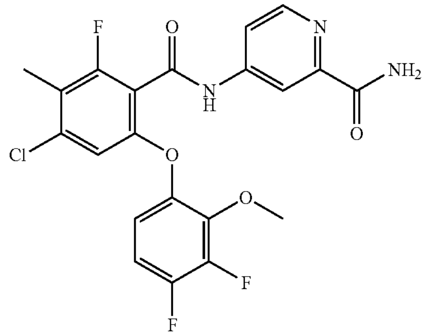 [SMILES: COc1c(Oc2cc(Cl)c(C)c(F)c2C(=O)Nc2ccnc(C(N)=O)c2)ccc(F)c1F]
374
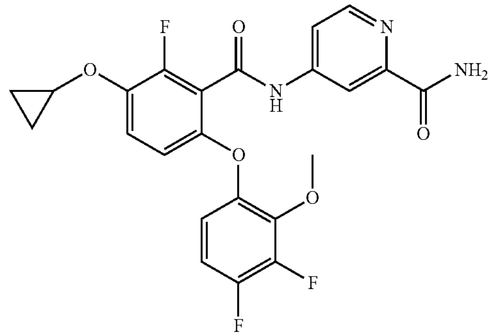 [SMILES: COc1c(Oc2ccc(OC3CC3)c(F)c2C(=O)Nc2ccnc(C(N)=O)c2)ccc(F)c1F]
375
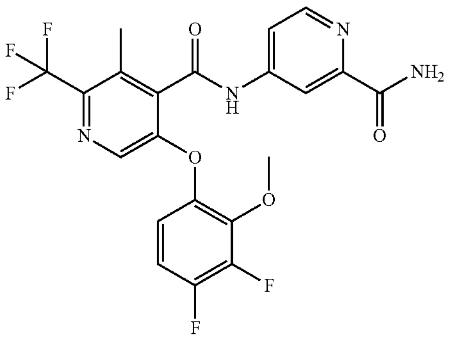 [SMILES: COc1c(Oc2cnc(C(F)(F)F)c(C)c2C(=O)Nc2ccnc(C(N)=O)c2)ccc(F)c1F]
376
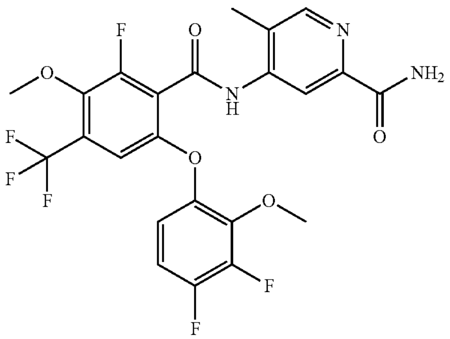 [SMILES: COc1c(Oc2cc(C(F)(F)F)c(OC)c(F)c2C(=O)Nc2cc(C(N)=O)ncc2C)ccc(F)c1F]
TABLE B-continued
Compound Numbers and Structures.
377
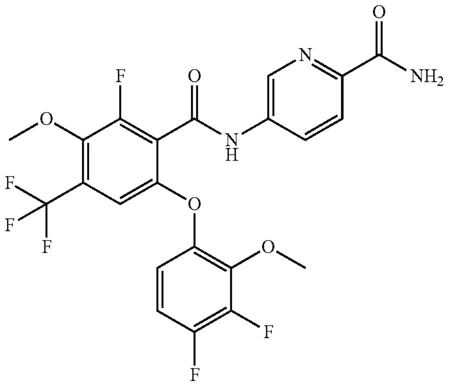 [SMILES: COc1c(Oc2cc(C(F)(F)F)c(OC)c(F)c2C(=O)Nc2ccc(C(N)=O)nc2)ccc(F)c1F]
378
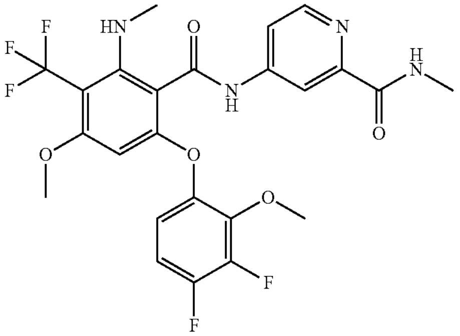
379
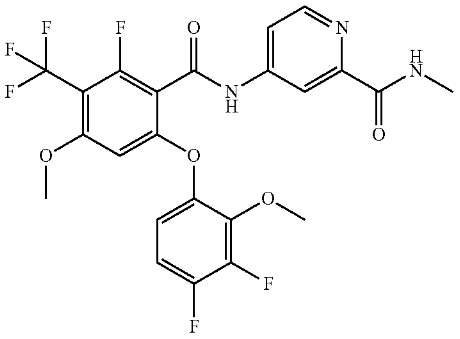 [SMILES: CNC(=O)c1cc(NC(=O)c2c(Oc3ccc(F)c(F)c3OC)cc(OC)c(C(F)(F)F)c2F)ccn1]
380
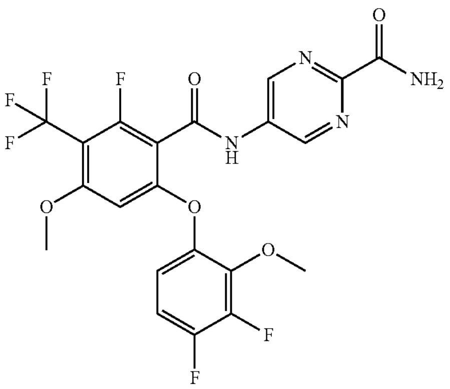 [SMILES: COc1cc(Oc2ccc(F)c(F)c2OC)c(C(=O)Nc2cnc(C(N)=O)nc2)c(F)c1C(F)(F)F]

TABLE B-continued
Compound Numbers and Structures.
381
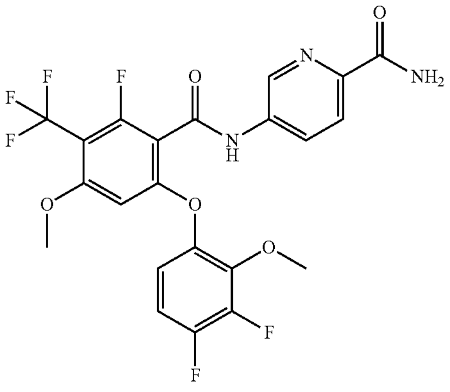 [SMILES: COc1cc(Oc2ccc(F)c(F)c2OC)c(C(=O)Nc2ccc(C(N)=O)nc2)c(F)c1C(F)(F)F]
382
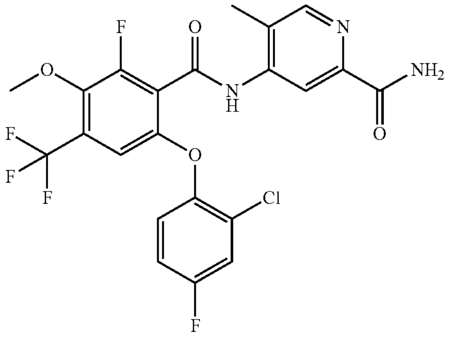 [SMILES: COc1c(C(F)(F)F)cc(Oc2ccc(F)cc2Cl)c(C(=O)Nc2cc(C(N)=O)ncc2C)c1F]
383
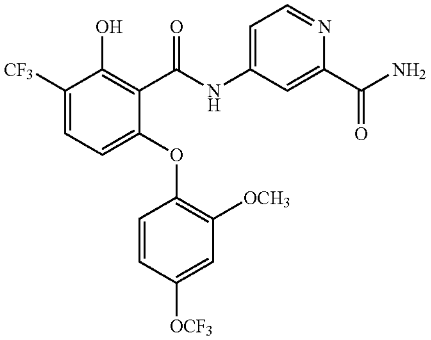 [SMILES: COc1cc(OC(F)(F)F)ccc1Oc1ccc(C(F)(F)F)c(O)c1C(=O)Nc1ccnc(C(N)=O)c1]
109
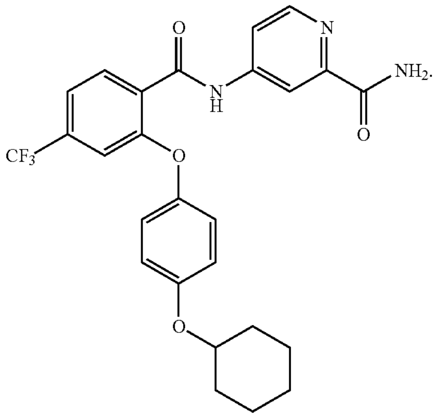 [SMILES: NC(=O)c1cc(NC(=O)c2ccc(C(F)(F)F)cc2Oc2ccc(OC3CCCCC3)cc2)ccn1]
In some embodiments, the invention relates to a compound selected from Table C or a pharmaceutically acceptable salt thereof. In other embodiments, the invention relates to a compound selected from Table C, i.e., the compound in non-salt form.
TABLE C
Compound Numbers and Structures.
1001
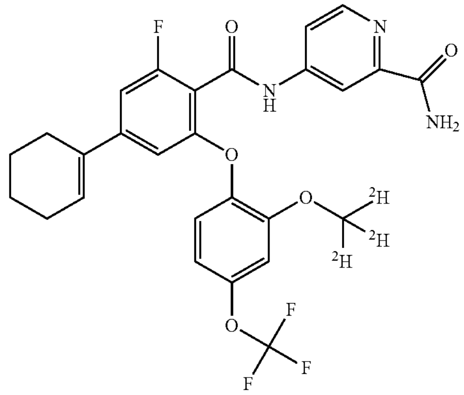 [SMILES: [2H]C([2H])([2H])Oc1cc(OC(F)(F)F)ccc1Oc1cc(C2=CCCCC2)cc(F)c1C(=O)Nc1ccnc(C(N)=O)c1]
1002
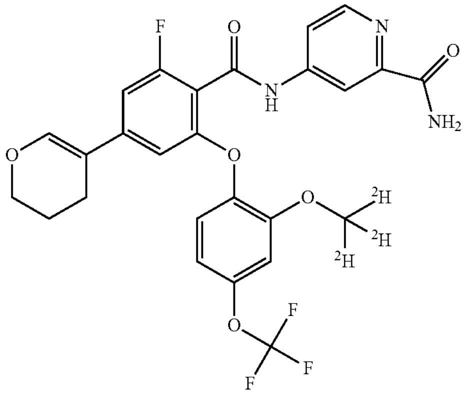 [SMILES: [2H]C([2H])([2H])Oc1cc(OC(F)(F)F)ccc1Oc1cc(C2=COCCC2)cc(F)c1C(=O)Nc1ccnc(C(N)=O)c1]
1003
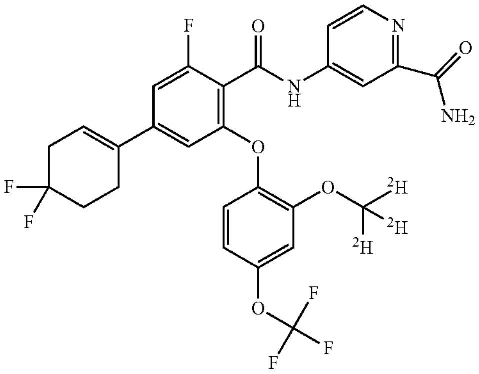 [SMILES: [2H]C([2H])([2H])Oc1cc(OC(F)(F)F)ccc1Oc1cc(C2=CCC(F)(F)CC2)cc(F)c1C(=O)Nc1ccnc(C(N)=O)c1]

TABLE C-continued
| Compound Numbers and Structures. | |
|---|---|
| 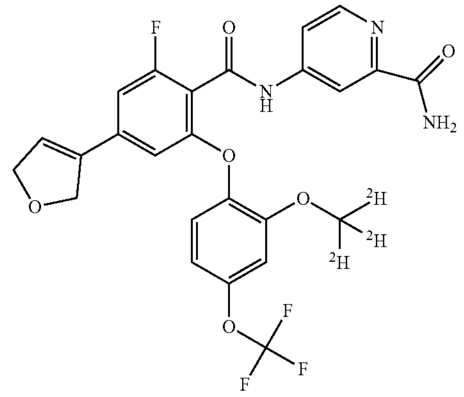 [SMILES: [2H]C([2H])([2H])Oc1cc(OC(F)(F)F)ccc1Oc1cc(C2=CCOC2)cc(F)c1C(=O)Nc1ccnc(C(N)=O)c1] | 1004 |
| 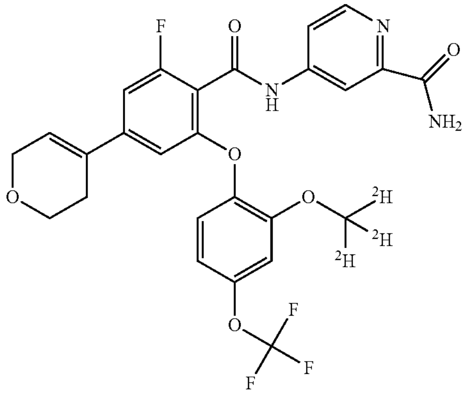 [SMILES: [2H]C([2H])([2H])Oc1cc(OC(F)(F)F)ccc1Oc1cc(C2=CCOCC2)cc(F)c1C(=O)Nc1ccnc(C(N)=O)c1] | 1005 |
| 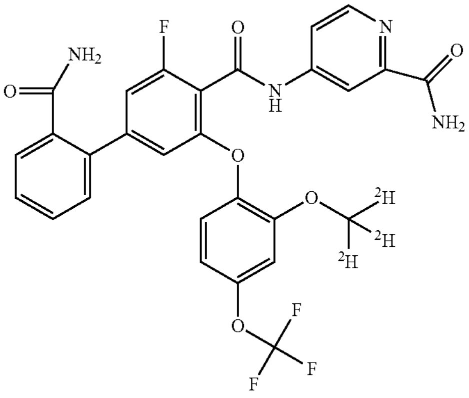 [SMILES: [2H]C([2H])([2H])Oc1cc(OC(F)(F)F)ccc1Oc1cc(-c2ccccc2C(N)=O)cc(F)c1C(=O)Nc1ccnc(C(N)=O)c1] | 1006 |
| 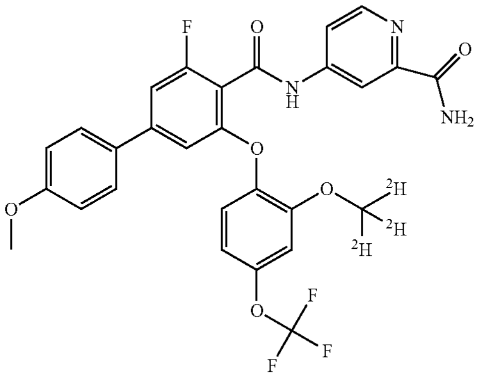 [SMILES: [2H]C([2H])([2H])Oc1cc(OC(F)(F)F)ccc1Oc1cc(-c2ccc(OC)cc2)cc(F)c1C(=O)Nc1ccnc(C(N)=O)c1] | 1007 |
TABLE C-continued
| Compound Numbers and Structures. | |
|---|---|
| 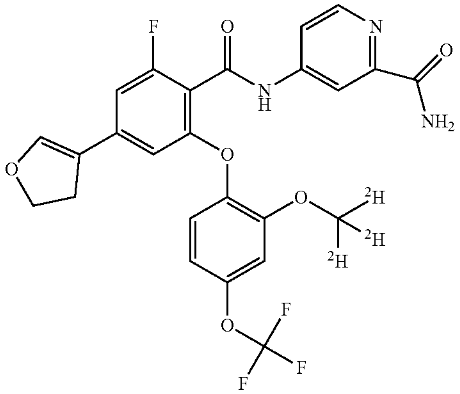 [SMILES: [2H]C([2H])([2H])Oc1cc(OC(F)(F)F)ccc1Oc1cc(C2=COCC2)cc(F)c1C(=O)Nc1ccnc(C(N)=O)c1] | 1008 |
| 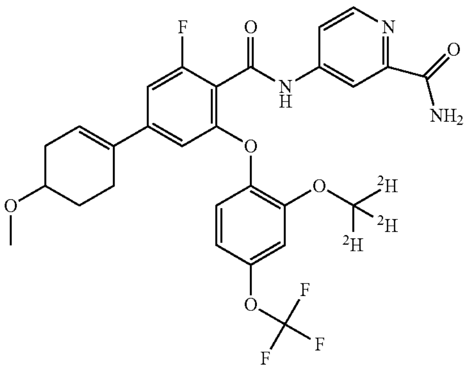 [SMILES: [2H]C([2H])([2H])Oc1cc(OC(F)(F)F)ccc1Oc1cc(C2=CCC(OC)CC2)cc(F)c1C(=O)Nc1ccnc(C(N)=O)c1] | 1009 |
| 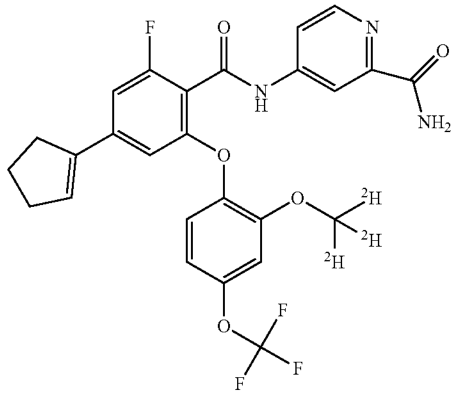 [SMILES: [2H]C([2H])([2H])Oc1cc(OC(F)(F)F)ccc1Oc1cc(C2=CCCC2)cc(F)c1C(=O)Nc1ccnc(C(N)=O)c1] | 1010 |
| 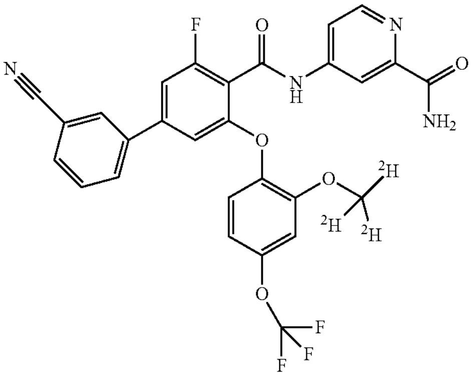 [SMILES: [2H]C([2H])([2H])Oc1cc(OC(F)(F)F)ccc1Oc1cc(-c2cccc(C#N)c2)cc(F)c1C(=O)Nc1ccnc(C(N)=O)c1] | 1011 |

TABLE C-continued
Compound Numbers and Structures.
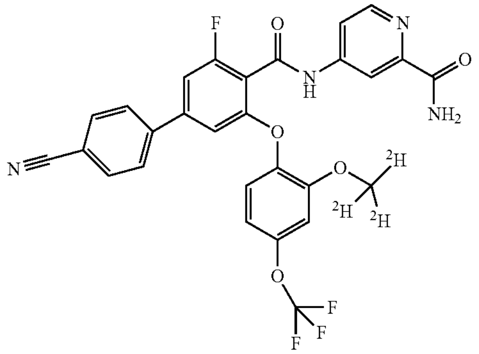 [SMILES: [2H]C([2H])([2H])Oc1cc(OC(F)(F)F)ccc1Oc1cc(-c2ccc(C#N)cc2)cc(F)c1C(=O)Nc1ccnc(C(N)=O)c1]
1012
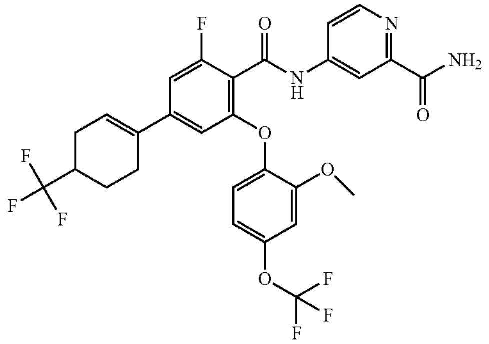 [SMILES: COc1cc(OC(F)(F)F)ccc1Oc1cc(C2=CCC(C(F)(F)F)CC2)cc(F)c1C(=O)Nc1ccnc(C(N)=O)c1]
1013
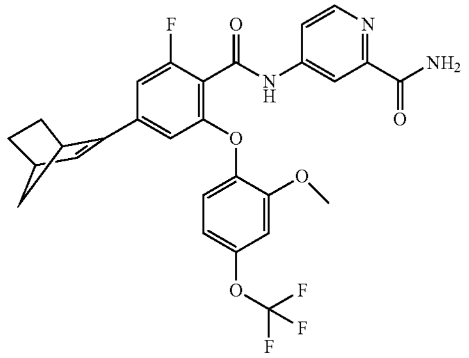 [SMILES: COc1cc(OC(F)(F)F)ccc1Oc1cc(C2=CC3CCC2C3)cc(F)c1C(=O)Nc1ccnc(C(N)=O)c1]
1014
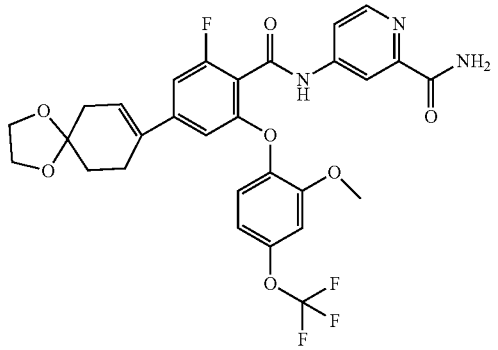 [SMILES: COc1cc(OC(F)(F)F)ccc1Oc1cc(C2=CCC3(CC2)OCCO3)cc(F)c1C(=O)Nc1ccnc(C(N)=O)c1]
1015
TABLE C-continued
Compound Numbers and Structures.
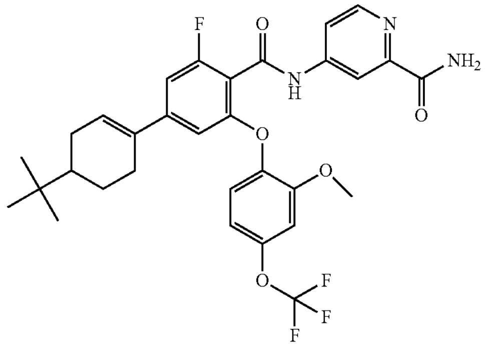 [SMILES: COc1cc(OC(F)(F)F)ccc1Oc1cc(C2=CCC(C(C)(C)C)CC2)cc(F)c1C(=O)Nc1ccnc(C(N)=O)c1]
1016
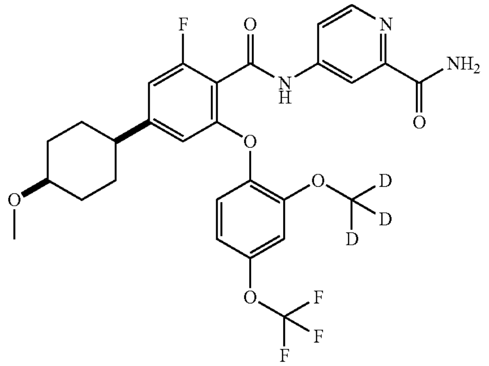
1017-a
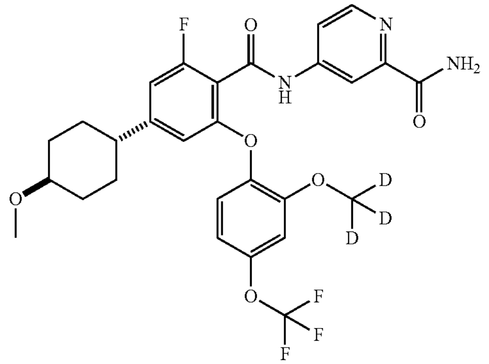
1017-b
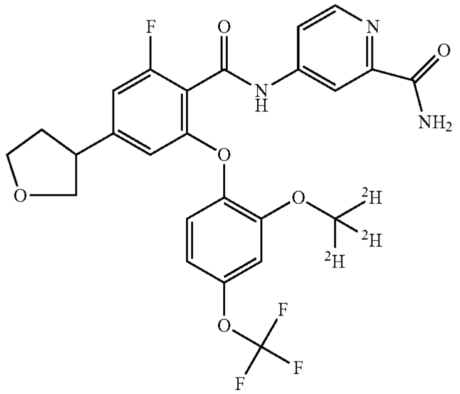 [SMILES: [2H]C([2H])([2H])Oc1cc(OC(F)(F)F)ccc1Oc1cc(C2CCOC2)cc(F)c1C(=O)Nc1ccnc(C(N)=O)c1]
1018

TABLE C-continued
Compound Numbers and Structures.
1019
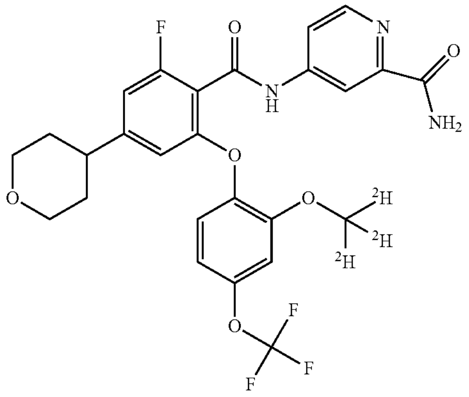 [SMILES: [2H]C([2H])([2H])Oc1cc(OC(F)(F)F)ccc1Oc1cc(C2CCOCC2)cc(F)c1C(=O)Nc1ccnc(C(N)=O)c1]
1020
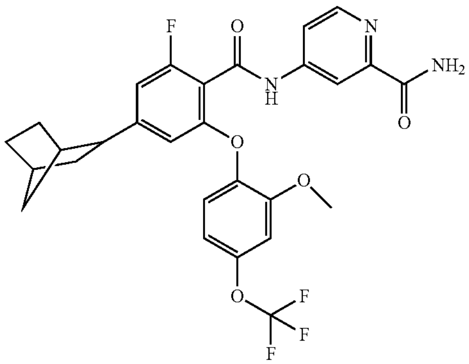 [SMILES: COc1cc(OC(F)(F)F)ccc1Oc1cc(C2CC3CCC2C3)cc(F)c1C(=O)Nc1ccnc(C(N)=O)c1]
1021
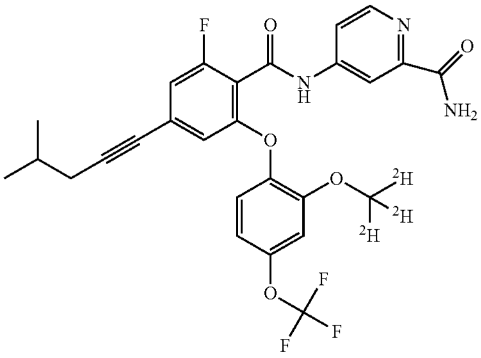 [SMILES: [2H]C([2H])([2H])Oc1cc(OC(F)(F)F)ccc1Oc1cc(C#CCC(C)C)cc(F)c1C(=O)Nc1ccnc(C(N)=O)c1]
1022
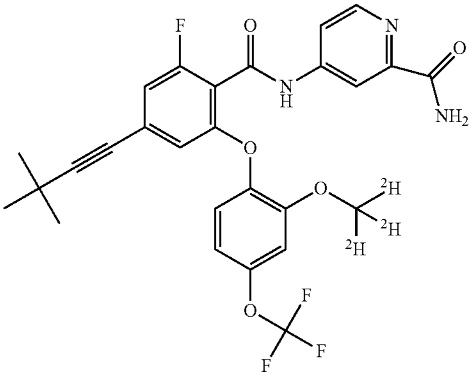 [SMILES: [2H]C([2H])([2H])Oc1cc(OC(F)(F)F)ccc1Oc1cc(C#CC(C)(C)C)cc(F)c1C(=O)Nc1ccnc(C(N)=O)c1]
1023
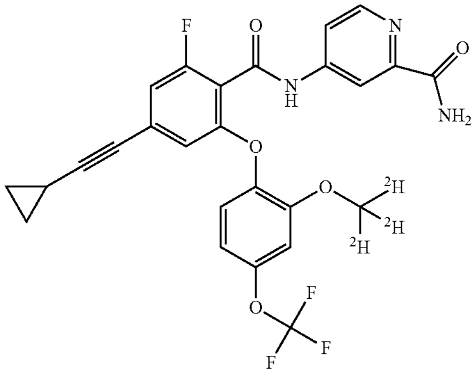 [SMILES: [2H]C([2H])([2H])Oc1cc(OC(F)(F)F)ccc1Oc1cc(C#CC2CC2)cc(F)c1C(=O)Nc1ccnc(C(N)=O)c1]
1024
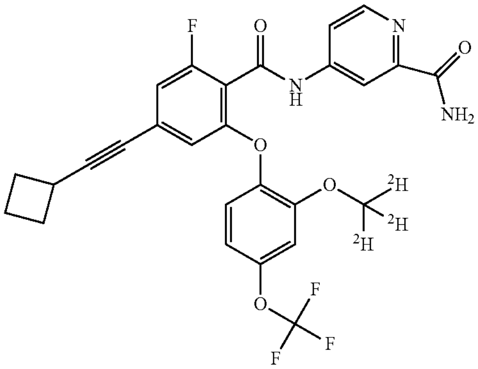 [SMILES: [2H]C([2H])([2H])Oc1cc(OC(F)(F)F)ccc1Oc1cc(C#CC2CCC2)cc(F)c1C(=O)Nc1ccnc(C(N)=O)c1]
1025
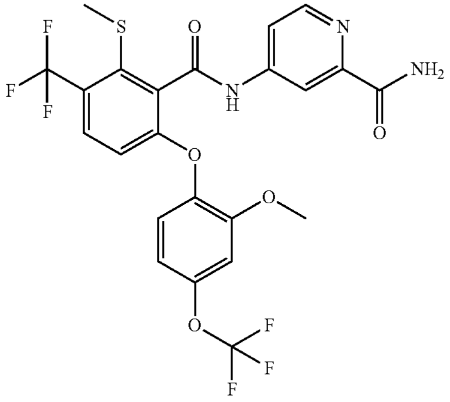 [SMILES: COc1cc(OC(F)(F)F)ccc1Oc1ccc(C(F)(F)F)c(SC)c1C(=O)Nc1ccnc(C(N)=O)c1]
1026
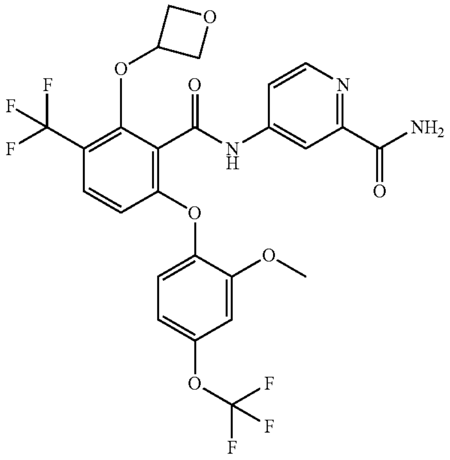 [SMILES: COc1cc(OC(F)(F)F)ccc1Oc1ccc(C(F)(F)F)c(OC2COC2)c1C(=O)Nc1ccnc(C(N)=O)c1]

TABLE C-continued
Compound Numbers and Structures.
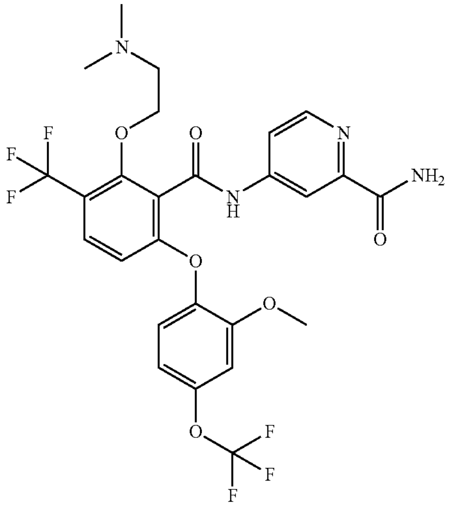 [SMILES: COc1cc(OC(F)(F)F)ccc1Oc1ccc(C(F)(F)F)c(OCCN(C)C)c1C(=O)Nc1ccnc(C(N)=O)c1]
1027
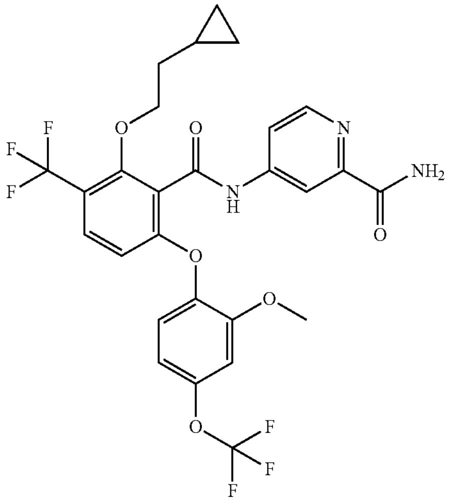 [SMILES: COc1cc(OC(F)(F)F)ccc1Oc1ccc(C(F)(F)F)c(OCCC2CC2)c1C(=O)Nc1ccnc(C(N)=O)c1]
1028
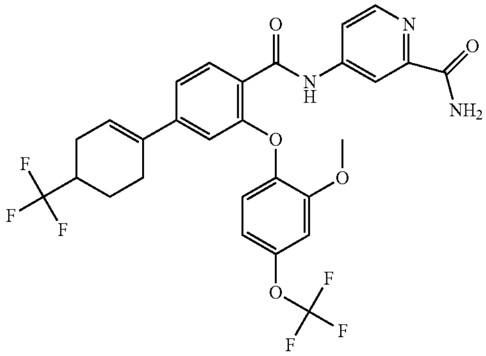 [SMILES: COc1cc(OC(F)(F)F)ccc1Oc1cc(C2=CCC(C(F)(F)F)CC2)ccc1C(=O)Nc1ccnc(C(N)=O)c1]
1029
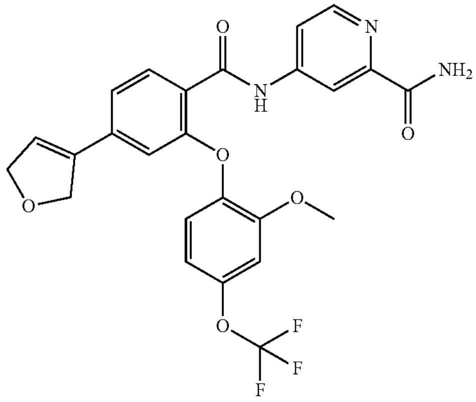 [SMILES: COc1cc(OC(F)(F)F)ccc1Oc1cc(C2=CCOC2)ccc1C(=O)Nc1ccnc(C(N)=O)c1]
1030
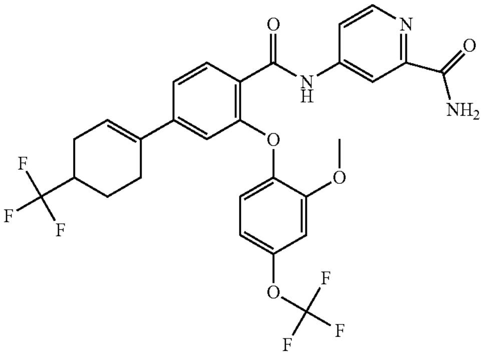 [SMILES: COc1cc(OC(F)(F)F)ccc1Oc1cc(C2=CCC(C(F)(F)F)CC2)ccc1C(=O)Nc1ccnc(C(N)=O)c1]
1031
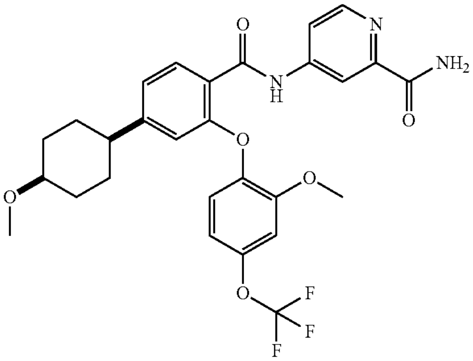
1032-a
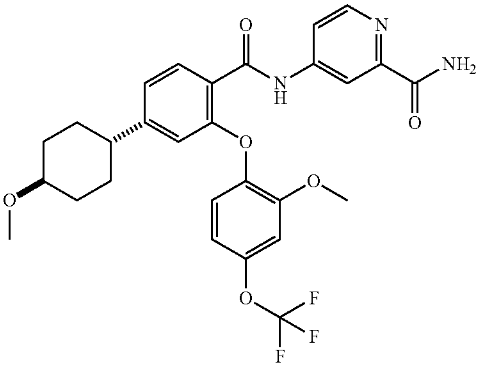
1032-b TABLE C-continued
Compound Numbers and Structures.
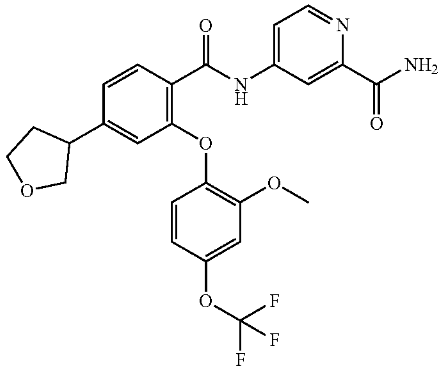 [SMILES: COc1cc(OC(F)(F)F)ccc1Oc1cc(C2CCOC2)ccc1C(=O)Nc1ccnc(C(N)=O)c1]
1033
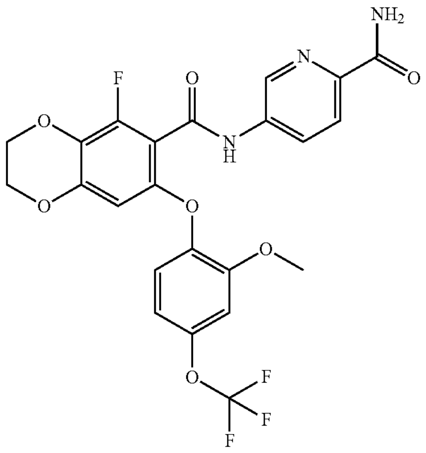 [SMILES: COc1cc(OC(F)(F)F)ccc1Oc1cc2c(c(F)c1C(=O)Nc1ccc(C(N)=O)nc1)OCCO2]
1034
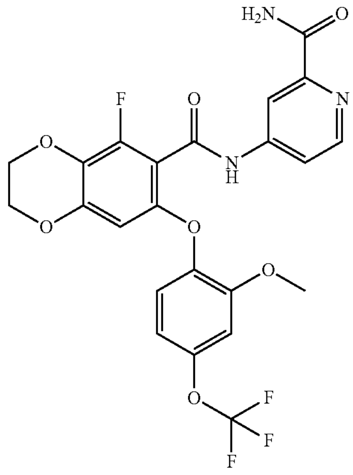 [SMILES: COc1cc(OC(F)(F)F)ccc1Oc1cc2c(c(F)c1C(=O)Nc1ccnc(C(N)=O)c1)OCCO2]
1035
TABLE C-continued
Compound Numbers and Structures.
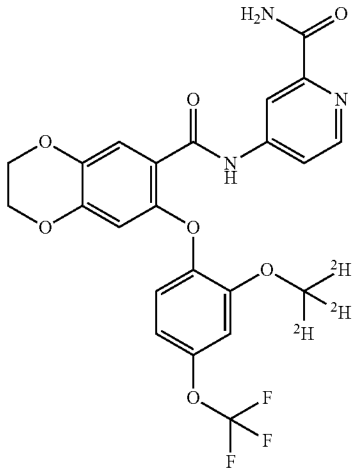 [SMILES: [2H]C([2H])([2H])Oc1cc(OC(F)(F)F)ccc1Oc1cc2c(cc1C(=O)Nc1ccnc(C(N)=O)c1)OCCO2]
1036
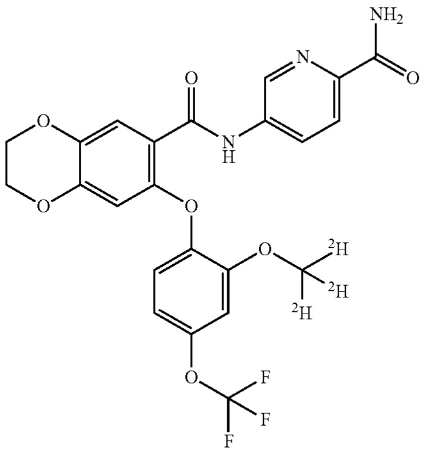 [SMILES: [2H]C([2H])([2H])Oc1cc(OC(F)(F)F)ccc1Oc1cc2c(cc1C(=O)Nc1ccc(C(N)=O)nc1)OCCO2]
1037
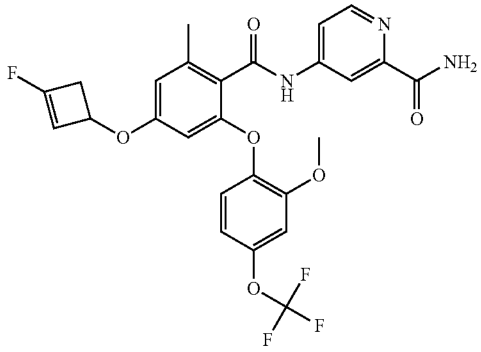 [SMILES: COc1cc(OC(F)(F)F)ccc1Oc1cc(OC2C=C(F)C2)cc(C)c1C(=O)Nc1ccnc(C(N)=O)c1]
1038

TABLE C-continued

| Compound Numbers and Structures. |
| --- |
| 1039 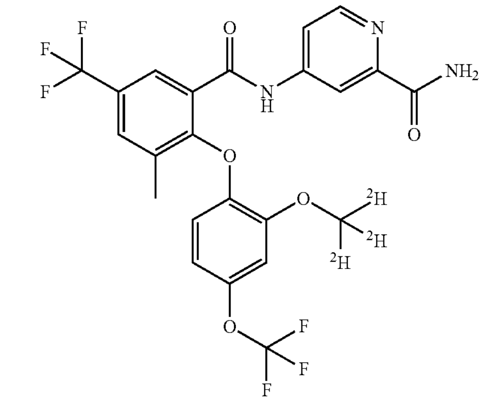 [SMILES: [2H]C([2H])([2H])Oc1cc(OC(F)(F)F)ccc1Oc1c(C)cc(C(F)(F)F)cc1C(=O)Nc1ccnc(C(N)=O)c1] |

In some embodiments, the invention relates to a compound selected from Table D or a pharmaceutically acceptable salt thereof. In other embodiments, the invention relates to a compound selected from Table D, i.e., the compound in non-salt form.

TABLE D

| Compound Numbers and Structures. |
| --- |
| 1040 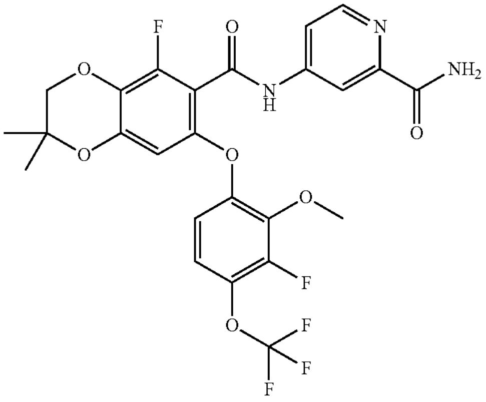 [SMILES: COc1c(Oc2cc3c(c(F)c2C(=O)Nc2ccnc(C(N)=O)c2)OCC(C)(C)O3)ccc(OC(F)(F)F)c1F] |
| 1041 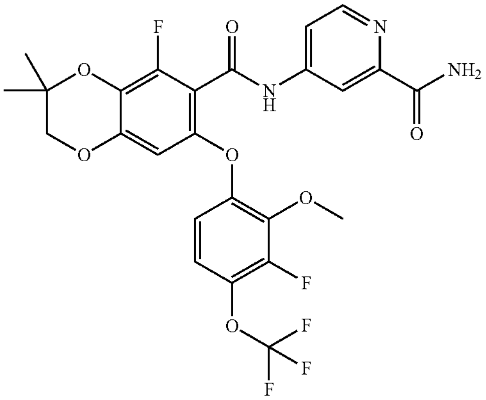 [SMILES: COc1c(Oc2cc3c(c(F)c2C(=O)Nc2ccnc(C(N)=O)c2)OC(C)(C)CO3)ccc(OC(F)(F)F)c1F] |

In some embodiments, the invention relates to a compound of formula

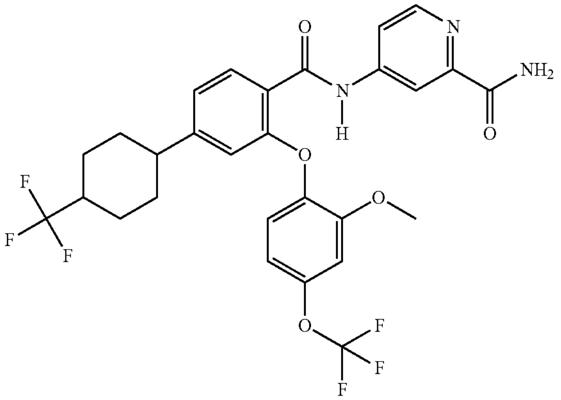 [SMILES: COc1cc(OC(F)(F)F)ccc1Oc1cc(C2CCC(C(F)(F)F)CC2)ccc1C(=O)Nc1ccnc(C(N)=O)c1]

or a pharmaceutically acceptable salt thereof, wherein the compound has the relative stereochemistry of the first eluting diastereomer when a mixture of the diastereomers is separated by HPLC Method B, as described in Example 68. Such compound is considered to be a "compound of the invention," as that term is used herein.

In some embodiments, the invention relates to a compound of formula

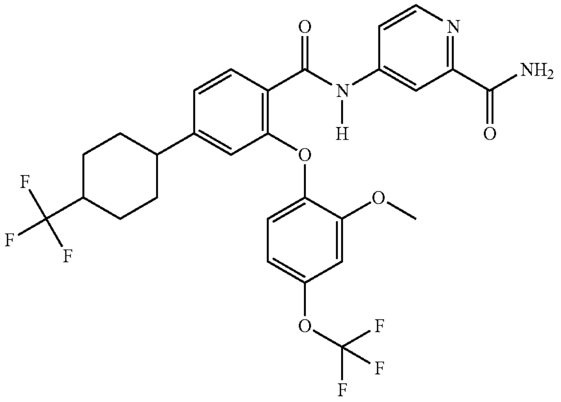 [SMILES: COc1cc(OC(F)(F)F)ccc1Oc1cc(C2CCC(C(F)(F)F)CC2)ccc1C(=O)Nc1ccnc(C(N)=O)c1]

or a pharmaceutically acceptable salt thereof, wherein the compound has the relative stereochemistry of the second eluting diastereomer when a mixture of the diastereomers is separated by HPLC Method B, as described in Example 68. Such compound is considered to be a "compound of the invention," as that term is used herein.

In some embodiments, the invention relates to a compound of formula

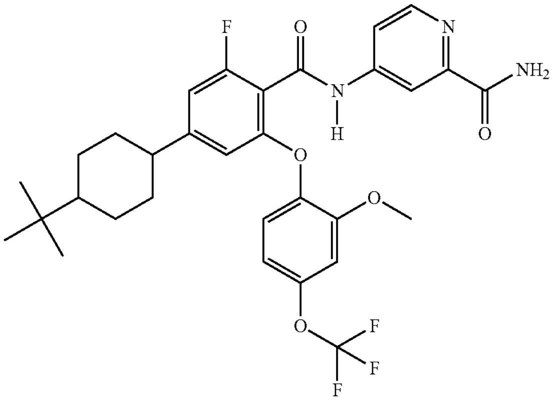 [SMILES: COc1cc(OC(F)(F)F)ccc1Oc1cc(C2CCC(C(C)(C)C)CC2)cc(F)c1C(=O)Nc1ccnc(C(N)=O)c1]

or a pharmaceutically acceptable salt thereof, wherein the compound has the relative stereochemistry of the first eluting diastereomer when a mixture of the diastereomers is separated by HPLC Method B, as described in Example 24. Such compound is considered to be a "compound of the invention," as that term is used herein.

In some embodiments, the invention relates to a compound of formula

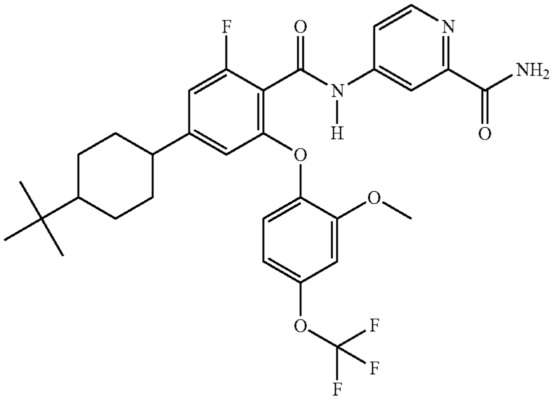 [SMILES: COc1cc(OC(F)(F)F)ccc1Oc1cc(C2CCC(C(C)(C)C)CC2)cc(F)c1C(=O)Nc1ccnc(C(N)=O)c1]

or a pharmaceutically acceptable salt thereof, wherein the compound has the relative stereochemistry of the second eluting diastereomer when a mixture of the diastereomers is separated by HPLC Method B, as described in Example 24. Such compound is considered to be a "compound of the invention," as that term is used herein.

In some embodiments, the invention relates to a compound of formula

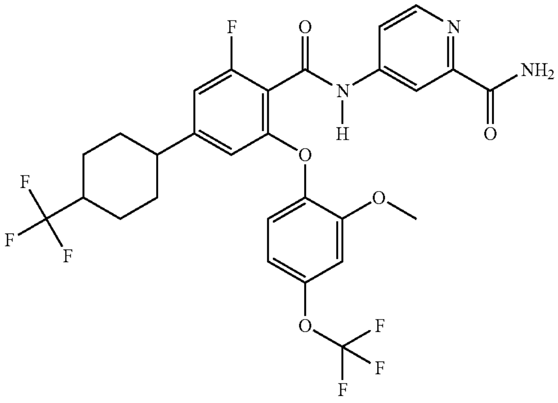 [SMILES: COc1cc(OC(F)(F)F)ccc1Oc1cc(C2CCC(C(F)(F)F)CC2)cc(F)c1C(=O)Nc1ccnc(C(N)=O)c1]

or a pharmaceutically acceptable salt thereof, wherein the compound has the relative stereochemistry of the first eluting diastereomer when a mixture of the diastereomers is separated by HPLC Method B, as described in Example 24. Such compound is considered to be a "compound of the invention," as that term is used herein.

In some embodiments, the invention relates to a compound of formula

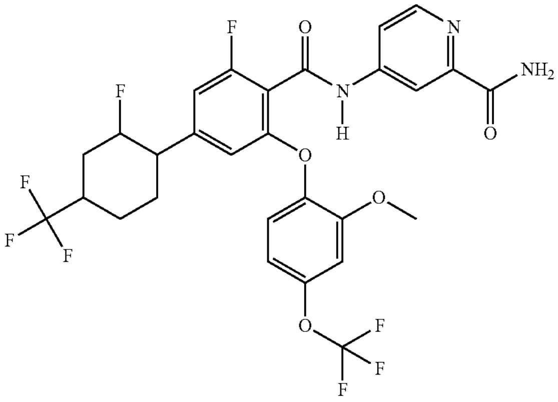 [SMILES: COc1cc(OC(F)(F)F)ccc1Oc1cc(C2CCC(C(F)(F)F)CC2F)cc(F)c1C(=O)Nc1ccnc(C(N)=O)c1]

or a pharmaceutically acceptable salt thereof, wherein the compound has the relative stereochemistry of the second eluting diastereomer when a mixture of the diastereomers is separated by HPLC Method B, as described in Example 24. Such compound is considered to be a "compound of the invention," as that term is used herein.

In some embodiments, the invention relates to a compound of formula (I), or a pharmaceutically acceptable salt thereof, wherein the compound has formula

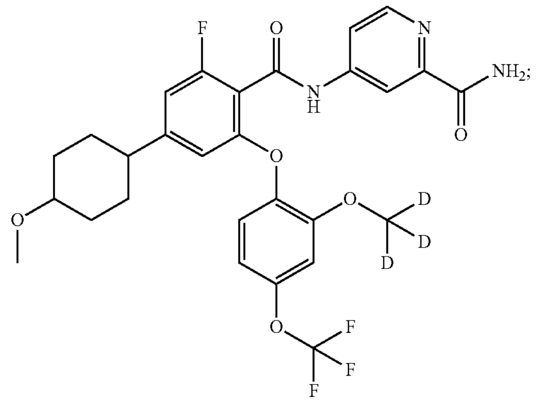 [SMILES: [2H]C([2H])([2H])Oc1cc(OC(F)(F)F)ccc1Oc1cc(C2CCC(OC)CC2)cc(F)c1C(=O)Nc1ccnc(C(N)=O)c1]

wherein the compound has the relative stereochemistry of the first eluting diastereomer when a mixture of the diastereomers is separated by HPLC Method B, as described in Example 204.

In some embodiments, the invention relates to a compound of formula (I), or a pharmaceutically acceptable salt thereof, wherein the compound has formula

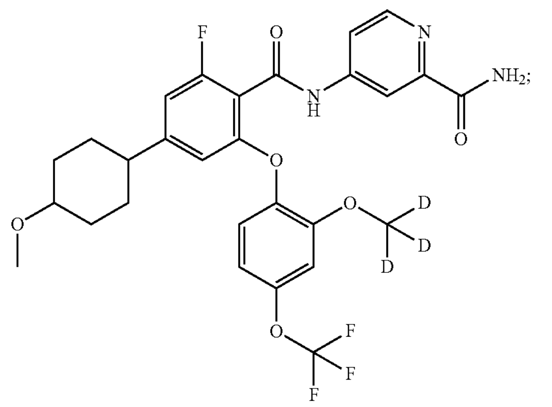 [SMILES: [2H]C([2H])([2H])Oc1cc(OC(F)(F)F)ccc1Oc1cc(C2CCC(OC)CC2)cc(F)c1C(=O)Nc1ccnc(C(N)=O)c1]

wherein the compound has the relative stereochemistry of the second eluting diastereomer when a mixture of the diastereomers is separated by HPLC Method B, as described in Example 204.

In some embodiments, the invention relates to a compound of formula (I), or a pharmaceutically acceptable salt thereof, wherein the compound has formula

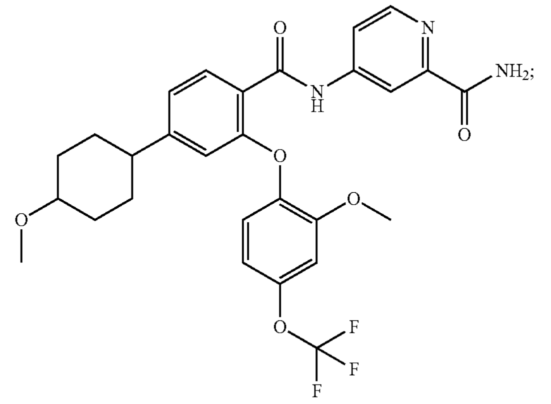 [SMILES: COc1cc(OC(F)(F)F)ccc1Oc1cc(C2CCC(OC)CC2)ccc1C(=O)Nc1ccnc(C(N)=O)c1]

wherein the compound has the relative stereochemistry of the first eluting diastereomer when a mixture of the diastereomers is separated by HPLC Method B, as described in Example 209.

In some embodiments, the invention relates to a compound of formula (I), or a pharmaceutically acceptable salt thereof, wherein the compound has formula

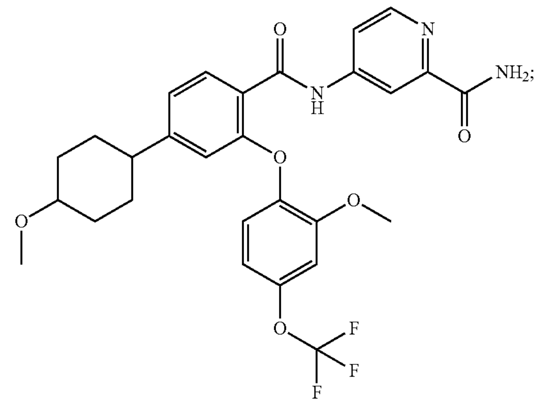 [SMILES: COc1cc(OC(F)(F)F)ccc1Oc1cc(C2CCC(OC)CC2)ccc1C(=O)Nc1ccnc(C(N)=O)c1]

wherein the compound has the relative stereochemistry of the second eluting diastereomer when a mixture of the diastereomers is separated by HPLC Method B, as described in Example 209.

Salts, Compositions, Uses, Formulation, Administration and Additional Agents

Pharmaceutically acceptable salts and compositions

As discussed herein, the invention provides compounds, and pharmaceutically acceptable salts thereof, that are inhibitors of voltage-gated sodium channels, and thus the present compounds, and pharmaceutically acceptable salts thereof, are useful for the treatment of diseases, disorders, and conditions including, but not limited to chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia. Accordingly, in another aspect of the invention, pharmaceutical compositions are provided, wherein these compositions comprise a compound as described herein, or a pharmaceutically acceptable salt thereof, and optionally comprise a pharmaceutically acceptable carrier, adjuvant or vehicle. In certain embodiments, these compositions optionally further comprise one or more additional therapeutic agents. In some embodiments, the additional therapeutic agent is a sodium channel inhibitor.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" of a compound of this invention includes any non-toxic salt that, upon administration to a recipient, is capable of providing, either directly or indirectly, a compound of this invention or an inhibitorily active metabolite or residue thereof. The salt may be in pure form, in a mixture (e.g., solution, suspension, or colloid) with one or more other substances, or in the form of a hydrate, solvate, or co-crystal. As used herein, the term "inhibitorily active metabolite or residue thereof" means that a metabolite or residue thereof is also an inhibitor of a voltage-gated sodium channel.

Pharmaceutically acceptable salts are well known in the art. For example, S. M. Berge, et al. describe pharmaceutically acceptable salts in detail in *J. Pharmaceutical Sciences,* 1977, 66, 1-19, incorporated herein by reference. Pharmaceutically acceptable salts of the compound of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising a compound of the invention, or a pharmaceutically acceptable salt thereof, and a pharmaceutically acceptable carrier.

In another aspect, the invention features a pharmaceutical composition comprising a therapeutically effective amount of a compound, or a pharmaceutically acceptable salt thereof, and one or more pharmaceutically acceptable carriers or vehicles.

Uses of Compounds and Pharmaceutically Acceptable Salts and Compositions

In another aspect, the invention features a method of inhibiting a voltage-gated sodium channel in a subject comprising administering to the subject a compound of the invention or a pharmaceutically acceptable salt thereof or a pharmaceutical composition thereof. In another aspect, the voltage-gated sodium channel is $Na_V1.8$.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of gut pain, wherein gut pain comprises inflammatory bowel disease pain, Crohn's disease pain or interstitial cystitis pain wherein said method comprises administering an effective amount of a compound of the invention, a pharmaceutically acceptable salt thereof or a pharmaceutical composition thereof.

In yet another aspect, the invention features a method of treating or lessening the severity in a subject of neuropathic pain comprising administering an effective amount of a compound of the invention, a pharmaceutically acceptable salt thereof or a pharmaceutical composition thereof. In some aspects, the neuropathic pain comprises post-herpetic neuralgia, small fiber neuropathy or idiopathic small-fiber neuropathy. As used herein, the phrase "idiopathic small-fiber neuropathy" shall be understood to include any small fiber neuropathy.

In yet another aspect, the invention features a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, small fiber neuropathy, idiopathic small-fiber neuropathy, idiopathic sensory neuropathy or trigeminal autonomic cephalalgia wherein said method comprises administering an effective amount of a compound of the invention, a pharmaceutically acceptable salt thereof or a pharmaceutical composition thereof.

In yet another aspect, the invention features a method of treating or lessening the severity in a subject of musculoskeletal pain comprising administering an effective amount of a compound of the invention, a pharmaceutically acceptable salt thereof or a pharmaceutical composition thereof. In some aspects, the musculoskeletal pain comprises osteoarthritis pain.

In yet another aspect, the invention features a method of treating or lessening the severity in a subject of musculoskeletal pain, wherein musculoskeletal pain comprises osteoarthritis pain, back pain, cold pain, burn pain or dental pain wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain or vulvodynia wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain wherein said method comprises administering an effective amount of a compound of the invention, a pharmaceutically acceptable salt thereof or a pharmaceutical composition thereof.

In yet another aspect, the invention features a method of treating or lessening the severity in a subject of idiopathic pain, wherein idiopathic pain comprises fibromyalgia pain wherein said method comprises administering an effective amount of a compound of the invention, a pharmaceutically acceptable salt thereof or a pharmaceutical composition thereof.

In yet another aspect, the invention features a method of treating or lessening the severity in a subject of pathological cough wherein said method comprises administering an effective amount of a compound of the invention, a pharmaceutically acceptable salt thereof or a pharmaceutical composition thereof.

In yet another aspect, the invention features a method of treating or lessening the severity in a subject of acute pain comprising administering an effective amount of a compound of the invention, a pharmaceutically acceptable salt thereof or a pharmaceutical composition thereof. In some aspects, the acute pain comprises acute post-operative pain.

In yet another aspect, the invention features a method of treating or lessening the severity in a subject of postsurgical pain (e.g., herniorrhaphy pain, bunionectomy pain or abdominoplasty pain) comprising administering an effective amount of a compound of the invention, a pharmaceutically acceptable salt thereof or a pharmaceutical composition thereof.

In yet another aspect, the invention features a method of treating or lessening the severity in a subject of bunionectomy pain comprising administering an effective amount of a compound of the invention, a pharmaceutically acceptable salt thereof or a pharmaceutical composition thereof.

In yet another aspect, the invention features a method of treating or lessening the severity in a subject of herniorrhaphy pain comprising administering an effective amount of a compound of the invention, a pharmaceutically acceptable salt thereof or a pharmaceutical composition thereof.

In yet another aspect, the invention features a method of treating or lessening the severity in a subject of abdominoplasty pain comprising administering an effective amount of a compound of the invention, a pharmaceutically acceptable salt thereof or a pharmaceutical composition thereof.

In yet another aspect, the invention features a method of treating or lessening the severity in a subject of visceral pain comprising administering an effective amount of a compound of the invention, a pharmaceutically acceptable salt thereof or a pharmaceutical composition thereof. In some aspects, the visceral pain comprises visceral pain from abdominoplasty.

In yet another aspect, the invention features a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., herniorrhaphy pain, bunionectomy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility, comprising administering an effective amount of a compound of the invention, a pharmaceutically acceptable salt thereof or a pharmaceutical composition thereof.

In another aspect, the invention features a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain, comprising administering an effective amount of a compound of the invention, a pharmaceutically acceptable salt thereof or a pharmaceutical composition thereof.

Compounds, Pharmaceutically Acceptable Salts, and Compositions for Use

In another aspect, the invention features a compound of the invention, or a pharmaceutically acceptable salt or pharmaceutical composition thereof, for use as a medicament.

In another aspect, the invention features a compound of the invention, or a pharmaceutically acceptable salt or pharmaceutical composition thereof, for use in a method of inhibiting a voltage-gated sodium channel in a subject. In another aspect, the voltage-gated sodium channel is $Na_V1.8$.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain (e.g., herniorrhaphy pain, bunionectomy pain or abdominoplasty pain), visceral pain, multiple sclerosis, Charcot-Marie-Tooth syndrome, incontinence, pathological cough, or cardiac arrhythmia.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia.

In another aspect, the invention features a compound of the invention, or a pharmaceutically acceptable salt or pharmaceutical composition thereof, for use in a method of treating or lessening the severity in a subject of gut pain, wherein gut pain comprises inflammatory bowel disease pain, Crohn's disease pain or interstitial cystitis pain.

In another aspect, the invention features a compound of the invention, or a pharmaceutically acceptable salt or pharmaceutical composition thereof, for use in a method of treating or lessening the severity in a subject of neuropathic pain. In some aspects, the neuropathic pain comprises post-herpetic neuralgia, small fiber neuropathy or idiopathic small-fiber neuropathy. As used herein, the phrase "idiopathic small-fiber neuropathy" shall be understood to include any small fiber neuropathy.

In another aspect, the invention features a compound of the invention, or a pharmaceutically acceptable salt or pharmaceutical composition thereof, for use in a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, small fiber neuropathy, idiopathic small-fiber neuropathy, idiopathic sensory neuropathy or trigeminal autonomic cephalalgia.

In another aspect, the invention features a compound of the invention, or a pharmaceutically acceptable salt or pharmaceutical composition thereof, for use in a method of treating or lessening the severity in a subject of musculoskeletal pain. In some aspects, the musculoskeletal pain comprises osteoarthritis pain.

In another aspect, the invention features a compound of the invention, or a pharmaceutically acceptable salt or pharmaceutical composition thereof, for use in a method of treating or lessening the severity in a subject of musculoskeletal pain, wherein musculoskeletal pain comprises osteoarthritis pain, back pain, cold pain, burn pain or dental pain.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain or vulvodynia.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain.

In another aspect, the invention features a compound of the invention, or a pharmaceutically acceptable salt or pharmaceutical composition thereof, for use in a method of treating or lessening the severity in a subject of idiopathic pain, wherein idiopathic pain comprises fibromyalgia pain.

In another aspect, the invention features a compound of the invention, or a pharmaceutically acceptable salt or pharmaceutical composition thereof, for use in a method of treating or lessening the severity in a subject of pathological cough.

In another aspect, the invention features a compound of the invention, or a pharmaceutically acceptable salt or pharmaceutical composition thereof, for use in a method of treating or lessening the severity in a subject of acute pain. In some aspects, the acute pain comprises acute post-operative pain.

In another aspect, the invention features a compound of the invention, or a pharmaceutically acceptable salt or pharmaceutical composition thereof, for use in a method of treating or lessening the severity in a subject of postsurgical pain (e.g., herniorrhaphy pain, bunionectomy pain or abdominoplasty pain).

In another aspect, the invention features a compound of the invention, or a pharmaceutically acceptable salt or pharmaceutical composition thereof, for use in a method of treating or lessening the severity in a subject of bunionectomy pain.

In another aspect, the invention features a compound of the invention, or a pharmaceutically acceptable salt or pharmaceutical composition thereof, for use in a method of treating or lessening the severity in a subject of heriorrhaphy pain.

In another aspect, the invention features a compound of the invention, or a pharmaceutically acceptable salt or pharmaceutical composition thereof, for use in a method of treating or lessening the severity in a subject of abdominoplasty pain.

In another aspect, the invention features a compound of the invention, or a pharmaceutically acceptable salt or pharmaceutical composition thereof, for use in a method of treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for use in a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a compound of the invention, or a pharmaceutically acceptable salt or pharmaceutical composition thereof, for use in a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a compound of the invention, or a pharmaceutically acceptable salt or pharmaceutical composition thereof, for use in a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., herniorrhaphy pain, bunionectomy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention features a compound of the invention, or a pharmaceutically acceptable salt or pharmaceutical composition thereof, for use in a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain.

Manufacture of Medicaments

In another aspect, the invention provides the use of a compound of the invention, or a pharmaceutically acceptable salt or pharmaceutical composition thereof, for the manufacture of a medicament.

In another aspect, the invention provides the use of a compound of the invention, a pharmaceutically acceptable salt thereof, or a pharmaceutical composition thereof for the manufacture of a medicament for use in inhibiting a voltage-gated sodium channel. In another aspect, the voltage-gated sodium channel is $Na_V1.8$.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain (e.g., herniorrhaphy pain, bunionectomy pain or abdominoplasty pain), visceral pain, multiple sclerosis, Charcot-Marie-Tooth syndrome, incontinence, pathological cough, or cardiac arrhythmia.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia.

In yet another aspect, the invention provides the use of the compound, pharmaceutically acceptable salt, or pharmaceutical composition described herein for the manufacture of a medicament for use in treating or lessening the severity in a subject of gut pain, wherein gut pain comprises inflammatory bowel disease pain, Crohn's disease pain or interstitial cystitis pain.

In yet another aspect, the invention provides a compound of the invention, a pharmaceutically acceptable salt thereof, or a pharmaceutical composition thereof for the manufacture of a medicament for use in treating or lessening the severity in a subject of neuropathic pain. In some aspects, the neuropathic pain comprises post-herpetic neuralgia, small fiber neuropathy or idiopathic small-fiber neuropathy.

In yet another aspect, the invention provides the use of a compound of the invention, a pharmaceutically acceptable salt thereof, or a pharmaceutical composition thereof for the manufacture of a medicament for use in a treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, small fiber neuropathy, idiopathic small-fiber neuropathy, idiopathic sensory neuropathy or trigeminal autonomic neuropathy.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain. In some aspects the musculoskeletal pain comprises osteoarthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain, wherein musculoskeletal pain comprises osteoarthritis pain, back pain, cold pain, burn pain or dental pain.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain or vulvodynia.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of idiopathic pain, wherein idiopathic pain comprises fibromyalgia pain.

In yet another aspect, the invention provides the use of a compound of the invention, a pharmaceutically acceptable salt thereof, or a pharmaceutical composition thereof for the manufacture of a medicament for use in treating or lessening the severity in a subject of pathological cough.

In yet another aspect, the invention provides the use of a compound of the invention, a pharmaceutically acceptable salt thereof, or a pharmaceutical composition thereof for the manufacture of a medicament for use in treating or lessening the severity in a subject of acute pain. In some aspects, the acute pain comprises acute post-operative pain.

In yet another aspect, the invention provides the use of a compound of the invention, a pharmaceutically acceptable salt thereof, or a pharmaceutical composition thereof for the manufacture of a medicament for use in treating or lessening the severity in a subject of postsurgical pain (e.g., herniorrhaphy pain, bunionectomy pain or abdominoplasty pain).

In yet another aspect, the invention provides the use of a compound of the invention, a pharmaceutically acceptable salt thereof, or a pharmaceutical composition thereof for the manufacture of a medicament for use in treating or lessening the severity in a subject of herniorrhaphy pain.

In yet another aspect, the invention provides the use of a compound of the invention, a pharmaceutically acceptable salt thereof, or a pharmaceutical composition thereof for the manufacture of a medicament for use in treating or lessening the severity in a subject of bunionectomy pain.

In yet another aspect, the invention provides the use of a compound of the invention, a pharmaceutically acceptable salt thereof, or a pharmaceutical composition thereof for the manufacture of a medicament for use in treating or lessening the severity in a subject of abdominoplasty pain.

In yet another aspect, the invention provides the use of a compound of the invention, a pharmaceutically acceptable salt thereof, or a pharmaceutical composition thereof for the manufacture of a medicament for use in treating or lessening the severity in a subject of visceral pain. In some aspects, the visceral pain comprises visceral pain from abdominoplasty.

In yet another aspect, the invention provides the use of a compound of the invention, a pharmaceutically acceptable salt thereof, or a pharmaceutical composition thereof for the manufacture of a medicament for use in combination with one or more additional therapeutic agents administered concurrently with, prior to, or subsequent to treatment with the compound or pharmaceutical composition. In some embodiments, the additional therapeutic agent is a sodium channel inhibitor.

In another aspect, the invention provides the use of a compound of the invention, a pharmaceutically acceptable salt thereof, or a pharmaceutical composition thereof for the manufacture of a medicament for use in treating or lessening the severity of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., herniorrhaphy pain, bunionectomy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention provides the use of a compound of the invention, a pharmaceutically acceptable salt thereof, or a pharmaceutical composition thereof for the manufacture of a medicament for use in treating or lessening the severity of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence; pathological cough; hyperactive bladder; painful bladder syndrome; interstitial cystitis (IC); prostatitis; complex regional pain syndrome (CRPS) type I; complex regional pain syndrome (CRPS) type II; widespread pain, paroxysmal extreme pain, pruritus, tinnitus, or angina-induced pain.

Administration of Pharmaceutically acceptable salts and compositions.

In certain embodiments of the invention an "effective amount" of a compound of the invention, a pharmaceutically acceptable salt thereof, or a pharmaceutical composition thereof is that amount effective for treating or lessening the severity of one or more of the conditions recited above.

The compounds, salts, and compositions, according to the method of the invention, may be administered using any amount and any route of administration effective for treating or lessening the severity of one or more of the pain or non-pain diseases recited herein. The exact amount required will vary from subject to subject, depending on the species, age, and general condition of the subject, the severity of the condition, the particular agent, its mode of administration, and the like. The compounds, salts, and compositions of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds, salts, and compositions of the invention will be decided by the attending physician within the scope of sound medical judgment. The specific effective dose level for any particular subject or organism will depend upon a variety of factors including the disorder being treated and the severity of the disorder; the activity of the specific compound or salt employed; the specific composition employed; the age, body weight, general health, sex and diet of the subject; the time of administration, route of administration, and rate of excretion of the specific compound or salt employed; the duration of the treatment; drugs used in combination or coincidental with the specific compound or salt employed, and like factors well known in the medical arts. The term "subject" or "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compound, salts, and compositions of the invention may be administered orally or parenterally at dosage levels of about 0.001 mg/kg to about 100 mg/kg, or about 0.01 mg/kg to about 50 mg/kg, of subject body weight per day, one or more times a day, effective to obtain the desired therapeutic effect.

Liquid dosage forms for oral administration include, but are not limited to, pharmaceutically acceptable emulsions, microemulsions, solutions, suspensions, syrups and elixirs. In addition to the active compound or salt, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the compounds of the invention, it is often desirable to slow the absorption of the compounds from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compound or salt of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound or salt is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragées, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compound or salt can also be in microencapsulated form with one or more excipients as noted above. The solid dosage forms of tablets, dragées, capsules, pills, and granules can be prepared with coatings and shells such as enteric coatings, release controlling coatings and other coatings well known in the pharmaceutical formulating art. In such solid dosage forms the active compound or salt may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound or salt of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium channels. In one embodiment, the compounds are inhibitors of $Na_V1.8$ and thus, without wishing to be bound by any particular theory, the compounds, salts, and compositions are particularly useful for treating or lessening the severity of a disease, condition, or disorder where activation or hyperactivity of $Na_V1.8$ is implicated in the disease, condition, or disorder. When activation or hyperactivity of $Na_V1.8$ is implicated in a particular disease, condition, or disorder, the disease, condition, or disorder may also be referred to as a "$Na_V$1.8-mediated disease, condition or disorder." Accordingly, in another aspect, the invention provides a method for treating or lessening the severity of a disease, condition, or disorder where activation or hyperactivity of $Na_V$1.8 is implicated in the disease state.

The activity of a compound utilized in this invention as an inhibitor of $Na_V$1.8 may be assayed according to methods described generally in International Publication No. WO 2014/120808 A9 and U.S. Publication No. 2014/0213616 A1, both of which are incorporated by reference in their entirety, methods described herein, and other methods known and available to one of ordinary skill in the art.

Additional Therapeutic Agents

It will also be appreciated that the compounds, salts, and pharmaceutically acceptable compositions of the invention can be employed in combination therapies, that is, the compounds, salts, and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: non-opioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Nineteenth Edition, Ed. Robert S. Porter and Justin L. Kaplan, Merck Sharp & Dohme Corp., a subsidiary of Merck & Co., Inc., 2011, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, pentazocine, or difelikefalin;

(2) a nonsteroidal antiinflammatory drug (NSAID), e.g. aspirin, diclofenac, diflunisal, etodolac, fenbufen, fenoprofen, flufenisal, flurbiprofen, ibuprofen (including without limitation intravenous ibuprofen (e.g., Caldolor®)), indomethacin, ketoprofen, ketorolac (including without limitation ketorolac tromethamine (e.g., Toradol®)), meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

(4) a benzodiazepine having a sedative action, e.g. chlordiazepoxide, clorazepate, diazepam, flurazepam, lorazepam, oxazepam, temazepam or triazolam;

(5) a histamine ($H_1$) antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphenadrine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmedetomidine, modafinil, or 4-amino-6,7-dimethoxy-2-(5-methane-sulfonamido-1, 2,3,4-tetrahydroisoquinolin-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine (Tegretol®), lamotrigine, topiramate, lacosamide (Vimpat®) or valproate;

(12) a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin or civamide) or antagonist (e.g. capsazepine, GRC-15300);

(18) a beta-adrenergic such as propranolol;

(19) a local anesthetic such as mexiletine;

(20) a corticosteroid such as dexamethasone;

(21) a 5-HT receptor agonist or antagonist, particularly a 5-$HT_{1B/1D}$ agonist such as eletriptan, sumatriptan, naratriptan, zolmitriptan or rizatriptan;

(22) a 5-$HT_{2A}$ receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®, Tramadol ER (Ultram ER®), Tapentadol ER (Nucynta®);

(25) a PDE5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d] pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-amino-methyl-bicyclo[3.2.0] hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid such as KHK-6188;

(28) metabotropic glutamate subtype 1 receptor (mGluR1) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, bupropion, bupropion metabolite hydroxybupropion, nomifensine and viloxazine (Vivalan®), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethylvenlafaxine, clomipramine, clomipramine metabolite desmethylclomipramine, duloxetine (Cymbalta®), milnacipran and imipramine;

(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl] phenyl]thiophene-2-carboxamidine, NXN-462, or guanidinoethyldisulfide;

(33) an acetylcholinesterase inhibitor such as donepezil;

(34) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy) pyridin-3-yl]carbonyl}amino)ethyl]benzoic acid;

(35) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

(36) a 5-lipoxygenase inhibitor, such as zileuton, 6-[(3-fluoro-5-[4-methoxy-3,4,5,6-tetrahydro-2H-pyran-4-yl]) phenoxy-methyl]-1-methyl-2-quinolone (ZD-2138), or 2,3,5-trimethyl-6-(3-pyridylmethyl)-1,4-benzoquinone (CV-6504);

(37) a sodium channel blocker, such as lidocaine, lidocaine plus tetracaine cream (ZRS-201) or eslicarbazepine acetate;

(38) a $Na_V1.7$ blocker, such as XEN-402, XEN403, TV-45070, PF-05089771, CNV1014802, GDC-0276, RG7893 BIIB-074, BIIB-095, ASP-1807, DSP-3905, OLP-1002, RQ-00432979, FX-301, DWP-17061, IMB-110, IMB-111, IMB-112 and such as those disclosed in WO2011/140425 (US2011/306607); WO2012/106499 (US2012196869); WO2012/112743 (US2012245136); WO2012/125613 (US2012264749), WO2012/116440 (US2014187533), WO2011026240 (US2012220605), U.S. Pat. Nos. 8,883,840, 8,466,188, or WO2013/109521 (US2015005304), the entire contents of each application hereby incorporated by reference.

(38a) a $Na_V1.7$ blocker such as (2-benzylspiro[3,4-dihydropyrrolo[1,2-a]pyrazine-1,4'-piperidine]-1'-yl)-(4-isopropoxy-3-methyl-phenyl)methanone, 2,2,2-trifluoro-1-[1'-[3-methoxy-4-[2-(trifluoromethoxy)ethoxy]benzoyl]-2,4-dimethyl-spiro[3,4-dihydropyrrolo[1,2-a]pyrazine-1,4'-piperidine]-6-yl]ethanone, [8-fluoro-2-methyl-6-(trifluoromethyl)spiro[3,4-dihydropyrrolo[1,2-a]pyrazine-1,4'-piperidine]-1'-yl]-(4-isobutoxy-3-methoxy-phenyl)methanone, 1-(4-benzhydrylpiperazin-1-yl)-3-[2-(3,4-dimethylphenoxy)ethoxy]propan-2-ol, (4-butoxy-3-methoxy-phenyl)-[2-methyl-6-(trifluoromethyl)spiro[3,4-dihydropyrrolo[1,2-a]pyrazine-1,4'-piperidine]-1'-yl]methanone, [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone, (4-isopropoxy-3-methyl-phenyl)-[2-methyl-6-(1,1,2,2,2-pentafluoroethyl)spiro[3,4-dihydropyrrolo[1,2-a]pyrazine-1,4'-piperidine]-1'-yl]methanone, 5-[2-methyl-4-[2-methyl-6-(2,2,2-trifluoroacetyl)spiro[3,4-dihydropyrrolo[1,2-a]pyrazine-1,4'-piperidine]-1'-carbonyl]phenyl]pyridine-2-carbonitrile, (4-isopropoxy-3-methyl-phenyl)-[6-(trifluoromethyl)spiro[3,4-dihydro-2H-pyrrolo[1,2-a]pyrazine-1,4'-piperidine]-1'-yl]methanone, 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl]ethanone, 2,2,2-trifluoro-1-[1'-(5-isopropoxy-6-methyl-pyridine-2-carbonyl)-3,3-dimethyl-spiro[2,4-dihydropyrrolo[1,2-a]pyrazine-1,4'-piperidine]-6-yl]ethanone, 2,2,2-trifluoro-1-[1'-(5-isopentyloxypyridine-2-carbonyl)-2-methyl-spiro[3,4-dihydropyrrolo[1,2-a]pyrazine-1,4'-piperidine]-6-yl]ethanone, (4-isopropoxy-3-methoxy-phenyl)-[2-methyl-6-(trifluoromethyl)spiro[3,4-dihydropyrrolo[1,2-a]pyrazine-1,4'-piperidine]-1'-yl]methanone, 2,2,2-trifluoro-1-[1'-(5-isopentyloxypyridine-2-carbonyl)-2,4-dimethyl-spiro[3,4-dihydropyrrolo[1,2-a]pyrazine-1,4'-piperidine]-6-yl]ethanone, 1-[(3S)-2,3-dimethyl-1'-[4-(3,3,3-trifluoropropoxymethyl)benzoyl]spiro[3,4-dihydropyrrolo[1,2-a]pyrazine-1,4'-piperidine]-6-yl]-2,2,2-trifluoro-ethanone, [8-fluoro-2-methyl-6-(trifluoromethyl)spiro[3,4-dihydropyrrolo[1,2-a]pyrazine-1,4'-piperidine]-1'-yl]-[3-methoxy-4-[(1R)-1-methylpropoxy]phenyl]methanone, 2,2,2-trifluoro-1-[1'-(5-isopropoxy-6-methyl-pyridine-2-carbonyl)-2,4-dimethyl-spiro[3,4-dihydropyrrolo[1,2-a]pyrazine-1,4'-piperidine]-6-yl]ethanone, 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one, (4-isopropoxy-3-methyl-phenyl)-[2-methyl-6-(trifluoromethyl)spiro[3,4-dihydropyrrolo[1,2-a]pyrazine-1,4'-piperidine]-1'-yl]methanone, [2-methyl-6-(1-methylcyclopropanecarbonyl)spiro[3,4-dihydropyrrolo[1,2-a]pyrazine-1,4'-piperidine]-1'-yl]-[4-(3,3,3-trifluoropropoxymethyl)phenyl]methanone, 4-bromo-N-(4-bromophenyl)-3-[(1-methyl-2-oxo-4-piperidyl)sulfamoyl]benzamide or (3-chloro-4-isopropoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone.

(39) a $Na_V1.8$ blocker, such as PF-04531083, PF-06372865 and such as those disclosed in WO2008/135826 (US2009048306), WO2006/011050 (US2008312235), WO2013/061205 (US2014296313), US20130303535, WO2013131018, U.S. Pat. No. 8,466,188, WO2013114250 (US2013274243), WO2014/120808 (US2014213616), WO2014/120815 (US2014228371) WO2014/120820 (US2014221435), WO2015/010065 (US20160152561), WO2015/089361 (US20150166589) and WO2019014352 (US20190016671), the entire contents of each application hereby incorporated by reference.

(39a) a $Na_V1.8$ blocker such as 4,5-dichloro-2-(4-fluoro-2-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-4-(perfluoroethyl)benzamide, 4,5-dichloro-2-(4-fluorophenoxy)-N-(2-oxo-1,2-dihydropyridin-4-yl)benzamide, 4,5-dichloro-2-(3-fluoro-4-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-5-(trifluoromethyl)benzamide, N-(2-oxo-1,2-dihydropyridin-4-yl)-2-(4-(trifluoromethoxy)phenoxy)-4-(trifluoromethyl)benzamide, 2-(4-fluorophenoxy)-N-(2-oxo-1,2-dihydropyridin-4-yl)-4-(perfluoroethyl)benzamide, 5-chloro-2-(4-fluoro-2-methoxyphenoxy)-N-(2-oxo-1,2-dihydropyridin-4-yl)benzamide, N-(2-oxo-1,2-dihydropyridin-4-yl)-2-(4-(trifluoromethoxy)phenoxy)-5-(trifluoromethyl)benzamide, 2-(4-fluoro-2-methylphenoxy)-N-(2-oxo-1,2-dihydropyridin-4-yl)-5-(trifluoromethyl)benzamide, 2-(2-chloro-4-fluorophenoxy)-N-(2-oxo-1,2-dihydropyridin-4-yl)-5-(trifluoromethyl)benzamide, 5-chloro-2-(4-fluoro-2-methylphenoxy)-N-(2-oxo-1,2-dihydropyridin-4-yl)benzamide, 4-chloro-2-(4-fluoro-2-methylphenoxy)-N-(2-oxo-1,2-dihydropyridin-4-yl)benzamide, 5-chloro-2-(2-chloro-4-fluorophenoxy)-N-(2-oxo-1,2-dihydropyridin-4-yl)benzamide, 2-((5-fluoro-2-hydroxybenzyl)oxy)-N-(2-oxo-1,2-dihydropyridin-4-yl)-4-(trifluoromethyl)benzamide, N-(2-oxo-1,2-dihydropyridin-4-yl)-2-(o-tolyloxy)-5-(trifluoromethyl)benzamide, 2-(2,4-difluorophenoxy)-N-(2-oxo-1,2-dihydropyridin-4-yl)-4-(trifluoromethyl)benzamide, N-(2-oxo-1,2-dihydropyridin-4-yl)-2-(2-(trifluoromethoxy)phenoxy)-5-(trifluoromethyl)benzamide, 2-(4-fluorophenoxy)-N-(2-oxo-1,2-dihydropyridin-4-yl)-5-(trifluoromethyl)benzamide, 2-(4-fluoro-2-methyl-phenoxy)-N-(2-oxo-1H-pyridin-4-yl)-4-(trifluoromethyl)benzamide, [4-[[2-(4-fluoro-2-methyl-phenoxy)-4-(trifluoromethyl)benzoyl]amino]-2-oxo-1-pyridyl]methyl dihydrogen phosphate, 3-(4-fluoro-2-methoxyphenoxy)-N-(3-(methylsulfonyl)phenyl)quinoxaline-2-carboxamide, 3-(2-chloro-4-fluorophenoxy)-N-(3-sulfamoylphenyl)quinoxaline-2-carboxamide, 3-(2-chloro-4-methoxyphenoxy)-N-(3-sulfamoylphenyl)quinoxaline-2-carboxamide, 3-(4-chloro-2-methoxyphenoxy)-N-(3-sulfamoylphenyl)quinoxaline-2-carboxamide, 4-(3-(4-(trifluoromethoxy)phenoxy)quinoxaline-2-carboxamido)picolinic acid, 2-(2,4-difluorophenoxy)-N-(3-sulfamoylphenyl)quinoline-3-carboxamide, 2-(4-fluoro-2-methoxyphenoxy)-N-(3-sulfamoylphenyl)quinoline-3-carboxamide, 3-(2,4-difluorophenoxy)-N-(3-sulfamoylphenyl)quinoxaline-2-carboxamide, N-(3-sulfamoylphenyl)-2-(4-(trifluoromethoxy)phenoxy)quinoline-3-carboxamide, N-(3-sulfamoylphenyl)-3-(4-(trifluoromethoxy)phenoxy)quinoxaline-2-carboxamide, 3-(4-chloro-2-methylphenoxy)-N-(3-sulfamoylphenyl)quinoxaline-2-carboxamide, 5-(3-(4-(trifluoromethoxy)phenoxy)quinoxaline-2-carboxamido)picolinic acid, 3-(4-fluoro-2-methoxyphenoxy)-N-(2-oxo-2,3-dihydro-1H-benzo[d]imidazol-5-yl)quinoxaline-2-carboxamide, 3-(4-fluoro-2-methoxyphenoxy)-N-(pyridin-4-yl)quinoxaline-2-carboxamide, 3-(4-fluorophenoxy)-N-(3-sulfamoylphenyl)quinoxaline-2-carboxamide, N-(3-cyanophenyl)-3-(4-fluoro-2-methoxyphenoxy)quinoxaline-2-carboxamide, N-(4-carbamoylphenyl)-3-(4-fluoro-2-methoxyphenoxy)quinoxaline-2-carboxamide, 4-(3-(4-(trifluoromethoxy)phenoxy)quinoxaline-2-carboxamido)benzoic acid, N-(4-cyanophenyl)-3-(4-fluoro-2-methoxyphenoxy)quinoxaline-2-carboxamide, 5-(4,5-dichloro-2-(4-fluoro-2-methoxyphenoxy)benzamido)picolinic acid, 5-(2-(2,4-dimethoxyphenoxy)-4,6-bis(trifluoromethyl)benzamido)picolinic acid, 4-(4,5-dichloro-2-(4-fluoro-2-methoxyphenoxy)benzamido)benzoic acid, 5-(2-(4-fluoro-2-methoxyphenoxy)-4,6-bis(trifluoromethyl)benzamido)picolinic acid, 4-(2-(4-fluoro-2-methoxyphenoxy)-4-(perfluoroethyl)benzamido)benzoic acid, 5-(2-(4-fluoro-2-methoxyphenoxy)-4-(perfluoroethyl)benzamido)picolinic acid, 4-(2-(4-fluoro-2-methylphenoxy)-4-(trifluoromethyl)benzamido)benzoic acid, 5-(4,5-dichloro-2-(4-fluoro-2-methoxyphenoxy)benzamido)picolinic acid, 4-(2-(2-chloro-4-fluorophenoxy)-4-(perfluoroethyl)benzamido)benzoic acid, 4-(2-(4-fluoro-2-methylphenoxy)-4-(perfluoroethyl)benzamido)benzoic acid, 4-(4,5-dichloro-2-(4-(trifluoromethoxy)phenoxy)benzamido)benzoic acid, 4-(4,5-dichloro-2-(4-chloro-2-methylphenoxy)benzamido)benzoic acid, 5-(4-(tert-butyl)-2-(4-fluoro-2-methoxyphenoxy)benzamido)picolinic acid, 5-(4,5-dichloro-2-(4-(trifluoromethoxy)phenoxy)benzamido)picolinic acid, 4-(4,5-dichloro-2-(4-fluoro-2-methylphenoxy)benzamido)benzoic acid, 5-(4,5-dichloro-2-(2,4-dimethoxyphenoxy)benzamido)picolinic acid, 5-(4,5-dichloro-2-(2-chloro-4-fluorophenoxy)benzamido)picolinic acid, 5-(4,5-dichloro-2-(4-fluoro-2-methylphenoxy)benzamido)picolinic acid, 4-(4,5-dichloro-2-(4-chloro-2-methoxyphenoxy)benzamido)benzoic acid, 5-(4,5-dichloro-2-(2,4-difluorophenoxy)benzamido)picolinic acid, 2-(4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-6-(trifluoromethyl)benzamide, 2-(2-chloro-4-fluorophenoxy)-5-(difluoromethyl)-N-(3-sulfamoylphenyl)benzamide, 2-(4-fluorophenoxy)-4-(perfluoroethyl)-N-(3-sulfamoylphenyl)benzamide, 2-(4-chloro-2-methoxyphenoxy)-4-(perfluoroethyl)-N-(3-sulfamoylphenyl)benzamide, 2-(4-fluoro-2-methoxyphenoxy)-N-(3-sulfamoylphenyl)-5-(trifluoromethyl)benzamide, 5-chloro-2-(4-fluoro-2-methylphenoxy)-N-(3-sulfamoylphenyl)benzamide, 4,5-dichloro-2-(4-fluoro-2-methoxyphenoxy)-N-(3-sulfamoylphenyl)benzamide, 2,4-dichloro-6-(4-chloro-2-methoxyphenoxy)-N-(3-sulfamoylphenyl)benzamide, 2,4-dichloro-6-(4-fluoro-2-methylphenoxy)-N-(3-sulfamoylphenyl)benzamide, 2-(4-fluoro-2-methoxyphenoxy)-N-(3-sulfamoylphenyl)-4,6-bis(trifluoromethyl)benzamide, 2-(4-fluoro-2-methylphenoxy)-N-(3-sulfamoylphenyl)-4,6-bis(trifluoromethyl)benzamide, 5-chloro-2-(2-chloro-4-fluorophenoxy)-N-(3-sulfamoylphenyl)benzamide, 2-(4-fluoro-2-methoxyphenoxy)-N-(3-sulfamoylphenyl)-4-(trifluoromethoxy)benzamide, 2-(4-fluoro-2-methoxyphenoxy)-N-(3-sulfamoylphenyl)-4-(trifluoromethyl)benzamide, 4,5-dichloro-2-(4-fluorophenoxy)-N-(3-sulfamoylphenyl)benzamide, 2-(4-fluoro-2-methoxyphenoxy)-4-(perfluoroethyl)-N-(3-sulfamoylphenyl)benzamide, 5-fluoro-2-(4-fluoro-2-methylphenoxy)-N-(3-sulfamoylphenyl)benzamide, 2-(2-chloro-4-fluorophenoxy)-4-cyano-N-(3-sulfamoylphenyl)benzamide, N-(3-sulfamoylphenyl)-2-(4-(trifluoromethoxy)phenoxy)-4-(trifluoromethyl)benzamide, N-(3-carbamoyl-4-fluoro-phenyl)-2-fluoro-6-[2-(trideuteriomethoxy)-4-(trifluoromethoxy)phenoxy]-3-(trifluoromethyl)benzamide, N-(3-carbamoyl-4-fluoro-phenyl)-2-fluoro-6-[2-methoxy-4-(trifluoromethoxy)phenoxy]-3-(trifluoromethyl)benzamide, N-(3-carbamoyl-4-fluoro-phenyl)-2-fluoro-6-[2-(trideuteriomethoxy)-4-(trifluoromethoxy)phenoxy]-3-(trifluoromethoxy)benzamide, 4-[[2-fluoro-6-[2-methoxy-4-(trifluoromethoxy)phenoxy]-3-(trifluoromethyl)benzoyl]amino]pyridine-2-carboxamide, 4-[[3-chloro-2-fluoro-6-[2-methoxy-4-(trifluoromethoxy)phenoxy]benzoyl]amino]pyridine-2-carboxamide, 4-[[2-fluoro-6-[2-(trideuteriomethoxy)-4-(trifluoromethoxy)phenoxy]-3-(trifluoromethyl)benzoyl]amino]pyridine-2-carboxamide, N-(3-carbamoyl-4-fluoro-phenyl)-3-(difluoromethyl)-2-fluoro-6-[2-methoxy-4-(trifluoromethoxy)phenoxy]benzamide, 4-[[2-fluoro-6-[2-(trideuteriomethoxy)-4-(trifluoromethoxy)phenoxy]-3-(trifluoromethoxy)benzoyl]amino]pyridine-2-carboxamide, N-(3-carbamoyl-4-fluoro-phenyl)-6-[2-chloro-4-(trifluoromethoxy)phenoxy]-2-fluoro-3-(trifluoromethyl)benzamide, N-(3-carbamoyl-4-fluoro-phenyl)-2-fluoro-6-[2-methyl-4-(trifluoromethoxy)phenoxy]-3-(trifluoromethyl)benzamide, N-(3-carbamoyl-4-fluoro-phenyl)-2,3,4-trifluoro-6-[2-methoxy-4-(trifluoromethoxy)phenoxy]benzamide, N-(2-carbamoyl-4-pyridyl)-3-fluoro-5-[2-methoxy-4-(trifluoromethoxy)phenoxy]-2-(trifluoromethyl)pyridine-4-carboxamide, 4-[[6-[2-(difluoromethoxy)-4-(trifluoromethoxy)phenoxy]-2-fluoro-3-(trifluoromethyl)benzoyl]amino]pyridine-2-carboxamide, N-(3-carbamoyl-4-fluoro-phenyl)-6-[3-chloro-4-(trifluoromethoxy)phenoxy]-2-fluoro-3-(trifluoromethyl)benzamide, N-(3-carbamoyl-4-fluoro-phenyl)-2-fluoro-6-[4-(trifluoromethoxy)phenoxy]-3-(trifluoromethyl)benzamide, N-(4-carbamoyl-3-fluoro-phenyl)-2-fluoro-6-[2-methoxy-4-(trifluoromethoxy)phenoxy]-3-(trifluoromethyl)benzamide, 4-[[2-fluoro-6-[2-(trideuteriomethoxy)-4-(trifluoromethoxy)phenoxy]-4-(trifluoromethyl)benzoyl]amino]pyridine-2-carboxamide, N-(3-carbamoyl-4-fluoro-phenyl)-2-fluoro-6-[3-fluoro-4-(trifluoromethoxy)phenoxy]-3-(trifluoromethyl)benzamide, N-(3-carbamoyl-4-fluoro-phenyl)-2-[2-methoxy-4-(trifluoromethoxy)phenoxy]-5-(1,1,2,2,2-pentafluoroethyl)benzamide, 4-[[4-(difluoromethoxy)-2-fluoro-6-[2-methoxy-4-(trifluoromethoxy)phenoxy]benzoyl]amino]pyridine-2-carboxamide, N-(3-carbamoyl-4-fluoro-phenyl)-2-fluoro-6-[2-fluoro-4-(trifluoromethoxy)phenoxy]-3-(trifluoromethyl)benzamide, 4-[[4-cyclopropyl-2-fluoro-6-[2-methoxy-4-(trifluoromethoxy)phenoxy]benzoyl]amino]pyridine-2-carboxamide, N-(3-carbamoyl-4-fluoro-phenyl)-5-fluoro-2-[2-methoxy-4-(trifluoromethoxy)phenoxy]-4-(trifluoromethyl)benzamide, 5-[[2-fluoro-6-[2-(trideuteriomethoxy)-4-(trifluoromethoxy)phenoxy]-3-(trifluoromethyl)benzoyl]amino]pyridine-2-carboxamide, N-(3-carbamoyl-4-fluoro-phenyl)-2-fluoro-6-(4-fluorophenoxy)-3-(trifluoromethyl)benzamide, or 4-[[2-fluoro-6-[3-fluoro-2-methoxy-4-(trifluoromethoxy)phenoxy]-3-(trifluoromethyl)benzoyl]amino]pyridine-2-carboxamide.

(40) a combined $Na_V1.7$ and $Na_V1.8$ blocker, such as DSP-2230, Lohocla201 or BL-1021;

(41) a 5-HT3 antagonist, such as ondansetron;

(42) a TPRV 1 receptor agonist, such as capsaicin (NeurogesX®, Qutenza®); and the pharmaceutically acceptable salts and solvates thereof,

(43) a nicotinic receptor antagonist, such as varenicline;

(44) an N-type calcium channel antagonist, such as Z-160;

(45) a nerve growth factor antagonist, such as tanezumab;

(46) an endopeptidase stimulant, such as senrebotase;

(47) an angiotensin II antagonist, such as EMA-401;

(48) acetaminophen (including without limitation intravenous acetaminophen (e.g., Ofirmev®));

(49) bupivacaine (including without limitation bupivacaine liposome injectable suspension (e.g., Exparel®) bupivacaine ER (Posimir), bupivacaine collagen (Xaracoll) and transdermal bupivacaine (Eladur®)); and

(50) bupivacaine and meloxicam combination (e.g., HTX-011).

In one embodiment, the additional appropriate therapeutic agents are selected from V-116517, Pregabalin, controlled release Pregabalin, Ezogabine (Potiga®). Ketamine/amitriptyline topical cream (Amiket®), AVP-923, Perampanel (E-2007), Ralfinamide, transdermal bupivacaine (Eladur®), CNV1014802, JNJ-10234094 (Carisbamate), BMS-954561 or ARC-4558.

In another embodiment, the additional appropriate therapeutic agents are selected from N-(6-amino-5-(2,3,5-trichlorophenyl)pyridin-2-yl)acetamide; N-(6-amino-5-(2-chloro-5-methoxyphenyl)pyridin-2-yl)-1-methyl-1H-pyrazole-5-carboxamide; or 3-((4-(4-(trifluoromethoxy)phenyl)-1H-imidazol-2-yl)methyl)oxetan-3-amine.

In another embodiment, the additional therapeutic agent is selected from a GlyT2/5HT2 inhibitor, such as Operanserin (VVZ149), a TRPV modulator such as CA008, CMX-020, NE06860, FTABS, CNTX4975, MCP101, MDR16523, or MDR652, a EGRI inhibitor such as Brivoglide (AYX1), an NGF inhibitor such as Tanezumab, Fasinumab, ASP6294, MEDI7352, a Mu opioid agonist such as Cebranopadol, NKTR181 (oxycodegol), a CB-1 agonist such as NEO1940 (AZN1940), an imidazoline 12 agonist such as CR4056 or a p75NTR-Fc modulator such as LEVI-04.

In another embodiment, the additional therapeutic agent is oliceridine or ropivacaine (TLC590).

In another embodiment, the additional therapeutic agent is a sodium channel inhibitor (also known as a sodium channel blocker), such as the $Na_V1.7$ and $Na_V1.8$ blockers identified above.

The amount of additional therapeutic agent present in the compositions of this invention may be no more than the amount that would normally be administered in a composition comprising that therapeutic agent as the only active agent. The amount of additional therapeutic agent in the presently disclosed compositions may range from about 10% to 100% of the amount normally present in a composition comprising that agent as the only therapeutically active agent.

The compounds and salts of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound or salt of the invention as described generally above, and in classes and subclasses herein, and a carrier suitable for coating said implantable device. In still another aspect, the invention includes an implantable device coated with a composition comprising a compound or salt of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting $Na_V1.8$ activity in a biological sample or a subject, which method comprises administering to the subject, or contacting said biological sample with a compound of the invention, a pharmaceutically acceptable salt thereof, or a pharmaceutical composition thereof. The term "biological sample," as used herein, includes, without limitation, cell cultures or extracts thereof, biopsied material obtained from a mammal or extracts thereof, and blood, saliva, urine, feces, semen, tears, or other body fluids or extracts thereof.

Inhibition of $Na_V1.8$ activity in a biological sample is useful for a variety of purposes that are known to one of skill in the art. Examples of such purposes include, but are not limited to, the study of sodium channels in biological and pathological phenomena; and the comparative evaluation of new sodium channel inhibitors.

Synthesis of the Compounds of the Invention

The compounds of the invention can be prepared from known materials by the methods described in the Examples, and other methods known to one skilled in the art.

The compounds of the invention also can be prepared from known materials by the following methods, similar methods, and other methods known to one skilled in the art. As one skilled in the art would appreciate, the functional groups of the intermediate compounds in the methods described below may need to be protected by suitable protecting groups. Protecting groups may be added or removed in accordance with standard techniques, which are well-known to those skilled in the art. The use of protecting groups is described in detail in T. G. M. Wuts et al., *Greene's Protective Groups in Organic Synthesis* (4th ed. 2006).

In general, the compounds of formulas (I) and (II) can be synthesized according to the general methods outlined in Scheme 1 and the specific procedures discussed in the Examples. Scheme 1 depicts the synthesis of the compounds of formula (I). The compounds of formula (II) can be synthesized by analogous methods. The starting materials for the synthesis described in Scheme 1 and the Examples are commercially available or can be prepared according to methods known to one skilled in the art.

Scheme 1. Synthesis of Compounds of Formula (I)

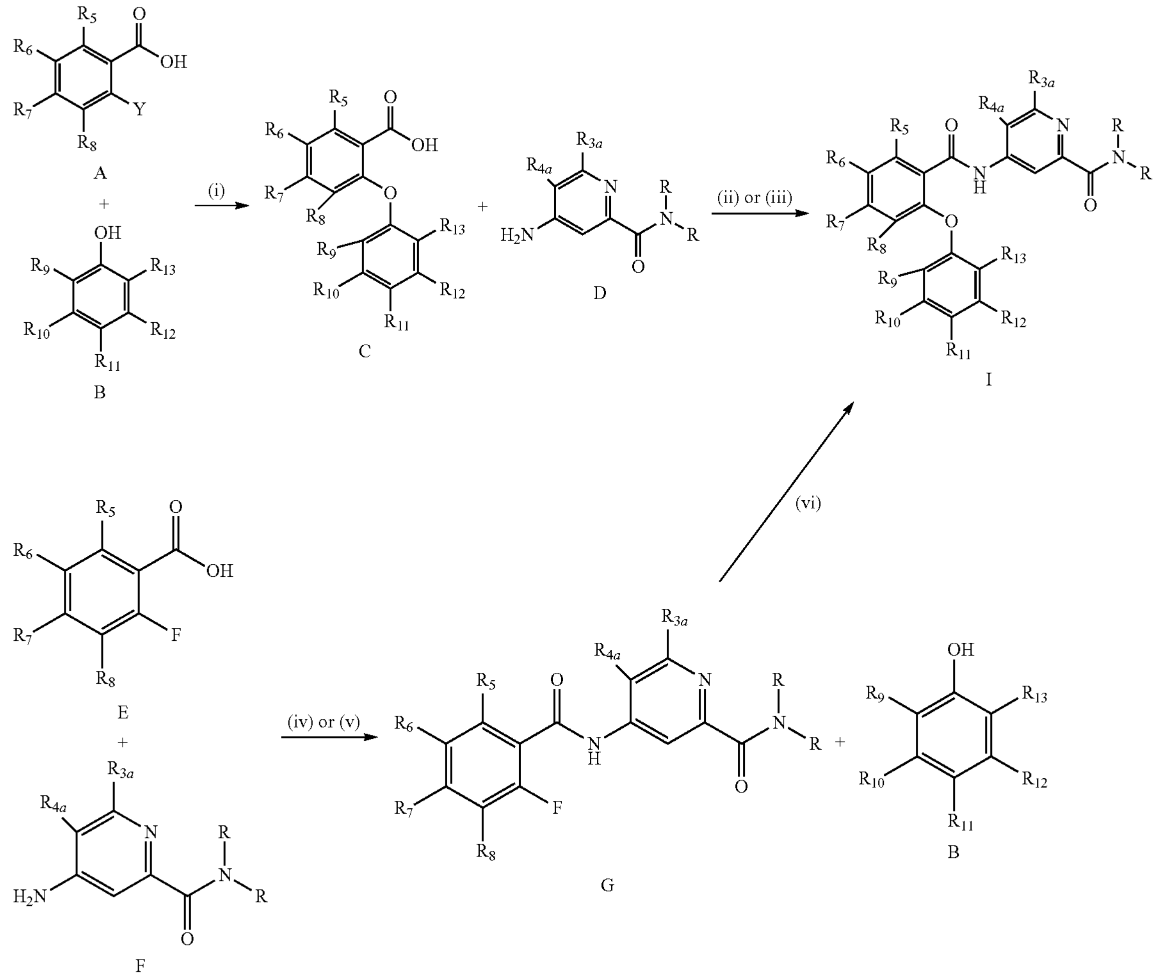

(i) base (e.g., $Cs_2CO_3$), solvent (e.g., toluene), and catalyst (e.g., CuI) (Y = Br, I); or base (e.g., $K_2CO_3$), solvent (e.g., DMF), and heat (Y = F); (ii) oxalyl chloride/thionyl chloride, DMF and solvent (e.g., $CH_2Cl_2$), then D, base (e.g., DIEA), and solvent (e.g., THF); (iii) coupling agent (e.g., HATU, EDCl, HOBT), base (e.g., N-methylmorpholine, $Et_3N$), solvent (e.g., DMF, dichloromethane); (iv) oxalyl chloride/thionyl chloride, DMF and solvent (e.g., $CH_2Cl_2$), then F, base (e.g., DIPEA), and solvent (e.g.,THF, $CH_2Cl_2$); (v) coupling agent (e.g., HATU, EDCl, HOBT), base (e.g., N-methylmorpholine, $Et_3N$), solvent (e.g., DMF, dichloromethane); (vi) base (e.g., $K_2CO_3$), solvent (e.g., DMF), and heat.

Radiolabeled Analogs of the Compounds of the Invention

In another aspect, the invention relates to radiolabeled analogs of the compounds of the invention. As used herein, the term "radiolabeled analogs of the compounds of the invention" refers to compounds that are identical to the compounds of the invention, including the compounds of formulas (I) and (II), and all of the embodiments thereof, as described herein, and the compounds identified in Tables A-D, as described herein, except that one or more atoms has been replaced with a radioisotope of the atom present in the compounds of the invention.

As used herein, the term "radioisotope" refers to an isotope of an element that is known to undergo spontaneous radioactive decay. Examples of radioisotopes include $^{3}H$, $^{4}C$, $^{32}P$ $^{35}S$, $^{18}F$, $^{36}Cl$, and the like, as well as the isotopes for which no decay mode is identified in V. S. Shirley & C. M. Lederer, Isotopes Project, Nuclear Science Division, Lawrence Berkeley Laboratory, Table of Nuclides (January 1980).

The radiolabeled analogs can be used in a number of beneficial ways, including in various types of assays, such as substrate tissue distribution assays. For example, tritium (3H)- and/or carbon-14 ($^{14}C$)-labeled compounds may be useful for various types of assays, such as substrate tissue distribution assays, due to relatively simple preparation and excellent detectability.

In another aspect, the invention relates to pharmaceutically acceptable salts of the radiolabeled analogs, in accordance with any of the embodiments described herein in connection with the compounds of the invention.

In another aspect, the invention relates to pharmaceutical compositions comprising the radiolabeled analogs, or pharmaceutically acceptable salts thereof, and a pharmaceutically acceptable carrier, adjuvant or vehicle, in accordance with any of the embodiments described herein in connection with the compounds of the invention.

In another aspect, the invention relates to methods of inhibiting voltage-gated sodium channels and methods of treating or lessening the severity of various diseases and disorders, including pain, in a subject comprising administering an effective amount of the radiolabeled analogs, pharmaceutically acceptable salts thereof, and pharmaceutical compositions thereof, in accordance with any of the embodiments described herein in connection with the compounds of the invention.

In another aspect, the invention relates to radiolabeled analogs, pharmaceutically acceptable salts thereof, and pharmaceutical compositions thereof, for use, in accordance with any of the embodiments described herein in connection with the compounds of the invention.

In another aspect, the invention relates to the use of the radiolabeled analogs, or pharmaceutically acceptable salts thereof, and pharmaceutical compositions thereof, for the manufacture of medicaments, in accordance with any of the embodiments described herein in connection with the compounds of the invention.

In another aspect, the radiolabeled analogs, pharmaceutically acceptable salts thereof, and pharmaceutical compositions thereof, can be employed in combination therapies, in accordance with any of the embodiments described herein in connection with the compounds of the invention.

EXAMPLES

General methods. $^1$H NMR (400 MHz) spectra were obtained as solutions in an appropriate deuterated solvent such as dimethyl sulfoxide-$d_6$ (DMSO-d6).

Compound purity, retention time, and electrospray mass spectrometry (ESI-MS) data were determined by LC/MS analysis using one of the following methods or in another method described in the individual examples.

LC/MS Method A. LC/MS analysis was conducted using a Waters Acquity Ultra Performance LC system by reverse phase UPLC using an Acquity UPLC BEH $C_{18}$ column (30×2.1 mm, 1.7 m particle) made by Waters (pn: 186002349), and a dual gradient run from 1-99% mobile phase B over 1.0-1.2 minutes. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.

LC/MS Method B. LC/MS analysis was conducted using a Waters Acquity Ultra Performance LC system by reverse phase UPLC using an Acquity UPLC BEH $C_{18}$ column (50×2.1 mm, 1.7 m particle) made by Waters (pn: 186002350), and a dual gradient run from 1-99% mobile phase B over 2.9-3.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

LC/MS Method C. LC/MS analysis was conducted using a Waters Acquity Ultra Performance LC system by reverse phase UPLC using an Acquity UPLC BEH $C_{18}$ column (50×2.1 mm, 1.7 m particle) made by Waters (pn: 186002350), and a dual gradient run from 1-99% mobile phase B over 4.5-5.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

LC/MS Method D. LC/MS analysis was conducted using an Acquity UPLC BEH $C_s$ column (50×2.1 mm, 1.7 μm particle) made by Waters (pn: 186002877) with a (2.1×5 mm, 1.7 m particle) guard column (pn: 186003978), and a dual gradient run from 2-98% mobile phase B over 1.15 minutes. Mobile phase A=$H_2O$ (10 mM ammonium formate with 0.05% ammonium hydroxide). Mobile phase B=acetonitrile. Flow rate=1.0 mL/min, injection volume=2 μL, and column temperature=45° C.

LC/MS Method E. LC/MS analysis was conducted using an Acquity UPLC BEH $C_8$ column (50×2.1 mm, 1.7 μm particle) made by Waters (pn: 186002877) with a (2.1×5 mm, 1.7 m particle) guard column (pn: 186003978), and a dual gradient run from 2-98% mobile phase B over 4.45 minutes. Mobile phase A=$H_2O$ (10 mM ammonium formate with 0.05% ammonium hydroxide). Mobile phase B=acetonitrile. Flow rate=0.6 mL/min, injection volume=2 μL, and column temperature=45° C.

LC/MS Method F. LC/MS analysis was conducted using an Acquity UPLC BEH $C_8$ column (50×2.1 mm, 1.7 μm particle) made by Waters (pn: 186002877) with a (2.1×5 mm, 1.7 m particle) guard column (pn: 186003978), and a dual gradient run from 2-98% mobile phase B over 1.5 minutes. Mobile phase A=$H_2O$ (10 mM ammonium formate with 0.05% ammonium hydroxide). Mobile phase B=acetonitrile. Flow rate=0.6 mL/min, injection volume=2 μL, and column temperature=45° C.

LC/MS Method G. LC/MS analysis was conducted using a Shimadzu 10-A LC system by reverse phase HPLC using an Onyx Monolithic $C_{18}$ column (50×4.6 mm) made by Phenomenex (pn:CHO-7644), and a dual gradient run from 5-100% mobile phase B over 4.2 minutes. Mobile phase A =$H_2O$ (0.1% $CF_3CO_2H$). Mobile phase B=$CH_3CN$ (0.1% $CF_3CO_2H$). Flow rate=1.5 mL/min, injection volume 10 μL and with the column at ambient temperature.

LC/MS Method H. LC/MS analysis was conducted using a Shimadzu 10-A LC system by reverse phase HPLC using an Onyx Monolithic $C_{18}$ column (50×4.6 mm) made by Phenomenex (pn:CHO-7644), and a dual gradient run from 5-100% mobile phase B over 12 minutes. Mobile phase A =$H_2O$ (0.1% $CF_3CO_2H$). Mobile phase B=$CH_3CN$ (0.1% $CF_3CO_2H$). Flow rate=1.5 mL/min, injection volume 10 μL and with the column at ambient temperature.

LC/MS Method I. LC/MS analysis was conducted using an Acquity UPLC HSS T3 $C_s$ column (50×2.1 mm, 1.8 μm particle) made by Waters (pn: 186003538), and a dual gradient run from 1-99% mobile phase B over 2.90 minutes. Mobile phase A=$H_2O$ (10 mM ammonium formate). Mobile phase B=acetonitrile. Flow rate=1.2 mL/min, injection volume=1.5 μL, and column temperature=60° C.

LC/MS Method J. LC/MS analysis was conducted using Cortex 2.7 M $C_{18}$ (3.0 mm×50 mm) column made by Waters, at a temperature of 55° C. with a flow rate of 1.2 mL/minutes and a dual gradient run from 5-100% mobile phase B over 4 minutes. Mobile phase A=water with 0.1% trifluoroacetic (TFA) acid. Mobile phase B=acetonitrile with 0.1% TFA acid.

LC/MS Method K. LC/MS analysis was conducted using a Phenomenex Luna $C_{18}$ column (3×50 mm, 3 m particle) over 2 minutes. Mobile phase conditions: 5-95% acetonitrile (0.1% formic acid) with water (0.1% formic acid) over 1 minute, then hold for 1 minute at 95% acetonitrile (0.1% formic acid). Flow rate=2 mL/min and column temperature 45° C.

LC/MS Method L: LC/MS analysis was conducted using a Phenomenex Kinetex Polar $C_{18}$ column (3×50 mm, 2.6 m particle) over 3 minutes. Mobile phase conditions: 5-95% acetonitrile (0.1% formic acid) in water (0.1% formic acid). Flow rate=1.2 mL/min.

LC/MS Method M: LC/MS analysis was conducted using a Phenomenex Kinetex Polar $C_{18}$ column (3×50 mm, 2.6 m particle, Phenomenex) over 6 minutes. Mobile phase conditions: 5-95% acetonitrile (0.1% formic acid) in water (0.1% formic acid). Flow rate=1.2 mL/min.

LC/MS Method N: LC/MS analysis was conducted using a Millipore Sigma Chromolith SpeedROD $C_{18}$ column (50×4.6 mm, 2 m particle) over 12 minutes. Mobile phase conditions: 5-100% acetonitrile (0.1% trifluoroacetic acid) in water (0.1% trifluoroacetic acid).

LC/MS Method O: LC/MS analysis was conducted using a Phenomenex Luna $C_{18}$ column (3×5 mm, 3 m particle) over 2.5 minutes. Mobile phase conditions: 5-100% acetonitrile (0.1% formic acid) in water (0.1% formic acid) over 1.3 minutes, then hold for 1.2 minutes at 95% acetonitrile (0.1% formic acid). Flow rate=1.5 mL/min and column temperature 45° C.

LC/MS Method P: LC/MS analysis was conducted using an Agilent ZORBAX Extend $C_{18}$ column (4.6×50 mm 1.8 m particle) over 5 minutes. Mobile phase conditions: 10-90% acetonitrile in water (10 mM ammonium acetate). Flow rate=1.2 mL/min.

LCMS Method Q: LC/MS analysis was conducted using a Waters Cortecs $C_{18}$ column (3×50 mm, 2.7 m particle) over 6 minutes. Mobile phase conditions: 5-100% acetonitrile (0.1% trifluoroacetic acid) in water (0.1% trifluoroacetic acid) over 4 minutes, then hold at 100% acetonitrile (0.1% trifluoroacetic acid) for 0.5 minutes, then equilibration to 5% acetonitrile (0.1% trifluoroacetic acid) over 1.5 minutes. Flow rate=1.2 mL/min and column temperature 55° C.

LC/MS Method R: LC/MS analysis was conducted using a YMC Triart $C_{18}$ column (2.1×33 mm. 3 m particle) over 3 minutes. Mobile phase conditions: 2-98% acetonitrile in water (5 mM ammonium acetate). Flow rate=1.0 mL/min.

LC/MS Method S: LC/MS analysis was conducted using a Millipore Sigma Chromolith SpeedROD $C_{18}$ column (4.6×50 mm) over 6 minutes. Mobile phase conditions: 5-95% acetonitrile (0.1% trifluoroacetic acid) in water (0.11% trifluoroacetic acid).

LC/MS Method T: LC/MS analysis was conducted using a Waters XBridge $C_{18}$ (4.6×50 mm, m particle) over 5 minutes. Mobile phase conditions 10-90% acetonitrile in water (10 mM ammonium acetate). Flow rate=1.2 mL/min.

LC/MS Method U: LC/MS analysis was conducted using a Waters Acquity BEH $C_{18}$ column (2.1×50 mm, 1.7 m particle) over 4.5 minutes. Mobile phase conditions 3-98% acetonitrile in water (0.1% formic acid). Flow rate=1.3 mL/min and column temperature 35° C.

LC/MS Method V. LC/MS analysis was conducted using a Merckmillipore Chromolith SpeedROD $C_{18}$ column (50×4.6 mm) and a dual gradient run from 5-100% mobile phase B over 6 minutes. Mobile phase A=$H_2O$ (0.1% TFA). Mobile phase B=$CH_3CN$ (0.1% TFA).

LC/MS Method W. LC/MS analysis was conducted using a Waters Cortex $C_{18}$ column (50 mm×3.0 mm, 2.7 m particle). Mobile phase A=$H_2O$ (0.1% TFA). Mobile phase B=$CH_3CN$ (0.1% TFA), dual gradient from 5% to 100% mobile phase B over 4 minutes, 100% B for 0.5 minutes, with equilibration to 5% B over 1.5 min. Flow rate=1.2 mL/min and column temperature=55° C.

Unless otherwise noted, where purification by reverse phase HPLC is indicated in the Examples below, samples were purified using a reverse phase HPLC-MS method using the general conditions as follows:

a. When using 5 mM HCl aqueous phase modifier: Phenomenex Luna $C_{18}$(2) column (30×75 mm, 5 μm particle size) using an acetonitrile gradient runtime ranging from 9.5 minutes up to 15 minutes. Initial gradient acetonitrile concentration ranged from 1 to 40%, and final acetonitrile gradient concentration ranged from 30 to 99%. Flow rate=50 mL/min, injection volume=950 μL, and column temperature=25° C.

b. When using 0.1% ammonium hydroxide aqueous phase modifier: Waters X-bridge OBD $C_{18}$ column (19×150 mm, 5 μm particle size) using an acetonitrile gradient run over 9 minutes. The acetonitrile gradient concentration was either 38-53% acetonitrile or 47-95% acetonitrile. Flow rate=19 mL/min.

c. When using 0.05% trifluoroacetic aqueous phase modifier: Waters Sunfire $C_{18}$ column (19×150 mm, 5 m particle size) with a gradient from 1-100% acetonitrile over 11 minutes. Flow rate=19 mL/min.

Abbreviations

Unless otherwise noted, or where the context dictates otherwise, the following abbreviations shall be understood to have the following meanings:

| Abbreviation | Meaning |
|---|---|
| % w/v | Weight-volume concentration |
| $[Ir(ppy)_2(dtbbpy)]PF_6$ | [4,4'-Bis(1,1-dimethylethyl)-2,2'-bipyridine-N1,N1']bis[2-(2-pyridinyl-N)phenyl-C] iridium (III) hexafluorophosphate |
| 2-MeTHF | 2-methyltetrahydrofuran |
| BSA | Bovine Serum Albumin |
| ca. | Circa (approximately) |
| CC2-DMPE | Chlorocoumarin-2-dimyristoyl phosphatidylethanolamine |
| DCM | Dichloromethane |
| DCE | Dichloroethane |
| DIEA, DIPEA | N, N-Diisopropyl ethyl amine |
| $DiSBAC_6(3)$ | Bis-(1,3-dihexyl-thiobarbituric acid) trimethine oxonol |
| DMA | N,N-Dimethylacetamide |
| DMAP | 4-Dimethylaminopyridine |
| DMEM | Dulbecco's Modified Eagle's Medium |
| DMF | N,N-Dimethylformamide |
| DMSO | Dimethyl sulfoxide |
| DRG | Dorsal root ganglia |
| EDCI | 1-Ethyl-3-(3-dimethylaminopropyl)carbodiimide |
| ESI | Electrospray ionization |
| ESI-MS | Electrospray mass spectrometry |
| EtOAc | Ethyl acetate |
| EtOH | Ethanol |
| E-VIPR | Electrical stimulation voltage ion probe reader |
| FBS | Fetal bovine serum |

-continued

| Abbreviation | Meaning |
|---|---|
| g | Grams |
| HATU | 1-[Bis(dimethylamino)methylene]-1H-1,2,3-triazolo[4,5-b]pyridinium 3-oxide hexafluorophosphate |
| HEK | Human embryonic kidney |
| HEPES | 2-[4-(2-hydroxyethyl)piperazin-1-yl]ethanesulfonic acid |
| HPLC | High performance liquid chromatography |
| HPLC/MS/MS | High performance liquid chromatography/tandem mass spectrometry |
| hr, h | Hours |
| HS | Human serum |
| Hz | Hertz |
| IS | Internal standard |
| KIR2.1 | Inward-rectifier potassium ion channel 2.1 |
| L | Liter(s) |
| LC/MS | Liquid chromatography-mass spectrometry |
| LDA | Lithium diisopropylamide |
| M | Molar (concentration) |
| MeOH | Methanol |
| mg | Milligrams |
| MHz | Megahertz |
| min | Minutes |
| mL | Milliliters |
| mm | Millimeters |
| mM | Millimolar (concentration) |
| mmol | Millimoles |
| ms | Millisecond |
| MTBE | Methyl tert-butyl ether |
| N | Normal (concentration) |
| NBS | N-Bromosuccinimide |
| NEAA | Non-essential amino acids |
| $Ni(TMHD)_2$ | Nickel (II) bis(2,2,6,6-tetramethyl-3,5-heptanedionate) |
| NIS | N-Iodosuccinimide |
| nL | Nanoliters |
| nm | Nanometer |
| NMP | N-Methylpyrrolidone |
| NMR | Nuclear magnetic resonance |
| $Pd(dba)_2$ | Palladium (0) bis(dibenzylideneacetone) |
| $Pd(t-Bu_3P)_2$ | Bis(tri-tert-butylphosphine) palladium (0) |
| ppm | Parts per million |
| RB | Round bottom (flask) |
| RT | Room temperature |
| SFC | Supercritical fluid chromatography |
| T3P | Propylphosphonic anhydride, i.e., 2,4,6-tripropyl-1,3,5,2,4,6-trioxatriphosphinane 2,4,6-trioxide |
| TBSCl | tert-Butyldimethylchlorosilane |
| t-BuOH | tert-butyl alcohol |
| tBuXPhos | 2-Di-tert-butylphosphino-2',4',6'-triisopropylbiphenyl |
| TEA | Triethylamine |
| TFA | Trifluoroacetic acid |
| THF | Tetrahydrofuran |
| UPLC | Ultra performance liquid chromatography |
| VABSC-1 | Voltage Assay Background Suppression Compound |
| μL | Microliters |
| μm | Micrometers |
| μM | Micromolar (concentration) |

Preparation 1

Methyl 4-Amino-5-Methyl-Pyridine-2-Carboxylate

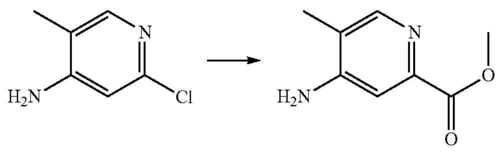

2-Chloro-5-methyl-pyridin-4-amine (0.5 g, 4 mmol) was diluted in methanol (6.6 mL) in an autoclave. $Pd(dppf)Cl_2$-dichloromethane (70 mg, 0.086 mmol) and TEA (1.0 mL, 7.2 mmol) were added and the autoclave was purged with nitrogen, then with carbon monoxide. The mixture was heated to 130° C. and the carbon monoxide pressure was adjusted to 120 psi. The mixture was stirred for 18 hours at 130° C., and then cooled to 25° C. The mixture was purged with nitrogen and concentrated in vacuo. After purification by silica gel chromatography (0-10% methanol/ethyl acetate), the resulting material was triturated with MTBE (10 mL) for 1 hour. The solid was isolated by filtration, washed with MTBE (5 mL) and dried under vacuum at 50° C. for 3 hours to provide methyl 4-amino-5-methyl-pyridine-2-carboxylate (380 mg, 64%) as a beige solid. $^1H$ NMR (400 MHz, $CDCl_3$) δ 8.20 (s, 1H), 7.39 (s, 1H), 4.31 (br s, 2H), 3.95 (s, 3H), 2.16 (s, 3H) ppm. ESI-MS m z calc. 166.07, found 167.4 $(M+1)^+$; LC/MS retention time (Method K): 0.2 minutes.

Preparation 2

3-Chloro-4-Fluoro-2-Methyl-Phenol

Step 1: (3-Chloro-4-Fluoro-Phenyl) N,N-Diethylcarbamate

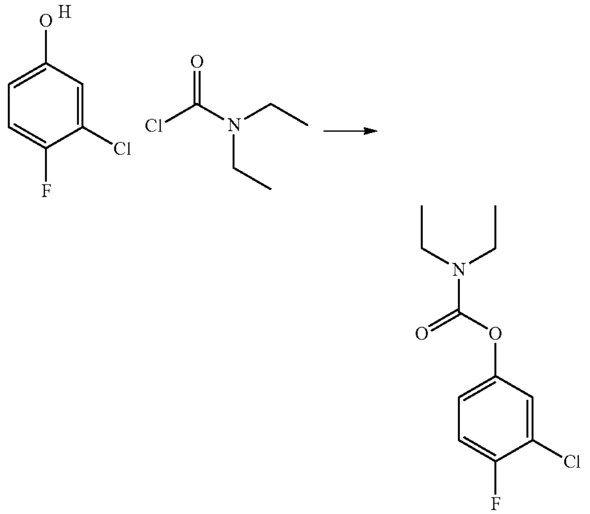

A 500-mL round-bottom flask was charged with 3-chloro-4-fluorophenol (25.0 g, 165.5 mmol), N,N-diethylcarbamoyl chloride (45.1 g, 43.0 mL, 326 mmol) and pyridine (125 mL). The resulting mixture was heated at 100° C. and stirred at this temperature for 21 hours. The mixture was cooled to room temperature and was poured into water (250 mL). The resulting solution was extracted with MTBE (2×125 mL). The combined organic layers were washed with 10% aqueous HCl (3×250 mL), 10% aqueous NaOH (2×250 mL), brine (125 mL), dried over $Na_2SO_4$, filtered and concentrated under reduced pressure to give (3-chloro-4-fluoro-phenyl) N,N-diethylcarbamate (41.2 g, 100%) as a yellow oil. ESI-MS m z calc. 245.06, found 246.1 $(M+1)^+$; LC/MS retention time (Method L): 2.06 minutes. $^1H$ NMR (300 MHz, $CDCl_3$) δ 7.22 (dd, J=6.2, 2.6 Hz, 1H), 7.17-7.07 (m, 1H), 7.06-6.97 (m, 1H), 3.48-3.33 (m, 4H), 1.32-1.15 (m, 6H) ppm. $^{19}F$ NMR (282 MHz, $CDCl_3$) δ −120.33--120.55 (m, 1F) ppm.

Step 2: (3-Chloro-4-Fluoro-2-Methyl-Phenyl) N,N-Diethylcarbamate

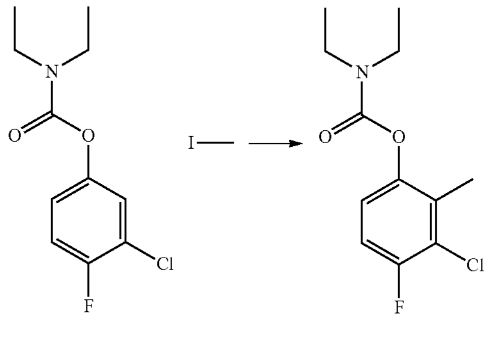

A 25-mL round-bottom flask under nitrogen was charged with (3-chloro-4-fluoro-phenyl) N,N-diethylcarbamate (500 mg, 1.97 mmol), THF (3 mL) and N,N,N,N-tetramethylethylenediamine (271 mg, 0.35 mL, 2.33 mmol). The mixture was cooled to −78° C. and sec-butyllithium (1.7 mL of 1.4 M solution in cyclohexane, 2.4 mmol) was then added slowly over ~ 15 minutes. The resulting mixture was stirred at −78° C. for 2 hours and then treated with methyl iodide (480 mg, 0.21 mL, 3.4 mmol). The resulting mixture was stirred for 2 hours while being allowed to warm to 0° C. Water (5 mL) was then added and the resulting solution extracted with MTBE (3×5 mL). The combined organic layers were washed with brine, dried over anhydrous $Na_2SO_4$, filtered and concentrated in vacuo to provide (3-chloro-4-fluoro-2-methyl-phenyl) N,N-diethylcarbamate (612 mg, 104% yield, purity 87%) as a yellow oil. ESI-MS m z calc. 259.08, found 260.1 $(M+1)^+$; LC/MS retention time (Method L): 2.11 minutes. $^1H$ NMR (300 MHz, $CDCl_3$) δ 7.05-6.93 (m, 2H), 3.47 (q, J=7.3 Hz, 2H), 3.39 (q, J=7.1 Hz, 2H), 2.27 (s, 3H), 1.28 (t, J=7.2 Hz, 3H), 1.21 (t, J=7.2 Hz, 3H) ppm. $^{19}F$ NMR (282 MHz, $CDCl_3$) δ −116.99-17.13 (m, 1F) ppm.

Step 3: 3-Chloro-4-Fluoro-2-Methyl-Phenol

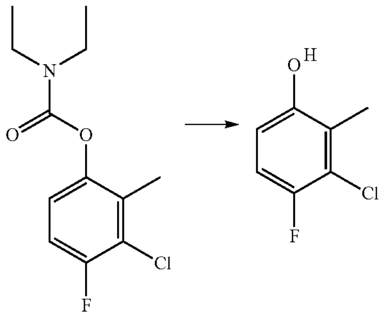

To a solution of (3-chloro-4-fluoro-2-methyl-phenyl) N,N-diethylcarbamate (508 mg, 1.96 mmol) in THF (3 mL) at room temperature was added $LiAlH_4$ (150 mg, 3.95 mmol) in one portion. The mixture was stirred at 50° C. for 6 hours and then at room temperature (~15° C.) overnight. A saturated aqueous $NH_4Cl$ solution (15 mL) was added dropwise to the mixture and the resulting suspension was stirred at room temperature for 20 minutes. The mixture was filtered over Celite and the solid washed with MTBE (35 mL) and water (5 mL). The layers were separated and the aqueous layer was extracted with MTBE (2×35 mL). The combined organic layers were extracted with aqueous 2 M NaOH solution (4×20 mL). The combined aqueous layers were acidified (pH<4) with aqueous concentrated HCl (~15 mL) and the resulting solution was extracted with MTBE (3×50 mL). The combined organic layers were washed with brine (25 mL), dried over $Na_2SO_4$ filtered and concentrated in vacuo to provide 3-chloro-4-fluoro-2-methyl-phenol (258 mg, 81%) as a light brown solid. ESI-MS m z calc. 160.01, found 159.1 $(M-1)^-$; LC/MS retention time (Method L): 1.82 minutes. $^1H$ NMR (300 MHz, $CDCl_3$) δ 6.88 (t, J=8.7 Hz, 1H), 6.65 (dd, J=8.8, 4.4 Hz, 1H), 4.70 (br. s., 1H), 2.32 (s, 3H) ppm. $^{19}F$ NMR (282 MHz, $CDCl_3$) δ −123.29 (d, J=12.2 Hz, 1F) ppm.

Preparation 3

2-Chloro-3,4-Difluoro-Phenol

Step 1: 1,2-Difluoro-4-(Methoxymethoxy)Benzene

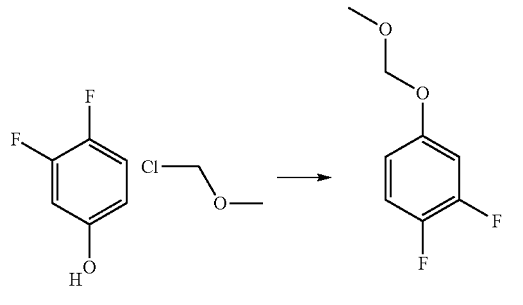

To a mixture of 3,4-difluorophenol (10.0 g, 76.9 mmol) and $K_2CO_3$ (13.9 g, 101 mmol) in acetone (100 mL) was added chloro(methoxy)methane (9.0 g, 8.5 mL, 112 mmol). The resulting mixture was stirred for 2 days at room temperature. Additional chloro(methoxy)methane (5.3 g, 5.0 mL, 66 mmol) and diisopropylethylamine (9.6 g, 13 mL, 75 mmol) were added and the mixture was stirred at 25° C. overnight. The mixture was filtered and the filtrate was concentrated in vacuo. The residue was purified by silica gel chromatography (0-20% ethyl acetate/heptane) to provide 1,2-difluoro-4-(methoxymethoxy)benzene (7.54 g, 56%) as a clear liquid. $^1H$ NMR (300 MHz, $CDCl_3$) δ 7.06 (dt, J=10.0, 9.1 Hz, 1H), 6.89 (ddd, J=12.0, 6.8, 2.9 Hz, 1H), 6.74 (dtd, J=9.0, 3.3, 1.8 Hz, 1H), 5.11 (s, 2H), 3.47 (s, 3H) ppm. $^{19}F$ NMR (282 MHz, $CDCl_3$) δ −135.51 (dt, J=21.4, 10.7 Hz, 1F), −146.74−−147.11 (m, 1F) ppm.

Step 2:
3-Chloro-1,2-Difluoro-4-(Methoxymethoxy)Benzene

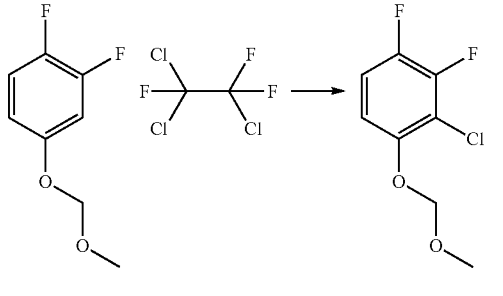

2,2,6,6-Tetramethylpiperidine (5.27 g, 6.3 mL, 37 mmol) and 1,2-difluoro-4-(methoxymethoxy)benzene (6.5 g, 37 mmol) were added consecutively to a solution of n-butyllithium (15 mL of 2.5 M in hexanes, 38 mmol) in THF (65 mL) at −78° C. After stirring for 2 hours at −78° C., 1,1,2-trichloro-1,2,2-trifluoroethane (7.1 g, 4.5 mL, 38 mmol) was added and the mixture was stirred at 0° C. for 1 hour. Water (100 mL) was added and the mixture was extracted with dichloromethane (3×100 mL). The combined organic layers were dried over $Na_2SO_4$, filtered and concentrated in vacuo. The residue was purified by silica gel chromatography (0-10% ethyl acetate/heptane) to provide 3-chloro-1,2-difluoro-4-(methoxymethoxy)benzene (9.43 g, 85%) as yellow oil. $^1H$ NMR (300 MHz, $CDCl_3$) δ 7.02 (td, J=9.4, 8.2 Hz, 1H), 6.96-6.88 (m, 1H), 5.21 (s, 2H), 3.52 (s, 3H) ppm. $^{19}F$ NMR (282 MHz, $CDCl_3$) δ −135.20 (dd, J=21.4, 9.2 Hz, 1F), −143.05−−143.37 (m, 1F) ppm.

Step 3: 2-Chloro-3,4-Difluoro-Phenol

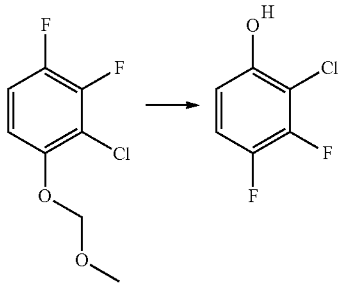

Aqueous HCl (50 mL of 6 M, 300 mmol) was added to a solution of 3-chloro-1,2-difluoro-4-(methoxymethoxy)benzene (9.43 g, 31.7 mmol) in THF (55 mL) and the mixture was stirred at 25° C. overnight. The mixture was diluted with water (100 mL) and extracted with diethyl ether (3×100 mL). The combined organic layers were washed with brine (50 mL), dried over $Na_2SO_4$, filtered and concentrated in vacuo. The residue was purified by silica gel chromatography (0-30% dichloromethane/pentane) to afford 2-chloro-3,4-difluoro-phenol (4.65 g, 66%) as yellow oil. ESI-MS m z calc. 163.984, found 163.0 $(M-1)^-$; LC/MS retention time (Method M): 2.34 minutes. $^1H$ NMR (300 MHz, $CDCl_3$) δ 7.02 (td, J=9.5, 8.5 Hz, 1H), 6.76 (ddd, J=9.3, 4.2, 2.3 Hz, 1H), 5.50 (s, 1H) ppm. $^{19}F$ NMR (282 MHz, $CDCl_3$) δ −136.22 (dd, J=21.4, 9.2 Hz, 1F), −144.97−−145.28 (m, 1F) ppm.

Preparation 4

2-Cyclopropyl-3,6-Difluoro-Phenol

Step 1: 2-Bromo-3,6-Difluoro-Phenol

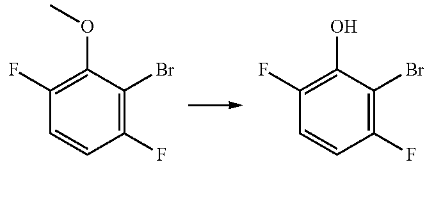

To a solution of 2-bromo-1,4-difluoro-3-methoxy-benzene (1.0 g, 4.5 mmol) in dichloromethane (5.0 mL) was added $BBr_3$ (4.5 g, 1.7 mL, 18 mmol) dropwise at 0° C. The mixture was stirred for 2 hours at room temperature. Water was then added dropwise at 0° C. and the layers separated. The organic layer was dried over anhydrous $MgSO_4$, filtered and concentrated in vacuo to provide 2-bromo-3,6-difluorophenol (1.04 g, 100%) as colorless oil. LC/MS retention time=3.94 minutes (Method N).

Step 2: 2-Cyclopropyl-3,6-Difluoro-Phenol

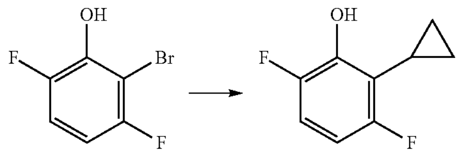 [SMILES: Oc1c(F)ccc(F)c1Br ; Oc1c(F)ccc(F)c1C1CC1]

Nitrogen was bubbled though a solution of 2-bromo-3,6-difluoro-phenol (14.27 g, 68.28 mmol), cyclopropyl boronic acid (11.73 g, 136.6 mmol), $K_3PO_4$ (58.0 g, 273 mmol), tricyclohexylphosphonium tetrafluoroborate (2.51 g, 6.84 mmol) and $Pd(OAc)_2$ (3.07 g, 13.7 mmol) in a mixture of toluene (265 mL) and water (65 mL) for 10 minutes in a pressure flask. The flask was sealed and heated at 100° C. overnight. After cooling, the mixture was diluted with ethyl acetate (700 mL), washed with water and brine, dried over $MgSO_4$ and filtered. The filtrate was concentrated in vacuo and purified using silica gel chromatography (0-40% ethyl acetate/hexane). The isolated product was dissolved in ethyl acetate (300 mL) and extracted with 1 M aqueous NaOH (4×50 mL). The combined aqueous layers were adjusted to pH~2 with 6 M aqueous HCl and extracted with ethyl acetate (2×150 mL). The combined organic layers were washed with water and brine, dried over $MgSO_4$ and filtered. The filtrate was concentrated in vacuo to obtain 2-cyclopropyl-3,6-difluoro-phenol (9.1 g, 74%) as yellow oil. ESI-MS m z calc. 170.05, found 171.2 $(M+1)^+$; LC/MS retention time (Method N): 4.86 minutes. $^1H$ NMR (500 MHz, $CDCl_3$) δ 6.93-6.84 (m, 1H), 6.56-6.48 (m, 1H), 5.51 (d, J=4.0 Hz, 1H), 1.84-1.75 (m, 1H), 1.05-0.97 (m, 2H), 0.97-0.89 (m, 2H) ppm.

Preparation 5

4-(Difluoromethyl)-2-Methoxy-Phenol

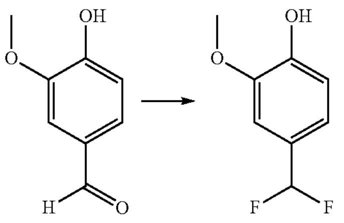

(Diethylamino)sulfur trifluoride (39 g, 32 mL, 242 mmol) was slowly added to a cold (10° C.) solution of 4-hydroxy-3-methoxy-benzaldehyde (18.0 g, 118 mmol) in dichloromethane (300 mL). The mixture was warmed to room temperature and stirred overnight. The mixture was treated with 5% aqueous $NaHCO_3$ (500 mL), stirred for 30 minutes, then extracted with dichloromethane (3×200 mL). The combined organic layers were dried over $Na_2SO_4$, filtered and concentrated in vacuo. The residue was purified by silica gel chromatography (0-30% ethyl acetate/heptane) to afford 4-(difluoromethyl)-2-methoxy-phenol (10.88 g, 47%) as an orange oil that crystallized on standing. ESI-MS m z calc. 174.0492, found 173.0 $(M-1)^-$; LC/MS retention time (Method M): 2.03 minutes. $^1H$ NMR (300 MHz, $CDCl_3$) δ 7.05-6.92 (m, 3H), 6.57 (t, J=61.1 Hz, 1H), 5.79 (s, 1H), 3.94 (s, 3H) ppm. $^{19}F$ NMR (282 MHz, $CDCl_3$) δ −107.50−−107.92 (m, 2F) ppm.

Preparation 6

2,3-Dichloro-4-Fluoro-Phenol

Step 1: (3-Chloro-4-Fluoro-Phenyl) N,N-Diethylcarbamate

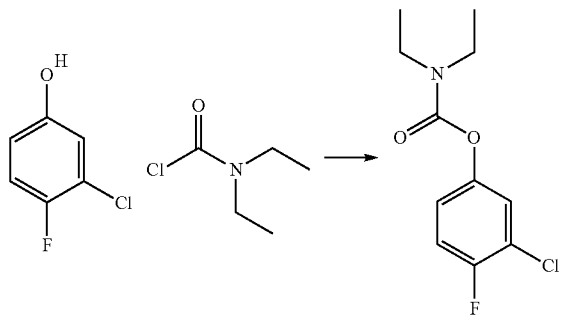

A 500-mL round-bottom flask was charged with 3-chloro-4-fluorophenol (25.0 g, 165.5 mmol), N,N-diethylcarbamoyl chloride (45 g, 43 mL, 326 mmol) and pyridine (125 mL). The mixture was stirred at 100° C. for 21 hours. The mixture was cooled to room temperature, poured into water (250 mL) and extracted with MTBE (2×125 mL). The combined organic layers were washed with 10% aqueous HCl (3×250 mL), 10% aqueous NaOH (2×250 mL) and brine (125 mL). The organic layer was dried over $Na_2SO_4$, filtered and concentrated in vacuo to provide (3-chloro-4-fluoro-phenyl) N,N-diethylcarbamate (41.2 g, 100%) as a yellow oil (99% purity). ESI-MS m z calc. 245.06, found 246.1 $(M+1)^+$; LC/MS retention time (Method L): 2.06 minutes. $^1H$ NMR (300 MHz, $CDCl_3$) δ 7.22 (dd, J=6.2, 2.6 Hz, 1H), 7.17-7.07 (m, 1H), 7.06-6.97 (m, 1H), 3.48-3.33 (m, 4H), 1.32-1.15 (m, 6H) ppm. $^{19}F$ NMR (282 MHz, $CDCl_3$) δ −120.33−−120.55 (m, 1F) ppm.

Step 2: (2,3-Dichloro-4-Fluoro-Phenyl) N,N-Diethylcarbamate

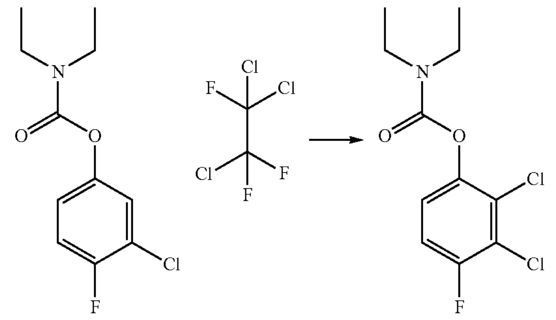 [SMILES: CCN(CC)C(=O)Oc1ccc(F)c(Cl)c1 ; FC(F)(Cl)C(F)(Cl)Cl ; CCN(CC)C(=O)Oc1ccc(F)c(Cl)c1Cl]

A flask under nitrogen was charged with (3-chloro-4-fluoro-phenyl) N,N-diethylcarbamate (10 g, 41 mmol), THF (60 mL) and N,N,N,N-tetramethylethylenediamine (5.4 g, 7.0 mL, 47 mmol). The mixture was cooled to −78° C. and sec-butyllithium (34 mL of 1.4 M in cyclohexane, 48 mmol) was then added slowly (over ~15 min). The mixture was stirred at −78° C. for 2 hours and then treated with 1,1,2-trichloro-1,2,2-trifluoro-ethane (8.4 g, 5.3 mL, 45 mmol). The resulting mixture was allowed to warm to 0° C. over 1 hour. Water (50 mL) was then added and the resulting solution extracted with diethyl ether (3×150 mL). The combined organic layers were washed with brine (50 mL), dried over anhydrous $Na_2SO_4$, filtered and concentrated in vacuo. The residue was purified by silica gel chromatography (0-10% ethyl acetate/heptane) to provide (2,3-dichloro-4-fluoro-phenyl) N,N-diethylcarbamate (8.92 g, 78%) as yellow oil. ESI-MS m z calc. 279.02, found 280.1 $(M+1)^+$; LC/MS retention time (Method L): 2.13 minutes. $^1H$ NMR (300 MHz, $CDCl_3$) δ 7.23-6.92 (m, 2H), 3.55-3.30 (m, 4H), 1.37-1.13 (m, 6H) ppm. $^{19}F$ NMR (282 MHz, $CDCl_3$) δ −113.45 (d, J=6.1 Hz, 1F) ppm.

Step 3: 2,3-Dichloro-4-Fluoro-Phenol

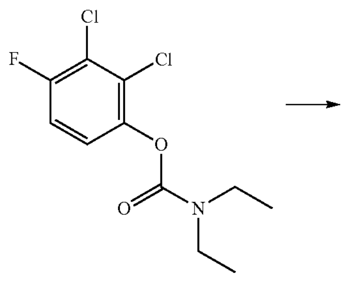

$LiAlH_4$ (45 mg, 1.3 mmol) was added to a solution of (2,3-dichloro-4-fluoro-phenyl) N,N-diethylcarbamate (300 mg, 1.07 mmol) in THF (5 mL) and the mixture was stirred at room temperature overnight. Additional $LiAlH_4$ (40 mg, 1.2 mmol) was added and the mixture was heated at 50° C. for 7 hours, and then at reflux for 2 hours. The mixture was cooled to room temperature, then treated slowly with a saturated aqueous $NH_4Cl$ solution (50 mL) and stirred at room temperature for 20 minutes. The mixture was filtered over Celite and the solid washed with MTBE (50 mL) and water (10 mL). The filtrate layers were separated and the aqueous layer was extracted with MTBE (2×50 mL). The combined organic layers were then extracted with 2 M aqueous NaOH (4×25 mL). The combined aqueous extracts were acidified (pH<4) with 6 M aqueous HCl and the resulting solution was extracted with diethyl ether (3×50 mL). The combined organic layers were washed with brine (10 mL), dried over $Na_2SO_4$, filtered and concentrated in vacuo. Silica gel chromatography (0-30% dichloromethane/pentane) provided 2,3-dichloro-4-fluoro-phenol (164 mg, 55%) as a yellow oil that solidified to an off-white solid upon standing. $^1H$ NMR (300 MHz, $CDCl_3$) δ 7.02-6.91 (m, 1H), 6.90-6.81 (m, 1H) ppm. $^{19}F$ NMR (282 MHz, $CDCl_3$) δ −120.56 (t, J=7.6 Hz, 1F) ppm.

Preparation 7

4-(Difluoromethoxy)-3-Fluoro-2-Methoxy-Phenol

Step 1: 1-Bromo-4-(Difluoromethoxy)-3-Fluoro-2-Methoxybenzene

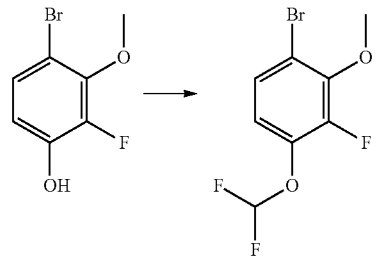

A mixture of 4-bromo-2-fluoro-3-methoxy-phenol (11.5 g, 52.0 mmol), $K_2CO_3$ (28.8 g, 208 mmol) and sodium 2-chloro-2,2-difluoro-acetate (23.8 g, 156 mmol) in DMF (200 mL) and water (50 mL) was degassed with nitrogen for 5 minutes and was heated at 100° C. for 18 hours. The mixture was cooled to room temperature, then extracted with diethyl ether (4×200 mL). The combined organic layers were washed with water (2×100 mL) and 1 M aqueous NaOH (2×100 mL). The organic phase was dried over anhydrous $Na_2SO_4$, filtered and concentrated in vacuo to provide 1-bromo-4-(difluoromethoxy)-3-fluoro-2-methoxy-benzene (9.62 g, 64%) as a yellow oil. $^1H$ NMR (300 MHz, $CDCl_3$): δ 7.33-7.26 (m, 1H), 6.92-6.84 (m, 1H), 6.53 (t, J=72.6 Hz, 1H), 3.99 (d, J=1.4 Hz, 3H) ppm. $^{19}F$ NMR (282 MHz, $CDCl_3$): δ −81.8 (dd J=72.4 Hz, 4.3 Hz, 2F), −143.1 (s, 1F) ppm.

Step 2: 4-(Difluoromethoxy)-3-Fluoro-2-Methoxy-Phenol

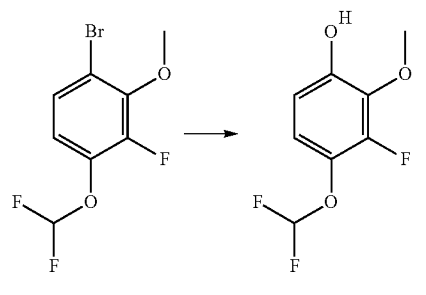

A mixture of 1-bromo-4-(difluoromethoxy)-3-fluoro-2-methoxy-benzene (9.1 g, 33.6 mmol), $Me_4$tButylXphos (493 mg, 1.03 mmol) and KOH (5.75 g, 102.5 mmol) in dioxane (28 mL) and water (28 mL) was degassed with nitrogen bubbling for 10 minutes. $Pd_2dba_3$ (474 mg, 0.518 mmol) was added and the reaction vessel purged with nitrogen (3×). The mixture was stirred at 90° C. for 3 hours, and then cooled to room temperature and diluted with water (100 mL). The aqueous mixture was washed with ether (4×200 mL). The aqueous phase was then acidified with 3 M aqueous HCl until pH 1-2 and extracted with ether (3×150 mL). The combined organic extracts were washed with saturated aqueous $NaHCO_3$ (3×50 mL) and brine (50 mL), dried over $Na_2SO_4$, filtered and concentrated in vacuo to provide 4-(difluoromethoxy)-3-fluoro-2-methoxy-phenol (5.90 g, 75%) as a light orange oil. ESI-MS m z calc. 208.03, found 207.0 $(M-1)^-$; LC/MS retention time (Method M): 2.33 minutes. $^1H$ NMR (300 MHz, $CDCl_3$) δ 6.90-6.79 (m, 1H), 6.73-6.18 (m, 2H), 5.73-5.65 (m, 1H), 4.03 (d, J=2.1 Hz, 3H) ppm. $^{19}F$ NMR (282 MHz, $CDCl_3$) δ −81.05--82.50 (m, 1F), −145.68--146.31 (m, 1F) ppm.

Preparation 8

2-Ethyl-3-Fluoro-4-(Trifluoromethoxy)Phenol

Step 1: 2-Fluoro-4-(Methoxymethoxy)-1-(Trifluoromethoxy)Benzene

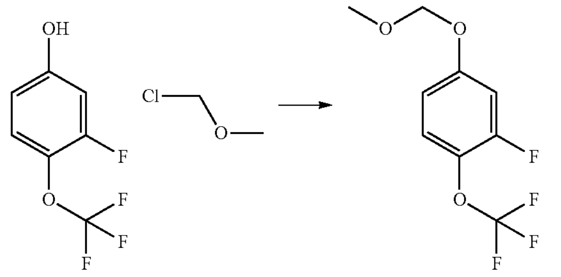

To a solution of 3-fluoro-4-(trifluoromethoxy)phenol (5.0 g, 25.5 mmol) and DIPEA (9.6 g, 13 mL, 75 mmol) in dichloromethane (130 mL) at 0° C. was added chloromethyl methyl ether (3.7 g, 3.9 mL, 42 mmol). The resulting mixture was stirred overnight at room temperature. The solvent was removed in vacuo and the residue purified by silica gel chromatography (0-40% dichloromethane/hexanes) to provide 2-fluoro-4-(methoxymethoxy)-1-(trifluoromethoxy)benzene (5.11 g, 83%) as a colorless oil. $^1H$ NMR (300 MHz, $CDCl_3$) δ 7.20 (td, J=8.9, 1.0 Hz, 1H), 6.91 (dd, J=11.6, 2.8 Hz, 1H), 6.81 (ddd, J=9.0, 2.9, 1.6 Hz, 1H), 5.15 (s, 2H), 3.48 (s, 3H) ppm. $^{19}F$ NMR (282 MHz, $CDCl_3$) δ −59.34 (br. s., 3F), −125.89--126.37 (m, 1F) ppm.

Step 2: 2-Ethyl-3-Fluoro-1-(Methoxymethoxy)-4-(Trifluoromethoxy)Benzene

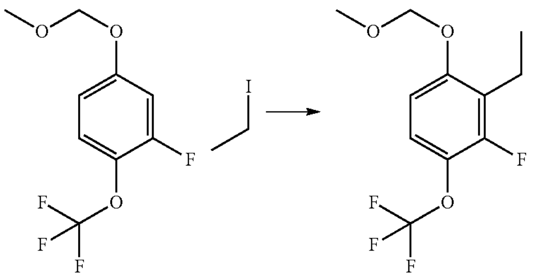

To a solution of 2-fluoro-4-(methoxymethoxy)-1-(trifluoromethoxy)benzene (5.0 g, 20.8 mmol) in THF (100 mL) at −78° C. was added n-butyllithium (10 mL of 2.5 M in hexanes, 25 mmol) dropwise over 20 minutes. After 30 minutes at this temperature, iodoethane (8.7 g, 4.5 mL, 56 mmol) was added dropwise over 10 minutes and the mixture was stirred at this temperature for 30 minutes. The mixture was allowed to warm to 0° C. and stirred for 2 hours, and then stirred at ~ 5° C. for 1.5 hours. The mixture was treated with saturated aqueous $NaHCO_3$ (75 mL) and water (50 mL) and concentrated in vacuo to remove the organic solvents. The remaining aqueous mixture was partitioned between water (100 mL) and dichloromethane (300 mL) and the layers separated. The aqueous layer was extracted with additional dichloromethane. The combined organic layers were dried over anhydrous $Na_2SO_4$, filtered and concentrated in vacuo. Reverse phase chromatography (5-95% acetonitrile/0.1% aqueous formic acid) product fractions were combined and concentrated in vacuo to remove the acetonitrile. Water (200 mL) was added to the remaining aqueous mixture which was extracted with dichloromethane (3×). The combined organic layers were dried over anhydrous $Na_2SO_4$, filtered and concentrated in vacuo to provide 2-ethyl-3-fluoro-1-(methoxymethoxy)-4-(trifluoromethoxy)benzene (4.08 g, 73%) as a pale yellow oil. $^1H$ NMR (300 MHz, $CDCl_3$) δ 7.11-6.99 (m, 1H), 6.84 (d, J=9.1 Hz, 1H), 5.20 (s, 2H), 3.48 (s, 3H), 2.78-2.64 (m, 2H), 1.16 (t, J=7.5 Hz, 3H) ppm. $^{19}F$ NMR (282 MHz, $CDCl_3$) δ −59.20 (s, 3F), −132.77 (s, 1F) ppm.

Step 3: 2-Ethyl-3-Fluoro-4-(Trifluoromethoxy)Phenol

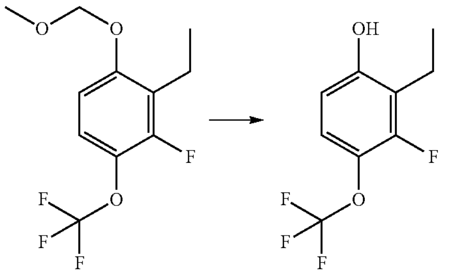 [SMILES: CCc1c(OCOC)ccc(OC(F)(F)F)c1F ; CCc1c(O)ccc(OC(F)(F)F)c1F]

To a solution of 2-ethyl-3-fluoro-1-(methoxymethoxy)-4-(trifluoromethoxy)benzene (4.08 g, 15.2 mmol) in dioxane (60 mL) at room temperature was added aqueous concentrated HCl (1.3 mL of 12 M, 15.6 mmol). The mixture was stirred at 40° C. for 5 hours, and then overnight at 35° C. The mixture was concentrated in vacuo and partitioned between water (300 mL) and dichloromethane (150 mL). The layers were separated and the aqueous layer was extracted with additional dichloromethane (100 mL). The combined organic extracts were dried over anhydrous $Na_2SO_4$, filtered and concentrated in vacuo. Reverse phase purification (5-95% acetonitrile/0.1% aqueous formic acid) provided product fractions which were combined and concentrated in vacuo to remove the acetonitrile. Water (200 mL) was added to the remaining aqueous mixture, which was extracted with dichloromethane (3×). The combined organic layers were dried over anhydrous $Na_2SO_4$, filtered and concentrated in vacuo to provide 2-ethyl-3-fluoro-4-(trifluoromethoxy)phenol (2.62 g, 76%) as a yellow oil. $^1H$ NMR (300 MHz, $CDCl_3$) δ 7.05-6.94 (m, 1H), 6.53 (dd, J=9.0, 1.9 Hz, 1H), 4.89 (d, J=1.2 Hz, 1H), 2.69 (qd, J=7.6, 1.9 Hz, 2H), 1.19 (t, J=7.5 Hz, 3H) ppm. $^{19}F$ NMR (282 MHz, $CDCl_3$) δ −59.32 (s, 3F), −132.31--132.53 (m, 1F) ppm.

Preparation 9

2-Cyclopropyl-3-Fluoro-4-(Trifluoromethoxy)Phenol

Step 1: 2-Bromo-3-Fluoro-1-(Methoxymethoxy)-4-(Trifluoromethoxy)Benzene

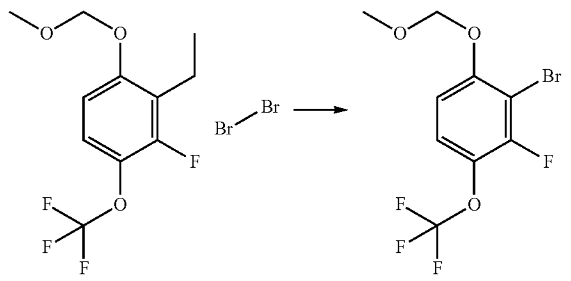

To a solution of 2-fluoro-4-(methoxymethoxy)-1-(trifluoromethoxy)benzene (5.0 g, 20.8 mmol, Preparation 8, Step 1) in THF (65 mL) at −78° C. under a nitrogen atmosphere was added dropwise n-butyllithium (10 mL of 2.5 M in hexanes, 25 mmol). The resulting mixture was stirred at this temperature for 1 hour, then bromine (5.0 g, 1.6 mL, 31 mmol) was slowly added over 10 minutes. The mixture was stirred at this temperature for 1 hour. The dry ice bath was removed and the mixture was treated with saturated aqueous $NaHCO_3$ (150 mL). The mixture was partitioned between dichloromethane (150 mL) and water (100 mL). The layers were separated and the aqueous layer was extracted with additional dichloromethane (150 mL). The combined organic layers were dried over anhydrous $Na_2SO_4$, filtered and concentrated in vacuo. Silica gel chromatography (0-20% ethyl acetate/heptane) provided 2-bromo-3-fluoro-1-(methoxymethoxy)-4-(trifluoromethoxy)benzene (6.51 g, 98%) as a colorless oil. $^1H$ NMR (300 MHz, $CDCl_3$) δ 7.22 (ddd, J=9.2, 8.2, 1.0 Hz, 1H), 6.96 (dd, J=9.4, 2.1 Hz, 1H), 5.26 (s, 2H), 3.52 (s, 3H) ppm. $^{19}F$ NMR (282 MHz, $CDCl_3$) δ −59.15--59.39 (m, 3F), −117.43 (d, J=6.1 Hz, 1F) ppm.

Step 2: 2-Cyclopropyl-3-Fluoro-1-(Methoxymethoxy)-4-(Trifluoromethoxy)Benzene

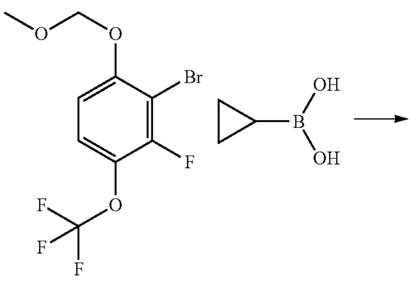

-continued

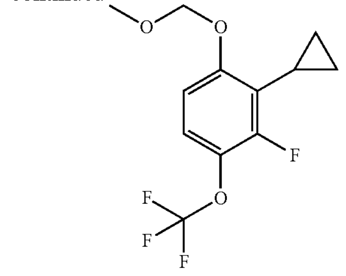

A solution of 2-bromo-3-fluoro-1-(methoxymethoxy)-4-(trifluoromethoxy)benzene (11.38 g, 33.53 mmol) in toluene (165 mL) was degassed by nitrogen bubbling for 1 hour, then cyclopropylboronic acid (6.0 g, 70 mmol), $K_3PO_4$ (18.3 g, 102 mmol), tricyclohexylphosphine tetrafluoroborate (2.5 g, 6.8 mmol), palladium (II) acetate (770 mg, 3.43 mmol) and nitrogen-degassed water (16.5 mL) were added. The mixture was stirred at 100° C. for 10 hours. The mixture was cooled to room temperature and filtered through a pad of Celite, rinsing with additional ethyl acetate (100 mL). The filtrate was dried over anhydrous $Na_2SO_4$, filtered and concentrated in vacuo. Silica gel chromatography (0-15% ethyl acetate/heptane), followed by reverse phase chromatography (5-95% acetonitrile/0.1% aqueous formic acid) provided 2-cyclopropyl-3-fluoro-1-(methoxymethoxy)-4-(trifluoromethoxy)benzene (6.62 g, 70%) as a colorless oil. $^1H$ NMR (300 MHz, $CDCl_3$) δ 7.07-6.98 (m, 1H), 6.82 (dd, J=9.2, 1.9 Hz, 1H), 5.19 (s, 2H), 3.50 (s, 3H), 1.94-1.83 (m, 1H), 1.03-0.90 (m, 4H) ppm. $^{19}F$ NMR (282 MHz, $CDCl_3$) δ −59.03--59.39 (m, 3F), −131.68--131.95 (m, 1F) ppm.

Step 4: 2-Cyclopropyl-3-Fluoro-4-(Trifluoromethoxy)Phenol

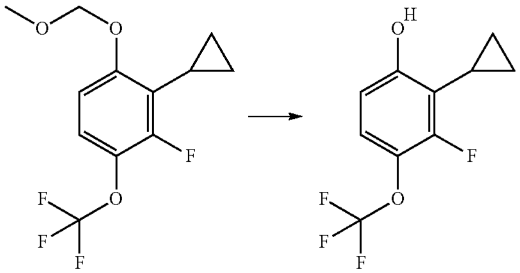

To a mixture of 2-cyclopropyl-3-fluoro-1-(methoxymethoxy)-4-(trifluoromethoxy)benzene (6.41 g, 22.9 mmol) in THF (80 mL) at room temperature was added concentrated aqueous HCl (3.3 mL of 12 M, 39.600 mmol) dropwise. The mixture was stirred at 40° C. for 5 hours, and then at room temperature overnight. Approximately half of the THF was removed under reduced pressure, and then the mixture was partitioned between water (200 mL) and dichloromethane (150 mL). The layers were separated and the aqueous layer was extracted with additional dichloromethane (2×100 mL). The combined organic layers were dried over anhydrous $Na_2SO_4$, filtered and concentrated in vacuo. Silica gel chromatography (0-30% ethyl acetate/heptane) followed by reverse phase chromatography (5-95% acetonitrile/0.1% aqueous formic acid) provided a product residue which was partitioned between water and dichloromethane.

The aqueous layer was extracted with additional dichloromethane (3×), and the combined organic layers were dried over anhydrous $Na_2SO_4$, filtered and concentrated in vacuo to provide 2-cyclopropyl-3-fluoro-4-(trifluoromethoxy)phenol (3.76 g, 68%) as a pale yellow oil. ESI-MS m z calc. 236.05, found 235.0 $(M-1)^-$; LC/MS retention time (Method M): 3.02 minutes. $^1$H NMR (300 MHz, $CDCl_3$) δ 7.07 (t, J=8.7 Hz, 1H), 6.64 (dd, J=9.1, 2.1 Hz, 1H), 5.75 (s, 1H), 1.66-1.56 (m, 1H), 1.14-1.06 (m, 2H), 0.78-0.70 (m, 2H) ppm. $^{19}$F NMR (282 MHz, $CDCl_3$) δ −59.36 (d, J=6.1 Hz, 3F), −129.15--129.33 (m, 1F) ppm.

Preparation 10

2-Ethoxy-4-(Trifluoromethoxy)Phenol

Step 1: 1-Bromo-2-Ethoxy-4-(Trifluoromethoxy)Benzene

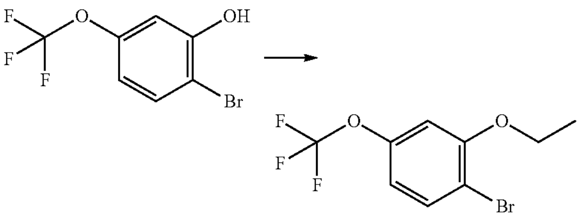

To a mixture of 2-bromo-5-(trifluoromethoxy)phenol (5.2 g, 20 mmol) and iodoethane (1.64 mL, 20.5 mmol) in DMF (20 mL) was added $K_2CO_3$ (3.38 g, 24.5 mmol). The mixture was stirred at room temperature overnight. Additional iodoethane (500 μL, 6.25 mmol) was added and the mixture stirred for 90 minutes, then allowed to stand overnight. The mixture was diluted with water (50 mL) and extracted with MTBE (3×50 mL). The combined organic extracts were washed with water (3×50 mL) and brine (50 mL), dried (phase separation cartridge) and concentrated in vacuo to afford 1-bromo-2-ethoxy-4-(trifluoromethoxy)benzene (5.587 g, 97%) as a pale yellow oil. $^1$H NMR (500 MHz, DMSO-$d_6$) δ 7.70 (d, J=8.7 Hz, 1H), 7.15-7.10 (m, 1H), 6.91 (ddq, J=8.7, 2.5, 1.2 Hz, 1H), 4.16 (q, J=7.0 Hz, 2H), 1.36 (t, J=7.0 Hz, 3H) ppm.

Step 2: [2-Ethoxy-4-(Trifluoromethoxy)Phenyl] Boronic Acid

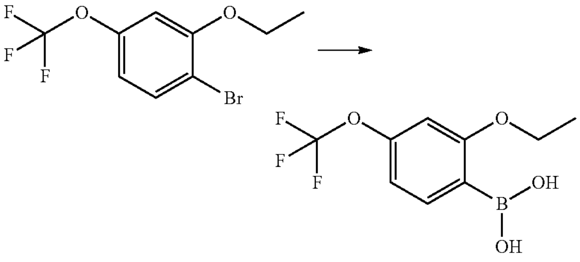

A three-necked flask with a thermometer and nitrogen inlet was charged under a nitrogen atmosphere with THF (150 mL) and was cooled to −78° C. n-Butyllithium (27 mL of 2.5 M in hexanes, 67.5 mmol) was added over 5 minutes while maintaining the internal temperature below −60° C. 1-Bromo-2-ethoxy-4-(trifluoromethoxy)benzene (16.9 g, 59.3 mmol) was added dropwise over 5 minutes while maintaining temperature below −65° C. The solution was stirred for 15 minutes, then treated with trimethyl borate (9 mL, 80 mmol) over 10 minutes, keeping the temperature below −65° C. After complete addition, the mixture was stirred at −78° C. for an additional hour. The mixture was treated dropwise with 2 M aqueous HCl (32 mL, 64 mmol) until pH=1 and the mixture was allowed to warm to room temperature. The aqueous phase was separated and extracted with MTBE (2×150 mL). The combined organic phases were washed with brine, dried over $MgSO_4$ and concentrated in vacuo to afford [2-ethoxy-4-(trifluoromethoxy) phenyl]boronic acid (14.1 g, 95%) as an off-white solid. $^1$H NMR (400 MHz, DMSO-$d_6$) δ 7.79 (s, 2H), 7.61 (d, J=8.0 Hz, 1H), 6.96-6.88 (m, 2H), 4.10 (q, J=7.0 Hz, 2H), 1.36 (t, J=6.9 Hz, 3H) ppm. $^{19}$F NMR (376 MHz, DMSO) δ −56.48 ppm.

Step 3: 2-Ethoxy-4-(Trifluoromethoxy)Phenol

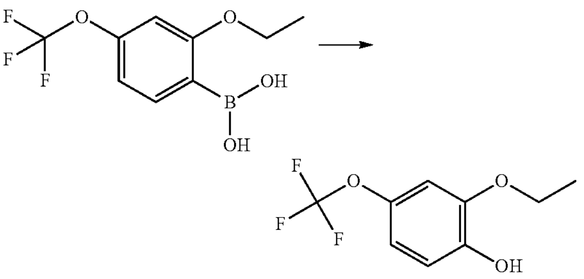

[2-Ethoxy-4-(trifluoromethoxy)phenyl]boronic acid (14.1 g, 54.5 mmol) was dissolved in THF (150 mL) and water (150 mL). Sodium perborate monohydrate (16.7 g, 167 mmol) was added in one portion, resulting in an exotherm to 37° C. after the addition. The mixture was stirred at room temperature for 20 minutes. The resulting white suspension was filtered, and the solid washed with water and MTBE. The filtrate phases were separated and the aqueous phase was extracted again with MTBE (100 mL). The combined organic phases were dried (phase separation cartridge) and concentrated in vacuo to afford 2-ethoxy-4-(trifluoromethoxy)phenol (12.4 g, 100%) as a yellow-orange oil. $^1$H NMR (400 MHz, DMSO-$d_6$) δ 9.25 (s, 1H), 6.90 (d, J=2.7 Hz, 1H), 6.83 (d, J=8.7 Hz, 1H), 6.78-6.70 (m, 1H), 4.04 (q, J=7.0 Hz, 2H), 1.33 (t, J=7.0 Hz, 3H) ppm. $^{19}$F NMR (376 MHz, DMSO) δ −57.17 ppm.

Preparation 11

3,4-Difluoro-2-Methyl-Phenol

Step 1: 1-Bromo-3,4-Difluoro-2-Methyl-Benzene

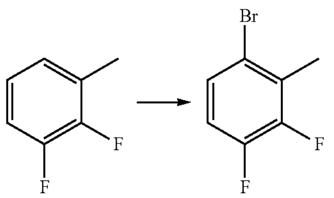

To a stirring suspension of 1,2-difluoro-3-methyl-benzene (10 g, 78 mmol) and iron powder (1.9 g, 7.5 mmol) in $CHCl_3$ (50 mL) under nitrogen was added $Br_2$ (12.1 g, 75.7 mmol) in a single portion. The mixture was stirred at room temperature for 19 hours, and then concentrated in vacuo to a volume of –25 mL. The residue was purified using silica gel column chromatography (100% hexanes) to provide 1-bromo-3,4-difluoro-2-methyl-benzene (15 g, 93%) as a clear oil. $^1H$ NMR (400 MHz, $CDCl_3$) δ 7.27 (ddd, J=8.9, 4.6, 2.2 Hz, 1H), 7.03-6.76 (m, 1H), 2.35 (s, 3H) ppm.

Step 2: 3,4-Difluoro-2-Methyl-Phenol

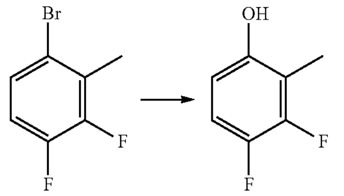

A mixture of 1-bromo-3,4-difluoro-2-methyl-benzene (22 g, 106 mmol), $Me_4$tButylXphos (1.51 g, 3.14 mmol) and KOH (18.2 g, 324 mmol) in dioxane (63 mL) and water (63 mL) was degassed with nitrogen bubbling for 10 minutes. $Pd_2dba_3$ (1.5 g, 1.6 mmol) was added and the mixture purged with nitrogen (3×). The mixture was stirred at 90° C. for 5 hours, and then diluted with water (100 mL) and washed with ether (3×80 mL). The aqueous layer was acidified with 3 M aqueous HCl to pH 1-2, and then extracted with ether (3×100 mL). The organic extracts were combined and washed with saturated aqueous $NaHCO_3$ (3×50 mL) and brine (50 mL), dried over $Na_2SO_4$, filtered and concentrated in vacuo to provide 3,4-difluoro-2-methyl-phenol (16.9 g, 85%) as a light orange oil. ESI-MS m z calc. 144.04, found 143.3 $(M-1)^-$; LC/MS retention time (Method M): 2.37 minutes. $^1H$ NMR (300 MHz, $CDCl_3$) δ 6.85 (q, J=9.1 Hz, 1H), 6.52-6.40 (m, 1H), 5.10-4.94 (m, 1H), 2.23-2.13 (m, 3H) ppm. $^{19}F$ NMR (282 MHz, $CDCl_3$) δ −139.60 (dd, J=21.4, 6.1 Hz, 1F), −148.15 (dd, J=21.4, 6.1 Hz, 1F) ppm.

Example 1

4-[[2-[(6-Chloro-2-Methoxy-3-Pyridyl)Oxy]-5-(Trifluoromethyl)Benzoyl]Amino]Pyridine-2-Carboxamide (1)

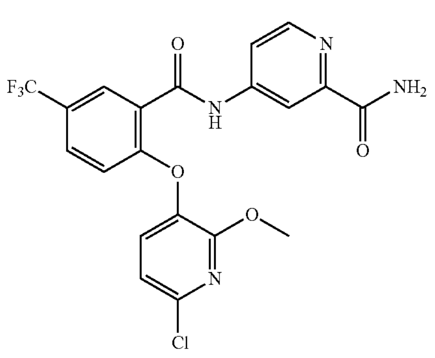 [SMILES: COc1nc(Cl)ccc1Oc1ccc(C(F)(F)F)cc1C(=O)Nc1ccnc(C(N)=O)c1]

Step 1: 2-Bromo-N-(2-Cyano-4-Pyridyl)-5-(Trifluoromethyl)Benzamide

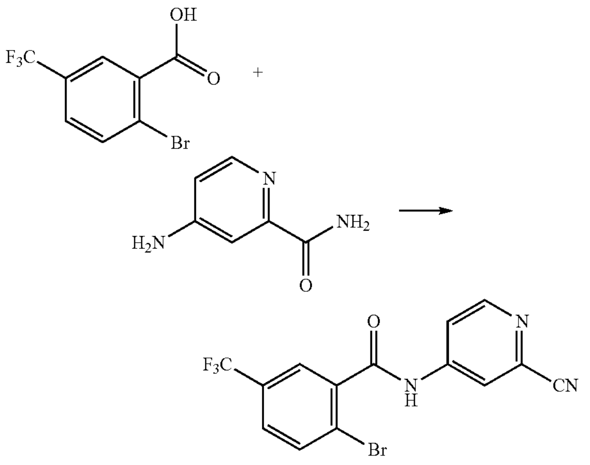

A solution of 2-bromo-5-(trifluoromethyl)benzoic acid (1 g, 3.7173 mmol) and 4-aminopyridine-2-carboxamide (515 mg, 3.7553 mmol) in pyridine (20.000 mL) was cooled to −10° C. followed by drop-wise addition of $POCl_3$ (855.40 mg, 520 μL, 5.5788 mmol) with stirring. Stirring was continued for 90 minutes at −10° C. The reaction was then quenched with water (20 mL) and extracted with ethyl acetate (100 mL). The organic layer was washed with water (30 mL×3) and brine, dried over anhydrous $MgSO_4$ and filtered. The filtrate was concentrated under vacuo, and the residue dried under vacuum to afford 2-bromo-N-(2-cyano-4-pyridyl)-5-(trifluoromethyl)benzamide (1.34 g, 88%) as an orange solid. ESI-MS m/z calc. 368.9725, found 369.9 $(M+1)^+$; Retention time: 5.27 minutes. LCMS Method: Merckmillipore Chromolith SpeedROD $C_{18}$ column (50×4.6 mm) and a dual gradient run from 5-100% mobile phase B over 12 minutes. Mobile phase A=water (0.1% CF3CO2H). Mobile phase B=acetonitrile (0.1% CF3CO2H); LCMS Method Detail: null.

Step 2: 4-[[2-Bromo-5-(Trifluoromethyl)Benzoyl]Amino]Pyridine-2-Carboxamide

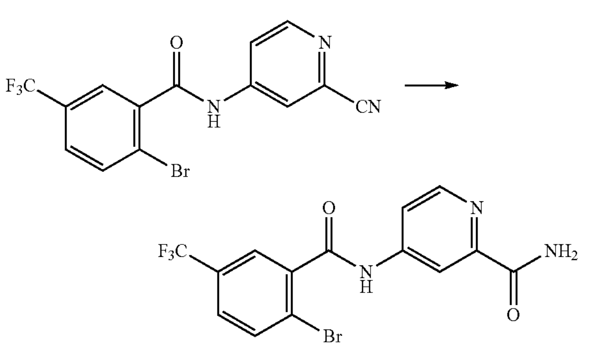

To a solution of mixture of 2-bromo-N-(2-cyano-4-pyridyl)-5-(trifluoromethyl)benzamide (13.01 g, 31.635 mmol) and $K_2CO_3$ (6.56 g, 47.465 mmol) in DMSO (390.30 mL) was added $H_2O_2$ (107.61 mL of 30% w/v, 949.05 mmol) dropwise at 10° C. with stirring. The reaction mixture was allowed to warm to ambient temperature and stirred for a further 30 minutes. The reaction mixture was then cooled to 4° C., diluted with ethyl acetate (600 mL) and quenched with 10% aqueous $Na_2S_2O_3$ (500 mL). The organic layer was washed with 10% aq. $Na_2S_2O_3$ (250 mL), water (250 mL×3), brine (250 mL), dried over anhydrous $MgSO_4$ and filtered. The filtrate was concentrated under reduced pressure to afford 4-[[2-bromo-5-(trifluoromethyl)benzoyl]amino]pyridine-2-carboxamide (9.28 g, 72%) as an orange solid. ESI-MS m/z calc. 386.983, found 388.2 $(M+1)^+$; Retention time: 1.83 minutes. 1H NMR (500 MHz, DMSO-d6) δ 11.20 (s, 1H), 8.57 (d, J=5.5 Hz, 1H), 8.38 (d, J=2.1 Hz, 1H), 8.11 (dd, J=8.4, 2.6 Hz, 2H), 8.02 (d, J=8.4 Hz, 1H), 7.88-7.81 (m, 2H), 7.67 (s, 1H) ppm. LCMS Method: Water Cortex 2.7u $C_{18}$ (3.0 mm×50 mm), Temp: 55c; Flow: 1.2 mL/minutes; MP: 100% water with 0.1% trifluoroacetic (TFA) acid then 100% acetonitrile with 0.1% TFA acid, grad:5% to 100% B over 4 min, with stay at 100% B for 0.5 min, equilibration to 5% B over 1.5 min; LCMS Method Detail: null.

Step 3: 4-[[2-[(6-Chloro-2-Methoxy-3-Pyridyl)Oxy]-5-(Trifluoromethyl)Benzoyl]Amino]Pyridine-2-Carboxamide (1)

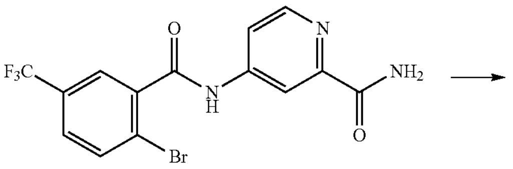

-continued

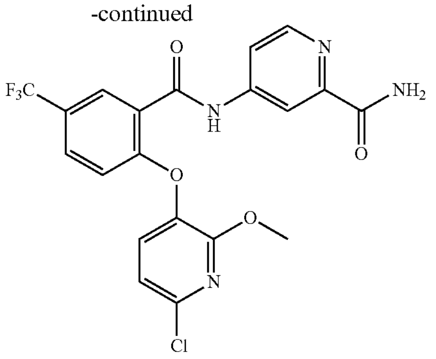

A solution of 4-[[2-bromo-5-(trifluoromethyl)benzoyl]amino]pyridine-2-carboxamide (40 mg, 0.1031 mmol) in DMSO (0.25 mL) was added to 6-chloro-2-methoxy-pyridin-3-ol (32.90 mg, 0.2062 mmol) followed by CsF (62.65 mg, 15.22 μL, 0.4124 mmol). The reaction mixture was capped and allowed to stir at 110° C. for 40 minutes. The product was purified by HPLC to provide 4-[[2-[(6-chloro-2-methoxy-3-pyridyl)oxy]-5-(trifluoromethyl)benzoyl]amino]pyridine-2-carboxamide (20.5 mg, 42%) was obtained. ESI-MS m/z calc. 466.06558, found 467.05 $(M+1)^+$; Retention time (Method B): 1.77 minutes. $^1$H NMR (400 MHz, DMSO-$d_6$) δ 11.08 (s, 1H), 8.54 (d, J=5.5 Hz, 1H), 8.33 (d, J=2.1 Hz, 11), 8.12 (d, J=2.8 Hz, 1), 8.06 (d, J 2.3 Hz, 1), 7.88 (dd, J 5.5, 2.2 Hz, 1H), 7.82 (dd, J 8.8, 2.4 Hz, 1H), 7.72 (d, J=8.1 Hz, 1), 7.66 (s, 11), 7.19 (d, J=8.2 Hz, 1H), 7.05 (d, J=8.8 Hz, 1), 3.83 (s, 3H).

The compounds set forth in Table 1 were prepared by methods analogous to the preparation of compound 1 in Example 1.

TABLE 1

Additional Compounds Prepared by Methods Analogous to Example 1.

| Cmpd No. | Compound Name | LC/MS | NMR (shifts in ppm) |
|---|---|---|---|
| 2 | 4-[[2-(3-chloro-4-isopropoxy-phenoxy)-5-(trifluoromethyl)benzoyl]amino]pyridine-2-carboxamide | ESI-MS m/z calc. 493.10162, found 493.95 (M + 1)+; Retention time (Method B): 1.96 minutes | $^1$H NMR (400 MHz, DMSO-$d_6$) δ 11.05 (s, 1H), 8.54 (d, J = 5.5 Hz, 1H), 8.33 (d, J = 2.2 Hz, 1H), 8.12 (s, 1H), 8.04 (d, J = 2.3 Hz, 1H), 7.89 (dd, J = 5.5, 2.2 Hz, 1H), 7.85 (dd, J = 9.0, 2.4 Hz, 1H), 7.67 (s, 1H), 7.40 (d, J = 2.8 Hz, 1H), 7.26 (d, J = 9.1 Hz, 1H), 7.18 (dd, J = 8.9, 2.9 Hz, 1H), 7.05 (d, J = 8.8 Hz, 1H), 4.63 (p, J = 6.0 Hz, 1H), 1.29 (d, J = 6.0 Hz, 6H). |
| 3 | 4-[[2-(4-fluoro-3-methyl-phenoxy)-5-(trifluoromethyl)benzoyl]amino]pyridine-2-carboxamide | ESI-MS m/z calc. 433.10495, found 434.05 (M + 1)+; Retention time (Method B): 1.82 minutes; | $^1$H NMR (400 MHz, DMSO-$d_6$) δ 11.09 (s, 1H), 8.54 (d, J = 5.5 Hz, 1H), 8.33 (d, J = 2.1 Hz, 1H), 8.13 (d, J = 2.8 Hz, 1H), 8.05 (d, J = 2.3 Hz, 1H), 7.89 (dd, J = 5.5, 2.2 Hz, 1H), 7.85 (dd, J = 8.8, 2.4 Hz, 1H), 7.68 (d, J = 2.7 Hz, 1H), 7.24 (t, J = 9.0 Hz, 1H), 7.18 (dd, J = 6.4, 3.0 Hz, 1H), 7.08 (dt, J = 8.2, 3.6 Hz, 1H), 7.02 (d, J = 8.7 Hz, 1H), 2.23 (d, J = 1.9 Hz, 3H). |
| 4 | 4-[[2-(4-fluoro-2-methyl-phenoxy)-5-(trifluoromethyl)benzoyl]amino]pyridine-2-carboxamide | ESI-MS m/z calc. 433.10495, found 434.1 (M + 1)+; Retention time (Method B): 1.81 minutes; | $^1$H NMR (400 MHz, DMSO-$d_6$) δ 11.13 (s, 1H), 8.55 (d, J = 5.5 Hz, 1H), 8.36 (d, J = 2.1 Hz, 1H), 8.14 (s, 1H), 8.06 (d, J = 2.3 Hz, 1H), 7.89 (dd, J = 5.5, 2.2 Hz, 1H), 7.82 (dd, J = 8.8, 2.4 Hz, 1H), 7.69 (s, 1H), 7.23 (ddd, J = 15.8, 9.1, 4.1 Hz, 2H), 7.14 (td, J = 8.5, 3.1 Hz, 1H), 6.85 (d, J = 8.8 Hz, 1H), 2.15 (s, 3H). |

TABLE 1-continued

Additional Compounds Prepared by Methods Analogous to Example 1.

| Cmpd No. | Compound Name | LC/MS | NMR (shifts in ppm) |
|---|---|---|---|
| 5 | 4-[[2-(2-chloro-4-fluoro-phenoxy)-5-(trifluoromethyl)benzoyl]amino]pyridine-2-carboxamide | ESI-MS m/z calc. 453.05032, found 454.0 (M + 1)+; Retention time (Method B): 1.78 minutes; | $^1$H NMR (400 MHz, DMSO-$d_6$) δ 11.16 (s, 1H), 8.55 (d, J = 5.5 Hz, 1H), 8.36 (d, J = 2.1 Hz, 1H), 8.15 (d, J = 2.6 Hz, 1H), 8.10 (d, J = 2.3 Hz, 1H), 7.91 (dd, J = 5.6, 2.2 Hz, 1H), 7.86 (dd, J = 8.7, 2.4 Hz, 1H), 7.69 (dd, J = 8.3, 3.0 Hz, 2H), 7.48 (dd, J = 9.1, 5.2 Hz, 1H), 7.37 (td, J = 8.5, 3.0 Hz, 1H), 6.94 (d, J = 8.7 Hz, 1H). |
| 6 | 4-[[2-(3,4-difluorophenoxy)-5-(trifluoromethyl)benzoyl]amino]pyridine-2-carboxamide | ESI-MS m/z calc. 437.0799, found 438.0 (M + 1)+; Retention time (Method B): 1.74 minutes; | $^1$H NMR (400 MHz, DMSO-$d_6$) δ 11.11 (s, 1H), 8.54 (d, J = 5.5 Hz, 1H), 8.33 (d, J = 2.1 Hz, 1H), 8.13 (d, J = 2.7 Hz, 1H), 8.09 (d, J = 2.3 Hz, 1H), 7.88 (dd, J = 8.6, 2.8 Hz, 2H), 7.68 (s, 1H), 7.55 (q, J = 9.5 Hz, 1H), 7.44 (ddd, J = 11.4, 6.8, 2.9 Hz, 1H), 7.14 (d, J = 8.7 Hz, 1H), 7.09 (d, J = 9.2 Hz, 1H). |
| 7 | 4-[[2-(3-fluoro-4-isopropoxy-phenoxy)-5-(trifluoromethyl)benzoyl]amino]pyridine-2-carboxamide | ESI-MS m/z calc. 477.13116, found 478.15 (M + 1)+; Retention time (Method B): 1.88 minutes; | $^1$H NMR (400 MHz, DMSO-$d_6$) δ 11.06 (s, 1H), 8.54 (d, J = 5.5 Hz, 1H), 8.33 (d, J = 2.2 Hz, 1H), 8.12 (d, J = 2.8 Hz, 1H), 8.05 (d, J = 2.3 Hz, 1H), 7.91-7.81 (m, 2H), 7.67 (d, J = 2.9 Hz, 1H), 7.30-7.19 (m, 2H), 7.06 (d, J = 8.7 Hz, 1H), 7.04-6.97 (m, 1H), 4.58 (p, J = 6.1 Hz, 1H), 1.27 (d, J = 6.1 Hz, 6H). |
| 8 | 4-[[2-(4-fluoro-2-methoxy-phenoxy)-5-(trifluoromethyl)benzoyl]amino]pyridine-2-carboxamide | ESI-MS m/z calc. 449.09988, found 450.05 (M + 1)+; Retention time (Method B): 1.76 minutes; | $^1$H NMR (400 MHz, DMSO-$d_6$) δ 11.04 (s, 1H), 8.55 (d, J = 5.4 Hz, 1H), 8.35 (d, J = 2.1 Hz, 1H), 8.12 (d, J = 2.9 Hz, 1H), 8.02 (d, J = 2.3 Hz, 1H), 7.92 (dd, J = 5.5, 2.2 Hz, 1H), 7.79 (dd, J = 8.8, 2.5 Hz, 1H), 7.67 (d, J = 2.9 Hz, 1H), 7.36 (dd, J = 8.8, 5.9 Hz, 1H), 7.17 (dd, J = 10.7, 3.0 Hz, 1H), 6.89 (td, J = 8.5, 2.9 Hz, 1H), 6.81 (d, J = 8.8 Hz, 1H), 3.75 (s, 3H). |
| 9 | 4-[[2-(4-isopropoxyphenoxy)-5-(trifluoromethyl)benzoyl]amino]pyridine-2-carboxamide | ESI-MS m/z calc. 459.1406, found 460.15 (M + 1)+; Retention time (Method B): 1.89 minutes; | $^1$H NMR (400 MHz, DMSO-$d_6$) δ 11.06 (s, 1H), 8.54 (d, J = 5.5 Hz, 1H), 8.34 (d, J = 2.2 Hz, 1H), 8.12 (d, J = 3.3 Hz, 1H), 8.02 (d, J = 2.3 Hz, 1H), 7.90 (dd, J = 5.6, 2.2 Hz, 1H), 7.83 (dd, J = 8.8, 2.5 Hz, 1H), 7.67 (d, J = 2.8 Hz, 1H), 7.16 (d, J = 9.0 Hz, 2H), 7.00 (d, J = 9.0 Hz, 2H), 6.95 (d, J = 8.8 Hz, 1H), 4.58 (p, J = 6.1 Hz, 1H), 1.26 (d, J = 5.9 Hz, 6H). |
| 10 | 4-[[2-[(4-fluoro-2,3-dihydrobenzofuran-7-yl)oxy]-5-(trifluoromethyl)benzoyl]amino]pyridine-2-carboxamide | ESI-MS m/z calc. 461.09988, found 462.05 (M + 1)+; Retention time (Method B): 1.77 minutes | $^1$H NMR (400 MHz, DMSO-$d_6$) δ 11.07 (s, 1H), 8.55 (d, J = 5.5 Hz, 1H), 8.35 (d, J = 2.1 Hz, 1H), 8.12 (d, J = 2.8 Hz, 1H), 8.02 (d, J = 2.3 Hz, 1H), 7.91 (dd, J = 5.6, 2.2 Hz, 1H), 7.82 (dd, J = 8.9, 2.4 Hz, 1H), 7.67 (d, J = 2.9 Hz, 1H), 7.14 (dd, J = 9.0, 4.7 Hz, 1H), 6.95 (d, J = 8.8 Hz, 1H), 6.78 (t, J = 8.5 Hz, 1H), 4.63 (t, J = 8.7 Hz, 2H), 3.29 (t, J = 8.7 Hz, 2H). |
| 11 | 4-[[2-(3-chloro-4-fluoro-phenoxy)-5-(trifluoromethyl)benzoyl]amino]pyridine-2-carboxamide | ESI-MS m/z calc. 453.05032, found 454.05 (M + 1)+; Retention time (Method B): 1.82 minutes; | $^1$H NMR (400 MHz, DMSO-$d_6$) δ 11.10 (s, 1H), 8.54 (d, J = 5.5 Hz, 1H), 8.33 (d, J = 2.1 Hz, 1H), 8.13 (s, 1H), 8.09 (d, J = 2.3 Hz, 1H), 7.91-7.84 (m, 2H), 7.68 (s, 1H), 7.58-7.47 (m, 2H), 7.27 (dt, J = 9.0, 3.5 Hz, 1H), 7.14 (d, J = 8.8 Hz, 1H). |
| 12 | 4-[[2-(3-fluoro-2-methoxy-phenoxy)-5-(trifluoromethyl)benzoyl]amino]pyridine-2-carboxamide | ESI-MS m/z calc. 449.09988, found 450.05 (M + 1)+; Retention time (Method B): 1.74 minutes; | $^1$H NMR (400 MHz, DMSO-$d_6$) δ 11.16 (s, 1H), 8.55 (d, J = 5.5 Hz, 1H), 8.38 (d, J = 2.1 Hz, 1H), 8.15 (s, 1H), 8.09 (d, J = 2.3 Hz, 1H), 7.90 (dd, J = 5.6, 2.2 Hz, 1H), 7.85 (dd, J = 8.9, 2.4 Hz, 1H), 7.69 (s, 1H), 7.28-7.16 (m, 2H), 7.10 (dd, J = 7.9, 2.2 Hz, 1H), 7.00 (d, J = 8.7 Hz, 1H), 3.77 (s, 3H). |
| 13 | 4-[[2-[4-(cyclohexoxy)phenoxy]-5-(trifluoromethyl)benzoyl]amino]pyridine-2-carboxamide | ESI-MS m/z calc. 499.1719, found 500.1 (M + 1)+; Retention time (Method B): 2.11 minutes | $^1$H NMR (400 MHz, DMSO-$d_6$) δ 11.05 (s, 1H), 8.53 (d, J = 5.5 Hz, 1H), 8.33 (d, J = 2.1 Hz, 1H), 8.11 (d, J = 2.7 Hz, 1H), 8.02 (d, J = 2.4 Hz, 1H), 7.90 (dd, J = 5.8, 2.2 Hz, 1H), 7.82 (dd, J = 8.9, 2.5 Hz, 1H), 7.66 (s, 1H), 7.15 (d, J = 8.9 Hz, 2H), 7.01 (d, J = 9.1 Hz, 2H), 6.95 (d, J = 8.8 Hz, 1H), 4.39-4.19 (m, 0H), |

TABLE 1-continued

Additional Compounds Prepared by Methods Analogous to Example 1.

| Cmpd No. | Compound Name | LC/MS | NMR (shifts in ppm) |
|---|---|---|---|
| | | | 1.97-1.85 (m, 2H), 1.76-1.66 (m, 2H), 1.60-1.49 (m, 1H), 1.45-1.25 (m, 5H). |
| 14 | 4-[[2-(3-cyclohexylphenoxy)-5-(trifluoromethyl)benzoyl]amino]pyridine-2-carboxamide | ESI-MS m/z calc. 483.17697, found 484.1 (M + 1)+; Retention time (Method B): 2.18 minutes | $^1$H NMR (400 MHz, DMSO-d$_6$) δ 11.07 (s, 1H), 8.52 (d, J = 5.5 Hz, 1H), 8.31 (s, 1H), 8.11 (s, 1H), 8.05 (d, J = 2.4 Hz, 1H), 7.86 (d, J = 7.3 Hz, 2H), 7.66 (s, 1H), 7.35 (t, J = 7.9 Hz, 1H), 7.09 (d, J = 7.7 Hz, 1H), 7.07-7.02 (m, 2H), 6.97 (dd, J = 8.2, 2.5 Hz, 1H), 2.46 (m, 1H, obscured by DMSO), 1.70 (d, J = 36.7 Hz, 5H), 1.40-1.16 (m, 5H). |
| 15 | 4-[[2-(5-chloro-2-methoxy-phenoxy)-5-(trifluoromethyl)benzoyl]amino]pyridine-2-carboxamide | ESI-MS m/z calc. 465.0703, found 466.1 (M + 1)+; Retention time (Method B): 1.84 minutes | $^1$H NMR (400 MHz, DMSO-d$_6$) δ 11.00 (s, 1H), 8.54 (d, J = 5.5 Hz, 1H), 8.35 (d, J = 2.1 Hz, 1H), 8.12 (d, J = 2.6 Hz, 1H), 8.03 (d, J = 2.4 Hz, 1H), 7.90 (dd, J = 5.6, 2.2 Hz, 1H), 7.82 (dd, J = 8.8, 2.4 Hz, 1H), 7.67 (s, 1H), 7.42 (d, J = 2.6 Hz, 1H), 7.35 (dd, J = 8.9, 2.6 Hz, 1H), 7.24 (d, J = 8.9 Hz, 1H), 6.90 (d, J = 8.8 Hz, 1H), 3.74 (s, 3H). |
| 16 | 4-[[2-(4-fluoro-3-methoxy-phenoxy)-5-(trifluoromethyl)benzoyl]amino]pyridine-2-carboxamide | ESI-MS m/z calc. 449.09988, found 450.0 (M + 1)+; Retention time (Method B): 1.74 minutes | $^1$H NMR (400 MHz, DMSO-d$_6$) δ 11.07 (s, 1H), 8.54 (d, J = 5.5 Hz, 1H), 8.34 (d, J = 2.1 Hz, 1H), 8.11 (s, 1H), 8.05 (d, J = 2.3 Hz, 1H), 7.88 (dd, J = 5.6, 2.2 Hz, 1H), 7.84 (dd, J = 9.0, 2.4 Hz, 1H), 7.67 (s, 1H), 7.30 (dd, J = 11.2, 8.8 Hz, 1H), 7.10 (dd, J = 7.4, 2.8 Hz, 1H), 7.04 (d, J = 8.7 Hz, 1H), 6.81-6.74 (m, 1H), 3.81 (s, 3H). |
| 17 | 4-[[2-(2,4-difluorophenoxy)-5-(trifluoromethyl)benzoyl]amino]pyridine-2-carboxamide | ESI-MS m/z calc. 437.0799, found 438.1 (M + 1)+; Retention time (Method B): 1.72 minutes | $^1$H NMR (400 MHz, DMSO-d$_6$) δ 11.16 (s, 1H), 8.55 (d, J = 5.5 Hz, 1H), 8.35 (d, J = 2.1 Hz, 1H), 8.13 (s, 1H), 8.08 (d, J = 2.3 Hz, 1H), 7.90 (dd, J = 5.5, 2.2 Hz, 1H), 7.88-7.83 (m, 1H), 7.68 (s, 1H), 7.54 (td, J = 11.3, 10.1, 3.0 Hz, 1H), 7.48 (td, J = 9.2, 5.6 Hz, 1H), 7.22 (t, J = 9.3 Hz, 1H), 7.05 (d, J = 8.8 Hz, 1H). |

Example 2

4-[[6-(2,3-Difluoro-4-Isopropoxy-Phenoxy)-2-Fluoro-3-(Trifluoromethyl)Benzoyl]Amino]Pyridine-2-Carboxamide (18)

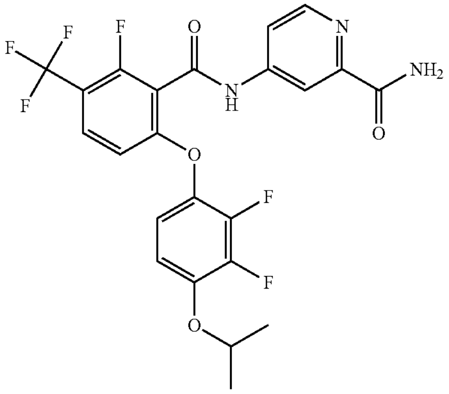 [SMILES: CC(C)Oc1ccc(Oc2ccc(C(F)(F)F)c(F)c2C(=O)Nc2ccnc(C(N)=O)c2)c(F)c1F]

Step 1: Methyl 4-[[6-Bromo-2-Fluoro-3-(Trifluoromethyl)Benzoyl]Amino]Pyridine-2-Carboxylate

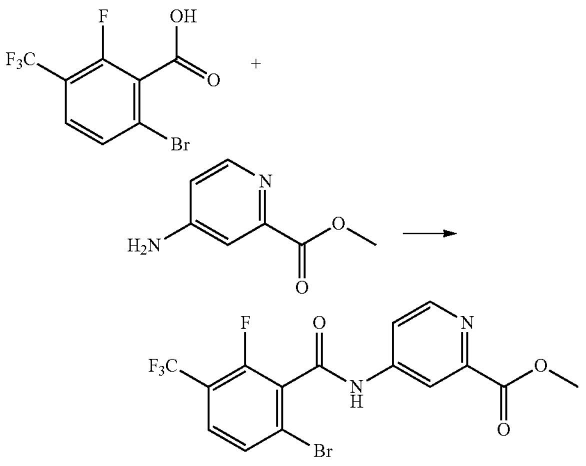

To an ice-cooled solution of 6-bromo-2-fluoro-3-(trifluoromethyl)benzoic acid (250 mg, 0.8711 mmol) in DCM (10 mL) was added DMF (5 μL, 0.06457 mmol) oxalyl chloride (230 μL, 2.637 mmol) and the mixture was stirred and warmed to RT over 3.5 h. The reaction mixture was concentrated in vacuo, dissolved in DCM (10 mL) and added drop-wise to a solution of methyl 4-aminopyridine-2-carboxylate (160 mg, 1.052 mmol) and TEA (610 μL, 4.377 mmol) in DCM (10 mL) at 0° C. The resulting mixture was stirred and warmed to ambient temperature over 18 h. The reaction mixture was quenched with water and the layers separated. The aqueous layer was extracted with DCM (×2) and the combined organics extracts were dried ($MgSO_4$), filtered and concentrated in vacuo. The residue was purified by column chromatography (0 to 75% EtOAc/Petroleum Ether) to give methyl 4-[[6-bromo-2-fluoro-3-(trifluoromethyl)benzoyl]amino]pyridine-2-carboxylate (98.1 mg, 27%) as a pale yellow solid. ESI-MS m/z calc. 419.97327, found 423.0 $(M+1)^+$; 421.0 $(M-1)^-$; Retention time (Method E): 0.78 minutes. $^1H$ NMR (500 MHz, Chloroform-d) δ 8.76 (d, J=5.4 Hz, 1H), 8.21 (d, J=1.9 Hz, 1H), 8.07 (dd, J=5.5, 2.1 Hz, 1H), 7.87 (s, 1H), 7.66-7.61 (m, 2H), 4.04 (s, 3H); 19F NMR (471 MHz, Chloroform-d) 6-61.47 (d, J=12.9 Hz), −112.56 (q, J=12.9 Hz) ppm.

Step 2: 4-[[6-Bromo-2-Fluoro-3-(Trifluoromethyl) Benzoyl]Amino]Pyridine-2-Carboxamide

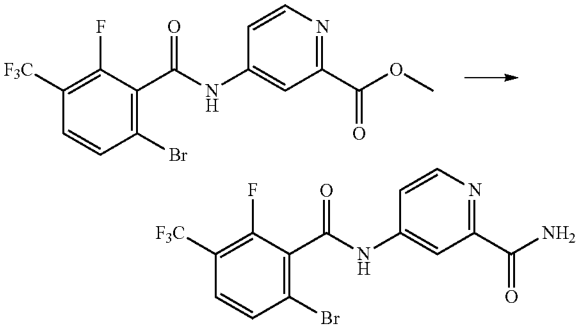

To a solution of methyl 4-[[6-bromo-2-fluoro-3-(trifluoromethyl)benzoyl]amino]pyridine-2-carboxylate (13.46 g, 31.961 mmol) in MeCN (160 mL) was added $NH_4Cl$ (600 mg, 11.217 mmol) and $NH_4OH$ (153.00 g, 170 mL of 28% w/v, 4.3657 mol) with stirring at ambient temperature. The reaction mixture was stirred at ambient temperature overnight then diluted with ethyl acetate (400 mL) and washed with water (150 mL×2), brine, dried over anhydrous $MgSO_4$ and filtered. Filtrate was evaporated, residue was subjected to flash purification (330 g SG column; dry loading; gradient 0->90% EtOAc/hexane/2%(7N $NH_3$/MeOH) in 60 minutes) to afford 4-[[6-bromo-2-fluoro-3-(trifluoromethyl)benzoyl]amino]pyridine-2-carboxamide (8.266 g, 60%) as off-white solid. ESI-MS m/z calc. 404.9736, found 406.0 $(M+1)^+$; Retention time: 1.87 minutes. 1H NMR (500 MHz, DMSO-d6) δ 11.53 (s, 1H), 8.60 (d, J=5.4 Hz, 1H), 8.35 (d, J=2.1 Hz, 1H), 8.14 (s, 1H), 7.98-7.85 (m, 2H), 7.81 (dd, J=5.4, 2.2 Hz, 1H), 7.70 (s, 1H) ppm. LCMS Method: Water Cortex 2.7u $C_{18}$ (3.0 mm×50 mm), Temp: 55c; Flow: 1.2 mL/minutes; MP: 100% water with 0.1% trifluoroacetic (TFA) acid then 100% acetonitrile with 0.10% TFA acid, grad:5% to 100% B over 4 min, with stay at 100% B for 0.5 min, equilibration to 5% B over 1.5 min; LCMS Method Detail: null.

Step 3: 4-[[6-(2,3-Difluoro-4-Isopropoxy-Phenoxy)-2-Fluoro-3-(Trifluoromethyl)Benzoyl]Amino]Pyridine-2-Carboxamide (18)

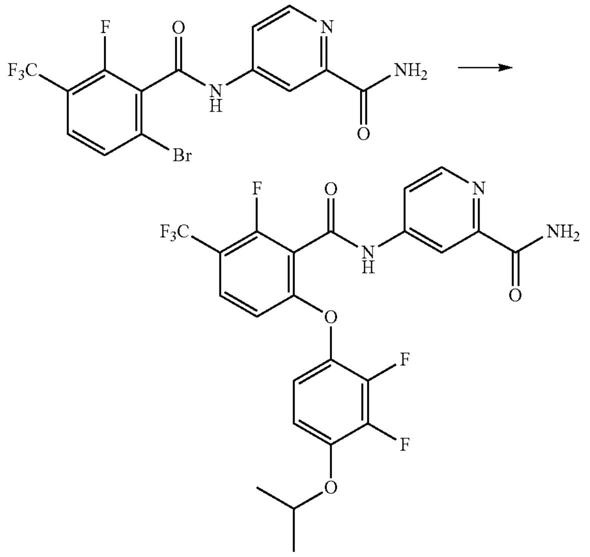

A mixture of 4-[[6-bromo-2-fluoro-3-(trifluoromethyl)benzoyl]amino]pyridine-2-carboxamide (50 mg, 0.1231 mmol), 2,3-difluoro-4-isopropoxy-phenol (23.16 mg, 0.1231 mmol), $Cs_2CO_3$ (80.22 mg, 0.2462 mmol), CuI (14.07 mg, 0.07386 mmol), and DMF (1.000 mL), was stirred at 100° C. for 1 hour. The reaction was diluted with DMSO (500 uL), filtered, and purified by reverse phase HPLC (gradient of 10-99% acetonitrile in water containing HCl as a modifier) to give 4-[[6-(2,3-difluoro-4-isopropoxy-phenoxy)-2-fluoro-3-(trifluoromethyl)benzoyl]amino]pyridine-2-carboxamide (23.8 mg, 37%) as a white solid. ESI-MS m/z calc. 513.1123, found 513.9 $(M+1)^+$; Retention time (Method B): 1.77 minutes. $^1H$ NMR (400 MHz, DMSO-d6) δ 11.54 (s, 1H), 8.57 (d, J=5.5 Hz, 1H), 8.33 (d, J=2.1 Hz, 1H), 8.14 (s, 1H), 7.86 (dd, J=10.5, 6.9 Hz, 2H), 7.69 (s, 1H), 7.31-7.06 (m, 2H), 6.95 (d, J=8.9 Hz, 1H), 4.67 (hept, J=6.1 Hz, 1H), 1.30 (d, J=6.0 Hz, 6H) ppm.

The compounds set forth in Table 2 were prepared by methods analogous to the preparation of compound 18 and Example 2.

TABLE 2

Additional Compounds Prepared by Methods Analogous to Example 2.

| Cmpd No. | Compound Name | LC/MS | NMR (shifts in ppm) |
|---|---|---|---|
| 19 | 4-[[6-(4-ethoxy-2,3-difluoro-phenoxy)-2-fluoro-3-(trifluoromethyl)benzoyl] | ESI-MS m/z calc. 499.09668, found 499.9 (M + 1)+; | $^1H$ NMR (400 MHz, DMSO-$d_6$) δ 11.54 (s, 1H), 8.57 (d, J = 5.5 Hz, 1H), 8.32 (s, 1H), 8.14 (s, 1H), 7.93-7.78 (m, 2H), 7.70 (s, 1H), 7.21 (t, J = 9.0 Hz, 1H), |

TABLE 2-continued

Additional Compounds Prepared by Methods Analogous to Example 2.

| Cmpd No. | Compound Name | LC/MS | NMR (shifts in ppm) |
|---|---|---|---|
| | amino]pyridine-2-carboxamide | Retention time (Method B): 1.7 minutes | 7.10 (t, J = 8.9 Hz, 1H), 6.93 (d, J = 8.9 Hz, 1H), 4.15 (q, J = 7.0 Hz, 2H), 1.36 (t, J = 6.9 Hz, 3H). |
| 20 | 4-[[6-(2-chloro-4-fluoro-phenoxy)-2-fluoro-3-(trifluoromethyl)benzoyl]amino]pyridine-2-carboxamide | ESI-MS m/z calc. 471.04092, found 472.04 (M + 1)+; Retention time (Method B): 1.61 minutes | 1H NMR (400 MHz, DMSO-d6) δ 11.51 (s, 1H), 8.58 (d, J = 5.5 Hz, 1H), 8.33 (s, 1H), 8.14 (s, 1H), 7.91-7.82 (m, 2H), 7.72 (dd, J = 8.4, 3.1 Hz, 2H), 7.51 (dd, J = 9.1, 5.2 Hz, 1H), 7.39 (td, J = 8.4, 3.0 Hz, 1H), 6.75 (d, J = 8.9 Hz, 1H). |
| 21 | 4-[[2-fluoro-6-(4-fluoro-3-methoxy-phenoxy)-3-(trifluoromethyl)benzoyl]amino]pyridine-2-carboxamide | ESI-MS m/z calc. 467.09045, found 468.07 (M + 1)+; Retention time (Method B): 1.56 minutes | $^{1}$H NMR (400 MHz, DMSO-$d_6$) δ 11.53 (s, 1H), 8.58 (s, 1H), 8.34 (s, 1H), 8.16 (s, 1H), 7.86 (t, J = 8.6 Hz, 2H), 7.72 (s, 1H), 7.33 (dd, J = 11.2, 8.8 Hz, 1H), 7.12 (dd, J = 7.4, 2.8 Hz, 1H), 6.84 (d, J = 8.9 Hz, 1H), 6.80 (dt, J = 8.9, 3.2 Hz, 1H), 3.83 (s, 3H). |
| 22 | 4-[[2-fluoro-6-phenoxy-3-(trifluoromethyl)benzoyl]amino]pyridine-2-carboxamide | ESI-MS m/z calc. 419.0893, found 420.0 (M + 1)+; Retention time (Method C): 2.12 minutes | $^{1}$H NMR (400 MHz, DMSO-$d_6$) δ 11.58 (s, 1H), 8.57 (d, J = 5.5 Hz, 1H), 8.34 (d, J = 2.2 Hz, 1H), 8.17 (s, 1H), 7.92-7.83 (m, 2H), 7.73 (s, 1H), 7.50 (t, J = 7.9 Hz, 2H), 7.31 (t, J = 7.4 Hz, 1H), 7.24 (d, J = 8.0 Hz, 2H), 6.80 (d, J = 8.9 Hz, 1H). |
| 23 | 4-[[6-(4-ethoxyphenoxy)-2-fluoro-3-(trifluoromethyl)benzoyl]amino]pyridine-2-carboxamide | ESI-MS m/z calc. 463.1155, found 464.0 (M + 1)+; Retention time (Method B): 1.66 minutes | 1H NMR (400 MHz, DMSO-d6) δ 11.53 (s, 1H), 8.57 (s, 1H), 8.34 (s, 1H), 8.16 (s, 1H), 7.97-7.79 (m, 2H), 7.72 (s, 1H), 7.17 (d, J = 9.0 Hz, 2H), 7.02 (d, J = 9.0 Hz, 2H), 6.72 (d, J = 8.9 Hz, 1H), 4.02 (q, J = 7.0 Hz, 2H), 1.32 (t, J = 7.0 Hz, 3H). |
| 24 | 4-[[6-(3,4-difluorophenoxy)-2-fluoro-3-(trifluoromethyl)benzoyl]amino]pyridine-2-carboxamide | ESI-MS m/z calc. 455.07047, found 456.05 (M + 1)+; Retention time (Method B): 1.58 minutes | $^{1}$H NMR (400 MHz, DMSO-$d_6$) δ 11.49 (s, 1H), 8.57 (d, J = 5.5 Hz, 1H), 8.31 (s, 1H), 8.14 (s, 1H), 7.89 (t, J = 8.7 Hz, 1H), 7.83 (d, J = 5.5 Hz, 1H), 7.70 (s, 1H), 7.57 (q, J = 9.5 Hz, 1H), 7.49 (ddd, J = 10.5, 6.8, 3.0 Hz, 1H), 7.13 (d, J = 9.4 Hz, 1H), 6.94 (d, J = 8.9 Hz, 1H). |
| 25 | 4-[[6-(3-chloro-4-fluoro-phenoxy)-2-fluoro-3-(trifluoromethyl)benzoyl]amino]pyridine-2-carboxamide | ESI-MS m/z calc. 471.04092, found 472.04 (M + 1)+; Retention time (Method B): 1.65 minutes; | $^{1}$H NMR (400 MHz, DMSO-$d_6$) δ 11.46 (s, 1H), 8.57 (d, J = 5.5 Hz, 1H), 8.31 (d, J = 2.1 Hz, 1H), 8.13 (s, 1H), 7.89 (t, J = 8.7 Hz, 1H), 7.82 (dd, J = 5.5, 2.2 Hz, 1H), 7.69 (s, 1H), 7.60 (dd, J = 6.2, 2.9 Hz, 1H), 7.55 (t, J = 9.0 Hz, 1H), 7.30 (dt, J = 9.1, 3.5 Hz, 1H), 6.94 (d, J = 8.9 Hz, 1H). |
| 26 | 4-[[2-fluoro-6-[[2-methyl-6-(trifluoromethyl)-3-pyridyl]oxy]-3-(trifluoromethyl)benzoyl]amino]pyridine-2-carboxamide | ESI-MS m/z calc. 502.0876, found 503.08 (M + 1)+; Retention time (Method B): 1.56 minutes; | 1H NMR (400 MHz, DMSO-d6) δ 11.61 (s, 1H), 8.56 (s, 1H), 8.30 (s, 1H), 8.16 (s, 1H), 7.94 (t, J = 8.6 Hz, 1H), 7.87-7.75 (m, 3H), 7.72 (s, 1H), 7.10 (d, J = 8.8 Hz, 1H), 2.45 (s, 3H). |
| 27 | 4-[[6-(5-chloro-2-methoxy-phenoxy)-2-fluoro-3-(trifluoromethyl)benzoyl]amino]pyridine-2-carboxamide | ESI-MS m/z calc. 483.06088, found 484.06 (M + 1)+; Retention time (Method B): 1.63 minutes; | $^{1}$H NMR (400 MHz, DMSO-$d_6$) δ 11.44 (s, 1H), 8.58 (s, 1H), 8.35 (s, 1H), 8.14 (s, 1H), 7.90-7.78 (m, 2H), 7.70 (s, 1H), 7.43-7.37 (m, 2H), 7.26 (d, J = 8.7 Hz, 1H), 6.71 (d, J = 8.9 Hz, 1H), 3.76 (s, 3H). |
| 28 | 4-[[2-fluoro-6-(3-fluoro-4-isopropoxy-phenoxy)-3-(trifluoromethyl)benzoyl]amino]pyridine-2-carboxamide | ESI-MS m/z calc. 495.12173, found 496.09 (M + 1)+; Retention time (Method B): 1.7 minutes | $^{1}$H NMR (400 MHz, DMSO-$d_6$) δ 11.46 (s, 1H), 8.57 (s, 1H), 8.32 (s, 0H), 8.15 (s, 2H), 7.86 (t, J = 8.6 Hz, 2H), 7.71 (s, 1H), 7.33-7.19 (m, 2H), 7.02 (d, J = 9.6 Hz, 1H), 6.86 (d, J = 8.9 Hz, 1H), 4.60 (p, J = 6.1 Hz, 1H), 1.28 (d, J = 6.0 Hz, 6H). |
| 29 | 4-[[6-(4-ethoxy-3-fluoro-phenoxy)-2-fluoro-3-(trifluoromethyl)benzoyl]amino]pyridine-2-carboxamide | ESI-MS m/z calc. 481.1061, found 481.9 (M + 1)+; Retention time (Method B): 1.67 minutes; | 1H NMR (400 MHz, DMSO-d6) δ 11.49 (s, 1H), 8.57 (d, J = 5.5 Hz, 1H), 8.32 (d, J = 2.2 Hz, 1H), 8.14 (s, 1H), 7.94-7.80 (m, 2H), 7.70 (s, 1H), 7.34-7.14 (m, 2H), 7.04 (ddd, J = 9.0, 2.9, 1.5 Hz, 1H), 6.83 (d, J = 8.9 Hz, 1H), 4.10 (q, J = 6.9 Hz, 2H), 1.34 (t, J = 6.9 Hz, 3H). |
| 30 | 4-[[2-fluoro-6-[(4-fluoro-2,3-dihydrobenzofuran-7- | ESI-MS m/z calc. 479.09045, | $^{1}$H NMR (400 MHz, DMSO-$d_6$) δ 11.49 (s, 1H), 8.57 (s, 1H), 8.33 (s, 1H), 8.14 |

TABLE 2-continued

Additional Compounds Prepared by Methods Analogous to Example 2.

| Cmpd No. | Compound Name | LC/MS | NMR (shifts in ppm) |
|---|---|---|---|
| | yl)oxy]-3-(trifluoromethyl)benzoyl]amino]pyridine-2-carboxamide | found 480.1 (M + 1)+; Retention time (Method B): 1.58 minutes; | (s, 1H), 7.88-7.79 (m, 2H), 7.70 (s, 1H), 7.11 (dd, J = 9.0, 4.7 Hz, 1H), 6.83-6.73 (m, 2H), 4.65 (t, J = 8.7 Hz, 2H), 3.30 (t, J = 8.7 Hz, 2H). |
| 31 | 4-[[6-(3,4-difluoro-2-methoxy-phenoxy)-2-fluoro-3-(trifluoromethyl)benzoyl]amino]pyridine-2-carboxamide | ESI-MS m/z calc. 485.08102, found 485.9 (M + 1)+; Retention time (Method B): 1.63 minutes; | $^1$H NMR (400 MHz, DMSO-$d_6$) δ 11.57 (s, 1H), 8.58 (d, J = 5.5 Hz, 1H), 8.36 (d, J = 2.1 Hz, 1H), 8.15 (s, 1H), 7.89-7.79 (m, 2H), 7.71 (s, 1H), 7.30 (q, J = 9.3 Hz, 1H), 7.19 (ddd, J = 9.3, 5.2, 2.1 Hz, 1H), 6.81 (d, J = 8.9 Hz, 1H), 3.85 (d, J = 1.2 Hz, 3H). |
| 32 | 4-[[2-fluoro-6-(4-fluoro-3-methyl-phenoxy)-3-(trifluoromethyl)benzoyl]amino]pyridine-2-carboxamide | ESI-MS m/z calc. 451.09552, found 452.09 (M + 1)+; Retention time (Method B): 1.65 minutes; | $^1$H NMR (400 MHz, DMSO-$d_6$) δ 11.47 (s, 1H), 8.57 (s, 1H), 8.32 (s, 1H), 8.14 (s, 1H), 7.91-7.82 (m, 2H), 7.70 (s, 1H), 7.26 (t, J = 9.0 Hz, 1H), 7.20 (dd, J = 6.4, 3.0 Hz, 1H), 7.10 (dd, J = 8.5, 4.1 Hz, 1H), 6.82 (d, J = 8.9 Hz, 1H), 2.27-2.20 (m, 3H). |
| 33 | 4-[[6-(3-chloro-4-isopropoxy-phenoxy)-2-fluoro-3-(trifluoromethyl)benzoyl]amino]pyridine-2-carboxamide | ESI-MS m/z calc. 511.0922, found 512.08 (M + 1)+; Retention time (Method B): 1.78 minutes; | $^1$H NMR (400 MHz, DMSO-$d_6$) δ 11.46 (s, 1H), 8.57 (s, 1H), 8.32 (s, 1H), 8.14 (s, 1H), 7.86 (t, J = 8.7 Hz, 2H), 7.70 (s, 1H), 7.41 (d, J = 2.8 Hz, 1H), 7.27 (d, J = 9.1 Hz, 1H), 7.20 (dd, J = 9.0, 2.9 Hz, 1H), 6.85 (d, J = 8.9 Hz, 1H), 4.64 (p, J = 6.1 Hz, 1H), 1.29 (d, J = 6.0 Hz, 6H). |
| 34 | 4-[[2-fluoro-6-(3-fluoro-2-methoxy-phenoxy)-3-(trifluoromethyl)benzoyl]amino]pyridine-2-carboxamide | ESI-MS m/z calc. 467.09045, found 468.07 (M + 1)+; Retention time (Method B): 1.56 minutes | $^1$H NMR (400 MHz, DMSO-$d_6$) δ 11.53 (s, 1H), 8.57 (d, J = 5.5 Hz, 1H), 8.35 (s, 1H), 8.14 (s, 1H), 7.90-7.80 (m, 2H), 7.70 (s, 1H), 7.32-7.25 (m, 1H), 7.22 (td, J = 8.3, 5.9 Hz, 1H), 7.13 (d, J = 7.9 Hz, 1H), 6.78 (d, J = 8.9 Hz, 1H), 3.78 (s, 3H). |
| 35 | 4-[[6-[4-(cyclohexoxy)phenoxy]-2-fluoro-3-(trifluoromethyl)benzoyl]amino]pyridine-2-carboxamide | ESI-MS m/z calc. 517.1625, found 518.13 (M + 1)+; Retention time (Method B): 1.9 minutes; | $^1$H NMR (400 MHz, DMSO-$d_6$) δ 11.47 (s, 1H), 8.57 (s, 1H), 8.32 (s, 1H), 8.13 (s, 1H), 7.84 (t, J = 8.6 Hz, 1H), 7.70 (s, 1H), 7.19-7.10 (m, 2H), 7.02 (d, J = 9.0 Hz, 2H), 6.75 (d, J = 8.9 Hz, 1H), 4.31 (m, 1H), 1.91 (m, 2H), 1.71 (m, 2H), 1.53 (m, 1H), 1.47-1.18 (m, 5H). |
| 36 | 4-[[6-[2-(1,1-difluoroethyl)-4-fluoro-phenoxy]-2-fluoro-3-(trifluoromethyl)benzoyl]amino]pyridine-2-carboxamide | ESI-MS m/z calc. 501.09235, found 501.9 (M + 1)+; Retention time (Method B): 1.69 minutes; | 1H NMR (400 MHz, DMSO-d6) δ 11.52 (s, 1H), 8.56 (s, 1H), 8.33 (s, 1H), 8.12 (s, 1H), 7.94-7.77 (m, 1H), 7.69 (s, 2H), 7.50 (ddd, J = 12.2, 9.0, 4.2 Hz, 1H), 7.40 (dd, J = 9.0, 4.6 Hz, 2H), 6.80 (d, J = 8.9 Hz, 1H), 1.90 (t, J = 19.2 Hz, 3H). |
| 37 | 4-[[2-fluoro-6-(4-isopropoxyphenoxy)-3-(trifluoromethyl)benzoyl]amino]pyridine-2-carboxamide | ESI-MS m/z calc. 477.13116, found 478.0 (M + 1)+; Retention time (Method B): 1.75 minutes. | 1H NMR (500 MHz, DMSO-d6) δ 11.49 (d, J = 1.9 Hz, 1H), 8.57 (d, J = 5.5 Hz, 1H), 8.33 (d, J = 2.2 Hz, 1H), 8.23-8.04 (m, 1H), 8.00-7.79 (m, 2H), 7.69 (d, J = 2.5 Hz, 1H), 7.25-7.09 (m, 2H), 7.09-6.93 (m, 2H), 6.86-6.66 (m, 1H), 4.59 (hept, J = 5.8 Hz, 1H), 1.26 (d, J = 6.0 Hz, 6H). |
| 38 | 4-[[6-(3-chloro-4-ethoxy-phenoxy)-2-fluoro-3-(trifluoromethyl)benzoyl]amino]pyridine-2-carboxamide | ESI-MS m/z calc. 497.07654, found 497.9 (M + 1)+; Retention time (Method B): 1.76 minutes; | 1H NMR (400 MHz, DMSO-d6) δ 11.49 (s, 1H), 8.57 (d, J = 5.5 Hz, 1H), 8.32 (d, J = 2.1 Hz, 1H), 8.15 (s, 1H), 7.91-7.79 (m, 2H), 7.74-7.67 (m, 1H), 7.43 (d, J = 2.1 Hz, 1H), 7.22 (d, J = 2.3 Hz, 2H), 6.82 (d, J = 8.9 Hz, 1H), 4.12 (q, J = 6.9 Hz, 2H), 1.35 (t, J = 6.9 Hz, 3H). |
| 39 | 4-[[2-fluoro-3-(trifluoromethyl)-6-[[6-(trifluoromethyl)-3-pyridyl]oxy]benzoyl]amino]pyridine-2-carboxamide | ESI-MS m/z calc. 488.07193, found 489.04 (M + 1)+; Retention time (Method B): 1.51 minutes | $^1$H NMR (400 MHz, DMSO-$d_6$) δ 11.58 (s, 1H), 8.71 (d, J = 2.7 Hz, 1H), 8.56 (s, 1H), 8.28 (s, 1H), 8.13 (s, 1H), 7.99 (m, 2H), 7.90 (dd, J = 8.6, 2.7 Hz, 1H), 7.79 (s, 1H), 7.71 (s, 1H), 7.23 (d, J = 8.8 Hz, 1H). |
| 40 | 4-[[6-(3-cyclohexylphenoxy)-2-fluoro-3-(trifluoromethyl)benzoyl]amino]pyridine-2-carboxamide | ESI-MS m/z calc. 501.16754, found 502.14 (M + 1)+; Retention time (Method B): 1.98 minutes | $^1$H NMR (400 MHz, DMSO-$d_6$) δ 11.46 (s, 1H), 8.56 (s, 1H), 8.32 (s, 1H), 8.13 (s, 1H), 7.93-7.81 (m, 2H), 7.69 (s, 1H), 7.38 (t, J = 7.8 Hz, 1H), 7.15 (d, J = 7.7 Hz, 1H), 7.09-6.98 (m, 2H), 6.81 (d, J = 8.9 Hz, 1H), 1.72 (dd, J = 32.4, 11.2 Hz, 6H), 1.28 (dt, J = 52.2, 11.5 Hz, 5H). |

TABLE 2-continued

Additional Compounds Prepared by Methods Analogous to Example 2.

| Cmpd No. | Compound Name | LC/MS | NMR (shifts in ppm) |
|---|---|---|---|
| 41 | 4-[[6-[2-cyclopropyl-4-(trifluoromethoxy)phenoxy]-2-fluoro-3-(trifluoromethyl)benzoyl]amino]pyridine-2-carboxamide | ESI-MS m/z calc. 543.1029, found 544.0 (M + 1)+; Retention time (Method B): 1.93 minutes | 1H NMR (400 MHz, DMSO-d6) δ 11.53 (s, 1H), 8.57 (d, J = 5.5 Hz, 1H), 8.33 (s, 1H), 8.12 (s, 1H), 7.86 (d, J = 8.7 Hz, 2H), 7.68 (s, 1H), 7.29 (d, J = 8.8 Hz, 2H), 7.02 (s, 1H), 6.73 (d, J = 8.9 Hz, 1H), 1.97 (s, 1H), 0.88 (d, J = 10.4 Hz, 2H), 0.70 (s, 2H). |
| 42 | 4-[[6-(3,4-difluoro-2-methyl-phenoxy)-2-fluoro-3-(trifluoromethyl)benzoyl]amino]pyridine-2-carboxamide | ESI-MS m/z calc. 469.08612, found 470.0 (M + 1)+; Retention time (Method B): 1.75 minutes | 1H NMR (400 MHz, DMSO-d6) δ 11.67 (s, 1H), 8.58 (d, J = 5.5 Hz, 1H), 8.36 (s, 1H), 8.19 (s, 1H), 7.86 (d, J = 12.4 Hz, 2H), 7.74 (s, 1H), 7.41 (d, J = 9.5 Hz, 1H), 7.11 (d, J = 7.6 Hz, 1H), 6.76 (d, J = 8.9 Hz, 1H), 2.11 (s, 3H). |
| 43 | 4-[[6-(4-chloro-2-methoxy-phenoxy)-2-fluoro-3-(trifluoromethyl)benzoyl]amino]pyridine-2-carboxamide | ESI-MS m/z calc. 483.06088, found 484.0 (M + 1)+; Retention time (Method B): 1.73 minutes | 1H NMR (400 MHz, DMSO-d6) δ 11.45 (s, 1H), 8.54 (s, 1H), 8.31 (s, 1H), 8.09 (s, 1H), 7.73 (d, J = 73.8 Hz, 3H), 7.28 (d, J = 27.7 Hz, 2H), 7.09 (d, J = 8.5 Hz, 1H), 6.66 (s, 1H), 3.78 (s, 3H). |
| 44 | 4-[[2-fluoro-6-[2-methoxy-4-(1,1,2,2,2-pentafluoroethyl)phenoxy]-3-(trifluoromethyl)benzoyl]amino]pyridine-2-carboxamide | ESI-MS m/z calc. 567.08405, found 568.0 (M + 1)+; Retention time (Method B): 1.83 minutes | 1H NMR (400 MHz, DMSO-d6) δ 11.47 (s, 1H), 8.55 (d, J = 5.4 Hz, 1H), 8.31 (s, 1H), 8.10 (s, 1H), 7.83 (d, J = 4.9 Hz, 2H), 7.66 (s, 1H), 7.47 (d, J = 8.4 Hz, 1H), 7.42-7.30 (m, 2H), 6.78 (d, J = 8.9 Hz, 1H), 3.83 (s, 3H). |
| 45 | 4-[[6-(2,6-dimethoxy-4-methyl-phenoxy)-2-fluoro-3-(trifluoromethyl)benzoyl]amino]pyridine-2-carboxamide | ESI-MS m/z calc. 493.1261, found 494.0 (M + 1)+; Retention time (Method B): 1.71 minutes | 1H NMR (400 MHz, DMSO-d6) δ 11.34 (s, 1H), 8.56 (d, J = 5.5 Hz, 1H), 8.35 (s, 1H), 8.10 (s, 1H), 7.84 (s, 1H), 7.75 (s, 1H), 7.66 (s, 1H), 6.65 (s, 2H), 6.54 (d, J = 8.9 Hz, 1H), 3.72 (s, 6H), 2.33 (s, 3H). |
| 46 | 4-[[2-fluoro-3-(trifluoromethyl)-6-(2,4,6-trifluorophenoxy)benzoyl]amino]pyridine-2-carboxamide | ESI-MS m/z calc. 473.06104, found 474.0 (M + 1)+; Retention time (Method B): 1.55 minutes | 1H NMR (400 MHz, DMSO-d6) δ 11.55 (s, 1H), 8.57 (d, J = 5.4 Hz, 1H), 8.32 (s, 1H), 8.11 (s, 1H), 7.93-7.76 (m, 2H), 7.68 (s, 1H), 7.52 (s, 2H), 7.00 (d, J = 8.9 Hz, 1H). |
| 47 | 4-[[6-(2,4-dichloro-6-methyl-phenoxy)-2-fluoro-3-(trifluoromethyl)benzoyl]amino]pyridine-2-carboxamide | ESI-MS m/z calc. 501.027, found 502.0 (M + 1)+; Retention time (Method B): 1.83 minutes | 1H NMR (400 MHz, DMSO-d6) δ 11.53 (s, 1H), 8.59 (s, 1H), 8.37 (s, 1H), 8.13 (s, 1H), 7.82 (d, J = 26.1 Hz, 2H), 7.70 (s, 2H), 7.53 (s, 1H), 6.60 (d, J = 8.9 Hz, 1H), 2.19 (s, 3H). |
| 48 | 4-[[2-fluoro-6-(4-fluoro-2,3-dimethyl-phenoxy)-3-(trifluoromethyl)benzoyl]amino]pyridine-2-carboxamide | ESI-MS m/z calc. 465.11118, found 466.0 (M + 1)+; Retention time (Method B): 1.74 minutes | 1H NMR (400 MHz, DMSO-d6) δ 11.50 (s, 1H), 8.57 (d, J = 5.5 Hz, 1H), 8.33 (s, 1H), 8.11 (s, 1H), 7.82 (d, J = 8.9 Hz, 2H), 7.67 (s, 1H), 7.10 (d, J = 23.4 Hz, 2H), 6.59 (d, J = 8.9 Hz, 1H), 2.17 (s, 3H), 2.08 (s, 3H). |
| 49 | 4-[[2-fluoro-3-(trifluoromethyl)-6-(2,3,4-trifluorophenoxy)benzoyl]amino]pyridine-2-carboxamide | ESI-MS m/z calc. 473.06104, found 474.0 (M + 1)+; Retention time (Method B): 1.6 minutes | 1H NMR (400 MHz, DMSO-d6) δ 11.56 (s, 1H), 8.57 (d, J = 5.5 Hz, 1H), 8.32 (s, 1H), 8.12 (s, 1H), 7.89 (s, 1H), 7.82 (s, 1H), 7.68 (s, 1H), 7.45 (d, J = 9.8 Hz, 1H), 7.30 (s, 1H), 7.04 (d, J = 8.9 Hz, 1H). |
| 50 | 4-[[6-(4-chloro-2-methyl-phenoxy)-2-fluoro-3-(trifluoromethyl)benzoyl]amino]pyridine-2-carboxamide | ESI-MS m/z calc. 467.06598, found 468.0 (M + 1)+; Retention time (Method B): 1.86 minutes | 1H NMR (400 MHz, DMSO-$d_6$) δ 11.50 (s, 1H), 8.57 (d, J = 5.5 Hz, 1H), 8.32 (d, J = 2.1 Hz, 1H), 8.23-8.03 (m, 1H), 7.94-7.78 (m, 2H), 7.69 (d, J = 2.6 Hz, 1H), 7.48 (d, J = 2.6 Hz, 1H), 7.37 (dd, J = 8.6, 2.7 Hz, 1H), 7.20 (d, J = 8.6 Hz, 1H), 6.71 (d, J = 8.8 Hz, 1H), 2.13 (s, 3H). |

TABLE 2-continued

Additional Compounds Prepared by Methods Analogous to Example 2.

| Cmpd No. | Compound Name | LC/MS | NMR (shifts in ppm) |
|---|---|---|---|
| 51 | 4-[[6-(4-chloro-2-fluoro-phenoxy)-2-fluoro-3-(trifluoromethyl)benzoyl] amino]pyridine-2-carboxamide | ESI-MS m/z calc. 471.04092, found 472.0 (M + 1)+; Retention time (Method B): 1.75 minutes | 1H NMR (400 MHz, DMSO-d6) δ 11.56 (s, 1H), 8.57 (d, J = 5.5 Hz, 1H), 8.32 (d, J = 1.9 Hz, 1H), 8.13 (s, 1H), 7.92-7.78 (m, 2H), 7.76-7.62 (m, 2H), 7.51-7.35 (m, 2H), 6.93 (d, J = 8.9 Hz, 1H). |
| 338 | 4-[[6-(3-chloro-4-fluoro-2-methyl-phenoxy)-2-fluoro-3-(trifluoromethyl)benzoyl] amino]pyridine-2-carboxamide (synthesized using 3-chloro-4-fluoro-2-methyl-phenol from Preparation 2) | ESI-MS m/z calc. 485.06, found 486.0 $(M + 1)^+$; LC/MS retention time (Method C): 2.47 minutes | $^1$H NMR (400 MHz, DMSO-$d_6$) δ 11.54 (s, 1H), 8.57 (d, J = 5.4 Hz, 1H), 8.33 (d, J = 2.2 Hz, 1H), 8.13 (s, 1H), 7.87-7.79 (m, 2H), 7.70 (s, 1H), 7.42 (t, J = 8.8 Hz, 1H), 7.27 (dd, J = 9.1, 4.6 Hz, 1H), 6.74 (d, J = 8.9 Hz, 1H), 2.22 (s, 3H). |
| 339 | 4-[[6-(2-chloro-3,4-difluoro-phenoxy)-2-fluoro-3-(trifluoromethyl)benzoyl] amino]pyridine-2-carboxamide (synthesized using 2-chloro-3,4-difluoro-phenol from Preparation 3) | ESI-MS m/z calc. 489.03, found 490.0 $(M + 1)^+$; LC/MS retention time (Method C): 2.31 minutes | $^1$H NMR (400 MHz, DMSO-$d_6$) δ 11.55 (s, 1H), 8.57 (d, J = 5.5 Hz, 1H), 8.32 (d, J = 2.1 Hz, 1H), 8.14 (s, 1H), 7.88 (t, J = 8.7 Hz, 1H), 7.84 (dd, J = 5.5, 2.2 Hz, 1H), 7.70 (s, 1H), 7.63 (q, J = 9.4 Hz, 1H), 7.40-7.30 (m, 1H), 6.91 (d, J = 8.9 Hz, 1H). |
| 340 | 4-[[6-(2-cyclopropyl-3,6-difluoro-phenoxy)-2-fluoro-3-(trifluoromethyl)benzoyl] amino]pyridine-2-carboxamide (synthesized using 2-cyclopropyl-3,6-difluoro-phenol from Preparation 4) | ESI-MS m/z calc. 495.10, found 496.0 $(M + 1)^+$; LC/MS retention time (Method C): 2.43 minutes | $^1$H NMR (400 MHz, DMSO-$d_6$) δ 11.52 (s, 1H), 8.58 (d, J = 5.5 Hz, 1H), 8.35 (d, J = 2.2 Hz, 1H), 8.12 (d, J = 2.7 Hz, 1H), 7.89-7.81 (m, 2H), 7.68 (d, J = 2.9 Hz, 1H), 7.36 (td, J = 9.5, 4.8 Hz, 1H), 7.21 (td, J = 9.8, 4.3 Hz, 1H), 6.77 (d, J = 8.9 Hz, 1H), 1.80-1.69 (m, 1H), 0.93-0.76 (m, 4H). |
| 341 | 4-[[6-[4-(difluoromethyl)-2-methoxy-phenoxy]-2-fluoro-3-(trifluoromethyl)benzoyl] amino]pyridine-2-carboxamide (synthesized using 4-(difluoromethyl)-2-methoxy-phenol from Preparation 5) | ESI-MS m/z calc. 499.10, found 500.5 $(M + 1)^+$; LC/MS retention time (Method B): 1.57 minutes | $^1$H NMR (400 MHz, DMSO-$d_6$) δ 11.47 (d, J = 3.5 Hz, 1H), 8.56 (d, J = 5.5 Hz, 1H), 8.33 (d, J = 2.2 Hz, 1H), 8.12 (d, J = 6.2 Hz, 1H), 7.88-7.75 (m, 2H), 7.68 (s, 1H), 7.46-7.34 (m, 2H), 7.26 (dd, J = 8.2, 1.8 Hz, 1H), 7.04 (t, J = 55.8 Hz, 1H), 6.67 (d, J = 8.9 Hz, 1H), 3.80 (s, 3H). |
| 342 | 4-[[6-(2,3-dichloro-4-fluoro-phenoxy)-2-fluoro-3-(trifluoromethyl)benzoyl] amino]pyridine-2-carboxamide (synthesized using 2,3-dichloro-4-fluoro-phenol from Preparation 6) | ESI-MS m/z calc. 505.00, found 506.0 $(M + 1)^+$; LC/MS retention time (Method C): 2.41 minutes | $^1$H NMR (400 MHz, DMSO-$d_6$) δ 11.55 (s, 1H), 8.58 (s, 1H), 8.33 (s, 1H), 8.14 (s, 1H), 7.84 (m, 2H), 7.78-7.46 (m, 3H), 6.88 (d, J = 8.9 Hz, 1H). |
| 343 | 4-[[6-[4-(difluoromethoxy)-3-fluoro-2-methoxy-phenoxy]-2-fluoro-3-(trifluoromethyl)benzoyl] amino]pyridine-2-carboxamide (synthesized using 4-(difluoromethoxy)-3-fluoro-2-methoxy-phenol from Preparation 7) | ESI-MS m/z calc. 533.08, found 534.0 $(M + 1)^+$; LC/MS retention time (Method C): 2.31 minutes | $^1$H NMR (400 MHz, DMSO-$d_6$) δ 11.51 (s, 1H), 8.57 (d, J = 5.5 Hz, 1H), 8.34 (s, 1H), 8.12 (s, 1H), 7.84 (d, J = 5.8 Hz, 2H), 7.68 (s, 1H), 7.35 (d, J = 73.0 Hz, 1H), 7.14 (d, J = 46.5 Hz, 2H), 6.82 (d, J = 8.9 Hz, 1H), 3.83 (s, 3H). |
| 344 | 4-[[6-[2-ethyl-3-fluoro-4-(trifluoromethoxy)phenoxy]-2-fluoro-3-(trifluoromethyl)benzoyl] amino]pyridine-2-carboxamide (synthesized using 2-ethyl-3-fluoro-4-(trifluoromethoxy)phenol from Preparation 8) | ESI-MS m/z calc. 549.09, found 550.0 $(M + 1)^+$; LC/MS retention time (Method C): 2.73 minutes | $^1$H NMR (400 MHz, DMSO-$d_6$) δ 11.51 (s, 1H), 8.56 (d, J = 5.4 Hz, 1H), 8.30 (d, J = 2.2 Hz, 1H), 8.11 (d, J = 2.7 Hz, 1H), 7.90 (t, J = 8.6 Hz, 1H), 7.80 (dd, J = 5.5, 2.2 Hz, 1H), 7.67 (d, J = 2.9 Hz, 1H), 7.53 (t, J = 8.8 Hz, 1H), 7.12 (dd, J = 9.2, 1.8 Hz, 1H), 6.95 (d, J = 8.9 Hz, 1H), 2.62 (q, J = 7.5 Hz, 2H), 1.01 (t, J = 7.5 Hz, 3H) |

TABLE 2-continued

| Additional Compounds Prepared by Methods Analogous to Example 2. | | | |
|---|---|---|---|
| Cmpd No. | Compound Name | LC/MS | NMR (shifts in ppm) |
| 345 | 4-[[6-[2-cyclopropyl-3-fluoro-4-(trifluoromethoxy)phenoxy]-2-fluoro-3-(trifluoromethyl)benzoyl]amino]pyridine-2-carboxamide (synthesized using 2-cyclopropyl-3-fluoro-4-(trifluoromethoxy)phenol from Preparation 9) | ESI-MS m/z calc. 561.09, found 562.0 $(M + 1)^+$; LC/MS retention time (Method C): 2.75 minutes | $^1H$ NMR (400 MHz, DMSO-$d_6$) δ 11.47 (s, 1H), 8.56 (d, J = 5.4 Hz, 1H), 8.31 (s, 1H), 8.11 (s, 1H), 7.88 (t, J = 8.6 Hz, 1H), 7.81 (dd, J = 5.5, 2.2 Hz, 1H), 7.67 (d, J = 2.9 Hz, 1H), 7.50 (t, J = 8.7 Hz, 1H), 7.09 (d, J = 9.0 Hz, 1H), 6.91 (d, J = 8.9 Hz, 1H), 1.81-1.69 (m, 1H), 0.92-0.83 (m, 2H), 0.83-0.74 (m, 2H). |

Example 3

4-[[6-(4-Fluoro-2-Methoxy-Phenoxy)-2-Methoxy-3-(Trifluoromethyl)Benzoyl]Amino]Pyridine-2-Carboxamide (52)

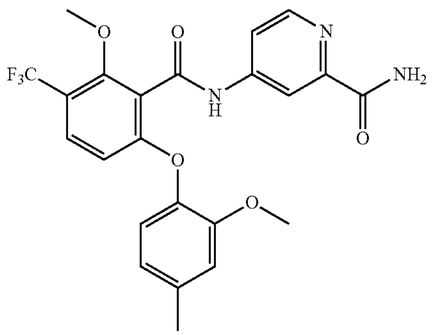 [SMILES: COc1cc(C)ccc1Oc1ccc(C(F)(F)F)c(OC)c1C(=O)Nc1ccnc(C(N)=O)c1]

Step 1: 4-[[6-Bromo-2-Methoxy-3-(Trifluoromethyl)Benzoyl]Amino]Pyridine-2-Carboxamide

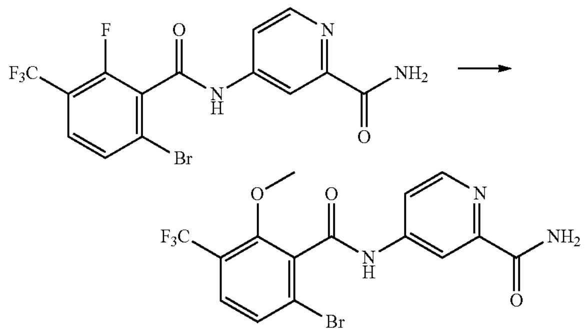

4-[[6-Bromo-2-fluoro-3-(trifluoromethyl)benzoyl]amino]pyridine-2-carboxamide (1.50 g, 3.693 mmol) was dissolved in MeOH (15 mL). Sodium methoxide (8.0 mL of 25% w/v, 37.02 mmol) was added and the reaction mixture allowed to stir at 85° C. for 5 h. The cooled reaction mixture was taken up in ethyl acetate (75 mL) and washed with aqueous HCl (0.5 M, 1×75 mL) and brine (1×75 mL). The organic layer was dried over $Na_2SO_4$, filtered and concentrated under reduced pressure. The crude product was chromatographed on silica gel eluting with a ethyl acetate-hexane gradient to yield 4-[[6-bromo-2-methoxy-3-(trifluoromethyl)benzoyl]amino]pyridine-2-carboxamide (620 mg, 40%) was obtained as a white foamy solid. ESI-MS m z calc. 416.9936, found 420.0 (M+3)+; Retention time (Method C): 1.31 minutes.

Step 2: 4-[[6-(4-Fluoro-2-Methoxy-Phenoxy)-2-Methoxy-3-(Trifluoromethyl)Benzoyl]Amino]Pyridine-2-Carboxamide (52)

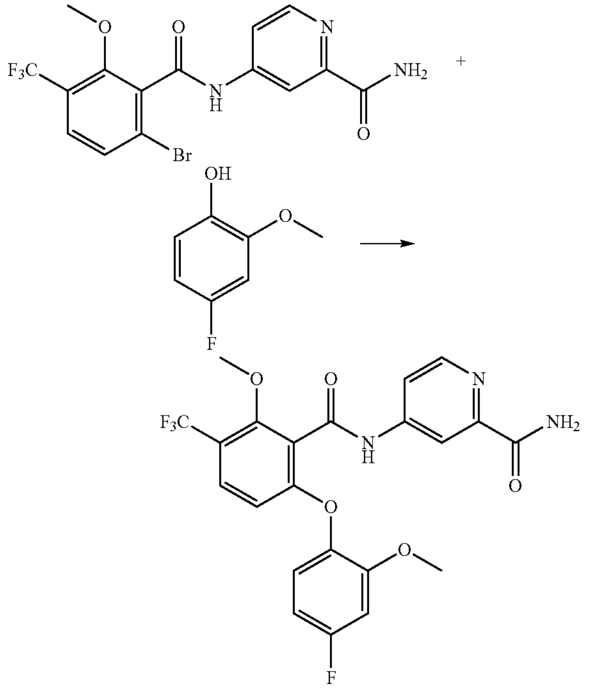

A vial was loaded with 4-[[6-bromo-2-methoxy-3-(trifluoromethyl)benzoyl]amino]pyridine-2-carboxamide (20 mg, 0.04783 mmol) and 4-fluoro-2-methoxy-phenol (33.98 mg, 27.25 μL, 0.2391 mmol). A solution of CsF (14.53 mg, 3.531 μL, 0.09566 mmol) in DMSO (0.25 mL) was added. $Cs_2CO_3$ (31.17 mg, 0.09566 mmol) was added under nitrogen gas. The vial was capped, and the reaction mixture was stirred at 100° C. for 20 minutes. The product was purified by reverse phase HPLC (gradient of 10-99% acetonitrile in water containing HCl as a modifier) to provide 4-[[6-(4-fluoro-2-methoxy-phenoxy)-2-methoxy-3-(trifluoromethyl) benzoyl]amino]pyridine-2-carboxamide (3.4 mg, 14%). ESI-MS m/z calc. 479.11044, found 480.0 $(M+1)^+$; Retention time (Method B): 1.71 minutes. $^1$H NMR (400 MHz, DMSO-$d_6$) δ 11.38 (s, 1H), 8.56 (s, 1H), 8.41 (s, 1H), 8.16 (s, 1H), 7.89 (s, 1H), 7.72 (s, 1H), 7.67 (d, J=8.9 Hz, 1H), 7.25 (dd, J=8.9, 5.8 Hz, 1H), 7.16 (dd, J=10.7, 2.9 Hz, 1H), 6.86 (td, J=8.5, 2.9 Hz, 1H), 6.48 (d, J=8.8 Hz, 1H), 3.90 (s, 3H), 3.77 (s, 3H) ppm.

The compounds set forth in Table 3 were prepared by methods analogous to the preparation of compound 52 in Example 3.

TABLE 3

Additional Compounds Prepared By Methods Analogous to Example 3.

| Cmpd No. | Compound Name | LC/MS | NMR (shifts in ppm) |
|---|---|---|---|
| 53 | 4-[[6-(4-isopropoxyphenoxy)-2-methoxy-3-(trifluoromethyl)benzoyl]amino]pyridine-2-carboxamide | ESI-MS m/z calc. 489.15115, found 490.05 (M + 1)+; Retention time (Method B): 1.85 minutes | $^1$H NMR (400 MHz, DMSO-$d_6$) δ 11.38 (s, 1H), 8.55 (s, 1H), 8.37 (s, 1H), 8.14 (s, 1H), 7.87 (s, 1H), 7.78-7.44 (m, 2H), 7.12 (d, J = 9.0 Hz, 2H), 6.99 (d, J = 9.0 Hz, 2H), 6.61 (d, J = 8.9 Hz, 1H), 4.58 (p, J = 6.0 Hz, 1H), 3.91 (s, 3H), 1.26 (d, J = 6.0 Hz, 6H). |
| 54 | 4-[[6-(5-chloro-2-methoxy-phenoxy)-2-methoxy-3-(trifluoromethyl)benzoyl]amino]pyridine-2-carboxamide | ESI-MS m/z calc. 495.08087, found 496.0 (M + 1)+; Retention time (Method B): 1.78 minutes | $^1$H NMR (400 MHz, DMSO-$d_6$) δ 11.34 (s, 1H), 8.56 (s, 1H), 8.40 (s, 1H), 8.15 (s, 1H), 7.86 (s, 1H), 7.70 (d, J = 8.9 Hz, 2H), 7.40-7.32 (m, 2H), 7.24 (d, J = 9.6 Hz, 1H), 6.57 (d, J = 8.9 Hz, 1H), 3.91 (s, 3H), 3.76 (s, 3H). |
| 55 | 4-[[6-(3,4-difluorophenoxy)-2-methoxy-3-(trifluoromethyl)benzoyl]amino]pyridine-2-carboxamide | ESI-MS m/z calc. 467.09045, found 468.0 (M + 1)+; Retention time (Method B): 1.74 minutes | $^1$H NMR (400 MHz, DMSO-$d_6$) δ 11.39 (s, 1H), 8.56 (s, 1H), 8.36 (s, 1H), 8.14 (s, 1H), 7.84 (s, 1H), 7.76 (d, J = 8.9 Hz, 1H), 7.70 (s, 1H), 7.55 (q, J = 9.5 Hz, 1H), 7.43 (ddd, J = 11.3, 6.8, 2.9 Hz, 1H), 7.08 (d, J = 9.3 Hz, 1H), 6.81 (d, J = 8.8 Hz, 1H), 3.92 (s, 3H). |
| 56 | 4-[[6-(3-chloro-4-isopropoxy-phenoxy)-2-methoxy-3-(trifluoromethyl)benzoyl]amino]pyridine-2-carboxamide | ESI-MS m/z calc. 523.1122, found 523.96 (M + 1)+; Retention time (Method B): 1.93 minutes | $^1$H NMR (400 MHz, DMSO-$d_6$) δ 11.34 (s, 1H), 8.55 (s, 1H), 8.36 (s, 1H), 8.13 (s, 1H), 7.84 (s, 1H), 7.73 (d, J = 8.9 Hz, 1H), 7.69 (s, 1H), 7.36 (d, J = 2.9 Hz, 1H), 7.25 (d, J = 9.1 Hz, 1H), 7.15 (dd, J = 9.1, 2.9 Hz, 1H), 6.74-6.66 (m, 1H), 4.80-4.51 (m, 1H), 3.91 (s, 3H), 1.28 (d, J = 6.1 Hz, 6H). |
| 57 | 4-[[6-(3-chloro-4-fluoro-phenoxy)-2-methoxy-3-(trifluoromethyl)benzoyl]amino]pyridine-2-carboxamide | ESI-MS m/z calc. 483.06088, found 484.0 (M + 1)+; Retention time (Method B): 1.81 minutes; | $^1$H NMR (400 MHz, DMSO-$d_6$) δ 11.36 (s, 1H), 8.55 (s, 1H), 8.35 (s, 1H), 8.13 (s, 1H), 7.83 (s, 1H), 7.76 (d, J = 8.9 Hz, 1H), 7.69 (s, 1H), 7.57-7.48 (m, 2H), 7.25 (dt, J = 9.0, 3.5 Hz, 1H), 6.80 (d, J = 8.8 Hz, 1H), 3.92 (s, 3H). |
| 58 | 4-[[6-(3,4-difluoro-2-methoxy-phenoxy)-2-methoxy-3-(trifluoromethyl)benzoyl]amino]pyridine-2-carboxamide | ESI-MS m/z calc. 497.101, found 497.9 (M + 1)+; Retention time (Method B): 1.77 minutes | |
| 59 | 4-[[6-(2-chloro-4-fluoro-phenoxy)-2-methoxy-3-(trifluoromethyl)benzoyl]amino]pyridine-2-carboxamide | ESI-MS m/z calc. 483.06088, found 484.0 (M + 1)+; Retention time (Method B): 1.75 minutes | 1H NMR (400 MHz, DMSO-d6) δ 11.35 (s, 1H), 8.55 (d, J = 5.5 Hz, 1H), 8.36 (s, 1H), 8.11 (s, 1H), 7.85 (d, J = 5.3 Hz, 1H), 7.73 (d, J = 9.0 Hz, 1H), 7.67 (dd, J = 8.3, 3.0 Hz, 2H), 7.44 (dd, J = 9.1, 5.3 Hz, 1H), 7.36 (ddd, J = 9.1, 8.0, 3.0 Hz, 1H), 6.60 (d, J = 8.8 Hz, 1H), 3.92 (s, 3H). |
| 60 | 4-[[6-[4-(cyclohexoxy)phenoxy]-2-methoxy-3-(trifluoromethyl)benzoyl]amino]pyridine-2-carboxamide | ESI-MS m/z calc. 529.18243, found 529.96 (M + 1)+; Retention time (Method B): 2.05 minutes | |
| 61 | 4-[[6-(4-fluoro-3-methyl-phenoxy)-2-methoxy-3-(trifluoromethyl)benzoyl]amino]pyridine-2-carboxamide | ESI-MS m/z calc. 463.1155, found 464.05 (M + 1)+; Retention time (Method B): 1.8 minutes | $^1$H NMR (400 MHz, DMSO-$d_6$) δ 11.37 (s, 1H), 8.55 (s, 1H), 8.36 (s, 1H), 8.13 (s, 1H), 7.85 (s, 1H), 7.73 (d, J = 8.9 Hz, 1H), 7.69 (s, 1H), 7.23 (t, J = 9.1 Hz, 1H), 7.16 (dd, J = 6.3, 3.0 Hz, 1H), 7.06 (dt, J = 8.4, 3.6 Hz, 1H), 6.69 (d, J = 8.9 Hz, 1H), 3.92 (s, 3H), 2.23 (s, 3H). |

TABLE 3-continued

| Additional Compounds Prepared By Methods Analogous to Example 3. | | | |
|---|---|---|---|
| Cmpd No. | Compound Name | LC/MS | NMR (shifts in ppm) |
| 62 | 4-[[6-(2,4-difluorophenoxy)-2-methoxy-3-(trifluoromethyl)benzoyl]amino]pyridine-2-carboxamide | ESI-MS m/z calc. 467.09045, found 468.0 (M + 1)+; Retention time (Method B): 1.71 minutes | $^1$H NMR (400 MHz, DMSO-$d_6$) δ 11.42 (s, 1H), 8.56 (s, 1H), 8.38 (s, 1H), 8.14 (s, 1H), 7.87 (s, 1H), 7.74 (d, J = 8.9 Hz, 1H), 7.69 (s, 1H), 7.55 (ddd, J = 11.4, 8.9, 3.0 Hz, 1H), 7.45 (td, J = 9.1, 5.5 Hz, 1H), 7.21 (t, J = 8.6 Hz, 1H), 6.70 (d, J = 8.8 Hz, 1H), 3.92 (s, 3H). |
| 63 | 4-[[2-methoxy-6-phenoxy-3-(trifluoromethyl)benzoyl]amino]pyridine-2-carboxamide | ESI-MS m/z calc. 431.10928, found 432.05 (M + 1)+; Retention time (Method B): 1.69 minutes | $^1$H NMR (400 MHz, DMSO-$d_6$) δ 11.47 (s, 1H), 8.56 (s, 1H), 8.39 (s, 1H), 8.18 (s, 1H), 7.87 (s, 1H), 7.74 (d, J = 8.9 Hz, 2H), 7.47 (t, J = 7.8 Hz, 2H), 7.27 (t, J = 7.4 Hz, 1H), 7.20 (d, J = 8.0 Hz, 2H), 6.68 (d, J = 8.8 Hz, 1H), 3.92 (s, 3H). |
| 64 | 4-[[6-(4-fluoro-2-methyl-phenoxy)-2-methoxy-3-(trifluoromethyl)benzoyl]amino]pyridine-2-carboxamide | ESI-MS m/z calc. 463.1155, found 464.05 (M + 1)+; Retention time (Method B): 1.77 minutes | $^1$H NMR (400 MHz, DMSO-$d_6$) δ 11.38 (s, 1H), 8.56 (s, 1H), 8.38 (s, 1H), 8.13 (s, 1H), 7.85 (d, J = 5.1 Hz, 1H), 7.74-7.66 (m, 2H), 7.25 (dd, J = 9.4, 3.0 Hz, 1H), 7.22-7.07 (m, 2H), 6.51 (d, J = 8.8 Hz, 1H), 3.93 (s, 3H), 2.13 (s, 3H). |
| 65 | 4-[[6-[3-fluoro-4-(trifluoromethoxy)phenoxy]-2-methoxy-3-(trifluoromethyl)benzoyl]amino]pyridine-2-carboxamide | ESI-MS m/z calc. 533.08215, found 533.86 (M + 1)+; Retention time (Method B): 1.91 minutes | |
| 66 | 4-[[6-[2-chloro-4-(trifluoromethoxy)phenoxy]-2-methoxy-3-(trifluoromethyl)benzoyl]amino]pyridine-2-carboxamide | ESI-MS m/z calc. 549.0526, found 549.86 (M + 1)+; Retention time (Method B): 1.92 minutes | $^1$H NMR (400 MHz, DMSO-$d_6$) δ 11.42 (s, 1H), 8.55 (s, 1H), 8.36 (s, 1H), 8.13 (s, 1H), 7.84 (s, 1H), 7.80 (d, J = 2.5 Hz, 1H), 7.77 (d, J = 8.9 Hz, 1H), 7.70 (s, 1H), 7.55-7.45 (m, 2H), 6.73 (d, J = 8.9 Hz, 1H), 3.93 (s, 3H). |
| 67 | 4-[[6-(3-fluoro-4-isopropoxy-phenoxy)-2-methoxy-3-(trifluoromethyl)benzoyl]amino]pyridine-2-carboxamide | ESI-MS m/z calc. 507.14172, found 508.05 (M + 1)+; Retention time (Method B): 1.85 minutes | |
| 68 | 4-[[6-[(4-fluoro-2,3-dihydrobenzofuran-7-yl)oxy]-2-methoxy-3-(trifluoromethyl)benzoyl]amino]pyridine-2-carboxamide | ESI-MS m/z calc. 491.11044, found 492.0 (M + 1)+; Retention time (Method B): 1.73 minutes | |
| 69 | 4-[[6-(4-fluoro-3-methoxy-phenoxy)-2-methoxy-3-(trifluoromethyl)benzoyl]amino]pyridine-2-carboxamide | ESI-MS m/z calc. 479.11044, found 479.95 (M + 1)+; Retention time (Method B): 1.72 minutes | $^1$H NMR (400 MHz, DMSO-$d_6$) δ 11.41 (s, 1H), 8.56 (s, 1H), 8.39 (s, 1H), 8.15 (s, 1H), 7.86 (s, 1H), 7.77-7.68 (m, 2H), 7.31 (dd, J = 11.2, 8.8 Hz, 1H), 7.07 (dd, J = 7.4, 2.8 Hz, 1H), 6.80-6.74 (m, 1H), 6.72 (d, J = 8.9 Hz, 1H), 3.92 (s, 3H), 3.82 (s, 3H). |
| 70 | 4-[[2-methoxy-3-(trifluoromethyl)-6-[[6-(trifluoromethyl)-3-pyridyl]oxy]benzoyl]amino]pyridine-2-carboxamide | ESI-MS m/z calc. 500.09192, found 501.0 (M + 1)+; Retention time (Method B): 1.67 minutes | |
| 71 | 4-[[6-[(6-chloro-2-methoxy-3-pyridyl)oxy]-2-methoxy-3-(trifluoromethyl)benzoyl]amino]pyridine-2-carboxamide | ESI-MS m/z calc. 496.07614, found 496.95 (M + 1)+; Retention time (Method B): 1.73 minutes | |
| 258 | 4-[[6-(3-cyclohexylphenoxy)-2-methoxy-3-(trifluoromethyl)benzoyl]amino]pyridine-2-carboxamide | ESI-MS m/z calc. 513.18756, found 514.05 (M + 1)+; Retention time | $^1$H NMR (400 MHz, DMSO-$d_6$) δ 11.34 (s, 1H), 8.54 (d, J = 5.5 Hz, 1H), 8.36 (s, 1H), 8.11 (s, 1H), 7.90-7.78 (m, 1H), 7.74 (d, J = 8.9 Hz, 1H), 7.67 (s, 1H), 7.36 (t, J = 7.8 Hz, 1H), 7.12 (d, J = |

TABLE 3-continued

Additional Compounds Prepared By Methods Analogous to Example 3.

| Cmpd No. | Compound Name | LC/MS | NMR (shifts in ppm) |
|---|---|---|---|
| | | (Method B): 2.14 minutes | 7.7 Hz, 1H), 7.04-6.95 (m, 2H), 6.68 (d, J = 8.9 Hz, 1H), 3.91 (s, 3H), 2.48 (m, 1H, obscured by solvent), 1.85-1.59 (m, 5H), 1.39-1.17 (m, 5H). |

Example 4

4-[[2-(2,3-Difluoro-4-Isopropoxy-Phenoxy)-6-(Trifluoromethyl)Benzoyl]Amino]Pyridine-2-Carboxamide (72)

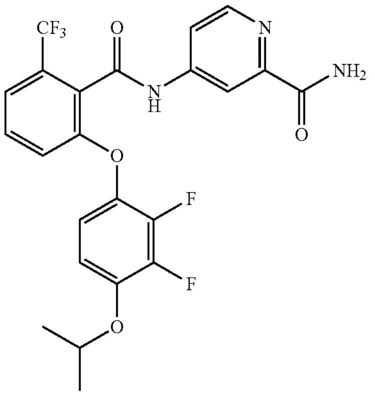 [SMILES: CC(C)Oc1ccc(Oc2cccc(C(F)(F)F)c2C(=O)Nc2ccnc(C(N)=O)c2)c(F)c1F]

Step 1: 4-[[2-Fluoro-6-(Trifluoromethyl)Benzoyl]Amino]Pyridine-2-Carboxamide

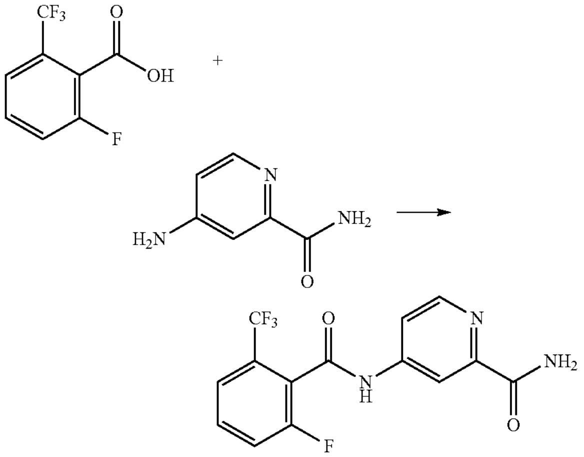

To a solution of 2-fluoro-6-(trifluoromethyl)benzoic acid (7.00 g, 33.64 mmol) in DCM (70 mL) and DMF (100 μL, 1.291 mmol) at 0° C. was added oxalyl chloride (23.5 mL, 269.4 mmol) drop-wise. The reaction mixture was allowed to stir at RT for 1 hour. The reaction mixture was concentrated under reduced pressure and taken up in NMP (7 mL). This acid chloride solution was then added to a prepared solution of 4-aminopyridine-2-carboxamide (4.61 g, 33.62 mmol) and DIEA (35. mL, 200.9 mmol) in NMP (70 mL) and DMF (7 mL) at 0° C. The final reaction mixture was allowed to slowly warm to RT and stirred overnight. The reaction mixture was diluted with ethyl acetate (100 mL) and washed with water (1×100 mL) and brine (1×100 mL). The organic layer was dried over $Na_2SO_4$, filtered and concentrated under reduced pressure. The crude product was chromatographed on a 120 gram silica gel column eluting with a 0-100% EtOAc/hexane gradient over 60 minutes. 4-[[2-fluoro-6-(trifluoromethyl)benzoyl]amino]pyridine-2-carboxamide (881 mg, 8%) was obtained as an orange oil. ESI-MS m/z calc. 327.06308, found 328.2 $(M+1)^+$; Retention time (Method B): 1.12 minutes. $^1H$ NMR (400 MHz, DMSO-d6) δ 11.44 (s, 1H), 8.57 (d, J=5.4 Hz, 1H), 8.32 (d, J=2.1 Hz, 1H), 8.12 (d, J=2.9 Hz, 1H), 7.87-7.74 (m, 4H), 7.72-7.62 (m, 1H) ppm.

Step 2: 4-[[2-(2,3-Difluoro-4-Isopropoxy-Phenoxy)-6-(Trifluoromethyl)Benzoyl]Amino]Pyridine-2-Carboxamide (72)

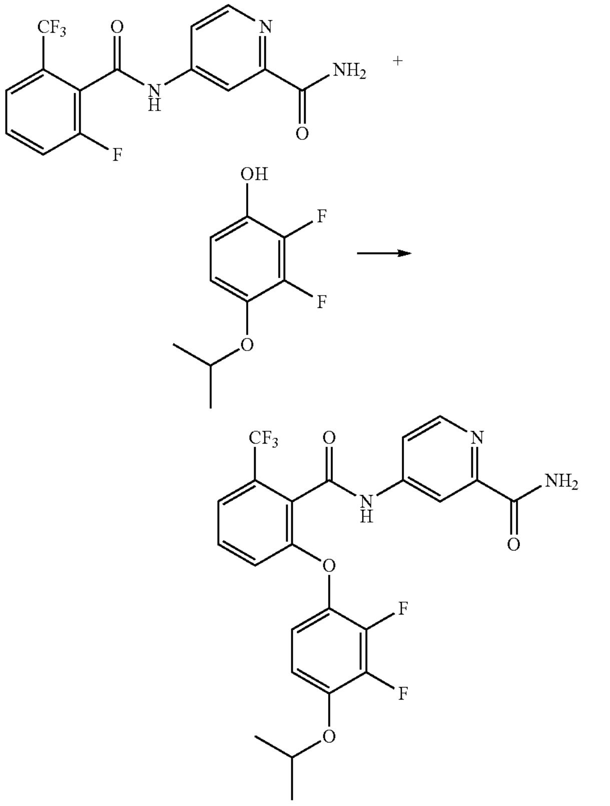

A solution of 4-[[2-fluoro-6-(trifluoromethyl)benzoyl]amino]pyridine-2-carboxamide (40 mg, 0.1222 mmol) in DMSO (0.5 mL) was added to 2,3-difluoro-4-isopropoxy-phenol (68.98 mg, 0.3666 mmol). Finely ground $K_2CO_3$ (50.67 mg, 0.3666 mmol) was then added. The reaction mixture was allowed to stir at 120° C. for 2 h. The mixture was purified by reverse phase HPLC (gradient of 10-99% acetonitrile in water containing HCl as a modifier) to afford 4-[[2-(2,3-difluoro-4-isopropoxy-phenoxy)-6-(trifluoromethyl)benzoyl]amino]pyridine-2-carboxamide (9.3 mg, 15%). ESI-MS m/z calc. 495.12173, found 496.31 $(M+1)^+$; Retention time (Method B): 1.63 minutes. $^1$H NMR (400 MHz, DMSO-$d_6$) δ 11.40 (s, 1H), 8.55 (d, J=5.5 Hz, 1H), 8.33 (d, J=2.1 Hz, 1H), 8.13 (d, J=2.8 Hz, 1H), 7.82 (dd, J=5.5, 2.2 Hz, 1H), 7.72-7.59 (m, 3H), 7.28 (d, J=8.0 Hz, 1H), 7.10 (t, J=5.2 Hz, 2H), 4.65 (p, J=6.1 Hz, 1H), 1.30 (d, J=6.0 Hz, 6H) ppm.

The compounds set forth in Table 4 were prepared by methods analogous to the preparation of compound 72 in Example 4.

TABLE 4

Additional Compounds Prepared By Methods Analogous to Example 4.

| Cmpd No. | Compound Name | LC/MS | NMR (shifts in ppm) |
|---|---|---|---|
| 73 | 4-[[2-[(6-chloro-2-methoxy-3-pyridyl)oxy]-6-(trifluoromethyl)benzoyl]amino]pyridine-2-carboxamide | ESI-MS m/z calc. 466.06558, found 467.25 (M + 1)+; Retention time (Method B): 1.46 minutes (3 minute run) | $^1$H NMR (400 MHz, DMSO-$d_6$) δ 11.40 (s, 1H), 8.54 (d, J = 5.5 Hz, 1H), 8.33 (d, J = 2.1 Hz, 1H), 8.16 (s, 1H), 7.81 (dd, J = 5.5, 2.2 Hz, 1H), 7.72 (s, 1H), 7.69-7.58 (m, 3H), 7.23 (d, J = 7.7 Hz, 1H), 7.16 (d, J = 8.1 Hz, 1H), 3.84 (s, 3H). |
| 74 | 4-[[2-(3-fluoro-4-isopropoxy-phenoxy)-6-(trifluoromethyl)benzoyl]amino]pyridine-2-carboxamide | ESI-MS m/z calc. 477.13116, found 478.31 (M + 1)+; Retention time (Method B): 1.59 minutes (3 minute run) | $^1$H NMR (400 MHz, DMSO-$d_6$) δ 11.31 (s, 1H), 8.53 (d, J = 5.5 Hz, 1H), 8.30 (d, J = 2.1 Hz, 1H), 8.12 (d, J = 2.8 Hz, 1H), 7.79 (dd, J = 5.5, 2.2 Hz, 1H), 7.71-7.58 (m, 3H), 7.26-7.20 (m, 2H), 7.14 (dd, J = 11.8, 2.9 Hz, 1H), 6.94 (dd, J = 8.9, 2.2 Hz, 1H), 4.56 (p, J = 6.0 Hz, 1H), 1.27 (d, J = 6.0 Hz, 6H). |
| 75 | 4-[[2-(4-fluoro-2-methoxy-phenoxy)-6-(trifluoromethyl)benzoyl]amino]pyridine-2-carboxamide | ESI-MS m/z calc. 449.09988, found 450.26 (M + 1)+; Retention time (Method B): 1.45 minutes (3 minute run) | $^1$H NMR (400 MHz, DMSO-$d_6$) δ 11.30 (s, 1H), 8.53 (d, J = 5.5 Hz, 1H), 8.34 (d, J = 2.1 Hz, 1H), 8.11 (s, 1H), 7.83 (dd, J = 5.4, 2.2 Hz, 1H), 7.67 (s, 1H), 7.60 (t, J = 8.1 Hz, 1H), 7.53 (d, J = 7.9 Hz, 1H), 7.21 (dd, J = 8.9, 5.8 Hz, 1H), 7.15 (dd, J = 10.7, 2.9 Hz, 1H), 6.95 (d, J = 8.3 Hz, 1H), 6.84 (td, J = 8.4, 2.9 Hz, 1H), 3.77 (s, 3H). |
| 76 | 4-[[2-[2-chloro-4-(trifluoromethoxy)phenoxy]-6-(trifluoromethyl)benzoyl]amino]pyridine-2-carboxamide | ESI-MS m/z calc. 519.04205, found 520.26 (M + 1)+; Retention time (Method B): 1.68 minutes. | |
| 77 | 4-[[2-(2,4-difluorophenoxy)-6-(trifluoromethyl)benzoyl]amino]pyridine-2-carboxamide | ESI-MS m/z calc. 437.0799, found 438.25 (M + 1)+; Retention time (Method B): 1.43 minutes | $^1$H NMR (400 MHz, DMSO-$d_6$) δ 11.43 (s, 1H), 8.55 (d, J = 5.5 Hz, 1H), 8.33 (d, J = 2.1 Hz, 1H), 8.16 (s, 1H), 7.83 (dd, J = 5.5, 2.2 Hz, 1H), 7.71 (s, 1H), 7.69-7.62 (m, 2H), 7.56-7.49 (m, 1H), 7.39 (td, J = 92, 5.5 Hz, 1H), 7.24-7.15 (m, 2H). |
| 78 | 4-[[2-[(4-fluoro-2,3-dihydrobenzofuran-7-yl)oxy]-6-(trifluoromethyl)benzoyl]amino]pyridine-2-carboxamide | ESI-MS m/z calc. 461.09988, found 462.27 (M + 1)+; Retention time (Method B): 1.46 minutes | $^1$H NMR (400 MHz, DMSO-$d_6$) δ 11.33 (s, 1H), 8.54 (d, J = 5.5 Hz, 1H), 8.33 (d, J = 2.1 Hz, 1H), 8.12 (s, 1H), 7.82 (dd, J = 5.6, 22 Hz, 1H), 7.67 (d, J = 2.9 Hz, 1H), 7.63 (t, J = 8.2 Hz, 1H), 7.56 (d, J = 7.9 Hz, 1H), 7.09 (d, J = 8.4 Hz, 1H), 7.01 (dd, J = 9.0, 4.7 Hz, 1H), 6.75 (t, J = 8.5 Hz, 1H), 4.64 (t, J = 8.7 Hz, 2H), 3.28 (t, J = 8.7 Hz, 2H). |
| 79 | 4-[[2-(2-chloro-4-fluoro-phenoxy)-6-(trifluoromethyl)benzoyl]amino]pyridine-2-carboxamide | ESI-MS m/z calc. 453.05032, found 454.22 (M + 1)+; Retention time (Method B): 1.5 minutes | |
| 80 | 4-[[2-(3-chloro-4-fluoro-phenoxy)-6-(trifluoromethyl)benzoyl]amino]pyridine-2-carboxamide | ESI-MS m/z calc. 453.05032, found 454.22 (M + 1)+; Retention time (Method B): 1.56 minutes | $^1$H NMR (400 MHz, DMSO-$d_6$) δ 11.32 (s, 1H), 8.53 (d, J = 5.5 Hz, 1H), 8.29 (d, J = 2.1 Hz, 1H), 8.12 (s, 1H), 7.77 (dd, J = 5.5, 2.2 Hz, 1H), 7.74-7.64 (m, 3H), 7.53-7.44 (m, 2H), 7.33 (d, J = 7.8 Hz, 1H), 7.20 (dt, J = 9.1, 3.5 Hz, 1H). |

TABLE 4-continued

Additional Compounds Prepared By Methods Analogous to Example 4.

| Cmpd No. | Compound Name | LC/MS | NMR (shifts in ppm) |
|---|---|---|---|
| 81 | 4-[[2-(2-fluoro-4-isopropoxy-phenoxy)-6-(trifluoromethyl)benzoyl]amino]pyridine-2-carboxamide | ESI-MS m/z calc. 477.13116, found 478.31 (M + 1)+; Retention time (Method B): 1.58 minutes | $^1H$ NMR (400 MHz, DMSO-$d_6$) δ 11.30 (s, 1H), 8.54 (d, J = 5.5 Hz, 1H), 8.37 (d, J = 2.1 Hz, 1H), 8.14 (s, 1H), 7.84 (dd, J = 5.5, 2.2 Hz, 1H), 7.69 (s, 1H), 7.61 (t, J = 8.1 Hz, 1H), 7.55 (d, J = 7.8 Hz, 1H), 7.34-7.20 (m, 1H), 7.06 (d, J = 8.5 Hz, 1H), 7.02-6.89 (m, 2H), 4.64-4.49 (m, 1H), 1.12 (d, J = 6.0 Hz, 6H). |
| 82 | 4-[[2-isobutoxy-6-[2-methoxy-4-(trifluoromethoxy)phenoxy]-3-(trifluoromethyl)benzoyl]amino]pyridine-2-carboxamide | ESI-MS m/z calc. 587.1491, found 588.2 (M + 1)+; Retention time (Method B): 2.05 minutes | $^1H$ NMR (400 MHz, DMSO-$d_6$) δ 11.32 (s, 1H), 8.55 (d, J = 5.5 Hz, 1H), 8.36 (d, J = 2.2 Hz, 1H), 8.15-8.07 (m, 1H), 7.86 (dd, J = 5.5, 2.2 Hz, 1H), 7.74-7.64 (m, 2H), 7.35-7.28 (m, 1H), 7.24 (d, J = 2.7 Hz, 1H), 7.09-6.97 (m, 1H), 6.54 (d, J = 8.9 Hz, 1H), 3.88 (d, J = 5.8 Hz, 2H), 3.79 (s, 3H), 2.08-1.74 (m, 1H), 0.85 (d, J = 6.7 Hz, 6H). |

Example 5

4-[[2-Ethoxy-6-[2-Methoxy-4-(Trifluoromethoxy)Phenoxy]-3-(Trifluoromethyl)Benzoyl]Amino]Pyridine-2-Carboxamide (83)

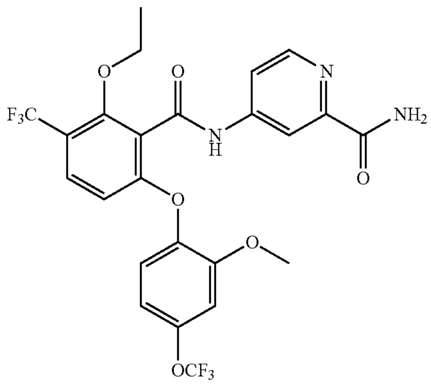 [SMILES: CCOc1c(C(F)(F)F)ccc(Oc2ccc(OC(F)(F)F)cc2OC)c1C(=O)Nc1ccnc(C(N)=O)c1]

Step 1: 4-[(Z)-[(Tert-Butylamino)-Phenylsulfanyl-Methylene]Amino]Pyridine-2-Carboxamide

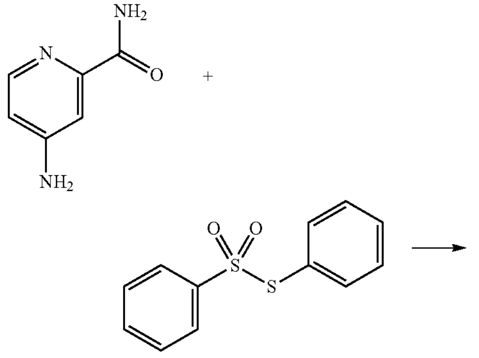

-continued

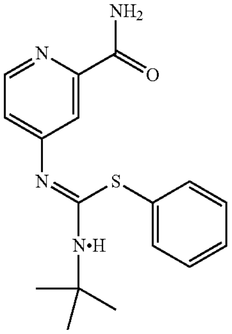

A flask equipped with a reflux condenser was charged with 4-aminopyridine-2-carboxamide (1.12 g, 8.17 mmol), benzenesulfonylsulfanylbenzene (1.85 g, 7.39 mmol), 2-isocyano-2-methyl-propane (3.0 mL, 27 mmol), copper (I) iodide (60 mg, 0.32 mmol) and molecular sieves (2.2 g) in 2-methyltetrahydrofuran (10 mL), and the mixture was heated at 75° C. for 24 hours. The reaction mixture was filtered through Celite and the cake was rinsed with ethyl acetate. The filtrate was concentrated and dried under vacuum. The residue was purified by silica gel chromatography (0-60% ethyl acetate/hexanes) to obtain 4-[(Z)-[(tert-butylamino)-phenylsulfanyl-methylene]amino]pyridine-2-carboxamide (1.25 g, 51%). ESI-MS m/z calc. 328.14, found 329.2 $(M+1)^+$; retention time (Method B): 1.07 minutes. $^1H$ NMR (400 MHz, DMSO-d6) δ 8.17 (dd, J=5.3, 0.6 Hz, 1H), 7.94 (d, J=3.0 Hz, 1H), 7.49 (s, 1H), 7.28 (dd, J=2.2, 0.6 Hz, 1H), 7.25-7.17 (m, 5H), 6.74 (dd, J=5.3, 2.2 Hz, 1H), 6.66 (s, 1H), 1.35 (s, 9H) ppm.

Step 2: 2-Fluoro-6-[2-Methoxy-4-(Trifluoromethoxy)Phenoxy]-3-(Trifluoromethyl)Benzoic Acid A pressure flask was charged with 6-bromo-2-fluoro-3-(trifluoromethyl)benzoic acid (5 g, 17.42 mmol), 2-methoxy-4-(trifluoromethoxy)phenol (4.35 g, 20.90 mmol), cesium carbonate (11.35 g, 34.84 mmol) and toluene (50 mL). The mixture was degassed with nitrogen. After ca. 2 minutes, copper (I) iodide (663 mg, 3.48 mmol) was added and the reaction was stirred at 100° C. for lhr. The reaction was diluted with 300 mL ethyl acetate and 200 mL of water and the phases were separated. The aqueous layer was acidified to pH-3 and extracted with ethyl acetate. The combined organic phases were dried over sodium sulfate, filtered and concentrated. The residue was purified by silica gel chromatography (ethyl acetate/hexane gradient, followed by 9:1 dichloromethane:methanol) to afford 2-fluoro-6-[2-methoxy-4-(trifluoromethoxy)phenoxy]-3-(trifluoromethyl)benzoic acid (5.4503 g, 76%) as a pale green solid. ESI-MS m/z calc. 414.03, found 415.0 $(M+1)^+$; retention time (Method B): 1.94 minutes. $^1H$ NMR (400 MHz, DMSO-d6) δ 7.53 (t, J=8.4 Hz, 1H), 7.27-7.11 (m, 2H), 6.99 (ddd, J=8.8, 2.7, 1.3 Hz, 1H), 6.49 (d, J=8.8 Hz, 1H), 3.80 (s, 3H) ppm.

Step 3: 4-[[2-Fluoro-6-[2-Methoxy-4-(Trifluoromethoxy)Phenoxy]-3-(Trifluoromethyl)Benzoyl] Amino]Pyridine-2-Carboxamide A microwave vial charged with 4-[(Z)-[(tert-butylamino)-phenylsulfanyl-methylene]amino]pyridine-2-carboxamide (75 mg, 0.29 mmol), tris[(Z)-1-methyl-3-oxo-but-1-enoxy] iron (approximately 2 mg, 0.0057 mmol) and 2-fluoro-6-[2-methoxy-4-(trifluoromethoxy)phenoxy]-3-(trifluoromethyl) benzoic acid (94 mg, 0.29 mmol) in isopropanol (2 mL) was heated at 83° C. for 16 hours. The reaction mixture was cooled to room temperature and the solvent evaporated. The crude material was taken up in dichloromethane and washed with 1N HCl. The organic layer was dried over $MgSO_4$, filtered and concentrated. The residue was purified by silica gel chromatography (ethyl acetate/hexane gradient) to afford 4-[[2-fluoro-6-[2-methoxy-4-(trifluoromethoxy)phenoxy]-3-(trifluoromethyl)benzoyl]amino]pyridine-2-carboxamide (80 mg, 64%). ESI-MS m/z calc. 533.08215, found 534.1 $(M+1)^+$; retention time (Method B): 1.77 minutes. $^1H$ NMR (400 MHz, DMSO-d6) δ 11.45 (s, 1H), 8.56 (d, J=5.5 Hz, 1H), 8.32 (d, J=2.2 Hz, 1H), 8.12 (d, J=2.7 Hz, 1H), 7.86-7.77 (m, 2H), 7.72-7.64 (m, 1H), 7.38 (d, J=8.8 Hz, 1H), 7.27 (d, J=2.8 Hz, 1H), 7.08-7.01 (m, 1H), 6.68 (d, J=8.9 Hz, 1H), 3.79 (s, 3H) ppm.

Step 4: 4-[[2-Ethoxy-6-[2-Methoxy-4-(Trifluoromethoxy)Phenoxy]-3-(Trifluoromethyl)Benzoyl] Amino]Pyridine-2-Carboxamide (83)

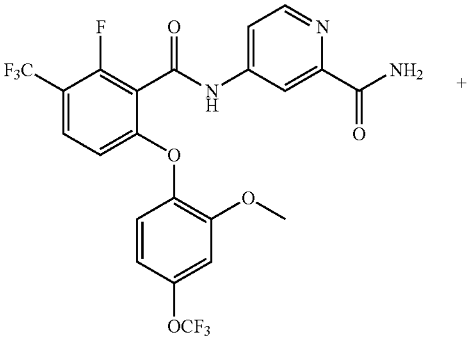

-continued

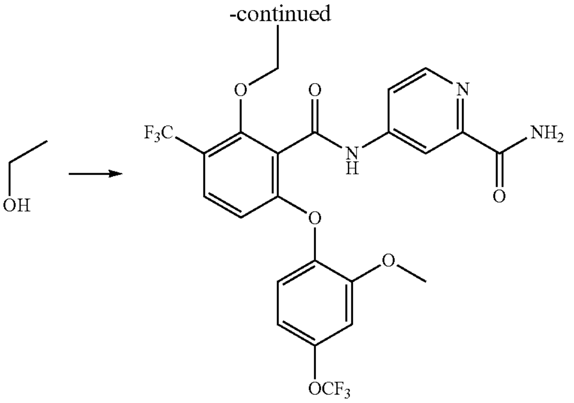

To ethanol (12.95 mg, 16.41 μL, 0.2812 mmol) was added a solution of 4-[[2-fluoro-6-[2-methoxy-4-(trifluoromethoxy)phenoxy]-3-(trifluoromethyl)benzoyl]amino] pyridine-2-carboxamide (30 mg, 0.05625 mmol) in DMSO (0.5 mL). Finely ground $K_2CO_3$ (31.10 mg, 0.2250 mmol) was then added. The reaction mixture was capped and allowed to stir at 140° C. for 30 minutes. The reaction mixture was purified by HPLC to afford 4-[[2-ethoxy-6-[2-methoxy-4-(trifluoromethoxy)phenoxy]-3-(trifluoromethyl) benzoyl]amino]pyridine-2-carboxamide (10.7 mg, 33%). ESI-MS m/z calc. 559.1178, found 560.3 $(M+1)^+$; Retention time (Method B): 1.88 minutes. 1H NMR (400 MHz, DMSO-$d_6$) δ 11.32 (s, 1H), 8.55 (d, J=5.5 Hz, 1H), 8.37 (d, J=2.1 Hz, 1H), 8.12 (s, 1H), 7.86 (dd, J=5.5, 2.2 Hz, 1H), 7.75-7.61 (m, 2H), 7.32 (d, J=8.8 Hz, 1H), 7.24 (d, J=2.7 Hz, 1H), 7.09-6.98 (m, 1H), 6.53 (d, J=8.9 Hz, 1H), 4.13 (q, J=7.0 Hz, 2H), 3.79 (s, 3H), 1.24 (t, J=7.0 Hz, 3H).

The compounds set forth in Table 5 were prepared by methods analogous to the preparation of compound 83 in Example 5.

TABLE 5

| Additional Compounds Prepared By Methods Analogous to Example 5. | | | |
|---|---|---|---|
| Cmpd No. | Compound Name | LC/MS | NMR (shifts in ppm) |
| 84 | 4-[[2-(cyclopropylmethoxy)-6-[2-methoxy-4-(trifluoromethoxy)phenoxy]-3-(trifluoromethyl)benzo-yl]amino]pyridine-2-carboxamide | ESI-MS m/z calc. 585.1335, found 586.2 (M + 1)+; Retention time (Method B): 1.96 minutes; | $^1$H NMR (400 MHz, DMSO-$d_6$) δ 11.11 (s, 1H), 8.36 (d, J = 5.5 Hz, 1H), 8.18 (d, J = 2.1 Hz, 1H), 7.93 (d, J = 2.8 Hz, 1H), 7.68 (dd, J = 5.6, 2.0 Hz, 1H), 7.54-7.45 (m, 2H), 7.12 (d, J = 8.9 Hz, 1H), 7.05 (d, J = 2.7 Hz, 1H), 6.88-6.80 (m, 1H), 6.35 (d, J = 8.8 Hz, 1H), 3.72 (d, J = 7.1 Hz, 2H), 3.60 (s, 3H), 0.99-0.87 (m, 1H), 0.32-0.23 (m, 2H), 0.03--0.05 (m, 2H). |
| 85 | 4-[[2-(cyclopropoxy)-6-[2-methoxy-4-(trifluoromethoxy)phenoxy]-3-(trifluoromethyl)benzo-yl]amino]pyridine-2-carboxamide | ESI-MS m/z calc. 571.1178, found 572.2 (M + 1)+; Retention time (Method B): 1.89 minutes; | $^1$H NMR (400 MHz, DMSO-$d_6$) δ 11.38 (s, 1H), 8.54 (d, J = 5.5 Hz, 1H), 8.37 (d, J = 2.1 Hz, 1H), 8.12 (d, J = 2.8 Hz, 1H), 7.88 (dd, J = 5.5, 2.2 Hz, 1H), 7.72-7.58 (m, 2H), 7.34 (d, J = 8.8 Hz, 1H), 7.24 (d, J = 2.7 Hz, 1H), 7.04 (d, J = 9.6 Hz, 1H), 6.47 (d, J = 8.9 Hz, 1H), 4.10 (tt, J = 5.9, 2.7 Hz, 1H), 3.78 (s, 3H), 0.76-0.69 (m, 2H), 0.68-0.56 (m, 2H). |
| 86 | 4-[[2-[(2,2-difluorocyclopropyl)me-thoxy]-6-[2-methoxy-4-(trifluoromethoxy)phenoxy]-3-(trifluoromethyl)benzo-yl]amino]pyridine-2-carboxamide | ESI-MS m/z calc. 621.1146, found 622.2 (M + 1)+; Retention time: 1.93 minutes (Method B); | $^1$H NMR (400 MHz, DMSO-$d_6$) δ 11.33 (s, 1H), 8.55 (d, J = 5.5 Hz, 1H), 8.35 (d, J = 2.1 Hz, 1H), 8.12 (d, J = 2.8 Hz, 1H), 7.87 (dd, J = 5.5, 2.2 Hz, 1H), 7.71 (d, J = 9.0 Hz, 1H), 7.68 (d, J = 2.7 Hz, 1H), 7.32 (d, J = 8.8 Hz, 1H), 7.24 (d, J = 2.7 Hz, 1H), 7.04 (d, J = 9.0 Hz, 1H), 6.57 (d, J = 8.9 Hz, 1H), 4.28-4.18 (m, 1H), 4.08 (t, J = 9.6 Hz, 1H), 3.79 (s, 3H), 2.17-1.98 (m, 1H), 1.75-1.58 (m, 1H), 1.42-1.28 (m, 1H). |
| 87 | 4-[[2-(isobutylamino)-6-[2-methoxy-4-(trifluoromethoxy)phenoxy]-3-(trifluoromethyl)benzo-yl]amino]pyridine-2-carboxamide | ESI-MS m/z calc. 586.1651, found 587.5 (M + 1)+; Retention time (Method B): 2.02 minutes | 1H NMR (400 MHz, DMSO-d6) δ 11.18 (s, 1H), 8.52 (d, J = 5.5 Hz, 1H), 8.34 (d, J = 2.1 Hz, 1H), 8.08 (d, J = 2.9 Hz, 1H), 7.86 (dd, J = 5.5, 2.1 Hz, 1H), 7.63 (d, J = 2.9 Hz, 1H), 7.48 (d, J = 8.9 Hz, 1H), 7.27 (d, J = 8.8 Hz, 1H), 7.19 (d, J = 2.7 Hz, 1H), 7.07-6.94 (m, 1H), 6.03 (d, J = 8.8 Hz, 1H), 5.01-4.86 (m, 1H), 3.77 (s, 3H), 3.00 (t, J = 6.4 Hz, 2H), 1.87 (dh, J = 13.3, 6.8 Hz, 1H), 0.77 (d, J = 6.6 Hz, 6H). |

Example 6

4-[[2-Fluoro-4-(p-Tolyl)-6-[2-(Trideuteriomethoxy)-4-(Trifluoromethoxy)Phenoxy]Benzoyl]Amino]Pyridine-2-Carboxamide (88)

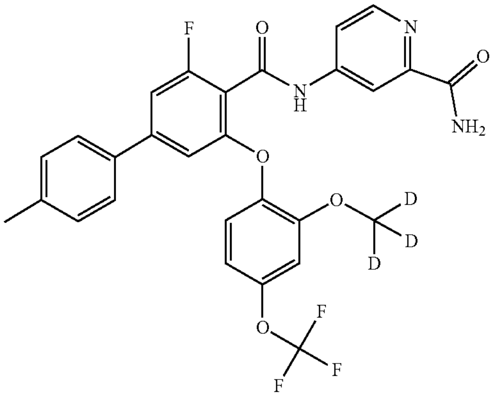 [SMILES: [2H]C([2H])([2H])Oc1cc(OC(F)(F)F)ccc1Oc1cc(-c2ccc(C)cc2)cc(F)c1C(=O)Nc1ccnc(C(N)=O)c1]

Step 1: 4-[[2-Fluoro-4-(p-Tolyl)-6-[2-(Trideuteriomethoxy)-4-(Trifluoromethoxy)Phenoxy]Benzoyl]Amino]Pyridine-2-Carboxamide (88)

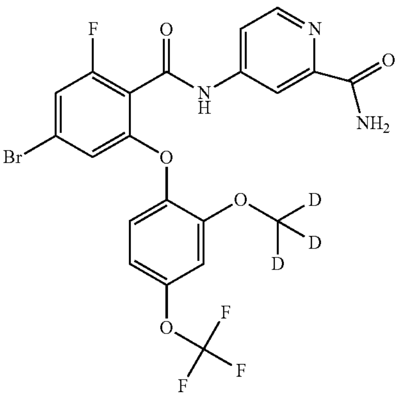

+

-continued

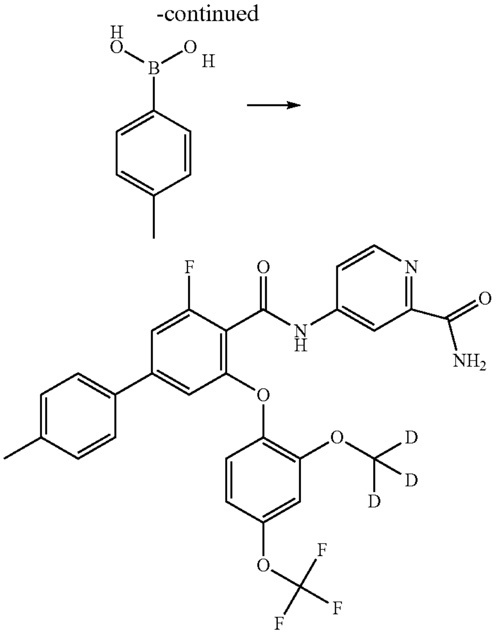

A solution of 4-(2-trideuteriomethoxy)-4-(trifluoromethoxy)phenoxy)-4-bromo-6-fluorobenzamido)picolinamide, p-tolylboronic acid (approximately 15 mg, 0.110 mmol), $K_2CO_3$ (approximately 15 mg, 0.110 mmol), $Pd(dppf)_2Cl_2$ (8 mg, 0.0098 mmol) in dioxane (500 μL) and water (50 μL) was flushed with $N_2$ and heated at 100° C. for 16 h. The reaction mixture was purified by reverse phase HPLC (gradient of 10-99% acetonitrile in water containing HCl as a modifier) to give 4-[[2-fluoro-4-(p-tolyl)-6-[2-(trideuteriomethoxy)-4-(trifluoromethoxy)phenoxy]benzoyl]amino]pyridine-2-carboxamide (22.6 mg, 74%). ESI-MS m/z calc. 558.1606, found 559.4 $(M+1)^+$; Retention time (Method B): 1.95 minutes. $^1H$ NMR (400 MHz, DMSO-$d_6$) δ 11.32 (s, 1H), 8.54 (d, J=5.4 Hz, 1H), 8.32 (s, 1H), 8.13 (s, 1H), 7.84 (d, J=4.2 Hz, 1H), 7.68 (s, 1H), 7.50 (d, J=7.8 Hz, 2H), 7.45 (d, J=10.4 Hz, 1H), 7.31-7.24 (m, 3H), 7.17 (d, J=2.6 Hz, 1H), 7.02-6.92 (m, 1H), 6.82 (s, 1H), 2.33 (s, 3H) ppm.

The compounds set forth in Table 6 were prepared by methods analogous to the preparation of compound 88 in Example 6.

TABLE 6

Additional Compounds Prepared By Methods Analogous to Example 6.

| Cmpd No. | Compound Name | LC/MS | NMR (shifts in ppm) |
|---|---|---|---|
| 89 | 4-[[2-fluoro-4-(4-fluorophenyl)-6-[2-(trideuteriomethoxy)-4-(trifluoromethoxy)phenoxy]benzoyl]amino]pyridine-2-carboxamide | ESI-MS m/z calc. 562.1355, found 563.3 (M + 1)+; Retention time (Method B): 1.85 minutes (3 minute run). | $^1H$ NMR (400 MHz, DMSO-$d_6$) δ 11.35 (s, 1H), 8.54 (d, J = 5.5 Hz, 1H), 8.33 (d, J = 2.1 Hz, 1H), 8.14 (s, 1H), 7.84 (dd, J = 5.7, 2.1 Hz, 1H), 7.73-7.64 (m, 3H), 7.49 (d, J = 9.9 Hz, 1H), 7.34-7.25 (m, 3H), 7.17 (d, J = 2.7 Hz, 1H), 6.98 (dd, J = 8.8, 2.5 Hz, 1H), 6.86 (s, 1H). |
| 90 | 4-[[2-fluoro-4-(3-pyridyl)-6-[2-(trideuteriomethoxy)-4-(trifluoromethoxy)phenoxy]benzoyl]amino]pyridine-2-carboxamide | ESI-MS m/z calc. 545.14014, found 545.96 (M + 1)+; Retention time (Method B): 1.41 minutes (3 minute run). | $^1H$ NMR (400 MHz, DMSO-$d_6$) δ 11.52 (s, 1H), 9.13-9.00 (m, 1H), 8.80 (d, J = 5.1 Hz, 1H), 8.56 (d, J = 5.6 Hz, 1H), 8.47 (d, J = 8.1 Hz, 1H), 8.35 (d, J = 2.1 Hz, 1H), 8.19 (s, 1H), 7.92-7.81 (m, 2H), 7.74 (s, 1H), 7.70 (dd, J = 10.0, 1.4 Hz, 1H), 7.30 (d, J = 8.8 Hz, 1H), 7.17 (d, J = 2.7 Hz, 1H), 7.11 (s, 1H), 6.97 (d, J = 9.4 Hz, 1H). |
| 91 | 4-[[2-fluoro-4-(4-pyridyl)-6-[2-(trideuteriomethoxy)-4-(trifluoromethoxy)phenoxy]benzoyl]amino]pyridine-2-carboxamide | ESI-MS m/z calc. 545.14014, found 546.01 (M + 1)+; Retention time (Method B): 1.38 minutes (3 minute run). | $^1H$ NMR (400 MHz, DMSO-$d_6$) δ 11.60 (s, 1H), 8.93 (d, J = 5.9 Hz, 2H), 8.56 (d, J = 5.5 Hz, 1H), 8.35 (s, 1H), 8.26-8.18 (m, 3H), 7.91-7.83 (m, 2H), 7.74 (s, 1H), 7.32 (d, J = 8.8 Hz, 1H), 7.22 (s, 1H), 7.18 (d, J = 2.7 Hz, 1H), 6.98 (d, J = 8.9 Hz, 1H). |
| 92 | 4-[[2-fluoro-4-phenyl-6-[2-(trideuteriomethoxy)-4-(trifluoromethoxy)phenoxy]benzoyl]amino]pyridine-2-carboxamide | ESI-MS m/z calc. 544.1449, found 545.3 (M + 1)+; Retention time (Method B): 2.1 minutes (3 minute run). | $^1H$ NMR (400 MHz, DMSO-$d_6$) δ 11.33 (s, 1H), 8.54 (d, J = 5.3 Hz, 1H), 8.32 (s, 1H), 8.12 (s, 1H), 7.85 (d, J = 4.4 Hz, 1H), 7.67 (s, 1H), 7.60 (d, J = 7.3 Hz, 2H), 7.52-7.37 (m, 4H), 7.29 (d, J = 8.7 Hz, 1H), 7.18 (d, J = 2.6 Hz, 1H), 6.99 (d, J = 8.7 Hz, 1H), 6.84 (s, 1H). |
| 93 | 4-[[2-fluoro-6-[2-(trideuteriomethoxy)-4-(trifluoromethoxy)phenoxy]-4-[4-(trifluoromethyl)phenyl]benzoyl]amino]pyridine-2-carboxamide | ESI-MS m/z calc. 612.1323, found 613.3 (M + 1)+; Retention time (Method B): 2.0 minutes (3 minute run). | $^1H$ NMR (400 MHz, DMSO-$d_6$) δ 11.37 (s, 1H), 8.55 (d, J = 5.5 Hz, 1H), 8.33 (d, J = 2.1 Hz, 1H), 8.14 (d, J = 2.8 Hz, 1H), 7.88-7.79 (m, 5H), 7.69 (d, J = 2.8 Hz, 1H), 7.63-7.56 (m, 1H), 7.30 (d, J = 8.8 Hz, 1H), 7.18 (d, J = 2.7 Hz, 1H), 6.99 (dd, J = 9.0, 2.3 Hz, 1H), 6.94 (s, 1H). |
| 94 | 4-[[2-fluoro-6-[2-(trideuteriomethoxy)-4-(trifluoromethoxy)phe- | ESI-MS m/z calc. 612.1323, found 613.2 | $^1H$ NMR (400 MHz, DMSO-$d_6$) δ 11.36 (s, 1H), 8.54 (d, J = 5.5 Hz, 1H), 8.32 (d, J = 2.1 Hz, 1H), 8.13 (s, 1H), 7.98-7.91 (m, |

TABLE 6-continued

| Additional Compounds Prepared By Methods Analogous to Example 6. | | | |
|---|---|---|---|
| Cmpd No. | Compound Name | LC/MS | NMR (shifts in ppm) |
| | noxy]-4-[3-(trifluoromethyl)phenyl]benzoyl]amino]pyridine-2-carboxamide | (M + 1)+; Retention time (Method B): 1.97 minutes (3 minute run). | 2H), 7.86-7.78 (m, 2H), 7.75-7.61 (m, 3H), 7.26 (d, J = 8.8 Hz, 1H), 7.17 (d, J = 2.6 Hz, 1H), 7.04-6.93 (m, 2H). |
| 95 | 4-[[2-fluoro-6-[2-(trideuteriomethoxy)-4-(trifluoromethoxy)phenoxy]-4-[2-(trifluoromethyl)phenyl]benzoyl]amino]pyridine-2-carboxamide | ESI-MS m/z calc. 612.1323, found 613.2 (M + 1)+; Retention time (Method B): 1.94 minutes. | $^1H$ NMR (400 MHz, DMSO-$d_6$) δ 11.42 (s, 1H), 8.56 (d, J = 5.4 Hz, 1H), 8.37 (s, 1H), 8.13 (s, 1H), 7.88 (d, J = 3.9 Hz, 1H), 7.83 (d, J = 7.8 Hz, 1H), 7.74 (t, J = 7.6 Hz, 1H), 7.70-7.60 (m, 2H), 7.41 (d, J = 7.6 Hz, 1H), 7.30 (d, J = 8.8 Hz, 1H), 7.19-7.12 (m, 2H), 6.98 (d, J = 8.2 Hz, 1H), 6.43 (s, 1H). |

Example 7

4-[[4-Cyclopentyl-2-Fluoro-6-[2-(Trideuteriomethoxy)-4-(Trifluoromethoxy)Phenoxy]Benzoyl]Amino]Pyridine-2-Carboxamide (96)

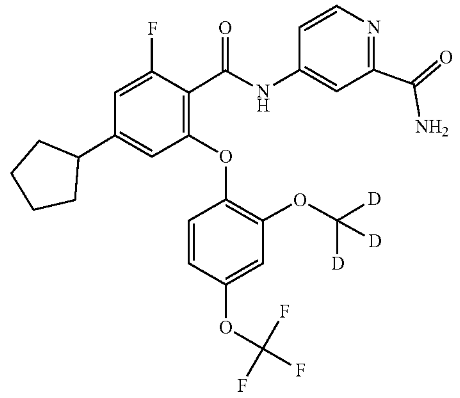 [SMILES: [2H]C([2H])([2H])Oc1cc(OC(F)(F)F)ccc1Oc1cc(C2CCCC2)cc(F)c1C(=O)Nc1ccnc(C(N)=O)c1]

Step 1: Methyl 4-Bromo-2-Fluoro-6-[2-(Trideuteriomethoxy)-4-(Trifluoromethoxy)Phenoxy]Benzoate

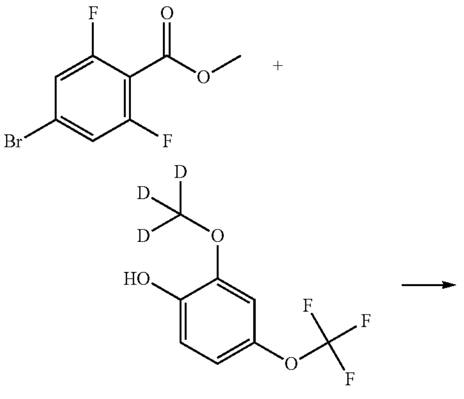

-continued

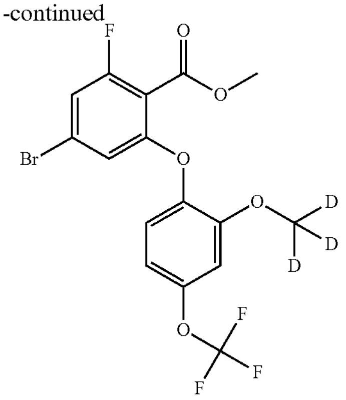

A mixture of $Cs_2CO_3$ (7.89 g, 24.22 mmol), 2-(trideuteriomethoxy)-4-(trifluoromethoxy)phenol (3.54 g, 16.77 mmol) and methyl 4-bromo-2,6-difluoro-benzoate (4.00 g, 15.93 mmol) in DMF (70 mL) was stirred at ambient temperature for 20 h. The reaction was diluted with ethyl acetate and washed with water (×3) and brine. The organic layer was dried over anhydrous $MgSO_4$, filtered and concentrated under reduced pressure. Silica gel chromatography (0-10% ethyl acetate/hexane) provided methyl 4-bromo-2-fluoro-6-[2-(trideuteriomethoxy)-4-(trifluoromethoxy)phenoxy]benzoate (6.091 g, 86%). ESI-MS m/z calc. 440.99142, found 443.1 $(M+1)^+$; Retention time (Method A): 0.82 minutes. $^1H$ NMR (400 MHz, DMSO-d6) δ 7.47 (dd, J=9.0, 1.7 Hz, 1H), 7.26 (d, J=8.8 Hz, 1H), 7.24 (d, J=2.8 Hz, 1H), 7.00 (ddd, J=8.8, 2.7, 1.3 Hz, 1H), 6.73 (t, J=1.5 Hz, 1H), 3.83 (s, 3H) ppm.

Step 2: 4-Bromo-2-Fluoro-6-[2-(Trideuteriomethoxy)-4-(Trifluoromethoxy)Phenoxy]Benzoic Acid

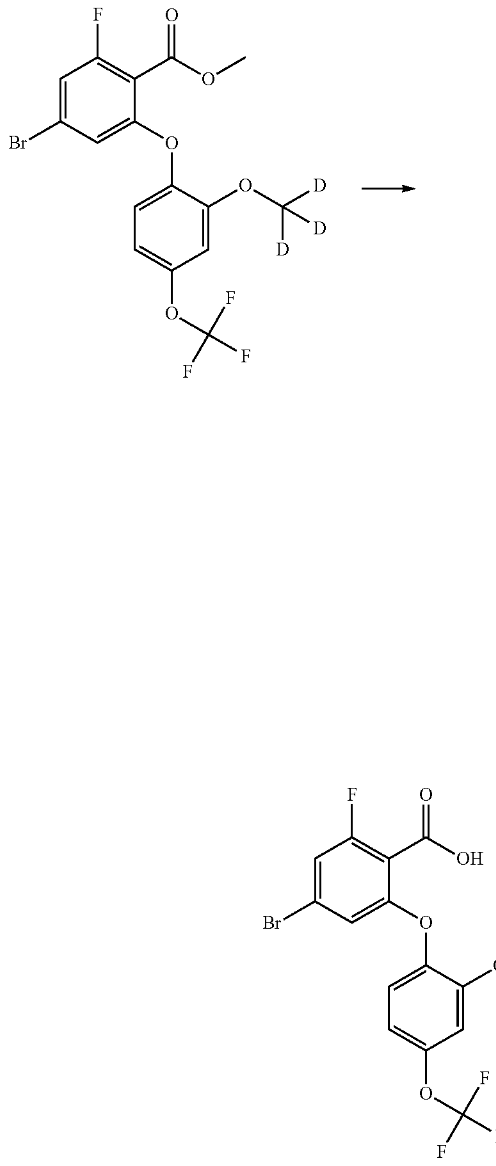

Methyl 4-bromo-2-fluoro-6-[2-(trideuteriomethoxy)-4-(trifluoromethoxy)phenoxy]benzoate (6.09 g, 13.77 mmol) was dissolved in MeOH (60 mL) and treated with NaOH (40 mL of 1 M, 40.00 mmol). The reaction was heated to 40° C. and stirred for 2 h resulting in partial hydrolysis. Additional NaOH (23 mL of 6 M, 138.0 mmol) was added and the reaction stirred at 45° C. for 1 hour. The reaction mixture was acidified with HCl (210 mL of 1 M, 210.0 mmol) and extracted into ethyl acetate (×3). The combined organic layers were dried over anhydrous $MgSO_4$, filtered and concentrated reduced pressure to provide 4-bromo-2-fluoro-6-[2-(trideuteriomethoxy)-4-(trifluoromethoxy)phenoxy] benzoic acid (5.81 g, 99%) as a glassy oil. ESI-MS m/z calc. 426.97577, found 429.0 $(M+1)^+$; Retention time (Method A): 0.72 minutes. $^1H$ NMR (400 MHz, DMSO-d6) δ 13.78 (s, 1H), 7.42 (dd, J=8.9, 1.6 Hz, 1H), 7.25-7.20 (m, 2H), 7.00 (ddd, J=8.8, 2.7, 1.3 Hz, 1H), 6.67 (t, J=1.4 Hz, 1H) ppm.

Step 3: 4-[[4-Bromo-2-Fluoro-6-[2-(Trideuteriomethoxy)-4-(Trifluoromethoxy)Phenoxy]Benzoyl] Amino]Pyridine-2-Carboxamide

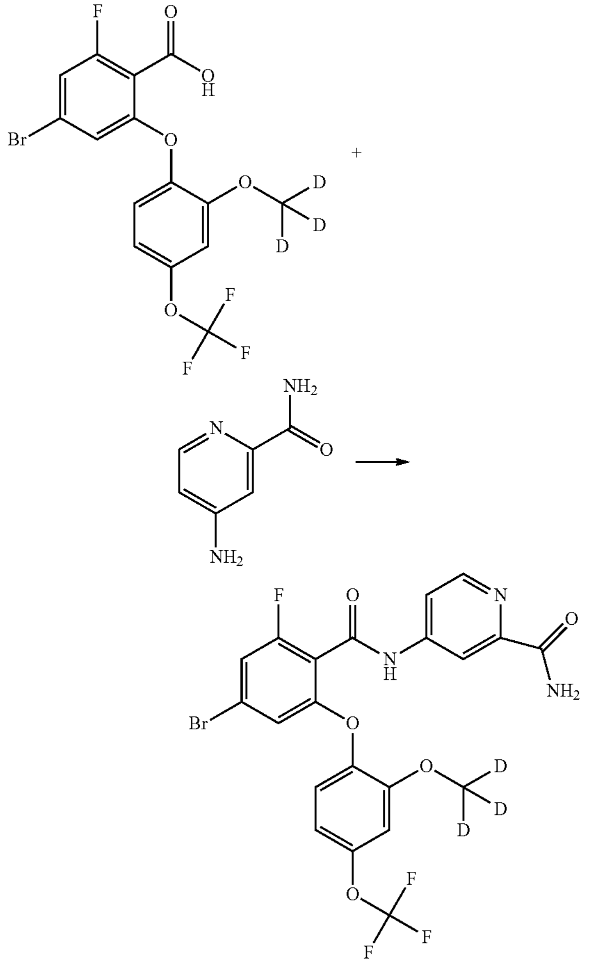

To a solution of 4-bromo-2-fluoro-6-[2-(trideuteriomethoxy)-4-(trifluoromethoxy)phenoxy]benzoic acid (4.0 g, 9.343 mmol), DMF (210 μL, 2.712 mmol) and DCM (48 mL) at 0° C. under $N_2$ (g) was added oxalyl dichloride (7 mL, 80.24 mmol). The reaction was stirred at 0° C. for 10 minutes and then at RT for additional 1 h. The mixture was concentrated under reduced pressure and redissolved in NMP (5 mL). This solution was added drop-wise to a suspension of 4-aminopyridine-2-carboxamide (1.28 g, 9.334 mmol), DMF (1.5 mL, 19.37 mmol), and DIEA (10 mL, 57.41 mmol) in NMP (10 mL) under $N_2$ atmosphere at 0° C. The resulting reaction mixture was slowly warmed to RT and stirred overnight. The mixture was partitioned between water and ethyl acetate. The phases were separated and the aqueous layer was extracted with ethyl acetate (1×). The combined organic layers were washed with brine (2×), water (2×) then brine (1×). The organic layer was dried over $Na_2SO_4$, filtered and concentrated to give a light brown foam. The crude was purified by silica chromatography eluting with a gradient of ethyl acetate-hexanes to give 4-[[4-bromo-2-fluoro-6-[2-(trideuteriomethoxy)-4-(trifluoromethoxy)phenoxy]benzoyl]amino]pyridine-2-carboxamide (1.26 g, 25%). ESI-MS m/z calc. 546.0241, found 549.0

$(M+1)^+$; Retention time (Method B): 1.94 minutes. $^1H$ NMR (400 MHz, DMSO-d6) δ 11.30 (s, 1H), 8.54 (d, J=5.4 Hz, 1H), 8.29 (d, J=2.1 Hz, 1H), 8.16-7.99 (m, 1H), 7.82 (dd, J=5.6, 2.2 Hz, 1H), 7.65 (d, J=2.8 Hz, 1H), 7.52 (dd, J=8.6, 1.5 Hz, 1H), 7.30 (d, J=8.8 Hz, 1H), 7.20 (d, J=2.7 Hz, 1H), 7.10-6.91 (m, 1H), 6.75 (s, 1H) ppm.

Step 4: 4-[[4-(Cyclopenten-1-Yl)-2-Fluoro-6-[2-(Trideuteriomethoxy)-4-(Trifluoromethoxy)Phenoxy]Benzoyl]Amino]Pyridine-2-Carboxamide

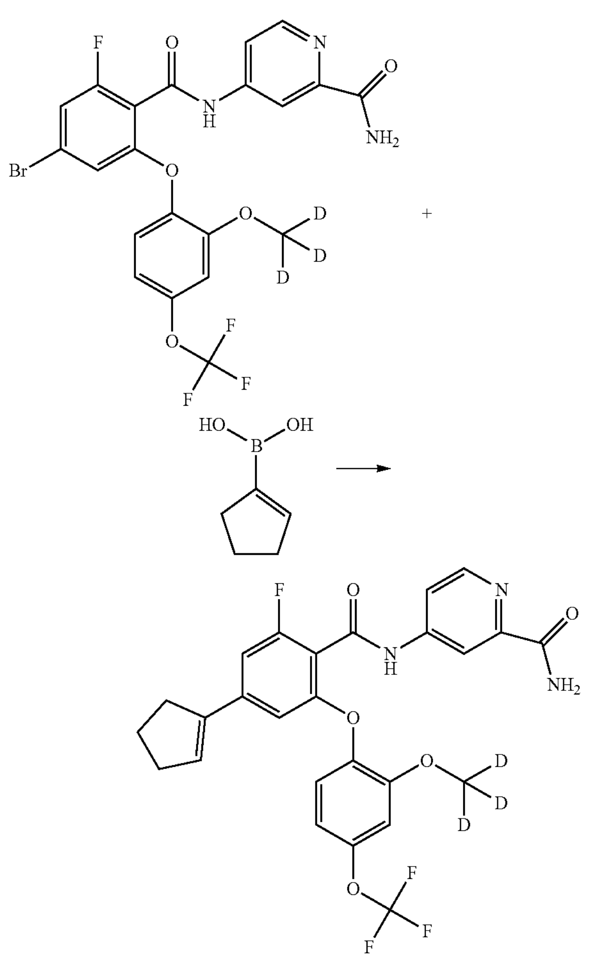

A solution of 4-[[4-bromo-2-fluoro-6-[2-(trideuteriomethoxy)-4-(trifluoromethoxy)phenoxy]benzoyl]amino] pyridine-2-carboxamide (25 mg, 0.04568 mmol), cyclopenten-1-ylboronic acid (13 mg, 0.1161 mmol), $K_2CO_3$ (13 mg, 0.09406 mmol), ferrous; cyclopenta-1,4-dien-1-yl(diphenyl)phosphane; DCM; dichloropalladium (8 mg, 0.009796 mmol) in dioxane (500 μL) and water (50 μL) was heated at 100° C. for 16 h. The reaction mixture was filtered and purified by reverse phase HPLC (gradient of 10-99% acetonitrile in water containing HCl as a modifier) to obtain 4-[[4-(cyclopenten-1-yl)-2-fluoro-6-[2-(trideuteriomethoxy)-4-(trifluoromethoxy)phenoxy]benzoyl]amino] pyridine-2-carboxamide (18.2 mg, 74%). ESI-MS m/z calc. 534.1606, found 534.96 $(M+1)^+$; Retention time (Method B): 2.01 minutes.

Step 5: 4-[[4-Cyclopentyl-2-Fluoro-6-[2-(Trideuteriomethoxy)-4-(Trifluoromethoxy)Phenoxy]Benzoyl] Amino]Pyridine-2-Carboxamide (96)

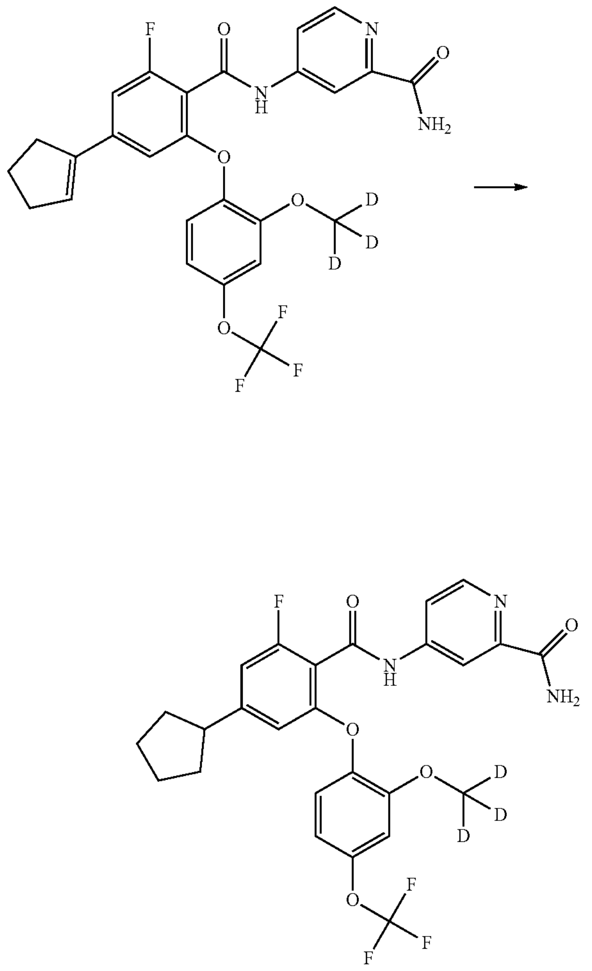

A solution of 4-[[4-(cyclopenten-1-yl)-2-fluoro-6-[2-(trideuteriomethoxy)-4-(trifluoromethoxy)phenoxy]benzoyl] amino]pyridine-2-carboxamide (9 mg, 0.01680 mmol) in ethyl acetate (250 μL) and MeOH (250 μL) was flushed with N2 (g). Palladium on Carbon (0.1788 mg, 0.001680 mmol) was added and the resulting mixture was purged with $H_2$ (balloon). The reaction was stirred at RT under a hydrogen atmosphere for 16 h. The mixture was filtered and purified by reverse phase HPLC (gradient of 10-99% acetonitrile in water containing HCl as a modifier) giving 4-[[14-cyclopentyl-2-fluoro-6-[2-(trideuteriomethoxy)-4-(trifluoromethoxy)phenoxy]benzoyl]amino]pyridine-2-carboxamide (6.6 mg, 73%). ESI-MS m/z cac. 536.1762, found 537.2 $(M+1)^+$; Retention time (Method B): 1.94 minutes. $^1HNMR$ (400 MHz, DMSO-$d_6$) δ 11.25 (s, 1H), 8.53 (d, J=5.5 Hz, 1H), 8.32 (d, J=2.1 Hz, 1H), 8.13 (s, 1H), 7.83 (dd, J=5.5, 2.2 Hz, 1H), 7.69 (s, 1H), 7.22 (d, J=8.7 Hz, 1H), 7.18 (d, J=2.7 Hz, 1H), 7.03 (d, J=10.2 Hz, 1H), 6.99 (d, J=8.9 Hz, 1H), 6.46 (s, 1H), 2.95 (p, J=9.0 Hz, 1H), 1.98-1.91 (m, 2H), 1.75-1.67 (min, 2H), 1.649-1.56 (i, 2H), 1.462-1.41 ((, 2H) ppm.

The compounds set forth in Table 7 were prepared by methods analogous to the preparation of compound 96.

TABLE 7

| Additional Compounds Prepared By Methods Analogous to Example 7. | | | |
|---|---|---|---|
| Cmpd No. | Compound Name | LC/MS | NMR (shifts in ppm) |
| 97 | 4-[[4-cyclohexyl-2-fluoro-6-[2-(trideuteriomethoxy)-4-(trifluoromethoxy)phenoxy]benzoyl]amino]pyridine-2-carboxamide | ESI-MS m/z calc. 550.19183, found 551.3 (M + 1)+; Retention time (Method B): 2.04 minutes; | $^1$H NMR (400 MHz, DMSO-d$_6$) δ 11.28 (s, 1H), 8.52 (d, J = 5.5 Hz, 1H), 8.33 (d, J = 2.1 Hz, 1H), 8.14 (s, 1H), 7.83 (dd, J = 5.8, 2.1 Hz, 1H), 7.77-7.66 (m, 1H), 7.22 (d, J = 8.8 Hz, 1H), 7.17 (d, J = 2.8 Hz, 1H), 7.00 (t, J = 9.9 Hz, 2H), 6.44 (s, 1H), 2.47 (m, 1H, obscured by DMSO), 1.85-1.60 (m, 5H), 1.44-1.10 (m, 5H). |
| 98 | 4-[[4-(4,4-difluorocyclohexyl)-2-fluoro-6-[2-(trideuteriomethoxy)-4-(trifluoromethoxy)phenoxy]benzoyl]amino]pyridine-2-carboxamide | ESI-MS m/z calc. 586.17303, found 587.3 (M + 1)+; Retention time (Method B): 1.83 minutes | $^1$H NMR (400 MHz, DMSO-d$_6$) δ 11.38 (s, 1H), 8.54 (d, J = 5.6 Hz, 1H), 8.36 (d, J = 2.1 Hz, 1H), 8.21 (s, 1H), 7.94-7.82 (m, 1H), 7.76 (s, 1H), 7.25 (d, J = 8.8 Hz, 1H), 7.19 (d, J = 2.7 Hz, 1H), 7.06 (d, J = 10.2 Hz, 1H), 7.04-6.92 (m, 1H), 6.46 (s, 1H), 2.82-2.63 (m, 1H), 2.18-1.71 (m, 6H), 1.67-1.47 (m, 2H). |

Example 8

4-[[5-Fluoro-2-[12-(Trideuteriomethoxy)-4-(Trifluoromethoxy)Phenoxy]-4-(Trifluoromethyl)Benzoyl]Amino]Pyridine-2-Carboxamide (99)

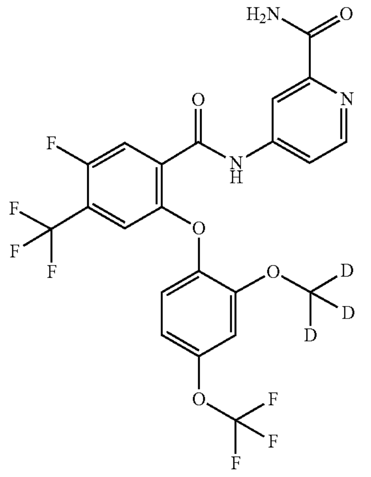 [SMILES: [2H]C([2H])([2H])Oc1cc(OC(F)(F)F)ccc1Oc1cc(C(F)(F)F)c(F)cc1C(=O)Nc1ccnc(C(N)=O)c1]

Step 1: Ethyl 2,5-Difluoro-4-(Trifluoromethyl)Benzoate

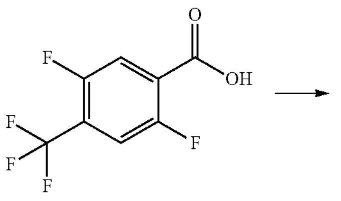

-continued

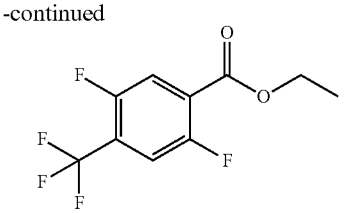

To a solution of 2,5-difluoro-4-(trifluoromethyl)benzoic acid (5 g, 22.11 mmol) in ethanol (50 mL) was added $H_2SO_4$ (1.5 mL, 28.14 mmol) dropwise over 5 minutes. The solution was heated at reflux for 48 h, then the reaction mixture was cooled to RT and concentrated under reduced pressure to provide ethyl 2,5-difluoro-4-(trifluoromethyl)benzoate (4.57 g, 81%) as a clear colorless liquid. ESI-MS m/z calc. 254.03662, Retention time (Method A): 0.71 minutes (product does not ionize). $^1$H NMR (400 MHz, DMSO-d6) δ 7.96 (dd, J=10.1, 5.6 Hz, 2H), 4.37 (q, J=7.1 Hz, 2H), 1.33 (t, J=7.1 Hz, 3H) ppm.

Step 2: 5-Fluoro-2-[2-(Trideuteriomethoxy)-4-(Trifluoromethoxy)Phenoxy]-4-(Trifluoromethyl)Benzoic Acid

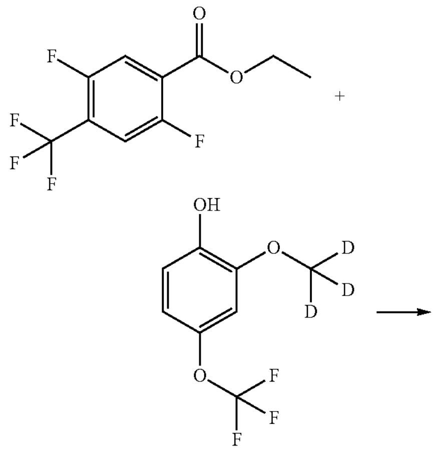

-continued

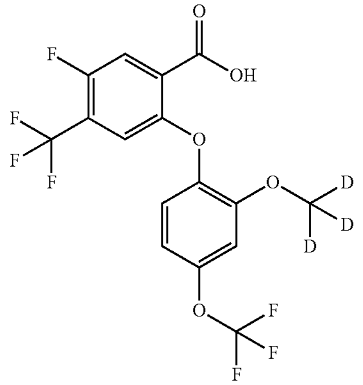

A mixture of 2-(trideuteriomethoxy)-4-(trifluoromethoxy)phenol (7.69 g, 36.42 mmol), ethyl 2,5-difluoro-4-(trifluoromethyl)benzoate (8.41 g, 33.09 mmol) and $Cs_2CO_3$ (16.17 g, 49.63 mmol) in acetonitrile (102.6 mL) was heated under reflux under $N_2$ overnight. The reaction mixture was diluted with water and acidified to ~pH 2 with 6 N HCl. The mixture was extracted with DCM (3×50 mL) and the combined organic layers dined over $MgSO_4$, filtered and concentrated. The residue was dissolved in MeOH (50 mL) and treated with solid NaOH (2.647 g, 66.18 mmol) dissolved in 50 mL water. The mixture was stirred for 20 minutes then acidified with an aqueous solution of HCl (9 mL of 12 M, 108.0 mmol). The aqueous mixture was extracted with ethyl acetate, and the organic layer dried over $MgSO_4$, filtered and concentrated under reduced pressure. The residue was purified by silica gel chromatography (0-3% MeOH/DCM with 0.2% AcOH) and product fractions were concentrated and the solid triturated 2× with hexanes to provide 5-fluoro-2-[2-(trideuteriomethoxy)-4-(trifluoromethoxy)phenoxy]-4-(trifluoromethyl)benzoic acid as a white solid. ESI-MS m/z calc. 417.05264, found 418.1 $(M+1)^+$; Retention time (Method A): 0.74 minutes. $^1H$ NMR (500 MHz, DMSO-d6) δ 13.69 (br s, 1H), 7.88 (d, J=10.4 Hz, 1H), 7.20 (d, J=2.7 Hz, 1H), 7.14 (d, J=5.7 Hz, 1H), 7.07 (d, J=8.8 Hz, 1H), 6.95 (d, J=8.8 Hz, 1H) ppm.

Step 3: 5-Fluoro-2-[2-(Trideuteriomethoxy)-4-(Trifluoromethoxy)Phenoxy]-4-(Trifluoromethyl)Benzoyl Chloride

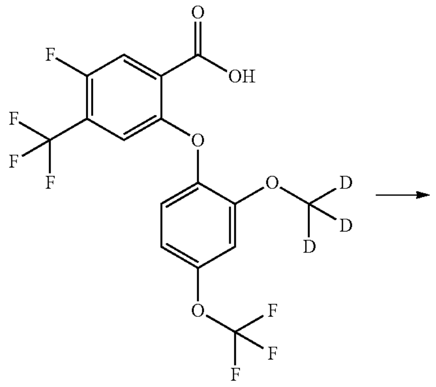

-continued

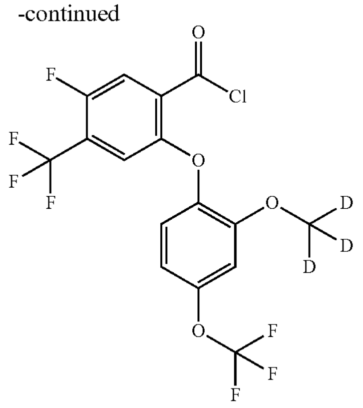

To a solution of 5-fluoro-2-[2-(trideuteriomethoxy)-4-(trifluoromethoxy)phenoxy]-4-(trifluoromethyl)benzoic acid (1.8 g, 4.314 mmol) and DMF (10 μL, 0.1291 mmol) in DCM (15 mL) at 0° C. was added oxalyl chloride (565 μL, 6.477 mmol) drop-wise under $N_2$ atmosphere. The ice bath was removed after 10 minutes and the reaction was stirred at RT for 1.5 h. The solvent was evaporated under reduced pressure to afford 5-fluoro-2-[2-(trideuteriomethoxy)-4-(trifluoromethoxy)phenoxy]-4-(trifluoromethyl)benzoyl chloride. The intermediate was used in the next step without further purification.

Step 4: 4-[[5-Fluoro-2-[2-(Trideuteriomethoxy)-4-(Trifluoromethoxy)Phenoxy]-4-(Trifluoromethyl) Benzoyl]Amino]Pyridine-2-Carboxamide (99)

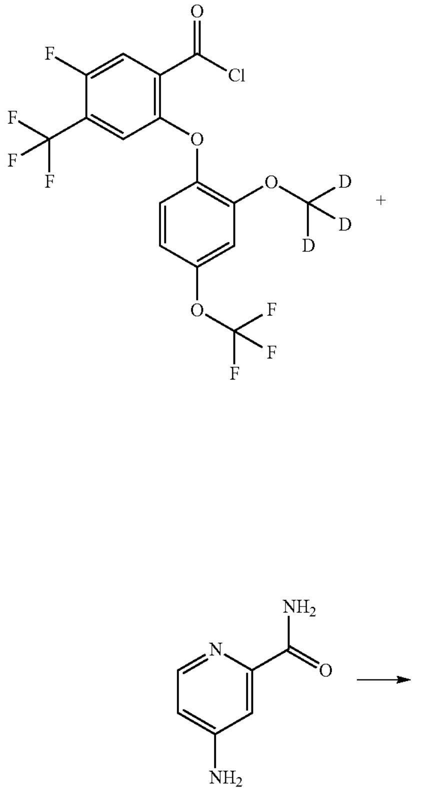

-continued

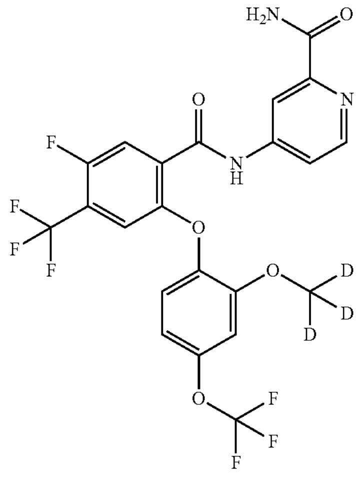

To 5-fluoro-2-[2-(trideuteriomethoxy)-4-(trifluoromethoxy)phenoxy]-4-(trifluoromethyl)benzoyl chloride (60 mg, 0.1377 mmol) in NMP (0.3 mL) was added to a mixture of 4-aminopyridine-2-carboxamide (28.32 mg, 0.2065 mmol) and DIEA (71.19 mg, 95.94 μL, 0.5508 mmol) in NMP (0.3 mL). The reaction was stirred at RT for 2 h. The crudes were filtered and purified by reverse phase HPLC (gradient of 10-99% acetonitrile in water containing HCl as a modifier) to give 4-[[5-fluoro-2-[2-(trideuteriomethoxy)-4-(trifluoromethoxy)phenoxy]-4-(trifluoromethyl)benzoyl]amino]pyridine-2-carboxamide (30.00 mg, 41%). ESI-MS m/z calc. 536.101, found 537.31 $(M+1)^+$; Retention time (Method B): 1.83 minutes.

Example 9

5-[[5-Fluoro-2-[2-(Trideuteriomethoxy)-4-(Trifluoromethoxy)Phenoxy]-4-(Trifluoromethyl)Benzoyl]Amino]Pyridine-2-Carboxamide (100)

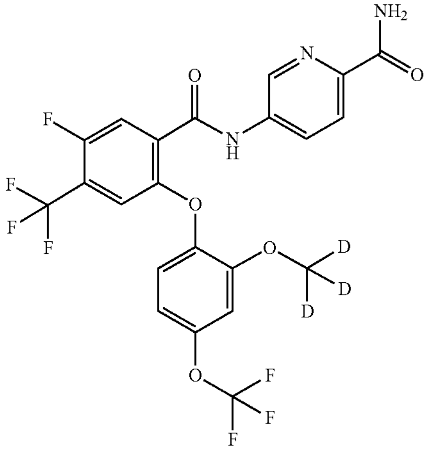 [SMILES: [2H]C([2H])([2H])Oc1cc(OC(F)(F)F)ccc1Oc1cc(C(F)(F)F)c(F)cc1C(=O)Nc1ccc(C(N)=O)nc1]

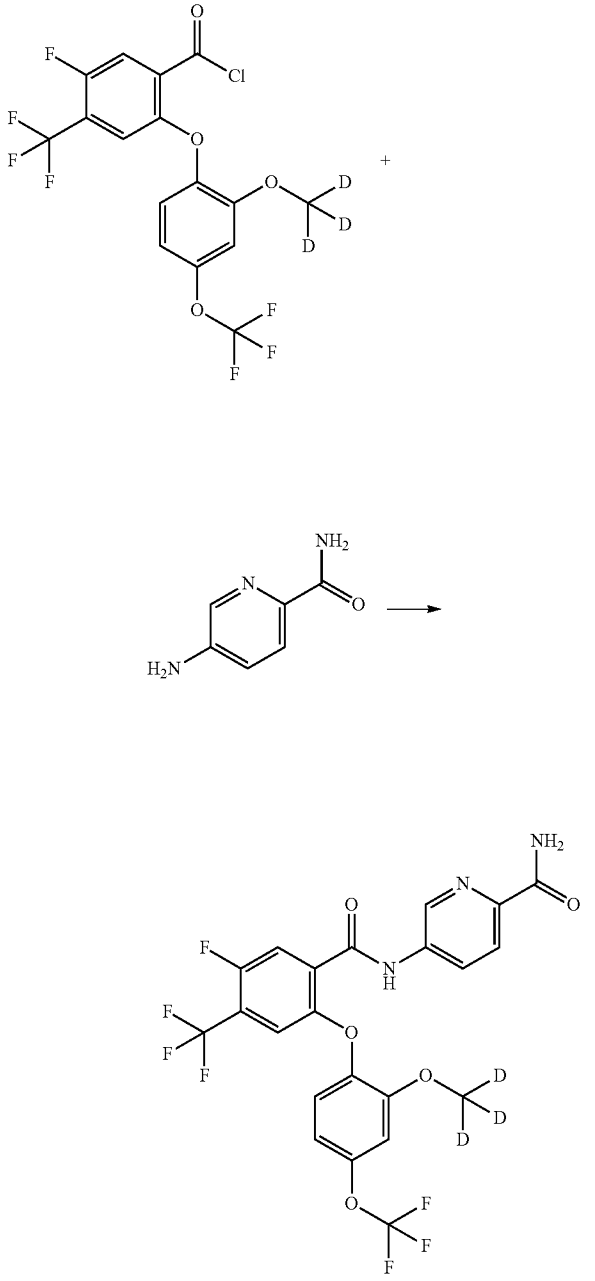

To a solution of 5-fluoro-2-[2-(trideuteriomethoxy)-4-(trifluoromethoxy)phenoxy]-4-(trifluoromethyl)benzoyl chloride (60 mg, 0.1377 mmol) in NMP (0.3 mL) was added a mixture of 5-aminopyridine-2-carboxamide (28.32 mg, 0.2065 mmol) and DIEA (71.19 mg, 95.94 μL, 0.5508 mmol) in NMP (0.3 mL). The reactions were stirred at RT for 2 h. The crude was filtered and purified by reverse phase HPLC (gradient of 10-99% acetonitrile in water containing HCl as a modifier) to give 5-[[5-fluoro-2-[2-(trideuteriomethoxy)-4-(trifluoromethoxy)phenoxy]-4-(trifluoromethyl)benzoyl]amino]pyridine-2-carboxamide (27.80 mg, 37%). ESI-MS m/z calc. 536.101, found 536.96 $(M+1)^+$; Retention time (Method B): 1.98 minutes. $^1H$ NMR (400 MHz, DMSO-$d_6$) δ 11.07 (s, 1H), 8.84 (d, J=2.4 Hz, 1H), 8.22 (dd, J=8.6, 2.5 Hz, 1H), 8.07-8.00 (m, 2H), 7.95 (d, J=10.1 Hz, 1H), 7.58 (s, 1H), 7.21 (dd, J=7.4, 5.3 Hz, 2H), 7.16 (d, J=2.7 Hz, 1H), 6.97 (dd, J=9.0, 2.3 Hz, 1H) ppm.

Example 10

5-[[2-Fluoro-6-(4-Fluoro-2-Methyl-Phenoxy)-3-(Trifluoromethyl)Benzoyl]Amino]Pyridine-2-Carboxamide (101)

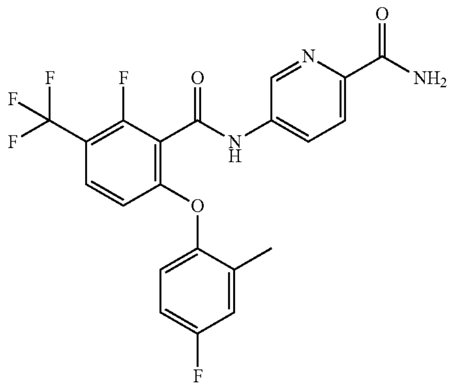 [SMILES: Cc1cc(F)ccc1Oc1ccc(C(F)(F)F)c(F)c1C(=O)Nc1ccc(C(N)=O)nc1]

Step 1: 2-Fluoro-6-(4-Fluoro-2-Methyl-Phenoxy)-3-(Trifluoromethyl)Benzoic Acid

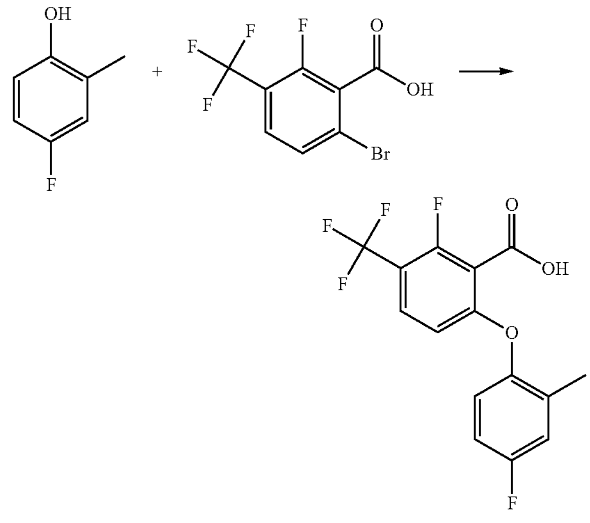

A solution of 6-bromo-2-fluoro-3-(trifluoromethyl)benzoic acid (24 g, 83.62 mmol), 4-fluoro-2-methyl-phenol (11.33 g, 89.83 mmol), $Cs_2CO_3$ (27.43 g, 84.19 mmol) in toluene (200 mL) was bubbled with $N_2$ for 10 minutes then CuI (3.1 g, 16.28 mmol) was added. The flask was flushed with $N_2$, capped, and heated at 100° C. with vigorous stirring for 3 h. The mixture was allowed to cool then diluted with ethyl acetate and water (350 mL). The two layers were separated, the aqueous was layer acidified with HCl (375 mL of 1 M, 375.0 mmol) and extracted with ethyl acetate (×3). The combined organic layer was washed with brine (×2), dried over $Na_2SO_4$, filtered through a plug of celite and concentrated undere reduced pressure. The crude product was titurated with hexane and filtered to obtain 2-fluoro-6-(4-fluoro-2-methyl-phenoxy)-3-(trifluoromethyl)benzoic acid (16 g, 58%) as a cream colored solid. ESI-MS m/z calc. 332.04718, found 333.1 $(M+1)^+$; Retention time (Method C): 2.39 minutes. $^1H$ NMR (500 MHz, DMSO-d6) δ 14.11 (s, 1H), 7.76 (t, J=8.6 Hz, 1H), 7.28 (dd, J=9.4, 3.0 Hz, 1H), 7.22-7.11 (m, 2H), 6.58 (d, J=8.9 Hz, 1H), 2.13 (s, 3H) ppm.

Step 2: 2-Fluoro-6-(4-Fluoro-2-Methyl-Phenoxy)-3-(Trifluoromethyl)Benzoyl Chloride

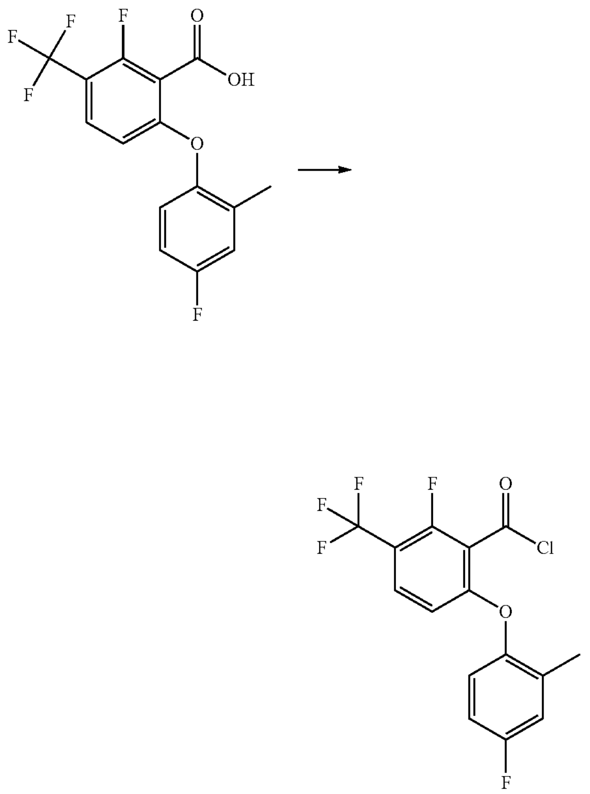 [SMILES: Cc1cc(F)ccc1Oc1ccc(C(F)(F)F)c(F)c1C(=O)O ; Cc1cc(F)ccc1Oc1ccc(C(F)(F)F)c(F)c1C(=O)Cl]

To 2-fluoro-6-(4-fluoro-2-methyl-phenoxy)-3-(trifluoromethyl)benzoic acid (600 mg, 1.806 mmol) and DMF (15 μL, 0.1937 mmol) in DCM (6 mL) at 0° C. was added oxalyl chloride (237 μL, 2.717 mmol) dropwise under $N_2$ atmosphere. The ice bath was removed after 10 minutes and the reaction was stirred at RT for 1 h. The solvent was evaporated under reduced pressure to afford 2-fluoro-6-(4-fluoro-2-methyl-phenoxy)-3-(trifluoromethyl)benzoyl chloride. The intermediate was used in the next step without further purification.

Step 3: 5-[[2-Fluoro-6-(4-Fluoro-2-Methyl-Phenoxy)-3-(Trifluoromethyl)Benzoyl]Amino]Pyridine-2-Carboxamide (101)

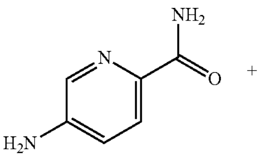

-continued

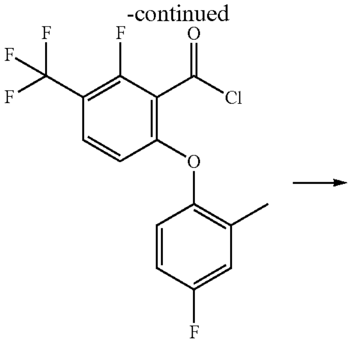

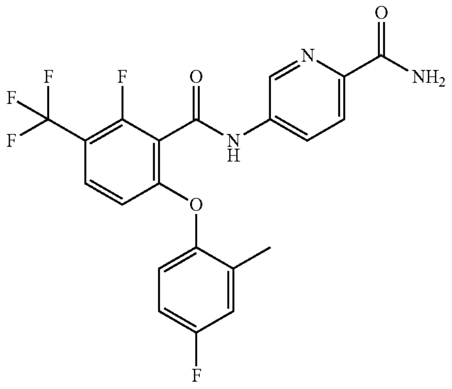

To 5-aminopyridine-2-carboxamide (28.15 mg, 0.2053 mmol) in NMP (400 µL), and DIEA (66.34 mg, 89.41 µL, 0.5133 mmol) at 0° C. was added a solution of 2-fluoro-6-(4-fluoro-2-methyl-phenoxy)-3-(trifluoromethyl)benzoyl chloride (60 mg, 0.1711 mmol) in NMP (200 µL) slowly. The reaction was stirred at RT for 16 h. The crude product was filtered and purified by reverse phase HPLC (gradient of 10-99% acetonitrile in water containing HCl as a modifier) yield 5-[[2-fluoro-6-(4-fluoro-2-methyl-phenoxy)-3-(trifluoromethyl)benzoyl]amino]pyridine-2-carboxamide (39.5 mg, 51%). ESI-MS m/z calc. 451.09552, found 452.0 $(M+1)^+$; Retention time (Method B): 1.81 minutes. $^1H$ NMR (400 MHz, DMSO-d6) δ 11.40 (s, 1H), 8.86 (d, J=2.4 Hz, 1H), 8.31 (dd, J=8.7, 2.4 Hz, 1H), 8.07 (d, J=8.6 Hz, 1H), 8.03 (s, 1H), 7.83 (t, J=8.7 Hz, 1H), 7.58 (s, 1H), 7.24 (ddd, J=17.5, 9.1, 4.0 Hz, 2H), 7.15 (td, J=8.5, 3.0 Hz, 1H), 6.65 (d, J=8.9 Hz, 1H), 2.14 (s, 3H) ppm.

Example 11

4-[[2-Fluoro-6-(4-Fluoro-2-Methyl-Phenoxy)-3-(Trifluoromethyl)Benzoyl]Amino]Pyridine-2-Carboxamide (102)

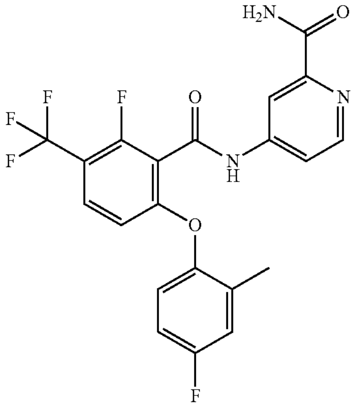 [SMILES: Cc1cc(F)ccc1Oc1ccc(C(F)(F)F)c(F)c1C(=O)Nc1ccnc(C(N)=O)c1]

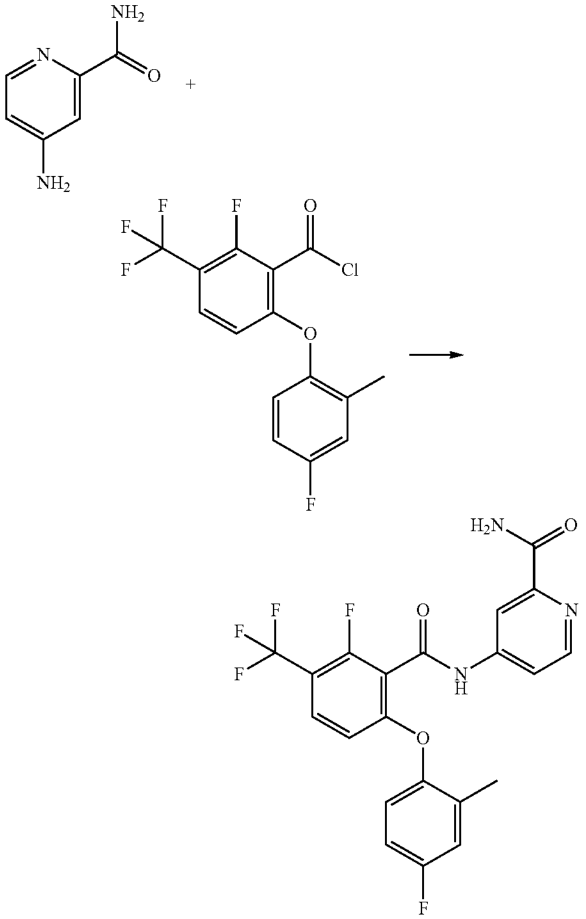

To 4-aminopyridine-2-carboxamide (28.15 mg, 0.2053 mmol) in NMP (400 µL) and DIEA (66.34 mg, 89.41 µL, 0.5133 mmol) at 0° C. was added a solution of 2-fluoro-6-(4-fluoro-2-methyl-phenoxy)-3-(trifluoromethyl)benzoyl chloride (60 mg, 0.1711 mmol) in NMP (200 µL) slowly.

The reaction was stirred at RT for 16 h. The crude product was filtered and purified by reverse phase HPLC (gradient of 10-99% acetonitrile in water containing HCl as a modifier) to yield 4-[[2-fluoro-6-(4-fluoro-2-methyl-phenoxy)-3-(trifluoromethyl)benzoyl]amino]pyridine-2-carboxamide (28.9 mg, 37%). ESI-MS m/z calc. 451.09552, found 452.0 $(M+1)^+$; Retention time (Method B): 1.8 minutes. $^1H$ NMR (400 MHz, DMSO-d6) δ 11.48 (s, 1H), 8.57 (d, J=5.4 Hz, 1H), 8.33 (d, J=2.1 Hz, 1H), 8.11 (d, J=2.8 Hz, 1H), 7.94-7.80 (m, 2H), 7.67 (s, 1H), 7.36-7.07 (m, 3H), 6.64 (d, J=8.9 Hz, 1H), 2.13 (d, J=5.0 Hz, 3H) ppm.

Example 12

4-[[2-Fluoro-6-(4-Fluoro-2-Methoxy-Phenoxy)-3-(Trifluoromethyl)Benzoyl]Amino]Pyridine-2-Carboxamide (103)

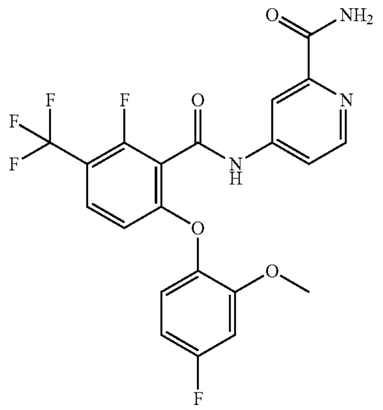 [SMILES: COc1cc(F)ccc1Oc1ccc(C(F)(F)F)c(F)c1C(=O)Nc1ccnc(C(N)=O)c1]

Step 1: 2-Fluoro-6-(4-Fluoro-2-Methoxy-Phenoxy)-3-(Trifluoromethyl)Benzoic Acid

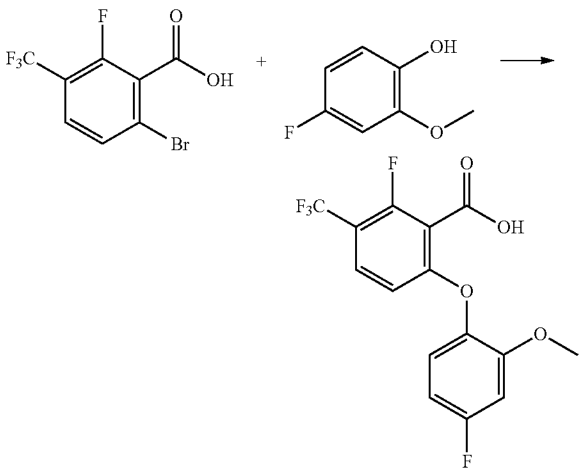

A solution of 6-bromo-2-fluoro-3-(trifluoromethyl)benzoic acid (20 g, 69.68 mmol), 4-fluoro-2-methoxy-phenol (10 g, 70.36 mmol), $Cs_2CO_3$ (25 g, 76.73 mmol) in toluene (250 mL) was bubbled with $N_2$ for 15 minutes then CuI (2.8 g, 14.70 mmol) added. The flask was flushed with $N_2$, and stirred at RT for 16 h, then heated to 100° C. with stirring for 5 h. The mixture was allowed to cool, then diluted with ethyl acetate and water. The water layer was acidified with HCl (142 mL of 1 M, 142.0 mmol) and the product extracted into ethyl acetate. The organic layer was washed with brine, dried over $Na_2SO_4$, filtered and concentrated. The resulting gummy residue was dissolved in ethyl acetate and filtered through a pad of celite and the filtrate was concentrated. The brown residue was dissolved in DCM/ethyl acetate and purified by silica chromatography in a 330 g silica column with a shallow (0-10%) gradient system of DCM/MeOH (0.5% AcOH). The resultant material was dissolved in a minimum amount of DCM and hexanes and allowed to stand overnight. The resultant precipitate was filtered, washed with hexane and dried under vacuum to give 2-fluoro-6-(4-fluoro-2-methoxy-phenoxy)-3-(trifluoromethyl)benzoic acid (9.8 g, 31%) as a light brown solid. ESI-MS m/z calc. 348.0421, found 349.1 $(M+1)^+$; Retention time (Method A): 0.58 minutes.

Step 2: 2-Fluoro-6-(4-Fluoro-2-Methoxy-Phenoxy)-3-(Trifluoromethyl)Benzoyl Chloride

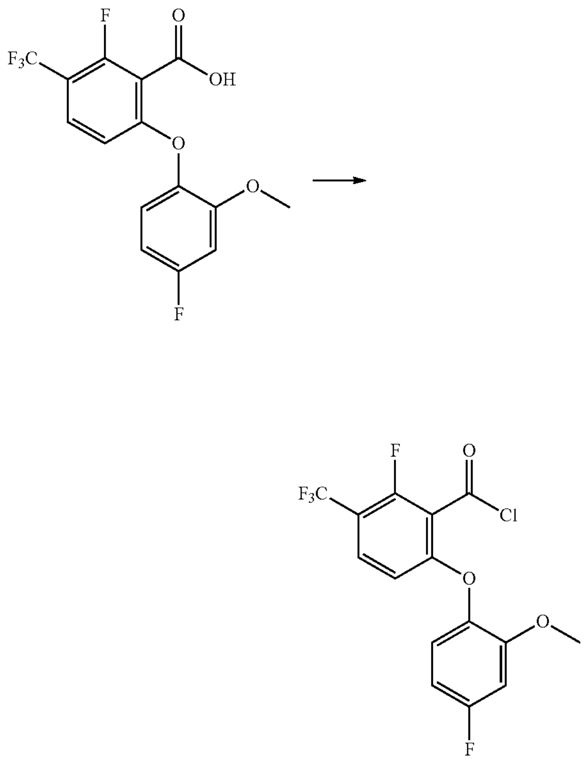

To a solution of 2-fluoro-6-(4-fluoro-2-methoxy-phenoxy)-3-(trifluoromethyl)benzoic acid (700 mg, 1.568 mmol) and DMF (34 μL, 0.4391 mmol) in DCM (6.5 mL) at 0° C. was added oxalyl chloride (1.1 mL, 12.61 mmol) dropwise under $N_2$ atmosphere. The ice bath was removed after 10 minutes and the reaction was stirred at RT for 50 minutes. The mixture was concentrated to dryness under reduced pressure to afford the crude 2-fluoro-6-(4-fluoro-2-methoxy-phenoxy)-3-(trifluoromethyl)benzoyl chloride. The intermediate was immediately used in the next step without purification.

Step 3: 4-[[2-Fluoro-6-(4-Fluoro-2-Methoxy-Phenoxy)-3-(Trifluoromethyl)Benzoyl]Amino]Pyridine-2-Carboxamide (103)

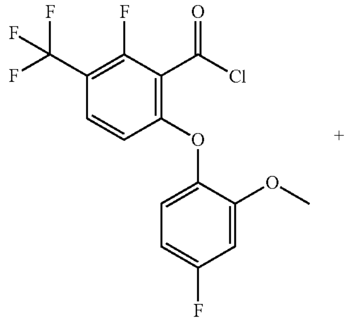

-continued

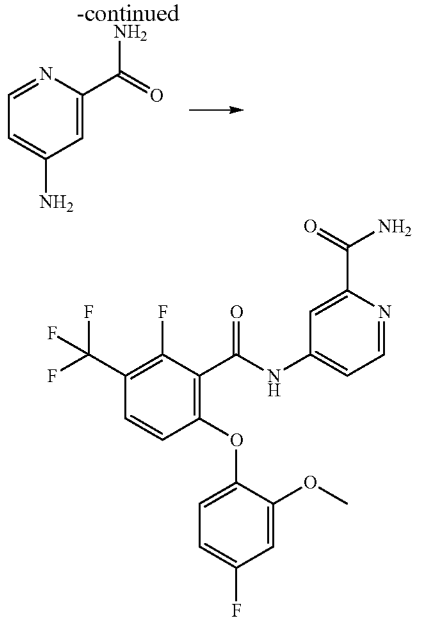

To a solution of 4-aminopyridine-2-carboxamide (13.46 mg, 0.09818 mmol), DMF (5.981 mg, 6.336 μL, 0.08182 mmol) and NMP (200 μL) was added DIEA (31.73 mg, 42.76 μL, 0.2455 mmol) under $N_2$ atmosphere and the resulting clear solution was cooled to 0° C. A solution of 2-fluoro-6-(4-fluoro-2-methoxy-phenoxy)-3-(trifluoromethyl)benzoyl chloride (30 mg, 0.08182 mmol) in NMP (200 μL) was added and the reaction was stirred at RT for 16 h. The mixture was filtered and purified by reverse phase HPLC (gradient of 10-99% acetonitrile in water containing HCl as a modifier) giving the desired product 4-[[2-fluoro-6-(4-fluoro-2-methoxy-phenoxy)-3-(trifluoromethyl)benzoyl]amino]pyridine-2-carboxamide (18.4 mg, 48%). ESI-MS m/z calc. 467.09045, found 468.0 $(M+1)^+$; Retention time (Method B): 1.73 minutes. $^1H$ NMR (400 MHz, DMSO-$d_6$) δ 11.47 (s, 1H), 8.57 (d, J=5.5 Hz, 1H), 8.34 (d, J=2.1 Hz, 1H), 8.14 (s, 1H), 7.86 (dd, J=5.5, 2.2 Hz, 1H), 7.80 (t, J=8.7 Hz, 1H), 7.76-7.65 (m, 1H), 7.34-7.08 (m, 2H), 6.88 (td, J=8.5, 2.8 Hz, 1H), 6.59 (dd, J=30.6, 8.9 Hz, 1H), 3.76 (d, J=2.2 Hz, 3H) ppm.

The compounds set forth in Table 8 were prepared by methods analogous to the preparation of compound 103 in example 12.

TABLE 8

Additional Compounds Prepared By Methods Analogous to Example 12.

| Cmpd No. | Compound Name | LC/MS | NMR (shifts in ppm) |
|---|---|---|---|
| 104 | 5-[[2-fluoro-6-(4-fluoro-2-methoxy-phenoxy)-3-(trifluoromethyl)benzoyl]amino]pyridine-2-carboxamide | ESI-MS m/z calc. 467.09045, found 468.0 (M + 1)+; Retention time (Method B): 1.72 minutes | |

Example 13

4-[[2-[2-(Trideuteriomethoxy)-4-(Trifluoromethoxy)Phenoxy]-5-(Trifluoromethyl)Benzoyl]Amino]Pyridine-2-Carboxamide (105)

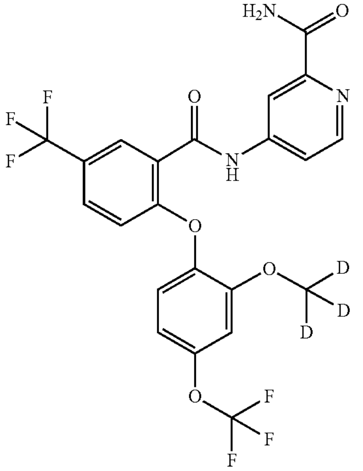

Step 1: 2-[2-(Trideuteriomethoxy)-4-(Trifluoromethoxy)Phenoxy]-5-(Trifluoromethyl)Benzaldehyde

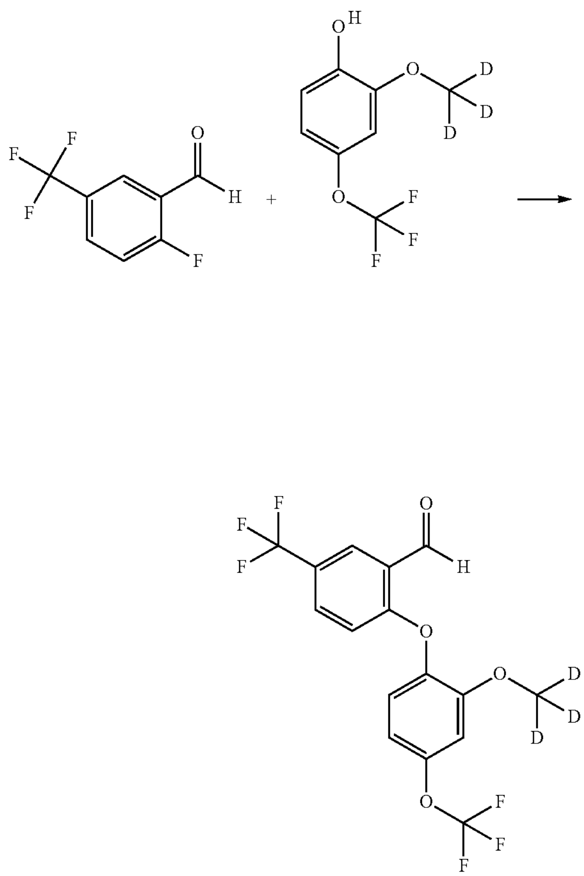

To a stirring solution of 2-fluoro-5-(trifluoromethyl)benzaldehyde (5.02 g, 26.13 mmol) in DMF (50 mL) in an ice bath was added $Cs_2CO_3$ (10.68 g, 32.78 mmol) and 2-(trideuteriomethoxy)-4-(trifluoromethoxy)phenol (6.50 g, 30.78 mmol). The reaction mixture was warmed to RT then stirred for 16 h. The reaction mixture was partitioned between ethyl acetate and water. The organic layer was washed with water, 50% saturated aqueous $NaHCO_3$ and brine, then dried over $MgSO_4$, filtered and concentrated in vacuo. Silica gel chromatography (220 g silica, 0-30% ethyl acetate/hexane) provided 2-[2-(trideuteriomethoxy)-4-(trifluoromethoxy)phenoxy]-5-(trifluoromethyl)benzaldehyde (8.84 g, 88%). ESI-MS m/z calc. 383.06717, found 384.0 $(M+1)^+$; Retention time (Method A): 0.81 minutes. $^1H$ NMR (500 MHz, DMSO-d6) δ 10.50 (s, 1H), 8.06 (s, 1H), 7.92 (dd, J=8.9, 2.4 Hz, 1H), 7.44 (d, J=8.7 Hz, 1H), 7.29 (d, J=2.5 Hz, 1H), 7.07 (d, J=8.7 Hz, 1H), 6.88 (d, J=8.8 Hz, 1H) ppm.

Step 2: 2-[2-(Trideuteriomethoxy)-4-(Trifluoromethoxy)Phenoxy]-5-(Trifluoromethyl)Benzoic Acid

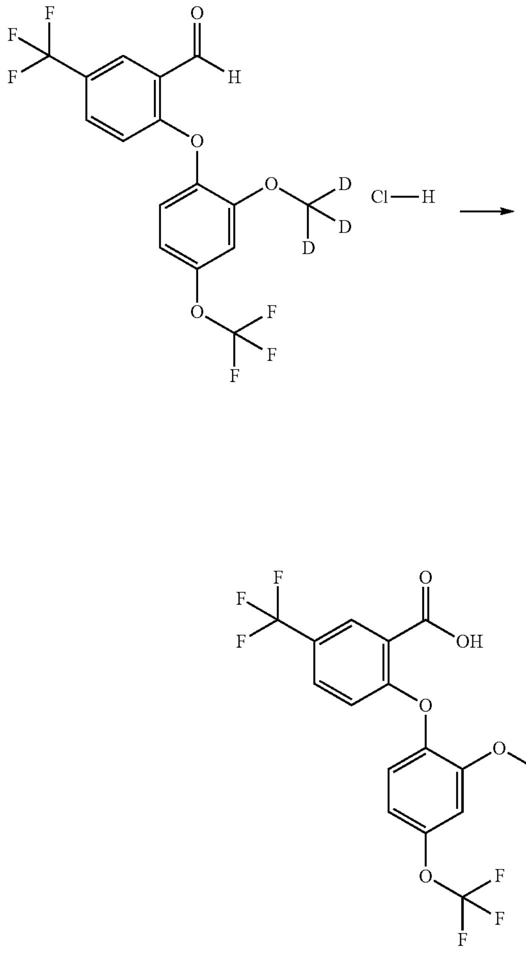

A mixture of 2-[2-(trideuteriomethoxy)-4-(trifluoromethoxy)phenoxy]-5-(trifluoromethyl)benzaldehyde (8.84 g, 23.07 mmol) and $NaH_2PO_4$ (2.92 g, 24.34 mmol) in tert-butyl alcohol (80 mL)/water (40 mL)/acetonitrile (40 mL) was cooled in an ice bath then 2-methy-2-butene (11 mL, 103.8 mmol) was added. Sodium chlorite (3.12 g, 27.60 mmol) was then added portion wise over 10 minutes. The mixture was allowed to warm to RT then stirred for 16 h. The reaction mixture was acidified to pH 1-2 using aqueous HCl (8 mL of 12 M, 96.00 mmol), and partitioned with ethyl acetate. The organic layer was separated, dried over $MgSO_4$ and concentrated in vacuo to afford 2-[2-(trideuterimethoxy)-4-(trifluoromethoxy)phenoxy]-5-(trifluoromethyl)benzoic acid (7.55 g, 82%) as a white solid. ESI-MS m/z calc. 399.06207, found 400.1 $(M+1)^+$; Retention time (Method A): 0.72 minutes. $^1H$ NMR (400 MHz, DMSO-d6) δ 13.38 (s, 1H), 8.07 (d, J=2.4 Hz, 1H), 7.81 (dd, J=8.9, 2.4 Hz, 1H), 7.28-7.20 (m, 2H), 7.01 (dd, J=8.9, 1.7 Hz, 1H), 6.83 (d, J=8.7 Hz, 1H) ppm.

Step 3: 2-[2-(Trideuteriomethoxy)-4-(Trifluoromethoxy)Phenoxy]-5-(Trifluoromethyl)Benzoyl Chloride

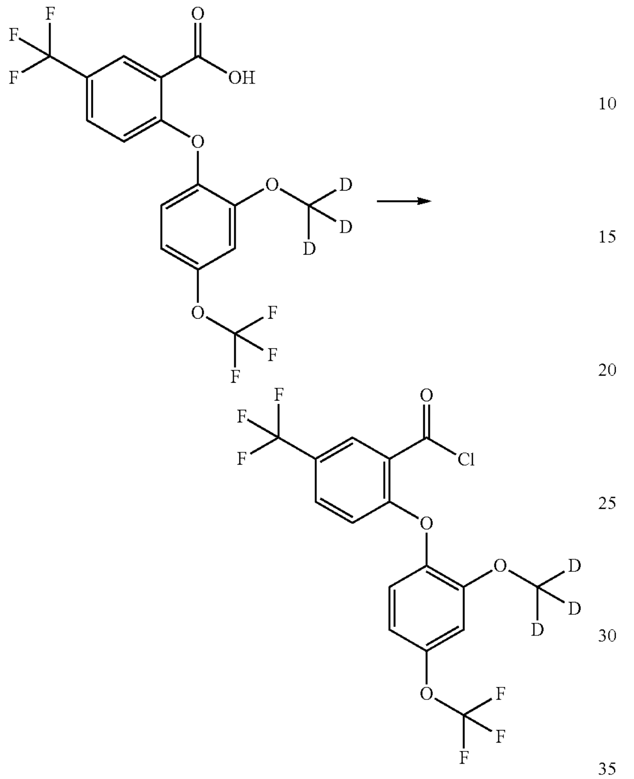

To 2-[2-(trideuteriomethoxy)-4-(trifluoromethoxy)phenoxy]-5-(trifluoromethyl)benzoic acid (1.5 g, 3.757 mmol) and DMF (10 μL, 0.1291 mmol) in DCM (12 mL) at 0° C. was added oxalyl chloride (492 μL, 5.640 mmol) dropwise under $N_2$ atmosphere. The ice bath was removed after 10 minutes and the reaction was stirred at RT for 1.5 h. The solvent was evaporated under reduced pressure to afford 2-[2-(trideuteriomethoxy)-4-(trifluoromethoxy)phenoxy]-5-(trifluoromethyl)benzoyl chloride. The intermediate was used in the next step without further purification.

Step 4: 4-[[2-[2-(Trideuteriomethoxy)-4-(Trifluoromethoxy)Phenoxy]-5-(Trifluoromethyl)Benzoyl]Amino]Pyridine-2-Carboxamide(105)

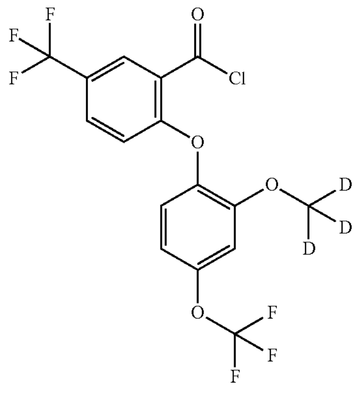

+

-continued

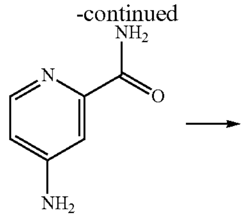

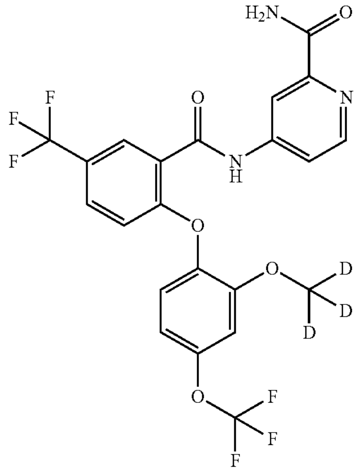 [SMILES: [2H]C([2H])([2H])Oc1cc(OC(F)(F)F)ccc1Oc1ccc(C(F)(F)F)cc1C(=O)Nc1ccnc(C(N)=O)c1]

2-[2-(trideuteriomethoxy)-4-(trifluoromethoxy)phenoxy]-5-(trifluoromethyl)benzoyl chloride (50 mg, 0.1197 mmol) in NMP (0.3 mL) was added to a mixture of 4-aminopyridine-2-carboxamide (16.42 mg, 0.1197 mmol) and DIEA (15.47 mg, 20.85 μL, 0.1197 mmol) in NMP (0.3 mL), and the reaction was stirred at RT for 2 h. The crude was filtered and purified by reverse phase HPLC (gradient of 10-99% acetonitrile in water containing HCl as a modifier) to give 4-[[2-[2-(trideuteriomethoxy)-4-(trifluoromethoxy)phenoxy]-5-(trifluoromethyl)benzoyl]amino]pyridine-2-carboxamide (34.70 mg, 56%). ESI-MS m/z calc. 518.1104, found 519.32 $(M+1)^+$; Retention time (Method B): 1.84 minutes.

The compounds set forth in Table 9 were prepared by methods analogous to the preparation of compound 105 in Example 13.

TABLE 9

| Additional Compounds Prepared By Methods Analogous to Example 13. | | | |
|---|---|---|---|
| Cmpd No. | Compound Name | LC/MS | NMR (shifts in ppm) |
| 106 | 5-[[2-[2-(trideuteriomethoxy)-4-(trifluoromethoxy)phenoxy]-5-(trifluoromethyl)benzoyl]amino]pyridine-2-carboxamide | ESI-MS m/z calc. 518.1104, found 519.32 (M + 1)+; Retention time (Method B): 1.83 minutes | 1H NMR (400 MHz, DMSO-d6) δ 10.95 (s, 1H), 8.91 (s, 1H), 8.29 (d, J = 10.8 Hz, 1H), 8.04 (s, 3H), 7.81 (d, J = 10.9 Hz, 1H), 7.55 (s, 1H), 7.39 (d, J = 8.8 Hz, 1H), 7.24 (s, 1H), 7.05 (d, J = 8.8 Hz, 1H), 6.89 (d, J = 8.7 Hz, 1H). |

Example 14

4-[[2-(3-Chloro-4-Fluoro-Phenoxy)-4-(Trifluoromethyl)Benzoyl]Amino]Pyridine-2-Carboxamide (107)

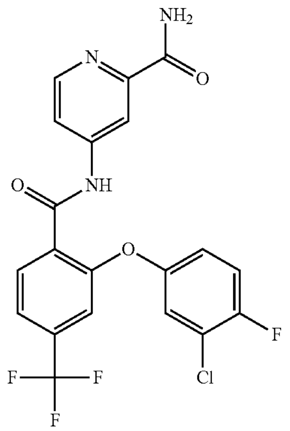 [SMILES: NC(=O)c1cc(NC(=O)c2ccc(C(F)(F)F)cc2Oc2ccc(F)c(Cl)c2)ccn1]

Step 1: 4-[[2-Bromo-4-(Trifluoromethyl)Benzoyl]Amino]Pyridine-2-Carboxamide

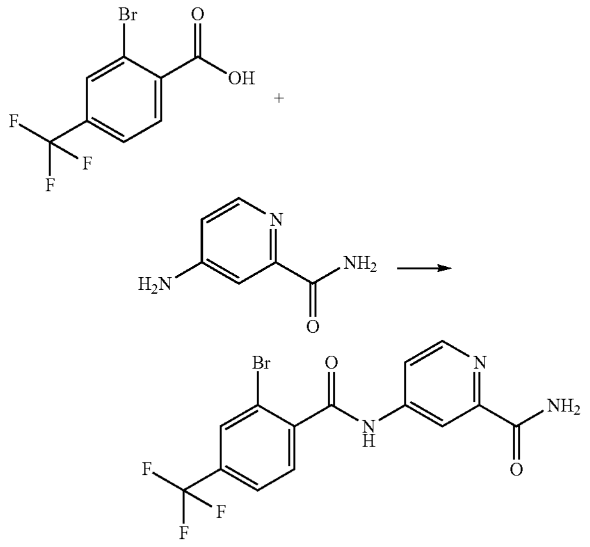

To a solution of 2-bromo-4-(trifluoromethyl)benzoic acid (1 g, 3.7173 mmol) and 4-aminopyridine-2-carboxamide (510 mg, 3.7189 mmol) in pyridine (30 mL) was added $POCl_3$ (575.75 mg, 0.350 mL, 3.7549 mmol) at −25° C. and stirred for 30 minutes at this temperature. The reaction was quenched by addition of water (20 mL) then extracted with ethyl acetate (100x2). The organics were washed with water (3x30 mL), brine, dried over $MgSO_4$, filtered then concentrated in vacuo to provide a 4-[[2-bromo-4-(trifluoromethyl)benzoyl]amino]pyridine-2-carboxamide. ESI-MS m/z calc. 386.983, found 388.6 $(M+1)^+$; Retention time (Method H): 4.18 minutes. Used directly in the next step without further purification.

Step 2: 4-[[2-(3-Chloro-4-Fluoro-Phenoxy)-4-(Trifluoromethyl)Benzoyl]Amino]Pyridine-2-Carboxamide (107)

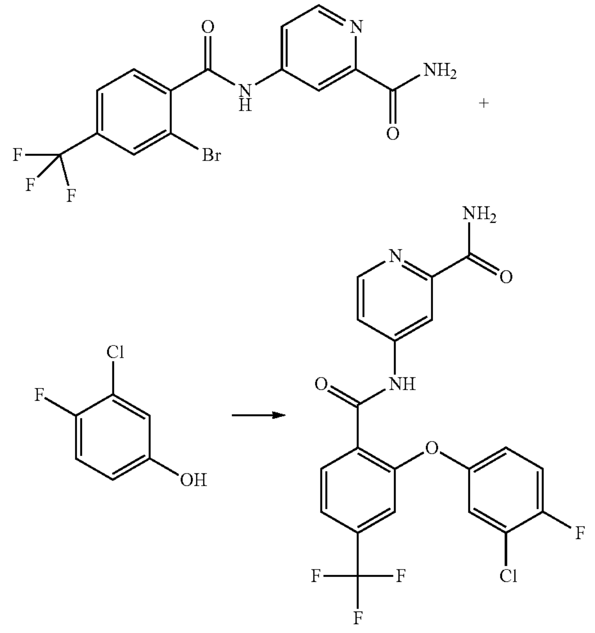 [SMILES: NC(=O)c1cc(NC(=O)c2ccc(C(F)(F)F)cc2Br)ccn1 ; Oc1ccc(F)c(Cl)c1 ; NC(=O)c1cc(NC(=O)c2ccc(C(F)(F)F)cc2Oc2ccc(F)c(Cl)c2)ccn1]

To a mixture of 4-[[2-bromo-4-(trifluoromethyl)benzoyl]amino]pyridine-2-carboxamide (25 mg, 0.06441 mmol), 3-chloro-4-fluoro-phenol (9.439 mg, 0.06441 mmol), $Cs_2CO_3$ (41.97 mg, 0.1288 mmol), CuI (7.361 mg, 0.03865 mmol), CsF (48.91 mg, 11.89 μL, 0.3220 mmol), and DMF (500.0 μL), was stirred at 150° C. for 1 h. The reaction was diluted with DMSO (500 uL), filtered, and purified by reverse phase HPLC (gradient of 10-99% acetonitrile in water containing HCl as a modifier) to give 4-[[2-(3-chloro- 4-fluoro-phenoxy)-4-(trifluoromethyl)benzoyl]amino]pyridine-2-carboxamide (11.9 mg, 39%) as a white solid. ESI-MS m/z calc. 453.05032, found 453.9 $(M+1)^+$; Retention time (Method B): 1.68 minutes. $^1H$ NMR (400 MHz, DMSO-d6) δ 11.11 (s, 1H), 8.53 (d, J=5.5 Hz, 1H), 8.30 (d, J=2.1 Hz, 1H), 8.10 (d, J=2.7 Hz, 1H), 8.02-7.88 (m, 1H), 7.82 (dd, J=5.5, 2.2 Hz, 1H), 7.74-7.68 (m, 1H), 7.66 (d, J=2.7 Hz, 1H), 7.52-7.40 (m, 2H), 7.36 (d, J=1.6 Hz, 1H), 7.17 (ddd, J=9.1, 3.9, 3.0 Hz, 1H) ppm.

The compounds set forth in Table 10 were prepared by methods analogous to the preparation of compound 107 in Example 13

TABLE 10

Additional Compounds Prepared By Methods Analogous to Example 13.

| Cmpd No. | Compound Name | LC/MS | NMR (shifts in ppm) |
|---|---|---|---|
| 108 | 4-[[2-(3-chloro-4-isopropoxy-phenoxy)-4-(trifluoromethyl)benzoyl]amino]pyridine-2-carboxamide | ESI-MS m/z calc. 493.10162, found 494.29 (M + 1)+; Retention time (Method B): 1.66 minutes | |
| 109 | 4-[[2-[4-(cyclohexoxy)phenoxy]-4-(trifluoromethyl)benzoyl]amino]pyridine-2-carboxamide | ESI-MS m/z calc. 499.1719, found 500.39 (M + 1)+; Retention time (Method B): 1.97 minutes | $^1H$ NMR (400 MHz, DMSO-$d_6$) δ 11.09 (s, 1H), 8.53 (d, J = 5.5 Hz, 1H), 8.32 (d, J = 2.1 Hz, 1H), 8.10 (d, J = 2.9 Hz, 1H), 7.90-7.82 (m, 2H), 7.66 (d, J = 2.9 Hz, 1H), 7.62-7.56 (m, 1H), 7.15-7.04 (m, 3H), 7.04-6.95 (m, 2H), 4.28 (dt, J = 8.4, 4.6 Hz, 1H), 1.90 (d, J = 10.9 Hz, 2H), 1.71 (s, 2H), 1.53 (d, J = 12.1 Hz, 1H), 1.42-1.23 (m, 5H). |
| 110 | 4-[[2-(3-cyclohexylphenoxy)-4-(trifluoromethyl)benzoyl]amino]pyridine-2-carboxamide | ESI-MS m/z calc. 483.17697, found 484.39 (M + 1)+; Retention time (Method B): 2.03 minutes | $^1H$ NMR (400 MHz, DMSO-$d_6$) δ 11.09 (s, 1H), 8.51 (d, J = 5.5 Hz, 1H), 8.29 (d, J = 2.1 Hz, 1H), 8.09 (s, 1H), 7.90 (d, J = 7.9 Hz, 1H), 7.82 (dd, J = 5.7, 2.2 Hz, 1H), 7.66 (d, J = 7.7 Hz, 2H), 7.31 (t, J = 7.9 Hz, 1H), 7.24 (s, 1H), 7.04 (d, J = 7.7 Hz, 1H), 6.97 (d, J = 2.5 Hz, 1H), 6.88 (dd, J = 8.2, 2.4 Hz, 1H), 2.49-2.39 (m, 1H), 1.77-1.61 (m, 5H), 1.37-1.13 (m, 5H). |
| 111 | 4-[[2-(2,4-difluorophenoxy)-4-(trifluoromethyl)benzoyl]amino]pyridine-2-carboxamide | ESI-MS m/z calc. 437.0799, found 436.3 (M + 1)+; Retention time (Method B): 1.27 minutes | $^1H$ NMR (400 MHz, DMSO-$d_6$) δ 11.27 (s, 1H), 8.71 (s, 1H), 8.29-8.13 (m, 3H), 7.96 (d, J = 1.5 Hz, 1H), 7.75 (s, 1H), 7.44 (s, 1H), 7.29 (s, 1H), 6.95 (s, 1H), 6.81 (td, J = 8.6, 2.9 Hz, 1H), 6.66 (s, 1H). |
| 112 | 4-[[2-[2-(1,1-difluoroethyl)-4-fluoro-phenoxy]-4-(trifluoromethyl)benzoyl]amino]pyridine-2-carboxamide | ESI-MS m/z calc. 483.10175, found 484.0 (M + 1)+; Retention time (Method B): 1.71 minutes | $^1H$ NMR (400 MHz, DMSO-d6) δ 11.12 (s, 1H), 8.53 (d, J = 5.4 Hz, 1H), 8.32 (s, 1H), 8.08 (s, 1H), 7.94 (d, J = 8.0 Hz, 1H), 7.83 (s, 1H), 7.71-7.63 (m, 2H), 7.44 (d, J = 8.6 Hz, 2H), 7.15 (s, 1H), 2.02-1.90 (m, 2H). |
| 113 | 4-[[2-(4-fluoro-2-methyl-phenoxy)-4-(trifluoromethyl)benzoyl]amino]pyridine-2-carboxamide | ESI-MS m/z calc. 433.10495, found 433.9 (M + 1)+; Retention time (Method B): 1.68 minutes | $^1H$ NMR (500 MHz, DMSO-d6) δ 11.12 (d, J = 2.7 Hz, 1H), 8.54 (d, J = 5.5 Hz, 1H), 8.33 (d, J = 2.2 Hz, 1H), 8.10 (d, J = 2.9 Hz, 1H), 7.91 (d, J = 7.9 Hz, 1H), 7.85 (dd, J = 5.4, 2.2 Hz, 1H), 7.70-7.59 (m, 2H), 7.24-7.18 (m, 1H), 7.15-7.07 (m, 2H), 6.99 (d, J = 1.7 Hz, 1H), 2.16 (s, 3H) |

Example 15

4-[[2,2-Difluoro-5-[2-(Trideuteriomethoxy)-4-(Trifluoromethoxy)Phenoxy]-1,3-Benzodioxole-4-Carbonyl]Amino]Pyridine-2-Carboxamide (114)

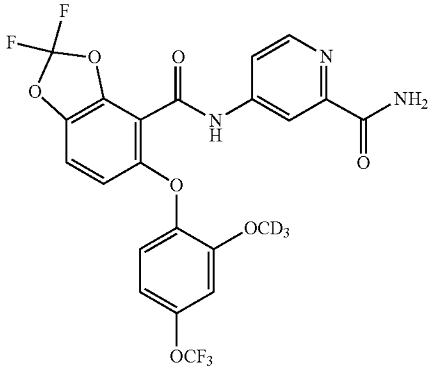

Step 1: 5-Bromo-2,2-Difluoro-1,3-Benzodioxole-4-Carboxylic Acid

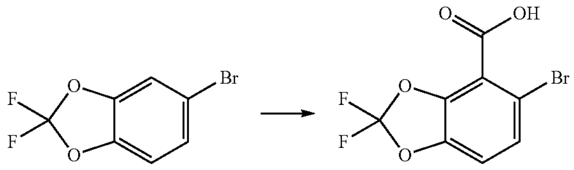 [SMILES: FC1(F)Oc2ccc(Br)cc2O1 ; O=C(O)c1c(Br)ccc2c1OC(F)(F)O2]

To a solution of 2, 2, 6, 6-tetramethylpiperidine (12.03 g, 14.5 mL, 85.20 mmol) in THF (170 mL) was added n-butyl lithium in hexanes (33.5 mL of 2.5 M, 83.75 mmol) at 0° C. and the mixture was stirred at this temperature for 30 minutes, then cooled to −78° C. and stirred for 30 minutes. To a −78° C. solution of 5-bromo-2,2-difluoro-1,3-benzodioxole (20 g, 84.389 mmol) in THF (30 mL) was added the previously prepared LiTMP via cannula at −78° C. over 25 minutes. The reaction was stirred at this temperature for 25 minutes, then the reaction mixture was transferred, using the same cannula, into a wide mouthed flask containing crushed $CO_2$ (200.00 g, 4.54 mol) and stirred gently. Then, the reaction was slowly warmed to room temperature over 12 h. The reaction was diluted with NaOH (1M, 950 mL), washed with $Et_2O$ (3×650 mL), and the aqueous phase was acidified at 0° C. with HCl (6 M, until pH=1, gas evolved) and extracted with $Et_2O$ (3×750 mL), dried over $MgSO_4$, then filtered and concentrated under reduced pressure to provide pure 5-bromo-2,2-difluoro-1,3-benzodioxole-4-carboxylic acid (19.27 g, 81%). $^1H$ NMR (500 MHz, DMSO-d6) δ 7.58 (d, J=9 Hz, 1H), 7.51 (d, J=9 Hz, 1H) ppm. ESI-MS m/z calc. 279.9183, found 281.1 $(M+1)^+$; Retention time: 1.87 minutes. LCMS Method: Water Cortex 2.7u $C_{18}$ (3.0 mm×50 mm), Temp: 55c; Flow: 1.2 mL/min; MP: 100% water with 0.1% trifluoroacetic (TFA) acid then 100% acetonitrile with 0.10% TFA acid, grad:5% to 100% B over 4 min, with stay at 100% B for 0.5 min, equilibration to 5% B over 1.5 min.

Step 2: 2,2-Difluoro-5-[2-(Trideuteriomethoxy)-4-(Trifluoromethoxy)Phenoxy]-1,3-Benzodioxole-4-Carboxylic Acid

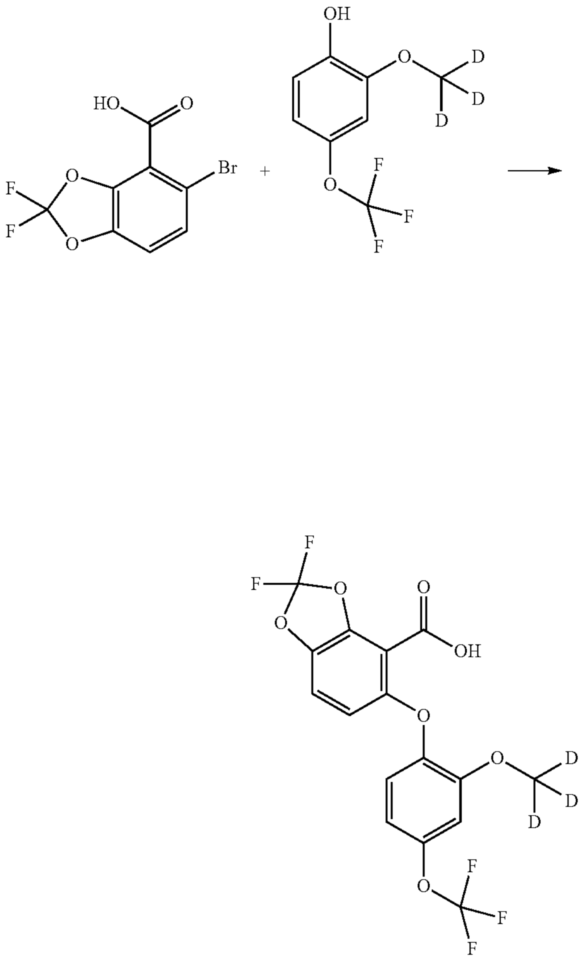

A solution of 5-bromo-2,2-difluoro-1,3-benzodioxole-4-carboxylic acid (2 g, 7.117 mmol), 2-(trideuteriomethoxy)-4-(trifluoromethoxy)phenol (1.52 g, 7.199 mmol), $Cs_2CO_3$ (2.38 g, 7.305 mmol) in toluene (15 mL) was bubbled with $N_2$ for 10 minutes, then CuI (286 mg, 1.502 mmol) added. The flask was flushed with $N_2$, capped, and heated at 100° C. with vigorous stirring for 7 h. The mixture was allowed to cool then diluted with ethyl acetate and 50 mL water. The two layers were separated. The organic layer contained some product. The water layer was acidified with HCl (30 mL of 1 M, 30.00 mmol) and the product was extracted into ethyl acetate (×3). The combined organic layer was washed with brine (×2), dried over $Na_2SO_4$, filtered through a plug of celite and concentrated. The crude product was purified on silica gel (gradient of 0-50% ethyl acetate in hexane). The product was titurated with hexane to yield 2,2-difluoro-5-[2-(trideuteriomethoxy)-4-(trifluoromethoxy)phenoxy]-1,3-benzodioxole-4-carboxylic acid (1.1206 g, 38%) as a light brown solid. ESI-MS m/z calc. 411.0457, found 412.2 $(M+1)^+$; Retention time (Method C): 2.48 minutes (5 minutes run).

Step 3: 2,2-Difluoro-5-[2-(Trideuteriomethoxy)-4-(Trifluoromethoxy)Phenoxy]-1,3-Benzodioxole-4-Carbonyl Chloride

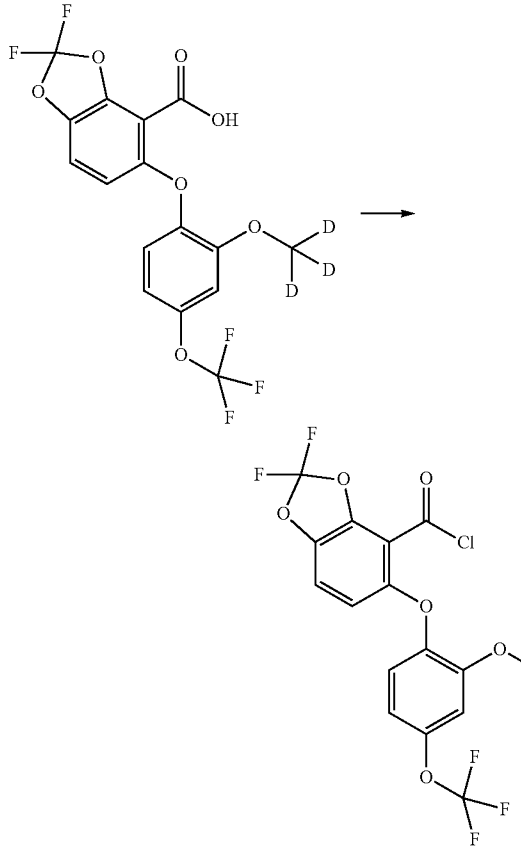

To a slurry of 2,2-difluoro-5-[2-(trideuteriomethoxy)-4-(trifluoromethoxy)phenoxy]-1,3-benzodioxole-4-carboxylic acid (300 mg, 0.7295 mmol) and DMF (15 μL, 0.1937 mmol) in DCM (2.5 mL) at 0° C. was added oxalyl chloride (192 μL, 2.201 mmol) dropwise under $N_2$ atmosphere. The ice bath was removed after 10 minutes and the reaction was stirred at RT for 1.5 h. The solvent was evaporated under reduced pressure to afford 2,2-difluoro-5-[2-(trideuteriomethoxy)-4-(trifluoromethoxy)phenoxy]-1,3-benzodioxole-4-carbonyl chloride. The intermediate was used in the next step without further purification. ESI-MS m/z calc. 478.12427, found 479.2 $(M+1)^+$; Retention time (Method A): 0.77 minutes.

Step 4: 4-[[2,2-Difluoro-5-[2-(Trideuteriomethoxy)-4-(Trifluoromethoxy)Phenoxy]-1,3-Benzodioxole-4-Carbonyl]Amino]Pyridine-2-Carboxamide (114)

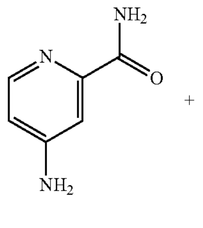

-continued

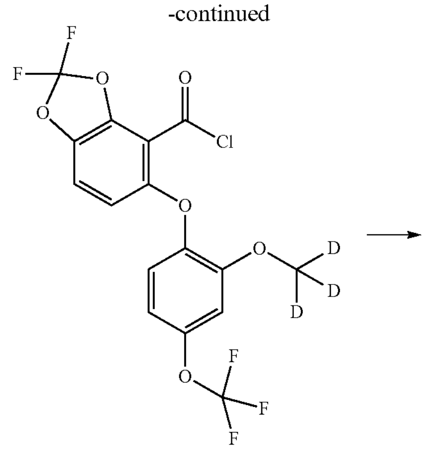

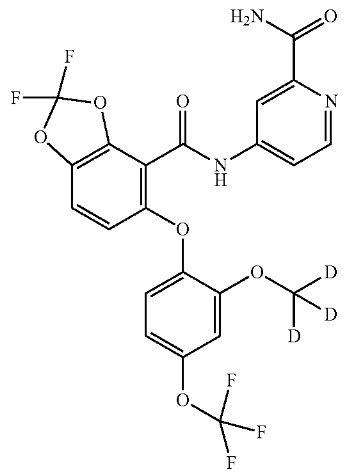

To 4-aminopyridine-2-carboxamide (22.97 mg, 0.1675 mmol) in NMP (500 μL), and DIEA (54.13 mg, 72.95 μL, 0.4188 mmol) at 0° C. was added a solution of 2,2-difluoro-5-[2-(trideuteriomethoxy)-4-(trifluoromethoxy)phenoxy]-1,3-benzodioxole-4-carbonyl chloride (60 mg, 0.1396 mmol) in NMP (200 μL) slowly. The mixture was stirred at RT for 16 h. The crude product was filtered and purified by reverse phase HPLC (gradient of 10-99% acetonitrile in water containing HCl as a modifier) to yield 4-[[2,2-difluoro-5-[2-(trideuteriomethoxy)-4-(trifluoromethoxy)phenoxy]-1,3-benzodioxole-4-carbonyl]amino]pyridine-2-carboxamide (24.0 mg, 32%). ESI-MS m/z calc. 530.094, found 530.96 $(M+1)^+$; Retention time (Method B): 1.85 minutes. $^1H$ NMR (400 MHz, DMSO-$d_6$) δ 11.32 (s, 1H), 8.55 (d, J=5.5 Hz, 1H), 8.27 (d, J=2.1 Hz, 1H), 8.12 (d, J=2.9 Hz, 1H), 7.82 (dd, J=5.6, 2.1 Hz, 1H), 7.68 (s, 1H), 7.50 (d, J=8.9 Hz, 1H), 7.20 (d, J=8.8 Hz, 1H), 7.15 (d, J=2.7 Hz, 1H), 6.96 (d, J=9.1 Hz, 1H), 6.67 (d, J=8.9 Hz, 1H) ppm.

The compounds set forth in Table 11 were prepared by methods analogous to the preparation of compound 114.

TABLE 11

| Additional Compounds Prepared By Methods Analogous to Example 15. | | | |
|---|---|---|---|
| Cmpd No. | Compound Name | LC/MS | NMR (shifts in ppm) |
| 115 | 5-[[2,2-difluoro-5-[2-(trideuteriomethoxy)-4-(trifluoromethoxy)phenoxy]-1,3-benzodioxole-4-carbonyl]amino]pyridine-2-carboxamide | ESI-MS m/z calc. 530.094, found 530.91 (M + 1)+; Retention time (Method B): 1.87 minutes | $^1$H NMR (400 MHz, DMSO-$d_6$) δ 11.26 (s, 1H), 8.84 (d, J = 2.4 Hz, 1H), 8.22 (dd, J = 8.6, 2.5 Hz, 1H), 8.08-8.01 (m, 2H), 7.59 (s, 1H), 7.50 (d, J = 8.9 Hz, 1H), 7.19 (d, J = 8.8 Hz, 1H), 7.15 (d, J = 2.7 Hz, 1H), 6.96 (d, J = 7.4 Hz, 1H), 6.69 (d, J = 8.9 Hz, 1H). |

Example 16

5-[[2-Methyl-6-[2-(Trideuteriomethoxy)-4-(Trifluoromethoxy)Phenoxy]-3-(Trifluoromethyl)Benzoyl]Amino]Pyridine-2-Carboxamide (116)

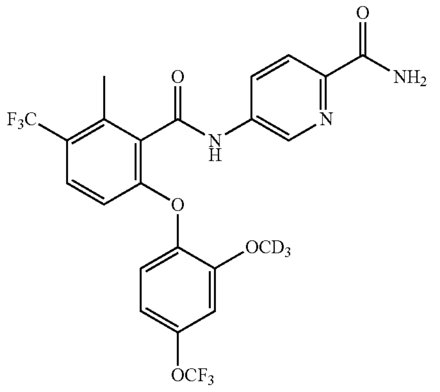

Step 1: 2-Bromo-6-Fluoro-3-(Trifluoromethyl)Benzoic Acid

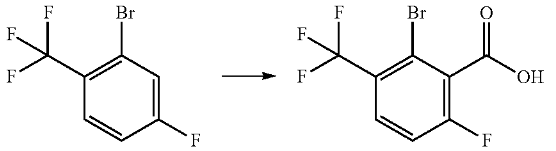 [SMILES: Fc1ccc(C(F)(F)F)c(Br)c1 ; O=C(O)c1c(F)ccc(C(F)(F)F)c1Br]

To a stirred solution of 2-bromo-4-fluoro-1-(trifluoromethyl)benzene (17.004 g, 10 mL, 67.877 mmol) in anhydrous THF (600 mL) was added LDA (37 mL of 2.0 M, 74.000 mmol) drop-wise over 15 minutes at −78° C. The reaction mixture was stirred at this temperature for 2 h. The resulting yellow solution was then transferred via cannula onto crushed $CO_2$ and the resulting emulsion was stirred gently for 17 h. The solvent was evaporated in vacuo and the slurry was taken up in NaOH solution (500 mL, 1M) and extracted once with diethyl ether (500 mL). The aqueous layer was acidified to pH=1 and then extracted with diethyl ether (3×500 mL). The combined organic layer was washed with brine (200 mL), dried over $Na_2SO_4$, filtered, and concentrated under reduced pressure to give 2-bromo-6-fluoro-3-(trifluoromethyl)benzoic acid (16.3 g, 79%) as an off-white solid. ESI-MS m/z calc. 285.9253, found 287.1 $(M+1)^+$; Retention time: 1.84 minutes. $^1$H NMR (500 MHz, DMSO-d6) δ 8.01 (dd, J=8.9, 5.6 Hz, 1H), 7.63 (t, J=8.6 Hz, 1H) ppm.

LCMS Method: Water Cortex 2.7u $C_{18}$ (3.0 mm×50 mm), Temp: 55c; Flow: 1.2 mL/minutes; MP: 100% water with 0.1% trifluoroacetic (TFA) acid then 100% acetonitrile with 0.1% TFA acid, grad:5% to 100% B over 4 min, with stay at 100% B for 0.5 min, equilibration to 5% B over 1.5 min.

Step 2: Tert-Butyl 2-Bromo-6-Fluoro-3-(Trifluoromethyl)Benzoate

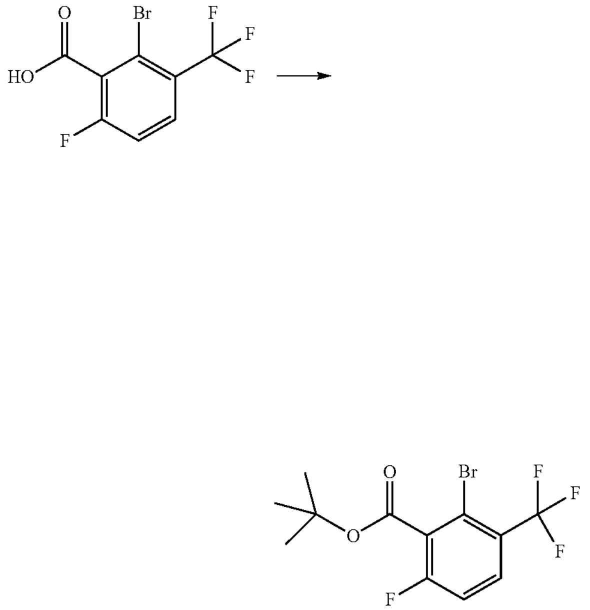

A stirring mixture of 2-bromo-6-fluoro-3-(trifluoromethyl)benzoic acid (8.0 g, 27.87 mmol), tert-butoxycarbonyl tert-butyl carbonate (9.1 g, 41.70 mmol), DMAP (680 mg, 5.566 mmol), and t-BuOH (8 mL) was heated at 90° C. for 1 hour. The reaction mixture cooled to RT and directly purified by silica gel column chromatography using a gradient of 1-10% EtOAc in Hexanes to give tert-butyl 2-bromo-6-fluoro-3-(trifluoromethyl)benzoate (8.1 g, 85%) as a white solid. ESI-MS m/z calc. 341.98785, found 344.8 $(M+1)^+$; Retention time (Method B): 2.02 minutes. $^1$H NMR (400 MHz, DMSO-d6) δ 8.03 (dd, J=9.0, 5.7 Hz, 1H), 7.64 (t, J=8.6 Hz, 1H), 1.58 (s, 9H) ppm.

Step 3: Tert-Butyl 2-Bromo-6-[2-(Trideuteriomethoxy)-4-(Trifluoromethoxy)Phenoxy]-3-(Trifluoromethyl)Benzoate

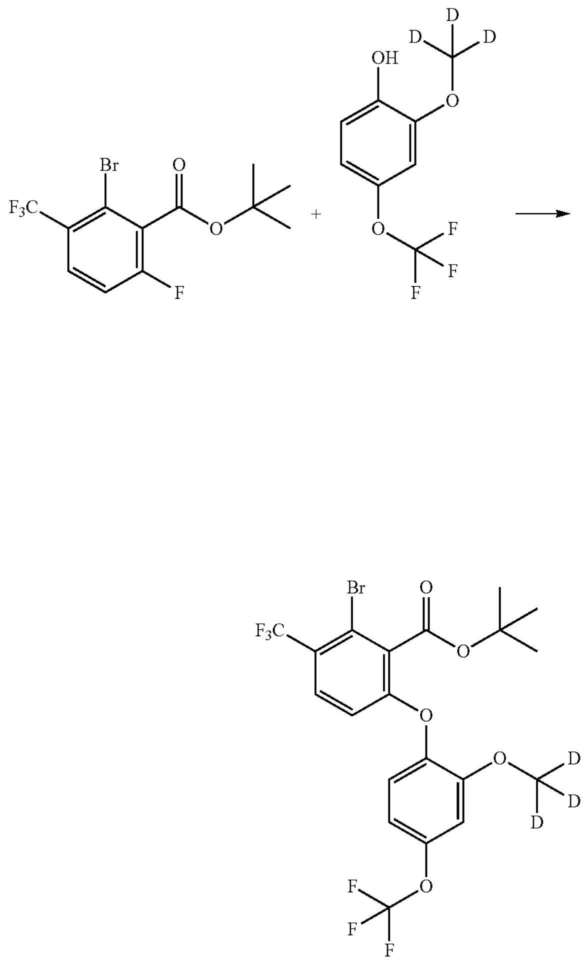

A mixture of tert-butyl 2-bromo-6-fluoro-3-(trifluoromethyl)benzoate (500 mg, 1.3115 mmol), 2-(trideuteriomethoxy)-4-(trifluoromethoxy)phenol (360.02 mg, 1.7050 mmol), and $K_2CO_3$ (362.51 mg, 2.6230 mmol) in DMSO (2 mL) was heated at 100° C. for 1 h. The reaction mixture was allowed to cool to RT, poured onto 50 mL of water and extracted with ethyl acetate (3×50 mL). The combined organic layer was washed with brine (50 mL), dried over $Na_2SO_4$, filtered and concentrated in vacuo to give crude tert-butyl 2-bromo-6-[2-(trideuteriomethoxy)-4-(trifluoromethoxy)phenoxy]-3-(trifluoromethyl)benzoate (800 mg, 103%) as a purple oil. ESI-MS m/z calc. 533.03516, found 534.3 $(M+1)^+$; Retention time: 4.39 minutes; LCMS Method: Merckmillipore Chromolith SpeedROD $C_{18}$ column (50×4.6 mm) and a dual gradient run from 5-100% mobile phase B over 6 minutes. Mobile phase A=water (0.1% $CF_3CO_2H$). Mobile phase B=acetonitrile (0.1% $CF_3CO_2H$); LCMS Method Detail: null.

Step 4: Tert-Butyl 2-Methyl-6-[2-(Trideuteriomethoxy)-4-(Trifluoromethoxy)Phenoxy]-3-(Trifluoromethyl)Benzoate

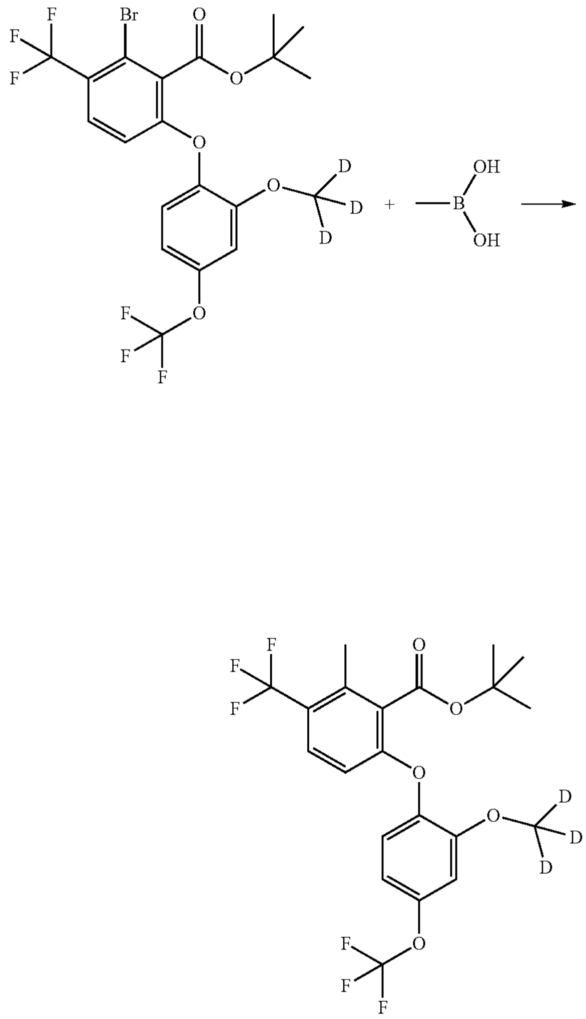

A mixture of tert-butyl 2-bromo-6-[2-(trideuteriomethoxy)-4-(trifluoromethoxy)phenoxy]-3-(trifluoromethyl)benzoate (1.6 g, 2.6953 mmol), methylboronic acid (1.06 g, 17.354 mmol), $K_2CO_3$ (1.2 g, 8.5090 mmol) and $Pd(dppf)_2Cl_2$ (200 mg, 0.2679 mmol) in dioxane (10 mL) and water (1 mL) was flushed with nitrogen, capped and heated at 120° C. for 30 minutes in microwave. The reaction mixture was allowed to cool to RT and diluted with water (50 mL) and extracted with ethyl acetate (3×50 mL). The combined organic layer was washed with brine, filtered, and concentrated in vacuo to give tert-butyl 2-methyl-6-[2-(trideuteriomethoxy)-4-(trifluoromethoxy)phenoxy]-3-(trifluoromethyl)benzoate (1.3 g, 98%) as a pale yellow solid which was used in next step without purification. ESI-MS m/z calc. 469.1403, found 470.5 $(M+1)^+$; Retention time: 4.42 minutes. LCMS Method: Merckmillipore Chromolith SpeedROD $C_{18}$ column (50×4.6 mm) and a dual gradient run from 5-100% mobile phase B over 6 minutes. Mobile phase A=water (0.1% $CF_3CO_2H$). Mobile phase B=acetonitrile (0.1% $CF_3CO_2H$).

Step 5: 2-Methyl-6-[2-(Trideuteriomethoxy)-4-(Trifluoromethoxy)Phenoxy]-3-(Trifluoromethyl)Benzoic Acid

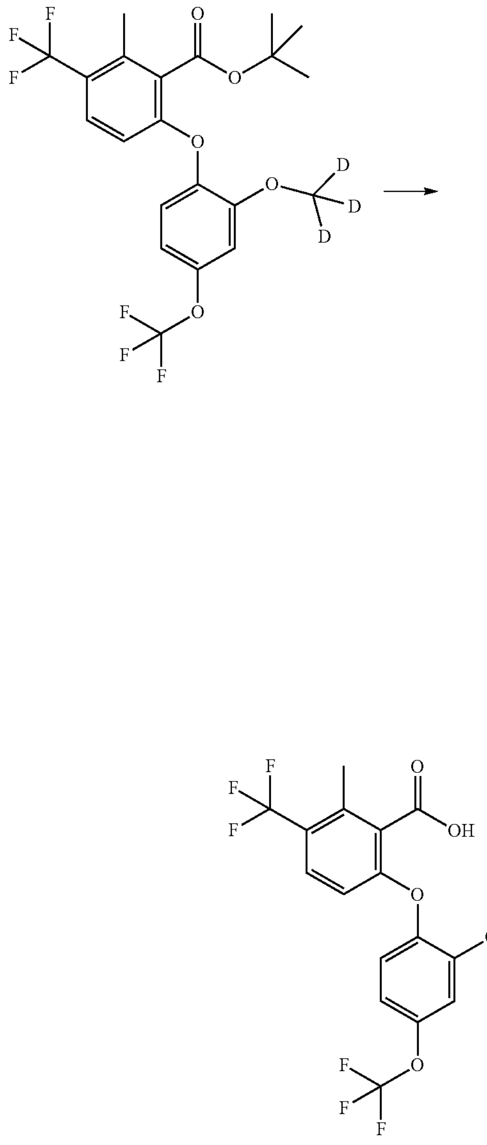

A solution of tert-butyl 2-methyl-6-[2-(trideuteriomethoxy)-4-(trifluoromethoxy)phenoxy]-3-(trifluoromethyl)benzoate (2.6 g, 4.4313 mmol) in THF (10 mL)/Water (5 mL) was added TFA (51.800 g, 35 mL, 454.29 mmol) and stirred at rt for 1 h. The reaction mixture was extracted with ether (3×100 mL). The combined organic layer was washed with 10% $NaHCO_3$ solution (50 mL), water (50 mL), brine (50 mL), dried over $Na_2SO_4$, filtered, and concentrated in vacuo. The resulting pale yellow oil was triturated with DCM (5 mL)/Hexanes (50 mL) and the resulting solid was filtered and dried in vacuo to give 2-methyl-6-[2-(trideuteriomethoxy)-4-(trifluoromethoxy)phenoxy]-3-(trifluoromethyl)benzoic acid (1.8 g, 93%) as a white solid. $^1H$ NMR (500 MHz, DMSO-d6) 7.64 (d, J=8.9 Hz, 1H), 7.26 (d, J=2.8 Hz, 1H), 7.21 (d, J=8.8 Hz, 1H), 7.01 (ddd, J=8.8, 2.8, 1.3 Hz, 1H), 6.59 (d, J=8.8 Hz, 1H), 2.40 (d, J=1.8 Hz, 3H) ppm.

Step 6: 5-[[2-Methyl-6-[2-(Trideuteriomethoxy)-4-(Trifluoromethoxy)Phenoxy]-3-(Trifluoromethyl)Benzoyl]Amino]Pyridine-2-Carboxamide (116)

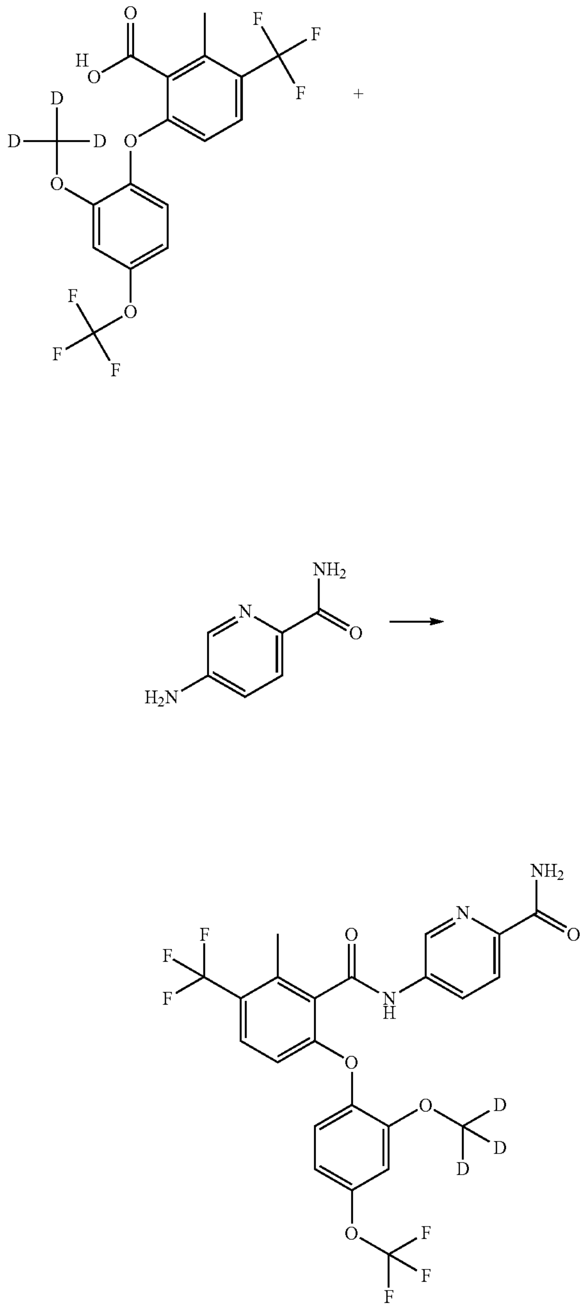

A solution of 2-methyl-6-[2-(trideuteriomethoxy)-4-(trifluoromethoxy)phenoxy]-3-(trifluoromethyl)benzoic acid (150 mg, 0.3629 mmol) and DMF (25 μL, 0.3229 mmol) were dissolved in DCM (3 mL). Oxalyl chloride (250 μL, 2.866 mmol) was slowly added dropwise to the reaction mixture at RT. After 1 h the reaction mixture was concentrated under vacuo to give 2-methyl-6-[2-(trideuteriomethoxy)-4-(trifluoromethoxy)phenoxy]-3-(trifluoromethyl)benzoyl chloride as an oil. This was dissolved in NMP (0.4 mL). This solution was slowly added to a prepared solution of 5-aminopyridine-2-carboxamide (19.91 mg, 0.1452 mmol) and DIEA (56.29 mg, 75.86 µL, 0.4355 mmol) in NMP (0.4 mL) at RT. The reaction mixture was allowed to stir overnight. The product was isolated by reverse-phase HPLC (gradient of 10-99% acetonitrile in water containing HCl as a modifier) to afford 5-[[2-methyl-6-[2-(trideuteriomethoxy)-4-(trifluoromethoxy)phenoxy]-3-(trifluoromethyl)benzoyl]amino]pyridine-2-carboxamide (28.2 mg, 73%). ESI-MS m/z calc. 532.1261, found 533.2 $(M+1)^+$; Retention time (Method B): 1.85 minutes. $^1$H NMR (400 MHz, DMSO-$d_6$) δ 11.18 (s, 1H), 8.90 (d, J=2.4 Hz, 1H), 8.34 (dd, J=8.6, 2.5 Hz, 1H), 8.08-8.01 (m, 2H), 7.72 (d, J=8.9 Hz, 1H), 7.57 (s, 1H), 7.31 (d, J=8.8 Hz, 1H), 7.24 (d, J=2.7 Hz, 1H), 7.07-6.95 (m, 1H), 6.64 (d, J=8.9 Hz, 1H), 2.46-2.41 (m, 3H) ppm.

The compounds set forth in Table 12 were prepared by methods analogous to the preparation of compound 116 in Example 16.

TABLE 12

Additional Compounds Prepared by Methods Analogous to Example 16.

| Cmpd No. | Compound Name | LC/MS | NMR (shifts in ppm) |
|---|---|---|---|
| 117 | 4-[[2-methyl-6-[2-(trideuteriomethoxy)-4-(trifluoromethoxy)phenoxy]-3-(trifluoromethyl)benzoyl]amino]pyridine-2-carboxamide | ESI-MS m/z calc. 532.1261, found 533.2 (M + 1)+; Retention time (Method C): 1.84 minutes | $^1$H NMR (400 MHz, DMSO-$d_6$) δ 11.28 (s, 1H), 8.55 (d, J = 5.5 Hz, 1H), 8.38 (d, J = 2.1 Hz, 1H), 8.12 (s, 1H), 7.87 (dd, J = 5.6, 2.1 Hz, 1H), 7.72 (d, J = 8.9 Hz, 1H), 7.67 (d, J = 2.9 Hz, 1H), 7.31 (d, J = 8.8 Hz, 1H), 7.24 (d, J = 2.7 Hz, 1H), 7.04 (d, J = 10.0 Hz, 1H), 6.64 (d, J = 8.8 Hz, 1H), 2.43 (s, 3H). |

Example 17

5-[[6-(3,4-Difluoro-2-Methoxy-Phenoxy)-2-Fluoro-3-(Trifluoromethyl)Benzoyl]Amino]Pyridine-2-Carboxamide (118)

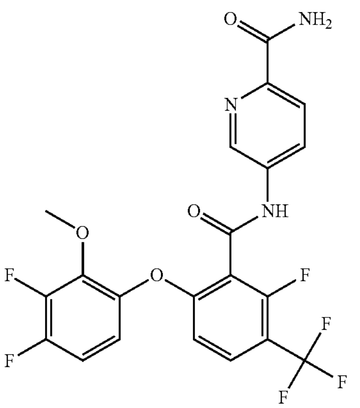 [SMILES: COc1c(Oc2ccc(C(F)(F)F)c(F)c2C(=O)Nc2ccc(C(N)=O)nc2)ccc(F)c1F]

Step 1: 6-(3,4-Difluoro-2-Methoxy-Phenoxy)-2-Fluoro-3-(Trifluoromethyl)Benzoic Acid

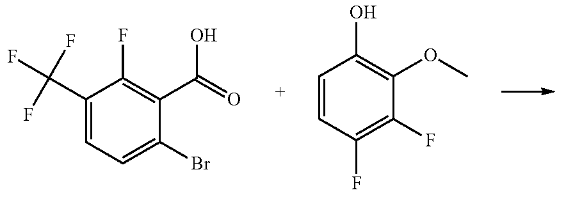

-continued

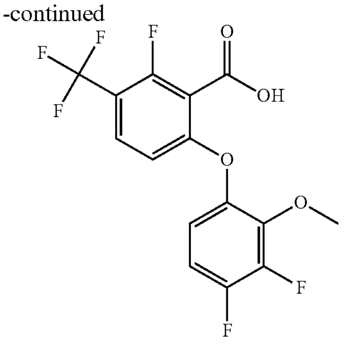

A solution of 6-bromo-2-fluoro-3-(trifluoromethyl)benzoic acid (1 g, 3.484 mmol), 3,4-difluoro-2-methoxy-phenol (557 mg, 3.479 mmol), $Cs_2CO_3$ (2.3 g, 7.059 mmol) in toluene (20 mL) was bubbled with $N_2$ for 10 minutes then CuI (132 mg, 0.6931 mmol) was added. The flask was flushed with $N_2$, capped, and heated at 100° C. with vigorous stirring for 1 h. The mixture was allowed to cool then diluted with ethyl acetate and water. The water layer was acidified with HCl (5.2 mL of 1 M, 5.200 mmol) and the product extracted into ethyl acetate. The organic layer was evaporated to dryness under reduced pressure and the residue was purified by silica gel column chromatography using a gradient eluent of 1-10% MeOH in DCM to give to provide 6-(3,4-difluoro-2-methoxy-phenoxy)-2-fluoro-3-(trifluoromethyl)benzoic acid (1.2 g, 92%) as a white solid. ESI-MS m/z calc. 366.03268, found 367.0 $(M+1)^+$; Retention time (Method B): 1.66 minutes. $^1$H NMR (400 MHz, DMSO-d6) δ 7.76 (t, J=8.6 Hz, 1H), 7.39-7.21 (m, 1H), 7.14 (ddd, J=9.3, 5.1, 2.2 Hz, 1H), 6.75 (d, J=8.9 Hz, 1H), 3.85 (s, 3H) ppm.

Step 2: 5-[[6-(3,4-Difluoro-2-Methoxy-Phenoxy)-2-Fluoro-3-(Trifluoromethyl)Benzoyl]Amino]Pyridine-2-Carboxamide (118)

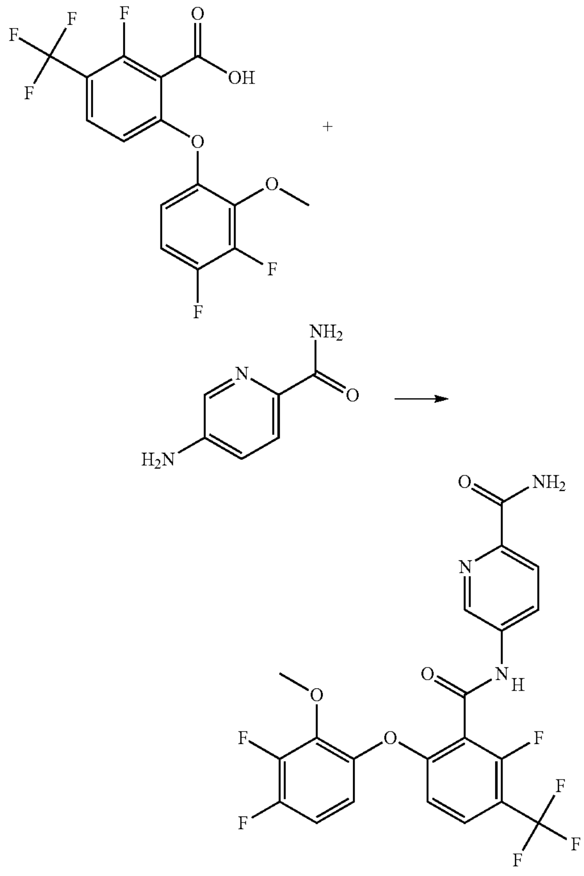

A mixture of 6-(3,4-difluoro-2-methoxy-phenoxy)-2-fluoro-3-(trifluoromethyl)benzoic acid (102.1 mg, 0.2731 mmol), oxalyl dichloride (23.11 mg, 15.88 μL, 0.1821 mmol), DMF (0.3328 mg, 0.3525 μL, 0.004553 mmol), and DCM (1.001 mL) was stirred under nitrogen at RT for 1 hour. The reaction mixture was evaporated to dryness under reduced pressure. To the residue was added DCM (500.5 μL), N-ethyl-N-isopropyl-propan-2-amine (35.30 mg, 47.57 μL, 0.2731 mmol), and 5-aminopyridine-2-carboxamide (18.73 mg, 0.1366 mmol). The reaction mixture was stirred at ambient temperature for 1 h. The reaction was diluted with DMSO (500 uL), filtered, and purified by HPLC (gradient of 10-99% acetonitrile in water containing HCl as a modifier) to give 5-[[6-(3,4-difluoro-2-methoxy-phenoxy)-2-fluoro-3-(trifluoromethyl)benzoyl]amino]pyridine-2-carboxamide (54.8 mg, 41%) as a white solid. ESI-MS m/z calc. 485.08102, found 486.0 $(M+1)^+$; Retention time (Method B): 1.62 minutes. $^1H$ NMR (400 MHz, DMSO-d6) δ 11.42 (s, 1H), 8.86 (d, J=2.4 Hz, 1H), 8.32 (dd, J=8.6, 2.5 Hz, 1H), 8.07 (d, J=8.5 Hz, 1H), 8.03 (d, J=2.7 Hz, 1H), 7.83 (t, J=8.6 Hz, 1H), 7.58 (d, J=2.8 Hz, 1H), 7.39-7.23 (m, 1H), 7.17 (ddd, J=9.3, 5.2, 2.1 Hz, 1H), 6.81 (d, J=8.9 Hz, 1H), 3.85 (d, J=1.2 Hz, 3H) ppm.

Example 18

4-[[4-Bromo-2-Fluoro-6-[2-Methoxy-4-(Trifluoromethoxy)Phenoxy]Benzoyl]Amino]Pyridine-2-Carboxamide (119)

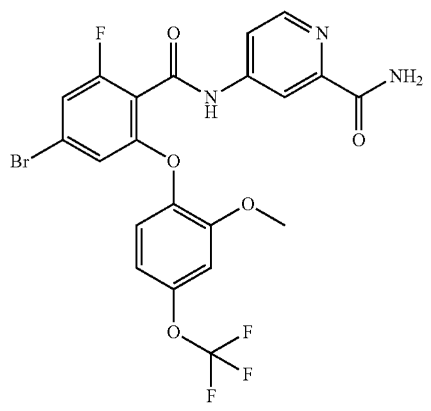 [SMILES: COc1cc(OC(F)(F)F)ccc1Oc1cc(Br)cc(F)c1C(=O)Nc1ccnc(C(N)=O)c1]

Step 1: Methyl 4-Bromo-2-Fluoro-6-[2-Methoxy-4-(Trifluoromethoxy)Phenoxy]Benzoate

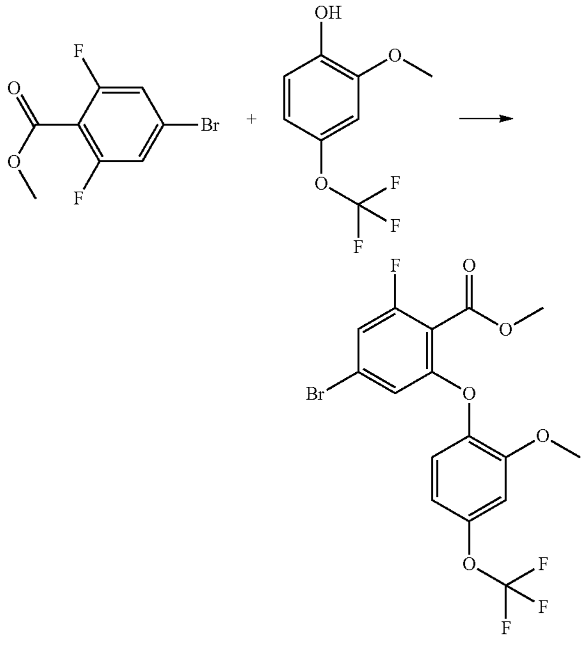

To methyl 4-bromo-2,6-difluoro-benzoate (6.1 g, 24.30 mmol) was added 2-methoxy-4-(trifluoromethoxy)phenol (5.2 g, 24.98 mmol), $Cs_2CO_3$ (6.3 g, 19.34 mmol) and DMF (74 mL). The vial was sealed, the reaction mixture stirred at 80° C. for 1 hour, and the crude mixture cooled to RT. Ethyl acetate (~150 mL) was added and the reaction mixture was washed with brine (3×75 ml). The organic layer was dried over $Na_2SO_4$, filtered and concentrated in vacuo. Column chromatography (silica, 100:0-80:20 hexanes:EtOAc) afforded methyl 4-bromo-2-fluoro-6-[2-methoxy-4-(trifluoromethoxy)phenoxy]benzoate (9.23 g, 87%) as a clear oil. ESI-MS m/z calc. 437.9726, found 463.1; Retention time (Method B): 2.09 minutes.

Step 2: 4-Bromo-2-Fluoro-6-[2-Methoxy-4-(Trifluoromethoxy)Phenoxy]Benzoic Acid

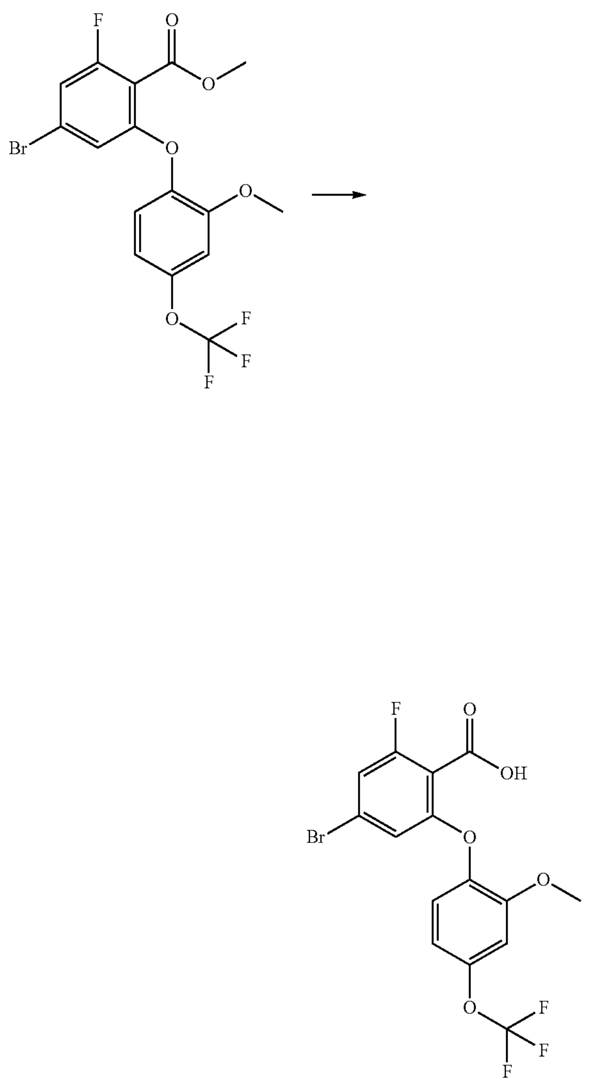

To a slurry of methyl 4-bromo-2-fluoro-6-[2-methoxy-4-(trifluoromethoxy)phenoxy]benzoate (6 g, 13.66 mmol) in MeOH (60 mL) and water (60 mL) was added NaOH (5.5 g, 137.5 mmol). The reaction mixture was stirred at RT for 5 h. The solvent was evaporated and the residue was taken up in water, cooled in an ice bath and quenched with 6N HCl (pH~ 2) slowly. The resultant solid product was filtered and washed with water. The residue was dissolved in DCM/ethyl acetate and dried over $MgSO_4$, filtered and concentrated. The filtrate was extracted by ethyl acetate and dried over $MgSO_4$ and combined with the residue to obtain 4-bromo-2-fluoro-6-[2-methoxy-4-(trifluoromethoxy)phenoxy]benzoic acid (5.6 g, 96%) as clear oil. ESI-MS m/z calc. 423.95694, found 427.0 $(M+1)^+$; Retention time (Method B):1.82 minutes. The oil was dried under high vacuum to for 24 h and taken on without further purification.

Step 3: 4-[[4-Bromo-2-Fluoro-6-[2-Methoxy-4-(Trifluoromethoxy)Phenoxy]Benzoyl]Amino]Pyridine-2-Carboxamide (119)

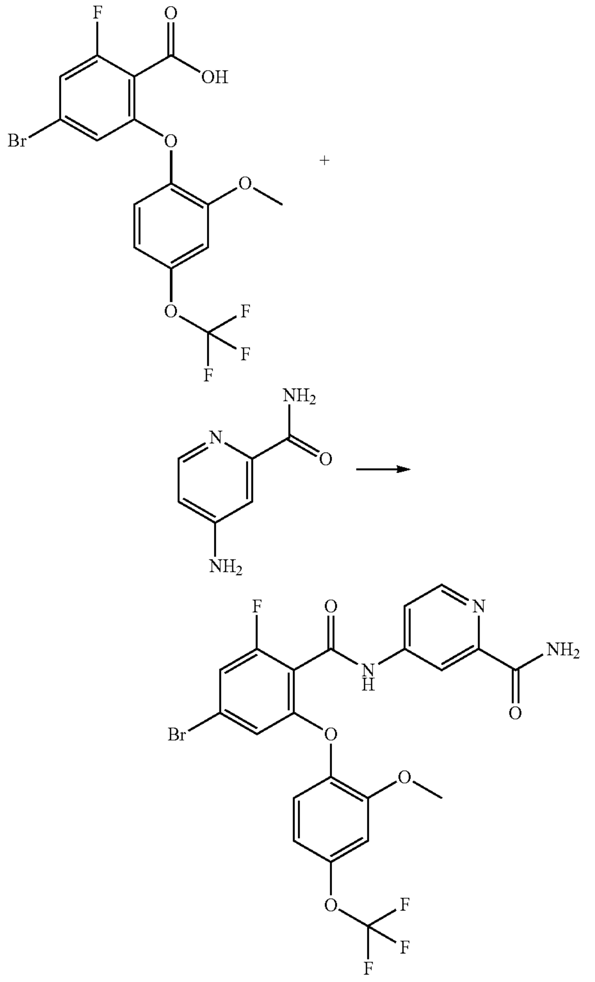

To a solution of 4-bromo-2-fluoro-6-[2-methoxy-4-(trifluoromethoxy)phenoxy]benzoic acid (2 g, 4.704 mmol), DMF (100 μL, 1.291 mmol) and DCM (24.0 mL) at 0° C. under $N_2$ (g) was added oxalyl dichloride (3.3 mL, 37.83 mmol). The reaction was stirred at 0° C. for 10 minutes and then at RT for 1 h. The mixture was concentrated under reduced pressure and redissolved in NMP (5 mL). This solution was added drop-wise to a suspension of 4-aminopyridine-2-carboxamide (700 mg, 5.104 mmol), DMF (720 μL, 9.299 mmol), DIEA (5 mL, 28.71 mmol) in NMP (10 mL) under $N_2$ atmosphere at 0° C. The resulting reaction mixture was slowly warmed to RT and stirred at RT for 18 h. The reaction mixture turned from light brown suspension into a dark brown solution with time. The mixture was partitioned between water and ethyl acetate. The phases were separated and the aqueous layer was extracted with ethyl acetate (1×). The combined organic layer was washed with brine (2×), water (2×) then brine (1×). The organic layer was dried over $Na_2SO_4$, filtered and concentrated to give light brown foam. The crude was purified by ISCO silica chromatography (80 g silica gel column) eluting with a gradient system of hexane/EtOAc starting from 100% hexane to 70% EtOAc over 30 minutes to afford 4-[[4-bromo-2-fluoro-6-[2-methoxy-4-(trifluoromethoxy)phenoxy]benzoyl]amino]pyridine-2-carboxamide (710 mg, 28%) as a white solid. ESI-MS m/z calc. 543.0053, found 546.1 $(M+1)^+$; Retention time (Method B): 1.72 minutes. $^1H$ NMR (400 MHz, DMSO-d6) δ 11.30 (s, 1H), 8.54 (d, J=5.5 Hz, 1H), 8.29 (d, J=2.1 Hz, 1H), 8.10 (d, J=2.8 Hz, 1H), 7.82 (dd, J=5.5, 2.2 Hz, 1H), 7.65 (d, J=2.8 Hz, 1H), 7.52 (dd, J=8.6, 1.6 Hz, 1H), 7.30 (d, J=8.8 Hz, 1H), 7.20 (d, J=2.7 Hz, 1H), 7.05-6.97 (m, 1H), 6.75 (d, J=1.6 Hz, 1H), 3.78 (s, 3H) ppm.

Example 19

4-[[6-(3,4-Difluoro-2-Methoxy-Phenoxy)-2-Methyl-3-(Trifluoromethyl)Benzoyl]Amino]Pyridine-2-Carboxamide (120)

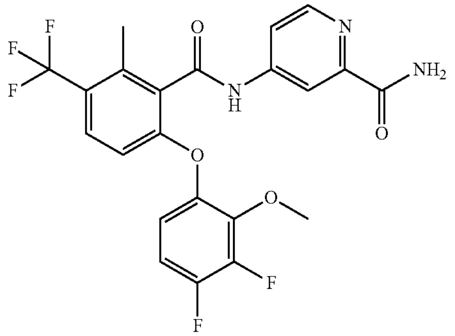 [SMILES: COc1c(Oc2ccc(C(F)(F)F)c(C)c2C(=O)Nc2ccnc(C(N)=O)c2)ccc(F)c1F]

Step 1: 6-Fluoro-2-Methyl-3-(Trifluoromethyl)Benzoic Acid

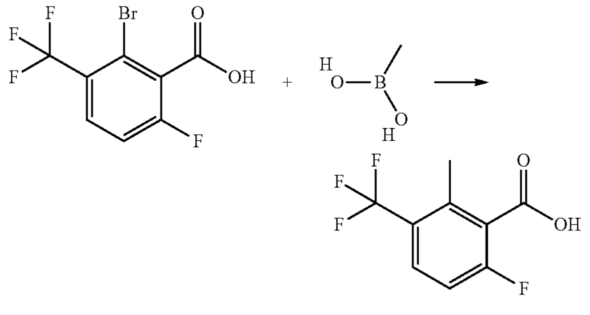

To a solution of 2-bromo-6-fluoro-3-(trifluoromethyl) benzoic acid (3.5 g, 12.19 mmol) and methylboronic acid (2.189 g, 36.57 mmol) in THF (35 mL) was added $Cs_2CO_3$ (12 g, 36.83 mmol) followed by $Pd(dppf)_2Cl_2$ (498 mg, 0.6098 mmol) under nitrogen gas. The reaction mixture was allowed to stir at 65° C. overnight and then heated under reflux in a 75° C. oil bath for 3 h. The reaction mixture was diluted with EtOAc (75 mL) and washed with aqueous HCl (0.5 M, 1x75 mL) and brine (1x75 mL). The organic layer was dried over $Na_2SO_4$, filtered and concentrated under reduced pressure. The resultant oil was purified by silica gel column chromatography using a MeOH/DCM eluent. 6-fluoro-2-methyl-3-(trifluoromethyl)benzoic acid (2.27 g, 84%) was obtained as a ~1.3:1 mixture of 6-fluoro-2-methyl-3-(trifluoromethyl)benzoic acid and 6-fluoro-3-(trifluoromethyl)benzoic acid as a crystalline solid. $^1H$ NMR (400 MHz, DMSO-d6) δ 13.95 (s, 1H), 7.85 (dd, J=8.9, 5.5 Hz, 1H), 7.38 (t, J=8.8 Hz, 1H), 2.42 (d, J=1.9 Hz, 3H) ppm.

Step 2: 4-[[6-Fluoro-2-Methyl-3-(Trifluoromethyl) Benzoyl]Amino]Pyridine-2-Carboxamide

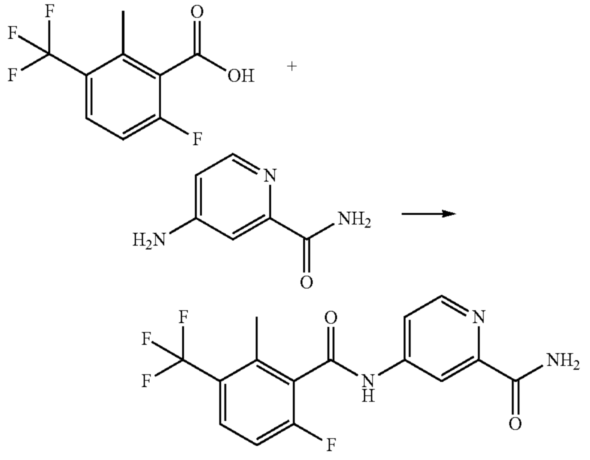

6-fluoro-2-methyl-3-(trifluoromethyl)benzoic acid (900 mg, 4.052 mmol) was dissolved in dichloromethane (13 mL). DMF (125 μL, 1.614 mmol) was added followed by the slow drop wise addition of oxalyl chloride (2.5 mL, 28.66 mmol). The reaction mixture was allowed to stir at RT for 30 minutes. The reaction mixture was concentrated under reduced pressure. Additional dichloromethane (~5 mL) was added, and the solution was again concentrated to dryness. The remaining residue was taken up in NMP (2.7 mL) and was added to a prepared solution of 4-aminopyridine-2-carboxamide (833 mg, 6.074 mmol) and DIEA (4.2 mL, 24.11 mmol) in NMP (2.7 mL). This reaction mixture was allowed to stir at RT overnight. The reaction mixture was diluted with EtOAc (75 mL) and washed with water (2×75 mL), aqueous HCl (2×75 mL, 0.5 M) and brine (2×75 mL). The organic layer was dried over sodium sulfate, filtered and concentrated under reduced pressure. The crude product was chromatographed on silica gel eluting with an EtOAc/hexane gradient to provide 4-[[6-fluoro-2-methyl-3-(trifluoromethyl)benzoyl]amino]pyridine-2-carboxamide (800 mg, 58%) as a white solid. ESI-MS m/z calc. 341.07874, found 342.1 $(M+1)^+$; Retention time (Method B): 1.25 minutes. $^1H$ NMR (400 MHz, DMSO-d6) δ 11.36 (s, 1H), 8.60-8.55 (m, 1H), 8.36 (d, J=2.1 Hz, 1H), 8.12 (d, J=2.8 Hz, 1H), 7.92 (dd, J=8.9, 5.5 Hz, 1H), 7.84 (dd, J=5.4, 2.2 Hz, 1H), 7.67 (d, J=2.9 Hz, 1H), 7.47 (t, J=8.7 Hz, 1H), 2.44 (d, J=1.8 Hz, 3H) ppm.

Step 3: 4-[[6-(3,4-Difluoro-2-Methoxy-Phenoxy)-2-Methyl-3-(Trifluoromethyl)Benzoyl]Amino]Pyridine-2-Carboxamide (120)

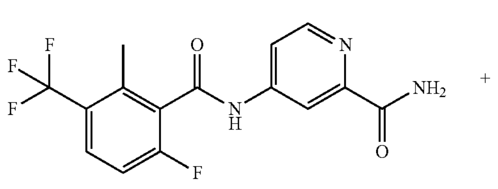

-continued

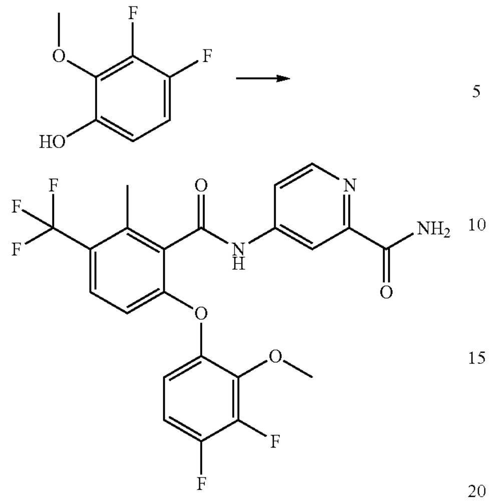

To a solution of 4-[[6-fluoro-2-methyl-3-(trifluoromethyl)benzoyl]amino]pyridine-2-carboxamide (25 mg, 0.07326 mmol) in DMSO (0.5 mL) was added to 3,4-difluoro-2-methoxy-phenol (approximately 35.19 mg, 0.2198 mmol). Finely ground $K_2CO_3$ (30.38 mg, 0.2198 mmol) was then added. The reaction mixture was capped and allowed to stir at 120° C. for 30 minutes then at 140° C. for 1.5 h. The product was isolated by mass-triggered reverse-phase HPLC. Samples were and purified by reverse phase HPLC (gradient of 10-99% acetonitrile in water containing HCl as a modifier) to afford 4-[[6-(3,4-difluoro-2-methoxy-phenoxy)-2-methyl-3-(trifluoromethyl)benzoyl]amino]pyridine-2-carboxamide (7.1 mg, 20%). ESI-MS m/z calc. 481.1061, found 482.2 $(M+1)^+$; Retention time (Method B): 1.65 minutes. $^1H$ NMR (400 MHz, DMSO-$d_6$) δ 11.33 (s, 1H), 8.55 (d, J=5.4 Hz, 1H), 8.39 (d, J=2.1 Hz, 1H), 8.12 (s, 1H), 7.86 (dd, J=5.5, 2.2 Hz, 1H), 7.73 (d, J=8.9 Hz, 1H), 7.67 (s, 1H), 7.28 (q, J=9.3 Hz, 1H), 7.14-7.06 (m, 1H), 6.77 (d, J=8.9 Hz, 1H), 3.83 (s, 3H), 2.44 (s, 3H) ppm.

The compounds set forth in Table 13 were prepared by methods analogous to the preparation of compound 120 in Example 19.

TABLE 13

Additional Compounds Prepared by Methods Analogous to Example 19.

| Cmpd No. | Compound Name | LC/MS | NMR (shifts in ppm) |
|---|---|---|---|
| 121 | 4-[[6-(2,3-difluoro-4-isopropoxy-phenoxy)-2-methyl-3-(trifluoromethyl)benzoyl]amino]pyridine-2-carboxamide | ESI-MS m/z calc. 509.1374, found 510.2 (M + 1)+; Retention time (Method B): 1.8 minutes | $^1H$ NMR (400 MHz, DMSO-$d_6$) δ 11.33 (s, 1H), 8.55 (d, J = 5.5 Hz, 1H), 8.36 (d, J = 2.1 Hz, 1H), 8.12 (d, J = 2.7 Hz, 1H), 7.86 (dd, J = 5.6, 2.2 Hz, 1H), 7.75 (d, J = 8.9 Hz, 1H), 7.67 (d, J = 2.8 Hz, 1H), 7.16-7.06 (m, 2H), 6.88 (d, J = 8.8 Hz, 1H), 4.82-4.54 (m, 1H), 2.43 (s, 3H), 1.30 (d, J = 6.0 Hz, 6H). |
| 122 | 4-[[6-(2-chloro-4-fluoro-phenoxy)-2-methyl-3-(trifluoromethyl)benzoyl]amino]pyridine-2-carboxamide | ESI-MS m/z calc. 467.06598, found 468.2 (M + 1)+; Retention time (Method B): 1.65 minutes | $^1H$ NMR (400 MHz, DMSO-$d_6$) δ 11.29 (s, 1H), 8.55 (d, J = 5.4 Hz, 1H), 8.37 (d, J = 2.1 Hz, 1H), 8.12 (d, 1H), 7.86 (dd, J = 5.5, 2.2 Hz, 1H), 7.75 (d, J = 8.9 Hz, 1H), 7.72-7.60 (m, 2H), 7.49-7.27 (m, 2H), 6.70 (d, J = 8.8 Hz, 1H), 2.45 (s, 3H). |
| 123 | 4-[[2-methyl-6-[4-(trifluoromethoxy)phenoxy]-3-(trifluoromethyl)benzoyl]amino]pyridine-2-carboxamide | ESI-MS m/z calc. 499.09668, found 500.2 (M + 1)+; Retention time (Method B): 1.79 minutes | $^1H$ NMR (400 MHz, DMSO-$d_6$) δ 11.31 (s, 1H), 8.53 (d, J = 5.5 Hz, 1H), 8.34 (d, J = 2.1 Hz, 1H), 8.11 (d, J = 2.7 Hz, 1H), 7.83 (dd, J = 5.5, 2.2 Hz, 1H), 7.79 (d, J = 8.9 Hz, 1H), 7.67 (d, J = 2.7 Hz, 1H), 7.46 (d, J = 8.6 Hz, 2H), 7.34-7.24 (m, 2H), 6.90 (d, J = 8.8 Hz, 1H), 2.44 (s, 3H). |
| 124 | 4-[[6-(3-chloro-4-isopropoxy-phenoxy)-2-methyl-3-(trifluoromethyl)benzoyl]amino]pyridine-2-carboxamide | ESI-MS m/z calc. 507.11728, found 508.2 (M + 1)+; Retention time (Method B): 1.85 minutes | $^1H$ NMR (400 MHz, DMSO-$d_6$) δ 11.26 (s, 1H), 8.54 (d, J = 5.5 Hz, 1H), 8.35 (d, J = 2.1 Hz, 1H), 8.11 (d, J = 2.8 Hz, 1H), 7.84 (dd, J = 5.5, 2.2 Hz, 1H), 7.75 (d, J = 8.9 Hz, 1H), 7.67 (d, J = 2.8 Hz, 1H), 7.34 (d, J = 2.8 Hz, 1H), 7.24 (d, J = 9.0 Hz, 1H), 7.14 (dd, J = 9.0, 2.9 Hz, 1H), 6.82 (d, J = 8.8 Hz, 1H), 4.72-4.55 (m, 1H), 2.43 (s, 3H), 1.28 (d, J = 6.0 Hz, 6H). |
| 125 | 4-[[6-[(4-fluoro-2,3-dihydrobenzofuran-7-yl)oxy]-2-methyl-3-(trifluoromethyl)benzoyl]amino]pyridine-2-carboxamide | ESI-MS m/z calc. 475.1155, found 476.3 (M + 1)+; Retention time (Method B): 1.62 minutes; | $^1H$ NMR (400 MHz, DMSO-$d_6$) δ 11.30 (s, 1H), 8.55 (d, J = 5.5 Hz, 1H), 8.38 (d, J = 2.1 Hz, 1H), 8.13 (s, 1H), 7.87 (dd, J = 5.5, 2.2 Hz, 1H), 7.72 (d, J = 8.9 Hz, 1H), 7.68 (s, 1H), 7.04 (dd, J = 9.0, 4.7 Hz, 1H), 6.83-6.62 (m, 2H), 4.64 (t, J = Hz, 2H), 3.29 (t, J = 8.7 Hz, 2H), 2.41 (s, 3H). |
| 126 | 4-[[6-(3,4-difluorophenoxy)-2-methyl-3-(trifluoromethyl)benzoyl]amino]pyridine-2-carboxamide | ESI-MS m/z calc. 451.09552, found 452.2 (M + 1)+; Retention time (Method B): 1.63 minutes | $^1H$ NMR (400 MHz, DMSO-$d_6$) δ 11.28 (s, 1H), 8.54 (d, J = 5.5 Hz, 1H), 8.34 (d, J = 2.2 Hz, 1H), 8.12 (s, 1H), 7.83 (dd, J = 5.5, 2.2 Hz, 1H), 7.78 (d, J = 8.9 Hz, 1H), 7.68 (s, 1H), 7.53 (q, J = 9.5 Hz, 1H), 7.47-7.32 (m, 1H), 7.12-6.99 (m, 1H), 6.92 (d, J = 8.8 Hz, 1H), 2.44 (s, 3H). |

TABLE 13-continued

Additional Compounds Prepared by Methods Analogous to Example 19.

| Cmpd No. | Compound Name | LC/MS | NMR (shifts in ppm) |
|---|---|---|---|
| 127 | 4-[[6-(3-chloro-4-fluoro-phenoxy)-2-methyl-3-(trifluoromethyl)benzoyl]amino]pyridine-2-carboxamide | ESI-MS m/z calc. 467.06598, found 468.2 (M + 1)+; Retention time (Method B): 1.71 minutes | $^1$H NMR (400 MHz, DMSO-$d_6$) δ 11.29 (s, 1H), 8.54 (d, J = 5.5 Hz, 1H), 8.35 (d, J = 2.1 Hz, 1H), 8.12 (s, 1H), 7.83 (dd, J = 5.5, 2.2 Hz, 1H), 7.78 (d, J = 8.9 Hz, 1H), 7.68 (s, 1H), 7.57-7.43 (m, 2H), 7.30-7.15 (m, 1H), 6.92 (d, J = 8.8 Hz, 1H), 2.44 (s, 3H). |
| 128 | 4-[[6-[2-fluoro-4-(trifluoromethoxy)phenoxy]-2-methyl-3-(trifluoromethyl)benzoyl]amino]pyridine-2-carboxamide | ESI-MS m/z calc. 517.0873, found 518.2 (M + 1)+; Retention time (Method B): 1.79 minutes | $^1$H NMR (400 MHz, DMSO-$d_6$) δ 11.42 (s, 1H), 8.55 (d, J = 5.5 Hz, 1H), 8.38 (d, J = 2.1 Hz, 1H), 8.16 (s, 1H), 7.86 (dd, J = 5.5, 2.2 Hz, 1H), 7.79 (d, J = 8.9 Hz, 1H), 7.75-7.64 (m, 2H), 7.48 (t, J = 9.0 Hz, 1H), 7.35 (d, J = 9.1 Hz, 1H), 6.91 (d, J = 8.8 Hz, 1H), 2.45 (s, 3H). |
| 129 | 4-[[6-(4-fluoro-2-methyl-phenoxy)-2-methyl-3-(trifluoromethyl)benzoyl]amino]pyridine-2-carboxamide | ESI-MS m/z calc. 447.1206, found 448.3 (M + 1)+; Retention time (Method B): 1.68 minutes | $^1$H NMR (400 MHz, DMSO-$d_6$) δ 11.31 (s, 1H), 8.54 (d, J = 5.4 Hz, 1H), 8.38 (d, J = 2.1 Hz, 1H), 8.12 (d, J = 2.8 Hz, 1H), 7.86 (dd, J = 5.5, 2.2 Hz, 1H), 7.72 (d, J = 8.9 Hz, 1H), 7.67 (d, 1H), 7.24 (dd, 1H), 7.20-7.07 (m, 2H), 6.60 (d, J = 8.8 Hz, 1H), 2.44 (s, 3H), 2.12 (s, 3H). |
| 130 | 4-[[6-(4-ethoxy-2,3-difluoro-phenoxy)-2-methyl-3-(trifluoromethyl)benzoyl]amino]pyridine-2-carboxamide | ESI-MS m/z calc. 495.12173, found 496.2 (M + 1)+; Retention time (Method B): 1.72 minutes | 1H NMR (400 MHz, DMSO-d6) δ 11.31 (s, 1H), 8.54 (d, J = 5.5 Hz, 1H), 8.36 (d, J = 2.0 Hz, 1H), 8.10 (d, J = 2.8 Hz, 1H), 7.86 (dd, J = 5.5, 2.1 Hz, 1H), 7.74 (d, J = 8.9 Hz, 1H), 7.65 (d, J = 2.9 Hz, 1H), 7.18-7.03 (m, 2H), 6.86 (d, J = 8.9 Hz, 1H), 4.14 (q, J = 7.0 Hz, 2H), 2.43 (s, 3H), 1.36 (t, J = 7.0 Hz, 3H). |
| 131 | 4-[[6-(2,4-difluorophenoxy)-2-methyl-3-(trifluoromethyl)benzoyl]amino]pyridine-2-carboxamide | ESI-MS m/z calc. 451.09552, found 452.2 (M + 1)+; Retention time (Method B): 1.59 minutes | $^1$H NMR (400 MHz, DMSO-$d_6$) δ 11.34 (s, 1H), 8.55 (d, J = 5.5 Hz, 1H), 8.37 (d, J = 2.1 Hz, 1H), 8.13 (s, 1H), 7.86 (dd, J = 5.5, 2.2 Hz, 1H), 7.76 (d, J = 8.9 Hz, 1H), 7.68 (d, J = 2.6 Hz, 1H), 7.61-7.49 (m, 1H), 7.49-7.37 (m, 1H), 7.20 (t, J = 8.6 Hz, 1H), 6.80 (d, J = 8.8 Hz, 1H), 2.44 (s, 3H). |
| 132 | 4-[[6-(2-fluoro-4-isopropoxy-phenoxy)-2-methyl-3-(trifluoromethyl)benzoyl]amino]pyridine-2-carboxamide | ESI-MS m/z calc. 491.14682, found 492.2 (M + 1)+; Retention time (Method B): 1.74 minutes | $^1$H NMR (400 MHz, DMSO-$d_6$) δ 11.22 (s, 1H), 8.55 (d, J = 5.5 Hz, 1H), 8.40 (d, J = 2.1 Hz, 1H), 8.11 (d, 1H), 7.87 (dd, J = 5.5, 2.2 Hz, 1H), 7.71 (d, J = 8.9 Hz, 1H), 7.66 (d, 1H), 7.36-7.17 (m, 1H), 7.07 (d, J = 8.5 Hz, 1H), 6.99 (t, J = 9.2 Hz, 1H), 6.62 (d, J = 8.8 Hz, 1H), 4.68-4.49 (m, 1H), 2.43 (s, 3H), 1.14 (d, J = 6.0 Hz, 6H). |
| 133 | 4-[[2-methyl-6-[2-methyl-4-(trifluoromethoxy)phenoxy]-3-(trifluoromethyl)benzoyl]amino]pyridine-2-carboxamide | ESI-MS m/z calc. 513.1123, found 513.95 (M + 1)+; Retention time (Method B): 1.96 minutes | 1H NMR (400 MHz, DMSO-d6) δ 11.30 (s, 1H), 8.54 (d, J = 5.5 Hz, 1H), 8.36 (d, J = 2.1 Hz, 1H), 8.10 (d, J = 2.9 Hz, 1H), 7.84 (dd, J = 5.5, 2.2 Hz, 1H), 7.75 (d, J = 8.9 Hz, 1H), 7.65 (d, J = 2.9 Hz, 1H), 7.39 (d, J = 2.9 Hz, 1H), 7.29 (dd, J = 8.9, 2.9 Hz, 1H), 7.22 (d, J = 8.9 Hz, 1H), 6.71 (d, J = 8.8 Hz, 1H), 2.44 (d, J = 1.7 Hz, 3H), 2.16 (s, 3H). |
| 134 | 4-[[6-(4-chloro-2-methoxy-phenoxy)-2-methyl-3-(trifluoromethyl)benzoyl]amino]pyridine-2-carboxamide | ESI-MS m/z calc. 479.08597, found 480.0 (M + 1)+; Retention time (Method B): 1.8 minutes | 1H NMR (400 MHz, DMSO-d6) δ 11.26 (d, J = 3.4 Hz, 1H), 8.54 (d, J = 5.5 Hz, 1H), 8.38 (t, J = 1.6 Hz, 1H), 8.11 (s, 1H), 7.87 (dd, J = 5.5, 2.1 Hz, 1H), 7.70 (d, J = 8.9 Hz, 1H), 7.66 (s, 1H), 7.29 (d, J = 2.4 Hz, 1H), 7.21 (d, J = 8.5 Hz, 1H), 7.08 (dd, J = 8.5, 2.4 Hz, 1H), 6.63 (d, J = 8.8 Hz, 1H), 3.77 (s, 3H), 2.42 (d, J = 1.7 Hz, 3H). |
| 135 | 4-[[6-(4-chloro-2-fluoro-phenoxy)-2-methyl-3-(trifluoromethyl)benzoyl]amino]pyridine-2-carboxamide | ESI-MS m/z calc. 467.06598, found 467.95 (M + 1)+; Retention time (Method B): 1.8 minutes | 1H NMR (400 MHz, DMSO-d6) δ 11.31 (s, 1H), 8.54 (d, J = 5.5 Hz, 1H), 8.35 (d, J = 2.1 Hz, 1H), 8.10 (d, J = 2.7 Hz, 1H), 7.85 (dd, J = 5.5, 2.2 Hz, 1H), 7.77 (d, J = 8.9 Hz, 1H), 7.73-7.62 (m, 2H), 7.42-7.32 (m, 2H), 6.88 (d, J = 8.8 Hz, 1H), 2.44 (d, J = 1.7 Hz, 3H). |

TABLE 13-continued

Additional Compounds Prepared by Methods Analogous to Example 19.

| Cmpd No. | Compound Name | LC/MS | NMR (shifts in ppm) |
|---|---|---|---|
| 136 | 4-[[6-(4-chloro-2-methyl-phenoxy)-2-methyl-3-(trifluoromethyl)benzoyl]amino]pyridine-2-carboxamide | ESI-MS m/z calc. 463.09106, found 463.95 (M + 1)+; Retention time (Method B): 1.88 minutes | 1H NMR (400 MHz, DMSO-d6) δ 11.30 (s, 1H), 8.54 (d, J = 5.5 Hz, 1H), 8.37 (d, J = 2.0 Hz, 1H), 8.10 (d, J = 2.8 Hz, 1H), 7.84 (dd, J = 5.5, 2.2 Hz, 1H), 7.73 (d, J = 8.9 Hz, 1H), 7.65 (d, J = 2.8 Hz, 1H), 7.44 (dd, J = 2.6, 0.9 Hz, 1H), 7.34 (dd, J = 8.7, 2.7 Hz, 1H), 7.13 (d, J = 8.6 Hz, 1H), 6.68 (d, J = 8.8 Hz, 1H), 2.44 (d, J = 1.7 Hz, 3H), 2.12 (s, 3H). |
| 137 | 4-[[6-(4-fluoro-2-methoxy-phenoxy)-2-methyl-3-(trifluoromethyl)benzoyl]amino]pyridine-2-carboxamide | ESI-MS m/z calc. 463.1155, found 464.05 (M + 1)+; Retention time (Method B): 1.73 minutes | 1H NMR (400 MHz, DMSO-d6) δ 11.25 (s, 1H), 8.55 (d, J = 5.5 Hz, 1H), 8.39 (d, J = 2.1 Hz, 1H), 8.11 (d, J = 2.8 Hz, 1H), 7.88 (dd, J = 5.5, 2.2 Hz, 1H), 7.73-7.63 (m, 2H), 7.23 (dd, J = 8.9, 5.9 Hz, 1H), 7.15 (dd, J = 10.7, 2.9 Hz, 1H), 6.85 (td, J = 8.5, 2.9 Hz, 1H), 6.58 (d, J = 8.8 Hz, 1H), 3.76 (s, 3H), 2.42 (d, J = 1.7 Hz, 3H). |
| 138 | 4-[[6-[3-chloro-4-(trifluoromethoxy)phenoxy]-2-methyl-3-(trifluoromethyl)benzoyl]amino]pyridine-2-carboxamide | ESI-MS m/z calc. 533.0577, found 533.91 (M + 1)+; Retention time (Method B): 1.97 minutes | $^1$H NMR (400 MHz, DMSO-$d_6$) δ 11.30 (s, 1H), 8.53 (d, J = 5.4 Hz, 1H), 8.33 (d, J = 2.1 Hz, 1H), 8.11 (d, J = 2.9 Hz, 1H), 7.87-7.75 (m, 2H), 7.72-7.60 (m, 2H), 7.56 (d, J = 2.9 Hz, 1H), 7.26 (dd, J = 9.1, 3.0 Hz, 1H), 7.05 (d, J = 8.8 Hz, 1H), 2.45 (s, 3H). |
| 139 | 4-[[6-[3-fluoro-4-(trifluoromethoxy)phenoxy]-2-methyl-3-(trifluoromethyl)benzoyl]amino]pyridine-2-carboxamide | ESI-MS m/z calc. 517.0873, found 518.0 (M + 1)+; Retention time (Method B): 1.91 minutes | |
| 140 | 4-[[2-methyl-3-(trifluoromethyl)-6-(2,3,4-trifluorophenoxy)benzoyl]amino]pyridine-2-carboxamide | ESI-MS m/z calc. 469.08612, found 470.0 (M + 1)+; Retention time (Method B): 1.76 minutes | $^1$H NMR (400 MHz, DMSO-$d_6$) δ 11.35 (s, 1H), 8.55 (d, J = 5.5 Hz, 1H), 8.36 (d, J = 2.1 Hz, 1H), 8.11 (d, 1H), 7.85 (dd, J = 5.5, 2.2 Hz, 1H), 7.77 (d, J = 8.9 Hz, 1H), 7.67 (d, J = 2.9 Hz, 1H), 7.51-7.35 (m, 1H), 7.33-7.15 (m, 1H), 6.98 (d, J = 8.8 Hz, 1H), 2.44 (s, 3H). |
| 141 | 4-[[6-(4-fluoro-2,3-dimethyl-phenoxy)-2-methyl-3-(trifluoromethyl)benzoyl]amino]pyridine-2-carboxamide | ESI-MS m/z calc. 461.13626, found 462.0 (M + 1)+; Retention time (Method B): 1.87 minutes | 1H NMR (400 MHz, DMSO-d6) δ 11.31 (s, 1H), 8.54 (d, J = 5.5 Hz, 1H), 8.38 (d, J = 2.1 Hz, 1H), 8.10 (d, J = 2.9 Hz, 1H), 7.86 (dd, J = 5.5, 2.2 Hz, 1H), 7.70 (d, J = 8.9 Hz, 1H), 7.65 (d, J = 3.0 Hz, 1H), 7.11 (t, J = 9.0 Hz, 1H), 7.01 (dd, J = 8.9, 4.9 Hz, 1H), 6.56 (d, J = 8.8 Hz, 1H), 2.44 (d, J = 1.7 Hz, 3H), 2.16 (d, J = 2.1 Hz, 3H), 2.07 (d, J = 4.7 Hz, 3H). |
| 142 | 4-[[6-(2,4-dichloro-6-methyl-phenoxy)-2-methyl-3-(trifluoromethyl)benzoyl]amino]pyridine-2-carboxamide | ESI-MS m/z calc. 497.0521, found 497.95 (M + 1)+; Retention time (Method B): 1.93 minutes | |
| 143 | 4-[[2-methyl-3-(trifluoromethyl)-6-(2,4,6-trifluorophenoxy)benzoyl]amino]pyridine-2-carboxamide | ESI-MS m/z calc. 469.08612, found 470.0 (M + 1)+; Retention time (Method B): 1.72 minutes | $^1$H NMR (400 MHz, DMSO-$d_6$) δ 11.39 (s, 1H), 8.56 (d, J = 5.5 Hz, 1H), 8.39 (d, J = 2.1 Hz, 1H), 8.14 (s, 1H), 7.87 (dd, J = 5.6, 2.2 Hz, 1H), 7.75 (d, J = 8.9 Hz, 1H), 7.69 (s, 1H), 7.60-7.39 (m, 2H), 6.90 (d, J = 8.9 Hz, 1H), 2.43 (s, 3H). |
| 144 | 4-[[6-(4-chloro-2,6-dimethyl-phenoxy)-2-methyl-3-(trifluoromethyl)benzoyl]amino]pyridine-2-carboxamide | ESI-MS m/z calc. 477.1067, found 478.0 (M + 1)+; Retention time (Method B): 1.96 minutes | 1H NMR (400 MHz, DMSO-d6) δ 11.32 (s, 1H), 8.55 (d, J = 5.5 Hz, 1H), 8.41 (d, J = 2.1 Hz, 1H), 8.11 (d, J = 2.8 Hz, 1H), 7.87 (dd, J = 5.5, 2.2 Hz, 1H), 7.71-7.63 (m, 2H), 7.29 (s, 2H), 6.42 (d, J = 8.8 Hz, 1H), 2.44 (d, J = 1.6 Hz, 3H), 2.07 (d, J = 1.4 Hz, 6H). |
| 145 | 4-[[6-(2,6-dimethoxy-4-methyl-phenoxy)-2-methyl-3-(trifluoromethyl)benzoyl]amino]pyridine-2-carboxamide | ESI-MS m/z calc. 489.15115, found 490.05 (M + 1)+; Retention time (Method B): 1.77 minutes | 1H NMR (400 MHz, DMSO-d6) δ 11.08 (s, 1H), 8.53 (d, J = 5.5 Hz, 1H), 8.41 (d, J = 2.1 Hz, 1H), 8.09 (d, J = 2.8 Hz, 1H), 7.88 (dd, J = 5.5, 2.2 Hz, 1H), 7.67-7.60 (m, 2H), 6.63 (s, 2H), 6.47 (d, J = 8.8 Hz, 1H), 3.70 (s, 6H), 2.40 (d, J = 1.7 Hz, 3H), 2.33 (s, 3H). |

TABLE 13-continued

Additional Compounds Prepared by Methods Analogous to Example 19.

| Cmpd No. | Compound Name | LC/MS | NMR (shifts in ppm) |
|---|---|---|---|
| 146 | 4-[[6-[2-chloro-4-(trifluoromethoxy)phenoxy]-2-methyl-3-(trifluoromethyl)benzoyl]amino]pyridine-2-carboxamide | ESI-MS m/z calc. 533.0577, found 534.0 (M + 1)+; Retention time (Method B): 1.84 minutes | 1H NMR (400 MHz, DMSO-d6) δ 11.30 (s, 1H), 8.54 (d, J = 5.5 Hz, 1H), 8.35 (d, J = 2.2 Hz, 1H), 8.19-8.00 (m, 1H), 7.84 (dd, J = 5.6, 2.2 Hz, 1H), 7.82-7.73 (m, 2H), 7.69-7.62 (m, 1H), 7.53-7.39 (m, 2H), 6.84 (d, J = 8.8 Hz, 1H), 2.45 (s, 3H). |
| 147 | 4-[[6-[3-fluoro-2-methoxy-4-(trifluoromethoxy)phenoxy]-2-methyl-3-(trifluoromethyl)benzoyl]amino]pyridine-2-carboxamide | ESI-MS m/z calc. 547.09784, found 548.2 (M + 1)+; Retention time (Method B): 1.83 minutes | 1H NMR (400 MHz, DMSO-d6) δ 11.31 (s, 1H), 8.54 (d, J = 5.5 Hz, 1H), 8.36 (d, J = 2.1 Hz, 1H), 8.09 (d, J = 2.9 Hz, 1H), 7.84 (dd, J = 5.5, 2.2 Hz, 1H), 7.76 (d, J = 8.9 Hz, 1H), 7.65 (d, J = 2.8 Hz, 1H), 7.38 (ddd, J = 9.4, 8.1, 1.3 Hz, 1H), 7.13 (dd, J = 9.3, 2.2 Hz, 1H), 6.89 (d, J = 8.8 Hz, 1H), 3.83 (d, J = 1.0 Hz, 3H), 2.45 (d, J = 1.7 Hz, 3H). |
| 148 | 4-[[6-[2-cyclopropyl-4-(trifluoromethoxy)phenoxy]-2-methyl-3-(trifluoromethyl)benzoyl]amino]pyridine-2-carboxamide | ESI-MS m/z calc. 539.128, found 540.3 (M + 1)+; Retention time (Method B): 2.02 minutes | 1H NMR (400 MHz, DMSO-d6) δ 11.30 (s, 1H), 8.54 (d, J = 5.5 Hz, 1H), 8.36 (d, J = 2.1 Hz, 1H), 8.10 (d, J = 2.8 Hz, 1H), 7.84 (dd, J = 5.5, 2.2 Hz, 1H), 7.76 (d, J = 8.9 Hz, 1H), 7.65 (d, J = 2.9 Hz, 1H), 7.29-7.19 (m, 2H), 6.98 (d, J = 2.4 Hz, 1H), 6.71 (d, J = 8.8 Hz, 1H), 2.44 (d, J = 1.6 Hz, 3H), 1.98 (tt, J = 8.4, 5.2 Hz, 1H), 0.91-0.81 (m, 2H), 0.74-0.65 (m, 2H). |
| 149 | 4-[[6-(3,4-difluoro-2-methyl-phenoxy)-2-methyl-3-(trifluoromethyl)benzoyl]amino]pyridine-2-carboxamide | ESI-MS m/z calc. 465.11118, found 466.1 (M + 1)+; Retention time (Method B): 1.79 minutes | 1H NMR (400 MHz, DMSO-d6) δ 11.31 (s, 1H), 8.54 (d, J = 5.5 Hz, 1H), 8.36 (d, J = 2.0 Hz, 1H), 8.09 (s, 1H), 7.84 (dd, J = 5.5, 2.2 Hz, 1H), 7.73 (d, J = 8.9 Hz, 1H), 7.65 (s, 1H), 7.38 (q, J = 9.4 Hz, 1H), 7.06-6.97 (m, 1H), 6.72 (d, J = 8.8 Hz, 1H), 2.44 (d, J = 1.8 Hz, 3H), 2.09 (d, J = 2.2 Hz, 3H). |

Example 20

4-[[2-Fluoro-6-[2-Methoxy-4-(Trifluoromethoxy) Phenoxy]-3-(Trifluoromethyl)Benzoyl]Amino]-1-Oxido-Pyridin-1-Ium-2-Carboxamide (150)

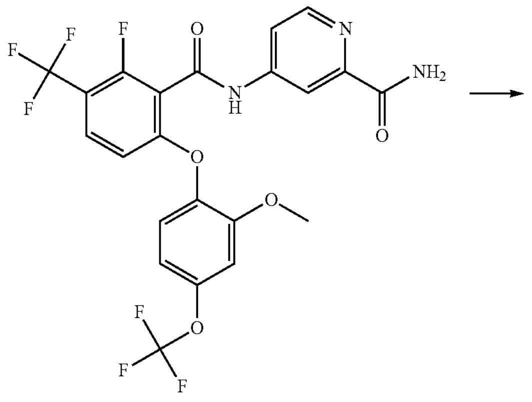

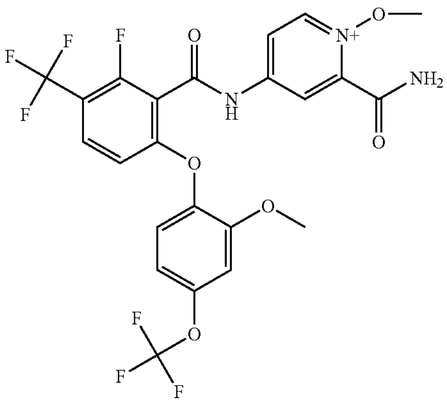 [SMILES: COc1cc(OC(F)(F)F)ccc1Oc1ccc(C(F)(F)F)c(F)c1C(=O)Nc1cc[n+](OC)c(C(N)=O)c1]

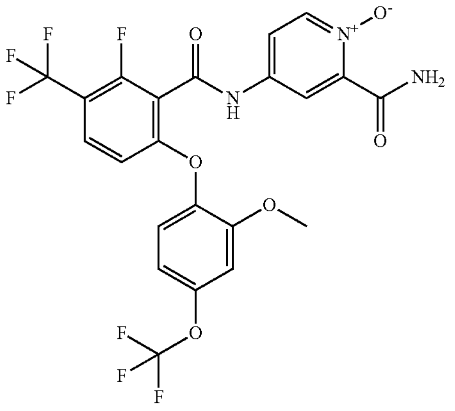

To a stirred slurry of 4-[[2-fluoro-6-[2-methoxy-4-(trifluoromethoxy)phenoxy]-3-(trifluoromethyl)benzoyl]amino]pyridine-2-carboxamide (200 mg, 0.3736 mmol) in anhydrous DCM (1.8 mL) under $N_2$ at 0° C. was added 3-chlorobenzenecarboperoxoic acid (253 mg, 1.129 mmol). The reaction was allowed to warm up to RT and stirred for 13 h. The solvent was evaporated under reduced pressure. The crude material was purified by silica gel chromatography EtOAc/hexanes as eluant to yield 4-[[2-fluoro-6-[2-methoxy-4-(trifluoromethoxy)phenoxy]-3-(trifluoromethyl)benzoyl]amino]-1-oxido-pyridin-1-ium-2-carboxamide (190 mg, 93%) as a white solid. ESI-MS m/z calc. 549.0771, found 549.9 $(M+1)^+$; Retention time (Method C): 2.36 minutes. $^1H$ NMR (400 MHz, DMSO-d6) δ 11.57 (s, 1H), 10.59 (d, J=4.6 Hz, 1H), 8.55 (d, J=3.2 Hz, 1H), 8.38 (d, J=7.2 Hz, 1H), 8.28 (d, J=4.5 Hz, 1H), 7.87 (dd, J=7.2, 3.2 Hz, 1H), 7.82 (t, J=8.6 Hz, 1H), 7.37 (d, J=8.8 Hz, 1H), 7.27 (d, J=2.7 Hz, 1H), 7.09-7.01 (m, 1H), 6.69 (d, J=8.9 Hz, 1H), 3.79 (s, 3H) ppm.

Example 21

4-[[6-[2-Methoxy-4-(Trifluoromethoxy)Phenoxy]-2-Methyl-3-(Trifluoromethyl)Benzoyl]Amino]Pyridine-2-Carboxamide (151)

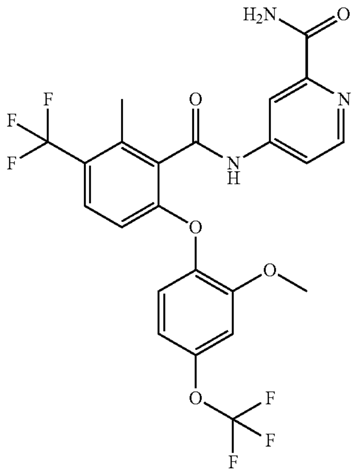 [SMILES: COc1cc(OC(F)(F)F)ccc1Oc1ccc(C(F)(F)F)c(C)c1C(=O)Nc1ccnc(C(N)=O)c1]

Step 1: Tert-Butyl 2-Bromo-6-[2-Methoxy-4-(Trifluoromethoxy)Phenoxy]-3-(Trifluoromethyl)Benzoate

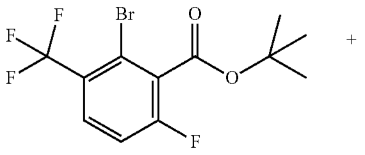

-continued

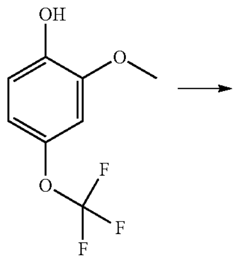

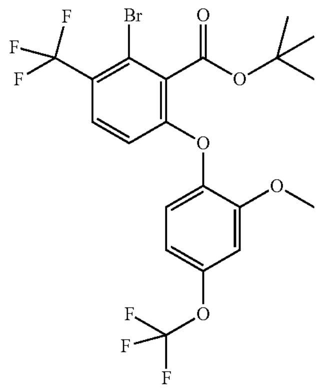

A stirring mixture of tert-butyl 2-bromo-6-fluoro-3-(trifluoromethyl)benzoate (3.0 g, 8.744 mmol), 2-methoxy-4-(trifluoromethoxy)phenol (2.1 g, 10.09 mmol), $K_2CO_3$ (2.4 g, 17.37 mmol), and DMSO (12 mL) was heated at 100° C. for 1 hour. The reaction mixture was cooled to room temperature and was then directly purified by silica gel column chromatography using a gradient of 1-100% EtOAc in hexanes to give tert-butyl 2-bromo-6-[2-methoxy-4-(trifluoromethoxy)phenoxy]-3-(trifluoromethyl)benzoate (4.1 g, 87%) as a clear oil. $^1H$ NMR (400 MHz, DMSO-d6) δ 7.79 (d, J=8.9 Hz, 1H), 7.36-7.17 (m, 2H), 7.12-6.94 (m, 1H), 6.83 (d, J=8.9 Hz, 1H), 3.81 (s, 3H), 1.53 (s, 9H) ppm.

Step 2: Tert-Butyl 6-[2-Methoxy-4-(Trifluoromethoxy)Phenoxy]-2-Methyl-3-(Trifluoromethyl)Benzoate

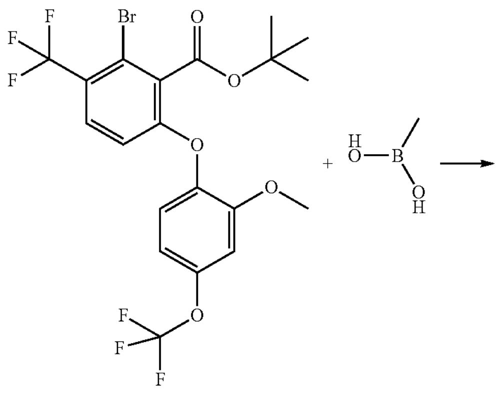

-continued

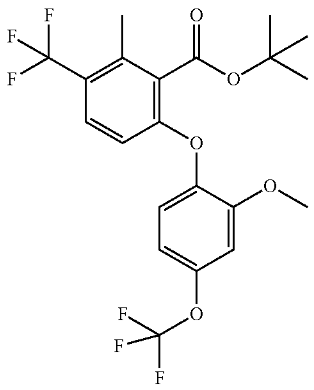

A microwave vial was loaded with tert-butyl 2-bromo-6-[2-methoxy-4-(trifluoromethoxy)phenoxy]-3-(trifluoromethyl)benzoate (1.0 g, 1.882 mmol), methylboronic acid (563 mg, 9.405 mmol), ferrous; cyclopenta-1,4-dien-1-yl (diphenyl)phosphane; dichloromethane; dichloropalladium (154 mg, 0.1886 mmol), and $K_2CO_3$ (780 mg, 5.644 mmol). The reaction vial was capped, purged with nitrogen, and 1,4-dioxane (6.0 mL) and water (600 μL) were added via syringe. The reaction was heated at 120° C. (oil bath) for 30 minutes. The reaction mixture was cooled to room temperature and was then directly purified by silica gel column chromatography using a gradient of 1-100% EtOAc in hexanes to give tert-butyl 6-[2-methoxy-4-(trifluoromethoxy)phenoxy]-2-methyl-3-(trifluoromethyl)benzoate (780 mg, 89%) as a clear oil. $^1$H NMR (400 MHz, DMSO-d6) δ 7.66 (d, J=8.9 Hz, 1H), 7.25 (d, J=2.7 Hz, 1H), 7.15 (d, J=8.8 Hz, 1H), 7.08-6.92 (m, 1H), 6.68 (d, J=8.8 Hz, 1H), 3.81 (s, 3H), 2.38 (d, J=2.1 Hz, 3H), 1.50 (s, 9H) ppm.

Step 3: 6-[2-Methoxy-4-(Trifluoromethoxy)Phenoxy]-2-Methyl-3-(Trifluoromethyl)Benzoic Acid

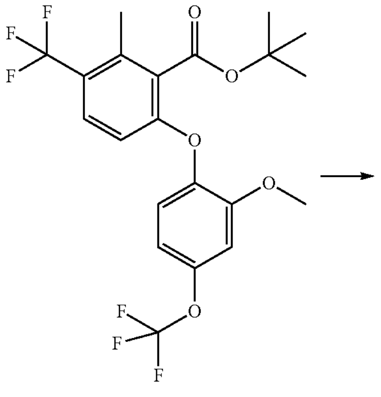

-continued

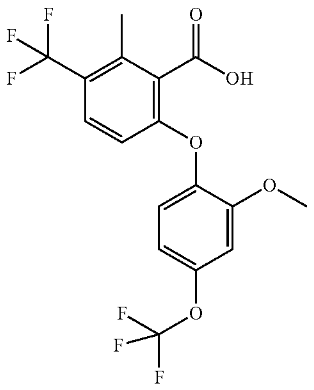

A solution of tert-butyl 6-[2-methoxy-4-(trifluoromethoxy)phenoxy]-2-methyl-3-(trifluoromethyl)benzoate (4.0 g, 8.577 mmol), TFA (100 mL, 1.298 mol), water (6 mL, 333.1 mmol), and THF (16 mL), was stirred at room temperature for 1 hour. The solution was evaporated to dryness under reduced pressure and the residue was purified by silica gel column chromatography using a gradient eluent of 1-10% MeOH in dichloromethane to give 6-[2-methoxy-4-(trifluoromethoxy)phenoxy]-2-methyl-3-(trifluoromethyl) benzoic acid (3.4 g, 92%) as a light brown semisolid. $^1$H NMR (400 MHz, DMSO-d6) δ 13.51 (s, 1H), 7.64 (d, J=8.8 Hz, 1H), 7.25 (d, J=2.7 Hz, 1H), 7.21 (d, J=8.8 Hz, 1H), 7.12-6.90 (m, 1H), 6.59 (d, J=8.8 Hz, 1H), 3.80 (s, 3H), 2.40 (s, 3H) ppm. ESI-MS m/z calc. 410.0589, found 411.0 $(M+1)^+$; Retention time (Method B): 1.87 minutes.

Step 4: 6-[2-Methoxy-4-(Trifluoromethoxy)Phenoxy]-2-Methyl-3-(Trifluoromethyl)Benzoyl Chloride

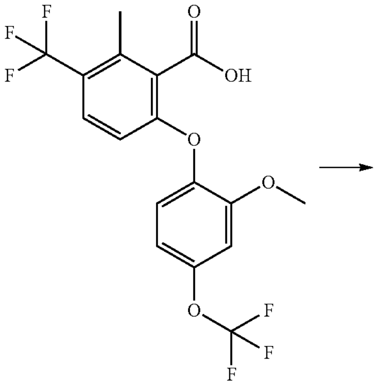

-continued

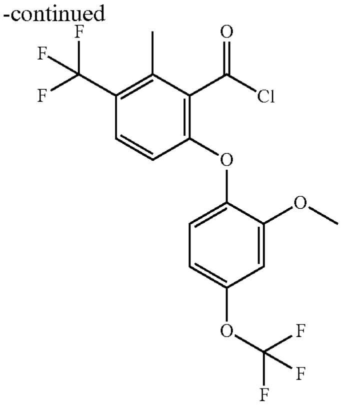

6-[2-methoxy-4-(trifluoromethoxy)phenoxy]-2-methyl-3-(trifluoromethyl)benzoic acid (1.11 g, 2.706 mmol) was dissolved in dichloromethane (18 mL). DMF (25 μL, 0.3229 mmol) was added. Oxalyl chloride (1.65 mL, 18.91 mmol) was slowly added dropwise while stirring the reaction mixture in a 0° C. ice bath. The ice bath was then removed, and the reaction mixture was allowed to stir at room temperature for 1 hour. Volatiles were then removed under reduced pressure. Additional dichloromethane was added (~20 mL), and the solution was again concentrated to dryness. 6-[2-Methoxy-4-(trifluoromethoxy)phenoxy]-2-methyl-3-(trifluoromethyl)benzoyl chloride was obtained as a colorless oil which was used directly in the next step.

Step 5: 4-[[6-[2-Methoxy-4-(Trifluoromethoxy)Phenoxy]-2-Methyl-3-(Trifluoromethyl)Benzoyl]Amino]Pyridine-2-Carboxamide (151)

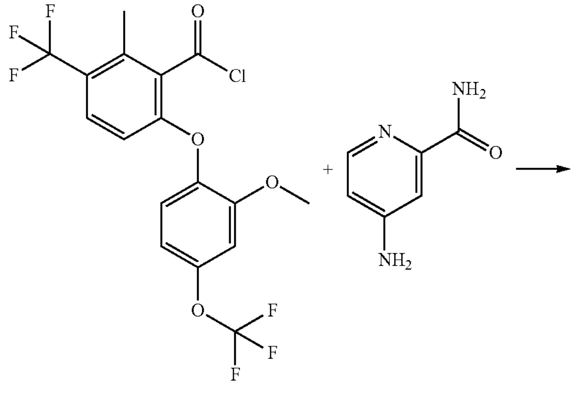

-continued

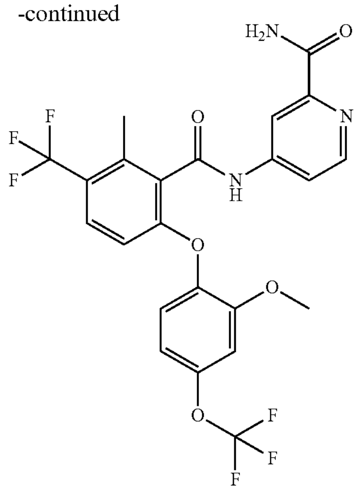

A solution of 6-[2-methoxy-4-(trifluoromethoxy)phenoxy]-2-methyl-3-(trifluoromethyl)benzoyl chloride (500 mg, 1.166 mmol) in NMP (4 mL) was added to a prepared solution of 4-aminopyridine-2-carboxamide (320 mg, 2.333 mmol) and DIEA (1.22 mL, 7.004 mmol) in NMP (4 mL). The reaction mixture was allowed to stir at room temperature overnight. It was then diluted with EtOAc (75 mL) and washed with water (2×75 mL) and brine (3×75 mL). The organic layer was dried over sodium sulfate, filtered and concentrated under reduced pressure. The crude product was chromatographed on silica gel column eluting with a 0-70% EtOAc/hexane gradient to provide 4-[[6-[2-methoxy-4-(trifluoromethoxy)phenoxy]-2-methyl-3-(trifluoromethyl)benzoyl]amino]pyridine-2-carboxamide (202 mg, 32%) as a white solid. $^1$H NMR (400 MHz, DMSO-d6) δ 11.25 (s, 1H), 8.54 (d, J=5.5 Hz, 1H), 8.37 (d, J=2.1 Hz, 1H), 8.09 (d, J=2.9 Hz, 1H), 7.86 (dd, J=5.5, 2.1 Hz, 1H), 7.71 (d, J=8.9 Hz, 1H), 7.64 (d, J=2.8 Hz, 1H), 7.30 (d, J=8.8 Hz, 1H), 7.23 (d, J=2.6 Hz, 1H), 7.06-7.00 (m, 1H), 6.64 (d, J=8.8 Hz, 1H), 3.78 (s, 3H), 2.43 (s, 3H) ppm. ESI-MS m/z calc. 529.10724, found 530.3 $(M+1)^+$; Retention time (Method B): 1.79 minutes.

The compounds set forth in Table 14 were prepared by methods analogous to the preparation of compound 151 in Example 21.

TABLE 14

Additional Compounds Prepared by Methods Analogous to Example 21.

| Cmpd No. | Compound Name | LC/MS | NMR (shifts in ppm) |
|---|---|---|---|
| 152 | 4-[[6-(2,3-difluoro-4-isopropoxy-phenoxy)-2-methyl-3-(trifluoromethyl)benzoyl]amino]pyridine-2-carboxamide | ESI-MS m/z calc. 529.10724, found 530.2 (M + 1)+; Retention time (Method B): 1.79 minutes | 1H NMR (400 MHz, DMSO-d6) δ 11.15 (s, 1H), 8.89 (d, J = 2.4 Hz, 1H), 8.33 (dd, J = 8.6, 2.4 Hz, 1H), 8.11-7.95 (m, 2H), 7.71 (d, J = 8.9 Hz, 1H), 7.55 (s, 1H), 7.30 (d, J = 8.8 Hz, 1H), 7.23 (d, J = 2.7 Hz, 1H), 7.08-6.99 (m, 1H), 6.64 (d, J = 8.8 Hz, 1H), 3.78 (s, 3H), 2.44 (s, 3H). |
| 153 | 4-[[6-[2-methoxy-4-(trifluoromethoxy)phenoxy]-2-methyl-3-(trifluoromethyl)benzo- | ESI-MS m/z calc. 543.12286, found 544.2 (M + 1)+; | 1H NMR (400 MHz, DMSO-d6) δ 10.45 (s, 1H), 8.48 (s, 1H), 8.45 (s, 1H), 8.06 (s, 1H), 7.70 (d, J = 8.9 Hz, 1H), 7.60 (s, 1H), 7.31 (d, J = 8.7 Hz, 1H), 7.25 (s, 1H), 7.04 (d, J = 8.9 |

TABLE 14-continued

Additional Compounds Prepared by Methods Analogous to Example 21.

| Cmpd No. | Compound Name | LC/MS | NMR (shifts in ppm) |
|---|---|---|---|
| | yl]amino]-5-methyl-pyridine-2-carboxamide | Retention time (Method B): 1.8 minutes | Hz, 1H), 6.63 (d, J = 8.9 Hz, 1H), 3.80 (s, 3H), 2.31 (s, 3H). |

Example 22

4-[[4-(3-Furyl)-2-[2-Methoxy-4-(Trifluoromethoxy) Phenoxy]Benzoyl]Amino]Pyridine-2-Carboxamide (154)

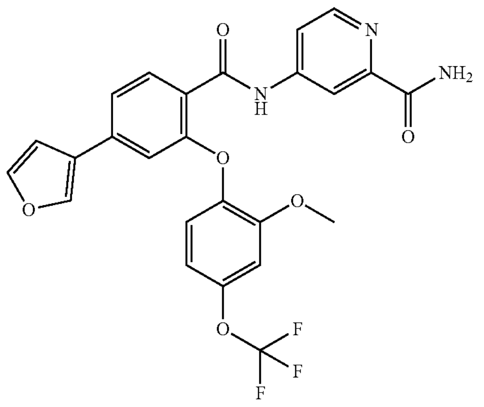 [SMILES: COc1cc(OC(F)(F)F)ccc1Oc1cc(-c2ccoc2)ccc1C(=O)Nc1ccnc(C(N)=O)c1]

Step 1: 4-Bromo-2-[2-Methoxy-4-(Trifluoromethoxy)Phenoxy]Benzaldehyde

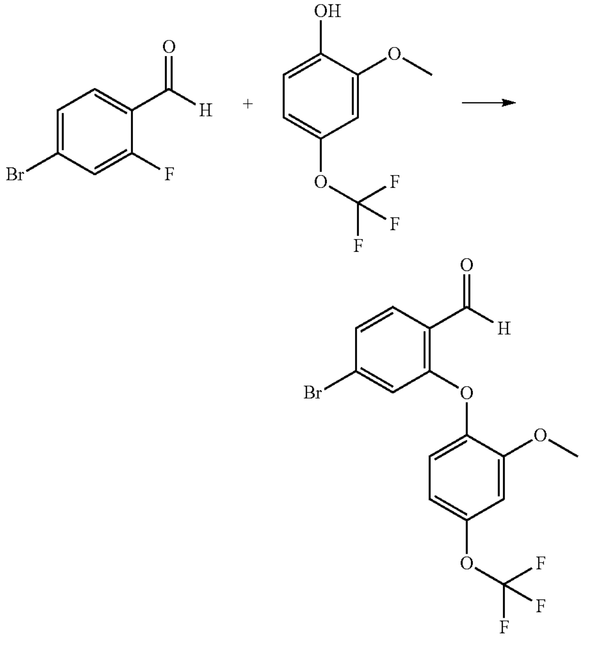

To a solution of 4-bromo-2-fluoro-benzaldehyde (3.70 g, 18.23 mmol) in DMF (35 mL) was added $Cs_2CO_3$ (7.50 g, 23.02 mmol) and 2-methoxy-4-(trifluoromethoxy)phenol (4.17 g, 20.04 mmol). The reaction mixture was stirred at RT for 16 h. The reaction mixture was partitioned between ethyl acetate and water. The organic layer was washed with water, aqueous $NaHCO_3$ (50%) and brine, then dried over $MgSO_4$, filtered and concentrated in vacuo. Purification by silica gel column chromatography using a EtOAc/hexanes eluent provided 4-bromo-2-[2-methoxy-4-(trifluoromethoxy)phenoxy]benzaldehyde (6.77 g, 95%). ESI-MS m/z calc. 389.97147, found 392.9 $(M+1)^+$; Retention time (Method A): 0.8 minutes. $^1H$ NMR (400 MHz, DMSO-d6) δ 10.43 (s, 1H), 7.75 (d, J=8.3 Hz, 1H), 7.48-7.43 (m, 1H), 7.40 (d, J=8.8 Hz, 1H), 7.28 (d, J=2.7 Hz, 1H), 7.05 (ddd, J=8.8, 2.8, 1.3 Hz, 1H), 6.88 (d, J=1.7 Hz, 1H), 3.80 (s, 3H) ppm.

Step 2: 4-Bromo-2-[2-Methoxy-4-(Trifluoromethoxy)Phenoxy]Benzoic Acid

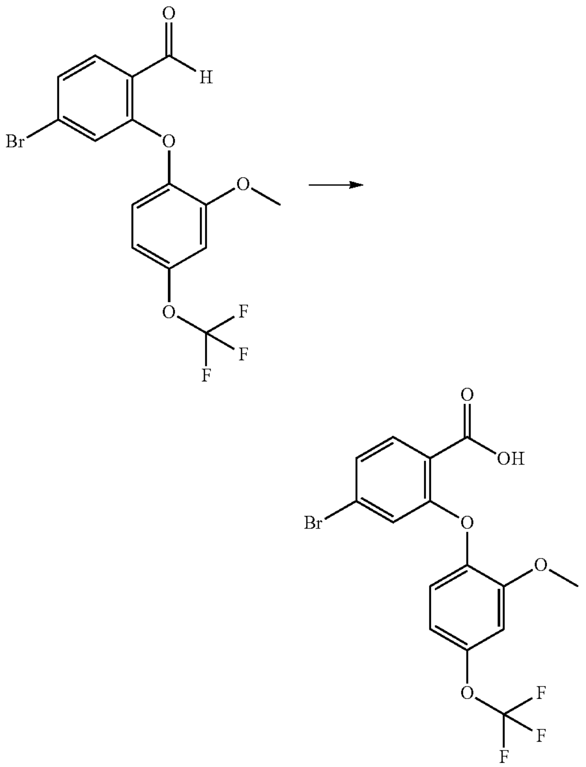

A mixture of 4-bromo-2-[2-methoxy-4-(trifluoromethoxy)phenoxy]benzaldehyde (6.74 g, 17.23 mmol) and $NaH_2PO_4$ (3.10 g, 25.84 mmol) in tert-butyl alcohol (60 mL)/water (35 mL)/acetonitrile (35 mL) at 0° C. was treated with 2-methylbut-2-ene (8.0 mL, 75.51 mmol) followed by the portion-wise addition of sodium chlorite (2.92 g, 25.83 mmol) over 10 minutes. The mixture was allowed to warm to RT and stirred for 16 h. Additional $NaH_2PO_4$ (3.10 g, 25.84 mmol) and sodium chlorite (2.92 g, 25.83 mmol) were added and the reaction mixture stirred for 30 minutes. The reaction mixture was acidified to pH 1-2 with aqueous HCl (175 mL of 1 M, 175.0 mmol) and partitioned with ethyl acetate. Excess sodium sulfite solid was added to the aqueous layer to remove the faint yellow color. The two layers were separated and the aqueous layer was extracted with ethyl acetate (3×25 mL). The combined organics were washed with brine, dried over $Na_2SO_4$, filtered and concentrated to an off-white solid. The solid was stirred/triturated with hexane (100 mL) for 1 h then filtered to provide 4-bromo-2-[2-methoxy-4-(trifluoromethoxy)phenoxy]benzoic acid (6.70 g, 96%) as a white solid. ESI-MS m/z calc. 405.96637, found 407.9 $(M+1)^+$; Retention time (Method A): 0.72 minutes. $^1H$ NMR (400 MHz, DMSO-d6) δ 13.03 (s, 1H), 7.75 (d, J=8.4 Hz, 1H), 7.39 (dd, J=8.3, 1.8 Hz, 1H), 7.21 (d, J=2.7 Hz, 1H), 7.09 (d, J=8.8 Hz, 1H), 6.99-6.94 (m, 1H), 6.88 (d, J=1.8 Hz, 1H), 3.80 (s, 3H) ppm.

Step 3: 4-[[4-Bromo-2-[2-Methoxy-4-(Trifluoromethoxy)Phenoxy]Benzoyl]Amino]Pyridine-2-Carboxamide

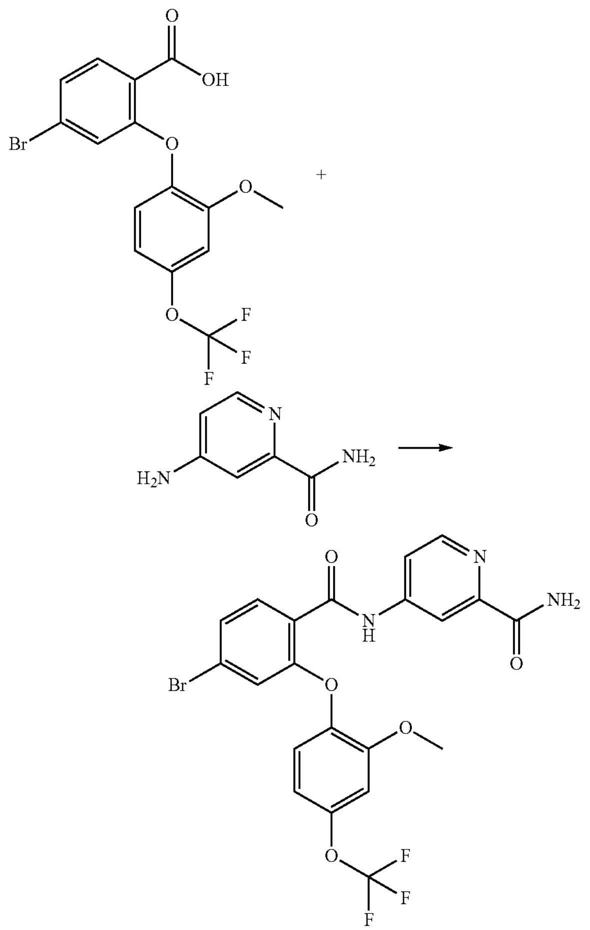

4-Bromo-2-[2-methoxy-4-(trifluoromethoxy)phenoxy]benzoic acid (2.011 g, 4.939 mmol) in anhydrous DCM (16 mL) under nitrogen was treated with DMF (20 μL, 0.2583 mmol), cooled in an ice bath and the suspension treated dropwise with oxalyl chloride (700 μL, 8.024 mmol). The solution was stirred for 15 minutes and then at 35° C. for 15 minutes (until no further gas evolution was observed). The acid chloride solution was concentrated under vacuo and the resulting solid was dissolved in DCM (5 mL) then added drop-wise to a cold solution of 4-aminopyridine-2-carboxamide (0.812 g, 5.921 mmol) and DIEA (2.2 mL, 12.63 mmol) in NMP (20 mL). The clear orange-colored reaction mixture was then stirred at RT for 2 h. The reaction was concentrated in vacuo, diluted with ethyl acetate and washed with water (2×), aqueous $NaHCO_3$ (50%) and brine. The organic phase was dried over Na2SO4, filtered and concentrated. The resulting light orange solid was triturated with cold DCM (25 mL) and filtered. The solid was rinsed with minimal cold DCM to remove color and air dried to provide 4-[[4-bromo-2-[2-methoxy-4-(trifluoromethoxy)phenoxy]benzoyl]amino]pyridine-2-carboxamide (1.210 g, 47%). ESI-MS m/z calc. 525.0147, found 527.0 $(M+1)^+$; Retention time (Method A): 0.71 minutes. $^1H$ NMR (400 MHz, DMSO-d6) δ 10.88 (s, 1H), 8.51 (d, J=5.5 Hz, 1H), 8.30 (d, J=2.1 Hz, 1H), 8.08 (d, J=2.9 Hz, 1H), 7.85 (dd, J=5.5, 2.1 Hz, 1H), 7.64 (d, J=8.1 Hz, 2H), 7.45 (dd, J=8.2, 1.7 Hz, 1H), 7.31 (d, J=8.8 Hz, 1H), 7.19 (d, J=2.6 Hz, 1H), 7.05-6.97 (m, 1H), 6.93 (d, J=1.7 Hz, 1H), 3.77 (s, 3H) ppm.

Step 4: 4-[[4-(3-Furyl)-2-[2-Methoxy-4-(Trifluoromethoxy)Phenoxy]Benzoyl]Amino]Pyridine-2-Carboxamide (154)

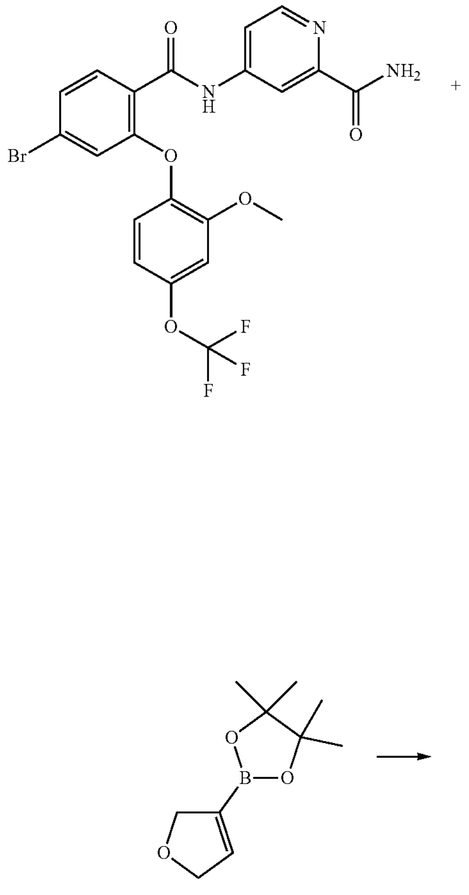

-continued

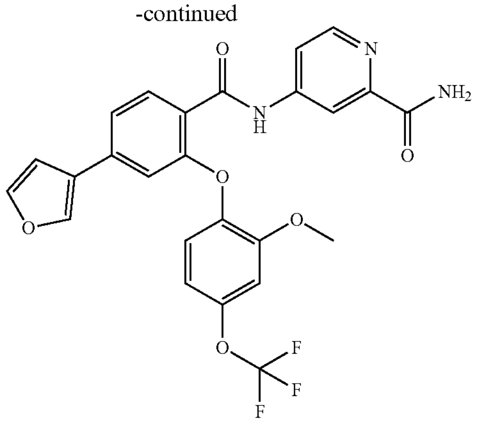

A solution of 4-[[4-bromo-2-[2-methoxy-4-(trifluoromethoxy)phenoxy]benzoyl]amino]pyridine-2-carboxamide (30 mg, 0.05701 mmol), 2-(2,5-dihydrofuran-3-yl)-4,4,5,5-tetramethyl-1,3,2-dioxaborolane (17 mg, 0.08671 mmol), $Pd(dppf)_2Cl_2$ (5 mg, 0.006123 mmol), $K_2CO_3$ (15 mg, 0.1085 mmol) in dioxane (500 μL)/water (50 μL) was flushed with $N_2$ and heated at 100° C. for 16 h. The reaction mixture was purified by reverse phase HPLC (gradient of 10-99% acetonitrile in water containing HCl as a modifier) to give 4-[[4-(3-furyl)-2-[2-methoxy-4-(trifluoromethoxy)phenoxy]benzoyl]amino]pyridine-2-carboxamide (1.0 mg, 3%), ESI-MS m/z calc. 513.11475, found 514.2 $(M+1)^+$; Retention time (Method B): 1.75 minutes.

The compounds set forth in Table 15 were prepared by methods analogous to the preparation of compound 154 and Example 22.

TABLE 15

Additional Compounds Prepared By Methods Analogous to Example 22.

| Cmpd No. | Compound Name | LC/MS | NMR (shifts in ppm) |
|---|---|---|---|
| 155 | 4-[[4-(4-chlorophenyl)-2-[2-methoxy-4-(trifluoromethoxy)phenoxy]benzoyl]amino]pyridine-2-carboxamide | ESI-MS m/z calc. 557.09656, found 558.3 (M + 1)+; Retention time (Method B): 1.48 minutes | 1H NMR (400 MHz, DMSO-d6) ä 10.88 (s, 1H), 8.51 (d, J = 5.5 Hz, 1H), 8.31 (d, J = 2.2 Hz, 1H), 8.11-8.06 (m, 1H), 7.86 (dd, J = 5.6, 2.2 Hz, 1H), 7.79 (d, J = 8.0 Hz, 1H), 7.68-7.60 (m, 3H), 7.60-7.49 (m, 3H), 7.23 (d, J = 8.8 Hz, 1H), 7.15 (d, J = 2.7 Hz, 1H), 7.10 (d, J = 1.6 Hz, 1H), 6.97 (d, J = 9.1 Hz, 1H), 3.77 (s, 3H). |
| 156 | 4-[[4-(4-fluorophenyl)-2-[2-methoxy-4-(trifluoromethoxy)phenoxy]benzoyl]amino]pyridine-2-carboxamide | ESI-MS m/z calc. 541.1261, found 542.1 (M + 1)+; Retention time (Method B): 1.32 minutes | $^1H$ NMR (400 MHz, DMSO-$d_6$) δ 10.89 (s, 1H), 8.51 (d, J = 5.5 Hz, 1H), 8.31 (s, 1H), 8.10 (s, 1H), 7.91-7.83 (m, 1H), 7.78 (d, J = 7.9 Hz, 1H), 7.72-7.60 (m, 3H), 7.56 (d, J = 7.9 Hz, 1H), 7.30 (t, J = 8.6 Hz, 2H), 7.23 (d, J = 8.8 Hz, 1H), 7.15 (d, J = 2.6 Hz, 1H), 7.08 (s, 1H), 6.98 (d, 1H), 3.77 (s, 3H). |
| 157 | 4-[[2-[2-methoxy-4-(trifluoromethoxy)phenoxy]-4-[4-(trifluoromethyl)phenyl]benzoyl]amino]pyridine-2-carboxamide | ESI-MS m/z calc. 591.12286, found 592.2 (M + 1)+; Retention time (Method B): 1.51 minutes | $^1H$ NMR (400 MHz, DMSO-$d_6$) δ 10.94 (s, 1H), 8.52 (d, J = 5.5 Hz, 1H), 8.32 (d, J = 2.1 Hz, 1H), 8.10 (s, 1H), 7.93-7.75 (m, 6H), 7.71-7.57 (m, 2H), 7.25 (d, J = 8.8 Hz, 1H), 7.21-7.09 (m, 2H), 6.98 (d, 1H), 3.77 (s, 3H). |

Example 23

4-[[2-(4-Fluoro-2-Methoxy-Phenoxy)-4-(Trifluoromethyl)Benzoyl]Amino]Pyridine-2-Carboxamide (159)

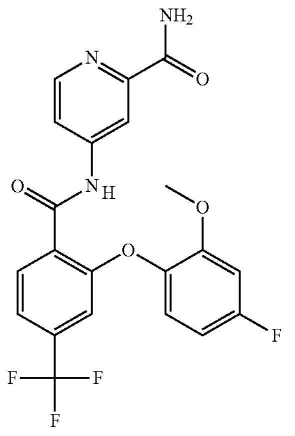

Step 1: 4-[[2-Bromo-4-(Trifluoromethyl)Benzoyl]Amino]Pyridine-2-Carboxamide

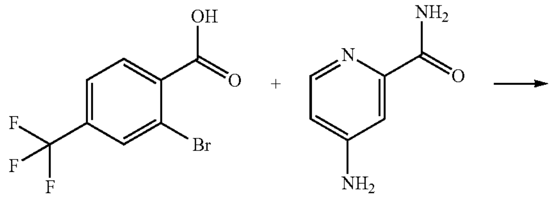

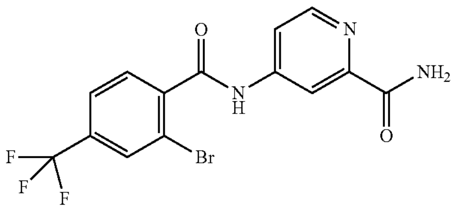

To a solution of 2-bromo-4-(trifluoromethyl)benzoic acid (5.0 g, 18.59 mmol) in DMF (135 μL, 1.744 mmol), and DCM (50 mL) at 0° C. was added oxalyl chloride (7.6 mL, 87.12 mmol) dropwise over 3 minutes. The mixture was stirred at RT for 2 h then concentrated in vacuo. The intermediate was taken up in DCM (5 mL) and added drop-wise to a solution of 4-aminopyridine-2-carboxamide (2.4 g, 17.50 mmol), DIEA (3.0 mL, 17.22 mmol), and DCM (25 mL) at 0° C. The reaction mixture was stirred at RT for 2 h. The reaction mixture concentrated under vacuo and purified by silica gel column chromatography using a MeOH/DCM eluent. The resultant material was triturated with diethyl ether (100 mL) and filtered to give 4-[[2-bromo-4-(trifluoromethyl)benzoyl]amino]pyridine-2-carboxamide (1.2 g, 17%) as a white solid. $^1$H NMR (500 MHz, DMSO-d6) δ 11.23 (s, 1H), 8.57 (d, J=5.5 Hz, 1H), 8.38 (d, J=2.3 Hz, 1H), 8.19 (d, J=1.7 Hz, 1H), 8.17-8.09 (m, 1H), 7.98-7.82 (m, 3H), 7.69 (d, J=2.8 Hz, 1H) ppm.

Step 2: 4-[[2-(4-Fluoro-2-Methoxy-Phenoxy)-4-(Trifluoromethyl)Benzoyl]Amino]Pyridine-2-Carboxamide (159)

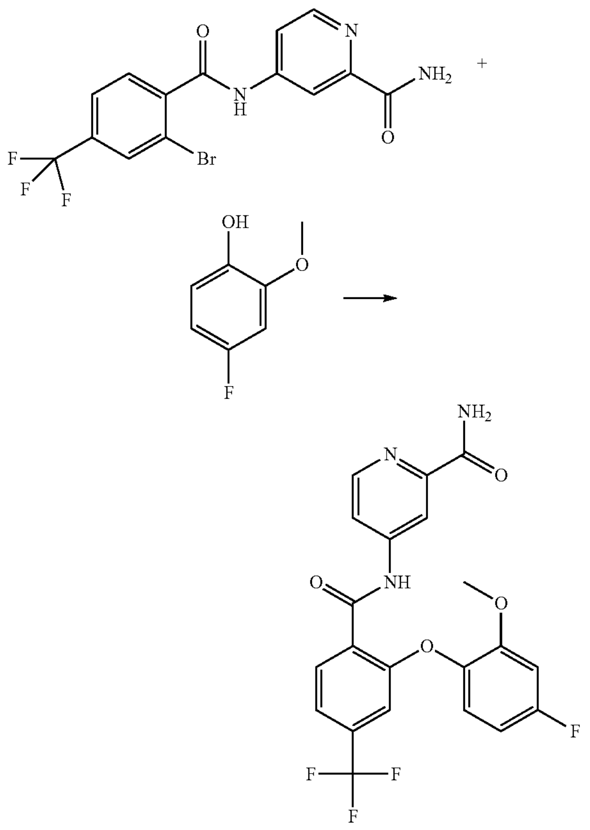

A mixture of 4-[[2-bromo-4-(trifluoromethyl)benzoyl]amino]pyridine-2-carboxamide (25 mg, 0.06441 mmol), 4-fluoro-2-methoxy-phenol (9.154 mg, 7.341 μL, 0.06441 mmol), $Cs_2CO_3$ (20.99 mg, 0.06441 mmol), CuI (3.679 mg, 0.01932 mmol), CsF (48.91 mg, 11.89 μL, 0.3220 mmol), and DMF (500.0 μL), was heated at 150° C. for 1 h. The crude was then purified by reverse phase HPLC (gradient of 10-99% acetonitrile in water containing HCl as a modifier) to give 4-[[2-(4-fluoro-2-methoxy-phenoxy)-4-(trifluoromethyl)benzoyl]amino]pyridine-2-carboxamide (8.0 mg, 25%) as a white solid. ESI-MS m/z calc. 449.09988, found 450.3 $(M+1)^+$; Retention time (Method B): 1.63 minutes. $^1$H NMR (400 MHz, DMSO-$d_6$) δ 11.08 (s, 1H), 8.54 (d, J=5.5 Hz, 1H), 8.35 (d, J=2.1 Hz, 1H), 8.12 (d, J=2.8 Hz, 1H), 7.88 (t, J=6.1 Hz, 2H), 7.67 (d, J=2.9 Hz, 1H), 7.57 (d, J=8.0 Hz, 1H), 7.32 (dd, J=8.9, 5.8 Hz, 1H), 7.16 (ddd, J=10.6, 7.6, 2.9 Hz, 1H), 6.91-6.83 (m, 2H), 3.74 (s, 3H) ppm.

The compounds set forth in Table 16 were prepared by methods analogous to the preparation of compound 159 and Example 23.

TABLE 16

| Additional Compounds Prepared By Methods Analogous to Example 23. | | | |
|---|---|---|---|
| Cmpd No. | Compound Name | LC/MS | NMR (shifts in ppm) |
| 160 | 4-[[2-(3-fluoro-4-isopropoxy-phenoxy)-4-(trifluoromethyl)benzoyl]amino]pyridine-2-carboxamide | ESI-MS m/z calc. 477.13116, found 478.33 (M + 1)+; Retention time (Method B): 1.59 minutes | |
| 161 | 4-[[2-(2-chloro-4-fluoro-phenoxy)-4-(trifluoromethyl)benzoyl]amino]pyridine-2-carboxamide | ESI-MS m/z calc. 453.05032, found 454.25 (M + 1)+; Retention time (Method B): 1.65 minutes | $^1$H NMR (400 MHz, DMSO-$d_6$) δ 11.23 (s, 1H), 8.55 (d, J = 5.6 Hz, 1H), 8.34 (d, J = 2.1 Hz, 1H), 8.18 (s, 1H), 7.93 (d, J = 7.9 Hz, 1H), 7.86 (dd, J = 5.6, 2.2 Hz, 1H), 7.71 (d, J = 8.3 Hz, 2H), 7.50 (q, J = 9.5 Hz, 1H), 7.40-7.32 (m, 2H), 7.01 (d, J = 9.6 Hz, 1H). |
| 162 | 4-[[2-(5-chloro-2-methoxy-phenoxy)-4-(trifluoromethyl)benzoyl]amino]pyridine-2-carboxamide | ESI-MS m/z calc. 465.0703, found 466.29 (M + 1)+; Retention time (Method B): 1.59 minutes | $^1$H NMR (400 MHz, DMSO-$d_6$) δ 11.10 (s, 1H), 8.53 (d, J = 5.5 Hz, 1H), 8.32 (d, J = 2.1 Hz, 1H), 8.11 (d, J = 2.9 Hz, 1H), 7.91-7.81 (m, 2H), 7.67 (d, J = 2.9 Hz, 1H), 7.63-7.56 (m, 1H), 7.12 (d, J = 9.0 Hz, 2H), 7.05 (s, 1H), 6.97 (d, J = 9.0 Hz, 2H), 4.57 (p, J = 6.0 Hz, 1H), 1.24 (d, J = 6.0 Hz, 6H). |
| 163 | 4-[[2-(3,4-difluorophenoxy)-4-(trifluoromethyl)benzoyl]amino]pyridine-2-carboxamide | ESI-MS m/z calc. 437.0799, found 438.29 (M + 1)+; Retention time: 1.62 minutes | $^1$H NMR (400 MHz, DMSO-$d_6$) δ 11.11 (s, 1H), 8.54 (d, J = 5.5 Hz, 1H), 8.33 (d, J = 2.1 Hz, 1H), 8.12 (d, J = 2.8 Hz, 1H), 7.90-7.82 (m, 2H), 7.67 (s, 1H), 7.60 (d, J = 8.0 Hz, 1H), 7.08 (dd, J = 9.0, 4.7 Hz, 1H), 7.03 (s, 1H), 6.75 (t, J = 8.6 Hz, 1H), 4.60 (t, J = 8.7 Hz, 2H), 3.26 (t, J = 8.7 Hz, 2H). |
| 164 | 4-[[2-(4-isopropoxyphenoxy)-4-(trifluoromethyl)benzoyl]amino]pyridine-2-carboxamide | ESI-MS m/z calc. 459.1406, found 460.34 (M + 1)+; Retention time (Method B): 1.74 minutes | $^1$H NMR (400 MHz, DMSO-$d_6$) δ 11.15 (s, 1H), 8.54 (d, J = 5.5 Hz, 1H), 8.32 (d, J = 2.1 Hz, 1H), 8.14 (s, 1H), 7.90 (d, J = 7.9 Hz, 1H), 7.85 (dd, J = 5.5, 2.2 Hz, 1H), 7.70 (s, 1H), 7.65 (d, J = 8.1 Hz, 1H), 7.24-7.15 (m, 2H), 7.12 (dd, J = 6.5, 3.0 Hz, 1H), 7.01 (dt, J = 8.3, 3.7 Hz, 1H), 2.20 (d, J = 1.9 Hz, 3H). |
| 165 | 4-[[2-[(4-fluoro-2,3-dihydrobenzofuran-7-yl)oxy]-4-(trifluoromethyl)benzoyl]amino]pyridine-2-carboxamide | ESI-MS m/z calc. 461.09988, found 462.3 (M + 1)+; Retention time (Method B): 1.63 minutes | $^1$H NMR (400 MHz, DMSO-$d_6$) δ 11.16 (s, 1H), 8.54 (d, J = 5.5 Hz, 1H), 8.34 (d, J = 2.1 Hz, 1H), 8.13 (d, J = 2.7 Hz, 1H), 7.91 (d, J = 7.9 Hz, 1H), 7.86 (dd, J = 5.6, 2.2 Hz, 1H), 7.72-7.67 (m, 1H), 7.64 (d, J = 7.8 Hz, 1H), 7.27 (dd, J = 11.2, 8.9 Hz, 1H), 7.21-7.15 (m, 1H), 7.06 (dd, J = 7.3, 2.8 Hz, 1H), 6.70 (dt, J = 8.9, 3.1 Hz, 1H), 3.79 (s, 3H). |
| 166 | 4-[[2-(4-fluoro-3-methyl-phenoxy)-4-(trifluoromethyl)benzoyl]amino]pyridine-2-carboxamide | ESI-MS m/z calc. 433.10495, found 434.3 (M + 1)+; Retention time (Method B): 1.68 minutes | $^1$H NMR (400 MHz, DMSO-$d_6$) δ 11.23 (s, 1H), 8.55 (d, J = 5.6 Hz, 1H), 8.34 (d, J = 2.1 Hz, 1H), 8.18 (s, 1H), 7.93 (d, J = 7.9 Hz, 1H), 7.86 (dd, J = 5.6, 2.2 Hz, 1H), 7.71 (d, J = 8.3 Hz, 2H), 7.50 (q, J = 9.5 Hz, 1H), 7.40-7.32 (m, 2H), 7.01 (d, J = 9.6 Hz, 1H). |
| 167 | 4-[[2-(4-fluoro-3-methoxy-phenoxy)-4-(trifluoromethyl)benzoyl]amino]pyridine-2-carboxamide | ESI-MS m/z calc. 449.09988, found 450.3 (M + 1)+; Retention time (Method B): 1.59 minutes | $^1$H NMR (400 MHz, DMSO-$d_6$) δ 11.10 (s, 1H), 8.53 (d, J = 5.5 Hz, 1H), 8.32 (d, J = 2.1 Hz, 1H), 8.11 (d, J = 2.9 Hz, 1H), 7.91-7.81 (m, 2H), 7.67 (d, J = 2.9 Hz, 1H), 7.63-7.56 (m, 1H), 7.12 (d, J = 9.0 Hz, 2H), 7.05 (s, 1H), 6.97 (d, J = 9.0 Hz, 2H), 4.57 (p, J = 6.0 Hz, 1H), 1.24 (d, J = 6.0 Hz, 6H). |

Example 24

4-[[2-Fluoro-6-[2-Methoxy-4-(Trifluoromethoxy) Phenoxy]-4-[4-(Trifluoromethyl)Cyclohexyl]Benzoyl]Amino]Pyridine-2-Carboxamide (Two Diastereoisomers) (168)

168-a

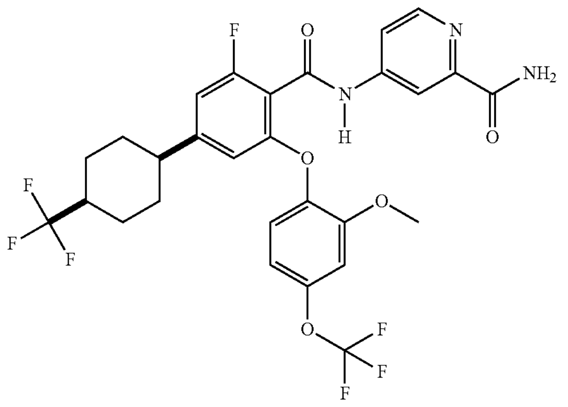

168-b

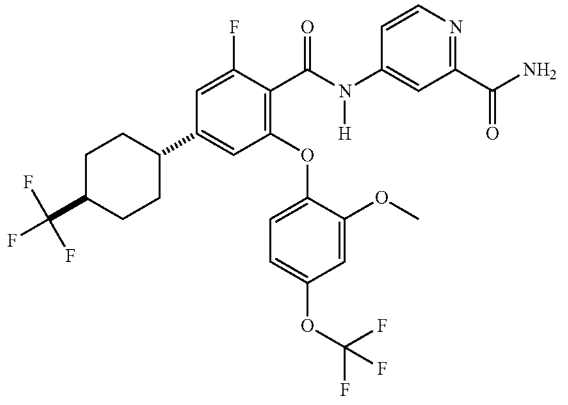

Step 1: 4-[[2-Fluoro-6-[2-Methoxy-4-(Trifluoromethoxy)Phenoxy]-4-[4-(Trifluoromethyl)Cyclohexen-1-Yl]Benzoyl]Amino]Pyridine-2-Carboxamide

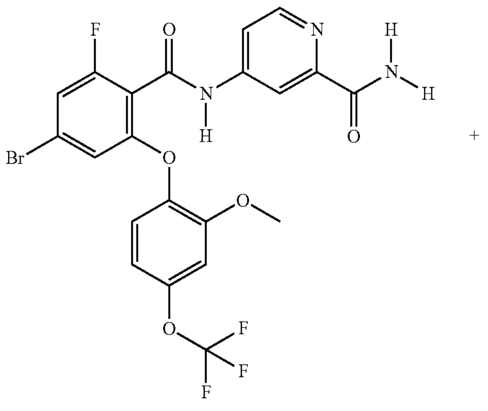

-continued

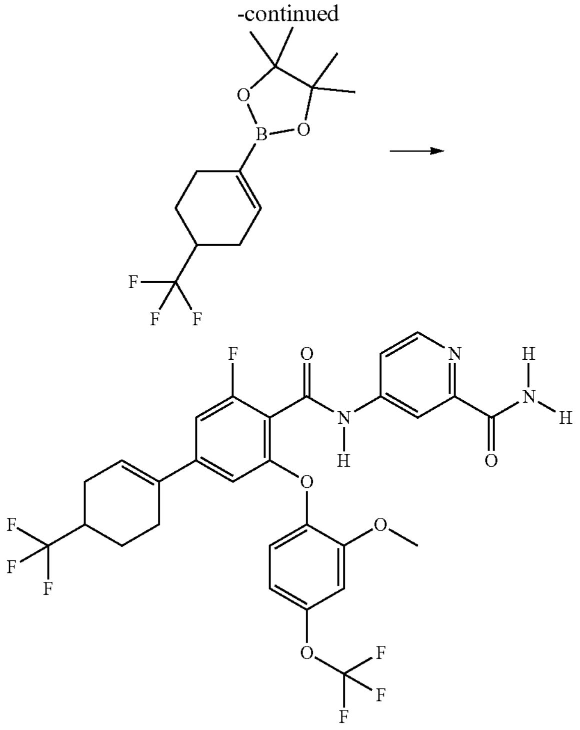

A solution of 4-[[4-bromo-2-fluoro-6-[2-methoxy-4-(trifluoromethoxy)phenoxy]benzoyl]amino]pyridine-2-carboxamide (25 mg, 0.046 mmol), 4,4,5,5-tetramethyl-2-[4-(trifluoromethyl)cyclohexen-1-yl]-1,3,2-dioxaborolane (25 mg, 0.092 mmol), $K_2CO_3$ (13 mg, 0.092 mmol), $Pd(dppf)_2Cl_2$ (7.5 mg, 0.0092 mmol), in dioxane (0.5 mL) and water (50 μL) was heated at 100° C. for 16 h. The reaction mixture was purified by reverse phase HPLC (gradient of 10-99% acetonitrile in water containing HCl as a modifier) to give 4-[[2-fluoro-6-[2-methoxy-4-(trifluoromethoxy)phenoxy]-4-[4-(trifluoromethyl)cyclohexen-1-yl]benzoyl]amino]pyridine-2-carboxamide (21.3 mg, 76%). ESI-MS m/z calc. 613.1448, found 614.3 $(M+1)^+$; Retention time (Method B): 2.01 minutes. $^1H$ NMR (400 MHz, DMSO-d6) δ 11.22 (s, 1H), 8.52 (d, J=5.5 Hz, 1H), 8.29 (d, J=2.2 Hz, 1H), 8.09 (d, J=2.9 Hz, 1H), 7.81 (dd, J=5.5, 2.2 Hz, 1H), 7.64 (d, J=2.9 Hz, 1H), 7.24-7.14 (m, 3H), 6.97 (dd, J=9.2, 2.3 Hz, 1H), 6.61 (s, 1H), 6.17 (s, 1H), 3.77 (s, 3H), 2.40 (d, J=7.3 Hz, 3H), 2.28-2.09 (m, 2H), 2.03 (d, J=12.4 Hz, 1H), 1.55 (td, J=12.4, 6.0 Hz, 1H) ppm.

Step 2: 4-[[2-Fluoro-6-[2-Methoxy-4-(Trifluoromethoxy)Phenoxy]-4-[4-(Trifluoromethyl)Cyclohexyl]Benzoyl]Amino]Pyridine-2-Carboxamide (Two Diastereoisomers) (168)

A solution of 4-[[2-fluoro-6-[2-methoxy-4-(trifluoromethoxy)phenoxy]-4-[4-(trifluoromethyl)cyclohexen-1-yl]benzoyl]amino]pyridine-2-carboxamide (15 mg, 0.02445 mmol) in EtOAc (250 μL)/MeOH (250 μL) was treated with Pd/C (1 mg, 0.009397 mmol). The mixture was degassed with a flow of $N_2$ (g) for 2 minutes, then purged with $H_2$ (balloon). The reaction was stirred at RT for 16 h. The mixture was purified by reverse phase HPLC Method B, resulting in two diastereoisomers. It is appreciated that both diastereomers of 4-[[2-fluoro-6-[2-methoxy-4-(trifluoromethoxy)phenoxy]-4-[4-(trifluoromethyl)cyclohexyl]benzoyl]amino]pyridine-2-carboxamide (168) were isolated and that those diastereomers have the structure of compounds 168-a and 168-b (above). However, the relative stereochemistry of diastereomers 1 and 2 was not determined.

Diastereomer 1: 4-[[2-fluoro-6-[2-methoxy-4-(trifluoromethoxy)phenoxy]-4-[4-(trifluoromethyl)cyclohexyl] benzoyl]amino]pyridine-2-carboxamide (4.1 mg, 71%). ESI-MS m/z calc. 615.1604, found 616.2 $(M+1)^+$; Retention time (Method B): 1.97 minutes. $^1H$ NMR (400 MHz, DMSO-$d_6$) δ 11.27 (s, 1H), 8.52 (d, J=5.5 Hz, 1H), 8.32 (d, J=2.1 Hz, 1H), 8.12 (s, 1H), 7.83 (dd, J=5.5, 2.2 Hz, 1H), 7.67 (s, 1H), 7.24 (d, J=8.8 Hz, 1H), 7.19 (d, J=2.7 Hz, 1H), 7.05-6.95 (m, 2H), 6.43 (s, 1H), 3.76 (s, 3H), 2.82-2.72 (m, 1H), 2.46 (m, 1H, obscured by DMSO), 1.75-1.55 (m, 8H) ppm.

Diastereomer 2: 4-[[2-fluoro-6-[2-methoxy-4-(trifluoromethoxy)phenoxy]-4-[4-(trifluoromethyl)cyclohexyl] benzoyl]amino]pyridine-2-carboxamide (1.7 mg, 29%), ESI-MS m/z calc. 615.1604, found 616.3 $(M+1)^+$; Retention time (Method B): 2.03 minutes respectively.

The compounds set forth in Table 17 were prepared by methods analogous to the preparation of compound 168. It is appreciated that both diastereomers of 4-[[4-(4-tert-butylcyclohexyl)-2-fluoro-6-[2-methoxy-4-(trifluoromethoxy) phenoxy]benzoyl]amino]pyridine-2-carboxamide (169) were isolated and that those diastereomers have the structure of compounds 169-a and 169-b (see Table A, above). However, the relative stereochemistry of the first and second eluting diastereomers was not determined.

TABLE 17

Additional Compounds Prepared By Methods Analogous to Example 24.

| Cmpd No. | Compound Name | LC/MS | NMR (shifts in ppm) |
|---|---|---|---|
| 169 (first diastereomer) | 4-[[4-(4-tert-butylcyclohexyl)-2-fluoro-6-[2-methoxy-4-(trifluoromethoxy)phenoxy] benzoyl]amino]pyridine-2-carboxamide | %), ESI-MS m/z calc. 603.23566, found 604.6 (M + 1)+; Retention time: (Method B) 2.3 minutes | |
| 169 (second diastereomer) | 4-[[4-(4-tert-butylcyclohexyl)-2-fluoro-6-[2-methoxy-4-(trifluoromethoxy)phenoxy] benzoyl]amino]pyridine-2-carboxamide | ESI-MS m/z calc. 603.23566, found 604.4 (M + 1)+; Retention time: (Method B) 2.37 minutes | $^1H$ NMR (400 MHz, DMSO-$d_6$) δ 11.22 (s, 1H), 8.51 (d, J = 5.5 Hz, 1H), 8.30 (d, J = 2.1 Hz, 1H), 8.10 (d, J = 2.9 Hz, 1H), 7.81 (dd, J = 5.6, 2.2 Hz, 1H), 7.65 (d, J = 2.8 Hz, 1H), 7.21 (d, J = 8.8 Hz, 1H), 7.18 (d, J = 2.8 Hz, 1H), 7.05-6.88 (m, 2H), 6.44 (s, 1H), 3.76 (s, 3H), 2.48-2.38 (m, 1H), 1.85-1.71 (m, 4H), 1.47-1.25 (m, 2H), 1.15-0.96 (m, 3H), 0.83 (s, 9H). |

Example 25

5-[[2-Fluoro-4-(4-Fluorophenyl)-6-[2-Methoxy-4-(Trifluoromethoxy)Phenoxy]Benzoyl]Amino]Pyridine-2-Carboxamide(170)

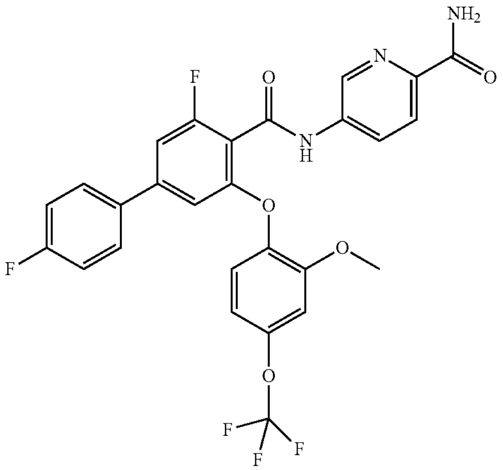 [SMILES: COc1cc(OC(F)(F)F)ccc1Oc1cc(-c2ccc(F)cc2)cc(F)c1C(=O)Nc1ccc(C(N)=O)nc1]

Step 1: 2-Fluoro-4-(4-Fluorophenyl)-6-[2-Methoxy-4-(Trifluoromethoxy)Phenoxy]Benzoic Acid

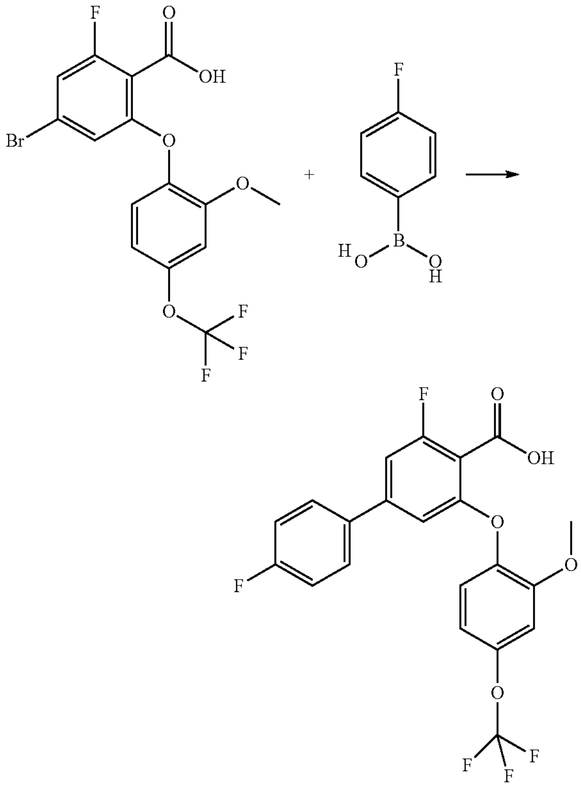

A solution of 4-bromo-2-fluoro-6-[2-methoxy-4-(trifluoromethoxy)phenoxy]benzoic acid (1.22 g, 2.870 mmol), (4-fluorophenyl)boronic acid (830 mg, 5.932 mmol), $Pd(PPh_3)_4$ (550 mg, 0.4760 mmol) and $Na_2CO_3$ (500 mg, 4.717 mmol) were combined in DMF (30 mL) and $H_2O$ (10 mL), then heated at 100° C. for 3 h. The reaction was poured carefully into 1N HCl (caution: gas evolution) then washed with DCM. The organic layer was dried over $Na_2SO_4$, filtered and concentrated in vacuo. Purification by silica gel column chromatography using a EtOAc/hexanes eluent gave 2-fluoro-4-(4-fluorophenyl)-6-[2-methoxy-4-(trifluoromethoxy)phenoxy]benzoic acid (970 mg, 77%). ESI-MS m/z calc. 440.06833, found 441.0 $(M+1)^+$; Retention time (Method B): 1.99.

Step 2: 2-Fluoro-4-(4-Fluorophenyl)-6-[2-Methoxy-4-(Trifluoromethoxy)Phenoxy]Benzoyl Chloride

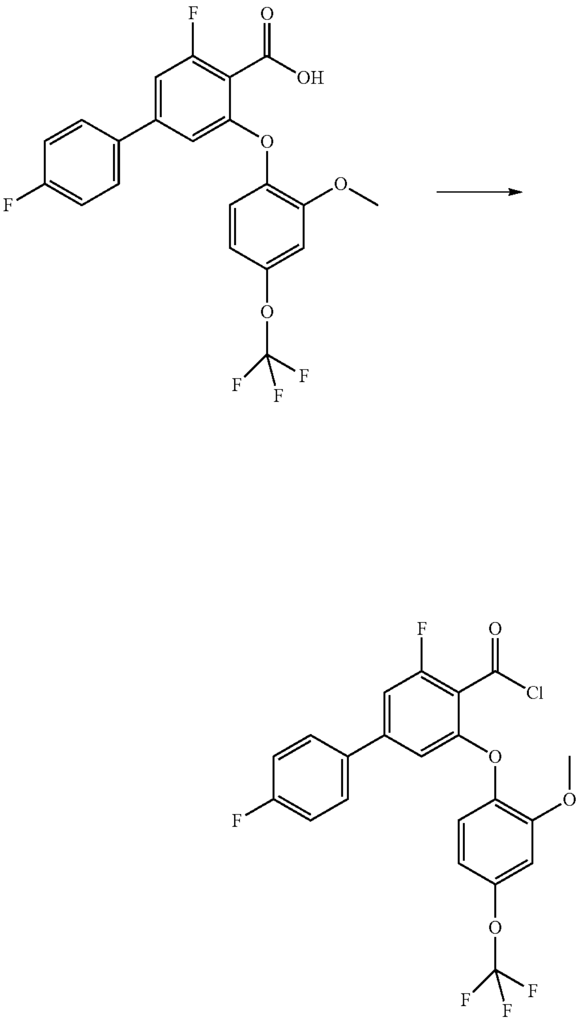

To a solution of 2-fluoro-4-(4-fluorophenyl)-6-[2-methoxy-4-(trifluoromethoxy)phenoxy]benzoic acid (500 mg, 1.136 mmol) and DMF (25 μL, 0.3229 mmol) in DCM (6 mL) at 0° C. was added oxalyl chloride (800 μL, 9.171 mmol) dropwise under a $N_2$ atmosphere. The ice bath was removed after 10 minutes and the reaction was stirred at RT for 50 minutes. The mixture was concentrated in vacuo to afford the crude 2-fluoro-4-(4-fluorophenyl)-6-[2-methoxy-4-(trifluoromethoxy)phenoxy]benzoyl chloride (520 mg, 100%) which was taken on without further purification.

Step 3: 5-[[2-Fluoro-4-(4-Fluorophenyl)-6-[2-Methoxy-4-(Trifluoromethoxy)Phenoxy]Benzoyl]Amino]Pyridine-2-Carboxamide (170)

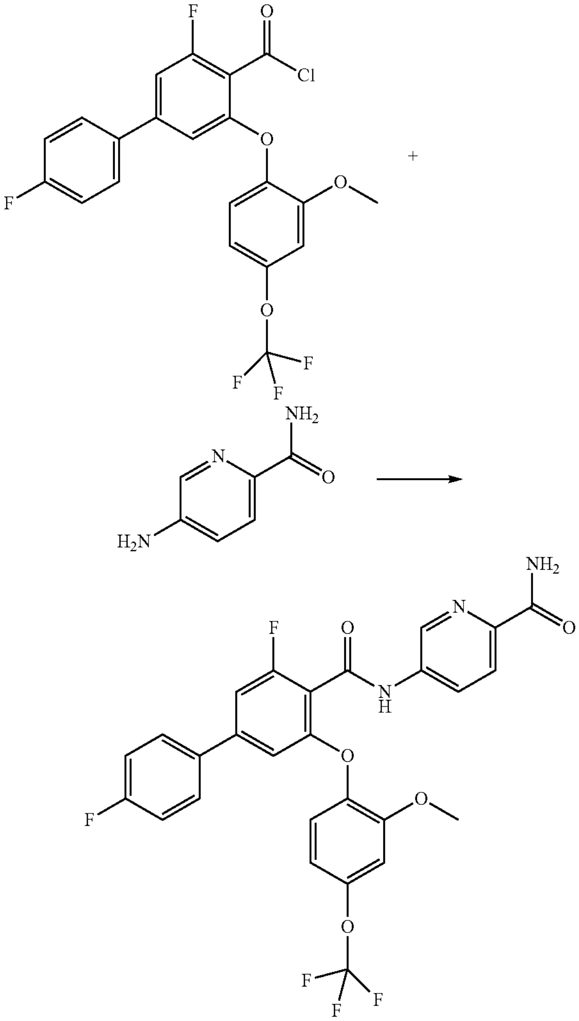

To a solution of 5-aminopyridine-2-carboxamide (9.715 mg, 0.07084 mmol), DMF (3.983 mg, 4.219 μL, 0.05449 mmol) and NMP (400 μL) was added DIEA (21.13 mg, 28.48 μL, 0.1635 mmol) under a $N_2$ atmosphere and the resulting clear solution was cooled to 0° C. A solution of 2-fluoro-4-(4-fluorophenyl)-6-[2-methoxy-4-(trifluoromethoxy)phenoxy]benzoyl chloride (25 mg, 0.05449 mmol) in NMP (200 μL) was then added and the reaction was stirred at RT for 16 h. The mixture was purified by reverse phase HPLC (gradient of 10-99% acetonitrile in water containing HCl as a modifier) to give 5-[[2-fluoro-4-(4-fluorophenyl)-6-[2-methoxy-4-(trifluoromethoxy)phenoxy]benzoyl]amino]pyridine-2-carboxamide (21.1 mg, 69%). ESI-MS m/z calc. 559.11664, found 559.91 $(M+1)^+$; Retention time (Method B): 1.97 minutes. $^1H$ NMR (400 MHz, DMSO-d6) δ 11.21 (s, 1H), 8.86 (d, J=2.4 Hz, 1H), 8.26 (dd, J=8.7, 2.4 Hz, 1H), 8.05 (s, 1H), 8.03 (s, 1H), 7.67 (dd, J=8.6, 5.4 Hz, 2H), 7.56 (s, 1H), 7.52-7.44 (m, 1H), 7.35-7.23 (m, 3H), 7.17 (d, J=2.7 Hz, 1H), 6.98 (d, J=8.8 Hz, 1H), 6.87 (s, 1H), 3.77 (s, 3H) ppm.

Example 26

4-[[4-(4-Chlorophenyl)-2-Fluoro-6-[2-Methoxy-4-(Trifluoromethoxy)Phenoxy]Benzoyl]Amino]Pyridine-2-Carboxamide (171)

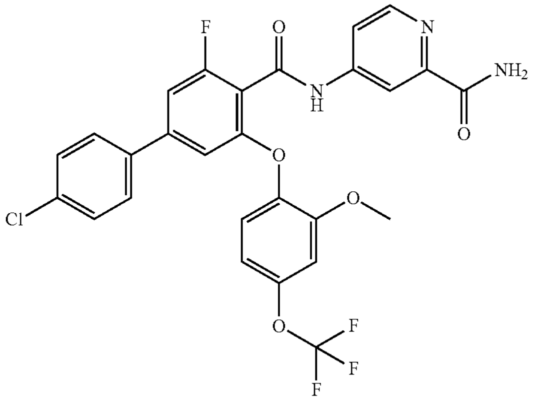 [SMILES: COc1cc(OC(F)(F)F)ccc1Oc1cc(-c2ccc(Cl)cc2)cc(F)c1C(=O)Nc1ccnc(C(N)=O)c1]

Step 1: 4-[[4-(4-Chlorophenyl)-2-Fluoro-6-[2-Methoxy-4-(Trifluoromethoxy)Phenoxy]Benzoyl]Amino]Pyridine-2-Carboxamide (171)

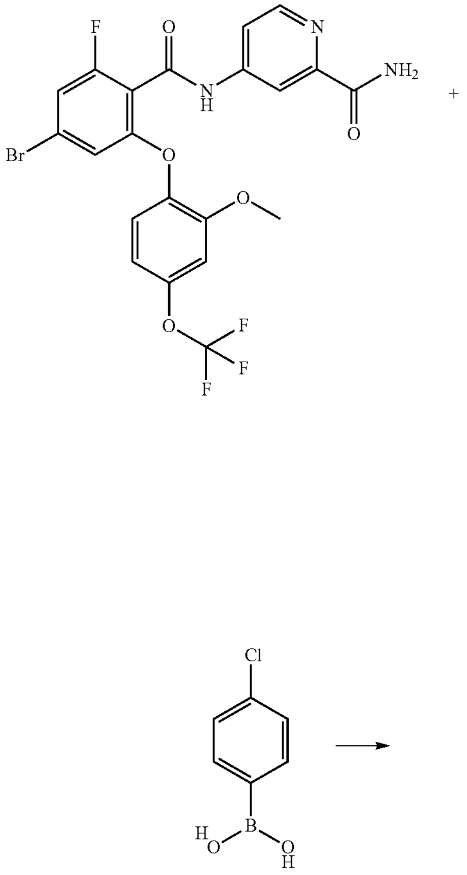

-continued

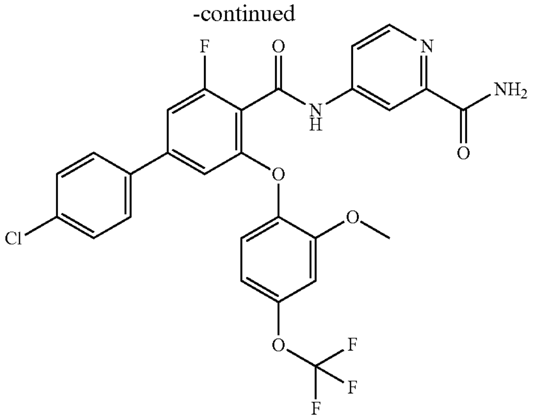

A solution of 4-[[4-bromo-2-fluoro-6-[2-methoxy-4-(trifluoromethoxy)phenoxy]benzoyl]amino]pyridine-2-carboxamide (25 mg, 0.04593 mmol), (4-chlorophenyl)boronic acid (approximately 14.36 mg, 0.09186 mmol), $K_2CO_3$ (12.70 mg, 0.09186 mmol), $Pd(dppf)_2Cl_2$ (7.502 mg, 0.009186 mmol) in dioxane (500 μL) and water (50 μL) was flushed with $N_2$ and heated at 100° C. for 16 h. The reaction mixture was purified by reverse phase HPLC (gradient of 10-99% acetonitrile in water containing HCl as a modifier) giving 4-[[4-(4-chlorophenyl)-2-fluoro-6-[2-methoxy-4-(trifluoromethoxy)phenoxy]benzoyl]amino]pyridine-2-carboxamide (14.6 mg, 55%). ESI-MS m/z calc. 575.0871, found 576.1 $(M+1)^+$; Retention time (Method B): 1.97 minutes. $^1H$ NMR (400 MHz, DMSO-$d_6$) δ 11.33 (s, 1H), 8.54 (d, J=5.4 Hz, 1H), 8.32 (d, J=2.0 Hz, 1H), 8.12 (d, J=2.7 Hz, 1H), 7.86-7.81 (m, 1H), 7.65 (d, J=8.9 Hz, 3H), 7.57-7.48 (m, 3H), 7.28 (d, J=8.8 Hz, 1H), 7.18 (d, J=2.6 Hz, 1H), 6.98 (d, J=8.8 Hz, 1H), 6.88 (s, 1H), 3.78 (s, 3H) ppm.

The compounds set forth in Table 18 were prepared by methods analogous to the preparation of compound 171 and Example 26.

Example 27

N-(2-Carbamoyl-4-Pyridyl)-3-[2-(Trideuterimethoxy)-4-(Trifluoromethoxy)Phenoxy]-5-(Trifluoromethyl)Pyridine-2-Carboxamide (173)

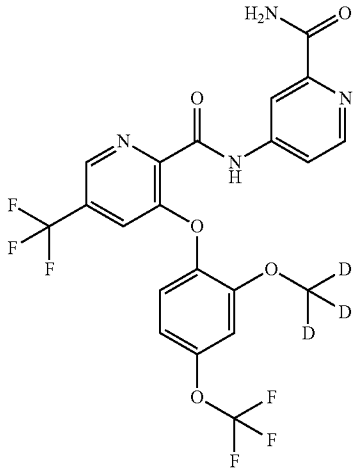

Step 1: Methyl 3-Fluoro-5-(Trifluoromethyl)Pyridine-2-Carboxylate

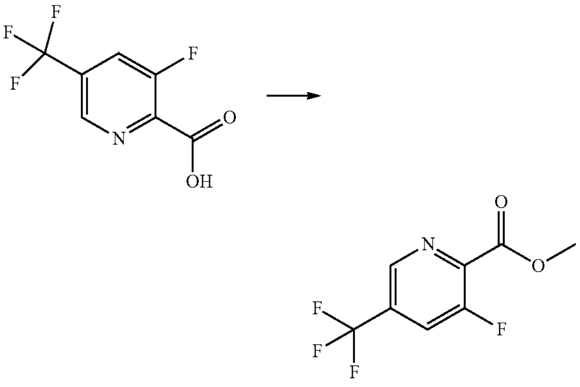

Concentrated sulfuric acid (8 mL, 150.1 mmol) was added to a solution of 3-fluoro-5-(trifluoromethyl)pyridine-2-carboxylic acid (10 g, 47.82 mmol) in methanol (200 mL) and

TABLE 18

Additional Compounds Prepared By Methods Analogous to Example 26.

| Cmpd No. | Compound Name | LC/MS | NMR (shifts in ppm) |
|---|---|---|---|
| 172 | 4-[[4-(4-tert-butylphenyl)-2-fluoro-6-[2-methoxy-4-(trifluoromethoxy)phenoxy]benzoyl]amino]pyridine-2-carboxamide | ESI-MS m/z calc. 597.18866, found 598.3 (M + 1)+; Retention time (Method B): 2.19 minutes | 1H NMR (400 MHz, DMSO-d6) ä 11.30 (s, 1H), 8.54 (d, J = 5.5 Hz, 1H), 8.32 (d, J = 2.1 Hz, 1H), 8.10 (d, J = 2.8 Hz, 1H), 7.84 (dd, J = 5.5, 2.2 Hz, 1H), 7.65 (d, J = 2.9 Hz, 1H), 7.56-7.40 (m, 5H), 7.29 (d, J = 8.8 Hz, 1H), 7.18 (d, J = 2.7 Hz, 1H), 7.02-6.95 (m, 1H), 6.80 (s, 1H), 3.78 (s, 3H), 1.29 (s, 9H). |

the resulting reaction was stirred at 65° C. for 19.5 h. The residue was taken up in ethyl acetate and water and the layers were separated. The organic layer was washed with saturated aqueous $NaHCO_3$ (×1) and brine (×1). The aqueous layer was extracted with EtOAc (×1) and the organic layer was washed with saturated aqueous $NaHCO_3$ (×1) and brine (×1). The combined organic layer was dried over $Na_2SO_4$ filtered and concentrated in vacuo to yield methyl 3-fluoro-5-(trifluoromethyl)pyridine-2-carboxylate (8.2311 g, 77%) as a cream colored solid. ESI-MS m/z calc. 223.02563, found 224.0 $(M+1)^+$; Retention time (Method C): 1.46 minutes.

Step 3: Methyl 3-[2-(Trideuteriomethoxy)-4-(Trifluoromethoxy)Phenoxy]-5-(Trifluoromethyl)Pyridine-2-Carboxylate

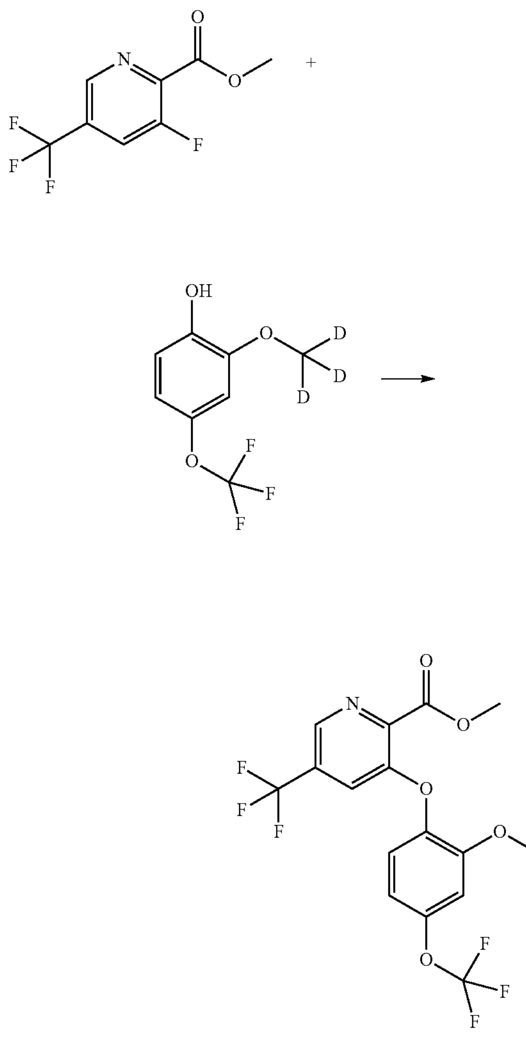

A solution of methyl 3-fluoro-5-(trifluoromethyl)pyridine-2-carboxylate (2 g, 8.964 mmol), 2-(trideuterimethoxy)-4-(trifluoromethoxy)phenol (2.06 g, 9.756 mmol), and $Cs_2CO_3$ (2.966 g, 9.103 mmol) in DMF (15 mL) was heated at 100° C. for 16 h. The reaction was diluted with EtOAc and washed with water (×3) and brine (×1). The organic layer was dried over $Na_2SO_4$, filtered and the concentrated in vacuo to yield methyl 3-[2-(trideuterimethoxy)-4-(trifluoromethoxy)phenoxy]-5-(trifluoromethyl)pyridine-2-carboxylate (3.44 g, 93%) as an orange viscous liquid. ESI-MS m/z calc. 414.07297, found 415.1 $(M+1)^+$; Retention time (Method C): 2.71 minutes. $^1H$ NMR (400 MHz, DMSO-d6) δ 8.77-8.70 (m, 1H), 7.61-7.53 (m, 1H), 7.31 (d, J=8.8 Hz, 1H), 7.22 (d, J=2.8 Hz, 1H), 7.01-6.93 (m, 1H), 3.88 (s, 3H) ppm.

Step 4: 3-[2-(Trideuteriomethoxy)-4-(Trifluoromethoxy)Phenoxy]-5-(Trifluoromethyl)Pyridine-2-Carboxylic Acid

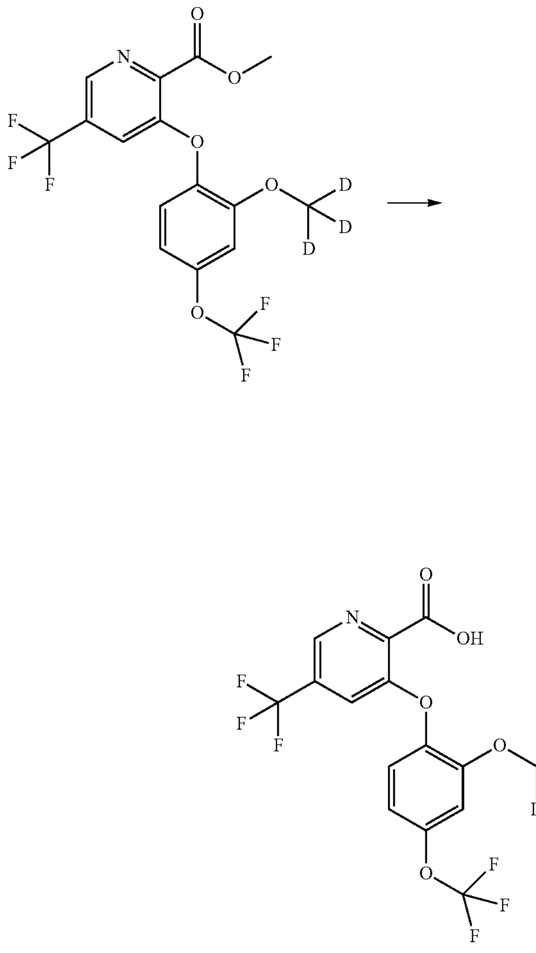

A solution of methyl 3-[2-(trideuteriomethoxy)-4-(trifluoromethoxy)phenoxy]-5-(trifluoromethyl)pyridine-2-carboxylate (3.14 g, 7.580 mmol) in methanol (30 mL) was treated with aqueous NaOH (30 mL of 1 M, 30.00 mmol). The reaction was stirred at 60° C. for 2 h. The reaction was acidified to pH~1 with concentrated HCl. The reaction was diluted with water and extracted with EtOAc (×1). The organic layer was washed with brine (×1), dried over $Na_2SO_4$, filtered and concentrated under vacuo to yield 3-[2-(trideuteriomethoxy)-4-(trifluoromethoxy)phenoxy]-5-(trifluoromethyl)pyridine-2-carboxylic acid (2.9 g, 96%) as a cream colored solid. ESI-MS m/z calc. 400.0573, found 401.1 $(M+1)^+$; Retention time (Method C): 2.39 minutes. $^1H$ NMR (400 MHz, DMSO-d6) δ 13.89 (s, 1H), 8.83-8.66 (m, 1H), 7.55 (d, J=1.8 Hz, 1H), 7.29-7.23 (m, 2H), 7.09-6.93 (m, 1H) ppm.

Step 5: 3-[2-(Trideuteriomethoxy)-4-(Trifluoromethoxy)Phenoxy]-5-(Trifluoromethyl)Pyridine-2-Carbonyl Chloride

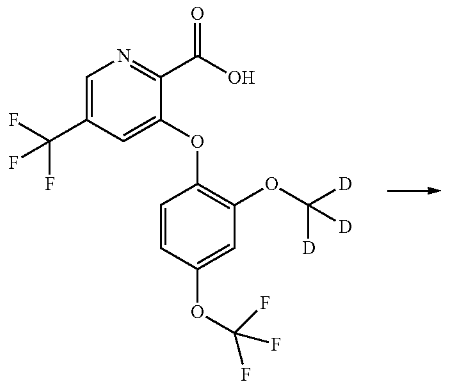

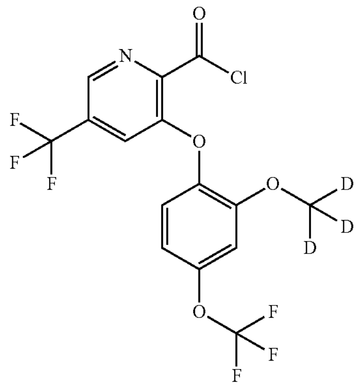

To 3-[2-(trideuteriomethoxy)-4-(trifluoromethoxy)phenoxy]-5-(trifluoromethyl)pyridine-2-carboxylic acid (540 mg, 1.349 mmol) and DMF (15 μL, 0.1937 mmol) in DCM (4 mL) at 0° C. was added oxalyl chloride (180 μL, 2.063 mmol) dropwise under a $N_2$ atmosphere. The ice bath was removed after 10 minutes and the reaction was stirred at RT for 30 minutes then at 50° C. for 2 h. The reaction mixture was concentrated in vacuo to afford 3-[2-(trideuteriomethoxy)-4-(trifluoromethoxy)phenoxy]-5-(trifluoromethyl)pyridine-2-carbonyl chloride. The intermediate was used in the next step without further purification.

Step 6: N-(2-Carbamoyl-4-Pyridyl)-3-[2-(Trideuteriomethoxy)-4-(Trifluoromethoxy)Phenoxy]-5-(Trifluoromethyl)Pyridine-2-Carboxamide (173)

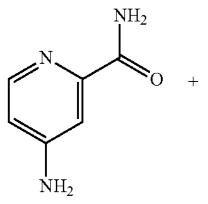

-continued

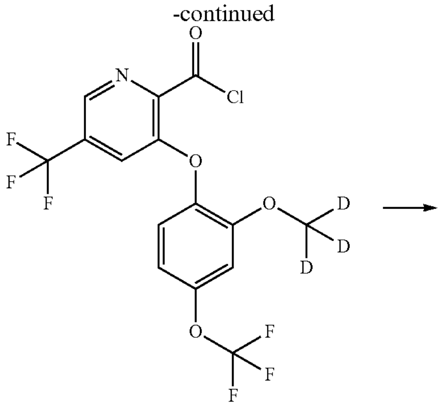

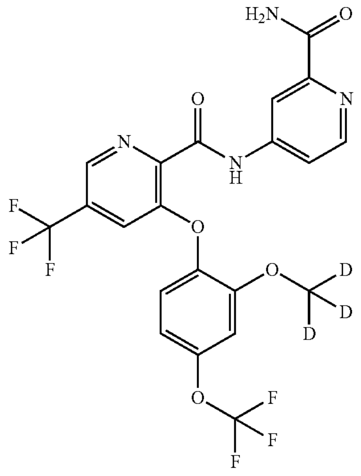 [SMILES: [2H]C([2H])([2H])Oc1cc(OC(F)(F)F)ccc1Oc1cc(C(F)(F)F)cnc1C(=O)Nc1ccnc(C(N)=O)c1]

To 4-aminopyridine-2-carboxamide (23.59 mg, 0.1720 mmol) in NMP (500 μL) and DIEA (55.56 mg, 74.88 μL, 0.4299 mmol) at 0° C. was added a solution of 3-[2-(trideuteriomethoxy)-4-(trifluoromethoxy)phenoxy]-5-(trifluoromethyl)pyridine-2-carbonyl chloride (60 mg, 0.1433 mmol) in NMP (200 μL) slowly. The mixture was stirred at RT for 16 h. The crude product was filtered and purified by reverse phase HPLC (gradient of 10-99% acetonitrile in water containing HCl as a modifier) to yield N-(2-carbamoyl-4-pyridyl)-3-[2-(trideuteriomethoxy)-4-(trifluoromethoxy)phenoxy]-5-(trifluoromethyl)pyridine-2-carboxamide (26.5 mg, 35%). ESI-MS m/z calc. 519.10565, found 519.9 $(M+1)^+$; Retention time (Method B): 1.77 minutes. 1H NMR (400 MHz, DMSO-d6) δ 11.31 (s, 1H), 8.85 (s, 1H), 8.55 (d, J=5.5 Hz, 1H), 8.40 (d, J=2.2 Hz, 1H), 8.10 (s, 1H), 7.92-7.86 (m, 1H), 7.70-7.61 (m, 2H), 7.31 (d, J=8.8 Hz, 1H), 7.22 (d, J=2.7 Hz, 1H), 7.03-6.99 (m, 1H) ppm.

The compounds set forth in Table 19 were prepared by methods analogous to the preparation of compound 173 and Example 27.

TABLE 19

| Additional Compounds Prepared By Methods Analogous to Example 27. | | | |
|---|---|---|---|
| Cmpd No. | Compound Name | LC/MS | NMR (shifts in ppm) |
| 174 | N-(6-carbamoyl-3-pyridyl)-3-[2-(trideuteriomethoxy)-4-(trifluoromethoxy)phenoxy]-5-(trifluoromethyl)pyridine-2-carboxamide | ESI-MS m/z calc. 519.10565, found 520.2 (M + 1)+; Retention time (Method C): 2.35 minutes | 1H NMR (400 MHz, DMSO-d6) δ 11.26 (s, 1H), 8.95 (d, J = 2.4 Hz, 1H), 8.86 (d, J = 1.7 Hz, 1H), 8.34 (dd, J = 8.6, 2.5 Hz, 1H), 8.09-7.98 (m, 2H), 7.69 (s, 1H), 7.59 (s, 1H), 7.31 (d, J = 8.8 Hz, 1H), 7.23 (d, J = 2.7 Hz, 1H), 7.01 (d, J = 9.4 Hz, 1H). |

Example 28

4-[[2-(4-Fluoro-2-Methoxy-Phenyl)-4-(Trifluoromethyl)Benzoyl]Amino]Pyridine-2-Carboxamide (175)

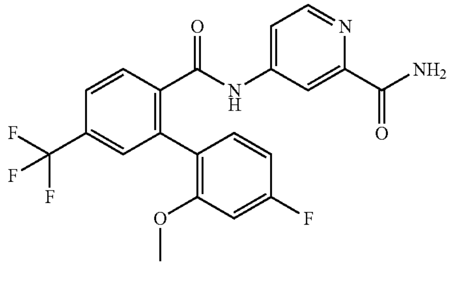 [SMILES: COc1cc(F)ccc1-c1cc(C(F)(F)F)ccc1C(=O)Nc1ccnc(C(N)=O)c1]

Step 1: Methyl 2-Bromo-4-(Trifluoromethyl)Benzoate

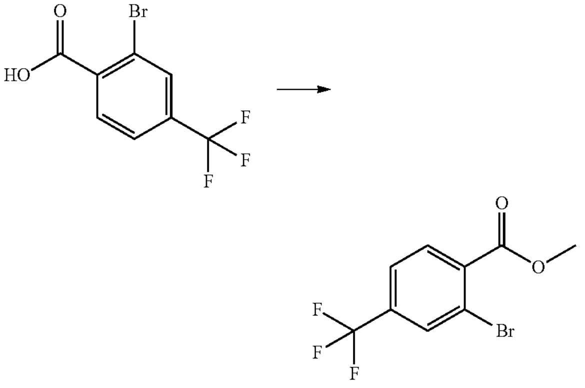

A solution of 2-bromo-4-(trifluoromethyl)benzoic acid (2 g, 7.435 mmol) and $H_2SO_4$ (1.094 g, 594.6 μL, 11.15 mmol) in MeOH (50 mL) was heated at 65° C. overnight. The reaction mixture was cooled to RT and concentrated in vacuo. The residue was taken up in ethyl acetate (20 mL) and water (20 mL) and the layers separated. The aqueous layer was extracted further with ethyl acetate (2×20 mL) and the combined organic layers washed with saturated aqueous $NaHCO_3$ (1×20 mL), dried over $MgSO_4$ and concentrated in vacuo to afford the product as a colorless oil. $^1$H NMR (500 MHz, Chloroform-d) δ 7.97-7.86 (m, 2H), 7.64 (ddt, J=8.0, 1.3, 0.7 Hz, 1H), 3.99 (s, 3H) ppm.

Step 2: Methyl 2-(4-Fluoro-2-Methoxy-Phenyl)-4-(Trifluoromethyl)Benzoate

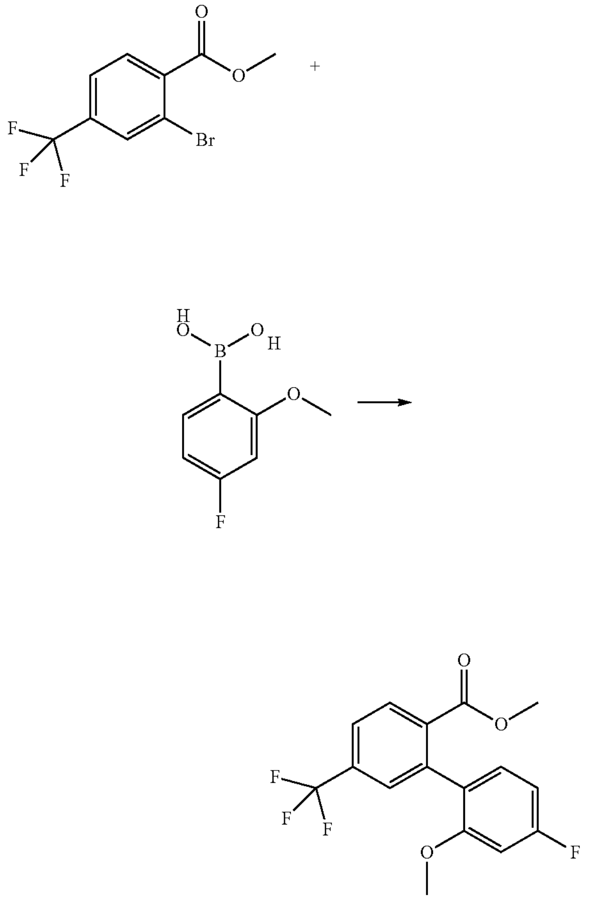

A mixture of methyl 2-bromo-4-(trifluoromethyl)benzoate (500 mg, 1.767 mmol), (4-fluoro-2-methoxy-phenyl) boronic acid (450 mg, 2.648 mmol), $K_2CO_3$ (488 mg, 3.531 mmol), $Pd(PPh_3)_4$ (41 mg, 0.03548 mmol), DMF (4.5 mL) and water (500 μL) was heated at 80° C. for 2 h. The solution was concentrated in vacuo and the residue was purified by silica gel column chromatography using a EtOAc/hexanes eluent to give methyl 2-(4-fluoro-2-methoxy-phenyl)-4-(trifluoromethyl)benzoate (510 mg, 88%) as a clear oil. $^1$H NMR (400 MHz, DMSO-d6) δ 7.95 (d, J=8.1 Hz, 1H), 7.90-7.78 (m, 1H), 7.64 (d, J=1.9 Hz, 1H), 7.35 (dd, J=8.4, 6.8 Hz, 1H), 6.98 (dd, J=11.3, 2.5 Hz, 1H), 6.88 (td, J=8.5, 2.5 Hz, 1H), 3.68 (s, 3H), 3.66 (s, 3H) ppm.

Step 3: 2-(4-Fluoro-2-Methoxy-Phenyl)-4-(Trifluoromethyl)Benzoic Acid

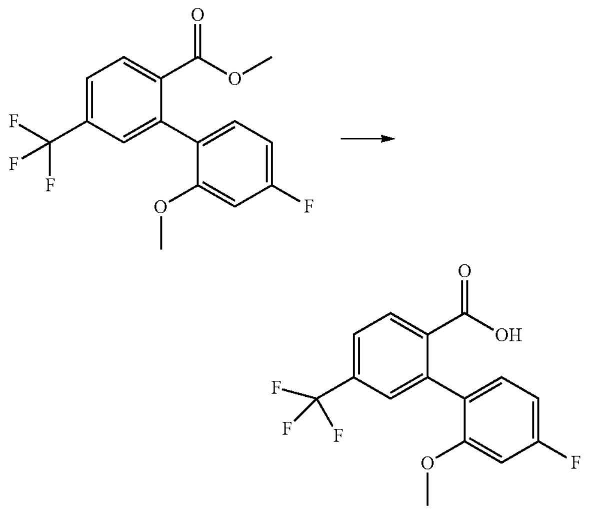

A mixture of methyl 2-(4-fluoro-2-methoxy-phenyl)-4-(trifluoromethyl)benzoate (500 mg, 1.523 mmol), NaOH (1.2 g, 30.00 mmol) in $H_2O$ (2.5 mL), and THF (2.5 mL) was heated at 100° C. for 2 h. The reaction mixture was acidified to pH=2 (1.0 N aqueous HCl) and partitioned between water (50 mL) and EtOAc (100 mL). The reaction was concentrated in vacuo and the residue purified by silica gel column chromatography using a EtOAc/hexanes eluent to give 2-(4-fluoro-2-methoxy-phenyl)-4-(trifluoromethyl)benzoic acid (230 mg, 48%) as a white solid. $^1$H NMR (400 MHz, DMSO-d6) δ 12.97 (s, 1H), 7.95 (d, J=8.1 Hz, 1H), 7.86-7.76 (m, 1H), 7.59 (d, J=1.9 Hz, 1H), 7.30 (dd, J=8.4, 6.8 Hz, 1H), 6.97 (dd, J=11.4, 2.5 Hz, 1H), 6.85 (td, J=8.5, 2.5 Hz, 1H), 3.69 (s, 3H) ppm.

Step 4: 4-[[2-(4-Fluoro-2-Methoxy-Phenyl)-4-(Trifluoromethyl)Benzoyl]Amino]Pyridine-2-Carboxamide (175)

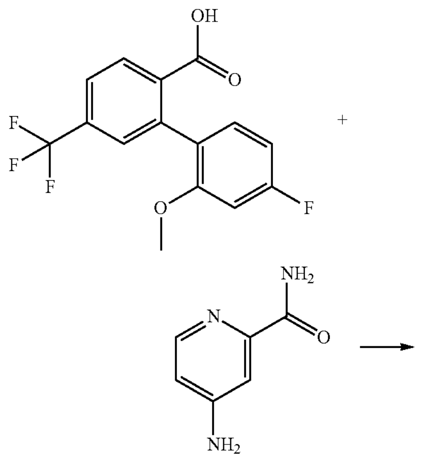

-continued

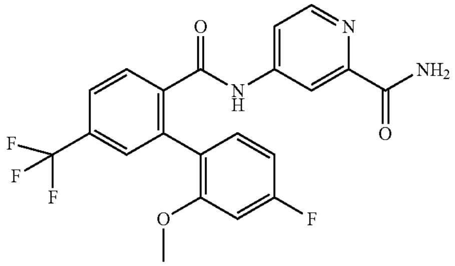

To a solution of 2-(4-fluoro-2-methoxy-phenyl)-4-(trifluoromethyl)benzoic acid (100 mg, 0.3182 mmol), DMF (3 μL, 0.03874 mmol), and DCM (1 mL), at 0° C. (ice-bath), was added oxalyl chloride (55 μL, 0.6305 mmol) dropwise over 3 minutes. The mixture was stirred at RT for 2 h then concentrated in vacuo. The intermediate was dissolved in DCM (5 mL) and added drop-wise to a solution of 4-aminopyridine-2-carboxamide (44 mg, 0.3208 mmol), DIEA (140 μL, 0.8038 mmol) in DCM (500 μL) at a 0° C. The reaction mixture was stirred at RT for 2 h. The reaction mixture was concentrated under vacuo and the residue purified by silica gel column chromatography using a EtOAc/hexanes eluent. The resultant material was triturated with diethyl ether (100 mL) and filtered to give 4-[[2-(4-fluoro-2-methoxy-phenyl)-4-(trifluoromethyl)benzoyl]amino]pyridine-2-carboxamide (13.1 mg, 9%) as a white solid. ESI-MS m/z calc. 433.10495, found 434.0 $(M+1)^+$; Retention time (Method B): 1.31 minutes. $^1$H NMR (400 MHz, DMSO-d6) δ 11.01 (s, 1H), 8.50 (d, J=5.6 Hz, 1H), 8.30 (d, J=2.2 Hz, 1H), 8.16 (s, 1H), 7.90 (d, J=1.4 Hz, 2H), 7.79 (dd, J=5.7, 2.2 Hz, 1H), 7.70 (d, J=7.3 Hz, 2H), 7.40 (dd, J=8.4, 6.7 Hz, 1H), 6.94-6.82 (m, 2H), 3.54 (s, 3H) ppm.

Example 29

5-[[6-(2-Chloro-4-Fluoro-Phenoxy)-2-Fluoro-3-(Trifluoromethyl)Benzoyl]Amino]Pyridine-2-Carboxamide(176)

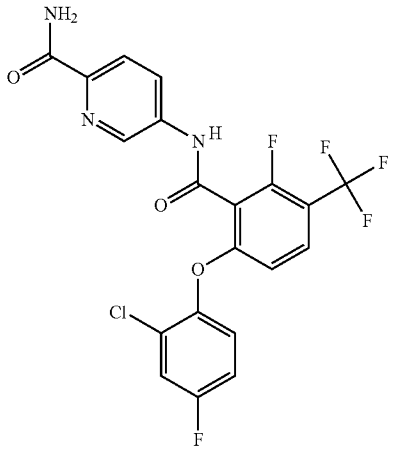

Step 1: 6-(2-Chloro-4-Fluoro-Phenoxy)-2-Fluoro-3-(Trifluoromethyl)Benzoic Acid

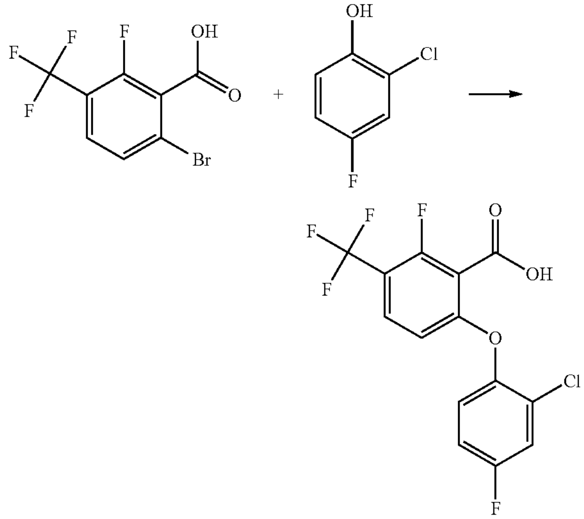

A solution of 6-bromo-2-fluoro-3-(trifluoromethyl)benzoic acid (5 g, 17.42 mmol), 2-chloro-4-fluoro-phenol (3.0 g, 20.47 mmol), $Cs_2CO_3$ (11.4 g, 34.99 mmol) in toluene (100 mL) was degassed with $N_2$ for 10 minutes, then CuI (664 mg, 3.486 mmol) was added. The reaction was flushed with $N_2$ then heated at 100° C. with vigorous stirring for 1 h. The mixture was allowed to cool then diluted with ethyl acetate and water. The water layer was acidified with HCl (26 mL of 1 M, 26.00 mmol) and the product extracted with ethyl acetate. The organic layer was concentrated under vacuo and the residue was purified by silica gel column chromatography using a MeOH/DCM eluent to provide 6-(2-chloro-4-fluoro-phenoxy)-2-fluoro-3-(trifluoromethyl) benzoic acid (5.1 g, 80%) as a white solid. ESI-MS m/z calc. 351.99255, found 353.0 $(M+1)^+$; Retention time (Method B): 1.66 minutes. $^1H$ NMR (400 MHz, DMSO-d6) δ 14.19 (s, 1H), 7.89-7.58 (m, 2H), 7.59-7.22 (m, 2H), 6.69 (d, J=8.9 Hz, 1H) ppm.

Step 2: 5-[[6-(2-Chloro-4-Fluoro-Phenoxy)-2-Fluoro-3-(Trifluoromethyl)Benzoyl]Amino]Pyridine-2-Carboxamide (176)

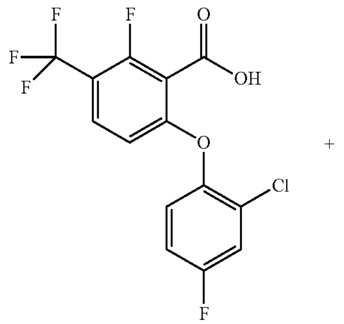

-continued

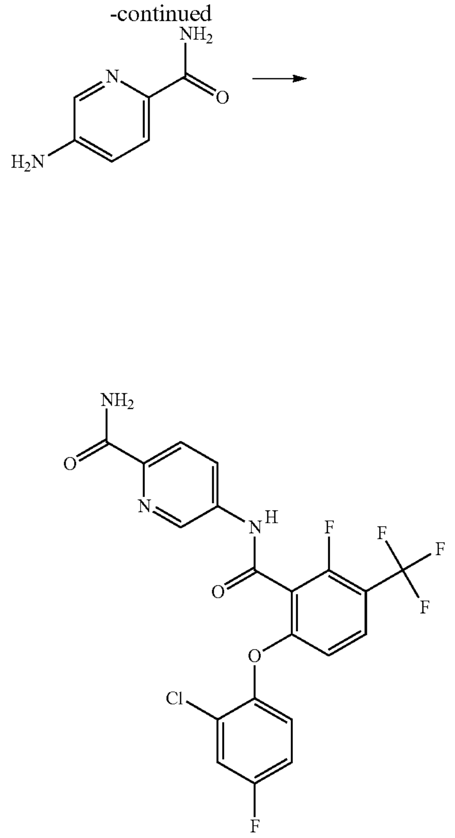

A mixture of 6-(2-chloro-4-fluoro-phenoxy)-2-fluoro-3-(trifluoromethyl)benzoic acid (50 mg, 0.1390 mmol), oxalyl chloride (17.64 mg, 12.12 μL, 0.1390 mmol), and DMF (0.2541 mg, 0.2692 μL, 0.003476 mmol) in DCM (285.9 μL) was stirred under nitrogen at RT for 1 h. The reaction mixture was concentrated in vacuo. To the residue was added DCM (143.0 μL), 5-aminopyridine-2-carboxamide (28.59 mg, 0.2085 mmol), and DIEA (26.95 mg, 36.32 μL, 0.2085 mmol). The reaction mixture was stirred at RT for 1 h. The crude mixture was purified by reverse phase HPLC (gradient of 10-99% acetonitrile in water containing HCl as a modifier) to give amide 5-[[6-(2-chloro-4-fluoro-phenoxy)-2-fluoro-3-(trifluoromethyl)benzoyl]amino]pyridine-2-carboxamide (8.7 mg, 9%) as a white solid. ESI-MS m/z calc. 471.04092, found 471.9 $(M+1)^+$; Retention time (Method B): 1.77 minutes. $^1H$ NMR (400 MHz, DMSO-d6) δ 11.42 (s, 1H), 8.87 (d, J=2.4 Hz, 1H), 8.31 (dd, J=8.6, 2.4 Hz, 1H), 8.07 (d, J=8.6 Hz, 1H), 8.04 (d, J=2.7 Hz, 1H), 7.86 (t, J=8.6 Hz, 1H), 7.70 (dd, J=8.3, 3.0 Hz, 1H), 7.64-7.54 (m, 1H), 7.50 (dd, J=9.1, 5.2 Hz, 1H), 7.38 (td, J=9.2, 8.7, 3.0 Hz, 1H), 6.76 (d, J=8.9 Hz, 1H) ppm.

Example 30

4-[[2-Fluoro-6-[2-Methoxy-4-(Trifluoromethoxy) Phenoxy]-3-Phenyl-Benzoyl]Amino]Pyridine-2-Carboxamide (177)

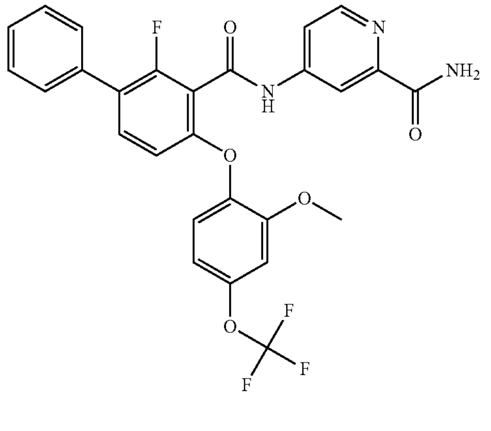 [SMILES: COc1cc(OC(F)(F)F)ccc1Oc1ccc(-c2ccccc2)c(F)c1C(=O)Nc1ccnc(C(N)=O)c1]

Step 1: 3-Chloro-2-Fluoro-6-[2-Methoxy-4-(Trifluoromethoxy)Phenoxy]Benzoic Acid

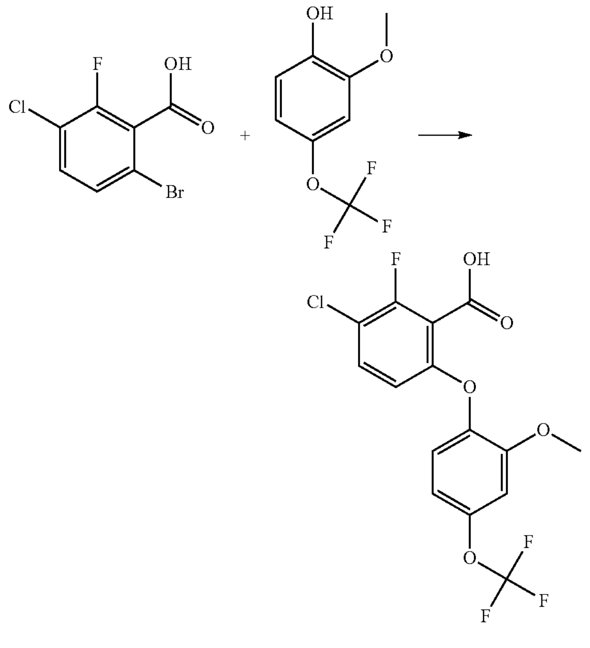

A solution of 6-bromo-3-chloro-2-fluoro-benzoic acid (2 g, 7.891 mmol), 2-methoxy-4-(trifluoromethoxy)phenol (1.66 g, 7.976 mmol), $Cs_2CO_3$ (2.69 g, 8.256 mmol) in toluene (15 mL) was bubbled with $N_2$ for 10 minutes, then CuI (359.6 mg, 1.888 mmol) was added. The reaction was heated at 100° C. with vigorous stirring for 3 h. The mixture was allowed to cool, then diluted with ethyl acetate and water (50 mL) and then acidified with 1 M HCl. The two layers were separated and the aqueous layer was extracted with EtOAc (×3). The combined organic layer was washed with water (×2), brine (×1), dried over $Na_2SO_4$, filtered through a plug of celite and concentrated in vacuo. Purification by silica gel column chromatography using a EtOAc/hexanes eluent followed by purification by reverse phase HPLC (gradient of 10-99% acetonitrile in water containing HCl as a modifier) to yield 3-chloro-2-fluoro-6-[2-methoxy-4-(trifluoromethoxy)phenoxy]benzoic acid (510.6 mg, 17%). ESI-MS m/z calc. 380.00748, found 381.1 $(M+1)^+$; Retention time (Method B): 2.53 minutes. $^1H$ NMR (400 MHz, DMSO-d6) δ 13.92 (s, 1H), 7.56 (t, J=8.8 Hz, 1H), 7.29-7.14 (m, 2H), 6.99 (dd, J=8.8, 2.5 Hz, 1H), 6.56 (d, J=9.0 Hz, 1H), 3.79 (s, 3H) ppm.

Step 2: 4-[[3-Chloro-2-Fluoro-6-[2-Methoxy-4-(Trifluoromethoxy)Phenoxy]Benzoyl]Amino]Pyridine-2-Carboxamide

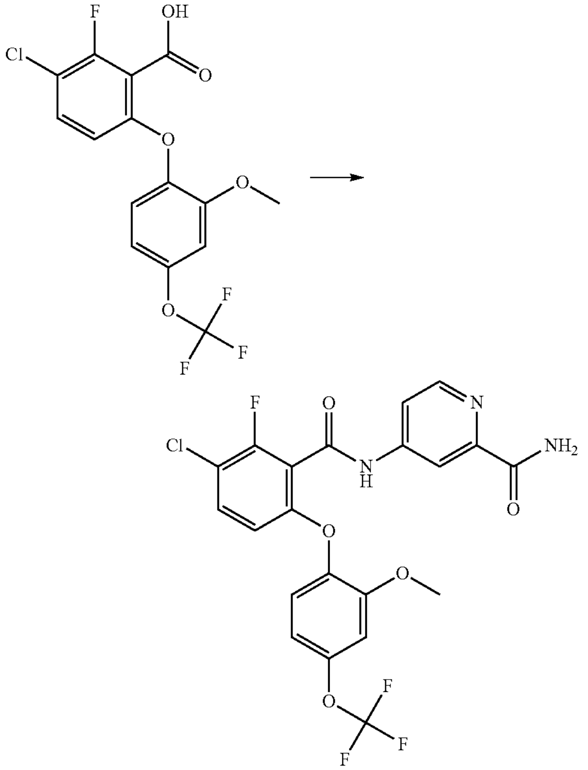

To 3-chloro-2-fluoro-6-[2-methoxy-4-(trifluoromethoxy) phenoxy]benzoic acid (83.8 mg, 0.2201 mmol) and DMF (15 μL, 0.1937 mmol) in DCM (1 mL) at 0° C. was added oxalyl chloride (53 μL, 0.6076 mmol) dropwise under a $N_2$ atmosphere. The ice bath was removed after 10 minutes and the reaction was stirred at RT for 2.5 h. The reaction was concentrated in vacuo to afford 3-chloro-2-fluoro-6-[2-methoxy-4-(trifluoromethoxy)phenoxy]benzoyl chloride. The intermediate was taken onto the next step without further purification.

To 4-aminopyridine-2-carboxamide (36.2 mg, 0.2640 mmol) in NMP (0.5 mL) and DIEA (115 μL, 0.6602 mmol) at 0° C. was added a solution of 3-chloro-2-fluoro-6-[2-methoxy-4-(trifluoromethoxy)phenoxy]benzoyl chloride in NMP (0.2 mL) slowly. The mixture was stirred at RT for 1 h. The crude product was purified by reverse phase HPLC (gradient of 10-99% acetonitrile in water containing HCl as a modifier) to yield 4-[[3-chloro-2-fluoro-6-[2-methoxy-4-(trifluoromethoxy)phenoxy]benzoyl]amino]pyridine-2-carboxamide (25.8 mg, 23%). ESI-MS m/z calc. 499.05582, found 500.0 $(M+1)^+$; Retention time (Method A): 0.55 minutes.

Step 3: 4-[[2-Fluoro-6-[2-Methoxy-4-(Trifluoromethoxy)Phenoxy]-3-Phenyl-Benzoyl]Amino]Pyridine-2-Carboxamide (177)

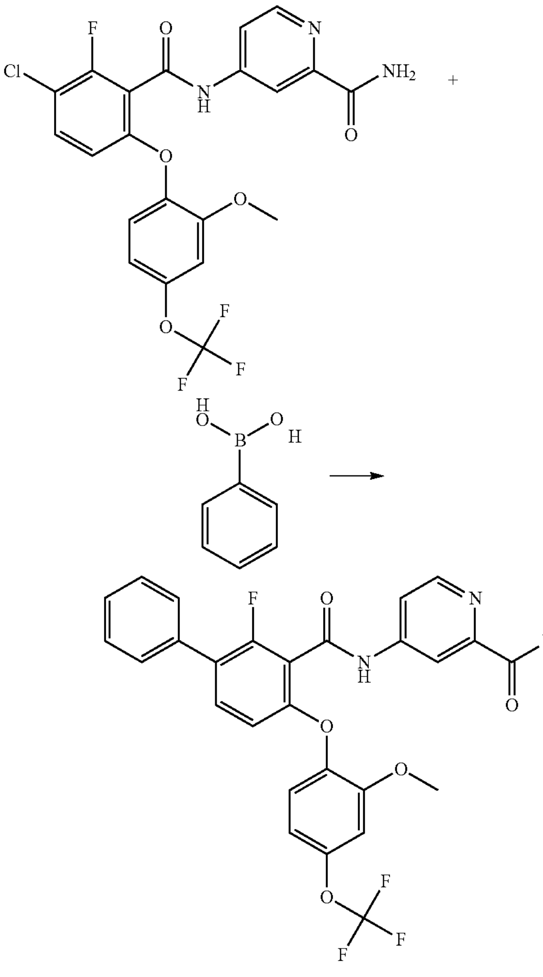

A solution of 4-[[3-chloro-2-fluoro-6-[2-methoxy-4-(trifluoromethoxy)phenoxy]benzoyl]amino]pyridine-2-carboxamide (26 mg, 0.05202 mmol), phenylboronic acid (19.5 mg, 0.1599 mmol), $Pd(dppf)_2Cl_2$ (4.1 mg, 0.005021 mmol) and $K_2CO_3$ (79 μL of 2 M, 0.1580 mmol) in dioxane (500 μL) was heated in the microwave at 120° C. for 20 minutes. Further $Pd(dppf)_2Cl_2$ (11 mg) and $K_2CO_3$ (79 μL of 2 M, 0.1580 mmol) were added to the reaction which was heated at 130° C. for 40 minutes in the microwave. Further $Pd(dppf)_2Cl_2$ (11 mg), $K_2CO_3$ (79 μL of 2 M, 0.1580 mmol), and phenylboronic acid (19.5 mg, 0.1599 mmol) were added to the reaction mixture which was then heated in the microwave at 130° C. for 40 minutes. The crude product was purified by reverse phase HPLC (gradient of 10-99% acetonitrile in water containing HCl as a modifier) to yield 4-[[2-fluoro-6-[2-methoxy-4-(trifluoromethoxy)phenoxy]-3-phenyl-benzoyl]amino]pyridine-2-carboxamide (2.8 mg, 10%). ESI-MS m/z calc. 541.1261, found 542.2 $(M+1)^+$; Retention time (Method C): 2.61 minutes (5 minutes run).

$^1H$ NMR (400 MHz, DMSO-d6) δ 11.40 (s, 1H), 8.54 (d, J=5.3 Hz, 1H), 8.35 (s, 1H), 8.12 (s, 1H), 7.92-7.80 (m, 1H), 7.67 (s, 1H), 7.61-7.48 (m, 5H), 7.48-7.38 (m, 1H), 7.32 (d, J=8.9 Hz, 1H), 7.23 (s, 1H), 7.03 (d, J=8.3 Hz, 1H), 6.64 (d, J=8.8 Hz, 1H), 3.80 (s, 3H) ppm.

Example 31

4-[[2-Ethyl-6-[2-Methoxy-4-(Trifluoromethoxy)Phenoxy]-4-(Trifluoromethyl)Benzoyl]Amino]Pyridine-2-Carboxamide (178)

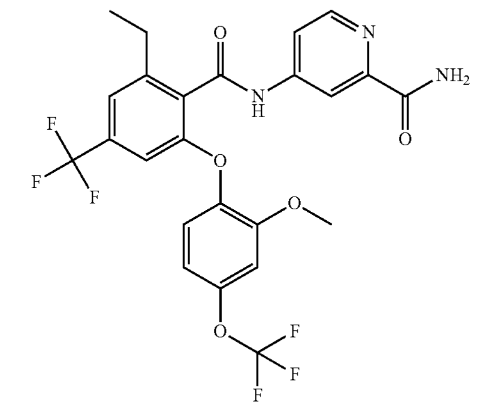 [SMILES: CCc1cc(C(F)(F)F)cc(Oc2ccc(OC(F)(F)F)cc2OC)c1C(=O)Nc1ccnc(C(N)=O)c1]

Step 1: 2-Bromo-6-Fluoro-4-(Trifluoromethyl)Benzoic Acid

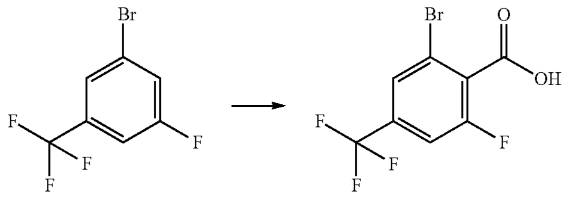 [SMILES: Fc1cc(Br)cc(C(F)(F)F)c1 ; O=C(O)c1c(F)cc(C(F)(F)F)cc1Br]

To a solution containing freshly distilled diisopropylamine (4 mL, 28.54 mmol) was added n-butyl lithium in hexanes (11 mL of 2.5 M, 27.5 mmol) over 10 minutes at 0° C. The mixture was then stirred at this temperature for 30 minutes, then cooled to −78° C., and stirred at this temperature for 30 minutes. This solution was then transferred via cannula into a solution of 1-bromo-3-fluoro-5-(trifluoromethyl)benzene (5 g, 20.576 mmol) in THF (20 mL) at −78° C. The resulting pale amber solution was transferred via cannula to crushed $CO_2$ and the resulting golden solution was stirred gently for 18 h. The reaction was diluted with NaOH (0.1M, 200 mL), and washed with $Et_2O$ (3×200 mL), the aqueous phase was acidified with HCl (3M, until pH=1), and was extracted with $Et_2O$ (3×200 mL), dried over $MgSO_4$, filtered and concentrated under reduced pressure to provide 2-bromo-6-fluoro-4-(trifluoromethyl)benzoic acid (5.34 g, 90%). ESI-MS m/z calc. 285.92526, found 287.0 $(M+1)^+$; Retention time: 4.4 minutes; LCMS Method: Merckmillipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$); LCMS Method Detail: null.

Step 2: 4-[[2-Bromo-6-Fluoro-4-(Trifluoromethyl) Benzoyl]Amino]Pyridine-2-Carboxamide

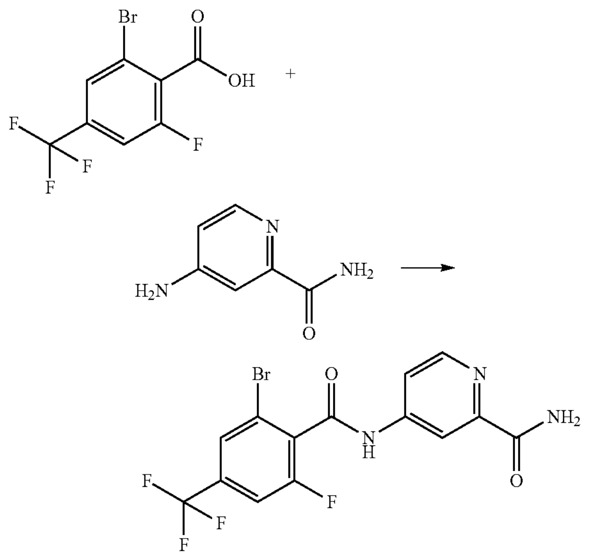

To a solution of 2-bromo-6-fluoro-4-(trifluoromethyl) benzoic acid (50 mg, 0.174 mmol) and 4-aminopyridine-2-carboxamide (24 mg, 0.175 mmol) in pyridine (1.5 mL) was added POCl3 (0.016 mL, 0.172 mmol) at −20° C. to −15° C. and stirred 30 min at this temperature. The reaction was quenched by addition of water (1 mL), then extracted with EtOAc (2×10 mL). The combined organic phases were washed with water (3×2 mL), brine, dried over $MgSO_4$, and concentrated under reduced pressure to give 4-[[2-bromo-6-fluoro-4-(trifluoromethyl)benzoyl]amino]pyridine-2-carboxamide (70 mg, 99%). ESI-MS m/z calc. 404.9736, found 406.0 $(M+1)^+$; Retention time: 3.78 minutes and used directly in the next step without further purification.

Step 3: 4-[[2-Bromo-6-[2-Methoxy-4-(Trifluoromethoxy)Phenoxy]-4-(Trifluoromethyl)Benzoyl] Amino]Pyridine-2-Carboxamide

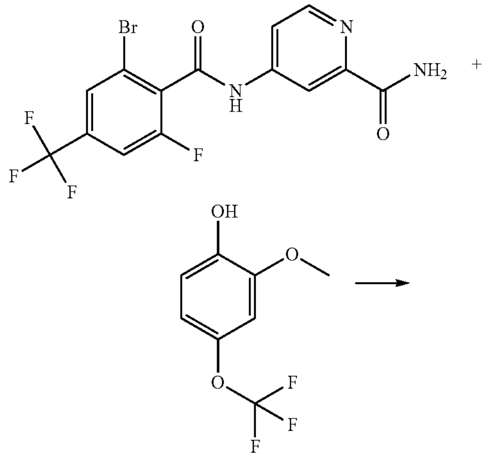

-continued

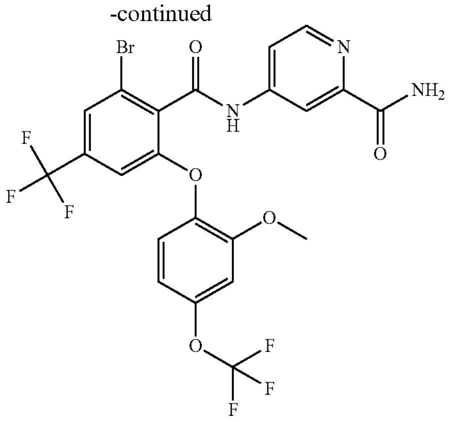

A solution of 4-[[2-bromo-6-fluoro-4-(trifluoromethyl) benzoyl]amino]pyridine-2-carboxamide (1.00 g, 2.46 mmol), 2-methoxy-4-(trifluoromethoxy)phenol (564 mg, 2.71 mmol) and $Cs_2CO_3$ (1.60 g, 4.91 mmol) in NMP (15 mL) was heated at 95° C. for 2 h. The reaction mixture was partitioned between ethyl acetate and water. The organic layer was separated and washed with water and brine. The organic layer was dried over $MgSO_4$, then purified by silica gel column chromatography using a ethyl acetate-dichloromethane gradient to give 4-[[2-bromo-6-[2-methoxy-4-(trifluoromethoxy)phenoxy]-4-(trifluoromethyl)benzoyl] amino]pyridine-2-carboxamide (690 mg, 47%). ESI-MS m/z calc. 593.0021, found 595.0 $(M+1)^+$; Retention time (Method B): 1.68 minutes. $^1H$ NMR (400 MHz, DMSO-d6) δ 11.14 (s, 1H), 8.44 (d, J=5.5 Hz, 1H), 8.05 (dd, J=13.5, 2.5 Hz, 2H), 7.93-7.81 (m, 2H), 7.63 (d, J=2.8 Hz, 1H), 7.48 (dd, J=5.6, 2.2 Hz, 1H), 6.86 (d, J=2.5 Hz, 1H), 6.79 (d, J=8.8 Hz, 1H), 6.73 (d, J=8.6 Hz, 1H), 3.50 (s, 3H) ppm.

Step 4: 4-[[2-Ethyl-6-[2-Methoxy-4-(Trifluoromethoxy)Phenoxy]-4-(Trifluoromethyl)Benzoyl] Amino]Pyridine-2-Carboxamide (178)

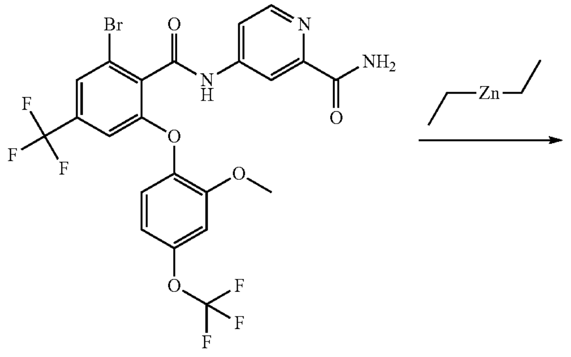

-continued

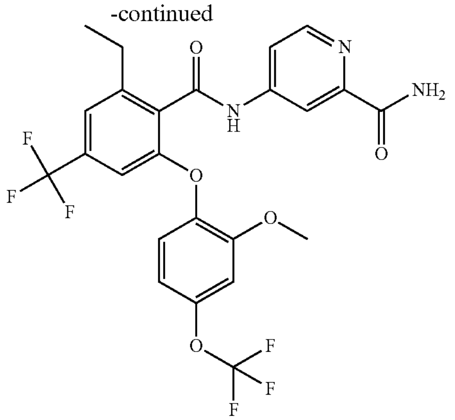

Diethylzinc (80 μL of 2 M, 0.1600 mmol) was added under nitrogen to a solution of 4-[[2-bromo-6-[2-methoxy-4-(trifluoromethoxy)phenoxy]-4-(trifluoromethyl)benzoyl]amino]pyridine-2-carboxamide (48 mg, 0.08077 mmol) and Pd(dppf)$Cl_2$ (3.1 mg, 0.004237 mmol) in dioxane (0.6 mL) in a capped vial and the resulting pale yellow solution heated at 100° C. for 1 h. Additional diethylzinc (80 μL of 2 M, 0.1600 mmol) was added and the solution heated at 100° C. for a further 1 h. The reaction was quenched with MeOH (500 uL) and partitioned between ethyl acetate and 1 M aqueous HCl. The organic layer was dried over $Na_2SO_4$, filtered and concentrated. HPLC purification (10-100% $CH_3CN$/5 mM HCl) gave partially purified product. The product fractions were concentrated to a cloudy white suspension with some solid precipitate. The cloudy solution was decanted from the white solid. The solid was dried under vacuum, then suspended in hexane and dissolved with the slow addition of DCM. The DCM was slowly removed under rotary vacuum until a white solid began to precipitate. The precipitate was allowed to settle and the mother liquor decanted. The isolated solid was dried under high vacuum to give 4-[[2-ethyl-6-[2-methoxy-4-(trifluoromethoxy)phenoxy]-4-(trifluoromethyl)benzoyl]amino]pyridine-2-carboxamide (7.1 mg, 15%). ESI-MS m/z calc. 543.12286, found 544.6 $(M+1)^+$; Retention time (Method B): 1.77 minutes. $^1$H NMR (400 MHz, Methanol-d4) δ 8.42 (d, J=5.5 Hz, 1H), 8.01 (d, J=2.1 Hz, 1H), 7.80 (d, J=8.2 Hz, 1H), 7.63 (dd, J=5.5, 2.1 Hz, 1H), 7.39 (d, J=8.2 Hz, 1H), 6.69-6.55 (m, 3H), 3.47 (s, 3H), 2.75 (q, J=7.6 Hz, 2H), 1.24 (t, J=7.6 Hz, 3H) ppm.

Example 32

5-[[6-(3,4-Difluoro-2-Methoxy-Phenoxy)-2-Methyl-3-(Trifluoromethyl)Benzoyl]Amino]Pyridine-2-Carboxamide (179)

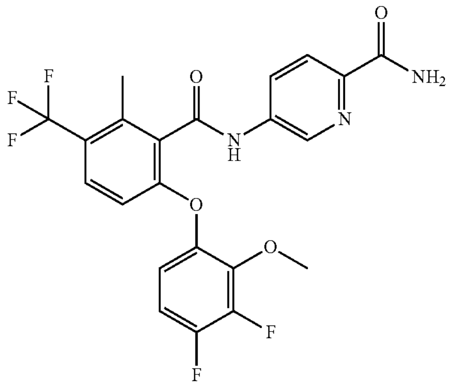 [SMILES: COc1c(Oc2ccc(C(F)(F)F)c(C)c2C(=O)Nc2ccc(C(N)=O)nc2)ccc(F)c1F]

Step 1: 2-Bromo-6-Fluoro-3-(Trifluoromethyl)Benzoic Acid

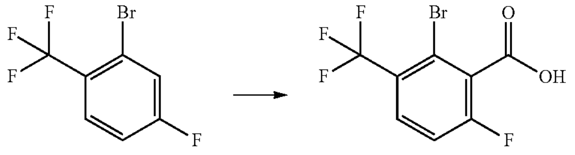 [SMILES: Fc1ccc(C(F)(F)F)c(Br)c1 ; O=C(O)c1c(F)ccc(C(F)(F)F)c1Br]

To a stirred solution of 2-bromo-4-fluoro-1-(trifluoromethyl)benzene (2.5 mL, 17 mmol) in anhydrous THF (150 mL) was added LDA (10 mL of 2.0 M, 20 mmol) at −78° C. The reaction mixture was stirred at this temperature for 2 h. The resulting yellow solution was then transferred via cannula onto crushed $CO_2$ and the resulting emulsion was stirred gently for 17 h. The slurry was taken up 0.2 M NaOH solution (150 mL) and extracted with diethyl ether (200 mL). The aqueous layer was acidified to pH=1 and then extracted with diethyl ether (3×250 mL). The combined organic layer was washed with brine (200 mL), dried over $Na_2SO_4$, filtered, and concentrated under reduced pressure to give 2-bromo-6-fluoro-3-(trifluoromethyl)benzoic acid (4.62 g, 90%) as an off-white solid. ESI-MS m/z calc. 285.9253, found 287.3 $(M+1)^+$; Retention time (Method G): 2.53 minutes.

Step 2: Tert-Butyl 2-Bromo-6-Fluoro-3-(Trifluoromethyl)Benzoate

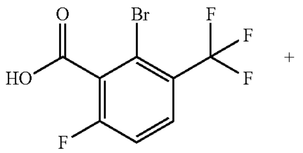

-continued

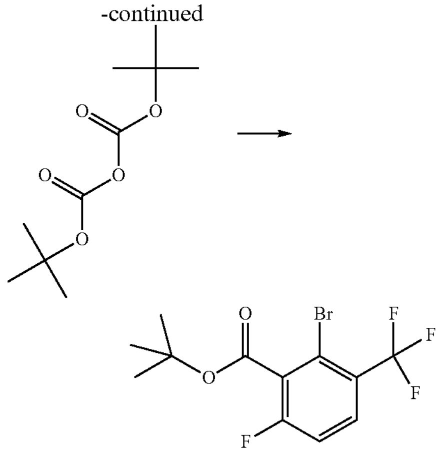

A solution of 2-bromo-6-fluoro-3-(trifluoromethyl)benzoic acid (8.0 g, 27.87 mmol), tert-butoxycarbonyl tert-butyl carbonate (9.1 g, 41.70 mmol), DMAP (680 mg, 5.566 mmol) and t-BuOH (8 mL) was heated at 90° C. for 1 h. The reaction mixture cooled to RT and directly purified by silica gel column chromatography using a EtOAc/hexanes eluent to give tert-butyl 2-bromo-6-fluoro-3-(trifluoromethyl)benzoate (8.1 g, 85%) as a white solid. ESI-MS m/z calc. 341.98785, found 344.8 $(M+1)^+$; Retention time (Method B): 2.02 minutes. $^1$H NMR (400 MHz, DMSO-d6) δ 8.03 (dd, J=9.0, 5.7 Hz, 1H), 7.64 (t, J=8.6 Hz, 1H), 1.58 (s, 9H) ppm.

Step 3: Tert-Butyl 2-Bromo-6-(3,4-Difluoro-2-Methoxy-Phenoxy)-3-(Trifluoromethyl)Benzoate

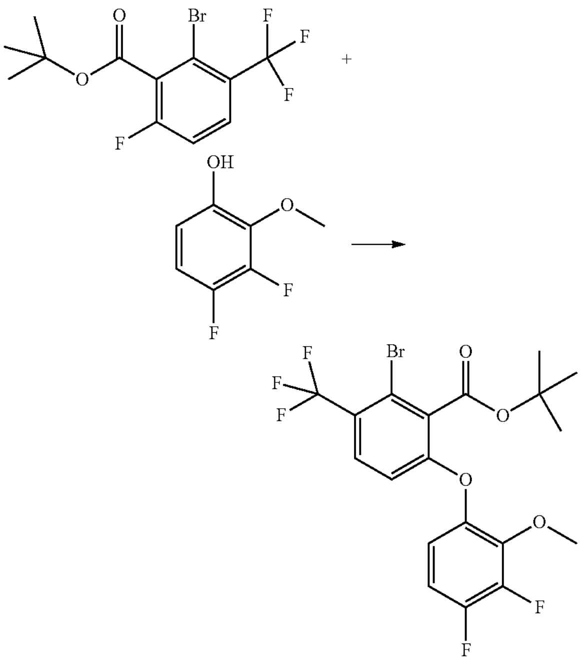

A solution of tert-butyl 2-bromo-6-fluoro-3-(trifluoromethyl)benzoate (1.0 g, 2.915 mmol), 3,4-difluoro-2-methoxy-phenol (700 mg, 4.372 mmol), $K_2CO_3$ (806 mg, 5.832 mmol), in DMF (3 mL) was purged with nitrogen and heated at 100° C. for 1 h. The reaction mixture was cooled to RT and then directly purified by silica gel column chromatography using a EtOAc/hexanes eluent. to give tert-butyl 2-bromo-6-(3,4-difluoro-2-methoxy-phenoxy)-3-(trifluoromethyl)benzoate (1.3 g, 92%) as a clear oil. $^1$H NMR (400 MHz, DMSO-d6) δ 7.80 (d, J=8.9 Hz, 1H), 7.29 (q, J=9.3 Hz, 1H), 7.20-7.05 (m, 1H), 6.92 (d, J=8.9 Hz, 1H), 3.86 (s, 3H), 1.55 (s, 9H) ppm.

Step 4: Tert-Butyl 6-(3,4-Difluoro-2-Methoxy-Phenoxy)-2-Methyl-3-(Trifluoromethyl)Benzoate

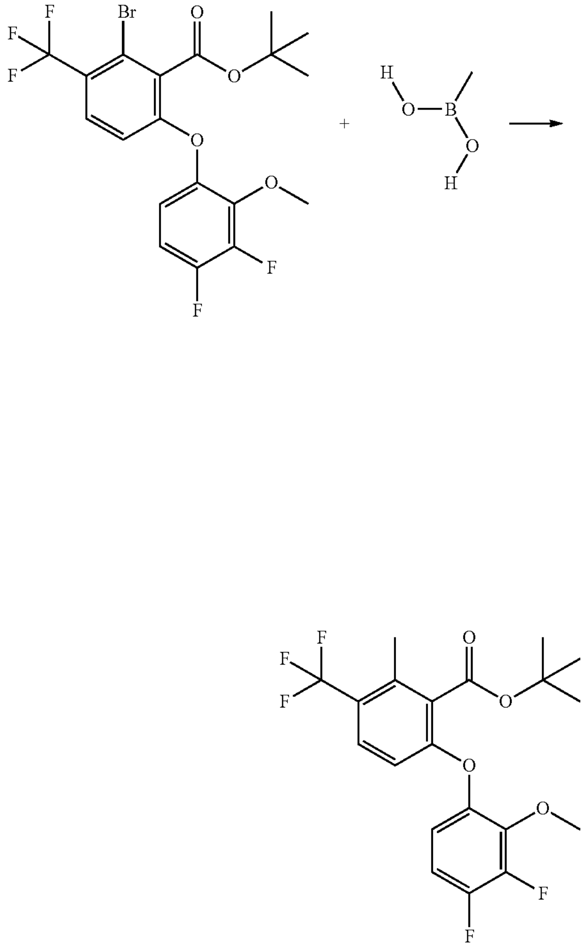

A solution of tert-butyl 2-bromo-6-(3,4-difluoro-2-methoxy-phenoxy)-3-(trifluoromethyl)benzoate (1.3 g, 2.690 mmol), methylboronic acid (829 mg, 13.85 mmol), $Pd(dppf)_2Cl_2$ (226 mg, 0.2767 mmol), and $K_2CO_3$ (1.1 g, 7.959 mmol) in dioxane (6.0 mL) and water (600 μL) was heated at 120° C. for 30 minutes. The reaction mixture was cooled to RT and then directly purified by silica gel column chromatography using a EtOAc/hexanes eluent to give tert-butyl 6-(3,4-difluoro-2-methoxy-phenoxy)-2-methyl-3-(trifluoromethyl)benzoate (1.0 g, 89%) as a clear oil. $^1$H NMR (400 MHz, DMSO-d6) δ 7.67 (d, J=8.9 Hz, 1H), 7.25 (q, J=9.3 Hz, 1H), 7.01 (ddd, J=9.3, 5.1, 2.2 Hz, 1H), 6.74 (d, J=8.8 Hz, 1H), 3.86 (s, 3H), 2.40 (s, 3H), 1.53 (s, 9H) ppm.

Step 5: 6-(3,4-Difluoro-2-Methoxy-Phenoxy)-2-Methyl-3-(Trifluoromethyl)Benzoic Acid

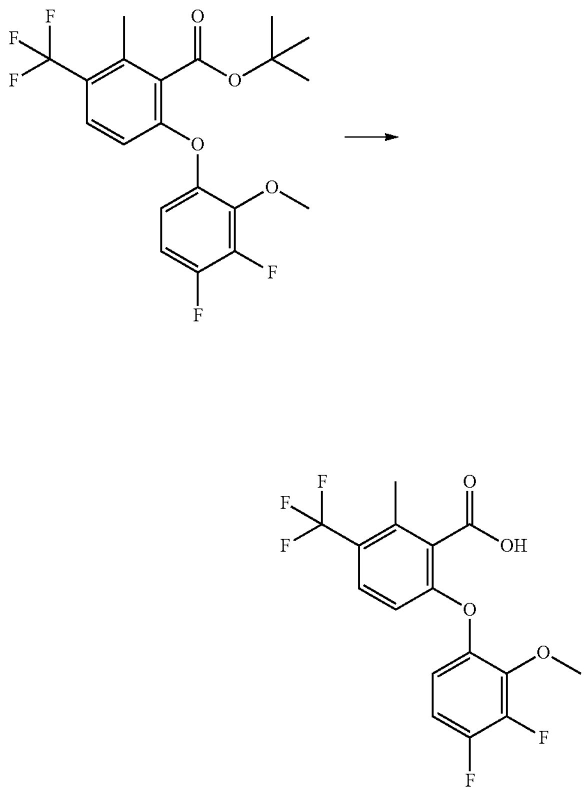 [SMILES: COc1c(Oc2ccc(C(F)(F)F)c(C)c2C(=O)OC(C)(C)C)ccc(F)c1F ; COc1c(Oc2ccc(C(F)(F)F)c(C)c2C(=O)O)ccc(F)c1F]

A solution of tert-butyl 6-(3,4-difluoro-2-methoxy-phenoxy)-2-methyl-3-(trifluoromethyl)benzoate (1.0 g, 2.390 mmol), TFA (27 mL, 350.5 mmol), water (1.7 mL, 94.36 mmol) and THF (5 mL) was stirred at RT for 1 h. The reaction was concentrated under vacuo and purified by silica gel column chromatography using a EtOAc/hexanes eluent to give 6-(3,4-difluoro-2-methoxy-phenoxy)-2-methyl-3-(trifluoromethyl)benzoic acid (390 mg, 45%) as a white solid. $^1H$ NMR (400 MHz, DMSO-d6) δ 13.75 (s, 1H), 7.65 (d, J=8.8 Hz, 1H), 7.25 (q, J=9.3 Hz, 1H), 7.03 (ddd, J=9.5, 5.1, 2.2 Hz, 1H), 6.72 (d, J=8.9 Hz, 1H), 3.85 (s, 3H), 2.47-2.29 (m, 3H) ppm.

Step 6: 5-[[6-(3,4-Difluoro-2-Methoxy-Phenoxy)-2-Methyl-3-(Trifluoromethyl)Benzoyl]Amino]Pyridine-2-Carboxamide (179)

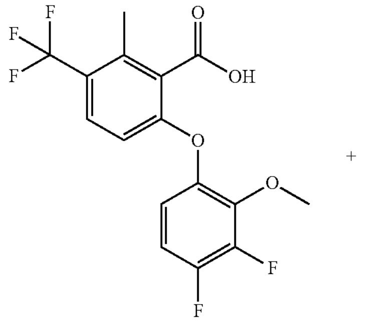

-continued

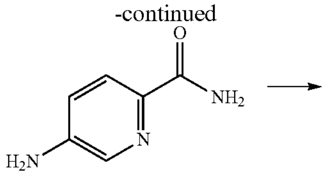

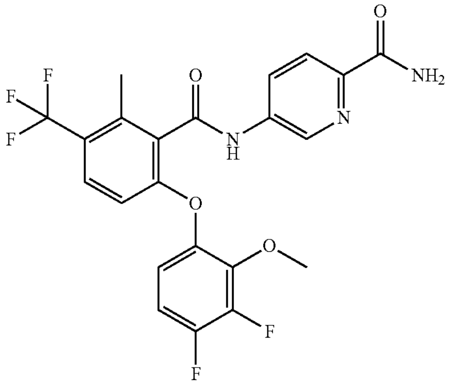

To a solution of 6-(3,4-difluoro-2-methoxy-phenoxy)-2-methyl-3-(trifluoromethyl)benzoic acid (50 mg, 0.1380 mmol) in DCM (750 μL) was added DMF (3 μL, 0.03874 mmol) followed by the slow dropwise addition of oxalyl chloride (72 μL, 0.8254 mmol). The reaction mixture was allowed to stir at RT for 30 minutes then concentrated in vacuo. Additional DCM (1 mL) was added, and the solution again concentrated in vacuo. The remaining residue was taken up in NMP (300 μL) and added to a solution of 5-aminopyridine-2-carboxamide (32 mg, 0.2333 mmol) and DIEA (120 μL, 0.6889 mmol) in NMP (300 μL). The reaction mixture was allowed to stir at 75° C. overnight then purified by reverse phase HPLC (gradient of 10-99% acetonitrile in water containing HCl as a modifier) to give 5-[[6-(3,4-difluoro-2-methoxy-phenoxy)-2-methyl-3-(trifluoromethyl)benzoyl]amino]pyridine-2-carboxamide (18 mg, 24%) as a white solid. ESI-MS m/z calc. 481.1061, found 482.5 $(M+1)^+$; Retention time (Method I): 1.65 minutes. $^1H$ NMR (400 MHz, DMSO-d6) δ 11.23 (s, 1H), 8.89 (d, J=2.4 Hz, 1H), 8.35 (dd, J=8.6, 2.4 Hz, 1H), 8.14-7.93 (m, 2H), 7.73 (d, J=8.9 Hz, 1H), 7.56 (s, 1H), 7.27 (q, J=9.3 Hz, 1H), 7.09 (ddd, J=9.4, 5.1, 2.1 Hz, 1H), 6.77 (d, J=8.8 Hz, 1H), 3.84 (s, 3H), 2.45 (s, 3H) ppm.

The compounds set forth in Table 20 were prepared by methods analogous to the preparation of compound 179.

TABLE 20

| Additional Compounds Prepared By Methods Analogous to Example 32. | | | |
|---|---|---|---|
| Cmpd No. | Compound Name | LC/MS | NMR (shifts in ppm) |
| 180 | 4-[[6-(3,4-difluoro-2-methoxy-phenoxy)-2-methyl-3-(trifluoromethyl)benzoyl]amino]-5-methyl-pyridine-2-carboxamide | ESI-MS m/z calc. 495.12173, found 496.2 (M + 1)+; Retention time (Method B): 1.65 minutes. | $^1$H NMR (400 MHz, DMSO-$d_6$) δ 10.54 (s, 1H), 8.48 (d, J = 8.2 Hz, 2H), 8.09 (s, 1H), 7.72 (d, J = 8.9 Hz, 1H), 7.63 (s, 1H), 7.37-7.21 (m, 1H), 7.21-6.98 (m, 1H), 6.77 (d, J = 8.8 Hz, 1H), 3.86 (s, 3H), 2.48 (s, 3H, obscured by solvent peak), 2.31 (s, 3H). |

Example 33

4-[[3-Cyclopropyl-6-[2-Methoxy-4-(Trifluoromethoxy)Phenoxy]-2-Methyl-Benzoyl]Amino] Pyridine-2-Carboxamide (181)

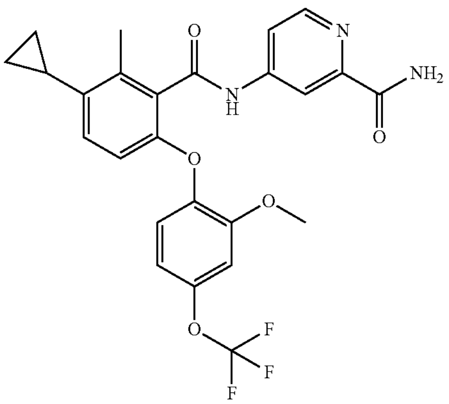 [SMILES: COc1cc(OC(F)(F)F)ccc1Oc1ccc(C2CC2)c(C)c1C(=O)Nc1ccnc(C(N)=O)c1]

Step 1: 3-Bromo-6-[2-Methoxy-4-(Trifluoromethoxy)Phenoxy]-2-Methyl-Benzaldehyde

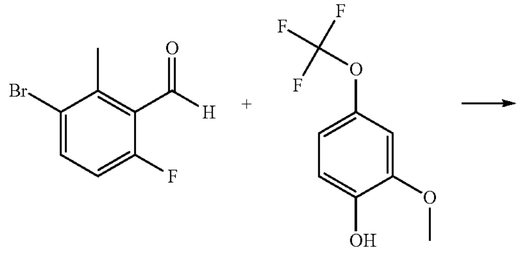

-continued

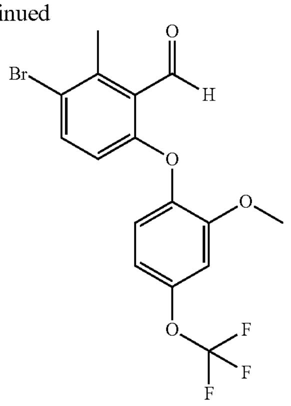

To 3-bromo-6-fluoro-2-methyl-benzaldehyde (2400 mg, 11.06 mmol) and 2-methoxy-4-(trifluoromethoxy)phenol (2.19 g, 10.52 mmol) in N,N-dimethylformamide (50 mL) was added $Cs_2CO_3$ (3.42 g, 10.50 mmol) under a $N_2$ atm. and the mixture was heated at 100° C. for 1.25 hours. After cooling to RT the mixture was diluted with ethyl acetate and wash with water, brine, dried over $Na_2SO_4$, and concentrated under reduced pressure. The residue was purified by column chromatography using a gradient of ethyl acetate in hexanes (0-15%) to yield 3-bromo-6-[2-methoxy-4-(trifluoromethoxy)phenoxy]-2-methyl-benzaldehyde (709 mg, 16%) as an off white solid. $^1$H NMR (400 MHz, Chloroform-d) δ 10.68 (s, 1H), 7.58 (d, J=8.9 Hz, 1H), 7.06 (d, J=8.4 Hz, 1H), 6.85 (d, J=9.5 Hz, 2H), 6.46 (d, J=8.9 Hz, 1H), 3.79 (s, 3H), 2.71 (s, 3H) ppm. ESI-MS m/z calc. 405.99, found 407.14 $(M+1)^+$; Retention time (Method A): 0.89 minutes.

Step 2: 3-Cyclopropyl-6-[2-Methoxy-4-(Trifluoromethoxy)Phenoxy]-2-Methyl-Benzaldehyde

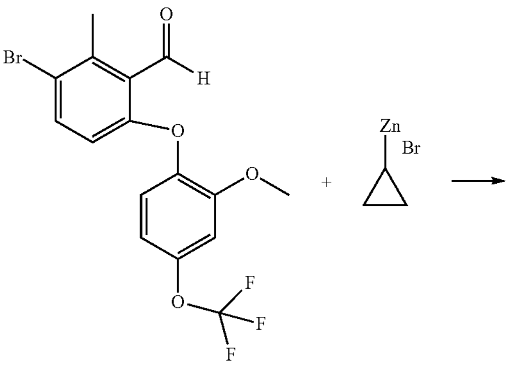

-continued

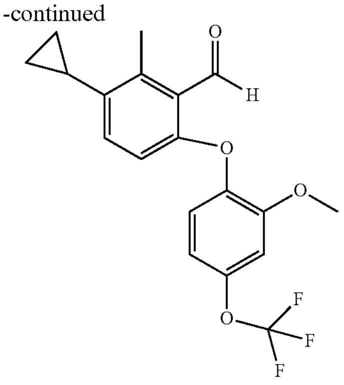

To a flask charged with 3-bromo-6-[2-methoxy-4-(trifluoromethoxy)phenoxy]-2-methyl-benzaldehyde (80 mg, 0.197 mmol) and palladium tri-tert-butylphosphane (18 mg, 0.0352 mmol), under an atmosphere of $N_2$ at 0° C. was added THF (1 mL) followed by bromo(cyclopropyl)zinc (600 μL of 0.5 M, 0.30 mmol) in THF and the reaction mixture was gradually warmed to room temperature over 1 h. The mixture as stirred at RT for 30 minutes. The reaction mixture was quenched with 1N HCl, the aq. layer was extracted with DCM (3×). The combined organic layers were dried over $Na_2SO_4$, filtered and concentrated. The residue was purified by column chromatography using a gradient of ethyl acetate in hexanes (0-15%) to yield 3-cyclopropyl-6-[2-methoxy-4-(trifluoromethoxy)phenoxy]-2-methyl-benzaldehyde (69 mg, 95%) as a white solid. $^1$H NMR (400 MHz, Chloroform-d) δ 10.72 (s, 1H), 7.16 (d, J=8.6 Hz, 1H), 6.95 (d, J=8.7 Hz, 1H), 6.85 (d, J=2.7 Hz, 1H), 6.80 (d, J=8.9 Hz, 1H), 6.51 (d, J=8.6 Hz, 1H), 3.82 (s, 3H), 2.72 (s, 3H), 1.86 (td, J=8.1, 4.1 Hz, 1H), 1.05-0.87 (m, 2H), 0.56 (h, J=4.3 Hz, 2H) ppm. ESI-MS m/z calc. 366.108, found 367.26 $(M+1)^+$; Retention time (Method A): 0.85 minutes.

Step 3: 3-Cyclopropyl-6-[2-Methoxy-4-(Trifluoromethoxy)Phenoxy]-2-Methyl-Benzoic Acid

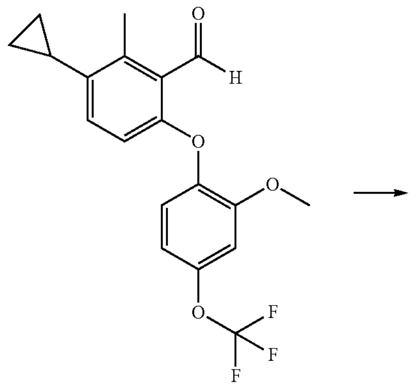

-continued

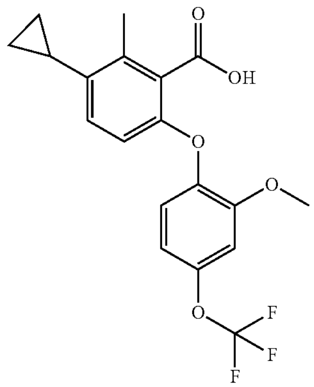

To a solution of 3-cyclopropyl-6-[2-methoxy-4-(trifluoromethoxy)phenoxy]-2-methyl-benzaldehyde (69 mg, 0.188 mmol) in tert-butyl alcohol (1 mL), acetonitrile (0.6 mL), and water (0.6 mL) was added sodium dihydrogen phosphate (26 mg, 0.217 mmol) and 2-methyl-2-butene (100 μL, 0.945 mmol) (cooled container in ice prior to syringing out). To this mixture was added sodium chlorite (22 mg, 0.243 mmol) and the reaction was stirred at RT for 1.75 h. The mixture was diluted with 1 N HCl (15 mL) and extracted with ethyl acetate (3×). The combined organics were dried over $Na_2SO_4$ and concentrated under reduced pressure to give 3-cyclopropyl-6-[2-methoxy-4-(trifluoromethoxy)phenoxy]-2-methyl-benzoic acid (71 mg, 94%). $^1$H NMR (400 MHz, Chloroform-d) δ 7.06 (d, J=8.3 Hz, 1H), 7.01 (d, J=8.6 Hz, 1H), 6.82 (d, J=9.0 Hz, 2H), 6.50 (d, J=8.6 Hz, 1H), 3.81 (s, 3H), 2.53 (s, 3H), 1.83 (td, J=9.1, 8.2, 4.6 Hz, 1H), 1.01-0.86 (m, 2H), 0.58 (t, J=5.2 Hz, 2H) ppm. ESI-MS m/z calc. 382.1028, found 383.25 $(M+1)^+$; Retention time (Method A): 0.74 minutes.

Step 4: 4-[[3-Cyclopropyl-6-[2-Methoxy-4-(Trifluoromethoxy)Phenoxy]-2-Methyl-Benzoyl]Amino]Pyridine-2-Carboxamide (181)

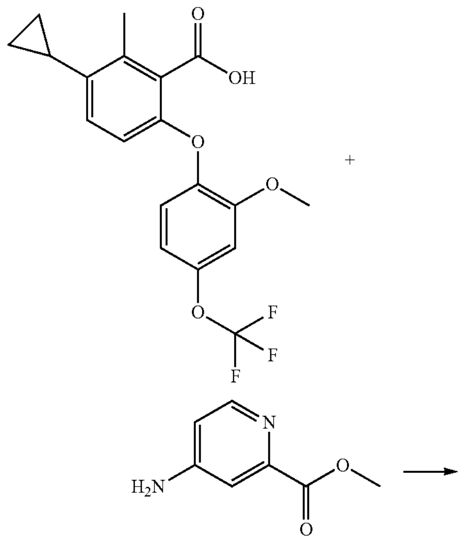

-continued

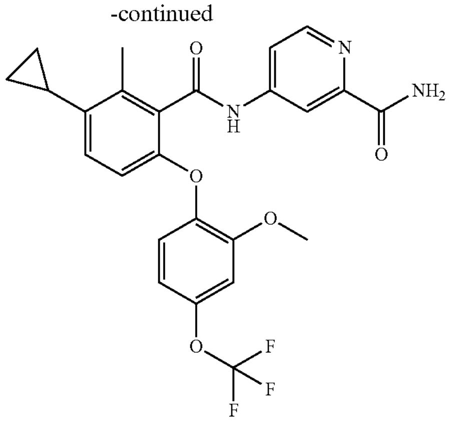

To a solution of 3-cyclopropyl-6-[2-methoxy-4-(trifluoromethoxy)phenoxy]-2-methyl-benzoic acid (70 mg, 0.1831 mmol) in DCM (2 mL) cooled in an ice bath was added DMF (2 μL, 0.0258 mmol) followed by the dropwise addition of oxalyl chloride (32 μL, 0.367 mmol). The mixture was stirred at on ice for 10 minutes and then at RT for 2 h. The reaction was concentrated under reduced pressure and flushed with $N_2$ to afford the acid chloride, which was taken directly into the next step.

A solution of methyl 4-aminopyridine-2-carboxylate (35 mg, 0.230 mmol) and DIEA (82 μL, 0.471 mmol) in DCM (2 mL) was cooled on ice and the crude acid chloride in DCM (2 mL) was added dropwise. The ice bath was removed and the reaction mixture was stirred at RT overnight. The reaction was quenched into water and extract with DCM (3×). The combined organics were dried over $Na_2SO_4$, and concentrated under reduced pressure. The major product was isolated by silica gel column chromatography using a gradient of ethyl acetate in hexanes and was used directly in the next step. The isolated material was treated with $NH_3$ (10 mL of 7 M, 70.00 mmol) in methanol for 28 hours. The solvent was removed under reduced pressure to give 4-[[3-cyclopropyl-6-[2-methoxy-4-(trifluoromethoxy)phenoxy]-2-methyl-benzoyl]amino]pyridine-2-carboxamide (39 mg, 40%) as an off white solid. $^1H$ NMR (400 MHz, DMSO-d6) δ 11.05 (s, 1H), 8.50 (d, J=5.5 Hz, 1H), 8.37 (d, J=2.1 Hz, 1H), 8.07 (d, J=3.1 Hz, 1H), 7.84 (dd, J=5.5, 2.2 Hz, 1H), 7.62 (d, J=3.0 Hz, 1H), 7.18-7.07 (m, 2H), 7.04 (d, J=8.7 Hz, 1H), 6.98-6.87 (m, 1H), 6.48 (d, J=8.6 Hz, 1H), 3.74 (s, 3H), 2.37 (s, 3H), 1.90 (h, J=6.0 Hz, 1H), 1.00-0.85 (m, 2H), 0.57 (h, J=4.0 Hz, 2H) ppm. ESI-MS m/z calc. 501.15115, found 502.42 $(M+1)^+$; Retention time (Method B): 1.87 minutes.

The compounds set forth in Table 21 were prepared by methods analogous to the preparation of compound 181.

TABLE 21

Additional Compounds Prepared By Methods Analogous to Example 33.

| Cmpd No. | Compound Name | LC/MS | NMR (shifts in ppm) |
| --- | --- | --- | --- |
| 182 | 5-[[3-cyclopropyl-6-[2-methoxy-4-(trifluoromethoxy)phenoxy]-2-methyl-benzoyl]amino]pyridine-2-carboxamide | ESI-MS m/z calc. 501.15115, found 502.0 (M + 1)+; Retention time (Method B): 1.8 minutes | 1H NMR (400 MHz, DMSO-d6) δ 10.95 (s, 1H), 8.87 (s, 1H), 8.30 (d, J = 11.0 Hz, 1H), 8.10-7.90 (m, 2H), 7.53 (s, 1H), 7.10 (d, J = 8.8 Hz, 2H), 7.04 (d, J = 8.6 Hz, 1H), 6.94 (d, J = 8.8 Hz, 1H), 6.49 (d, J = 8.6 Hz, 1H), 3.74 (s, 3H), 2.38 (s, 3H), 1.90 (s, 1H), 0.93 (d, J = 18.5 Hz, 2H), 0.57 (d, J = 5.5 Hz, 2H). |

Example 34

4-[[2-Ethyl-6-[2-Methoxy-4-(Trifluoromethoxy)Phenoxy]-3-(Trifluoromethyl)Benzoyl]Amino]Pyridine-2-Carboxamide (183)

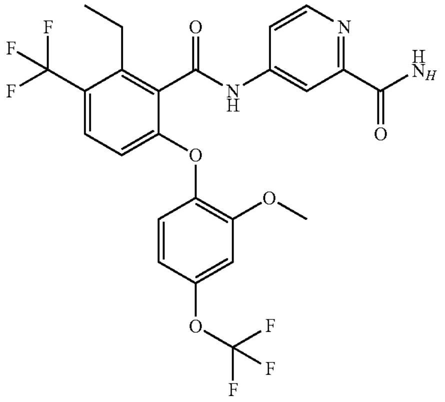

Step 1: Tert-Butyl 2-Bromo-6-[2-Methoxy-4-(Trifluoromethoxy)Phenoxy]-3-(Trifluoromethyl)Benzoate

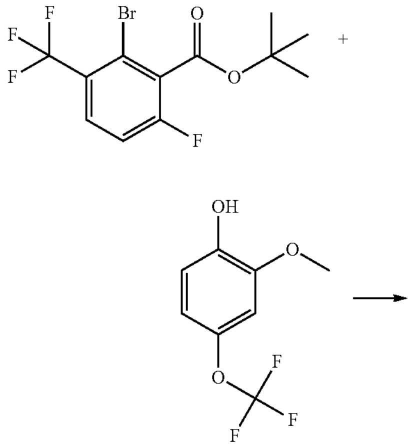

-continued

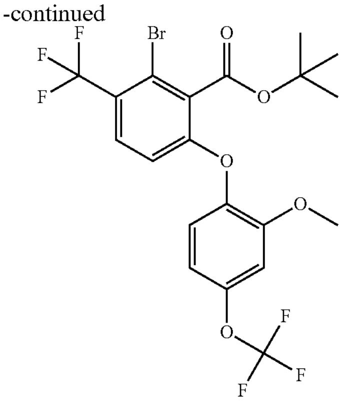

$K_2CO_3$ (6.3 g, 45.58 mmol) was added to a completely soluble solution of tert-butyl 2-bromo-6-fluoro-3-(trifluoromethyl)benzoate (7.7 g, 22.44 mmol) and 2-methoxy-4-(trifluoromethoxy)phenol (4.8 g, 23.06 mmol) in DMSO (27.0 mL). The mixture was heated at 100° C. for 1.25 hours and then cooled to RT. To the mixture was added heptane (58 mL) and water (38 mL). The layers were separated and the organic layer was washed with water, dried over MgSO4, concentrated under reduced pressure to give tert-butyl 2-bromo-6-[2-methoxy-4-(trifluoromethoxy)phenoxy]-3-(trifluoromethyl)benzoate (12.19 g, 102%). $^1H$ NMR (400 MHz, DMSO-d6) δ 7.79 (d, J=8.9 Hz, 1H), 7.32-7.22 (m, 2H), 7.07-6.98 (m, 1H), 6.83 (d, J=8.9 Hz, 1H), 3.81 (s, 3H), 1.53 (s, 9H) ppm.

Step 2: Tert-Butyl 6-[2-Methoxy-4-(Trifluoromethoxy)Phenoxy]-3-(Trifluoromethyl)-2-Vinyl-Benzoate

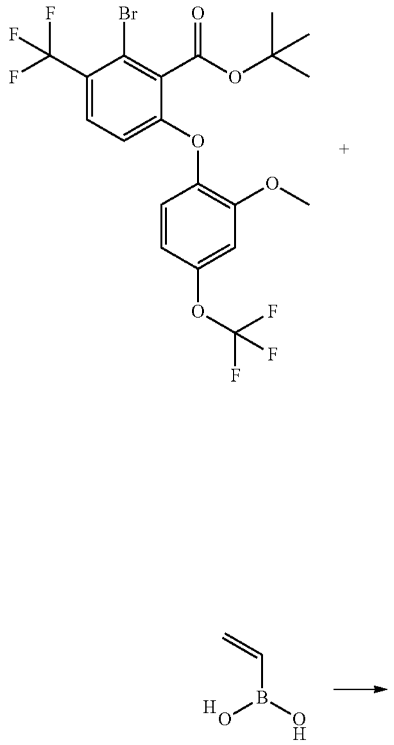

-continued

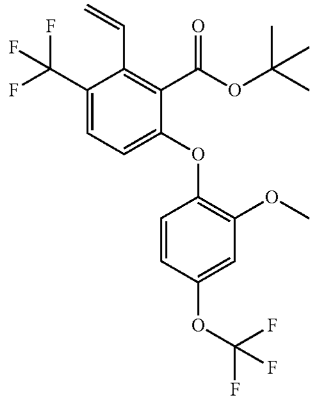

tert-Butyl 2-bromo-6-[2-methoxy-4-(trifluoromethoxy)phenoxy]-3-(trifluoromethyl)benzoate (1.00 g, 1.88 mmol) and vinylboronic acid (203 mg, 2.82 mmol) were combined and dissolved in DMSO (10 mL). Aqueous potassium carbonate (2.8 mL of 2 M, 5.600 mmol) was added followed by ferrous; cyclopenta-1,4-dien-1-yl(diphenyl)phosphane; dichloromethane; dichloropalladium (77 mg, 0.0943 mmol). The reaction mixture was stirred at 75° C. for 1 hour. The reaction mixture was diluted with EtOAc (75 mL) and washed with water (1×75 mL) and brine (1×75 mL). The organic layer was dried over sodium sulfate, filtered and concentrated under reduced pressure. The crude product was chromatographed on a silica gel column eluting with a EtOAc/hexane gradient to give tert-butyl 6-[2-methoxy-4-(trifluoromethoxy)phenoxy]-3-(trifluoromethyl)-2-vinyl-benzoate (644 mg, 72%) as a clear colorless oil. $^1H$ NMR (400 MHz, DMSO-d6) δ 7.70 (d, J=8.8 Hz, 1H), 7.26 (d, J=2.4 Hz, 1H), 7.19 (d, J=8.8 Hz, 1H), 7.00 (d, J=9.7 Hz, 1H), 6.91-6.83 (m, 1H), 6.76 (d, J=8.8 Hz, 1H), 5.64 (d, J=11.6 Hz, 1H), 5.56 (d, J=17.6 Hz, 1H), 1.53 (s, 3H), 1.45 (s, 9H) ppm. ESI-MS m/z calc. 478.1215, found 423.1 (M−55)+; Retention time (Method B): 2.37 minutes

Step 3: Tert-Butyl 2-Ethyl-6-[2-Methoxy-4-(Trifluoromethoxy)Phenoxy]-3-(Trifluoromethyl)Benzoate

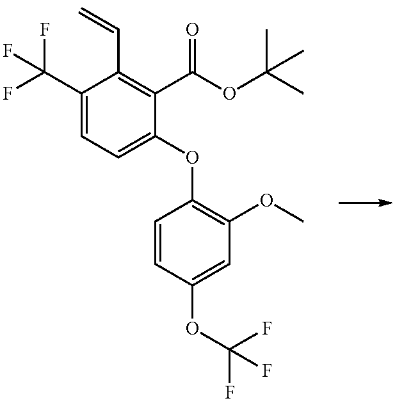

-continued

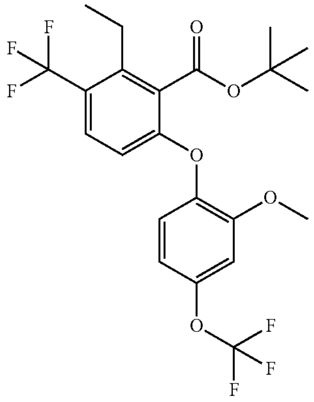

tert-Butyl 6-[2-methoxy-4-(trifluoromethoxy)phenoxy]-3-(trifluoromethyl)-2-vinyl-benzoate (644 mg, 1.346 mmol) was dissolved in ethanol (15 mL) and the reaction was flushed with $N_2$. Palladium (32 mg, 0.3007 mmol) (10 wt % on carbon, wet, degussa) was added. The reaction mixture was allowed to stir under an atmosphere of hydrogen gas overnight. The reaction mixture was filtered through celite, and the filtrate was concentrated under reduced pressure. The crude product was chromatographed on a silica gel column eluting with a 0-10% EtOAc/hexane gradient to give tert-butyl 2-ethyl-6-[2-methoxy-4-(trifluoromethoxy)phenoxy]-3-(trifluoromethyl)benzoate (522 mg, 81%) as a clear colorless oil. ESI-MS m/z calc. 480.13715, found 407.1 (M−73)+; Retention time (Method B): 2.46 minutes.

Step 4: 2-Ethyl-6-[2-Methoxy-4-(Trifluoromethoxy) Phenoxyl-3-(Trifluoromethyl)Benzoic Acid

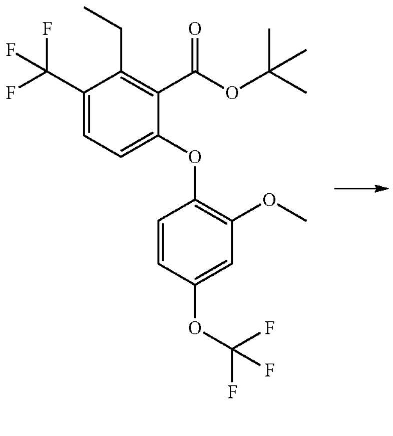

-continued

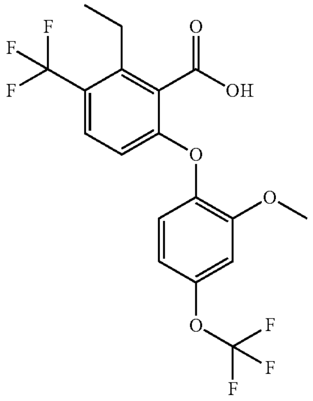

tert-Butyl 2-ethyl-6-[2-methoxy-4-(trifluoromethoxy) phenoxy]-3-(trifluoromethyl)benzoate (544 mg, 1.132 mmol) was dissolved into a prepared solution of TFA (1 mL, 12.98 mmol) in DCM (2 mL). The reaction mixture was allowed to stir at room temperature for 30 minutes. The reaction mixture was diluted with EtOAc (75 mL) and washed with water (1×75 mL) and brine (1×75 mL). The organic layer was dried over sodium sulfate, filtered and concentrated under reduced pressure. The crude product was purified by reverse-phase HPLC eluting with a 35-99% acetonitrile/water (0.5 mM HC 1) gradient to give 2-ethyl-6-[2-methoxy-4-(trifluoromethoxy)phenoxy]-3-(trifluoromethyl)benzoic acid (297 mg, 62%) as a white sticky foam. $^1$H NMR (400 MHz, DMSO-d6) δ 13.67 (s, 1H), 7.64 (d, J=8.9 Hz, 1H), 7.25 (d, J=2.7 Hz, 1H), 7.21 (d, J=8.8 Hz, 1H), 7.05-6.97 (m, 1H), 6.60 (d, J=8.9 Hz, 1H), 3.80 (s, 3H), 2.78 (q, J=7.5 Hz, 2H), 1.22 (t, J=7.5 Hz, 3H) ppm.

Step 5: 4-[[2-Ethyl-6-[2-Methoxy-4-(Trifluoromethoxy)Phenoxy]-3-(Trifluoromethyl)Benzoyl] Amino]Pyridine-2-Carboxamide (183)

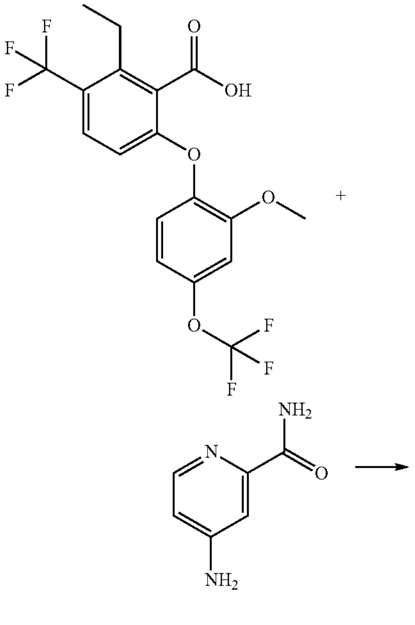

-continued

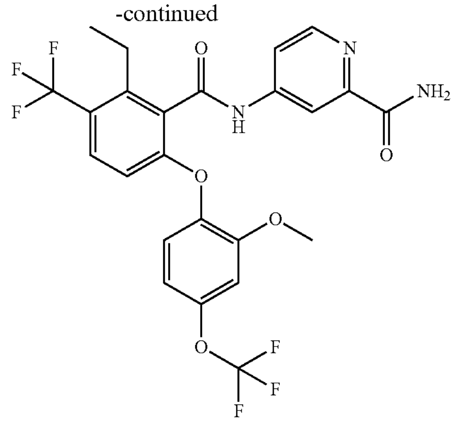

2-Ethyl-6-[2-methoxy-4-(trifluoromethoxy)phenoxy]-3-(trifluoromethyl)benzoic acid (43 mg, 0.101 mmol) was dissolved in dichloromethane (0.5 mL). DMF (approximately 0.37 mg, 0.39 μL, 0.0051 mmol) was added followed by the slow dropwise addition of oxalyl chloride (approximately 35 μL, 0.405 mmol). The reaction mixture was allowed to stir at room temperature for 1 hour. The reaction mixture was concentrated under reduced pressure. Additional dichloromethane (~5 mL) was added, and the solution was again concentrated to dryness. The remaining residue was taken up in NMP (0.5 mL) and added to a mixture of 4-aminopyridine-2-carboxamide (approximately 21 mg, 0.152 mmol) and DIEA (approximately 106 μL, 0.608 mmol). The reaction mixture was allowed to stir at 70° C. overnight. The product was isolated by reverse-phase HPLC eluting with a 30-99% acetonitrile/water (5 mM HCl) gradient to give 4-[[2-ethyl-6-[2-methoxy-4-(trifluoromethoxy)phenoxy]-3-(trifluoromethyl)benzoyl]amino]pyridine-2-carboxamide (16.3 mg, 28%). $^1$H NMR (400 MHz, DMSO-d6) δ 11.28 (s, 1H), 8.54 (d, J=5.5 Hz, 1H), 8.39 (d, J=2.2 Hz, 1H), 8.16-8.07 (m, 1H), 7.86 (dd, J=5.6, 2.1 Hz, 1H), 7.72 (d, J=8.9 Hz, 1H), 7.66 (s, 1H), 7.32 (d, J=8.8 Hz, 1H), 7.24 (d, J=2.6 Hz, 1H), 7.04 (d, J=9.1 Hz, 1H), 6.65 (d, J=8.9 Hz, 1H), 3.78 (s, 3H), 2.81 (q, J=7.5 Hz, 2H), 1.23 (t, J=7.4 Hz, 3H) ppm. ESI-MS m/z calc. 543.12286, found 544.2 $(M+1)^+$; Retention time (Method B): 1.88 minutes.

The compounds set forth in Table 22 were prepared by methods analogous to the preparation of compound 183.

Example 35

4-[[3-Isobutyl-6-[2-Methoxy-4-(Trifluoromethoxy)Phenoxy]-2-Methyl-Benzoyl]Amino]Pyridine-2-Carboxamide (185)

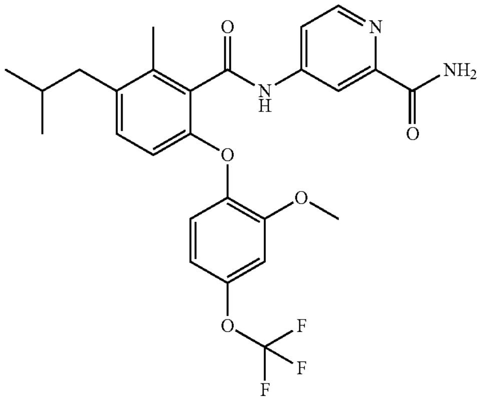 [SMILES: COc1cc(OC(F)(F)F)ccc1Oc1ccc(CC(C)C)c(C)c1C(=O)Nc1ccnc(C(N)=O)c1]

Step 1: 3-Isobutyl-6-[2-Methoxy-4-(Trifluoromethoxy)Phenoxy]-2-Methyl-Benzaldehyde

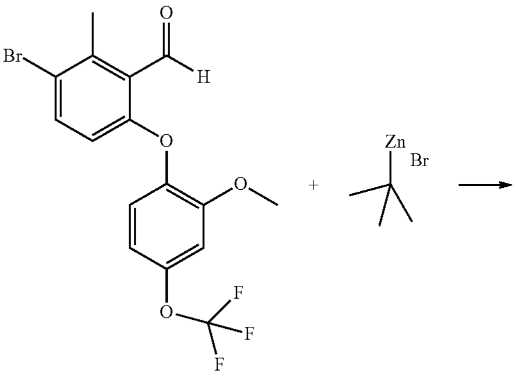

TABLE 22

Additional Compounds Prepared By Methods Analogous to Example 34.

| Cmpd No. | Compound Name | LC/MS | NMR (shifts in ppm) |
|---|---|---|---|
| 184 | 5-[[2-ethyl-6-[2-methoxy-4-(trifluoromethoxy)phenoxy]-3-(trifluoromethyl)benzoyl]amino]pyridine-2-carboxamide | ESI-MS m/z calc. 543.12286, found 544.2 (M + 1)+; Retention time: 1.88 minutes | 1H NMR (400 MHz, DMSO-d6) δ 11.16 (s, 1H), 8.88 (d, J = 2.4 Hz, 1H), 8.34 (dd, J = 8.6, 2.3 Hz, 1H), 8.05 (d, J = 8.6 Hz, 1H), 8.00 (s, 1H), 7.72 (d, J = 9.0 Hz, 1H), 7.59-7.51 (m, 1H), 7.32 (d, J = 8.8 Hz, 1H), 7.24 (d, J = 2.7 Hz, 1H), 7.04 (d, J = 8.4 Hz, 1H), 6.66 (d, J = 8.9 Hz, 1H), 3.79 (s, 3H), 2.82 (d, J = 7.9 Hz, 2H), 1.24 (t, J = 7.5 Hz, 3H). |

-continued

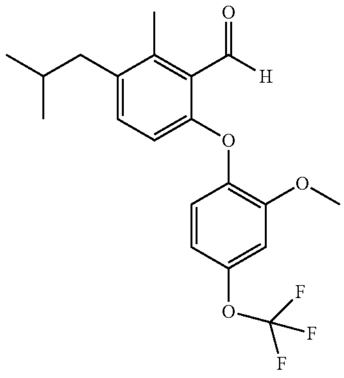

-continued

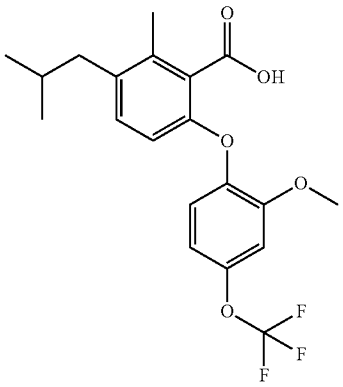

To a flask charged with 3-bromo-6-[2-methoxy-4-(trifluoromethoxy)phenoxy]-2-methyl-benzaldehyde (250 mg, 0.617 mmol) and palladium tri-tert-butylphosphane (56 mg, 0.11 mmol), under an atmosphere of $N_2$ at 0° C. was added THF (3 mL) followed by bromo(tert-butyl)zinc (1.9 mL of 0.5 M, 0.950 mmol) in THF and the reaction mixture was gradually warmed to room temperature over 1 h. The reaction mixture was quenched with 1N HCl, the aq. layer was extracted with DCM (3×). The combined organic layers were dried over $Na_2SO_4$, filtered and concentrated. The residue was purified by column chromatography using a gradient of ethyl acetate in hexanes to yield 3-isobutyl-6-[2-methoxy-4-(trifluoromethoxy)phenoxy]-2-methyl-benzaldehyde (65 mg, 22%). $^1$H NMR (400 MHz, Chloroform-d) δ 10.73 (d, J=5.6 Hz, 1H), 7.16 (d, J=8.5 Hz, 1H), 6.97 (d, J=8.7 Hz, 1H), 6.89-6.84 (m, 1H), 6.84-6.78 (m, 1H), 6.53 (d, J=8.3 Hz, 1H), 3.82 (s, 3H), 2.55 (s, 3H), 2.50 (d, J=7.8 Hz, 2H), 1.81 (hept, J=6.7 Hz, 1H), 0.91 (d, J=6.6 Hz, 6H) ppm. ESI-MS m/z calc. 382.1392, found 383.29 $(M+1)^+$; Retention time (Method A): 0.94 minutes.

Step 2: 3-Isobutyl-6-[2-Methoxy-4-(Trifluoromethoxy)Phenoxy]-2-Methyl-Benzoic Acid

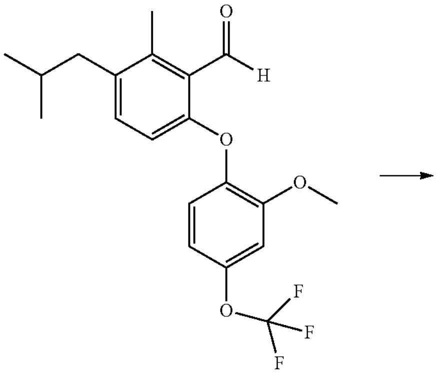

To a solution of 3-tert-butyl-6-[2-methoxy-4-(trifluoromethoxy)phenoxy]-2-methyl-benzaldehyde (60 mg, 0.126 mmol) in tert-butyl alcohol (1 mL), acetonitrile (0.5 mL), and water (0.5 mL) was added sodium dihydrogen phosphate (22 mg, 0.183 mmol) and 2-methyl-2-butene (83 μL, 0.785 mmol). To this mixture was added sodium chlorite (19 mg, 0.210 mmol) and the reaction was stirred at RT for 1.75 h. The mixture was diluted with 1 N HCl (15 mL) and extracted with ethyl acetate (3×). The combined organics were dried over $Na_2SO_4$ and concentrated under reduced pressure to give 3-isobutyl-6-[2-methoxy-4-(trifluoromethoxy)phenoxy]-2-methyl-benzoic acid (63 mg, 101%). ESI-MS m/z calc. 398.1341, found 399.29 $(M+1)^+$; Retention time (Method A): 0.84 minutes.

Step 3: 4-[[3-Isobutyl-6-[2-Methoxy-4-(Trifluoromethoxy)Phenoxy]-2-Methyl-Benzoyl]Amino] Pyridine-2-Carboxamide (185)

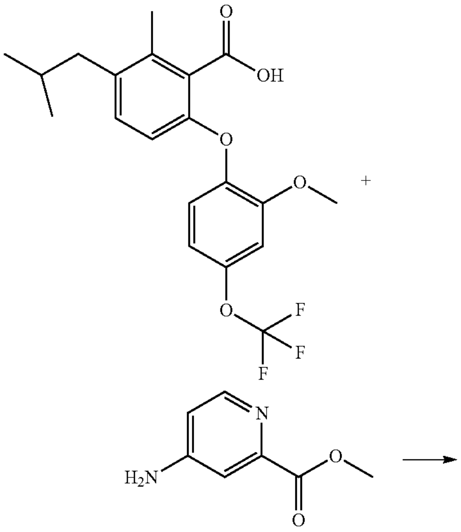

-continued

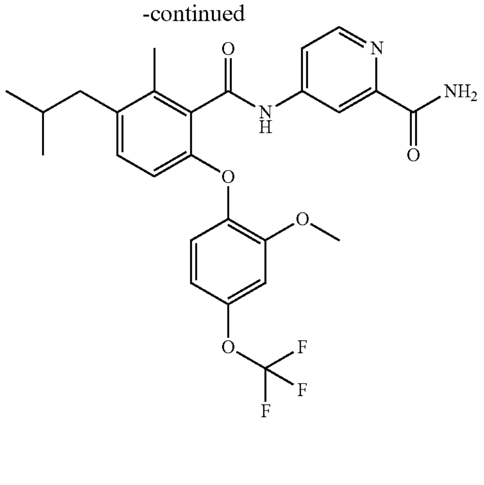

To a solution of 3-isobutyl-6-[2-methoxy-4-(trifluoromethoxy)phenoxy]-2-methyl-benzoic acid (60 mg, 0.121 mmol) in DCM (2 mL) cooled in an ice bath was added DMF (2 μL, 0.02583 mmol) followed by the dropwise addition of oxalyl chloride (26 μL, 0.298 mmol). The mixture was stirred on ice for 10 mins then at RT for 1.5 h. The reaction was concentrated under reduced pressure and flushed with $N_2$ to afford the acid chloride, which was taken directly into the next step.

A solution of methyl 4-aminopyridine-2-carboxylate (46 mg, 0.302 mmol) and DIEA (67 μL, 0.385 mmol) in DCM (2 mL) was cooled on ice and the crude acid chloride in DCM (2 mL) was added dropwise. The ice bath was removed and the reaction mixture was stirred at RT overnight. The reaction was quenched into water and extract with DCM (3×). The combined organics were dried over $Na_2SO_4$, and concentrated under reduced pressure. The residue was purified by silica gel column chromatography using a gradient of ethyl acetate in hexanes and was used directly in the next step. The isolated material was treated with $NH_3$ (7 mL of 7 M, 49.00 mmol) in methanol for 28 hours. The solvent was removed under reduced pressure and the residue as purified by medium pressure $C_{18}$ reverse phase chromatography (acetonitrile, water (5 mMHCl) gradient) to give 4-[[3-isobutyl-6-[2-methoxy-4-(trifluoromethoxy)phenoxy]-2-methyl-benzoyl]amino]pyridine-2-carboxamide (6 mg, 10%). $^1H$ NMR (400 MHz, Chloroform-d) δ 9.55 (s, 1H), 9.08 (s, 1H), 8.71 (s, 1H), 8.53 (d, J=5.5 Hz, 1H), 8.11 (s, 1H), 7.14 (d, J=8.4 Hz, 1H), 7.09 (d, J=8.5 Hz, 1H), 6.88 (d, J=8.5 Hz, 2H), 6.52 (d, J=8.5 Hz, 1H), 5.81 (s, 1H), 3.88 (s, 3H), 2.49 (d, J=7.1 Hz, 2H), 2.40 (s, 3H), 1.83 (p, J=6.5 Hz, 1H), 0.92 (d, J=6.5 Hz, 6H) ppm. ESI-MS m/z calc. 517.18243, found 518.45 $(M+1)^+$; Retention time (Method B): 2.06 minutes.

Example 36

4-[[2-[2-Methoxy-4-(Trifluoromethoxy)Phenoxy]-6-Methyl-4-(Trifluoromethyl)Benzoyl]Amino]-5-Methyl-Pyridine-2-Carboxamide (186)

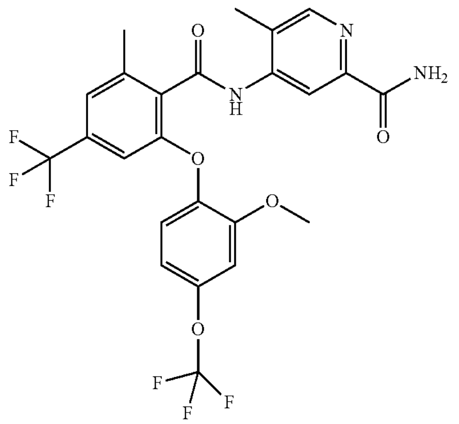 [SMILES: COc1cc(OC(F)(F)F)ccc1Oc1cc(C(F)(F)F)cc(C)c1C(=O)Nc1cc(C(N)=O)ncc1C]

Step 1: Tert-Butyl 2-Bromo-6-Fluoro-4-(Trifluoromethyl)Benzoate

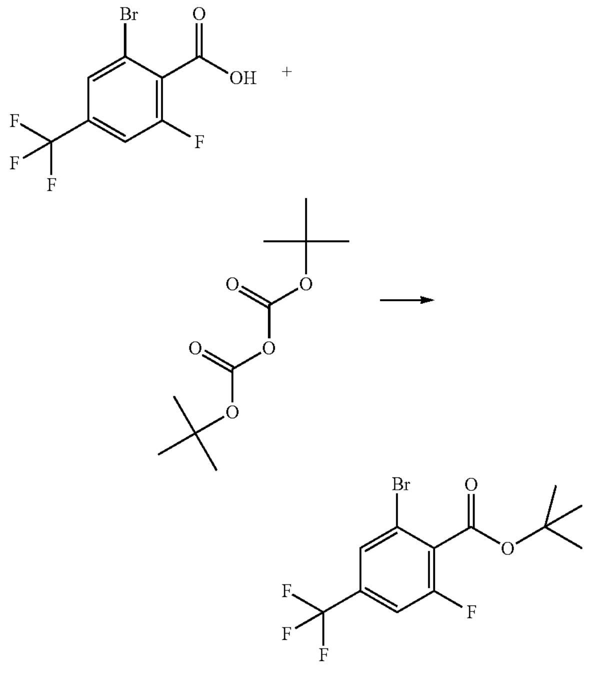

To a solution of 2-bromo-6-fluoro-4-(trifluoromethyl)benzoic acid (15 g, 49.65 mmol) in tert-butanol (285 mL) was added DMAP (607 mg, 4.919 mmol) followed by tert-butoxycarbonyl tert-butyl carbonate (21.7 g, 96.45 mmol) at room temperature. The reaction mixture was stirred at 40° C. overnight. The mixture was cooled to RT and concentrated under reduced pressure. The residue was triturated with 50 mL of hexanes and filtered. The filtrate was concentrated under reduced pressure to give tert-butyl 2-bromo-6-fluoro-4-(trifluoromethyl)benzoate (14.94 g, 88%) as a pale yellow oil, which was used in next step without purification. $^1$H NMR (400 MHz, DMSO-d6) δ 8.03 (s, 1H), 7.95 (d, J=9.0 Hz, 1H), 1.57 (s, 9H) ppm.

Step 2: Tert-Butyl 2-Bromo-6-[2-Methoxy-4-(Trifluoromethoxy)Phenoxy]-4-(Trifluoromethyl)Benzoate

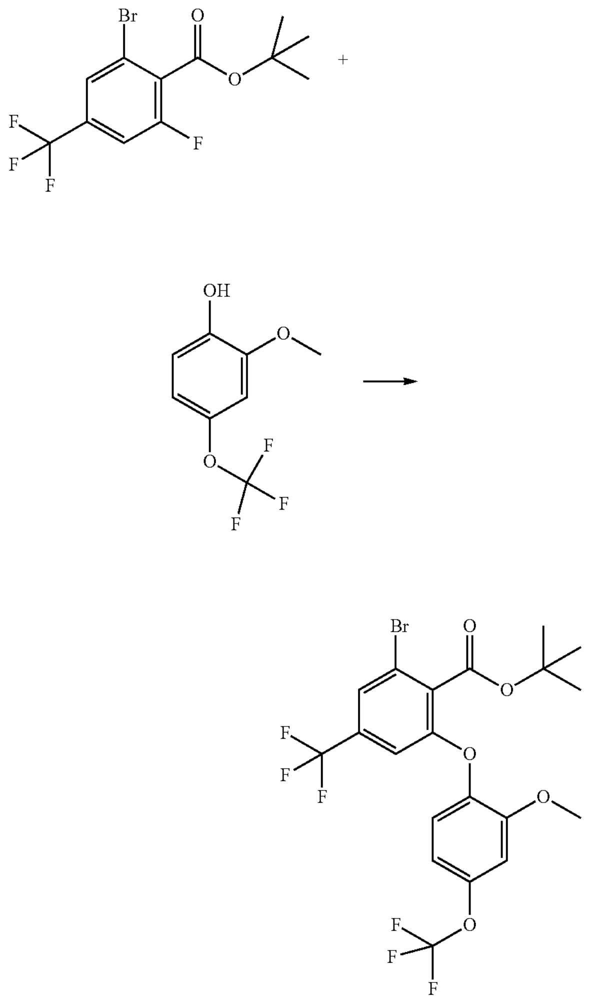

A mixture of tert-butyl 2-bromo-6-fluoro-4-(trifluoromethyl)benzoate (2.97 g, 8.66 mmol), 2-methoxy-4-(trifluoromethoxy)phenol (2.4 g, 11.53 mmol) and potassium carbonate (2.4 g, 17.37 mmol) in DMSO (12 mL) was heated at 100° C. for 1 h. The reaction mixture was allowed to cool to RT, was poured onto 50 mL of water and extracted with ethyl acetate (3×50 mL). The combined organic layers were washed with brine (50 mL), dried over sodium sulfate, filtered and concentrated under reduced pressure. The residue was purified by silica chromatography eluting with gradient of EtOAc and hexanes to give tert-butyl 2-bromo-6-[2-methoxy-4-(trifluoromethoxy)phenoxy]-4-(trifluoromethyl)benzoate (4.10 g, 89%). $^1$H NMR (400 MHz, DMSO-d6) δ 7.85 (s, 1H), 7.25 (d, J=2.8 Hz, 1H), 7.17 (d, J=8.8 Hz, 1H), 7.06 (s, 1H), 7.04-6.93 (m, 1H), 3.81 (s, 3H), 1.48 (s, 9H) ppm.

Step 3: Tert-Butyl 2-[2-Methoxy-4-(Trifluoromethoxy)Phenoxy]-6-Methyl-4-(Trifluoromethyl)Benzoate

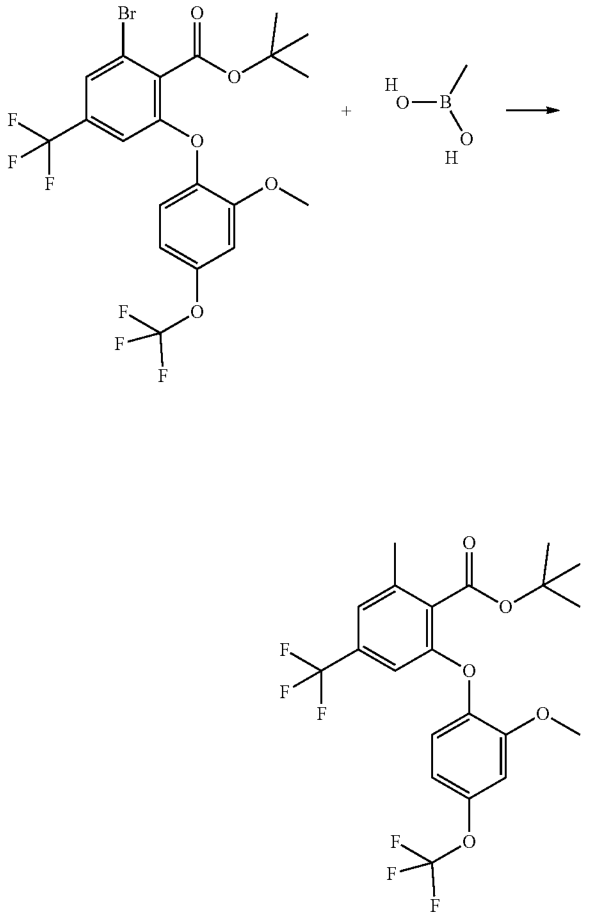

A mixture of tert-butyl 2-bromo-6-[2-methoxy-4-(trifluoromethoxy)phenoxy]-4-(trifluoromethyl)benzoate (1 g, 1.882 mmol), methylboronic acid (740 mg, 12.11 mmol), potassium carbonate (838 mg, 5.942 mmol) and ferrous; cyclopenta-1,4-dien-1-yl(diphenyl)phosphane dichloromethane dichloropalladium (154 mg, 0.1886 mmol) in dioxane (6 mL)/water (600 μL) was flushed with nitrogen, capped and heated at 120° C. for 30 minutes in an oil bath. The reaction mixture was allowed to cool to room temperature and was diluted with water (50 mL) and extracted with ethyl acetate (3×50 mL). The combined organic layers were washed with brine, filtered, and concentrated reduced pressure. The residue was purified by silica column chromatography eluting with a EtOAc/hexanes gradient to giving tert-butyl 2-[2-methoxy-4-(trifluoromethoxy)phenoxy]-6-methyl-4-(trifluoromethyl)benzoate (693 mg, 79%). $^1$H NMR (400 MHz, DMSO-d6) δ 7.46 (s, 1H), 7.22 (d, J=2.6 Hz, 1H), 7.04-6.89 (m, 3H), 3.81 (s, 3H), 2.38 (s, 3H), 1.43 (s, 9H) ppm.

Step 4: 2-[2-Methoxy-4-(Trifluoromethoxy)Phenoxy]-6-Methyl-4-(Trifluoromethyl)Benzoic Acid

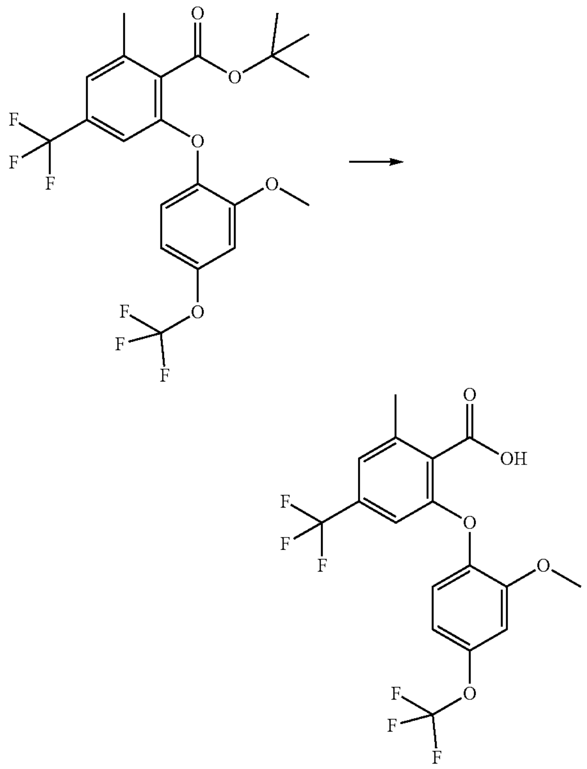

tert-Butyl 2-[2-methoxy-4-(trifluoromethoxy)phenoxy]-6-methyl-4-(trifluoromethyl)benzoate (693 mg, 1.49 mmol) was dissolved in a solution of TFA (2 mL, 25.96 mmol) in DCM (6 mL). The mixture was stirred at room temperature for 16 h. The mixture was concentrated under reduced pressure to give 2-[2-methoxy-4-(trifluoromethoxy)phenoxy]-6-methyl-4-(trifluoromethyl)benzoic acid (610 mg, 79%), which was used directly in the next step. ESI-MS m/z calc. 410.0589, found 411.3 $(M+1)^+$; Retention time (Method B): 1.87 minutes.

Step 5: 2-[2-Methoxy-4-(Trifluoromethoxy)Phenoxy]-6-Methyl-4-(Trifluoromethyl)Benzoyl Chloride

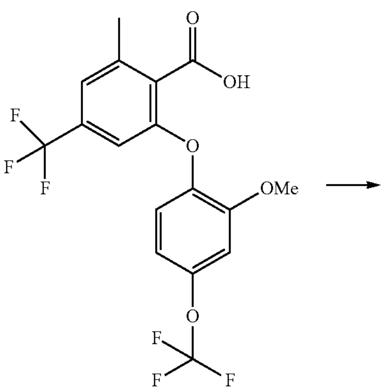

-continued

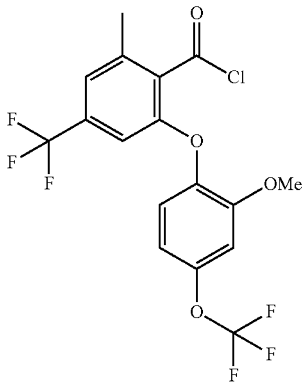

To a solution of 2-[2-methoxy-4-(trifluoromethoxy)phenoxy]-6-methyl-4-(trifluoromethyl)benzoic acid (500 mg, 1.219 mmol), DMF (26 μL, 0.3358 mmol) and DCM (8 mL) at 0° C. under $N_2$ (g) was added oxalyl chloride (855 μL, 9.801 mmol). The reaction was stirred at 0° C. for 10 min and then at RT for 1 h. The reaction was concentrated under reduced pressure and the residue was used directly in the next step.

Step 6: Methyl 4-[[2-[2-Methoxy-4-(Trifluoromethoxy)Phenoxy]-6-Methyl-4-(Trifluoromethyl)Benzoyl]Amino]-5-Methyl-Pyridine-2-Carboxylate

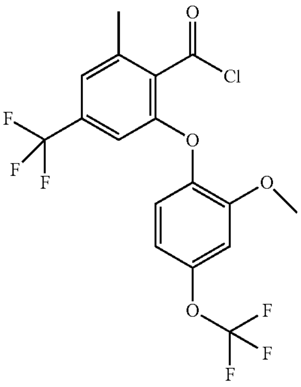

+

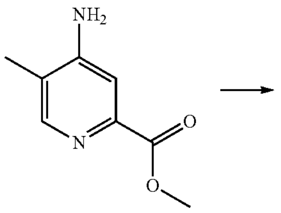

-continued

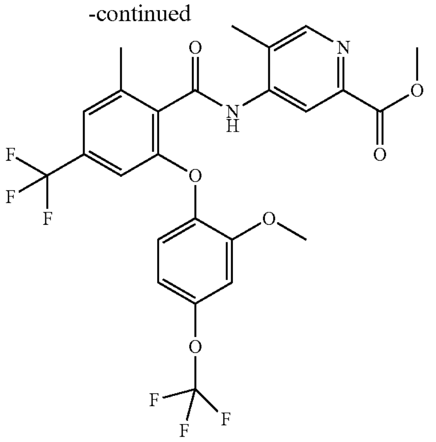

In a vial was combined methyl 4-amino-5-methylpicolinate, DIEA (61 μL) and NMP (400 μL). The mixture was cooled in ice bath and a solution of 2-[2-methoxy-4-(trifluoromethoxy)phenoxy]-6-methyl-4-(trifluoromethyl)benzoyl chloride (50 mg) in NMP (200 μL) was added drop wise. The resulting mixture was stirred at RT for 16 h. The reaction was purified directly by reverse phase HPLC (C-18 Column and gradient system of 1-99% ACN/H2O with 5 mM HCl modifier) giving methyl 4-[[2-[2-methoxy-4-(trifluoromethoxy)phenoxy]-6-methyl-4-(trifluoromethyl)benzoyl]amino]-5-methyl-pyridine-2-carboxylate (11 mg, 17%). ESI-MS m/z calc. 558.12256, found 559.3 $(M+1)^+$; Retention time (Method B): 1.6 minutes. $^1H$ NMR (400 MHz, DMSO-d6) δ 10.48 (s, 1H), 8.57 (d, J=7.2 Hz, 2H), 7.50 (d, J=1.6 Hz, 1H), 7.29-7.19 (m, 2H), 7.02 (ddd, J=8.9, 2.8, 1.3 Hz, 1H), 6.78 (s, 1H), 3.89 (s, 3H), 3.79 (s, 3H), 2.47 (s, 3H), 2.31 (s, 3H) ppm.

Step 7: 4-[[2-[2-Methoxy-4-(Trifluoromethoxy)Phenoxy]-6-Methyl-4-(Trifluoromethyl)Benzoyl]Amino]-5-Methyl-Pyridine-2-Carboxamide (186)

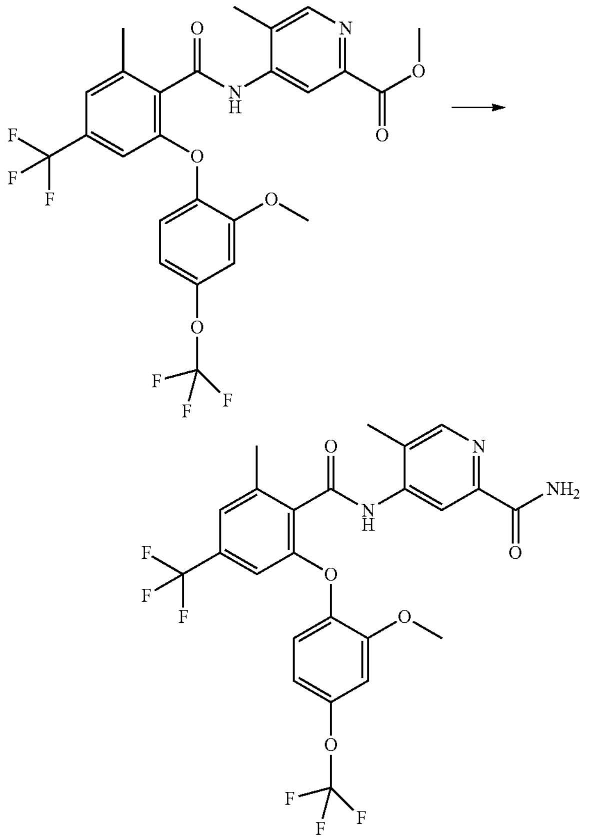

A vial containing methyl 4-[[2-[2-methoxy-4-(trifluoromethoxy)phenoxy]-6-methyl-4-(trifluoromethyl)benzoyl]amino]-5-methyl-pyridine-2-carboxylate (10 mg, 0.0179 mmol) was treated with ammonia in methanol (500 μL of 7 M, 3.50 mmol). The solution was stirred at RT for 18 h. Solvent was evaporated and the residue was purified by reverse phase LC-MS on C-18 column with gradient of 1-99% ACN/$H_2O$ (5 mM HCl) to give 4-[[2-[2-methoxy-4-(trifluoromethoxy)phenoxy]-6-methyl-4-(trifluoromethyl)benzoyl]amino]-5-methyl-pyridine-2-carboxamide (6.0 mg, 62%) as a white solid. $^1H$ NMR (400 MHz, DMSO-d6) δ 10.38 (s, 1H), 8.46 (d, J=5.7 Hz, 2H), 8.07 (s, 1H), 7.61 (s, 1H), 7.50 (s, 1H), 7.30-7.20 (m, 2H), 7.06-6.99 (m, 1H), 6.77 (s, 1H), 3.80 (s, 3H), 2.48 (s, 3H), 2.29 (s, 3H) ppm. ESI-MS m/z calc. 543.12286, found 544.2 $(M+1)^+$; Retention time (Method B): 1.35 minutes.

The compounds set forth in Table 23 were prepared by methods analogous to the preparation of compound 186.

TABLE 23

Additional Compounds Prepared By Methods Analogous to Example 36.

| Cmpd No. | Compound Name | LC/MS | NMR (shifts in ppm) |
|---|---|---|---|
| 187 | 5-[[2-[2-methoxy-4-(trifluoromethoxy)phenoxy]-6-methyl-4- | ESI-MS m/z calc. 529.10724, found 530.2 | 1H NMR (400 MHz, DMSO-d6) δ 11.11 (s, 1H), 8.87 (s, 1H), 8.29 (d, J = 9.0 Hz, 1H), 8.08-7.99 (m, 2H), 7.55 |

TABLE 23-continued

Additional Compounds Prepared By Methods Analogous to Example 36.

| Cmpd No. | Compound Name | LC/MS | NMR (shifts in ppm) |
|---|---|---|---|
| | (trifluoromethyl)benzoyl]amino]pyridine-2-carboxamide | (M + 1)+; Retention time (Method B): 1.87 minutes | (s, 1H), 7.50 (s, 1H), 7.25 (d, J = 8.8 Hz, 1H), 7.20 (s, 1H), 7.01 (d, J = 8.8 Hz, 1H), 6.79 (s, 1H), 3.76 (s, 3H), 2.43 (s, 3H). |
| 188 | 4-[[2-[2-methoxy-4-(trifluoromethoxy)phenoxy]-6-methyl-4-(trifluoromethyl)benzoyl]amino]pyridine-2-carboxamide | ESI-MS m/z calc. 529.10724, found 530.2 (M + 1)+; Retention time (Method B): 1.56 minutes | 1H NMR (400 MHz, DMSO-d6) δ 11.21 (s, 1H), 8.53 (d, J = 5.5 Hz, 1H), 8.35 (d, J = 2.1 Hz, 1H), 8.10 (s, 1H), 7.83 (dd, J = 5.5, 2.2 Hz, 1H), 7.65 (s, 1H), 7.50 (s, 1H), 7.26 (d, J = 8.8 Hz, 1H), 7.20 (d, J = 2.7 Hz, 1H), 7.01 (d, J = 8.7 Hz, 1H), 6.77 (s, 1H), 3.77 (s, 3H), 2.42 (s, 3H). |

Example 37

4-[[2-(3,4-Difluoro-2-Methoxy-Phenoxy)-6-Methyl-4-(Trifluoromethyl)Benzoyl]Amino]Pyridine-2-Carboxamide (189)

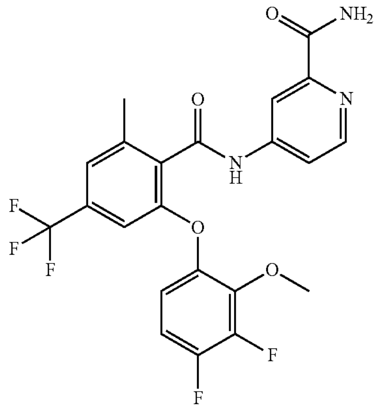 [SMILES: COc1c(Oc2cc(C(F)(F)F)cc(C)c2C(=O)Nc2ccnc(C(N)=O)c2)ccc(F)c1F]

Step 1: Tert-Butyl 2-Bromo-6-(3,4-Difluoro-2-Methoxy-Phenoxy)-4-(Trifluoromethyl)Benzoate

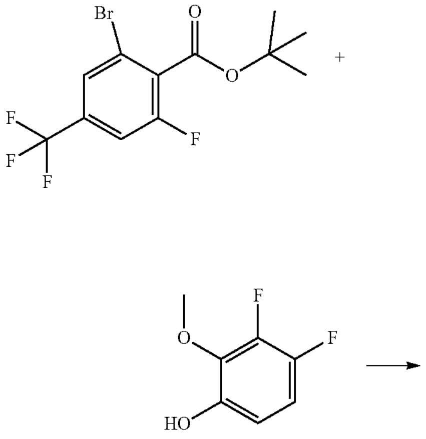

-continued

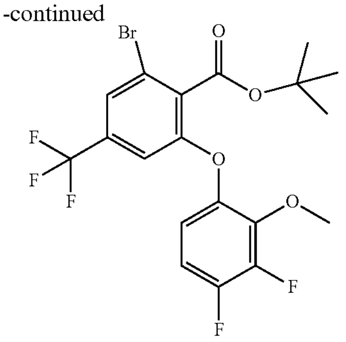

A mixture of tert-butyl 2-bromo-6-fluoro-4-(trifluoromethyl)benzoate (5 g, 14.57 mmol), 3,4-difluoro-2-methoxy-phenol (3.03 g, 18.92 mmol) and potassium carbonate (4.03 g, 29.16 mmol) in DMSO (20 mL) was heated at 100° C. for 1 h. The reaction mixture was cooled to RT, poured onto 50 mL of water and extracted with ethyl acetate (3×50 mL). The combined organic layers were washed with brine (50 mL), dried over sodium sulfate, filtered and concentrated in under reduced pressure. The residue was purified by silica chromatography on eluting with gradient of EtOAc/hexanes to give tert-butyl 2-bromo-6-(3,4-difluoro-2-methoxy-phenoxy)-4-(trifluoromethyl)benzoate (5.74 g, 82%) as an oil. $^1$H NMR (400 MHz, DMSO-d6) δ 7.86 (s, 1H), 7.24 (q, J=9.3 Hz, 1H), 7.16 (s, 1H), 7.02 (ddd, J=9.4, 5.1, 2.3 Hz, 1H), 3.87 (s, 3H), 1.51 (s, 9H) ppm.

Step 2: Tert-Butyl 2-(3,4-Difluoro-2-Methoxy-Phenoxy)-6-Methyl-4-(Trifluoromethyl)Benzoate

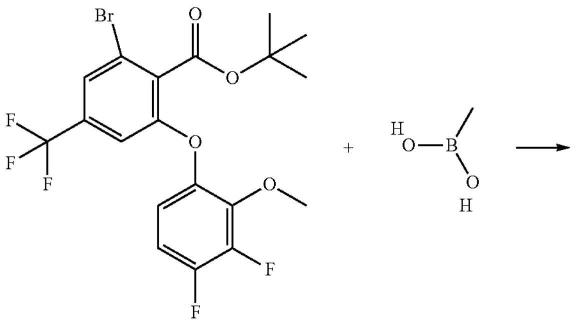

-continued

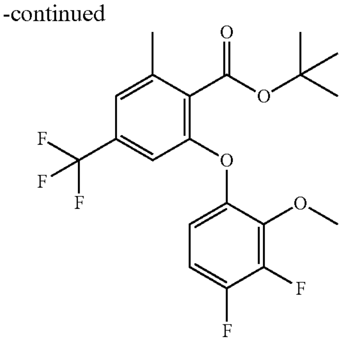

A mixture of tert-butyl 2-bromo-6-(3,4-difluoro-2-methoxy-phenoxy)-4-(trifluoromethyl)benzoate (1 g, 2.069 mmol), methylboronic acid (815 mg, 13.34 mmol), potassium carbonate (921 mg, 6.53 mmol) and ferrous; cyclopenta-1,4-dien-1-yl(diphenyl)phosphane; dichloromethane; dichloropalladium (170 mg, 0.208 mmol) in dioxane (6 mL) and water (600 μL) was flushed with nitrogen, capped and heated at 120° C. for 30 minutes in oil bath. The reaction mixture was allowed to cool to room temperature and diluted with water (50 mL) and extracted with ethyl acetate (2×50 mL). The combined organic layers were washed with brine, filtered, and concentrated under reduced pressure. The residue was then purified by silica column chromatography eluting with a EtOAc/hexanes gradient to give tert-butyl 2-(3,4-difluoro-2-methoxy-phenoxy)-6-methyl-4-(trifluoromethyl)benzoate (388 mg, 45%) as clear colorless oil. $^1$H NMR (400 MHz, DMSO-d6) δ 7.48 (s, 1H), 7.21 (q, J=9.3 Hz, 1H), 6.96 (s, 1H), 6.93-6.84 (m, 1H), 3.87 (s, 3H), 2.40 (d, J=3.7 Hz, 3H), 1.48 (s, 9H) ppm.

Step 3: 2-(3,4-Difluoro-2-Methoxy-Phenoxy)-6-Methyl-4-(Trifluoromethyl)Benzoic Acid

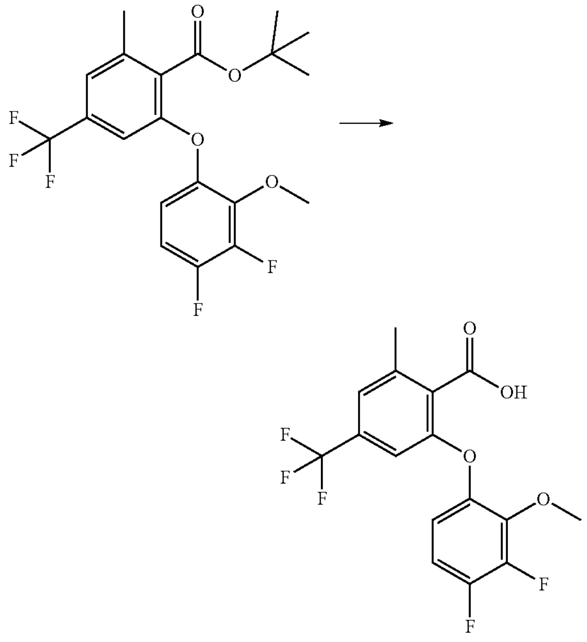

tert-butyl 2-(3,4-difluoro-2-methoxy-phenoxy)-6-methyl-4-(trifluoromethyl)benzoate (388 mg, 0.93 mmol) was dissolved in a solution of TFA (2 mL, 25.96 mmol) in DCM (6 mL). The mixture was stirred at RT for 16 h. The mixture was concentrated under reduced pressure to give a thick oil. The oil was titurated with hexanes to give 2-(3,4-difluoro-2-methoxy-phenoxy)-6-methyl-4-(trifluoromethyl)benzoic acid (204 mg, 27%) as a white solid. ESI-MS m/z calc. 362.05774, found 363.1 (M+1)$^+$; Retention time (Method B): 1.78 minutes.

Step 4: 4-[[2-(3,4-Difluoro-2-Methoxy-Phenoxy)-6-Methyl-4-(Trifluoromethyl)Benzoyl]Amino]Pyridine-2-Carboxamide (189)

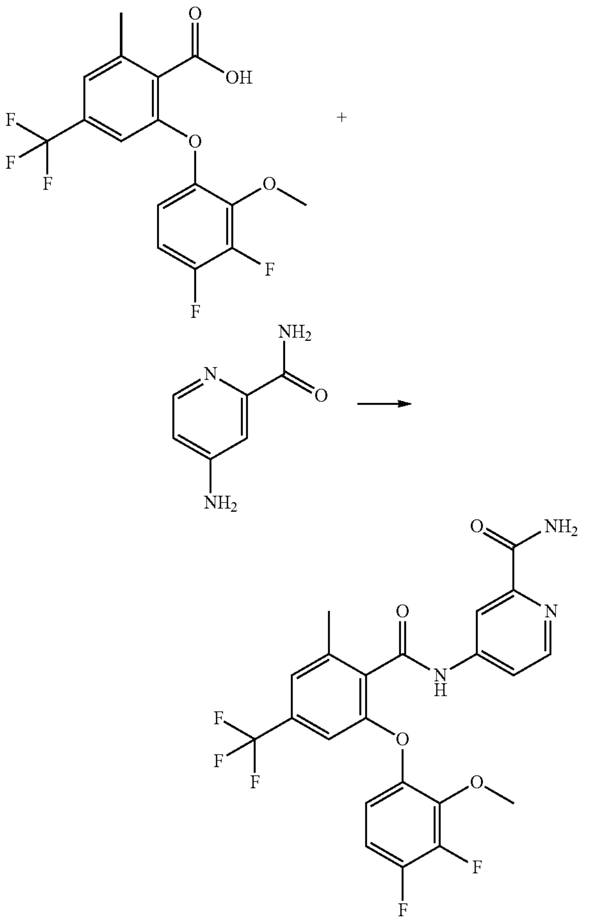

A solution of 2-(3,4-difluoro-2-methoxy-phenoxy)-6-methyl-4-(trifluoromethyl)benzoic acid (25 mg, 0.06901 mmol) in DCM (75.00 μL) was treated with DMF (approximately 5 μL, 0.069 mmol), and the mixture was cooled in an ice bath. To this solution was added oxalyl chloride (approximately 18 μL, 0.207 mmol) dropwise. The resulting mixture was stirred in an ice bath for 10 min, and then allowed to stir at RT for 1 h. The mixture was concentrated to dryness under vacuum to give a light yellow solid which was used directly in the next step.

The acid chloride intermediate was dissolved in NMP (300 μL) and added dropwise to a cooled solution of 4-aminopyridine-2-carboxamide (approximately 19 mg, 0.138 mmol) and DIEA (approximately 36 μL, 0.207 mmol) in NMP (250 μL). The reaction mixture was stirred at RT for 16 h. The mixture was filtered and purified by reverse phase HPLC on C-18 column eluting with gradient 1-99% ACN/$H_2O$ (5 mM HCl) to give 4-[[2-(3,4-difluoro-2-methoxy-phenoxy)-6-methyl-4-(trifluoromethyl)benzoyl]amino]pyridine-2-carboxamide (17 mg, 50%) as a white solid. ESI-MS m/z calc. 481.1061, found 482.2 $(M+1)^+$; Retention time (Method B): 1.66 minutes. $^1H$ NMR (400 MHz, DMSO-d6) δ 11.26 (s, 1H), 8.54 (d, J=5.4 Hz, 1H), 8.36 (d, J=2.2 Hz, 1H), 8.12-8.07 (m, 1H), 7.86-7.80 (m, 1H), 7.65 (s, 1H), 7.53 (s, 1H), 7.24 (q, J=9.3 Hz, 1H), 7.03 (s, 1H), 6.93 (s, 1H), 3.82 (s, 3H), 2.43 (s, 3H) ppm.

Example 38

5-[[6-(2-Chloro-4-Fluoro-Phenoxy)-2-Methyl-3-(Trifluoromethyl)Benzoyl]Amino]Pyridine-2-Carboxamide (190)

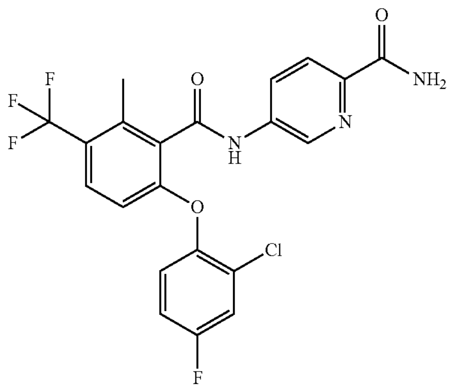 [SMILES: Cc1c(C(F)(F)F)ccc(Oc2ccc(F)cc2Cl)c1C(=O)Nc1ccc(C(N)=O)nc1]

Step 1: Tert-Butyl 2-Bromo-6-(2-Chloro-4-Fluoro-Phenoxy)-3-(Trifluoromethyl)Benzoate

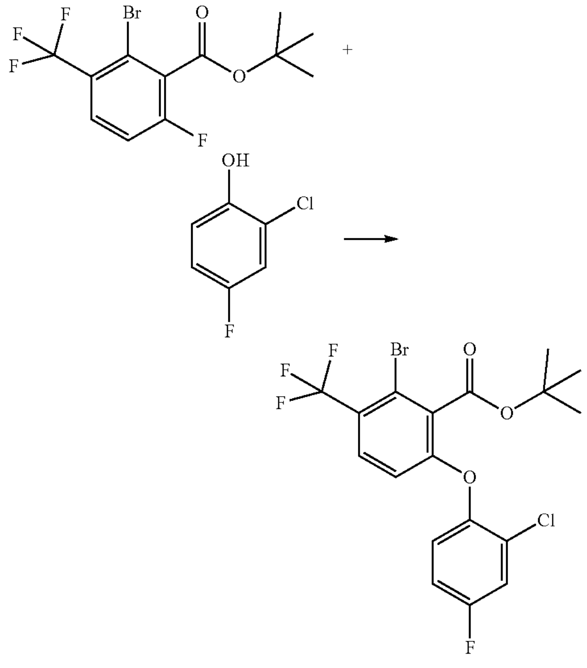

A stirring mixture of tert-butyl 2-bromo-6-fluoro-3-(trifluoromethyl)benzoate (1.0 g, 2.91 mmol), 2-chloro-4-fluoro-phenol (493 mg, 3.364 mmol), $K_2CO_3$ (800 mg, 5.788 mmol), and DMSO (4 mL) was heated at 100° C. for 1 hour. The reaction mixture was cooled to RT and was then directly purified by silica gel column chromatography using a gradient of EtOAc in hexanes to give tert-butyl 2-bromo-6-(2-chloro-4-fluoro-phenoxy)-3-(trifluoromethyl)benzoate (1.3 g, 95%) as a clear oil. $^1H$ NMR (400 MHz, DMSO-d6) δ 7.84 (d, J=8.9 Hz, 1H), 7.72 (dd, J=8.4, 2.9 Hz, 1H), 7.52-7.23 (m, 2H), 6.92 (d, J=8.9 Hz, 1H), 1.53 (s, 9H) ppm.

Step 2: Tert-Butyl 6-(2-Chloro-4-Fluoro-Phenoxy)-2-Methyl-3-(Trifluoromethyl)Benzoate

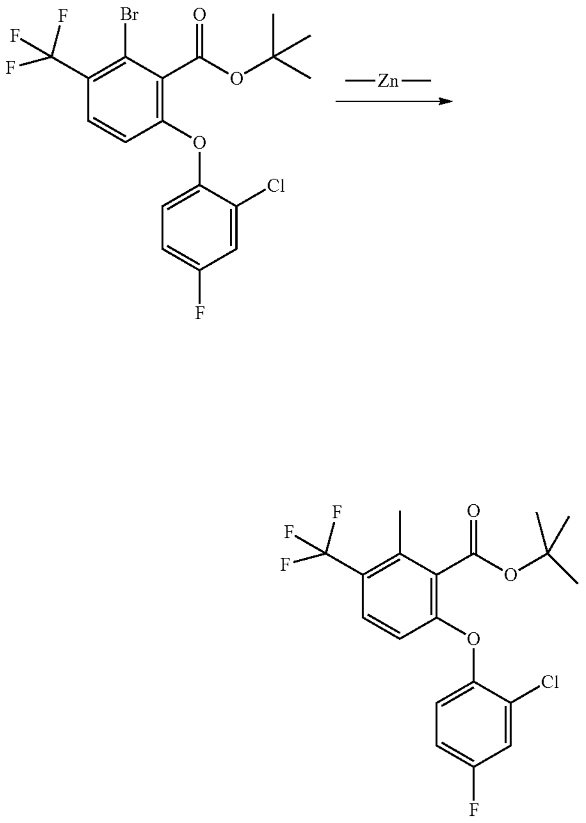

To a stirring solution of tert-butyl 2-bromo-6-(2-chloro-4-fluoro-phenoxy)-3-(trifluoromethyl)benzoate (800 mg, 1.703 mmol), $Pd(dppf)C_{12}$ (16 mg, 0.02187 mmol), and 1,4-dioxane (8 mL), under nitrogen, was added dimethylzinc (450 μL, 3.393 mmol). The reaction mixture was heated at 100° C. for 2 hours. The cooled reaction was directly purified by silica gel column chromatography using a gradient of 1-100% EtOAc in hexanes to give tert-butyl 6-(2-chloro-4-fluoro-phenoxy)-2-methyl-3-(trifluoromethyl)benzoate (450 mg, 65%) as a clear oil. $^1H$ NMR (400 MHz, DMSO-d6) δ 7.76-7.64 (m, 2H), 7.35-7.22 (m, 2H), 6.77 (d, J=8.8 Hz, 1H), 2.40 (s, 3H), 1.50 (s, 9H) ppm.

Step 3: 6-(2-Chloro-4-Fluoro-Phenoxy)-2-Methyl-3-(Trifluoromethyl)Benzoic Acid

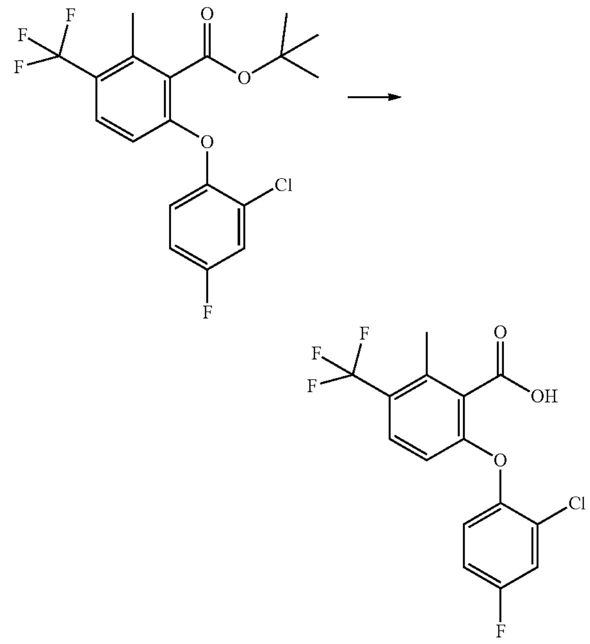

A solution of tert-butyl 6-(2-chloro-4-fluoro-phenoxy)-2-methyl-3-(trifluoromethyl)benzoate (400 mg, 0.9882 mmol), TFA (11.4 mL, 148.0 mmol), water (700 µL, 38.86 mmol), and THF (400 µL), was stirred at room temperature for 1 hour. The solution was evaporated to dryness under reduced pressure and the residue was diluted with DMSO (500 uL), filtered, and purified by reverse phase preparative chromatography using a $C_{18}$ column and a gradient eluent of 1 to 99% acetonitrile in water (5 mM HCl) to give 6-(2-chloro-4-fluoro-phenoxy)-2-methyl-3-(trifluoromethyl)benzoic acid (180 mg, 34%) as a clear oil. ESI-MS m/z calc. 348.01764, found 351.0 $(M+1)^+$; Retention time (Method B): 1.87 minutes. $^1$H NMR (400 MHz, DMSO-d6) δ 14.12-13.25 (m, 1H), 7.68 (dd, J=8.8, 5.7 Hz, 2H), 7.45-7.17 (m, 2H), 6.66 (d, J=8.8 Hz, 1H), 2.41 (s, 3H) ppm.

Step 4: 5-[[6-(2-Chloro-4-Fluoro-Phenoxy)-2-Methyl-3-(Trifluoromethyl)Benzoyl]Amino]Pyridine-2-Carboxamide (190)

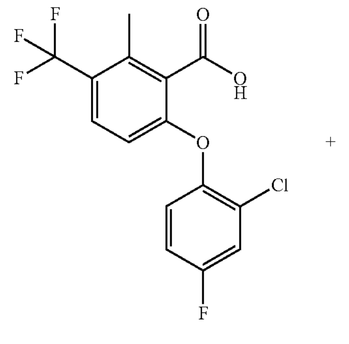

-continued

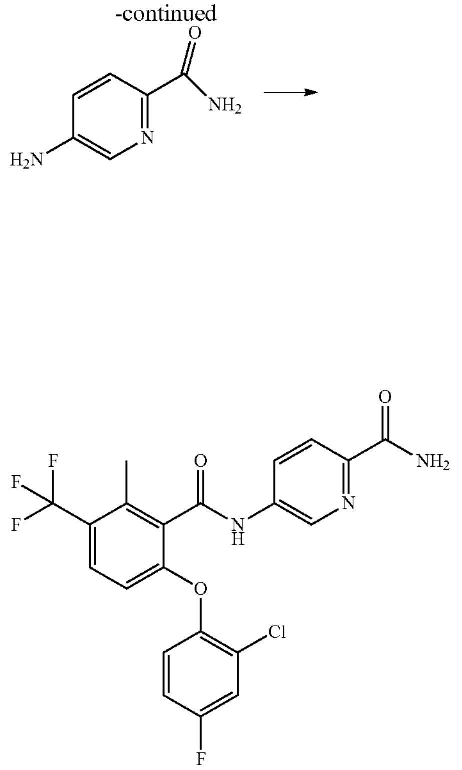

6-(2-Chloro-4-fluoro-phenoxy)-2-methyl-3-(trifluoromethyl)benzoic acid (25 mg, 0.0717 mmol) was dissolved in dichloromethane (375 µL). DMF (2 µL, 0.0258 mmol) was added followed by the slow dropwise addition of oxalyl chloride (40 µL, 0.4585 mmol). The reaction mixture was allowed to stir at room temperature for 30 minutes. The reaction mixture was concentrated under reduced pressure. Additional dichloromethane (~1 mL) was added, and the solution was again concentrated to dryness. The remaining residue was taken up in NMP (150 µL) and added to a prepared solution of 5-aminopyridine-2-carboxamide (17 mg, 0.124 mmol) and DIEA (62 µL, 0.356 mmol) in NMP (150 µL). This reaction mixture was allowed to stir at 75° C. overnight. The reaction was diluted with DMSO (500 uL), filtered, and purified by reverse phase preparative chromatography using a $C_{18}$ column and a gradient eluent of 1 to 99% acetonitrile in water (5 mM HCl) to give 5-[[6-(2-chloro-4-fluoro-phenoxy)-2-methyl-3-(trifluoromethyl)benzoyl]amino]pyridine-2-carboxamide (16 mg, 47%) as a white solid. ESI-MS m/z calc. 467.06598, found 468.0 $(M+1)^+$; Retention time (Method B): 1.65 minutes. $^1$H NMR (400 MHz, DMSO-d6) δ 11.19 (s, 1H), 8.88 (d, J=2.4 Hz, 1H), 8.33 (dd, J=8.6, 2.4 Hz, 1H), 8.06 (d, J=8.6 Hz, 1H), 8.04-7.97 (m, 1H), 7.75 (d, J=8.9 Hz, 1H), 7.67 (dd, J=8.4, 2.9 Hz, 1H), 7.61-7.49 (m, 1H), 7.41 (dd, J=9.1, 5.3 Hz, 1H), 7.35 (td, J=8.5, 2.8 Hz, 1H), 6.72 (d, J=8.8 Hz, 1H), 2.46 (s, 3H) ppm.

Example 39

4-[[2-Chloro-6-[2-Methoxy-4-(Trifluoromethoxy) Phenoxy]-3-(Trifluoromethyl)Benzoyl]Amino]Pyridine-2-Carboxamide (191)

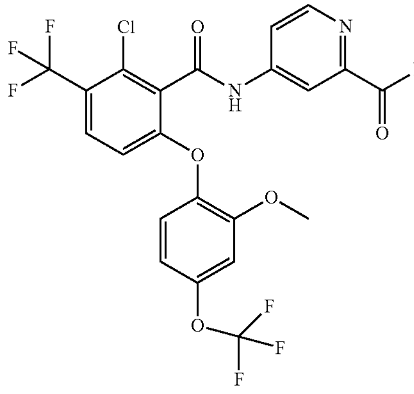

Step 1: 4-[[2-Chloro-6-Fluoro-3-(Trifluoromethyl) Benzoyl]Amino]Pyridine-2-Carboxamide

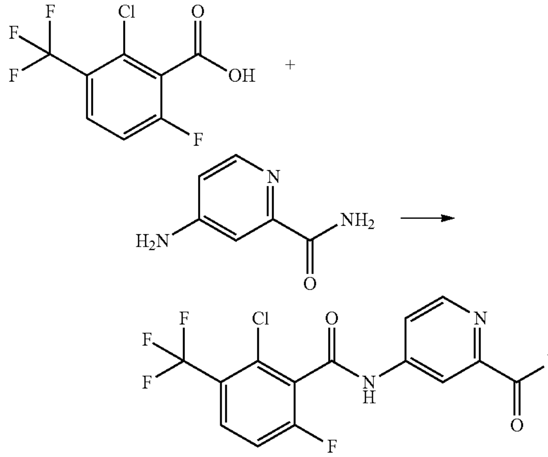

2-Chloro-6-fluoro-3-(trifluoromethyl)benzoic acid (900 mg, 3.710 mmol) was dissolved in dichloromethane (13 mL). DMF (125 μL, 1.614 mmol) was added followed by the slow dropwise addition of oxalyl chloride (2.5 mL, 28.66 mmol). The reaction mixture was allowed to stir at room temperature for 30 minutes. The reaction mixture was concentrated under reduced pressure. Additional dichloromethane (~5 mL) was added, and the solution was again concentrated to dryness. The remaining residue was taken up in NMP (2.7 mL) and added to a prepared solution of 4-aminopyridine-2-carboxamide (833 mg, 6.074 mmol) and DIEA (4.2 mL, 24.11 mmol) in NMP (2.7 mL). This reaction mixture was allowed to stir at 25° C. overnight. The reaction mixture was diluted with EtOAc (75 mL) and washed with water (2×75 mL), aqueous HCl (2×75 mL, 0.5 M) and brine (2×75 mL). The organic layer was dried over sodium sulfate, filtered and concentrated under reduced pressure. The crude product was chromatographed on a silica gel column eluting with a EtOAc/hexane gradient to provide 4-[[2-chloro-6-fluoro-3-(trifluoromethyl)benzoyl]amino]pyridine-2-carboxamide (430 mg, 32%) as a white solid. ESI-MS m/z calc. 361.0241, found 362.1 $(M+1)^+$; Retention time (Method B): 1.25 minutes. $^1$H NMR (400 MHz, DMSO-d6) δ 11.54 (s, 1H), 8.59 (d, J=5.4 Hz, 1H), 8.34 (d, J=2.2 Hz, 1H), 8.22-8.05 (m, 2H), 7.81 (dd, J=5.5, 2.2 Hz, 1H), 7.77-7.59 (m, 2H) ppm.

Step 2: 4-[[2-Chloro-6-[2-Methoxy-4-(Trifluoromethoxy)Phenoxy]-3-(Trifluoromethyl)Benzoyl] Amino]Pyridine-2-Carboxamide (191)

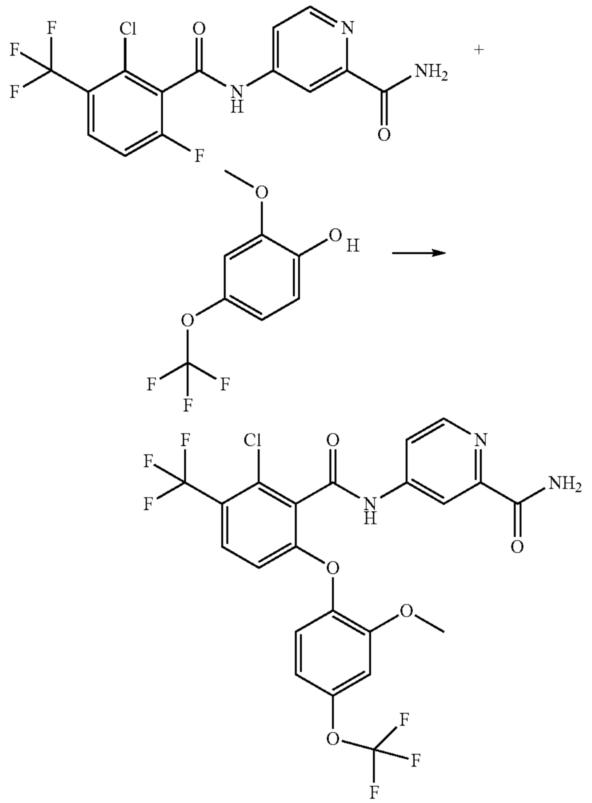

A mixture of 4-[[2-chloro-6-fluoro-3-(trifluoromethyl) benzoyl]amino]pyridine-2-carboxamide (30 mg, 0.0829 mmol), 2-methoxy-4-(trifluoromethoxy)phenol (56 mg, 0.269 mmol), $K_2CO_3$ (36 mg, 0.261 mmol), and DMSO (150 μL) was stirred at 120° C. for 30 minutes. The reaction was diluted with DMSO (500 uL), filtered, and purified by reverse phase preparative chromatography using a $C_{18}$ column and a gradient eluent of 1 to 99% acetonitrile in water (5 mM hydrochloric acid) to give 4-[[2-chloro-6-[2-methoxy-4-(trifluoromethoxy)phenoxy]-3-(trifluoromethyl) benzoyl]amino]pyridine-2-carboxamide (29 mg, 61%) as a white solid. ESI-MS m/z calc. 549.0526, found 550.0 $(M+1)^+$; Retention time (Method B): 1.78 minutes. $^1$H NMR (400 MHz, DMSO-d6) δ 11.50 (s, 1H), 8.57 (d, J=5.5 Hz, 1H), 8.38 (d, J=2.1 Hz, 1H), 8.29-8.07 (m, 1H), 8.03-7.81 (m, 2H), 7.81-7.60 (m, 1H), 7.35 (d, J=8.8 Hz, 1H), 7.27 (d, J=2.7 Hz, 1H), 7.05 (ddq, J=8.8, 2.5, 1.2 Hz, 1H), 6.81 (d, J=8.9 Hz, 1H), 3.80 (s, 3H) ppm.

The compounds set forth in Table 24 were prepared by methods analogous to the preparation of compound 191.

TABLE 24

Additional Compounds Prepared By Methods Analogous to Example 39.

| Cmpd No. | Compound Name | LC/MS | NMR (shifts in ppm) |
|---|---|---|---|
| 192 | 4-[[2-chloro-6-[2-chloro-4-(trifluoromethoxy)phenoxy]-3-(trifluoromethyl)benzoyl]amino]pyridine-2-carboxamide | ESI-MS m/z calc. 553.00305, found 553.9 (M + 1)+; Retention time (Method B): 1.83 minutes | 1H NMR (400 MHz, DMSO-d6) δ 11.52 (d, J = 3.1 Hz, 1H), 8.56 (d, J = 5.5 Hz, 1H), 8.35 (d, J = 2.2 Hz, 1H), 8.14 (s, 1H), 7.94 (d, J = 9.0 Hz, 1H), 7.90-7.78 (m, 2H), 7.70 (s, 1H), 7.52 (d, J = 1.6 Hz, 2H), 7.00 (d, J = 8.9 Hz, 1H). |
| 193 | 4-[[2-chloro-6-(3,4-difluoro-2-methoxy-phenoxy)-3-(trifluoromethyl)benzoyl]amino]pyridine-2-carboxamide | ESI-MS m/z calc. 501.05148, found 502.0 (M + 1)+; Retention time Method B): 1.65 minutes. | 1H NMR (400 MHz, DMSO-d6) δ 11.54 (s, 1H), 8.57 (d, J = 5.5 Hz, 1H), 8.38 (d, J = 2.1 Hz, 1H), 8.27-8.00 (m, 1H), 8.00-7.79 (m, 2H), 7.79-7.64 (m, 1H), 7.29 (td, J = 9.7, 8.4 Hz, 1H), 7.15 (ddd, J = 9.3, 5.1, 2.2 Hz, 1H), 6.94 (d, J = 8.8 Hz, 1H), 3.85 (d, J = 1.2 Hz, 3H). |

Example 40

4-[[2-Bromo-6-[2-Methoxy-4-(Trifluoromethoxy) Phenoxy]-3-(Trifluoromethyl)Benzoyl]Amino]Pyridine-2-Carboxamide (194)

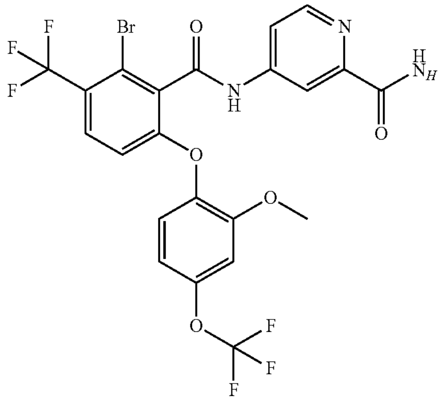

Step 1: Methyl 4-[[2-Bromo-6-Fluoro-3-(Trifluoromethyl)Benzoyl]Amino]Pyridine-2-Carboxylate

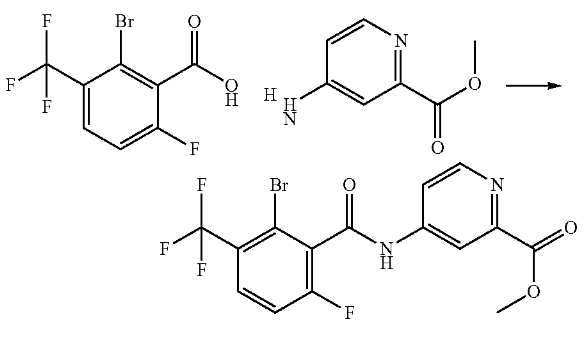

To a solution of 2-bromo-6-fluoro-3-(trifluoromethyl) benzoic acid (25 g, 87.106 mmol) in anhydrous pyridine (800 mL) (dried over $CaH_2$ for 18 h) was added methyl 4-aminopyridine-2-carboxylate (13.87 g, 91.159 mmol). The mixture was cooled to −14° C. and $POCl_3$ (8.4 mL, 90.119 mmol) was added dropwise. The reaction was stirred at −14° C. to −10° C. for 30 minutes then warmed to RT and stirred for 3 h. The reaction was quenched with water (800 mL), extracted with EtOAc (2×1.2 L), and the combined organic layers were washed with water (3×500 mL), brine, dried over $MgSO_4$, filtered and concentrated under reduced pressure to provide methyl 4-[[2-bromo-6-fluoro-3-(trifluoromethyl)benzoyl]amino]pyridine-2-carboxylate (26.47 g, 72%) as an amber oil. ESI-MS m/z calc. 419.9733, found 421.0 $(M+1)^+$; Retention time (Method H): 4.31 minutes. This material was used directly in the next step without further purification.

Step 2: 4-[[2-Bromo-6-Fluoro-3-(Trifluoromethyl) Benzoyl]Amino]Pyridine-2-Carboxamide

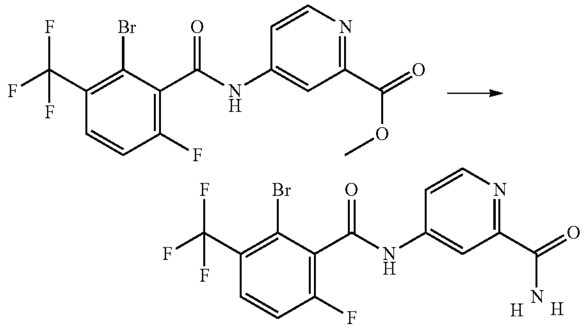

To a solution of methyl 4-[[2-bromo-6-fluoro-3-(trifluoromethyl)benzoyl]amino]pyridine-2-carboxylate (26.47 g, 62.85 mmol) in $CH_3CN$ (312 mL) was added $NH_4Cl$ (1.18 g, 22.06 mmol) and $NH_4OH$ (334 mL of 28% w/v, 2.669 mol) and the reaction was stirred at RT for 5 h. Reaction mixture was diluted with EtOAc (1 L) and washed with water (350 mL×2), brine, dried over $MgSO_4$, filtered, and concentrated under reduced pressure. The residue was purified by silica gel chromatography using an EtOAc (containing 2% of 7N $NH_3$/MeOH)/hexanes gradient) to provide 8.69 g of product as a sticky off-white foam. An additional 5 g of product containing fractions contaminated with an impurity were re-purified by silica gel chromatography using an EtOAc (containing 2% of 7N $NH_3$/MeOH)—hexanes gradient and the purified samples were combined to give 4-[[2-bromo-6-fluoro-3-(trifluoromethyl)benzoyl]

amino]pyridine-2-carboxamide (12.699 g, 49%). ESI-MS m/z calc. 404.9736, found 406.8 $(M+1)^+$; Retention time (Method H): 4.18 minutes.

Step 3: 4-[[2-Bromo-6-[2-Methoxy-4-(Trifluoromethoxy)Phenoxy]-3-(Trifluoromethyl)Benzoyl]Amino]Pyridine-2-Carboxamide (194)

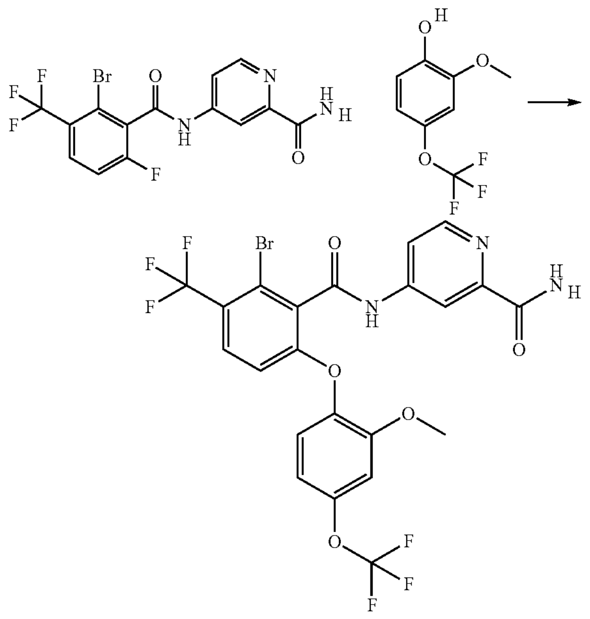

4-[[2-bromo-6-fluoro-3-(trifluoromethyl)benzoyl]amino]pyridine-2-carboxamide (250 mg, 0.616 mmol) and 2-methoxy-4-(trifluoromethoxy)phenol (141 mg, 0.677 mmol) were combined and dissolved in DMSO (0.5 mL). Solid potassium carbonate (255 mg, 1.845 mmol) was added. The reaction mixture was allowed to stir overnight at 75° C. The reaction mixture was filtered purified by silica gel chromatography using a EtOAc/hexane gradient to give 4-[[2-bromo-6-[2-methoxy-4-(trifluoromethoxy)phenoxy]-3-(trifluoromethyl)benzoyl]amino]pyridine-2-carboxamide (325 mg, 82%) as a white solid. $^1H$ NMR (400 MHz, DMSO-d6) δ 11.39 (s, 1H), 8.55 (d, J=5.5 Hz, 1H), 8.36 (d, J=2.1 Hz, 1H), 8.10 (d, J=2.9 Hz, 1H), 7.88-7.82 (m, 2H), 7.66 (d, J=2.9 Hz, 1H), 7.32 (d, J=8.8 Hz, 1H), 7.26 (d, J=2.7 Hz, 1H), 7.04 (ddq, J=8.8, 2.4, 1.2 Hz, 1H), 6.83 (d, J=8.8 Hz, 1H), 3.80 (s, 3H) ppm. ESI-MS m/z calc. 593.0021, found 596.1 (M+3)+; Retention time (Method B): 1.52 minutes.

The compounds set forth in Table 25 were prepared by methods analogous to the preparation of compound 194.

TABLE 25

Additional Compounds Prepared By Methods Analogous to Example 40.

| Cmpd No. | Compound Name | LC/MS | NMR (shifts in ppm) |
|---|---|---|---|
| 195 | 4-[[2-bromo-6-[3-fluoro-2-methoxy-4-(trifluoromethoxy)phenoxy]-3-(trifluoromethyl)benzoyl]amino]pyridine-2-carboxamide | ESI-MS m/z calc. 610.9927, found 614.1 (M + 1)+; Retention time (Method B): 1.82 minutes | $^1H$ NMR (400 MHz, DMSO-$d_6$) δ 11.48 (s, 1H), 8.56 (d, J = 5.5 Hz, 1H), 8.36 (d, J = 2.1 Hz, 1H), 8.12 (s, 1H), 7.89 (d, J = 9.0 Hz, 1H), 7.82 (dd, J = 5.6, 2.2 Hz, 1H), 7.68 (s, 1H), 7.41 (t, J = 8.7 Hz, 1H), 7.19 (dd, J = 9.2, 2.1 Hz, 1H), 7.07 (d, J = 8.9 Hz, 1H), 3.85 (s, 3H). |

Example 41

4-[[3-Cyclopropyl-6-[3-Fluoro-2-Methoxy-4-(Trifluoromethoxy)Phenoxy]-2-Methyl-Benzoyl]Amino] Pyridine-2-Carboxamide (196)

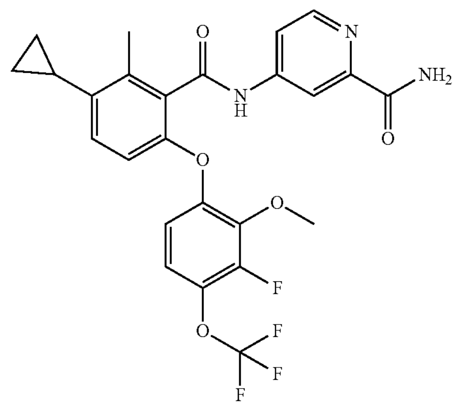 [SMILES: COc1c(Oc2ccc(C3CC3)c(C)c2C(=O)Nc2ccnc(C(N)=O)c2)ccc(OC(F)(F)F)c1F]

Step 1: 3-Bromo-6-Iodo-2-Methyl-Benzoic Acid

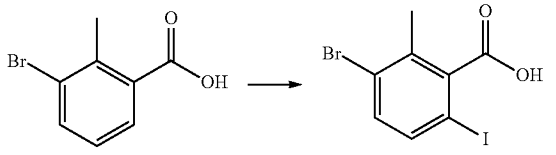

A solution of 3-bromo-2-methyl-benzoic acid (5000 mg, 23.25 mmol), $Pd(OAc)_2$ (262 mg, 1.166 mmol), $I_2$ (7.67 g, 30.22 mmol), and $PhI(OAc)_2$ (9.74 g, 30.22 mmol) in DMF (130 mL) was heated at 100° C. for 16 hours. The mixture was cooled to RT and the DMF was removed under reduced pressure. To the residue was added DCM and sat. $Na_2S_2O_3$ and the mixture as stirred for 15 minutes. To the mixture was added 1N HCl until the pH was <3 and the layers were separated. The aqueous layer was extracted with DCM (3×) and the combined organics were washed with a mixture of sat. $Na_2SO_3$ and 1 N HCl. The organic phase was dried over $Na_2SO_4$ and concentrated under reduced pressure. The residue was purified by medium pressure reverse phase chromatography ($C_{18}$, $CH_3CN$/water (5 mM HCl)) to give 3-bromo-6-iodo-2-methyl-benzoic acid (5.43 g, 69%) as a white solid. $^1H$ NMR (400 MHz, Chloroform-d) δ 7.60-7.47 (m, 1H), 7.33 (dd, J=8.5, 1.8 Hz, 1H), 2.49 (s, 3H) ppm.

Step 2: 1-Bromo-3-Fluoro-2-Methoxy-4-(Trifluoromethoxy)Benzene

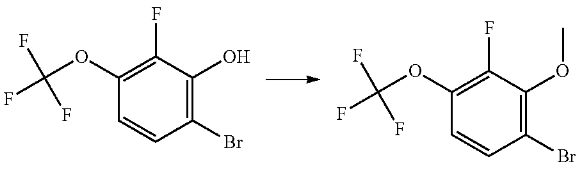

To a solution of 6-bromo-2-fluoro-3-(trifluoromethoxy) phenol (10 g, 36.36 mmol) in DMF (20 mL) was added $K_2CO_3$ (6.5 g, 47.03 mmol) and iodomethane (4.1 mL, 65.86 mmol) and the mixture heated to 50° C. for 2 h. The reaction mixture was allowed to cool down, filtered, concentrated under reduced pressure and the residue was partitioned between diethyl ether (30 ml) and water (30 ml). The aqueous layer was further extracted with diethyl ether (10 mL). Combined organic fractions were washed with brine, dried over magnesium sulfate and concentrated under reduce pressure to an oil. The product was purified by silica gel chromatography eluting with 100% petroleum ether to give 1-bromo-3-fluoro-2-methoxy-4-(trifluoromethoxy)benzene (8.1 g, 77%) as an oil. $^1H$ NMR (400 MHz, Chloroform-d) δ 7.34 (dd, J=9.0, 2.4 Hz, 1H), 6.95 (ddq, J=8.5, 7.2, 1.2 Hz, 1H), 4.01 (d, J=1.7 Hz, 3H) ppm.

Step 3: 3-Fluoro-2-Methoxy-4-(Trifluoromethoxy)Phenol

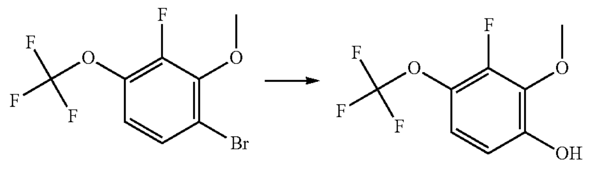

To a solution of 1-bromo-3-fluoro-2-methoxy-4-(trifluoromethoxy)benzene (7 g, 24.22 mmol) in dioxane (84 mL) was added (1E,4E)-1,5-diphenylpenta-1,4-dien-3-one palladium (554 mg, 0.6050 mmol), di-tert-butyl-[2-(2,4,6-triisopropylphenyl)phenyl]phosphane (709 mg, 1.670 mmol) and KOH (2.8 g, 49.91 mmol) followed by water (56 mL) and the mixture heated to 90° C. for 5 hours. The reaction mixture was allowed to cool to RT, filtered and partitioned between diethyl ether (30 ml) and water (100 ml). The aqueous fraction was separated and was acidified to ~ pH 1 with 2M HCl and extracted twice with diethyl ether (2×50 ml). The combined organics where dried ($MgSO_4$) and concentrated under reduced pressure to afford 3-fluoro-2-methoxy-4-(trifluoromethoxy)phenol (3.6 g, 66%). $^1H$ NMR (400 MHz, Chloroform-d) δ 6.91 (ddq, J=9.1, 7.8, 1.2 Hz, 1H), 6.70 (dd, J=9.1, 2.2 Hz, 1H), 5.92 (s, 1H), 4.04 (d, J=2.0 Hz, 3H) ppm.

Step 4: 3-Bromo-6-[3-Fluoro-2-Methoxy-4-(Trifluoromethoxy)Phenoxy]-2-Methyl-Benzoic Acid

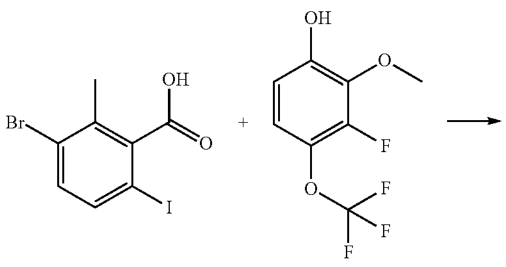

-continued

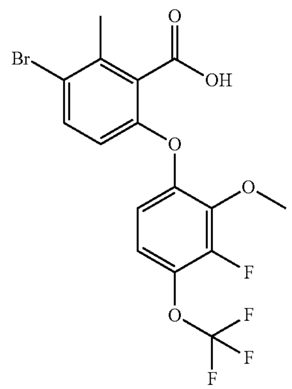

To a pressure flask was added 3-bromo-6-iodo-2-methyl-benzoic acid (1000 mg, 2.933 mmol), 3-fluoro-2-methoxy-4-(trifluoromethoxy)phenol (530 mg, 2.344 mmol), cesium carbonate (1.2 g, 3.683 mmol), toluene (5.3 mL) and a stir bar. The reaction mixture was bubbled with nitrogen for 10 minutes, then copper (I) iodide (446 mg, 2.342 mmol) was added. The flask was flushed with nitrogen, capped, and heated at 100° C. with vigorous stirring for 16 hours. The mixture was allowed to cool, then diluted with ethyl acetate and water. The water layer was acidified with 1 M HCl and the product extracted into ethyl acetate. The biphasic mixture was filtered and the layers separated. The organic layer was washed with brine, dried over $MgSO_4$, filtered and concentrated under reduced pressure. The residue was purified by silica gel chromatography using a gradient of MeOH in dichloromethane to give 3-bromo-6-[3-fluoro-2-methoxy-4-(trifluoromethoxy)phenoxy]-2-methyl-benzoic acid (453 mg, 44%) as a light yellow oil. ESI-MS m/z calc. 437.9726, found 439.0 $(M+1)^+$; Retention time (Method B): 1.55 minutes. $^1H$ NMR (400 MHz, DMSO-d6) δ 13.66 (s, 1H), 7.63 (d, J=8.9 Hz, 1H), 7.30 (ddq, J=9.5, 8.4, 1.2 Hz, 1H), 6.87 (dd, J=9.3, 2.2 Hz, 1H), 6.78 (dd, J=8.8, 0.7 Hz, 1H), 3.89 (s, 3H), 2.36 (s, 3H) ppm.

Step 5: Tert-Butyl 3-Bromo-6-[3-Fluoro-2-Methoxy-4-(Trifluoromethoxy)Phenoxy]-2-Methyl-Benzoate

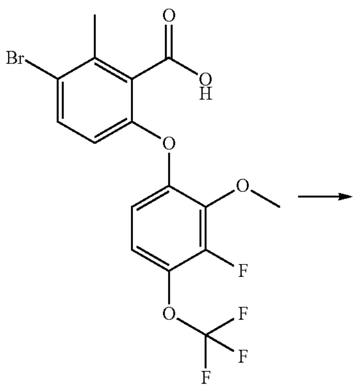

-continued

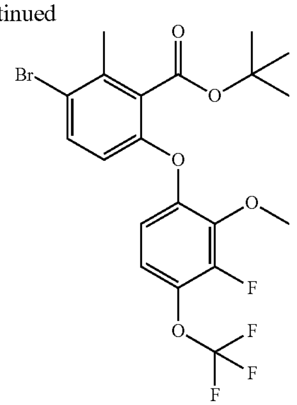

A mixture of 3-bromo-6-[3-fluoro-2-methoxy-4-(trifluoromethoxy)phenoxy]-2-methyl-benzoic acid (900 mg, 2.049 mmol), di-tert-butyl dicarbonate (670 mg, 3.070 mmol), DMAP (50 mg, 0.4093 mmol), and tert-BuOH (900 μL), was heated at 90° C. for 2 hours. The reaction mixture was directly purified by silica gel column chromatography using a gradient of EtOAc in hexanes to give tert-butyl 3-bromo-6-[3-fluoro-2-methoxy-4-(trifluoromethoxy)phenoxy]-2-methyl-benzoate (340 mg, 34%) as a clear oil. $^1H$ NMR (400 MHz, DMSO-d6) δ 7.67 (d, J=8.8 Hz, 1H), 7.35-7.20 (m, 1H), 6.85 (dd, J=8.8, 0.7 Hz, 1H), 6.78 (dd, J=9.4, 2.2 Hz, 1H), 3.90 (d, J=0.8 Hz, 3H), 2.34 (s, 3H), 1.41 (s, 9H) ppm.

Step 6: Tert-Butyl 3-Cyclopropyl-6-[3-Fluoro-2-Methoxy-4-(Trifluoromethoxy)Phenoxy]-2-Methyl-Benzoate

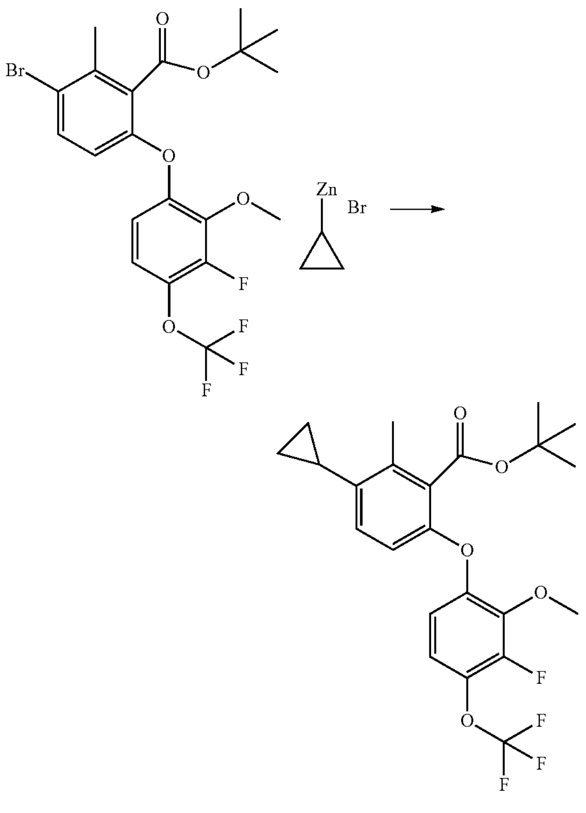

To a vial charged with tert-butyl 3-bromo-6-[3-fluoro-2-methoxy-4-(trifluoromethoxy)phenoxy]-2-methyl-benzoate (140 mg, 0.2827 mmol), palladium tritert-butylphosphane (approximately 7 mg, 0.0141 mmol), and THF (1 mL) under an atmosphere of $N_2$ at 0° C. was added bromo(cyclopropyl) zinc (approximately 735 μL of 0.5 M, 0.367 mmol) in THF slowly and the reaction mixture was gradually warmed to room temperature over 1 h and stirred at RT for 15 minutes. The reaction mixture was quenched with 1N HCl, and the aq. layer was extracted with DCM (3×). The combined organic layers were dried over $Na_2SO_4$, filtered and concentrated. The residue was purified by column chromatography using a gradient of ethyl acetate in hexanes to yield tert-butyl 3-cyclopropyl-6-[3-fluoro-2-methoxy-4-(trifluoromethoxy)phenoxy]-2-methyl-benzoate (104 mg, 81%). $^1H$ NMR (400 MHz, Chloroform-d) δ 7.00 (d, J=8.5 Hz, 1H), 6.89 (ddq, J=9.1, 7.9, 1.2 Hz, 1H), 6.62 (d, J=8.5 Hz, 1H), 6.59 (dd, J=9.3, 2.3 Hz, 1H), 3.98 (d, J=0.8 Hz, 3H), 2.43 (s, 3H), 1.84 (tt, J=8.5, 5.4 Hz, 1H), 1.47 (s, 9H), 1.02-0.87 (m, 2H), 0.67-0.53 (m, 2H) ppm.

Step 7: 3-Cyclopropyl-6-[3-Fluoro-2-Methoxy-4-(Trifluoromethoxy)Phenoxy]-2-Methyl-Benzoic Acid

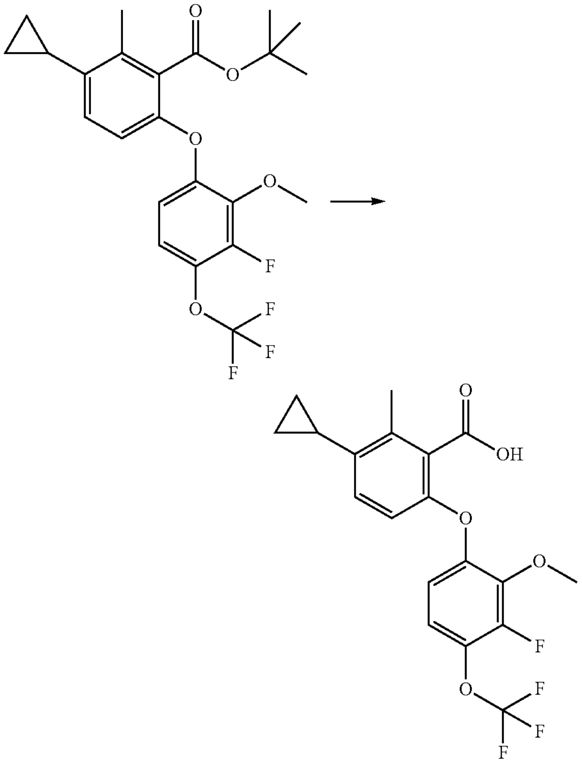

To a solution of tert-butyl 3-cyclopropyl-6-[3-fluoro-2-methoxy-4-(trifluoromethoxy)phenoxy]-2-methyl-benzoate (105 mg, 0.230 mmol) in THF (0.75 mL) and water (165 μL, 9.203 mmol) cooled on ice was added TFA (2.65 mL, 34.50 mmol) over approximately 4 minutes dropwise. The ice bath was removed and the solution was stirred at RT for 1 h. The stir bar was removed and the mixture was concentrated under reduced pressure to give 3-cyclopropyl-6-[3-fluoro-2-methoxy-4-(trifluoromethoxy)phenoxy]-2-methyl-benzoic acid (89 mg, 92%). ESI-MS m/z calc. 400.09338, found 401.23 $(M+1)^+$; Retention time (Method A): 0.81 minutes.

Step 8: 4-[[3-Cyclopropyl-6-[3-Fluoro-2-Methoxy-4-(Trifluoromethoxy)Phenoxy]-2-Methyl-Benzoyl]Amino]Pyridine-2-Carboxamide (196)

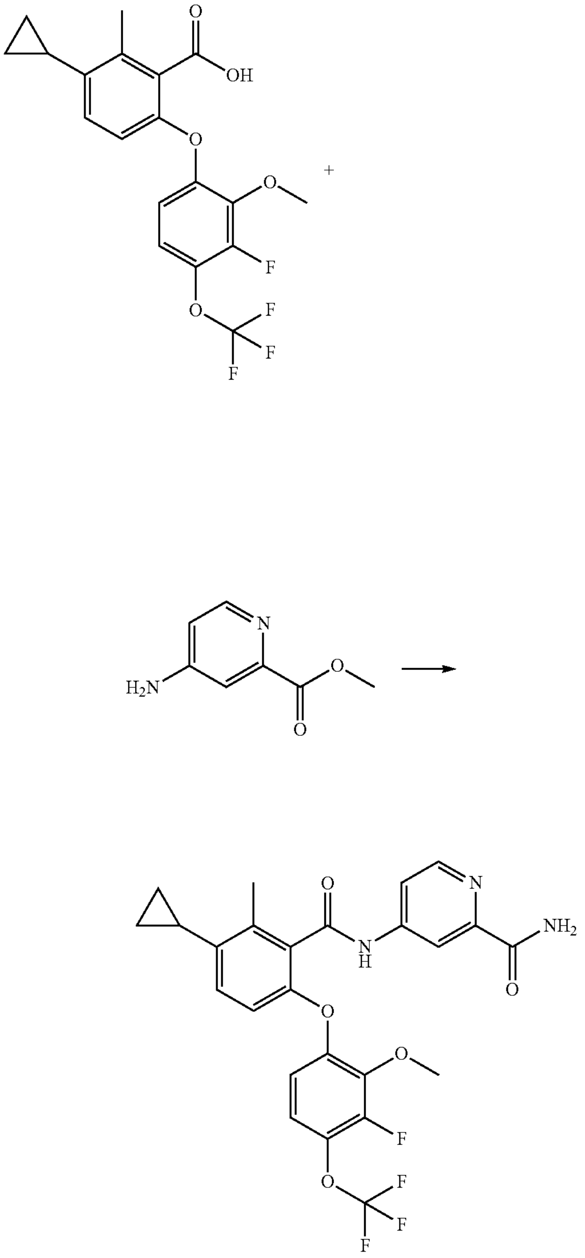

To a solution of 3-cyclopropyl-6-[3-fluoro-2-methoxy-4-(trifluoromethoxy)phenoxy]-2-methyl-benzoic acid (88 mg, 0.209 mmol) in DCM (2.5 mL) cooled in an ice bath was added DMF (approximately 2 μL, 0.0295 mmol) followed by the dropwise addition of oxalyl chloride (approximately 36 μL, 0.418 mmol). The mixture was stirred at on ice for 10 minutes then at RT for 2 h. The reaction was concentrated under reduced pressure and flushed with $N_2$ to afford the acid chloride, which was taken directly into the next step.

A solution of methyl 4-aminopyridine-2-carboxylate (approximately 79 mg, 0.522 mmol) and DIEA (93 μL, 0.537 mmol) in DCM (2.5 mL) was cooled on ice and the crude acid chloride in DCM (2.5 mL) was added dropwise. The ice bath was removed and the reaction mixture was stirred at RT overnight, and then at 50° C. for 2 hours. The reaction was cooled to RT and quenched into water and extract with DCM (3×). The combined organics were dried over $Na_2SO_4$, filter and concentrated under reduced pressure. The major product was isolated by silica gel column chromatography using a gradient of ethyl acetate in hexanes and was used directly in the next step. The isolated material was treated with $NH_3$ (10 mL of 7 M, 70.00 mmol) in methanol for 8 hours. The solvent was removed under reduced pressure to give 4-[[3-cyclopropyl-6-[3-fluoro-2-methoxy-4-(trifluoromethoxy)phenoxy]-2-methyl-benzoyl]amino]pyridine-2-carboxamide (39 mg, 36%). $^1H$ NMR (400 MHz, Chloroform-d) δ 8.99 (s, 1H), 8.50 (d, J=5.6 Hz, 1H), 8.38 (s, 1H), 8.14-7.89 (m, 2H), 7.06 (d, J=8.6 Hz, 1H), 6.99 (td, J=8.4, 7.8, 1.3 Hz, 1H), 6.85 (dd, J=9.2, 2.2 Hz, 1H), 6.58 (d, J=8.5 Hz, 1H), 5.35 (s, 1H), 3.75 (d, J=1.5 Hz, 3H), 2.52 (s, 3H), 1.87 (ddd, J=13.9, 8.5, 5.5 Hz, 1H), 1.03-0.91 (m, 2H), 0.60 (td, J=6.0, 4.4 Hz, 2H) ppm. ESI-MS m/z calc. 519.1417, found 520.43 $(M+1)^+$; Retention time Method B): 1.79 minutes.

The compounds set forth in Table 26 were prepared by methods analogous to the preparation of compound 196.

Step 1: 3-Bromo-6-[2-Chloro-4-(Trifluoromethoxy)Phenoxy]-2-Methyl-Benzoic Acid

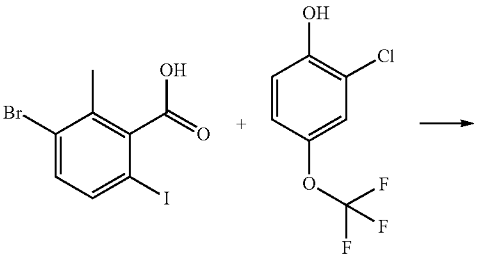

TABLE 26

Additional Compounds Prepared By Methods Analogous to Example 41.

| Cmpd No. | Compound Name | LC/MS | NMR (shifts in ppm) |
|---|---|---|---|
| 197 | 5-[[3-cyclopropyl-6-[3-fluoro-2-methoxy-4-(trifluoromethoxy)phenoxy]-2-methyl-benzoyl]amino]pyridine-2-carboxamide | ESI-MS m/z calc. 519.1417, found 520.0 (M + 1)+; Retention time (Method B): 1.9 minutes | 1H NMR (400 MHz, DMSO-d6) δ 11.03 (s, 1H), 8.84 (s, 1H), 8.28 (d, J = 11.0 Hz, 1H), 8.00 (d, J = 13.4 Hz, 2H), 7.53 (s, 1H), 7.27 (s, 1H), 7.11 (d, J = 8.6 Hz, 1H), 6.85 (d, J = 11.4 Hz, 1H), 6.77 (d, J = 8.5 Hz, 1H), 3.81 (s, 3H), 2.41 (s, 3H), 1.93 (s, 1H), 0.96 (d, J = 14.5 Hz, 2H), 0.62 (d, J = 11.1 Hz, 2H). |
| 198 | 4-[[3-cyclopropyl-6-[2-methoxy-4-(trifluoromethoxy)phenoxy]-2-methyl-benzoyl]amino]-5-methyl-pyridine-2-carboxamide | ESI-MS m/z calc. 515.1668, found 516.0 (M + 1)+; Retention time (Method B): 1.85 minutes | $^1H$ NMR (400 MHz, DMSO-$d_6$) δ 10.32 (s, 1H), 8.48 (d, J = 17.8 Hz, 2H), 8.17 (s, 1H), 7.69 (s, 1H), 7.19-7.09 (m, 2H), 7.09-7.04 (m, 1H), 7.00-6.90 (m, 1H), 6.50 (d, J = 8.6 Hz, 1H), 3.78 (s, 3H), 2.45 (s, 3H), 2.27 (s, 3H), 1.92 (qd, J = 8.2, 5.2 Hz, 1H), 1.07-0.82 (m, 2H), 0.68-0.45 (m, 2H). |

Example 42

4-[[6-[2-Chloro-4-(Trifluoromethoxy)Phenoxy]-3-Cyclopropyl-2-Methyl-Benzoyl]Amino]Pyridine-2-Carboxamide (199)

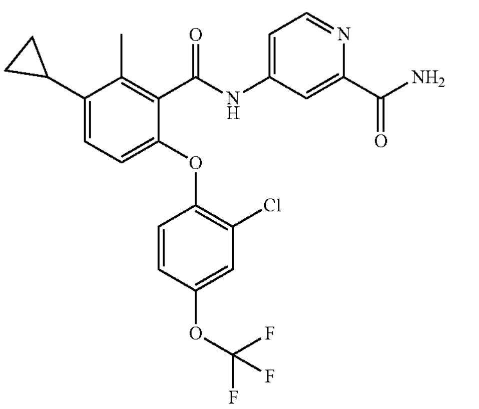 [SMILES: Cc1c(C2CC2)ccc(Oc2ccc(OC(F)(F)F)cc2Cl)c1C(=O)Nc1ccnc(C(N)=O)c1]

-continued

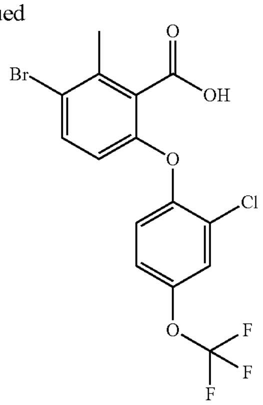

To a pressure flask was added 3-bromo-6-iodo-2-methylbenzoic acid (1.170 g, 3.43 mmol), 2-chloro-4-(trifluoromethoxy)phenol (730 mg, 3.434 mmol), cesium carbonate (1.8 g, 5.53 mmol), toluene (22 mL) and a stir bar. The reaction mixture was bubbled with nitrogen for 10 minutes, then copper (I) iodide (660 mg, 3.465 mmol) was added. The flask was flushed with nitrogen, capped, and heated at 100° C. with vigorous stirring for 16 hours. The mixture was allowed to cool, then diluted with ethyl acetate and water. The water layer was acidified with 1 M HCl and the product extracted into ethyl acetate. The aqueous layer was extracted with additional ethyl acetate (3×50 mL). The combined organic layers were washed with brine, dried over $MgSO_4$, filtered and concentrated under reduced pressure. HPLC purification (30-99% $CH_3CN$/water (5 mM HCl)) provided 3-bromo-6-[2-chloro-4-(trifluoromethoxy)phenoxy]-2-methyl-benzoic acid (800 mg, 55%) as a white solid. ESI-MS m/z calc. 423.9325, found 426.9 $(M+1)^+$; Retention time (Method A): 0.75 minutes. $^1H$ NMR (400 MHz, DMSO-d6) δ 13.65 (s, 1H), 7.76 (dd, J=2.9, 0.8 Hz, 1H), 7.66 (d, J=8.8 Hz, 1H), 7.39 (ddd, J=9.0, 2.8, 1.1 Hz, 1H), 7.10 (d, J=9.0 Hz, 1H), 6.77 (d, J=8.7 Hz, 1H), 2.36 (s, 3H) ppm.

Step 2: Tert-Butyl 3-Bromo-6-[2-Chloro-4-(Trifluoromethoxy)Phenoxy]-2-Methyl-Benzoate

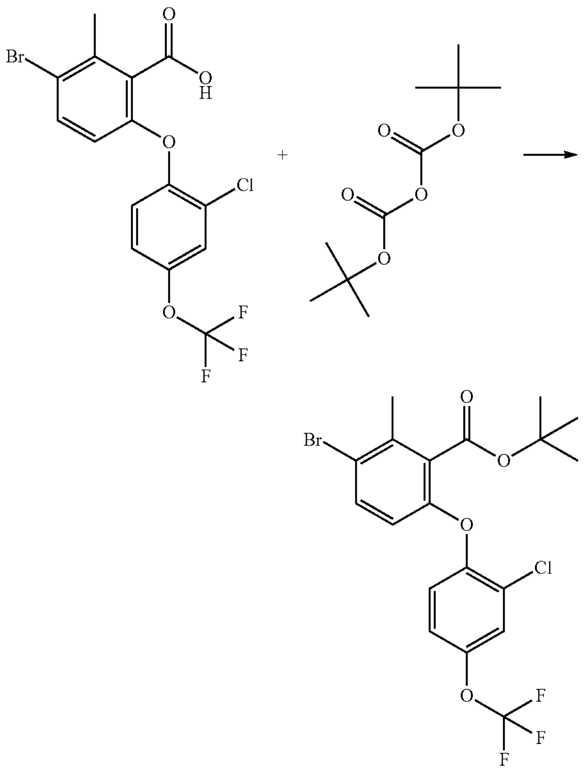

A mixture of 3-bromo-6-[2-chloro-4-(trifluoromethoxy) phenoxy]-2-methyl-benzoic acid (795 mg, 1.868 mmol), tert-butoxycarbonyl tert-butyl carbonate (610 mg, 2.795 mmol), DMAP (46 mg, 0.377 mmol), and t-BuOH (800 μL) was heated at 90° C. for 1 hour (gas evolution during first several minutes). The reaction mixture was cooled and additional tert-butoxycarbonyl tert-butyl carbonate (610 mg, 2.795 mmol) added. The reaction was stirred at 90° C. for 5 minutes with gas evolution. After gas evolution had ceased (5 min) the reaction mixture cooled to RT and directly purified by silica gel column chromatography with an ethyl acetate/hexanes gradient to provide tert-butyl 3-bromo-6-[2-chloro-4-(trifluoromethoxy)phenoxy]-2-methyl-benzoate (845 mg, 94%) as a clear, colorless oil. ESI-MS m z calc. 479.9951, found 426.8 (M-tBu+1)+; Retention time (Method A): 0.84 minutes. $^1H$ NMR (400 MHz, DMSO-d6) δ 7.76 (dd, J=3.0, 0.8 Hz, 1H), 7.73 (d, J=8.8 Hz, 1H), 7.39-7.31 (m, 1H), 6.94 (dd, J=9.0, 1.4 Hz, 2H), 2.35 (s, 3H), 1.35 (s, 9H) ppm.

Step 3: Tert-Butyl 6-[2-Chloro-4-(Trifluoromethoxy)Phenoxy]-3-Cyclopropyl-2-Methyl-Benzoate

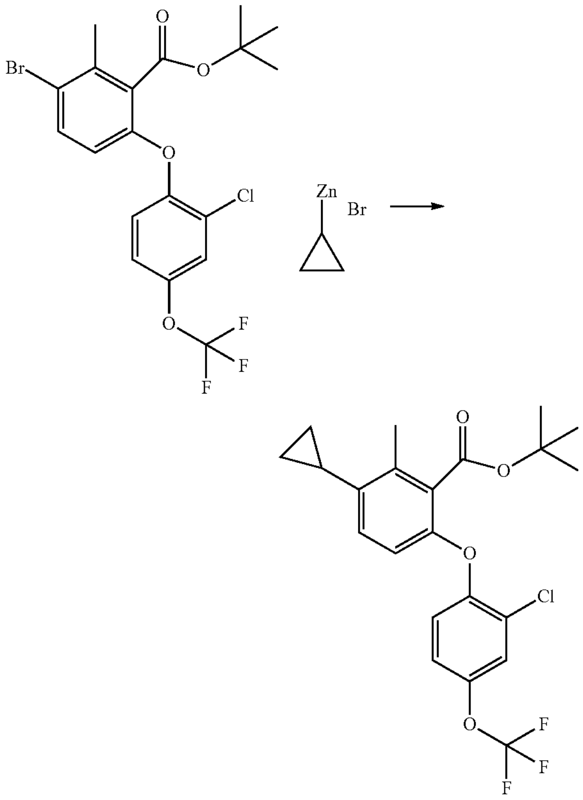

To a vial charged with tert-butyl 3-bromo-6-[2-chloro-4-(trifluoromethoxy)phenoxy]-2-methyl-benzoate (140 mg, 0.291 mmol), palladium tritert-butylphosphane (approximately 7 mg, 0.0145 mmol), and THF (1 mL) under an atmosphere of $N_2$ at 0° C. was added bromo(cyclopropyl) zinc (639 μL of 0.5 M, 0.320 mmol) in THF slowly and the reaction mixture was gradually warmed to room temperature over 1 h and stirred at RT for 15 minutes. The reaction mixture was quenched with 1N HCl, the aqueous layer was extracted with DCM (3×). The combined organic layers were dried over $Na_2SO_4$, filtered and concentrated under reduced pressure. The residue was purified by silica gel chromatography using a gradient of ethyl acetate in hexanes to yield tert-butyl 6-[2-chloro-4-(trifluoromethoxy)phenoxy]-3-cyclopropyl-2-methyl-benzoate (98 mg, 76%). 1H NMR (400 MHz, Chloroform-d) δ 7.33 (dq, J=2.9, 0.9 Hz, 1H), 7.06-6.97 (m, 2H), 6.80 (d, J=9.0 Hz, 1H), 6.67 (d, J=8.5 Hz, 1H), 2.44 (s, 3H), 1.85 (tt, J=8.5, 5.4 Hz, 1H), 1.44 (s, 9H), 1.00-0.87 (m, 2H), 0.67-0.58 (m, 2H) ppm.

Step 4: 6-[2-Chloro-4-(Trifluoromethoxy)Phenoxy]-3-Cyclopropyl-2-Methyl-Benzoic Acid

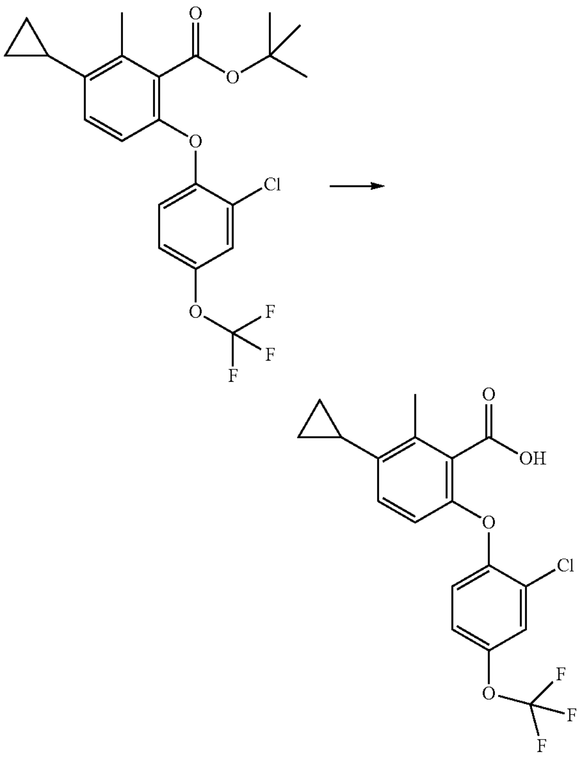

To a solution of tert-butyl 6-[2-chloro-4-(trifluoromethoxy)phenoxy]-3-cyclopropyl-2-methyl-benzoate (95 mg, 0.2145 mmol) in THF (750 μL) and water (150 μL) cooled on ice was added TFA (2.5 mL, 32.45 mmol) over approximately 4 minutes dropwise. The ice bath was removed and the solution was stirred at RT for 1.25 h. The reaction was concentrated under reduced pressure to give 6-[2-chloro-4-(trifluoromethoxy)phenoxy]-3-cyclopropyl-2-methyl-benzoic acid (83 mg, 100%). ESI-MS m/z calc. 386.05328, found 387.23 $(M+1)^+$; Retention time (Method B): 0.83 minutes.

Step 5: 4-[[6-[2-Chloro-4-(Trifluoromethoxy)Phenoxy]-3-Cyclopropyl-2-Methyl-Benzoyl]Amino]Pyridine-2-Carboxamide (199)

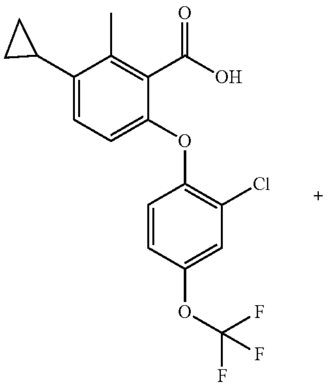

+

-continued

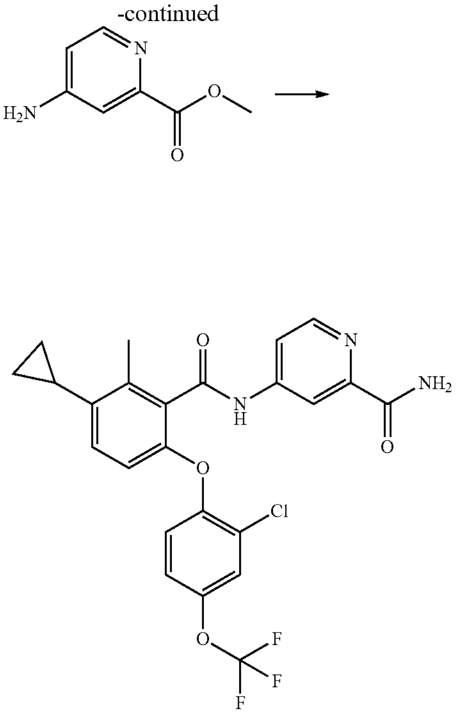

To a solution of 6-[2-chloro-4-(trifluoromethoxy)phenoxy]-3-cyclopropyl-2-methyl-benzoic acid (82 mg, 0.212 mmol) in DCM (2.5 mL) cooled in an ice bath was added DMF (2 μL, 0.03 mmol) followed by the dropwise addition of oxalyl chloride (37 μL, 0.425 mmol). The mixture was stirred at on ice for 10 mins then at RT for 1.25 h. The reaction was concentrated under reduced pressure and flushed with $N_2$ to afford the acid chloride, which was taken directly into the next step.

A solution of methyl 4-aminopyridine-2-carboxylate (80 mg, 0.53 mmol) and DIEA (94 μL, 0.545 mmol) in DCM (2.5 mL) was cool on ice and the crude acid chloride in DCM (2.5 mL) was added drop wise. The ice bath was removed and the reaction mixture was stirred at RT overnight, then at 50° C. for 2 hours. The reaction was quenched into water and extract with DCM (3×). The combined organics were dried over $Na_2SO_4$, filter and concentrated under reduced pressure. The major product was isolated by silica gel chromatography using a gradient of ethyl acetate in hexanes which was used directly in the next step. The isolated material was treated with $NH_3$ (11.6 mL of 7 M, 81 mmol) in methanol for 28 hours. The solvent was removed under reduced pressure to give 4-[[6-[2-chloro-4-(trifluoromethoxy)phenoxy]-3-cyclopropyl-2-methyl-benzoyl]amino]pyridine-2-carboxamide (53 mg, 49%). 1H NMR (400 MHz, Chloroform-d) δ 8.74 (s, 1H), 8.50 (d, J=5.6 Hz, 1H), 8.35 (s, 1H), 8.10 (s, 1H), 7.92 (s, 1H), 7.29 (d, J=2.3 Hz, 1H), 7.16-6.91 (m, 3H), 6.57 (d, J=8.5 Hz, 1H), 5.25 (s, 1H), 2.51 (s, 3H), 1.87 (td, J=8.4, 4.2 Hz, 1H), 1.04-0.93 (m, 2H), 0.70-0.53 (m, 2H) ppm. ESI-MS m/z calc. 505.10162, found 506.38 $(M+1)^+$; Retention time (Method B): 1.81 minutes.

Example 43

4-[[4-(Difluoromethyl)-2-[2-Methoxy-4-(Trifluoromethoxy)Phenoxy]-6-Methyl-Benzoyl]Amino]Pyridine-2-Carboxamide (200)

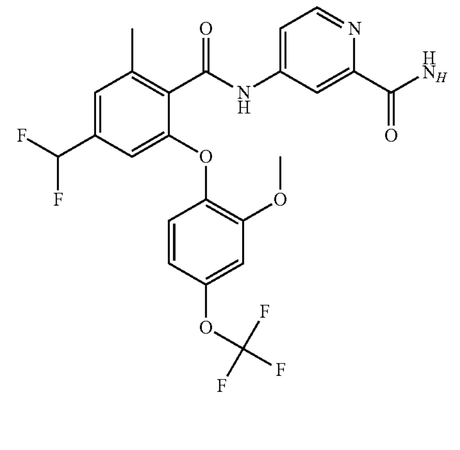

Step 1: 2-Bromo-5-(Difluoromethyl)-1-Fluoro-3-Methyl-Benzene

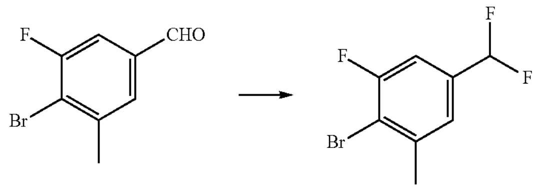

To 4-bromo-3-fluoro-5-methyl-benzaldehyde (5 g, 23.04 mmol) in dichloromethane (30 mL) was added diethylaminosulfur trifluoride (36 mL, 272.5 mmol) dropwise and the mixture was stirred under nitrogen for 5 hours. The reaction was quenched whilst ice-cooled by drop wise addition of aqueous NaOH (2 M) until basic. The organic layer was separated, dried (MgSO4) and concentrated to give an orange oil. Purification by silica gel chromatography with a ethyl acetate in heptane gradient gave 2-bromo-5-(difluoromethyl)-1-fluoro-3-methyl-benzene (5.02 g, 91%). 1H NMR (500 MHz, DMSO-d6) δ 7.50-7.39 (m, 2H), 7.02 (t, J=55.5 Hz, 1H), 2.46 (s, 3H) ppm.

Step 2: 4-(Difluoromethyl)-2-Fluoro-6-Methyl-Benzonitrile

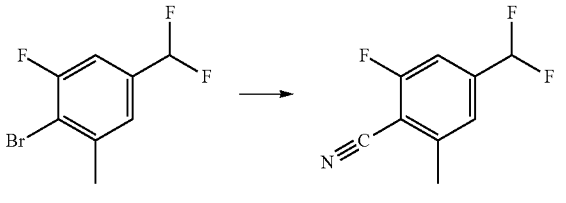

2-bromo-5-(difluoromethyl)-1-fluoro-3-methyl-benzene (4.5 g, 18.83 mmol) in DMF (45 mL) was treated with $Pd(PPh_3)_4$ (1.12 g, 0.969 mmol) and $Zn(CN)_2$ (2.641 g, 22.49 mmol) then degassed by a nitrogen purge and heated at 120° C. under nitrogen for 5 hours. The cooled mixture was diluted with EtOAc and washed with sat. aq. $NaHCO_3$ (2×), brine (2×) and water. The organic layer was dried over $MgSO_4$ and concentrated under reduced pressure. The residue as purified by silica gel chromatography with an ethyl acetate in heptane gradient to give 4-(difluoromethyl)-2-fluoro-6-methyl-benzonitrile (2.908 g, 83%). 1H NMR (500 MHz, DMSO-d6) δ 7.59 (d, J=9.5 Hz, 1H), 7.57 (s, 1H), 7.10 (t, J=55.1 Hz, 1H), 2.57 (s, 3H) ppm.

Step 3: 4-(Difluoromethyl)-2-[2-Methoxy-4-(Trifluoromethoxy)Phenoxy]-6-Methyl-Benzonitrile

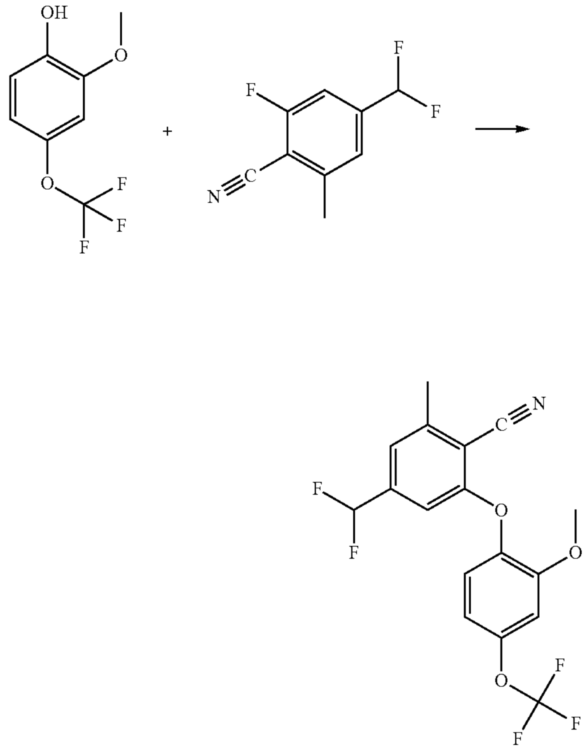

2-Methoxy-4-(trifluoromethoxy)phenol (670.7 mg, 3.222 mmol), 4-(difluoromethyl)-2-fluoro-6-methyl-benzonitrile (571 mg, 3.085 mmol) and $Cs_2CO_3$ (1.12 g, 3.437 mmol) were combined in DMF (3.5 mL), degassed by multiple $N_2$ flush and vacuum cycles and then heated at 80° C. for 2.5 hours. Additional $Cs_2CO_3$ (203 mg, 0.624 mmol) and 2-methoxy-4-(trifluoromethoxy)phenol (130 mg, 0.624 mmol) were added and heating was continued for 2 hours. The mixture was allowed to cool. The mixture was diluted with EtOAc and washed with 2M NaOH (2×) and brine (2×). The organic layer dried over $MgSO_4$ and concentrated under reduced pressure to give 4-(difluoromethyl)-2-[2-methoxy-4-(trifluoromethoxy)phenoxy]-6-methyl-benzonitrile (1.316 g, 114%). This was used without further purification. 1H NMR (500 MHz, DMSO-d6) δ 7.41 (d, J=8.8 Hz, 1H), 7.36 (s, 1H), 7.30 (d, J=2.7 Hz, 1H), 7.07 (ddq, J=8.7, 2.4, 1.1 Hz, 1H), 6.99 (t, J=55.2 Hz, 1H), 6.68 (s, 1H), 3.79 (s, 3H), 2.58 (s, 3H) ppm.

Step 4: 4-(Difluoromethyl)-2-[2-Methoxy-4-(Trifluoromethoxy)Phenoxy]-6-Methyl-Benzamide

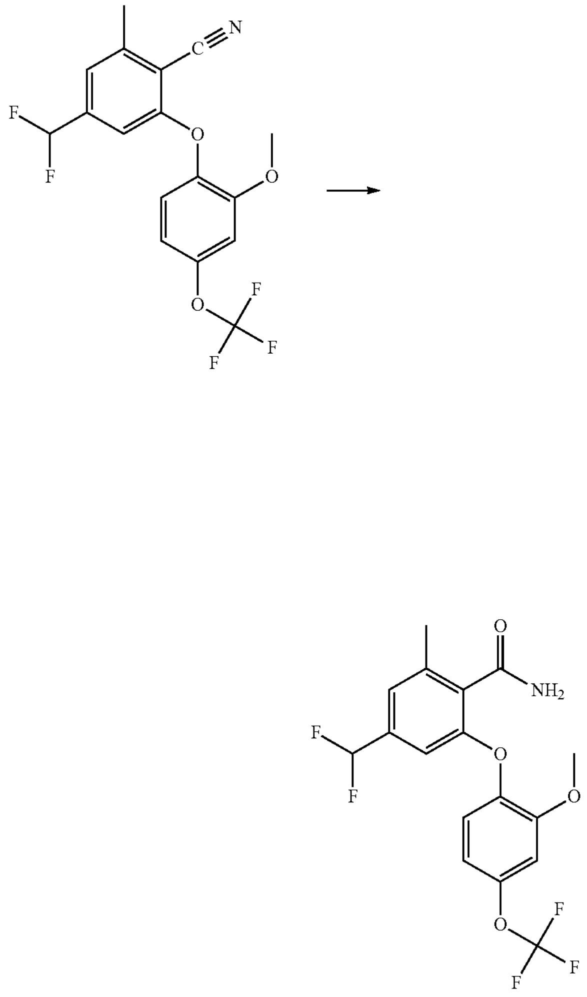

4-(Difluoromethyl)-2-[2-methoxy-4-(trifluoromethoxy)phenoxy]-6-methyl-benzonitrile (1.316 g, 3.526 mmol) in EtOH (13 mL) and NaOH (17 mL of 2 M, 34.00 mmol) was stirred at 90° C. for 1.5 hours. Additional NaOH (2 g, 50.00 mmol) was added and heating was continued for 6 hours. The mixture was allowed to cool and then diluted with EtOAc and washed with brine. The organic layer was dried (MgSO4) and concentrated under reduced pressure to give 4-(difluoromethyl)-2-[2-methoxy-4-(trifluoromethoxy)phenoxy]-6-methyl-benzamide (1.34 g, 97%). 1H NMR (500 MHz, DMSO-d6) δ 7.83 (t, J=2.2 Hz, 1H), 7.65-7.55 (m, 1H), 7.21 (d, J=2.8 Hz, 1H), 7.18 (s, 1H), 7.14 (d, J=8.8 Hz, 1H), 7.01-6.96 (m, 1H), 6.86 (d, J=55.7 Hz, 1H), 6.63 (s, 1H), 3.82 (s, 3H), 2.36 (s, 3H) ppm.

Step 5: Methyl 4-[[4-(Difluoromethyl)-2-[2-Methoxy-4-(Trifluoromethoxy)Phenoxy]-6-Methyl-Benzoyl]Amino]Pyridine-2-Carboxylate

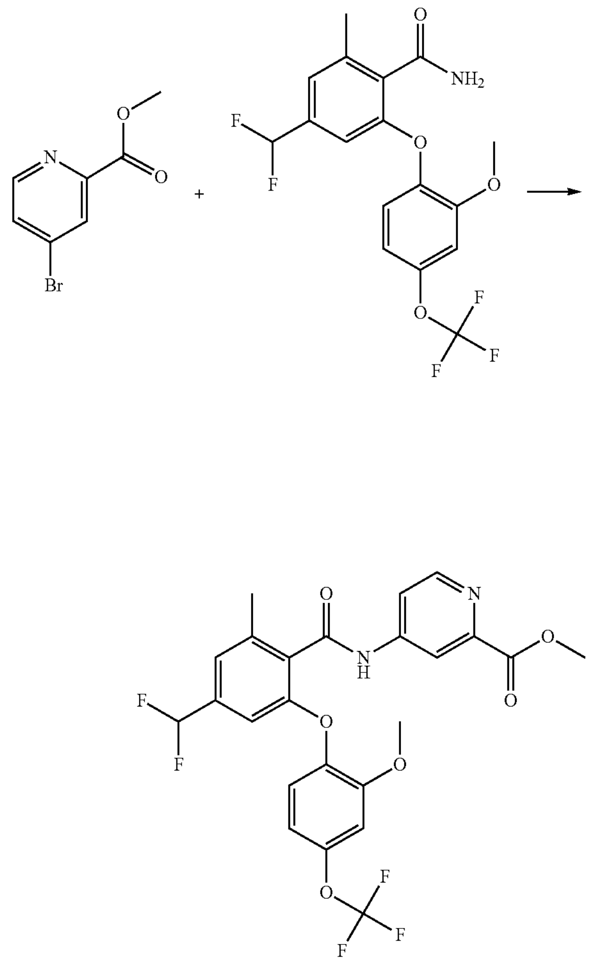

A solution of methyl 4-bromopyridine-2-carboxylate (87.2 mg, 0.404 mmol), Xantphos (36.4 mg, 0.0629 mmol), cesium carbonate (246 mg, 0.755 mmol), $Pd(OAc)_2$ (11.2 mg, 0.0499 mmol) and 4-(difluoromethyl)-2-[2-methoxy-4-(trifluoromethoxy)phenoxy]-6-methyl-benzamide (130 mg, 0.332 mmol) in dioxane (3 mL) was degassed with multiple nitrogen flush-vacuum cycles and then heated at 100° C. under nitrogen for 2.75 hours. The mixture was diluted with EtOAc and washed with sat. aq. $NaHCO_3$. The organic layer was dried over $MgSO_4$ and concentrated under reduced pressure to give methyl 4-[[4-(difluoromethyl)-2-[2-methoxy-4-(trifluoromethoxy)phenoxy]-6-methyl-benzoyl]amino]pyridine-2-carboxylate (174.9 mg, 100%). ESI-MS m/z calc. 526.11633, found 527.6 $(M+1)^+$; Retention time (Method D): 0.91 minutes.

Step 6: 4-[[4-(Difluoromethyl)-2-[2-Methoxy-4-(Trifluoromethoxy)Phenoxy]-6-Methyl-Benzoyl]Amino]Pyridine-2-Carboxamide (200)

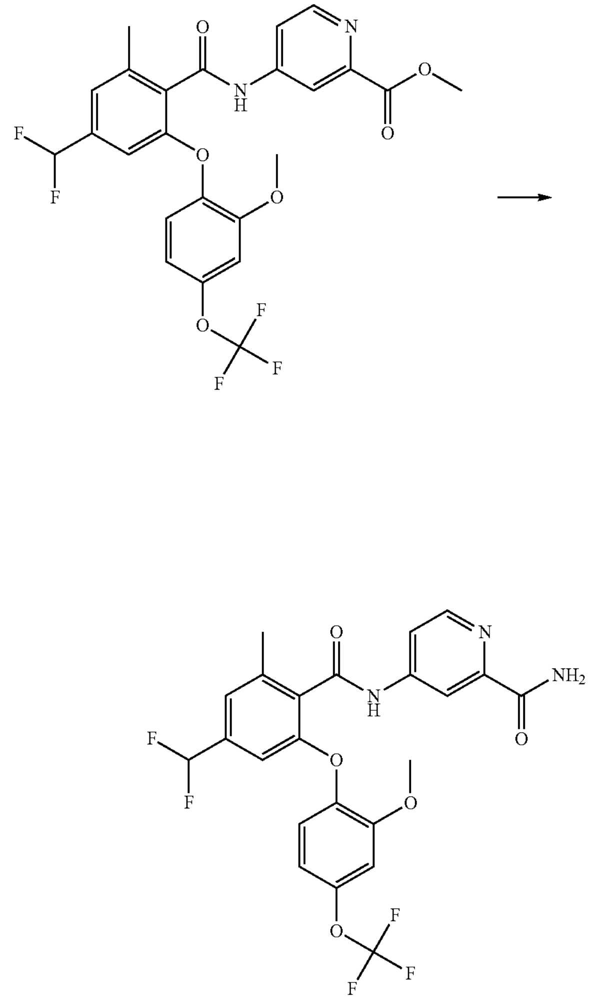

Methyl 4-[[4-(difluoromethyl)-2-[2-methoxy-4-(trifluoromethoxy)phenoxy]-6-methyl-benzoyl]amino]pyridine-2-carboxylate (175 mg, 0.3324 mmol) was dissolved in ammonia (in methanol) (3 mL of 7 M, 21.00 mmol) and stirred at RT overnight. Purification by $C_{18}$ reverse phase HPLC gave 4-[[4-(difluoromethyl)-2-[2-methoxy-4-(trifluoromethoxy)phenoxy]-6-methyl-benzoyl]amino]pyridine-2-carboxamide (68.2 mg, 40%). 1H NMR (500 MHz, DMSO-d6) δ 11.13 (s, 1H), 8.53 (d, J=5.4 Hz, 1H), 8.36 (d, J=2.2 Hz, 1H), 8.07 (d, J=2.9 Hz, 1H), 7.85 (dd, J=5.5, 2.2 Hz, 1H), 7.63 (d, J=2.9 Hz, 1H), 7.28 (s, 1H), 7.25 (d, J=8.8 Hz, 1H), 7.20 (d, J=2.7 Hz, 1H), 7.01 (ddd, J=8.8, 2.7, 1.3 Hz, 1H), 6.93 (d, J=55.6 Hz, 1H), 6.71 (s, 1H), 3.78 (s, 3H), 2.39 (s, 3H) ppm. ESI-MS m/z calc. 511.11667, found 512.5 $(M+1)^+$; Retention time (Method E): 3.08 minutes.

Example 44

N-(2-Carbamoyl-4-Pyridyl)-5,6-Dicyclopropyl-3-[2-Methoxy-4-(Trifluoromethoxy)Phenoxy]Pyridine-2-Carboxamide (201)

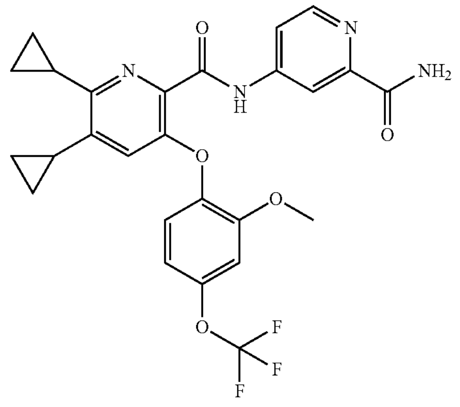 [SMILES: COc1cc(OC(F)(F)F)ccc1Oc1cc(C2CC2)c(C2CC2)nc1C(=O)Nc1ccnc(C(N)=O)c1]

Step 1: Methyl 5,6-Dicyclopropyl-3-Fluoro-Pyridine-2-Carboxylate

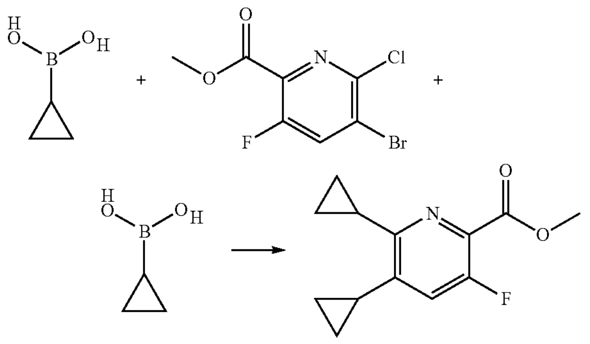

A mixture of methyl 5-bromo-6-chloro-3-fluoro-pyridine-2-carboxylate (1 g, 3.725 mmol), cyclopropyl boronic acid (2 g, 23.28 mmol), $K_3PO_4$ (2.8 g, 13.19 mmol), $Pd(OAc)_2$ (170 mg, 0.757 mmol) and tricyclohexylphosphane (105 mg, 0.374 mmol) in toluene (20 mL) and water (5 mL) was heated at 100° C. for 24 hours. Additional cyclopropylboronic acid (640 mg, 7.451 mmol) was added and the reaction mixture heated for a further 24 h. The reaction mixture was cooled to RT and diluted with water (20 mL) and EtOAc (20 mL) and the layers were separated. The aqueous layer was extracted with EtOAc (2×25 mL) and the combined organic layers were washed with saturated aqueous sodium carbonate solution, dried ($MgSO_4$) and concentrated under reduced pressure to give methyl 5,6-dicyclopropyl-3-fluoro-pyridine-2-carboxylate (910 mg, 68%) as a pale brown oil. This was used without purification. ESI-MS m/z calc. 235.10086, found 236.6 $(M+1)^+$; Retention time (Method D): 0.87 minutes.

Step 2: 5,6-Dicyclopropyl-3-[2-Methoxy-4-(Trifluoromethoxy)Phenoxy]Pyridine-2-Carboxylic Acid

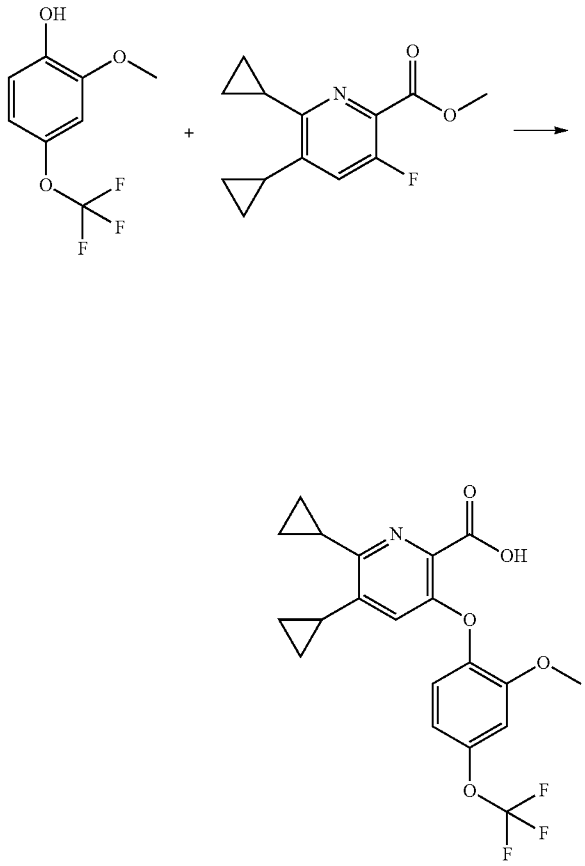

To methyl 5,6-dicyclopropyl-3-fluoro-pyridine-2-carboxylate (300 mg, 0.8289 mmol) in DMF (5 mL) was added 2-methoxy-4-(trifluoromethoxy)phenol (173 mg, 0.831 mmol) and cesium carbonate (810 mg, 2.486 mmol) and the resulting mixture was heated at 90° C. for 48 h. The reaction mixture was cooled to RT and diluted with water (10 mL) and ethyl acetate (10 mL) and the layers were separated. The aqueous layer was extracted with EtOAc (2x5 mL). The aqueous layer was acidified to pH3 by addition of 1N HCl and then extracted with EtOAc (3x10 mL). The combined organic extracts were dried over $MgSO_4$ and concentrated under reduced pressure to give crude (approximately 60% pure) of 5,6-dicyclopropyl-3-[2-methoxy-4-(trifluoromethoxy)phenoxy]pyridine-2-carboxylic acid (190 mg, 52%) as a dark oil which was taken on into the next step without purification. ESI-MS m/z calc. 409.1137, found 410.6 $(M+1)^+$; Retention time (Method D): 0.64 minutes.

Step 3: N-(2-Carbamoyl-4-Pyridyl)-5,6-Dicyclopropyl-3-[2-Methoxy-4-(Trifluoromethoxy)Phenoxy]Pyridine-2-Carboxamide (201)

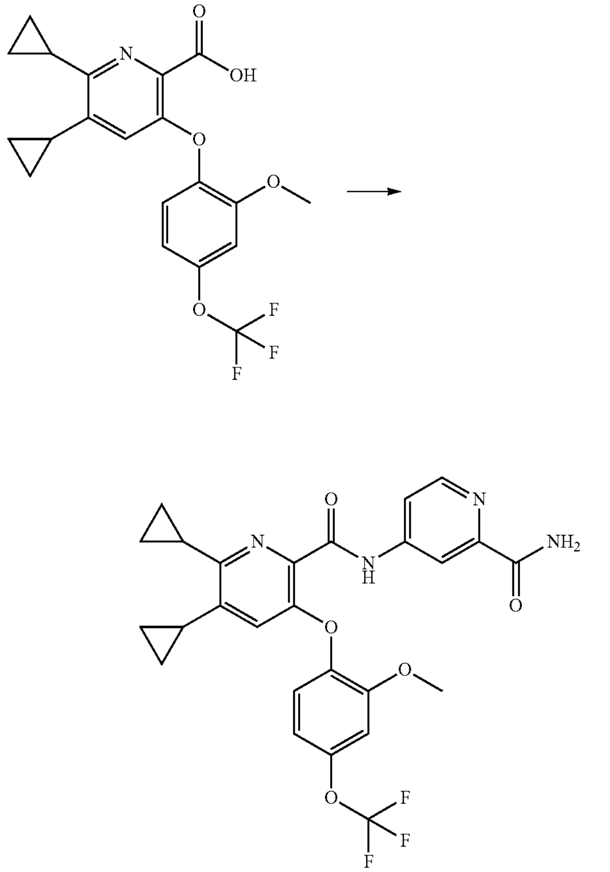

DMF (5 μL, 0.0646 mmol) and oxalyl chloride (0.15 mL, 1.72 mmol) was added to an ice cooled solution of crude 5,6-dicyclopropyl-3-fluoro-pyridine-2-carboxylic acid (187 mg, approximately 60% pure) in DCM (4 mL) and the resulting mixture stirred at RT for 2 h. The reaction mixture was concentrated under reduced pressure and the residue dissolved in DCM (4 mL) and methyl 4-aminopyridine-2-carboxylate (250 mg, 1.643 mmol) and $Et_3N$ (100 μL, 0.718 mmol) was added and the resulting mixture stirred at RT overnight. The reaction mixture was concentrated under reduced pressure and then ammonia in MeOH (3 mL of 7 M, 21.00 mmol) was added and the resulting mixture stirred at RT overnight. The reaction mixture was concentrated under reduced pressure and purified by $C_{18}$ HPLC to yield N-(2-carbamoyl-4-pyridyl)-5,6-dicyclopropyl-3-[2-methoxy-4-(trifluoromethoxy)phenoxy]pyridine-2-carboxamide (4.96 mg, 7%) as a white powder. 1H NMR (500 MHz, DMSO-d6) δ 10.69 (s, 1H), 8.50 (d, J=5.3 Hz, 1H), 8.34 (d, J=2.1 Hz, 1H), 8.07 (d, J=2.8 Hz, 1H), 7.90 (dd, J=5.5, 2.2 Hz, 1H), 7.61 (d, J=2.9 Hz, 1H), 7.14 (d, J=2.5 Hz, 1H), 6.95-6.84 (m, 3H), 3.79 (s, 3H), 2.55 (td, J=8.1, 4.1 Hz, 1H), 2.24 (tt, J=8.5, 5.4 Hz, 1H), 1.15 (dq, J=4.9, 3.4 Hz, 2H), 1.02 (ddt, J=8.5, 6.5, 4.1 Hz, 4H), 0.67-0.60 (m, 2H) ppm. ESI-MS m/z calc. 528.16205, found 529.6 $(M+1)^+$; 527.8 $(M-1)^-$; Retention time (Method E): 3.51 minutes.

Example 45

4-[[2,2-Difluoro-6-[2-Methoxy-4-(Trifluoromethoxy)Phenoxy]-4-Methyl-1,3-Benzodioxole-5-Carbonyl]Amino]Pyridine-2-Carboxamide (202)

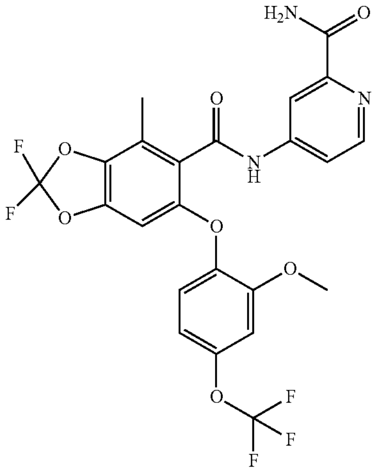 [SMILES: COc1cc(OC(F)(F)F)ccc1Oc1cc2c(c(C)c1C(=O)Nc1ccnc(C(N)=O)c1)OC(F)(F)O2]

Step 1: 2,2-Difluoro-6-Iodo-4-Methyl-1,3-Benzodioxole-5-Carboxylic Acid

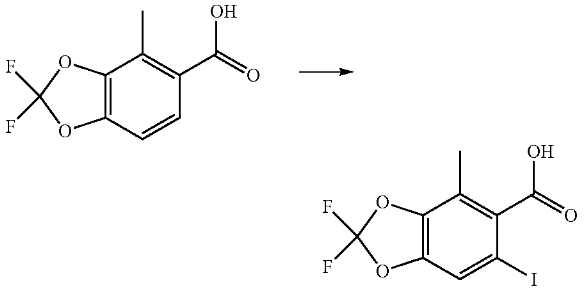

To 2,2-difluoro-4-methyl-1,3-benzodioxole-5-carboxylic acid (2 g, 9.253 mmol), was added palladium(II) acetate (340 mg, 1.514 mmol), tetrabutylammonium iodide (3.6 g, 9.746 mmol), (acetyloxy)(phenyl)-lambda3-iodanyl acetate (6.28 g, 19.50 mmol), iodine (4.94 g, 19.46 mmol) and DCE (20 mL) and the reaction was stirred at 60° C. for 14 h. Additional palladium(II) acetate (340 mg, 1.514 mmol), tetrabutylammonium iodide (3.6 g, 9.746 mmol), (acetyloxy)(phenyl)-lambda3-iodanyl acetate (6.28 g, 19.50 mmol) and iodine (4.94 g, 19.46 mmol) were added and to the reaction and stirred at 60° C. for 93 h. The reaction was acidified with 1 M HCl and a saturated aqueous solution of sodium bisulfite was added. The reaction was extracted with DCM (x3). The combined organic layers were washed with brine and dried over $Na_2SO_4$, filtered and the solvent was evaporated under reduced pressure. The crude product was dissolved in DMSO, filtered and purified using a reverse phase HPLC $C_{18}$ column ($CH_3CN$/water (5 mM HCi) gradient) to yield 2,2-difluoro-6-iodo-4-methyl-1,3-benzodioxole-5-carboxylic acid (1.59 g, 50%) as a brown solid. $^1H$ NMR (400 MHz, DMSO-d6) δ 13.80 (s, 1H), 7.82 (s, 1H), 2.26 (s, 3H) ppm. ESI-MS m/z calc. 341.92004, found 343.0 $(M+1)^+$; Retention time (Method C): 2.02 minutes.

Step 2: 2,2-Difluoro-6-[2-Methoxy-4-(Trifluoromethoxy)Phenoxy]-4-Methyl-1,3-Benzodioxole-5-Carboxylic Acid

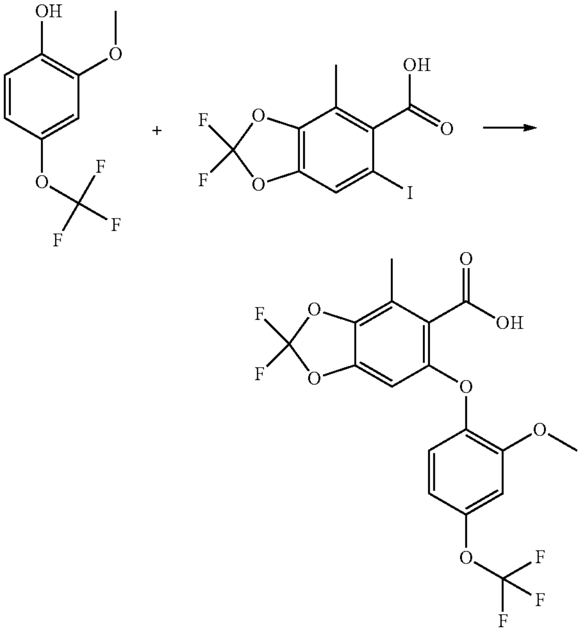

A flask containing 2,2-difluoro-6-iodo-4-methyl-1,3-benzodioxole-5-carboxylic acid (1.47 g, 4.298 mmol), toluene (30 mL) and a stirrer bar was flushed with $N_2$ for 10 min. 2-Methoxy-4-(trifluoromethoxy)phenol (901.4 mg, 4.331 mmol) and cesium carbonate (2.89 g, 8.87 mmol) were added to the reaction and flushed with $N_2$ for 10 min. Copper (I) iodide (177 mg, 0.933 mmol) was added to the reaction and flushed with $N_2$ for 10 min. The reaction was stirred at 60° C. with vigorous stirring under $N_2$ for 14 h. Additional 2-methoxy-4-(trifluoromethoxy)phenol (901 mg, 4.331 mmol), cesium carbonate (2.89 g, 8.870 mmol), iodocopper (177 mg, 0.933 mmol) and toluene (24 mL) were added to the reaction, which was flushed with $N_2$ for 10 min and the reaction was stirred at 60° C. for 1 h. The mixture was allowed to cool, and then diluted with ethyl acetate and water and acidified with 1 M HCl. The two layers were separated. The aqueous layer was extracted with EtOAc (3×). The combined organic layers were filtered and the filtrate was washed with water and brine, dried over sodium sulfate, filtered through a plug of celite and concentrated under reduced pressure. The crude product was dissolved in DMSO, filtered and purified using a reverse phase HPLC $C_{18}$ column ($CH_3CN$/water (5 mM HCl) gradient) to yield 2,2-difluoro-6-[2-methoxy-4-(trifluoromethoxy)phenoxy]-4-methyl-1,3-benzodioxole-5-carboxylic acid (370.0 mg, 20%) as a brown solid. ESI-MS m/z calc. 422.04248, found 423.4 $(M+1)^+$; Retention time (Method C): 2.75 minutes.

Step 3: 2,2-Difluoro-6-[2-Methoxy-4-(Trifluoromethoxy)Phenoxy]-4-Methyl-1,3-Benzodioxole-5-Carbonyl Chloride

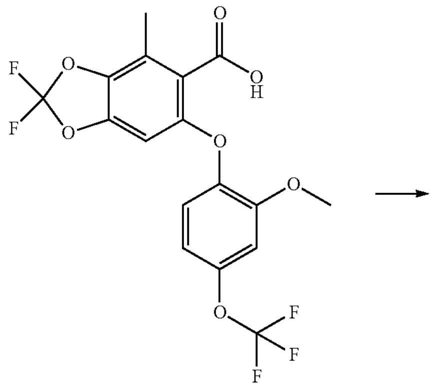

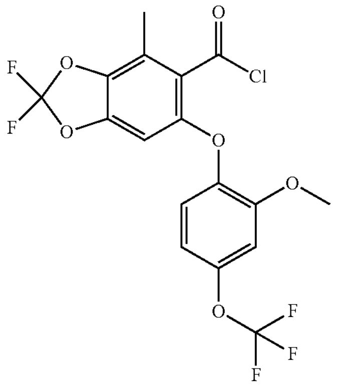

To 2,2-difluoro-6-[2-methoxy-4-(trifluoromethoxy)phenoxy]-4-methyl-1,3-benzodioxole-5-carboxylic acid (370 mg, 0.8762 mmol) and DMF (15 µL, 0.194 mmol) in DCM (3.5 mL) at 0° C. was added oxalyl chloride (216 µL, 2.476 mmol) dropwise under a $N_2$ atmosphere. The ice bath was removed after 10 min and the reaction was stirred at room temperature for 1.5 h. The mixture was concentrated under reduced pressure to afford 2,2-difluoro-6-[2-methoxy-4-(trifluoromethoxy)phenoxy]-4-methyl-1,3-benzodioxole-5-carbonyl chloride, which was used directly in the next step.

Step 4: 4-[[2,2-Difluoro-6-[2-Methoxy-4-(Trifluoromethoxy)Phenoxy]-4-Methyl-1,3-Benzodioxole-5-Carbonyl]Amino]Pyridine-2-Carboxamide (202)

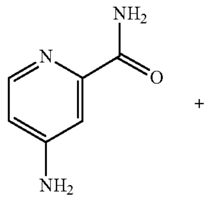

-continued

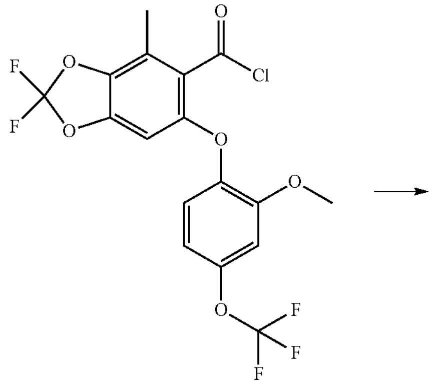

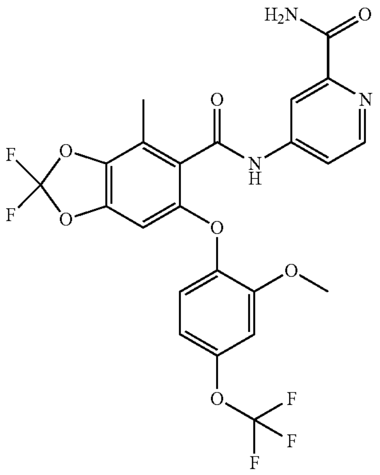

To 4-aminopyridine-2-carboxamide (approximately 39 mg, 0.281 mmol) in NMP (500 µL), and DIEA (approximately 122 µL, 0.704 mmol) at 0° C. was added a solution of 2,2-difluoro-6-[2-methoxy-4-(trifluoromethoxy)phenoxy]-4-methyl-1,3-benzodioxole-5-carbonyl chloride (62 mg, 0.1407 mmol) in NMP (500 µL) slowly. The reaction was stirred at RT for 19 hours follow by 75° C. for 7 hours. The crude product was filtered and purified using a reverse phase HPLC $C_{18}$ column ($CH_3CN$/water (5 mM HCl) gradient) to yield 4-[[2,2-difluoro-6-[2-methoxy-4-(trifluoromethoxy)phenoxy]-4-methyl-1,3-benzodioxole-5-carbonyl]amino]pyridine-2-carboxamide (23.0 mg, 30%). 1H NMR (400 MHz, DMSO-d6) δ 11.10 (s, 1H), 8.51 (d, J=5.5 Hz, 1H), 8.31 (d, J=2.1 Hz, 1H), 8.09 (d, J=2.8 Hz, 1H), 7.80 (dd, J=5.5, 2.2 Hz, 1H), 7.64 (d, J=2.8 Hz, 1H), 7.16-7.10 (m, 2H), 7.01-6.86 (m, 2H), 3.74 (s, 3H), 2.29 (s, 3H) ppm. ESI-MS m/z calc. 541.0908, found 542.1 $(M+1)^+$; Retention time (Method C): 2.67 minutes.

The compounds set forth in Table 27 were prepared by methods analogous to the preparation of compound 202.

TABLE 27

| Additional Compounds Prepared By Methods Analogous to Example 45. | | | |
|---|---|---|---|
| Cmpd No. | Compound Name | LC/MS | NMR (shifts in ppm) |
| 203 | 5-[[2,2-difluoro-6-[2-methoxy-4-(trifluoromethoxy)phenoxy]-4-methyl-1,3-benzodioxole-5-carbonyl]amino]pyridine-2-carboxamide | ESI-MS m/z calc. 541.0908, found 542.2 (M + 1)+; Retention time (Method C): 2.67 minutes | 1H NMR (400 MHz, DMSO-d6) δ 10.99 (s, 1H), 8.82 (dd, J = 2.5, 0.7 Hz, 1H), 8.23 (dd, J = 8.6, 2.5 Hz, 1H), 8.09-7.93 (m, 2H), 7.54 (s, 1H), 7.18-7.06 (m, 2H), 7.02-6.86 (m, 2H), 3.73 (s, 3H), 2.30 (s, 3H). |

Example 46

4-[[3-(3,3-Difluorocyclobutoxy)-6-[2-Methoxy-4-(Trifluoromethoxy)Phenoxy]-2-Methyl-Benzoyl]Amino]Pyridine-2-Carboxamide (204)

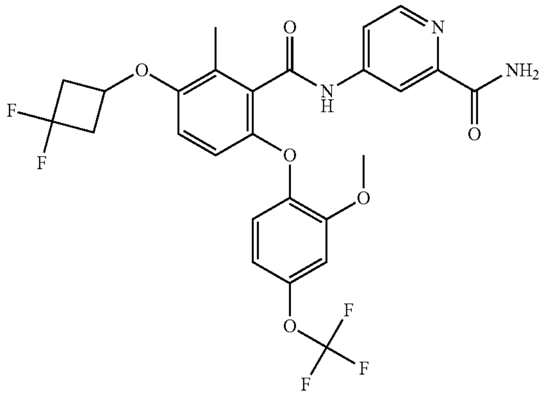 [SMILES: COc1cc(OC(F)(F)F)ccc1Oc1ccc(OC2CC(F)(F)C2)c(C)c1C(=O)Nc1ccnc(C(N)=O)c1]

Step 1: 3-(3,3-Difluorocyclobutoxy)-2-Methyl-Benzoic Acid

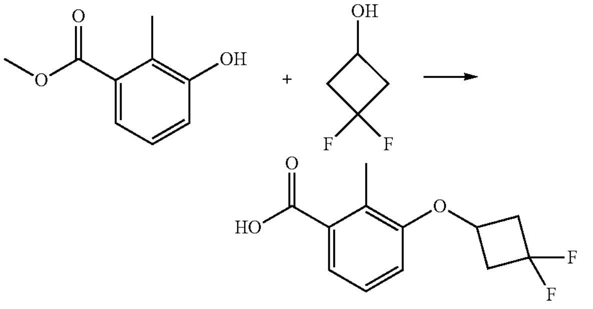

A solution of 3,3-difluorocyclobutanol (2 g, 18.50 mmol) and pyridine (4.9 mL, 60.58 mmol) in DCM (20 mL) was cooled to −78° C. and triflic anhydride (4.1 mL, 24.37 mmol) was added dropwise. After the addition, the cooling bath was replaced with and ice bath and the reaction mixture stirred for an additional 20 minutes. The reaction mixture was poured in to 0.1N HCl and extracted with DCM (3×). The combined organics were washed with 0.1N HCl (2×), water, brine, dried over $Na_2SO_4$, filtered through a short plug of silica and evaporated to dryness to give (3,3-difluorocyclobutyl) trifluoromethanesulfonate that was used directly in the next step.

A solution of methyl 3-hydroxy-2-methyl-benzoate (2 g, 12.04 mmol) in DMF (20 mL) was cooled to 0° C., NaH (950 mg of 60% w/w, 23.75 mmol) was added in portions and the reaction mixture stirred at this temperature for 10 minutes. A solution of (3,3-difluorocyclobutyl) trifluoromethanesulfonate in DMF (5 mL) was added dropwise over 5 minutes, the cooling bath was removed and the reaction mixture was stirred at RT for 16 hours. The reaction mixture was poured in to water, the pH was adjusted with 1N HCl to ~2 and the mixture was extracted with EtOAc (3×). The organics phases were combined washed with 0.1N HCl (2×), brine and concentrated under reduced pressure. The residue was purified by silica gel column chromatography using a EtOAc in hexane gradient to give 3-(3,3-difluorocyclobutoxy)-2-methyl-benzoic acid (1.11 g, 38%) as an off-white solid. 1H NMR (400 MHz, DMSO-d6) δ 12.88 (s, 1H), 7.34 (d, J=8.1 Hz, 1H), 7.22 (dd, J=8.0 Hz, 1H), 7.01 (dd, J=8.2, 1.2 Hz, 1H), 4.86-4.71 (m, 1H), 3.29-3.14 (m, 2H), 2.80-2.61 (m, 2H), 2.34 (s, 3H) ppm.

Step 2: 3-(3,3-Difluorocyclobutoxy)-6-Iodo-2-Methyl-Benzoic Acid

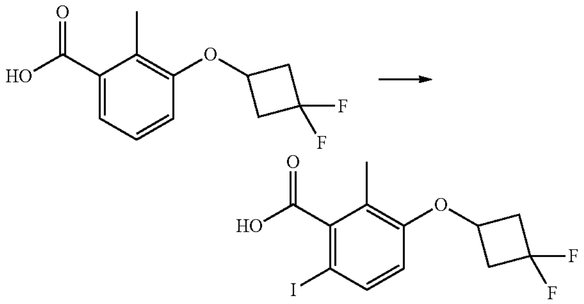

To a solution of 3-(3,3-difluorocyclobutoxy)-2-methyl-benzoic acid (220 mg, 0.908 mmol), iodine (461 mg, 1.817 mmol), and (acetyloxy)(phenyl)-lambda3-iodanyl acetate (585 mg, 1.816 mmol) in DMF (2.5 mL) was degased by bubbling nitrogen through the solution for 5 min. To the reaction mixture was added palladium (II) acetate (33 mg, 0.1470 mmol) and the reaction mixture was stirred at 100° C. for 45 min. The reaction mixture was poured into 0.1 N HCl and extracted with EtOAc (3×). The organics phases were combined, washed with brine, dried over $Na_2SO_4$ and concentrated under reduced pressure. The residue was purified by silica gel column chromatography with a MeOH in DCM gradient to give 3-(3,3-difluorocyclobutoxy)-6-iodo-2-methyl-benzoic acid (160 mg, 48%) as a cream solid. ESI-MS m/z calc. 367.9721, found 369.0 $(M+1)^+$; Retention time (Method A): 0.55 minutes.

Step 3: 3-(3,3-Difluorocyclobutoxy)-6-[2-Methoxy-4-(Trifluoromethoxy)Phenoxy]-2-Methyl-Benzoic Acid

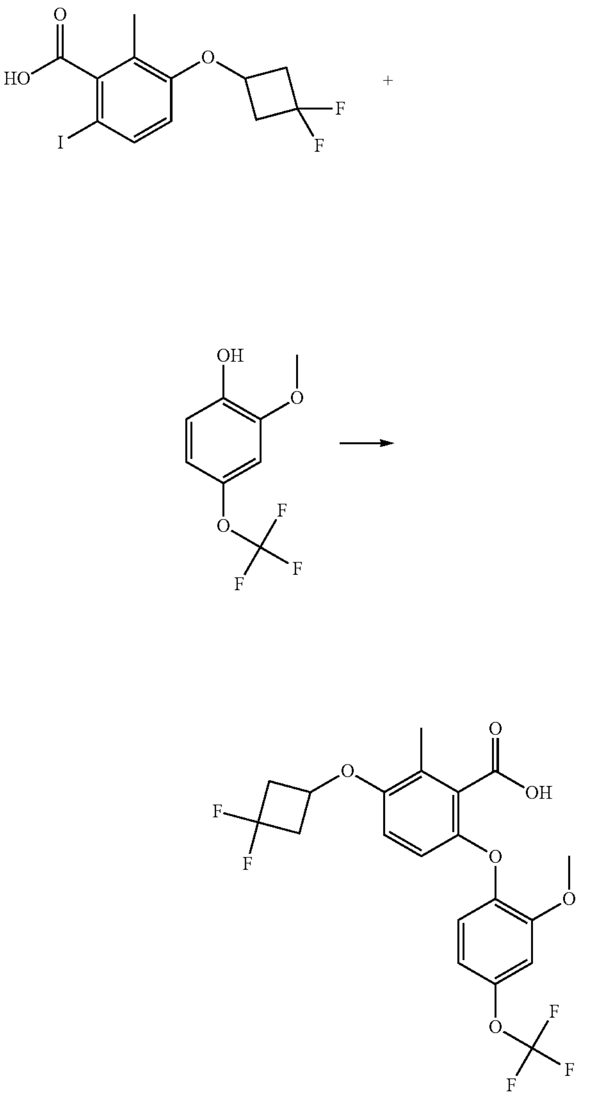

A suspension of 3-(3,3-difluorocyclobutoxy)-6-iodo-2-methyl-benzoic acid (160 mg, 0.435 mmol), 2-methoxy-4-(trifluoromethoxy)phenol (145 mg, 0.697 mmol) and $Cs_2CO_3$ (296 mg, 0.909 mmol) was degassed by bubbling nitrogen through the solution for 3 min, copper (I) iodide (19 mg, 0.0998 mmol) was added and the reaction mixture stirred at 100° C. for 1 hour. The reaction mixture was poured into water, the pH was adjusted to 2 with 1N HCl and the mixture was extracted with EtOAc (3×). The organic phases were combined, washed with 0.1N HCl, brine, dried over sodium sulfate and concentrated under reduced pressure. The residue was purified by silica gel column chromatography with a EtOAc in hexanes gradient to give 3-(3,3-difluorocyclobutoxy)-6-[2-methoxy-4-(trifluoromethoxy)phenoxy]-2-methyl-benzoic acid (58 mg, 30%) as an off-white solid. ESI-MS m/z calc. 448.09454, found 449.1 $(M+1)^+$; Retention time (Method A): 0.68 minutes.

Step 4: 4-[[3-(3,3-Difluorocyclobutoxy)-6-[2-Methoxy-4-(Trifluoromethoxy)Phenoxy]-2-Methyl-Benzoyl]Amino]Pyridine-2-Carboxamide (204)

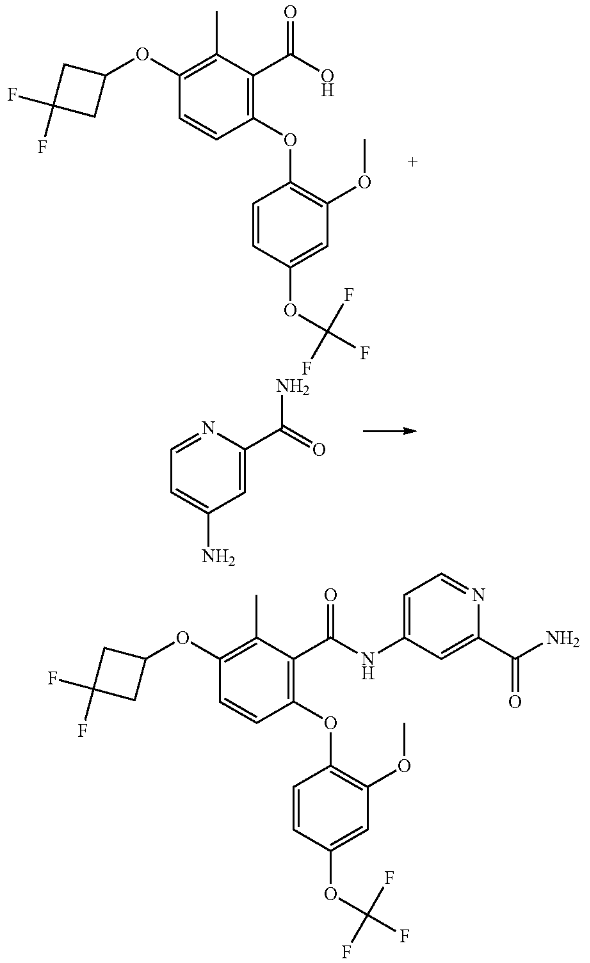

To a solution of 3-(3,3-difluorocyclobutoxy)-6-[2-methoxy-4-(trifluoromethoxy)phenoxy]-2-methyl-benzoic acid (58 mg, 0.129 mmol) in DCM (1 mL) and DMF (12 μL, 0.155 mmol) was added oxalyl chloride (25 μL, 0.287 mmol) and the reaction mixture was stirred at RT for 15 min. The reaction mixture was then concentrated under reduced pressure, toluene was added and the mixture was concentrated again under reduced pressure. The residue was taken up in DCM and added dropwise to a solution of 4-aminopyridine-2-carboxamide (29 mg, 0.212 mmol) and DIEA (68 μL, 0.390 mmol) in NMP (580.0 μL) and the reaction mixture was stirred at RT for 16 hours. The reaction mixture was evaporated to half its original volume, diluted with MeOH, filtered and purification by HPLC ($CH_3CN$/Water (5 mM HCl) gradient) to give 4-[[3-(3,3-difluorocyclobutoxy)-6-[2-methoxy-4-(trifluoromethoxy)phenoxy]-2-methyl-benzoyl]amino]pyridine-2-carboxamide (Hydrochloride salt) (8.2 mg, 10%) as a white solid. ESI-MS m/z calc. 567.1429, found 568.1 $(M+1)^+$; Retention time (Method B): 1.76 minutes. 1H NMR (400 MHz, DMSO-d6) δ 11.07 (s, 1H), 8.50 (d, J=5.5 Hz, 1H), 8.33 (d, J=2.1 Hz, 1H), 8.08 (s, 1H), 7.81 (dd, J=5.5, 2.2 Hz, 1H), 7.63 (s, 1H), 7.10 (d, J=2.7 Hz, 1H), 7.05 (d, J=8.8 Hz, 1H), 6.95-6.88 (m, 2H), 6.62 (d, J=8.9 Hz, 1H), 4.76 (m, J=11.7, 7.3 Hz, 1H), 3.73 (s, 3H), 3.28-3.18 (m, 2H), 2.78-2.60 (m, 2H), 2.17 (s, 3H) ppm.

Example 47

N-(6-Carbamoyl-3-Pyridyl)-5,6-Dicyclopropyl-3-[2-Methoxy-4-(Trifluoromethoxy)Phenoxy]Pyridine-2-Carboxamide (205)

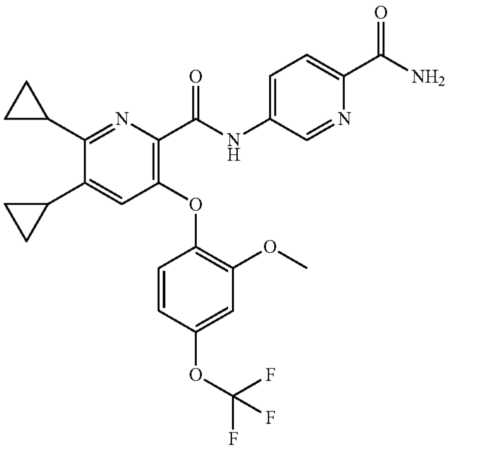 [SMILES: COc1cc(OC(F)(F)F)ccc1Oc1cc(C2CC2)c(C2CC2)nc1C(=O)Nc1ccc(C(N)=O)nc1]

Step 1: N-(6-Carbamoyl-3-Pyridyl)-5,6-Dicyclopropyl-3-Fluoro-Pyridine-2-Carboxamide

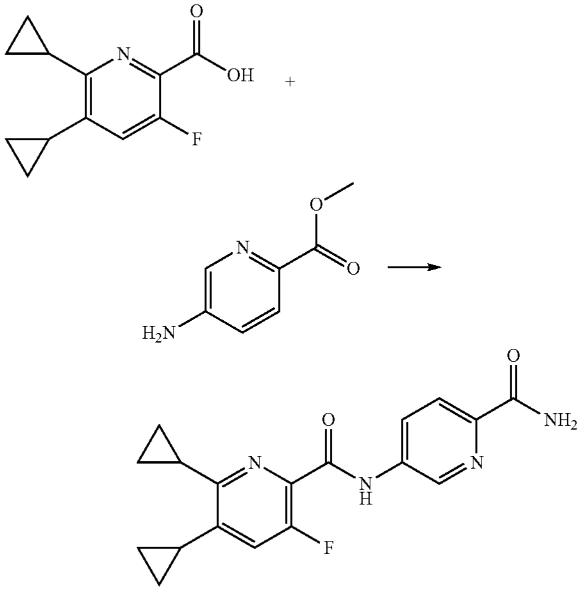

DMF (5 μL, 0.0646 mmol) was added to an ice cooled solution of 5,6-dicyclopropyl-3-fluoro-pyridine-2-carboxylic acid (70 mg, 0.316 mmol) (side product from example 44, step 1) and oxalyl chloride (100 μL, 1.146 mmol) in DCM (2 mL) and the resulting mixture stirred at RT for 2 h. The solvent was removed under reduced pressure and the residue dissolved in DCM (2 mL) and methyl 5-aminopyridine-2-carboxylate (50 mg, 0.329 mmol) and $Et_3N$ (100 μL, 0.718 mmol) were added and the resulting mixture stirred at RT overnight. The reaction mixture was concentrated under reduced pressure and ammonia in methanol (2.5 mL of 7 M, 17.50 mmol) was added and the resulting mixture stirred at RT over the weekend. The reaction mixture was concentrated under reduced pressure to leave a dark brown oil which was dissolved in DCM (10 mL) and water (10 mL) and the layers separated. The organic layer was washed with additional water (1×10 mL), dried over $MgSO_4$ and concentrated under reduced pressure. The residue was purified by chromatography on silica gel eluting with a EtOAc in petroleum ether gradient to give N-(6-carbamoyl-3-pyridyl)-5,6-dicyclopropyl-3-fluoro-pyridine-2-carboxamide (56 mg, 42%) as a white powder. 1H NMR (500 MHz, DMSO-d6) δ 10.53 (s, 1H), 8.99 (d, J=2.4 Hz, 1H), 8.33 (dd, J=8.5, 2.5 Hz, 1H), 8.09-8.02 (m, 2H), 7.54 (s, 1H), 7.43 (d, J=11.7 Hz, 1H), 2.60-2.52 (m, 1H), 2.31 (ddd, J=13.5, 8.4, 5.1 Hz, 1H), 1.23-1.15 (m, 2H), 1.14-1.06 (m, 2H), 1.02 (dq, J=8.2, 3.5 Hz, 2H), 0.88-0.81 (m, 2H) ppm. ESI-MS m/z calc. 340.13354, found 314.6 $(M+1)^+$; 339.8 $(M-1)^-$; Retention time (Method D): 0.79 minutes.

Step 3: N-(6-Carbamoyl-3-Pyridyl)-5,6-Dicyclopropyl-3-[2-Methoxy-4-(Trifluoromethoxy)Phenoxy]Pyridine-2-Carboxamide (205)

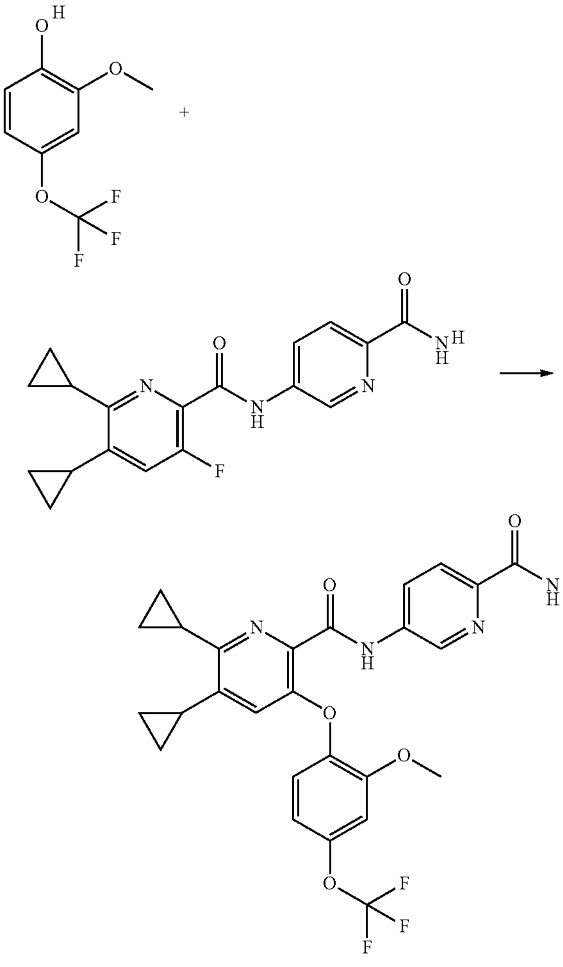

A mixture of 2-methoxy-4-(trifluoromethoxy)phenol (15 mg, 0.0721 mmol), N-(6-carbamoyl-3-pyridyl)-5,6-dicyclopropyl-3-fluoro-pyridine-2-carboxamide (22 mg, 0.0646 mmol) and $Cs_2CO_3$ (63 mg, 0.193 mmol) in DMF (2 mL) was heated at 100° C. overnight. The reaction mixture was cooled to RT and purified by HPLC to give N-(6-carbamoyl-3-pyridyl)-5,6-dicyclopropyl-3-[2-methoxy-4-(trifluoromethoxy)phenoxy]pyridine-2-carboxamide (trifluoroacetic acid (2)) (4.8 mg, 10%) as a white powder. 1H NMR (500 MHz, DMSO-d6) δ 10.61 (s, 1H), 8.90 (d, J=2.5 Hz, 1H), 8.26 (dd, J=8.5, 2.4 Hz, 1H), 8.02 (d, J=8.6 Hz, 2H), 7.52 (s, 1H), 7.14 (d, J=2.5 Hz, 1H), 6.95-6.86 (m, 3H), 3.78 (s, 3H), 2.56 (td, J=8.1, 4.0 Hz, 1H), 2.24 (tt, J=8.4, 5.3 Hz, 1H), 1.15 (dd, J=5.0, 2.5 Hz, 2H), 1.08-0.96 (m, 4H), 0.67-0.58 (m, 2H) ppm. ESI-MS m/z calc. 528.16205, found 529.6 $(M+1)^+$; 527.7 $(M-1)^-$; Retention time (Method E): 3.49 minutes.

Example 48

5-[[6-[2-Cyclopropyl-4-(Trifluoromethoxy)Phenoxy]-2-Fluoro-3-(Trifluoromethyl)Benzoyl]Amino]Pyridine-2-Carboxamide (206)

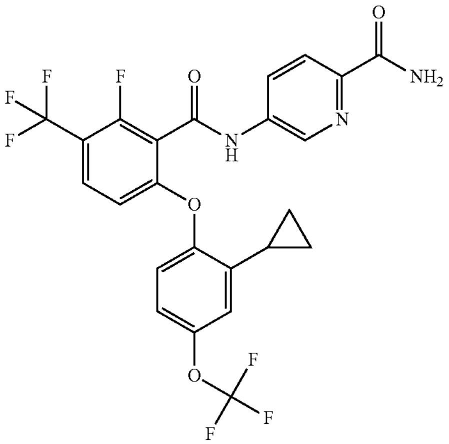 [SMILES: NC(=O)c1ccc(NC(=O)c2c(Oc3ccc(OC(F)(F)F)cc3C3CC3)ccc(C(F)(F)F)c2F)cn1]

Step 1: 5-[[6-Bromo-2-Fluoro-3-(Trifluoromethyl)Benzoyl]Amino]Pyridine-2-Carboxamide

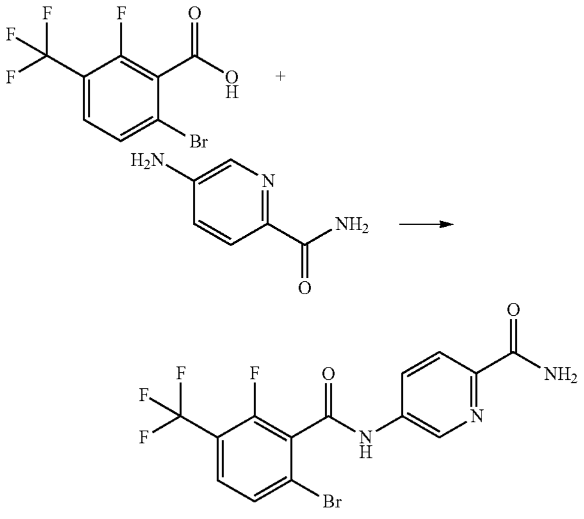

6-Bromo-2-fluoro-3-(trifluoromethyl)benzoic acid (2.0 g, 6.968 mmol) was dissolved in dichloromethane (28 mL). DMF (215 μL, 2.777 mmol) was added followed by the slow dropwise addition of oxalyl chloride (2.7 mL, 30.95 mmol). The reaction mixture was allowed to stir at RT for 30 minutes. The reaction mixture was concentrated under reduced pressure. Additional dichloromethane (~5 mL) was added, and the solution was again concentrated to dryness. The remaining residue was taken up in NMP (6 mL) and added to a prepared solution of 5-aminopyridine-2-carboxamide (1.4 g, 10.21 mmol) and DIEA (7.3 mL, 41.91 mmol) in NMP (6 mL). This reaction mixture was allowed to stir at 25° C. for 4 hours. The reaction mixture was purified by silica gel column chromatography using a gradient of EtOAc in hexanes to give 5-[[6-bromo-2-fluoro-3-(trifluoromethyl)benzoyl]amino]pyridine-2-carboxamide (1.5 g, 53%) as a white solid. ESI-MS m/z calc. 404.9736, found 406.1 $(M+1)^+$; Retention time (Method B): 1.01 minutes. 1H NMR (400 MHz, DMSO-d6) δ 11.45 (s, 1H), 8.86 (d, J=2.4 Hz, 1H), 8.31 (dd, J=8.5, 2.5 Hz, 1H), 8.20-7.99 (m, 2H), 8.00-7.79 (m, 2H), 7.71-7.41 (m, 1H) ppm.

Step 2: 5-[[6-[2-Cyclopropyl-4-(Trifluoromethoxy)Phenoxy]-2-Fluoro-3-(Trifluoromethyl)Benzoyl]Amino]Pyridine-2-Carboxamide (206)

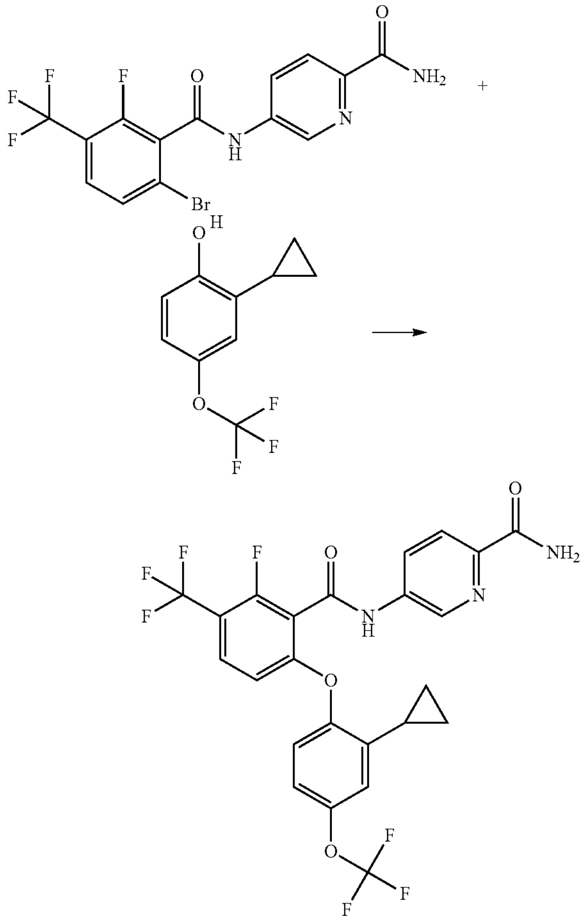

5-[[6-Bromo-2-fluoro-3-(trifluoromethyl)benzoyl]amino]pyridine-2-carboxamide (50 mg, 0.123 mmol), 2-cyclopropyl-4-(trifluoromethoxy)phenol (approximately 32 mg, 0.148 mmol), $Cs_2CO_3$ (approximately 60 mg, 0.185 mmol), and copper (I) iodide (approximately 9 mg, 0.0492 mmol) in toluene (0.5 mL) were purged with nitrogen. The mixture was stirred at 100° C. for 60 minutes. The reaction mixture was allowed to cool to RT, filtered, and purified by reverse phase chromatography using a $C_{18}$ column and a gradient of acetonitrile in water (5 mM hydrochloric acid) to give 5-[[6-[2-cyclopropyl-4-(trifluoromethoxy)phenoxy]-2-fluoro-3-(trifluoromethyl)benzoyl]amino]pyridine-2-carboxamide (4.7 mg, 7%). ESI-MS m/z calc. 543.1029, found 544.0 $(M+1)^+$; Retention time (Method B): 1.92 minutes. 1H NMR (400 MHz, DMSO-d6) δ 11.43 (s, 1H), 8.85 (s, 1H), 8.30 (d, J=10.8 Hz, 1H), 8.10-7.96 (m, 2H), 7.87 (s, 1H), 7.57 (s, 1H), 7.29 (s, 2H), 7.01 (s, 1H), 6.74 (d, J=8.9 Hz, 1H), 1.98 (s, 1H), 0.87 (d, J=10.1 Hz, 2H), 0.71 (d, J=5.3 Hz, 2H) ppm.

The compounds set forth in Table 28 were prepared by methods analogous to the preparation of compound 206.

TABLE 28

Additional Compounds Prepared By Methods Analogous to Example 48.

| Cmpd No. | Compound Name | LC/MS | NMR (shifts in ppm) |
|---|---|---|---|
| 207 | 5-[[6-(3,4-difluoro-2-methyl-phenoxy)-2-fluoro-3-(trifluoromethyl)benzoyl]amino]pyridine-2-carboxamide | ESI-MS m/z calc. 469.08612, found 470.0 (M + 1)+; Retention time (Method B): 1.68 minutes | 1H NMR (400 MHz, DMSO-d6) δ 11.44 (s, 1H), 8.85 (s, 1H), 8.30 (d, J = 6.1 Hz, 1H), 8.15-7.98 (m, 2H), 7.84 (s, 1H), 7.58 (s, 1H), 7.41 (q, J = 9.4 Hz, 1H), 7.08 (d, J = 13.2 Hz, 1H), 6.77 (d, J = 8.9 Hz, 1H), 2.11 (s, 3H). |
| 208 | 5-[[6-(4-chloro-2,6-dimethyl-phenoxy)-2-fluoro-3-(trifluoromethyl)benzoyl]amino]pyridine-2-carboxamide | ESI-MS m/z calc. 481.08163, found 482.0 (M + 1)+; Retention time (Method B) 1.86 minutes | $^1$H NMR (400 MHz, DMSO-$d_6$) δ 11.49 (s, 1H), 8.88 (d, J = 2.4 Hz, 1H), 8.35 (dd, J = 8.7, 2.5 Hz, 1H), 8.20-8.00 (m, 2H), 7.79 (t, J = 8.7 Hz, 1H), 7.71-7.52 (m, 1H), 7.33 (s, 2H), 6.48 (d, J = 8.9 Hz, 1H), 2.10 (s, 6H). |
| 209 | 5-[[2-fluoro-6-[3-fluoro-2-methoxy-4-(trifluoromethoxy)phenoxy]-3-(trifluoromethyl)benzoyl]amino]pyridine-2-carboxamide | ESI-MS m/z calc. 551.07275, found 552.0 (M + 1)+; Retention time (Method B): 1.86 minutes | $^1$H NMR (400 MHz, DMSO-$d_6$) δ 11.45 (s, 1H), 8.85 (d, J = 2.4 Hz, 1H), 8.30 (dd, J = 8.6, 2.5 Hz, 1H), 8.17-7.98 (m, 2H), 7.87 (t, J = 8.6 Hz, 1H), 7.60 (s, 1H), 7.41 (t, J = 8.6 Hz, 1H), 7.23 (dd, J = 9.3, 2.1 Hz, 1H), 6.93 (d, J = 8.9 Hz, 1H), 3.86 (s, 3H). |
| 210 | 5-[[2-fluoro-6-[2-methoxy-4-(1,1,2,2,2-pentafluoroethyl)phenoxy]-3-(trifluoromethyl)benzoyl]amino]pyridine-2-carboxamide | ESI-MS m/z calc. 567.08405, found 568.0 (M + 1)+; Retention time (Method B): 1.89 minutes | $^1$H NMR (400 MHz, DMSO-$d_6$) δ 11.42 (s, 1H), 8.86 (d, J = 2.5 Hz, 1H), 8.28 (dd, J = 8.6, 2.5 Hz, 1H), 8.06 (d, J = 8.7 Hz, 2H), 7.85 (t, J = 8.6 Hz, 1H), 7.69-7.55 (m, 1H), 7.47 (d, J = 8.4 Hz, 1H), 7.42 (d, J = 2.2 Hz, 1H), 7.37 (dd, J = 8.7, 2.1 Hz, 1H), 6.79 (d, J = 8.9 Hz, 1H), 3.83 (s, 3H). |
| 211 | 5-[[6-(2, 6-dimethoxy-4-methyl-phenoxy)-2-fluoro-3-(trifluoromethyl)benzoyl]amino]pyridine-2-carboxamide | ESI-MS m/z calc. 493.1261, found 494.0 (M + 1)+; Retention time (Method B): 1.71 minutes | $^1$H NMR (400 MHz, DMSO-$d_6$) δ 11.28 (s, 1H), 8.90 (d, J = 2.5 Hz, 1H), 8.34 (dd, J = 8.6, 2.5 Hz, 1H), 8.07 (d, J = 8.6 Hz, 2H), 7.75 (t, J = 8.7 Hz, 1H), 7.68-7.52 (m, 1H), 6.65 (s, 2H), 6.54 (d, J = 8.9 Hz, 1H), 3.72 (s, 6H), 2.33 (s, 3H). |
| 212 | 5-[[2-fluoro-3-(trifluoromethyl)-6-(2,4,6-trifluorophenoxy)benzoyl]amino]pyridine-2-carboxamide | ESI-MS m/z calc. 473.06104, found 474.0 (M + 1)+; Retention time (Method B): 1.54 minutes | $^1$H NMR (400 MHz, DMSO-$d_6$) δ 11.51 (s, 1H), 8.87 (d, J = 2.5 Hz, 1H), 8.31 (dd, J = 8.5, 2.5 Hz, 1H), 8.08 (d, J = 8.6 Hz, 2H), 7.88 (t, J = 8.6 Hz, 1H), 7.60 (s, 1H), 7.57-7.47 (m, 2H), 7.01 (d, J = 8.9 Hz, 1H). |
| 213 | 5-[[6-(2,4-dichloro-6-methyl-phenoxy)-2-fluoro-3-(trifluoromethyl)benzoyl]amino]pyridine-2-carboxamide | ESI-MS m/z calc. 501.027, found 502.0 (M + 1)+; Retention time (Method B): 1.89 minutes | $^1$H NMR (400 MHz, DMSO-$d_6$) δ 11.46 (s, 1H), 8.87 (d, J = 2.5 Hz, 1H), 8.35 (dd, J = 8.6, 2.5 Hz, 1H), 8.21-7.97 (m, 2H), 7.81 (t, J = 8.6 Hz, 1H), 7.70 (d, J = 2.5 Hz, 1H), 7.60 (s, 1H), 7.54 (d, J = 2.5 Hz, 1H), 6.60 (d, J = 8.9 Hz, 1H), 2.19 (s, 3H). |
| 214 | 5-[[2-fluoro-6-(4-fluoro-2,3-dimethyl-phenoxy)-3-(trifluoromethyl)benzoyl]amino]pyridine-2-carboxamide | ESI-MS m/z calc. 465.11118, found 466.0 (M + 1)+; Retention time (Method B): 1.81 minutes | $^1$H NMR (400 MHz, DMSO-$d_6$) δ 11.45 (s, 1H), 8.87 (d, J = 2.5 Hz, 1H), 8.32 (dd, J = 8.7, 2.5 Hz, 1H), 8.20-7.96 (m, 2H), 7.82 (t, J = 8.6 Hz, 1H), 7.60 (s, 1H), 7.24-6.97 (m, 2H), 6.60 (d, J = 8.9 Hz, 1H), 2.17 (d, J = 2.1 Hz, 3H), 2.08 (s, 3H). |
| 215 | 5-[[2-fluoro-3-(trifluoromethyl)-6-(2,3,4-trifluorophenoxy)benzoyl]amino]pyridine-2-carboxamide | ESI-MS m/z calc. 473.06104, found 474.0 (M + 1)+; Retention time (Method B): 1.66 minutes | $^1$H NMR (400 MHz, DMSO-$d_6$) δ 11.47 (s, 1H), 8.85 (d, J = 2.4 Hz, 1H), 8.30 (dd, J = 8.6, 2.5 Hz, 1H), 8.19-8.01 (m, 2H), 7.89 (t, J = 8.6 Hz, 1H), 7.60 (s, 1H), 7.55-7.40 (m, 1H), 7.40-7.23 (m, 1H), 7.05 (d, J = 8.9 Hz, 1H). |

TABLE 28-continued

| Additional Compounds Prepared By Methods Analogous to Example 48. | | | |
|---|---|---|---|
| Cmpd No. | Compound Name | LC/MS | NMR (shifts in ppm) |
| 216 | 5-[[2-fluoro-6-[3-fluoro-4-(trifluoromethoxy)phenoxy]-3-(trifluoromethyl)benzoyl]amino]pyridine-2-carboxamide | ESI-MS m/z calc. 521.0622, found 522.0 (M + 1)+; Retention time (Method B): 1.82 minutes | $^{1}$H NMR (400 MHz, DMSO-$d_6$) δ 11.40 (s, 1H), 8.82 (d, J = 2.4 Hz, 1H), 8.26 (dd, J = 8.6, 2.5 Hz, 1H), 8.05 (d, J = 8.6 Hz, 2H), 7.94 (t, J = 8.6 Hz, 1H), 7.67 (t, J = 9.2 Hz, 1H), 7.63-7.55 (m, 1H), 7.51 (dd, J = 11.1, 2.9 Hz, 1H), 7.17 (d, J = 9.0 Hz, 1H), 7.10 (d, J = 8.8 Hz, 1H). |
| 217 | 5-[[6-[3-chloro-4-(trifluoromethoxy)phenoxy]-2-fluoro-3-(trifluoromethyl)benzoyl]amino]pyridine-2-carboxamide | ESI-MS m/z calc. 537.03265, found 538.0 (M + 1)+; Retention time (Method B): 1.89 minutes | $^{1}$H NMR (400 MHz, DMSO-$d_6$) δ 11.43 (s, 1H), 8.82 (d, J = 2.4 Hz, 1H), 8.26 (dd, J = 8.6, 2.5 Hz, 1H), 8.05 (d, J = 8.7 Hz, 2H), 7.93 (t, J = 8.6 Hz, 1H), 7.66 (d, J = 10.6 Hz, 2H), 7.59 (s, 1H), 7.34 (dd, J = 9.0, 2.9 Hz, 1H), 7.09 (d, J = 8.8 Hz, 1H). |
| 218 | 5-[[6-(4-chloro-2-methyl-phenoxy)-2-fluoro-3-(trifluoromethyl)benzoyl]amino]pyridine-2-carboxamide | ESI-MS m/z calc. 467.06598, found 468.0 (M + 1)+; Retention time (Method B): 1.82 minutes | $^{1}$H NMR (400 MHz, DMSO-$d_6$) δ 11.42 (s, 1H), 8.85 (d, J = 2.5 Hz, 1H), 8.30 (dd, J = 8.5, 2.5 Hz, 1H), 8.20-7.98 (m, 2H), 7.84 (t, J = 8.7 Hz, 1H), 7.59 (s, 1H), 7.48 (d, J = 2.6 Hz, 1H), 7.37 (dd, J = 8.6, 2.6 Hz, 1H), 7.19 (d, J = 8.7 Hz, 1H), 6.72 (d, J = 8.9 Hz, 1H), 2.14 (s, 3H). |
| 219 | 5-[[6-(4-chloro-2-fluoro-phenoxy)-2-fluoro-3-(trifluoromethyl)benzoyl]amino]pyridine-2-carboxamide | ESI-MS m/z calc. 471.04092, found 472.0 (M + 1)+; Retention time (Method B): 1.72 minutes | 1H NMR (400 MHz, DMSO-d6) δ 11.48 (s, 1H), 8.55 (d, J = 5.5 Hz, 1H), 8.28 (s, 1H), 8.10 (s, 1H), 7.93 (s, 1H), 7.78 (s, 1H), 7.67 (s, 2H), 7.51 (d, J = 12.9 Hz, 1H), 7.17 (d, J = 9.3 Hz, 1H), 7.08 (d, J = 8.7 Hz, 1H). |
| 220 | 5-[[6-(4-chloro-2-methoxy-phenoxy)-2-fluoro-3-(trifluoromethyl)benzoyl]amino]pyridine-2-carboxamide | ESI-MS m/z calc. 483.06088, found 484.0 (M + 1)+; Retention time (Method B): 1.75 minutes | 1H NMR (400 MHz, DMSO-d6) δ 11.36 (s, 1H), 8.87 (s, 1H), 8.30 (d, J = 10.9 Hz, 1H), 8.14-7.94 (m, 2H), 7.79 (s, 1H), 7.57 (s, 1H), 7.36-7.21 (m, 2H), 7.10 (d, J = 10.9 Hz, 1H), 6.67 (d, J = 8.9 Hz, 1H), 3.78 (s, 3H). |
| 221 | 5-[[2-fluoro-6-[2-fluoro-4-(trifluoromethoxy)phenoxy]-3-(trifluoromethyl)benzoyl]amino]pyridine-2-carboxamide | ESI-MS m/z calc. 521.0622, found 522.0 (M + 1)+; Retention time (Method B): 1.73 minutes | 1H NMR (400 MHz, DMSO-d6) δ 11.45 (s, 1H), 8.84 (s, 1H), 8.28 (d, J = 11.0 Hz, 1H), 8.13-7.98 (m, 2H), 7.90 (s, 1H), 7.71 (d, J = 13.4 Hz, 1H), 7.64-7.47 (m, 2H), 7.36 (d, J = 9.0 Hz, 1H), 6.98 (d, J = 8.8 Hz, 1H). |
| 222 | 5-[[2-fluoro-6-[2-methyl-4-(trifluoromethoxy)phenoxy]-3-(trifluoromethyl)benzoyl]amino]pyridine-2-carboxamide | ESI-MS m/z calc. 517.0873, found 518.0 (M + 1)+; Retention time (Method B): 1.82 minutes | 1H NMR (400 MHz, DMSO-d6) δ 11.42 (s, 1H), 8.84 (s, 1H), 8.29 (d, J = 8.6 Hz, 1H), 8.13-7.95 (m, 2H), 7.86 (s, 1H), 7.57 (s, 1H), 7.42 (s, 1H), 7.30 (d, J = 5.5 Hz, 2H), 6.75 (d, J = 8.8 Hz, 1H), 2.18 (s, 3H). |
| 223 | 5-[[6-[2-chloro-4-(trifluoromethoxy)phenoxy]-2-fluoro-3-(trifluoromethyl)benzoyl]amino]pyridine-2-carboxamide | ESI-MS m/z calc. 537.03265, found 538.0 (M + 1)+; Retention time (Method B): 1.8 minutes | 1H NMR (400 MHz, DMSO-d6) δ 11.42 (s, 1H), 8.84 (s, 1H), 8.27 (d, J = 8.6 Hz, 1H), 8.13-7.97 (m, 2H), 7.90 (s, 1H), 7.82 (s, 1H), 7.55 (d, J = 21.6 Hz, 3H), 6.89 (d, J = 8.8 Hz, 1H). |

Example 49

5-[[6-[3-Fluoro-2-Methoxy-4-(Trifluoromethoxy) Phenoxy]-2-Methyl-3-(Trifluoromethyl)Benzoyl] Amino]Pyridine-2-Carboxamide (224)

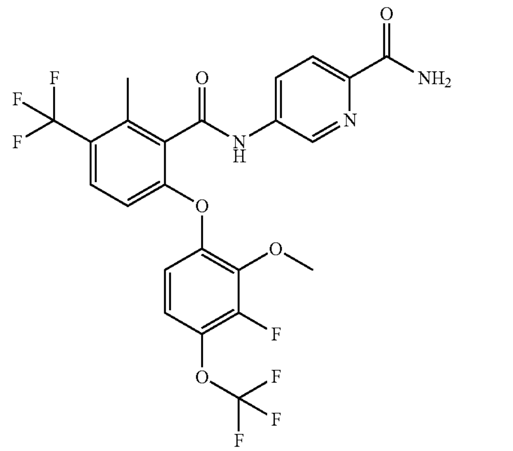 [SMILES: COc1c(Oc2ccc(C(F)(F)F)c(C)c2C(=O)Nc2ccc(C(N)=O)nc2)ccc(OC(F)(F)F)c1F]

Step 1: 5-[[6-Fluoro-2-Methyl-3-(Trifluoromethyl) Benzoyl]Amino]Pyridine-2-Carboxamide

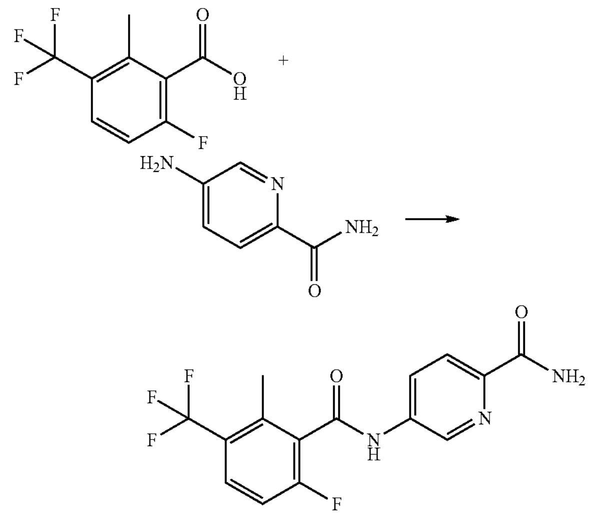

6-Fluoro-2-methyl-3-(trifluoromethyl)benzoic acid (2.95 g, 13.28 mmol) in anhydrous DCM (30 mL) under nitrogen was treated with DMF (50 μL, 0.646 mmol), cooled in an ice bath and treated dropwise with oxalyl chloride (2.2 mL, 25.22 mmol). The reaction was stirred for 10 minutes in the ice bath then the bath was removed. The clear solution was stirred at RT for 1 hour. The mixture was concentrated to dryness under reduced pressure. The orange residue was dissolved in DCM (7.5 mL) and the solution was added dropwise to a cold mixture of 5-aminopyridine-2-carboxamide (2.2 g, 16.04 mmol) and DIEA (7 mL, 40.19 mmol) in NMP (30 mL). The mixture was stirred at RT for 16 h. The mixture was concentrated under reduced pressure and the residue was diluted with EtOAc and water. The aqueous phase was extracted with EtOAc (1×75 mL). The combined organic layers were washed with brine (2×), dried over $Na_2SO_4$, filtered and concentrated to give white solid. The crude material was purified by silica chromatography eluting with a gradient of methanol in DCM to give 5-[[6-fluoro-2-methyl-3-(trifluoromethyl)benzoyl]amino]pyridine-2-carboxamide (3.14 g, 69%) as off-white solid. ESI-MS m/z calc. 341.07874, found 342.2 $(M+1)^+$; Retention time (Method B): 0.87 minutes. 1H NMR (400 MHz, DMSO-d6) δ 11.29 (s, 1H), 8.87 (d, J=2.4 Hz, 1H), 8.33 (dd, J=8.6, 2.5 Hz, 1H), 8.15-8.00 (m, 2H), 7.92 (dd, J=9.0, 5.5 Hz, 1H), 7.58 (s, 1H), 7.46 (t, J=8.7 Hz, 1H), 2.45 (d, J=1.8 Hz, 3H) ppm.

Step 2: 5-[[6-[3-Fluoro-2-Methoxy-4-(Trifluoromethoxy)Phenoxy]-2-Methyl-3-(Trifluoromethyl) Benzoyl]Amino]Pyridine-2-Carboxamide (224)

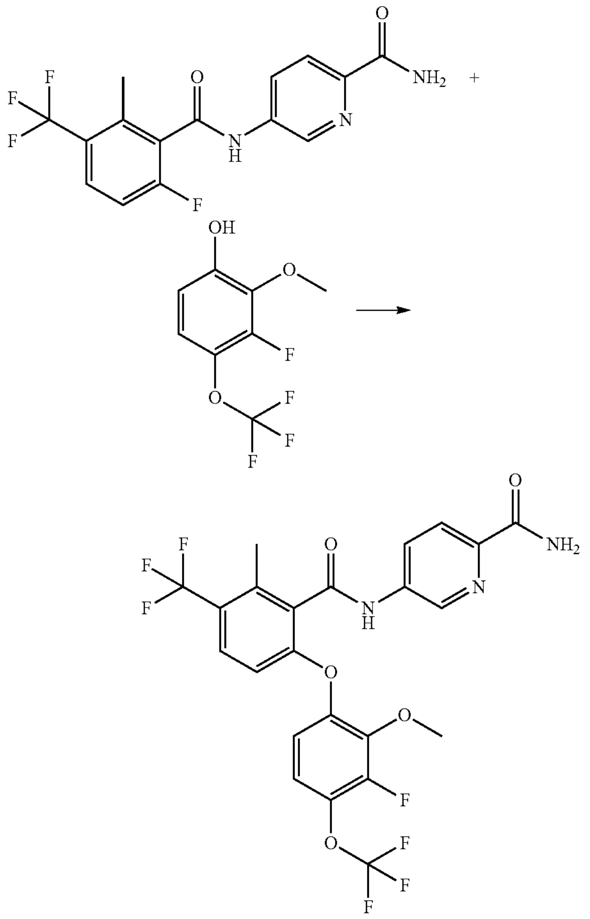

5-[[6-Fluoro-2-methyl-3-(trifluoromethyl)benzoyl] amino]pyridine-2-carboxamide (75 mg, 0.220 mmol) and 3-fluoro-2-methoxy-4-(trifluoromethoxy)phenol (150 mg, 0.663 mmol) were dissolved in DMSO (200 L). To this clear solution was added finely ground potassium carbonate (92 mg, 0.666 mmol). The reaction mixture was stirred at 125° C. for 5 h. The mixture was cooled to RT, filtered and purified by reverse phase HPLC (C18, 1M99% $CH_3CN/H_2O$ with 5 mM HCl) to give 5-[[6-[3-fluoro-2-methoxy-4-(trifluoromethoxy)phenoxy]-2-methyl-3-(trifluoromethyl)benzoyl]amino]pyridine-2-carboxamide (11.3 mg, 9%) as an off-white solid. ESI-MS m/z calc. 547.09784, found 548.2 $(M+1)^+$; Retention time (Method B): 1.82 minutes. $^1$H NMR (400 MHz, DMSO-d6) δ 11.22 (s, 1H), 8.87 (d, J=2.4 Hz, 1H), 8.32 (dd, J=8.6, 2.5 Hz, 1H), 8.05 (d, 9=8.5 Hz, 1H), 8.01 (s, 1H), 7.76 (d, (=8.9 Hz, 1H), 7.55 (sc, 1H), 7.42-7.33 (m, 1H), 7.13 (dd, ==9.4, 2.2 Hz, 1H), 6.90 (d, 7=8.8 Hz, 1H), 3.84 (d, J=0.9 Hz, 3H), 2.46 (d, J=1.9 Hz, 3H) ppm.

The compounds set forth in Table 29 were prepared by methods analogous to the preparation of compound 224.

TABLE 29

Additional Compounds Prepared By Methods Analogous to Example 49.

| Cmpd No. | Compound Name | LC/MS | NMR (shifts in ppm) |
|---|---|---|---|
| 225 | 5-[[2-methyl-3-(trifluoromethyl)-6-(2,3,4-trifluorophenoxy)benzoyl]amino]pyridine-2-carboxamide | ESI-MS m/z calc. 469.08612, found 470.2 (M + 1)+; Retention time (Method B): 1.63 minutes | |
| 226 | 5-[[6-[2-cyclopropyl-4-(trifluoromethoxy)phenoxy]-2-methyl-3-(trifluoromethyl)benzoyl]amino]pyridine-2-carboxamide | ESI-MS m/z calc. 539.128, found 540.1 (M + 1)+; Retention time (Method B): 2.02 minutes | 1H NMR (400 MHz, DMSO-d6) δ 11.22 (s, 1H), 8.87 (dd, J = 2.5, 0.7 Hz, 1H), 8.33 (dd, J = 8.6, 2.5 Hz, 1H), 8.09-8.03 (m, 1H), 8.03-7.99 (m, 1H), 7.77 (d, J = 8.9 Hz, 1H), 7.56 (s, 1H), 7.29-7.18 (m, 2H), 6.98 (d, J = 2.5 Hz, 1H), 6.73 (d, J = 8.8 Hz, 1H), 2.46 (d, J = 1.7 Hz, 3H), 1.99 (tt, J = 8.4, 5.2 Hz, 1H), 0.91-0.80 (m, 2H), 0.74-0.66 (m, 2H). |
| 227 | : 5-[[6-(3,4-difluoro-2-methyl-phenoxy)-2-methyl-3-(trifluoromethyl)benzoyl]amino]pyridine-2-carboxamide | ESI-MS m/z calc. 465.11118, found 466.1 (M + 1)+; Retention time (Method B): 1.79 minutes | 1H NMR (400 MHz, DMSO-d6) δ 11.23 (s, 1H), 8.90-8.85 (m, 1H), 8.33 (dd, J = 8.6, 2.5 Hz, 1H), 8.06 (d, J = 8.6 Hz, 1H), 8.02 (s, 1H), 7.73 (d, J = 8.9 Hz, 1H), 7.56 (s, 1H), 7.38 (q, J = 9.4 Hz, 1H), 7.05-6.98 (m, 1H), 6.74 (d, J = 8.9 Hz, 1H), 2.45 (d, J = 1.7 Hz, 3H), 2.10 (d, J = 2.1 Hz, 3H). |
| 228 | 5-[[6-(2,6-dimethoxy-4-methyl-phenoxy)-2-methyl-3-(trifluoromethyl)benzoyl]amino]pyridine-2-carboxamide | ESI-MS m/z calc. 489.15115, found 490.0 (M + 1)+; Retention time (Method B): 1.79 minutes | 1H NMR (400 MHz, DMSO-d6) δ 10.97 (s, 1H), 8.92 (d, J = 2.4 Hz, 1H), 8.38 (dd, J = 8.6, 2.5 Hz, 1H), 8.09-7.99 (m, 2H), 7.64 (d, J = 8.9 Hz, 1H), 7.54 (d, J = 2.7 Hz, 1H), 6.63 (s, 2H), 6.47 (d, J = 8.8 Hz, 1H), 3.71 (s, 6H), 2.41 (d, J = 1.6 Hz, 3H), 2.33 (s, 3H). |
| 229 | 5-[[6-(4-chloro-2,6-dimethyl-phenoxy)-2-methyl-3-(trifluoromethyl)benzoyl]amino]pyridine-2-carboxamide | ESI-MS m/z calc. 477.1067, found 478.05 (M + 1)+; Retention time (Method B): 1.97 minutes | 1H NMR (400 MHz, DMSO-d6) δ 11.23 (s, 1H), 8.89 (d, J = 2.4 Hz, 1H), 8.38 (dd, J = 8.6, 2.5 Hz, 1H), 8.06 (d, J = 8.6 Hz, 1H), 8.01 (s, 1H), 7.67 (d, J = 8.9 Hz, 1H), 7.56 (d, J = 2.7 Hz, 1H), 7.29 (s, 2H), 6.42 (d, J = 8.8 Hz, 1H), 2.45 (d, J = 1.7 Hz, 3H), 2.07 (s, 6H). |
| 230 | 5-[[2-methyl-3-(trifluoromethyl)-6-(2,4,6-trifluorophenoxy)benzoyl]amino]pyridine-2-carboxamide | ESI-MS m/z calc. 469.08612, found 469.95 (M + 1)+; Retention time (Method B): 1.73 minutes | |
| 231 | 5-[[6-(4-fluoro-2,3-dimethyl-phenoxy)-2-methyl-3-(trifluoromethyl)benzoyl]amino]pyridine-2-carboxamide | ESI-MS m/z calc. 461.13626, found 462.0 (M + 1)+; Retention time (Method B): 1.88 minutes | 1H NMR (400 MHz, DMSO-d6) δ 11.22 (s, 1H), 8.91-8.86 (m, 1H), 8.34 (dd, J = 8.6, 2.5 Hz, 1H), 8.05 (d, J = 8.6 Hz, 1H), 8.01 (d, J = 2.9 Hz, 1H), 7.70 (d, J = 8.9 Hz, 1H), 7.55 (s, 1H), 7.11 (t, J = 9.0 Hz, 1H), 7.01 (dd, J = 8.9, 4.9 Hz, 1H), 6.56 (d, J = 8.8 Hz, 1H), 2.44 (d, J = 1.8 Hz, 3H), 2.17 (d, J = 2.1 Hz, 3H), 2.07 (s, 3H). |
| 232 | 5-[[6-(4-fluoro-2-methoxy-phenoxy)-2-methyl-3-(trifluoromethyl)benzoyl]amino]pyridine-2-carboxamide | ESI-MS m/z calc. 463.1155, found 464.0 (M + 1)+; Retention time (Method B): 1.74 minutes | 1H NMR (400 MHz, DMSO-d6) δ 11.14 (s, 1H), 8.91 (d, J = 2.4 Hz, 1H), 8.35 (dd, J = 8.6, 2.5 Hz, 1H), 8.09-7.99 (m, 2H), 7.69 (d, J = 8.9 Hz, 1H), 7.55 (d, J = 2.9 Hz, 1H), 7.23 (dd, J = 8.8, 5.9 Hz, 1H), 7.15 (dd, J = 10.7, 2.9 Hz, 1H), 6.85 (td, J = 8.5, 2.9 Hz, 1H), 6.58 (d, J = 8.8 Hz, 1H), 3.76 (s, 3H), 2.43 (d, J = 1.8 Hz, 3H). |
| 233 | 5-[[6-(4-chloro-2-methyl-phenoxy)-2-methyl-3-(trifluoromethyl)benzoyl]amino]pyridine-2-carboxamide | ESI-MS m/z calc. 463.09106, found 463.95 (M + 1)+; Retention time (Method B): 1.89 minutes | 1H NMR (400 MHz, DMSO-d6) δ 11.20 (s, 1H), 8.87 (d, J = 2.3 Hz, 1H), 8.32 (dd, J = 8.6, 2.5 Hz, 1H), 8.05 (d, J = 8.6 Hz, 1H), 8.01 (s, 1H), 7.73 (d, J = 8.9 Hz, 1H), 7.57-7.53 (m, 1H), 7.44 (d, J = 2.6 Hz, 1H), 7.34 (dd, J = 8.5, 2.7 Hz, 1H), 7.12 (d, J = 8.6 Hz, 1H), 6.70 (d, J = 8.8 Hz, 1H), 2.45 (d, J = 1.7 Hz, 3H), 2.12 (s, 3H). |

TABLE 29-continued

Additional Compounds Prepared By Methods Analogous to Example 49.

| Cmpd No. | Compound Name | LC/MS | NMR (shifts in ppm) |
|---|---|---|---|
| 234 | 5-[[6-(4-chloro-2-fluoro-phenoxy)-2-methyl-3-(trifluoromethyl)benzoyl]amino]pyridine-2-carboxamide | ESI-MS m/z calc. 467.06598, found 468.1 (M + 1)+; Retention time (Method B): 1.76 minutes | $^1$H NMR (400 MHz, DMSO-$d_6$) δ 11.26 (s, 1H), 8.88 (d, J = 2.5 Hz, 1H), 8.32 (dd, J = 8.5, 2.5 Hz, 1H), 8.16-7.95 (m, 2H), 7.77 (d, J = 8.9 Hz, 1H), 7.74-7.64 (m, 1H), 7.64-7.52 (m, 1H), 7.45-7.36 (m, 2H), 6.89 (d, J = 8.8 Hz, 1H), 2.43 (s, 3H). |
| 235 | 5-[[6-(2-chloro-4-methoxy-phenoxy)-2-methyl-3-(trifluoromethyl)benzoyl]amino]pyridine-2-carboxamide | ESI-MS m/z calc. 479.08597, found 479.95 (M + 1)+; Retention time (Method B): 1.82 minutes | 1H NMR (400 MHz, DMSO-d6) δ 11.14 (s, 1H), 8.90 (d, J = 2.4 Hz, 1H), 8.34 (dd, J = 8.5, 2.5 Hz, 1H), 8.05 (d, J = 8.5 Hz, 1H), 8.01 (s, 1H), 7.69 (d, J = 8.9 Hz, 1H), 7.55 (s, 1H), 7.30 (d, J = 2.4 Hz, 1H), 7.21 (d, J = 8.5 Hz, 1H), 7.08 (dd, J = 8.5, 2.4 Hz, 1H), 6.63 (d, J = 8.8 Hz, 1H), 3.77 (s, 3H), 2.43 (d, J = 1.7 Hz, 3H). |
| 236 | 5-[[2-methyl-6-[2-methyl-4-(trifluoromethoxy)phenoxy]-3-(trifluoromethyl)benzoyl]amino]pyridine-2-carboxamide | ESI-MS m/z calc. 513.1123, found 513.9 (M + 1)+; Retention time (Method B): 1.96 minutes | 1H NMR (400 MHz, DMSO-d6) δ 11.21 (s, 1H), 8.89-8.84 (m, 1H), 8.31 (dd, J = 8.6, 2.5 Hz, 1H), 8.08-7.98 (m, 2H), 7.75 (d, J = 8.9 Hz, 1H), 7.55 (d, J = 2.9 Hz, 1H), 7.39 (d, J = 3.0 Hz, 1H), 7.29 (dd, J = 8.8, 2.9 Hz, 1H), 7.21 (d, J = 8.9 Hz, 1H), 6.73 (d, J = 8.8 Hz, 1H), 2.45 (d, J = 1.7 Hz, 3H), 2.17 (s, 3H). |

Example 50

4-[[4-Tert-Butyl-2-[2-Methoxy-4-(Trifluoromethoxy)Phenoxy]-6-Methyl-Benzoyl]Amino]Pyridine-2-Carboxamide (237)

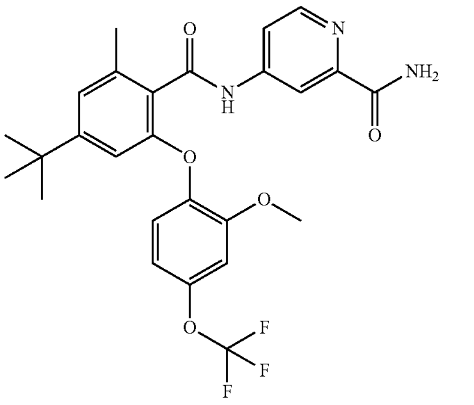 [SMILES: COc1cc(OC(F)(F)F)ccc1Oc1cc(C(C)(C)C)cc(C)c1C(=O)Nc1ccnc(C(N)=O)c1]

Step 1: Methyl 4-Bromo-2-[2-Methoxy-4-(Trifluoromethoxy)Phenoxy]-6-Methyl-Benzoate

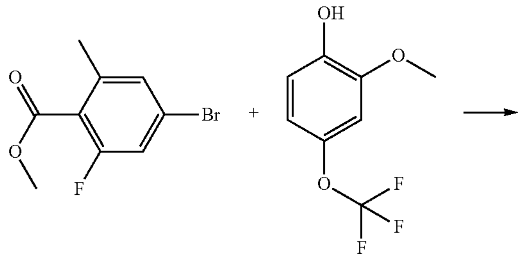

-continued

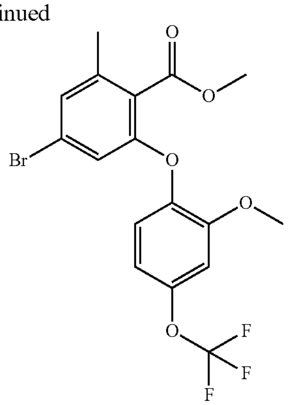

A pressure vessel was charged with methyl 4-bromo-2-fluoro-6-methyl-benzoate (5 g, 20.24 mmol), 2-methoxy-4-(trifluoromethoxy)phenol (4.4 g, 21.14 mmol), $Cs_2CO_3$ (6.6 g, 20.26 mmol) and DMF (61 mL). The vessel was sealed, the reaction mixture stirred at 100° C. for 16 hours, and the mixture was cooled to RT. The mixture was diluted with EtOAc, washed with brine (3×100 ml), and the organic layer dried over $Na_2SO_4$, filtered and concentrated under reduced pressure. The residue was purified by silica gel chromatography with a EtOAc in hexanes gradient to give methyl 4-bromo-2-[2-methoxy-4-(trifluoromethoxy)phenoxy]-6-methyl-benzoate (2.9 g, 33%) as a clear oil. $^1$H NMR (400 MHz, DMSO-d6) δ 7.29 (d, J=1.8 Hz, 1H), 7.21 (d, J=2.7 Hz, 1H), 7.13 (d, J=8.8 Hz, 1H), 6.97 (ddd, J=8.9, 2.7, 1.4 Hz, 1H), 6.68 (d, J=1.8 Hz, 1H), 3.80 (s, 6H), 2.27 (s, 3H) ppm.

Step 2: Methyl 4-Tert-Butyl-2-[2-Methoxy-4-(Trifluoromethoxy)Phenoxy]-6-Methyl-Benzoate

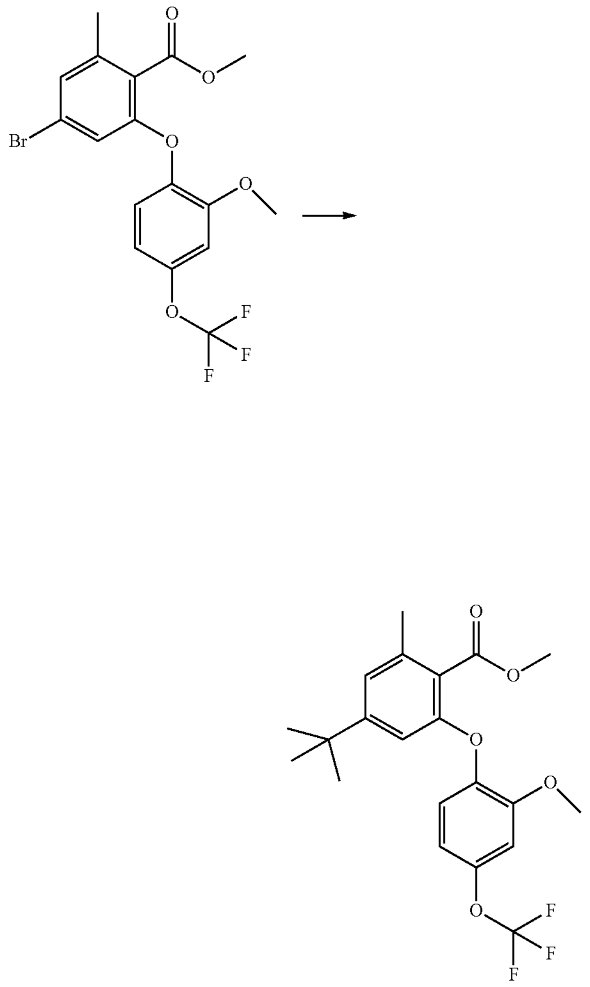

To a solution of methyl 4-bromo-2-[2-methoxy-4-(trifluoromethoxy)phenoxy]-6-methyl-benzoate (300 mg, 0.689 mmol), 1,3-dicyclohexylimidazol-1-ium tetrafluoroborate (44 mg, 0.137 mmol) and dichloronickel 1,2-dimethoxyethane (30 mg, 0.137 mmol) in THF (20 mL) cooled to −15° C. was added tert-butyl(chloro)magnesium (861 μL of 1 M, 0.861 mmol) in portions over 5 minutes. The mixture was allowed to stir at −15 C for 30 minutes. Additional tert-butyl (chloro)magnesium (861 μL of 1 M, 0.8610 mmol) was added over 5 mins at −10° C. The reaction mixture was quenched with aqueous $NH_4Cl$ and partitioned between ethyl acetate (30 ml) and water (30 ml). The aqueous layer was further extracted with EtOAc (50 mL). The combined organic layers were washed with brine, dried over magnesium sulfate and concentrated under reduced pressure. The product was purified by silica gel chromatography with a EtOAc in petroleum ether gradient to give methyl 4-tert-butyl-2-[2-methoxy-4-(trifluoromethoxy)phenoxy]-6-methyl-benzoate (170 mg, 48%) as an oil. 1H NMR (500 MHz, Chloroform-d) δ 7.00 (dd, J=1.7, 0.8 Hz, 1H), 6.90-6.83 (m, 2H), 6.79-6.74 (m, 1H), 6.72 (d, J=1.9 Hz, 1H), 3.88 (s, 3H), 3.81 (s, 3H), 2.42-2.37 (m, 3H), 1.25 (s, 9H) ppm. ESI-MS m/z calc. 412.14975, found 413.5 $(M+1)^+$; Retention time (Method E): 3.21 minutes.

Step 3: 4-Tert-Butyl-2-[2-Methoxy-4-(Trifluoromethoxy)Phenoxy]-6-Methyl-Benzoic Acid

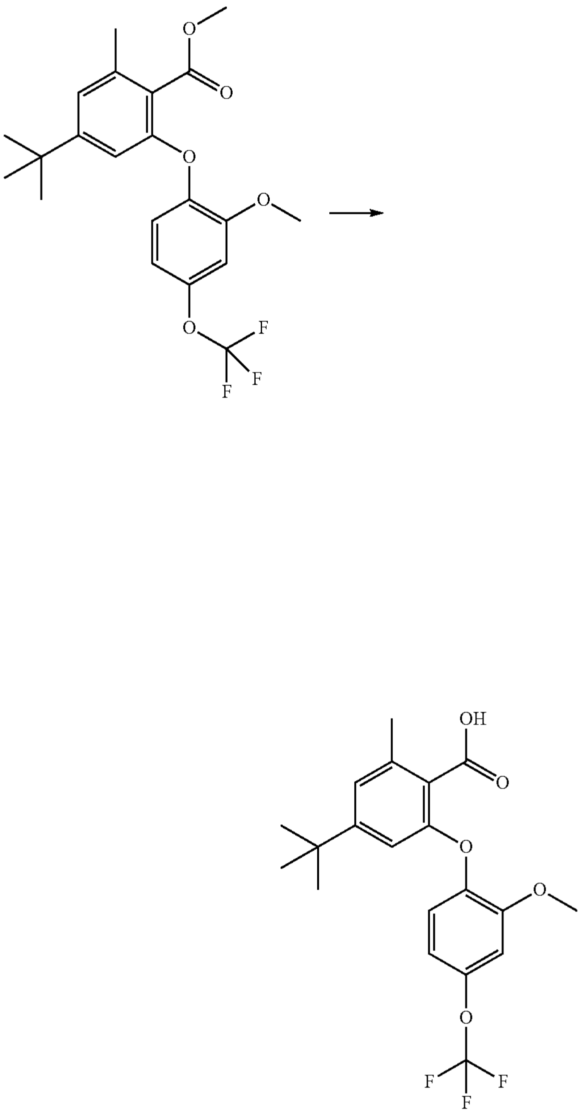

Methyl 4-tert-butyl-2-[2-methoxy-4-(trifluoromethoxy) phenoxy]-6-methyl-benzoate (225 mg, 0.546 mmol) was dissolved in ethanol (10 mL) and then aqueous LiOH (1000 μL of 2 M, 2.000 mmol) was added and the mixture heated to 60 C for 1 h. An additional 2 mL aqueous LiOH (2M) was added and heating was continued for 5 h. The reaction was quenched with 2M HCl and the mixture was concentrated under reduced pressure to give 4-tert-butyl-2-[2-methoxy-4-(trifluoromethoxy)phenoxy]-6-methyl-benzoic acid (200 mg, 92%). 1H NMR (400 MHz, Chloroform-d) δ 7.28 (s, 1H), 7.12-6.99 (m, 2H), 6.87 (s, 1H), 6.84-6.77 (m, 1H), 6.68 (dd, J=1.8, 0.6 Hz, 1H), 3.85 (s, 3H), 2.55 (d, J=1.2 Hz, 1H), 2.55 (s, 2H), 1.23 (s, 9H) ppm. ESI-MS m/z calc. 398.1341, found 397.2 $(M-1)^-$; Retention time (Method D): 0.67 minutes.

Step 4: 4-Tert-Butyl-2-[2-Methoxy-4-(Trifluoromethoxy)Phenoxy]-6-Methyl-Benzamide

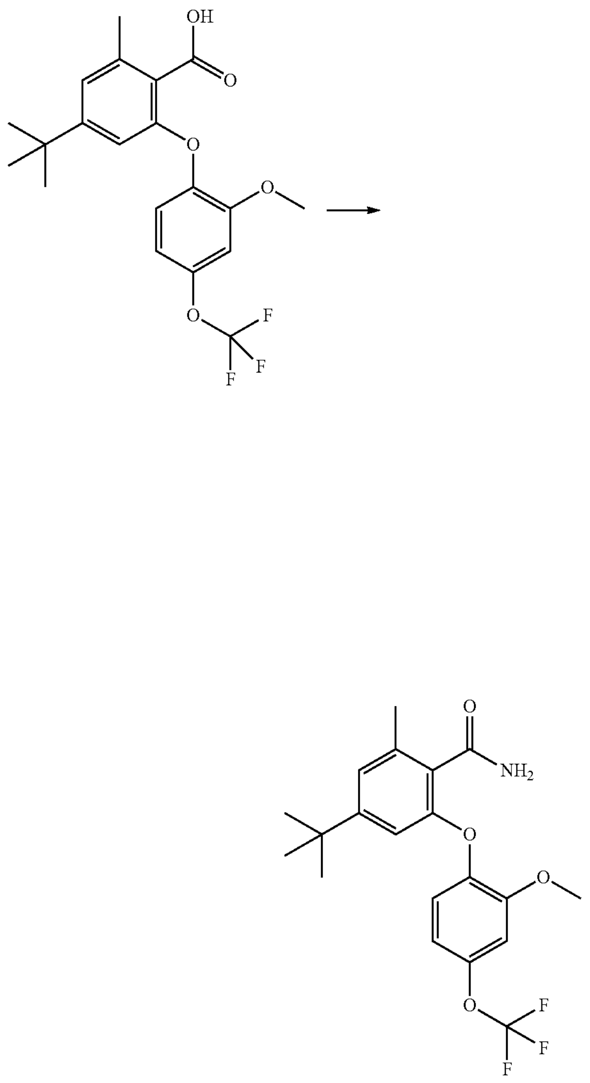

4-tert-Butyl-2-[2-methoxy-4-(trifluoromethoxy)phenoxy]-6-methyl-benzoic acid (200 mg, 0.502 mmol) was dissolved in DCM (10 mL) at 0° C., DMF (4 μL, 0.0517 mmol) was added, followed by the dropwise addition of oxalyl chloride (440 μL, 5.044 mmol). After 1 h, the mixture was concentrated under reduced pressure, and the residue was taken up in DCM (10 mL) and added dropwise to a stirring solution of $NH_3$ in dioxane (10 mL of 0.5 M, 5.000 mmol). The mixture was stirred overnight and concentrated under reduced pressure. The residue was purified by silica gel chromatography with a EtOAc in heptanes gradient to give 4-tert-butyl-2-[2-methoxy-4-(trifluoromethoxy)phenoxy]-6-methyl-benzamide (35 mg, 18%). $^1H$ NMR (400 MHz, Chloroform-d) δ 6.99-6.83 (m, 2H), 6.78-6.64 (m, 2H), 6.53 (dd, J=1.8, 0.6 Hz, 1H), 6.28 (s, 1H), 5.97 (s, 1H), 3.73 (s, 3H), 2.39 (s, 3H), 1.67 (dt, J=13.6, 6.8 Hz, OH), 1.13 (s, 9H) ppm. ESI-MS m/z calc. 397.1501, found 398.1 $(M+1)^+$; Retention time (Method D): 0.97 minutes.

Step 5: 4-[[4-Tert-Butyl-2-[2-Methoxy-4-(Trifluoromethoxy)Phenoxy]-6-Methyl-Benzoyl]Amino] Pyridine-2-Carboxamide (237)

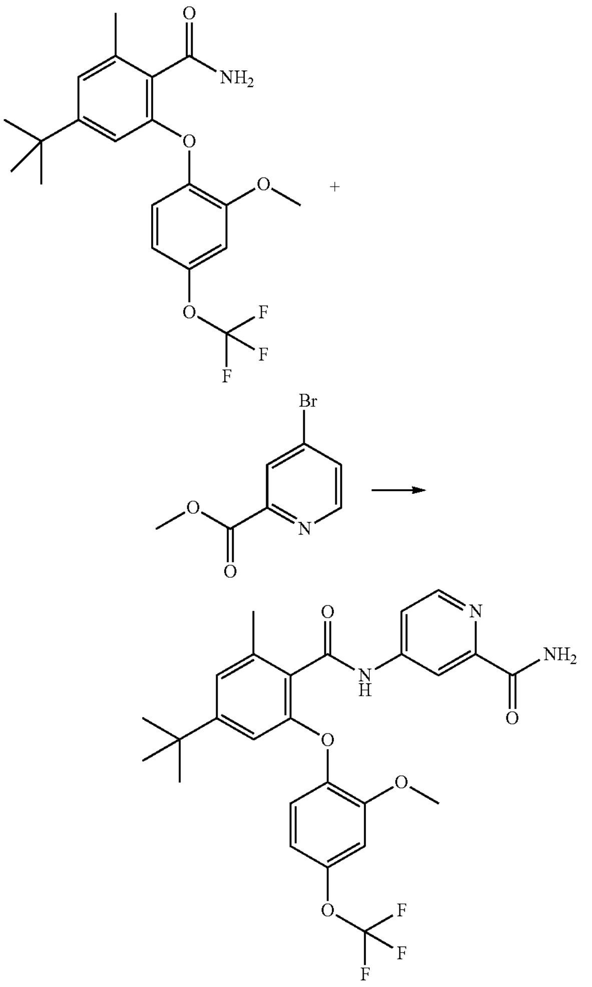

4-tert-Butyl-2-[2-methoxy-4-(trifluoromethoxy)phenoxy]-6-methyl-benzamide (40 mg, 0.101 mmol), methyl 4-bromopyridine-2-carboxylate (26 mg, 0.120 mmol), (5-diphenylphosphanyl-9,9-dimethyl-xanthen-4-yl)-diphenyl-phosphane (12 mg, 0.0207 mmol) and cesium carbonate (75 mg, 0.230 mmol) were suspended in dioxane (2 mL), then degassed with $N_2$ (flush and evacuation cycles). Then palladium(II) acetate (5 mg, 0.0223 mmol) was added and additional degassing was done. The mixture was heated to 100° C. The mixture was concentrated under reduced pressure and the residue dissolved in 5 mL 7M ammonia in MeOH and stirred overnight at 45° C. The material was purified by reverse phase HPLC to give 4-[[4-tert-butyl-2-[2-methoxy-4-(trifluoromethoxy)phenoxy]-6-methyl-benzoyl]amino]pyridine-2-carboxamide (0.5 mg, 1%). 1H NMR (400 MHz, Chloroform-d) δ 8.93 (s, 1H), 8.50 (d, J=5.6 Hz, 1H), 8.38 (s, 1H), 8.03 (s, 1H), 7.87 (s, 1H), 7.13-7.02 (m, 2H), 6.93-6.80 (m, 3H), 6.69 (d, J=1.7 Hz, 1H), 3.90 (d, J=2.7 Hz, 3H), 2.55 (s, 3H), 1.25 (s, 9H) ppm. ESI-MS m/z calc. 517.18243, found 518.1 $(M+1)^+$; Retention time (Method E): 1.02 minutes.

Example 51

5-Tert-Butyl-N-(2-Carbamoyl-4-Pyridyl)-3-[2-Methoxy-4-(Trifluoromethoxy)Phenoxy]Pyridine-2-Carboxamide (238)

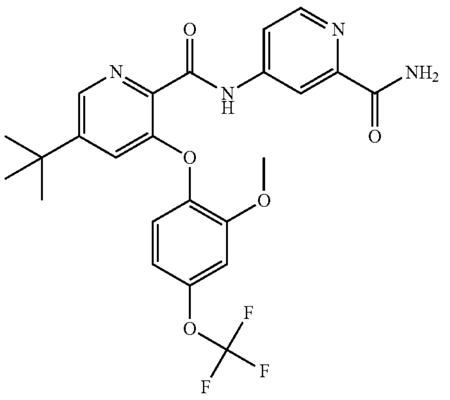 [SMILES: COc1cc(OC(F)(F)F)ccc1Oc1cc(C(C)(C)C)cnc1C(=O)Nc1ccnc(C(N)=O)c1]

Step 1: 5-Tert-Butyl-3-Fluoro-Pyridine-2-Carbonitrile

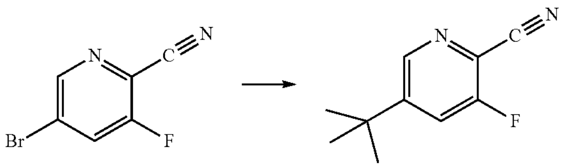

To a solution of 5-bromo-3-fluoro-pyridine-2-carbonitrile (500 mg, 2.488 mmol), 1,3-diisopropylimidazol-1-ium chloride (approximately 188 mg, 0.995 mmol) and dichloronickel 1,2-dimethoxyethane (approximately 219 mg, 0.995 mmol) in THF (10 mL) cooled to −15° C. was added tert-butylchloromagnesium (approximately 3.1 mL of 1 M, 3.1 mmol) in portions over 2-3 minutes. The mixture was allowed to stir at −15° C. for 30 minutes and then allowed to warm to RT. The mixture was cooled to −20° C. and additional tert-butylchloromagnesium (approximately 3.1 mL of 1 M, 3.1 mmol) was added. The reaction mixture was quenched with aqueous $NH_4Cl$ and partitioned between ethyl acetate (30 ml) and water (30 ml). The aqueous layer was extracted with EtOAc (50 mL) and the combined organic layers were washed with brine (1×20 mL), dried over magnesium sulfate and concentrated under reduced pressure. The residue was purified by silica gel chromatography with a EtOAc in petroleum ether gradient to give 5-tert-butyl-3-fluoro-pyridine-2-carbonitrile (90 mg, 19%) as an oil. 1H NMR (500 MHz, Chloroform-d) δ 8.61 (t, J=1.7 Hz, 1H), 7.56 (dd, J=10.1, 1.9 Hz, 1H), 1.41 (s, 9H) ppm. ESI-MS m/z calc. 178.09062, found 179.3 $(M+1)^+$; Retention time (Method E): 2.26 minutes.

Step 2: 5-Tert-Butyl-3-[2-Methoxy-4-(Trifluoromethoxy)Phenoxy]Pyridine-2-Carbonitrile

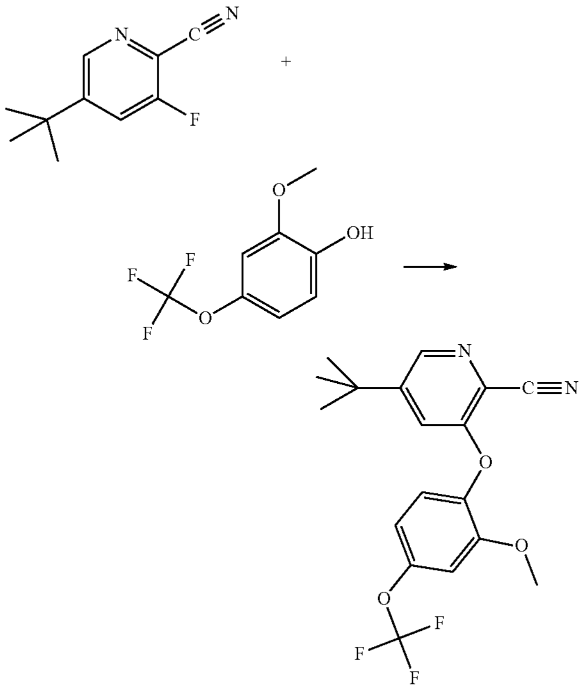

2-Methoxy-4-(trifluoromethoxy)phenol (53.2 mg, 0.256 mmol), 5-tert-butyl-3-fluoro-pyridine-2-carbonitrile (40 mg, 0.213 mmol) and $Cs_2CO_3$ (approximately 104 mg, 0.320 mmol) were combined in DMF (456 μL) and sealed and heated at 70° C. for 1 hour. The reaction mixture was allowed to cool to RT and partitioned between ethyl acetate (30 ml) and water (30 ml). The aqueous layer was extracted with EtOAc (50 mL). The combined organic layers were washed with brine (1×20 mL), dried over magnesium sulfate and concentrated under reduced pressure. The residue was purified by silica gel chromatography eluting with a EtOAc in petroleum ether gradient to give 5-tert-butyl-3-[2-methoxy-4-(trifluoromethoxy)phenoxy]pyridine-2-carbonitrile (61 mg, 66%). ESI-MS m/z calc. 366.11914, found 367.5 $(M+1)^+$; Retention time (Method E): 2.91 minutes.

Step 3: 5-Tert-Butyl-3-[2-Methoxy-4-(Trifluoromethoxy)Phenoxy]Pyridine-2-Carboxamide

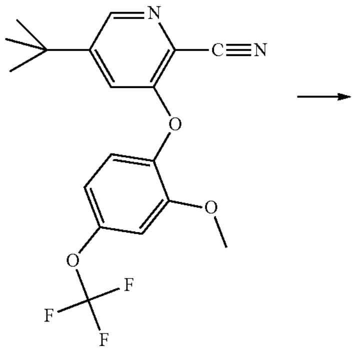

-continued

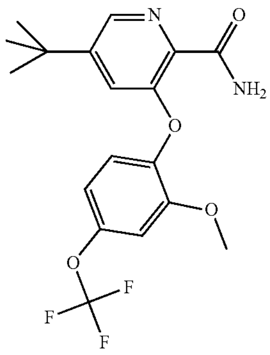

To 5-tert-butyl-3-[2-methoxy-4-(trifluoromethoxy)phenoxy]pyridine-2-carbonitrile (75 mg, 0.205 mmol) was added HCl (341 μL of 12 M, 4.09 mmol) and the mixture stirred overnight at RT. To the mixture was added some ice and then 5N NaOH until the pH was 8-9. The reaction mixture was partitioned between ethyl acetate (5 ml) and water (5 ml). The aqueous layer was extracted with EtOAc (5 mL). The combined organic layers were washed with brine, dried over magnesium sulfate and concentrated under reduced pressure and used as such in the next step. 5-tert-Butyl-3-[2-methoxy-4-(trifluoromethoxy)phenoxy]pyridine-2-carboxamide (81 mg, 79%). ESI-MS m/z calc. 384.1297, found 385.5 $(M+1)^+$; Retention time (Method E): 2.26 minutes.

Step 4: Methyl 4-[[5-Tert-Butyl-3-[2-Methoxy-4-(Trifluoromethoxy)Phenoxy]Pyridine-2-Carbonyl]Amino]Pyridine-2-Carboxylate

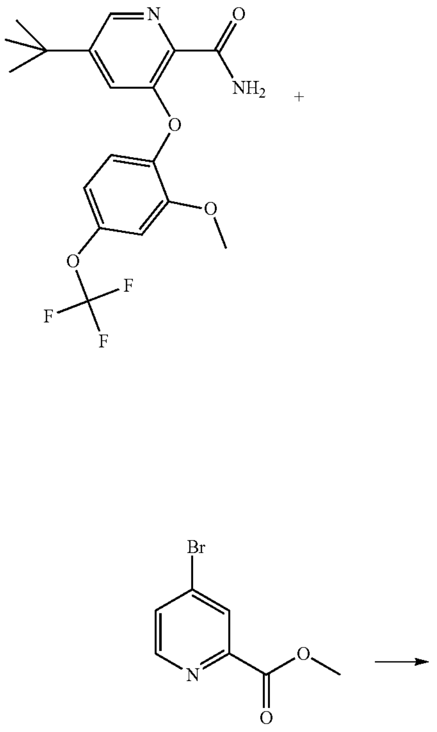

-continued

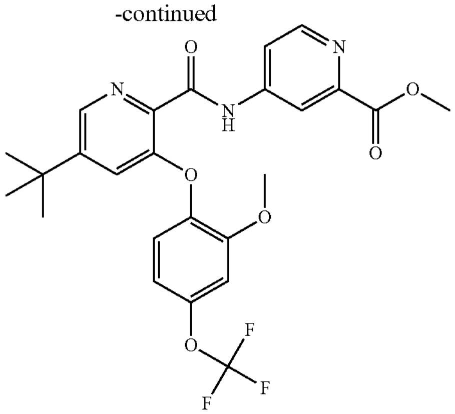

5-tert-Butyl-3-[2-methoxy-4-(trifluoromethoxy)phenoxy]pyridine-2-carboxamide (80 mg, 0.208 mmol), Xantphos (18 mg, 0.0311 mmol), cesium carbonate (149 mg, 0.457 mmol), $Pd(OAc)_2$ (7 mg, 0.0312 mmol) and methyl 4-bromopyridine-2-carboxylate (58 mg, 0.269 mmol) were combined in dioxane (3 mL) and heated at 100° C. for 3 hours. The reaction mixture was allowed to cool to RT and was partitioned between ethyl acetate (30 ml) and water (30 ml). The aqueous layer was extracted with EtOAc (50 mL) and the combined organic layers were washed with brine (1×20 mL), dried over magnesium sulfate and concentrated under reduced pressure. The residue was purified by silica gel chromatography eluting with a EtOAc in petroleum ether gradient to give methyl 4-[[5-tert-butyl-3-[2-methoxy-4-(trifluoromethoxy)phenoxy]pyridine-2-carbonyl]amino]pyridine-2-carboxylate (65 mg, 60%). ESI-MS m/z calc. 519.16174, found 520.5 $(M+1)^+$; Retention time (Method D): 1.01 minutes

Step 5: 5-Tert-Butyl-N-(2-Carbamoyl-4-Pyridyl)-3-[2-Methoxy-4-(Trifluoromethoxy)Phenoxy]Pyridine-2-Carboxamide (238)

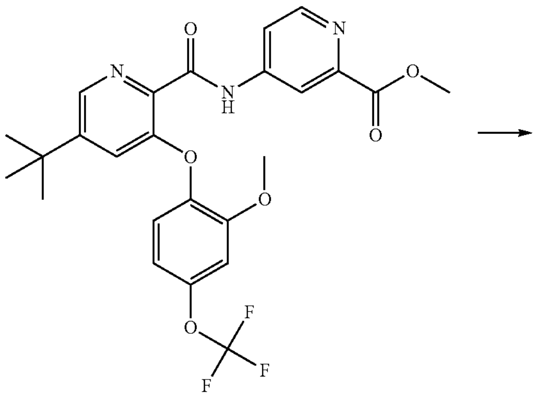

-continued

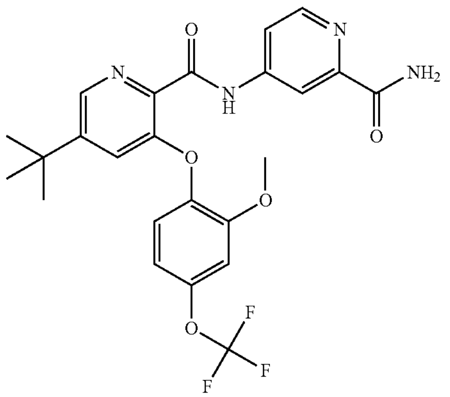

Methyl 4-[[5-tert-butyl-3-[2-methoxy-4-(trifluoromethoxy)phenoxy]pyridine-2-carbonyl]amino]pyridine-2-carboxylate (70 mg, 0.1348 mmol) was added to ammonia (2.6 mL, 18.32 mmol) (7N in methanol) and the mixture was stirred overnight at RT. The mixture was concentrated under reduced pressure to give 5-tert-butyl-N-(2-carbamoyl-4-pyridyl)-3-[2-methoxy-4-(trifluoromethoxy)phenoxy]pyridine-2-carboxamide (35 mg, 41%). 1H NMR (500 MHz, DMSO-d6) δ 8.55 (d, J=1.9 Hz, 1H), 8.51 (d, J=5.4 Hz, 1H), 8.44 (d, J=2.1 Hz, 1H), 8.06 (d, J=2.8 Hz, 1H), 7.90 (dd, J=5.6, 2.1 Hz, 1H), 7.61 (d, J=2.8 Hz, 1H), 7.30 (d, J=1.9 Hz, 1H), 7.24-7.16 (m, 2H), 7.13-7.05 (m, 2H), 6.99-6.87 (m, 1H), 3.79 (s, 3H), 1.29 (s, 7H) ppm. ESI-MS m/z calc. 504.16205, found 505.6 $(M+1)^+$; Retention time (Method E): 3.34 minutes.

Example 52

4-[[6-[2-Chloro-4-(Trifluoromethoxy)Phenoxy]-2,2-Difluoro-4-Methyl-1,3-Benzodioxole-5-Carbonyl]Amino]Pyridine-2-Carboxamide (239)

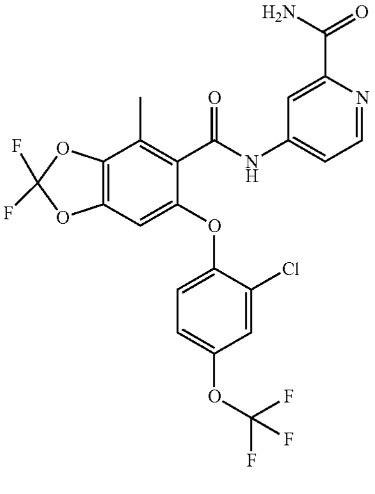 [SMILES: Cc1c2c(cc(Oc3ccc(OC(F)(F)F)cc3Cl)c1C(=O)Nc1ccnc(C(N)=O)c1)OC(F)(F)O2]

Step 1: 6-Bromo-2,2-Difluoro-4-Methyl-1,3-Benzodioxole-5-Carboxylic Acid

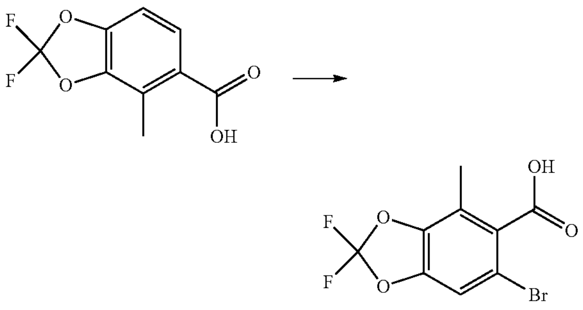

To 2,2-difluoro-4-methyl-1,3-benzodioxole-5-carboxylic acid (2.5 g, 11.57 mmol) was added palladium(II) acetate (610 mg, 2.717 mmol), tetramethylammonium bromide (2.9 g, 18.83 mmol), (acetyloxy)(phenyl)-lambda3-iodanyl acetate (7.9 g, 24.53 mmol), iodine (6.5 g, 25.61 mmol) and DCE (25 mL) and the reaction was stirred at 60° C. for 16 h. Additional palladium(II) acetate (610 mg, 2.717 mmol), tetramethylammonium bromide (2.9 g, 18.83 mmol), (acetyloxy)(phenyl)-lambda3-iodanyl acetate (7.9 g, 24.53 mmol), and iodine (6.5 g, 25.61 mmol) were added to the reaction and it was and heated at 60° C. for 68 h. The reaction was allowed to cool to RT and was acidified with 1 M HCl. A solution of sodium bisulfite (~ 40%) was added to the mixture and it was extracted with DCM (3×). The combined organic layers were dried over $Na_2SO_4$, filtered and the solvent was evaporated under reduced pressure. The crude product was dissolved in DMSO, filtered and purified by reverse phase HPLC ($C_{18}$ column, gradient of $CH_3CN$ and water (5 mM HCl)) to yield 6-bromo-2,2-difluoro-4-methyl-1,3-benzodioxole-5-carboxylic acid (1.3118 g, 38%) as a white solid. ESI-MS m/z calc. 293.93393, found 295.0 $(M+1)^+$; Retention time (Method A): 0.56 minutes.

Step 2: 6-[2-Chloro-4-(Trifluoromethoxy)Phenoxy]-2,2-Difluoro-4-Methyl-1,3-Benzodioxole-5-Carboxylic Acid

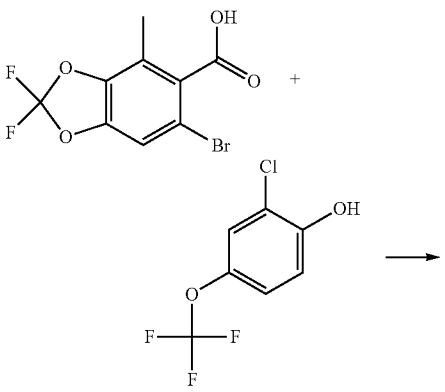

-continued

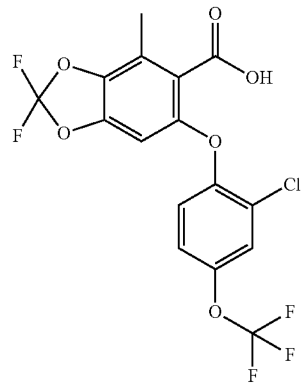

A flask containing 6-bromo-2,2-difluoro-4-methyl-1,3-benzodioxole-5-carboxylic acid (1.3 g, 4.406 mmol), toluene (30 mL) and a stirrer bar was flushed with $N_2$ for 10 min. 2-Chloro-4-(trifluoromethoxy)phenol (1.01 g, 4.752 mmol) and cesium carbonate (3.04 g, 9.33 mmol) were added to the mixture and it was flushed with $N_2$ for 10 min. Copper iodide (186 mg, 0.977 mmol) was added and the mixture was flushed with $N_2$ for 10 min. The reaction was stirred at 80° C. with vigorous stirring under $N_2$ for 14 h. The mixture was allowed to cool to RT, and then diluted with ethyl acetate and water, and acidified with 1 M HCl. The layers were separated and the aqueous layer was extracted with EtOAc (3×). The combined organic layers were filtered and the filtrate was washed with water and brine, dried over sodium sulfate, filtered through a plug of celite and concentrated under reduced pressure. The crude product was dissolved in DMSO, filtered and purified by reverse phase HPLC ($C_{18}$ column, gradient of $CH_3CN$ and water (5 mM HCl)) to yield 6-[2-chloro-4-(trifluoromethoxy)phenoxy]-2,2-difluoro-4-methyl-1,3-benzodioxole-5-carboxylic acid (482.5 mg, 26%) as an off-white solid. ESI-MS m/z calc. 425.99295, found 427.1 $(M+1)^+$; Retention time (Method A): 0.77 minutes.

Step 3: 6-[2-Chloro-4-(Trifluoromethoxy)Phenoxy]-2,2-Difluoro-4-Methyl-1,3-Benzodioxole-5-Carbonyl Chloride

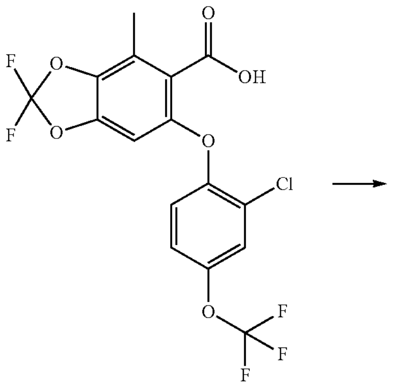

-continued

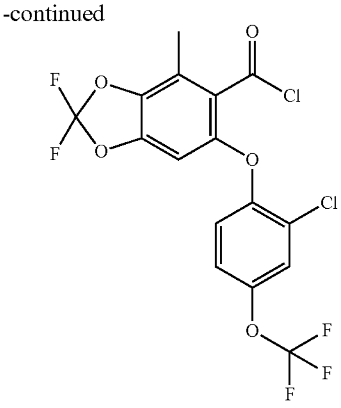

To 6-[2-chloro-4-(trifluoromethoxy)phenoxy]-2,2-difluoro-4-methyl-1,3-benzodioxole-5-carboxylic acid (203 mg, 0.476 mmol) and DMF (15 μL, 0.194 mmol) in DCM (2 mL) at 0° C. was added oxalyl chloride (120 μL, 1.376 mmol) dropwise under a $N_2$ atmosphere. The ice bath was removed after 10 min and the reaction was stirred at RT for 1.5 h. The solvent was evaporated under reduced pressure to afford 6-[2-chloro-4-(trifluoromethoxy)phenoxy]-2,2-difluoro-4-methyl-1,3-benzodioxole-5-carbonyl chloride, which was used directly in the next step.

Step 4: 4-[[6-[2-Chloro-4-(Trifluoromethoxy)Phenoxy]-2,2-Difluoro-4-Methyl-1,3-Benzodioxole-5-Carbonyl]Amino]Pyridine-2-Carboxamide (239)

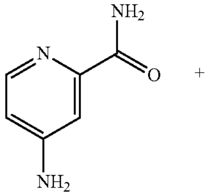

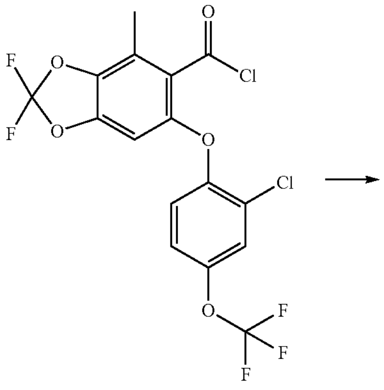

-continued

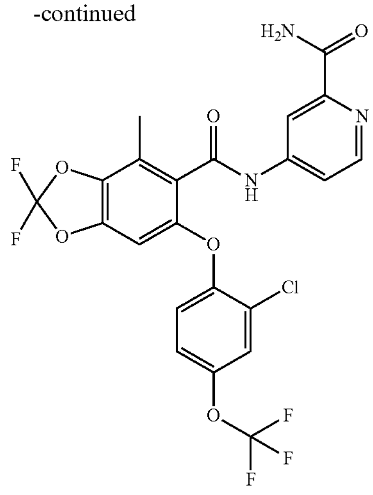

To 4-aminopyridine-2-carboxamide (approximately 41.9 mg, 0.306 mmol) in NMP (500 μL), and DIEA (133 μL, 0.764 mmol) at 0° C. was added a solution of the above acid chloride (68 mg, 0.153 mmol) in NMP (500 μL) slowly. The reaction was stirred at RT for 2.5 h and at 75° C. for 1 h. The crude product was filtered and purified by reverse phase HPLC ($C_{18}$ column, gradient of $CH_3CN$ and water (5 mM HCl)) to yield 4-[[6-[2-chloro-4-(trifluoromethoxy)phenoxy]-2,2-difluoro-4-methyl-1,3-benzodioxole-5-carbonyl]amino]pyridine-2-carboxamide (17.1 mg, 21%). ESI-MS m/z calc. 545.0413, found 546.1 $(M+1)^+$; Retention time (Method C): 2.72 minutes. 1H NMR (400 MHz, DMSO-d6) δ 11.16 (s, 1H), 8.51 (d, J=5.5 Hz, 1H), 8.27 (d, J=2.1 Hz, 1H), 8.09 (d, J=2.8 Hz, 1H), 7.75 (dd, J=5.5, 2.2 Hz, 1H), 7.69-7.60 (m, 2H), 7.40-7.34 (m, 1H), 7.30 (s, 1H), 7.19 (d, J=9.1 Hz, 1H), 2.31 (s, 3H) ppm.

The compounds set forth in Table 30 were prepared by methods analogous to the preparation of compound 239.

TABLE 30

Additional Compounds Prepared By Methods Analogous to Example 52.

| Cmpd No. | Compound Name | LC/MS | NMR (shifts in ppm) |
|---|---|---|---|
| 240 | 5-[[6-[2-chloro-4-(trifluoromethoxy)phenoxy]-2,2-difluoro-4-methyl-1,3-benzodioxole-5-carbonyl]amino]pyridine-2-carboxamide | ESI-MS m/z calc. 545.0413, found 546.1 (M + 1)+; Retention time (Method C): 2.72 minutes | 1H NMR (400 MHz, DMSO-d6) δ 11.04 (s, 1H), 8.77 (dd, J = 2.5, 0.7 Hz, 1H), 8.18 (dd, J = 8.6, 2.4 Hz, 1H), 8.06-7.94 (m, 2H), 7.72-7.60 (m, 1H), 7.59-7.49 (m, 1H), 7.41-7.28 (m, 2H), 7.16 (d, J = 9.1 Hz, 1H), 2.34-2.27 (m, 3H). |

Example 53

4-[[2-[2-Chloro-4-(Trifluoromethoxy)Phenoxy]-6-Methyl-4-(Trifluoromethoxy)Benzoyl]Amino]Pyridine-2-Carboxamide (241)

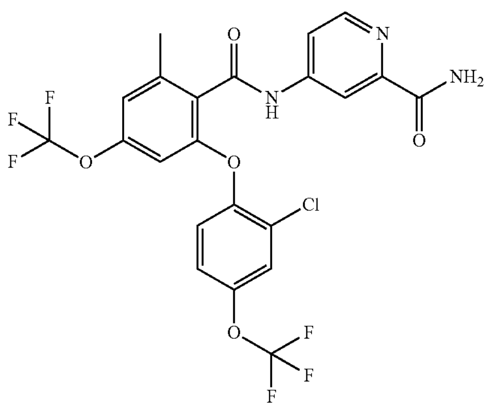 [SMILES: Cc1cc(OC(F)(F)F)cc(Oc2ccc(OC(F)(F)F)cc2Cl)c1C(=O)Nc1ccnc(C(N)=O)c1]

Step 1: 2-Iodo-6-Methyl-4-(Trifluoromethoxy)Benzoic Acid

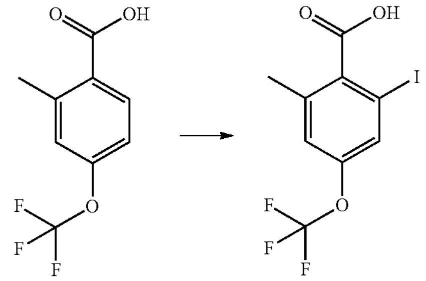 [SMILES: Cc1cc(OC(F)(F)F)ccc1C(=O)O ; Cc1cc(OC(F)(F)F)cc(I)c1C(=O)O]

2-Methyl-4-(trifluoromethoxy)benzoic acid (7.0 g, 31.80 mmol), (diacetoxyiodo)benzene (12.3 g, 38.19 mmol), $I_2$ (9.7 g, 38.22 mmol) and $Pd(OAc)_2$ (380 mg, 1.693 mmol) were combined in DMF (100 mL) under $N_2$. The mixture was de-gassed (×3 vacuum-$N_2$ flush cycles). $N_2$ was replaced with Ar and the mixture was stirred overnight at 105° C. The mixture was cooled to RT and partitioned between EtOAc and saturated sodium thiosulfate solution. The aqueous phase was extracted with EtOAc (2×) and the combined organics were dried ($Na_2SO_4$), filtered and concentrated under reduced pressure. The residue was purified by silica gel chromatography eluting with an EtOAc-heptane gradient to give 2-iodo-6-methyl-4-(trifluoromethoxy)benzoic acid (3.57 g, 30%) as a white solid. 1H NMR (400 MHz, DMSO-d6) δ 13.75 (s, 1H), 7.71 (dt, J=2.5, 0.9 Hz, 1H), 7.37 (ddt, J=3.1, 2.2, 1.1 Hz, 1H), 2.51 (p, J=1.8 Hz, 3H) ppm. ESI-MS m/z calc. 345.93137, found 345.0 $(M-1)^-$; Retention time (Method E): 0.84 minutes.

Step 2: 2-[2-Chloro-4-(Trifluoromethoxy)Phenoxy]-6-Methyl-4-(Trifluoromethoxy)Benzoic Acid

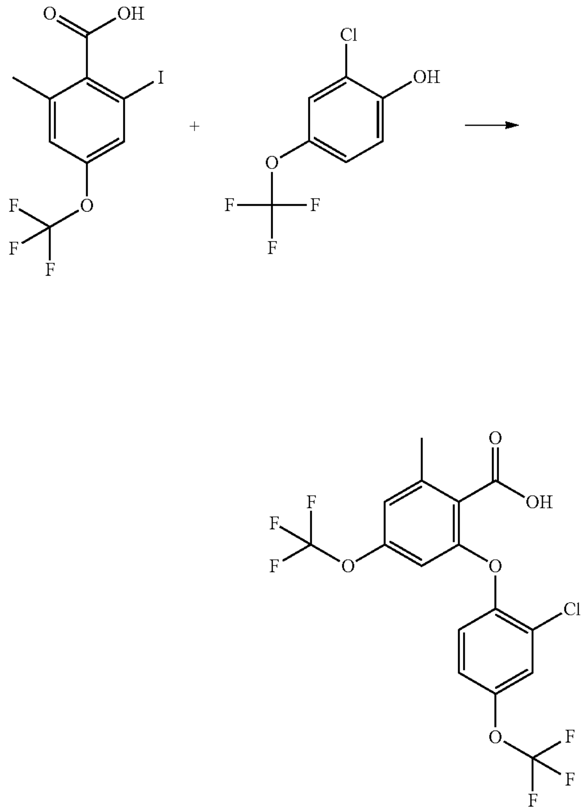 [SMILES: Cc1cc(OC(F)(F)F)cc(I)c1C(=O)O ; Oc1ccc(OC(F)(F)F)cc1Cl ; Cc1cc(OC(F)(F)F)cc(Oc2ccc(OC(F)(F)F)cc2Cl)c1C(=O)O]

2-Iodo-6-methyl-4-(trifluoromethoxy)benzoic acid (1.0 g, 2.688 mmol) and 2-chloro-4-(trifluoromethoxy)phenol (686 mg, 3.227 mmol) were dissolved in toluene (20 mL) and $Cs_2CO_3$ (2.3 g, 7.06 mmol) was added. The mixture was de-gassed (×2 vacuum-$N_2$ flush cycles) and tetrakis(acetonitrile)copper(I) hexafluorophosphate (246 mg, 0.660 mmol) was added. The mixture was de-gassed and heated at reflux overnight. The mixture was cooled to RT and partitioned between EtOAc and 2M HCl. The aqueous phase was extracted with EtOAc and the combined organics were dried ($Na_2SO_4$), filtered and concentrated under reduced pressure. The residue was purified by silica gel chromatography eluting with an EtOAc-heptane gradient to give 2-[2-chloro-4-(trifluoromethoxy)phenoxy]-6-methyl-4-(trifluoromethoxy)benzoic acid (433 mg, 37%). 1H NMR (400 MHz, DMSO-d6) δ 13.55 (s, 1H), 7.77 (dd, J=2.9, 0.8 Hz, 1H), 7.41 (ddq, J=9.0, 3.0, 1.0 Hz, 1H), 7.20 (dt, J=2.3, 1.1 Hz, 1H), 7.13 (d, J=9.0 Hz, 1H), 6.84 (d, J=2.1 Hz, 1H), 2.39 (s, 3H) ppm. ESI-MS m/z calc. 430.00427, found 431.0 $(M+1)^+$; 429.0 $(M-1)^-$; Retention time (Method D): 0.68 minutes.

Step 3: 2-[2-Chloro-4-(Trifluoromethoxy)Phenoxy]-6-Methyl-4-(Trifluoromethoxy)Benzamide

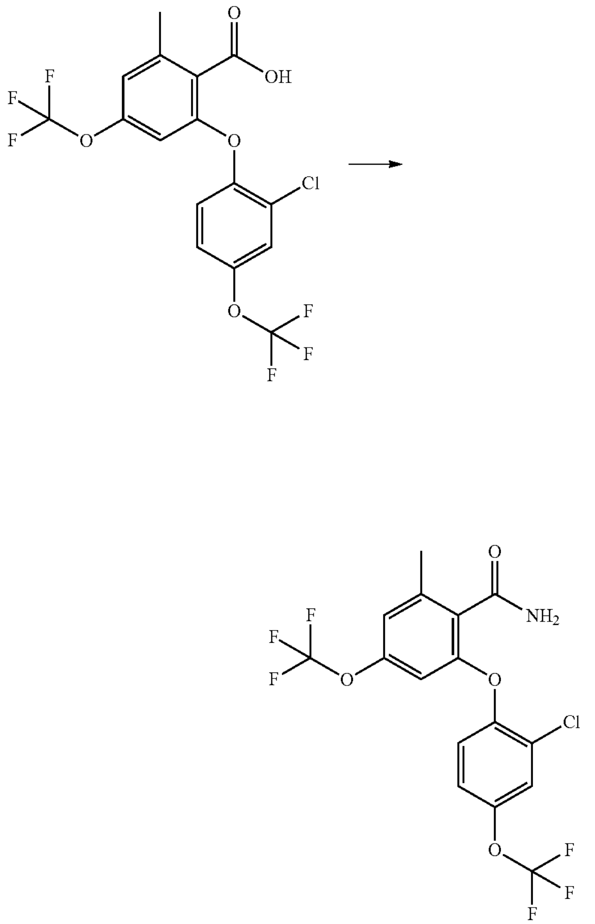

2-[2-Chloro-4-(trifluoromethoxy)phenoxy]-6-methyl-4-(trifluoromethoxy)benzoic acid (200 mg, 0.4644 mmol) was dissolved in DCM (3 mL) under $N_2$ and the solution cooled in an ice bath. Oxalyl chloride (120 μL, 1.376 mmol) was added dropwise with stirring, followed by the addition of DMF (3 μL, 0.0387 mmol). After stirring for 35 minutes, the mixture was concentrated and the residue re-dissolved in DCM (3 mL) under $N_2$. Ammonia in dioxane (10 mL of 0.5 M, 5.000 mmol) was added with cooling in an ice bath, and after 5 minutes the ice bath was removed and the resulting cloudy solution stirred for 30 minutes. The mixture was concentrated under reduced pressure and the residue partitioned was between EtOAc and water. The aqueous phase was extracted with EtOAc and the combined organics were washed with brine, dried ($Na_2SO_4$), filtered and concentrated under reduced pressure to give 2-[2-chloro-4-(trifluoromethoxy)phenoxy]-6-methyl-4-(trifluoromethoxy)benzamide (153 mg, 73%) which was taken directly on to the next reaction without further purification. 1H NMR (400 MHz, DMSO-d6) δ 7.91 (s, 1H), 7.75 (dt, J=2.8, 0.8 Hz, 1H), 7.65 (s, 1H), 7.42 (ddt, J=9.0, 2.9, 1.1 Hz, 1H), 7.24-7.07 (m, 2H), 6.81-6.68 (m, 1H), 2.41-2.34 (m, 3H) ppm. ESI-MS m/z calc. 429.02026, found 430.0 $(M+1)^+$; 428.0 $(M-1)^-$; Retention time (Method D): 0.97 minutes.

Step 4: 4-[[2-[2-Chloro-4-(Trifluoromethoxy)Phenoxy]-6-Methyl-4-(Trifluoromethoxy)Benzoyl]Amino]Pyridine-2-Carboxamide (241)

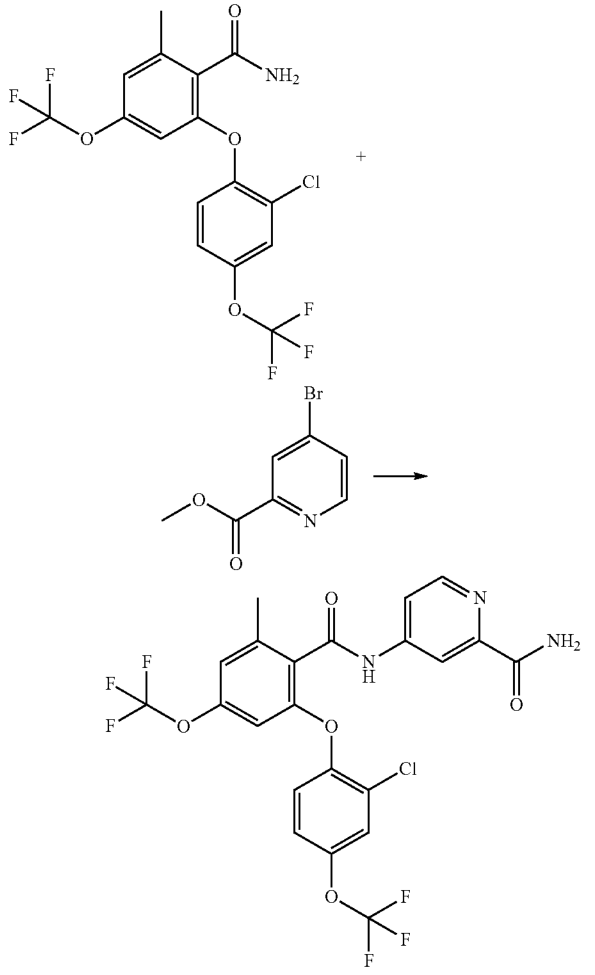

2-[2-Chloro-4-(trifluoromethoxy)phenoxy]-6-methyl-4-(trifluoromethoxy)benzamide (153 mg, 0.338 mmol), methyl 4-bromopyridine-2-carboxylate (90 mg, 0.417 mmol), Xantphos (40 mg, 0.0691 mmol) and $Cs_2CO_3$ (245 mg, 0.752 mmol) were combined in dioxane (4 mL) under $N_2$. The mixture was de-gassed (×2 vacuum-$N_2$ flush cycles) and $Pd(OAc)_2$ (14 mg, 0.0624 mmol) was added. The mixture was de-gassed (×2 cycles) then heated at 100° C. for 3 hours. The mixture was cooled to RT and partitioned between EtOAc and water. The aqueous phase was extracted with EtOAc and the combined organics washed with brine, dried ($Na_2SO_4$), filtered and concentrated under reduced pressure. The residue was stirred with ammonia in MeOH (5 mL of 7 M) under $N_2$ over the weekend. The mixture was concentrated and the residue taken up in DMSO, filtered and purified by HPLC. The resulting white solid was only ~90% pure and was taken up in MeOH and passed through SPE bicarbonate cartridges. The filtrate was concentrated and the residue further purified by silica gel chromatography eluting with an EtOAc-heptane gradient. This material was also ~90% pure. A final purification by HPLC was carried out to give 4-[[2-[2-chloro-4-(trifluoromethoxy)phenoxy]-6-methyl-4-(trifluoromethoxy)benzoyl]amino]pyridine-2-carboxamide (34.13 mg, 18%) as a white solid. 1H NMR (500 MHz, DMSO-d6) δ 11.17 (s, 1H), 8.51 (d, J=5.5 Hz, 1H), 8.31 (d, J=2.1 Hz, 1H), 8.07 (s, 1H), 7.79 (dd, J=5.5, 2.2 Hz, 1H), 7.71 (d, J=2.9 Hz, 1H), 7.63 (s, 1H), 7.49-7.40 (m, 1H), 7.30 (d, J=9.0 Hz, 1H), 7.26 (s, 1H), 6.85 (s, 1H), 2.40 (s, 3H) ppm. ESI-MS m/z calc. 549.0526, found 550.0 $(M+1)^+$; 548.0 $(M-1)^-$; Retention time (Method E): 3.46 minutes.

Example 54

4-[[2-[2-Methoxy-4-(Trifluoromethoxy)Phenoxy]-6-Methyl-4-(Trifluoromethoxy)Benzoyl]Amino]Pyridine-2-Carboxamide (242)

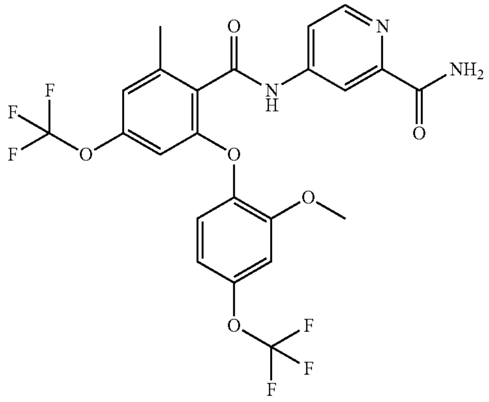 [SMILES: COc1cc(OC(F)(F)F)ccc1Oc1cc(OC(F)(F)F)cc(C)c1C(=O)Nc1ccnc(C(N)=O)c1]

Step 1: 2-[2-Methoxy-4-(Trifluoromethoxy)Phenoxy]-6-Methyl-4-(Trifluoromethoxy)Benzoic Acid

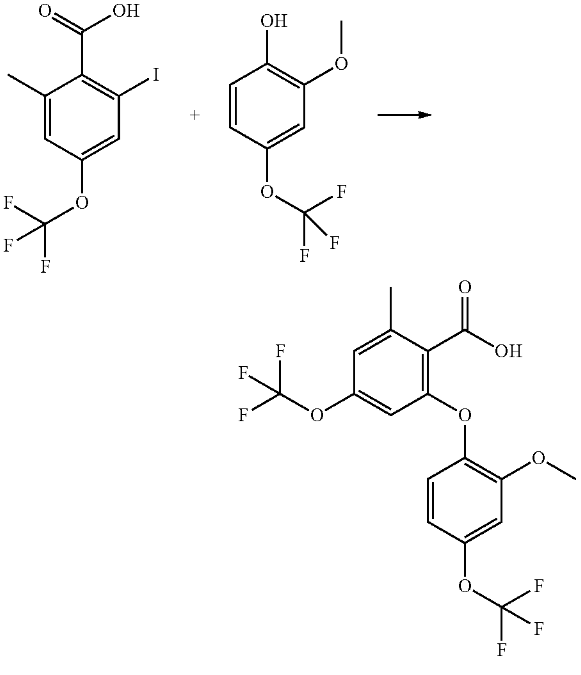

2-Iodo-6-methyl-4-(trifluoromethoxy)benzoic acid (1.0 g, 2.312 mmol) and 2-methoxy-4-(trifluoromethoxy)phenol (600 mg, 2.883 mmol) were dissolved in toluene (20 mL) and $Cs_2CO_3$ (1.9 g, 5.831 mmol) was added. The mixture was de-gassed (×2 vacuum-$N_2$ flush cycles) and tetrakis (acetonitrile)copper(I) hexafluorophosphate (212 mg, 0.5688 mmol) was added. The mixture was de-gassed and heated at reflux overnight. The mixture was cooled to RT and partitioned between EtOAc and 2M HCl. The aqueous phase was extracted with EtOAc and the combined organics were dried ($Na_2SO_4$), filtered and concentrated under reduced pressure. The residue was purified by silica gel chromatography using an EtOAc-heptane gradient to give 2-[2-methoxy-4-(trifluoromethoxy)phenoxy]-6-methyl-4-(trifluoromethoxy)benzoic acid (651 mg, 66%). 1H NMR (400 MHz, DMSO-d6) δ 13.44 (s, 1H), 7.22 (d, J=2.8 Hz, 1H), 7.13 (d, J=8.8 Hz, 1H), 7.05 (dt, J=2.2, 1.0 Hz, 1H), 6.99 (ddq, J=8.8, 2.4, 1.2 Hz, 1H), 6.43 (dt, J=2.2, 0.9 Hz, 1H), 3.80 (s, 3H), 2.36 (s, 3H) ppm. ESI-MS m/z calc. 426.0538, found 427.0 $(M+1)^+$; 425.0 $(M-1)^-$; Retention time (Method D): 0.67 minutes.

Step 2: 2-[2-Methoxy-4-(Trifluoromethoxy)Phenoxy]-6-Methyl-4-(Trifluoromethoxy)Benzamide

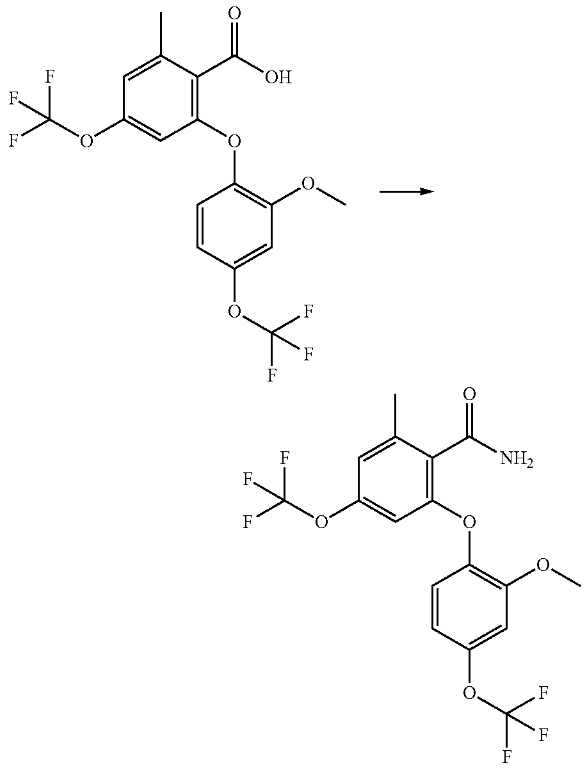

2-[2-Methoxy-4-(trifluoromethoxy)phenoxy]-6-methyl-4-(trifluoromethoxy)benzoic acid (200 mg, 0.4692 mmol) was dissolved in DCM (3 mL) under $N_2$, the solution was cooled in an ice bath, and oxalyl chloride (120 μL, 1.376 mmol) was added dropwise with stirring followed by the addition of DMF (3 μL, 0.03874 mmol). After stirring for 35 minutes the mixture was concentrated and the residue dissolved in DCM (3 mL) under $N_2$. Ammonia in dioxane (10 mL of 0.5 M, 5.000 mmol) was added with cooling in an ice bath. After 5 minutes the ice bath was removed and the resulting cloudy solution stirred for 30 minutes. The mixture was concentrated under reduced pressure and the residue was partitioned between EtOAc and water. The aqueous phase was extracted with EtOAc and the combined organics were washed with brine, dried ($Na_2SO_4$), filtered and concentrated under reduced pressure to give 2-[2-methoxy-4-(trifluoromethoxy)phenoxy]-6-methyl-4-(trifluoromethoxy)benzamide (184 mg, 83%) which was taken directly on to the next step without further purification. 1H NMR (400 MHz, DMSO-d6) δ 7.84 (s, 1H), 7.61 (s, 1H), 7.21 (d, J=2.7 Hz, 1H), 7.16 (d, J=8.8 Hz, 1H), 7.04-6.97 (m, 2H), 6.39-6.35 (m, 1H), 3.81 (s, 3H), 2.34 (d, J=0.7 Hz, 3H) ppm. ESI-MS m/z calc. 425.0698, found 426.0 $(M+1)^+$; 424.0 $(M-1)^-$; Retention time (Method D): 0.94 minutes.

Step 3: 4-[[2-[2-Methoxy-4-(Trifluoromethoxy)Phenoxy]-6-Methyl-4-(Trifluoromethoxy)Benzoyl]Amino]Pyridine-2-Carboxamide (242)

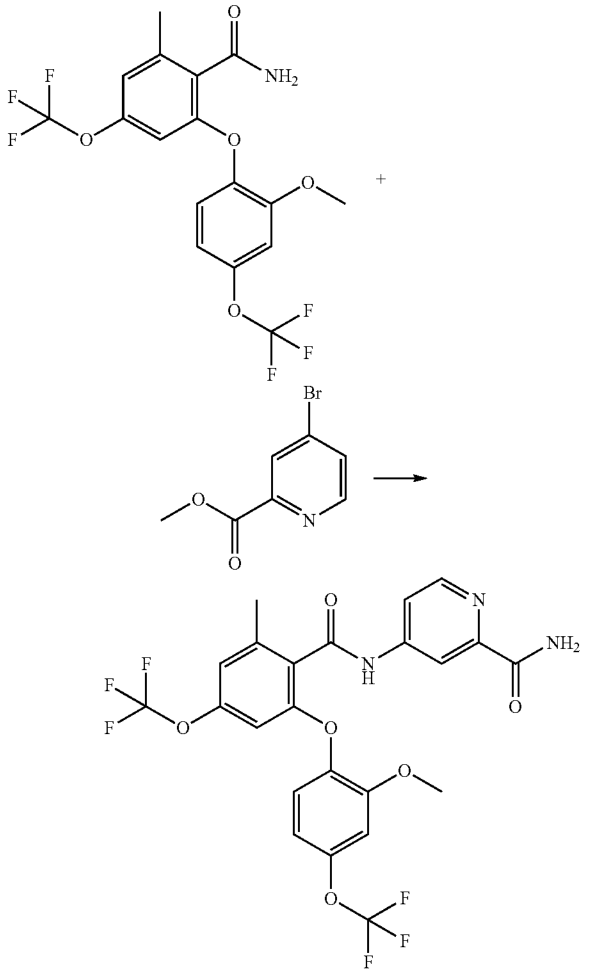

2-[2-Methoxy-4-(trifluoromethoxy)phenoxy]-6-methyl-4-(trifluoromethoxy)benzamide (184 mg, 0.389 mmol), methyl 4-bromopyridine-2-carboxylate (102 mg, 0.472 mmol), Xantphos (45 mg, 0.0777 mmol) and $Cs_2CO_3$ (280 mg, 0.859 mmol) were combined in dioxane (5 mL) under $N_2$. The mixture was de-gassed (×2 vacuum-$N_2$ flush cycles) and $Pd(OAc)_2$ (15 mg, 0.0661 mmol) added. The mixture was de-gassed (×2 cycles) then heated at 100° C. for 90 minutes. The mixture was cooled to RT and partitioned between EtOAc and water. The aqueous phase was extracted with EtOAc and the combined organics were washed with brine, dried ($Na_2SO_4$), filtered and concentrated under reduced pressure. The residue was stirred with ammonia in MeOH (5 mL of 7 M) under $N_2$ over the weekend. The mixture was concentrated and the residue taken up in DMSO, filtered and purified by HPLC. The resulting white solid was only ~90% pure by UV. Further purification by silica gel chromatography using an EtOAc-heptane elution gave 4-[[2-[2-methoxy-4-(trifluoromethoxy)phenoxy]-6-methyl-4-(trifluoromethoxy)benzoyl]amino]pyridine-2-carboxamide (63.50 mg, 29%) as a white solid. 1H NMR (500 MHz, DMSO-d6) δ 11.13 (s, 1H), 8.52 (d, J=5.6 Hz, 1H), 8.35 (d, J=2.1 Hz, 1H), 8.07 (d, J=2.8 Hz, 1H), 7.84 (dd, J=5.6, 2.2 Hz, 1H), 7.63 (d, J=2.8 Hz, 1H), 7.26 (d, J=8.8 Hz, 1H), 7.19 (d, J=2.7 Hz, 1H), 7.12 (s, 1H), 7.04-6.97 (m, 1H), 6.48 (s, 1H), 3.77 (s, 3H), 2.38 (s, 3H) ppm. ESI-MS m/z calc. 545.1022, found 546.0 $(M+1)^+$; 544.0 $(M-1)^-$; Retention time (Method E): 3.38 minutes.

Example 55

5-[[2-[2-Chloro-4-(Trifluoromethoxy)Phenoxy]-6-Methyl-4-(Trifluoromethoxy)Benzoyl]Amino]Pyridine-2-Carboxamide (243)

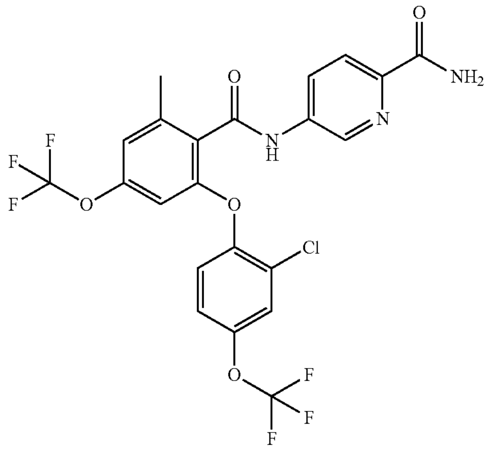 [SMILES: Cc1cc(OC(F)(F)F)cc(Oc2ccc(OC(F)(F)F)cc2Cl)c1C(=O)Nc1ccc(C(N)=O)nc1]

Step 1: Methyl 5-Bromopyridine-2-Carboxylate

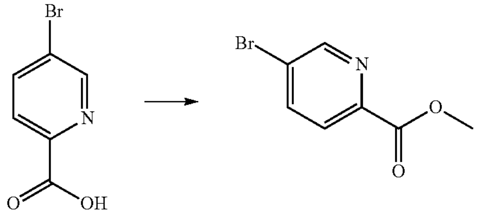

A solution of 5-bromopyridine-2-carboxylic acid (10 g, 49.5 mmol) in methanol (165 mL) was treated with sulfuric acid (4.9 g, 2.6 mL, 49.5 mmol) and refluxed overnight. The solution was concentrated and the resulting product partitioned between saturated aqueous sodium bicarbonate and ethyl acetate. The organic layer was separated and the aqueous layer extracted with additional ethyl acetate (2×). The combined organic layers were dried and concentrated to provide methyl 5-bromopyridine-2-carboxylate (10 g).

Step 2: 5-[[2-[2-Chloro-4-(Trifluoromethoxy)Phenoxy]-6-Methyl-4-(Trifluoromethoxy)Benzoyl]Amino]Pyridine-2-Carboxamide (243)

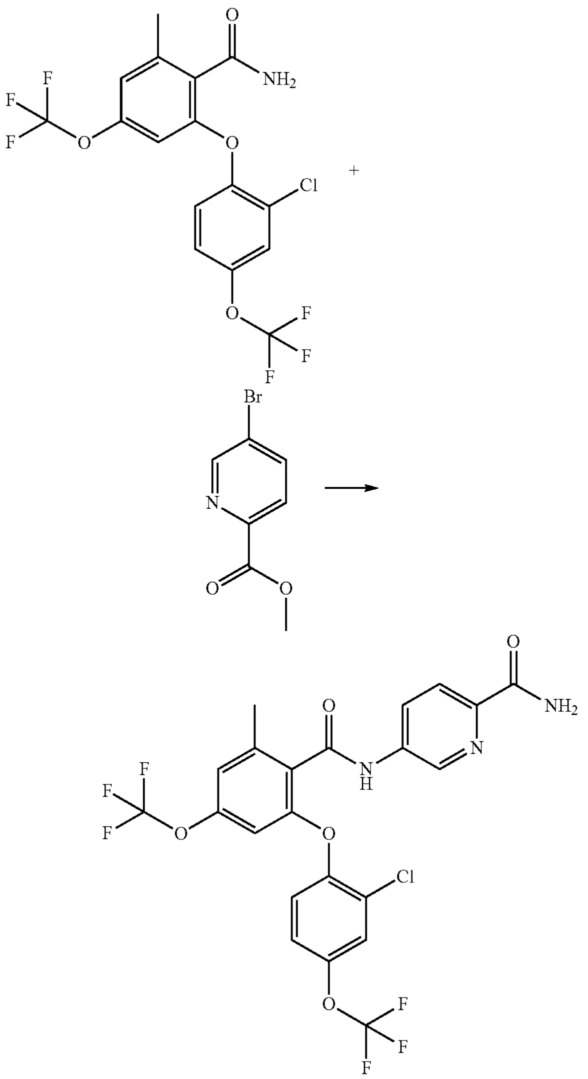

2-[2-Chloro-4-(trifluoromethoxy)phenoxy]-6-methyl-4-(trifluoromethoxy)benzamide (179 mg, 0.354 mmol), methyl 5-bromopyridine-2-carboxylate (92 mg, 0.43 mmol), Xantphos (41 mg, 0.07 mmol) and $Cs_2CO_3$ (255 mg, 0.783 mmol) were combined in dioxane (4 mL) under nitrogen. The mixture was degassed (2×vacuum-nitrogen cycles) and $Pd(OAc)_2$ (13 mg, 0.058 mmol) added. The mixture was again degassed (2×vacuum-nitrogen cycles) then heated at 100° C. for 2 hours. The reaction mixture was cooled to RT and partitioned between ethyl acetate and water. The aqueous phase was extracted with additional ethyl acetate and the combined organics washed with brine, dried over $Na_2SO_4$, filtered and concentrated under reduced pressure. The residue was stirred with ammonia in methanol (5 mL, 7 M) under nitrogen overnight. The reaction mixture was concentrated and purified sequentially by silica gel chromatography (ethyl acetate-heptane gradient) and HPLC (acetonitrile/water gradient with ammonia modifier) to provide 5-[[2-[2-chloro-4-(trifluoromethoxy)phenoxy]-6-methyl-4-(trifluoromethoxy)benzoyl]amino]pyridine-2-carboxamide (23 mg, 12%). ESI-MS m/z calc. 549.05, found 550.0 $(M+1)^+$; 548.0 $(M-1)^-$; Retention time (Method E): 3.41 minutes. $^1$H NMR (500 MHz, DMSO-d6) δ 11.07 (s, 1H), 8.82 (d, J=2.5 Hz, 1H), 8.23 (dd, J=8.7, 2.4 Hz, 1H), 8.02 (d, J=8.6 Hz, 1H), 7.99 (s, 1H), 7.71 (d, J=2.8 Hz, 1H), 7.53 (s, 1H), 7.44 (d, J=9.4 Hz, 1H), 7.28 (d, J=9.0 Hz, 2H), 6.89 (s, 1H), 2.41 (s, 3H) ppm.

Example 56

4-[[3-(Difluoromethyl)-6-[2-Methoxy-4-(Trifluoromethoxy)Phenoxy]-2-Methyl-Benzoyl]Amino]Pyridine-2-Carboxamide (244)

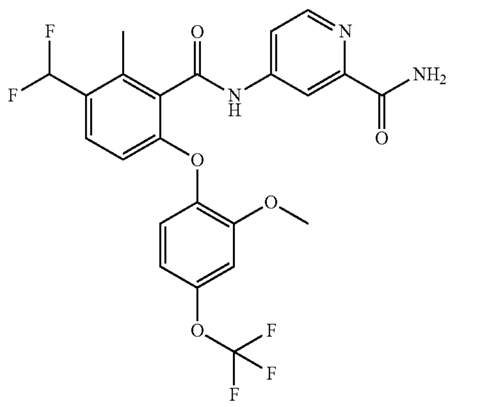 [SMILES: COc1cc(OC(F)(F)F)ccc1Oc1ccc(C(F)F)c(C)c1C(=O)Nc1ccnc(C(N)=O)c1]

Step 1: 3-Bromo-6-[2-Methoxy-4-(Trifluoromethoxy)Phenoxy]-2-Methyl-Benzoic Acid

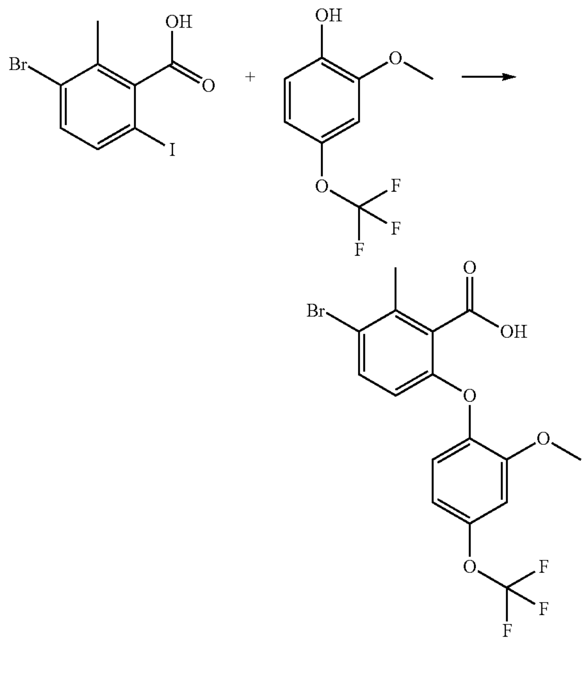

To a pressure flask was added 3-bromo-6-iodo-2-methyl-benzoic acid (1000 mg, 2.933 mmol), 2-methoxy-4-(trifluoromethoxy)phenol (611 mg, 2.94 mmol), $Cs_2CO_3$ (1.44 g, 4.42 mmol), toluene (18 mL) and a stir bar. The reaction mixture was bubbled with nitrogen for 10 minutes, then copper (I) iodide (563 mg, 2.96 mmol) added. The flask was flushed with nitrogen, capped, and heated at 100° C. with vigorous stirring for 16 hours. The mixture was allowed to cool, and then diluted with ethyl acetate and water. The water layer was acidified with 1 M HCl and the product extracted into ethyl acetate (3×). The combined organics were dried over $Na_2SO_4$, filtered and concentrated under reduced pressure. Medium pressure reverse phase chromatography ($C_{18}$, $CH_3CN$/water (5 mM HCl) gradient) provided 3-bromo-6-[2-methoxy-4-(trifluoromethoxy)phenoxy]-2-methyl-benzoic acid (455 mg, 37%). $^1$H NMR (400 MHz, Chloroform-d) δ 7.47 (d, J=8.8 Hz, 1H), 7.15-7.06 (m, 1H), 6.85 (ddd, J=6.9, 2.4, 1.1 Hz, 2H), 6.46 (dd, J=8.9, 0.7 Hz, 1H), 3.81 (s, 3H), 2.52 (s, 3H) ppm.

Step 2: Methyl 3-Bromo-6-[2-Methoxy-4-(Trifluoromethoxy)Phenoxy]-2-Methyl-Benzoate

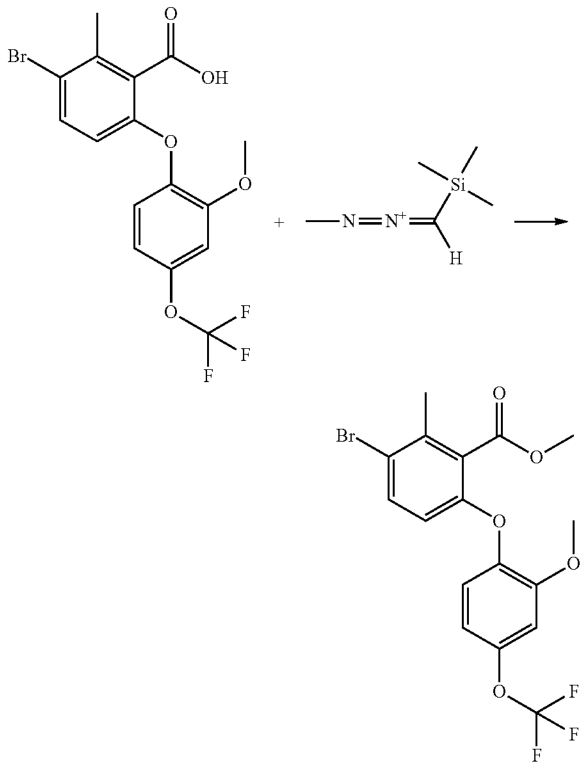

3-Bromo-6-[2-methoxy-4-(trifluoromethoxy)phenoxy]-2-methyl-benzoic acid (450 mg, 1.07 mmol) was dissolved in a mixture of dichloromethane (7 mL) and methanol (1.1 mL, 27.16 mmol) and cooled in an ice bath under nitrogen. Diazomethyl(trimethyl)silane in hexanes (1.4 mL of 2 M, 2.8 mmol) was added dropwise and the reaction was stirred on ice for 15 minutes. A solution of acetic acid in methanol (1:5) was added dropwise to quench excess reagent (removal of yellow color and bubbling). The reaction was concentrated and the crude material was purified by silica gel chromatography (ethyl acetate/hexanes gradient) to provide methyl 3-bromo-6-[2-methoxy-4-(trifluoromethoxy)phenoxy]-2-methyl-benzoate (423 mg, 91%) as a clear oil. ESI-MS m/z calc. 434.00, found 435.1 $(M+1)^+$; Retention time (Method A): 0.82 minutes. $^1H$ NMR (400 MHz, Chloroform-d) δ 7.43 (d, J=8.8 Hz, 1H), 6.99 (d, J=8.7 Hz, 1H), 6.83 (d, J=2.7 Hz, 1H), 6.81-6.76 (m, 1H), 6.44 (d, J=8.8, 0.7 Hz, 1H), 3.90 (s, 3H), 3.81 (s, 3H), 2.38 (s, 3H) ppm.

Step 3: Methyl 3-Formyl-6-[2-Methoxy-4-(Trifluoromethoxy)Phenoxy]-2-Methyl-Benzoate

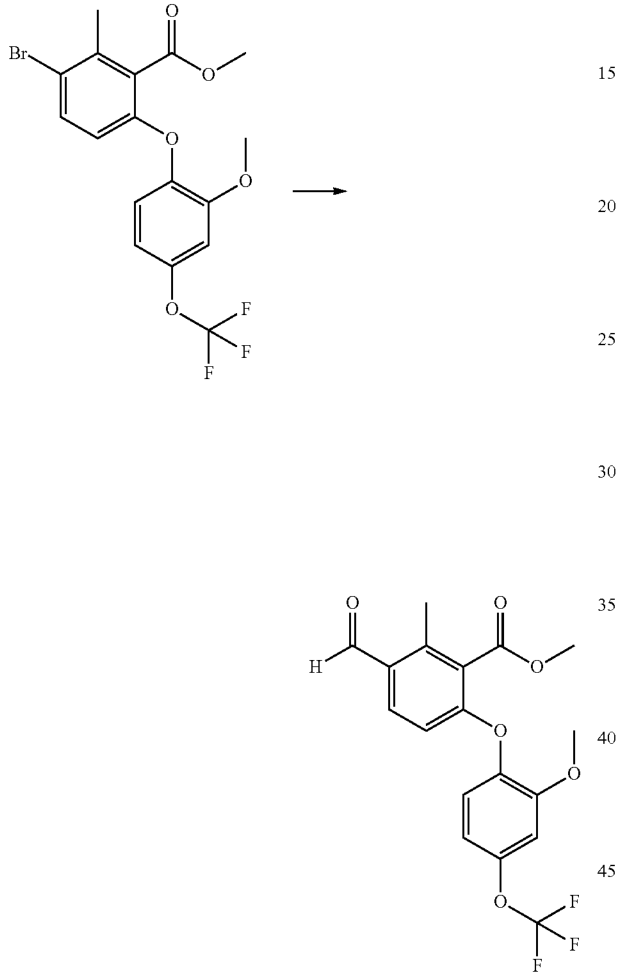

Methyl 3-bromo-6-[2-methoxy-4-(trifluoromethoxy)phenoxy]-2-methyl-benzoate (260 mg, 0.597 mmol) was dissolved in THF (1 mL) and cooled in an ice bath under nitrogen. Isopropylmagnesium chloride in THF (150 μL of 2 M, 0.3 mmol) was added and the reaction mixture was stirred for 5 minutes. n-Butyllithium (240 μL of 2.5 M, 0.6000 mmol) was then added and the reaction was stirred an additional 10 minutes. DMF (100 μL, 1.29 mmol) was added dropwise and the reaction was stirred for 30 minutes. The mixture was quenched with a saturated citric acid solution and extracted with ethyl acetate. The organics were washed with brine, dried over $Na_2SO_4$, filtered and concentrated. Silica gel chromatography (ethyl acetate/hexanes gradient) provided methyl 3-formyl-6-[2-methoxy-4-(trifluoromethoxy)phenoxy]-2-methyl-benzoate (103 mg, 45%) as a clear oil. ESI-MS m/z calc. 384.08, found 385.0 $(M+1)^+$; Retention time (Method A): 0.7 minutes. $^1H$ NMR (400 MHz, Chloroform-d) δ 10.18 (s, 1H), 7.73 (d, J=8.7 Hz, 1H), 7.13-7.08 (m, 1H), 6.88-6.82 (m, 2H), 6.56 (d, J=8.7 Hz, 1H), 3.96 (s, 3H), 3.79 (s, 3H), 2.65 (s, 3H) ppm.

Step 4: Methyl 3-(Difluoromethyl)-6-[2-Methoxy-4-(Trifluoromethoxy)Phenoxy]-2-Methyl-Benzoate

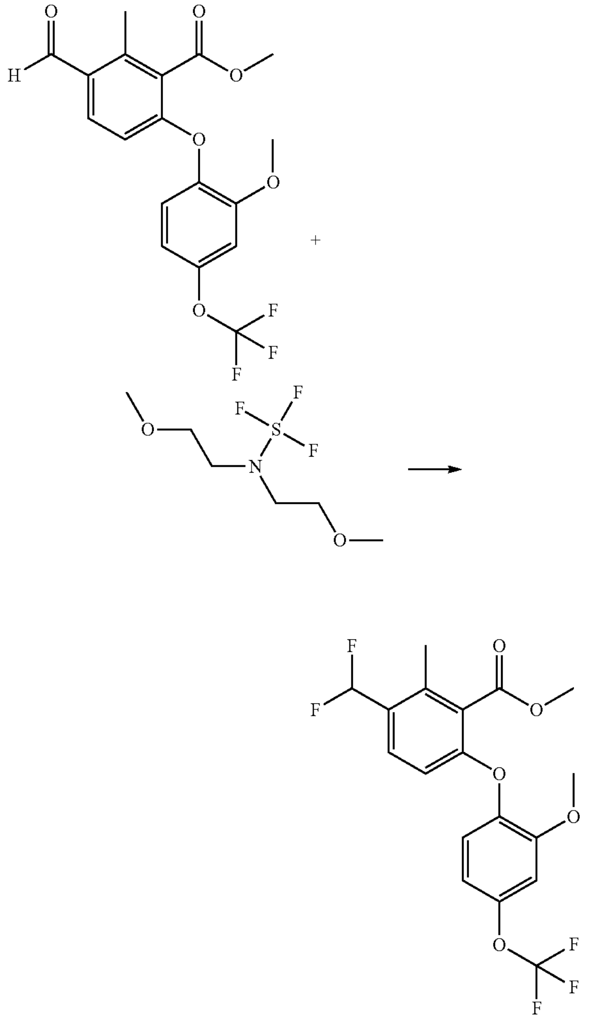

Methyl 3-formyl-6-[2-methoxy-4-(trifluoromethoxy)phenoxy]-2-methyl-benzoate (100 mg, 0.260 mmol) was dissolved in dichloromethane (1 mL) and bis(2-methoxyethyl) aminosulfur trifluoride (240 μL, 1.30 mmol) was added dropwise and the solution was allowed to stir at RT for 3 hours. The reaction was cooled in an ice bath and a saturated solution of sodium bicarbonate was added dropwise until bubbling had ceased. The reaction mixture was extracted with dichloromethane. The organic phase was washed with brine, dried over $Na_2SO_4$ and evaporated. Silica gel chromatography (ethyl acetate/hexanes gradient) provided methyl 3-(difluoromethyl)-6-[2-methoxy-4-(trifluoromethoxy)phenoxy]-2-methyl-benzoate (83 mg, 79%) as a clear oil. $^1H$ NMR (400 MHz, Chloroform-d) δ 7.41 (d, J=8.6 Hz, 1H), 7.05 (d, J=8.6 Hz, 1H), 6.85-6.79 (m, 2H), 6.72 (t, J=55.4 Hz, 1H), 6.55 (d, J=8.7 Hz, 1H), 3.93 (s, 3H), 3.80 (s, 3H), 2.39 (d, J=1.3 Hz, 3H) ppm.

Step 5: 3-(Difluoromethyl)-6-[2-Methoxy-4-(Trifluoromethoxy)Phenoxy]-2-Methyl-Benzoic Acid

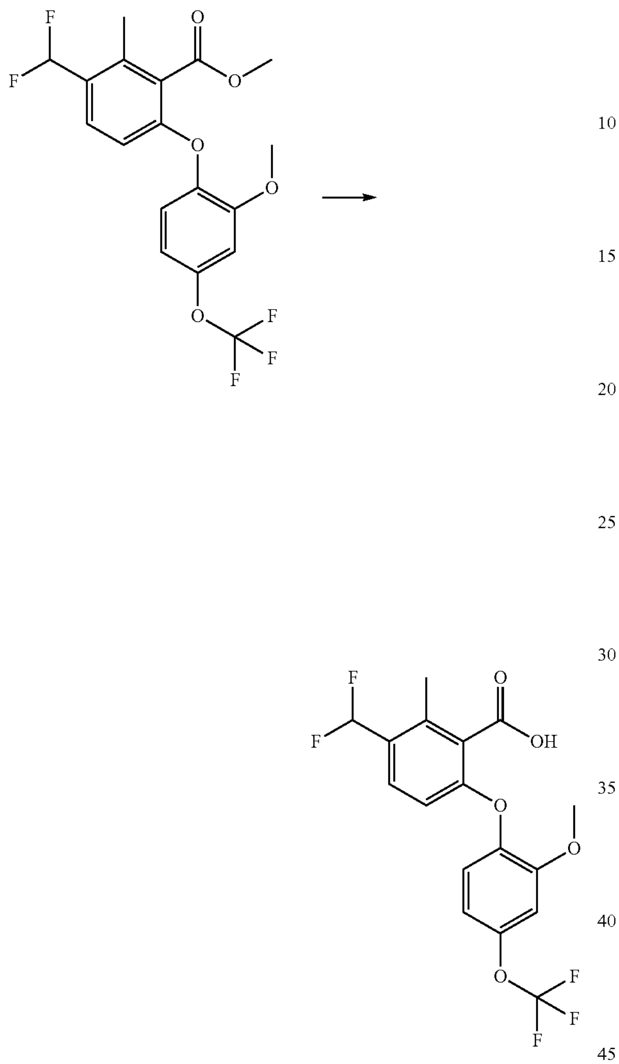

Methyl 3-(difluoromethyl)-6-[2-methoxy-4-(trifluoromethoxy)phenoxy]-2-methyl-benzoate (80 mg, 0.20 mmol) and NaOH (500 mg, 12.5 mmol) were combined in a mixture of DMF (5 mL)/water (5 mL) and heated in a sealed vial at 120° C. for 16 hours. The reaction was acidified with conc. HCl to a pH of ~1 and extracted with ethyl acetate (3×10 mL). The combined organics were washed with brine, dried over $Na_2SO_4$, filtered and concentrated. HPLC purification ($CH_3CN$/water (5 mM HCl) gradient) provided 3-(difluoromethyl)-6-[2-methoxy-4-(trifluoromethoxy)phenoxy]-2-methyl-benzoic acid (39.6 mg, 51%). ESI-MS m/z calc. 392.07, found 393.3 $(M+1)^+$; Retention time (Method A): 0.69 minutes.

Step 6: 4-[[3-(Difluoromethyl)-6-[2-Methoxy-4-(Trifluoromethoxy)Phenoxy]-2-Methyl-Benzoyl]Amino]Pyridine-2-Carboxamide (244)

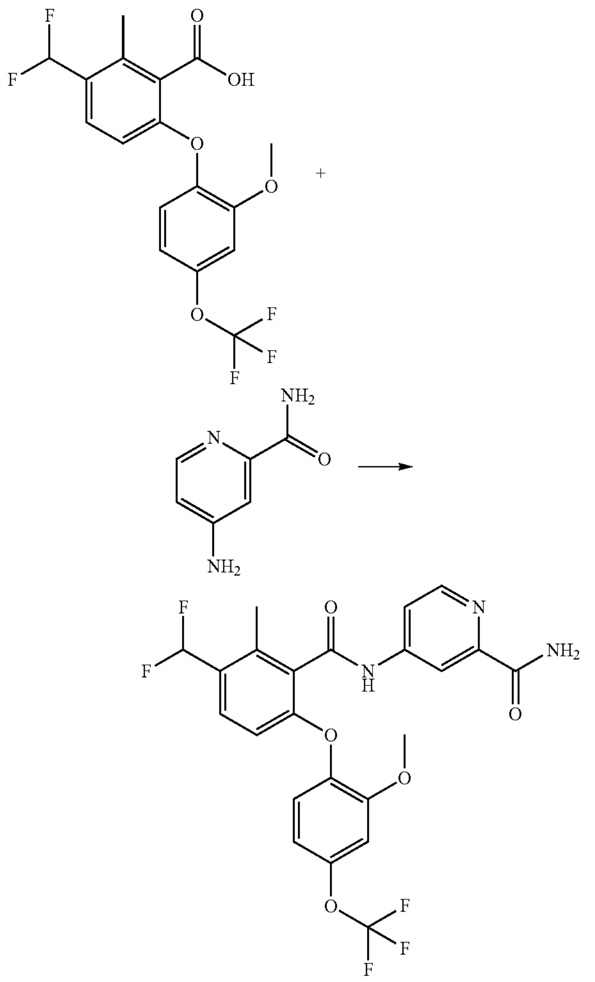

3-(Difluoromethyl)-6-[2-methoxy-4-(trifluoromethoxy)phenoxy]-2-methyl-benzoic acid (36.6 mg, 0.093 mmol) and oxalyl chloride (50 µL, 0.57 mmol) were combined in dichloromethane (800 µL) and a drop of DMF was added. The reaction was stirred at 50° C. for 30 minutes then evaporated to dryness to provide the corresponding acid chloride. The acid chloride was dissolved in dichloromethane (0.5 mL) and added to a solution of 4-aminopyridine-2-carboxamide (14 mg, 0.10 mmol) and DIEA (50 µL, 0.29 mmol) in NMP (0.5 mL). The reaction mixture was stirred at RT for 24 hours. The mixture was filtered and purified by HPLC ($CH_3CN$/water (5 mM HCl) gradient) to provide 4-[[3-(difluoromethyl)-6-[2-methoxy-4-(trifluoromethoxy)phenoxy]-2-methyl-benzoyl]amino]pyridine-2-carboxamide (6.4 mg, 13%). ESI-MS m/z calc. 511.12, found 512.0 $(M+1)^+$; Retention time (Method B): 1.64 minutes. $^1H$ NMR (400 MHz, DMSO-d6) δ 11.23 (s, 1H), 8.53 (d, J=5.5 Hz, 1H), 8.39 (d, J=2.1 Hz, 1H), 8.12 (s, 1H), 7.87 (dd, J=5.5, 2.2 Hz, 1H), 7.67 (s, 1H), 7.55 (d, J=8.8 Hz, 1H), 7.26 (d, J=8.8 Hz, 1H), 7.20 (t, J=55 Hz, 1H), 7.20 (s, 1H), 7.03-6.98 (m, 1H), 6.61 (d, J=8.6 Hz, 1H), 3.77 (s, 3H), 2.39 (s, 3H) ppm.

Example 57

5-[[2-[2-Methoxy-4-(Trifluoromethoxy)Phenoxy]-6-Methyl-4-(Trifluoromethoxy)Benzoyl]Amino]Pyridine-2-Carboxamide (245)

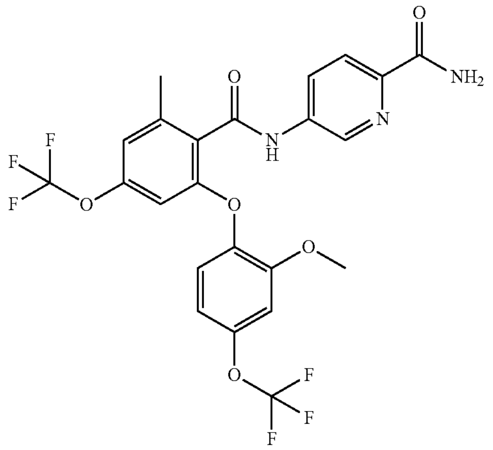 [SMILES: COc1cc(OC(F)(F)F)ccc1Oc1cc(OC(F)(F)F)cc(C)c1C(=O)Nc1ccc(C(N)=O)nc1]

Step 1: 2-[2-Methoxy-4-(Trifluoromethoxy)Phenoxy]-6-Methyl-4-(Trifluoromethoxy)Benzoic Acid

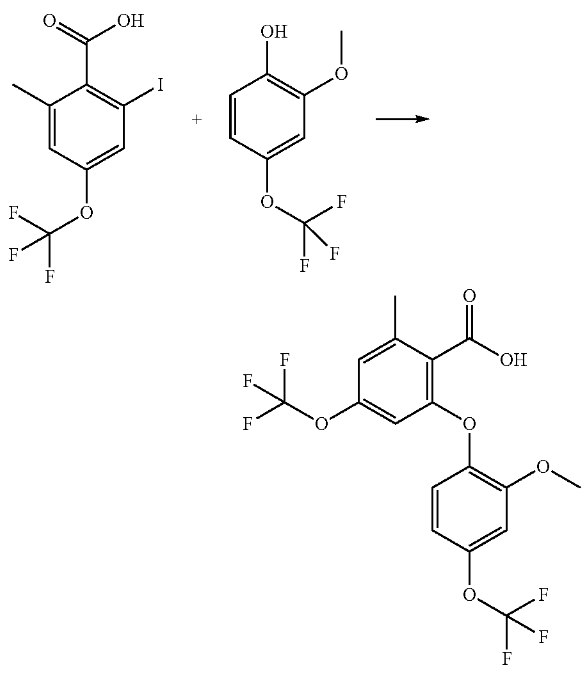

2-Iodo-6-methyl-4-(trifluoromethoxy)benzoic acid (1.0 g, 2.3 mmol) and 2-methoxy-4-(trifluoromethoxy)phenol (600 mg, 2.88 mmol) were dissolved in toluene (20 mL) and $Cs_2CO_3$ (1.9 g, 5.8 mmol) added. The mixture was degassed (2×vacuum-nitrogen cycles) and tetrakis(acetonitrile) copper(I) hexafluorophosphate (212 mg, 0.569 mmol) added. The mixture was again degassed and heated at reflux overnight. The reaction mixture was cooled to RT and partitioned between ethyl acetate and 2 M HCl. The aqueous phase was extracted with additional ethyl acetate and the combined organics dried over $Na_2SO_4$, filtered and concentrated under reduced pressure. Silica gel chromatography (ethyl acetate/heptane gradient) provided 2-[2-methoxy-4-(trifluoromethoxy)phenoxy]-6-methyl-4-(trifluoromethoxy)benzoic acid (651 mg, 66%). $^1$H NMR (400 MHz, DMSO-d6) δ 13.44 (s, 1H), 7.22 (d, J=2.8 Hz, 1H), 7.13 (d, J=8.8 Hz, 1H), 7.05 (dt, J=2.2, 1.0 Hz, 1H), 6.99 (ddq, J=8.8, 2.4, 1.2 Hz, 1H), 6.43 (dt, J=2.2, 0.9 Hz, 1H), 3.80 (s, 3H), 2.36 (s, 3H) ppm.

Step 2: 2-[2-Methoxy-4-(Trifluoromethoxy)Phenoxy]-6-Methyl-4-(Trifluoromethoxy)Benzamide

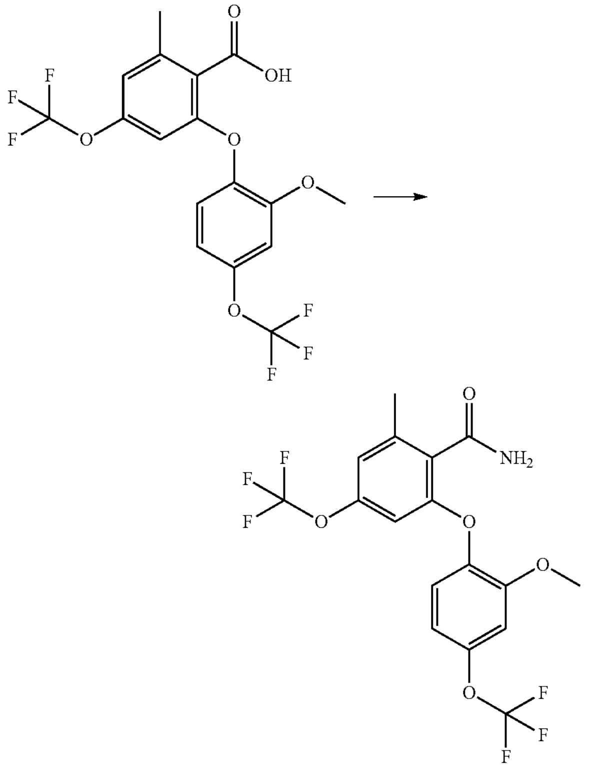

2-[2-Methoxy-4-(trifluoromethoxy)phenoxy]-6-methyl-4-(trifluoromethoxy)benzoic acid (200 mg, 0.469 mmol) was dissolved in dichloromethane (3 mL) and the solution cooled in an ice bath under nitrogen atmosphere. Oxalyl chloride (120 μL, 1.38 mmol) was added dropwise with stirring, followed by the addition of DMF (3 μL, 0.04 mmol). After stirring for 35 minutes, the reaction mixture was concentrated. The residue was redissolved in dichloromethane (3 mL), cooled to 0° C. under nitrogen, and treated with ammonia in dioxane (10 mL of 0.5 M, 5 mmol). After 5 minutes the ice bath was removed and the resulting cloudy solution stirred for 30 minutes. The reaction mixture was concentrated under reduced pressure and the residue partitioned between ethyl acetate and water. The aqueous phase was extracted with ethyl acetate and the combined organics washed with brine, dried over $Na_2SO_4$, filtered and concentrated under reduced pressure to provide 2-[2-methoxy-4-(trifluoromethoxy)phenoxy]-6-methyl-4-(trifluoromethoxy)benzamide (184 mg, 83%). ESI-MS m/z calc.

425.07, found 426.0 $(M+1)^+$; 424.0 $(M-1)^-$; Retention time (Method D): 0.94 minutes. $^1$H NMR (400 MHz, DMSO-d6) δ 7.84 (s, 1H), 7.61 (s, 1H), 7.21 (d, J=2.7 Hz, 1H), 7.16 (d, J=8.8 Hz, 1H), 7.04-6.97 (m, 2H), 6.39-6.35 (m, 1H), 3.81 (s, 3H), 2.34 (d, J=0.7 Hz, 3H) ppm.

Step 3: 5-[[2-[2-Methoxy-4-(Trifluoromethoxy)Phenoxy]-6-Methyl-4-(Trifluoromethoxy)Benzoyl]Amino]Pyridine-2-Carboxamide (245)

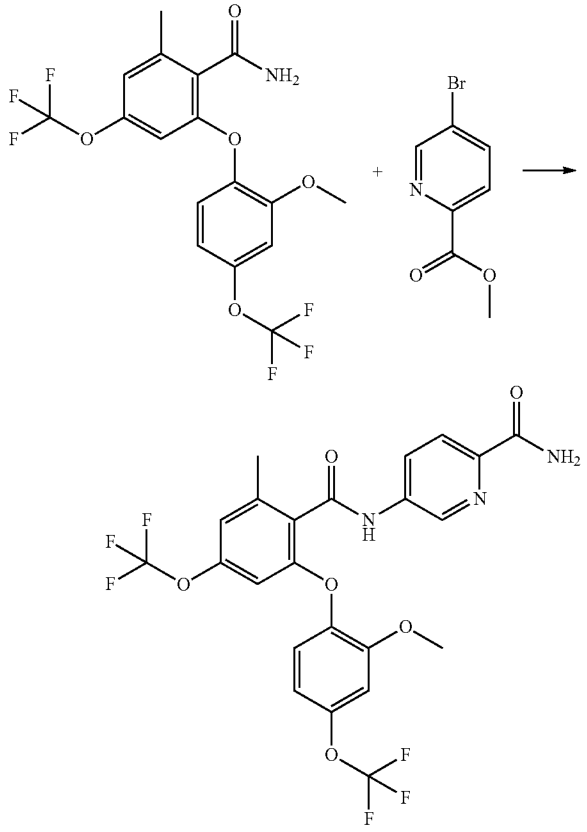 [SMILES: COc1cc(OC(F)(F)F)ccc1Oc1cc(OC(F)(F)F)cc(C)c1C(N)=O ; COC(=O)c1ccc(Br)cn1 ; COc1cc(OC(F)(F)F)ccc1Oc1cc(OC(F)(F)F)cc(C)c1C(=O)Nc1ccc(C(N)=O)nc1]

2-[2-Methoxy-4-(trifluoromethoxy)phenoxy]-6-methyl-4-(trifluoromethoxy)benzamide (185 mg, 0.370 mmol), methyl 5-bromopyridine-2-carboxylate (96 mg, 0.44 mmol), Xantphos (43 mg, 0.0743 mmol) and $Cs_2CO_3$ (266 mg, 0.816 mmol) were combined in dioxane (4 mL) under nitrogen. The mixture was degassed (2×vacuum-nitrogen cycles) and $Pd(OAc)_2$ (14 mg, 0.062 mmol) added. The mixture was again degassed (2×cycles) then heated at 100° C. for 60 minutes. The reaction mixture was cooled to RT and partitioned between ethyl acetate and water. The aqueous phase was extracted with additional ethyl acetate and the combined organics washed with brine, dried $Na_2SO_4$, filtered and concentrated under reduced pressure. The residue was purified via silica gel chromatography (0-100% ethyl acetate/heptane) to provide methyl 5-(2-(2-methoxy-4-(trifluoromethoxy)phenoxy)-6-methyl-4-(trifluoromethoxy)benzamido)picolinate. The ester product was stirred with ammonia in methanol (5 mL of 7 M) under nitrogen overnight. The reaction mixture was concentrated and purified by HPLC to provide 5-[[2-[2-methoxy-4-(trifluoromethoxy)phenoxy]-6-methyl-4-(trifluoromethoxy)benzoyl]amino]pyridine-2-carboxamide (98.5 mg, 48%). ESI-MS m/z calc. 545.10, found 546.0 $(M+1)^+$; 544.0 $(M-1)^-$; Retention time (Method E): 3.35 minutes. $^1$H NMR (500 MHz, DMSO-d6) δ 11.04 (s, 1H), 8.88 (dd, J=2.5, 0.7 Hz, 1H), 8.30 (dd, J=8.6, 2.5 Hz, 1H), 8.08-8.01 (m, 1H), 7.99 (s, 1H), 7.53 (s, 1H), 7.25 (d, J=8.8 Hz, 1H), 7.19 (d, J=2.8 Hz, 1H), 7.13 (dd, J=2.2, 1.2 Hz, 1H), 7.00 (ddd, J=8.9, 2.7, 1.3 Hz, 1H), 6.49 (d, J=2.0 Hz, 1H), 3.77 (s, 3H), 2.39 (s, 3H) ppm.

Example 58

N-(2-Carbamoyl-4-Pyridyl)-6-Cyclopropyl-3-[2-Methoxy-4-(Trifluoromethoxy)Phenoxy]-5-(Trifluoromethyl)Pyridine-2-Carboxamide (246)

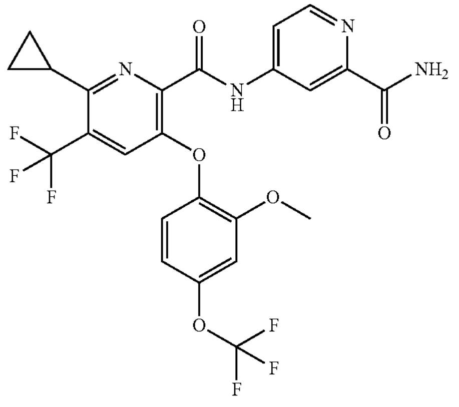 [SMILES: COc1cc(OC(F)(F)F)ccc1Oc1cc(C(F)(F)F)c(C2CC2)nc1C(=O)Nc1ccnc(C(N)=O)c1]

Step 1: 3-[2-Methoxy-4-(Trifluoromethoxy)Phenoxy]-5-(Trifluoromethyl)Pyridine-2-Carboxylic Acid

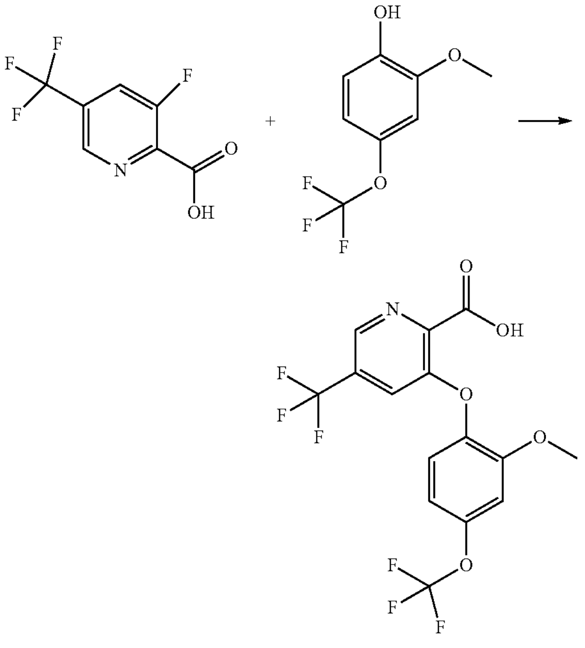

To 3-fluoro-5-(trifluoromethyl)pyridine-2-carboxylic acid (1.40 g, 6.70 mmol) in DMF (14 mL) was added 2-methoxy- 4-(trifluoromethoxy)phenol (1.39 g, 6.69 mmol) and $Cs_2CO_3$ (6.54 g, 20.1 mmol). The reaction was stirred at 90° C. for 72 hours. The reaction was filtered through a pad of Celite and the filtrate was partitioned between water and ethyl acetate. The organic layer was washed with water, aqueous $NaHCO_3$ and brine, dried over $Na_2SO_4$, filtered and concentrated under reduced pressure. Silica gel chromatography (10-100% ethyl acetate/hexanes) provided 3-[2-methoxy-4-(trifluoromethoxy)phenoxy]-5-(trifluoromethyl)pyridine-2-carboxylic acid (1.80 g, 68%) as a white solid. ESI-MS m/z calc. 397.04, found 398.2 $(M+1)^+$; retention time (Method A): 0.61 minutes.

Step 2: Methyl 3-[2-Methoxy-4-(Trifluoromethoxy)Phenoxy]-5-(Trifluoromethyl)Pyridine-2-Carboxylate

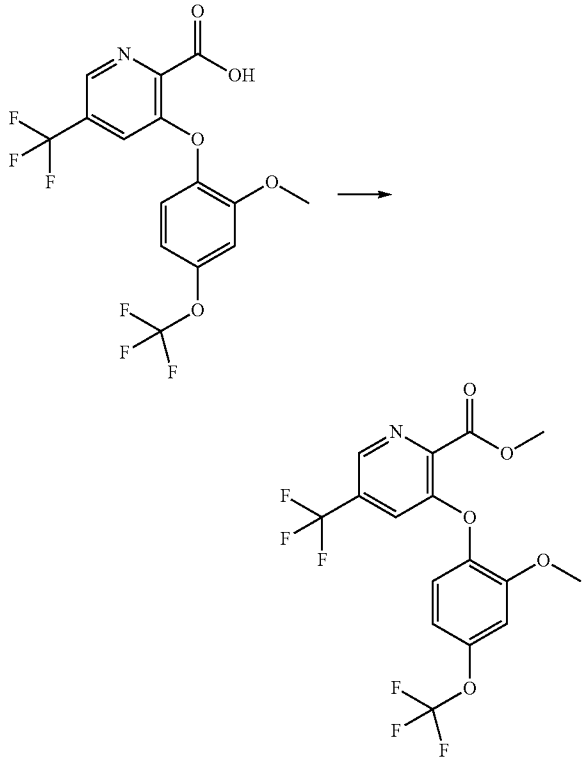

To an ice-cooled solution of 3-[2-methoxy-4-(trifluoromethoxy)phenoxy]-5-(trifluoromethyl)pyridine-2-carboxylic acid (4 g, 10.07 mmol) in dichloromethane (50 mL) was added DMF (50 μL, 0.65 mmol) and carefully oxalyl chloride (2.7 mL, 31 mmol). The reaction mixture was allowed to warm to room temperature over 30 minutes. Methanol (15 mL, 370 mmol) was cautiously added and the resulting mixture was stirred at room temperature for 2 hours. The reaction mixture was concentrated under reduced pressure. The residue was dissolved in ethyl acetate and washed with water (3×30 mL), dried over $MgSO_4$ and concentrated under reduced pressure to provide methyl 3-[2-methoxy-4-(trifluoromethoxy)phenoxy]-5-(trifluoromethyl)pyridine-2-carboxylate (3.8 g, 92%). ESI-MS m/z calc. 411.05, found 412.5 $(M+1)^+$; Retention time (Method D): 0.96 minutes. $^1H$ NMR (500 MHz, Chloroform-d) δ 8.60 (d, J=1.6 Hz, 1H), 7.23 (dd, J=1.7, 0.7 Hz, 1H), 7.17-7.12 (m, 1H), 6.92-6.85 (m, 2H), 4.00 (s, 3H), 3.77 (s, 3H) ppm.

Step 3: Methyl 3-[2-Methoxy-4-(Trifluoromethoxy)Phenoxy]-1-Oxido-5-(Trifluoromethyl)Pyridin-1-Ium-2-Carboxylate

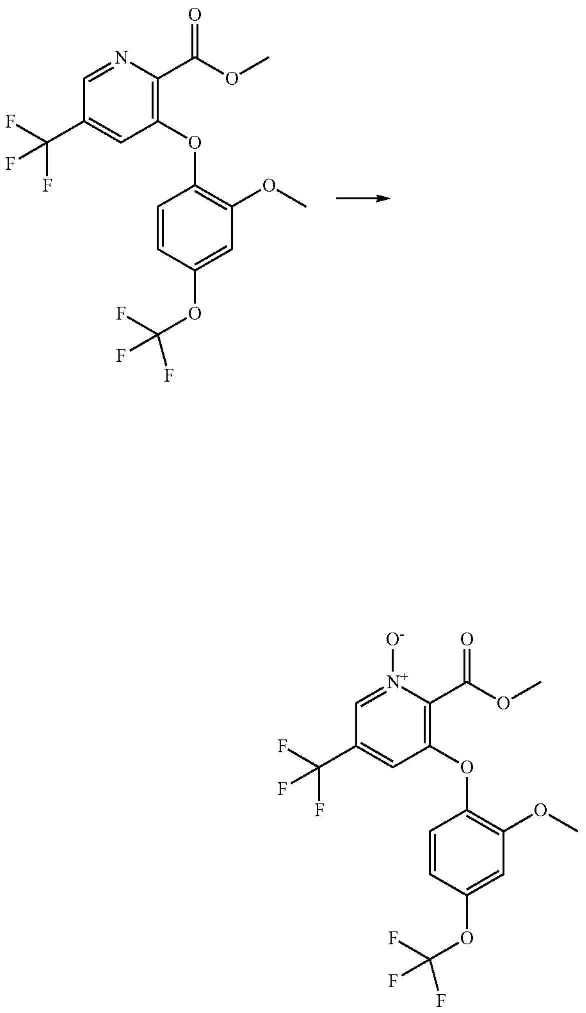

To a solution of methyl 3-[2-methoxy-4-(trifluoromethoxy)phenoxy]-5-(trifluoromethyl)pyridine-2-carboxylate (1.9 g, 4.6 mmol) in dichloromethane (30 mL) at 0° C. was added urea hydrogen peroxide (915 mg, 9.73 mmol) followed by the slow addition of trifluoroacetic anhydride (1.3 mL, 9.4 mmol). The resulting mixture was stirred at room temperature for 2 hours, then diluted with dichloromethane (30 mL) and treated with a saturated aqueous solution of $NaHCO_3$ (50 mL). The mixture was stirred for 40 minutes at room temperature. Additional dichloromethane (100 mL) was added and layers were separated. The organic phase was washed with saturated aqueous $NaHCO_3$ (50 mL), 10% aqueous $Na_2S_2O_3$ (50 mL) and brine (50 mL), then dried over $MgSO_4$, filtered and concentrated under reduced pressure to afford methyl 3-[2-methoxy-4-(trifluoromethoxy)phenoxy]-1-oxido-5-(trifluoromethyl)pyridin-1-ium-2-carboxylate (1.95 g, 99%). ESI-MS m/z calc. 427.05, found 428.5 $(M+1)^+$; 426.6 $(M-1)^-$; Retention time (Method D): 0.88 minutes. $^1H$ NMR (500 MHz, Chloroform-d) δ 8.21 (dd, J=1.3, 0.7 Hz, 1H), 7.19 (dd, J=8.2, 0.8 Hz, 1H), 6.93-6.86 (m, 2H), 6.68 (dd, J=1.4, 0.7 Hz, 1H), 4.03 (s, 3H), 3.81 (s, 3H) ppm.

Step 4: Methyl 6-Chloro-3-[2-Methoxy-4-(Trifluoromethoxy)Phenoxy]-5-(Trifluoromethyl)Pyridine-2-Carboxylate

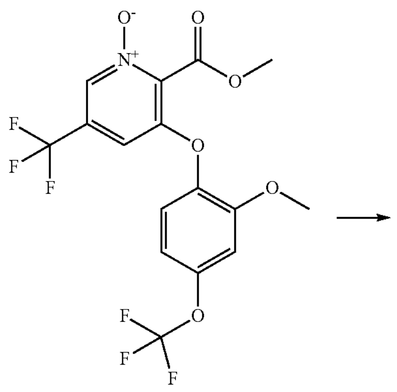

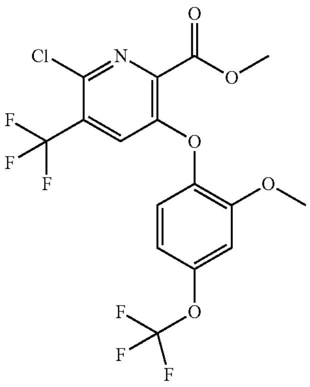

Methyl 3-[2-methoxy-4-(trifluoromethoxy)phenoxy]-1-oxido-5-(trifluoromethyl)pyridin-1-ium-2-carboxylate (1.0 g, 2.3 mmol) in phosphoryl trichloride (10 mL, 107 mmol) was stirred at 50° C. overnight. The reaction mixture was cooled to room temperature and concentrated under reduced pressure. The residue was partitioned between ethyl acetate (80 mL) and saturated aqueous $NaHCO_3$ (50 mL) and the layers separated. The organic layer was washed with brine (50 mL), dried over $MgSO_4$, filtered and evaporated under reduced pressure to provide methyl 6-chloro-3-[2-methoxy-4-(trifluoromethoxy)phenoxy]-5-(trifluoromethyl)pyridine-2-carboxylate (874 mg, 84%). ESI-MS m/z calc. 445.02, found 446.4 $(M+1)^+$; Retention time (Method D): 1.08 minutes. $^1H$ NMR (500 MHz, Chloroform-d) δ 7.35 (s, 1H), 7.18-7.12 (m, 1H), 6.92-6.82 (m, 2H), 3.99 (s, 3H), 3.79 (s, 3H) ppm.

Step 5: Methyl 6-Cyclopropyl-3-[2-Methoxy-4-(Trifluoromethoxy)Phenoxy]-5-(Trifluoromethyl) Pyridine-2-Carboxylate

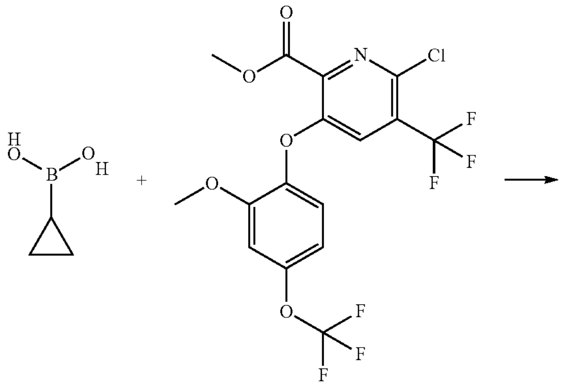

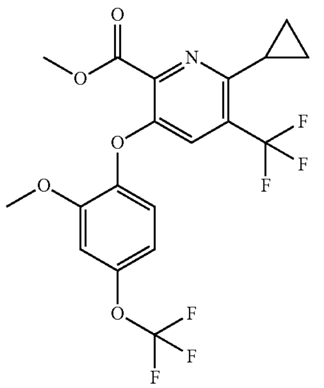

A mixture of methyl 6-chloro-3-[2-methoxy-4-(trifluoromethoxy)phenoxy]-5-(trifluoromethyl)pyridine-2-carboxylate (690 mg, 1.55 mmol), cyclopropyl boronic acid (1.20 g, 14.0 mmol), $K_3PO_4$ (1.50 g, 7.07 mmol), $Pd(OAc)_2$ (175 mg, 0.780 mmol) and tricyclohexylphosphane (240 μL, 0.780 mmol) in toluene (14 mL) and water (3.5 mL) was heated at 100° C. for 1 hour. The reaction mixture was cooled to room temperature and filtered through Celite. HPLC purification provided methyl 6-cyclopropyl-3-[2-methoxy-4-(trifluoromethoxy)phenoxy]-5-(trifluoromethyl) pyridine-2-carboxylate (522 mg, 75%). $^1H$ NMR (500 MHz, Chloroform-d) δ 7.28 (s, 1H), 7.04 (d, J=8.7 Hz, 1H), 6.88 (d, J=2.6 Hz, 1H), 6.85 (ddd, J=8.7, 2.7, 1.1 Hz, 1H), 3.94 (s, 3H), 3.83 (s, 3H), 2.36-2.23 (m, 1H), 1.28-1.20 (m, 2H), 1.11-1.01 (m, 2H) ppm.

Step 6: 6-Cyclopropyl-3-[2-Methoxy-4-(Trifluoromethoxy)Phenoxy]-5-(Trifluoromethyl)Pyridine-2-Carboxylic Acid

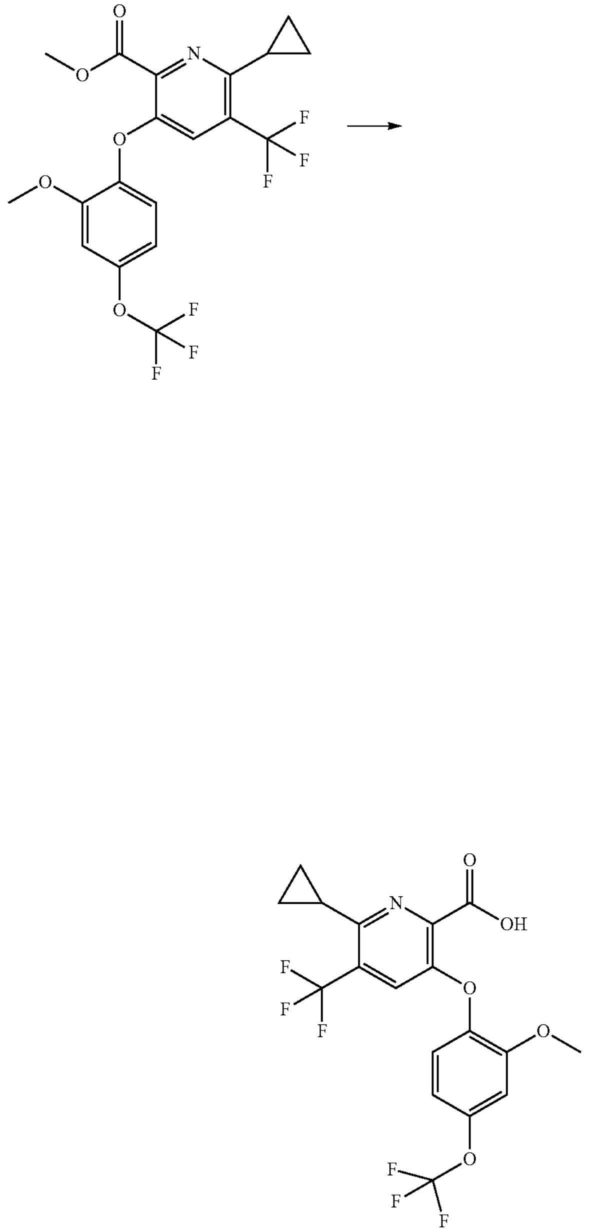

Sodium hydroxide (in water) (12 mL of 2 M, 24.00 mmol) was added to a solution of methyl 6-cyclopropyl-3-[2-methoxy-4-(trifluoromethoxy)phenoxy]-5-(trifluoromethyl) pyridine-2-carboxylate (600 mg, 1.329 mmol) in tetrahydrofuran (30 mL) at 0° C. and the resulting mixture stirred at RT for 2 h. The solvent was removed in vacuo and the residual aqueous mixture was acidified to pH-2 by careful addition of 1N HCl. The resulting mixture was extracted with ethyl acetate (3×30 mL) and the combined organic extracts were dried over $MgSO_4$ and concentrated under reduced pressure to leave 6-cyclopropyl-3-[2-methoxy-4-(trifluoromethoxy)phenoxy]-5-(trifluoromethyl)pyridine-2-carboxylic acid (560 mg, 96%). $^1H$ NMR (500 MHz, Chloroform-d) δ 10.53 (s, 1H), 7.24 (s, 1H), 7.15-6.98 (m, 1H), 6.87-6.64 (m, 2H), 3.71 (s, 3H), 2.27 (tdd, J=7.9, 6.4, 3.2 Hz, 1H), 1.11 (d, J=6.3 Hz, 4H) ppm.

Step 7: Methyl 4-[[6-Cyclopropyl-3-[2-Methoxy-4-(Trifluoromethoxy)Phenoxy]-5-(Trifluoromethyl) Pyridine-2-Carbonyl]Amino]Pyridine-2-Carboxylate

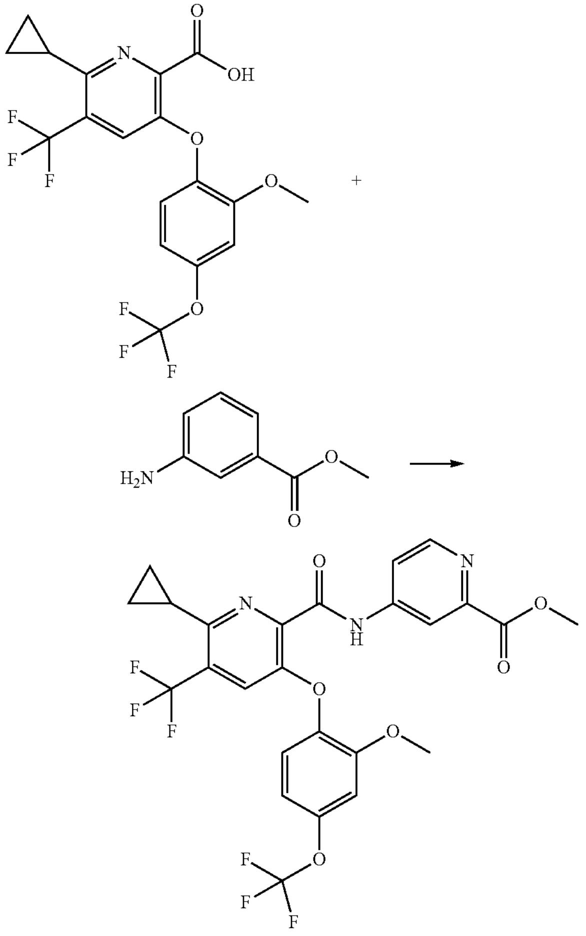

To an ice cold solution of methyl 4-aminopyridine-2-carboxylate (47 mg, 0.1043 mmol) in DCM (2.8 mL) was added oxalyl chloride (20 uL, 0.229 mmol) and DMF (0.5 uL, 0.0065 mmol) and the mixture was stirred at RT for 30 minutes. The mixture was concentrated under reduced pressure and the residue was dissolved in DCM (2.8 mL) and methyl 4-aminopyridine-2-carboxylate (19 mg, 0.125 mmol) and DIEA (29 uL, 0.167 mmol) were added and the mixture was stirred at RT for 30 minutes. The mixture was concentrated under reduced pressure and the residue was purified by silica gel chromatography (EtOAc—heptane gradient) to give methyl 4-[[6-cyclopropyl-3-[2-methoxy-4-(trifluoromethoxy)phenoxy]-5-(trifluoromethyl)pyridine-2-carbonyl]amino]pyridine-2-carboxylate (50 mg, 84%). ESI-MS m z calc. 571.1178, found 572.5 $(M+1)^+$; Retention time (Method F): 1.06 minutes.

Step 8: N-(2-Carbamoyl-4-Pyridyl)-6-Cyclopropyl-3-[2-Methoxy-4-(Trifluoromethoxy)Phenoxy]-5-(Trifluoromethyl)Pyridine-2-Carboxamide (246)

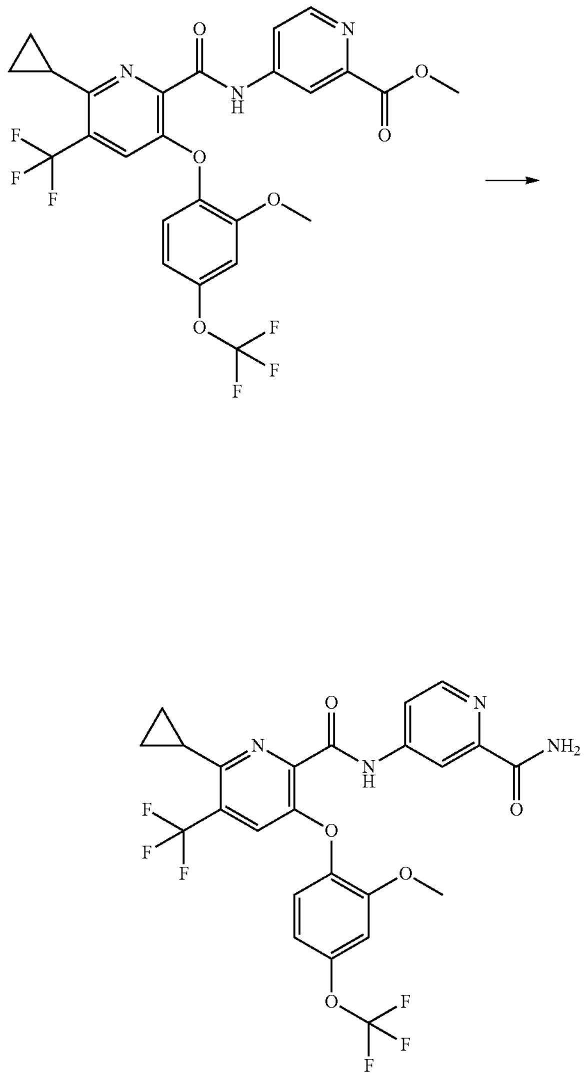

Methyl 4-[[6-cyclopropyl-3-[2-methoxy-4-(trifluoromethoxy)phenoxy]-5-(trifluoromethyl)pyridine-2-carbonyl]amino]pyridine-2-carboxylate (50 mg, 0.088 mmol) was dissolved in a solution of ammonia in methanol (2.5 mL of 7 M, 17.5 mmol) and stirred at room temperature overnight. The reaction was evaporated under reduced pressure and purified via silica gel chromatography (methanol/dichloromethane gradient). Additional purification via HPLC ($CH_3CN$ gradient with ammonia modifier) provided N-(2-carbamoyl-4-pyridyl)-6-cyclopropyl-3-[2-methoxy-4-(trifluoromethoxy)phenoxy]-5-(trifluoromethyl)pyridine-2-carboxamide (45 mg, 92%). ESI-MS m/z calc. 556.12, found 557.5 $(M+1)^+$; 555.5 $(M-1)^-$; Retention time (Method E): 3.54 minutes. $^1H$ NMR (500 MHz, DMSO-d6) δ 11.01 (s, 1H), 8.54 (d, J=5.4 Hz, 1H), 8.32 (d, J=2.2 Hz, 1H), 8.09 (d, J=2.8 Hz, 1H), 7.88 (dd, J=5.5, 2.2 Hz, 1H), 7.64 (d, J=2.8 Hz, 1H), 7.54 (s, 1H), 7.23-7.17 (m, 2H), 6.96 (ddt, J=8.9, 2.5, 1.2 Hz, 1H), 3.78 (s, 3H), 3.18 (d, J=5.2 Hz, 1H), 1.22 (dt, J=6.1, 3.0 Hz, 2H), 1.12 (dt, J=8.1, 3.3 Hz, 2H) ppm.

Example 59

N-(2-Carbamoyl-4-Pyridyl)-3-[2-Methoxy-4-(Trifluoromethoxy)Phenoxy]-6-Methyl-5-(Trifluoromethyl)Pyridine-2-Carboxamide (247)

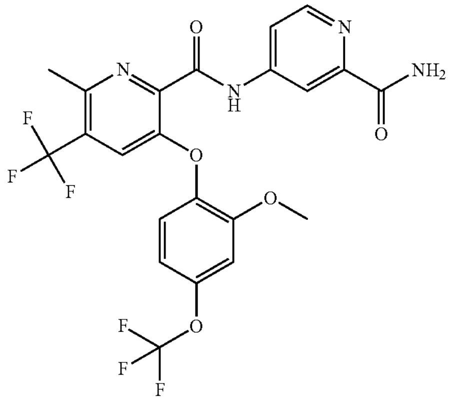

Step 1: 3-[2-Methoxy-4-(Trifluoromethoxy)Phenoxy]-6-Methyl-5-(Trifluoromethyl)Pyridine-2-Carboxylic Acid

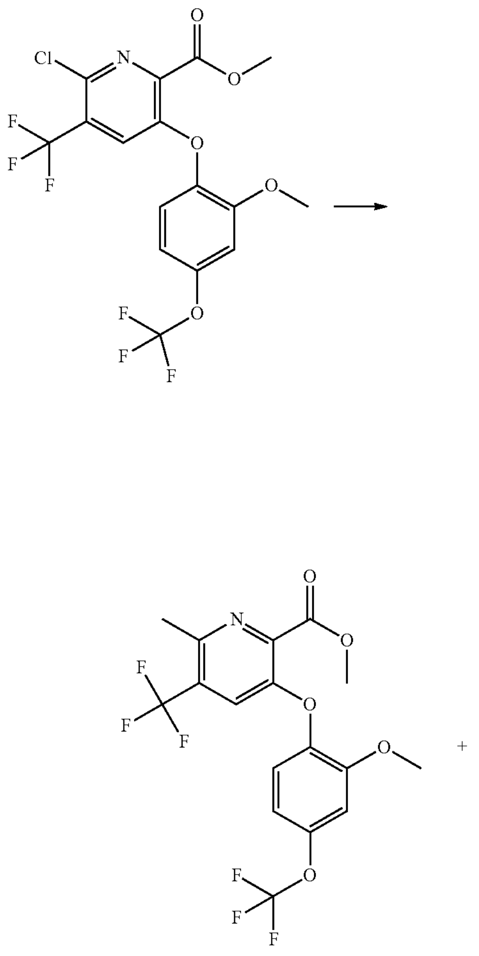

-continued

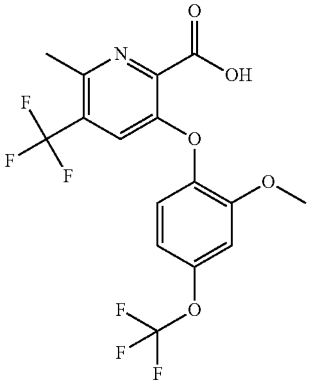

Methyl 6-chloro-3-[2-methoxy-4-(trifluoromethoxy)phenoxy]-5-(trifluoromethyl)pyridine-2-carboxylate (295 mg, 0.662 mmol), Pd(dppf)$Cl_2$ (56 mg, 0.069 mmol), $Cs_2CO_3$ (646 mg, 1.98 mmol) and potassium methyltrifluoroborate (81 mg, 0.67 mmol) in THF (10 mL) and water (1 mL) was heated to 80° C. and stirred for 68 hours. The reaction mixture was partitioned between ethyl acetate and water. The organic layer containing the ester product was concentrated and the crude product purified via silica gel chromatography (0-20% ethyl acetate/heptane gradient) to provide methyl 3-[2-methoxy-4-(trifluoromethoxy)phenoxy]-6-methyl-5-(trifluoromethyl)pyridine-2-carboxylate (97 mg, 34%). $^1$H NMR (500 MHz, DMSO-d6) δ 7.52 (s, 1H), 7.28-7.17 (m, 2H), 6.98 (ddt, J=8.8, 2.4, 1.1 Hz, 1H), 3.84 (s, 3H), 3.79 (s, 3H), 2.62 (q, J=1.7 Hz, 3H) ppm. The aqueous layer was acidified to pH3 with 2 M HCl and extracted with ethyl acetate. The organic layer was dried over $MgSO_4$, filtered and concentrated under reduced pressure to provide 3-[2-methoxy-4-(trifluoromethoxy)phenoxy]-6-methyl-5-(trifluoromethyl)pyridine-2-carboxylic acid (200 mg). ESI-MS m/z calc. 411.05, found 412.5 $(M+1)^+$; 410.6 $(M-1)^-$; Retention time (Method D): 0.59 minutes.

Step 2: 3-[2-Methoxy-4-(Trifluoromethoxy)Phenoxy]-6-Methyl-5-(Trifluoromethyl)Pyridine-2-Carboxylic Acid

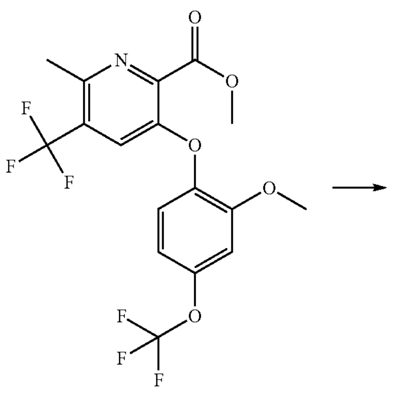

-continued

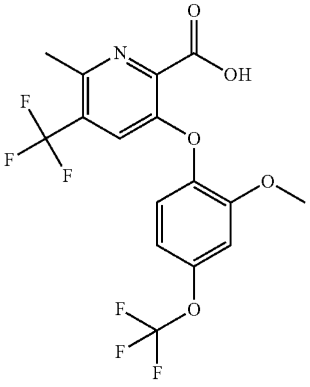

To a solution of methyl 3-[2-methoxy-4-(trifluoromethoxy)phenoxy]-6-methyl-5-(trifluoromethyl)pyridine-2-carboxylate (97 mg, 0.23 mmol) in THF (2 mL) was added NaOH (2 mL of 2 M, 4 mmol) and the reaction mixture was stirred at room temperature for 1 hour. The reaction mixture was diluted with water and acidified to pH-3 with 2 M HCl. The aqueous layer was extracted with ethyl acetate. The organic layer was dried over $MgSO_4$, filtered and concentrated under reduced pressure to provide 3-[2-methoxy-4-(trifluoromethoxy)phenoxy]-6-methyl-5-(trifluoromethyl)pyridine-2-carboxylic acid (116 mg, 100%). ESI-MS m/z calc. 411.05, found 412.5 $(M+1)^+$; 410.7 $(M-1)^-$; Retention time (Method D): 0.59 minutes. $^1$H NMR (500 MHz, DMSO-d6) δ 7.45 (s, 1H), 7.23 (d, J=2.8 Hz, 1H), 7.17 (d, J=8.8 Hz, 1H), 6.98 (ddd, J=8.8, 2.8, 1.3 Hz, 1H), 3.80 (s, 3H), 2.62 (d, J=1.8 Hz, 3H) ppm.

Step 3: Methyl 4-[[3-[2-Methoxy-4-(Trifluoromethoxy)Phenoxy]-6-Methyl-5-(Trifluoromethyl)Pyridine-2-Carbonyl]Amino]Pyridine-2-Carboxylate

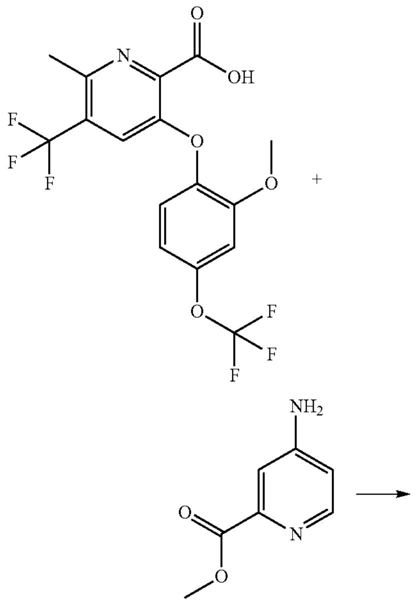

-continued

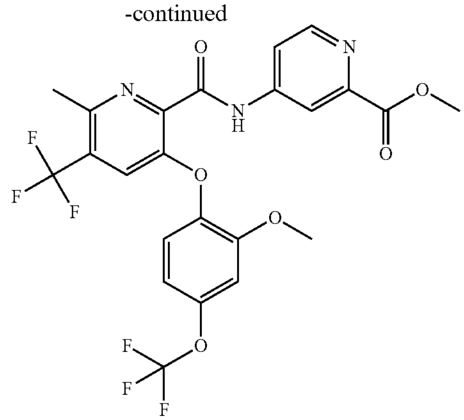

To a solution of 3-[2-methoxy-4-(trifluoromethoxy)phenoxy]-6-methyl-5-(trifluoromethyl)pyridine-2-carboxylic acid (109 mg, 0.239 mmol) in dichloromethane (1.5 mL) and DMF (2 μL, 0.02 mmol) at 0° C. was added oxalyl chloride (6 mL, 69 mmol) and the reaction mixture was warmed to room temperature for 2 hours. The reaction mixture was concentrate under reduced pressure. The residue was dissolved in dichloromethane (1 mL) and added to a solution of methyl 4-aminopyridine-2-carboxylate (33.6 mg, 0.2208 mmol) and $Et_3N$ (100 μL, 0.718 mmol) in dichloromethane (1 mL) at 0° C. The reaction was allowed to warm to RT and stirred for 1 hour. The reaction mixture partitioned between dichloromethane and water and the layers separated. The aqueous layer was extracted with additional dichloromethane, and the combined organic extracts were dried over $Na_2SO_4$, filtered and concentrated under reduced pressure. Silica gel chromatography (0-60% ethyl acetate/heptane gradient) provided methyl 4-[[3-[2-methoxy-4-(trifluoromethoxy)phenoxy]-6-methyl-5-(trifluoromethyl)pyridine-2-carbonyl]amino]pyridine-2-carboxylate (37 mg, 28%). ESI-MS m/z calc. 545.10, found 546.5 $(M+1)^+$; 544.7 $(M-1)^-$; Retention time (Method D): 0.97 minutes. $^1H$ NMR (500 MHz, DMSO-d6) δ 11.25 (s, 1H), 8.62 (d, J=5.5 Hz, 1H), 8.44 (d, J=2.1 Hz, 1H), 7.90 (dd, J=5.5, 2.1 Hz, 1H), 7.58 (s, 1H), 7.29-7.14 (m, 2H), 6.96 (ddt, J=8.8, 2.5, 1.3 Hz, 1H), 3.89 (s, 3H), 3.76 (s, 3H), 2.69 (q, J=1.6 Hz, 3H) ppm.

Step 4: N-(2-Carbamoyl-4-Pyridyl)-3-[2-Methoxy-4-(Trifluoromethoxy)Phenoxy]-6-Methyl-5-(Trifluoromethyl)Pyridine-2-Carboxamide (247)

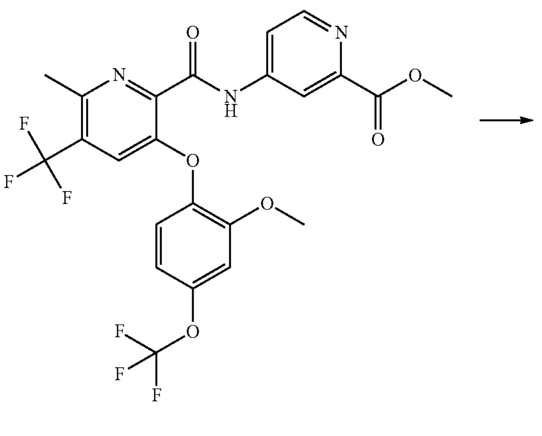

-continued

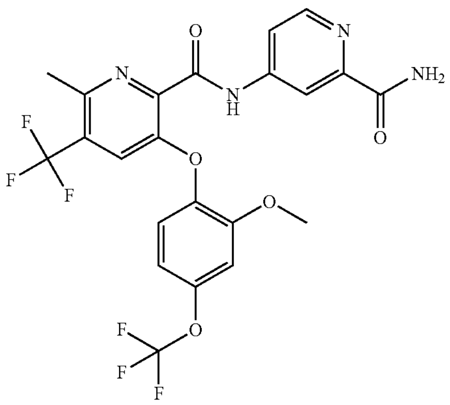 [SMILES: COc1cc(OC(F)(F)F)ccc1Oc1cc(C(F)(F)F)c(C)nc1C(=O)Nc1ccnc(C(N)=O)c1]

A solution of methyl 4-[[3-[2-methoxy-4-(trifluoromethoxy)phenoxy]-6-methyl-5-(trifluoromethyl)pyridine-2-carbonyl]amino]pyridine-2-carboxylate (35 mg, 0.064 mmol) and ammonia in methanol (1 mL of 7 M, 7 mmol) was stirred at RT for 20 hours. The reaction mixture was concentrated under reduced pressure. The residue was dissolved in dichloromethane (20 mL) and washed with water (3×15 mL). The organic layer was dried and concentrated under reduced pressure. Silica gel chromatography (ethyl acetate/heptane gradient) provided N-(2-carbamoyl-4-pyridyl)-3-[2-methoxy-4-(trifluoromethoxy)phenoxy]-6-methyl-5-(trifluoromethyl)pyridine-2-carboxamide (13 mg, 36%). ESI-MS m/z calc. 530.10, found 531.6 $(M+1)^+$; 529.7 $(M-1)^-$; Retention time (Method E): 3.34 minutes. $^1H$ NMR (500 MHz, DMSO-d6) δ 11.20 (s, 1H), 8.54 (d, J=5.4 Hz, 1H), 8.38 (d, J=2.3 Hz, 1H), 8.08 (d, J=2.8 Hz, 1H), 7.89 (dd, J=5.4, 2.2 Hz, 1H), 7.63 (d, J=2.8 Hz, 1H), 7.57 (s, 1H), 7.23 (d, J=8.8 Hz, 1H), 7.19 (d, J=2.8 Hz, 1H), 6.96 (ddt, J=8.7, 2.3, 1.2 Hz, 1H), 3.77 (s, 3H), 2.69 (q, J=1.7 Hz, 3H) ppm.

Example 60

4-[[4-Cyclopropyl-2-[2-Methoxy-4-(Trifluoromethoxy)Phenoxy]-6-Methyl-Benzoyl]Amino]Pyridine-2-Carboxamide (248)

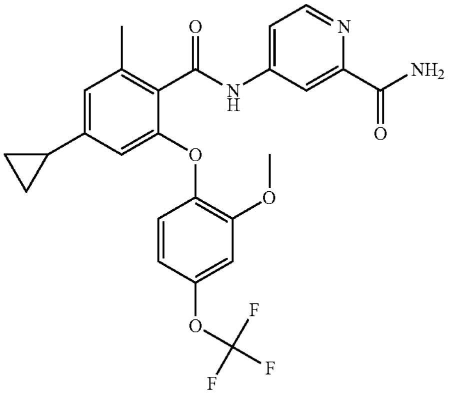 [SMILES: COc1cc(OC(F)(F)F)ccc1Oc1cc(C2CC2)cc(C)c1C(=O)Nc1ccnc(C(N)=O)c1]

Step 1: 4-Bromo-2-[2-Methoxy-4-(Trifluoromethoxy)Phenoxy]-6-Methyl-Benzonitrile

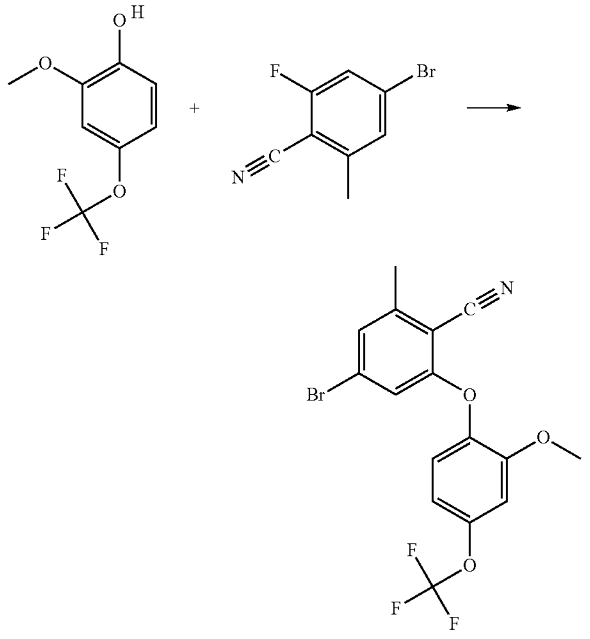

2-methoxy-4-(trifluoromethoxy)phenol (575.2 mg, 2.764 mmol), 4-bromo-2-fluoro-6-methyl-benzonitrile (500 mg, 2.336 mmol) and $Cs_2CO_3$ (908.8 mg, 2.789 mmol) in DMF (2.5 mL) were degassed with an $N_2$ purge and heated at 90° C. in a sealed tube for 24 hours. The mixture was allowed to cool and was diluted with EtOAc and washed with 2M NaOH (2×) and brine (2×). The organic layer was, dried ($MgSO_4$) and concentrated to give 4-bromo-2-[2-methoxy-4-(trifluoromethoxy)phenoxy]-6-methyl-benzonitrile (910.5 mg, 97%). $^1$H NMR (500 MHz, DMSO-d6) δ 7.44 (dd, J=1.7, 0.8 Hz, 1H), 7.39 (d, J=8.8 Hz, 1H), 7.28 (d, J=2.7 Hz, 1H), 7.05 (ddq, J=8.8, 2.5, 1.2 Hz, 1H), 6.73-6.65 (m, 1H), 3.81 (s, 3H) ppm. This was used in the next step without further purification.

Step 2: 4-Cyclopropyl-2-[2-Methoxy-4-(Trifluoromethoxy)Phenoxy]-6-Methyl-Benzonitrile

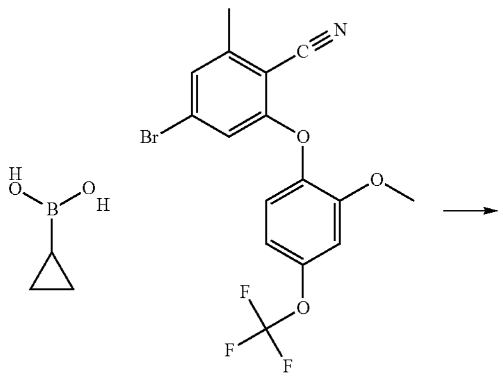

-continued

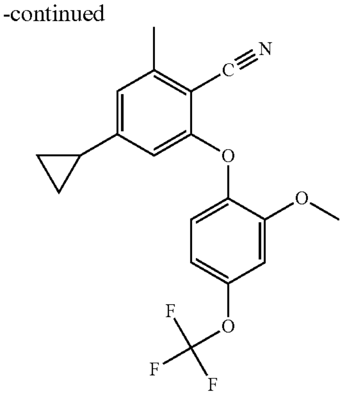

4-bromo-2-[2-methoxy-4-(trifluoromethoxy)phenoxy]-6-methyl-benzonitrile (469 mg, 1.166 mmol) in toluene (10 mL) and water (2.5 mL) was degassed with $N_2$/vacuum cycles before the addition of cyclopropylboronic acid (305 mg, 3.551 mmol), palladium acetate (20.3 mg, 0.09042 mmol), $K_3PO_4$ (502.2 mg, 2.366 mmol) and tricyclohexylphosphine (49.8 mg, 0.1776 mmol). The mixture was heated at 100° C. under nitrogen for 1.5 hours. The mixture was allowed to cool and diluted with water (20 mL) and EtOAc (20 mL) and the layers were separated. The organic layer was dried ($MgSO_4$) and concentrated under reduced pressure. The material was purified by chromatography on silica gel with an EtOAc/heptane gradient to give 4-cyclopropyl-2-[2-methoxy-4-(trifluoromethoxy)phenoxy]-6-methyl-benzonitrile (284 mg, 67%). ESI-MS m/z calc. 363.10822, found 364.5 $(M+1)^+$; Retention time (Method F): 1.07 minutes.

Step 3: 4-Cyclopropyl-2-[2-Methoxy-4-(Trifluoromethoxy)Phenoxy]-6-Methyl-Benzamide

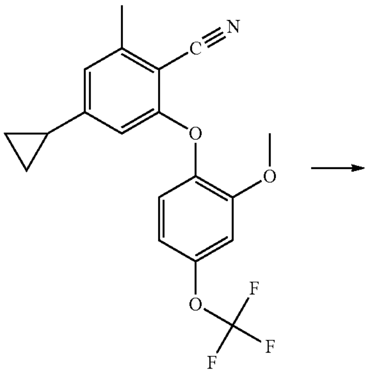

-continued

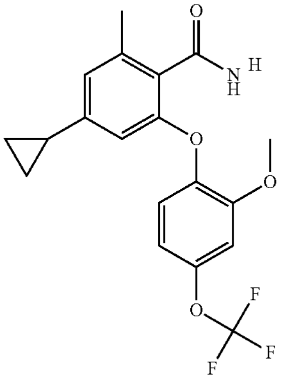

4-cyclopropyl-2-[2-methoxy-4-(trifluoromethoxy)phenoxy]-6-methyl-benzonitrile (284 mg, 0.782 mmol) in EtOH (3 mL) and NaOH (5.8 mL of 2 M, 11.60 mmol) was stirred at reflux for 3 hours. Additional solid NaOH (300 mg, 7.501 mmol) was carefully added and the mixture was returned to reflux for 3 hours. The mixture was allowed to cool and then diluted with EtOAc and washed with brine. The organic layer was dried ($MgSO_4$) and concentrated to give 4-cyclopropyl-2-[2-methoxy-4-(trifluoromethoxy)phenoxy]-6-methyl-benzamide. ESI-MS m/z calc. 381.1188, found 382.6 $(M+1)^+$; Retention time (Method F): 0.89 minutes. The material was taken directly into the next step.

Step 4: 4-[[4-Cyclopropyl-2-[2-Methoxy-4-(Trifluoromethoxy)Phenoxy]-6-Methyl-Benzoyl]Amino]Pyridine-2-Carboxamide (248)

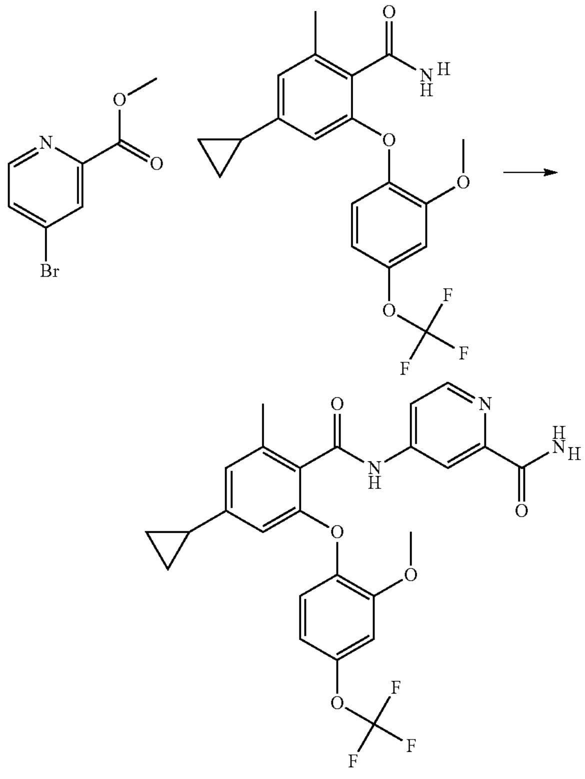

Methyl 4-bromopyridine-2-carboxylate (208.3 mg, 0.964 mmol), Xantphos (96.6 mg, 0.167 mmol), cesium carbonate (613 mg, 1.881 mmol), $Pd(OAc)_2$ (18.2 mg, 0.0811 mmol) and 4-cyclopropyl-2-[2-methoxy-4-(trifluoromethoxy)phenoxy]-6-methyl-benzamide (298 mg, 0.782 mmol) were combined in dioxane (10 mL) and heated at 100° C. overnight. The mixture was allowed to cool and then diluted with EtOAc and washed with sat. aq. $NaHCO_3$. The organic layer was separated, dried ($MgSO_4$) and concentrate. Purification by silica gel chromatography using an EtOAc/heptane gradient gave the major product, which was treated with $NH_3$ (in methanol) (6 mL of 7 M, 42.00 mmol) at RT for 3 days. The mixture was concentrated and purified directly by HPLC to give 4-[[4-cyclopropyl-2-[2-methoxy-4-(trifluoromethoxy)phenoxy]-6-methyl-benzoyl]amino]pyridine-2-carboxamide (26.5 mg, 7%). $^1H$ NMR (500 MHz, DMSO-d6) δ 10.93 (s, 1H), 8.49 (d, J=5.5 Hz, 1H), 8.33 (d, J=2.1 Hz, 1H), 8.05 (d, J=2.9 Hz, 1H), 7.81 (dd, J=5.5, 2.2 Hz, 1H), 7.60 (d, J=2.9 Hz, 1H), 7.15-7.04 (m, 2H), 7.03-6.88 (m, 1H), 6.73 (d, J=1.4 Hz, 1H), 6.37 (d, J=1.4 Hz, 1H), 3.75 (s, 3H), 2.28 (s, 3H), 1.87 (tt, J=8.4, 5.0 Hz, 1H), 0.98-0.85 (m, 2H), 0.74-0.53 (m, 2H) ppm. ESI-MS m/z calc. 501.15115, found 502.6 $(M+1)^+$; Retention time (Method E): 3.31 minutes.

Example 61

4-[[2-Fluoro-6-[2-Hydroxy-4-(Trifluoromethoxy)Phenoxy]-3-(Trifluoromethyl)Benzoyl]Amino]-1-Oxido-Pyridin-1-Ium-2-Carboxamide (249)

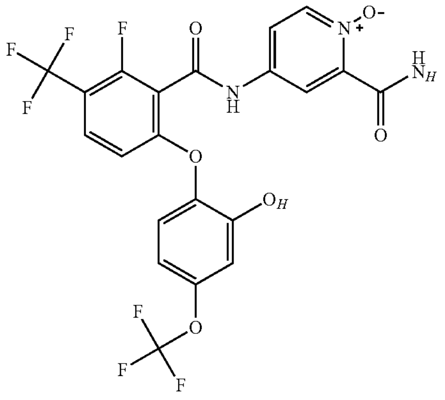

Step 1: 4-[[2-Fluoro-6-[2-Hydroxy-4-(Trifluoromethoxy)Phenoxy]-3-(Trifluoromethyl)Benzoyl]Amino]Pyridine-2-Carboxamide

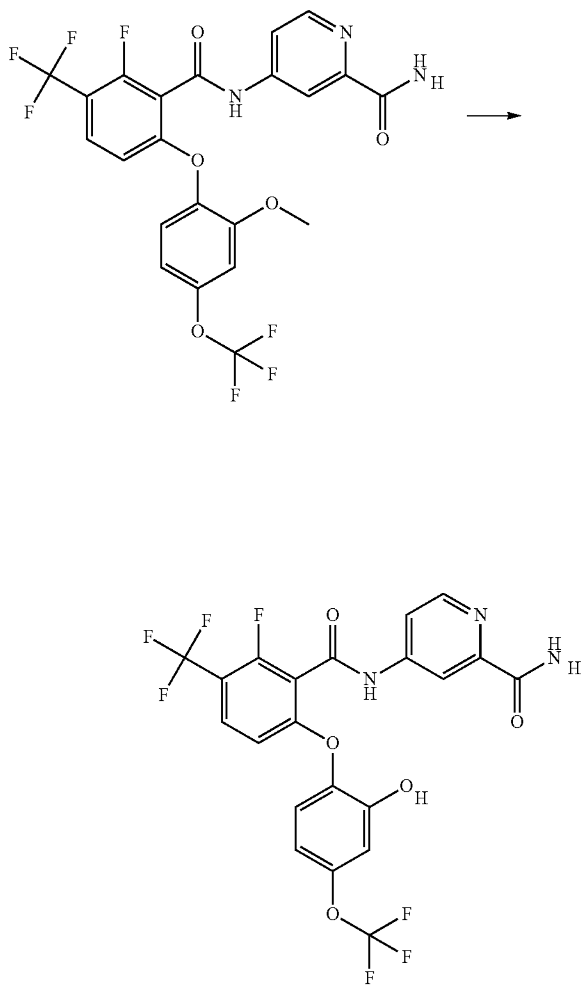

To a stirred mixture of 4-[[2-fluoro-6-[2-methoxy-4-(trifluoromethoxy)phenoxy]-3-(trifluoromethyl)benzoyl]amino]pyridine-2-carboxamide (200 mg, 0.375 mmol) in dichloromethane (2 mL) was added $BBr_3$ in dichloromethane (approximately 1.509 mL of 1 M, 1.509 mmol) dropwise at −78° C. The reaction mixture was stirred at −78° C. for 5 min then allowed to warm to RT and stirred overnight. The mixture was diluted with isopropyl acetate, washed with 50% of sat.d $NaHCO_3$, brine, dried over $Na_2SO_4$, and concentrated under reduced pressure. Purification by silica gel chromatography eluting with an EtOAc/Hexane gradient, and triturated with IPAc/heptane gave 4-[[2-fluoro-6-[2-hydroxy-4-(trifluoromethoxy)phenoxy]-3-(trifluoromethyl)benzoyl]amino]pyridine-2-carboxamide 64 mg, 33%) as white solid. $^1$H NMR (400 MHz, DMSO-d6) δ 11.42 (s, 1H), 10.62 (s, 1H), 8.56 (d, J=5.4 Hz, 1H), 8.33 (d, J=2.1 Hz, 1H), 8.10 (d, J=2.9 Hz, 1H), 7.86 (dd, J=5.5, 2.2 Hz, 1H), 7.82 (t, J=8.6 Hz, 1H), 7.66 (d, J=2.8 Hz, 1H), 7.31 (d, J=8.8 Hz, 1H), 6.99-6.92 (m, 1H), 6.91-6.85 (m, 1H), 6.67 (d, J=8.9 Hz, 1H) ppm. ESI-MS m/z calc. 519.0665, found 520.1 $(M+1)^+$; Retention time (Method B): 1.67 minutes.

Step 2: 4-[[2-Fluoro-6-[2-Hydroxy-4-(Trifluoromethoxy)Phenoxy]-3-(Trifluoromethyl)Benzoyl]Amino]-1-Oxido-Pyridin-1-Ium-2-Carboxamide (249)

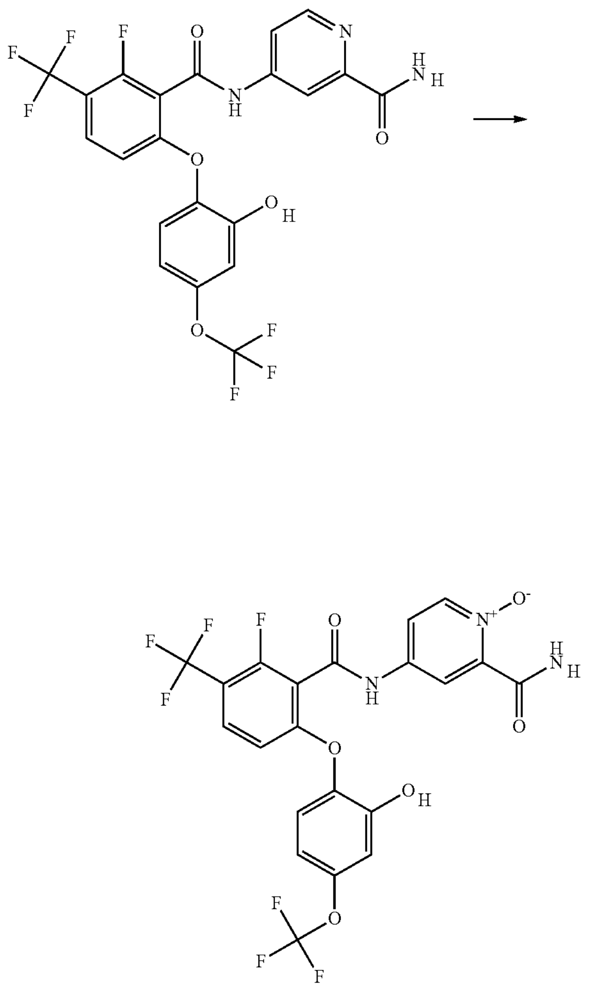

To a stirring slurry of 4-[[2-fluoro-6-[2-hydroxy-4-(trifluoromethoxy)phenoxy]-3-(trifluoromethyl)benzoyl]amino]pyridine-2-carboxamide (208 mg, 0.401 mmol) in anhydrous DCM (2 mL) under $N_2$ at 0° C. was added 3-chlorobenzenecarboperoxoic acid (304.4 mg, 1.358 mmol). Then, the reaction was allowed to warm to RT and stirred for 23 h. The solvent was evaporated under reduced pressure. The crude material was purified by silica gel chromatography eluting with an ethyl acetate in hexanes gradient. The product was impure. It was re-purified by SFC to yield 4-[[2-fluoro-6-[2-hydroxy-4-(trifluoromethoxy)phenoxy]-3-(trifluoromethyl)benzoyl]amino]-1-oxido-pyridin-1-ium-2-carboxamide (103.6 mg, 48%) as a white solid. $^1$H NMR (400 MHz, DMSO-d6) δ 11.58 (s, 1H), 10.63 (s, 1H), 10.60 (d, J=4.5 Hz, 1H), 8.56 (d, J=3.2 Hz, 1H), 8.38 (d, J=7.2 Hz, 1H), 8.28 (d, J=4.5 Hz, 1H), 7.88 (dd, J=7.2, 3.2 Hz, 1H), 7.83 (t, J=8.6 Hz, 1H), 7.31 (d, J=8.8 Hz, 1H), 6.96 (d, J=2.8 Hz, 1H), 6.93-6.83 (m, 1H), 6.68 (d, J=8.9 Hz, 1H) ppm. ESI-MS m/z calc. 535.06146, found 536.13 $(M+1)^+$; Retention time (Method C): 2.24 minutes.

Example 62

4-[[2-Fluoro-6-[4-(Trifluoromethoxy)Phenyl]-3-(Trifluoromethyl)Benzoyl]Amino]Pyridine-2-Carboxamide (250)

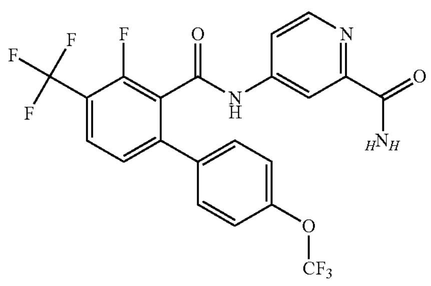

Step 1: 4-[[2-Fluoro-6-[4-(Trifluoromethoxy)Phenyl]-3-(Trifluoromethyl)Benzoyl]Amino]Pyridine-2-Carboxamide (250)

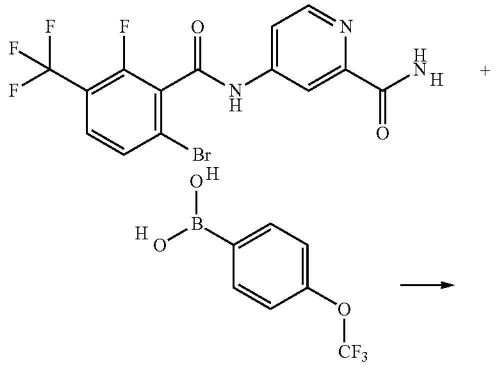

-continued

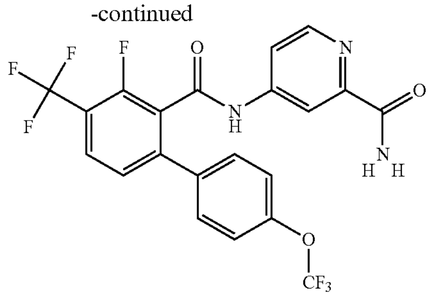

A microwave vial was loaded with 4-[[6-bromo-2-fluoro-3-(trifluoromethyl)benzoyl]amino]pyridine-2-carboxamide (100 mg, 0.246 mmol), [4-(trifluoromethoxy)phenyl]boronic acid (51 mg, 0.248 mmol), potassium carbonate (68 mg, 0.4920 mmol), $Pd(PPh_3)_4$ (28 mg, 0.0242 mmol), water (50 μL), and DMF (500 μL). The reaction mixture was degassed under nitrogen and stirred at 150° C. for 2 hours. The reaction was diluted with DMSO (500 μL), filtered, and purified by reverse phase preparative chromatography using a $C_{18}$ column and a gradient eluent of acetonitrile in water (5 mM HCl) to obtain 4-[[2-fluoro-6-[4-(trifluoromethoxy)phenyl]-3-(trifluoromethyl)benzoyl]amino]pyridine-2-carboxamide (11.4 mg, 9%). ESI-MS m/z calc. 487.0767, found 488.5 $(M+1)^+$; Retention time (Method C): 2.41 minutes. $^1H$ NMR (400 MHz, DMSO-d6) δ 11.40 (s, 1H), 8.51 (d, J=5.5 Hz, 1H), 8.17 (d, J=2.1 Hz, 1H), 8.11 (s, 1H), 8.04 (t, J=7.9 Hz, 1H), 7.71-7.64 (m, 2H), 7.64-7.58 (m, 3H), 7.45 (d, J=8.2 Hz, 2H) ppm.

The compounds set forth in Table 31 were prepared by methods analogous to the preparation of compound 250.

TABLE 31

Additional Compounds Prepared by Methods Analogous to Example 62.

| Cmpd No. | Compound Name | LC/MS | NMR (shifts in ppm) |
|---|---|---|---|
| 251 | 4-[[2-fluoro-6-(4-fluoro-2-methoxy-phenyl)-3-(trifluoromethyl)benzoyl]amino]pyridine-2-carboxamide | ESI-MS m/z calc. 451.09552, found 452.2 (M + 1)+; Retention time (Method B): 1.53 minutes | $^1H$ NMR (400 MHz, DMSO-$d_6$) δ 11.34 (s, 1H), 8.52 (d, J = 5.6 Hz, 1H), 8.24 (d, J = 2.2 Hz, 1H), 8.17 (s, 1H), 7.99 (t, J = 7.8 Hz, 1H), 7.78-7.68 (m, 2H), 7.45 (d, J = 8.1 Hz, 1H), 7.33 (dd, J = 8.5, 6.7 Hz, 1H), 7.00-6.94 (m, 1H), 6.91-6.83 (m, 1H), 3.60 (s, 3H). |

Example 63

4-[[2-(4-Fluoro-2-Methoxy-Phenyl)-5-(Trifluoromethyl)Benzoyl]Amino]Pyridine-2-Carboxamide (252)

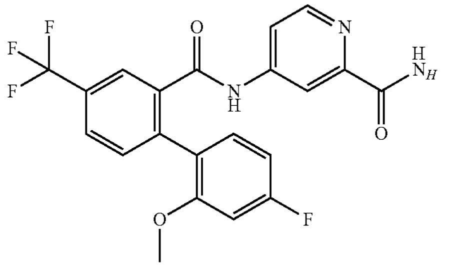

Step 1: Methyl 2-Bromo-5-(Trifluoromethyl)Benzoate

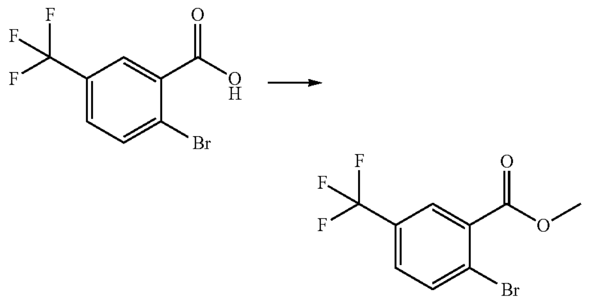

To a suspension of 2-bromo-5-(trifluoromethyl)benzoic acid (5.0 g, 18.59 mmol), N,N-dimethylformamide (144 μL, 1.860 mmol), and DCM (50 mL), under nitrogen and at RT, was added oxalyl chloride (1.6 mL, 18.34 mmol), in a single portion. The reaction was stirred at RT for 2 hours. The reaction mixture was concentrated to dryness under reduced pressure. To the residue was added DCM (50 mL) followed by methanol (7.5 mL, 185.1 mmol) and the solution was stirred at RT for 1 hour. The reaction mixture was evaporated to dryness under reduced pressure and the residue was purified by silica gel column chromatography using a gradient eluent of EtOAc in hexanes to give methyl 2-bromo-5-(trifluoromethyl)benzoate (4.3 g, 82%) as a clear oil. $^1$H NMR (400 MHz, DMSO-d6) δ 8.11 (d, J=2.4 Hz, 1H), 8.02 (dd, J=8.6, 1.1 Hz, 1H), 7.95-7.74 (m, 1H), 3.91 (s, 3H) ppm.

Step 2: Methyl 2-(4-Fluoro-2-Methoxy-Phenyl)-5-(Trifluoromethyl)Benzoate

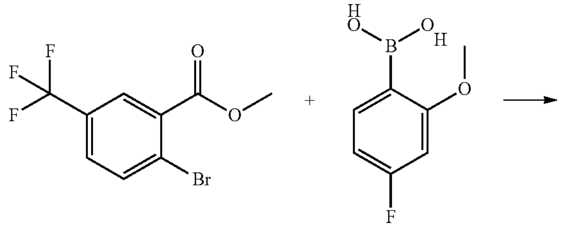

-continued

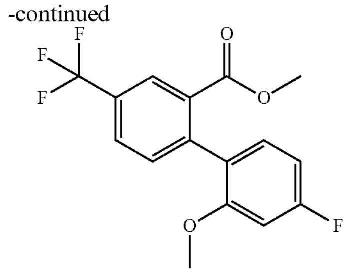

A mixture of methyl 2-bromo-5-(trifluoromethyl)benzoate (500 mg, 1.77 mmol), (4-fluoro-2-methoxy-phenyl)boronic acid (450 mg, 2.648 mmol), $K_2CO_3$ (488 mg, 3.531 mmol), $Pd(PPh_3)_4$ (41 mg, 0.0355 mmol), DMF (4.5 mL), and water (500 μL) was stirred under nitrogen at 80° C. for 2 hours. The solution was evaporated to dryness under reduced pressure and the residue was purified by silica gel column chromatography using a gradient eluent of EtOAc in hexanes to give methyl 2-(4-fluoro-2-methoxy-phenyl)-5-(trifluoromethyl)benzoate (510 mg, 88%) as a clear oil. $^1$H NMR (400 MHz, DMSO-d6) δ 8.02 (d, J=2.1 Hz, 1H), 8.01-7.95 (m, 1H), 7.57 (d, J=8.0 Hz, 1H), 7.32 (dd, J=8.4, 6.8 Hz, 1H), 6.98 (dd, J=11.3, 2.5 Hz, 1H), 6.89 (td, J=8.5, 2.5 Hz, 1H), 3.68 (s, 3H), 3.66 (s, 3H) ppm.

Step 3: 2-(4-Fluoro-2-Methoxy-Phenyl)-5-(Trifluoromethyl)Benzoic Acid

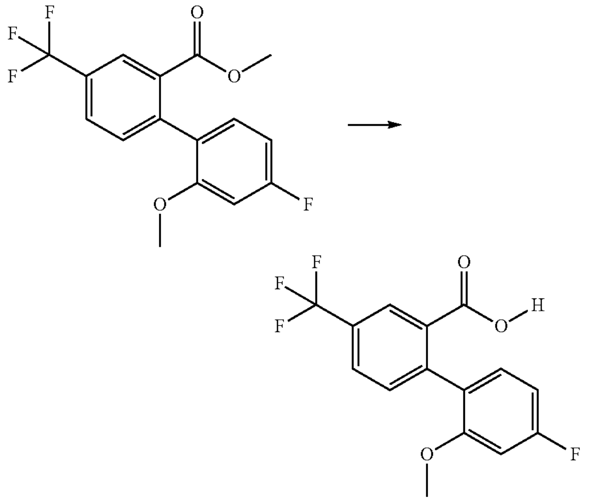

A mixture of methyl 2-(4-fluoro-2-methoxy-phenyl)-5-(trifluoromethyl)benzoate (500 mg, 1.523 mmol), NaOH (609 mg, 15.23 mmol), $H_2O$ (2.5 mL), and THF (2.5 mL) was loaded into a sealed vessel and heated at 100° C. for 2 hours. The reaction mixture was acidified to pH=2 (1.0 N aqueous HCl) and partitioned between water (50 mL) and EtOAc (100 mL). The organic phase was evaporated to dryness under reduced pressure and the residue was purified by silica gel column chromatography using a gradient of EtOAc in hexanes to give 2-(4-fluoro-2-methoxy-phenyl)-5-(trifluoromethyl)benzoic acid (340 mg, 71%) as a white solid. $^1$H NMR (400 MHz, DMSO-d6) δ 12.97 (s, 1H), 8.02 (d, J=2.1 Hz, 1H), 7.93 (dd, J=8.2, 2.1 Hz, 1H), 7.53 (d, J=8.0 Hz, 1H), 7.27 (dd, J=8.4, 6.8 Hz, 1H), 6.97 (dd, J=11.4, 2.5 Hz, 1H), 6.86 (td, J=8.4, 2.4 Hz, 1H), 3.69 (s, 3H) ppm.

Step 4: 4-[[2-(4-Fluoro-2-Methoxy-Phenyl)-5-(Trifluoromethyl)Benzoyl]Amino]Pyridine-2-Carboxamide (252)

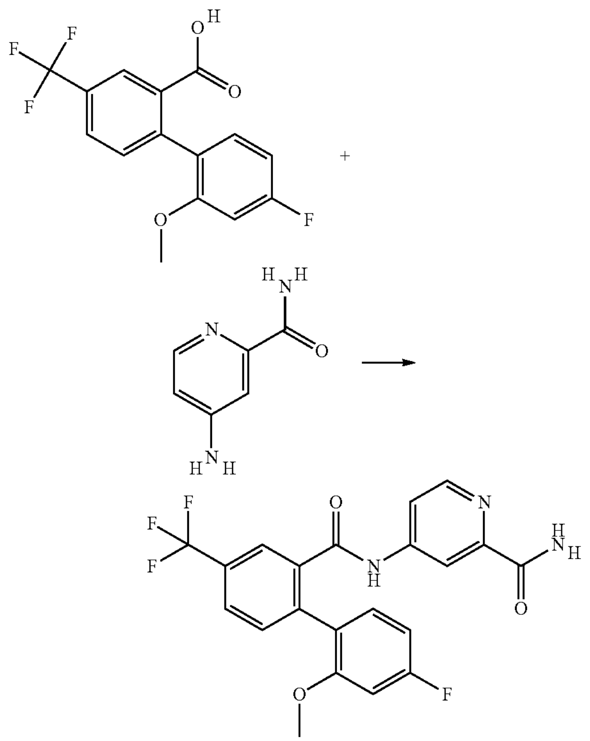

To a stirring solution of 2-(4-fluoro-2-methoxy-phenyl)-5-(trifluoromethyl)benzoic acid (150 mg, 0.477 mmol), DMF (4 μL, 0.0517 mmol), and dichloromethane (2 mL), at 0° C. (ice-bath), was added oxalyl chloride (83 μL, 0.925 mmol) dropwise over 3 minutes. The mixture was stirred at RT for 2 hours and the solvent was evaporated under reduced pressure to afford the acid chloride intermediate. This intermediate was dissolved in DCM (5 mL) and added dropwise to a 0° C. (ice-bath) solution of 4-aminopyridine-2-carboxamide (66 mg, 0.481 mmol), DIEA (208 μL, 1.194 mmol), and dichloromethane (1 mL). The reaction mixture was stirred at RT for 2 hours. The reaction mixture was concentrated under reduced pressure and the residue was purified by silica gel column chromatography using a gradient of MeOH in dichloromethane to give an orange semisolid. This material was triturated with diethyl ether (100 mL) and filtered to give 4-[[2-(4-fluoro-2-methoxy-phenyl)-5-(trifluoromethyl)benzoyl]amino]pyridine-2-carboxamide (16 mg, 8%) as a white solid. ESI-MS m/z calc. 433.10495, found 434.0 $(M+1)^+$; Retention time (Method B): 1.5 minutes. $^1H$ NMR (400 MHz, DMSO-d6) δ 11.05 (s, 1H), 8.51 (d, J=5.7 Hz, 1H), 8.31 (d, J=2.2 Hz, 1H), 8.20 (s, 1H), 8.02 (d, J=2.0 Hz, 1H), 7.97 (dd, J=8.1, 2.0 Hz, 1H), 7.82 (dd, J=5.7, 2.1 Hz, 1H), 7.74 (s, 1H), 7.62 (d, J=8.1 Hz, 1H), 7.37 (dd, J=8.3, 6.8 Hz, 1H), 7.00-6.75 (m, 2H), 3.54 (s, 3H) ppm.

The compounds set forth in Table 32 were prepared by methods analogous to the preparation of compound 252.

TABLE 32

Additional Compounds Prepared by Methods Analogous to Example 63.

| Cmpd No. | Compound Name | LC/MS | NMR (shifts in ppm) |
|---|---|---|---|
| 253 | N-(3-carbamoyl-4-fluoro-phenyl)-2-(4-fluoro-2-methoxy-phenyl)-5-(trifluoromethyl)benzamide | ESI-MS m/z calc. 450.10028, found 451.0 (M + 1)+; Retention time (Method B): 1.56 minutes | 1H NMR (400 MHz, DMSO-d6) δ 10.45 (s, 1H), 7.97-7.87 (m, 3H), 7.75-7.62 (m, 3H), 7.59 (d, J = 7.9 Hz, 1H), 7.33 (dd, J = 8.4, 6.8 Hz, 1H), 7.23 (dd, J = 10.2, 8.9 Hz, 1H), 6.92 (dd, J = 11.3, 2.4 Hz, 1H), 6.86 (td, J = 8.4, 2.4 Hz, 1H), 3.59 (s, 3H). |

Example 64

4-[[2-[4-(Trifluoromethoxy)Phenyl]-4-(Trifluoromethyl)Benzoyl]Amino]Pyridine-2-Carboxamide (254)

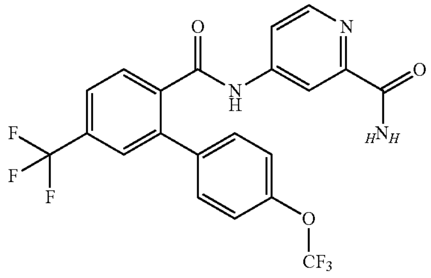

Step 1: 4-[[2-[4-(Trifluoromethoxy)Phenyl]-4-(Trifluoromethyl)Benzoyl]Amino]Pyridine-2-Carboxamide (254)

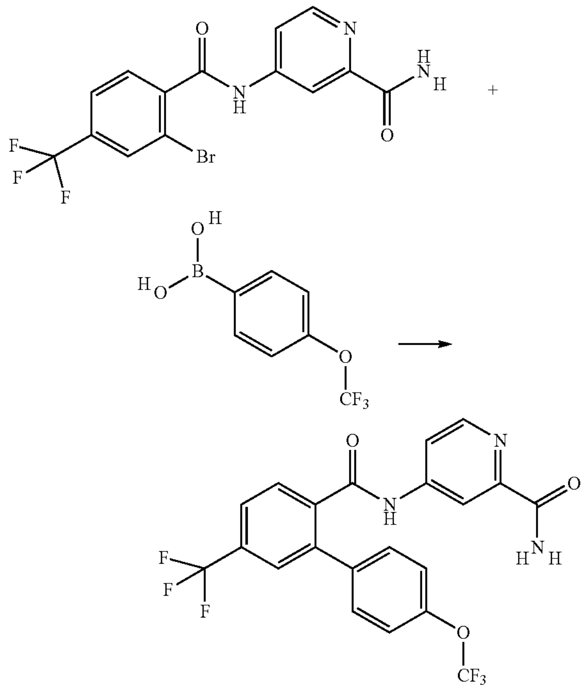

A microwave vial was loaded with 4-[[2-bromo-4-(trifluoromethyl)benzoyl]amino]pyridine-2-carboxamide (100 mg, 0.2576 mmol), [4-(trifluoromethoxy)phenyl]boronic acid (53 mg, 0.2574 mmol), potassium carbonate (71 mg, 0.5137 mmol), $Pd(PPh_3)_4$ (30 mg, 0.0260 mmol), water (50 μL), and DMF (500 μL). The reaction mixture was degassed under nitrogen and stirred at 150° C. for 2 hours. The reaction was diluted with DMSO (500 μL), filtered, and purified by reverse phase preparative chromatography using a $C_{18}$ column and a gradient eluent of acetonitrile in water (5 mM HCl) to obtain 4-[[2-[4-(trifluoromethoxy)phenyl]-4-(trifluoromethyl)benzoyl]amino]pyridine-2-carboxamide (2.0 mg, 2%). ESI-MS m/z calc. 469.08612, found 470.3

$(M+1)^+$; Retention time (Method B): 1.72 minutes. $^1H$ NMR (400 MHz, DMSO-$d_6$) δ 11.10 (s, 1H), 8.49 (d, J=5.5 Hz, 1H), 8.21 (s, 1H), 8.13 (s, 1H), 8.00-7.91 (m, 2H), 7.88 (s, 1H), 7.75-7.64 (m, 2H), 7.64-7.53 (m, 2H), 7.43 (s, 1H), 7.41 (s, 1H) ppm.

Example 65

4-[[2-Bromo-6-[2-Methoxy-4-(Trifluoromethoxy)Phenoxy]-4-(Trifluoromethyl)Benzoyl]Amino]Pyridine-2-Carboxamide (255)

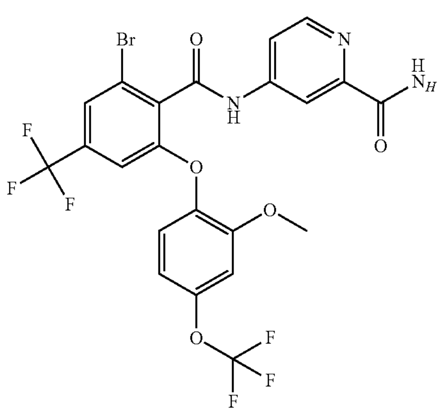

Step 1: 4-[[2-Bromo-6-[2-Methoxy-4-(Trifluoromethoxy)Phenoxy]-4-(Trifluoromethyl)Benzoyl]Amino]Pyridine-2-Carboxamide (255)

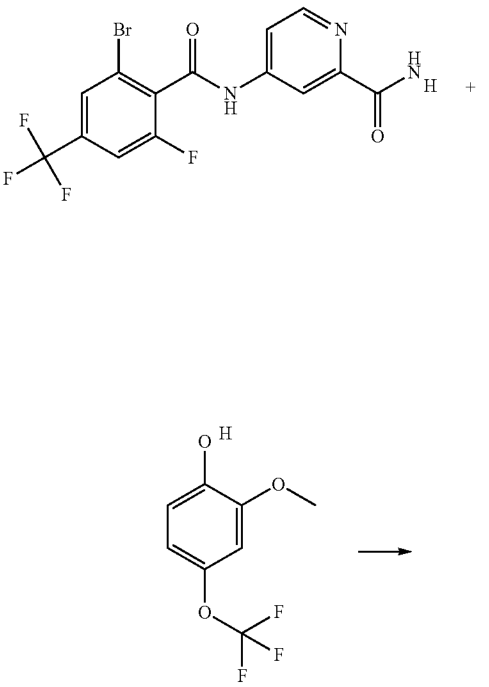

-continued

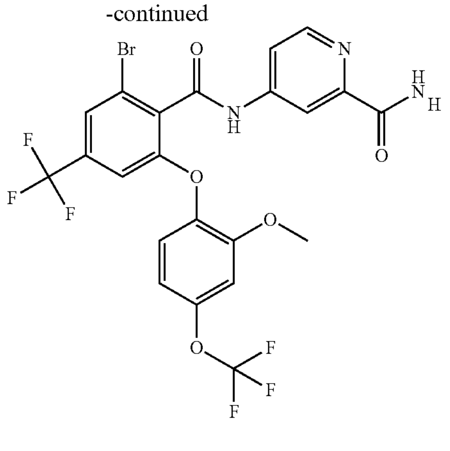

4-[[2-Bromo-6-fluoro-4-(trifluoromethyl)benzoyl]amino]pyridine-2-carboxamide (1.00 g, 2.462 mmol), 2-methoxy-4-(trifluoromethoxy)phenol (564 mg, 2.710 mmol) and $Cs_2CO_3$ (1.60 g, 4.911 mmol) were combined in NMP (15 mL) and heated at 95° C. for 2 hours. The reaction mixture was partitioned between ethyl acetate and water. The organic layer was separated and washed with water and brine. The organic layer was dried over $MgSO_4$, filtered and concentrated. Silica gel chromatography (ethyl acetate/dichloromethane gradient) provided 4-[[2-bromo-6-[2-methoxy-4-(trifluoromethoxy)phenoxy]-4-(trifluoromethyl)benzoyl]amino]pyridine-2-carboxamide (690 mg, 47%). ESI-MS m/z calc. 593.0021, found 595.0 $(M+1)^+$; Retention time (Method B): 1.68 minutes. $^1H$ NMR (400 MHz, DMSO-d6) δ 11.14 (s, 1H), 8.44 (d, J=5.5 Hz, 1H), 8.05 (dd, J=13.5, 2.5 Hz, 2H), 7.93-7.81 (m, 2H), 7.63 (d, J=2.8 Hz, 1H), 7.48 (dd, J=5.6, 2.2 Hz, 1H), 6.86 (d, J=2.5 Hz, 1H), 6.79 (d, J=8.8 Hz, 1H), 6.73 (d, J=8.6 Hz, 1H), 3.50 (s, 3H) ppm.

Example 66

5-[[5-Chloro-2-[[5-(Trifluoromethoxy)-2-Pyridyl]Oxy]Benzoyl]Amino]-2-Fluoro-Benzamide (256)

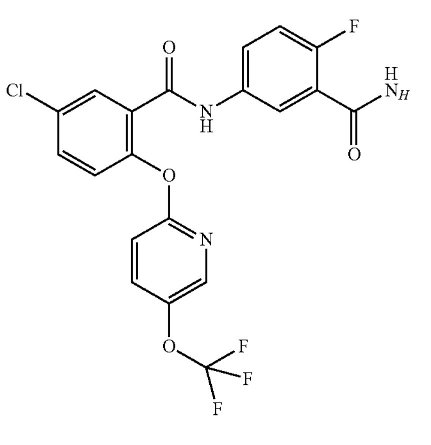

Step 1: Methyl 5-Chloro-2-[[5-(Trifluoromethoxy)-2-Pyridyl]Oxy]Benzoate

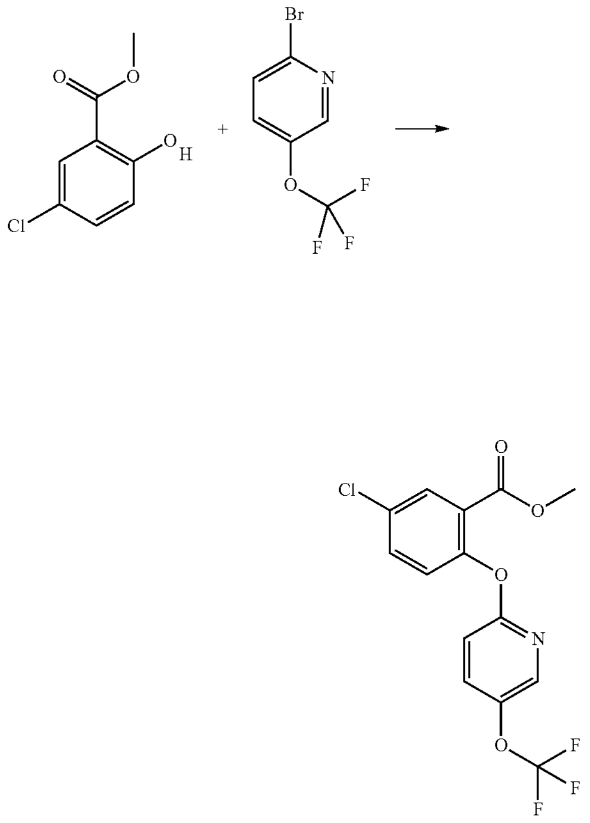

A microwave vial was loaded with methyl 5-chloro-2-hydroxy-benzoate (100 mg, 0.536 mmol), 2-bromo-5-(trifluoromethoxy)pyridine (155 mg, 0.6405 mmol), iodocopper (10 mg, 0.05251 mmol), $K_3PO_4$ (353 mg, 1.071 mmol), and pyridine-2-carboxylic acid (13 mg, 0.1056 mmol). The vial was capped, flushed with nitrogen and anhydrous DMSO (500 μL) was added via syringe. The reaction mixture was heated at 80° C. for 19 hours. The reaction was diluted with DMSO (500 μL), filtered, and purified by reverse phase preparative chromatography using a $C_{18}$ column and a gradient of acetonitrile in water (5 mM HCl) to give methyl 5-chloro-2-[[5-(trifluoromethoxy)-2-pyridyl]oxy]benzoate (58 mg, 31%) as a clear oil. ESI-MS m/z calc. 347.0172, found 347.9 $(M+1)^+$; Retention time (Method B): 1.92 minutes. $^1H$ NMR (400 MHz, DMSO-d6) δ 8.17 (d, J=2.9 Hz, 1H), 8.03-7.95 (m, 1H), 7.90 (d, J=2.7 Hz, 1H), 7.76 (dd, J=8.7, 2.7 Hz, 1H), 7.39 (d, J=8.7 Hz, 1H), 7.25 (d, J=9.0 Hz, 1H), 3.61 (s, 3H) ppm.

Step 2: 5-Chloro-2-[[5-(Trifluoromethoxy)-2-Pyridyl]Oxy]Benzoic Acid

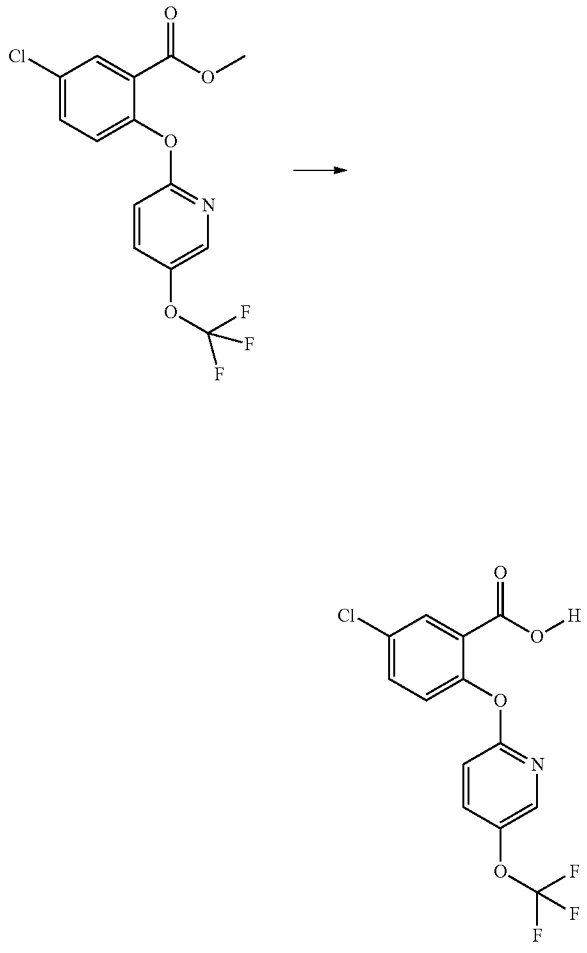 [SMILES: COC(=O)c1cc(Cl)ccc1Oc1ccc(OC(F)(F)F)cn1 ; O=C(O)c1cc(Cl)ccc1Oc1ccc(OC(F)(F)F)cn1]

A mixture of methyl 5-chloro-2-[[5-(trifluoromethoxy)-2-pyridyl]oxy]benzoate (50 mg, 0.141 mmol), NaOH (113 mg, 2.825 mmol), $H_2O$ (500 μL), and THF (500 μL) was loaded into a microwave vessel and heated at 100° C. for 2 hours. The reaction mixture was acidified to pH=2 (1.0 N aqueous HCl) and partitioned between water (50 mL) and EtOAc (100 mL). The organic portion was evaporated to dryness under reduced pressure and the residue was purified by silica gel column chromatography using a gradient of EtOAc in hexanes to give 5-chloro-2-[[5-(trifluoromethoxy)-2-pyridyl]oxy]benzoic acid (32 mg, 67%) as a white solid. ESI-MS m/z calc. 333.00156, found 333.8 $(M+1)^+$; Retention time (Method B): 1.61 minutes. $^1H$ NMR (400 MHz, DMSO-d6) δ 13.17 (s, 1H), 8.17 (d, J=2.9 Hz, 1H), 7.96 (dd, J=9.0, 2.9 Hz, 1H), 7.88 (d, J=2.7 Hz, 1H), 7.72 (dd, J=8.7, 2.7 Hz, 1H), 7.34 (d, J=8.7 Hz, 1H), 7.22 (d, J=9.0 Hz, 1H) ppm.

Step 3: 5-[[5-Chloro-2-[[5-(Trifluoromethoxy)-2-Pyridyl]Oxy]Benzoyl]Amino]-2-Fluoro-Benzamide (256)

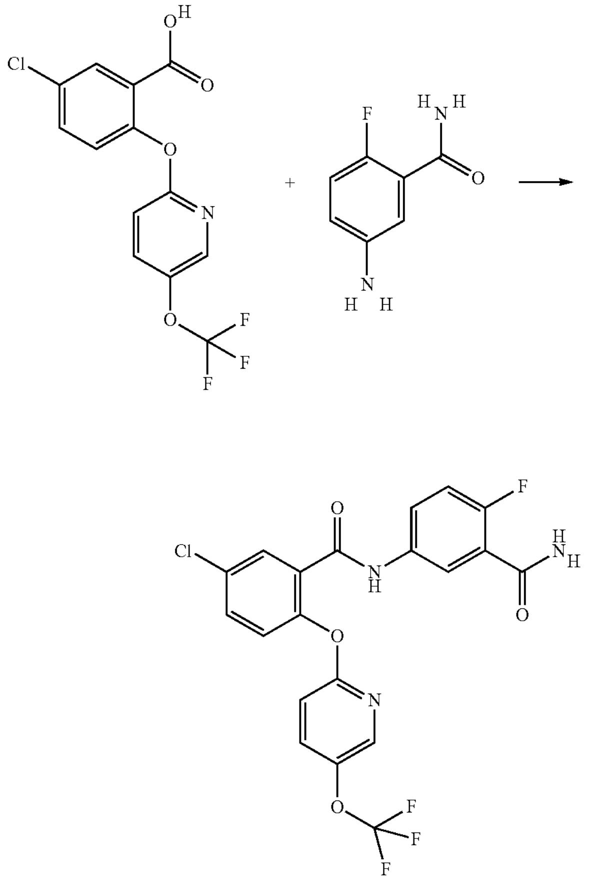

To a stirring solution of 5-chloro-2-[[5-(trifluoromethoxy)-2-pyridyl]oxy]benzoic acid (50 mg, 0.147 mmol), N,N-dimethylformamide (0.6 μL, 0.00775 mmol), and DCM (500 μL) was added oxalyl chloride (130 μL, 1.490 mmol) portion wise over 3 minutes. The mixture was stirred at RT for 2 hours and the solvent was evaporated under reduced pressure to afford the acid chloride intermediate. The intermediate was dissolved in DCM (200 μL) and added dropwise to a 0° C. (ice-bath) solution of 5-amino-2-fluoro-benzamide (34 mg, 0.221 mmol), $Et_3N$ (52 μL, 0.373 mmol), HATU (56 mg, 0.147 mmol), and DCM (500 μL). The reaction mixture was stirred at RT for 2 hours. The reaction mixture was concentrated under reduced pressure and the residue was purified by silica gel column chromatography using a gradient of MeOH in dichloromethane to give an orange semisolid. This material was triturated with diethyl ether (100 mL) and filtered to give 5-[[5-chloro-2-[[5-(trifluoromethoxy)-2-pyridyl]oxy]benzoyl]amino]-2-fluoro-benzamide (38 mg, 53%) as a white solid. ESI-MS m/z calc. 469.04526, found 469.9 $(M+1)^+$; Retention time (Method B): 1.57 minutes. $^1H$ NMR (400 MHz, DMSO-d6) δ 10.54 (s, 1H), 8.18 (d, J=3.0 Hz, 1H), 7.92 (dd, J=9.0, 2.9 Hz, 1H), 7.88 (dd, J=6.5, 2.7 Hz, 1H), 7.76 (d, J=2.7 Hz, 1H), 7.64 (dtt, J=7.3, 4.5, 2.7 Hz, 4H), 7.38 (d, J=8.7 Hz, 1H), 7.25-7.12 (m, 2H) ppm.

Example 67

4-[[3-Cyclobutyl-6-[2-Methoxy-4-(Trifluoromethoxy)Phenoxy]-2-Methyl-Benzoyl]Amino]Pyridine-2-Carboxamide (257)

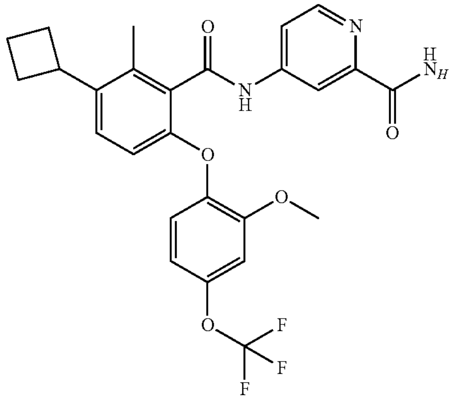

Step 1: Methyl 3-Cyclobutyl-6-[2-Methoxy-4-(Trifluoromethoxy)Phenoxy]-2-Methyl-Benzoate

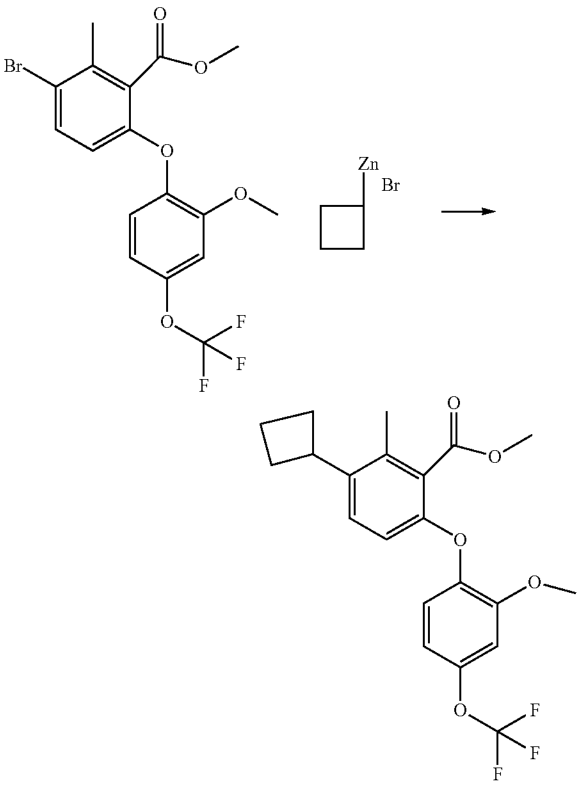

To a vial charged with methyl 3-bromo-6-[2-methoxy-4-(trifluoromethoxy)phenoxy]-2-methyl-benzoate (75 mg, 0.172 mmol), palladium tritert-butylphosphane (4 mg, 0.00783 mmol), and THF (0.5 mL) under an atmosphere of $N_2$ at 0° C. was added bromo(cyclobutyl)zinc (448 μL of 0.5 M, 0.2240 mmol) in THF slowly and the reaction mixture was gradually warmed to RT over 1 h. Stirring was continued at RT for 30 minutes. The reaction mixture was quenched with 1N HCl, and the aq. layer was extracted with DCM (3×). The combined organic layers were dried over $Na_2SO_4$, filtered and concentrated under reduced pressure. The residue was purified by silica gel chromatography using a gradient of ethyl acetate in hexanes to yield methyl 3-cyclobutyl-6-[2-methoxy-4-(trifluoromethoxy)phenoxy]-2-methyl-benzoate (65 mg, 87%). $^1H$ NMR (400 MHz, Chloroform-d) δ 7.15 (d, J=8.6 Hz, 1H), 6.92 (d, J=8.8 Hz, 1H), 6.85-6.81 (m, 1H), 6.75 (ddt, J=8.7, 2.7, 1.1 Hz, 1H), 6.58 (d, J=8.5 Hz, 1H), 3.85 (s, 3H), 3.83 (s, 3H), 3.59 (p, J=8.8 Hz, 1H), 2.41-2.28 (m, 2H), 2.20 (s, 3H), 2.15-1.95 (m, 3H), 1.89-1.74 (m, 1H) ppm. ESI-MS m/z calc. 410.1341, found 411.28 $(M+1)^+$; Retention time (Method A): 0.88 minutes.

Step 2: 3-Cyclobutyl-6-[2-Methoxy-4-(Trifluoromethoxy)Phenoxy]-2-Methyl-Benzoic Acid

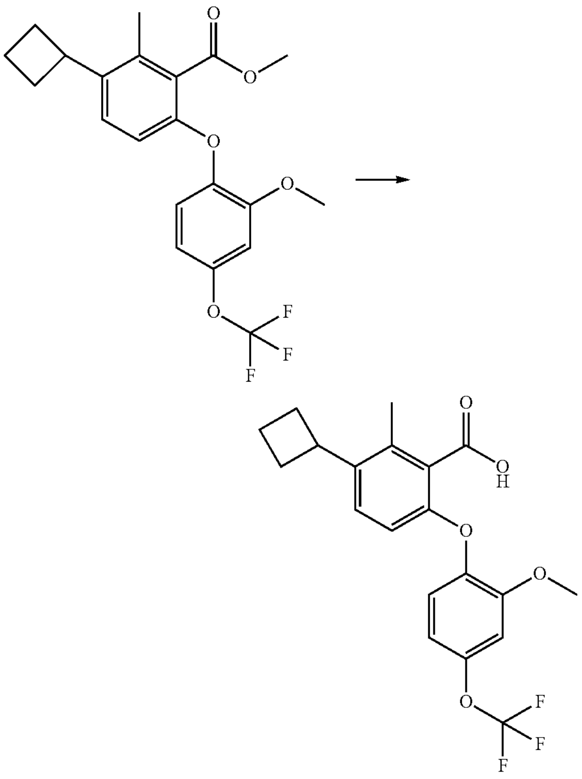

To a solution of methyl 3-cyclobutyl-6-[2-methoxy-4-(trifluoromethoxy)phenoxy]-2-methyl-benzoate (63 mg, 0.146 mmol) in DMSO (2 mL) was added lithium hydroxide monohydrate (75 mg, 1.787 mmol) in water (1.5 mL) and mixture was heated at 140° C. for 4 hours. After cooling to RT, 1 N HCl was added to acidify the mixture and it was extracted with DCM (3×). The combined organics were dried over $Na_2SO_4$, and concentrated under reduced pressure to give 3-cyclobutyl-6-[2-methoxy-4-(trifluoromethoxy)phenoxy]-2-methyl-benzoic acid (52 mg, 83%). ESI-MS m/z calc. 396.11847, found 397.27 $(M+1)^+$; Retention time (Method A): 0.84 minutes.

Step 3: 4-[[3-Cyclobutyl-6-[2-Methoxy-4-(Trifluoromethoxy)Phenoxy]-2-Methyl-Benzoyl]Amino] Pyridine-2-Carboxamide (257)

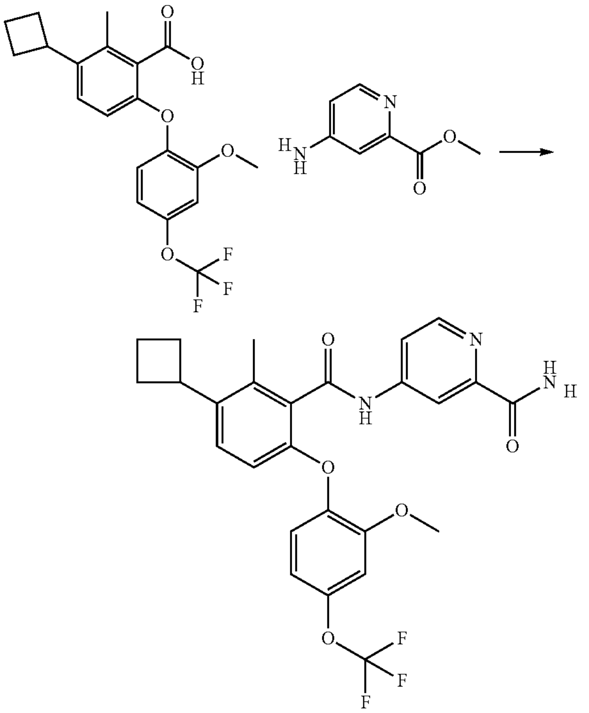

To a solution of 3-cyclobutyl-6-[2-methoxy-4-(trifluoromethoxy)phenoxy]-2-methyl-benzoic acid (50 mg, 0.126 mmol) in DCM (1.5 mL) cooled in an ice bath was added DMF (1.3 μL, 0.0168 mmol) followed by the drop wise addition of oxalyl chloride (22 μL, 0.252 mmol). The mixture was stirred at on ice for 10 minutes then at RT for 2 h. The reaction was concentrated under reduced pressure and flushed with $N_2$ to afford the acid chloride, which was taken directly into the next step. A solution of methyl 4-aminopyridine-2-carboxylate (19 mg, 0.1249 mmol) and DIEA (56 μL, 0.321 mmol) in DCM (1.5 mL) was cool on ice and the crude acid chloride in DCM (1.5 mL) was added drop wise. The ice bath was removed and the reaction mixture was stirred at RT overnight. The reaction was quenched into water and extract with DCM (3×). The combined organics were dried over $Na_2SO_4$, filter and concentrated under reduced pressure. The major product was isolated by silica gel column chromatography using a gradient of ethyl acetate in hexanes which was used directly in the next step. The isolated material was treated with $NH_3$ (7 mL of 7 M, 49.00 mmol) in methanol for 16 hours. The solvent was removed under reduced pressure to give 4-[[3-cyclobutyl-6-[2-methoxy-4-(trifluoromethoxy)phenoxy]-2-methyl-benzoyl]amino]pyridine-2-carboxamide (31 mg, 48%). $^1H$ NMR (400 MHz, Chloroform-d) δ 8.71 (s, 1H), 8.49 (d, J=5.6 Hz, 1H), 8.36 (s, 1H), 7.87 (d, J=2.1 Hz, 2H), 7.18 (d, J=8.6 Hz, 1H), 7.13-7.01 (m, 1H), 6.84 (d, J=7.6 Hz, 2H), 6.56 (d, J=8.6 Hz, 1H), 5.48 (s, 1H), 3.85 (s, 3H), 3.62 (p, J=9.1 Hz, 1H), 2.34 (s, 4H), 2.18-1.93 (m, 3H), 1.90-1.73 (m, 1H), 1.25 (s, 1H) ppm. ESI-MS m/z calc. 515.1668, found 516.4 $(M+1)^+$; Retention time (Method B): 1.87.

Example 68

4-[[2-[2-Methoxy-4-(Trifluoromethoxy)Phenoxy]-4-[4-(Trifluoromethyl)Cyclohexyl]Benzoyl]Amino] Pyridine-2-Carboxamide (Two Diastereoisomers) (158)

158-a

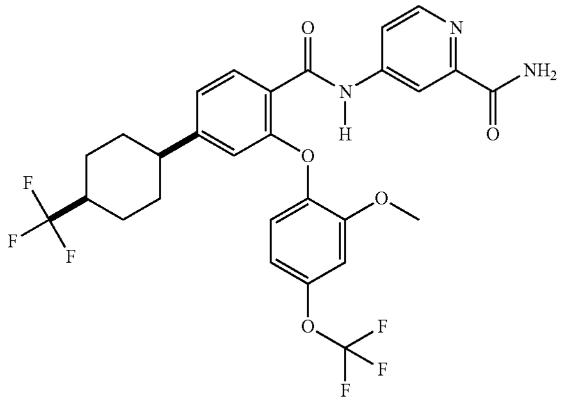

158-b

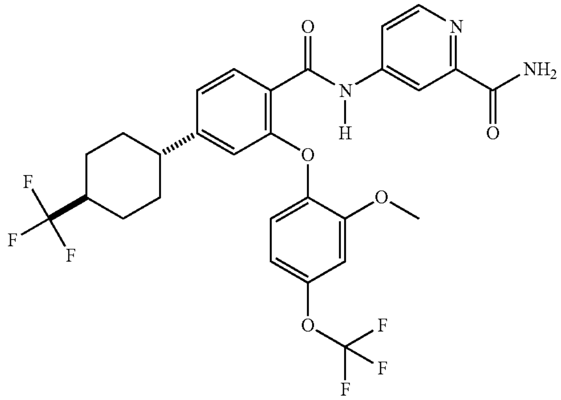

Step 1. 4-[[2-[2-Methoxy-4-(Trifluoromethoxy)Phenoxy]-4-[4-(Trifluoromethyl)Cyclohexen-1-Yl]Benzoyl]Amino]Pyridine-2-Carboxamide

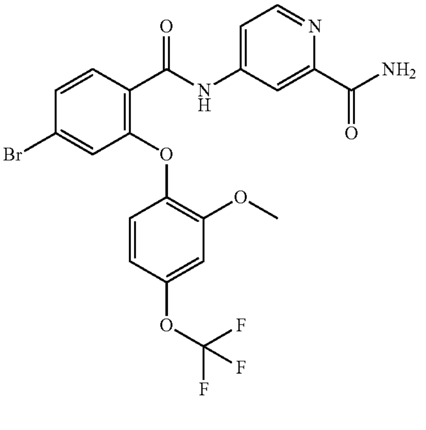

+

-continued

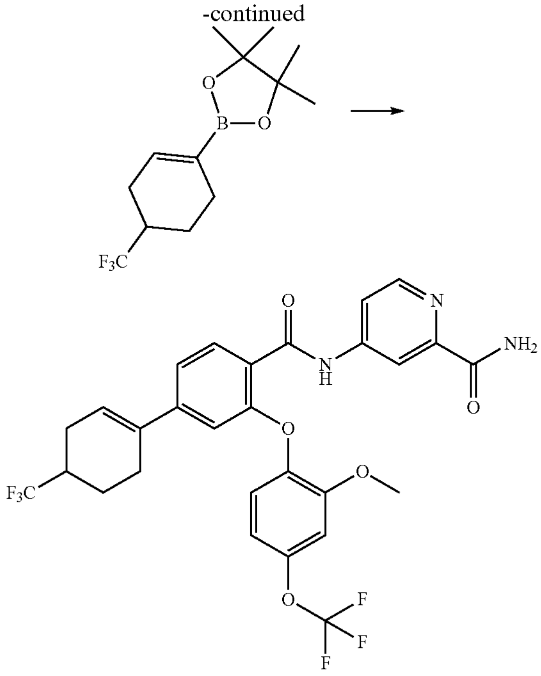

A 4-mL vial charged with 4-[[4-bromo-2-[2-methoxy-4-(trifluoromethoxy)phenoxy]benzoyl]amino]pyridine-2-carboxamide (30 mg, 0.057 mmol), 4,4,5,5-tetramethyl-2-[4-(trifluoromethyl)cyclohexen-1-yl]-1,3,2-dioxaborolane (31.5 mg, 0.114 mmol), $K_2CO_3$ (8 mg, 0.06 mmol), Pd(dppf)$Cl_2$.DCM (5 mg, 0.006 mmol) in dioxane (500 μL) and water (50 μL) was flushed with nitrogen and heated at 100° C. for 16 hours. The reaction mixture was filtered and purified by HPLC ($CH_3CN$/5 mM HCl) to provide 4-[[2-[2-methoxy-4-(trifluoromethoxy)phenoxy]-4-[4-(trifluoromethyl)cyclohexen-1-yl]benzoyl]amino]pyridine-2-carboxamide (33 mg, 97%). ESI-MS m/z calc. 584.48, found 585.1 $(M+1)^+$; Retention time (Method B): 1.94 minutes.

Step 2. 4-[[2-[2-Methoxy-4-(Trifluoromethoxy)Phenoxy]-4-[4-(Trifluoromethyl)Cyclohexyl]Benzoyl]Amino]Pyridine-2-Carboxamide (Two Diastereoisomers) (158)

4-[[2-[2-Methoxy-4-(trifluoromethoxy)phenoxy]-4-[4-(trifluoromethyl)cyclohexen-1-yl]benzoyl]amino]pyridine-2-carboxamide (20 mg, 0.034 mmol) was dissolved in ethyl acetate (500 μL) and methanol (500 μL) and treated with 10% Pd/C (10 mg, 0.009 mmol). The mixture was degassed with a flow of nitrogen for 2 minutes, and then stirred at room temperature under hydrogen atmosphere (balloon) for 16 hours. The reaction mixture was filtered and purified HPLC (1-99% $CH_3CN$/5 mM HCl) to provide the two diastereomers. It is appreciated that both diastereomers of 4-[[2-[2-methoxy-4-(trifluoromethoxy)phenoxy]-4-[4-(trifluoromethyl)cyclohexyl]benzoyl]amino]pyridine-2-carboxamide (158) were isolated and that those diastereomers have the structure of compounds 158-a and 158-b (above). However, the relative stereochemistry of the first and second eluting diastereomers was not determined.

Diastereomer 1: 4-[[2-[2-methoxy-4-(trifluoromethoxy)phenoxy]-4-[4-(trifluoromethyl)cyclohexyl]benzoyl]amino]pyridine-2-carboxamide (8.5 mg, 42%). ESI-MS m/z calc. 597.17, found 598.2 $(M+1)^+$; Retention time (Method B): 2.02 minutes. $^1H$ NMR (400 MHz, DMSO-$d_6$) δ 10.85 (s, 1H), 8.51 (d, J=5.6 Hz, 1H), 8.33 (d, J=2.2 Hz, 1H), 8.14 (s, 1H), 7.87 (dd, J=5.6, 2.2 Hz, 1H), 7.71-7.60 (m, 2H), 7.22 (d, J=8.8 Hz, 1H), 7.19-7.12 (m, 2H), 6.99 (d, J=8.8 Hz, 1H), 6.65 (d, J=1.5 Hz, 1H), 3.74 (s, 3H), 2.78 (s, 1H), 2.48 (m, 1H, obscured by solvent peak), 1.70 (d, J=8.6 Hz, 8H) ppm.

Diastereomer 2: 4-[[2-[2-methoxy-4-(trifluoromethoxy)phenoxy]-4-[4-(trifluoromethyl)cyclohexyl]benzoyl]amino]pyridine-2-carboxamide (4.5 mg, 22%). ESI-MS m/z calc. 597.17, found 598.3 $(M+1)^+$; Retention time (Method B): 2.08 minutes. $^1H$ NMR (400 MHz, DMSO-$d_6$) δ 10.90 (s, 1H), 8.51 (d, J=5.6 Hz, 1H), 8.34 (d, J=2.1 Hz, 1H), 8.18 (s, 1H), 7.87 (dd, J=5.7, 2.2 Hz, 1H), 7.72 (s, 1H), 7.62 (d, J=7.9 Hz, 1H), 7.28-7.06 (m, 3H), 6.98 (d, J=8.8 Hz, 1H), 6.70 (s, 1H), 3.75 (s, 3H), 2.43-2.23 (m, 1H), 2.02-1.73 (m, 4H), 1.58-1.28 (m, 4H) ppm.

Example 69

4-[[2,3-Difluoro-6-[2-Methoxy-4-(Trifluoromethoxy)Phenoxy]Benzoyl]Amino]Pyridine-2-Carboxamide (259)

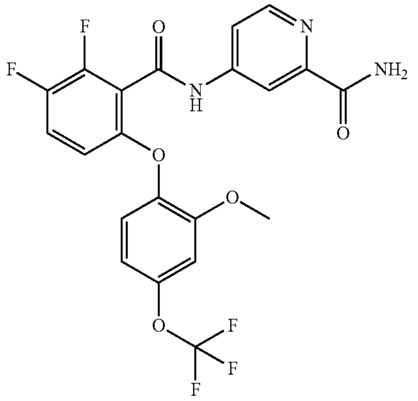 [SMILES: COc1cc(OC(F)(F)F)ccc1Oc1ccc(F)c(F)c1C(=O)Nc1ccnc(C(N)=O)c1]

Step 1: 2,3-Difluoro-6-[2-Methoxy-4-(Trifluoromethoxy)Phenoxy]Benzoic Acid

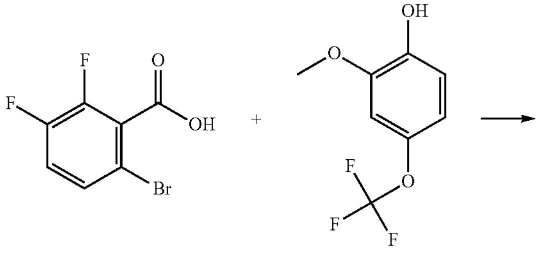

-continued

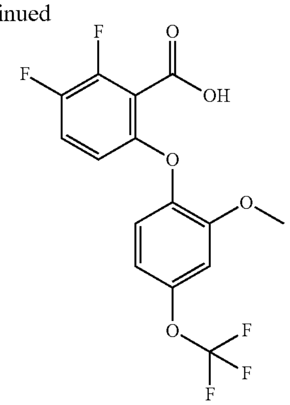

6-Bromo-2,3-difluoro-benzoic acid (2.97 g, 12.5 mmol) and 2-methoxy-4-(trifluoromethoxy)phenol (3.28 g, 15.8 mmol) were dissolved in toluene (60 mL) and the solution was purged with nitrogen (3×vacuum/nitrogen backfill). $Cs_2CO_3$ (8.22 g, 25.2 mmol) was added and the mixture was stirred for 5 minutes. Copper (I) iodide (486 mg, 2.55 mmol) was added and the mixture again purged with nitrogen (3×). The mixture was stirred at 100° C. overnight. After cooling to room temperature, the mixture was acidified to pH 2 with 1 M aqueous HCl and partitioned between ethyl acetate and water. The layers were separated and the aqueous layer was extracted with additional ethyl acetate. The combined organic layers were washed with brine and aqueous $Na_2S2O_3$, dried over $MgSO_4$ and concentrated in vacuo. Silica gel chromatography (0-5% methanol/dichloromethane) provided 2,3-difluoro-6-[2-methoxy-4-(trifluoromethoxy)phenoxy]benzoic acid (1.93 g, 42%). ESI-MS m z calc. 364.04, found 363.3 $(M-1)^-$; LC/MS retention time (Method F): 0.55 minutes. $^1H$ NMR (500 MHz, $CDCl_3$) δ 7.17 (td, J=9.3, 8.4 Hz, 1H), 7.13-7.09 (m, 1H), 6.85 (qt, J=2.7, 1.3 Hz, 2H), 6.50 (ddd, J=9.3, 3.5, 2.0 Hz, 1H), 3.81 (s, 3H) ppm.

Step 2: Methyl 4-[[2,3-Difluoro-6-[2-Methoxy-4-(Trifluoromethoxy)Phenoxy]Benzoyl]Amino]Pyridine-2-Carboxylate A solution of 2,3-difluoro-6-[2-methoxy-4-(trifluoromethoxy)phenoxy]benzoic acid (306 mg, 0.840 mmol) and DMF (5 μL, 0.07 mmol) in dichloromethane (7.5 mL) at 0° C. was treated dropwise with oxalyl chloride (190 μL, 2.18 mmol). The mixture was allowed to warm to room temperature and stirred for 1 hour. The mixture was then concentrated in vacuo, redissolved in dichloromethane (4.5 mL) and added dropwise to a solution of methyl 4-aminopyridine-2-carboxylate (138 mg, 0.907 mmol) and TEA (300 μL, 2.15 mmol) in dichloromethane (4.5 mL) at 0° C. The mixture was allowed to come to room temperature and stirred overnight. The mixture was partitioned between dichloromethane and water and filtered through a phase separator cartridge. The organic phase was concentrated in vacuo. Silica gel chromatography (0-100% ethyl acetate/heptane) provided methyl 4-[[2,3-difluoro-6-[2-methoxy-4-(trifluoromethoxy)phenoxy]benzoyl]amino]pyridine-2-carboxylate (134 mg, 32%). ESI-MS m z calc. 498.08502, found 499.5 $(M+1)^+$; 497.4 $(M-1)^-$; LC/MS retention time (Method F): 0.91 minutes. $^1H$ NMR (500 MHz, $CDCl_3$) δ 8.98 (s, 1H), 8.68 (d, J=5.5 Hz, 1H), 8.13-8.09 (m, 1H), 8.03 (d, J=2.1 Hz, 1H), 7.23-7.13 (m, 2H), 6.96-6.90 (m, 2H), 6.52 (ddd, J=9.3, 3.5, 1.9 Hz, 1H), 4.01 (s, 3H), 3.92 (s, 3H) ppm.

Step 3: 4-[[2,3-Difluoro-6-[2-Methoxy-4-(Trifluoromethoxy)Phenoxy]Benzoyl]Amino]Pyridine-2-Carboxamide (259)

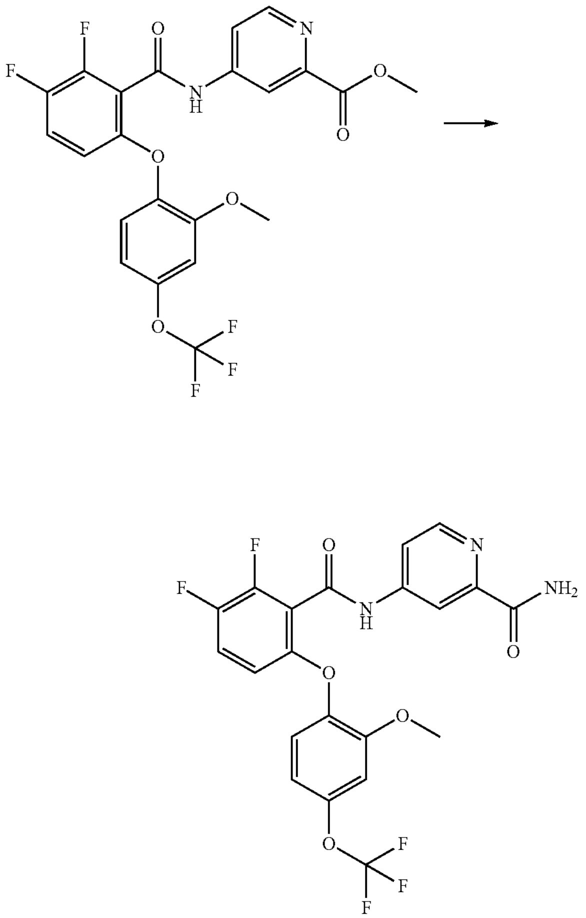

Methyl 4-[[2,3-difluoro-6-[2-methoxy-4-(trifluoromethoxy)phenoxy]benzoyl]amino]pyridine-2-carboxylate (134 mg, 0.269 mmol) was dissolved in a solution of ammonia in methanol (4 mL of 7 M, 28 mmol) and stirred at room temperature overnight. The mixture was concentrated in vacuo and treated with additional ammonia in methanol (4 mL of 7 M, 28 mmol) and stirred at room temperature for 5 hours. The mixture was concentrated in vacuo and purified by reverse phase HPLC (38-53% acetonitrile/0.1% ammonium hydroxide) to provide 4-[[2,3-difluoro-6-[2-methoxy-4-(trifluoromethoxy)phenoxy]benzoyl]amino]pyridine-2-carboxamide (70 mg, 54%) as an off white solid. ESI-MS m z calc. 483.09, found 484.5 $(M+1)^+$; 482.4 $(M-1)^-$; LC/MS retention time (Method E): 3.01 minutes. $^1H$ NMR (500 MHz, $CDCl_3$) δ 8.97 (s, 1H), 8.53 (d, J=5.6 Hz, 1H), 8.39 (dd, J=5.6, 2.2 Hz, 1H), 7.85 (s, 1H), 7.79 (d, J=2.2 Hz, 1H), 7.21-7.14 (m, 2H), 6.92 (d, J=8.1 Hz, 2H), 6.52 (dt, J=9.5, 2.8 Hz, 1H), 5.50 (s, 1H), 3.92 (s, 3H) ppm.

Example 70

4-[[2,3-Difluoro-6-[2-Methoxy-4-(Trifluoromethoxy)Phenoxy]Benzoyl]Amino]-5-Methyl-Pyridine-2-Carboxamide (260)

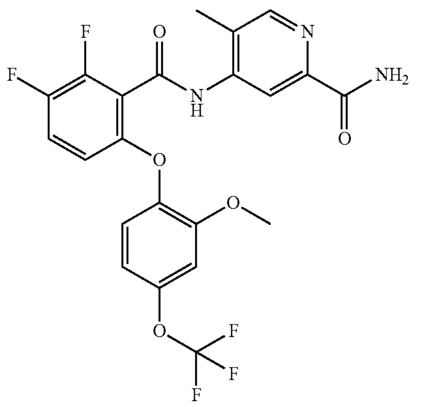 [SMILES: COc1cc(OC(F)(F)F)ccc1Oc1ccc(F)c(F)c1C(=O)Nc1cc(C(N)=O)ncc1C]

Step 1: Methyl 4-[[2,3-Difluoro-6-[2-Methoxy-4-(Trifluoromethoxy)Phenoxy]Benzoyl]Amino]-5-Methyl-Pyridine-2-Carboxylate

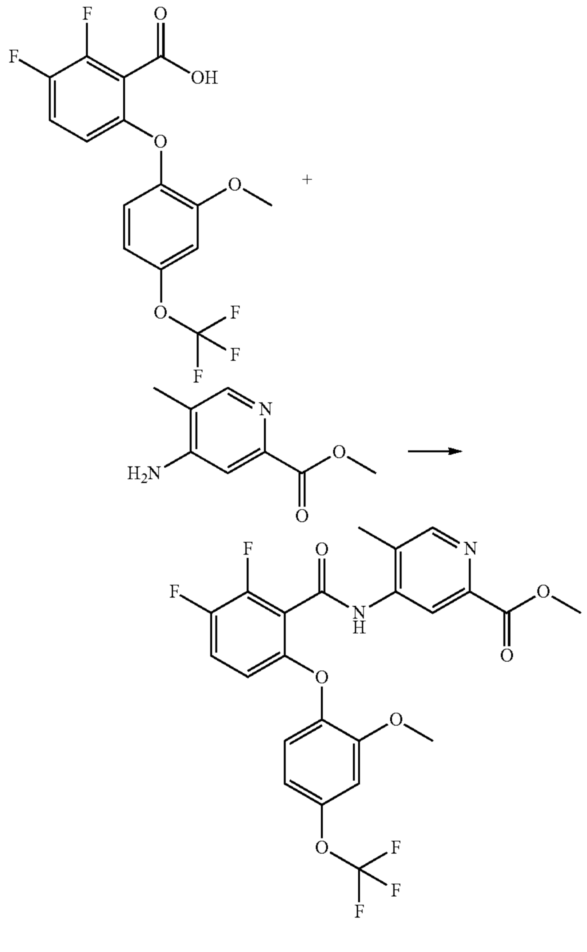

A solution of 2,3-difluoro-6-[2-methoxy-4-(trifluoromethoxy)phenoxy]benzoic acid (293 mg, 0.805 mmol) and DMF (5 μL, 0.07 mmol) in dichloromethane (6.5 mL) at 0° C. was treated dropwise with oxalyl chloride (180 μL, 2.06 mmol). The mixture was allowed to warm to room temperature and stirred for 1 hour. The mixture was concentrated in vacuo, redissolved in dichloromethane (4 mL) and added dropwise to a solution of methyl 4-amino-5-methyl-pyridine-2-carboxylate (136 mg, 0.818 mmol, Preparation 1) and TEA (290 μL, 2.08 mmol) in dichloromethane (4 mL) at 0° C. The solution was allowed to come to room temperature and stirred overnight. The mixture was partitioned between dichloromethane and water and filtered through a phase separator cartridge. The organic phase was concentrated in vacuo. Silica gel chromatography (0-100% ethyl acetate/heptane) provided methyl 4-[[2,3-difluoro-6-[2-methoxy-4-(trifluoromethoxy)phenoxy]benzoyl]amino]-5-methyl-pyridine-2-carboxylate (120 mg, 29%). ESI-MS m z calc. 512.10, found 511.4 $(M-1)^-$; LC/MS retention time (Method F): 0.93 minutes. $^1H$ NMR (500 MHz, $CDCl_3$) δ 9.07 (s, 1H), 8.51 (s, 2H), 7.17 (dd, J=8.7, 5.7 Hz, 2H), 6.95-6.88 (m, 2H), 6.48-6.44 (m, 1H), 4.01 (s, 3H), 3.79 (s, 3H), 2.25 (s, 3H) ppm.

Step 2: 4-[[2,3-Difluoro-6-[2-Methoxy-4-(Trifluoromethoxy)Phenoxy]Benzoyl]Amino]-5-Methyl-Pyridine-2-Carboxamide (260)

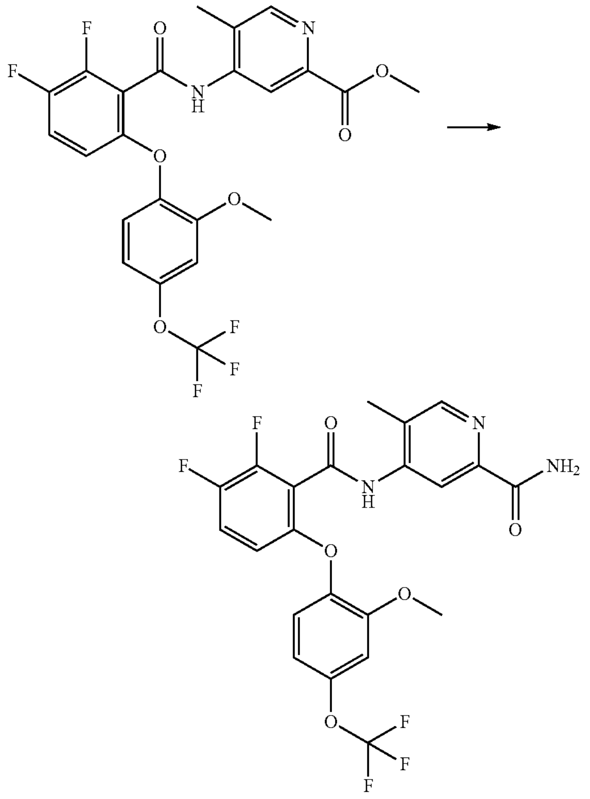

Methyl 4-[[2,3-difluoro-6-[2-methoxy-4-(trifluoromethoxy)phenoxy]benzoyl]amino]-5-methyl-pyridine-2-carboxylate (120 mg, 0.234 mmol) was dissolved in a solution of ammonia in methanol (3.5 mL of 7 M, 24.5 mmol) and stirred at room temperature overnight. The mixture was concentrated in vacuo and purified by reverse phase HPLC (38-53% acetonitrile/0.1% ammonium hydroxide) to provide 4-[[2,3-difluoro-6-[2-methoxy-4-(trifluoromethoxy)phenoxy]benzoyl]amino]-5-methyl-pyridine-2-carboxamide (78 mg, 65%) as an off-white solid. ESI-MS m z calc. 497.10, found 498.2 $(M+1)^+$; 496.4 $(M-1)^-$; LC/MS retention time (Method E): 3.05 minutes. H NMR (500 MHz, $CDCl_3$) δ 8.98 (s, 1H), 8.43 (s, 1H), 8.34 (s, 1H), 7.84 (s, 1H), 7.16 (dd, J=16.1, 8.6 Hz, 2H), 6.93-6.87 (m, 2H), 6.47-6.42 (m, 1H), 5.54 (s, 1H), 3.79 (s, 3H), 2.26 (s, 3H) ppm.

Example 71

4-[[3-Chloro-6-[2-Methoxy-4-(Trifluoromethoxy) Phenoxy]-2-Methyl-Benzoyl]Amino]Pyridine-2-Carboxamide (261)

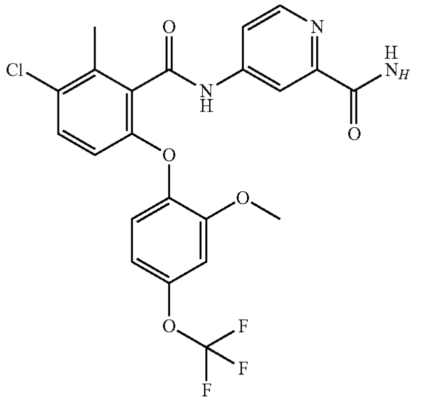

Step 1: 3-Chloro-6-Iodo-2-Methyl-Benzoic Acid

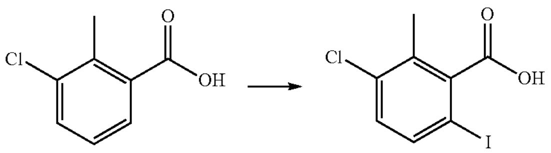

3-Chloro-2-methyl-benzoic acid (4.9 g, 29 mmol), N-iodosuccinimide (9.2 g, 41 mmol) and $Pd(OAc)_2$ (320 mg, 1.43 mmol) were added to a flask, which was evacuated/backfilled with nitrogen (3×). DMF (30 mL) was added and the mixture was heated at 100° C. for 4 hours. The mixture was cooled, then diluted with ethyl acetate (250 mL) and washed with water (5×100 mL). The organic layer was dried over $MgSO_4$, filtered and concentrated in vacuo to provide 3-chloro-6-iodo-2-methyl-benzoic acid (8.22 g, 97%). ESI-MS m z calc. 295.91, found 295.4 $(M-1)^-$; LC/MS retention time (Method F): 0.34 minutes. $^1H$ NMR (500 MHz, DMSO-$d_6$) δ 13.81 (s, 1H), 7.71 (d, J=8.4 Hz, 1H), 7.25 (d, J=8.4 Hz, 1H), 2.31 (s, 3H) ppm.

Step 2: 3-Chloro-6-[2-Methoxy-4-(Trifluoromethoxy)Phenoxy]-2-Methyl-Benzoic Acid

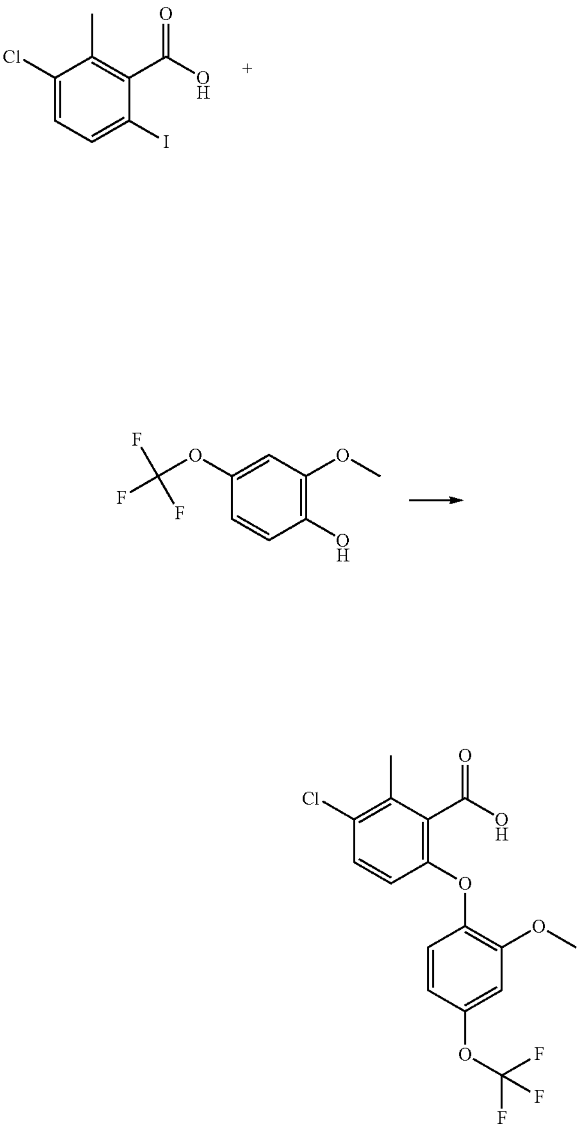

A solution of 3-chloro-6-iodo-2-methyl-benzoic acid (2.21 g, 7.45 mmol) in toluene (10 mL) was treated with copper (I) iodide (152 mg, 0.798 mmol), $Cs_2CO_3$ (4.82 g, 14.8 mmol) and 2-methoxy-4-(trifluoromethoxy)phenol (1.97 g, 9.47 mmol), then degassed via vacuum/nitrogen backfill. The flask was sealed and heated at 100° C. for 5 hours. The mixture was diluted with ethyl acetate and washed with brine (2×) and saturated aqueous $NaHCO_3$ (2×). The organic layer was dried over $MgSO_4$, filtered and concentrated. The residue was purified by silica gel chromatography (0-100% ethyl acetate/heptane) to provide 3-chloro-6-[2-methoxy-4-(trifluoromethoxy)phenoxy]-2-methyl-benzoic acid (2.26 g, 80%). ESI-MS m z calc. 376.03, found 375.5 $(M-1)^-$; LC/MS retention time (Method F): 0.6 minutes.

Step 3: 4-[[3-Chloro-6-[2-Methoxy-4-(Trifluoromethoxy)Phenoxy]-2-Methyl-Benzoyl]Amino]Pyridine-2-Carboxamide (261)

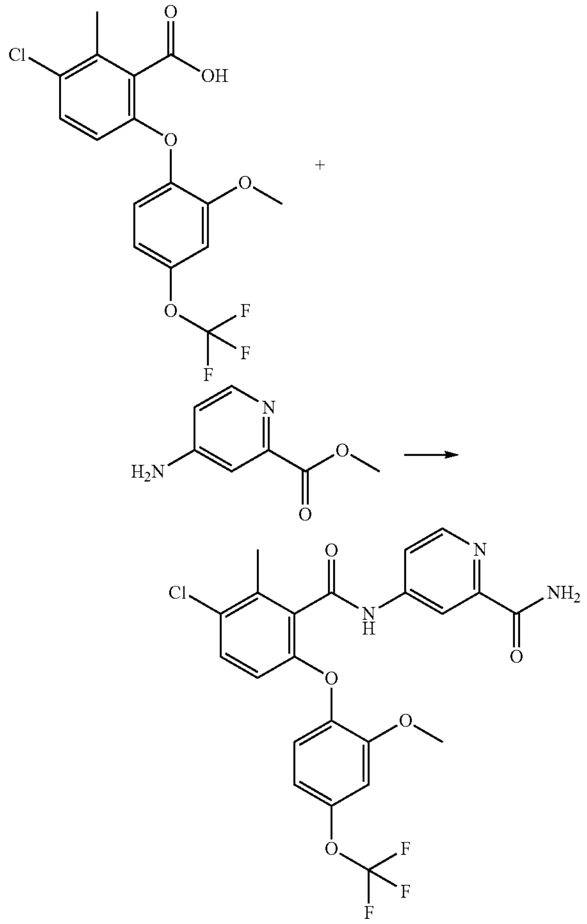

To a solution of 3-chloro-6-[2-methoxy-4-(trifluoromethoxy)phenoxy]-2-methyl-benzoic acid (100 mg, 0.266 mmol) and DMF (2 μL, 0.03 mmol) in dichloromethane (2 mL) at 0° C. was added oxalyl chloride (70 μL, 0.83 mmol) dropwise. The mixture was stirred for 1 hour, then concentrated in vacuo. The residue was redissolved in dichloromethane (2 mL) and added dropwise to a mixture of methyl 4-aminopyridine-2-carboxylate (50 mg, 0.33 mmol) and TEA (220 μL, 1.58 mmol) in dichloromethane (2 mL) at 0° C. The resulting mixture was stirred and warmed to room temperature overnight. The mixture was concentrated in vacuo and treated with a solution of ammonia in methanol (5 mL of 7 M, 35.00 mmol) and stirred at room temperature overnight. The mixture was concentrated in vacuo and the residue purified by reverse phase HPLC (47-95% acetonitrile/0.1% ammonium hydroxide) to provide 4-[[3-chloro-6-[2-methoxy-4-(trifluoromethoxy)phenoxy]-2-methyl-benzoyl]amino]pyridine-2-carboxamide (1.4 mg, 1%) as an off-white solid. ESI-MS m z calc. 495.08, found 496.1 $(M+1)^+$; 494.2 $(M-1)^-$; LC/MS retention time (Method F): 0.91 minutes. $^1H$ NMR (400 MHz, $CDCl_3$) δ 8.92 (s, 1H), 8.54 (d, J=5.6 Hz, 1H), 8.40 (d, J=5.5 Hz, 1H), 7.94 (d, J=2.1 Hz, 1H), 7.33 (d, J=8.9 Hz, 1H), 7.29-7.13 (m, 1H), 6.93-6.84 (m, 2H), 6.56 (dd, J=9.0, 0.7 Hz, 1H), 5.47 (s, 1H), 3.89 (s, 3H), 2.52 (s, 3H) ppm.

Example 72

5-[[2,3,4-Trifluoro-6-[2-Methoxy-4-(Trifluoromethoxy)Phenoxy]Benzoyl]Amino]Pyrimidine-2-Carboxamide (262)

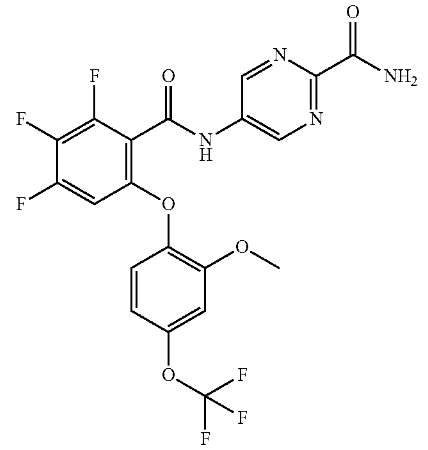 [SMILES: COc1cc(OC(F)(F)F)ccc1Oc1cc(F)c(F)c(F)c1C(=O)Nc1cnc(C(N)=O)nc1]

Step 1: 6-Bromo-2,3,4-Trifluoro-Benzoic Acid

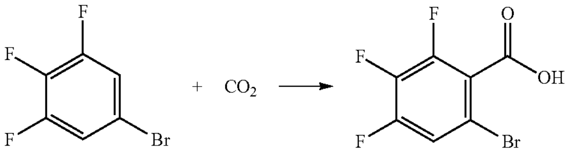 [SMILES: Fc1cc(Br)cc(F)c1F ; "CO2" ; O=C(O)c1c(Br)cc(F)c(F)c1F]

Diisopropylamine (2.87 g, 3.98 mL, 28.4 mmol) was diluted in 2-MeTHF (40 mL) and the solution was cooled to −20° C. A solution of n-butyllithium (10.4 mL of 2.5 M in hexanes, 26 mmol) was added over 15 minutes and the mixture was stirred for 15 minutes at −20° C. The solution was cooled to −78° C. and treated with a solution of 5-bromo-1,2,3-trifluoro-benzene (4.97 g, 23.6 mmol) in 2-MeTHF (2 mL) over 15 minutes. The mixture was stirred for 90 minutes, and then carbon dioxide (8 g, 182 mmol) pellets were added in one portion at −78° C. After the carbon dioxide addition, an exotherm reaching −59° C. was observed and the mixture was cooled back to −78° C. The mixture was warmed to −20° C. over 15 minutes, then treated with water (20 mL) and 3 M aqueous HCl (10 mL) over 5 minutes until the pH was about 1. The phases were separated and the aqueous layer was extracted with MTBE (25 mL). Combined organic layers were extracted with 2 M aqueous NaOH (2×25 mL). The combined aqueous layers were acidified with concentrated aqueous HCl (12 M, 10 mL) to pH=1. The aqueous layer was extracted with MTBE (2×25 mL). The organic layer was washed with 1 M aqueous HCl (30 mL) and brine, dried over anhydrous $Na_2SO_4$, filtered and concentrated in vacuo to provide 6-bromo-2,3,4-trifluoro-benzoic acid (4.8 g, 78%) as a white solid. ESI-MS m z calc. 253.92, found 253.0 $(M-1)^-$; LC/MS retention time (Method O): 1.51 minutes. $^1H$ NMR (400 MHz, DMSO-$d_6$) δ 14.90-14.09 (m, 1H), 7.94-7.84 (m, 1H)

ppm. $^{19}$F NMR (377 MHz, DMSO-$d_6$) δ −131.44 (dd, J=21.8, 6.8 Hz, 1F), −134.62–−134.89 (m, 1F), −159.54–−159.74 (m, 1F) ppm.

Step 2: 2,3,4-Trifluoro-6-[2-Methoxy-4-(Trifluoromethoxy)Phenoxy]Benzoic Acid

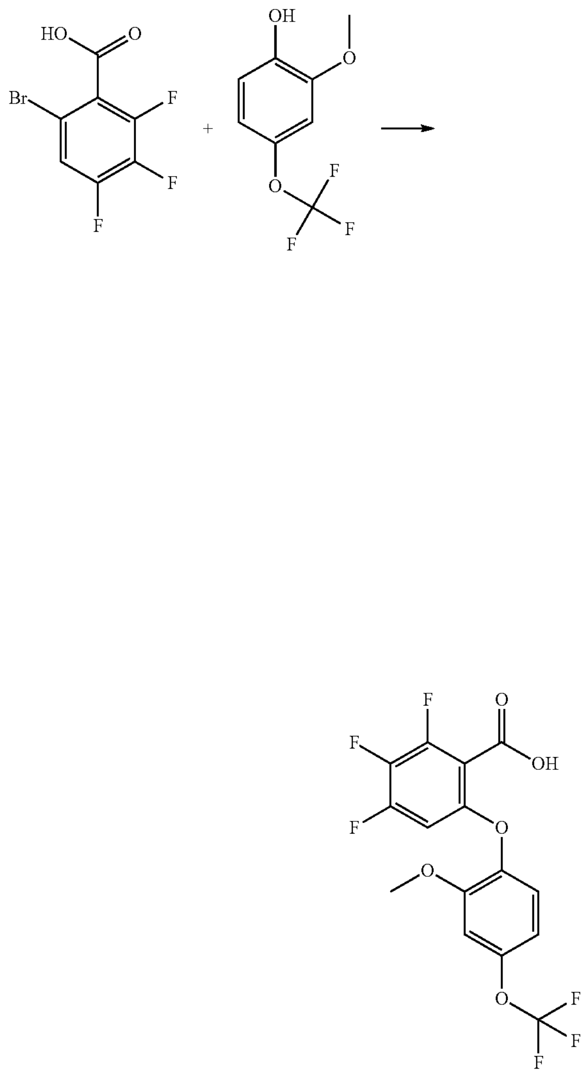

A mixture of 6-bromo-2,3,4-trifluoro-benzoic acid (544 mg, 2.13 mmol), $Cs_2CO_3$ (1.4 g, 4.3 mmol), copper (I) iodide (92 mg, 0.49 mmol) and 2-methoxy-4-(trifluoromethoxy)phenol (675 mg, 3.24 mmol) in toluene (5.5 mL) was flushed with nitrogen and stirred at 100° C. for 6 hours. After cooling to room temperature, water and ethyl acetate were added to the mixture and the layers were separated. The aqueous layer was acidified with concentrated HCl to ~pH 1 and extracted with ethyl acetate (3×). The combined organic phases were dried over $Na_2SO_4$, filtered and concentrated in vacuo. Silica gel chromatography (ethyl acetate/hexane gradient) provided 2,3,4-trifluoro-6-[2-methoxy-4-(trifluoromethoxy)phenoxy]benzoic acid (143.6 mg, 18%). ESI-MS m z calc. 382.03, found 383.1 $(M+1)^+$; LC/MS retention time (Method B): 1.82 minutes.

Step 3: 5-[[2,3,4-Trifluoro-6-[2-Methoxy-4-(Trifluoromethoxy)Phenoxy]Benzoyl]Amino]Pyrimidine-2-Carboxamide (262)

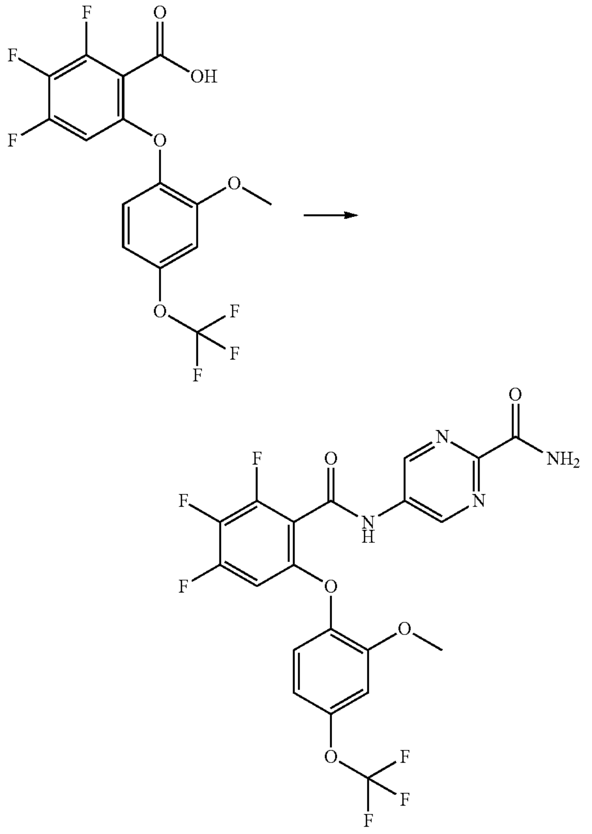

To a solution of 2,3,4-trifluoro-6-[2-methoxy-4-(trifluoromethoxy)phenoxy]benzoic acid (162 mg, 0.424 mmol) and DMF (15 μL, 0.19 mmol) in dichloromethane (3.0 mL) at 0° C. was added oxalyl chloride (105 μL, 1.20 mmol) dropwise under nitrogen atmosphere. The ice bath was removed after 10 minutes and the mixture was stirred at room temperature for 1 hour. The mixture was concentrated in vacuo to afford 2,3,4-trifluoro-6-[2-methoxy-4-(trifluoromethoxy)phenoxy]benzoyl chloride. The acid chloride was dissolved in NMP (1 mL), cooled to 0° C. and treated with a solution of methyl 5-aminopyrimidine-2-carboxylate (131 mg, 0.855 mmol) and DIEA (370 μL, 2.12 mmol) in NMP (1 mL). The mixture was stirred at room temperature for 1 hour, and then heated at 75° C. for 1 hour. Purification by reverse phase HPLC (10-99% acetonitrile/5 mM HCl) provided methyl 5-[[2,3,4-trifluoro-6-[2-methoxy-4-(trifluoromethoxy)phenoxy]benzoyl]amino]pyrimidine-2-carboxylate (75.1 mg, 34%). The solid was treated with a solution of ammonia in methanol (2 mL of 7 M, 14 mmol) and the mixture was stirred at 75° C. for 1.5 hours in a pressure vessel. The mixture was concentrated in vacuo, filtered and purified by reverse phase HPLC (10-99% acetonitrile/5 mM HCl) to provide 5-[[2,3,4-trifluoro-6-[2-methoxy-4-(trifluoromethoxy)phenoxy]benzoyl]amino]pyrimidine-2-carboxamide (37.6 mg, 18%) as a white solid. ESI-MS m z calc. 502.07, found 503.0 $(M+1)^+$; LC/MS retention time (Method C): 2.17 minutes. $^1$H NMR (400 MHz, DMSO-$d_6$) δ 11.50 (s, 1H), 9.15 (s, 2H), 8.13 (s, 1H), 7.74 (s, 1H), 7.26 (d, J=8.8 Hz, 1H), 7.18 (d, J=2.8 Hz, 1H), 7.01-6.95 (m, 1H), 6.95-6.88 (m, 1H), 3.76 (s, 3H) ppm.

Example 73

4-[[2,3-Difluoro-4-Methoxy-6-[2-Methoxy-4-(Trifluoromethoxy)Phenoxy]Benzoyl]Amino]Pyridine-2-Carboxamide (263)

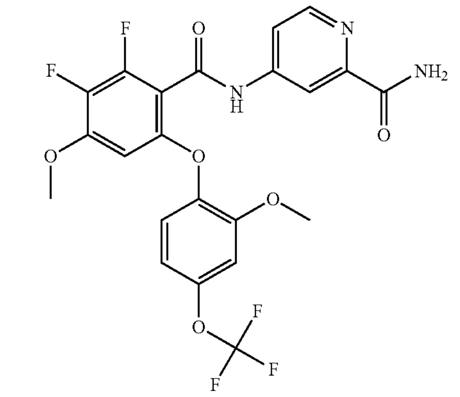 [SMILES: COc1cc(OC(F)(F)F)ccc1Oc1cc(OC)c(F)c(F)c1C(=O)Nc1ccnc(C(N)=O)c1]

Step 1: 6-Bromo-2,3-Difluoro-4-Methoxy-Benzoic Acid

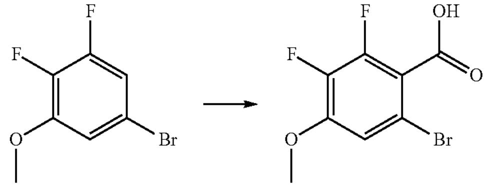

A solution of diisopropylamine (11.6 g, 16 mL, 114 mmol) in THF (160 mL) was cooled to −20° C. n-Butyllithium (42 mL of 2.3 M, 96.6 mmol) was added at such a rate to maintain the internal temperature below −15° C. The cooling bath was then removed and the mixture was allowed to warm to 0° C. and stirred at room temperature for 15 minutes. The mixture was cooled to −78° C. and treated dropwise with a solution of 5-bromo-1,2-difluoro-3-methoxy-benzene (20.0 g, 89.7 mmol) in THF (80 mL) over 30 minutes. The mixture was stirred for an additional 30 minutes at −78° C. Excess solid carbon dioxide was added to the mixture. The mixture was allowed to warm to room temperature and stirred for 30 minutes. A solution of 2 M aqueous HCl (100 mL) was added and the mixture extracted with ethyl acetate (500 mL). The organic phase was dried over $Na_2SO_4$ and concentrated in vacuo. The residue was dissolved in 2 M aqueous NaOH (100 mL) and washed with ethyl acetate (500 mL). The aqueous phase was acidified with 2 M aqueous HCl and extracted with ethyl acetate (2×300 mL). The organic layer was dried over $Na_2SO_4$, filtered and concentrated in vacuo to provide 6-bromo-2,3-difluoro-4-methoxy-benzoic acid (13 g, 54%) as a white solid. ESI-MS m z calc. 265.94, found 264.8 $(M-1)^-$; LC/MS retention time (Method P): 1.67 minutes. $^1H$ NMR (400 MHz, DMSO-$d_6$) δ 14.06 (s, 1H), 7.39 (d, J=6.76 Hz, 1H), 3.93 (s, 3H) ppm.

Step 2: 2,3-Difluoro-4-Methoxy-6-[2-Methoxy-4-(Trifluoromethoxy)Phenoxy]Benzoic Acid

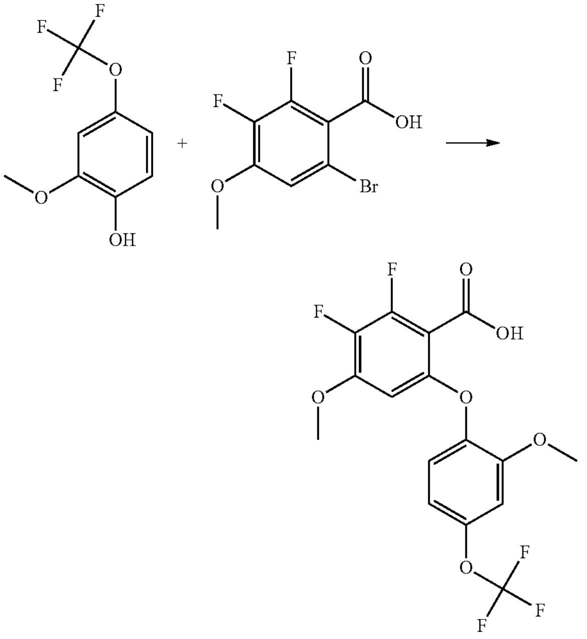

A mixture of 6-bromo-2,3-difluoro-4-methoxy-benzoic acid (1.5 g, 5.6 mmol), 2-methoxy-4-(trifluoromethoxy) phenol (1.0 g, 4.8 mmol) and $Cs_2CO_3$ (1.98 g, 6.08 mmol) in toluene (25 mL) was bubbled with nitrogen for 10 minutes, then copper (I) iodide (375 mg, 1.97 mmol) was added and the mixture heated at 100° C. with vigorous stirring for 30 minutes. The mixture was cooled to room temperature and acidified with aqueous HCl, filtered and the aqueous layer extracted with ethyl acetate (3×50 mL). The combined organic layers were washed with brine, dried over $MgSO_4$, filtered and concentrated. Silica chromatography (0-100% ethyl acetate/hexanes) provided 2,3-difluoro-4-methoxy-6-[2-methoxy-4-(trifluoromethoxy)phenoxy]benzoic acid (488 mg, 22%) as a pale yellow powder. ESI-MS m z calc. 394.05, found 395.5 $(M+1)^+$; 393.6 $(M-1)^-$; LC/MS retention time (Method F): 0.55 minutes. $^1H$ NMR (500 MHz, DMSO-$d_6$) δ 13.48 (s, 1H), 7.18 (d, J=2.7 Hz, 1H), 6.98 (d, J=8.8 Hz, 1H), 6.92 (ddd, J=8.8, 2.7, 1.2 Hz, 1H), 6.54 (dd, J=6.6, 1.9 Hz, 1H), 3.83 (s, 3H), 3.79 (s, 3H) ppm.

Step 3: Methyl 4-[[2,3-Difluoro-4-Methoxy-6-[2-Methoxy-4-(Trifluoromethoxy)Phenoxy]Benzoyl]Amino]Pyridine-2-Carboxylate

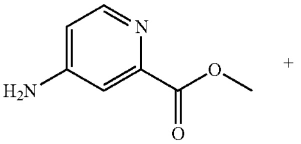

-continued

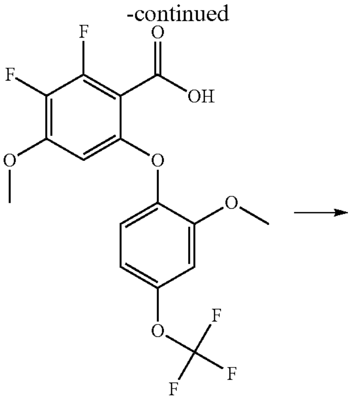

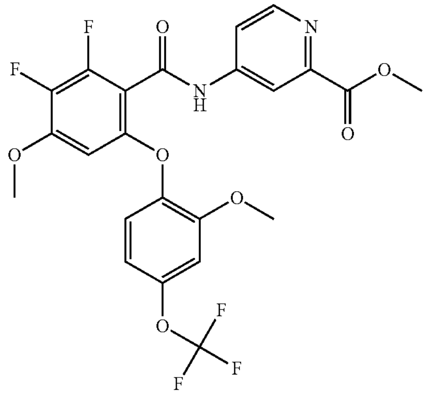

A solution of 2,3-difluoro-4-methoxy-6-[2-methoxy-4-(trifluoromethoxy)phenoxy]benzoic acid (80 mg, 0.20 mmol) was dissolved in dichloromethane (2.7 mL), cooled to 0° C. and treated with oxalyl chloride (47 μL, 0.54 mmol) followed by addition of DMF (1.7 μL, 0.02 mmol). The resulting mixture was stirred for 1 hour and concentrated in vacuo. The residue was dissolved in dichloromethane (2.7 mL) and methyl 4-aminopyridine-2-carboxylate (31 mg, 0.20 mmol) and triethylamine (63 μL, 0.45 mmol) added. The resulting mixture was stirred at room temperature overnight, and then concentrated in vacuo and purified by silica gel chromatography (0-100% ethyl acetate/heptane) to provide methyl 4-[[2,3-difluoro-4-methoxy-6-[2-methoxy-4-(trifluoromethoxy)phenoxy]benzoyl]amino]pyridine-2-carboxylate (24 mg, 22%) as a white powder. ESI-MS m z calc. 528.10, found 529.5 $(M+1)^+$; 527.6 $(M-1)^-$; LC/MS retention time (Method F): 0.89 minutes.

Step 4: 4-[[2,3-Difluoro-4-Methoxy-6-[2-Methoxy-4-(Trifluoromethoxy)Phenoxy]Benzoyl]Amino]Pyridine-2-Carboxamide (263)

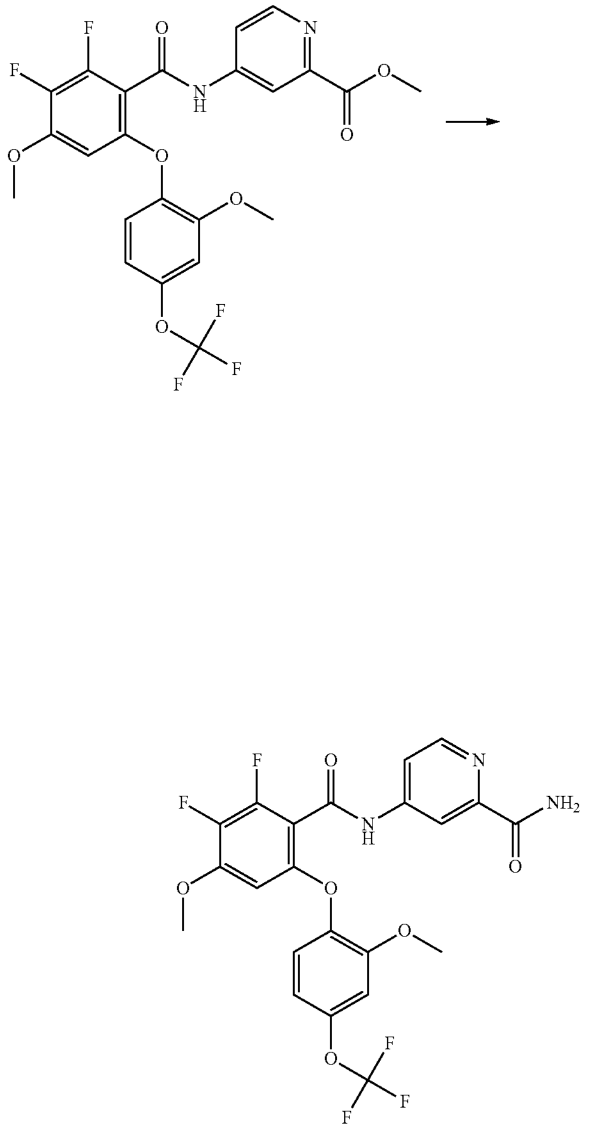

A solution of ammonia in methanol (1 mL of 7 M, 7 mmol) was added to methyl 4-[[2,3-difluoro-4-methoxy-6-[2-methoxy-4-(trifluoromethoxy)phenoxy]benzoyl]amino]pyridine-2-carboxylate (24 mg, 0.045 mmol) and the resulting mixture was stirred at room temperature for 3 hours. The mixture was concentrated in vacuo and purified by reverse phase HPLC (38-53% acetonitrile/0.1% ammonium hydroxide) to provide 4-[[2,3-difluoro-4-methoxy-6-[2-methoxy-4-(trifluoromethoxy)phenoxy]benzoyl]amino]pyridine-2-carboxamide (8.4 mg, 35%) as a white powder. ESI-MS m z calc. 513.10, found 514.5 $(M+1)^+$; 512.6 $(M-1)^-$; LC/MS retention time (Method E): 3.03 minutes. H NMR (500 MHz, DMSO-$d_6$) δ 11.17 (s, 1H), 8.51 (d, J=5.5 Hz, 1H), 8.24 (d, J=2.1 Hz, 1H), 8.07 (d, J=2.9 Hz, 1H), 7.76 (dd, J=5.4, 2.2 Hz, 1H), 7.63 (d, J=2.8 Hz, 1H), 7.15-7.08 (m, 2H), 6.92 (ddd, J=8.9, 2.8, 1.2 Hz, 1H), 6.60 (dd, J=6.5, 1.8 Hz, 1H), 3.83 (s, 3H), 3.75 (s, 3H) ppm.

Example 74

4-[[4-Cyclopropyl-3-Fluoro-6-[2-Methoxy-4-(Trifluoromethoxy)Phenoxy]-2-Methyl-Benzoyl]Amino] Pyridine-2-Carboxamide (264)

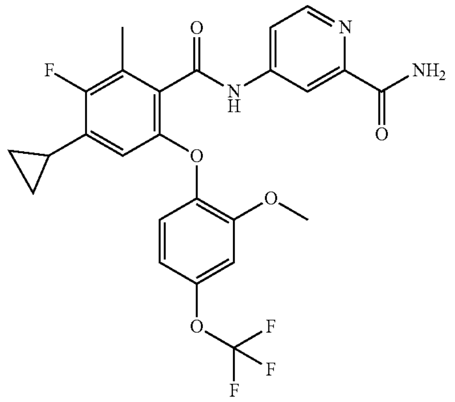 [SMILES: COc1cc(OC(F)(F)F)ccc1Oc1cc(C2CC2)c(F)c(C)c1C(=O)Nc1ccnc(C(N)=O)c1]

Step 1: 4-Cyclopropyl-3-Fluoro-2-Methyl-Benzoic Acid

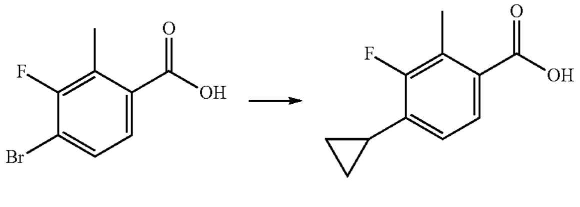

A mixture of 4-bromo-3-fluoro-2-methyl-benzoic acid (2.238 g, 9.604 mmol), cyclopropylboronic acid (1.648 g, 19.19 mmol), tricyclohexylphosphine (270 mg, 0.963 mmol), $K_3PO4$ (7.144 g, 33.66 mmol) and $Pd(OAc)_2$ (110 mg, 0.490 mmol) in toluene (50 mL) and water (12.5 mL) was purged with nitrogen and stirred at 100° C. for 60 hours. The mixture was diluted with water (75 mL) and washed with ethyl acetate (3x75 mL). The aqueous layer was acidified to pH 3 and extracted with ethyl acetate (3×100 mL). The combined organic extracts were dried and concentrated in vacuo to provide 4-cyclopropyl-3-fluoro-2-methyl-benzoic acid (1.816 g, 97%). ESI-MS m z calc. 194.07, found 193.7 $(M-1)^-$; LC/MS retention time (Method F): 0.35 minutes. $^1H$ NMR (500 MHz, DMSO-$d_6$) δ 12.88 (s, 1H), 7.55 (dd, J=8.2, 1.1 Hz, 1H), 6.87 (t, J=7.9 Hz, 1H), 2.43 (d, J=2.7 Hz, 3H), 2.08 (tt, J=8.5, 5.2 Hz, 1H), 1.10-0.92 (m, 2H), 0.82-0.69 (m, 2H) ppm.

Step 2: 4-Cyclopropyl-3-Fluoro-6-Iodo-2-Methyl-Benzoic Acid

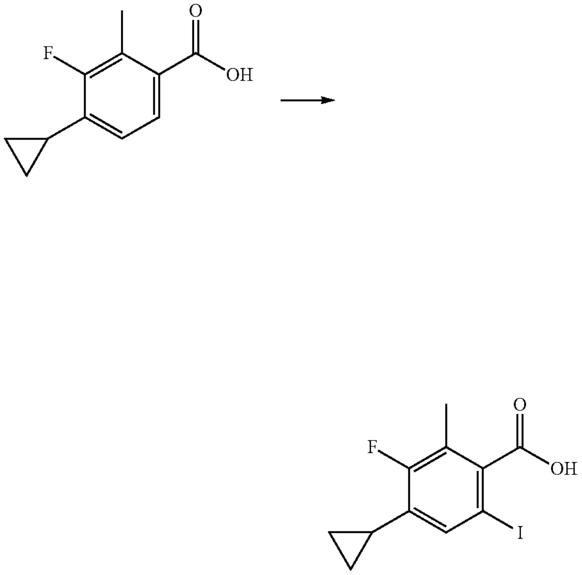

To a vial was added 4-cyclopropyl-3-fluoro-2-methyl-benzoic acid (1.0 g, 5.2 mmol), N-iodosuccinimide (1.280 g, 5.689 mmol) and $Pd(OAc)_2$ (110 mg, 0.490 mmol). The vial was evacuated and filled with nitrogen three times. DMF (40 mL) was added and the mixture was heated at 110° C. for 30 minutes. The mixture was diluted with water (100 mL) and extracted with ethyl acetate (100 mL). The organic layer was washed with water (3×100 mL), dried, filtered and concentrated in vacuo to provide 4-cyclopropyl-3-fluoro-6-iodo-2-methyl-benzoic acid (1.442 g, 88%). ESI-MS m z calc. 319.97, found 319.3 $(M-1)^-$; LC/MS retention time: 0.43 minutes (Method F). $^1H$ NMR (500 MHz, DMSO-$d_6$) δ 13.61 (s, 1H), 7.25 (d, J=6.9 Hz, 1H), 2.19 (d, J=2.5 Hz, 3H), 2.04-1.93 (m, 1H), 1.04-0.90 (m, 2H), 0.84-0.69 (m, 2H) ppm.

Step 3: 4-Cyclopropyl-3-Fluoro-6-[2-Methoxy-4-(Trifluoromethoxy)Phenoxy]-2-Methyl-Benzoic Acid

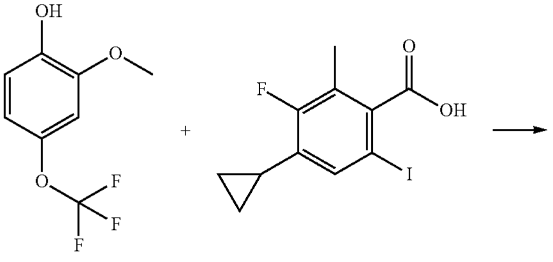

-continued

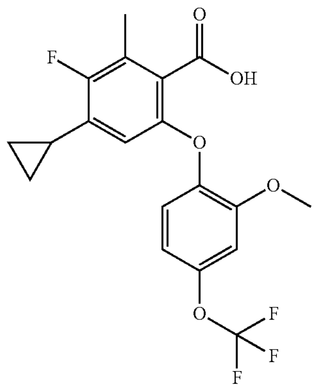

A vial containing 2-methoxy-4-(trifluoromethoxy)phenol (480 mg, 2.31 mmol), copper (I) iodide (425 mg, 2.23 mmol) and $Cs_2CO_3$ (1.093 g, 3.355 mmol) was evacuated and purged with nitrogen. A solution of 4-cyclopropyl-3-fluoro-6-iodo-2-methyl-benzoic acid (715 mg, 2.23 mmol) in toluene (12.5 mL) was added and the mixture heated at 100° C. for 20 hours. The mixture was diluted with water and extracted with ethyl acetate (4×20 mL). The combined organic extracts were dried and concentrated in vacuo. The residue was purified by silica gel chromatography (0-100% ethyl acetate/heptane) to provide 4-cyclopropyl-3-fluoro-6-[2-methoxy-4-(trifluoromethoxy)phenoxy]-2-methyl-benzoic acid (292 mg, 33%). ESI-MS m z calc. 400.09, found 399.5 $(M-1)^-$; LC/MS retention time (Method F): 0.62 minutes. $^1H$ NMR (500 MHz, DMSO-$d_6$) δ 13.29 (s, 1H), 7.13 (d, J=2.7 Hz, 1H), 6.88 (d, J=9.1 Hz, 1H), 6.79 (d, J=8.8 Hz, 1H), 6.32 (d, J=6.0 Hz, 1H), 3.82 (s, 3H), 2.21 (d, J=2.4 Hz, 3H), 2.08-1.95 (m, 1H), 1.01-0.87 (m, 2H), 0.66-0.52 (m, 2H) ppm.

Step 4: Methyl 4-[[4-Cyclopropyl-3-Fluoro-6-[2-Methoxy-4-(Trifluoromethoxy)Phenoxy]-2-Methyl-Benzoyl]Amino]Pyridine-2-Carboxylate

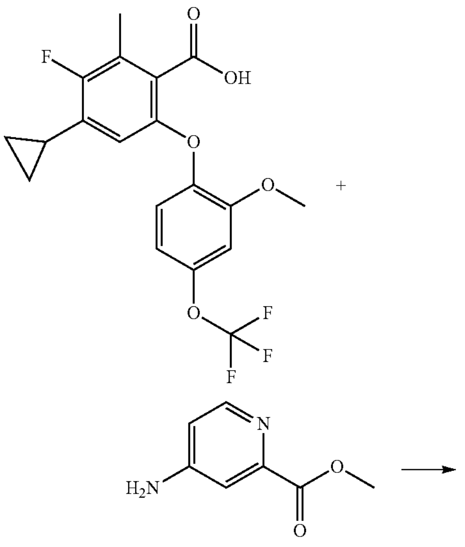

-continued

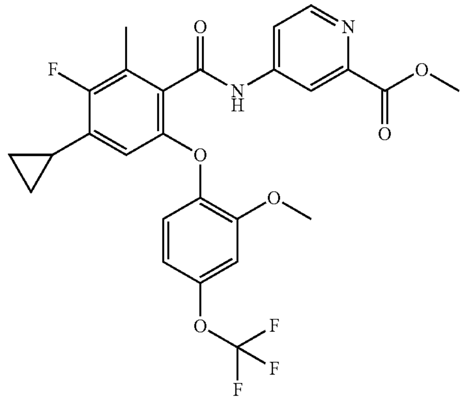

A solution of 4-cyclopropyl-3-fluoro-6-[2-methoxy-4-(trifluoromethoxy)phenoxy]-2-methyl-benzoic acid (140 mg, 0.35 mmol) and DMF (3 μL, 0.04 mmol) in dichloromethane (3 mL) was treated with oxalyl chloride (90 μL, 1.0 mmol) at 0° C. The mixture was allowed to warm to room temperature and stirred for 30 minutes. The mixture was then concentrated in vacuo. The residue was dissolved in dichloromethane (2 mL) and added to a solution of methyl 4-aminopyridine-2-carboxylate (64.1 mg, 0.421 mmol) and TEA (150 μL, 1.076 mmol) in dichloromethane (2 mL) at 0° C. The mixture was warmed to room temperature and stirred for 2 hours. The mixture was diluted with dichloromethane (30 mL) and washed with water (25 mL). The aqueous layer was extracted with additional dichloromethane (3×20 mL), and the combined organic extracts dried and concentrated in vacuo. The residue was purified by silica gel chromatography (0-70% ethyl acetate/heptane) to provide methyl 4-[[4-cyclopropyl-3-fluoro-6-[2-methoxy-4-(trifluoromethoxy)phenoxy]-2-methyl-benzoyl]amino]pyridine-2-carboxylate (68 mg, 36%). ESI-MS m z calc. 534.14, found 535.6 $(M+1)^+$; 533.6 $(M-1)^-$; LC/MS retention time (Method F): 0.95 minutes.

Step 5: 4-[[4-Cyclopropyl-3-Fluoro-6-[2-Methoxy-4-(Trifluoromethoxy)Phenoxy]-2-Methyl-Benzoyl]Amino]Pyridine-2-Carboxamide (264)

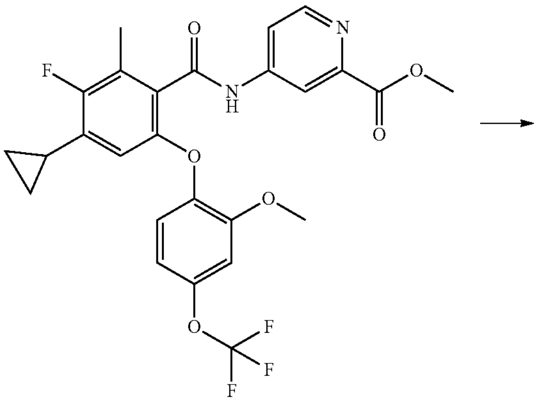

-continued

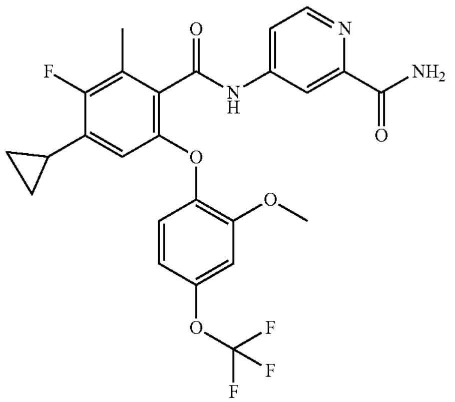

Methyl 4-[[4-cyclopropyl-3-fluoro-6-[2-methoxy-4-(trifluoromethoxy)phenoxy]-2-methyl-benzoyl]amino]pyridine-2-carboxylate (67 mg, 0.13 mmol) was dissolved in a solution of ammonia in methanol (2 mL of 7 M, 14 mmol) and stirred at room temperature for 20 hours. The mixture was concentrated in vacuo and purified by reverse phase HPLC (47-95% acetonitrile/0.1% ammonium hydroxide) to provide 4-[[4-cyclopropyl-3-fluoro-6-[2-methoxy-4-(trifluoromethoxy)phenoxy]-2-methyl-benzoyl]amino]pyridine-2-carboxamide (33 mg, 50%). ESI-MS m z calc. 519.14, found 520.6 $(M+1)^+$; 518.7 $(M-1)^-$; LC/MS retention time (Method E): 3.39 minutes. $^1H$ NMR (500 MHz, DMSO-$d_6$) δ 11.00 (s, 1H), 8.48 (d, J=5.5 Hz, 1H), 8.27 (d, J=2.1 Hz, 1H), 8.05 (d, J=2.9 Hz, 1H), 7.76 (dd, J=5.5, 2.2 Hz, 1H), 7.60 (d, J=2.9 Hz, 1H), 7.06 (d, J=2.7 Hz, 1H), 6.97 (d, J=8.8 Hz, 1H), 6.92-6.86 (m, 1H), 6.34 (d, J=5.9 Hz, 1H), 3.70 (s, 3H), 2.22 (d, J=2.3 Hz, 3H), 2.05 (ddd, J=13.5, 8.6, 5.1 Hz, 1H), 1.02-0.91 (m, 2H), 0.69-0.56 (m, 2H) ppm.

Example 75

4-[[3-Chloro-4-Methoxy-6-[2-Methoxy-4-(Trifluoromethoxy)Phenoxy]-2-Methyl-Benzoyl]Amino]Pyridine-2-Carboxamide (265)

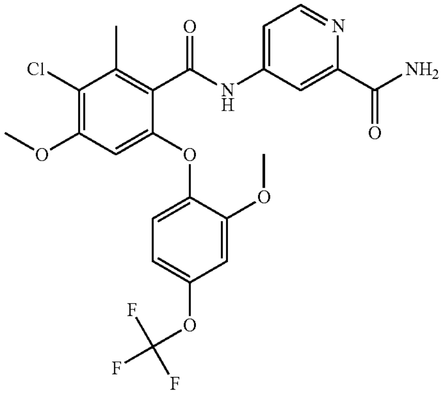 [SMILES: COc1cc(OC(F)(F)F)ccc1Oc1cc(OC)c(Cl)c(C)c1C(=O)Nc1ccnc(C(N)=O)c1]

Step 1: (4-Bromo-2-Chloro-Phenoxy)-Tert-Butyl-Dimethyl-Silane

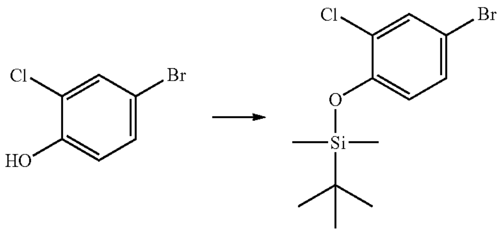 [SMILES: Oc1ccc(Br)cc1Cl ; CC(C)(C)[Si](C)(C)Oc1ccc(Br)cc1Cl]

To a solution of 4-bromo-2-chloro-phenol (1.0 g, 4.8 mmol) in DMF (4 mL) was added imidazole (660 mg, 9.70 mmol) and TBSCl (727 mg, 4.82 mmol) and the mixture was stirred at room temperature for 4 hours. Additional TBSCl (727 mg, 4.82 mmol) and imidazole (660 mg, 9.70 mmol) were added and the mixture was stirred for 12 hours. The mixture was diluted with ethyl acetate (100 mL) and washed with saturated aqueous $NH_4Cl$ (2×200 mL), water (3×200 mL) and brine, dried over $Na_2SO_4$, filtered and concentrated in vacuo. The residue was purified by silica gel chromatography (100% hexanes) to provide (4-bromo-2-chloro-phenoxy)-tert-butyl-dimethyl-silane (1.35 g, 86%) as a colorless oil. $^1H$ NMR (250 MHz, $CDCl_3$) δ 7.48 (d, J=2.5 Hz, 1H), 7.22 (dd, J=8.6, 2.4 Hz, 1H), 6.75 (d, J=8.6 Hz, 1H), 1.02 (s, 9H), 0.22 (s, 6H) ppm.

Step 2: (4-Bromo-2-Chloro-3-Methyl-Phenoxy)-Tert-Butyl-Dimethyl-Silane

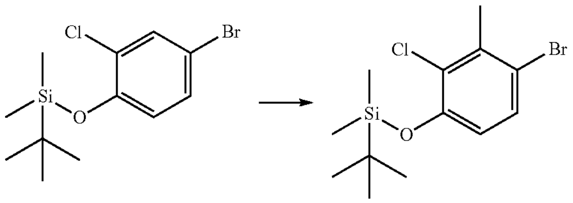 [SMILES: CC(C)(C)[Si](C)(C)Oc1ccc(Br)cc1Cl ; Cc1c(Br)ccc(O[Si](C)(C)C(C)(C)C)c1Cl]

To a solution of diisopropylamine (10.3 g, 14.2 mL, 101 mmol, freshly distilled from $CaH_2$) in THF (222 mL) at 0° C. was added n-butyllithium (40 mL of 2.5 M in hexanes, 100 mmol). The solution was stirred for 20 minutes at this temperature, then cooled to −78° C. and stirred for 15 minutes. A solution of (4-bromo-2-chloro-phenoxy)-tert-butyl-dimethyl-silane (30.0 g, 92.3 mmol) in THF (66 mL) was transferred to the LDA solution dropwise via cannula and the mixture stirred at −78° C. for 4 hours. Methyl iodide (22.8 g, 10 mL, 160 mmol) was then added dropwise. The mixture was stirred for 30 minutes at −78° C. then the cooling bath was removed and stirred for 30 minutes at room temperature. The mixture was diluted with saturated aqueous $NH_4Cl$ (150 mL) and extracted with ethyl acetate (3×500 mL). The combined organic layers were washed with 0.1 M aqueous HCl, saturated aqueous $NaHCO_3$, and brine, dried over $Na_2SO_4$, filtered and concentrated in vacuo to provide (4-bromo-2-chloro-3-methyl-phenoxy)-tert-butyl-dimethyl-silane (34 g, 77%) as a colorless oil. $^1H$ NMR (250 MHz, $CDCl_3$) δ 7.30 (d, J=8.7 Hz, 1H), 6.63 (d, J=8.7 Hz, 1H), 2.50 (s, 3H), 1.02 (s, 9H), 0.21 (s, 6H) ppm.

Step 3:
1-Bromo-3-Chloro-4-Methoxy-2-Methyl-Benzene

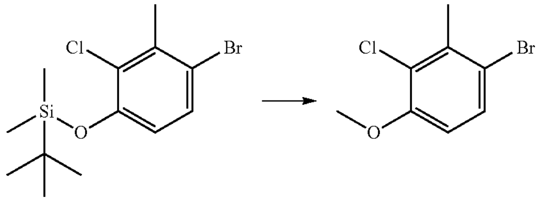 [SMILES: Cc1c(Br)ccc(O[Si](C)(C)C(C)(C)C)c1Cl ; COc1ccc(Br)c(C)c1Cl]

To a flask containing neat (4-bromo-2-chloro-3-methyl-phenoxy)-tert-butyl-dimethyl-silane (29.99 g, 89.33 mmol) was added methyl iodide (25.1 g, 11.0 mL, 177 mmol). The mixture was stirred for 5 minutes then treated with a solution of TBAF in THF (160 mL of 1 M, 160 mmol). The mixture was stirred for 12 hours at room temperature, then diluted with 0.5 M aqueous HCl (200 mL) and extracted with MTBE (3×750 mL). The combined organic extracts were washed with water (3×700 mL) and brine, dried over $MgSO_4$, filtered and concentrated in vacuo. The residue was purified by silica gel chromatography (0-5% diethyl ether/hexanes) to provide 1-bromo-3-chloro-4-methoxy-2-methyl-benzene (15.85 g, 65%) as a colorless oil. $^1H$ NMR (500 MHz, $CDCl_3$) δ 7.41 (d, J=8.9 Hz, 1H), 6.68 (d, J=8.9 Hz, 1H), 3.88 (s, 3H), 2.52 (s, 3H) ppm.

Step 4: 3-Chloro-4-Methoxy-2-Methyl-Benzoic Acid

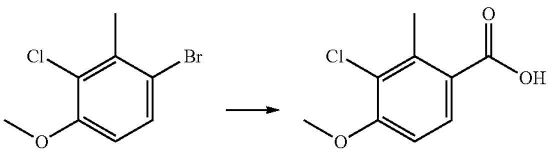

A solution of 1-bromo-3-chloro-4-methoxy-2-methyl-benzene (310 mg, 1.30 mmol) in THF (10 mL) was stirred at −78° C. for 15 minutes under nitrogen, then n-butyllithium (0.54 mL of 2.5 M, 1.35 mmol) was added and the mixture stirred at this temperature for 9 minutes. The suspension was transferred via cannula onto solid crushed carbon dioxide (dry ice) and the mixture allowed to warm to room temperature. The resulting solution was diluted with 0.5 M aqueous HCl (until pH=3) and extracted with ethyl acetate (3×50 mL). The combined organic extracts were dried over $MgSO_4$, filtered and concentrated in vacuo to provide 3-chloro-4-methoxy-2-methyl-benzoic acid (180 mg, 68%) as a white solid. ESI-MS m z calc. 200.02, found 201.3 $(M+1)^+$; LC/MS retention time (Method Q): 1.85 minutes. $^1H$ NMR (500 MHz, $CDCl_3$) δ 8.01 (d, J=8.9 Hz, 1H), 6.85 (d, J=8.8 Hz, 1H), 3.97 (s, 3H), 2.74 (s, 3H), 1.65 (br s, 1H) ppm.

Step 5:
3-Chloro-6-Iodo-4-Methoxy-2-Methyl-Benzoic Acid

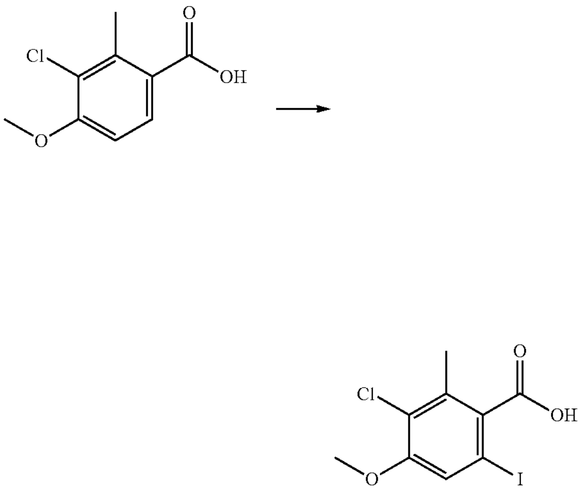

A solution of 3-chloro-4-methoxy-2-methyl-benzoic acid (4.25 g, 21.2 mmol), N-iodosuccinimide (5.24 g, 23.3 mmol) and $Pd(OAc)_2$ (1.19 g, 5.30 mmol) in DMF (24 mL) was heated at 65° C. for 22 hours under nitrogen. Additional N-iodosuccinimide (1.19 g, 5.29 mmol) and $Pd(OAc)_2$ (238 mg, 1.06 mmol) were added at room temperature and the mixture heated at 55° C. for an additional 12 hours. The mixture was cooled to 0° C., diluted with 1 M aqueous HCl (150 mL) and extracted with ethyl acetate (3×100 mL). The combined organics were extracted with 1 M aqueous NaOH (2×100 mL) and the combined aqueous extracts washed with hexanes (3×100 mL). The aqueous phase was acidified with 3 M aqueous HCl at 0° C. and extracted with ethyl acetate (50 mL). The combined organic extracts were washed with aqueous sodium metabisulfite (10%, 2×40 mL), 0.1 M HCl (2×200 mL) and brine, dried over $Na_2SO_4$, filtered and concentrated in vacuo to provide 3-chloro-6-iodo-4-methoxy-2-methyl-benzoic acid (4.81 g, 61%) as a white solid. ESI-MS m z calc. 325.92, found 327.3 $(M+1)^+$; LC/MS retention time (Method N): 4.46 minutes. $^1H$ NMR (500 MHz, DMSO-$d_6$) δ 13.55 (s, 1H), 7.41 (s, 1H), 3.87 (s, 3H), 2.30 (s, 3H) ppm.

Step 6: 3-Chloro-4-Methoxy-6-[2-Methoxy-4-(Trifluoromethoxy)Phenoxy]-2-Methyl-Benzoic Acid

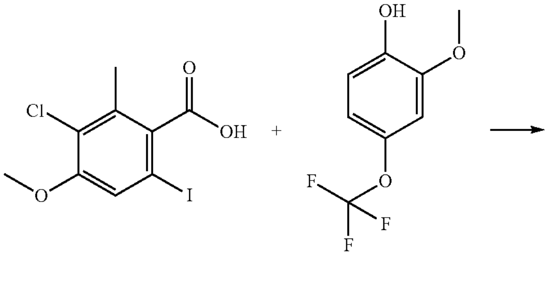

-continued

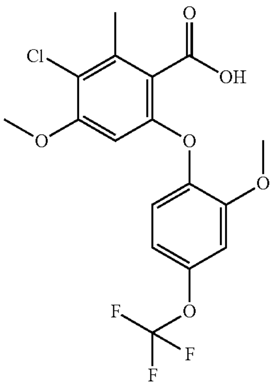

To a solution of 3-chloro-6-iodo-4-methoxy-2-methyl-benzoic acid (2.0 g, 6.1 mmol) in DMF (6 mL) was added $Cs_2CO_3$ (6.0 g, 18.4 mmol), 2-methoxy-4-(trifluoromethoxy)phenol (1.91 g, 9.18 mmol), copper (I) iodide (58 mg, 0.31 mmol) and pyridine (1.0 mL, 12.4 mmol). The mixture was heated at 80° C. under nitrogen for 4 hours. The mixture was cooled to room temperature, treated with additional 2-methoxy-4-(trifluoromethoxy)phenol (1.79 g, 8.60 mmol) and copper (29 mg, 0.46 mmol), and then heated at 100° C. for 1 hour. The mixture was cooled to 0° C., acidified with 1 M aqueous HCl (until pH=2) and extracted with ethyl acetate (200 mL). The organic layer was washed with 0.1 M aqueous HCl (3×75 mL) and brine, dried over $Na_2SO_4$, filtered and concentrated in vacuo. The resulting residue was brought up in dichloromethane and filtered. The filtrate was concentrated in vacuo and purified by silica gel chromatography (0-20% ethyl acetate/hexanes containing 1.5% acetic acid) to provide 3-chloro-4-methoxy-6-[2-methoxy-4-(trifluoromethoxy)phenoxy]-2-methyl-benzoic acid (640 mg, 25%) as a crystalline solid. ESI-MS m z calc. 406.04, found 407.2 $(M+1)^+$; LC/MS retention time (Method Q): 2.61 minutes. $^1H$ NMR (500 MHz, DMSO-$d_6$) δ 13.21 (s, 1H), 7.17 (d, J=2.5 Hz, 1H), 6.98-6.83 (m, 2H), 6.46 (s, 1H), 3.83 (s, 3H), 3.72 (s, 3H), 2.33 (s, 3H) ppm.

Step 7: Methyl 4-[[3-Chloro-4-Methoxy-6-[2-Methoxy-4-(Trifluoromethoxy)Phenoxy]-2-Methyl-Benzoyl]Amino]Pyridine-2-Carboxylate

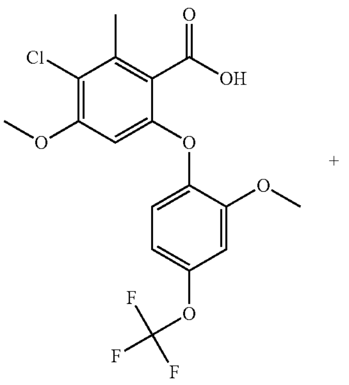

-continued

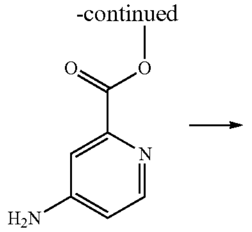

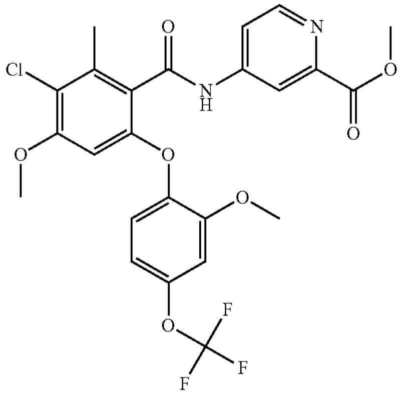

A solution of 3-chloro-4-methoxy-6-[2-methoxy-4-(trifluoromethoxy)phenoxy]-2-methyl-benzoic acid (135 mg, 0.331 mmol) and DMF (0.6 μL, 0.008 mmol) in dichloromethane (2.5 mL) was cooled to 0° C. and treated with oxalyl chloride (105 μL, 1.204 mmol). The mixture was stirred for 1 hour, then concentrated in vacuo. The residue was dissolved in a minimum amount of dichloromethane and added to a suspension of methyl 4-aminopyridine-2-carboxylate (68 mg, 0.44 mmol) in minimal dichloromethane and TEA (66 μL, 0.47 mmol) at 0° C. The reaction flask was removed from the ice bath after 10 minutes and the mixture stirred at room temperature overnight. The mixture was heated at 40° C. for 1 hour, then cooled to room temperature and diluted with dichloromethane. The organic solution was washed with brine (2×), dried over $MgSO_4$, filtered and concentrated in vacuo. Purification by silica gel chromatography (0-30% ethyl acetate/heptane) provided methyl 4-[[3-chloro-4-methoxy-6-[2-methoxy-4-(trifluoromethoxy)phenoxy]-2-methyl-benzoyl]amino]pyridine-2-carboxylate (59.9 mg, 33%). ESI-MS m z calc. 540.09, found 541.7 $(M+1)^+$; LC/MS retention time (Method F): 0.94 minutes.

Step 8: 4-[[3-Chloro-4-Methoxy-6-[2-Methoxy-4-(Trifluoromethoxy)Phenoxy]-2-Methyl-Benzoyl]Amino]Pyridine-2-Carboxamide (265)

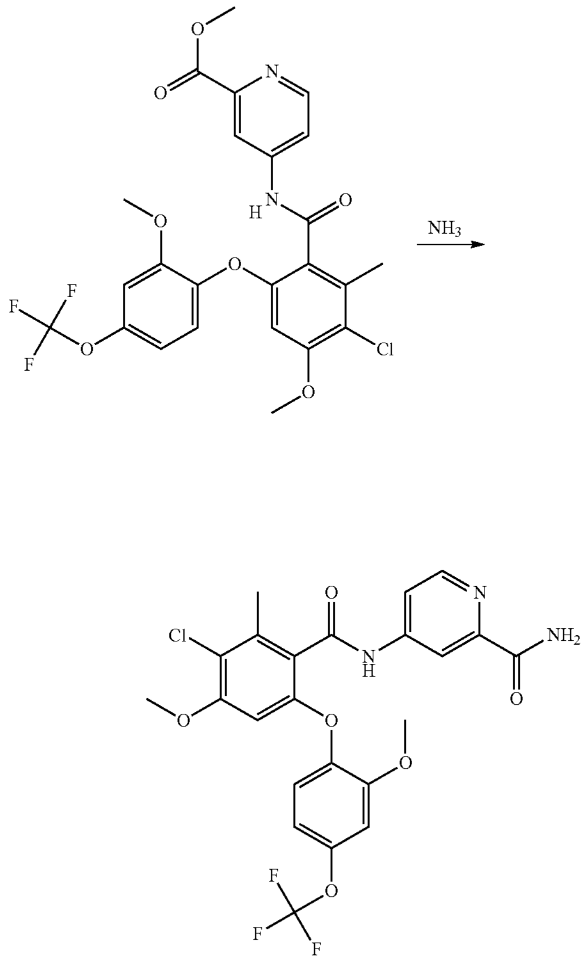

Methyl 4-[[3-chloro-4-methoxy-6-[2-methoxy-4-(trifluoromethoxy)phenoxy]-2-methyl-benzoyl]amino]pyridine-2-carboxylate (59.9 mg, 0.111 mmol) was dissolved in a solution of ammonia in methanol (6.5 mL of 7 M, 45.5 mmol) and stirred at room temperature for 1 hour. Additional ammonia solution (5 mL of 7 M, 35.00 mmol) was added and the mixture stirred for 16 hours. The solution was partially concentrated under vacuum, and then diluted with ethyl acetate and then washed with 2 M aqueous NaOH and water. The organic layer was concentrated in vacuo and purified by reverse phase HPLC (38-53% acetonitrile/0.1% ammonium hydroxide) to provide 4-[[3-chloro-4-methoxy-6-[2-methoxy-4-(trifluoromethoxy)phenoxy]-2-methyl-benzoyl]amino]pyridine-2-carboxamide (37.9 mg, 63%). ESI-MS m z calc. 525.09, found 526.6 $(M+1)^+$; LC/MS retention time (Method E): 3.16 minutes. $^1H$ NMR (500 MHz, DMSO-$d_6$) δ 11.00 (s, 1H), 8.50 (d, J=5.5 Hz, 1H), 8.29 (d, J=2.2 Hz, 1H), 8.06 (d, J=2.8 Hz, 1H), 7.79 (dd, J=5.5, 2.2 Hz, 1H), 7.61 (d, J=2.9 Hz, 1H), 7.11 (dd, J=5.8, 3.0 Hz, 2H), 6.93 (ddd, J=8.8, 2.8, 1.3 Hz, 1H), 6.49 (s, 1H), 3.75 (s, 3H), 3.74 (s, 3H), 2.34 (s, 3H) ppm.

Example 76

4-[[3-Chloro-2-Fluoro-4-Methoxy-6-[2-Methoxy-4-(Trifluoromethoxy)Phenoxy]Benzoyl]Amino]Pyridine-2-Carboxamide (266)

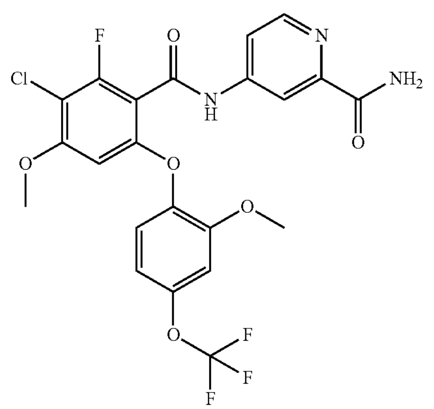 [SMILES: COc1cc(OC(F)(F)F)ccc1Oc1cc(OC)c(Cl)c(F)c1C(=O)Nc1ccnc(C(N)=O)c1]

Step 1: 5-Bromo-2-Chloro-1-Fluoro-3-Methoxy-Benzene

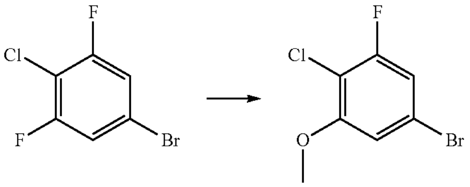

To a solution of 5-bromo-2-chloro-1,3-difluoro-benzene (1.033 g, 4.542 mmol) in DMF (15 mL) at 0° C. was added sodium methoxide (10 mL of 0.5 M in methanol, 5 mmol). The mixture was warmed to room temperature and stirred for 16 hours. The mixture was diluted with water (200 mL) and extracted with ethyl acetate (200 mL). The organic layer was washed with water (3×200 mL), dried over $MgSO_4$, filtered and concentrated in vacuo to provide 5-bromo-2-chloro-1-fluoro-3-methoxy-benzene (1.021 g, 94%). $^1H$ NMR (500 MHz, $CDCl_3$) δ 6.98 (dd, J=8.0, 2.0 Hz, 1H), 6.87 (t, J=1.9 Hz, 1H), 3.91 (s, 3H) ppm.

Step 2: 6-Bromo-3-Chloro-2-Fluoro-4-Methoxy-Benzoic Acid

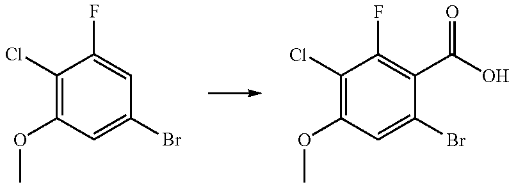

To a solution of 5-bromo-2-chloro-1-fluoro-3-methoxy-benzene (9.811 g, 40.97 mmol) in THF (125 mL) under nitrogen at −78° C. was added LDA (24 mL of 2 M in THF/heptane/ethylbenzene, 48 mmol) and the mixture stirred for 30 minutes. The solution was added to solid carbon dioxide (dry ice) and allowed to warm to room temperature and stirred for 1 hour. The mixture was diluted with water (150 mL) and washed with ethyl acetate (4×). The aqueous layer was then acidified to pH=3 and extracted with ethyl acetate (3×75 mL). The combined organic extracts were washed with water (2×50 mL), dried over $MgSO_4$, filtered and concentrated in vacuo to provide 6-bromo-3-chloro-2-fluoro-4-methoxy-benzoic acid (7.91 g, 68%). $^1$H NMR (500 MHz, DMSO-$d_6$) δ 14.01 (s, 1H), 7.36 (d, J=1.8 Hz, 1H), 3.95 (s, 3H) ppm.

Step 3: 3-Chloro-2-Fluoro-4-Methoxy-6-[2-Methoxy-4-(Trifluoromethoxy)Phenoxy]Benzoic Acid

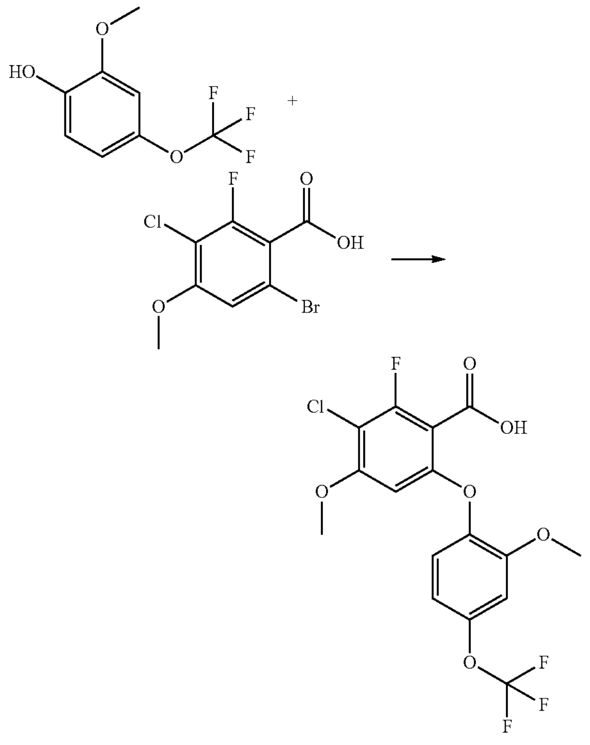

A solution of 2-methoxy-4-(trifluoromethoxy)phenol (2.289 g, 11.00 mmol) in toluene (100 mL) was bubbled with nitrogen for 10 minutes. 6-Bromo-3-chloro-2-fluoro-4-methoxy-benzoic acid (3.006 g, 10.60 mmol), $Cs_2CO_3$ (6.913 g, 21.22 mmol) and copper (I) iodide (404 mg, 2.12 mmol) were added and the mixture was bubbled with nitrogen for an additional 10 minutes. The mixture was heated at 100° C. for 20 hours, and then cooled and partitioned between ethyl acetate and water. The aqueous layer was separated, acidified to pH=3 with 2 M aqueous HCl, and extracted with ethyl acetate (3×150 mL). The combined organic extracts were dried over $MgSO_4$, filtered and concentrated in vacuo. The solid was triturated twice with dichloromethane to provide 3-chloro-2-fluoro-4-methoxy-6-[2-methoxy-4-(trifluoromethoxy)phenoxy]benzoic acid (1.187 g, 22%). ESI-MS m z calc. 410.02, found 411.3 $(M+1)^+$; 409.5 $(M-1)^-$; LC/MS retention time (Method F): 0.56 minutes.

Step 4: Methyl 4-[[3-Chloro-2-Fluoro-4-Methoxy-6-[2-Methoxy-4-(Trifluoromethoxy)Phenoxy]Benzoyl]Amino]Pyridine-2-Carboxylate

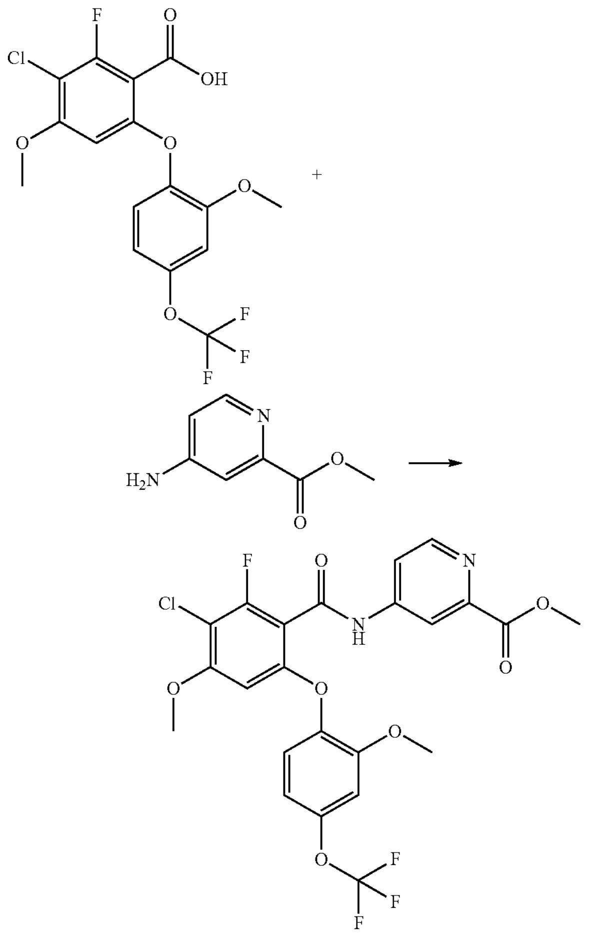

To a solution of 3-chloro-2-fluoro-4-methoxy-6-[2-methoxy-4-(trifluoromethoxy)phenoxy]benzoic acid (200 mg, 0.487 mmol) and DMF (4 μL, 0.05 mmol) in dichloromethane (5 mL) at 0° C. was added oxalyl chloride (130 μL, 1.49 mmol). The mixture was warmed to room temperature, stirred for 1 hour and then concentrated in vacuo. The residue was redissolved in dichloromethane (3 mL) and added to a solution of methyl 4-aminopyridine-2-carboxylate (82.1 mg, 0.540 mmol) and TEA (250 μL, 1.80 mmol) in dichloromethane (3 mL) at 0° C. The mixture was warmed to room temperature and stirred for 2 hours. The mixture was diluted with dichloromethane (30 mL) and washed with water (20 mL). The aqueous layer was extracted with additional dichloromethane (2×20 mL), and the combined organic extracts dried over $MgSO_4$, filtered and concentrated in vacuo. Silica gel chromatography (0-60% ethyl acetate/heptane) provided methyl 4-[[3-chloro-2-fluoro-4-methoxy-6-[2-methoxy-4-(trifluoromethoxy)phenoxy]benzoyl]amino]pyridine-2-carboxylate (74 mg, 28%). ESI-MS m z calc. 544.07, found 545.4 $(M+1)^+$; 543.4 $(M-1)^-$; LC/MS retention time (Method F): 0.94 minutes. $^1$H NMR (500 MHz, DMSO-$d_6$) δ 11.21 (s, 1H), 8.58 (d, J=5.4 Hz, 1H), 8.30 (s, 1H), 7.75 (d, J=5.2 Hz, 1H), 7.17 (d, J=8.9 Hz, 1H), 7.12 (d, J=2.7 Hz, 1H), 6.93 (d, J=9.0 Hz, 1H), 6.51 (d, J=1.4 Hz, 1H), 3.87 (s, 3H), 3.81 (s, 3H), 3.74 (s, 3H) ppm.

Step 5: 4-[[3-Chloro-2-Fluoro-4-Methoxy-6-[2-Methoxy-4-(Trifluoromethoxy)Phenoxy]Benzoyl]Amino]Pyridine-2-Carboxamide (266)

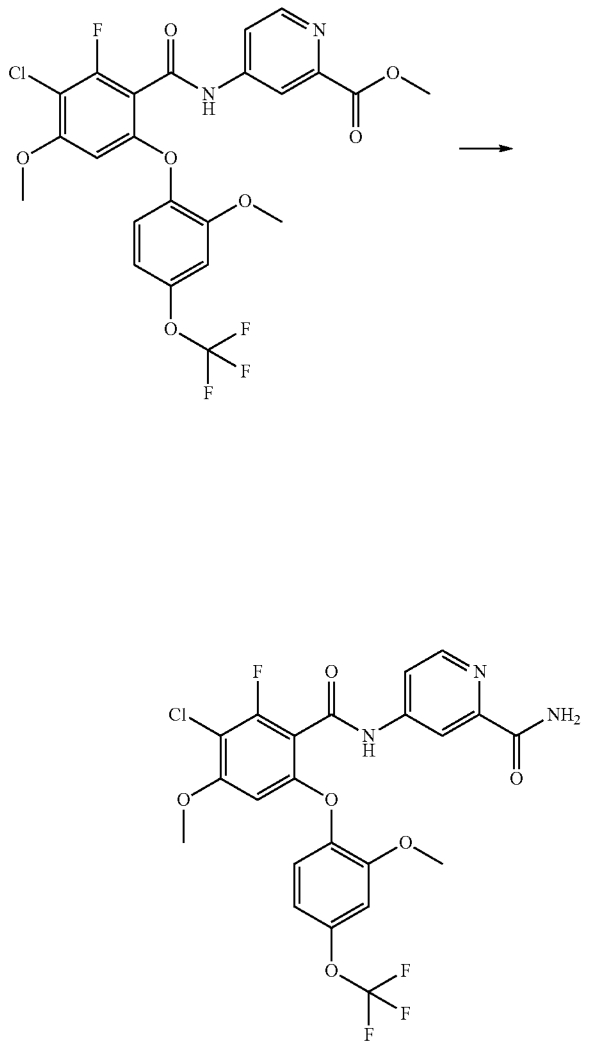

Methyl 4-[[3-chloro-2-fluoro-4-methoxy-6-[2-methoxy-4-(trifluoromethoxy)phenoxy]benzoyl]amino]pyridine-2-carboxylate (74 mg, 0.14 mmol) was dissolved in a solution of ammonia in methanol (1 mL of 7 M, 7 mmol) and stirred at room temperature for 20 hours. The mixture was concentrated in vacuo and the residue partitioned between ethyl acetate (20 mL) and water (20 mL). The layers were separated and the aqueous layer extracted with additional ethyl acetate (2×20 mL). The combined organic extracts were dried over $MgSO_4$, filtered and concentrated in vacuo. The residue was purified by reverse phase HPLC (47-95% acetonitrile/0.1% ammonium hydroxide) to provide 4-[[3-chloro-2-fluoro-4-methoxy-6-[2-methoxy-4-(trifluoromethoxy)phenoxy]benzoyl]amino]pyridine-2-carboxamide (22 mg, 29%). ESI-MS m z calc. 529.07, found 530.5 $(M+1)^+$; 528.6 $(M-1)^-$; LC/MS retention time (Method E): 3.13 minutes. $^1H$ NMR (500 MHz, DMSO-$d_6$) δ 11.16 (s, 1H), 8.51 (d, J=5.4 Hz, 1H), 8.24 (d, J=2.1 Hz, 1H), 8.07 (d, J=2.8 Hz, 1H), 7.77 (dd, J=5.5, 2.2 Hz, 1H), 7.62 (d, J=2.9 Hz, 1H), 7.19 (d, J=8.8 Hz, 1H), 7.13 (s, 1H), 6.94 (ddd, J=8.8, 2.7, 1.3 Hz, 1H), 6.49 (d, J=1.6 Hz, 1H), 3.80 (s, 3H), 3.75 (s, 3H) ppm.

Example 77

4-[[4-Chloro-2-Fluoro-6-[2-Methoxy-4-(Trifluoromethoxy)Phenoxy]Benzoyl]Amino]-5-Methyl-1-Oxido-Pyridin-1-Ium-2-Carboxamide (267)

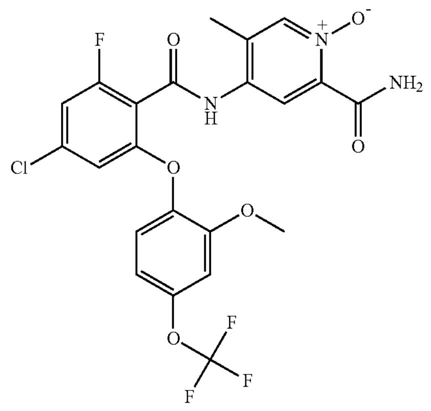

4-[[4-Chloro-2-fluoro-6-[2-methoxy-4-(trifluoromethoxy)phenoxy]benzoyl]amino]-5-methyl-pyridine-2-carboxamide (8.9 mg, 0.017 mmol, see US 2019/0016671, Example 60, which is incorporated by reference) was dissolved in dichloromethane (2 mL) at 0° C. The solution was treated with meta-chloroperoxybenzoic acid (17 mg, 0.076 mmol), and then allowed to warm to room temperature and stirred for 72 hours. The mixture was partitioned between dichloromethane and water and the phases separated (phase separation cartridge). The filtrate was concentrated in vacuo. Purification by reverse phase HPLC (38-53% acetonitrile/0.1% ammonium hydroxide) provided 4-[[4-chloro-2-fluoro-6-[2-methoxy-4-(trifluoromethoxy)phenoxy]benzoyl]amino]-5-methyl-1-oxido-pyridin-1-ium-2-carboxamide (6 mg, 62%). ESI-MS m z calc. 529.07, found 530.4 $(M+1)^+$; 528.3 $(M-1)^-$; LC/MS retention time: 3.01 minutes (Method E). $^1H$ NMR (500 MHz, $CDCl_3$) δ 10.83 (s, 1H), 9.09 (s, 1H), 8.35 (s, 1H), 8.12 (s, 1H), 7.22 (d, J=8.7 Hz, 1H), 6.99-6.90 (m, 3H), 6.46 (t, J=1.6 Hz, 1H), 6.00 (s, 1H), 3.83 (s, 3H), 2.23 (d, J=0.8 Hz, 3H) ppm.

Example 78

4-[[3-Chloro-2-Fluoro-6-[2-Methoxy-4-(Trifluoromethoxy)Phenoxy]Benzoyl]Amino]-5-Methyl-1-Oxido-Pyridin-1-Ium-2-Carboxamide (268)

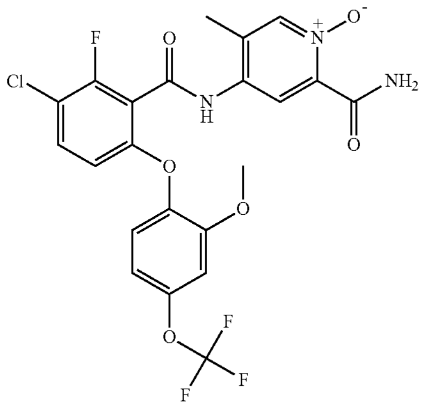

4-[[3-Chloro-2-fluoro-6-[2-methoxy-4-(trifluoromethoxy)phenoxy]benzoyl]amino]-5-methyl-pyridine-2-carboxamide (22.5 mg, 0.0434 mmol, see US 2019/0016671, Example 38, which is incorporated by reference) was dissolved in dichloromethane (4.5 mL) and cooled to 0° C. The solution was treated with meta-chloroperoxybenzoic acid (40 mg, 0.18 mmol) and the mixture brought to room temperature and stirred for 72 hours. The mixture was partitioned between dichloromethane and water and the phases separated (phase separation cartridge). The filtrate was concentrated in vacuo and the residue purified by reverse phase HPLC (38-53% acetonitrile/0.1% ammonium hydroxide) to provide 4-[[3-chloro-2-fluoro-6-[2-methoxy-4-(trifluoromethoxy)phenoxy]benzoyl]amino]-5-methyl-1-oxido-pyridin-1-ium-2-carboxamide (14 mg, 61%). ESI-MS m z calc. 529.07, found 530.4 $(M+1)^+$; 528.4 $(M-1)^-$; LC/MS retention time (Method E): 2.96 minutes. $^1H$ NMR (500 MHz, $CDCl_3$) δ 10.85 (s, 1H), 9.06 (s, 1H), 8.33 (s, 1H), 8.12 (s, 1H), 7.35 (dd, J=9.1, 7.8 Hz, 1H), 7.20 (d, J=8.7 Hz, 1H), 6.94-6.89 (m, 2H), 6.45 (dd, J=9.1, 1.5 Hz, 1H), 6.03 (s, 1H), 3.80 (s, 3H), 2.27-2.23 (m, 3H) ppm.

Example 79

4-[[2-Cyano-6-[2-Methoxy-4-(Trifluoromethoxy)Phenoxy]-3-(Trifluoromethyl)Benzoyl]Amino]Pyridine-2-Carboxamide (269)

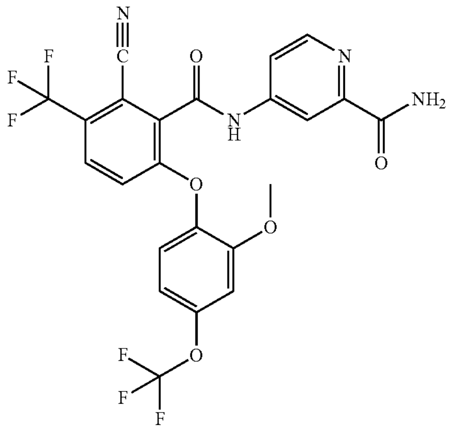 [SMILES: COc1cc(OC(F)(F)F)ccc1Oc1ccc(C(F)(F)F)c(C#N)c1C(=O)Nc1ccnc(C(N)=O)c1]

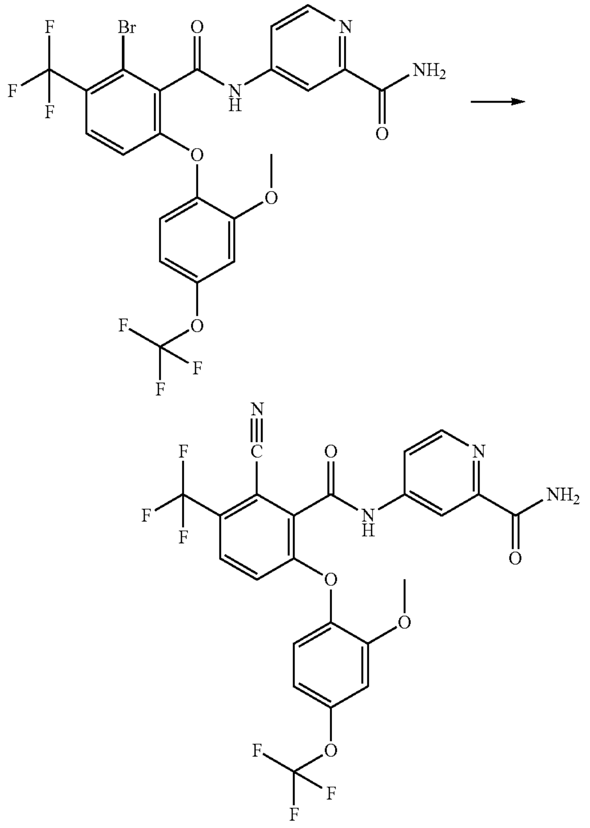

A suspension of 4-[[2-bromo-6-[2-methoxy-4-(trifluoromethoxy)phenoxy]-3-(trifluoromethyl)benzoyl]amino]pyridine-2-carboxamide (600 mg, 0.990 mmol, see Example 40), CuCN (178 mg, 1.99 mmol) and $Pd(PPh_3)_4$ (172 mg, 0.150 mmol) in DMF (10 mL) was bubbled with nitrogen for 5 minutes in a pressure tube. The tube was sealed and the mixture was heated at 150° C. for 1 hour. The mixture was diluted with ethyl acetate (250 mL) and solids removed by filtration. The filtrate was washed with water (2×100 mL) and brine, dried over anhydrous $MgSO_4$ and filtered and concentrated in vacuo. The residue was purified by reverse phase HPLC (Higgins Analytical $C_{18}$ column, 30×100 mm, 15-75% acetonitrile/5 mM HCl over 30 minutes, flow-rate=40 mL/min) to provide 4-[[2-cyano-6-[2-methoxy-4-(trifluoromethoxy)phenoxy]-3-(trifluoromethyl)benzoyl]amino]pyridine-2-carboxamide hydrochloride (53.1 mg, 9%) as a white powder. ESI-MS m z calc. 540.09, found 541.3 $(M+1)^+$; LC/MS retention time (Method Q): 2.52 minutes. $^1H$ NMR (500 MHz, DMSO-$d_6$) δ 11.60 (s, 1H), 8.60 (d, J=5.5 Hz, 1H), 8.35 (d, J=2.1 Hz, 1H), 8.15 (d, J=2.8 Hz, 1H), 8.02 (d, J=9.0 Hz, 1H), 7.86 (dd, J=5.5, 2.2 Hz, 1H), 7.71 (d, J=2.9 Hz, 1H), 7.41 (d, J=8.8 Hz, 1H), 7.29 (d, J=2.8 Hz, 1H), 7.21 (d, J=9.0 Hz, 1H), 7.10-7.04 (m, 1H), 3.79 (s, 3H) ppm.

Example 80

5-[[5-[2-Methoxy-4-(Trifluoromethoxy)Phenoxy]-3-Methyl-2-(Trifluoromethyl)Pyridine-4-Carbonyl]Amino]Pyrimidine-2-Carboxamide (270)

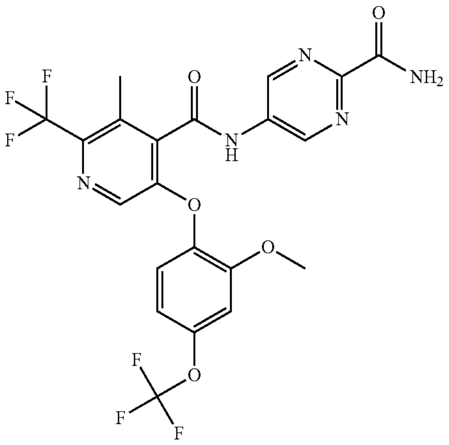 [SMILES: COc1cc(OC(F)(F)F)ccc1Oc1cnc(C(F)(F)F)c(C)c1C(=O)Nc1cnc(C(N)=O)nc1]

Step 1: 5-[2-Methoxy-4-(Trifluoromethoxy)Phenoxy]-3-Methyl-2-(Trifluoromethyl)Pyridine-4-Carboxylic Acid

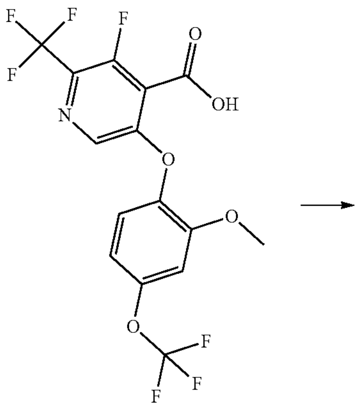

-continued

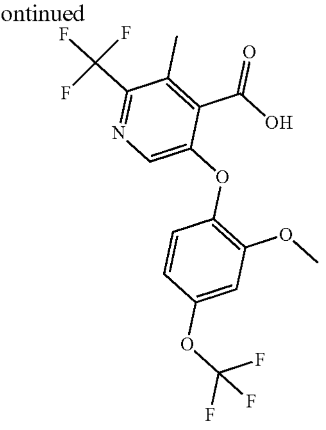

To a solution of 3-fluoro-5-[2-methoxy-4-(trifluoromethoxy)phenoxy]-2-(trifluoromethyl)pyridine-4-carboxylic acid (0.80 g, 1.9 mmol, see US 2019/0016671, Example 12, Steps 1-3, which is incorporated by reference) in THF (4.0 mL) was slowly added bromo(methyl)magnesium (1.1 mL, 9.5 mmol) under nitrogen atmosphere. The resulting mixture was stirred at room temperature for 30 minutes then heated to 55° C. for 18 hours. The mixture was allowed to cool to room temperature and additional bromo(methyl)magnesium (1.1 mL, 9.5 mmol) was slowly added. The resulting mixture was stirred at 55° C. for an additional 18 hours. The mixture was diluted with 1 M aqueous HCl and extracted with ethyl acetate (3×). The combined organic layers were concentrated in vacuo and purified by reverse phase HPLC (10-99% acetonitrile/5 mM HCl) to provide 5-[2-methoxy-4-(trifluoromethoxy)phenoxy]-3-methyl-2-(trifluoromethyl)pyridine-4-carboxylic acid (120.5 mg, 15%) as a white solid. ESI-MS m z calc. 411.05, found 412.0 $(M+1)^+$; LC/MS retention time (Method B): 1.75 minutes. $^1H$ NMR (400 MHz, DMSO-$d_6$) δ 14.31 (s, 1H), 7.96 (s, 1H), 7.37-7.18 (m, 2H), 7.07-6.92 (m, 1H), 3.81 (s, 3H), 2.42 (d, J=1.9 Hz, 3H) ppm.

Step 2: Methyl 5-[[5-[2-Methoxy-4-(Trifluoromethoxy)Phenoxy]-3-Methyl-2-(Trifluoromethyl)Pyridine-4-Carbonyl]Amino]Pyrimidine-2-Carboxylate

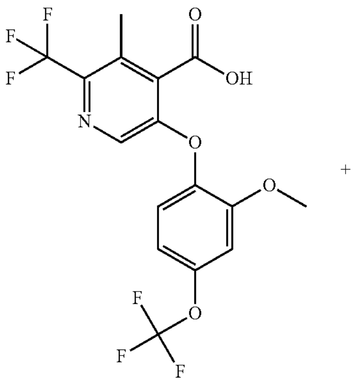

-continued

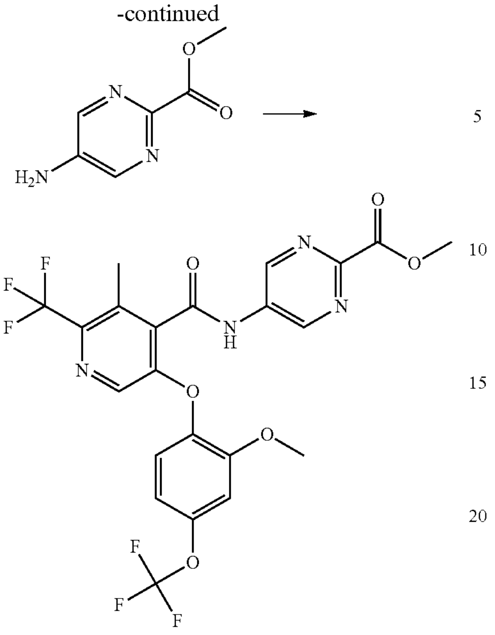

To a solution of 5-[2-methoxy-4-(trifluoromethoxy)phenoxy]-3-methyl-2-(trifluoromethyl)pyridine-4-carboxylic acid (33 mg, 0.08 mmol) and DMF (6 μL, 0.08 mmol) in dichloromethane (660 μL) at 0° C. was slowly added oxalyl dichloride (61 mg, 42 μL, 0.48 mmol) and the mixture stirred at room temperature for 30 minutes. The solvent was removed in vacuo. The resulting acid chloride was dissolved in NMP (165 μL) added to a solution of methyl 5-aminopyrimidine-2-carboxylate (37 mg, 0.24 mmol) and DIEA (62 mg, 84 μL, 0.48 mmol) in NMP (165 μL) at 0° C. The mixture was stirred at room temperature for 16 hours, and then filtered and purified by reverse phase HPLC (1-99% acetonitrile/5 mM HCl) to provide methyl 5-[[5-[2-methoxy-4-(trifluoromethoxy)phenoxy]-3-methyl-2-(trifluoromethyl)pyridine-4-carbonyl]amino]pyrimidine-2-carboxylate (26 mg, 59%). ESI-MS m z calc. 546.10, found 547.0 $(M+1)^+$; LC/MS retention time (Method A): 0.43 minutes.

Step 3: 5-[[5-[2-Methoxy-4-(Trifluoromethoxy)Phenoxy]-3-Methyl-2-(Trifluoromethyl)Pyridine-4-Carbonyl]Amino]Pyrimidine-2-Carboxamide (270)

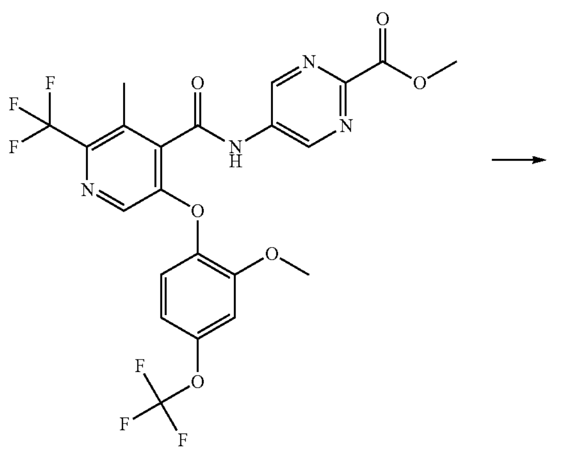

-continued

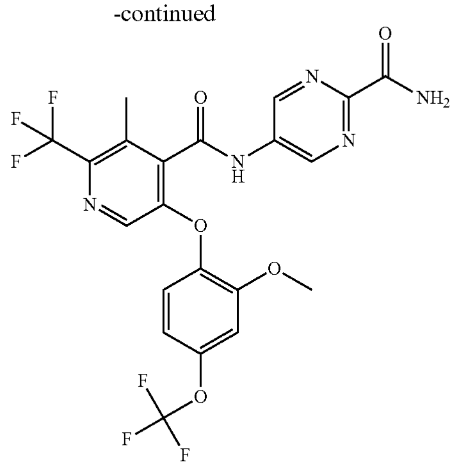

Methyl 5-[[5-[2-methoxy-4-(trifluoromethoxy)phenoxy]-3-methyl-2-(trifluoromethyl)pyridine-4-carbonyl]amino] pyrimidine-2-carboxylate (25 mg, 0.046 mmol) was dissolved in a solution of ammonia in methanol (800 μL of 7 M, 5.6 mmol) and stirred at room temperature for 18 hours. The solvent was removed in vacuo. The residue was dissolved in DMSO, filtered and purified by reverse phase HPLC (10-99% acetonitrile/5 mM HCl) to provide 5-[[5-[2-methoxy-4-(trifluoromethoxy)phenoxy]-3-methyl-2-(trifluoromethyl)pyridine-4-carbonyl]amino]pyrimidine-2-carboxamide (21.0 mg, 86%). ESI-MS m z calc. 531.10, found 532.1 $(M+1)^+$; LC/MS retention time (Method C): 2.18 minutes. $^1H$ NMR (400 MHz, DMSO-$d_6$) δ 11.53 (s, 1H), 9.18 (s, 2H), 8.16-8.09 (m, 1H), 8.07 (s, 1H), 7.78-7.69 (m, 1H), 7.35 (d, J=8.8 Hz, 1H), 7.23 (d, J=2.7 Hz, 1H), 7.01 (ddd, J=8.9, 2.7, 1.3 Hz, 1H), 3.79 (s, 3H), 2.47 (d, J=2.0 Hz, 3H) ppm.

Example 81

N-(2-Carbamoyl-5-Methyl-4-Pyridyl)-5-[2-Methoxy-4-(Trifluoromethoxy)Phenoxy]-3-Methyl-2-(Trifluoromethyl)Pyridine-4-Carboxamide (271)

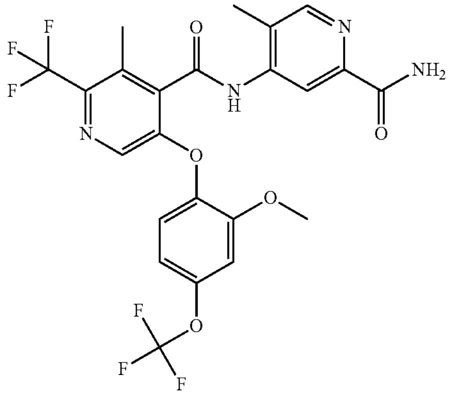 [SMILES: COc1cc(OC(F)(F)F)ccc1Oc1cnc(C(F)(F)F)c(C)c1C(=O)Nc1cc(C(N)=O)ncc1C]

Step 1: Methyl 4-[[5-[2-Methoxy-4-(Trifluoromethoxy)Phenoxy]-3-Methyl-2-(Trifluoromethyl) Pyridine-4-Carbonyl]Amino]-5-Methyl-Pyridine-2-Carboxylate

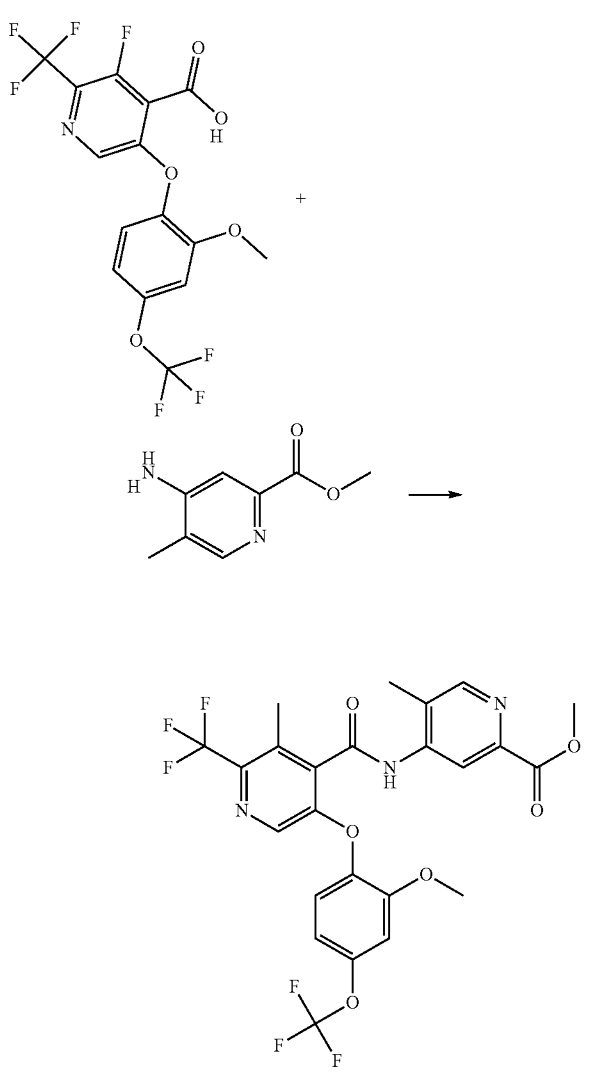

A solution of 5-[2-methoxy-4-(trifluoromethoxy)phenoxy]-3-methyl-2-(trifluoromethyl)pyridine-4-carboxylic acid (20 mg, 0.049 mmol, see Example 80 above, Step 4) and DMF (4 μL, 0.05 mmol) in dichloromethane at 0° C. was treated with oxalyl dichloride (37 mg, 26 μL, 0.29 mmol) dropwise and the resulting mixture stirred at room temperature for 20 minutes. The mixture was concentrated in vacuo. The resulting acid chloride was dissolved in NMP and added to a solution of methyl 4-amino-5-methyl-pyridine-2-carboxylate (24 mg, 0.15 mmol, Preparation 1) and DIEA (38 mg, 51 μL, 0.29 mmol) in NMP. The mixture was stirred at room temperature for 16 hours, and then filtered and purified by reverse phase HPLC (30-99% acetonitrile/5 mM HCl) to provide methyl 4-[[5-[2-methoxy-4-(trifluoromethoxy)phenoxy]-3-methyl-2-(trifluoromethyl)pyridine-4-carbonyl]amino]-5-methyl-pyridine-2-carboxylate (10.6 mg, 39%). ESI-MS m z calc. 559.12, found 560.1 $(M+1)^+$; LC/MS retention time (Method C): 2.55 minutes.

Step 2: N-(2-Carbamoyl-5-Methyl-4-Pyridyl)-5-[2-Methoxy-4-(Trifluoromethoxy)Phenoxy]-3-Methyl-2-(Trifluoromethyl)Pyridine-4-Carboxamide (271)

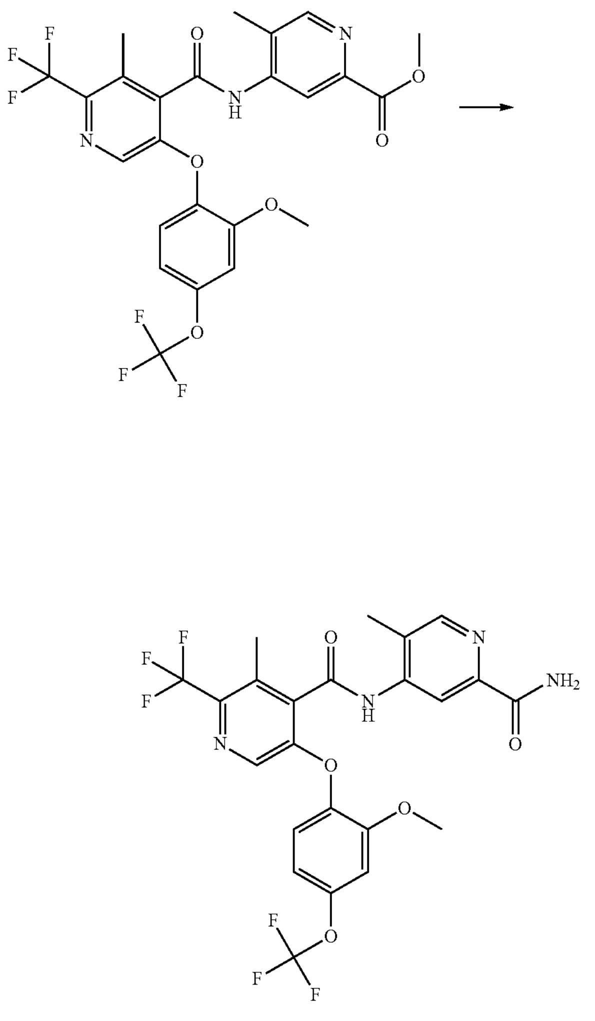

Methyl 4-[[5-[2-methoxy-4-(trifluoromethoxy)phenoxy]-3-methyl-2-(trifluoromethyl)pyridine-4-carbonyl]amino]-5-methyl-pyridine-2-carboxylate (10 mg, 0.018 mmol) was dissolved in a solution of ammonia in methanol (1.2 mL of 7 M, 8.4 mmol) and stirred at room temperature for 18 hours. The mixture was concentrated in vacuo. The residue was dissolved in DMSO, filtered and purified by reverse phase HPLC (1-99% acetonitrile/5 mM HCl) to provide N-(2-carbamoyl-5-methyl-4-pyridyl)-5-[2-methoxy-4-(trifluoromethoxy)phenoxy]-3-methyl-2-(trifluoromethyl)pyridine-4-carboxamide (6.0 mg, 62%) as a white solid. ESI-MS m z calc. 544.12, found 545.1 $(M+1)^+$; LC/MS retention time (Method C): 2.35 minutes. $^1H$ NMR (400 MHz, DMSO-$d_6$) δ 10.59 (s, 1H), 8.49 (d, J=6.6 Hz, 2H), 8.07 (s, 1H), 8.01 (s, 1H), 7.62 (s, 1H), 7.34 (d, J=8.8 Hz, 1H), 7.26 (d, J=2.7 Hz, 1H), 7.04 (d, J=8.7 Hz, 1H), 3.82 (s, 3H), 2.31 (s, 3H), 2.07 (s, 3H) ppm.

Example 82

N-(2-Carbamoyl-5-Methyl-4-Pyridyl)-2-Methoxy-4-[2-Methoxy-4-(Trifluoromethoxy)Phenoxy]-6-(Trifluoromethyl)Pyridine-3-Carboxamide (272)

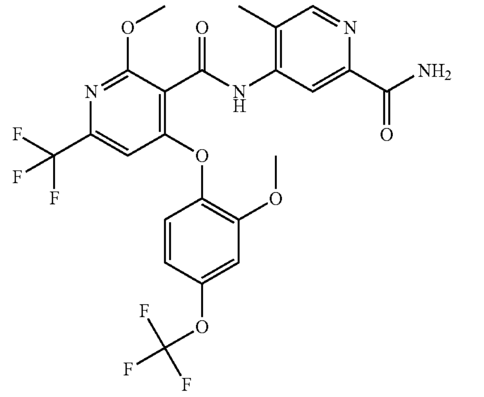 [SMILES: COc1cc(OC(F)(F)F)ccc1Oc1cc(C(F)(F)F)nc(OC)c1C(=O)Nc1cc(C(N)=O)ncc1C]

Step 1: 2-Methoxy-6-(Trifluoromethyl)Pyridine-3-Carboxylic Acid

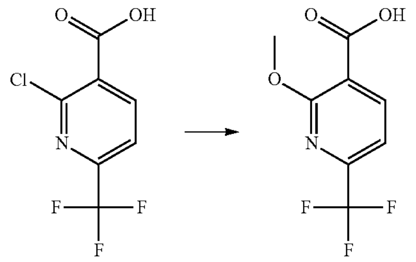

To the a stirring solution of sodium methoxide (2.9 g, 54 mmol) in methanol (24 mL) at 0° C. was added a solution of 2-chloro-6-(trifluoromethyl)pyridine-3-carboxylic acid (3.0 g, 13 mmol) in methanol (6 mL). The mixture was refluxed for 16 hours, and then cooled and diluted with water (10 mL) and dichloromethane (50 mL). The mixture acidified with 2 M aqueous HCl at 0° C. The organic layer was separated, dried over $MgSO_4$, filtered and concentrated in vacuo to provide 2-methoxy-6-(trifluoromethyl)pyridine-3-carboxylic acid (2.6 g, 88%) as a light yellow solid. $^1H$ NMR (400 MHz, $CDCl_3$) δ 8.59 (d, J=8 Hz, 1H), 7.46 (d, J=8 Hz, 1H), 4.23 (s, 3H) ppm. The acid proton was absent. ESI-MS m z calc. 221.03, found 220.0 $(M-1)^-$; LC/MS retention time (Method R): 1.27 minutes.

Step 2: 4-Chloro-2-Methoxy-6-(Trifluoromethyl) Pyridine-3-Carboxylic Acid

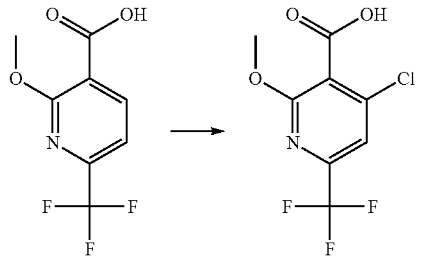 [SMILES: COc1nc(C(F)(F)F)ccc1C(=O)O ; COc1nc(C(F)(F)F)cc(Cl)c1C(=O)O]

To a stirring solution of 2,2,6,6-tetramethylpiperidine (7.0 g, 49.6 mmol) in THF (40 mL) at −50° C. was added n-butyllithium (28 mL of 1.8 M, 50.4 mmol) and the mixture stirred for 10 minutes. The solution was cooled to −78° C. and treated with a solution of 2-methoxy-6-(trifluoromethyl) pyridine-3-carboxylic acid (2.5 g, 11 mmol) in THF (40 mL). The mixture was stirred at −78° C. for 2 hours, and then transferred to a solution of hexachloroethane (12.0 g, 50.7 mmol) in THF (40 mL) at −50° C. The mixture was gradually warmed to room temperature and stirred for 1 hour. The mixture was washed with 2 M aqueous HCl (4×). The organic layer separated, dried over $MgSO_4$, filtered and concentrated in vacuo. Purification by silica gel chromatography (5-20% ethyl acetate/hexane) provided 4-chloro-2-methoxy-6-(trifluoromethyl)pyridine-3-carboxylic acid (2.1 g, 63%). $^1H$ NMR (400 MHz, $CDCl_3$) δ 7.25 (s, 1H), 3.95 (s, 3H) ppm. The acid proton was absent. ESI-MS m z calc. 254.99, found 254.2 $(M-1)^-$; LC/MS retention time (Method R): 1.36 minutes.

Step 3: Methyl 4-Chloro-2-Methoxy-6-(Trifluoromethyl)Pyridine-3-Carboxylate

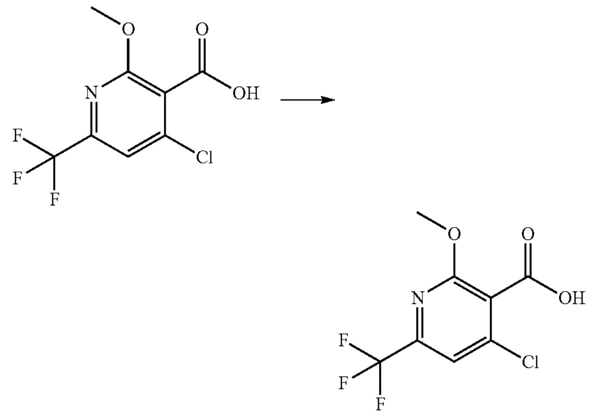

A solution of 4-chloro-2-methoxy-6-(trifluoromethyl) pyridine-3-carboxylic acid (3.23 g, 12.6 mmol) in DMF (30 mL) was treated with sodium carbonate (2.78 g, 26.2 mmol) followed by methyl iodide (5.43 g, 38.3 mmol). The mixture was stirred at room temperature overnight, then diluted with ethyl acetate and washed with saturated aqueous $NaHCO_3$ (3×) and brine. The organic layer was separated, dried over $MgSO_4$, filtered and concentrated in vacuo to provide methyl 4-chloro-2-methoxy-6-(trifluoromethyl)pyridine-3-carboxylate (2.68 g, 79%). $^1H$ NMR (400 MHz, DMSO-$d_6$) δ 7.88 (s, 1H), 3.98 (s, 3H), 3.93 (s, 3H) ppm.

Step 4: Methyl 2-Methoxy-4-[2-Methoxy-4-(Trifluoromethoxy)Phenoxy]-6-(Trifluoromethyl)Pyridine-3-Carboxylate

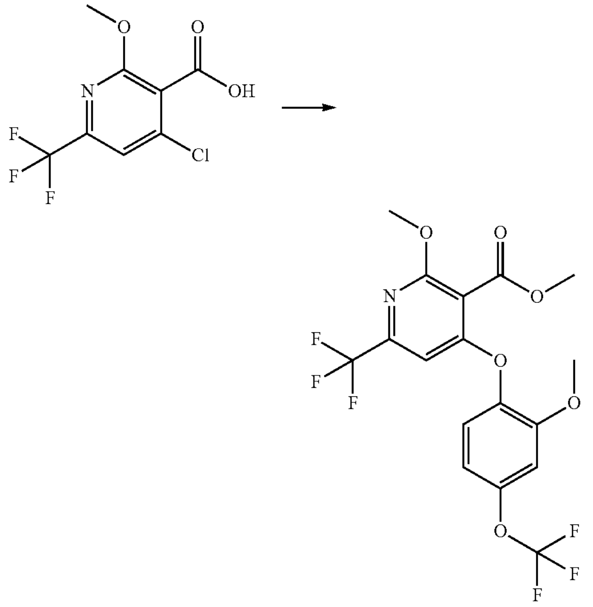

A mixture of methyl 4-chloro-2-methoxy-6-(trifluoromethyl)pyridine-3-carboxylate (2.68 g, 9.94 mmol), $K_2CO_3$ (1.82 g, 13.2 mmol) and 2-methoxy-4-(trifluoromethoxy)phenol (2.18 g, 10.5 mmol) in acetonitrile (15 mL) was heated in a pressure vessel at 90° C. for 8 hours. The mixture was diluted with ethyl acetate and washed with 2 M aqueous NaOH (2×). The organic layer was separated, dried over $MgSO_4$, filtered and concentrated to provide methyl 2-methoxy-4-[2-methoxy-4-(trifluoromethoxy)phenoxy]-6-(trifluoromethyl)pyridine-3-carboxylate (3.9 g, 89%). ESI-MS m z calc. 441.07, found 442.1 $(M+1)^+$; LC/MS retention time (Method F): 1.08 minutes.

Step 5: 2-Methoxy-4-[2-Methoxy-4-(Trifluoromethoxy)Phenoxy]-6-(Trifluoromethyl)Pyridine-3-Carboxylic Acid

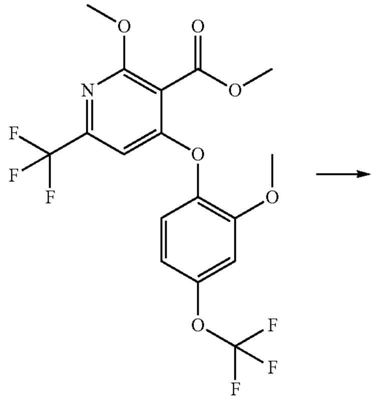

-continued

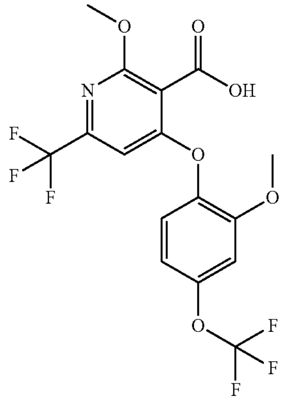

A solution of methyl 2-methoxy-4-[2-methoxy-4-(trifluoromethoxy)phenoxy]-6-(trifluoromethyl)pyridine-3-carboxylate (3.9 g, 8.8 mmol) in THF (20 mL) was treated with 2 M aqueous NaOH (34 mL of 2 M, 68 mmol). The mixture was heated at 50° C. for 20 hours. Additional aqueous NaOH (13 mL of 2 M, 26 mmol) was added and the mixture refluxed for 7 hours. The mixture was allowed to cool and acidified with 4 M aqueous HCl to pH=4. The organic layer was separated, dried over $MgSO_4$, filtered and concentrated in vacuo to provide 2-methoxy-4-[2-methoxy-4-(trifluoromethoxy)phenoxy]-6-(trifluoromethyl)pyridine-3-carboxylic acid (3.92 g, 104%). ESI-MS m z calc. 427.05, found 428.4 $(M+1)^+$; LC/MS retention time (Method F): 0.59 minutes.

Step 6: N-(2-Carbamoyl-5-Methyl-4-Pyridyl)-2-Methoxy-4-[2-Methoxy-4-(Trifluoromethoxy)Phenoxy]-6-(Trifluoromethyl)Pyridine-3-Carboxamide (272)

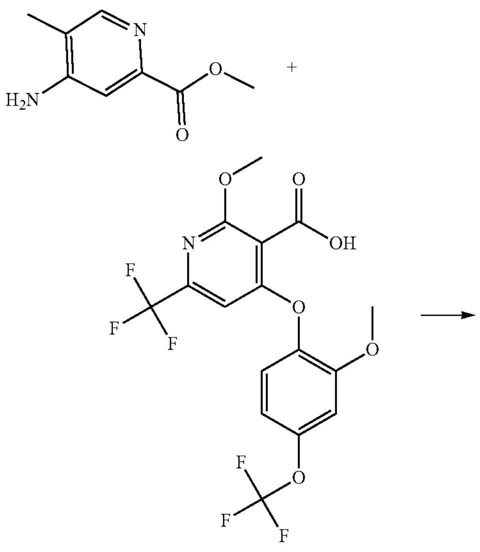

-continued

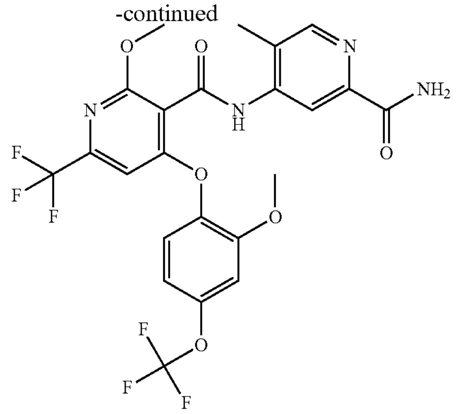

A solution of 2-methoxy-4-[2-methoxy-4-(trifluoromethoxy)phenoxy]-6-(trifluoromethyl)pyridine-3-carboxylic acid (400 mg, 0.936 mmol) in dichloromethane (10 mL) was treated with DMF (5 μL, 0.07 mmol) and oxalyl chloride (160 μL, 1.83 mmol) and stirred at room temperature for 1 hour before concentrating. The residue was redissolved in dichloromethane (10 mL) and treated with TEA (400 μL, 2.87 mmol) followed by methyl 4-amino-5-methyl-pyridine-2-carboxylate (17.3 mg, 0.104 mmol, Preparation 1). The mixture was stirred at room temperature for 2 hours. The mixture was then concentrated, treated with a solution of ammonia in methanol (5 mL of 7 M, 35 mmol) and stirred at room temperature for 20 hours. The mixture was concentrated in vacuo. Purification by reverse phase HPLC 38-53% acetonitrile/0.1% ammonium hydroxide), followed by additional reverse phase HPLC purification (0-100% acetonitrile/0.05% trifluoroacetic acid) provided N-(2-carbamoyl-5-methyl-4-pyridyl)-2-methoxy-4-[2-methoxy-4-(trifluoromethoxy)phenoxy]-6-(trifluoromethyl)pyridine-3-carboxamide (82.3 mg, 15%). ESI-MS m z calc. 560.11, found 561.4 $(M+1)^+$; LC/MS retention time (Method E): 3.34 minutes. $^1H$ NMR (500 MHz, DMSO-$d_6$) δ 10.31 (s, 1H), 8.54 (s, 1H), 8.45 (s, 1H), 8.04 (d, J=2.8 Hz, 1H), 7.58 (d, J=2.8 Hz, 1H), 7.38 (d, J=8.8 Hz, 1H), 7.28 (d, J=2.7 Hz, 1H), 7.05 (ddt, J=8.9, 2.5, 1.3 Hz, 1H), 6.70 (s, 1H), 4.00 (s, 3H), 3.82 (s, 3H), 2.31 (s, 3H) ppm.

Example 83

3-Methoxy-5-[2-Methoxy-4-(Trifluoromethoxy)Phenoxy]-N-[2-(Methylcarbamoyl)-4-Pyridyl]-2-(Trifluoromethyl)Pyridine-4-Carboxamide (273)

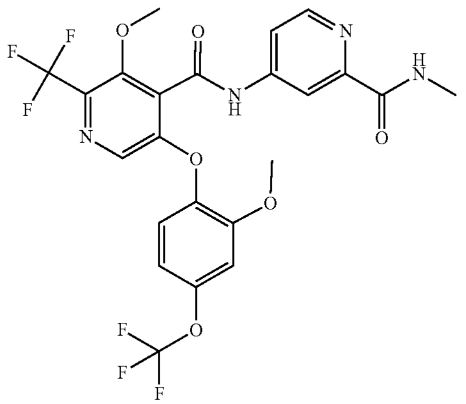

Step 1: Methyl 4-[[3-Methoxy-5-[2-Methoxy-4-(Trifluoromethoxy)Phenoxy]-2-(Trifluoromethyl)Pyridine-4-Carbonyl]Amino]Pyridine-2-Carboxylate

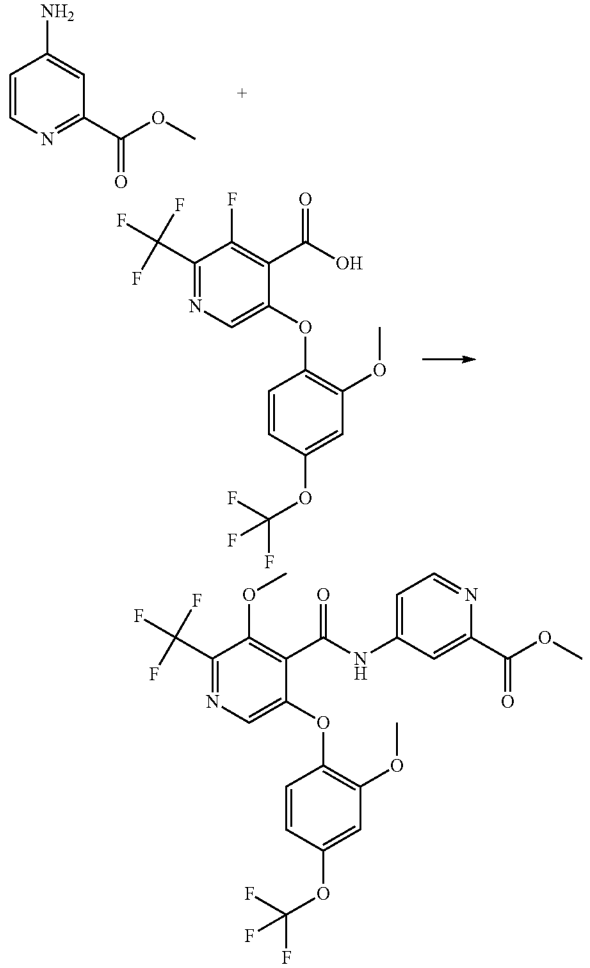

A solution of 3-fluoro-5-[2-methoxy-4-(trifluoromethoxy)phenoxy]-2-(trifluoromethyl)pyridine-4-carboxylic acid (625 mg, 1.51 mmol, see Example 80, Step 3) in dichloromethane (18 mL) at 0° C. under nitrogen was treated with DMF (10 μL, 0.13 mmol) followed by oxalyl chloride (175 μL, 2.01 mmol). The mixture was allowed to warm to room temperature over 40 minutes before concentrating. The acid chloride was redissolved in dichloromethane, treated with methyl 4-aminopyridine-2-carboxylate (278 mg, 1.83 mmol) and TEA (420 μL, 3.01 mmol), and stirred at room temperature for 16 hours. The mixture was diluted with saturated aqueous $NaHCO_3$ and the layers separated. The organic layer was dried over $MgSO_4$, filtered and concentrated. The residue was then dissolved in methanol (6 mL) and TEA (2 mL, 14 mmol) and heated at 70° C. for 4 hours. The mixture was allowed to cool and was then concentrated. Silica gel chromatography (0-55% ethyl acetate/heptane) provided methyl 4-[[3-methoxy-5-[2-methoxy-4-(trifluoromethoxy)phenoxy]-2-(trifluoromethyl)pyridine-4-carbonyl]amino]pyridine-2-carboxylate (380 mg, 45%). ESI-MS m z calc. 561.10, found 562.4 $(M+1)^+$; LC/MS retention time (Method F): 0.93 minutes.

Step 2: 3-Methoxy-5-[2-Methoxy-4-(Trifluoromethoxy)Phenoxy]-N-[2-(Methylcarbamoyl)-4-Pyridyl]-2-(Trifluoromethyl)Pyridine-4-Carboxamide (273)

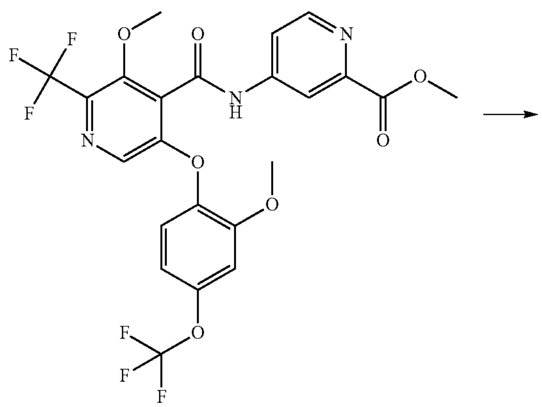

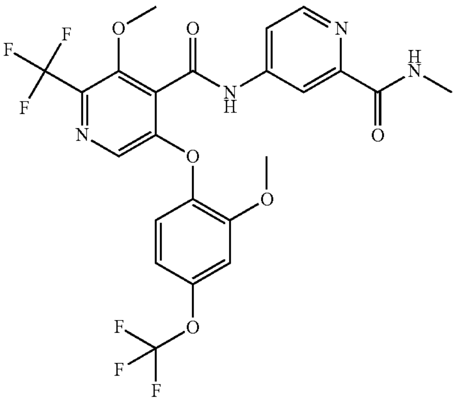 [SMILES: CNC(=O)c1cc(NC(=O)c2c(Oc3ccc(OC(F)(F)F)cc3OC)cnc(C(F)(F)F)c2OC)ccn1]

A solution of methyl 4-[[3-methoxy-5-[2-methoxy-4-(trifluoromethoxy)phenoxy]-2-(trifluoromethyl)pyridine-4-carbonyl]amino]pyridine-2-carboxylate (20 mg, 0.036 mmol) in methanol (150 µL) was treated with a solution of methylamine in water (200 µL of 40% w/v, 2.576 mmol). The mixture was stirred for 40 minutes, and then purified directly by reverse phase HPLC (47-95% acetonitrile/0.1% ammonium hydroxide) to provide 3-methoxy-5-[2-methoxy-4-(trifluoromethoxy)phenoxy]-N-[2-(methylcarbamoyl)-4-pyridyl]-2-(trifluoromethyl)pyridine-4-carboxamide (10.2 mg, 46%). ESI-MS m z calc. 560.11, found 561.5 $(M+1)^+$; LC/MS retention time (Method E): 3.28 minutes. $^1H$ NMR (500 MHz, DMSO-$d_6$) δ 11.49 (s, 1H), 8.76 (q, J=4.8 Hz, 1H), 8.57 (d, J=5.5 Hz, 1H), 8.29 (d, J=2.1 Hz, 1H), 7.97 (s, 1H), 7.84 (dd, J=5.5, 2.2 Hz, 1H), 7.36 (d, J=8.8 Hz, 1H), 7.23 (d, J=2.7 Hz, 1H), 7.01 (ddd, J=8.7, 2.7, 1.3 Hz, 1H), 3.96 (s, 3H), 3.80 (s, 3H), 2.83 (d, J=4.9 Hz, 3H) ppm.

Example 84

N-(2-Carbamoyl-4-Pyridyl)-6-Ethyl-3-[2-Methoxy-4-(Trifluoromethoxy)Phenoxy]-5-(Trifluoromethyl) Pyridine-2-Carboxamide (274)

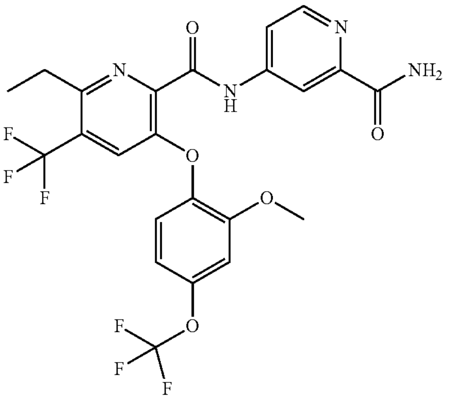 [SMILES: CCc1nc(C(=O)Nc2ccnc(C(N)=O)c2)c(Oc2ccc(OC(F)(F)F)cc2OC)cc1C(F)(F)F]

Step 1: Methyl 3-[2-Methoxy-4-(Trifluoromethoxy) Phenoxy]-5-(Trifluoromethyl)-6-Vinyl-Pyridine-2-Carboxylate

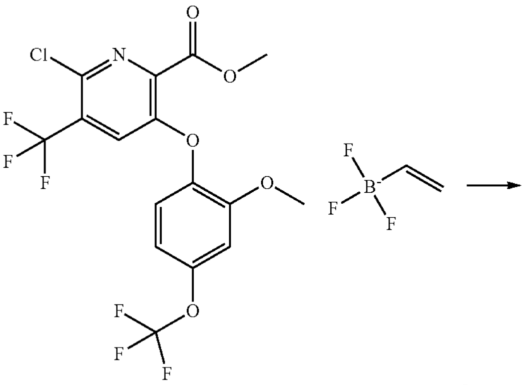

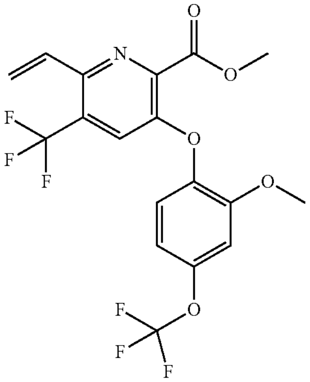

A mixture of methyl 6-chloro-3-[2-methoxy-4-(trifluoromethoxy)phenoxy]-5-(trifluoromethyl)pyridine-2-carboxylate (230 mg, 0.516 mmol, see Example 58, Step 4), potassium vinyltrifluoroborate (84 mg, 0.63 mmol), Pd(dppf)$Cl_2$ (27 mg, 0.037 mmol) and TEA (100 µL, 0.718 mmol) in 2-propanol (4.5 mL) was heated at 90° C. for 1 hour. The mixture was diluted with water (20 mL) and extracted with ethyl acetate (3×20 mL). The combined organic extracts were dried over $MgSO_4$, filtered and concentrated in vacuo to provide methyl 3-[2-methoxy-4-(trifluoromethoxy)phenoxy]-5-(trifluoromethyl)-6-vinyl-pyridine-2-carboxylate (205 mg, 91%). ESI-MS m z calc. 437.07, found 438.5 $(M+1)^+$; LC/MS retention time (Method F): 1.05 minutes.

Step 2: Methyl 6-Ethyl-3-[2-Methoxy-4-(Trifluoromethoxy)Phenoxy]-5-(Trifluoromethyl)Pyridine-2-Carboxylate

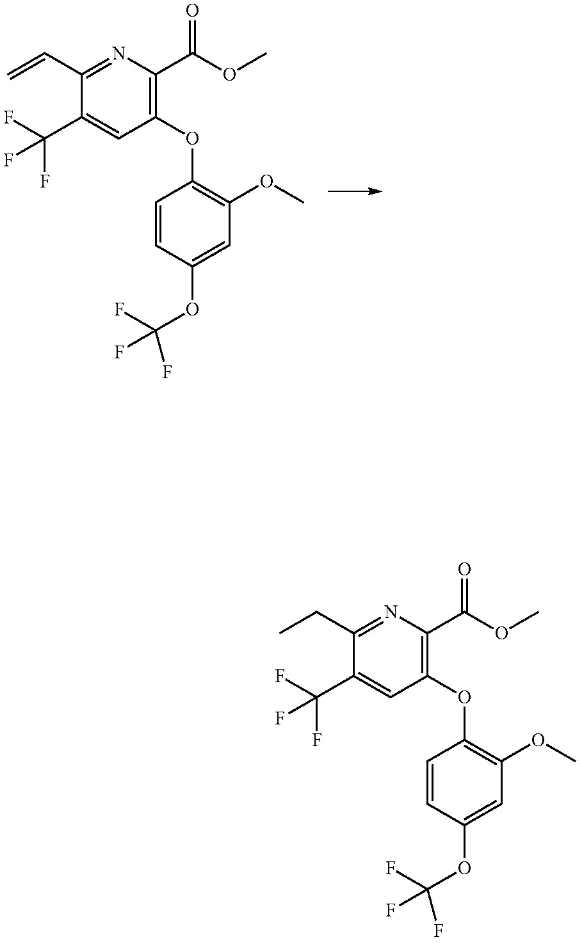 [SMILES: C=Cc1nc(C(=O)OC)c(Oc2ccc(OC(F)(F)F)cc2OC)cc1C(F)(F)F ; CCc1nc(C(=O)OC)c(Oc2ccc(OC(F)(F)F)cc2OC)cc1C(F)(F)F]

A solution of methyl 3-[2-methoxy-4-(trifluoromethoxy) phenoxy]-5-(trifluoromethyl)-6-vinyl-pyridine-2-carboxylate (200 mg, 0.457 mmol) in ethanol (5 mL) was stirred with 10% palladium on carbon (201 mg) under hydrogen atmosphere at room temperature for 20 hours. The mixture was filtered through Celite and the filtrate concentrated in vacuo to provide methyl 6-ethyl-3-[2-methoxy-4-(trifluoromethoxy)phenoxy]-5-(trifluoromethyl)pyridine-2-carboxylate (159 mg, 79%). ESI-MS m z calc. 439.09, found 440.5 $(M+1)^+$; LC/MS retention time (Method F): 1.05 minutes. $^1H$ NMR (500 MHz, $CDCl_3$) δ 7.28 (s, 1H), 7.10-7.02 (m, 1H), 6.85 (d, J=11.6 Hz, 2H), 3.97 (s, 3H), 3.80 (s, 3H), 2.98 (d, J=8.0 Hz, 2H), 1.33 (t, J=6.8 Hz, 3H) ppm.

Step 3: 6-Ethyl-3-[2-Methoxy-4-(Trifluoromethoxy) Phenoxy]-5-(Trifluoromethyl)Pyridine-2-Carboxylic Acid

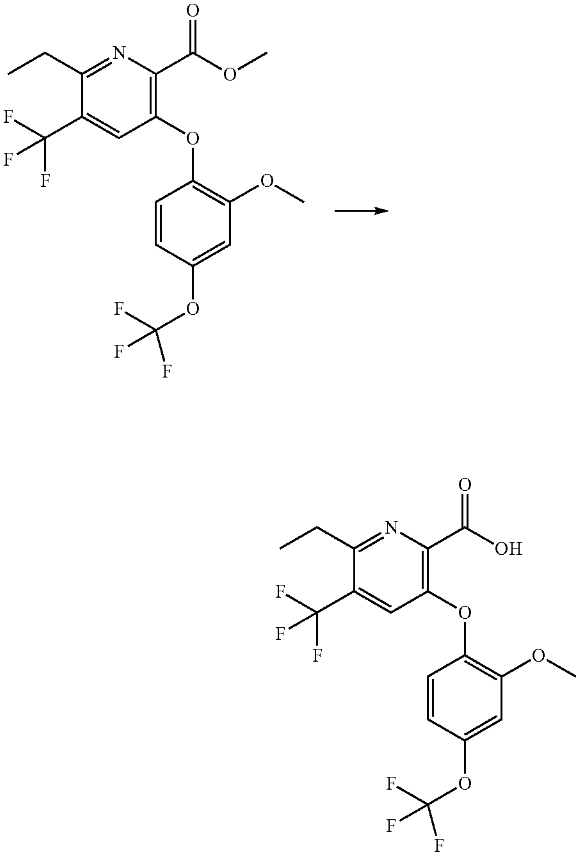 [SMILES: CCc1nc(C(=O)OC)c(Oc2ccc(OC(F)(F)F)cc2OC)cc1C(F)(F)F ; CCc1nc(C(=O)O)c(Oc2ccc(OC(F)(F)F)cc2OC)cc1C(F)(F)F]

To a solution of methyl 6-ethyl-3-[2-methoxy-4-(trifluoromethoxy)phenoxy]-5-(trifluoromethyl)pyridine-2-carboxylate (157 mg, 0.357 mmol) in THF (3 mL) was added 2 M aqueous NaOH (3 mL of 2 M, 6 mmol) and the mixture stirred at room temperature for 1 hour. The mixture was acidified to pH=3 with 2 M aqueous HCl and extracted with ethyl acetate (4×). The combined organic extracts were dried over $MgSO_4$, filtered and concentrated in vacuo to provide 6-ethyl-3-[2-methoxy-4-(trifluoromethoxy)phenoxy]-5-(trifluoromethyl)pyridine-2-carboxylic acid (150 mg, 99%). ESI-MS m z calc. 425.07, found 426.5 $(M+1)^+$; 424.6 $(M-1)^-$; LC/MS retention time (Method F): 0.59 minutes.

Step 4: N-(2-Carbamoyl-4-Pyridyl)-6-Ethyl-3-[2-Methoxy-4-(Trifluoromethoxy)Phenoxy]-5-(Trifluoromethyl)Pyridine-2-Carboxamide (274)

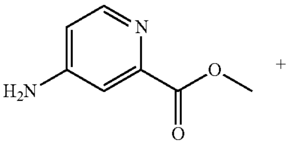

-continued

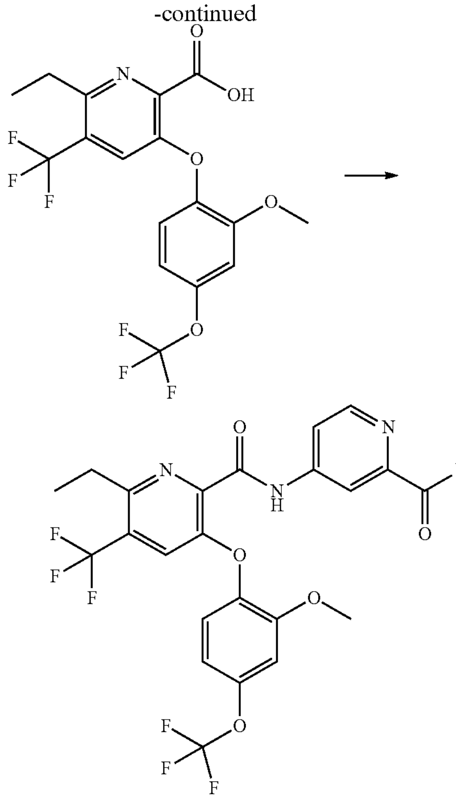

To a solution of 6-ethyl-3-[2-methoxy-4-(trifluoromethoxy)phenoxy]-5-(trifluoromethyl)pyridine-2-carboxylic acid (50 mg, 0.12 mmol) in dichloromethane (1 mL) and DMF (1 µL, 0.013 mmol) at 0° C. was added oxalyl chloride (40 µL, 0.46 mmol) and the mixture was warmed to room temperature and stirred for 30 minutes. The mixture was concentrated in vacuo. The acid chloride was redissolved in dichloromethane (1 mL) and added to a solution of methyl 4-aminopyridine-2-carboxylate (18 mg, 0.12 mmol) and TEA (50 µL, 0.36 mmol) in dichloromethane (1 mL) at 0° C. The mixture was warmed to room temperature and stirred for 1 hour. The mixture was partitioned between dichloromethane (20 mL) and water (25 mL) and the layers separated. The aqueous layer extracted with additional dichloromethane (2×20 mL), and the combined organic extracts were dried and concentrated in vacuo. The crude product was treated with a solution of ammonia in methanol (1 mL of 7 M, 7 mmol) and stirred for 6 hours at room temperature. The mixture was concentrated in vacuo and purified by reverse phase HPLC (47-95% acetonitrile/0.1% ammonium hydroxide) to provide N-(2-carbamoyl-4-pyridyl)-6-ethyl-3-[2-methoxy-4-(trifluoromethoxy)phenoxy]-5-(trifluoromethyl)pyridine-2-carboxamide (10 mg, 16%). ESI-MS m z calc. 544.12, found 545.3 $(M+1)^+$; 543.6 $(M-1)^-$; LC/MS retention time (Method E): 3.52 minutes. $^1H$ NMR (500 MHz, DMSO-$d_6$) δ 11.16 (s, 1H), 8.55 (dd, J=5.5, 0.6 Hz, 1H), 8.36 (d, J=2.2 Hz, 1H), 8.09 (d, J=2.8 Hz, 1H), 7.90 (dd, J=5.5, 2.2 Hz, 1H), 7.64 (d, J=2.8 Hz, 1H), 7.53 (s, 1H), 7.25 (d, J=8.8 Hz, 1H), 7.20 (d, J=2.8 Hz, 1H), 6.98 (ddt, J=8.7, 2.3, 1.2 Hz, 1H), 3.77 (s, 3H), 3.00-2.86 (m, 2H), 1.31 (t, J=7.4 Hz, 3H) ppm.

Example 85

N-(2-Carbamoyl-4-Pyridyl)-6-Methoxy-3-[2-Methoxy-4-(Trifluoromethoxy)Phenoxy]-5-(Trifluoromethyl)Pyridine-2-Carboxamide (275)

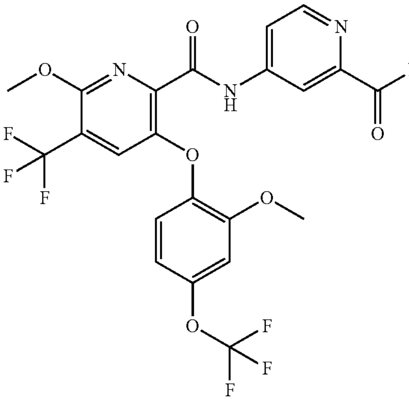

Step 1: Methyl 1-Oxido-5-(Trifluoromethyl)Pyridin-1-Ium-2-Carboxylate

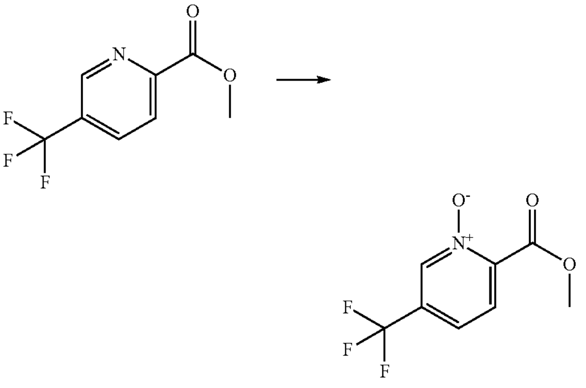

Urea hydrogen peroxide (31.37 g, 323.5 mmol) was added portion-wise to a stirring solution of methyl 5-(trifluoromethyl)pyridine-2-carboxylate (20.0 g, 95.6 mmol) in DCE (150 mL) at 0° C. Trifluoroacetic anhydride (54 g, 36 mL, 254 mmol) was then added over 30 minutes at −10° C. The mixture was stirred for an additional 30 minutes at 0° C. and then allowed to warm to room temperature and stirred for 1 hour. The mixture was then poured into ice-cold 0.5 M aqueous HCl (320 mL). The mixture was diluted with dichloromethane (160 mL) and layers were separated. The aqueous phase was extracted with additional dichloromethane (2×160 mL). The combined organic extracts were washed with water (2×300 mL) and brine (200 mL), dried over anhydrous $Na_2SO_4$, filtered and concentrated in vacuo to provide methyl 1-oxido-5-(trifluoromethyl)pyridin-1-ium-2-carboxylate (20.65 g, 98%) as light yellow solid. ESI-MS m z calc. 221.03, found 222.1 $(M+1)^+$; LC/MS retention time (Method L): 1.26 minutes. $^1H$ NMR (300 MHz, $CDCl_3$) δ 8.51 (s, 1H), 7.74 (d, J=8.2 Hz, 1H), 7.47 (d, J=8.2 Hz, 1H), 4.04 (s, 3H) ppm. $^{19}F$ NMR (282 MHz, $CDCl_3$) δ −63.61 (s, 3F) ppm.

Step 2: Methyl 6-Hydroxy-5-(Trifluoromethyl)Pyridine-2-Carboxylate

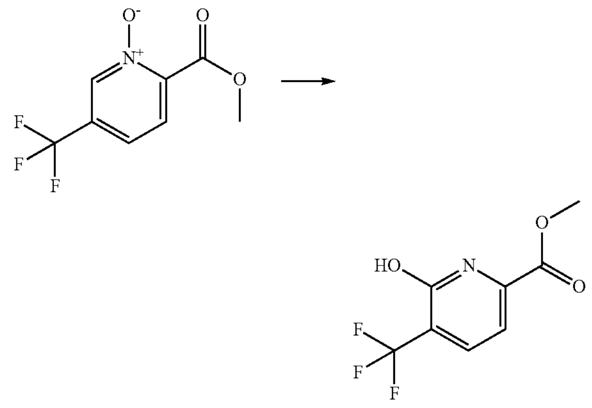

Trifluoroacetic anhydride (292 g, 193 mL, 1.39 mol) was added dropwise to a solution of methyl 1-oxido-5-(trifluoromethyl)pyridin-1-ium-2-carboxylate (51.06 g, 230.7 mmol) in DMF (305 mL) at 0° C. The mixture was stirred at room temperature overnight, then concentrated in vacuo to remove excess trifluoroacetic acid. The residual DMF solution was poured dropwise into stirring water (1000 mL) at 0° C. The resulting precipitate was collected by filtration. The solid was washed with water (300 mL) and dried under high vacuum to provide methyl 6-hydroxy-5-(trifluoromethyl)pyridine-2-carboxylate (45.24 g, 86%) as white solid. ESI-MS m z calc. 221.03, found 222.1 $(M+1)^+$; LC/MS retention time (Method L): 1.43 minutes. $^1H$ NMR (300 MHz, DMSO-$d_6$) δ 7.90 (d, J=7.2 Hz, 1H), 7.03 (d, J=7.2 Hz, 1H), 4.02 (s, 3H) ppm. $^{19}F$ NMR (282 MHz, DMSO-$d_6$) δ −66.39 (s, 3F) ppm.

Step 3: Methyl 3-Bromo-6-Hydroxy-5-(Trifluoromethyl)Pyridine-2-Carboxylate

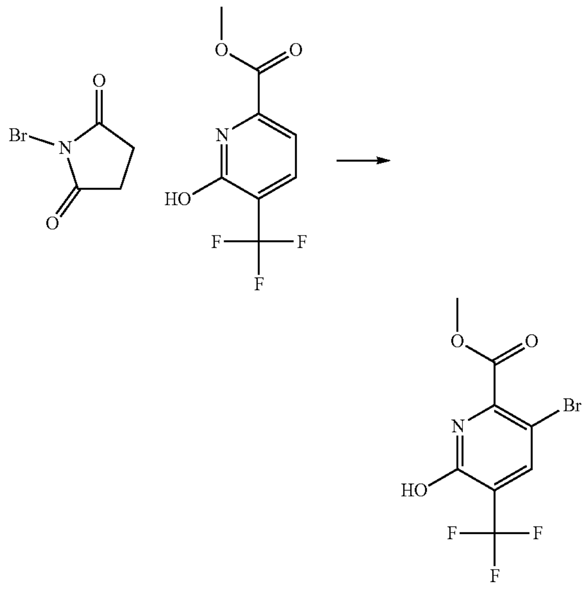

N-Bromosuccinimide (18.3 g, 104 mmol) was added in three equal portions over 45 minutes to a solution of methyl 6-hydroxy-5-(trifluoromethyl)pyridine-2-carboxylate (20.6 g, 93.2 mmol) in DMF (160 mL). A slight exotherm was observed during the NBS addition. The mixture was stirred at room temperature for 60 minutes, then diluted with water (1 L) and the resulting precipitate collected by filtration. The solid was washed with water (3×100 mL) and dried under high vacuum to provide methyl 3-bromo-6-hydroxy-5-(trifluoromethyl)pyridine-2-carboxylate (26.61 g, 95%) as a white powder. ESI-MS m z calc. 298.94, found 300.0 $(M+1)^+$; LC/MS retention time (Method L): 1.64 minutes. $^1H$ NMR (300 MHz, $CDCl_3$) δ 4.03 (s, 3H), 7.98 (s, 1H), 11.53 (br s, 1H) ppm. $^{19}F$ NMR (282 MHz, $CDCl_3$) δ −66.4 (s, 3F) ppm.

Step 4: Methyl 3-Bromo-6-Methoxy-5-(Trifluoromethyl)Pyridine-2-Carboxylate

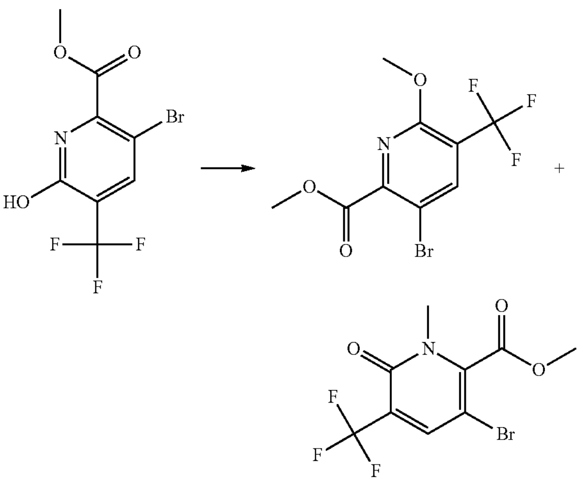

A mixture of methyl 3-bromo-6-hydroxy-5-(trifluoromethyl)pyridine-2-carboxylate (2.4 g, 8.0 mmol), iodomethane (3.4 g, 1.5 mL, 24 mmol) and silver carbonate (2.7 g, 9.8 mmol) in dioxane (35 mL) was heated at 50° C. in a sealed tube overnight. The mixture was filtered through Celite and the solids washed with ethyl acetate (150 mL). The filtrate was concentrated in vacuo. The residue was purified using silica gel chromatography (0-50% ethyl acetate/heptane) to provide methyl 3-bromo-6-methoxy-5-(trifluoromethyl) pyridine-2-carboxylate (2.25 g, 90%). ESI-MS m z calc. 312.96, found 314.0 $(M+1)^+$; LC/MS retention time (Method L): 2.1 minutes. $^1H$ NMR (300 MHz, $CDCl_3$) δ 4.00 (s, 3H), 4.05 (s, 3H), 8.06 (s, 1H) ppm. $^{19}F$ NMR (282 MHz, $CDCl_3$) δ −64.4 (s, 3F) ppm.

Step 5: 3-Bromo-6-Methoxy-5-(Trifluoromethyl) Pyridine-2-Carboxylic Acid

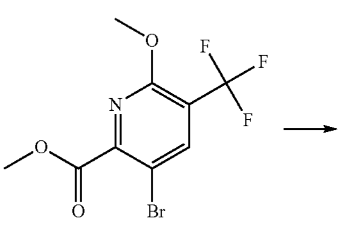

-continued

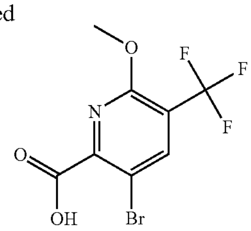

To a solution of methyl 3-bromo-6-methoxy-5-(trifluoromethyl)pyridine-2-carboxylate (9.2 g, 29 mmol) in 2-propanol (270 mL) was added NaOH (7.11 g, 178 mmol) and the mixture stirred at room temperature for 1 hour. The mixture was diluted with 3 M aqueous HCl (49 mL) then partially concentrated in vacuo to remove isopropanol. Additional 3 M aqueous HCl (10 mL) was added and the resulting solid collected by filtration and washed with water (150 mL). The solid was dissolved in ethyl acetate and washed with 0.1 M aqueous HCl (100 mL). The organic phase was dried over anhydrous $Na_2SO_4$, filtered and concentrated in vacuo to provide 3-bromo-6-methoxy-5-(trifluoromethyl)pyridine-2-carboxylic acid (6.73 g, 76%) as a white solid. ESI-MS m z calc. 298.94, found 300.0 $(M+1)^+$; LC/MS retention time (Method M): 2.43 minutes. $^1H$ NMR (300 MHz, $CDCl_3$) δ 4.09 (s, 3H), 6.18 (br. s., 1H), 8.18 (s, 1H) ppm. $^{19}F$ NMR (282 MHz, $CDCl_3$) δ −64.4 (s, 3F) ppm.

Step 6: Methyl 4-[[3-Bromo-6-Methoxy-5-(Trifluoromethyl)Pyridine-2-Carbonyl]Amino]Pyridine-2-Carboxylate

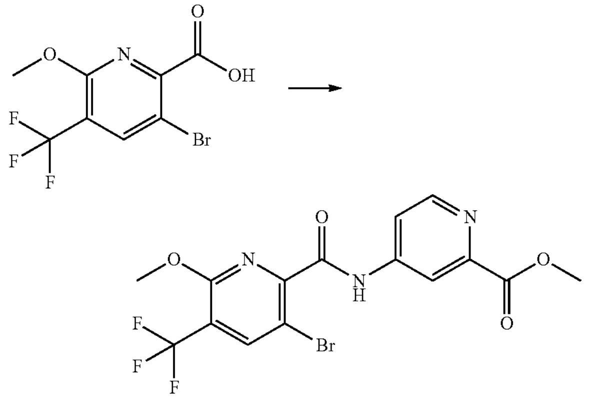

DMF (10 μL, 0.13 mmol) was added to a solution of 3-bromo-6-methoxy-5-(trifluoromethyl)pyridine-2-carboxylic acid (167 mg, 0.557 mmol) and oxalyl chloride (200 μL, 2.29 mmol) in dichloromethane (5 mL) at 0° C. and the resulting mixture stirred at room temperature for 2 hours. The solvent was removed in vacuo and the acid chloride redissolved in dichloromethane (5 mL). Methyl 4-aminopyridine-2-carboxylate (90 mg, 0.59 mmol) and TEA (180 μL, 1.29 mmol) were added and the resulting mixture stirred at room temperature for 2 hours. The mixture was concentrated in vacuo and purified by silica gel chromatography (0-70% ethyl acetate/petroleum ether) to provide methyl 4-[[3-bromo-6-methoxy-5-(trifluoromethyl)pyridine-2-carbonyl]amino]pyridine-2-carboxylate (127 mg, 53%) as a pale yellow solid. ESI-MS m z calc. 432.99, found 434.4 $(M+1)^+$; 432.5 $(M-1)^-$; LC/MS retention time (Method F): 0.81 minutes. $^1H$ NMR (500 MHz, DMSO-$d_6$) δ 11.29 (s, 1H), 8.67 (d, J=5.4 Hz, 1H), 8.56 (s, 1H), 8.44 (d, J=2.1 Hz, 1H), 7.91 (dd, J=5.4, 2.2 Hz, 1H), 4.07 (s, 3H), 3.91 (s, 3H) ppm.

Step 7: Methyl 4-[[6-Methoxy-3-[2-Methoxy-4-(Trifluoromethoxy)Phenoxy]-5-(Trifluoromethyl)Pyridine-2-Carbonyl]Amino]Pyridine-2-Carboxylate

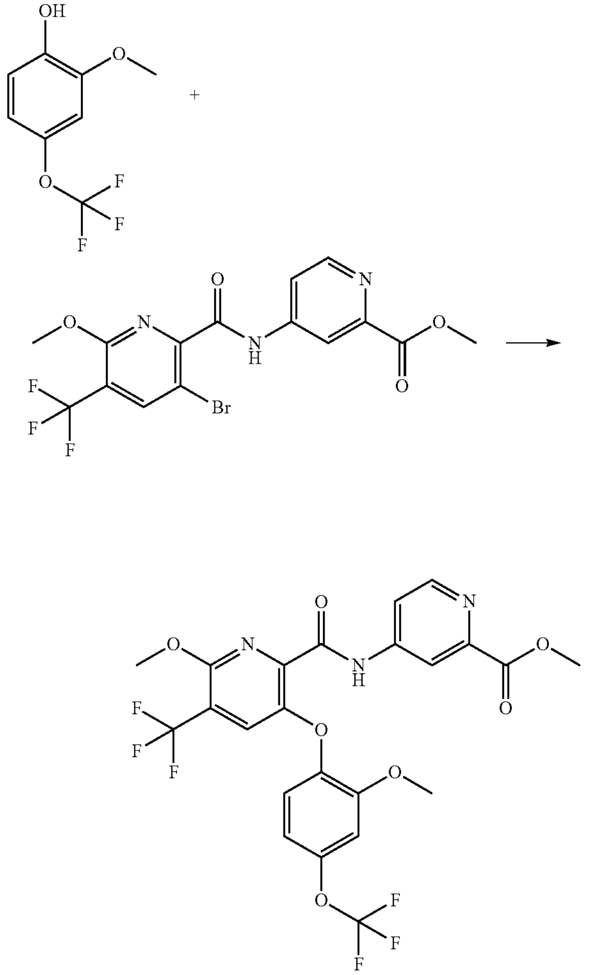

A mixture of 2-methoxy-4-(trifluoromethoxy)phenol (291 mg, 0.140 mmol), methyl 4-[[3-bromo-6-methoxy-5-(trifluoromethyl)pyridine-2-carbonyl]amino]pyridine-2-carboxylate (55 mg, 0.13 mmol), $Cs_2CO_3$ (63 mg, 0.19 mmol) and copper (I) iodide (5.3 mg, 0.028 mmol) in toluene (2 mL) was heated under nitrogen at 100° C. for 60 hours. The mixture was diluted with water (20 mL) and extracted with ethyl acetate (3×25 mL). The combined organic extracts were dried over $MgSO_4$, filtered and concentrated in vacuo. The residue was purified by silica gel chromatography (0-60% ethyl acetate/heptane) to provide methyl 4-[[6-methoxy-3-[2-methoxy-4-(trifluoromethoxy)phenoxy]-5-(trifluoromethyl)pyridine-2-carbonyl]amino]pyridine-2-carboxylate (9 mg, 13%). ESI-MS m z calc. 561.10, found 562.5 $(M+1)^+$; 560.5 $(M-1)^-$; LC/MS retention time (Method F): 0.96 minutes.

Step 8: N-(2-Carbamoyl-4-Pyridyl)-6-Methoxy-3-[2-Methoxy-4-(Trifluoromethoxy)Phenoxy]-5-(Trifluoromethyl)Pyridine-2-Carboxamide (275)

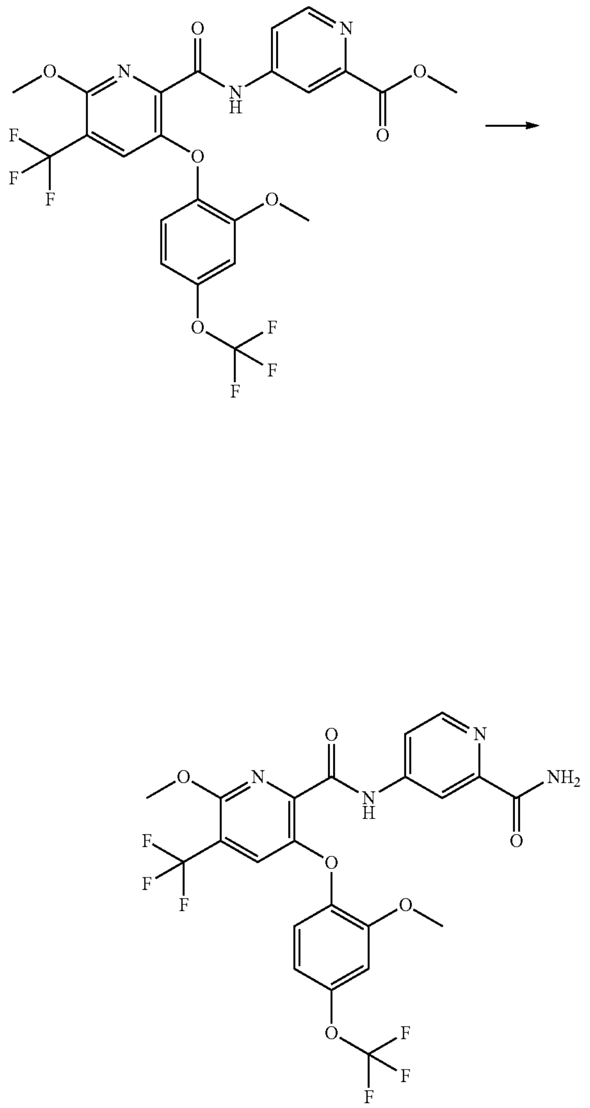

Methyl 4-[[6-methoxy-3-[2-methoxy-4-(trifluoromethoxy)phenoxy]-5-(trifluoromethyl)pyridine-2-carbonyl]amino]pyridine-2-carboxylate (9 mg, 0.02 mmol) was dissolved in a solution of ammonia in methanol (200 μL of 7 M, 1.4 mmol) and the mixture stirred at room temperature for 20 hours. The mixture was concentrated in vacuo and purified by reverse phase HPLC (47-95% acetonitrile/0.1% ammonium hydroxide) to provide N-(2-carbamoyl-4-pyridyl)-6-methoxy-3-[2-methoxy-4-(trifluoromethoxy)phenoxy]-5-(trifluoromethyl)pyridine-2-carboxamide (2 mg, 23%). ESI-MS m z calc. 546.10, found 547.5 $(M+1)^+$; 545.6 $(M-1)^-$; LC/MS retention time (Method E): 3.38 minutes. $^1H$ NMR (500 MHz, methanol-$d_4$) δ 8.59-8.50 (m, 2H), 8.30 (d, J=2.1 Hz, 1H), 8.02 (dd, J=5.5, 2.2 Hz, 1H), 7.60 (s, 1H), 7.15 (d, J=8.8 Hz, 1H), 7.03 (d, J=2.7 Hz, 1H), 6.89 (ddd, J=8.8, 2.7, 1.3 Hz, 1H), 4.15 (s, 3H), 3.80 (s, 3H) ppm.

Example 86

4-[[5-Methoxy-2-[2-Methoxy-4-(Trifluoromethoxy)Phenoxy]-4-(Trifluoromethyl)Benzoyl]Amino]Pyridine-2-Carboxamide (276)

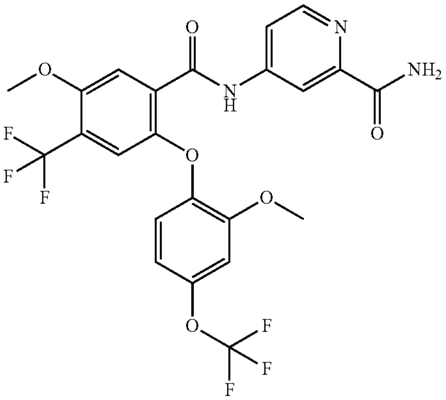 [SMILES: COc1cc(OC(F)(F)F)ccc1Oc1cc(C(F)(F)F)c(OC)cc1C(=O)Nc1ccnc(C(N)=O)c1]

Step 1: 2-Iodo-5-Methoxy-4-(Trifluoromethyl)Benzoic Acid

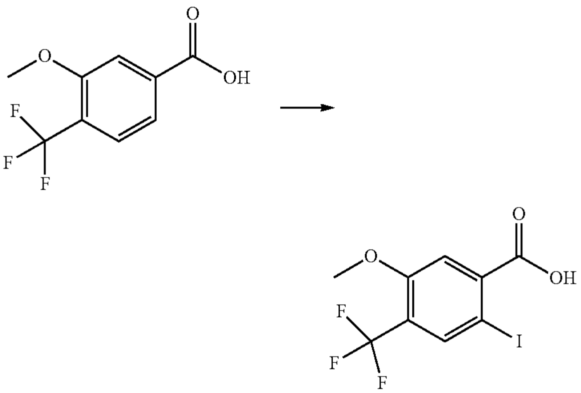

3-Methoxy-4-(trifluoromethyl)benzoic acid (5.02 g, 22.8 mmol), $PhI(OAc)_2$ (11.01 g, 34.18 mmol) and iodine (8.78 g, 34.6 mmol) were combined in DMF (100 mL) and the reaction vessel flushed with nitrogen. $Pd(OAc)_2$ (261 mg, 1.16 mmol) was added and the mixture heated under nitrogen at 100° C. for 90 minutes. The mixture was cooled to room temperature and partitioned between ethyl acetate and water. The layers were separated and the organic layer washed with additional water (5×). The organic layer was washed with brine, dried over $MgSO_4$, filtered and concentrated in vacuo. Silica gel chromatography (0-10% methanol/dichloromethane) provided 2-iodo-5-methoxy-4-(trifluoromethyl)benzoic acid (4.63 g, 59%) as a white solid. ESI-MS m z calc. 345.93, found 345.2 $(M-1)^-$; LC/MS retention time (Method F): 0.48 minutes. $^1H$ NMR (500 MHz, $CDCl_3$) δ 8.16 (d, J=0.8 Hz, 1H), 7.60 (s, 1H), 3.96 (s, 3H) ppm.

Step 2: 5-Methoxy-2-[2-Methoxy-4-(Trifluoromethoxy)Phenoxy]-4-(Trifluoromethyl)Benzoic Acid

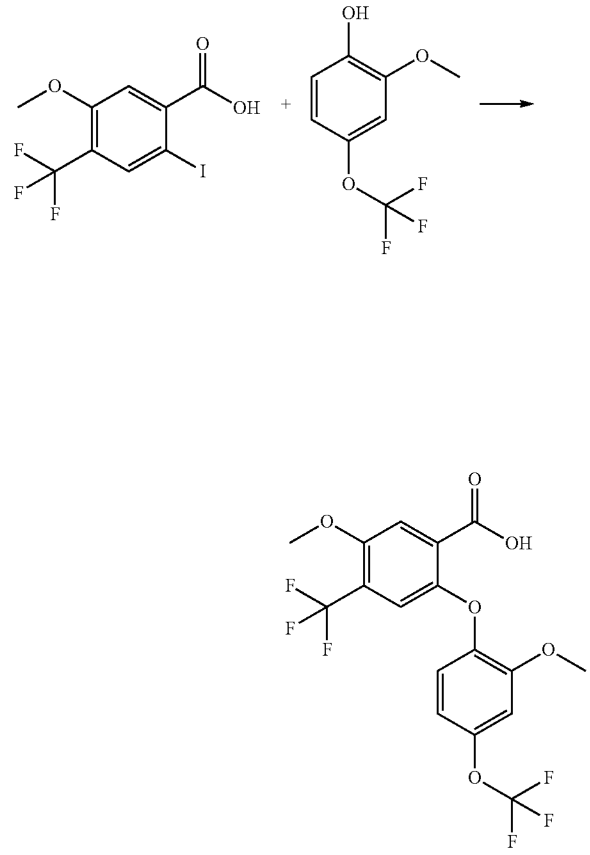

2-Iodo-5-methoxy-4-(trifluoromethyl)benzoic acid (4.63 g, 13.4 mmol) and 2-methoxy-4-(trifluoromethoxy)phenol (3.05 g, 14.7 mmol) were combined in toluene (100 mL) and the solution purged with nitrogen (3×vacuum/nitrogen fill). $Cs_2CO_3$ (6.45 g, 19.8 mmol) was added, and the mixture was stirred for 5 minutes. Copper (I) iodide (2.58 g, 13.6 mmol) was added and the mixture again purged with nitrogen. The mixture was heated at 100° C. overnight. Additional copper (I) iodide (1.44 g, 7.56 mmol) and 2-methoxy-4-(trifluoromethoxy)phenol (1.7 g, 8.2 mmol) were added and the mixture was heated at 100° C. for 5 hours. The mixture was then cooled to room temperature, acidified to pH=1 with 1 M aqueous HCl and partitioned between ethyl acetate and water. The layers were separated, and the aqueous layer was extracted with ethyl acetate (3×). The combined organic extracts were washed with brine, dried over $MgSO_4$, filtered and concentrated in vacuo. Two sequential silica gel chromatography purifications (0-5% methanol/dichloromethane) provided 5-methoxy-2-[2-methoxy-4-(trifluoromethoxy)phenoxy]-4-(trifluoromethyl)benzoic acid (1.13 g, 20%). ESI-MS m z calc. 426.05, found 425.4 $(M-1)^-$; LC/MS retention time (Method F): 0.65 minutes. $^1H$ NMR (500 MHz, DMSO-$d_6$) δ 13.44 (s, 1H), 7.57 (s, 1H), 7.16 (d, J=2.5 Hz, 1H), 7.12 (s, 1H), 6.93-6.85 (m, 2H), 3.94 (s, 3H), 3.82 (s, 3H) ppm.

Step 3: Methyl 4-[[5-Methoxy-2-[2-Methoxy-4-(Trifluoromethoxy)Phenoxy]-4-(Trifluoromethyl)Benzoyl]Amino]Pyridine-2-Carboxylate

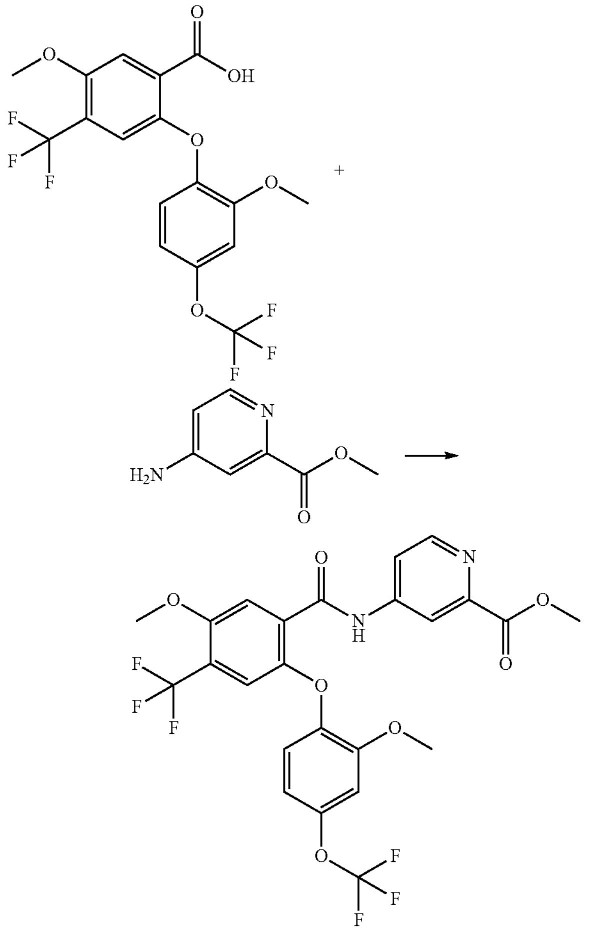

A solution of 5-methoxy-2-[2-methoxy-4-(trifluoromethoxy)phenoxy]-4-(trifluoromethyl)benzoic acid (281 mg, 0.659 mmol) and DMF (5 μL, 0.07 mmol) in dichloromethane (6 mL) at 0° C. was treated with oxalyl chloride (160 μL, 1.83 mmol) then brought to room temperature and stirred for 45 minutes. The mixture was concentrated in vacuo, redissolved in dichloromethane (4 mL) and added dropwise to a solution of methyl 4-aminopyridine-2-carboxylate (123 mg, 0.808 mmol) and TEA (280 μL, 2.01 mmol) in dichloromethane (4 mL) at 0° C. The mixture was brought to room temperature and stirred for 2 hours. The mixture was partitioned between dichloromethane and water and the phases separated (phase separation cartridge). The organic filtrate was concentrated in vacuo and purified by silica gel chromatography (0-10% methanol/dichloromethane) to provide methyl 4-[[5-methoxy-2-[2-methoxy-4-(trifluoromethoxy)phenoxy]-4-(trifluoromethyl)benzoyl]amino]pyridine-2-carboxylate (190 mg, 51%) as a white solid. ESI-MS m/z calc. 560.10, found 561.4 $(M+1)^+$; 559.4 $(M-1)^-$; LC/MS retention time (Method F): 0.98 minutes. $^1H$ NMR (500 MHz, DMSO-$d_6$) δ 11.08 (s, 1H), 8.59 (d, J=5.4 Hz, 1H), 8.34 (d, J=2.1 Hz, 1H), 7.81 (dd, J=5.5, 2.2 Hz, 1H), 7.58 (s, 1H), 7.16 (s, 1H), 7.10 (d, J=2.8 Hz, 1H), 7.06 (d, J=8.8 Hz, 1H), 6.92 (ddd, J=8.7, 2.6, 1.2 Hz, 1H), 3.95 (s, 3H), 3.88 (s, 3H), 3.72 (s, 3H) ppm.

Step 4: 4-[[5-Methoxy-2-[2-Methoxy-4-(Trifluoromethoxy)Phenoxy]-4-(Trifluoromethyl)Benzoyl]Amino]Pyridine-2-Carboxamide (276)

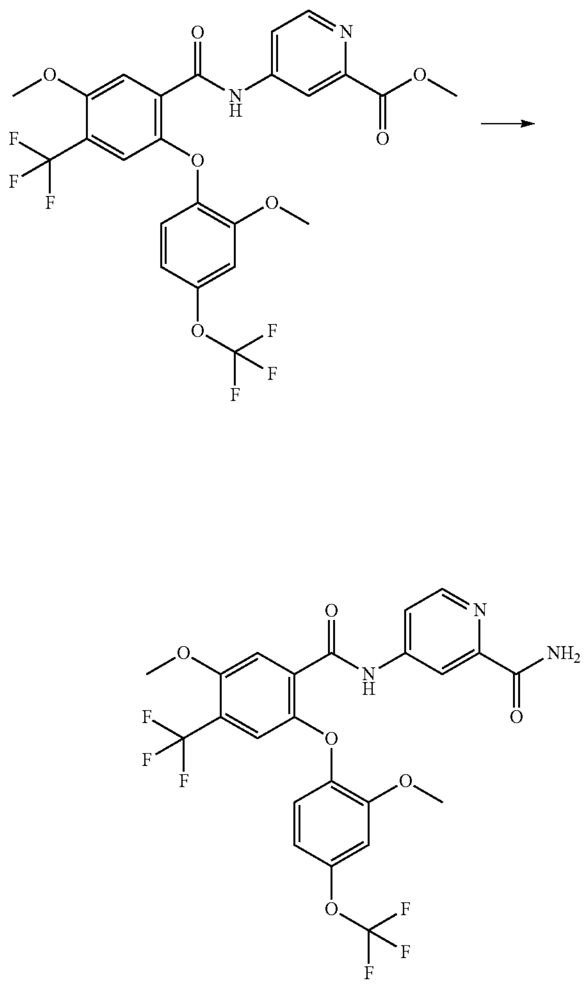

Methyl 4-[[5-methoxy-2-[2-methoxy-4-(trifluoromethoxy)phenoxy]-4-(trifluoromethyl)benzoyl]amino]pyridine-2-carboxylate (190 mg, 0.339 mmol) was dissolved in a solution of ammonia in methanol (5 mL of 7 M, 35 mmol) and stirred at room temperature for 8 hours. The mixture was concentrated in vacuo and purified by reverse phase HPLC (47-95% acetonitrile/0.1% ammonium hydroxide) to provide 4-[[5-methoxy-2-[2-methoxy-4-(trifluoromethoxy)phenoxy]-4-(trifluoromethyl)benzoyl]amino]pyridine-2-carboxamide (128 mg, 69%) as a white solid. ESI-MS m z calc. 545.10, found 546.5 $(M+1)^+$; 544.4 $(M-1)^-$; LC/MS retention time (Method E): 3.39 minutes. $^1H$ NMR (500 MHz, DMSO-$d_6$) δ 11.02 (s, 1H), 8.52 (d, J=5.5 Hz, 1H), 8.29 (d, J=2.1 Hz, 1H), 8.08 (d, J=2.8 Hz, 1H), 7.82 (dd, J=5.7, 2.2 Hz, 1H), 7.63 (d, J=2.8 Hz, 1H), 7.59 (s, 1H), 7.15 (s, 1H), 7.11 (d, J=2.8 Hz, 1H), 7.08 (d, J=8.9 Hz, 1H), 6.93 (ddd, J=8.9, 2.8, 1.2 Hz, 1H), 3.96 (s, 3H), 3.74 (s, 3H) ppm.

Example 87

4-[[2-Methoxy-6-[2-Methoxy-4-(Trifluoromethoxy)Phenoxy]-4-(Trifluoromethyl)Benzoyl]Amino]Pyridine-2-Carboxamide (277)

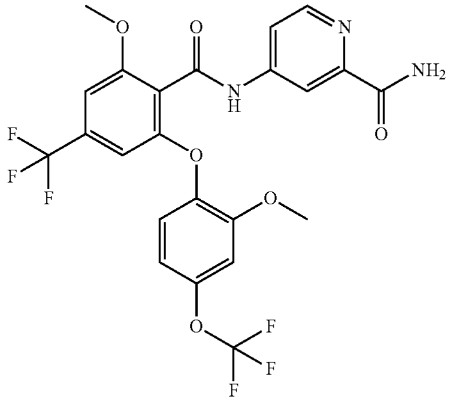

Step 1: 2,6-Difluoro-4-(Trifluoromethyl)Benzoic Acid

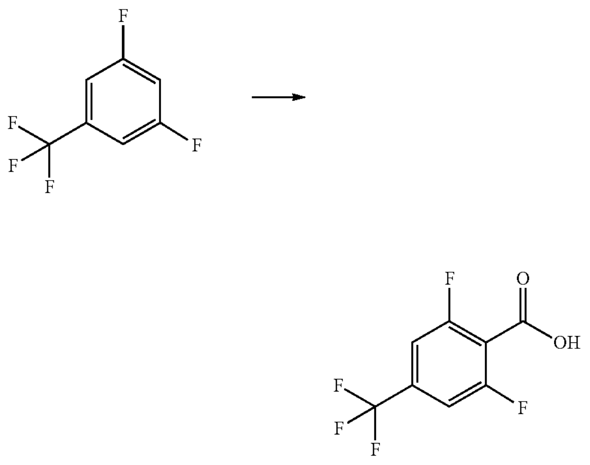

To a solution of 1,3-difluoro-5-(trifluoromethyl)benzene (1.0 mL, 10.3 mmol) in THF (100 mL) at −78° C. was added LDA (6 mL of 2 M in THF/heptane/ethylbenzene, 12 mmol) and the mixture stirred at −78° C. for 30 minutes. The mixture was poured into a beaker containing solid carbon dioxide (dry ice) and allowed to warm to room temperature over 2 hours. The mixture was partitioned between ethyl acetate (150 mL) and water (200 mL) and the layers separated. The aqueous layer was washed with additional ethyl acetate (150 mL) and then acidified with 2 M aqueous HCl to pH=3. The aqueous layer was extracted with ethyl acetate (3×150 mL), and the combined organic extracts dried over $MgSO_4$, filtered and concentrated in vacuo to provide 2,6-difluoro-4-(trifluoromethyl)benzoic acid (1.023 g, 44%). $^1H$ NMR (500 MHz, DMSO-$d_6$) δ 14.42 (s, 1H), 7.81-7.74 (m, 2H) ppm.

Step 2: Methyl 2,6-Difluoro-4-(Trifluoromethyl)Benzoate

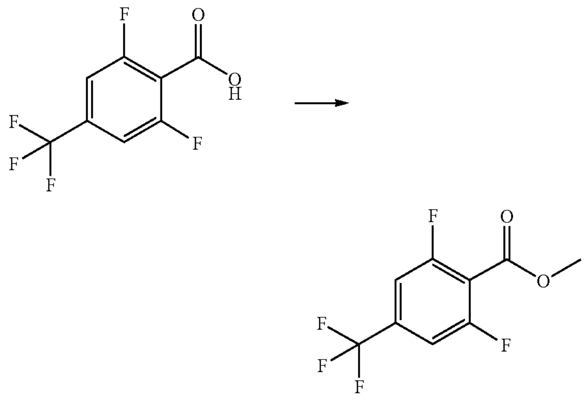

To a solution of 2,6-difluoro-4-(trifluoromethyl)benzoic acid (5.6 g, 25 mmol) in methanol (140 mL) was added $H_2SO_4$ (2 mL, 38 mmol) and the mixture heated at 70° C. for 20 hours. Additional $H_2SO_4$ (1 mL, 19 mmol) was added and mixture was heated for 48 hours. The solution was concentrated in vacuo. The residue was dissolved in ethyl acetate (300 mL) and washed with $NaHCO_3$ (2×250 mL) and brine, dried over $MgSO_4$, filtered and concentrated in vacuo to provide methyl 2,6-difluoro-4-(trifluoromethyl)benzoate (4.44 g, 75%). H NMR (500 MHz, DMSO-$d_6$) δ 7.88-7.81 (m, 2H), 3.94 (s, 3H) ppm.

Step 3: 2-Methoxy-6-[2-Methoxy-4-(Trifluoromethoxy)Phenoxy]-4-(Trifluoromethyl)Benzoic Acid

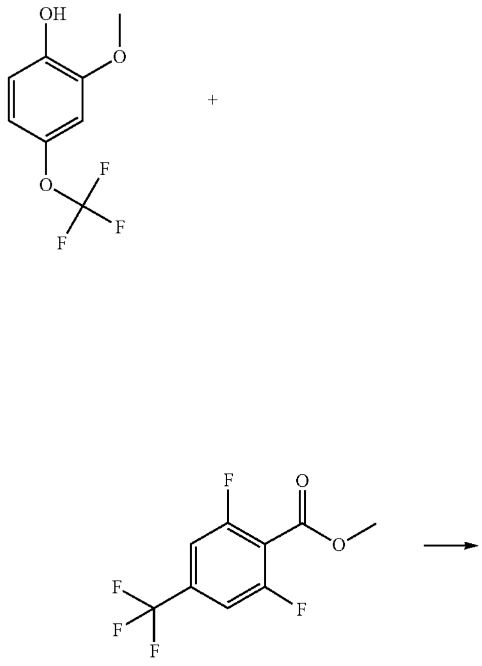

-continued

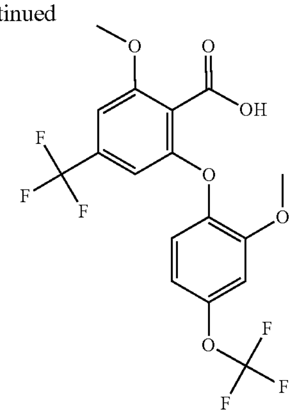

A mixture of methyl 2,6-difluoro-4-(trifluoromethyl)benzoate (962 mg, 4.01 mmol) and $Cs_2CO_3$ (1.46 g, 4.48 mmol) in DMF (10 mL) was heated at 70° C. in a sealed tube and treated portion-wise with 2-methoxy-4-(trifluoromethoxy) phenol (840 mg, 4.04 mmol) over 10 minutes. The mixture was heated at 70° C. for 10 hours. The mixture was diluted with ethyl acetate and washed with 2 M aqueous NaOH and brine (2×). The organic layer was dried over $MgSO_4$, filtered and concentrated in vacuo to afford crude methyl 2-methoxy-6-[2-methoxy-4-(trifluoromethoxy)phenoxy]-4-(trifluoromethyl)benzoate. The residue was dissolved in DMF (10 mL), treated with sodium methoxide solution (8.5 mL of 25% w/v in methanol, 39 mmol) and heated at 50° C. overnight. The mixture was concentrated and partitioned between ethyl acetate and 2 M aqueous HCl. The organic layer was separated, dried over $MgSO_4$, filtered and concentrated. Purification by silica chromatography (0-100% ethyl acetate/heptane) provided 2-methoxy-6-[2-methoxy-4-(trifluoromethoxy)phenoxy]-4-(trifluoromethyl)benzoic acid (82.8 mg). ESI-MS m z calc. 426.05, found 427.5 $(M+1)^+$; LC/MS retention time (Method F): 0.58 minutes.

Step 4: 4-[[2-Methoxy-6-[2-Methoxy-4-(Trifluoromethoxy)Phenoxy]-4-(Trifluoromethyl)Benzoyl]Amino]Pyridine-2-Carboxamide (277)

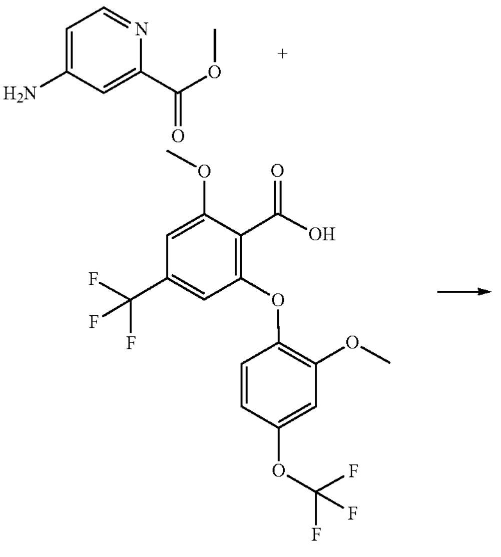

-continued

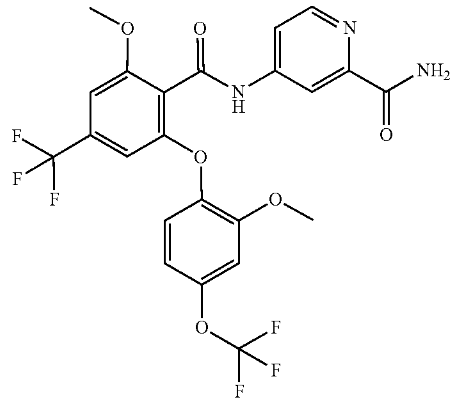 [SMILES: COc1cc(OC(F)(F)F)ccc1Oc1cc(C(F)(F)F)cc(OC)c1C(=O)Nc1ccnc(C(N)=O)c1]

A solution of 2-methoxy-6-[2-methoxy-4-(trifluoromethoxy)phenoxy]-4-(trifluoromethyl)benzoic acid (83 mg, 0.19 mmol) in dichloromethane (2 mL) and DMF (5 µL, 0.07 mmol) was dropwise treated with oxalyl chloride (120 µL of 2 M, 0.24 mmol). The mixture was stirred for 30 minutes then concentrated in vacuo. The residue was redissolved in dichloromethane (2 mL) and was treated with TEA (40 µL, 0.29 mmol) and methyl 4-aminopyridine-2-carboxylate (38 mg, 0.25 mmol). The mixture was stirred overnight then diluted with dichloromethane and washed with saturated aqueous $NaHCO_3$. The organic layer was separated, dried over $MgSO_4$, filtered and concentrated. The residue was dissolved in a solution of ammonia in methanol (5 mL of 7 M, 35 mmol) and stirred at room temperature for 6 hours. The mixture was concentrated and purified by reverse phase HPLC (47-95% acetonitrile/0.1% ammonium hydroxide) to provide 4-[[2-methoxy-6-[2-methoxy-4-(trifluoromethoxy)phenoxy]-4-(trifluoromethyl)benzoyl]amino]pyridine-2-carboxamide (24.8 mg, 23%). ESI-MS m z calc. 545.10, found 546.5 $(M+1)^+$; LC/MS retention time (Method E): 3.26 minutes. $^1H$ NMR (400 MHz, DMSO-$d_6$) δ 11.12 (s, 1H), 8.51 (d, J=5.5 Hz, 1H), 8.31 (d, J=2.1 Hz, 1H), 8.07 (d, J=2.9 Hz, 1H), 7.81 (dd, J=5.5, 2.2 Hz, 1H), 7.63 (d, J=2.8 Hz, 1H), 7.32-7.12 (m, 3H), 7.00 (ddd, J=8.8, 2.7, 1.2 Hz, 1H), 6.56 (d, J=1.3 Hz, 1H), 3.94 (s, 3H), 3.78 (s, 3H) ppm.

Example 88

4-[[2-Fluoro-6-[2-Methoxy-4-(Trifluoromethoxy)Phenoxy]-3-Methyl-4-(Trifluoromethyl)Benzoyl]Amino]Pyridine-2-Carboxamide (278)

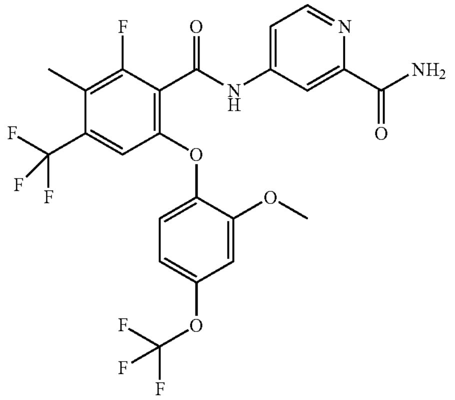 [SMILES: COc1cc(OC(F)(F)F)ccc1Oc1cc(C(F)(F)F)c(C)c(F)c1C(=O)Nc1ccnc(C(N)=O)c1]

Step 1: Methyl 2,6-Difluoro-3-Methyl-4-(Trifluoromethyl)Benzoate

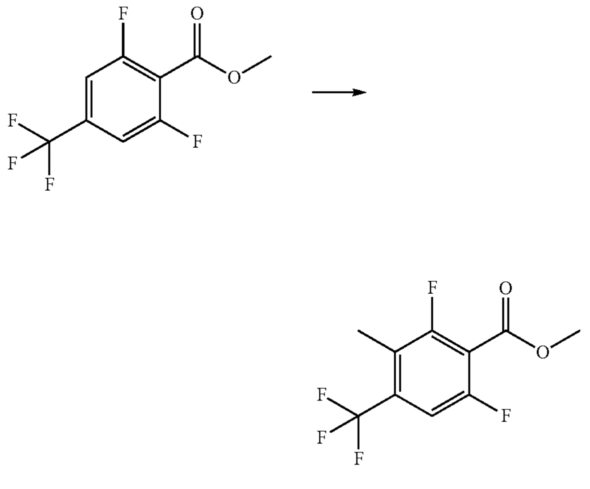

A solution of LDA (2.1 mL of 2 M in THF/heptane/ethylbenzene, 4.2 mmol) was added dropwise to a solution of methyl 2,6-difluoro-4-(trifluoromethyl)benzoate (1000 mg, 4.164 mmol, Example 87, Step 2) in THF (8 mL) at −78° C. The mixture was stirred for 10 minutes and was then treated with methyl iodide (400 µL, 6.43 mmol). The mixture was stirred at −78° C. for 30 minutes then allowed to warm to room temperature. The mixture was diluted with water and extracted with ethyl acetate (3×). The combined organic extracts were dried over $MgSO_4$, filtered and concentrated in vacuo. Silica gel chromatography (0-15% ethyl acetate/petroleum ether) provided methyl 2,6-difluoro-3-methyl-4-(trifluoromethyl)benzoate (700 mg, 66%, contaminated with residual starting material). The material was taken to the next step without further purification.

Step 2: 2-Fluoro-6-[2-Methoxy-4-(Trifluoromethoxy)Phenoxy]-3-Methyl-4-(Trifluoromethyl) Benzoic Acid

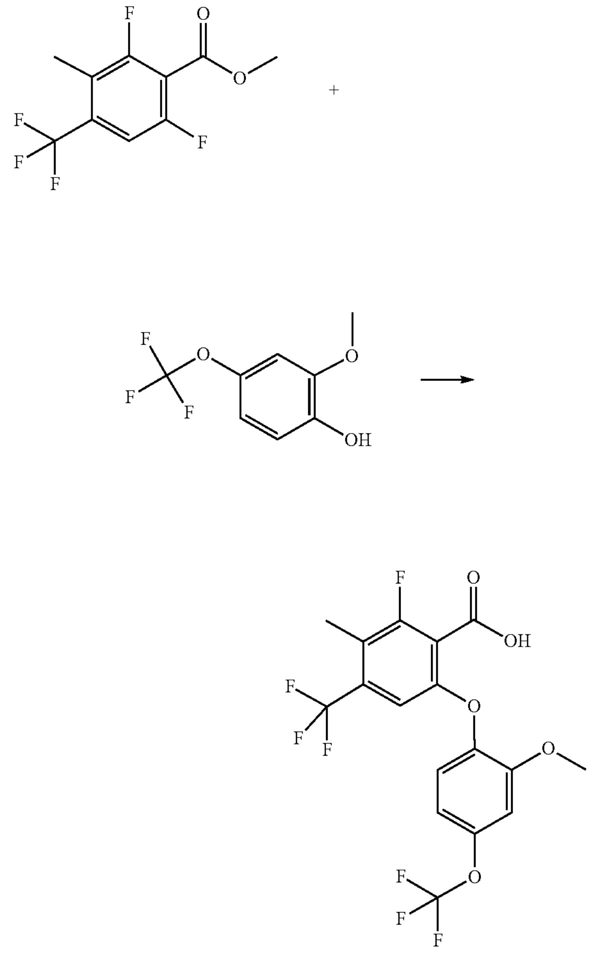

Methyl 2,6-difluoro-3-methyl-4-(trifluoromethyl)benzoate (700 mg, 2.75 mmol), 2-methoxy-4-(trifluoromethoxy) phenol (560 mg, 2.69 mmol) and $Cs_2CO_3$ (1.4 g, 4.3 mmol) were combined in DMF (28 mL) and stirred at 70° C. for 48 hours. The mixture was partitioned between ethyl acetate and brine and the layers separated. The organic layer was washed with brine, dried over $MgSO_4$, filtered and concentrated to afford crude methyl 2-fluoro-6-[2-methoxy-4-(trifluoromethoxy)phenoxy]-3-methyl-4-(trifluoromethyl)benzoate. The residue was then dissolved in ethanol (5 mL) and aqueous LiOH (1.4 mL of 2 M, 2.8 mmol) and the mixture heated at 60° C. overnight. The solution was cooled to room temperature and acidified with 2 M aqueous HCl (~10 mL). The cloudy aqueous mixture was extracted with ethyl acetate (2×50 mL), and the combined extracts dried over $Na_2SO_4$, filtered and concentrated in vacuo to provide 2-fluoro-6-[2-methoxy-4-(trifluoromethoxy)phenoxy]-3-methyl-4-(trifluoromethyl)benzoic acid (0.8 g, 68%, contaminated with 2-fluoro-6-[2-methoxy-4-(trifluoromethoxy) phenoxy]-4-(trifluoromethyl)benzoic acid). ESI-MS m z calc. 428.05, found 427.2 $(M-1)^-$; LC/MS retention time (Method E): 0.64 minutes. The material was taken to the next step without further purification.

Step 3: 4-[[2-Fluoro-6-[2-Methoxy-4-(Trifluoromethoxy)Phenoxy]-3-Methyl-4-(Trifluoromethyl) Benzoyl]Amino]Pyridine-2-Carboxamide (278)

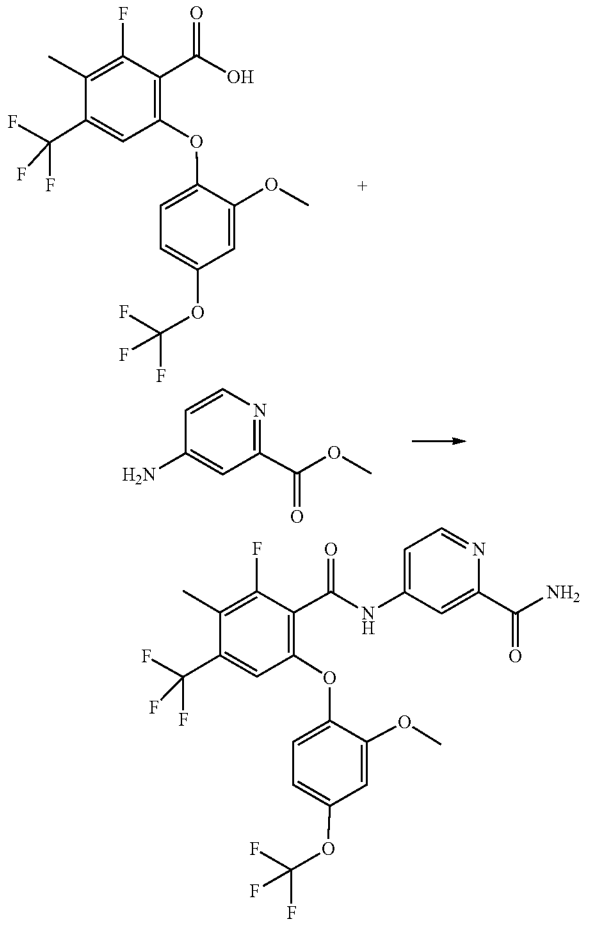

To a solution of 2-fluoro-6-[2-methoxy-4-(trifluoromethoxy)phenoxy]-3-methyl-4-(trifluoromethyl)benzoic acid (1.07 g, 2.50 mmol) and DMF (20 μL, 0.26 mmol) in dichloromethane (25 mL) at 0° C. was added and oxalyl chloride (655 μL, 7.51 mmol) dropwise. The mixture was stirred for 2 hours, and then concentrated in vacuo. The acid chloride was redissolved in dichloromethane (25 mL) and added dropwise to a mixture of methyl 4-aminopyridine-2-carboxylate (540 mg, 3.55 mmol) and TEA (2.1 mL, 15 mmol) in dichloromethane (25 mL) at 0° C. The resulting mixture was stirred at room temperature overnight. The mixture was concentrated in vacuo, then dissolved in a solution of ammonia in methanol (5 mL of 7 M, 35 mmol) and stirred for 24 hours. The mixture was concentrated and purified by reverse phase HPLC (47-95% acetonitrile/0.1% ammonium hydroxide) to provide 4-[[2-fluoro-6-[2-methoxy-4-(trifluoromethoxy)phenoxy]-3-methyl-4-(trifluoromethyl)benzoyl]amino]pyridine-2-carboxamide (26.4 mg, 2%) as an off-white solid. ESI-MS m z calc. 547.10, found 548.1 $(M+1)^+$; 546.2 $(M-1)^-$; LC/MS retention time (Method E): 3.38 minutes. $^1H$ NMR (400 MHz, $CDCl_3$) δ 8.85 (s, 1H), 8.56 (d, J=5.6 Hz, 1H), 8.40 (dd, J=5.6, 2.3 Hz, 1H), 7.90-7.80 (m, 2H), 7.24 (d, J=9.3 Hz, 1H), 6.96 (q, J=2.5 Hz, 2H), 6.82 (s, 1H), 5.53 (s, 1H), 3.95 (s, 3H), 2.43-2.37 (m, 3H) ppm.

Example 89

4-[[5-Fluoro-2-[2-Methoxy-4-(Trifluoromethoxy) Phenoxy]-4-(Trifluoromethyl)Benzoyl]Amino]-1-Oxido-Pyridin-1-Ium-2-Carboxamide (279)

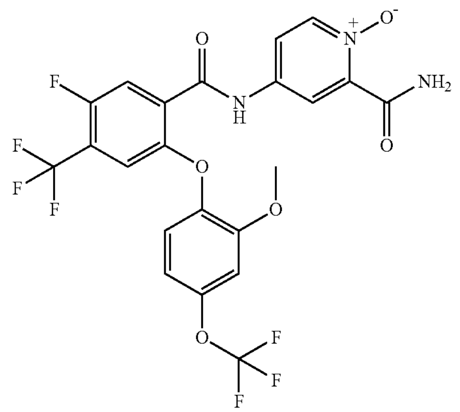

A solution of 4-[[5-fluoro-2-[2-methoxy-4-(trifluoromethoxy)phenoxy]-4-(trifluoromethyl)benzoyl]amino] pyridine-2-carboxamide (50.2 mg, 0.0941 mmol, see US 2019/0016671, Example 42, which is incorporated by reference) in dichloromethane (2 mL) was treated with 3-chloroperbenzoic acid (58.9 mg, 0.341 mmol). The mixture was stirred at room temperature for 16 hours, and then diluted with 2 M aqueous NaOH. The organic layer was separated, dried over $MgSO_4$, filtered and concentrated. The residue was purified by reverse phase HPLC (38-53% acetonitrile/ 0.1% ammonium hydroxide) to provide 4-[[5-fluoro-2-[2-methoxy-4-(trifluoromethoxy)phenoxy]-4-(trifluoromethyl) benzoyl]amino]-1-oxido-pyridin-1-ium-2-carboxamide (10.3 mg, 20%). ESI-MS m z calc. 549.08, found 550.5 $(M+1)^+$; LC/MS retention time (Method E): 3.22 minutes. $^1H$ NMR (400 MHz, DMSO-$d_6$) δ 11.20 (s, 1H), 10.62 (d, J=4.6 Hz, 1H), 8.53 (d, J=3.2 Hz, 1H), 8.37 (d, J=7.1 Hz, 1H), 8.26 (d, J=4.6 Hz, 1H), 7.95 (d, J=10.1 Hz, 1H), 7.84 (dd, J=7.2, 3.3 Hz, 1H), 7.30-7.12 (m, 3H), 6.97 (ddd, J=8.9, 2.8, 1.3 Hz, 1H), 3.76 (s, 3H) ppm.

Example 90

4-[[2-Fluoro-6-[2-Methoxy-4-(Trifluoromethoxy) Phenoxy]-3-(Trifluoromethoxy)Benzoyl]Amino] Pyridine-2-Carboxamide (280)

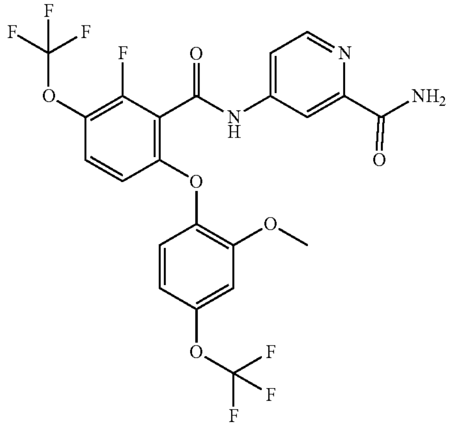 [SMILES: COc1cc(OC(F)(F)F)ccc1Oc1ccc(OC(F)(F)F)c(F)c1C(=O)Nc1ccnc(C(N)=O)c1]

Step 1: 6-Bromo-2-Fluoro-3-(Trifluoromethoxy)Benzoic Acid

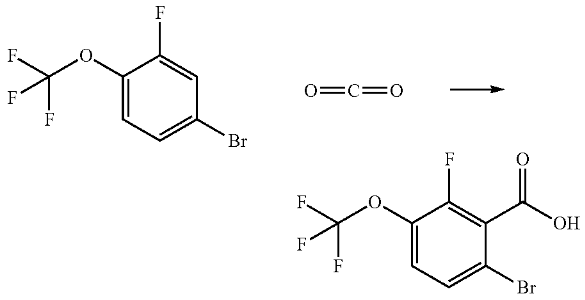

To a solution of diisopropylamine (27.7 g, 274 mmol) in THF (262 mL) was added a solution of n-butyllithium (105 mL of 2.5 M in hexanes, 262.5 mmol) over 45 minutes while maintaining the temperature below −70° C. At the end of addition, the yellow solution was stirred for 15 minutes and warmed to 0° C. and stirred for 10 minutes. The solution was cooled to −70° C. and a solution of 4-bromo-2-fluoro-1-(trifluoromethoxy)benzene (64.5 g, 249 mmol) in THF (60 mL) was added dropwise over 1 hour. The solution was stirred for 1 hour at −70° C. The solution was poured into a slurry of solid carbon dioxide (dry ice) (150 g, 3.408 mol) in THF (100 mL) and the solution was slowly warmed to room temperature over 1 hour, then stirred at room temperature for 2 days. The mixture was diluted with MTBE (200 mL) and 2 M aqueous HCl (150 mL). The phases were separated and the acidic layer was extracted with additional MTBE (100 mL). The combined MTBE layers were extracted with 2 M aqueous NaOH (3×). The combined aqueous extracts were acidified with 2 M aqueous HCl (150 mL) until the pH is 1 and extracted with MTBE (3×200 mL). The combined organic extracts were dried over $Na_2SO_4$, filtered and concentrated to an oil. The oil was treated with seed crystals (100 mg) and stirred for 1 hour. The suspension was diluted with heptane (65 mL) and filtered. The solid was washed with heptane and air dried to provide 58.2 g of product. The filtrate was concentrated in vacuo and another crop of product obtained in a similar fashion to obtain 4.6 g of product. The two crops of solid were combined to provide 6-bromo-2-fluoro-3-(trifluoromethoxy)benzoic acid (58.2 g, 77%). $^1H$ NMR (400 MHz, $CDCl_3$) δ 11.62 (s, 1H), 7.51 (dd, J=8.8, 1.8 Hz, 1H), 7.41-7.30 (m, 1H) ppm.

Step 2: 2-Fluoro-6-[2-Methoxy-4-(Trifluoromethoxy)Phenoxy]-3-(Trifluoromethoxy)Benzoic Acid

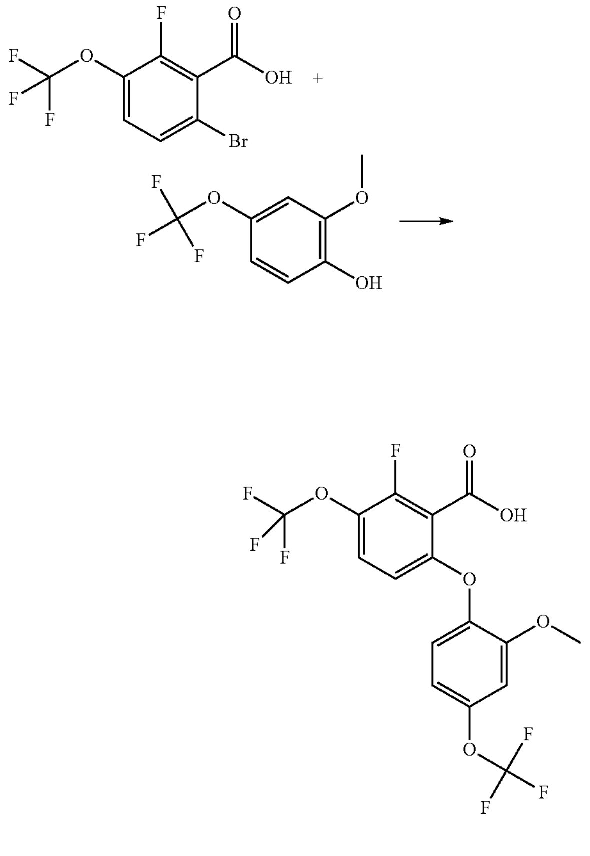

A mixture of 6-bromo-2-fluoro-3-(trifluoromethoxy)benzoic acid (500 mg, 1.65 mmol), 2-methoxy-4-(trifluoromethoxy)phenol (330 mg, 1.59 mmol) and $Cs_2CO_3$ (575 mg, 1.77 mmol) toluene (20 mL) was bubbled with nitrogen for 10 minutes, then treated with copper (I) iodide (112 mg, 0.588 mmol). The mixture was heated at 100° C. with vigorous stirring overnight. The mixture was acidified with 2 M aqueous HCl and the aqueous layer was extracted with ethyl acetate. The combined organic layers were washed with brine, dried over $MgSO_4$, filtered and concentrated to provide 2-fluoro-6-[2-methoxy-4-(trifluoromethoxy)phenoxy]-3-(trifluoromethoxy)benzoic acid (700 mg, 99%). ESI-MS m z calc. 430.03, no ionization observed; LC/MS retention time (Method F): 0.63 minutes. $^1H$ NMR (400 MHz, $CDCl_3$) δ 10.01-9.93 (m, 2H), 7.21-7.12 (m, 1H), 7.06-7.00 (m, 1H), 6.76 (dtd, J=9.4, 2.5, 1.4 Hz, 2H), 6.40 (dd, J=9.3, 1.8 Hz, 1H), 3.71 (s, 3H) ppm.

Step 3: 4-[[2-Fluoro-6-[2-Methoxy-4-(Trifluoromethoxy)Phenoxy]-3-(Trifluoromethoxy)Benzoyl]Amino]Pyridine-2-Carboxamide (280)

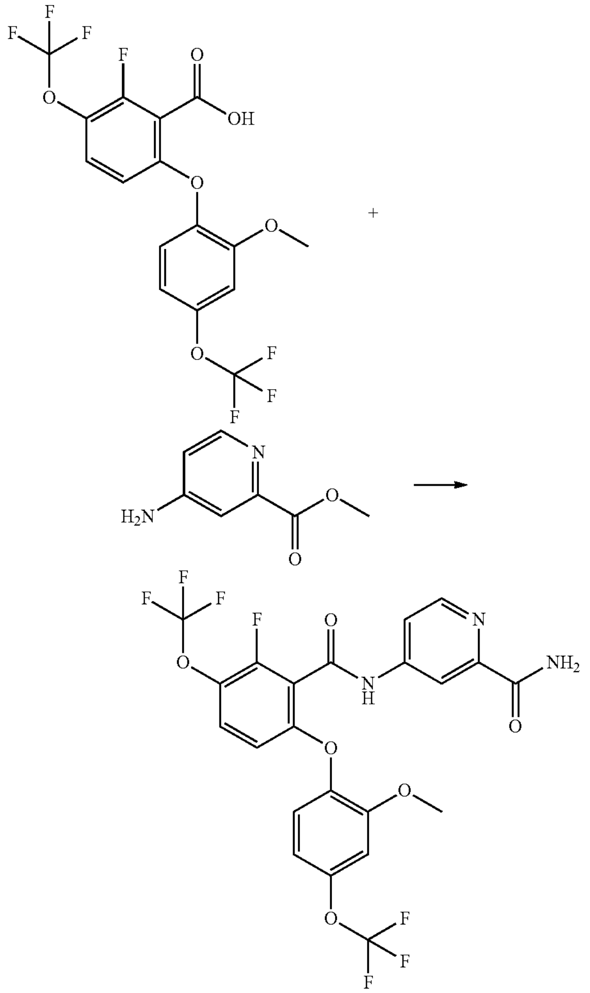

To a solution of 2-fluoro-6-[2-methoxy-4-(trifluoromethoxy)phenoxy]-3-(trifluoromethoxy)benzoic acid (167 mg, 0.388 mmol) and DMF (3 μL, 0.04 mmol) in dichloromethane (4 mL) at 0° C. was added oxalyl chloride (100 μL, 1.15 mmol) dropwise and the solution stirred for 2 hours. The mixture was concentrated in vacuo to afford the acid chloride. The residue was redissolved in dichloromethane (4 mL) and added dropwise to a mixture of methyl 4-aminopyridine-2-carboxylate (85 mg, 0.56 mmol) and TEA (325 μL, 2.33 mmol) in dichloromethane (4 mL) at 0° C. The resulting mixture was allowed to warm to room temperature and stirred overnight. The mixture was concentrated in vacuo to provide the intermediate methyl 4-[[2-fluoro-6-[2-methoxy-4-(trifluoromethoxy)phenoxy]-3-(trifluoromethoxy)benzoyl]amino]pyridine-2-carboxylate. The residue was dissolved in a solution of ammonia in methanol (7 M) in methanol and stirred overnight. The mixture was concentrated in vacuo and purified by reverse phase HPLC (47-95% acetonitrile/0.1% ammonium hydroxide) to provide 4-[[2-fluoro-6-[2-methoxy-4-(trifluoromethoxy)phenoxy]-3-(trifluoromethoxy)benzoyl]amino]pyridine-2-carboxamide (31.7 mg, 14%). ESI-MS m z calc. 549.08, found 550.1 (M+1)$^+$; 548.1 (M−1)$^-$; LC/MS retention time (Method F): 0.94 minutes. $^1$H NMR (400 MHz, $CDCl_3$) δ 9.28 (s, 1H), 8.56 (d, J=5.5 Hz, 1H), 8.46 (dd, J=5.7, 2.1 Hz, 1H), 7.98-7.89 (m, 2H), 7.36-7.26 (m, 1H), 7.27-7.17 (m, 1H), 6.96-6.87 (m, 2H), 6.57 (dd, J=9.2, 1.8 Hz, 1H), 5.47 (d, J=4.5 Hz, 1H), 3.91 (s, 3H) ppm.

Example 91

4-[[2-Cyclopropyl-6-[2-Methoxy-4-(Trifluoromethoxy)Phenoxy]-3-(Trifluoromethyl)Benzoyl]Amino]Pyridine-2-Carboxamide (281)

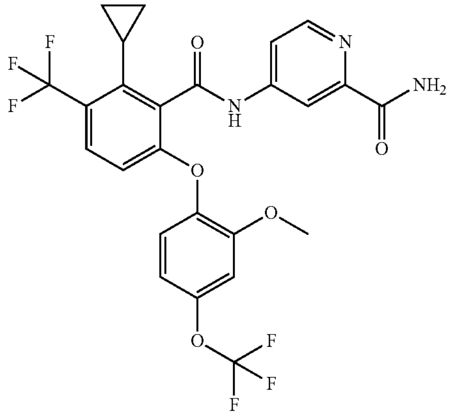 [SMILES: COc1cc(OC(F)(F)F)ccc1Oc1ccc(C(F)(F)F)c(C2CC2)c1C(=O)Nc1ccnc(C(N)=O)c1]

Step 1: 2-Cyclopropyl-6-[2-Methoxy-4-(Trifluoromethoxy)Phenoxy]-3-(Trifluoromethyl)Benzoic Acid

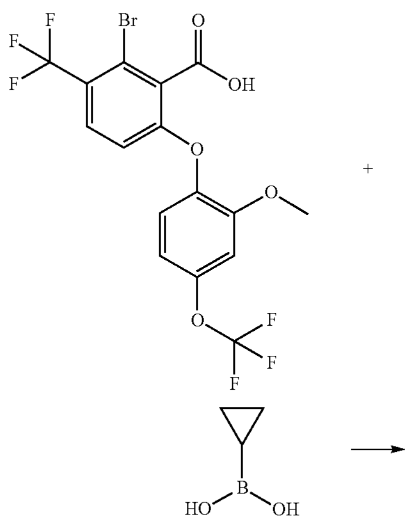

-continued

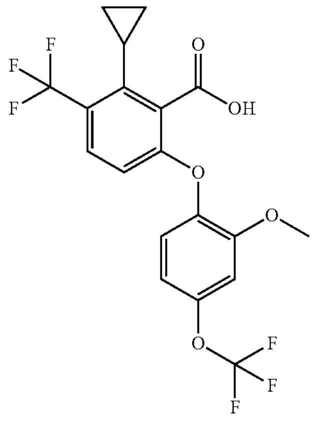

A solution of 2-bromo-6-[2-methoxy-4-(trifluoromethoxy)phenoxy]-3-(trifluoromethyl)benzoic acid (313 mg, 0.659 mmol, see Example 40) in DMSO (3 mL) was treated with cyclopropylboronic acid (85 mg, 0.99 mmol) and aqueous $K_2CO_3$ (1 mL of 2 M, 2 mmol). Pd(dppf)$Cl_2$-dichloromethane (27 mg, 0.033 mmol) was added and the mixture stirred under nitrogen at 60° C. for 1 hour. The mixture was diluted with ethyl acetate (75 mL) and washed with water (2×75 mL) and brine (75 mL). The organic layer was dried over $Na_2SO_4$, filtered and concentrated in vacuo. Reverse phase HPLC purification (10-99% acetonitrile/5 mM HCl) provided 2-cyclopropyl-6-[2-methoxy-4-(trifluoromethoxy)phenoxy]-3-(trifluoromethyl)benzoic acid (53 mg, 18%) as a white solid. ESI-MS m z calc. 436.08, found 437.1 (M+1)$^+$; LC/MS retention time (Method B): 2.27 minutes.

Step 2: 4-[[2-Cyclopropyl-6-[2-Methoxy-4-(Trifluoromethoxy)Phenoxy]-3-(Trifluoromethyl)Benzoyl]Amino]Pyridine-2-Carboxamide (281)

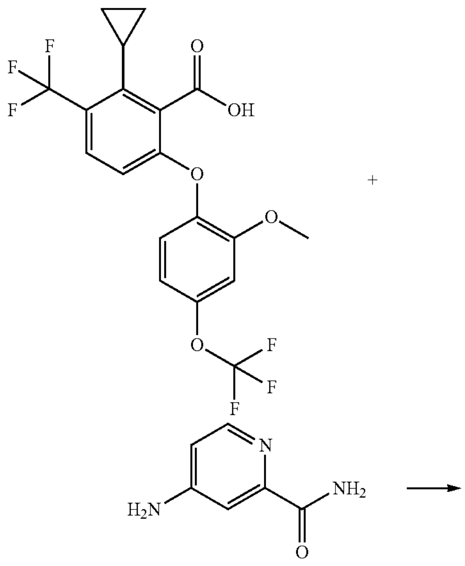

-continued

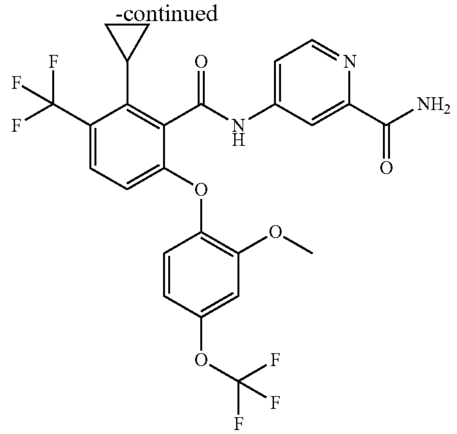

A solution of 2-cyclopropyl-6-[2-methoxy-4-(trifluoromethoxy)phenoxy]-3-(trifluoromethyl)benzoic acid (25 mg, 0.057 mmol) and DMF (1 μL, 0.01 mmol) in dichloromethane (2 mL) was treated dropwise with oxalyl chloride (30 μL, 0.34 mmol). The mixture was allowed to stir at room temperature for 1 hour and then concentrated in vacuo. The acid chloride intermediate was redissolved in NMP (0.5 mL) and added to a mixture of 4-aminopyridine-2-carboxamide (12 mg, 0.088 mmol) and DIEA (50 μL, 0.29 mmol). This mixture was stirred at 75° C. overnight, then cooled and purified by reverse phase HPLC (1-99% acetonitrile/5 mM HCl) to provide 4-[[2-cyclopropyl-6-[2-methoxy-4-(trifluoromethoxy)phenoxy]-3-(trifluoromethyl)benzoyl]amino]pyridine-2-carboxamide (4.5 mg, 14%) as a white solid. ESI-MS m z calc. 555.12, found 556.2 $(M+1)^+$; LC/MS retention time (Method B): 1.88 minutes. $^1H$ NMR (400 MHz, DMSO-$d_6$) δ 11.20 (s, 1H), 8.54 (d, J=5.5 Hz, 1H), 8.38 (d, J=2.0 Hz, 1H), 8.13 (s, 1H), 7.92-7.85 (m, 1H), 7.72 (d, J=9.0 Hz, 1H), 7.68 (s, 1H), 7.28 (d, J=8.8 Hz, 1H), 7.23 (d, J=2.7 Hz, 1H), 7.05-6.99 (m, 1H), 6.67 (d, J=8.8 Hz, 1H), 3.78 (s, 3H), 2.13 (d, J=8.0 Hz, 1H), 0.88 (dd, J=8.6, 4.6 Hz, 2H), 0.77 (d, J=6.2 Hz, 2H) ppm.

Example 92

N-(2-Carbamoyl-4-Pyridyl)-5-Cyclopropyl-3-[2-Methoxy-4-(Trifluoromethoxy)Phenoxy]-6-(Trifluoromethyl)Pyridine-2-Carboxamide (282)

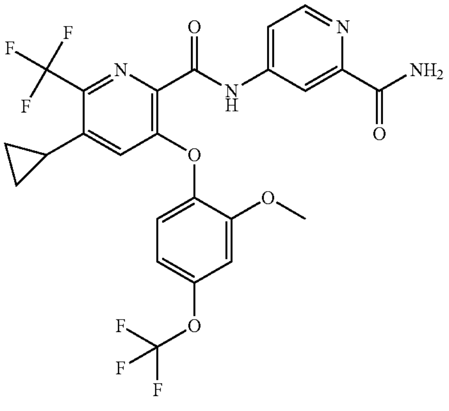 [SMILES: COc1cc(OC(F)(F)F)ccc1Oc1cc(C2CC2)c(C(F)(F)F)nc1C(=O)Nc1ccnc(C(N)=O)c1]

Step 1: 3-Bromo-5-Fluoro-2-Iodo-Pyridine

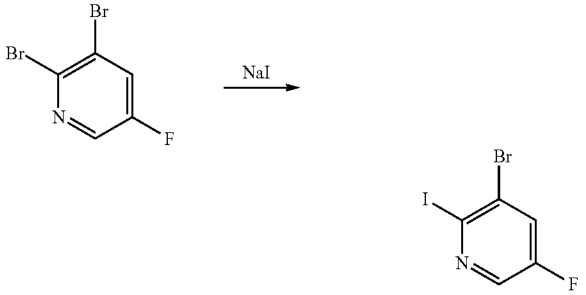

A mixture of 2,3-dibromo-5-fluoro-pyridine (10.54 g, 41.35 mmol), sodium iodide (6.1 g, 41 mmol), copper (I) iodide (390 mg, 2.05 mmol) and N,N-dimethylethylenediamine (363 mg, 0.45 mL, 4.12 mmol) in dioxane (60 mL) was stirred overnight at 100° C. under nitrogen atmosphere. The mixture was cooled to room temperature, diluted with ethyl acetate (50 mL) and filtered through Celite. The filtrate was concentrated in vacuo and purified by silica gel chromatography (0-20% ethyl acetate/heptane) to give 10.5 g of a white solid. The solid was dissolved in MTBE (50 mL) at 40° C., cooled to room temperature and precipitated by addition of pentane (50 mL). The resulting solid was filtered to provide 3-bromo-5-fluoro-2-iodo-pyridine (3.43 g, 25%) as a white solid. The filtrate was concentrated in vacuo to provide additional 3-bromo-5-fluoro-2-iodo-pyridine (6.95 g, 48%) as a white solid. $^1H$ NMR (300 MHz, $CDCl_3$) δ 8.27 (d, J=2.6 Hz, 1H), 7.63 (dd, J=7.6, 2.6 Hz, 1H) ppm. $^{19}F$ NMR (282 MHz, $CDCl_3$) δ −126.32-−126.45 (m, 1F) ppm.

Step 2: 3-Bromo-5-Fluoro-2-(Trifluoromethyl)Pyridine

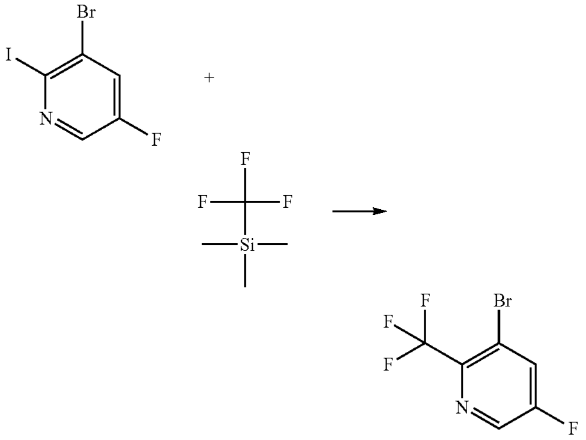

A mixture of potassium fluoride (360 mg, 6.20 mmol) and copper (I) iodide (1.15 g, 6.04 mmol) were heated under vacuum with gentle shaking until a yellow/greenish color was obtained. Once back to room temperature, nitrogen-degassed NMP (17 mL) and trimethyl(trifluoromethyl)silane (847 mg, 0.88 mL, 5.95 mmol) were added to the solid. The resulting mixture was stirred at 50° C. for 45 minutes, then 3-bromo-5-fluoro-2-iodo-pyridine (1.0 g, 2.8 mmol) was added. The mixture was stirred at 80° C. for 3 hours. The stirring mixture was cooled to room temperature and diluted with diethyl ether (150 mL) and aqueous $NH_4OH$ (150 mL, 9% solution). The aqueous layer was separated and extracted with additional diethyl ether (60 mL). The combined organic layers were washed with aqueous $NH_4OH$ (3×50 mL, 9% solution), water (50 mL) and brine (100 mL). The solution was dried over anhydrous $Na_2SO_4$, filtered and concentrated in vacuo to provide 3-bromo-5-fluoro-2-(trifluoromethyl) pyridine (641 mg, 85%). $^1H$ NMR (300 MHz, $CDCl_3$) δ 8.53-8.45 (m, 1H), 7.88-7.79 (m, 1H) ppm. $^{19}F$ NMR (282 MHz, $CDCl_3$) δ −65.44 (s, 3F), −118.93 (d, J=6.1 Hz, 1F) ppm.

Step 3: 3-Bromo-5-[2-Methoxy-4-(Trifluoromethoxy)Phenoxy]-2-(Trifluoromethyl)Pyridine

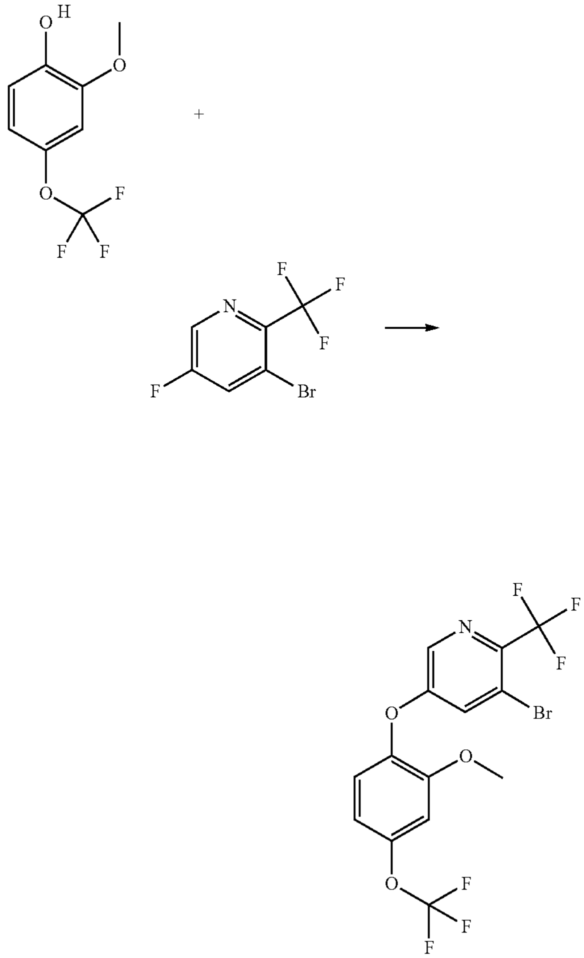

A vial of 3-bromo-5-fluoro-2-(trifluoromethyl)pyridine (1.0 g, 4.1 mmol), 2-methoxy-4-(trifluoromethoxy)phenol (853 mg, 4.10 mmol) and $Cs_2CO_3$ (1.48 g, 4.55 mmol) was flushed with nitrogen and DMF (33 mL) was added. The mixture was heated at 100° C. for 1 hour, then diluted with ethyl acetate and washed with water. The organic layer was dried and concentrated in vacuo to provide 3-bromo-5-[2-methoxy-4-(trifluoromethoxy)phenoxy]-2-(trifluoromethyl) pyridine (1.83 g, 97%). ESI-MS m z calc. 430.96, found 432.4 $(M+1)^+$; LC/MS retention time (Method F): 1.09 minutes. $^1H$ NMR (500 MHz, $CDCl_3$) δ 8.19 (d, J=2.4 Hz, 1H), 7.34 (dd, J=2.5, 0.6 Hz, 1H), 7.08 (d, J=9.4 Hz, 1H), 6.89-6.77 (m, 2H), 3.74 (s, 3H) ppm.

Step 4: 3-Cyclopropyl-5-[2-Methoxy-4-(Trifluoromethoxy)Phenoxy]-2-(Trifluoromethyl)Pyridine

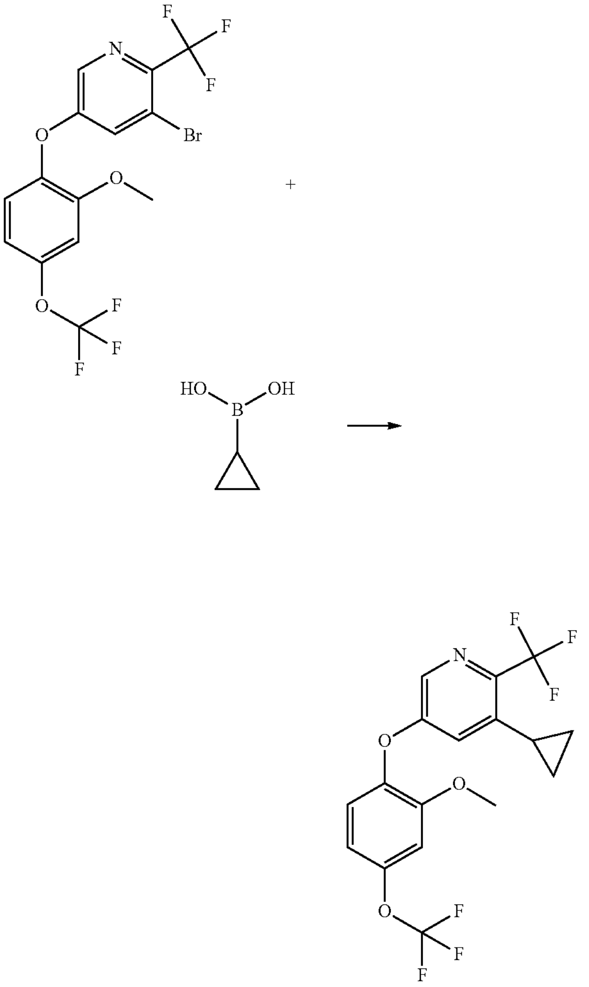

A mixture of 3-bromo-5-[2-methoxy-4-(trifluoromethoxy)phenoxy]-2-(trifluoromethyl)pyridine (1.871 g, 3.897 mmol), cyclopropylboronic acid (1.103 g, 12.84 mmol), $Pd(OAc)_2$ (200 mg, 0.891 mmol), tricyclohexylphosphine (120 mg, 0.428 mmol) and $K_3PO_4$ (2.87 g, 13.5 mmol) in toluene (30 mL) and water (7.5 mL) was purged with nitrogen and heated at 100° C. for 2 hours. The mixture was diluted with ethyl acetate and washed with water (3×). The organic layer was dried over $MgSO_4$, filtered and concentrated in vacuo. Purification by silica gel chromatography (0-20% ethyl acetate/heptane) provided 3-cyclopropyl-5-[2-methoxy-4-(trifluoromethoxy)phenoxy]-2-(trifluoromethyl)pyridine (1.413 g, 92%). ESI-MS m z calc. 393.08, found 394.6 $(M+1)^+$; LC/MS retention time (Method F): 1.09 minutes. $^1H$ NMR (500 MHz, $CDCl_3$) δ 7.95 (d, J=2.6 Hz, 1H), 7.00 (dd, J=8.4, 0.6 Hz, 1H), 6.85-6.73 (m, 3H), 3.73 (s, 3H), 2.15 (dddd, J=12.0, 8.5, 4.3, 1.7 Hz, 1H), 1.09-0.91 (m, 2H), 0.62 (dt, J=6.7, 5.0 Hz, 2H) ppm.

Step 5: 3-Cyclopropyl-5-[2-Methoxy-4-(Trifluoromethoxy)Phenoxy]-1-Oxido-2-(Trifluoromethyl) Pyridin-1-Ium

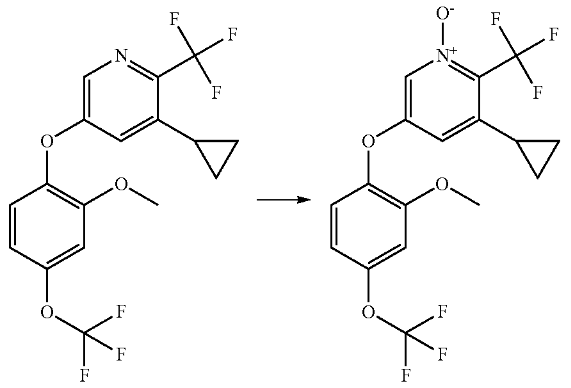 [SMILES: COc1cc(OC(F)(F)F)ccc1Oc1cnc(C(F)(F)F)c(C2CC2)c1 ; COc1cc(OC(F)(F)F)ccc1Oc1cc(C2CC2)c(C(F)(F)F)[n+]([O-])c1]

To a solution of 3-cyclopropyl-5-[2-methoxy-4-(trifluoromethoxy)phenoxy]-2-(trifluoromethyl)pyridine (1.305 g, 3.318 mmol) in dichloromethane (25 mL) at 0° C. was added hydrogen peroxide urea (1.116 g, 11.86 mmol) followed by the dropwise addition of trifluoroacetic anhydride (2.56 g, 1.69 mL, 12.2 mmol). The mixture was warmed to room temperature and stirred for 20 hours. The mixture was diluted with ethyl acetate and washed with water. The aqueous layer was extracted with additional ethyl acetate, and the combined organic extracts dried and concentrated in vacuo. Purification by silica gel chromatography (0-20% ethyl acetate/heptane) provided 3-cyclopropyl-5-[2-methoxy-4-(trifluoromethoxy)phenoxy]-1-oxido-2-(trifluoromethyl)pyridin-1-ium (915 mg, 58%). ESI-MS m z calc. 409.08, found 410.5 $(M+1)^+$; 408.6 $(M-1)^-$; LC/MS retention time (Method F): 0.94 minutes.

Step 6: 2-Bromo-5-Cyclopropyl-3-[2-Methoxy-4-(Trifluoromethoxy)Phenoxy]-6-(Trifluoromethyl) Pyridine

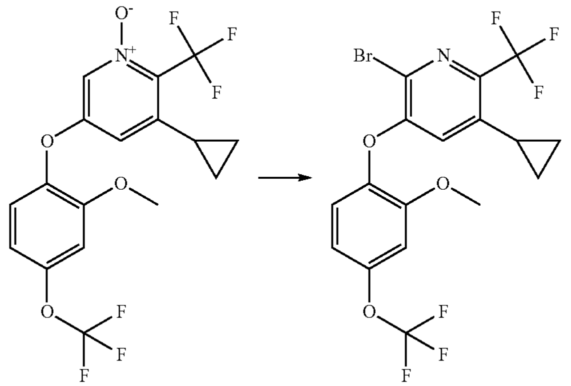 [SMILES: COc1cc(OC(F)(F)F)ccc1Oc1cc(C2CC2)c(C(F)(F)F)[n+]([O-])c1 ; COc1cc(OC(F)(F)F)ccc1Oc1cc(C2CC2)c(C(F)(F)F)nc1Br]

To a solution of 3-cyclopropyl-5-[2-methoxy-4-(trifluoromethoxy)phenoxy]-1-oxido-2-(trifluoromethyl)pyridin-1-ium (1.0 g, 2.1 mmol) in toluene (25 mL) was added $POBr_3$ (611 mg, 2.131 mmol). The mixture was heated at 100° C. for 2 hours, and then cooled and partitioned between ethyl acetate and water. The layers were separated and the aqueous layer extracted with additional ethyl acetate. The combined organic extracts were dried over $MgSO_4$, filtered and concentrated in vacuo. The residue was purified by silica gel chromatography (0-10% ethyl acetate/heptane) to provide 2-bromo-5-cyclopropyl-3-[2-methoxy-4-(trifluoromethoxy)phenoxy]-6-(trifluoromethyl)pyridine (782 mg, 79%). ESI-MS m z calc. 471.00, found 474.4 $(M+1)^+$; LC/MS retention time (Method F): 1.14 minutes. $^1$H NMR (500 MHz, $CDCl_3$) δ 7.12-7.04 (m, 1H), 6.93-6.83 (m, 2H), 6.46 (s, 1H), 3.80 (s, 3H), 2.14 (td, J=6.4, 5.8, 2.8 Hz, 1H), 1.10-0.99 (m, 2H), 0.52 (dt, J=6.6, 5.0 Hz, 2H) ppm.

Step 7: 5-Cyclopropyl-3-[2-Methoxy-4-(Trifluoromethoxy)Phenoxy]-6-(Trifluoromethyl)Pyridine-2-Carbonitrile

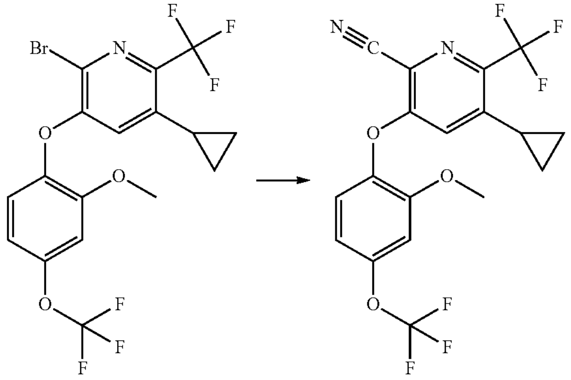 [SMILES: COc1cc(OC(F)(F)F)ccc1Oc1cc(C2CC2)c(C(F)(F)F)nc1Br ; COc1cc(OC(F)(F)F)ccc1Oc1cc(C2CC2)c(C(F)(F)F)nc1C#N]

A solution of 2-bromo-5-cyclopropyl-3-[2-methoxy-4-(trifluoromethoxy)phenoxy]-6-(trifluoromethyl)pyridine (500 mg, 1.06 mmol), $Zn(CN)_2$ (113 mg, 0.962 mmol), $Pd(dppf)Cl_2$ (57 mg, 0.077 mmol), $Pd_2dba_3$ (53 mg, 0.058 mmol) and zinc (32 mg, 0.49 mmol) in DMF (10 mL) was heated at 100° C. for 20 hours. Additional $Zn(CN)_2$ (75 mg, 0.64 mmol) was added and the mixture heated at 100° C. for 1 hour. Additional $Pd(dppf)Cl_2$ (42 mg, 0.058 mmol) and $Pd_2dba_3$ (41 mg, 0.045 mmol) was then added and heating continued at 100° C. for 1 hour. The mixture was cooled, diluted with saturated aqueous $NaHCO_3$ and extracted with ethyl acetate. The organic layer was washed with water (3×), dried over $MgSO_4$, filtered and concentrated in vacuo. The residue was purified by silica gel chromatography (0-10% ethyl acetate/heptane) to provide 5-cyclopropyl-3-[2-methoxy-4-(trifluoromethoxy)phenoxy]-6-(trifluoromethyl)pyridine-2-carbonitrile (257 mg, 45%). ESI-MS m z calc. 418.08, found 419.6 $(M+1)^+$; LC/MS retention time (Method F): 1.07 minutes.

Step 8: 5-Cyclopropyl-3-[2-Methoxy-4-(Trifluoromethoxy)Phenoxy]-6-(Trifluoromethyl)Pyridine-2-Carboxylic Acid

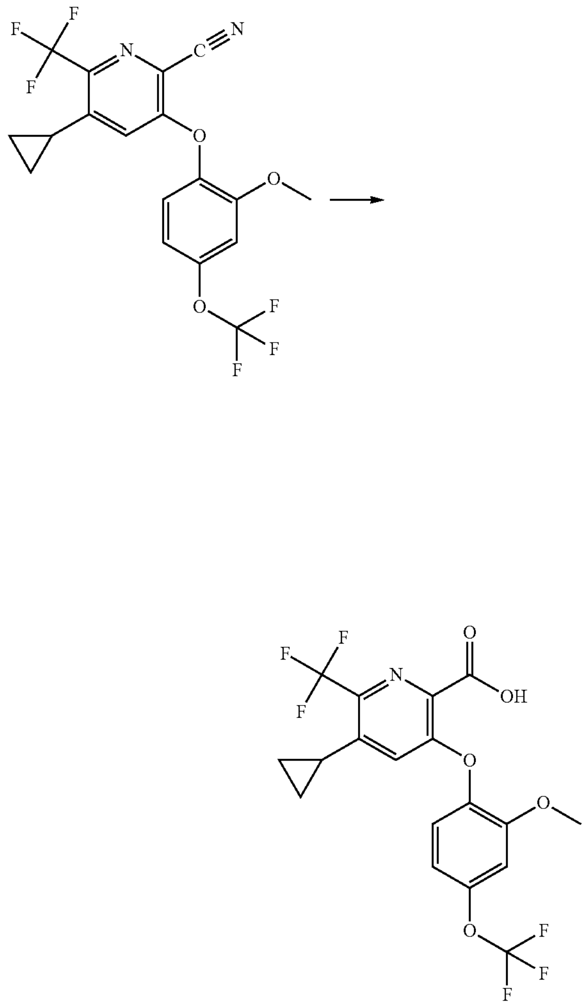

To a solution of 5-cyclopropyl-3-[2-methoxy-4-(trifluoromethoxy)phenoxy]-6-(trifluoromethyl)pyridine-2-carbonitrile (91 mg, 0.17 mmol) in ethanol (750 μL) was added aqueous NaOH (500 μL of 5 M, 2.5 mmol). The mixture was heated at 80° C. for 30 minutes, and then was diluted with water and extracted with ethyl acetate. The organic extract was dried over $MgSO_4$, filtered and concentrated in vacuo to provide 5-cyclopropyl-3-[2-methoxy-4-(trifluoromethoxy)phenoxy]-6-(trifluoromethyl)pyridine-2-carboxylic acid (69 mg, 81%). ESI-MS m z calc. 437.07, found 438.5 $(M+1)^+$; 436.7 $(M-1)^-$; LC/MS retention time (Method F): 0.64 minutes.

Step 9: N-(2-Carbamoyl-4-Pyridyl)-5-Cyclopropyl-3-[2-Methoxy-4-(Trifluoromethoxy)Phenoxy]-6-(Trifluoromethyl)Pyridine-2-Carboxamide (282)

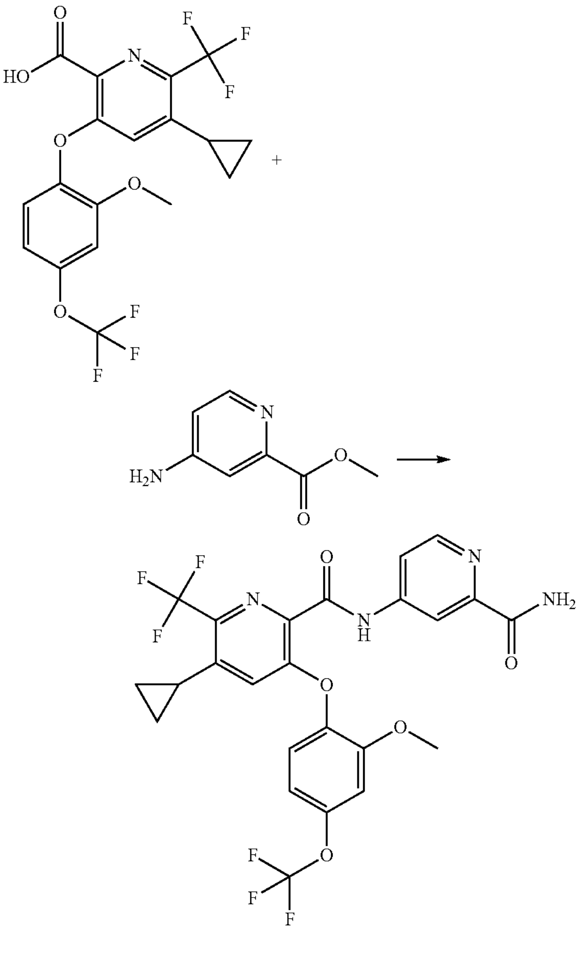

To a solution of 5-cyclopropyl-3-[2-methoxy-4-(trifluoromethoxy)phenoxy]-6-(trifluoromethyl)pyridine-2-carboxylic acid (13 mg, 0.026 mmol) in dichloromethane (300 μL) and DMF (0.2 μL, 0.003 mmol) at 0° C. was added oxalyl chloride (9 μL, 0.1 mmol) and the solution was warmed to room temperature and stirred for 1 hour. The mixture was concentrated in vacuo, redissolved in dichloromethane (300 μL) and added to a solution of methyl 4-aminopyridine-2-carboxylate (4 mg, 0.03 mmol) and TEA (10 μL, 0.072 mmol) in dichloromethane (200 μL) at 0° C. The mixture was warmed to room temperature and stirred for 3 hours. The mixture was diluted with dichloromethane and washed with water. The organic layer was dried and concentrated in vacuo. The residue was dissolved in a solution of ammonia in methanol (1 mL of 7 M, 7 mmol) and stirred at room temperature for 60 hours. The mixture was concentrated in vacuo and purified by reverse phase HPLC (47-95% acetonitrile/0.1% ammonium hydroxide) to provide N-(2-carbamoyl-4-pyridyl)-5-cyclopropyl-3-[2-methoxy-4-(trifluoromethoxy)phenoxy]-6-(trifluoromethyl)pyridine-2-carboxamide (2 mg, 14%). ESI-MS m z calc. 556.12, found 557.5 $(M+1)^+$; 555.6 $(M-1)^-$; LC/MS retention time (Method E): 3.45 minutes.

Example 93

4-[[4-Methoxy-6-[2-Methoxy-4-(Trifluoromethoxy) Phenoxy]-2-Methyl-3-(Trifluoromethyl)Benzoyl] Amino]Pyridine-2-Carboxamide (283)

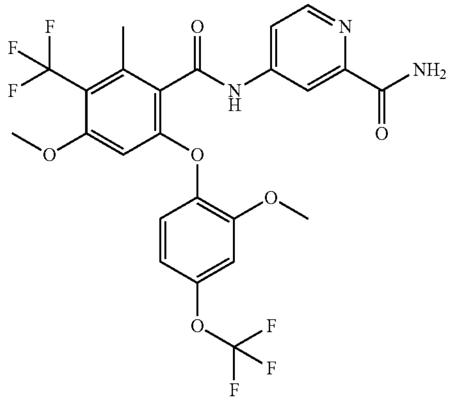 [SMILES: COc1cc(OC(F)(F)F)ccc1Oc1cc(OC)c(C(F)(F)F)c(C)c1C(=O)Nc1ccnc(C(N)=O)c1]

Step 1: Methyl 4-Methoxy-2-Methyl-3-(Trifluoromethyl)Benzoate

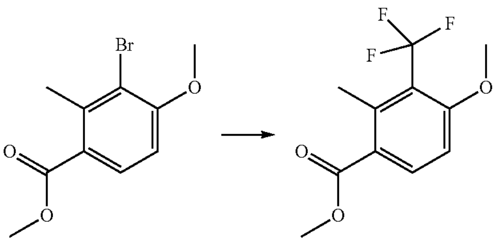 [SMILES: COC(=O)c1ccc(OC)c(Br)c1C ; COC(=O)c1ccc(OC)c(C(F)(F)F)c1C]

To a solution of methyl 3-bromo-4-methoxy-2-methyl-benzoate (3.964 g, 15.30 mmol) and copper (I) iodide (615 mg, 3.23 mmol) in DMF (38 mL) under nitrogen was added methyl 2,2-difluoro-2-(fluorosulfonyl)acetate (4.2 mL, 33 mmol). The mixture was heated at 120° C. for 3 hours. Additional copper (I) iodide (596 mg, 3.13 mmol) was added and the mixture was heated at 120° C. for an additional 30 minutes. Additional copper (I) iodide (1.746 g, 9.168 mmol) and methyl 2,2-difluoro-2-fluorosulfonyl-acetate (4.2 mL, 33 mmol) were added and the mixture was then heated at 120° C. for 20 hours. The mixture was added to ice-cold saturated aqueous $NaHCO_3$ (300 mL) and extracted with ethyl acetate (2×175 mL). The combined organic extracts were washed with water (5×100 mL), dried over $MgSO_4$, filtered and concentrated in vacuo. Two sequential purifications by silica gel chromatography (0-5% ethyl acetate/heptane) provided methyl 4-methoxy-2-methyl-3-(trifluoromethyl)benzoate (1.114 g, 29%). ESI-MS m z calc. 248.07, found 249.5 $(M+1)^+$; LC/MS retention time (Method F): 0.87 minutes. $^1H$ NMR (500 MHz, $CDCl_3$) δ 7.89 (d, J=8.8 Hz, 1H), 6.87 (d, J=8.8 Hz, 1H), 3.91 (s, 3H), 3.89 (s, 3H), 2.63 (q, J=3.3 Hz, 3H) ppm.

Step 2: 4-Methoxy-2-Methyl-3-(Trifluoromethyl)Benzoic Acid

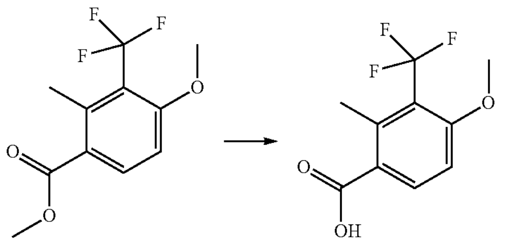 [SMILES: COC(=O)c1ccc(OC)c(C(F)(F)F)c1C ; COc1ccc(C(=O)O)c(C)c1C(F)(F)F]

To a solution of methyl 4-methoxy-2-methyl-3-(trifluoromethyl)benzoate (317 mg, 1.28 mmol) in THF (12 mL) and methanol (4 mL) at 0° C. was added aqueous NaOH (9 mL of 2 M, 18.00 mmol). The mixture was stirred at room temperature for 2 hours and then concentrated to remove organic solvents. The remaining aqueous solution was diluted with water (200 mL) and washed with ethyl acetate (3×100 mL). The aqueous solution was acidified to pH 3 and extracted with ethyl acetate (3×100 mL). The combined organic extracts were washed with water (2×75 mL), dried over $MgSO_4$, filtered and concentrated in vacuo to provide 4-methoxy-2-methyl-3-(trifluoromethyl)benzoic acid (285 mg, 95%). ESI-MS m z calc. 234.05, found 233.6 $(M-1)^-$; LC/MS retention time (Method F): 0.4 minutes. $^1H$ NMR (500 MHz, DMSO-$d_6$) δ 13.02 (s, 1H), 7.93 (d, J=8.8 Hz, 1H), 7.18 (d, J=8.8 Hz, 1H), 3.90 (s, 3H), 2.56 (q, J=3.4 Hz, 3H) ppm.

Step 3: 6-Iodo-4-Methoxy-2-Methyl-3-(Trifluoromethyl)Benzoic Acid

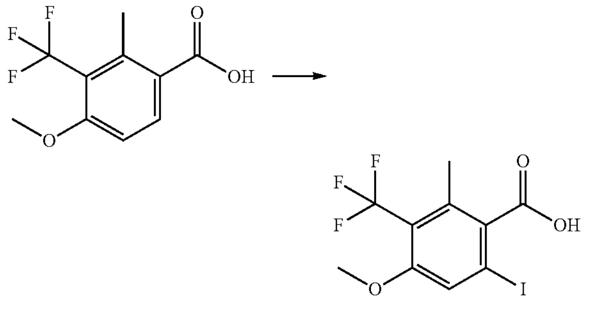

A mixture of 4-methoxy-2-methyl-3-(trifluoromethyl) benzoic acid (475 mg, 2.03 mmol), N-iodosuccinimide (502 mg, 2.23 mmol) and $Pd(OAc)_2$ (45 mg, 0.20 mmol) in DMF (10 mL) was heated under nitrogen at 100° C. for 90 minutes. The mixture was diluted with ethyl acetate (25 mL) and washed with water (5×20 mL) and brine (20 mL). The organic phase was dried over $MgSO_4$, filtered and concentrated in vacuo to provide 6-iodo-4-methoxy-2-methyl-3-(trifluoromethyl)benzoic acid (360 mg, 28%, contaminated with unreacted starting material). ESI-MS m z calc. 359.95, found 359.5 $(M-1)^-$; LC/MS retention time (Method F): 0.41 minutes. The material was used without additional purification.

Step 4: 4-Methoxy-6-[2-Methoxy-4-(Trifluoromethoxy)Phenoxy]-2-Methyl-3-(Trifluoromethyl) Benzoic Acid

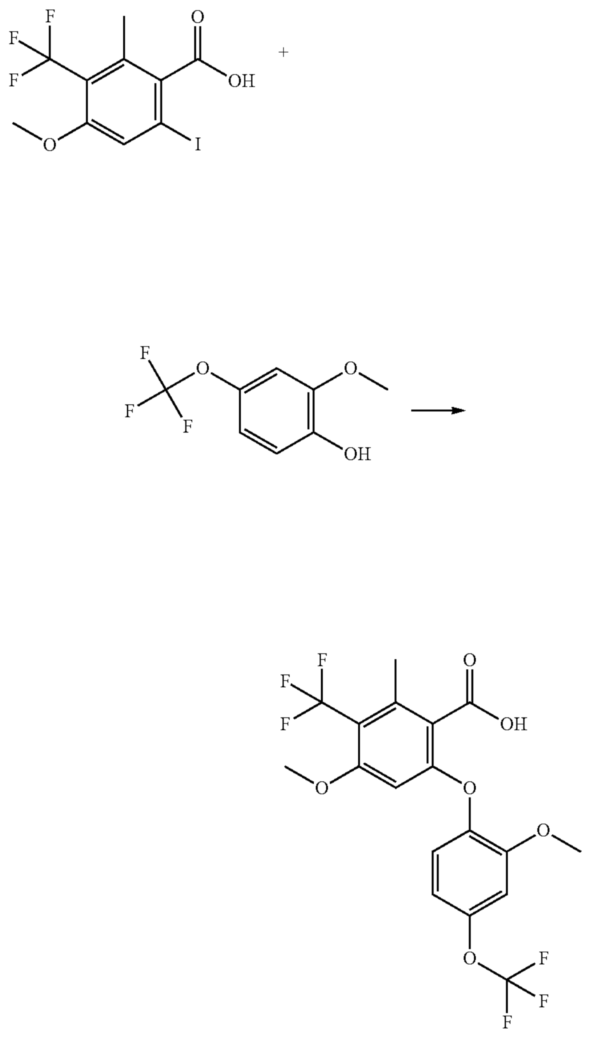

A solution of 6-iodo-4-methoxy-2-methyl-3-(trifluoromethyl)benzoic acid (360 mg, 0.640 mmol), 2-methoxy-4-(trifluoromethoxy)phenol (216 mg, 1.04 mmol) and $Cs_2CO_3$ (524 mg, 1.61 mmol) in toluene (8 mL) was flushed with nitrogen for 10 minutes. Copper (I) iodide (34 mg, 0.18 mmol) was added and the mixture heated at 100° C. for 16 hours under nitrogen. The mixture was diluted with water (100 mL) and extracted with ethyl acetate (100 mL). The organic layer was washed with saturated aqueous $NaHCO_3$ (75 mL), 1 M aqueous NaOH (75 mL×3) and brine (30 mL). The organic layer was dried over $MgSO_4$, filtered and concentrated in vacuo to provide 4-methoxy-6-[2-methoxy-4-(trifluoromethoxy)phenoxy]-2-methyl-3-(trifluoromethyl) benzoic acid (183 mg, 53%). ESI-MS m z calc. 440.07, found 441.5 $(M+1)^+$; 439.6 $(M-1)^-$; LC/MS retention time (Method F): 0.62 minutes.

Step 5: Methyl 4-[[4-Methoxy-6-[2-Methoxy-4-(Trifluoromethoxy)Phenoxy]-2-Methyl-3-(Trifluoromethyl)Benzoyl]Amino]Pyridine-2-Carboxylate

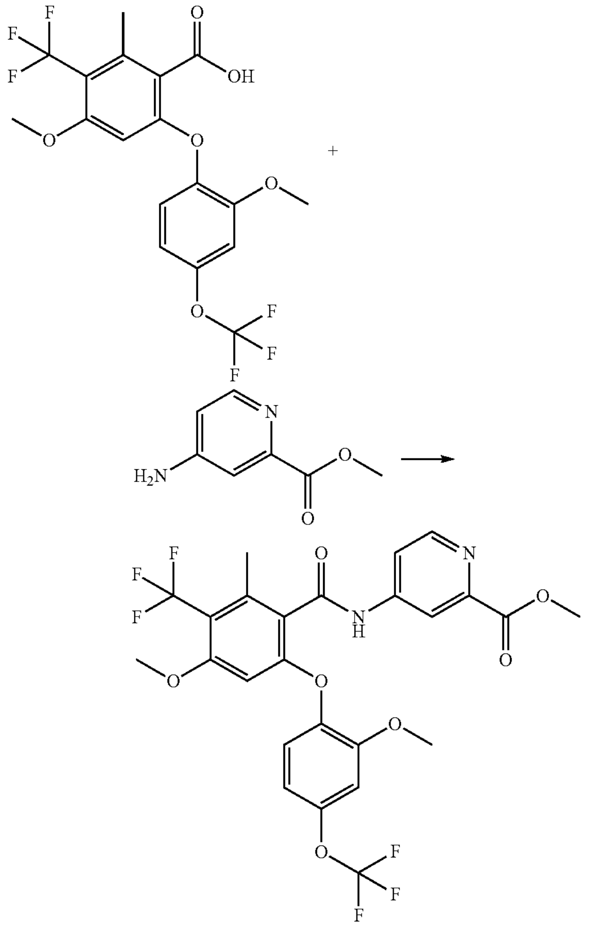

To a solution of 4-methoxy-6-[2-methoxy-4-(trifluoromethoxy)phenoxy]-2-methyl-3-(trifluoromethyl)benzoic acid (188 mg, 0.350 mmol) and DMF (3 μL, 0.04 mmol) in dichloromethane (3 mL) at 0° C. was added oxalyl chloride (100 μL, 1.15 mmol). The mixture was warmed to room temperature and stirred for 20 minutes. The mixture was concentrated in vacuo, then redissolved in dichloromethane (2 mL) and added dropwise to a solution of methyl 4-aminopyridine-2-carboxylate (52.8 mg, 0.347 mmol) and TEA (150 μL, 1.08 mmol) in dichloromethane (2 mL) at 0° C. The mixture was allowed to warm to room temperature and stirred for 20 hours. The mixture was diluted with dichloromethane (20 mL) and washed with water (20 mL). The aqueous layer was extracted with additional dichloromethane (2×20 mL), and then the combined organic extracts dried over $MgSO_4$, filtered and concentrated in vacuo. Purification by column chromatography (0-60% ethyl acetate/heptane) provided methyl 4-[[4-methoxy-6-[2-methoxy-4-(trifluoromethoxy)phenoxy]-2-methyl-3-(trifluoromethyl)benzoyl]amino]pyridine-2-carboxylate (43 mg, 21%). ESI-MS m z calc. 574.12, found 575.5 $(M+1)^+$; 573.6 $(M-1)^-$; LC/MS retention time (Method F): 0.98 minutes. $^1H$ NMR (500 MHz, DMSO-$d_6$) δ 11.14 (s, 1H), 8.59 (d, J=5.5 Hz, 1H), 8.40 (d, J=2.0 Hz, 1H), 7.81 (dd, J=5.4, 2.2

Hz, 1H), 7.23 (d, J=8.8 Hz, 1H), 7.18 (d, J=2.8 Hz, 1H), 6.98 (d, J=8.6 Hz, 1H), 6.36 (s, 1H), 3.87 (s, 3H), 3.77 (s, 3H), 3.70 (s, 3H), 2.38 (q, J=3.3 Hz, 3H) ppm.

Step 6: 4-[[4-Methoxy-6-[2-Methoxy-4-(Trifluoromethoxy)Phenoxy]-2-Methyl-3-(Trifluoromethyl) Benzoyl]Amino]Pyridine-2-Carboxamide (283)

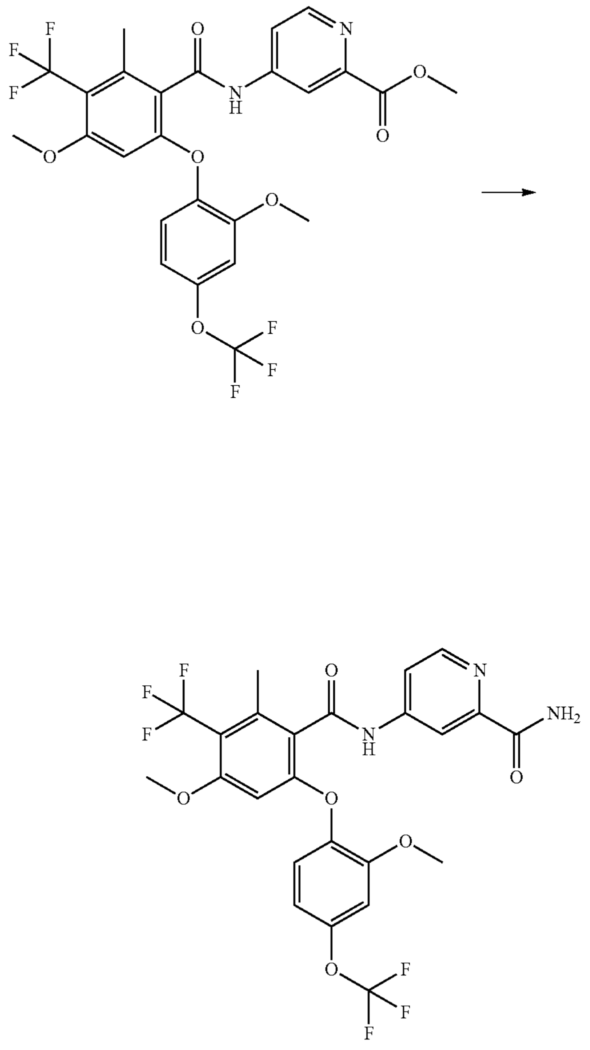

Methyl 4-[[4-methoxy-6-[2-methoxy-4-(trifluoromethoxy)phenoxy]-2-methyl-3-(trifluoromethyl)benzoyl] amino]pyridine-2-carboxylate (40 mg, 0.070 mmol) was dissolved in a solution of ammonia in methanol (1 mL of 7 M, 7 mmol) and stirred at room temperature for 24 hours. The mixture was concentrated in vacuo and partitioned between dichloromethane and water. The layers were separated, and the aqueous layer extracted with additional dichloromethane (2×20 mL). The combined organic extracts were dried over $MgSO_4$, filtered and concentrated in vacuo to provide 4-[[4-methoxy-6-[2-methoxy-4-(trifluoromethoxy)phenoxy]-2-methyl-3-(trifluoromethyl)benzoyl] amino]pyridine-2-carboxamide (20 mg, 49%). ESI-MS m z calc. 559.12, found 560.3 $(M+1)^+$; 558.4 $(M-1)^-$; LC/MS retention time (Method E): 3.31 minutes. $^1$H NMR (500 MHz, DMSO-$d_6$) δ 11.09 (s, 1H), 8.51 (d, J=5.6 Hz, 1H), 8.32 (d, J=2.1 Hz, 1H), 8.06 (d, J=2.9 Hz, 1H), 7.82 (dd, J=5.5, 2.2 Hz, 1H), 7.61 (d, J=2.9 Hz, 1H), 7.25 (d, J=8.8 Hz, 1H), 7.18 (d, J=2.8 Hz, 1H), 6.99 (ddd, J=8.8, 2.8, 1.3 Hz, 1H), 6.34 (s, 1H), 3.78 (s, 3H), 3.70 (s, 3H), 2.39 (q, J=3.3 Hz, 3H) ppm.

Example 94

4-[[2-Fluoro-3-Methoxy-6-[2-Methoxy-4-(Trifluoromethoxy)Phenoxy]-4-(Trifluoromethyl)Benzoyl] Amino]Pyridine-2-Carboxamide (284)

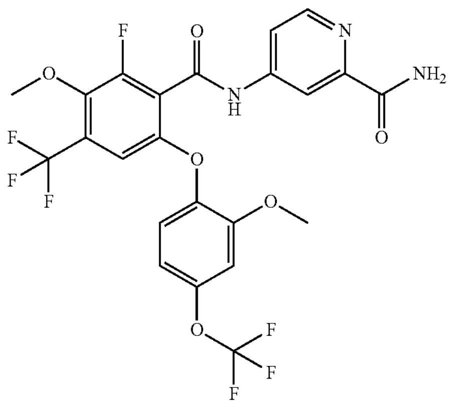 [SMILES: COc1cc(OC(F)(F)F)ccc1Oc1cc(C(F)(F)F)c(OC)c(F)c1C(=O)Nc1ccnc(C(N)=O)c1]

Step 1: 1-Fluoro-2-Methoxy-3-(Trifluoromethyl)Benzene

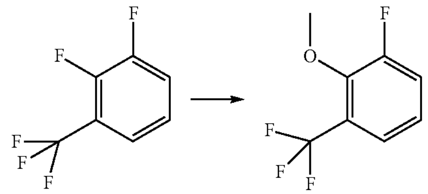

A solution of 1,2-difluoro-3-(trifluoromethyl)benzene (101.2 g, 555.8 mmol) in MTBE (800 mL) was treated with a solution of sodium methoxide (180 mL of 25% w/v, 833 mmol) at room temperature, with a slight endotherm observed. The mixture was heated at 43° C. for 30 hours, and then treated with additional sodium methoxide solution (40 mL of 25% w/v, 185.1 mmol) and heated at 50° C. overnight. The mixture was cooled to room temperature, diluted with water (830 mL) and the biphasic mixture filtered. The aqueous phase was separated and extracted with additional MTBE (2×300 mL). The combined organic layers were dried over $MgSO_4$, filtered and concentrated in vacuo to provide 1-fluoro-2-methoxy-3-(trifluoromethyl)benzene (103.9 g, 90%) as a colorless oil. $^1$H NMR (400 MHz, DMSO-$d_6$) δ 7.69-7.59 (m, 1H), 7.49 (ddq, J=7.9, 1.4, 0.7 Hz, 1H), 7.35-7.24 (m, 1H), 3.95 (d, J=2.0 Hz, 3H) ppm.

Step 2: 2-Fluoro-3-Methoxy-4-(Trifluoromethyl)Benzoic Acid

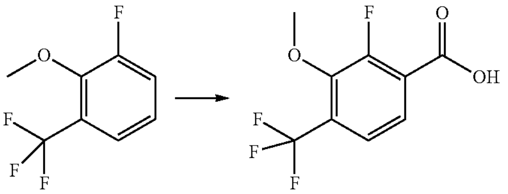 [SMILES: COc1c(F)cccc1C(F)(F)F ; COc1c(C(F)(F)F)ccc(C(=O)O)c1F]

A solution of diisopropylamine (80 mL, 571 mmol) in THF (620 mL) was cooled to −20° C. and treated with n-butyllithium (225 mL of 2.5 M in hexane, 562.5 mmol) at a rate to maintain the internal temperature below −15° C. After complete addition, the cooling bath was removed and the mixture was allowed to warm to 0° C. The mixture was then cooled to −74° C. and treated with a solution of 1-fluoro-2-methoxy-3-(trifluoromethyl)benzene (103.9 g, 498.7 mmol) in THF (210 mL) over 25 minutes while maintaining the internal temperature below −69° C. The mixture was stirred for an additional 30 minutes at −74° C., then poured into a slurry of excess solid carbon dioxide (dry ice) in THF (320 mL). The mixture was stirred until room temperature had been reached and no more effervescence was observed. The mixture was partitioned between 2 M aqueous NaOH (500 mL) and MTBE (130 mL), and then further diluted with water (450 mL). The aqueous phase was separated and washed with additional MTBE (130 mL). The aqueous phase was then acidified with 2 M aqueous HCl and extracted with MTBE (2×250 mL). The combined organic extracts were dried over $MgSO_4$, filtered and concentrated in vacuo to provide 2-fluoro-3-methoxy-4-(trifluoromethyl) benzoic acid (110 g, 93%) as a white solid. ESI-MS m z calc. 238.03, found 237.0 $(M-1)^-$; LC/MS retention time (Method F): 0.46 minutes. $^1H$ NMR (400 MHz, DMSO-$d_6$) δ 13.80 (s, 1H), 7.75-7.64 (m, 1H), 7.57 (dd, J=8.4, 1.4 Hz, 1H), 3.97 (d, J=1.8 Hz, 3H) ppm.

Step 3: 2-Fluoro-6-Iodo-3-Methoxy-4-(Trifluoromethyl)Benzoic Acid

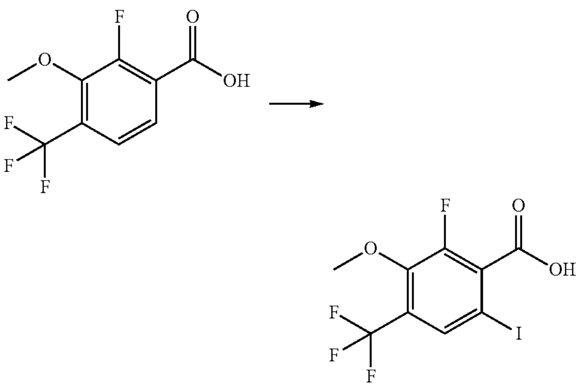

A solution of 2-fluoro-3-methoxy-4-(trifluoromethyl)benzoic acid (497 mg, 2.09 mmol) in trifluoroacetic acid (1 mL) and sulfuric acid (300 μL) was treated with N-iodosuccinimide (800 mg, 3.56 mmol) in one portion and stirred at room temperature for 3 hours. The mixture was diluted with dichloromethane and water (exothermic). The phases were separated and the aqueous layer was extracted with additional dichloromethane. The combined organic phases were washed with saturated aqueous $Na_2S_2O_3$, dried over $MgSO_4$, filtered and concentrated in vacuo. Purification using silica gel chromatography (0-100% ethyl acetate/heptane) provided 2-fluoro-6-iodo-3-methoxy-4-(trifluoromethyl)benzoic acid (708 mg, 93%). ESI-MS m z calc. 363.92, no ionization observed; LC/MS retention time (Method F): 0.45 minutes. $^1H$ NMR (400 MHz, $CDCl_3$) δ 7.86 (dd, J=1.7, 0.7 Hz, 1H), 4.07 (d, J=2.4 Hz, 3H), 2.85 (s, 1H) ppm.

Step 4: 2-Fluoro-3-Methoxy-6-[2-Methoxy-4-(Trifluoromethoxy)Phenoxy]-4-(Trifluoromethyl)Benzoic Acid

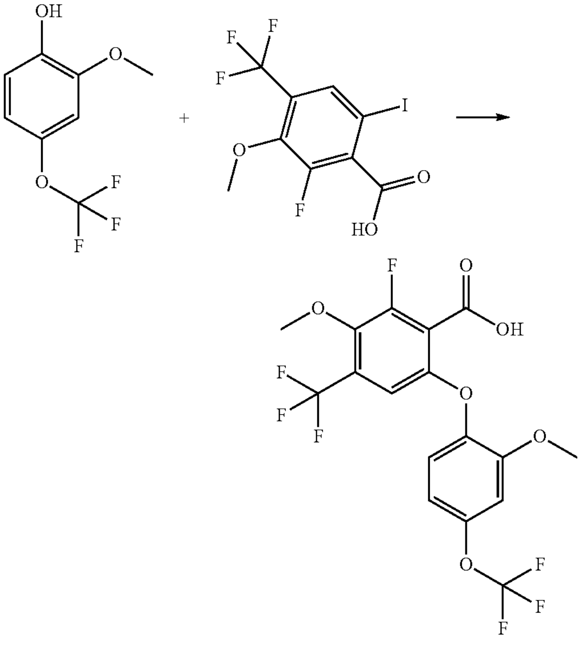

A mixture of 2-fluoro-6-iodo-3-methoxy-4-(trifluoromethyl)benzoic acid (300 mg, 0.618 mmol), 2-methoxy-4-(trifluoromethoxy)phenol (257 mg, 1.24 mmol) and $Cs_2CO_3$ (537 mg, 1.65 mmol) in toluene (11 mL) was bubbled with nitrogen for 10 minutes, then copper (I) iodide (31.39 mg, 0.1648 mmol) added. The mixture was heated at 100° C. under nitrogen with vigorous stirring for 16 hours. The mixture was allowed to cool and was partitioned between ethyl acetate and water. The separated aqueous layer was acidified with aqueous HCl and extracted with ethyl acetate. The organic layer was washed with brine, dried over $MgSO_4$, filtered and concentrated in vacuo. Purification by silica gel chromatography (0-60% ethyl acetate/heptane) provided 2-fluoro-3-methoxy-6-[2-methoxy-4-(trifluoromethoxy)phenoxy]-4-(trifluoromethyl)benzoic acid (160 mg, 58%) as a pale orange oil that crystallized on standing. ESI-MS m z calc. 444.04, found 443.4 $(M-1)^-$; LC/MS retention time (Method F): 0.62 minutes. $^1H$ NMR (500 MHz, $CDCl_3$) δ 7.23-7.06 (m, 1H), 6.91 (ddd, J=7.1, 2.3, 1.1 Hz, 2H), 6.73 (d, J=1.8 Hz, 1H), 4.02 (d, J=1.5 Hz, 3H), 3.85 (s, 3H) ppm.

Step 5: Methyl 4-[[2-Fluoro-3-Methoxy-6-[2-Methoxy-4-(Trifluoromethoxy)Phenoxy]-4-(Trifluoromethyl)Benzoyl]Amino]Pyridine-2-Carboxylate

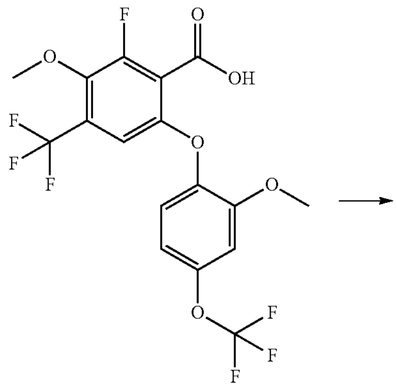

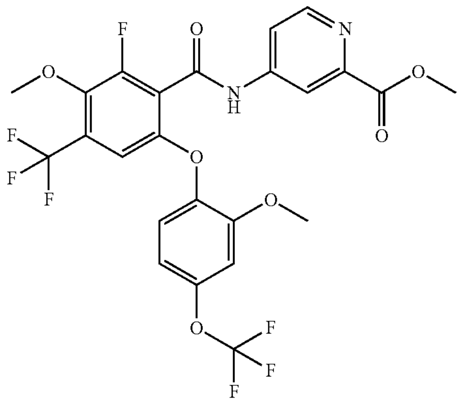

A solution of 2-fluoro-3-methoxy-6-[2-methoxy-4-(trifluoromethoxy)phenoxy]-4-(trifluoromethyl)benzoic acid (55 mg, 0.12 mmol) and DMF (0.5 μL, 0.007 mmol) in dichloromethane (3 mL) at 0° C. was treated with oxalyl chloride (2.5 mL, 29 mmol). The mixture was stirred for 1 hour before being concentrated in vacuo. The residue was redissolved in dichloromethane (3 mL) and treated with DIPEA (36 μL, 0.21 mmol) and methyl 4-aminopyridine-2-carboxylate (21 mg, 0.14 mmol). The mixture was stirred overnight, then concentrated in vacuo and purified by reverse phase HPLC (47-95% acetonitrile/0.1% ammonium hydroxide) to provide methyl 4-[[2-fluoro-3-methoxy-6-[2-methoxy-4-(trifluoromethoxy)phenoxy]-4-(trifluoromethyl)benzoyl]amino]pyridine-2-carboxylate (56 mg, 78%). ESI-MS m z calc. 578.09, found 579.5 $(M+1)^+$; 577.5 $(M-1)^-$; LC/MS retention time (Method F): 0.96 minutes.

Step 6: 4-[[2-Fluoro-3-Methoxy-6-[2-Methoxy-4-(Trifluoromethoxy)Phenoxy]-4-(Trifluoromethyl)Benzoyl]Amino]Pyridine-2-Carboxamide (284)

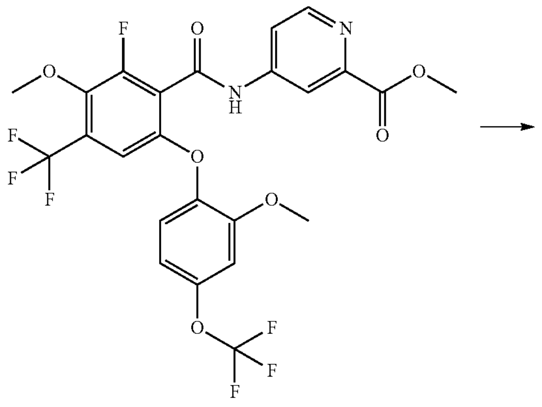

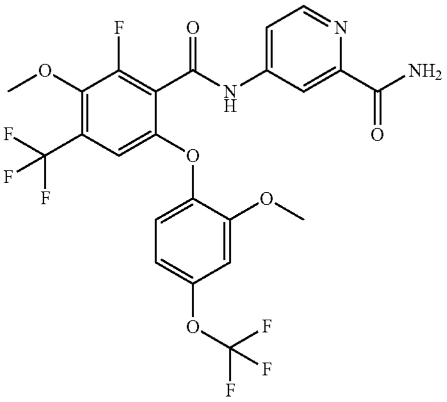

Methyl 4-[[2-fluoro-3-methoxy-6-[2-methoxy-4-(trifluoromethoxy)phenoxy]-4-(trifluoromethyl)benzoyl]amino]pyridine-2-carboxylate (56 mg, 0.10 mmol) was dissolved in a solution of ammonia in methanol (2.8 mL of 7 M, 19.6 mmol) and stirred at room temperature overnight. The mixture was concentrated in vacuo to provide 4-[[2-fluoro-3-methoxy-6-[2-methoxy-4-(trifluoromethoxy)phenoxy]-4-(trifluoromethyl)benzoyl]amino]pyridine-2-carboxamide (40 mg, 71%). ESI-MS m z calc. 563.09, found 564.5 $(M+1)^+$; 562.4 $(M-1)^-$; LC/MS retention time (Method E): 3.37 minutes. $^1H$ NMR (500 MHz, $CDCl_3$) δ 9.19 (s, 1H), 8.56 (d, J=5.5 Hz, 1H), 8.41 (dd, J=5.6, 2.2 Hz, 1H), 7.92 (d, J=2.2 Hz, 2H), 7.26-7.15 (m, 1H), 7.02-6.86 (m, 2H), 6.76 (d, J=1.9 Hz, 1H), 5.57 (d, J=4.5 Hz, 1H), 4.03 (d, J=1.5 Hz, 3H), 3.93 (s, 3H) ppm.

Example 95

4-[[2-Fluoro-6-[2-Methyl-4-(Trifluoromethoxy)Phenoxy]-3-(Trifluoromethyl)Benzoyl]Amino]-5-Methyl-Pyridine-2-Carboxamide (285)

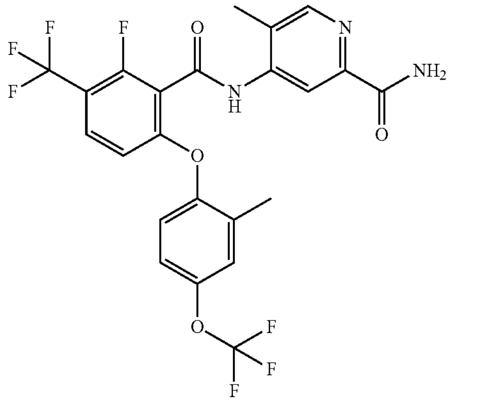 [SMILES: Cc1cnc(C(N)=O)cc1NC(=O)c1c(Oc2ccc(OC(F)(F)F)cc2C)ccc(C(F)(F)F)c1F]

To a solution of 2-fluoro-6-[2-methyl-4-(trifluoromethoxy)phenoxy]-3-(trifluoromethyl)benzoic acid (300 mg, 0.753 mmol, see US 2019/0016671, Example 10, Step 1, which is incorporated by reference) and DMF (6 μL, 0.08 mmol) in dichloromethane (7 mL) at 0° C. was added oxalyl chloride (190 μL, 2.25 mmol) dropwise. The mixture was stirred for 2 hours, and then concentrated in vacuo. The residue was redissolved in dichloromethane (7 mL) and added dropwise to a mixture of methyl 4-amino-5-methyl-pyridine-2-carboxylate (175 mg, 1.053 mmol, Preparation 1) and TEA (630 μL, 4.520 mmol) in dichloromethane (7 mL) at 0° C. The resulting mixture allowed to warm to room temperature and stirred overnight. The mixture was concentrated in vacuo and purified by reverse phase HPLC (47-95% acetonitrile/0.1% ammonium hydroxide) to provide 4-[[2-fluoro-6-[2-methyl-4-(trifluoromethoxy)phenoxy]-3-(trifluoromethyl)benzoyl]amino]-5-methyl-pyridine-2-carboxamide (66 mg, 16%). ESI-MS m z calc. 531.10, found 532.1 $(M+1)^+$; 530.2 $(M-1)^-$; LC/MS retention time (Method F): 0.95 minutes. $^1H$ NMR (400 MHz, DMSO-$d_6$) δ 10.65 (s, 1H), 8.48 (s, 2H), 8.06 (d, J=2.5 Hz, 1H), 7.84 (t, J=8.7 Hz, 1H), 7.61 (d, J=2.7 Hz, 1H), 7.45 (dd, J=2.7, 1.6 Hz, 1H), 7.38-7.24 (m, 2H), 6.71 (d, J=8.9 Hz, 1H), 2.31 (s, 3H), 2.22 (s, 3H) ppm.

Example 96

4-[[3-Chloro-2-Fluoro-6-[2-Methyl-4-(Trifluoromethoxy)Phenoxy]Benzoyl]Amino]Pyridine-2-Carboxamide (286)

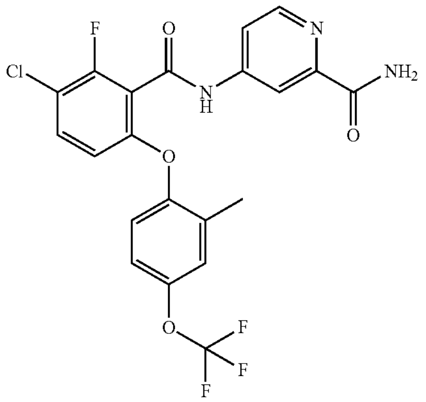 [SMILES: Cc1cc(OC(F)(F)F)ccc1Oc1ccc(Cl)c(F)c1C(=O)Nc1ccnc(C(N)=O)c1]

Step 1: 6-Bromo-3-Chloro-2-Fluoro-Benzoic Acid

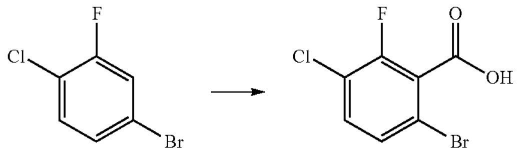 [SMILES: Fc1cc(Br)ccc1Cl ; O=C(O)c1c(Br)ccc(Cl)c1F]

A solution of diisopropylamine (94 mL, 671 mmol) in THF (840 mL) was cooled to −20° C. A solution of n-butyllithium (264 mL of 2.5 M in hexanes, 660 mmol) was added at such a rate to keep the internal temperature below −15° C. After complete addition, the cooling bath was removed and the mixture allowed to warm to 0° C. The mixture then was cooled to −74° C. and treated with a solution of 4-bromo-1-chloro-2-fluoro-benzene (120.2 g, 573.9 mmol) in THF (200 mL) over 30 minutes while maintaining the internal temperature below −70° C. The mixture was stirred for an additional 30 minutes at −74° C., then poured into a slurry of excess solid carbon dioxide (dry ice) in THF (320 mL). The mixture was stirred until room temperature had been reached and no more effervescence was observed. The mixture was partitioned between 2 M aqueous NaOH (600 mL) and MTBE (200 mL), and then further diluted with water (240 mL). The aqueous phase was separated and washed with additional MTBE (200 mL). The aqueous phase was then acidified with 2 M aqueous HCl and extracted with MTBE (2×400 mL). The combined organic extracts were dried over $MgSO_4$, filtered and concentrated in vacuo to provide 6-bromo-3-chloro-2-fluoro-benzoic acid (135.4 g, 93%). $^1H$ NMR (400 MHz, DMSO-$d_6$) δ 14.38 (s, 1H), 7.95-7.23 (m, 2H) ppm.

Step 2: 3-Chloro-2-Fluoro-6-[2-Methyl-4-(Trifluoromethoxy)Phenoxy]Benzoic Acid

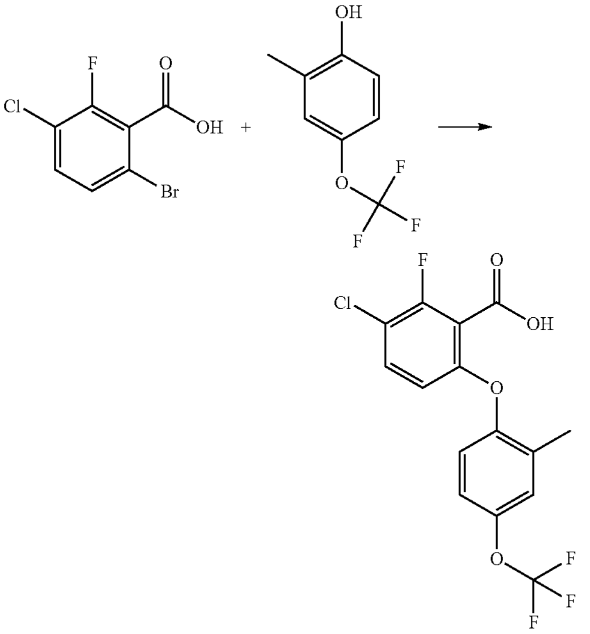

A mixture of 6-bromo-3-chloro-2-fluoro-benzoic acid (800 mg, 3.16 mmol), 2-methyl-4-(trifluoromethoxy)phenol (800 mg, 3.54 mmol) and $Cs_2CO_3$ (2.0 g, 6.1 mmol) in toluene (12 mL) was heated at 100° C. and then treated with copper (I) iodide (120 mg, 0.630 mmol). The mixture was heated at 100° C. overnight, then cooled and diluted with water and ethyl acetate. The aqueous layer was acidified with 2 M aqueous HCl and the layers separated. The organic layer was washed with water, dried over $Na_2SO_4$, filtered and concentrated in vacuo to provide 3-chloro-2-fluoro-6-[2-methyl-4-(trifluoromethoxy)phenoxy]benzoic acid (1.3 g, 90%). $^1H$ NMR (400 MHz, DMSO-$d_6$) δ 14.05 (s, 2H), 9.65 (s, 1H), 7.40 (d, J=2.9 Hz, 1H), 7.24 (dd, J=8.9, 2.9 Hz, 1H), 7.07 (d, J=3.2 Hz, 1H), 6.98 (dd, J=8.7, 3.0 Hz, 1H), 6.82 (d, J=8.7 Hz, 1H), 6.69 (dd, J=9.0, 1.5 Hz, 1H) ppm.

Step 3: 4-[[3-Chloro-2-Fluoro-6-[2-Methyl-4-(Trifluoromethoxy)Phenoxy]Benzoyl]Amino]Pyridine-2-Carboxamide (286)

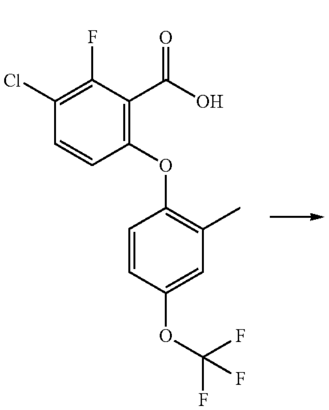

-continued

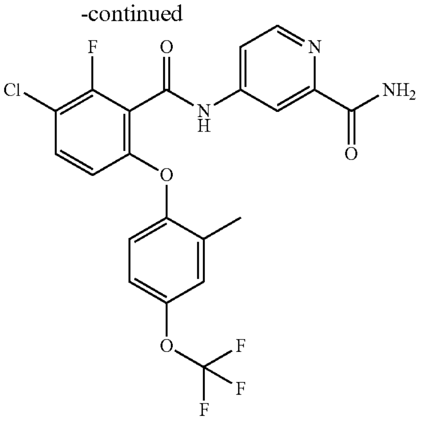

A solution of 3-chloro-2-fluoro-6-[2-methyl-4-(trifluoromethoxy)phenoxy]benzoic acid (260 mg, 0.570 mmol) and DMF (45 μL, 0.58 mmol) in dichloromethane (3 mL) at 0° C. was treated with oxalyl chloride (200 μL, 2.29 mmol). The mixture was stirred for 1 hour, and then concentrated in vacuo. The residue was redissolved in dichloromethane (3 mL) and added dropwise to a stirring solution of methyl 4-aminopyridine-2-carboxylate (100 mg, 0.624 mmol), DIPEA (303 μL, 1.74 mmol) and DMAP (70 mg, 0.57 mmol) in dichloromethane (3 mL). The mixture was stirred overnight then concentrated in vacuo. The residue was dissolved in a solution of ammonia in methanol (7 M) and stirred overnight. The mixture was concentrated and purified by reverse phase HPLC (47-95% acetonitrile/0.1% ammonium hydroxide) to provide 4-[[3-chloro-2-fluoro-6-[2-methyl-4-(trifluoromethoxy)phenoxy]benzoyl]amino]pyridine-2-carboxamide (13.9 mg, 5%). ESI-MS m z calc. 483.06, found 484.1 $(M+1)^+$; 482.1 $(M-1)^-$; LC/MS retention time (Method F): 0.91 minutes. $^1H$ NMR (400 MHz, $CDCl_3$) δ 9.66 (s, 1H), 8.58-8.47 (m, 2H), 8.20 (d, J=2.1 Hz, 1H), 7.93 (s, 1H), 7.43 (dd, J=9.0, 8.0 Hz, 1H), 7.14-7.00 (m, 3H), 6.54 (dd, J=8.9, 1.4 Hz, 1H), 5.16 (s, 1H), 2.22 (s, 3H) ppm.

Example 97

5-[[6-[2-Chloro-4-(Trifluoromethoxy)Phenoxy]-3-Cyclopropyl-2-Methyl-Benzoyl]Amino]Pyridine-2-Carboxamide (287)

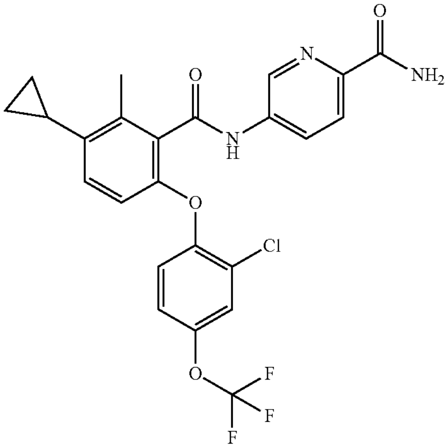 [SMILES: Cc1c(C2CC2)ccc(Oc2ccc(OC(F)(F)F)cc2Cl)c1C(=O)Nc1ccc(C(N)=O)nc1]

A solution of 6-[2-chloro-4-(trifluoromethoxy)phenoxy]-3-cyclopropyl-2-methyl-benzoyl chloride (40 mg, 0.10 mmol, see Example 42, Step 5) in NMP (0.3 mL) was added to a mixture of 5-aminopyridine-2-carboxamide (20.3 mg, 0.148 mmol) and DIEA (69 μL, 0.40 mmol) in NMP (0.3 mL). The mixture was stirred at room temperature for 16 hours. HATU (75 mg, 0.20 mmol) and DIEA (69 μL, 0.40 mmol) were added and the mixture stirred at 60° C. for 16 hours. The mixture was filtered and purified by reverse phase HPLC (30-99% acetonitrile/5 mM HCl) to provide 5-[[6-[2-chloro-4-(trifluoromethoxy)phenoxy]-3-cyclopropyl-2-methyl-benzoyl]amino]pyridine-2-carboxamide (6.4 mg, 13%). ESI-MS m z calc. 505.10, found 506.0 $(M+1)^+$; LC/MS retention time (Method B): 1.91 minutes. $^1H$ NMR (400 MHz, DMSO-$d_6$) δ 11.00 (s, 1H), 8.82 (s, 1H), 8.25 (d, J=10.4 Hz, 1H), 8.01 (d, J=8.8 Hz, 2H), 7.65 (s, 1H), 7.53 (s, 1H), 7.37 (d, J=10.4 Hz, 1H), 7.13 (d, J=8.7 Hz, 2H), 6.77 (d, J=8.5 Hz, 1H), 2.41 (s, 3H), 1.95 (s, 1H), 0.96 (d, J=8.3 Hz, 2H), 0.62 (d, J=5.0 Hz, 2H) ppm.

Example 98

4-[[6-[3-Fluoro-2-Methyl-4-(Trifluoromethoxy)Phenoxy]-2-Methyl-3-(Trifluoromethyl)Benzoyl]Amino]-5-Methyl-Pyridine-2-Carboxamide (288)

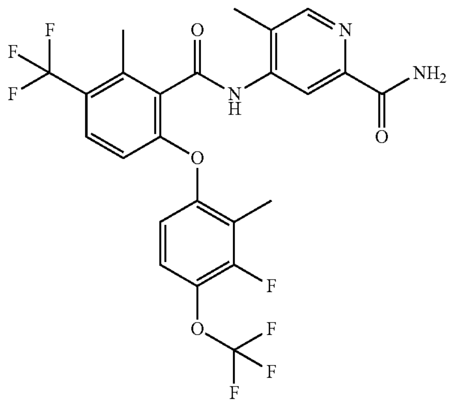 [SMILES: Cc1cnc(C(N)=O)cc1NC(=O)c1c(Oc2ccc(OC(F)(F)F)c(F)c2C)ccc(C(F)(F)F)c1C]

Step 1: 1-Bromo-3-Fluoro-2-Methyl-4-(Trifluoromethoxy)Benzene

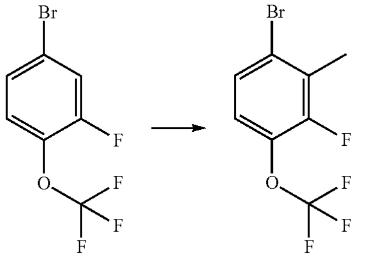

n-Butyllithium (14.5 mL of 1.6 M in hexanes, 23.2 mmol) was added to a stirring solution of diisopropylamine (3.0 mL, 21.4 mmol) in THF (50 mL) at −78° C. The mixture stirred for 20 minutes, then treated dropwise with 4-bromo-2-fluoro-1-(trifluoromethoxy)benzene (5.0 g, 19.3 mmol).

The mixture was stirred at −78° C. for 20 minutes then treated with iodomethane (1.85 mL, 29.7 mmol). The mixture was stirred at −78° C. for an additional 30 minutes then allowed to warm to room temperature overnight. The mixture was diluted with aqueous $NH_4Cl$ (50 mL) and water and extracted with ethyl acetate (2×50 mL). The combined organic layers were concentrated in vacuo to provide 1-bromo-3-fluoro-2-methyl-4-(trifluoromethoxy)benzene (4.7 g, 89%). $^1H$ NMR (400 MHz, $CDCl_3$) δ 7.28 (dd, J=8.9, 2.0 Hz, 1H), 6.96 (dddt, J=9.0, 7.7, 1.3, 0.7 Hz, 1H), 2.30 (d, J=2.7 Hz, 3H) ppm.

Step 2: 3-Fluoro-2-Methyl-4-(Trifluoromethoxy)Phenol

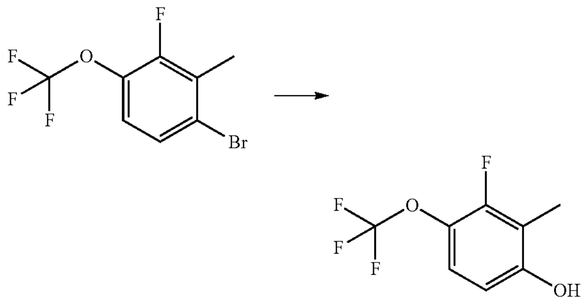

To a solution of 1-bromo-3-fluoro-2-methyl-4-(trifluoromethoxy)benzene (2.184 g, 7.999 mmol) in dioxane (11.4 mL) and water (7 mL) was added solid KOH (2.3 g, 41 mmol). The resulting solution was stirred for 15 minutes (until solids were dissolved). $Pd(dba)_2$ (115 mg, 0.200 mmol) and tBuXPhos (85 mg, 0.20 mmol) were added and the resulting solution was heated at 90° C. for 12 hours. The mixture was cooled to room temperature, partitioned between water and MTBE, and the biphasic mixture filtered. The layers were separated and the organic phase was concentrated in vacuo. The resulting oil was purified by silica gel chromatography (ethyl acetate/heptane gradient) to provide 3-fluoro-2-methyl-4-(trifluoromethoxy)phenol (1.57 g, 93%). ESI-MS m z calc. 210.03, found 209.3 $(M-1)^-$; LC/MS retention time (Method E): 1.99 minutes. $^1H$ NMR (400 MHz, $CDCl_3$) δ 7.02 (ddtd, J=9.0, 8.4, 1.2, 0.6 Hz, 1H), 6.56 (dd, J=8.9, 1.9 Hz, 1H), 5.38 (s, 1H), 2.21 (dt, J=2.2, 0.5 Hz, 3H) ppm.

Step 3: Tert-Butyl 2-Bromo-6-[3-Fluoro-2-Methyl-4-(Trifluoromethoxy)Phenoxy]-3-(Trifluoromethyl)Benzoate

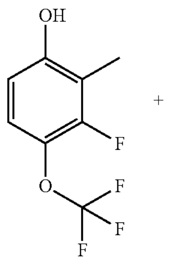

-continued

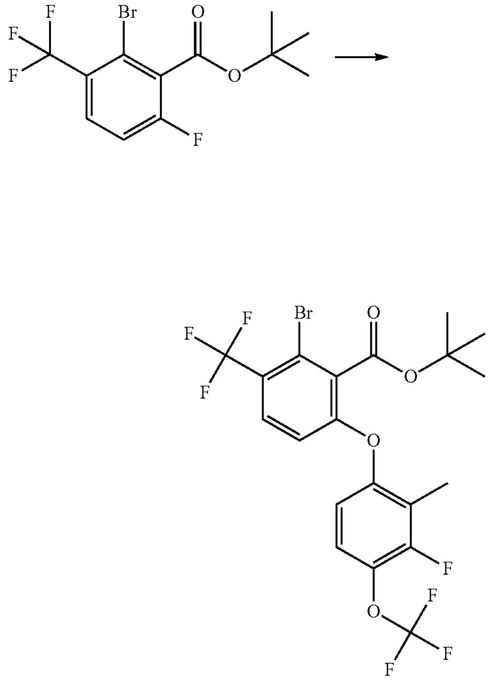

To a stirring solution of tert-butyl 2-bromo-6-fluoro-3-(trifluoromethyl)benzoate (1.66 g, 4.84 mmol) and 3-fluoro-2-methyl-4-(trifluoromethoxy)phenol (1.03 g, 4.90 mmol, Example 98, Step 2) in DMSO (6.5 mL) in a pressure vessel was added $K_2CO_3$ (1.35 g, 9.77 mmol) (325 mesh). The vessel was sealed and the suspension heated at 100° C. for 16 hours. After cooling to room temperature, the mixture was diluted with ethyl acetate and washed with water and brine. The organic layer was dried over $Na_2SO_4$, filtered and concentrated in vacuo. The crude material was purified by silica gel chromatography (0-10% ethyl acetate/hexanes) to provide tert-butyl 2-bromo-6-[3-fluoro-2-methyl-4-(trifluoromethoxy)phenoxy]-3-(trifluoromethyl)benzoate (1.49 g, 58%). ESI-MS m z calc. 532.01, found 476.9 (M-tert-butyl+1)+; LC/MS retention time (Method A): 0.92 minutes.

Step 4: Tert-Butyl 6-[3-Fluoro-2-Methyl-4-(Trifluoromethoxy)Phenoxy]-2-Methyl-3-(Trifluoromethyl) Benzoate

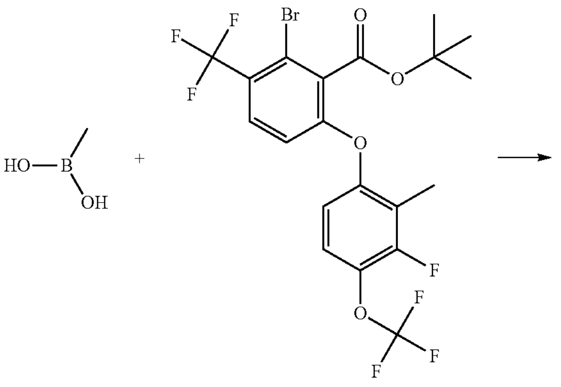

-continued

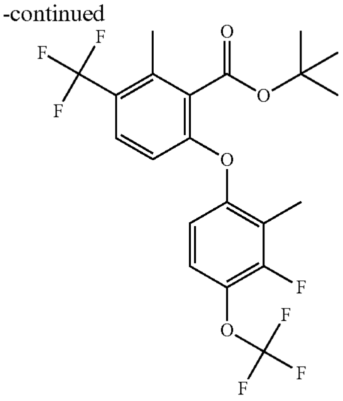

A mixture of tert-butyl 2-bromo-6-[3-fluoro-2-methyl-4-(trifluoromethoxy)phenoxy]-3-(trifluoromethyl)benzoate (1.49 g, 2.79 mmol), $Cs_2CO_3$ (2.736 g, 8.397 mmol) and methylboronic acid (841 mg, 14.1 mmol) in dioxane (22 mL) was sparged with nitrogen for 10 minutes. Pd(dppf)$Cl_2$ (52 mg, 0.071 mmol) was added and the mixture stirred at 90° C. for 4 hours. The mixture was filtered over Celite and the solids washed with dioxane. The filtrate was concentrated in vacuo, then partitioned between heptane/MTBE 4:1 (100 mL) and water (100 mL) and the layers separated. The organic layer was washed with water and brine, dried over $Na_2SO_4$, filtered and concentrated in vacuo to provide tert-butyl 6-[3-fluoro-2-methyl-4-(trifluoromethoxy)phenoxy]-2-methyl-3-(trifluoromethyl)benzoate (1.23 g, 94%) as a yellow liquid. ESI-MS m z calc. 468.12, found 413.1 (M-tert-butyl+1)+; LC/MS retention time (Method A): 0.96 minutes.

Step 5: 6-[3-Fluoro-2-Methyl-4-(Trifluoromethoxy) Phenoxy]-2-Methyl-3-(Trifluoromethyl)Benzoic Acid

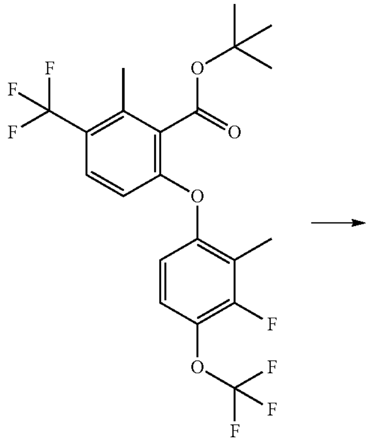

-continued

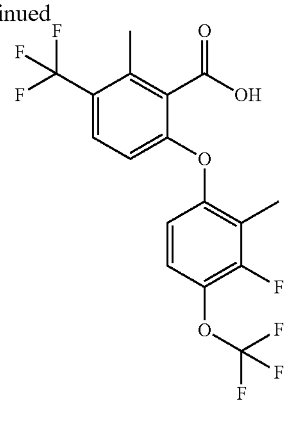

A solution of tert-butyl 6-[3-fluoro-2-methyl-4-(trifluoromethoxy)phenoxy]-2-methyl-3-(trifluoromethyl)benzoate (1.23 g, 2.63 mmol) in 2-propanol (6 mL) was treated with aqueous HCl (3 mL of 6 M, 18 mmol) and stirred at 90° C. for 1 hour. The mixture was allowed to cool and partitioned between ethyl acetate and water. The layers were separated and the aqueous layer was extracted with additional ethyl acetate (3×). The combined organic layers were washed with water and brine, dried over $Na_2SO_4$, filtered through Celite and concentrated in vacuo. Purification by reverse phase HPLC (1-99% acetonitrile/5 mM HCl) provided 6-[3-fluoro-2-methyl-4-(trifluoromethoxy)phenoxy]-2-methyl-3-(trifluoromethyl)benzoic acid (579.3 mg, 53%) as an orange viscous liquid. ESI-MS m z calc. 412.05, found 413.1 $(M+1)^+$; LC/MS retention time (Method C): 2.86 minutes.

Step 6: 6-[3-Fluoro-2-Methyl-4-(Trifluoromethoxy) Phenoxy]-2-Methyl-3-(Trifluoromethyl)Benzoyl

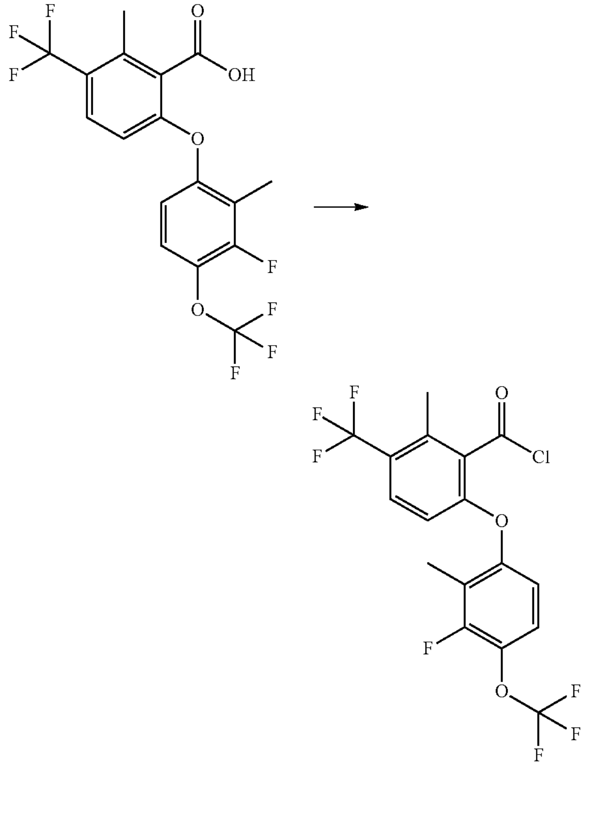

To a solution of 6-[3-fluoro-2-methyl-4-(trifluoromethoxy)phenoxy]-2-methyl-3-(trifluoromethyl)benzoic acid (480 mg, 1.16 mmol) and DMF (15 μL, 0.19 mmol) in dichloromethane (8 mL) at 0° C. was added oxalyl chloride (285 μL, 3.26 mmol) dropwise under nitrogen. The ice bath was removed after 10 minutes and the mixture was stirred at room temperature for 1 hour. The solvent was concentrated in vacuo to provide 6-[3-fluoro-2-methyl-4-(trifluoromethoxy)phenoxy]-2-methyl-3-(trifluoromethyl)benzoyl chloride.

Step 7: Methyl 4-[[6-[3-Fluoro-2-Methyl-4-(Trifluoromethoxy)Phenoxy]-2-Methyl-3-(Trifluoromethyl) Benzoyl]Amino]-5-Methyl-Pyridine-2-Carboxylate (Hydrochloride Salt)

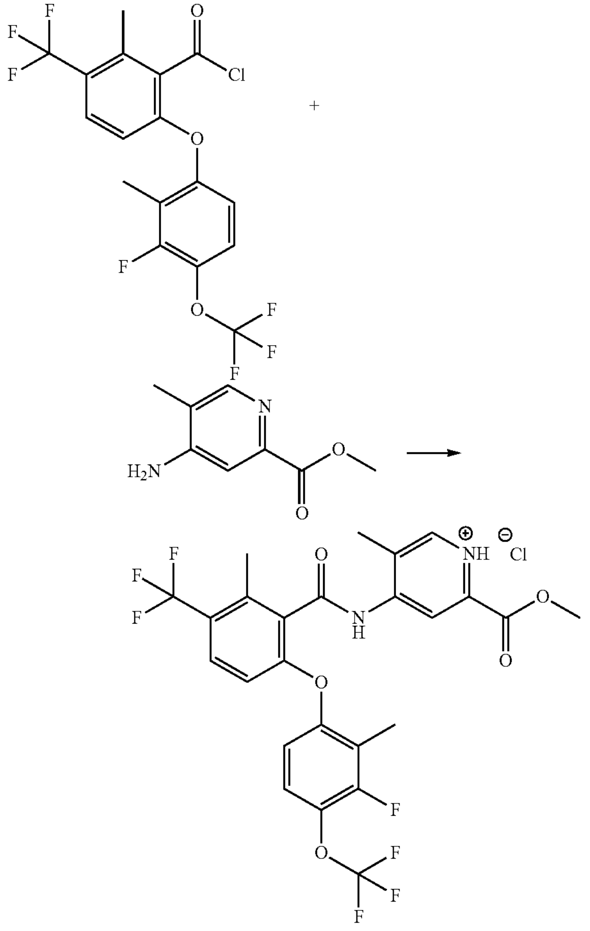

To a solution of methyl 4-amino-5-methyl-pyridine-2-carboxylate (46 mg, 0.28 mmol, Preparation 1) and DIEA (121 μL, 0.697 mmol) in NMP (500 μL) at 0° C. was added a solution of 6-[3-fluoro-2-methyl-4-(trifluoromethoxy)phenoxy]-2-methyl-3-(trifluoromethyl)benzoyl chloride (60 mg, 0.14 mmol) in NMP (500 μL). The mixture was stirred at 75° C. for 11 hours. The mixture was filtered and purified by reverse phase HPLC (1-99% acetonitrile/5 mM HCl) to provide methyl 4-[[6-[3-fluoro-2-methyl-4-(trifluoromethoxy)phenoxy]-2-methyl-3-(trifluoromethyl)benzoyl]amino]-5-methyl-pyridine-2-carboxylate (hydrochloride salt) (14.2 mg, 18%). ESI-MS m/z calc. 560.12, found 561.2

(M+1)$^+$; LC/MS retention time (Method C): 2.81 minutes. $^1$H NMR (400 MHz, DMSO-$d_6$) δ 10.57 (s, 1H), 8.54 (s, 1H), 8.53 (s, 1H), 7.76 (d, J=8.8 Hz, 1H), 7.50 (t, J=8.9 Hz, 1H), 7.05 (dd, J=9.1, 1.8 Hz, 1H), 6.85 (d, J=8.8 Hz, 1H), 3.87 (s, 3H), 2.49 (s, 3H), 2.28 (s, 3H), 2.15 (d, J=2.1 Hz, 3H) ppm.

Step 8: 4-[[6-[3-Fluoro-2-Methyl-4-(Trifluoromethoxy)Phenoxy]-2-Methyl-3-(Trifluoromethyl) Benzoyl]Amino]-5-Methyl-Pyridine-2-Carboxamide (288)

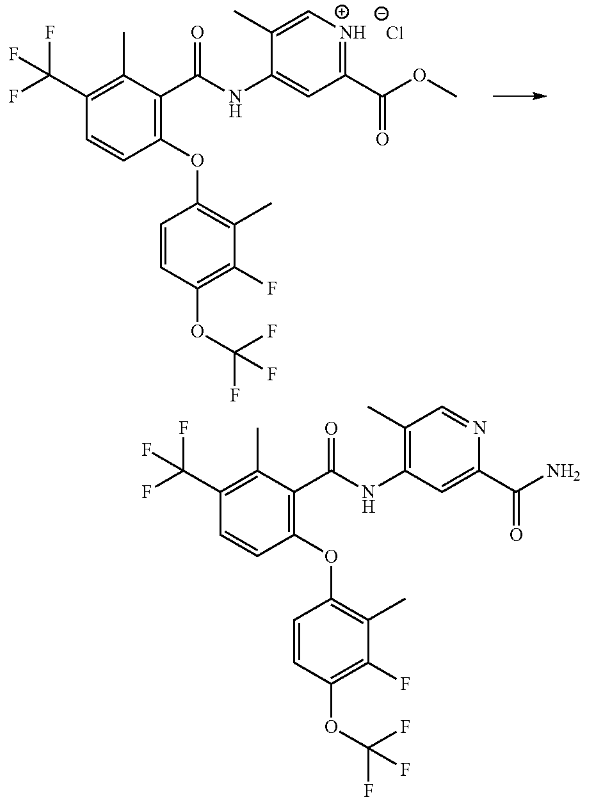

Methyl 4-[[6-[3-fluoro-2-methyl-4-(trifluoromethoxy) phenoxy]-2-methyl-3-(trifluoromethyl)benzoyl]amino]-5-methyl-pyridine-2-carboxylate (hydrochloride salt) (7.7 mg, 0.013 mmol) was dissolved in a solution of ammonia in methanol (2 mL of 7 M, 14 mmol) and stirred at 75° C. for 1 hour in a sealed vial, then at room temperature for 60 hours. Purification by reverse phase HPLC (10-99% acetonitrile/5 mM HCl) provided 4-[[6-[3-fluoro-2-methyl-4-(trifluoromethoxy)phenoxy]-2-methyl-3-(trifluoromethyl)benzoyl]amino]-5-methyl-pyridine-2-carboxamide (Hydrochloride salt) (6.0 mg, 80%). ESI-MS m z calc. 545.12, found 546.2 (M+1)$^+$; LC/MS retention time (Method C): 2.71 minutes. $^1$H NMR (400 MHz, DMSO-$d_6$) δ 10.54 (s, 1H), 8.48 (s, 1H), 8.46 (s, 1H), 8.07 (d, J=2.9 Hz, 1H), 7.75 (d, J=8.8 Hz, 1H), 7.61 (d, J=2.9 Hz, 1H), 7.51 (t, J=8.9 Hz, 1H), 7.06 (dd, J=9.1, 1.8 Hz, 1H), 6.84 (d, J=8.8 Hz, 1H), 2.49 (s, 3H), 2.27 (s, 3H), 2.15 (d, J=2.0 Hz, 3H) ppm.

Example 99

5-[[6-[3-Fluoro-2-Methyl-4-(Trifluoromethoxy)Phenoxy]-2-Methyl-3-(Trifluoromethyl)Benzoyl] Amino]Pyridine-2-Carboxamide (289)

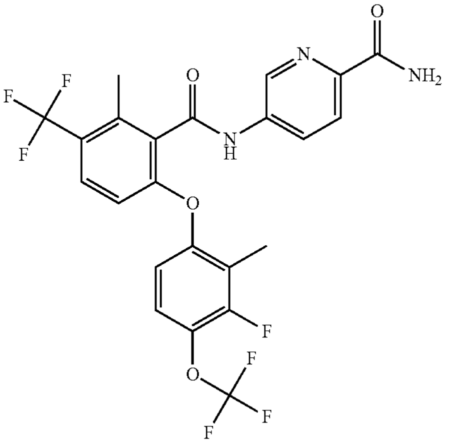 [SMILES: Cc1c(Oc2ccc(C(F)(F)F)c(C)c2C(=O)Nc2ccc(C(N)=O)nc2)ccc(OC(F)(F)F)c1F]

This compound was made in an analogous fashion to the synthesis of compound 288 in Example 98, except employing 5-aminopyridine-2-carboxamide in the amide formation step (Step 7). The yield of 5-[[6-[3-fluoro-2-methyl-4-(trifluoromethoxy)phenoxy]-2-methyl-3-(trifluoromethyl)benzoyl]amino]pyridine-2-carboxamide after purification was 48.5 mg (66%). ESI-MS m z calc. 531.10, found 532.1 (M+1)$^+$; LC/MS retention time (Method C): 2.72 minutes. $^1$H NMR (400 MHz, DMSO-$d_6$) δ 11.23 (s, 1H), 8.85 (d, J=2.4 Hz, 1H), 8.30 (dd, J=8.5, 2.5 Hz, 1H), 8.04 (d, J=8.5 Hz, 1H), 8.01 (s, 1H), 7.77 (d, J=8.9 Hz, 1H), 7.56 (s, 1H), 7.49 (t, J=8.9 Hz, 1H), 7.05 (dd, J=9.1, 1.8 Hz, 1H), 6.87 (d, J=8.8 Hz, 1H), 2.46 (s, 3H), 2.12 (d, J=2.1 Hz, 3H) ppm.

Example 100

4-[[6-[3-Fluoro-2-Methyl-4-(Trifluoromethoxy)Phenoxy]-2-Methyl-3-(Trifluoromethyl)Benzoyl] Amino]Pyridine-2-Carboxamide (290)

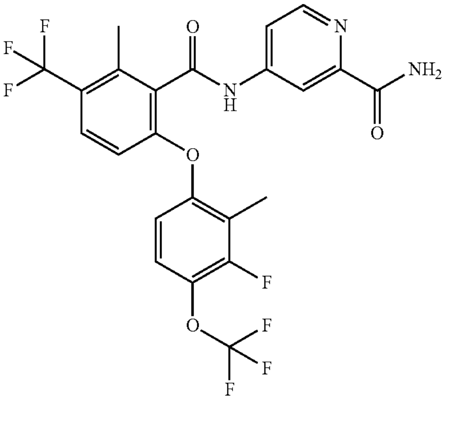 [SMILES: Cc1c(Oc2ccc(C(F)(F)F)c(C)c2C(=O)Nc2ccnc(C(N)=O)c2)ccc(OC(F)(F)F)c1F]

This compound was made in an analogous fashion to the synthesis of compound 288 in Example 98, except employing 4-aminopyridine-2-carboxamide in the amide formation step (Step 5). The yield of 4-[[6-[3-fluoro-2-methyl-4-(trifluoromethoxy)phenoxy]-2-methyl-3-(trifluoromethyl)benzoyl]amino]pyridine-2-carboxamide was 19.7 mg (27% yield). ESI-MS m z calc. 531.10, found 532.1 $(M+1)^+$; LC/MS retention time (Method C): 2.73 minutes. $^1H$ NMR (400 MHz, DMSO-$d_6$) δ 11.36 (s, 1H), 8.54 (d, J=5.5 Hz, 1H), 8.36 (d, J=2.1 Hz, 1H), 8.12 (s, 1H), 7.83 (dd, J=5.5, 2.2 Hz, 1H), 7.77 (d, J=8.9 Hz, 1H), 7.67 (s, 1H), 7.49 (t, J=8.9 Hz, 1H), 7.06 (dd, J=9.1, 1.8 Hz, 1H), 6.86 (d, J=8.8 Hz, 1H), 2.45 (s, 3H), 2.11 (d, J=2.0 Hz, 3H) ppm.

Example 101

4-[[2-Fluoro-6-[3-Fluoro-2-Methyl-4-(Trifluoromethoxy)Phenoxy]-3-(Trifluoromethyl)Benzoyl]Amino]-5-Methyl-Pyridine-2-Carboxamide (291)

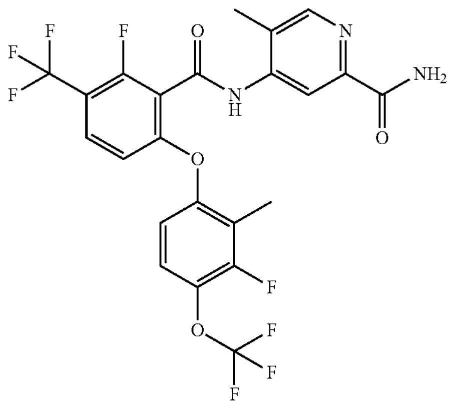 [SMILES: Cc1cnc(C(N)=O)cc1NC(=O)c1c(Oc2ccc(OC(F)(F)F)c(F)c2C)ccc(C(F)(F)F)c1F]

Step 1: 2-Fluoro-6-[3-Fluoro-2-Methyl-4-(Trifluoromethoxy)Phenoxy]-3-(Trifluoromethyl)Benzoic Acid

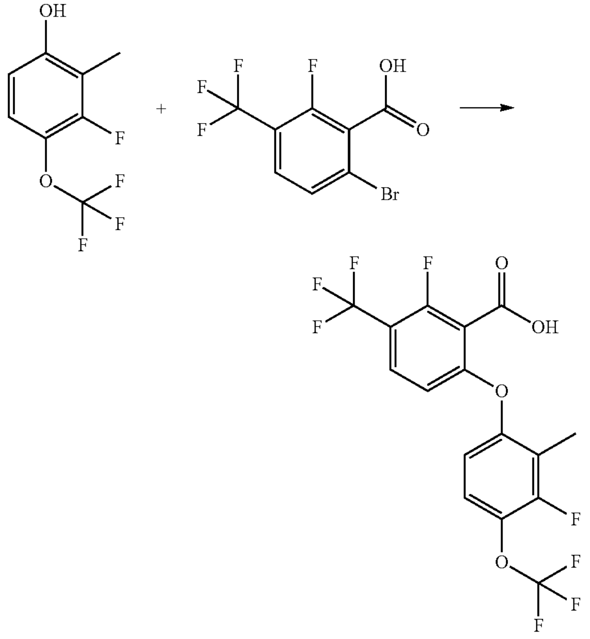

To a pressure flask was added 6-bromo-2-fluoro-3-(trifluoromethyl)benzoic acid (663 mg, 2.31 mmol), 3-fluoro-2-methyl-4-(trifluoromethoxy)phenol (450 mg, 2.14 mmol, see Example 98, Step 2), $Cs_2CO_3$ (1.07 g, 3.28 mmol) and toluene (15 mL). The mixture was bubbled with nitrogen for 10 minutes, then copper (I) iodide (420 mg, 2.21 mmol) added. The flask was flushed with nitrogen, capped and heated at 100° C. with vigorous stirring for 16 hours. The mixture was allowed to cool, and then diluted with ethyl acetate and water. The water layer was acidified with 1 M aqueous HCl and the product extracted with ethyl acetate (3×). The combined organic layers were washed with brine, dried over $Na_2SO_4$ and concentrated in vacuo. Purification by reverse phase HPLC (10-99% acetonitrile/5 mM HCl) provided 2-fluoro-6-[3-fluoro-2-methyl-4-(trifluoromethoxy)phenoxy]-3-(trifluoromethyl)benzoic acid (437 mg, 49%). ESI-MS m z calc. 416.03, found 417.1 $(M+1)^+$; LC/MS retention time (Method B): 1.92 minutes. $^1H$ NMR (400 MHz, DMSO-$d_6$) δ 14.22 (s, 1H), 7.81 (t, J=8.6 Hz, 1H), 7.50 (t, J=8.8 Hz, 1H), 7.06 (dd, J=9.2, 1.8 Hz, 1H), 6.85 (d, J=8.8 Hz, 1H), 2.15 (d, J=2.1 Hz, 3H) ppm.

Step 2: Methyl 4-[[2-Fluoro-6-[3-Fluoro-2-Methyl-4-(Trifluoromethoxy)Phenoxy]-3-(Trifluoromethyl)Benzoyl]Amino]-5-Methyl-Pyridine-2-Carboxylate

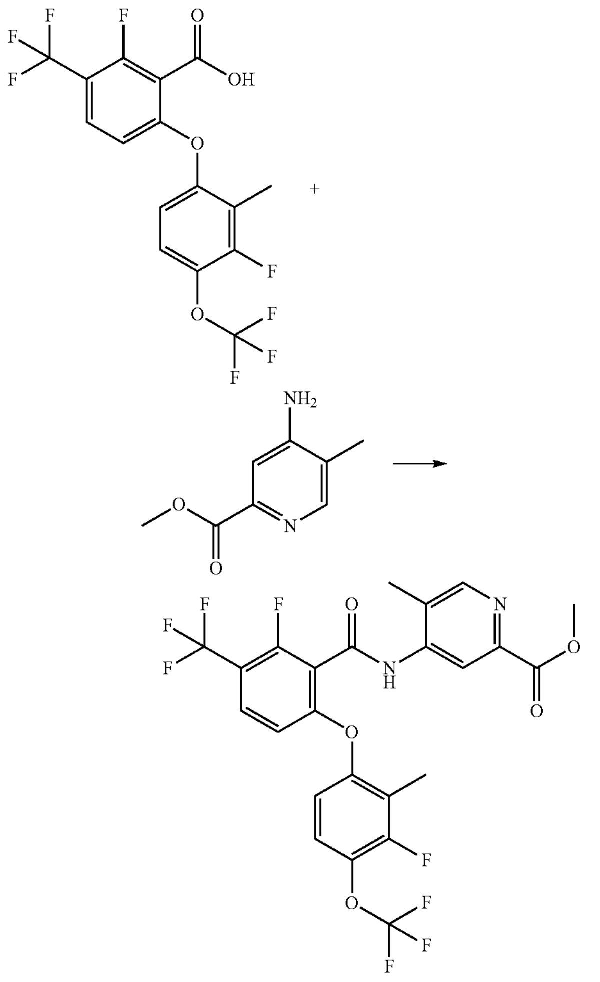

A solution of 2-fluoro-6-[3-fluoro-2-methyl-4-(trifluoromethoxy)phenoxy]-3-(trifluoromethyl)benzoic acid (40 mg, 0.096 mmol), DMF (0.6 μL, 0.007 mmol) and dichloromethane (0.5 mL) was cooled to 0° C. in an ice bath. To this solution was added oxalyl chloride (17 μL, 0.19 mmol). The resulting mixture was stirred in the ice bath for 10 minutes and then at room temperature for 50 minutes. The mixture was concentrated in vacuo. The resulting acid chloride was dissolved in NMP (0.4 mL) and slowly added to a solution of methyl 4-amino-5-methyl-pyridine-2-carboxylate (48 mg, 0.29 mmol, Preparation 1), DIEA (100 μL, 0.58 mmol) and NMP (0.2 mL). The mixture was allowed to warm to room temperature and stirred for 16 hours at room temperature. The mixture was filtered and purified by reverse phase HPLC (acetonitrile/5 mM HCl gradient) to provide methyl 4-[[2-fluoro-6-[3-fluoro-2-methyl-4-(trifluoromethoxy)phenoxy]-3-(trifluoromethyl)benzoyl]amino]-5-methyl-pyridine-2-carboxylate (28 mg, 52%). ESI-MS m z calc. 564.09, found 565.2 $(M+1)^+$; LC/MS retention time (Method B): 1.94 minutes. $^1H$ NMR (400 MHz, DMSO-$d_6$) δ 10.70 (s, 1H), 8.56 (s, 1H), 8.49 (s, 1H), 7.87 (t, J=8.6 Hz, 1H), 7.53 (t, J=8.9 Hz, 1H), 7.13 (d, J=9.3 Hz, 1H), 6.87 (d, J=8.9 Hz, 1H), 3.88 (s, 3H), 2.30 (s, 3H), 2.16 (d, J=2.1 Hz, 3H) ppm.

Step 3: 4-[[2-Fluoro-6-[3-Fluoro-2-Methyl-4-(Trifluoromethoxy)Phenoxy]-3-(Trifluoromethyl)Benzoyl]Amino]-5-Methyl-Pyridine-2-Carboxamide (291)

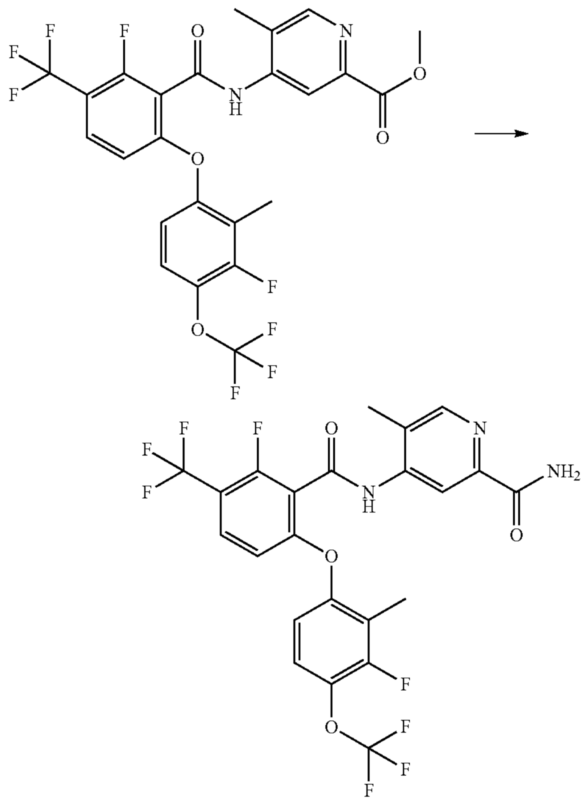

Methyl 4-[[2-fluoro-6-[3-fluoro-2-methyl-4-(trifluoromethoxy)phenoxy]-3-(trifluoromethyl)benzoyl]amino]-5-methyl-pyridine-2-carboxylate (20 mg, 0.03544 mmol) was dissolved in a solution of ammonia in methanol (3 mL of 7 M, 21 mmol) and stirred at room temperature for 48 hours. The solvent was removed in vacuo and the residue was purified by reverse phase HPLC (acetonitrile/5 mM HCl gradient). Additional purification by SFC ([R, R]-Whelk-O (150×2.1 mm) column; eluting with 8% methanol (20 mM ammonia)/92% $CO_2$) provided 4-[[2-fluoro-6-[3-fluoro-2-methyl-4-(trifluoromethoxy)phenoxy]-3-(trifluoromethyl)benzoyl]amino]-5-methyl-pyridine-2-carboxamide (5.6 mg, 29%). ESI-MS m z calc. 549.09, found 550.1 $(M+1)^+$; LC/MS retention time (Method B): 1.35 minutes. $^1H$ NMR (400 MHz, DMSO-$d_6$) δ 10.69 (s, 1H), 8.48 (s, 2H), 8.09 (s, 1H), 7.86 (t, J=8.6 Hz, 1H), 7.63 (s, 1H), 7.55 (t, J=8.8 Hz, 1H), 7.16 (d, J=9.1 Hz, 1H), 6.86 (d, J=8.9 Hz, 1H), 2.30 (s, 3H), 2.17 (d, J=2.1 Hz, 3H) ppm.

Example 102

5-[[2-Fluoro-6-[3-Fluoro-2-Methyl-4-(Trifluoromethoxy)Phenoxy]-3-(Trifluoromethyl)Benzoyl]Amino]Pyridine-2-Carboxamide (292)

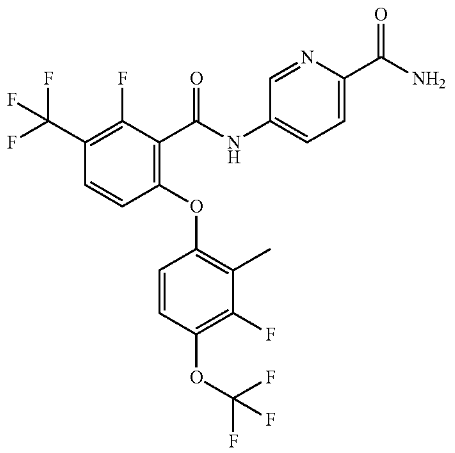 [SMILES: Cc1c(Oc2ccc(C(F)(F)F)c(F)c2C(=O)Nc2ccc(C(N)=O)nc2)ccc(OC(F)(F)F)c1F]

This compound was made in an analogous fashion to the synthesis of compound 288 in Example 98, except employing 5-aminopyridine-2-carboxamide in the amide formation step (Step 7). The yield of 5-[[2-fluoro-6-[3-fluoro-2-methyl-4-(trifluoromethoxy)phenoxy]-3-(trifluoromethyl)benzoyl]amino]pyridine-2-carboxamide was 33.8 mg (66% yield). ESI-MS m z calc. 535.08, found 536.3 $(M+1)^+$; LC/MS retention time (Method B): 1.87 minutes. $^1H$ NMR (400 MHz, DMSO-$d_6$) δ 11.42 (s, 1H), 8.83 (d, J=2.4 Hz, 1H), 8.27 (dd, J=8.6, 2.5 Hz, 1H), 8.09-8.00 (m, 2H), 7.88 (t, J=8.7 Hz, 1H), 7.58 (d, J=2.8 Hz, 1H), 7.52 (t, J=8.8 Hz, 1H), 7.13 (dd, J=9.1, 1.8 Hz, 1H), 6.91 (d, J=8.9 Hz, 1H), 2.14 (d, J=2.1 Hz, 3H) ppm.

Example 103

4-[[2-Fluoro-6-[3-Fluoro-2-Methyl-4-(Trifluoromethoxy)Phenoxy]-3-(Trifluoromethyl)Benzoyl]Amino]Pyridine-2-Carboxamide (293)

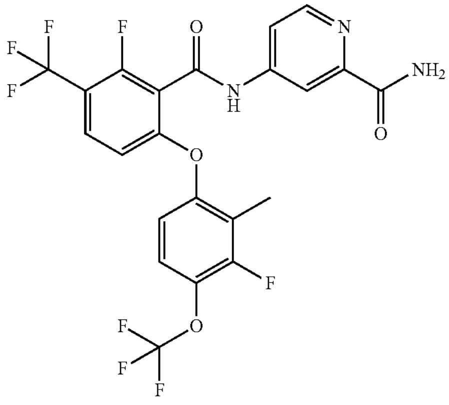 [SMILES: Cc1c(Oc2ccc(C(F)(F)F)c(F)c2C(=O)Nc2ccnc(C(N)=O)c2)ccc(OC(F)(F)F)c1F]

A mixture of methyl 4-[[2,6-difluoro-3-(trifluoromethyl)benzoyl]amino]pyridine-2-carboxylate (100 mg, 0.278 mmol, see US 2019/0016671, Example 169, Step 3, which is incorporated by reference), 3-fluoro-2-methyl-4-(trifluoromethoxy)phenol (56 mg, 0.27 mmol, see Example 98, Step 2) and $Cs_2CO_3$ (142 mg, 0.4358 mmol) in DMF (3 mL) and stirred overnight at 70° C. The mixture was partitioned between ethyl acetate and brine and the layers separated. The organic layer was washed with brine, dried over $MgSO_4$, filtered and concentrated in vacuo. Purification by reverse phase HPLC (47-95% acetonitrile/0.1% ammonium hydroxide) provided methyl 4-[[2-fluoro-6-[3-fluoro-2-methyl-4-(trifluoromethoxy)phenoxy]-3-(trifluoromethyl)benzoyl]amino]pyridine-2-carboxylate. The material was dissolved in a solution of ammonia in methanol (2 mL of 7 M, 14 mmol) and stirred overnight at room temperature. The mixture was concentrated in vacuo to provide 4-[[2-fluoro-6-[3-fluoro-2-methyl-4-(trifluoromethoxy)phenoxy]-3-(trifluoromethyl)benzoyl]amino]pyridine-2-carboxamide (32.7 mg, 22%). ESI-MS m z calc. 535.08, found 536.1 $(M+1)^+$; 534.2 $(M-1)^-$; LC/MS retention time (Method E): 3.39 minutes. $^{1}$H NMR (400 MHz, $CDCl_3$) δ 10.28 (s, 1H), 8.60-8.51 (m, 2H), 8.30-8.24 (m, 1H), 7.89 (d, J=4.6 Hz, 1H), 7.66 (t, J=8.3 Hz, 1H), 7.16 (t, J=8.7 Hz, 1H), 6.91 (dd, J=9.0, 1.9 Hz, 1H), 6.64 (d, J=8.8 Hz, 1H), 4.92 (d, J=4.6 Hz, 1H), 2.18 (d, J=2.1 Hz, 3H) ppm.

Example 104

4-[[2-Fluoro-6-[3-Fluoro-2-Methyl-4-(Trifluoromethoxy)Phenoxy]-3-(Trifluoromethoxy)Benzoyl]Amino]Pyridine-2-Carboxamide (294)

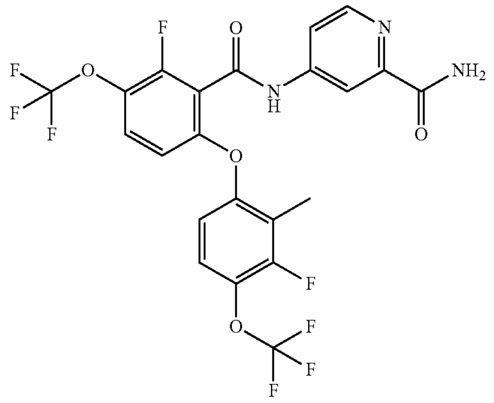 [SMILES: Cc1c(Oc2ccc(OC(F)(F)F)c(F)c2C(=O)Nc2ccnc(C(N)=O)c2)ccc(OC(F)(F)F)c1F]

Step 1: 2-Fluoro-6-[3-Fluoro-2-Methyl-4-(Trifluoromethoxy)Phenoxy]-3-(Trifluoromethoxy)Benzoic Acid

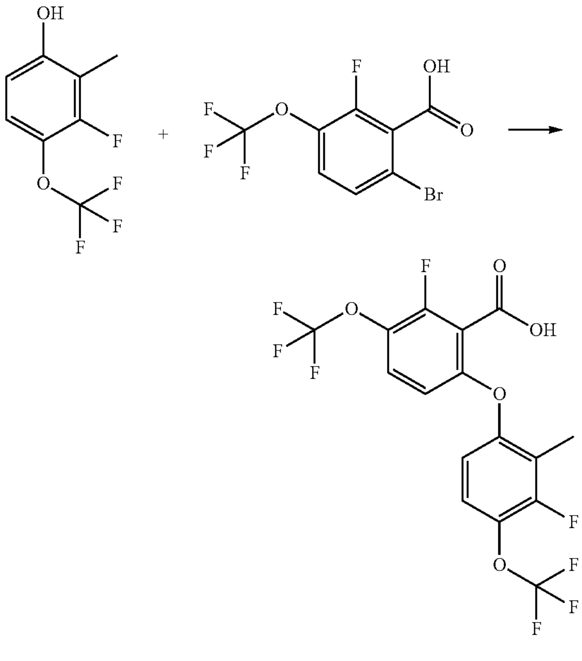

A mixture of 3-fluoro-2-methyl-4-(trifluoromethoxy)phenol (690 mg, 2.79 mmol, see Example 98, Step 2), 6-bromo-2-fluoro-3-(trifluoromethoxy)benzoic acid (702 mg, 2.32 mmol, see Example 90, Step 1) and $Cs_2CO_3$ (1.8 g, 5.5 mmol) in toluene (12 mL) was heated at 100° C. for 10 minutes, then treated with copper (I) iodide (90 mg, 0.47 mmol) and stirred at 100° C. for 1 hour. The mixture was acidified with 2 M aqueous HCl and partitioned between ethyl acetate and water. The organic layer was washed with brine, dried over $MgSO_4$, filtered and concentrated in vacuo to provide crude 2-fluoro-6-[3-fluoro-2-methyl-4-(trifluoromethoxy)phenoxy]-3-(trifluoromethoxy)benzoic acid (1.14 g, 114%). ESI-MS m z calc. 432.02, no ionization observed; LC/MS retention time (Method F): 0.63 minutes. $^1$H NMR (400 MHz, $CDCl_3$) δ 7.37 (ddq, J=9.4, 8.2, 1.2 Hz, 1H), 7.22-7.14 (m, 1H), 6.78 (dd, J=9.0, 2.0 Hz, 1H), 6.58 (dd, J=9.2, 1.9 Hz, 1H), 2.24 (d, J=2.2 Hz, 3H) ppm. The isolated product was used without further purification.

Step 2: 4-[[2-Fluoro-6-[3-Fluoro-2-Methyl-4-(Trifluoromethoxy)Phenoxy]-3-(Trifluoromethoxy)Benzoyl]Amino]Pyridine-2-Carboxamide (294)

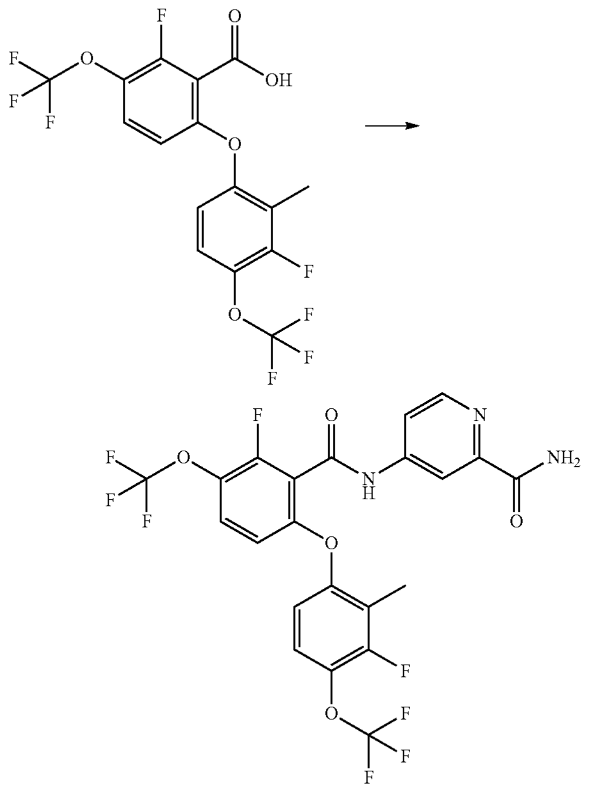

A mixture of 2-fluoro-6-[3-fluoro-2-methyl-4-(trifluoromethoxy)phenoxy]-3-(trifluoromethoxy)benzoic acid (200 mg, 0.463 mmol) and DMF (3.5 μL, 0.045 mmol) in dichloromethane (3 mL) at 0° C. was treated dropwise with oxalyl chloride (170 μL, 1.95 mmol). The mixture was stirred for 1 hour, and then concentrated in vacuo. The residue was redissolved in dichloromethane (3 mL) and added dropwise to a stirring solution of methyl 4-aminopyridine-2-carboxylate (82 mg, 0.51 mmol), DIPEA (250 μL, 1.44 mmol) and DMAP (57 mg, 0.47 mmol) in dichloromethane (3 mL). The mixture was stirred overnight and concentrated in vacuo. The residue was dissolved in a solution of ammonia in methanol (7 M) and stirred for 3 days. The mixture was concentrated and purified by HPLC (47-95% acetonitrile/0.1% ammonium hydroxide) to provide 4-[[2-fluoro-6-[3-fluoro-2-methyl-4-(trifluoromethoxy)phenoxy]-3-(trifluoromethoxy)benzoyl]amino]pyridine-2-carboxamide (28.0 mg, 11%). ESI-MS m z calc. 551.07, found 552.1 $(M+1)^+$; 550.1 $(M-1)^-$; LC/MS retention time (Method F): 0.96 minutes. $^1$H NMR (400 MHz, DMSO-$d_6$) δ 11.46 (s, 1H), 8.55 (dd, J=5.4, 0.6 Hz, 1H), 8.30-8.25 (m, 1H), 8.10 (d, J=2.9 Hz, 1H), 7.82-7.63 (m, 3H), 7.47 (t, J=8.8 Hz, 1H), 7.03 (dd, J=9.1, 1.8 Hz, 1H), 6.93 (dd, J=9.2, 1.6 Hz, 1H), 2.15 (d, J=2.1 Hz, 3H) ppm.

Example 105

4-[[3-Chloro-2-Fluoro-6-[3-Fluoro-2-Methyl-4-(Trifluoromethoxy)Phenoxy]Benzoyl]Amino]Pyridine-2-Carboxamide (295)

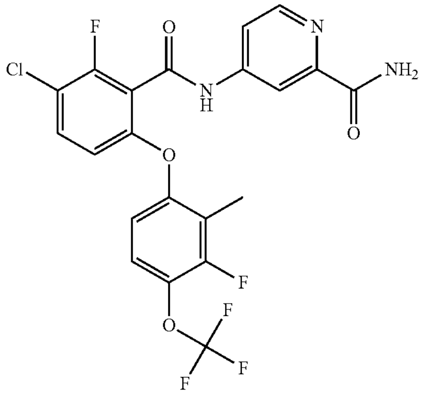 [SMILES: Cc1c(Oc2ccc(Cl)c(F)c2C(=O)Nc2ccnc(C(N)=O)c2)ccc(OC(F)(F)F)c1F]

Step 1: 3-Chloro-2-Fluoro-6-[3-Fluoro-2-Methyl-4-(Trifluoromethoxy)Phenoxy]Benzoic Acid

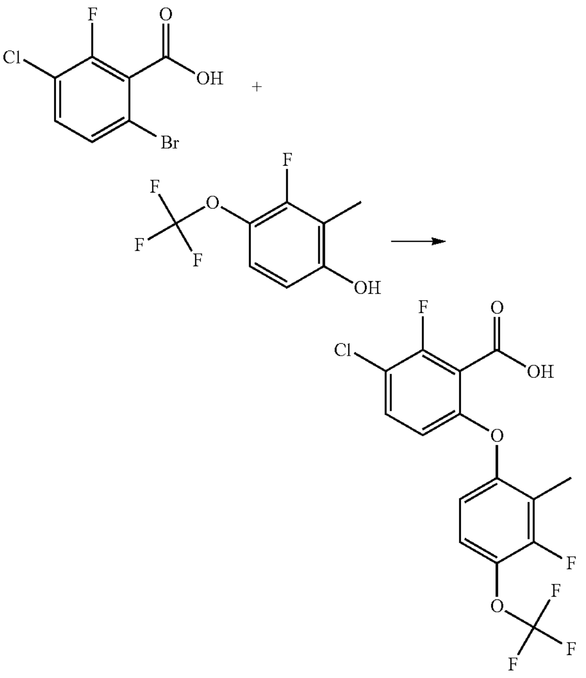

A mixture of 6-bromo-3-chloro-2-fluoro-benzoic acid (1000 mg, 3.946 mmol, see Example 96, step 1), 3-fluoro-2-methyl-4-(trifluoromethoxy)phenol (862 mg, 4.10 mmol, see Example 98, Step 2) and $Cs_2CO_3$ (1.49 g, 4.57 mmol) in toluene (15 mL) was stirred for 10 minutes then treated with copper (I) iodide (290 mg, 1.52 mmol). The mixture was heated at 100° C. with vigorous stirring overnight. The mixture was cooled, acidified with 2 M aqueous HCl and filtered and partitioned with ethyl acetate. The organic layer was washed with brine, dried over $MgSO_4$, filtered and concentrated to provide 3-chloro-2-fluoro-6-[3-fluoro-2-methyl-4-(trifluoromethoxy)phenoxy]benzoic acid (1.5 g, 86%). $^1$H NMR (400 MHz, $CDCl_3$) δ 9.90 (s, 1H), 7.44 (dd, J=9.0, 8.0 Hz, 1H), 7.22-7.13 (m, 1H, obscured by residual toluene), 6.76 (dd, J=9.0, 1.9 Hz, 1H), 6.56 (dd, J=9.0, 1.6 Hz, 1H), 2.23 (d, J=2.2 Hz, 3H) ppm.

Step 2: 4-[[3-Chloro-2-Fluoro-6-[3-Fluoro-2-Methyl-4-(Trifluoromethoxy)Phenoxy]Benzoyl]Amino]Pyridine-2-Carboxamide (295)

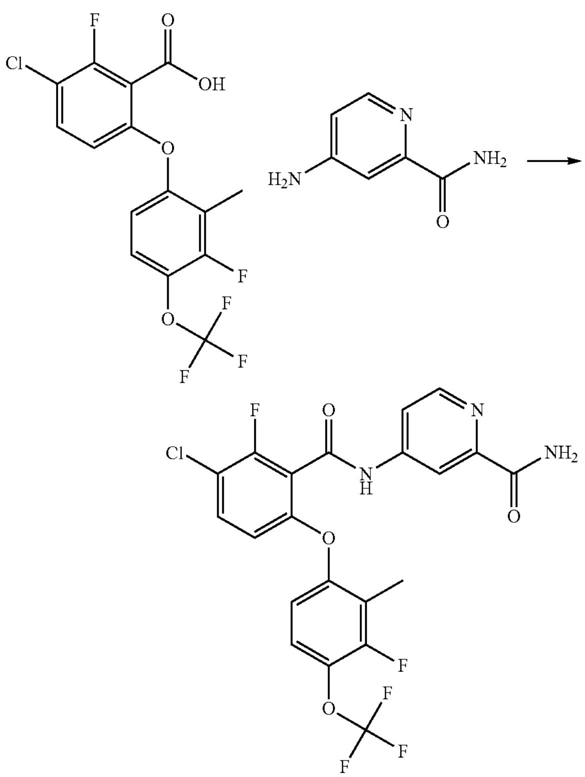

A solution of 3-chloro-2-fluoro-6-[3-fluoro-2-methyl-4-(trifluoromethoxy)phenoxy]benzoic acid (200 mg, 0.418 mmol) and DMF (33 μL, 0.43 mmol) in dichloromethane (3 mL) at 0° C. was treated dropwise with oxalyl chloride (150 μL, 1.720 mmol). The mixture was stirred for 1 hour and concentrated in vacuo. The residue was redissolved in dichloromethane (3 mL) and added dropwise to a stirring solution of methyl 4-aminopyridine-2-carboxylate (75 mg, 0.47 mmol), DIPEA (230 μL, 1.32 mmol) and DMAP (52 mg, 0.43 mmol) in dichloromethane (3 mL). The mixture was stirred overnight then concentrated. The residue was dissolved in dichloromethane (3 mL) and treated with a solution of ammonia in methanol (7 M). The mixture was stirred for three days, then concentrated and purified by reverse phase HPLC (47-95% acetonitrile/0.1% ammonium hydroxide) to provide 4-[[3-chloro-2-fluoro-6-[3-fluoro-2-methyl-4-(trifluoromethoxy)phenoxy]benzoyl]amino]pyridine-2-carboxamide (32.5 mg, 15%). ESI-MS m z calc. 501.05, found 502.1 $(M+1)^+$; 500.1 $(M-1)^-$; LC/MS retention time (Method F): 0.92 minutes. $^1$H NMR (400 MHz, $CDCl_3$) δ 9.90 (s, 1H), 8.58-8.48 (m, 2H), 8.24 (d, J=2.4 Hz, 1H), 7.93 (d, J=4.6 Hz, 1H), 7.47 (dd, J=9.0, 8.0 Hz, 1H), 7.12 (t, J=8.6 Hz, 1H), 6.81 (dd, J=9.0, 1.9 Hz, 1H), 6.62 (dd, J=8.9, 1.5 Hz, 1H), 5.09 (d, J=4.6 Hz, 1H), 2.18 (d, J=2.2 Hz, 3H) ppm.

Example 106

4-[[6-[2-Chloro-3-Fluoro-4-(Trifluoromethoxy)Phenoxy]-2-Fluoro-3-(Trifluoromethyl)Benzoyl]Amino]-5-Methyl-Pyridine-2-Carboxamide (296)

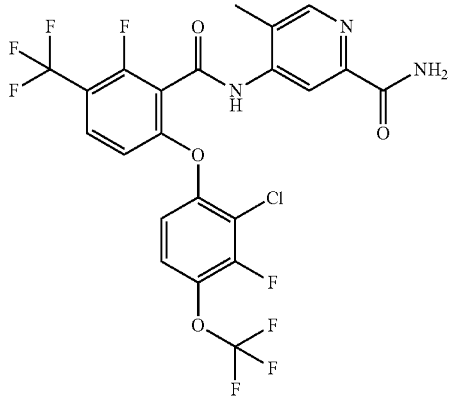

Step 1: 2-[3-Fluoro-4-(Trifluoromethoxy)Phenoxy]Tetrahydropyran

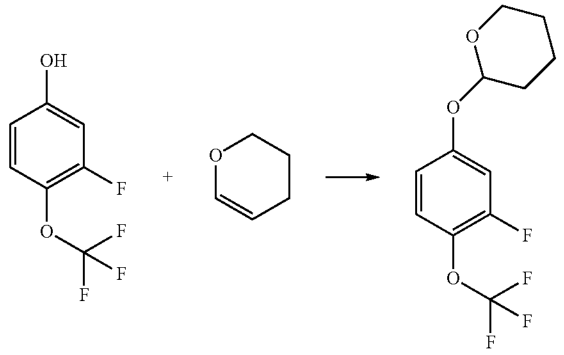 [SMILES: Oc1ccc(OC(F)(F)F)c(F)c1 ; C1=COCCC1 ; Fc1cc(OC2CCCCO2)ccc1OC(F)(F)F]

To a stirring solution of 3-fluoro-4-(trifluoromethoxy)phenol (10.0 g, 51.0 mmol) and concentrated HCl (43 μL of 12 M, 0.52 mmol) and dichloromethane (150 mL) was added a solution of 3,4-dihydro-2H-pyran (7.0 mL, 76.7 mmol) in dichloromethane (40 mL) dropwise. The mixture was stirred at room temperature for 2 hours, and then washed with 1 M aqueous NaOH (2×). The organic layer was dried over $MgSO_4$, filtered and concentrated in vacuo. Silica gel chromatography (0-20% ethyl acetate/hexanes gradient) provided 2-[3-fluoro-4-(trifluoromethoxy)phenoxy]tetrahydropyran (10.4 g, 73%) as a colorless oil. $^1$H NMR (400 MHz, $CDCl_3$) δ 7.19 (td, J=8.8, 1.2 Hz, 1H), 6.92 (dd, J=11.8, 2.8 Hz, 1H), 6.81 (ddd, J=9.1, 2.9, 1.6 Hz, 1H), 5.37 (t, J=3.2 Hz, 1H), 3.85 (ddd, J=11.3, 9.9, 3.1 Hz, 1H), 3.62 (dtd, J=11.4, 4.1, 1.4 Hz, 1H), 2.04-1.91 (m, 1H), 1.89-1.83 (m, 2H), 1.77-1.55 (m, 3H) ppm.

Step 2: 2-[2-Chloro-3-Fluoro-4-(Trifluoromethoxy) Phenoxy]Tetrahydropyran

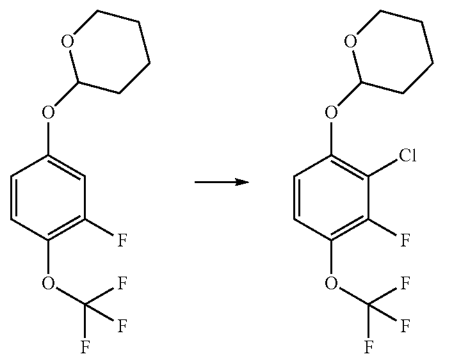 [SMILES: Fc1cc(OC2CCCCO2)ccc1OC(F)(F)F ; Fc1c(OC(F)(F)F)ccc(OC2CCCCO2)c1Cl]

A solution of 2-[3-fluoro-4-(trifluoromethoxy)phenoxy] tetrahydropyran (3.0 g, 10.7 mmol) in THF (48 mL) was cooled to −78° C. To this solution was added a solution of (diisopropylamino)lithium (7.0 mL of 2.0 M in THF/heptane/ethylbenzene, 14.0 mmol) over 5 minutes. After stirring for 1 hour at −78° C., a suspension of N-chlorosuccinimide (2.15 g, 16.1 mmol) in THF (1 mL) was added dropwise. The resulting mixture was stirred at −78° C. for 30 minutes then slowly warmed up to room temperature. The mixture was stirred at room temperature for 16 hours, and then diluted with saturated aqueous $NH_4Cl$ solution. The layers were separated and the aqueous layer was extracted with diethyl ether (3×). The combined organic layers were dried over $Na_2SO_4$, filtered and concentrated in vacuo. Silica gel chromatography (ethyl acetate/hexanes gradient) provided a colorless oil, which was further purified by reverse phase HPLC (acetonitrile/water gradient) to provide 2-[2-chloro-3-fluoro-4-(trifluoromethoxy)phenoxy]tetrahydropyran (1.0 g, 30%) as a colorless oil. $^1H$ NMR (400 MHz, $CDCl_3$) δ 7.15 (ddd, J=9.4, 8.2, 1.3 Hz, 1H), 6.98 (dd, J=9.4, 2.1 Hz, 1H), 5.51 (t, J=2.8 Hz, 1H), 3.84 (td, J=11.0, 3.0 Hz, 1H), 3.67-3.60 (m, 1H), 2.14-1.94 (m, 2H), 1.95-1.83 (m, 1H), 1.80-1.58 (m, 3H) ppm.

Step 3: 2-Chloro-3-Fluoro-4-(Trifluoromethoxy)Phenol

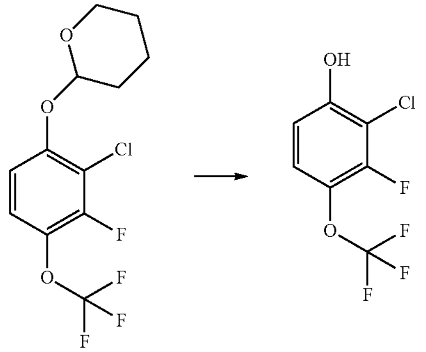 [SMILES: Fc1c(OC(F)(F)F)ccc(OC2CCCCO2)c1Cl ; Oc1ccc(OC(F)(F)F)c(F)c1Cl]

2-[2-Chloro-3-fluoro-4-(trifluoromethoxy)phenoxy]tetrahydropyran (2.5 g, 7.9 mmol) was dissolved in a solution of HCl in dioxane (40 mL of 4.0 M, 160 mmol). The resulting mixture was stirred at room temperature for 16 hours. The mixture was concentrated in vacuo. The residue was treated with 2 M aqueous NaOH (pH~10) and washed with diethyl ether. The aqueous layer was acidified with 1 M aqueous HCl and extracted with diethyl ether (3×). The combined organic layers were dried over $MgSO_4$, filtered and concentrated in vacuo to provide 2-chloro-3-fluoro-4-(trifluoromethoxy)phenol (1.7 g, 93%) as a colorless oil. $^1H$ NMR (400 MHz, $CDCl_3$) δ 7.16 (ddd, J=9.3, 8.0, 1.1 Hz, 1H), 6.84 (dd, J=9.2, 2.2 Hz, 1H), 5.67 (s, 1H) ppm.

Step 4: 6-[2-Chloro-3-Fluoro-4-(Trifluoromethoxy) Phenoxy]-2-Fluoro-3-(Trifluoromethyl)Benzoic Acid

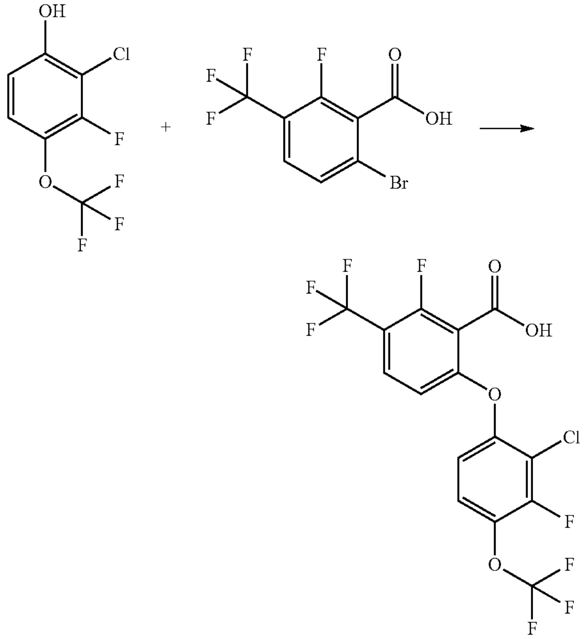

To a pressure flask was added 6-bromo-2-fluoro-3-(trifluoromethyl)benzoic acid (818 mg, 2.85 mmol), 2-chloro-3-fluoro-4-(trifluoromethoxy)phenol (610 mg, 2.65 mmol), $Cs_2CO_3$ (1.3 g, 4.0 mmol) and toluene (20 mL). The mixture was bubbled with nitrogen for 10 minutes, then copper (I) iodide (520 mg, 2.73 mmol) added. The flask was flushed with nitrogen, capped and heated at 100° C. with vigorous stirring for 16 hours. The mixture was allowed to cool, and then partitioned between water and ethyl acetate and the layers separated. The water layer was acidified with 1 M aqueous HCl and the product extracted into ethyl acetate (3×). The combined organic layers were washed with brine, dried over $Na_2SO_4$ and concentrated in vacuo. Purification by reverse phase HPLC (acetonitrile/water gradient) provided 6-[2-chloro-3-fluoro-4-(trifluoromethoxy)phenoxy]-2-fluoro-3-(trifluoromethyl)benzoic acid (724 mg, 63%). $^1H$ NMR (400 MHz, DMSO-$d_6$) δ 14.26 (s, 1H), 7.86 (t, J=8.6 Hz, 1H), 7.69 (t, J=8.8 Hz, 1H), 7.25 (dd, J=9.3, 2.1 Hz, 1H), 7.03 (d, J=8.8 Hz, 1H) ppm.

Step 5: Methyl 4-[[6-[2-Chloro-3-Fluoro-4-(Trifluoromethoxy)Phenoxy]-2-Fluoro-3-(Trifluoromethyl) Benzoyl]Amino]-5-Methyl-Pyridine-2-Carboxylate

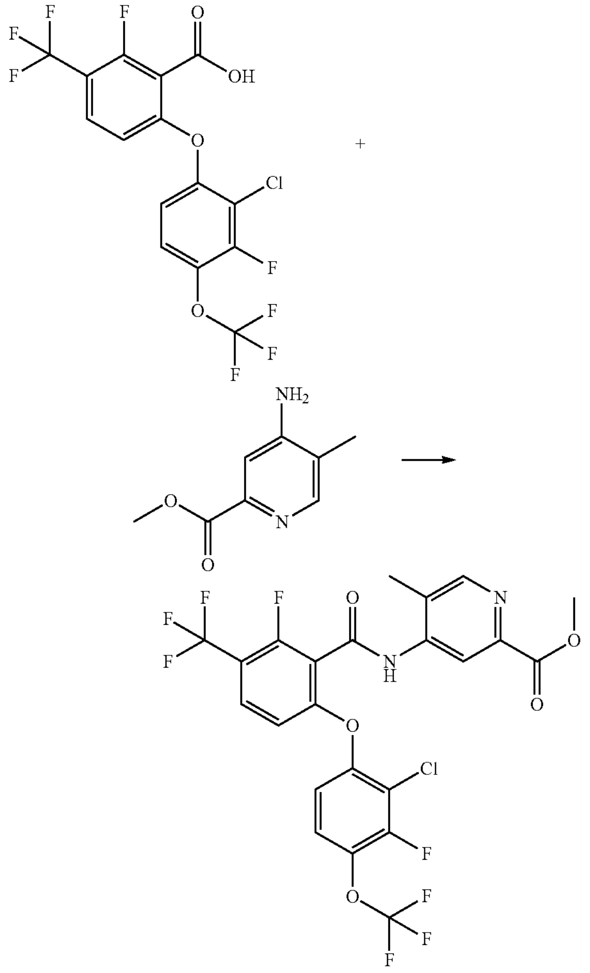

A solution of 6-[2-chloro-3-fluoro-4-(trifluoromethoxy) phenoxy]-2-fluoro-3-(trifluoromethyl)benzoic acid (40 mg, 0.092 mmol), DMF (0.2 μL, 0.002 mmol) and dichloromethane (0.4 mL) was cooled to 0° C. in an ice bath. To this solution was added oxalyl chloride (5.3 μL, 0.061 mmol). The resulting mixture was stirred at room temperature for 20 minutes then concentrated in vacuo. The resulting acid chloride was dissolved in NMP (400 μL) and slowly added to a solution of methyl 4-amino-5-methyl-pyridine-2-carboxylate (46 mg, 0.27 mmol, Preparation 1) and DIEA (10.6 μL, 0.061 mmol) in NMP (200 μL) at 0° C. The mixture was allowed to warm to room temperature and stirred for 16 hours. Purification by reverse phase HPLC (acetonitrile/5 mM HCl gradient) provided methyl 4-[[6-[2-chloro-3-fluoro-4-(trifluoromethoxy)phenoxy]-2-fluoro-3-(trifluoromethyl)benzoyl]amino]-5-methyl-pyridine-2-carboxylate (34 mg, 63%). ESI-MS m z calc. 584.04, found 585.1 $(M+1)^+$; LC/MS retention time (Method B): 1.45 minutes. $^1H$ NMR (400 MHz, DMSO-$d_6$) δ 10.71 (s, 1H), 8.57 (s, 1H), 8.47 (s, 1H), 7.91 (t, J=8.6 Hz, 1H), 7.73 (t, J=8.8 Hz, 1H), 7.34 (dd, J=9.3, 2.0 Hz, 1H), 7.07 (d, J=8.8 Hz, 1H), 3.88 (s, 3H), 2.31 (s, 3H) ppm.

Step 6: 4-[[6-[2-Chloro-3-Fluoro-4-(Trifluoromethoxy)Phenoxy]-2-Fluoro-3-(Trifluoromethyl) Benzoyl]Amino]-5-Methyl-Pyridine-2-Carboxamide (296)

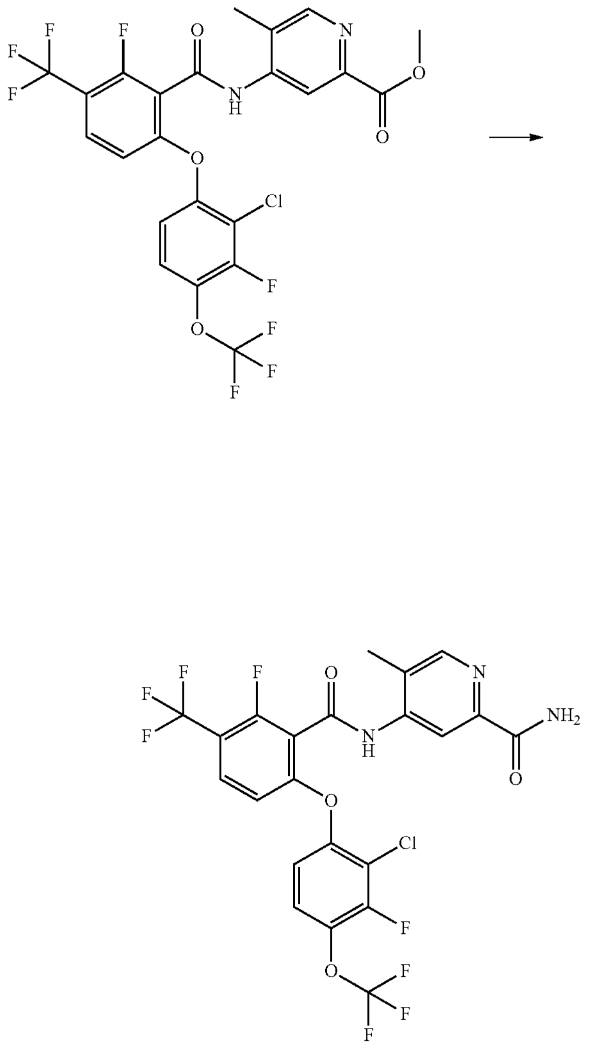

To a suspension of methyl 4-[[6-[2-chloro-3-fluoro-4-(trifluoromethoxy)phenoxy]-2-fluoro-3-(trifluoromethyl) benzoyl]amino]-5-methyl-pyridine-2-carboxylate (30 mg, 0.05 mmol) in methanol (0.5 mL) was added a solution ammonia in methanol (2 mL of 7 M, 14 mmol). The mixture was stirred for 24 hours, and then concentrated in vacuo. The residue was purified by reverse phase HPLC (30-99% acetonitrile/5 mM HCl), followed by SFC purification ([R, R]-Whelk-O column, eluting with 10% methanol (20 mM ammonia), 90% $CO_2$) to provide 4-[[6-[2-chloro-3-fluoro-4-(trifluoromethoxy)phenoxy]-2-fluoro-3-(trifluoromethyl) benzoyl]amino]-5-methyl-pyridine-2-carboxamide (12.9 mg, 44%) as a white solid. ESI-MS m z calc. 569.04, found 570.0 $(M+1)^+$; LC/MS retention time (Method B): 1.22 minutes. $^1H$ NMR (400 MHz, DMSO-$d_6$) δ 10.67 (s, 1H), 8.46 (d, J=18.0 Hz, 2H), 8.07 (d, J=2.7 Hz, 1H), 7.90 (t, J=8.6 Hz, 1H), 7.74 (t, J=8.9 Hz, 1H), 7.64-7.59 (m, 1H), 7.35 (dd, J=9.4, 2.0 Hz, 1H), 7.05 (d, J=8.8 Hz, 1H), 2.29 (s, 3H) ppm.

Example 107

5-[[6-[2-Chloro-3-Fluoro-4-(Trifluoromethoxy)Phenoxy]-2-Fluoro-3-(Trifluoromethyl)Benzoyl]Amino] Pyridine-2-Carboxamide (297)

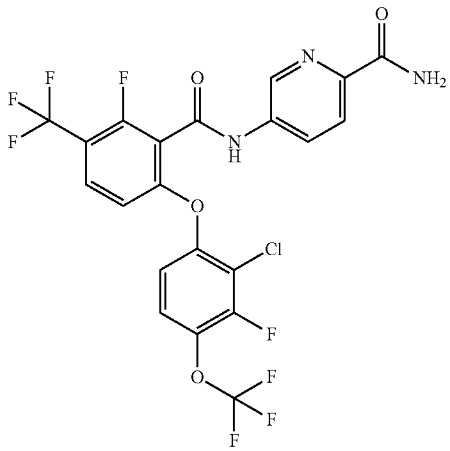

This compound was made in an analogous fashion to the synthesis of compound 296 in Example 106, except employing 5-aminopyridine-2-carboxamide in Step 5. The yield of 5-[[2-fluoro-6-[3-fluoro-2-methyl-4-(trifluoromethoxy)phenoxy]-3-(trifluoromethyl)benzoyl]amino]pyridine-2-carboxamide was 36.5 mg (70% yield). ESI-MS m z calc. 555.02, found 556.1 $(M+1)^+$; LC/MS retention time (Method B): 1.40 minutes. $^1H$ NMR (400 MHz, DMSO-$d_6$) δ 11.46 (s, 1H), 8.83 (d, J=2.4 Hz, 1H), 8.27 (dd, J=8.6, 2.5 Hz, 1H), 8.09-8.01 (m, 2H), 7.92 (t, J=8.6 Hz, 1H), 7.72 (t, J=8.8 Hz, 1H), 7.58 (s, 1H), 7.35 (dd, J=9.3, 2.0 Hz, 1H), 7.08 (d, J=8.8 Hz, 1H) ppm.

Example 108

4-[[6-[2-Chloro-3-Fluoro-4-(Trifluoromethoxy)Phenoxy]-2-Fluoro-3-(Trifluoromethyl)Benzoyl]Amino] Pyridine-2-Carboxamide (298)

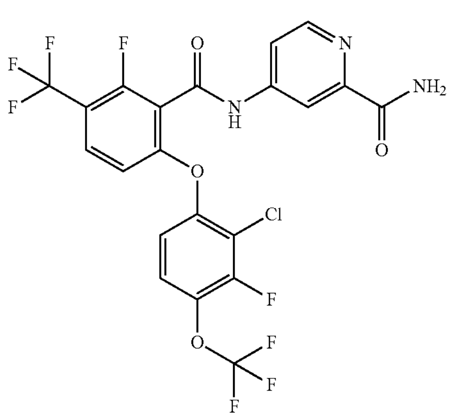

This compound was made in an analogous fashion to the synthesis of compound 296 in Example 106, except employing 4-aminopyridine-2-carboxamide in Step 5. The yield of 4-[[6-[2-chloro-3-fluoro-4-(trifluoromethoxy)phenoxy]-2-fluoro-3-(trifluoromethyl)benzoyl]amino]pyridine-2-carboxamide was 25.4 mg (49% yield). ESI-MS m z calc. 555.02, found 556.0 $(M+1)^+$; LC/MS retention time (Method B): 1.44 minutes. $^1H$ NMR (400 MHz, DMSO-$d_6$) δ 11.49 (s, 1H), 8.56 (d, J=5.5 Hz, 1H), 8.28 (d, J=2.2 Hz, 1H), 8.11 (d, J=2.7 Hz, 1H), 7.92 (t, J=8.6 Hz, 1H), 7.80 (dd, J=5.5, 2.2 Hz, 1H), 7.72 (t, J=8.8 Hz, 1H), 7.67 (d, J=2.9 Hz, 1H), 7.35 (dd, J=9.3, 2.1 Hz, 1H), 7.07 (d, J=8.8 Hz, 1H) ppm.

Example 109

4-[[6-(3,4-Difluoro-2-Methoxy-Phenoxy)-2-Fluoro-4-Methoxy-3-(Trifluoromethyl)Benzoyl]Amino] Pyridine-2-Carboxamide (299)

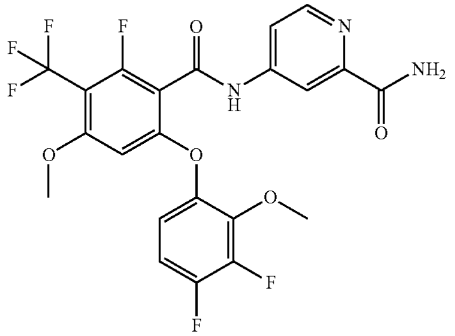 [SMILES: COc1cc(Oc2ccc(F)c(F)c2OC)c(C(=O)Nc2ccnc(C(N)=O)c2)c(F)c1C(F)(F)F]

Step 1: Methyl 4-[[6-Bromo-2-Fluoro-4-Methoxy-3-(Trifluoromethyl)Benzoyl]Amino]Pyridine-2-Carboxylate

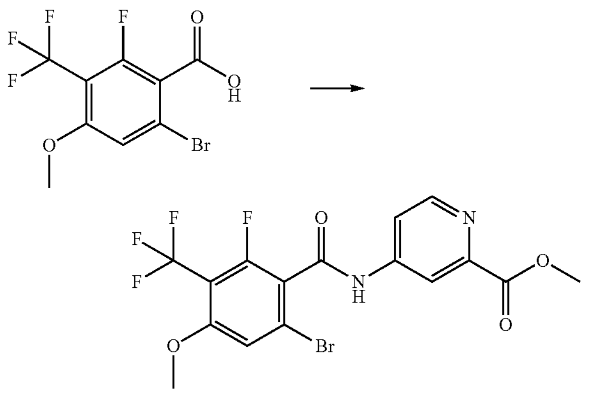

DMF (50 μL, 0.65 mmol) was added to a solution of oxalyl chloride (2.0 mL, 23 mmol) and 6-bromo-2-fluoro-4-methoxy-3-(trifluoromethyl)benzoic acid (2.0 g, 6.3 mmol, see US 2019/0016671, Example 129, Step 3, which is incorporated by reference) in dichloromethane (40 mL) at 0° C. and the resulting mixture stirred at room temperature for 2 hours. The solvent was removed in vacuo and redissolved in dichloromethane (40 mL). Methyl 4-aminopyridine-2-carboxylate (1.0 g, 6.6 mmol) and TEA (2.0 mL, 14 mmol) were added and the resulting mixture stirred at room temperature for 2 hours. The mixture was concentrated in vacuo and the residue purified by silica gel chromatography (0-70% ethyl acetate/petroleum ether) to provide methyl 4-[[6-bromo-2-fluoro-4-methoxy-3-(trifluoromethyl)benzoyl]amino]pyridine-2-carboxylate (1.37 g, 48%) as a pale yellow solid. ESI-MS m z calc. 449.98, found 453.3 $(M+1)^+$; 449.3 $(M-1)^-$; LC/MS retention time (Method F): 0.81 minutes. $^1H$ NMR (500 MHz, DMSO-$d_6$) δ 11.40 (s, 1H), 8.66 (d, J=5.4 Hz, 1H), 8.38 (d, J=2.0 Hz, 1H), 7.82 (dd, J=5.4, 2.2 Hz, 1H), 7.59 (s, 1H), 4.02 (s, 3H), 3.90 (s, 3H) ppm.

Step 2: 4-[[6-Bromo-2-Fluoro-4-Methoxy-3-(Trifluoromethyl)Benzoyl]Amino]Pyridine-2-Carboxamide

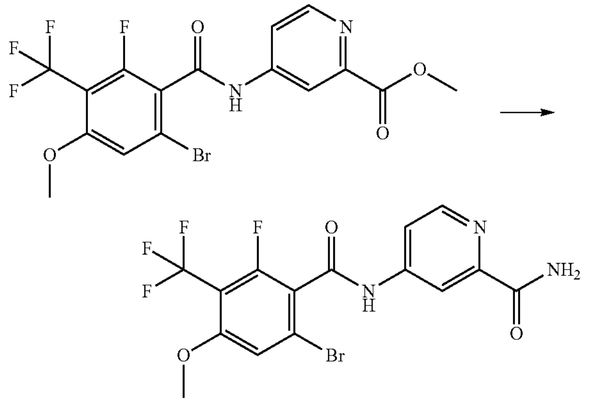

A solution of ammonia in methanol (20 mL of 7 M, 140 mmol) was added to methyl 4-[[6-bromo-2-fluoro-4-methoxy-3-(trifluoromethyl)benzoyl]amino]pyridine-2-carboxylate (1.35 g, 2.992 mmol) and the resulting mixture was stirred at room temperature over 3 days. The mixture was concentrated in vacuo to provide 4-[[6-bromo-2-fluoro-4-methoxy-3-(trifluoromethyl)benzoyl]amino]pyridine-2-carboxamide (1.25 g, 96%) as a yellow powder. ESI-MS m z calc. 434.98, found 436.4 $(M+1)^+$; 434.5 $(M-1)^-$; LC/MS retention time (Method E): 0.76 minutes.

Step 3: 4-[[6-(3,4-Difluoro-2-Methoxy-Phenoxy)-2-Fluoro-4-Methoxy-3-(Trifluoromethyl)Benzoyl]Amino]Pyridine-2-Carboxamide (299)

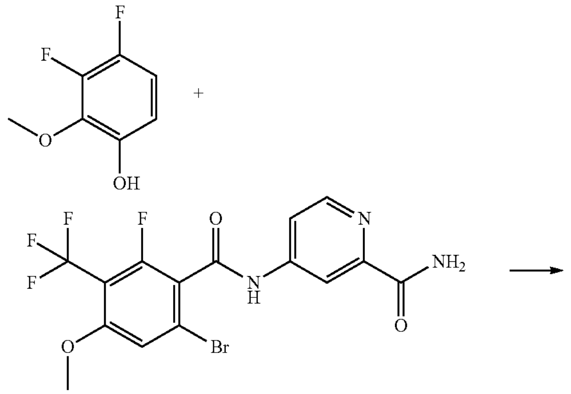

-continued

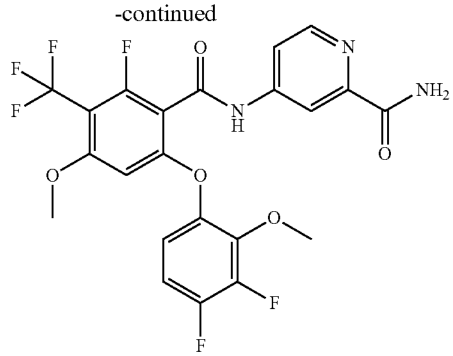

A mixture of 4-[[6-bromo-2-fluoro-4-methoxy-3-(trifluoromethyl)benzoyl]amino]pyridine-2-carboxamide (350 mg, 0.803 mmol), 3,4-difluoro-2-methoxy-phenol (120 mg, 0.749 mmol) and $Cs_2CO_3$ (280 mg, 0.859 mmol) in toluene (10 mL) was bubbled with nitrogen for 10 minutes, then copper (I) iodide (53 mg, 0.28 mmol) was added. The mixture was heated at 100° C. with vigorous stirring for 1 hour. The mixture was cooled to room temperature and partitioned between water (30 mL) and ethyl acetate (30 mL). The layers were separated and the aqueous layer was extracted with additional ethyl acetate (2×50 mL). The combined organic extracts were washed with brine, dried over $MgSO_4$, filtered and concentrated. Silica gel column chromatography (0-100% ethyl acetate/heptane), followed by reverse phase HPLC purification (47-95% acetonitrile/0.1% ammonium hydroxide) provided 4-[[6-(3,4-difluoro-2-methoxy-phenoxy)-2-fluoro-4-methoxy-3-(trifluoromethyl)benzoyl]amino]pyridine-2-carboxamide (18.2 mg, 4%) as a white powder. ESI-MS m z calc. 515.09, found 516.4 $(M+1)^+$; 514.4 $(M-1)^-$; LC/MS retention time (Method E): 3.09 minutes. $^1H$ NMR (500 MHz, DMSO-$d_6$) δ 11.34 (s, 1H), 8.55 (d, J=5.5 Hz, 1H), 8.31 (d, J=2.1 Hz, 1H), 8.14 (d, J=2.6 Hz, 1H), 7.82 (dd, J=5.5, 2.2 Hz, 1H), 7.69 (d, J=2.8 Hz, 1H), 7.26 (td, J=9.7, 8.3 Hz, 1H), 7.13 (ddd, J=9.4, 5.1, 2.1 Hz, 1H), 6.44 (s, 1H), 3.86 (d, J=1.1 Hz, 3H), 3.81 (s, 3H) ppm.

Example 110 and Example 111

4-[[6-(3,4-Difluoro-2-Methoxy-Phenoxy)-4-Methoxy-2-(Methylamino)-3-(Trifluoromethyl)Benzoyl]Amino]-N-Methyl-Pyridine-2-Carboxamide (300)

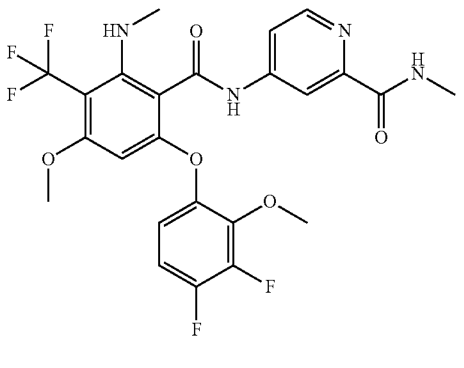 [SMILES: CNC(=O)c1cc(NC(=O)c2c(Oc3ccc(F)c(F)c3OC)cc(OC)c(C(F)(F)F)c2NC)ccn1]

And

4-[[6-(3,4-Difluoro-2-Methoxy-Phenoxy)-2-Fluoro-4-Methoxy-3-(Trifluoromethyl)Benzoyl]Amino]-N-Methyl-Pyridine-2-Carboxamide (301)

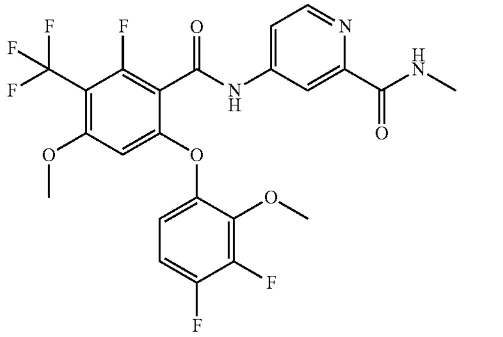

Step 1: 6-(3,4-Difluoro-2-Methoxy-Phenoxy)-2-Fluoro-4-Methoxy-3-(Trifluoromethyl)Benzoic Acid

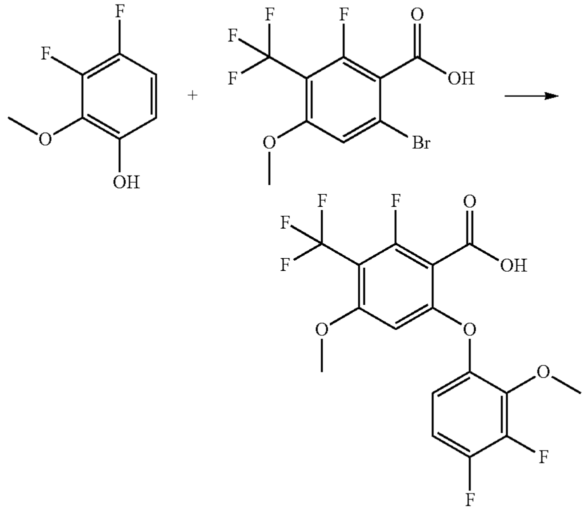

A mixture of 6-bromo-2-fluoro-4-methoxy-3-(trifluoromethyl)benzoic acid (6.5 g, 20.5 mmol, see Example 109, Step 3), 3,4-difluoro-2-methoxy-phenol (3.0 g, 19 mmol) and $Cs_2CO_3$ (7.0 g, 21.5 mmol), in toluene (30 mL) was bubbled with nitrogen for 10 minutes, then copper (I) iodide (1.37 g, 7.19 mmol) was added. The mixture was heated at 100° C. with vigorous stirring for 1.5 hours. The mixture was cooled to ambient temperature, acidified with 1 M aqueous HCl (15 mL) and filtered. The mixture was then extracted with ethyl acetate (3×50 mL). The combined organic extracts were washed with brine (10 mL), dried over $MgSO_4$, filtered and concentrated in vacuo. The residue was purified by silica gel chromatography (0-100% ethyl acetate/heptane) to provide 6-(3,4-difluoro-2-methoxy-phenoxy)-2-fluoro-4-methoxy-3-(trifluoromethyl)benzoic acid (6.0 g, 81%). ESI-MS m z calc. 396.04, found 396.8 $(M+1)^+$; 395.0 $(M-1)^-$; LC/MS retention time (Method E): 2.07 minutes.

Step 2: Methyl 4-[[6-(3,4-Difluoro-2-Methoxy-Phenoxy)-2-Fluoro-4-Methoxy-3-(Trifluoromethyl)Benzoyl]Amino]Pyridine-2-Carboxylate

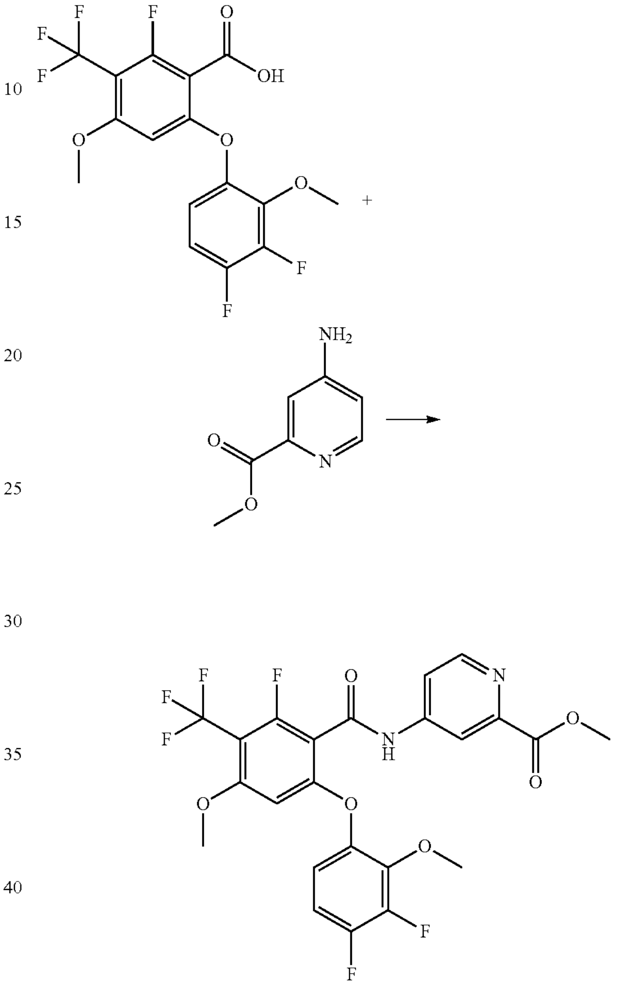

To a solution of 6-(3,4-difluoro-2-methoxy-phenoxy)-2-fluoro-4-methoxy-3-(trifluoromethyl)benzoic acid (500 mg, 1.26 mmol) and DMF (10 μL, 0.13 mmol) in dichloromethane (6 mL) at 0° C. was added oxalyl chloride (250 μL, 2.87 mmol). The mixture was warmed to room temperature over 30 minutes, then concentrated in vacuo. The residue was redissolved in dichloromethane (3 mL) and the solution was added to a solution of methyl 4-aminopyridine-2-carboxylate (240 mg, 1.577 mmol) and TEA (250 μL, 1.794 mmol) in dichloromethane (3 mL) at 0° C. The resulting mixture was stirred and warmed to room temperature over 2 hours. The mixture was diluted with aqueous $NH_4Cl$ solution and extracted with dichloromethane (2×5 mL). The combined organic extracts were dried over $MgSO_4$, filtered and concentrated in vacuo. Purification by silica gel chromatography (0-100% ethyl acetate/heptane) provided methyl 4-[[6-(3,4-difluoro-2-methoxy-phenoxy)-2-fluoro-4-methoxy-3-(trifluoromethyl)benzoyl]amino]pyridine-2-carboxylate (200 mg, 30%). ESI-MS m z calc. 530.09, found 531.0 $(M+1)^+$; 529.1 $(M-1)^-$; LC/MS retention time (Method E): 3.21 minutes.

Step 3: 4-[[6-(3,4-Difluoro-2-Methoxy-Phenoxy)-4-Methoxy-2-(Methylamino)-3-(Trifluoromethyl)Benzoyl]Amino]-N-Methyl-Pyridine-2-Carboxamide (300) and 4-[[6-(3,4-Difluoro-2-Methoxy-Phenoxy)-2-Fluoro-4-Methoxy-3-(Trifluoromethyl)Benzoyl]Amino]-N-Methyl-Pyridine-2-Carboxamide (301)

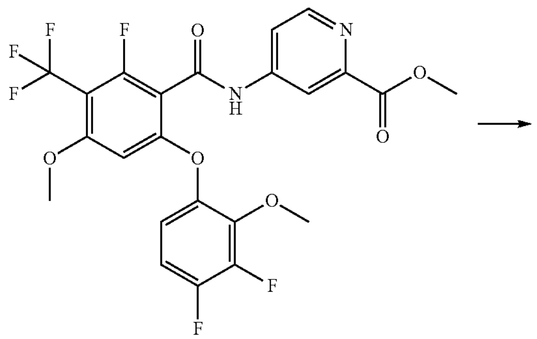

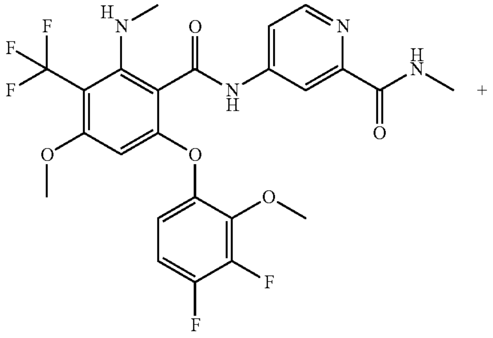

300

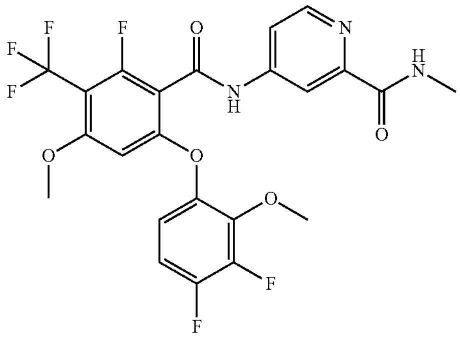 [SMILES: CNC(=O)c1cc(NC(=O)c2c(Oc3ccc(F)c(F)c3OC)cc(OC)c(C(F)(F)F)c2F)ccn1]

301

Methyl 4-[[6-(3,4-difluoro-2-methoxy-phenoxy)-2-fluoro-4-methoxy-3-(trifluoromethyl)benzoyl]amino]pyridine-2-carboxylate (100 mg, 0.189 mmol) was dissolved in a solution of methylamine (20 mL of 2 M, 40 mmol) and stirred for 60 hours at room temperature. The mixture was concentrated in vacuo to afford a mixture of products. The mixture was purified by reverse phase HPLC (acetonitrile+0.05% TFA/water+0.05% TFA gradient) to provide the following isolated components: 4-[[6-(3,4-difluoro-2-methoxy-phenoxy)-4-methoxy-2-(methylamino)-3-(trifluoromethyl)benzoyl]amino]-N-methyl-pyridine-2-carboxamide (16.3 mg, 16%) (300). ESI-MS m z calc. 540.14, found 541.1 $(M+1)^+$; 539.2 $(M-1)^-$; LC/MS retention time (Method E): 3.12 minutes. $^1$H NMR (500 MHz, DMSO-$d_6$) δ 11.09 (s, 1H), 8.71 (d, J=4.9 Hz, 1H), 8.49 (d, J=5.5 Hz, 1H), 8.30 (d, J=2.5 Hz, 1H), 7.84 (dd, J=5.4, 2.1 Hz, 1H), 7.27-7.12 (m, 1H), 7.06-6.89 (m, 1H), 5.85 (s, 1H), 5.60 (s, 1H), 3.81 (s, 3H), 3.65 (s, 3H), 2.84 (s, 3H), 2.81 (d, J=4.9 Hz, 3H) ppm.

and

4-[[6-(3,4-difluoro-2-methoxy-phenoxy)-2-fluoro-4-methoxy-3-(trifluoromethyl)benzoyl]amino]-N-methyl-pyridine-2-carboxamide (301) (2.7 mg, 3%). ESI-MS m z calc. 529.10, found 530.1 $(M+1)^+$; 528.2 $(M-1)^-$; LC/MS retention time (Method E): 3.18 minutes. $^1$H NMR (400 MHz, DMSO-$d_6$) δ 11.34 (s, 1H), 8.82-8.73 (m, 1H), 8.55 (d, J=5.5 Hz, 1H), 8.27 (d, J=2.2 Hz, 1H), 7.84 (dd, J=5.8, 2.2 Hz, 1H), 7.25 (q, J=9.3 Hz, 1H), 7.20-7.08 (m, 1H), 6.44 (s, 1H), 3.86 (s, 3H), 3.81 (s, 3H), 2.82 (d, J=4.7 Hz, 3H).

Example 112

N-(2-Carbamoyl-5-Methyl-4-Pyridyl)-5-(3,4-Difluoro-2-Methoxy-Phenoxy)-3-Methoxy-2-(Trifluoromethyl)Pyridine-4-Carboxamide (302)

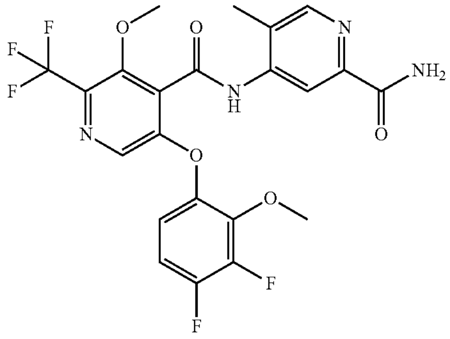 [SMILES: COc1c(Oc2cnc(C(F)(F)F)c(OC)c2C(=O)Nc2cc(C(N)=O)ncc2C)ccc(F)c1F]

Step 1: Ethyl 5-(3,4-Difluoro-2-Methoxy-Phenoxy)-3-Fluoro-2-(Trifluoromethyl)Pyridine-4-Carboxylate

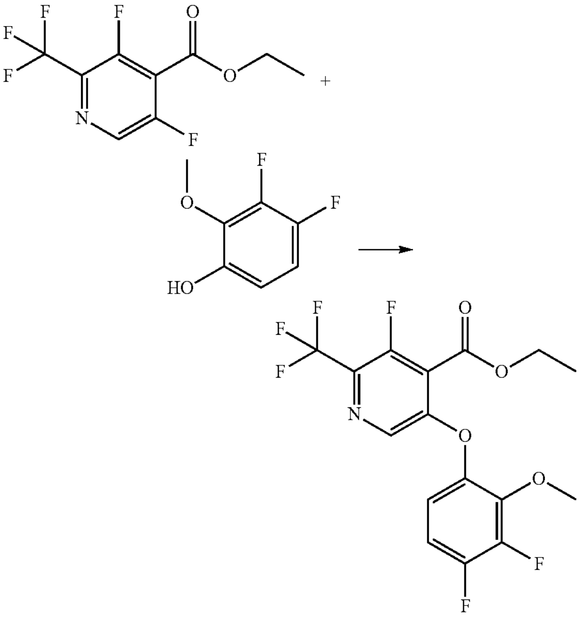

A solution of ethyl 3,5-difluoro-2-(trifluoromethyl)pyridine-4-carboxylate (1.00 g, 3.92 mmol, see US 2019/0016671, Example 148, Step 1, which is incorporated by reference) and 3,4-difluoro-2-methoxy-phenol (623 mg, 3.89 mmol) in DMF (6 mL) was cooled to −10° C. $Cs_2CO_3$ (2.553 g, 7.836 mmol) was added to the solution in one portion, and the mixture gradually warmed to room temperature and stirred for 16 hours. The mixture was diluted with water (40 mL) and extracted with ethyl acetate. The organic layer was washed with brine, dried over $Na_2SO_4$, filtered and concentrated to provide ethyl 5-(3,4-difluoro-2-methoxy-phenoxy)-3-fluoro-2-(trifluoromethyl)pyridine-4-carboxylate (1.5 g, 97%). ESI-MS m z calc. 395.06, found 396.5 $(M+1)^+$; LC/MS retention time (Method A): 0.77 minutes.

Step 2: 5-(3,4-Difluoro-2-Methoxy-Phenoxy)-3-Methoxy-2-(Trifluoromethyl)Pyridine-4-Carboxylic Acid

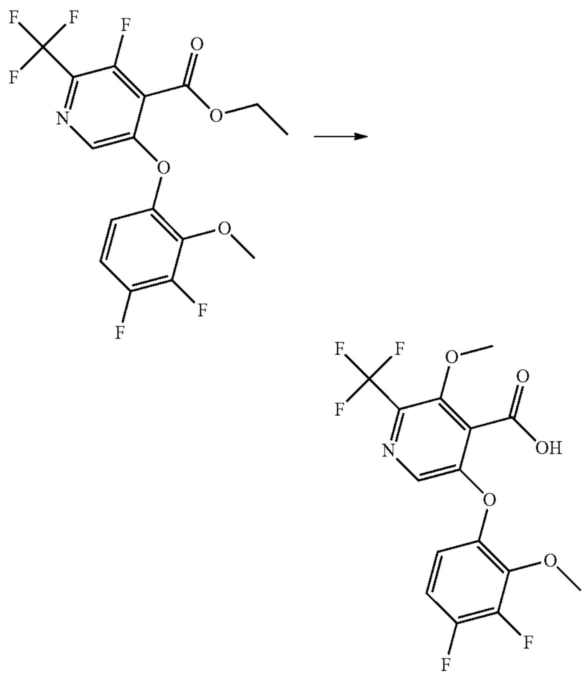

Ethyl 5-(3,4-difluoro-2-methoxy-phenoxy)-3-fluoro-2-(trifluoromethyl)pyridine-4-carboxylate (1.55 g, 3.92 mmol) was dissolved in a solution of sodium methoxide (30 mL of 25% w/w in methanol, 131 mmol) and stirred at room temperature for 70 minutes. Aqueous 1 M NaOH was added and the suspension heated at 45° C. until clear (~1 hour). The mixture was concentrated in vacuo and acidified with 1 M aqueous HCl. The aqueous mixture was extracted with ethyl acetate (3×). The combined extracts were washed with brine, dried over $Na_2SO_4$, filtered and concentrated. The colorless thick oil was triturated with dichloromethane/hexane to obtain 5-(3,4-difluoro-2-methoxy-phenoxy)-3-methoxy-2-(trifluoromethyl)pyridine-4-carboxylic acid (568 mg, 38%) as a white solid. ESI-MS m z calc. 379.05, found 380.5 $(M+1)^+$; LC/MS retention time (Method A): 0.61 minutes. $^1H$ NMR (400 MHz, DMSO-$d_6$) δ 14.55 (br s, 1H), 8.02 (s, 1H), 7.26 (td, J=9.7, 8.3 Hz, 1H), 7.14 (ddd, J=9.4, 5.1, 2.2 Hz, 1H), 3.97 (s, 3H), 3.87 (d, J=1.4 Hz, 3H) ppm.

Step 4: 5-(3,4-Difluoro-2-Methoxy-Phenoxy)-3-Methoxy-2-(Trifluoromethyl)Pyridine-4-Carbonyl Chloride

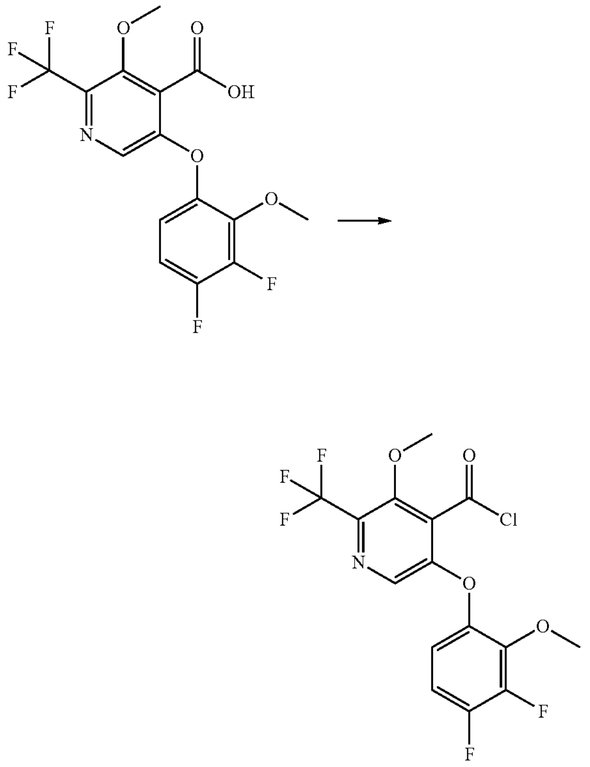 [SMILES: COc1c(Oc2cnc(C(F)(F)F)c(OC)c2C(=O)O)ccc(F)c1F ; COc1c(Oc2cnc(C(F)(F)F)c(OC)c2C(=O)Cl)ccc(F)c1F]

To a solution of 5-(3,4-difluoro-2-methoxy-phenoxy)-3-methoxy-2-(trifluoromethyl)pyridine-4-carboxylic acid (156 mg, 0.411 mmol) and DMF (3 μL, 0.04 mmol) in dichloromethane (1.5 mL) was added oxalyl chloride (52 μL, 0.60 mmol) dropwise at 0° C. The mixture was stirred at room temperature for 30 minutes until gas evolution had ceased. The solvent was removed in vacuo to afford 5-(3,4-difluoro-2-methoxy-phenoxy)-3-methoxy-2-(trifluoromethyl)pyridine-4-carbonyl chloride.

Step 5: Methyl 4-[[5-(3,4-Difluoro-2-Methoxy-Phenoxy)-3-Methoxy-2-(Trifluoromethyl)Pyridine-4-Carbonyl]Amino]-5-Methyl-Pyridine-2-Carboxylate

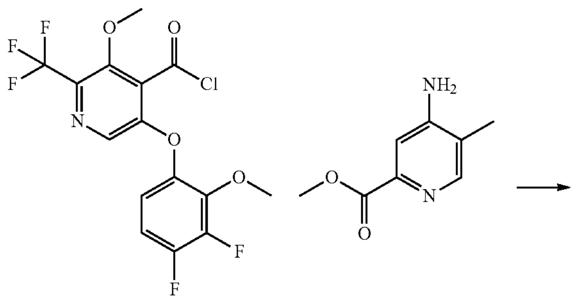

-continued

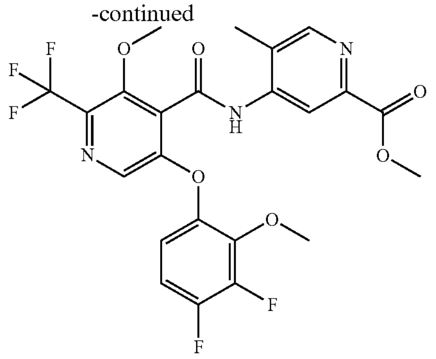

A solution of methyl 4-amino-5-methyl-pyridine-2-carboxylate (41 mg, 0.25 mmol, Preparation 1) and DIEA (106 μL, 0.609 mmol) in NMP (0.5 mL) at 0° C. was treated dropwise with a solution of 5-(3,4-difluoro-2-methoxy-phenoxy)-3-methoxy-2-(trifluoromethyl)pyridine-4-carbonyl chloride (81 mg, 0.2037 mmol) in dichloromethane (1.5 mL). The mixture was allowed to warm to room temperature over 16 hours. The mixture was concentrated to provide methyl 4-[[5-(3,4-difluoro-2-methoxy-phenoxy)-3-methoxy-2-(trifluoromethyl)pyridine-4-carbonyl]amino]-5-methyl-pyridine-2-carboxylate (92 mg, 86%). ESI-MS m z calc. 527.11, found 528.6 $(M+1)^+$; LC/MS retention time (Method A): 0.65 minutes.

Step 6: N-(2-Carbamoyl-5-Methyl-4-Pyridyl)-5-(3,4-Difluoro-2-Methoxy-Phenoxy)-3-Methoxy-2-(Trifluoromethyl)Pyridine-4-Carboxamide (302)

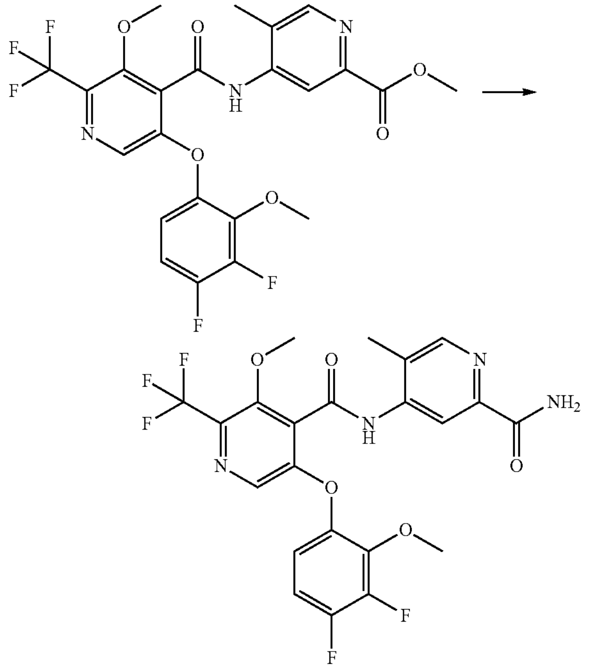

Methyl 4-[[5-(3,4-difluoro-2-methoxy-phenoxy)-3-methoxy-2-(trifluoromethyl)pyridine-4-carbonyl]amino]-5-methyl-pyridine-2-carboxylate (75 mg, 0.14 mmol) was dissolved in a solution of ammonia in methanol (3.0 mL of 7 M, 21 mmol) and stirred for 2 hours at room temperature, then treated with additional ammonia in methanol (3.0 mL of 7 M, 21 mmol) and heated at 50° C. in a sealed vial 16 hours. The mixture was cooled to room temperature and concentrated in vacuo. Purification by reverse phase HPLC (10-99% acetonitrile/5 mM HCl) provided N-(2-carbamoyl-5-methyl-4-pyridyl)-5-(3,4-difluoro-2-methoxy-phenoxy)-3-methoxy-2-(trifluoromethyl)pyridine-4-carboxamide (30.6 mg, 42%). ESI-MS m/z calc. 512.11, found 513.1 $(M+1)^+$; LC/MS retention time (Method C): 2.14 minutes. $^1H$ NMR (400 MHz, DMSO-$d_6$) δ 10.70 (s, 1H), 8.49 (s, 2H), 8.07 (s, 1H), 7.63 (d, J=2.8 Hz, 1H), 7.33-7.24 (m, 1H), 7.16 (ddd, J=9.4, 5.2, 2.1 Hz, 1H), 7.09 (br s, 1H), 4.03 (s, 3H), 3.89 (d, J=1.4 Hz, 3H), 2.32 (s, 3H) ppm.

Example 113

4-[[2,3-Difluoro-6-[3-Fluoro-2-Methoxy-4-(Trifluoromethoxy)Phenoxy]Benzoyl]Amino]Pyridine-2-Carboxamide (303)

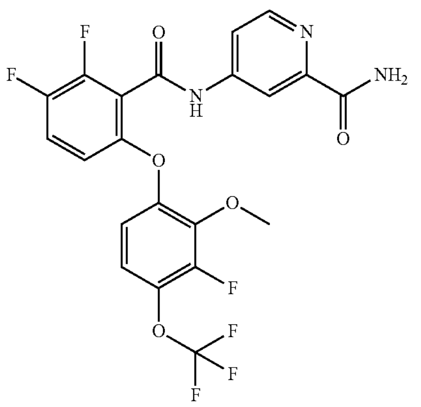 [SMILES: COc1c(Oc2ccc(F)c(F)c2C(=O)Nc2ccnc(C(N)=O)c2)ccc(OC(F)(F)F)c1F]

Step 1: 3-Fluoro-2-Methoxy-4-(Trifluoromethoxy)Phenol

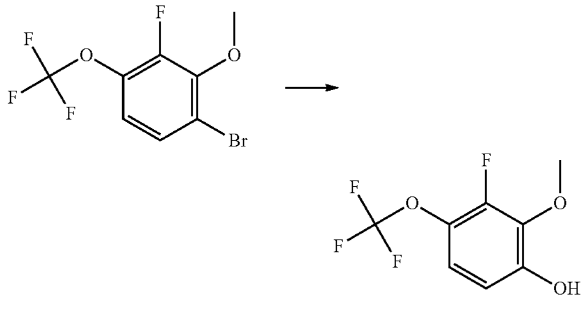

To a solution of 1-bromo-3-fluoro-2-methoxy-4-(trifluoromethoxy)benzene (900 mg, 2.52 mmol) in dioxane (4 mL) was added tris(dibenzylideneacetone)dipalladium (116 mg, 0.127 mmol), tBuXPhos (112 mg, 0.264 mmol) and KOH (425 mg, 7.58 mmol) followed by water (2 mL). The mixture was heated at 90° C. overnight, then cooled to room temperature and partitioned between MTBE (20 mL) and water (10 mL). The aqueous layer was separated and acidified to pH 1 by addition of 2 M aqueous HCl. The aqueous layer was then extracted with MTBE (2×20 mL). The combined organics were washed with brine (10 mL), dried over $MgSO_4$, filtered and concentrated in vacuo to provide 3-fluoro-2-methoxy-4-(trifluoromethoxy)phenol (456 mg, 75%) as an orange oil. ESI-MS m z calc. 226.03, found 225.6 $(M-1)^-$; LC/MS retention time (Method F): 0.87 minutes. $^1H$ NMR (400 MHz, DMSO-$d_6$) δ 10.18 (s, 1H), 7.14-7.01 (m, 1H), 6.73 (dd, J=9.2, 2.2 Hz, 1H), 3.83 (s, 3H) ppm.

Step 2: 2,3-Difluoro-6-[3-Fluoro-2-Methoxy-4-(Trifluoromethoxy)Phenoxy]Benzoic Acid

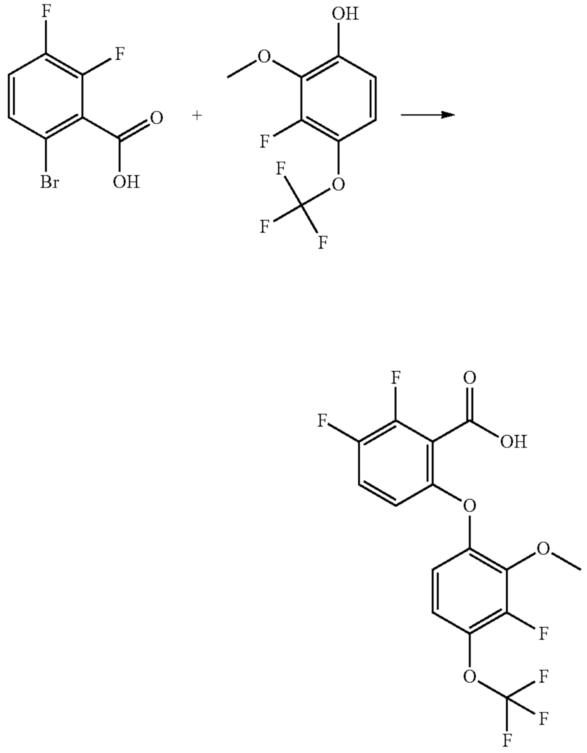 [SMILES: O=C(O)c1c(Br)ccc(F)c1F ; COc1c(O)ccc(OC(F)(F)F)c1F ; COc1c(Oc2ccc(F)c(F)c2C(=O)O)ccc(OC(F)(F)F)c1F]

6-Bromo-2,3-difluoro-benzoic acid (2.0 g, 8.4 mmol) and 3-fluoro-2-methoxy-4-(trifluoromethoxy)phenol (2.36 g, 10.4 mmol,) were dissolved in toluene (40 mL) and the solution was purged with nitrogen (3×vacuum/nitrogen flush). $Cs_2CO_3$ (5.54 g, 17.0 mmol) was added and the mixture was stirred for 5 minutes. Copper (I) iodide (325 mg, 1.76 mmol) was added and the mixture stirred at 100° C. overnight. The mixture was acidified to pH=2 with 1 M aqueous HCl and partitioned between ethyl acetate and water. The aqueous layer was extracted with additional ethyl acetate (2×). The combined organic extracts were washed with brine, dried over $MgSO_4$, filtered and concentrated in vacuo. Purification by silica gel chromatography (0-50% ethyl acetate/heptane) provided 2,3-difluoro-6-[3-fluoro-2-methoxy-4-(trifluoromethoxy)phenoxy]benzoic acid (1.63 g, 45%) as a yellow waxy solid. ESI-MS m z calc. 382.03, found 381.3 $(M-1)^-$; LC/MS retention time (Method F): 0.55 minutes. H NMR (500 MHz, $CDCl_3$) δ 7.23 (td, J=9.3, 8.5 Hz, 1H), 7.02 (tt, J=7.9, 1.3 Hz, 1H), 6.82 (dd, J=9.2, 2.3 Hz, 1H), 6.57 (ddd, J=9.3, 3.5, 2.0 Hz, 1H), 3.93 (d, J=1.4 Hz, 3H) ppm.

Step 3: Methyl 4-[[2,3-Difluoro-6-[3-Fluoro-2-Methoxy-4-(Trifluoromethoxy)Phenoxy]Benzoyl]Amino]Pyridine-2-Carboxylate

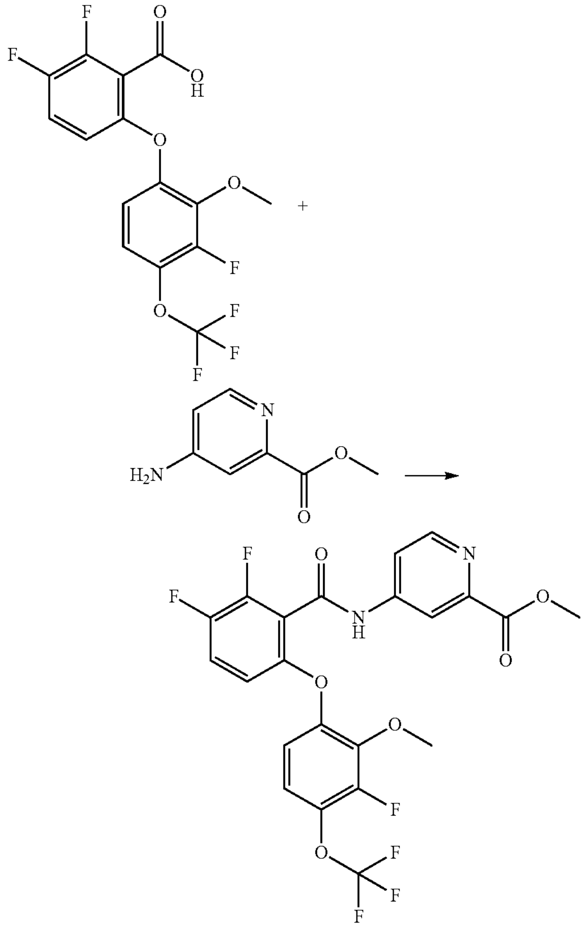

One drop of DMF (5 μL, 0.06 mmol) was added to a solution of 2,3-difluoro-6-[3-fluoro-2-methoxy-4-(trifluoromethoxy)phenoxy]benzoic acid (298 mg, 0.702 mmol) in dichloromethane (5 mL) at 0° C., followed by a dropwise addition of oxalyl chloride (190 μL, 2.18 mmol). The mixture was allowed to warm to room temperature and stirred for 1 hour. The mixture was concentrated in vacuo, dissolved in dichloromethane (3 mL) and added dropwise to a solution of methyl 4-aminopyridine-2-carboxylate (120 mg, 0.789 mmol) and TEA (300 μL, 2.15 mmol) in dichloromethane (3.5 mL) at 0° C. The mixture allowed to come to room temperature and stirred overnight. The mixture diluted with dichloromethane and water and filtered through a phase separator cartridge. The organic filtrate was concentrated in vacuo. Due to only partial conversion to product, the residue was dissolved in acetonitrile (2.7 mL) and treated with 1-methylimidazole (140 μL, 1.76 mmol) followed by [chloro(dimethylamino)methylene]-dimethyl-ammonium (Phosphorus Hexafluoride Ion) (238 mg, 0.848 mmol). The mixture was stirred at room temperature for 30 minutes and concentrated in vacuo. The mixture was partitioned between dichloromethane and water and filtered through a phase separator. The organic filtrate was concentrated in vacuo and purified by silica gel chromatography (30-100% ethyl acetate/heptane) to provide methyl 4-[[2,3-difluoro-6-[3-fluoro-2-methoxy-4-(trifluoromethoxy)phenoxy]benzoyl]amino]pyridine-2-carboxylate (105.4 mg, 29%) as a waxy solid. ESI-MS m z calc. 516.08, found 517.4 $(M+1)^+$; 515.4 $(M-1)^-$; LC/MS retention time (Method F): 0.92 minutes. $^1H$ NMR (500 MHz, $CDCl_3$) δ 8.90 (s, 1H), 8.69 (d, J=5.5 Hz, 1H), 8.21 (s, 1H), 8.06-8.01 (m, 1H), 7.22 (t, J=8.8 Hz, 1H), 7.09 (td, J=8.3, 7.6, 1.2 Hz, 1H), 7.00 (dd, J=9.2, 2.1 Hz, 1H), 6.61-6.57 (m, 1H), 4.01 (s, 3H), 3.87 (d, J=2.0 Hz, 3H) ppm.

Step 4: 4-[[2,3-Difluoro-6-[3-Fluoro-2-Methoxy-4-(Trifluoromethoxy)Phenoxy]Benzoyl]Amino]Pyridine-2-Carboxamide (303)

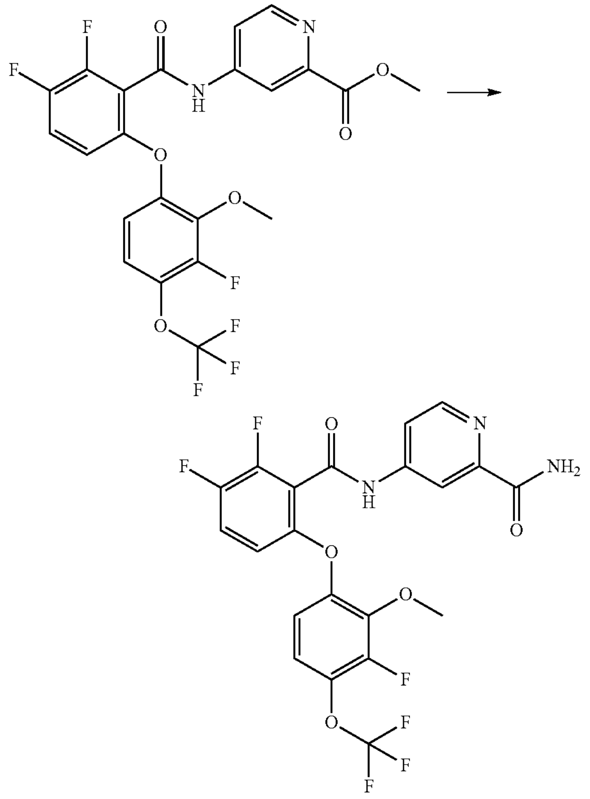

Methyl 4-[[2,3-difluoro-6-[3-fluoro-2-methoxy-4-(trifluoromethoxy)phenoxy]benzoyl]amino]pyridine-2-carboxylate (105 mg, 0.203 mmol) was dissolved in a solution of ammonia in methanol (4 mL of 7 M, 28 mmol) and stirred at room temperature for 4 hours. The mixture concentrated in vacuo and purified by reverse phase HPLC (38-53% acetonitrile/0.1% ammonium hydroxide) to provide 4-[[2,3-difluoro-6-[3-fluoro-2-methoxy-4-(trifluoromethoxy)phenoxy]benzoyl]amino]pyridine-2-carboxamide (53 mg, 51%) as a white solid. ESI-MS m z calc. 501.08, found 502.5 $(M+1)^+$; 500.4 $(M-1)^-$; LC/MS retention time (Method E): 3.09 minutes. $^1H$ NMR (500 MHz, $CDCl_3$) δ 9.12 (s, 1H), 8.52 (d, J=5.5 Hz, 1H), 8.33 (dd, J=5.5, 2.2 Hz, 1H), 8.07 (d, J=2.2 Hz, 1H), 7.83 (s, 1H), 7.21 (q, J=9.1 Hz, 1H), 7.02 (tq, J=7.6, 1.3 Hz, 1H), 6.91 (dd, J=9.2, 2.2 Hz, 1H), 6.59 (ddd, J=9.2, 3.5, 2.0 Hz, 1H), 5.33 (s, 1H), 3.88 (d, J=1.9 Hz, 3H) ppm.

Example 114

4-[[2,3-Difluoro-6-[3-Fluoro-2-Methoxy-4-(Trifluoromethoxy)Phenoxy]Benzoyl]Amino]-5-Methyl-Pyridine-2-Carboxamide (304)

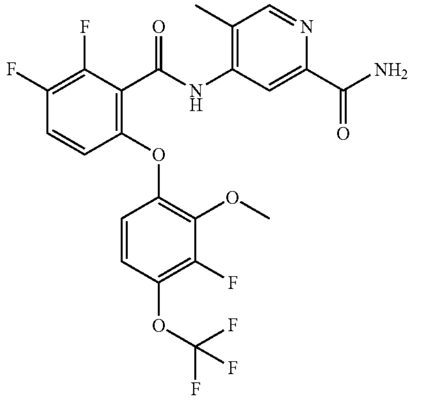 [SMILES: COc1c(Oc2ccc(F)c(F)c2C(=O)Nc2cc(C(N)=O)ncc2C)ccc(OC(F)(F)F)c1F]

Step 1: Methyl 4-[[2,3-Difluoro-6-[3-Fluoro-2-Methoxy-4-(Trifluoromethoxy)Phenoxy]Benzoyl]Amino]-5-Methyl-Pyridine-2-Carboxylate

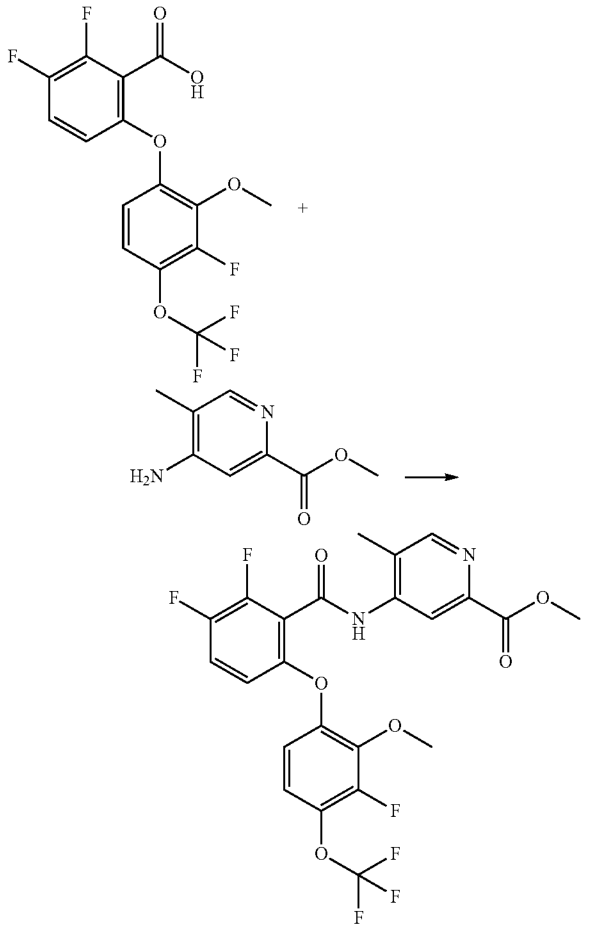

This compound was made in an analogous fashion to Example 113, Step 3, except employing methyl 4-amino-5-methyl-pyridine-2-carboxylate (Preparation 1) in place of methyl 4-aminopyridine-2-carboxylate in Step 3. The yield of 5-[[3-chloro-2-fluoro-6-[3-fluoro-2-methoxy-4-(trifluoromethoxy)phenoxy]benzoyl]amino]pyridine-2-carboxamide after purification was 109 mg (29%). ESI-MS m z calc. 530.09, found 531.4 $(M+1)^+$; 529.4 $(M-1)^-$; LC/MS retention time (Method F): 0.94 minutes as a white solid. $^1H$ NMR (500 MHz, $CDCl_3$) δ 9.07 (s, 1H), 8.53 (s, 1H), 8.35 (s, 1H), 7.26-7.20 (m, 1H), 7.09 (t, J=8.4 Hz, 1H), 6.98 (dd, J=9.2, 2.1 Hz, 1H), 6.60-6.56 (m, 1H), 4.01 (s, 3H), 3.82 (d, J=2.0 Hz, 3H), 2.29 (s, 3H) ppm.

Step 2: 4-[[2,3-Difluoro-6-[3-Fluoro-2-Methoxy-4-(Trifluoromethoxy)Phenoxy]Benzoyl]Amino]-5-Methyl-Pyridine-2-Carboxamide (304)

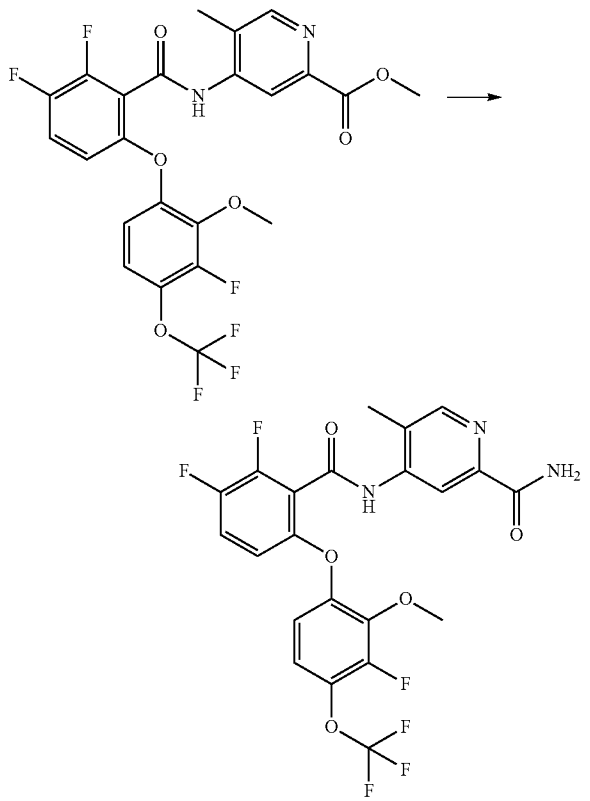

Methyl 4-[[2,3-difluoro-6-[3-fluoro-2-methoxy-4-(trifluoromethoxy)phenoxy]benzoyl]amino]-5-methyl-pyridine-2-carboxylate (109 mg, 0.2055 mmol) was dissolved in a solution of ammonia in methanol (4 mL of 7 M, 28 mmol) and stirred at room temperature for 5 hours. The mixture was concentrated in vacuo and redissolved in ammonia in methanol (4 mL of 7 M, 28 mmol) and stirred at room temperature for 3 days. Purification by reverse phase HPLC (38-53% acetonitrile/0.1% ammonium hydroxide) provided 4-[[2,3-difluoro-6-[3-fluoro-2-methoxy-4-(trifluoromethoxy)phenoxy]benzoyl]amino]-5-methyl-pyridine-2-carboxamide (51 mg, 48%) as a white solid. ESI-MS m z calc. 515.09, found 516.4 $(M+1)^+$; 514.4 $(M-1)^-$; LC/MS retention time (Method E): 3.11 minutes. $^1H$ NMR (500 MHz, $CDCl_3$) δ 8.87 (s, 1H), 8.36 (s, 1H), 8.06 (s, 1H), 7.73 (s, 1H), 7.20 (q, J=9.0 Hz, 1H), 7.09-7.02 (m, 1H), 6.95 (dd, J=9.2, 2.2 Hz, 1H), 6.57 (ddd, J=9.2, 3.5, 2.0 Hz, 1H), 5.45 (s, 1H), 3.85 (d, J=1.9 Hz, 3H), 2.29 (s, 3H) ppm.

Example 115

4-[[3-Chloro-2-Fluoro-6-[3-Fluoro-2-Methoxy-4-(Trifluoromethoxy)Phenoxy]Benzoyl]Amino]Pyridine-2-Carboxamide (305)

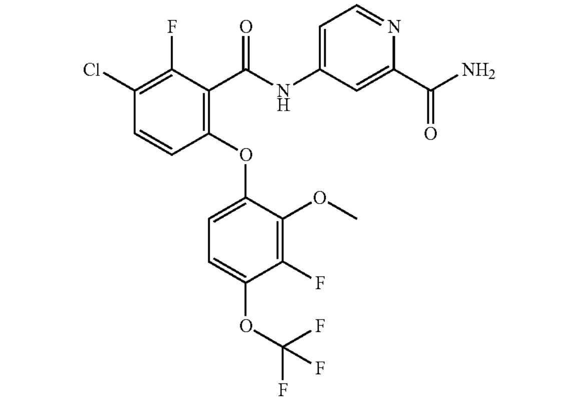 [SMILES: COc1c(Oc2ccc(Cl)c(F)c2C(=O)Nc2ccnc(C(N)=O)c2)ccc(OC(F)(F)F)c1F]

Step 1: 3-Chloro-2-Fluoro-6-[3-Fluoro-2-Methoxy-4-(Trifluoromethoxy)Phenoxy]Benzoic Acid

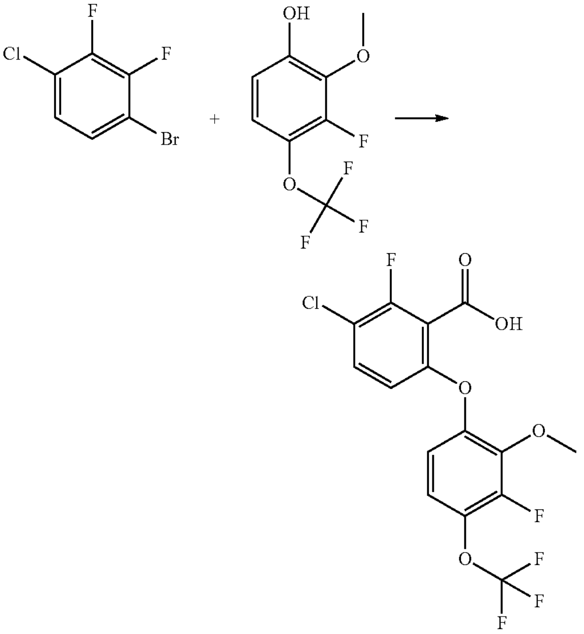

A mixture of 6-bromo-3-chloro-2-fluoro-benzoic acid (2.0 g, 7.9 mmol, see US 2019/0016671, Example 82, Step 1, which is incorporated by reference), 3-fluoro-2-methoxy-4-(trifluoromethoxy)phenol (1.98 g, 8.76 mmol, see Example 113, Step 1) and $Cs_2CO_3$ (5.14 g, 15.8 mmol) and toluene (15 mL) in a pressure flask was bubbled with nitrogen for 10 minutes, then copper (I) iodide (360 mg, 1.89 mmol) added. The flask was sealed and heated at 100° C. with vigorous stirring for 16 hours under nitrogen. The cooled mixture diluted with ethyl acetate and water, and then acidified with 1 M aqueous HCl. The layers were separated, and the aqueous layer was extracted with additional ethyl acetate (3×). The combined organic layers were washed with water (2×) and brine, dried over $Na_2SO_4$, filtered through Celite and concentrated. Purification by reverse phase HPLC (1-99% acetonitrile/5 mM HCl) provided 3-chloro-2-fluoro-6-[3-fluoro-2-methoxy-4-(trifluoromethoxy)phenoxy]benzoic acid (1.302 g, 41%). ESI-MS m/z calc. 398.00, found 399.1 $(M+1)^+$; LC/MS retention time (Method B): 1.19 minutes. $^1H$ NMR (400 MHz, DMSO-$d_6$) δ 7.65 (t, J=8.7 Hz, 1H), 7.32 (ddd, J=9.4, 8.1, 1.3 Hz, 1H), 7.01 (dd, J=9.3, 2.2 Hz, 1H), 6.85 (dd, J=9.1, 1.5 Hz, 1H), 3.88 (d, J=1.0 Hz, 3H) ppm.

Step 2: 4-[[3-Chloro-2-Fluoro-6-[3-Fluoro-2-Methoxy-4-(Trifluoromethoxy)Phenoxy]Benzoyl]Amino]Pyridine-2-Carboxamide (305)

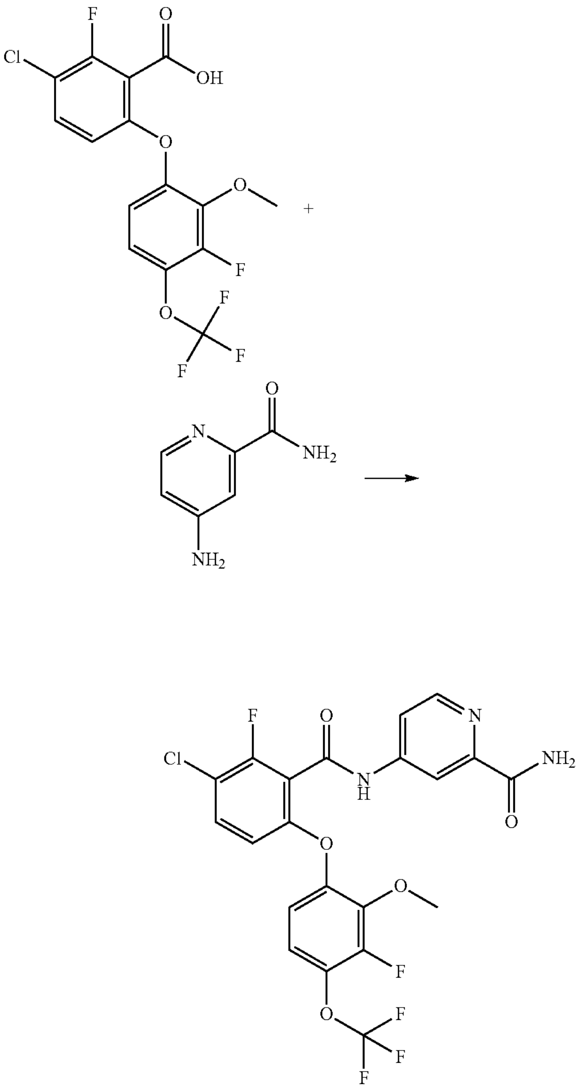

A solution of 3-chloro-2-fluoro-6-[3-fluoro-2-methoxy-4-(trifluoromethoxy)phenoxy]benzoic acid (30 mg, 0.075 mmol) and DMF (6 μL, 0.08 mmol) in dichloromethane (200 μL) at 0° C. was treated with oxalyl dichloride (39 μL, 0.45 mmol). The mixture was stirred at 0° C. for 5 minutes and for 30 minutes at room temperature. The mixture was concentrated in vacuo. The residue was dissolved in NMP (250 mL) and slowly added to mixture of 4-aminopyridine-2-carboxamide (20.6 mg, 0.151 mmol) and DIEA (79 μL, 0.45 mmol) in NMP (250 mL) at 0° C. The mixture was allowed to warm to room temperature and stirred for 16 hours. The mixture was filtered and purified by reverse phase HPLC (acetonitrile/5 mM HCl gradient) to provide 4-[[3-chloro-2-fluoro-6-[3-fluoro-2-methoxy-4-(trifluoromethoxy)phenoxy]benzoyl]amino]pyridine-2-carboxamide (28.2 mg, 72%). ESI-MS m z calc. 517.05, found 518.1 $(M+1)^+$; LC/MS retention time (Method B): 1.1 minutes. $^1H$ NMR (400 MHz, DMSO-$d_6$) δ 11.42 (s, 1H), 8.54 (d, J=5.4 Hz, 1H), 8.30 (d, J=2.1 Hz, 1H), 8.10 (d, J=2.8 Hz, 1H), 7.80 (dd, J=5.5, 2.2 Hz, 1H), 7.71 (t, J=8.8 Hz, 1H), 7.66 (d, J=2.8 Hz, 1H), 7.39-7.30 (m, 1H), 7.09 (dd, J=9.3, 2.1 Hz, 1H), 6.89 (dd, J=9.0, 1.4 Hz, 1H), 3.84 (d, J=1.0 Hz, 3H) ppm.

Example 116

5-[[3-Chloro-2-Fluoro-6-[3-Fluoro-2-Methoxy-4-(Trifluoromethoxy)Phenoxy]Benzoyl]Amino]Pyridine-2-Carboxamide (306)

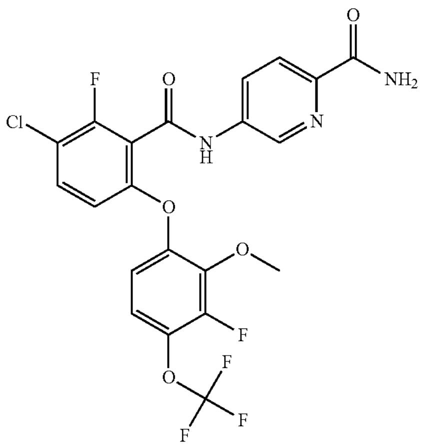 [SMILES: COc1c(Oc2ccc(Cl)c(F)c2C(=O)Nc2ccc(C(N)=O)nc2)ccc(OC(F)(F)F)c1F]

This compound was made in an analogous fashion to the synthesis of compound 305 in Example 115, except employing 5-aminopyridine-2-carboxamide in the amide formation step. The yield of 5-[[3-chloro-2-fluoro-6-[3-fluoro-2-methoxy-4-(trifluoromethoxy)phenoxy]benzoyl]amino]pyridine-2-carboxamide after purification was 29 mg (73%). ESI-MS m z calc. 517.05, found 518.0 $(M+1)^+$; LC/MS retention time (Method B): 1.09 minutes. $^1H$ NMR (400 MHz, DMSO-$d_6$) δ 11.36 (s, 1H), 8.83 (d, J=2.4 Hz, 1H), 8.27 (dd, J=8.6, 2.5 Hz, 1H), 8.08-8.00 (m, 2H), 7.71 (t, J=8.8 Hz, 1H), 7.57 (s, 1H), 7.34 (t, J=8.4 Hz, 1H), 7.09 (dd, J=9.4, 2.2 Hz, 1H), 6.91 (dd, J=9.1, 1.4 Hz, 1H), 3.85 (d, J=1.0 Hz, 3H) ppm.

Example 117

4-[[2,3,4-Trifluoro-6-[3-Fluoro-2-Methoxy-4-(Trifluoromethoxy)Phenoxy]Benzoyl]Amino]Pyridine-2-Carboxamide (307)

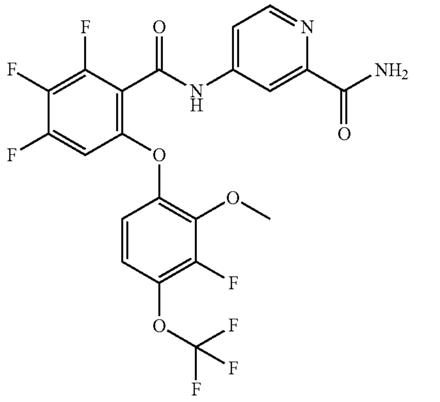 [SMILES: COc1c(Oc2cc(F)c(F)c(F)c2C(=O)Nc2ccnc(C(N)=O)c2)ccc(OC(F)(F)F)c1F]

Step 1: 2,3,4-Trifluoro-6-[3-Fluoro-2-Methoxy-4-(Trifluoromethoxy)Phenoxy]Benzoic Acid

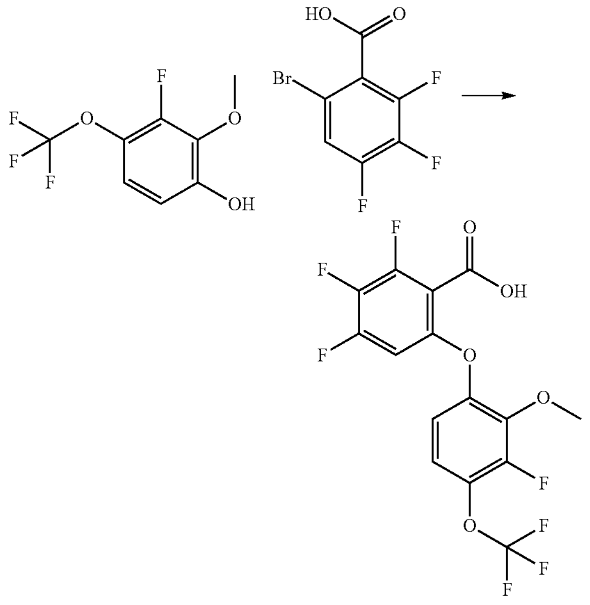

A solution of 6-bromo-2,3,4-trifluoro-benzoic acid (3.0 g, 11.8 mmol) in toluene (93 mL) was bubbled with nitrogen for 10 minutes. 3-Fluoro-2-methoxy-4-(trifluoromethoxy) phenol (4.0 g, 17.7 mmol, see Example 113, Step 1) and $Cs_2CO_3$ (8.05 g, 24.7 mmol) were added solution and bubbled with nitrogen for 10 minutes. Copper (I) iodide (2.32 g, 12.2 mmol) was added and the mixture bubbled with nitrogen for 10 minutes. The mixture was heated at 100° C. with vigorous stirring under nitrogen for 6.5 hours. The mixture was allowed to cool, partitioned between ethyl acetate and water and acidified with 1 M aqueous HCl. The layers were separated and the aqueous layer was extracted with additional ethyl acetate (3×). The combined organic layers were washed with water and brine, dried over $Na_2SO_4$, filtered through Celite and concentrated. Purification by reverse phase HPLC (1-99% acetonitrile/5 mM HCl) provided 2,3,4-trifluoro-6-[3-fluoro-2-methoxy-4-(trifluoromethoxy)phenoxy]benzoic acid (2.211 g, 47%). ESI-MS m z calc. 400.02, found 401.1 $(M+1)^+$; LC/MS retention time (Method C): 2.56 minutes. $^1H$ NMR (400 MHz, DMSO-$d_6$) δ 14.08 (s, 1H), 7.31 (t, J=8.9 Hz, 1H), 7.26-7.13 (m, 1H), 6.96 (dd, J=9.4, 2.2 Hz, 1H), 3.89 (s, 3H) ppm.

Step 2: 2,3,4-Trifluoro-6-[3-Fluoro-2-Methoxy-4-(Trifluoromethoxy)Phenoxy]Benzoyl Chloride

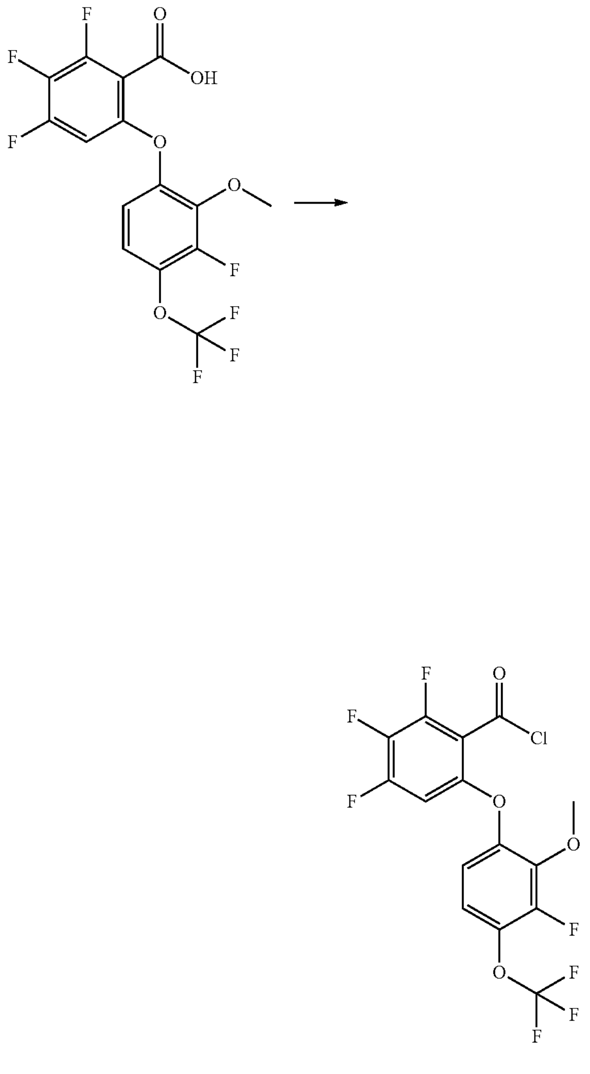

To 2,3,4-trifluoro-6-[3-fluoro-2-methoxy-4-(trifluoromethoxy)phenoxy]benzoic acid (100 mg, 0.250 mmol) and DMF (15 μL, 0.19 mmol) in dichloromethane (2 mL) at 0° C. was added oxalyl chloride (63 μL, 0.72 mmol) dropwise under nitrogen atmosphere. The ice bath was removed after 10 minutes and the mixture was stirred at room temperature for 1 hour. The concentrated in vacuo to afford 2,3,4-trifluoro-6-[3-fluoro-2-methoxy-4-(trifluoromethoxy)phenoxy]benzoyl chloride which was used in the next step without further purification.

Step 3: 4-[[2,3,4-Trifluoro-6-[3-Fluoro-2-Methoxy-4-(Trifluoromethoxy)Phenoxy]Benzoyl]Amino]Pyridine-2-Carboxamide (307)

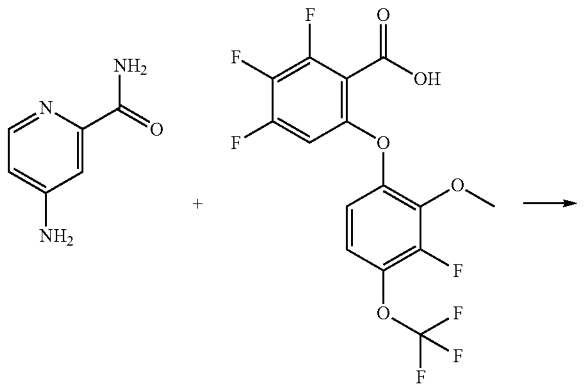

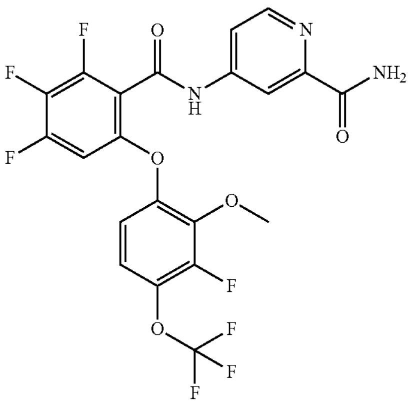

To a solution of 4-aminopyridine-2-carboxamide (41 mg, 0.30 mmol) and DIEA (131 µL, 0.750 mmol) in NMP (0.5 mL) at 0° C. was slowly added a solution of 2,3,4-trifluoro-6-[3-fluoro-2-methoxy-4-(trifluoromethoxy)phenoxy]benzoyl chloride (63 mg, 0.15 mmol) in NMP (0.5 mL). The mixture was stirred at room temperature for 19 hours. Purification by reverse phase HPLC (10-99% acetonitrile/5 mM HCl) provided 4-[[2,3,4-trifluoro-6-[3-fluoro-2-methoxy-4-(trifluoromethoxy)phenoxy]benzoyl]amino]pyridine-2-carboxamide (13.4 mg, 17%). ESI-MS m z calc. 519.07, found 520.1 $(M+1)^+$; LC/MS retention time (Method C): 2.44 minutes. $^1H$ NMR (400 MHz, DMSO-$d_6$) δ 11.46 (s, 1H), 8.55 (d, J=5.5 Hz, 1H), 8.28 (d, J=2.1 Hz, 1H), 8.10 (s, 1H), 7.79 (dd, J=5.5, 2.1 Hz, 1H), 7.67 (s, 1H), 7.32 (t, J=8.7 Hz, 1H), 7.29-7.19 (m, 1H), 7.08 (dd, J=9.4, 2.1 Hz, 1H), 3.85 (s, 3H) ppm.

Example 118

5-[[2,3,4-Trifluoro-6-[3-Fluoro-2-Methoxy-4-(Trifluoromethoxy)Phenoxy]Benzoyl]Amino]Pyrimidine-2-Carboxamide (308)

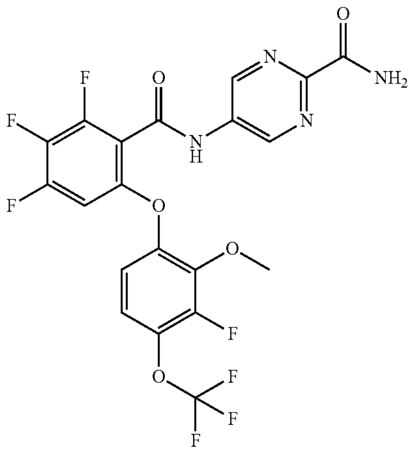 [SMILES: COc1c(Oc2cc(F)c(F)c(F)c2C(=O)Nc2cnc(C(N)=O)nc2)ccc(OC(F)(F)F)c1F]

This compound was made in an analogous fashion to the synthesis of compound 307 in Example 117, except employing methyl 5-aminopyrimidine-2-carboxylate in the amide formation step. The yield of methyl 5-[[2,3,4-trifluoro-6-[3-fluoro-2-methoxy-4-(trifluoromethoxy)phenoxy]benzoyl]amino]pyrimidine-2-carboxylate after purification was 112.3 mg (42%). ESI-MS m z calc. 535.06, found 536.1 $(M+1)^+$; LC/MS retention time (Method A): 0.65 minutes. Analogous treatment with methanolic ammonia provided 5-[[2,3,4-trifluoro-6-[3-fluoro-2-methoxy-4-(trifluoromethoxy)phenoxy]benzoyl]amino]pyrimidine-2-carboxamide (73.8 mg, 28%) as an off-white solid. ESI-MS m z calc. 520.06, found 521.1 $(M+1)^+$; LC/MS retention time (Method E): 2.23 minutes. $^1H$ NMR (400 MHz, DMSO-$d_6$) δ 11.56 (s, 1H), 9.14 (s, 2H), 8.13 (s, 1H), 7.74 (s, 1H), 7.40-7.20 (m, 2H), 7.08 (dd, J=9.3, 2.1 Hz, 1H), 3.86 (s, 3H) ppm.

Example 119

4-[[4-Chloro-2-Fluoro-6-[3-Fluoro-2-Methoxy-4-(Trifluoromethoxy)Phenoxy]-3-Methyl-Benzoyl]Amino]Pyridine-2-Carboxamide (309)

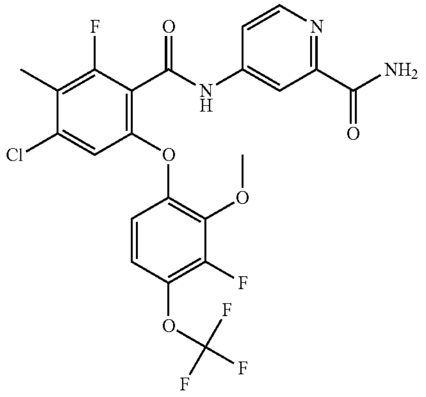

Step 1: Methyl 4-Chloro-2-Fluoro-6-[3-Fluoro-2-Methoxy-4-(Trifluoromethoxy)Phenoxy]Benzoate

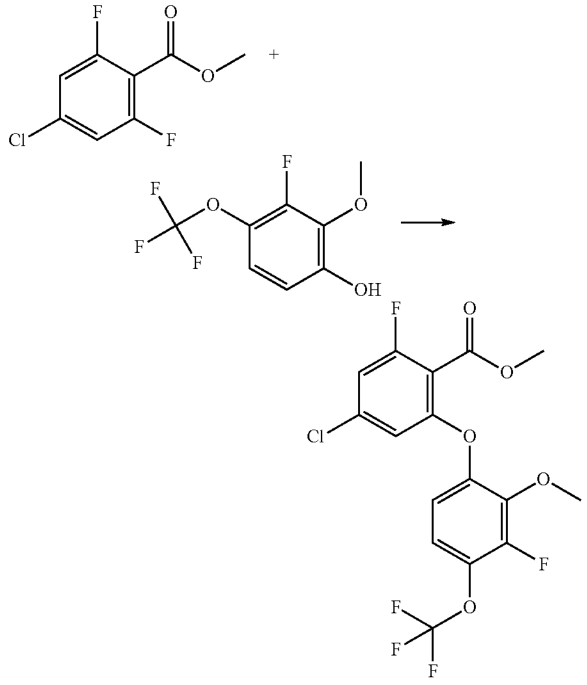

A mixture of methyl 4-chloro-2,6-difluoro-benzoate (1000 mg, 4.841 mmol), 3-fluoro-2-methoxy-4-(trifluoromethoxy)phenol (1.07 g, 4.73 mmol, see Example 113, Step 1) and $Cs_2CO_3$ (2.5 g, 7.7 mmol) in DMF (40 mL) was stirred at 70° C. for 48 hours. The mixture was partitioned between ethyl acetate and brine and the layers separated. The organic layer was washed with brine, dried over $MgSO_4$, filtered and evaporated. Purification by silica gel chromatography (0-20% ethyl acetate) provided methyl 4-chloro-2-fluoro-6-[3-fluoro-2-methoxy-4-(trifluoromethoxy)phenoxy]benzoate (540 mg, 27%). $^1H$ NMR (400 MHz, $CDCl_3$) δ 7.06 (tq, J=7.7, 1.3 Hz, 1H), 6.91 (ddd, J=22.5, 9.1, 2.1 Hz, 2H), 6.56 (t, J=1.6 Hz, 1H), 3.99-3.88 (m, 6H) ppm.

Step 2: Methyl 4-Chloro-2-Fluoro-6-[3-Fluoro-2-Methoxy-4-(Trifluoromethoxy)Phenoxy]-3-Methyl-Benzoate

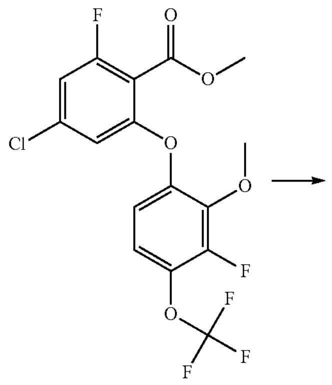

-continued

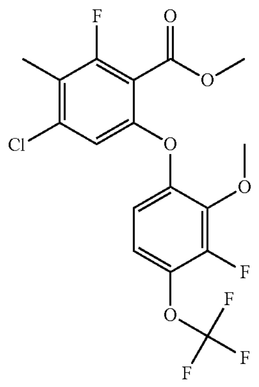

A solution of n-butyllithium (570 μL of 1.6 M in hexanes, 0.9120 mmol) was added to a stirring solution of diisopropylamine (120 μL, 0.856 mmol) in THF (7 mL) at −78° C. The mixture was then stirred at 0° C. for 20 minutes. The resulting LDA solution was added dropwise to a solution methyl 4-chloro-2-fluoro-6-[3-fluoro-2-methoxy-4-(trifluoromethoxy)phenoxy]benzoate (250 mg, 0.606 mmol) in THF (5 mL) at −78° C. The mixture was stirred at this temperature for 10 minutes then methyl iodide (102 μL, 1.64 mmol) was added. The mixture was stirred at −78° C. for 30 minutes then allowed to warm to room temperature. The mixture was diluted with water and extracted with ethyl acetate (3×). The combined organic extracts were dried over $MgSO_4$, filtered and concentrated in vacuo to provide methyl 4-chloro-2-fluoro-6-[3-fluoro-2-methoxy-4-(trifluoromethoxy)phenoxy]-3-methyl-benzoate (225 mg, 44%). $^1H$ NMR (400 MHz, $CDCl_3$) δ 6.95-6.91 (m, 1H), 6.74 (dd, J=9.2, 2.3 Hz, 1H), 6.54 (d, J=1.8 Hz, 1H), 3.86 (d, J=1.3 Hz, 3H), 3.82 (s, 3H), 2.20 (d, J=2.4 Hz, 3H) ppm. The isolated product contained unreacted starting material but was taken forward to the next step without additional purification.

Step 3: 4-Chloro-2-Fluoro-6-[3-Fluoro-2-Methoxy-4-(Trifluoromethoxy)Phenoxy]-3-Methyl-Benzoic Acid

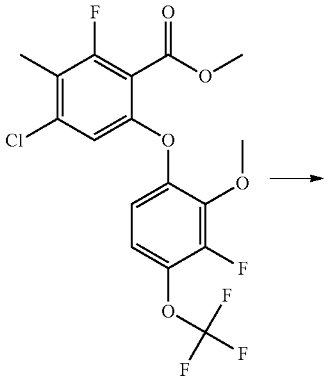

-continued

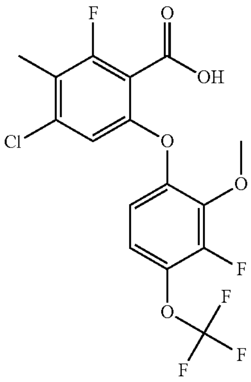

To a slurry of methyl 4-chloro-2-fluoro-6-[3-fluoro-2-methoxy-4-(trifluoromethoxy)phenoxy]-3-methyl-benzoate (300 mg, 0.253 mmol) in methanol (10 mL) and water (10 mL) was added NaOH (307 mg, 7.68 mmol) and the mixture was stirred at 50° C. for 18 hours. The mixture was cooled to room temperature, partially concentrated in vacuo to remove the methanol, and acidified with 2 M aqueous HCl. The mixture was extracted with ethyl acetate (3×), and the combined organic extracts were dried over $MgSO_4$, filtered and concentrated in vacuo to provide 4-chloro-2-fluoro-6-[3-fluoro-2-methoxy-4-(trifluoromethoxy)phenoxy]-3-methyl-benzoic acid (245 mg, 30%) as a white solid. ESI-MS m z calc. 412.01, found 413.0 $(M+1)^+$; LC/MS retention time (Method F): 0.62 minutes.

Step 4: 4-[[4-Chloro-2-Fluoro-6-[3-Fluoro-2-Methoxy-4-(Trifluoromethoxy)Phenoxy]-3-Methyl-Benzoyl]Amino]Pyridine-2-Carboxamide (309)

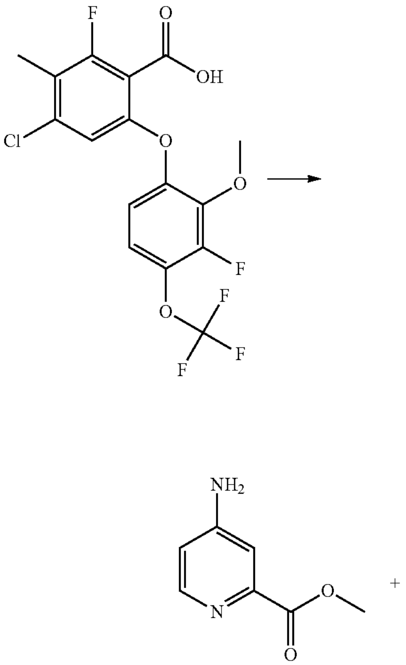

-continued

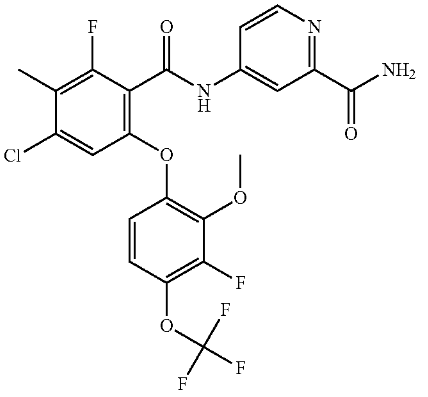 [SMILES: COc1c(Oc2cc(Cl)c(C)c(F)c2C(=O)Nc2ccnc(C(N)=O)c2)ccc(OC(F)(F)F)c1F]

To a solution of 4-chloro-2-fluoro-6-[3-fluoro-2-methoxy-4-(trifluoromethoxy)phenoxy]-3-methyl-benzoic acid (245 mg, 0.5937 mmol) and DMF (10 μL, 0.1291 mmol) in dichloromethane (2 mL) at 0° C. was carefully added oxalyl chloride (160 μL, 1.834 mmol) and the mixture allowed to warmed to room temperature over 1 hour. The mixture was concentrated in vacuo, dissolved in dichloromethane (2 mL) and added dropwise to a solution of methyl 4-aminopyridine-2-carboxylate (110 mg, 0.723 mmol), DMAP (1 mg, 0.008 mmol) and TEA (415 μL, 2.98 mmol) in dichloromethane (2 mL) at 0° C. The resulting mixture was stirred and warmed to ambient temperature overnight. The mixture was diluted with water and the layers separated. The aqueous layer was extracted with additional dichloromethane (2×) and the combined organics extracts were dried over $MgSO_4$, filtered and concentrated in vacuo. A solution of ammonia (3 mL of 3 M in methanol, 9 mmol) was then added to the residue and the mixture stirred overnight. The mixture was concentrated in vacuo and purified by reverse phase HPLC (47-95% acetonitrile/0.1% ammonium hydroxide) to provide 4-[[4-chloro-2-fluoro-6-[3-fluoro-2-methoxy-4-(trifluoromethoxy)phenoxy]-3-methyl-benzoyl]amino]pyridine-2-carboxamide (6.7 mg, 2%). ESI-MS m z calc. 531.06, found 532.1 $(M+1)^+$; 530.2 $(M-1)^-$; LC/MS retention time (Method E): 3.32 minutes. $^1H$ NMR (400 MHz, $CDCl_3$) δ 8.86 (s, 1H), 8.54 (d, J=5.6 Hz, 1H), 8.35 (dd, J=5.6, 2.2 Hz, 1H), 7.99 (d, J=2.2 Hz, 1H), 7.87 (d, J=4.6 Hz, 1H), 7.09 (ddd, J=9.0, 7.7, 1.3 Hz, 1H), 6.99 (dd, J=9.2, 2.2 Hz, 1H), 6.65 (d, J=1.8 Hz, 1H), 5.47 (s, 1H), 3.91 (d, J=2.1 Hz, 3H), 2.33 (d, J=2.5 Hz, 3H) ppm.

Example 120

4-[[3-Cyclobutyl-2-Fluoro-6-[3-Fluoro-2-Methoxy-4-(Trifluoromethoxy)Phenoxy]Benzoyl]Amino]Pyridine-2-Carboxamide (310)

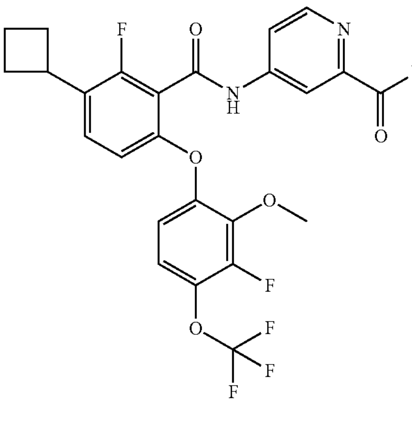

Step 1: 3-Bromo-2-Fluoro-6-[3-Fluoro-2-Methoxy-4-(Trifluoromethoxy)Phenoxy]Benzoic Acid

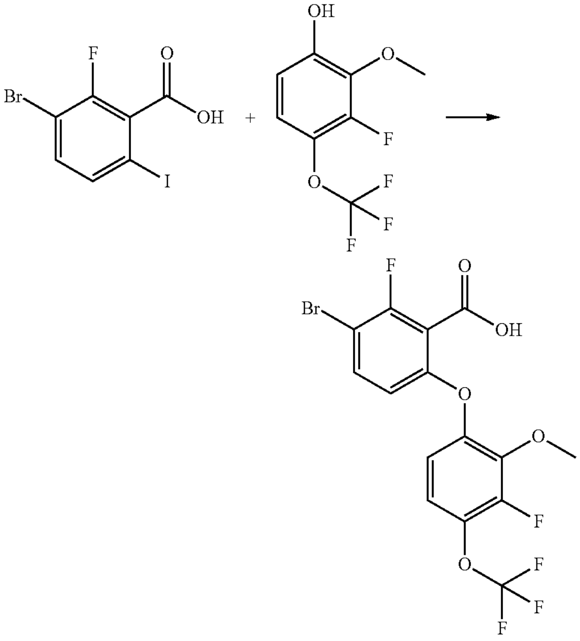

To a pressure flask was added 3-bromo-2-fluoro-6-iodobenzoic acid (2.0 g, 5.8 mmol), 3-fluoro-2-methoxy-4-(trifluoromethoxy)phenol (1.31 g, 5.79 mmol, see Example 113, Step 1), $Cs_2CO_3$ (2.83 g, 8.69 mmol) and toluene (36 mL). The mixture was bubbled with nitrogen for 15 minutes, then copper (I) iodide (1.10 g, 5.78 mmol) was added. The mixture was heated at 100° C. with vigorous stirring for 16 hours under nitrogen. The cooled mixture was partitioned between ethyl acetate and water, and the water layer acidified with 1 M aqueous HCl. The layers were separated, and the aqueous layer extracted with additional ethyl acetate (3×). The combined organic extracts were dried over $Na_2SO_4$, filtered and concentrated in vacuo. The residue was purified by reverse phase chromatography (acetonitrile/5 mM HCl) to provide 3-bromo-2-fluoro-6-[3-fluoro-2-methoxy-4-(trifluoromethoxy)phenoxy]benzoic acid (1.57 g, 61%). ESI-MS m z calc. 441.95, found 445.15 $(M+1)^+$; LC/MS retention time (Method A): 0.7 minutes. $^1H$ NMR (400 MHz, $CDCl_3$) δ 7.55 (dd, J=9.0, 7.5 Hz, 1H), 7.04 (ddd, J=9.3, 7.8, 1.5 Hz, 1H), 6.89 (dd, J=9.2, 2.2 Hz, 1H), 6.50 (dd, J=8.9, 1.5 Hz, 1H), 3.92 (d, J=1.5 Hz, 3H) ppm.

Step 2: Tert-Butyl 3-Bromo-2-Fluoro-6-[3-Fluoro-2-Methoxy-4-(Trifluoromethoxy)Phenoxy]Benzoate

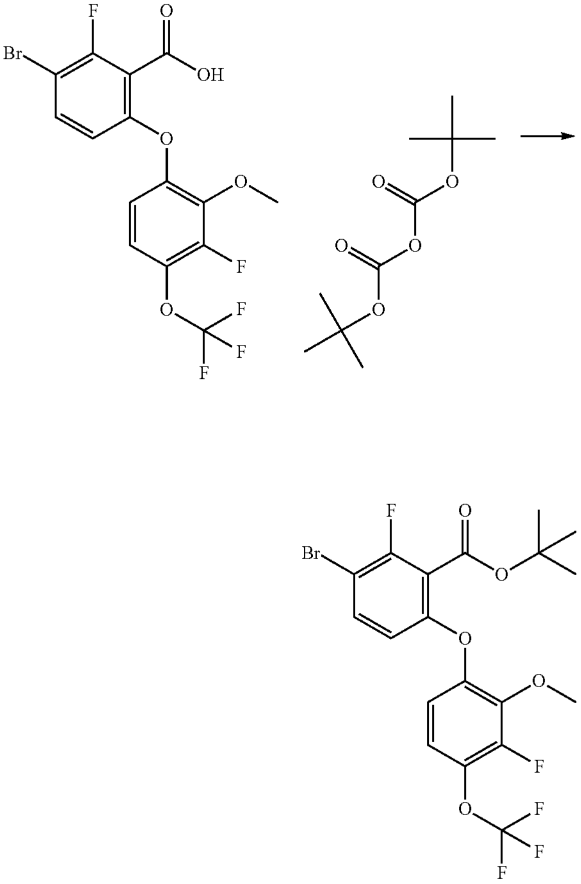

A mixture of 3-bromo-2-fluoro-6-[3-fluoro-2-methoxy-4-(trifluoromethoxy)phenoxy]benzoic acid (1570 mg, 3.543 mmol), tert-butoxycarbonyl tert-butyl carbonate (1158 mg, 5.306 mmol), DMAP (88 mg, 0.72 mmol), and t-BuOH (5 mL) was heated at 90° C. for 1 hour. The mixture was cooled and additional tert-butoxycarbonyl tert-butyl carbonate (1158 mg, 5.306 mmol) added. The mixture was stirred at 90° C. for 10 minutes, then cooled to room temperature and concentrated in vacuo. The residue was purified by silica gel chromatography (1-10% ethyl acetate/hexanes) to provide tert-butyl 3-bromo-2-fluoro-6-[3-fluoro-2-methoxy-4-(trifluoromethoxy)phenoxy]benzoate (1.65 g, 93%). $^1H$ NMR (400 MHz, $CDCl_3$) δ 7.48 (dd, J=8.9, 7.6 Hz, 1H), 6.99 (tt, J=7.8, 1.2 Hz, 1H), 6.76 (dd, J=9.2, 2.3 Hz, 1H), 6.52 (dd, J=8.9, 1.5 Hz, 1H), 3.95 (d, J=1.2 Hz, 3H), 1.52 (s, 9H) ppm.

Step 3: Tert-Butyl 3-Cyclobutyl-2-Fluoro-6-[3-Fluoro-2-Methoxy-4-(Trifluoromethoxy)Phenoxy] Benzoate

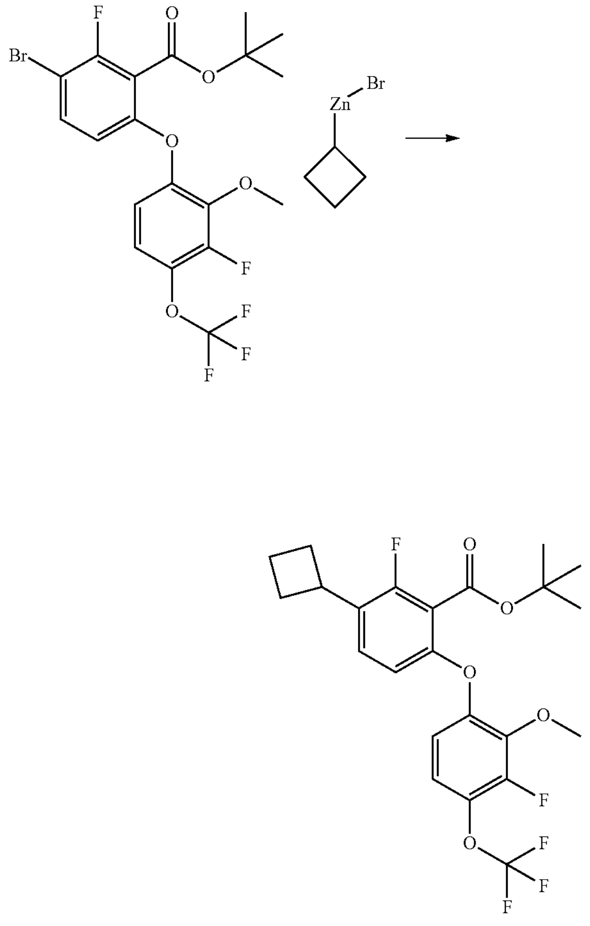

A mixture of tert-butyl 3-bromo-2-fluoro-6-[3-fluoro-2-methoxy-4-(trifluoromethoxy)phenoxy]benzoate (330 mg, 0.661 mmol) and $Pd(t\text{-}Bu_3P)_2$ (16 mg, 0.031 mmol) in THF (2.75 mL) at 0° C. under nitrogen was slowly treated with a solution of cyclobutylzinc bromide (2.6 mL of 0.5 M, 1.3 mmol) in THF. The mixture was allowed to warm to room temperature over 1 hour, then diluted with 1 M aqueous HCl and extracted with dichloromethane (2×). The combined organic extracts were dried over $Na_2SO_4$, filtered and concentrated. The residue was purified by silica gel chromatography (1-15% ethyl acetate/hexanes) to provide tert-butyl 3-cyclobutyl-2-fluoro-6-[3-fluoro-2-methoxy-4-(trifluoromethoxy)phenoxy]benzoate (215 mg, 69%). $^1H$ NMR (400 MHz, $CDCl_3$) δ 7.21 (t, J=8.4 Hz, 1H), 6.94 (ddd, J=9.2, 7.9, 1.3 Hz, 1H), 6.66 (dd, J=9.3, 2.3 Hz, 1H), 6.62 (dd, J=8.6, 1.2 Hz, 1H), 3.98 (d, J=1.0 Hz, 3H), 3.70 (p, J=8.6 Hz, 1H), 2.44-2.29 (m, 2H), 2.25-1.97 (m, 3H), 1.94-1.81 (m, 1H), 1.48 (s, 9H) ppm.

Step 4: 3-Cyclobutyl-2-Fluoro-6-[3-Fluoro-2-Methoxy-4-(Trifluoromethoxy)Phenoxy]Benzoic Acid

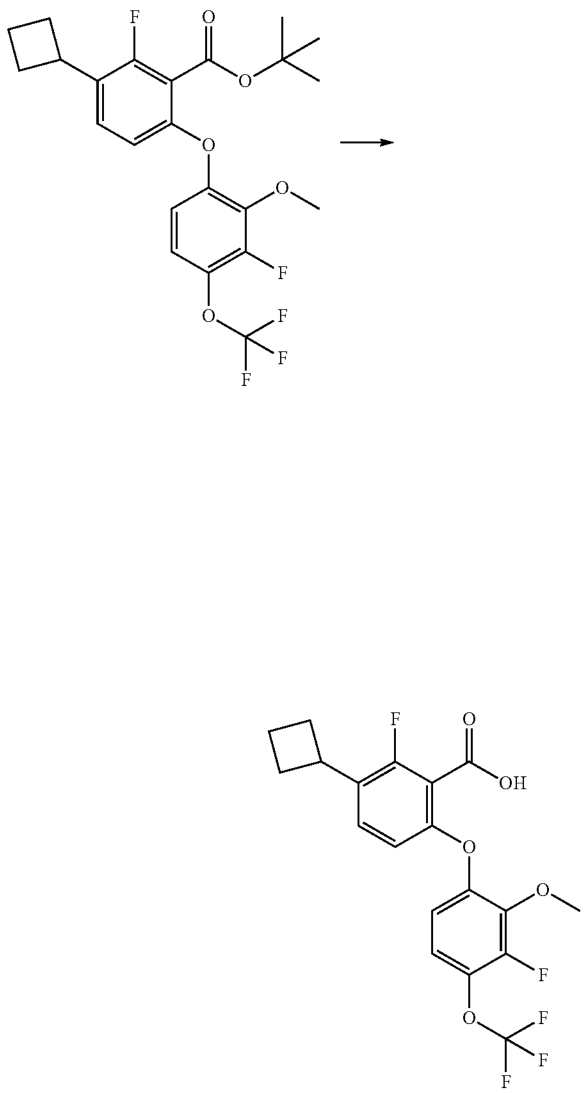

To a solution of tert-butyl 3-cyclobutyl-2-fluoro-6-[3-fluoro-2-methoxy-4-(trifluoromethoxy)phenoxy]benzoate (205 mg, 0.432 mmol) in THF (8 mL) and water (0.3 mL, 16.65 mmol) at 0° C. was added TFA (8 mL, 103.8 mmol) dropwise over approximately 4 minutes. The ice bath was removed and the solution stirred at room temperature for 2.5 hours. The mixture was concentrated in vacuo to provide 3-cyclobutyl-2-fluoro-6-[3-fluoro-2-methoxy-4-(trifluoromethoxy)phenoxy]benzoic acid (175 mg, 92%). ESI-MS m z calc. 418.08, found 419.28 $(M+1)^+$; LC/MS retention time (Method B): 1.98 minutes. $^1H$ NMR (400 MHz, $CDCl_3$) δ 7.28 (t, J=8.5 Hz, 1H), 7.00 (ddd, J=9.2, 7.9, 1.3 Hz, 1H), 6.81 (dd, J=9.2, 2.2 Hz, 1H), 6.58 (dd, J=8.7, 1.3 Hz, 1H), 3.93 (d, J=1.3 Hz, 3H), 3.71 (p, J=8.8 Hz, 1H), 2.41-2.31 (m, 2H), 2.21-1.99 (m, 3H), 1.88 (td, J=7.9, 3.0 Hz, 1H) ppm.

Step 5: 4-[[3-Cyclobutyl-2-Fluoro-6-[3-Fluoro-2-Methoxy-4-(Trifluoromethoxy)Phenoxy]Benzoyl]Amino]Pyridine-2-Carboxamide (310)

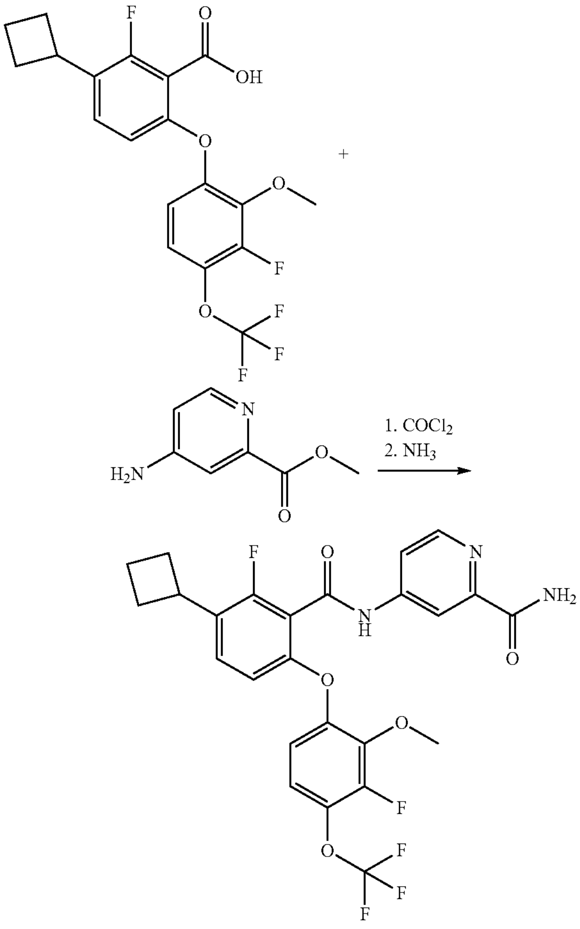

To a solution of 3-cyclobutyl-2-fluoro-6-[3-fluoro-2-methoxy-4-(trifluoromethoxy)phenoxy]benzoic acid (50 mg, 0.12 mmol) in dichloromethane (2 mL) at 0° C. was added DMF (2 μL, 0.03 mmol) followed by the dropwise addition of oxalyl chloride (21 μL, 0.24 mmol). The mixture was stirred at 0° C. for 10 minutes then at room temperature for 4 hours. The mixture was concentrated in vacuo to afford the acid chloride. The acid chloride was dissolved in 2-MeTHF (2 mL) and added dropwise to a solution of methyl 4-aminopyridine-2-carboxylate (20 mg, 0.13 mmol) and DIEA (53 μL, 0.30 mmol) in 2-MeTHF (800 μL). The mixture was heated at 60° C. for 16 hours. The cooled mixture was diluted with ethyl acetate and washed with 1 M aqueous HCl (2×) and brine. The organic phase was dried over $Na_2SO_4$, filtered and concentrated in vacuo. The residue was purified by silica gel chromatography (ethyl acetate/hexanes gradient) to provide methyl 4-[[3-cyclobutyl-2-fluoro-6-[3-fluoro-2-methoxy-4-(trifluoromethoxy)phenoxy]benzoyl]amino]pyridine-2-carboxylate. The material was stirred in a solution of ammonia in methanol (7 mL of 7 M, 49 mmol) at room temperature for 16 hours. The mixture was concentrated in vacuo to provide 4-[[3-cyclobutyl-2-fluoro-6-[3-fluoro-2-methoxy-4-(trifluoromethoxy)phenoxy]benzoyl]amino]pyridine-2-carboxamide (31 mg, 48%). ESI-MS m z calc. 537.13, found 538.34 $(M+1)^+$; LC/MS retention time (Method B): 1.90 minutes. $^1H$ NMR (400 MHz, $CDCl_3$) δ 8.78 (s, 1H), 8.51 (d, J=5.6 Hz, 1H), 8.41-8.31 (m, 1H), 7.95 (d, J=2.2 Hz, 1H), 7.91 (s, 1H), 7.29 (d, J=8.4 Hz, 1H), 7.05 (t, J=8.5 Hz, 1H), 6.94 (dd, J=9.3, 2.1 Hz, 1H), 6.57 (d, J=8.6 Hz, 1H), 5.45 (s, 1H), 3.84 (d, J=1.8 Hz, 3H), 3.71 (q, J=8.8 Hz, 1H), 2.37 (m, 2H), 2.11 (m, 3H), 1.88 (m, 1H) ppm.

Example 121

4-[[2,2-Difluoro-6-[3-Fluoro-2-Methoxy-4-(Trifluoromethoxy)Phenoxy]-1,3-Benzodioxole-5-Carbonyl]Amino]Pyridine-2-Carboxamide (311)

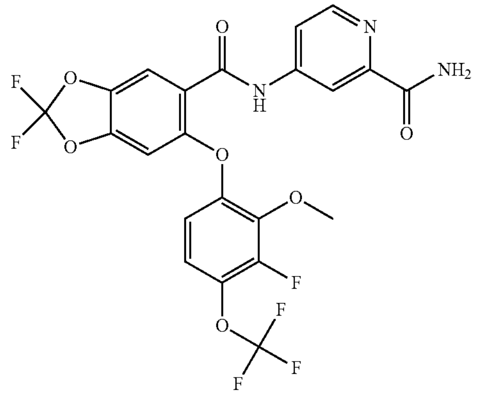 [SMILES: COc1c(Oc2cc3c(cc2C(=O)Nc2ccnc(C(N)=O)c2)OC(F)(F)O3)ccc(OC(F)(F)F)c1F]

Step 1: Ethyl 2-Bromo-4,5-Dimethoxy-Benzoate

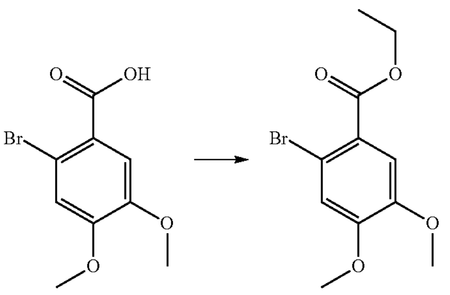 [SMILES: COc1cc(Br)c(C(=O)O)cc1OC ; CCOC(=O)c1cc(OC)c(OC)cc1Br]

A solution of 2-bromo-4,5-dimethoxy-benzoic acid (30.0 g, 115 mmol) and sulfuric acid (2.8 g, 1.5 mL, 28 mmol) in ethanol (300 mL) was heated to reflux and stirred for 72 hours. The mixture was concentrated to approximately 20 mL in vacuo, diluted with saturated aqueous $NaHCO_3$ (300 mL) and extracted with ethyl acetate (3×300 mL). The combined organic phases were washed with brine (300 mL), dried over $Na_2SO_4$, filtered and concentrated to provide ethyl 2-bromo-4,5-dimethoxy-benzoate (27.97 g, 83%) as a yellow solid. ESI-MS m z calc. 288.00, no ionization observed; LC/MS retention time (Method N): 4.98 minutes.

Step 2: Ethyl 2-Bromo-4,5-Dihydroxy-Benzoate

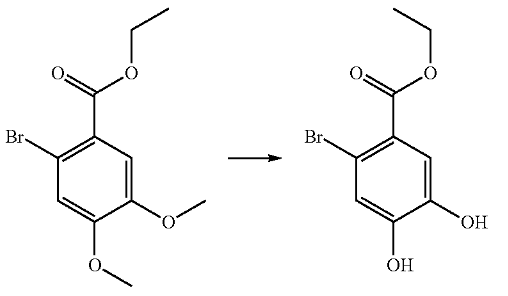 [SMILES: CCOC(=O)c1cc(OC)c(OC)cc1Br ; CCOC(=O)c1cc(O)c(O)cc1Br]

To a solution of ethyl 2-bromo-4,5-dimethoxy-benzoate (28.0 g, 96.8 mmol) in dichloromethane (500 mL) at −78° C. under nitrogen was added $BBr_3$ (79.2 g, 30 mL, 316 mmol) dropwise. The mixture was allowed to slowly warm to room temperature and stirred overnight, after which it was cautiously added into absolute ethanol at 0° C. The mixture was evaporated and the residue was partitioned between ethyl acetate (1 L) and 1 M aqueous potassium phosphate buffer with pH=7 (1 L). The organic phase was separated, washed with brine (500 mL), dried over $Na_2SO_4$, filtered and concentrated in vacuo. The residue was recrystallized from ethyl acetate/hexanes to provide ethyl 2-bromo-4,5-dihydroxy-benzoate (20.7 g, 80%) as an off-white solid. ESI-MS m z calc. 259.97, no ionization observed; LC/MS retention time (Method N): 3.65 minutes.

Step 3: Ethyl 6-Bromo-2-Thioxo-1,3-Benzodioxole-5-Carboxylate

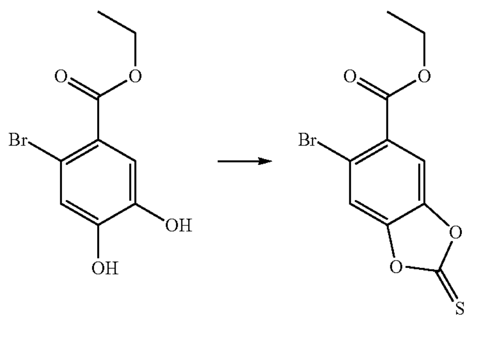 [SMILES: CCOC(=O)c1cc(O)c(O)cc1Br ; CCOC(=O)c1cc2oc(=S)oc2cc1Br]

A solution of imidazole (2.816 g, 41.37 mmol) in dichloromethane (100 mL) at 0° C. was treated dropwise with thiophosgene (1.28 g, 0.85 mL, 11.1 mmol). The mixture was allowed to stir for 15 minutes and then treated portionwise with ethyl 2-bromo-4,5-dihydroxy-benzoate (2.7 g, 10.342 mmol). The mixture was allowed to slowly warm to room temperature and stir for 2 hours. The mixture was washed with saturated aqueous $NaHCO_3$ (100 mL) and the layers separated. The organic phase was dried over $Na_2SO_4$, filtered and concentrated in vacuo to provide ethyl 6-bromo-2-thioxo-1,3-benzodioxole-5-carboxylate (2.95 g, 89%) as an off-white solid. ESI-MS m z calc. 301.92, no ionization observed; LC/MS retention time (Method N): 5.95 minutes.

Step 4: Ethyl 6-Bromo-2,2-Difluoro-1,3-Benzodioxole-5-Carboxylate

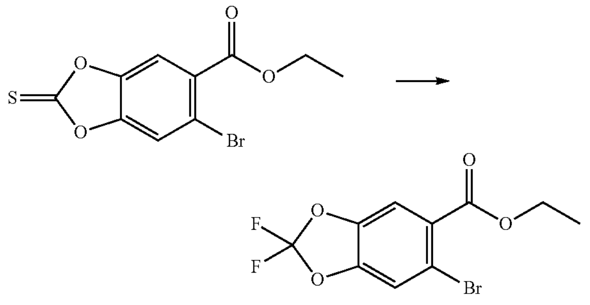

A solution of ethyl 6-bromo-2-thioxo-1,3-benzodioxole-5-carboxylate (19.1 g, 63.0 mmol) in dichloromethane (500 mL) was cooled to −40° C. using a dry ice/acetonitrile bath and treated with HF-pyridine (100 g, 90.9 mL, 718.81 mmol) followed by the portion-wise addition of N-iodosuccinimide (42.53 g, 189.0 mmol). The mixture was stirred at −40° C. for 1 hour, then diluted with saturated aqueous $NaHSO_3$ (5 mL) and water (30 mL). The organic phase was separated, dried over $Na_2SO_4$, filtered and concentrated in vacuo. Purification by silica gel chromatography (5% ethyl acetate/hexanes) provided ethyl 6-bromo-2,2-difluoro-1,3-benzodioxole-5-carboxylate (9.8 g, 50%) as a colorless oil. ESI-MS m z calc. 309.95, found 311.6 $(M+1)^+$; LC/MS retention time (Method N): 6.34 minutes

Step 5: 6-Bromo-2,2-Difluoro-1,3-Benzodioxole-5-Carboxylic Acid

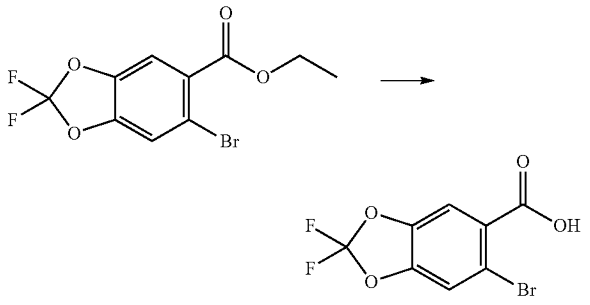

To a solution of ethyl 6-bromo-2,2-difluoro-1,3-benzodioxole-5-carboxylate (9.8 g, 31.7 mmol) in methanol (100 mL) and water (11.5 g, 11.5 mL, 638 mmol) was added LiOH monohydrate (13.3 g, 317 mmol). The mixture was stirred 15 minutes then concentrated in vacuo. The residue was diluted with water (250 mL) and washed with diethyl ether (3×250 mL). The aqueous phase was acidified with 3 M aqueous HCl until pH=1 and extracted with ethyl acetate (3×300 mL). The combined organic extracts were dried over $MgSO_4$, filtered and concentrated in vacuo to provide 6-bromo-2,2-difluoro-1,3-benzodioxole-5-carboxylic acid (7.74 g, 87%) as an off white solid. $^1H$ NMR (500 MHz, DMSO-$d_6$) δ 7.92 (s, 1H), 7.84 (s, 1H) ppm. ESI-MS m z calc. 279.92, no ionization observed; LC/MS retention time (Method Q): 2.01 minutes.

Step 6: 2,2-Difluoro-6-[3-Fluoro-2-Methoxy-4-(Trifluoromethoxy)Phenoxy]-1,3-Benzodioxole-5-Carboxylic Acid

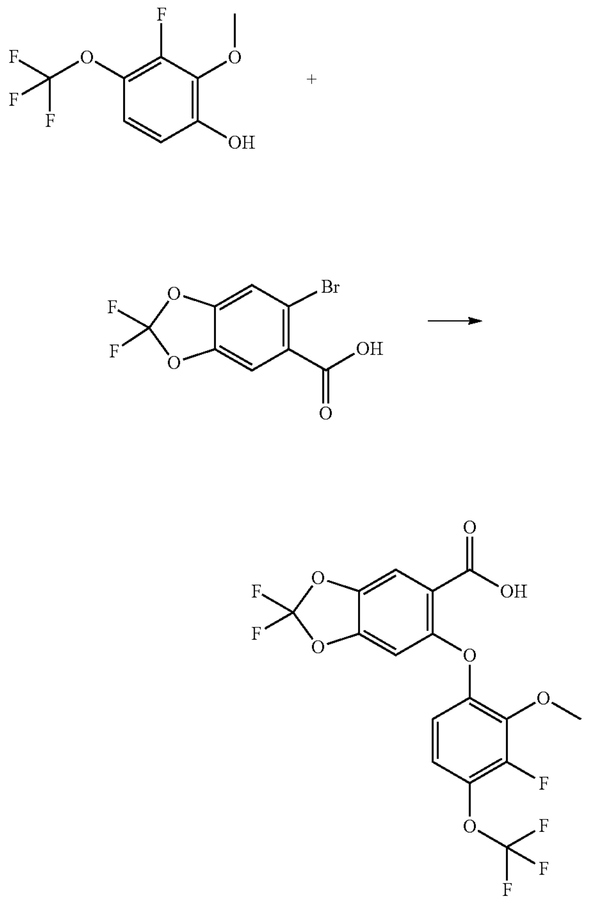

A mixture of 6-bromo-2,2-difluoro-1,3-benzodioxole-5-carboxylic acid (2.0 g, 7.1 mmol) in toluene (45 mL) was bubbled with nitrogen for 10 minutes. 3-Fluoro-2-methoxy-4-(trifluoromethoxy)phenol (2.516 g, 11.13 mmol, see Example 113, Step 1) and $Cs_2CO_3$ (5.14 g, 15.8 mmol) were added and the mixture bubbled with nitrogen for 10 minutes. Copper (I) iodide (317 mg, 1.66 mmol) was added to the mixture and bubbled with nitrogen for 10 minutes. The mixture was then heated at 100° C. under nitrogen with vigorous stirring for 72 hours. The cooled mixture was partitioned between ethyl acetate and water, and acidified with 1 M aqueous HCl. The layers were separated, and the aqueous layer was extracted with additional ethyl acetate (3×). The combined organic extracts were washed with water and brine, dried over $Na_2SO_4$, filtered through Celite and concentrated in vacuo. The residue was purified by reverse phase HPLC (1-99% acetonitrile/5 mM HCl) to provide 2,2-difluoro-6-[3-fluoro-2-methoxy-4-(trifluoromethoxy)phenoxy]-1,3-benzodioxole-5-carboxylic acid (1.085 g, 36%) as a yellow solid. ESI-MS m z calc. 426.02, found 427.3 $(M+1)^+$; LC/MS retention time (Method C): 2.74 minutes. $^1H$ NMR (400 MHz, DMSO-$d_6$) δ 13.27 (s, 1H), 7.89 (s, 1H), 7.46 (s, 1H), 7.21 (t, J=8.8 Hz, 1H), 6.68 (dd, J=9.4, 2.1 Hz, 1H), 3.94 (s, 3H) ppm.

Step 7: 4-[[2,2-Difluoro-6-[3-Fluoro-2-Methoxy-4-(Trifluoromethoxy)Phenoxy]-1,3-Benzodioxole-5-Carbonyl]Amino]Pyridine-2-Carboxamide (311)

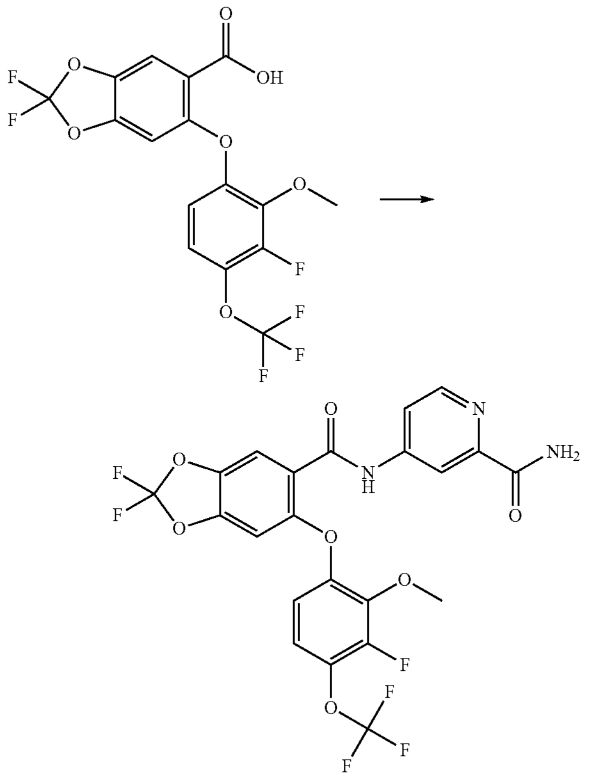

To a solution of 2,2-difluoro-6-[3-fluoro-2-methoxy-4-(trifluoromethoxy)phenoxy]-1,3-benzodioxole-5-carboxylic acid (70 mg, 0.16 mmol) and DMF (15 μL, 0.19 mmol) in dichloromethane (2.0 mL) at 0° C. was added oxalyl chloride (41 μL, 0.47 mmol) dropwise under a nitrogen atmosphere. The ice bath was removed after 10 minutes and the mixture was stirred at room temperature for 1 hour. The mixture was concentrated in vacuo to afford 2,2-difluoro-6-[3-fluoro-2-methoxy-4-(trifluoromethoxy)phenoxy]-1,3-benzodioxole-5-carbonyl chloride. The acid chloride was suspended in 2-MeTHF (1 mL), cooled to 0° C., and treated with a suspension of 4-aminopyridine-2-carboxamide (34.8 mg, 0.254 mmol) in 2-methyltetrahydrofuran (1.0 mL) and DIEA (72 μL, 0.4134 mmol) at 0° C. The mixture was stirred at 75° C. for 21 hours. The mixture was concentrated in vacuo and purified using reverse phase HPLC (1-99% acetonitrile/5 mM HCl) to provide 4-[[2,2-difluoro-6-[3-fluoro-2-methoxy-4-(trifluoromethoxy)phenoxy]-1,3-benzodioxole-5-carbonyl]amino]pyridine-2-carboxamide (7.0 mg, 8%) as a white solid. ESI-MS m z calc. 545.07, found 546.1 $(M+1)^+$; LC/MS retention time (Method C): 2.61 minutes. $^1H$ NMR (400 MHz, DMSO-$d_6$) δ 10.99 (s, 1H), 8.49 (d, J=5.5 Hz, 1H), 8.28 (d, J=2.1 Hz, 1H), 8.07 (d, J=2.9 Hz, 1H), 7.88 (s, 1H), 7.79 (dd, J=5.6, 2.2 Hz, 1H), 7.62 (d, J=2.8 Hz, 1H), 7.45 (s, 1H), 7.26 (t, J=8.7 Hz, 1H), 6.91 (dd, J=9.4, 2.1 Hz, 1H), 3.86 (s, 3H) ppm.

Example 122

4-[[6-[3-Fluoro-2-Methoxy-4-(Trifluoromethoxy) Phenoxy]-2-Methyl-3-(Trifluoromethyl)Benzoyl] Amino]-5-Methyl-Pyridine-2-Carboxamide (312)

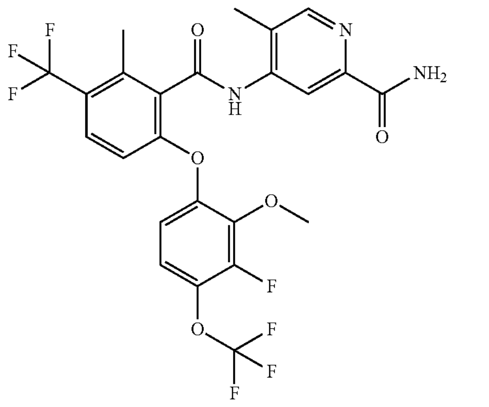 [SMILES: COc1c(Oc2ccc(C(F)(F)F)c(C)c2C(=O)Nc2cc(C(N)=O)ncc2C)ccc(OC(F)(F)F)c1F]

Step 1. 2-Bromo-6-Fluoro-3-(Trifluoromethyl)Benzoic Acid

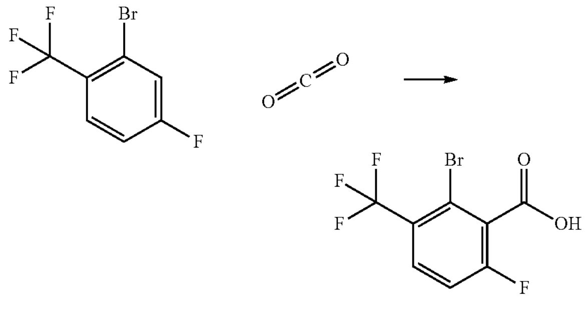

Diisopropylamine (49.96 g, 69.2 mL, 493.7 mmol) was diluted in tetrahydrofuran (1000 mL) and the mixture cooled to −20° C. n-Butyllithium (181 mL of 2.5 M in hexanes, 452 mmol) was added over 30 minutes and the mixture was stirred at −20° C. for 30 minutes. The solution was cooled to −78° C. and treated with a solution of 2-bromo-4-fluoro-1-(trifluoromethyl)benzene (100 g, 411.5 mmol) in tetrahydrofuran (100 mL) over 30 minutes. The mixture was stirred 1 hour, then carbon dioxide (181 g, 4.11 mol) pellets (dry ice) added over 20 minutes at −78° C. The mixture was stirred at −78° C. for 30 minutes, and then warmed to 0° C. over 1 hour. The mixture was diluted with water (200 mL) and MTBE (200 mL) and the aqueous layer adjusted to pH 2 with 3 M aqueous HCl (250 mL). The phases were separated and the aqueous phase was extracted with additional MTBE (3×200 mL). The combined organic layers were washed with brine (250 mL), dried over anhydrous $Na_2SO_4$ and filtered. The solution was concentrated in vacuo, then redissolved in MTBE (200 mL) and a solution of 2 M aqueous NaOH (300 mL) was added. Phases were separated and the aqueous phase washed with MTBE (2×100 mL). The aqueous solution was acidified with 12 M aqueous HCl (100 mL) and extracted with MTBE (3×100 mL). The combined organic layers were washed with brine (250 mL), dried over anhydrous $Na_2SO_4$ and concentrated in vacuo to provide 2-bromo-6-fluoro-3-(trifluoromethyl)benzoic acid (111.7 g, 89%) as a beige solid. ESI-MS m z calc. 285.93, found 570.8 $(2M-1)^-$. LC/MS retention time (Method O): 1.19 minutes. $^1H$ NMR (400 MHz, DMSO-$d_6$) δ 14.84-14.11 (m, 1H), 8.00 (dd, J=9.0, 5.6 Hz, 1H), 7.62 (t, J=8.7 Hz, 1H) ppm. $^{19}F$ NMR (377 MHz, DMSO-$d_6$) δ −60.63 (s, 3F), −107.91 (s, 1F) ppm.

Step 2: Tert-Butyl 2-Bromo-6-Fluoro-3-(Trifluoromethyl)Benzoate

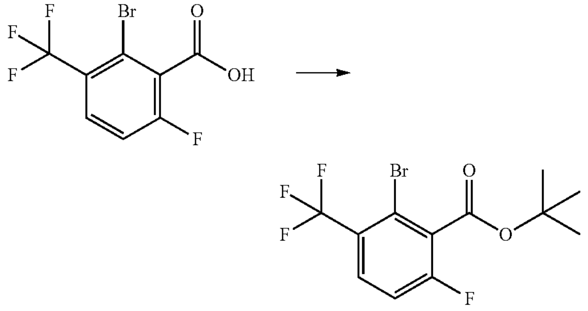

To a stirring suspension of $MgSO_4$ (8484 g, 70.48 mol) in dichloromethane (380 mL) under nitrogen atmosphere was slowly added $H_2SO_4$ (9.3 mL of 100% w/w, 174.5 mmol) via syringe. The mixture was stirred at room temperature for 30 minutes. Solid 2-bromo-6-fluoro-3-(trifluoromethyl)benzoic acid (50 g, 174 mmol) was slowly added to the stirring solution, followed by the dropwise addition of a solution of tert-butanol (83 mL, 867.8 mmol) in dichloromethane (15 mL) over 1 hour. The mixture was stirred at room temperature for 24 hours. The mixture was filtered and the solids washed with dichloromethane (100 mL). The filtrate was added to a cold, stirring solution of $K_2CO_3$ (48 g, 347 mmol) in water (480 mL, pH~10) and stirred for 10 minutes. The phases were separated and the organic phase washed with brine (150 mL). The combined aqueous phases were extracted with additional dichloromethane (100 mL), and the combined organics were then dried, filtered and concentrated in vacuo to provide the product as a pale yellow oil (59 g). The oil was crystallized from cold heptane to provide tert-butyl 2-bromo-6-fluoro-3-(trifluoromethyl)benzoate as an off-white solid (45 g, 75%). $^1H$ NMR (400 MHz, DMSO-$d_6$) δ 8.03 (dd, J=9.0, 5.6 Hz, 1H), 7.68-7.59 (m, 1H), 1.58 (s, 9H) ppm.

Step 3: Tert-Butyl 2-Bromo-6-[3-Fluoro-2-Methoxy-4-(Trifluoromethoxy)Phenoxy]-3-(Trifluoromethyl)Benzoate

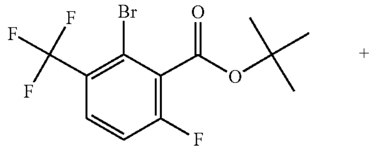

-continued

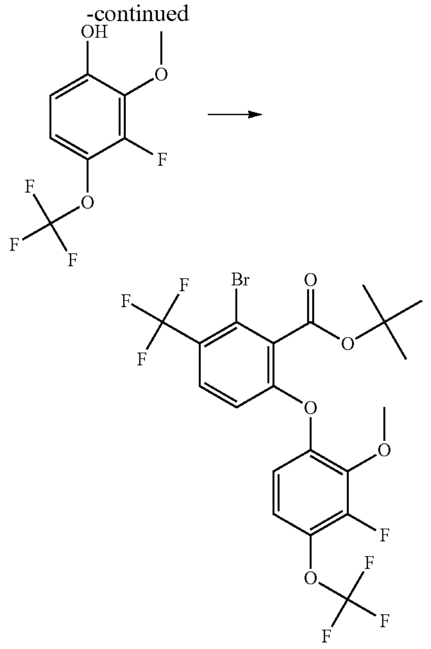

tert-Butyl 2-bromo-6-fluoro-3-(trifluoromethyl)benzoate (10 g, 29 mmol) and 3-fluoro-2-methoxy-4-(trifluoromethoxy)phenol (6.8 g, 30 mmol, see Example 113, Step 1) were dissolved in DMSO (40 mL) and $K_2CO_3$ (8.1 g, 58.6 mmol) (325 mesh) was added under stirring. The yellow suspension was heated at 100° C. (internal temperature) for 2 hours. After cooling, the suspension was partitioned between water (200 mL) and 4:1 heptane/MTBE (200 mL). The organic phase was washed –20 wt % aqueous $K_2CO_3$ (2×100 mL), dried, filtered and concentrated in vacuo. Silica gel chromatography (product loaded onto the column with 95:5 hexane/dichloromethane; 0-20% ethyl acetate/hexane gradient) provided tert-butyl 2-bromo-6-[3-fluoro-2-methoxy-4-(trifluoromethoxy)phenoxy]-3-(trifluoromethyl) benzoate (13.5 g, 84%). ESI-MS m z calc. 548.01, no ionization observed; LC/MS retention time (Method B): 2.07 minutes. $^1H$ NMR (400 MHz, DMSO-$d_6$) δ 7.84 (d, J=8.9 Hz, 1H), 7.39 (ddd, J=9.3, 8.1, 1.3 Hz, 1H), 7.15 (dd, J=9.3, 2.2 Hz, 1H), 7.06 (d, J=8.8 Hz, 1H), 3.88 (d, J=1.0 Hz, 3H), 1.52 (s, 9H) ppm.

Step 4: Tert-Butyl 6-[3-Fluoro-2-Methoxy-4-(Trifluoromethoxy)Phenoxy]-2-Methyl-3-(Trifluoromethyl)Benzoate -continued

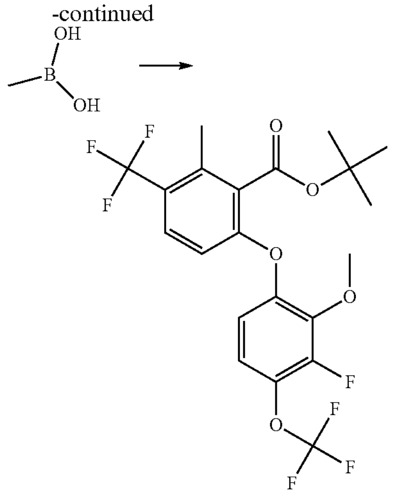

tert-Butyl 2-bromo-6-[3-fluoro-2-methoxy-4-(trifluoromethoxy)phenoxy]-3-(trifluoromethyl)benzoate (143.8 g, 261.8 mmol) was dissolved in 2-methyltetrahydrofuran (2.2 L) and treated with methylboronic acid (78.5 g, 1.31 mol) and $Cs_2CO_3$ (256 g, 786 mmol) under stirring. The suspension was purged with nitrogen for 30 minutes, treated with Pd(dppf)$Cl_2$ (2.88 g, 3.94 mmol) and heated at 80° C. (internal temperature) for 1 hour. The mixture was cooled to room temperature and diluted with water (1 L). The phases were separated and the organic phase washed water (2×1 L) and brine (500 mL). The organic phase was dried, filtered and concentrated in vacuo. The material was partitioned between 4:1 heptane/MTBE (500 mL) and water and the phases separated. The organic phase was washed with water (2×500 mL). The aqueous phases were back extracted with heptane (200 mL). The combined organic phases were stirred with $MgSO_4$ and charcoal for 30 minutes, filtered over a bed of $MgSO_4$ and concentrated in vacuo to provide tert-butyl 6-[3-fluoro-2-methoxy-4-(trifluoromethoxy)phenoxy]-2-methyl-3-(trifluoromethyl)benzoate (127 g, 100%). ESI-MS m z calc. 484.11, no ionization observed; LC/MS retention time (Method B): 2.05 minutes. $^1H$ NMR (400 MHz, DMSO-$d_6$) δ 7.72 (d, J=8.8 Hz, 1H), 7.35 (ddd, J=9.4, 8.1, 1.3 Hz, 1H), 7.00 (dd, J=9.3, 2.2 Hz, 1H), 6.91 (d, J=8.8 Hz, 1H), 3.89 (d, J=0.9 Hz, 3H), 2.41 (d, J=1.7 Hz, 3H), 1.49 (s, 9H) ppm.

Step 5: 6-[3-Fluoro-2-Methoxy-4-(Trifluoromethoxy)Phenoxy]-2-Methyl-3-(Trifluoromethyl) Benzoic Acid

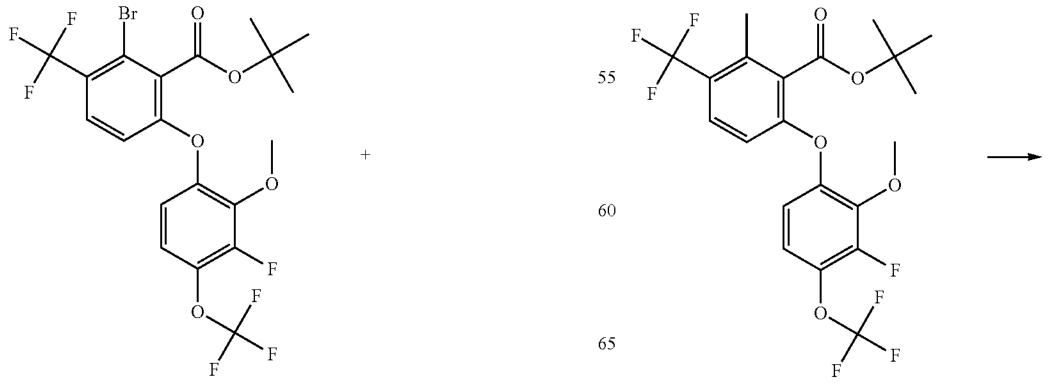

-continued

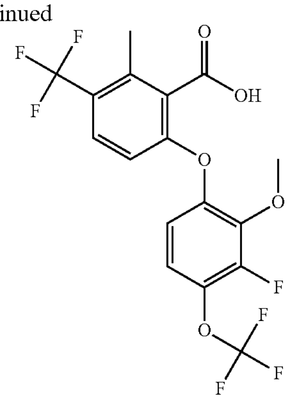

tert-Butyl 6-[3-fluoro-2-methoxy-4-(trifluoromethoxy)phenoxy]-2-methyl-3-(trifluoromethyl)benzoate (125 g, 258 mmol) was dissolved in isopropanol (625 mL), treated with 6 M aqueous HCl (260 mL, 1.56 mol) and heated at 80-90° C. for 2 hours. The solution was evaporated and azeotroped with isopropanol. The crude material was crystallized twice from heptane and once from toluene to provide 6-[3-fluoro-2-methoxy-4-(trifluoromethoxy)phenoxy]-2-methyl-3-(trifluoromethyl)benzoic acid (91.8 g, 82%) as a white solid. ESI-MS m z calc. 428.05, found 427.0 $(M-1)^-$; LC/MS retention time (Method C): 2.14 minutes. $^1$H NMR (400 MHz, DMSO-$d_6$) δ 13.80 (s, 1H), 7.69 (d, J=8.9 Hz, 1H), 7.36 (ddd, J=9.4, 8.2, 1.3 Hz, 1H), 7.06 (dd, J=9.3, 2.2 Hz, 1H), 6.86 (d, J=8.8 Hz, 1H), 3.87 (d, J=1.0 Hz, 3H), 2.43 (d, J=1.7 Hz, 3H) ppm.

Step 6: 4-[[6-[3-Fluoro-2-Methoxy-4-(Trifluoromethoxy)Phenoxy]-2-Methyl-3-(Trifluoromethyl)Benzoyl]Amino]-5-Methyl-Pyridine-2-Carboxamide (312)

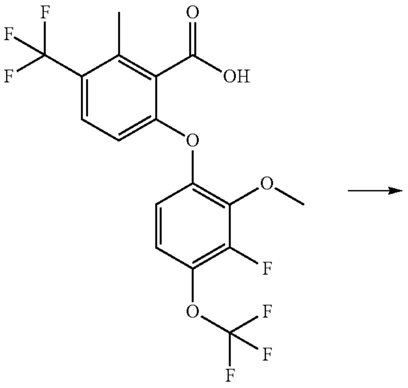

-continued

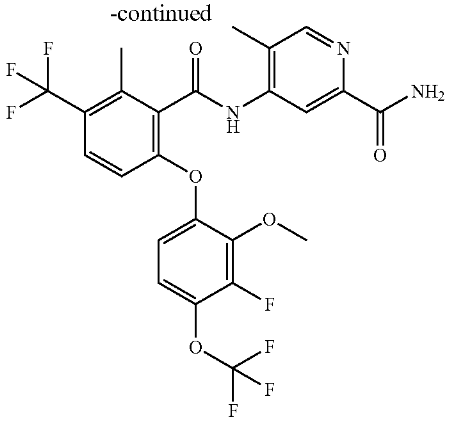

A solution of 6-[3-fluoro-2-methoxy-4-(trifluoromethoxy)phenoxy]-2-methyl-3-(trifluoromethyl)benzoic acid (50 mg, 0.12 mmol) and a drop of DMF in dichloromethane (5 mL) was treated dropwise with oxalyl chloride (89 mg, 61 μL, 0.70 mmol) and stirred at room temperature for 1 hour. The mixture was concentrated in vacuo to provide 6-[3-fluoro-2-methoxy-4-(trifluoromethoxy)phenoxy]-2-methyl-3-(trifluoromethyl)benzoyl chloride. The acid chloride was dissolved in NMP (0.5 mL) and added to a mixture of methyl 4-amino-5-methyl-pyridine-2-carboxylate (29 mg, 0.18 mmol, Preparation 1) and DIEA (143 μL, 0.818 mmol). The mixture was allowed to stir overnight at 75° C. Purification by reverse phase HPLC (10-99% acetonitrile/5 mM HCl) provided the intermediate methyl 4-[[6-[3-fluoro-2-methoxy-4-(trifluoromethoxy)phenoxy]-2-methyl-3-(trifluoromethyl)benzoyl]amino]-5-methyl-pyridine-2-carboxylate (36.1 mg, 0.0626 mmol). The material was dissolved in a solution of ammonia in methanol (600 μL of 7 M, 4.2 mmol) and stirred overnight resulting in a slurry. The solid was collected by filtration, re-dissolved in minimal hot methanol, and the resulting clear solution allowed to slowly cool to room temperature. The resulting solid was collected by filtration to provide 4-[[6-[3-fluoro-2-methoxy-4-(trifluoromethoxy)phenoxy]-2-methyl-3-(trifluoromethyl)benzoyl]amino]-5-methyl-pyridine-2-carboxamide (11.2 mg, 32%) as a white solid. ESI-MS m z calc. 561.11, found 562.2 $(M+1)^+$; LC/MS retention time (Method B): 1.82 minutes. $^1$H NMR (400 MHz, DMSO-$d_6$) δ 10.52 (s, 1H), 8.47 (d, J=6.6 Hz, 2H), 8.06 (d, J=2.8 Hz, 1H), 7.75 (d, J=8.9 Hz, 1H), 7.61 (d, J=2.9 Hz, 1H), 7.39 (t, J=8.7 Hz, 1H), 7.13 (dd, J=9.3, 2.1 Hz, 1H), 6.89 (d, J=8.8 Hz, 1H), 3.86 (s, 3H), 2.29 (s, 3H) ppm.

The compounds set forth in Table 33 were prepared by methods analogous to the preparation of compound 312, Example 122, i.e., amide coupling followed by conversion of the ester to the corresponding carboxamide via treatment with methanolic ammonia, except that compound 317 was synthesized via a one-step amide coupling with 6-amino-pyridazine-3-carboxamide

TABLE 33

Additional Compounds Prepared by Methods Analogous to Example 122

| Cmpd No. | Compound Name | LC/MS | NMR (shifts in ppm) |
|---|---|---|---|
| 313 | 2-[[6-[3-fluoro-2-methoxy-4-(trifluoromethoxy)phenoxy]-2-methyl-3-(trifluoromethyl)benzoyl]amino]pyridine-4-carboxamide | ESI-MS m/z calc. 547.10, found 548.0 $(M + 1)^+$; LC/MS retention time | $^1$H NMR (400 MHz, DMSO-$d_6$) δ 11.34 (s, 1H), 8.58 (s, 1H), 8.45 (d, J = 5.1 Hz, 1H), 8.24 (s, 1H), 7.75-7.68 (m, 2H), 7.54 (dd, J = 5.1, 1.6 Hz, 1H), 7.37 (t, J = 8.6 Hz, 1H), 7.14 |

TABLE 33-continued

| Additional Compounds Prepared by Methods Analogous to Example 122 | | | |
|---|---|---|---|
| Cmpd No. | Compound Name | LC/MS | NMR (shifts in ppm) |
| | | (Method B): 1.81 minutes | (dd, J = 9.3, 2.1 Hz, 1H), 6.86 (d, J = 8.8 Hz, 1H), 3.84 (s, 3H), 2.44 (d, J = 1.9 Hz, 3H). |
| 314 | 5-[[6-[3-fluoro-2-methoxy-4-(trifluoromethoxy)phenoxy]-2-methyl-3-(trifluoromethyl)benzoyl]amino]pyrimidine-2-carboxamide | ESI-MS m/z calc. 548.09, found 549.0 $(M + 1)^+$; LC/MS retention time (Method B): 1.77 minutes | $^1H$ NMR (400 MHz, DMSO-$d_6$) δ 11.43 (s, 1H), 9.21 (s, 2H), 8.12 (s, 1H), 7.77 (d, J = 8.9 Hz, 1H), 7.73 (s, 1H), 7.38 (ddd, J = 9.4, 8.1, 1.4 Hz, 1H), 7.14 (dd, J = 9.3, 2.1 Hz, 1H), 6.90 (d, J = 8.8 Hz, 1H), 3.84 (d, J = 1.0 Hz, 3H), 2.46 (d, J = 1.8 Hz, 3H). |
| 315 | 6-[[6-[3-fluoro-2-methoxy-4-(trifluoromethoxy)phenoxy]-2-methyl-3-(trifluoromethyl)benzoyl]amino]pyrimidine-4-carboxamide | ESI-MS m/z calc. 548.09, found 549.0 $(M + 1)^+$; LC/MS retention time (Method C): 2.79 minutes | $^1H$ NMR (400 MHz, DMSO-$d_6$) δ 11.85 (s, 1H), 9.46 (s, 1H), 8.95 (s, 1H), 8.16 (s, 1H), 7.79-7.70 (m, 2H), 7.37 (t, J = 8.7 Hz, 1H), 7.14 (d, J = 9.3 Hz, 1H), 6.88 (d, J = 8.8 Hz, 1H), 3.83 (s, 3H), 2.45 (s, 3H). |
| 316 | 5-[[6-[3-fluoro-2-methoxy-4-(trifluoromethoxy)phenoxy]-2-methyl-3-(trifluoromethyl)benzoyl]amino]pyrazine-2-carboxamide | ESI-MS m/z calc. 548.09, found 549.0 $(M + 1)^+$; LC/MS retention time (Method C): 2.73 minutes | |
| 317 | 6-[[6-[3-fluoro-2-methoxy-4-(trifluoromethoxy)phenoxy]-2-methyl-3-(trifluoromethyl)benzoyl]amino]pyridazine-3-carboxamide | ESI-MS m/z calc. 548.09, found 549.0 $(M + 1)^+$; LC/MS retention time (Method B): 1.93 minutes | $^1H$ NMR (400 MHz, DMSO-$d_6$) δ 12.13 (s, 1H), 8.61 (d, J = 9.3 Hz, 1H), 8.40 (s, 1H), 8.25 (d, J = 9.2 Hz, 1H), 7.84 (s, 1H), 7.75 (d, J = 8.9 Hz, 1H), 7.37 (t, J = 8.7 Hz, 1H), 7.15 (d, J = 9.2 Hz, 1H), 6.89 (d, J = 8.8 Hz, 1H), 3.84 (s, 3H), 2.46 (s, 3H). |

Example 123

4-[[2-Fluoro-6-[3-Fluoro-2-Methoxy-4-(Trifluoromethoxy)Phenoxy]-4-(Trifluoromethyl)Benzoyl]Amino]-5-Methyl-Pyridine-2-Carboxamide (318)

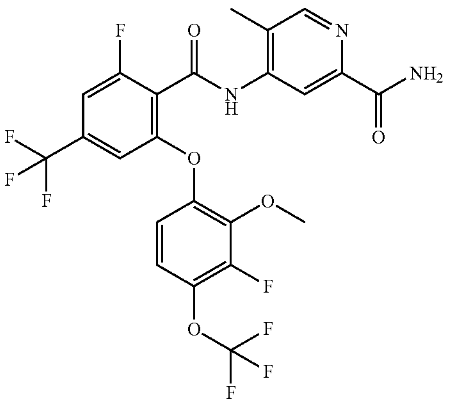 [SMILES: COc1c(Oc2cc(C(F)(F)F)cc(F)c2C(=O)Nc2cc(C(N)=O)ncc2C)ccc(OC(F)(F)F)c1F]

Step 1. Methyl 2-Fluoro-6-[3-Fluoro-2-Methoxy-4-(Trifluoromethoxy)Phenoxy]-4-(Trifluoromethyl)Benzoate

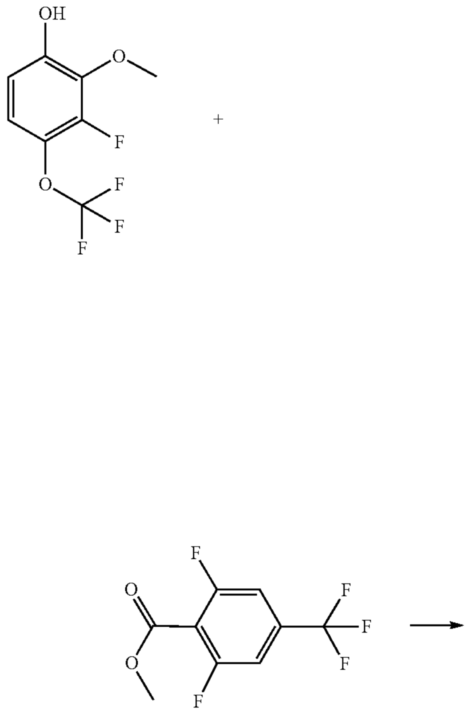

-continued

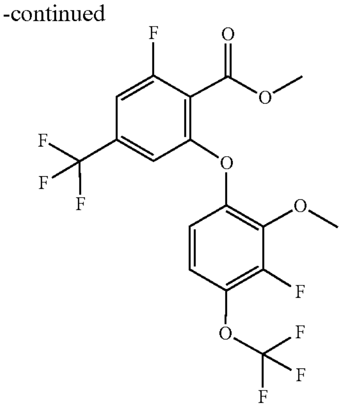

To a solution of methyl 2,6-difluoro-4-(trifluoromethyl) benzoate (1.000 g, 4.164 mmol) in DMF (12 mL) was added 3-fluoro-2-methoxy-4-(trifluoromethoxy)phenol (942 mg, 4.17 mmol, see Example 113, Step 1) and $Cs_2CO_3$ (4.10 g, 12.6 mmol) and the mixture was heated at 70° C. for 20 minutes. The cooled mixture was diluted with ethyl acetate and washed with water and brine. The organic layer was dried over $Na_2SO_4$, filtered and concentrated in vacuo. Purification by silica gel chromatography (0-15% ethyl acetate/hexanes) provided methyl 2-fluoro-6-[3-fluoro-2-methoxy-4-(trifluoromethoxy)phenoxy]-4-(trifluoromethyl) benzoate (1.162 g, 63%). ESI-MS m z calc. 446.04, found 447.2 $(M+1)^+$; LC/MS retention time (Method A): 0.83 minutes.

Step 2. 2-Fluoro-6-[3-Fluoro-2-Methoxy-4-(Trifluoromethoxy)Phenoxy]-4-(Trifluoromethyl)Benzoic Acid

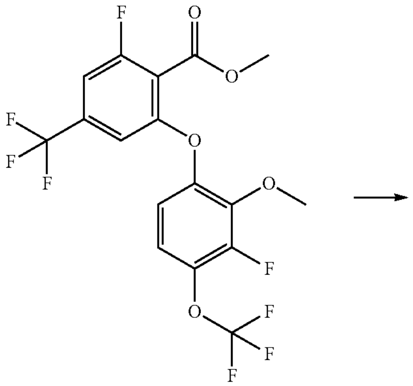

-continued

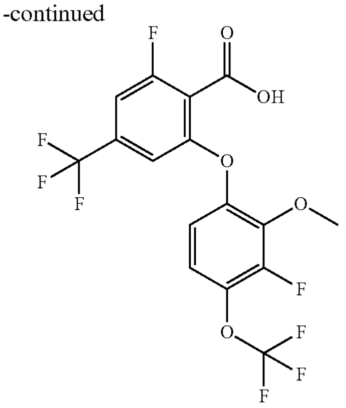

A solution of methyl 2-fluoro-6-[3-fluoro-2-methoxy-4-(trifluoromethoxy)phenoxy]-4-(trifluoromethyl)benzoate (1.16 g, 2.60 mmol) in methanol (8 mL) was treated with aqueous KOH (6 mL of 3 M, 18.00 mmol) at 0° C. The cloudy white mixture was allowed to come to room temperature then heated at 55° C. for 1 hour. The mixture was partitioned between 1 M aqueous HCl and diethyl ether. The organic layer was dried over $Na_2SO_4$, filtered and concentrated in vacuo to provide a viscous oil. The oil was suspended in hexane and stirred until a thick slurry had formed. The solid was collected by filtration and air dried to provide 2-fluoro-6-[3-fluoro-2-methoxy-4-(trifluoromethoxy)phenoxy]-4-(trifluoromethyl)benzoic acid (745 mg, 66%) as a white solid. ESI-MS m z calc. 432.02, found 433.2 $(M+1)^+$; LC/MS retention time (Method A): 0.74 minutes. $^1H$ NMR (400 MHz, DMSO-$d_6$) δ 14.22 (s, 1H), 7.69 (d, J=8.8 Hz, 1H), 7.35 (ddd, J=9.3, 8.0, 1.4 Hz, 1H), 7.04 (dd, J=9.4, 2.2 Hz, 1H), 3.88 (s, 4H) ppm.

Step 3: 4-[[2-Fluoro-6-[3-Fluoro-2-Methoxy-4-(Trifluoromethoxy)Phenoxy]-4-(Trifluoromethyl)Benzoyl]Amino]-5-Methyl-Pyridine-2-Carboxamide (318)

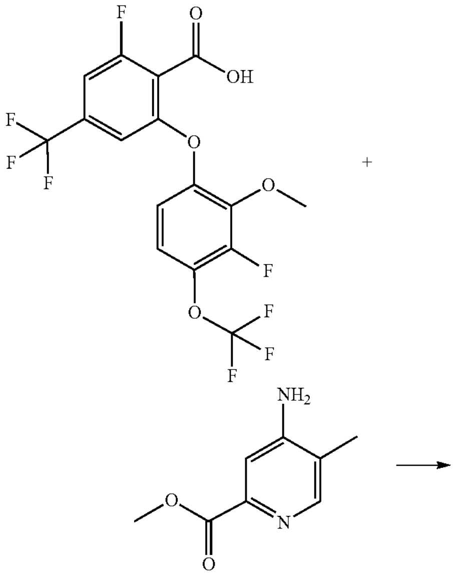

-continued

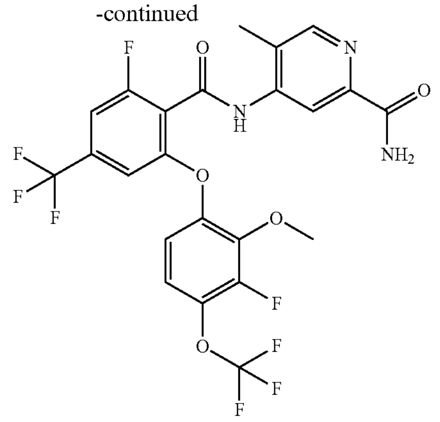

A solution of 2-fluoro-6-[3-fluoro-2-methoxy-4-(trifluoromethoxy)phenoxy]-4-(trifluoromethyl)benzoic acid (25 mg, 0.058 mmol) and DMF (1 μL, 0.01 mmol) in dichloromethane (400 μL) at 0° C. was treated slowly with oxalyl dichloride (30 μL, 0.34 mmol). The ice-bath was removed and the mixture was stirred at room temperature for 30 minutes. The mixture was concentrated in vacuo. The resulting acid chloride intermediate was dissolved in NMP (200 μL) and added dropwise to solution of methyl 4-amino-5-methyl-pyridine-2-carboxylate (25 mg, 0.1504 mmol, Preparation 1) and DIEA (60 μL, 0.3445 mmol) in NMP (200 μL) at 0° C. The resulting mixture was stirred at room temperature for 16 hours. Purification by reverse phase HPLC (30-99% acetonitrile/5 mM HCl) provided methyl 4-[[2-fluoro-6-[3-fluoro-2-methoxy-4-(trifluoromethoxy)phenoxy]-4-(trifluoromethyl)benzoyl]amino]-5-methyl-pyridine-2-carboxylate. The material was dissolved in a solution of ammonia in methanol (1.65 mL of 7 M, 11.6 mmol) and stirred at room temperature for 24 hours. The solution was concentrated in vacuo and purified by reverse phase HPLC (30-99% acetonitrile/5 mM HCl) to provide 4-[[2-fluoro-6-[3-fluoro-2-methoxy-4-(trifluoromethoxy)phenoxy]-4-(trifluoromethyl)benzoyl]amino]-5-methyl-pyridine-2-carboxamide (7.6 mg, 23%) as a white solid. ESI-MS m z calc. 565.09, found 566.2 $(M+1)^+$; LC/MS retention time (Method B): 1.27 minutes. $^1H$ NMR (400 MHz, DMSO-$d_6$) δ 10.60 (s, 1H), 8.45 (d, J=12.1 Hz, 2H), 8.05 (s, 1H), 7.76 (d, J=8.6 Hz, 1H), 7.60 (s, 1H), 7.36 (t, J=8.6 Hz, 1H), 7.25 (s, 1H), 7.10 (d, J=9.3 Hz, 1H), 3.89 (s, 3H), 2.27 (s, 3H) ppm.

Example 124

4-[[3-(Difluoromethyl)-6-[3-Fluoro-2-(Trideuteriomethoxy)-4-(Trifluoromethoxy)Phenoxy]-2-Methoxy-Benzoyl]Amino]Pyridine-2-Carboxamide (319)

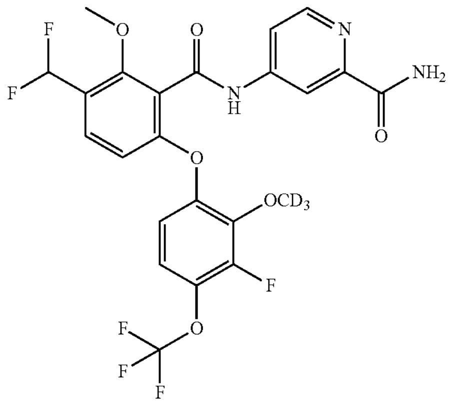

4-[[4-Chloro-3-(difluoromethyl)-6-[3-fluoro-2-(trideuteriomethoxy)-4-(trifluoromethoxy)phenoxy]-2-methoxy-benzoyl]amino]pyridine-2-carboxamide (52.5 mg, 0.090 mmol, see US 2019/0016671, Example 178, which is incorporated by reference) and 10% Pd/C (16 mg) were stirred in methanol (2 mL) under a hydrogen atmosphere (balloon) for 20 minutes. The mixture was filtered through Celite and concentrated in vacuo. Purification by reverse phase HPLC (47-95% acetonitrile/0.1% ammonium hydroxide) provided 4-[[3-(difluoromethyl)-6-[3-fluoro-2-(trideuteriomethoxy)-4-(trifluoromethoxy)phenoxy]-2-methoxy-benzoyl]amino]pyridine-2-carboxamide (20.2 mg, 38%) ESI-MS m z calc. 548.12, found 549.5 $(M+1)^+$; Retention time (Method E): 3.22 minutes.

Example 125

4-[[2-Fluoro-6-[3-Fluoro-2-Methoxy-4-(Trifluoromethoxy)Phenoxy]-4-Methoxy-3-(Trifluoromethyl)Benzoyl]Amino]Pyridine-2-Carboxamide (320)

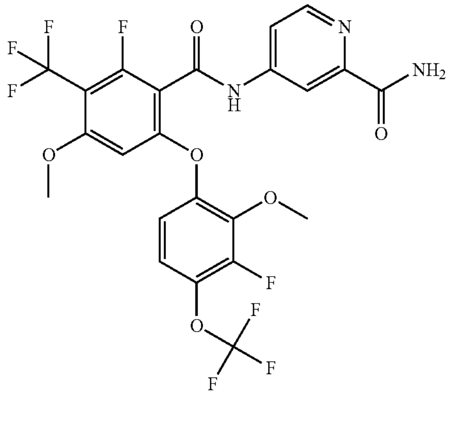

Step 1: 2-Fluoro-6-[3-Fluoro-2-Methoxy-4-(Trifluoromethoxy)Phenoxy]-4-Methoxy-3-(Trifluoromethyl)Benzoic Acid

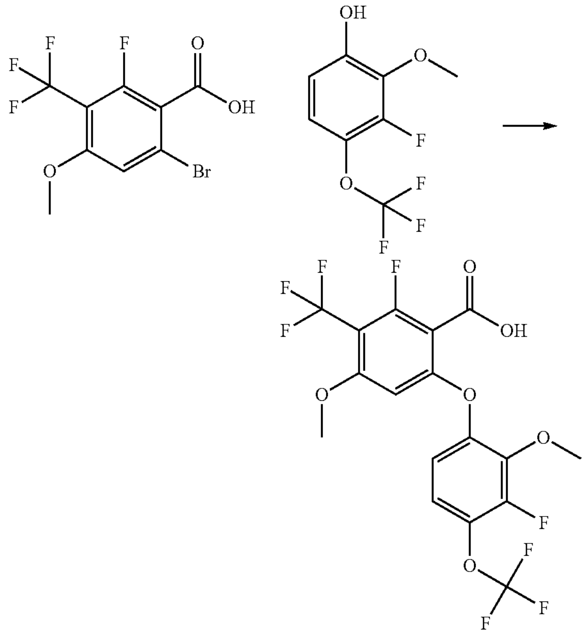

A mixture of 6-bromo-2-fluoro-4-methoxy-3-(trifluoromethyl)benzoic acid (1.5 g, 4.7 mmol, see US 2019/0016671, Example 129, Step 3, which is incorporated by reference), 3-fluoro-2-methoxy-4-(trifluoromethoxy)phenol (1.070 g, 4.732 mmol, see Example 113, Step 1) and $Cs_2CO_3$ (1.850 g, 5.678 mmol) in toluene (12 mL) was bubbled with nitrogen for 10 minutes, then copper (I) iodide (350 mg, 1.84 mmol) added. The mixture was heated at 100° C. under nitrogen with vigorous stirring for 1 hour. The cooled mixture was acidified with 1 M HCl, filtered and the layers separated. The aqueous layer was extracted with additional ethyl acetate (3×). The combined organic layers were washed with brine, dried over $MgSO_4$, filtered and concentrated in vacuo. Silica gel column chromatography (20-100% ethyl acetate/hexane) provided 2-fluoro-6-[3-fluoro-2-methoxy-4-(trifluoromethoxy)phenoxy]-4-methoxy-3-(trifluoromethyl)benzoic acid (1.674 g, 77%). ESI-MS m z calc. 462.04, found 463.2 $(M+1)^+$; LC/MS retention time (Method A): 0.71 minutes. $^1H$ NMR (400 MHz, DMSO-$d_6$) δ 13.76 (s, 1H), 7.33 (t, J=8.7 Hz, 1H), 7.05 (dd, J=9.3, 2.1 Hz, 1H), 6.65 (s, 1H), 3.91 (s, 3H), 3.81 (s, 3H) ppm.

Step 2: Methyl 4-[[2-Fluoro-6-[3-Fluoro-2-Methoxy-4-(Trifluoromethoxy)Phenoxy]-4-Methoxy-3-(Trifluoromethyl)Benzoyl]Amino]Pyridine-2-Carboxylate

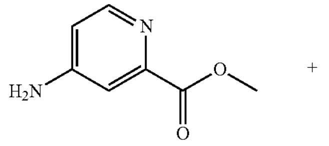

-continued

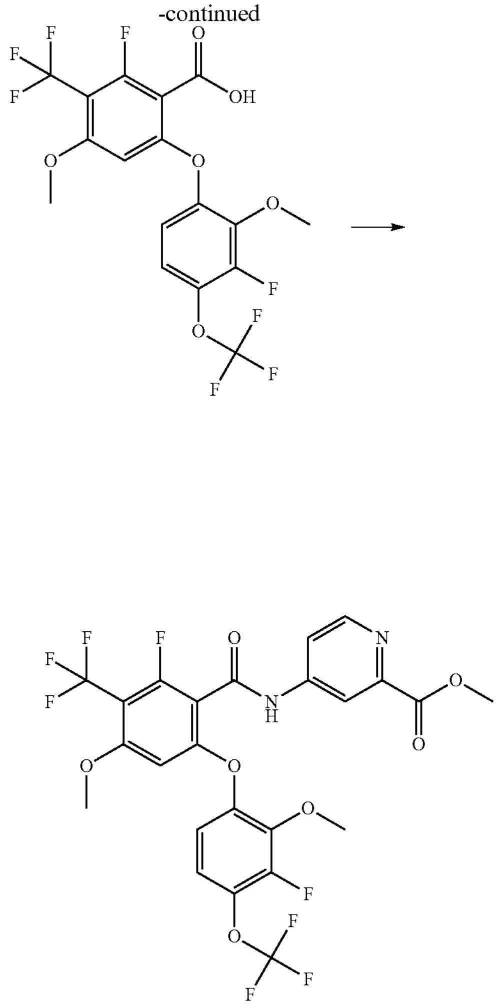

2-Fluoro-6-[3-fluoro-2-methoxy-4-(trifluoromethoxy)phenoxy]-4-methoxy-3-(trifluoromethyl)benzoic acid (300 mg, 0.649 mmol) was dissolved in dichloromethane (10 mL) and cooled to 0° C. Oxalyl chloride (150 μL, 1.72 mmol) was added followed by addition of DMF (5 μL, 0.07 mmol). The resulting mixture was stirred for 1 hour and concentrated in vacuo. The residue was dissolved in dichloromethane (10 mL) and methyl 4-aminopyridine-2-carboxylate (99 mg, 0.65 mmol) and TEA (200 μL, 1.44 mmol) added. The resulting mixture was stirred at room temperature overnight, then concentrated in vacuo. Purification by silica gel chromatography (0-100% ethyl acetate/heptane) provided methyl 4-[[2-fluoro-6-[3-fluoro-2-methoxy-4-(trifluoromethoxy)phenoxy]-4-methoxy-3-(trifluoromethyl)benzoyl]amino]pyridine-2-carboxylate (234 mg, 60%). ESI-MS m z calc. 596.08, found 597.5 $(M+1)^+$; 595.6 $(M-1)^-$; LC/MS retention time (Method F): 1.0 minutes. $^1H$ NMR (500 MHz, DMSO-$d_6$) δ 11.33 (s, 1H), 8.61 (d, J=5.3 Hz, 1H), 8.31 (d, J=2.1 Hz, 1H), 7.78 (dd, J=5.5, 2.1 Hz, 1H), 7.36-7.28 (m, 1H), 7.13 (dd, J=9.2, 2.0 Hz, 1H), 6.69 (s, 1H), 3.92-3.84 (m, 9H) ppm.

Step 3: 4-[[2-Fluoro-6-[3-Fluoro-2-Methoxy-4-(Trifluoromethoxy)Phenoxy]-4-Methoxy-3-(Trifluoromethyl)Benzoyl]Amino]Pyridine-2-Carboxamide (320)

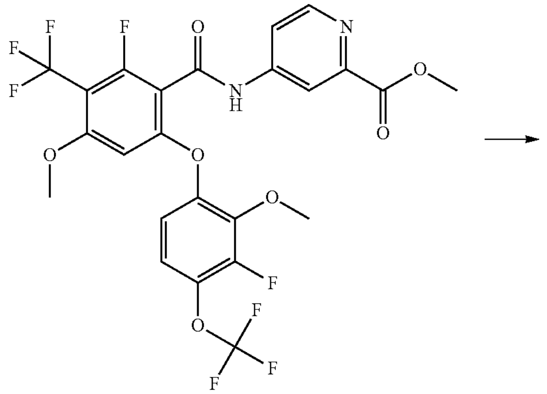

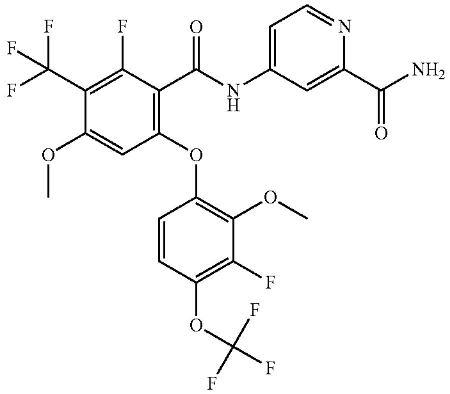 [SMILES: COc1cc(Oc2ccc(OC(F)(F)F)c(F)c2OC)c(C(=O)Nc2ccnc(C(N)=O)c2)c(F)c1C(F)(F)F]

A solution of ammonia in methanol (5 mL of 7 M, 35 mmol) was added to methyl 4-[[2-fluoro-6-[3-fluoro-2-methoxy-4-(trifluoromethoxy)phenoxy]-4-methoxy-3-(trifluoromethyl)benzoyl]amino]pyridine-2-carboxylate (234 mg, 0.3924 mmol) and the resulting mixture was stirred at room temperature overnight. The mixture was concentrated in vacuo to provide 4-[[2-fluoro-6-[3-fluoro-2-methoxy-4-(trifluoromethoxy)phenoxy]-4-methoxy-3-(trifluoromethyl)benzoyl]amino]pyridine-2-carboxamide (151.9 mg, 64%) as an off-white powder. ESI-MS m z calc. 581.08, found 582.5 $(M+1)^+$; 580.6 $(M-1)^-$; LC/MS retention time (Method E): 3.37 minutes. $^1H$ NMR (500 MHz, DMSO-$d_6$) δ 11.28 (s, 1H), 8.53 (d, J=5.5 Hz, 1H), 8.27 (d, J=2.1 Hz, 1H), 8.08 (d, J=2.9 Hz, 1H), 7.78 (dd, J=5.6, 2.2 Hz, 1H), 7.64 (d, J=2.9 Hz, 1H), 7.33 (tt, J=8.0, 1.2 Hz, 1H), 7.14 (dd, J=9.3, 2.1 Hz, 1H), 6.67 (s, 1H), 3.89-3.84 (m, 6H) ppm.

Example 126

5-[[2-Fluoro-6-[3-Fluoro-2-Methoxy-4-(Trifluoromethoxy)Phenoxy]-4-Methoxy-3-(Trifluoromethyl)Benzoyl]Amino]Pyridine-2-Carboxamide (321)

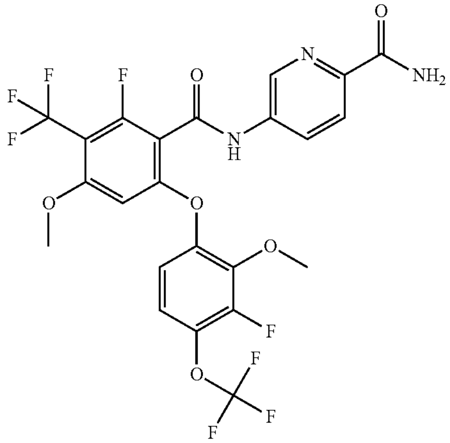 [SMILES: COc1cc(Oc2ccc(OC(F)(F)F)c(F)c2OC)c(C(=O)Nc2ccc(C(N)=O)nc2)c(F)c1C(F)(F)F]

This compound was made in an analogous fashion to the synthesis of compound 320 in Example 125, except employing 5-aminopyridine-2-carboxamide in the amide formation step. The yield 5-[[2-fluoro-6-[3-fluoro-2-methoxy-4-(trifluoromethoxy)phenoxy]-4-methoxy-3-(trifluoromethyl)benzoyl]amino]pyridine-2-carboxamide after purification was 171 mg (44%). ESI-MS m z calc. 581.08, found 582.5 $(M+1)^+$; 580.6 $(M-1)^-$; LC/MS retention time (Method E): 3.32 minutes. 1H NMR (500 MHz, DMSO-$d_6$) δ 11.21 (s, 1H), 8.80 (d, J=2.4 Hz, 1H), 8.22 (dd, J=8.6, 2.5 Hz, 1H), 8.06-7.98 (m, 2H), 7.55 (d, J=2.9 Hz, 1H), 7.33 (ddd, J=9.4, 8.1, 1.4 Hz, 1H), 7.14 (dd, J=9.3, 2.1 Hz, 1H), 6.70 (s, 1H), 3.94-3.80 (m, 6H) ppm.

Example 127

4-[[2-Fluoro-6-[3-Fluoro-2-Methoxy-4-(Trifluoromethoxy)Phenoxy]-3-(Trifluoromethoxy)Benzoyl]Amino]Pyridine-2-Carboxamide (322)

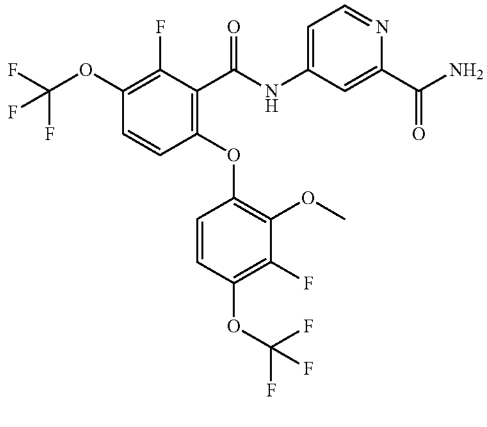 [SMILES: COc1c(Oc2ccc(OC(F)(F)F)c(F)c2C(=O)Nc2ccnc(C(N)=O)c2)ccc(OC(F)(F)F)c1F]

Step 1: 2-Fluoro-6-[3-Fluoro-2-Methoxy-4-(Trifluoromethoxy)Phenoxy]-3-(Trifluoromethoxy)Benzoic Acid

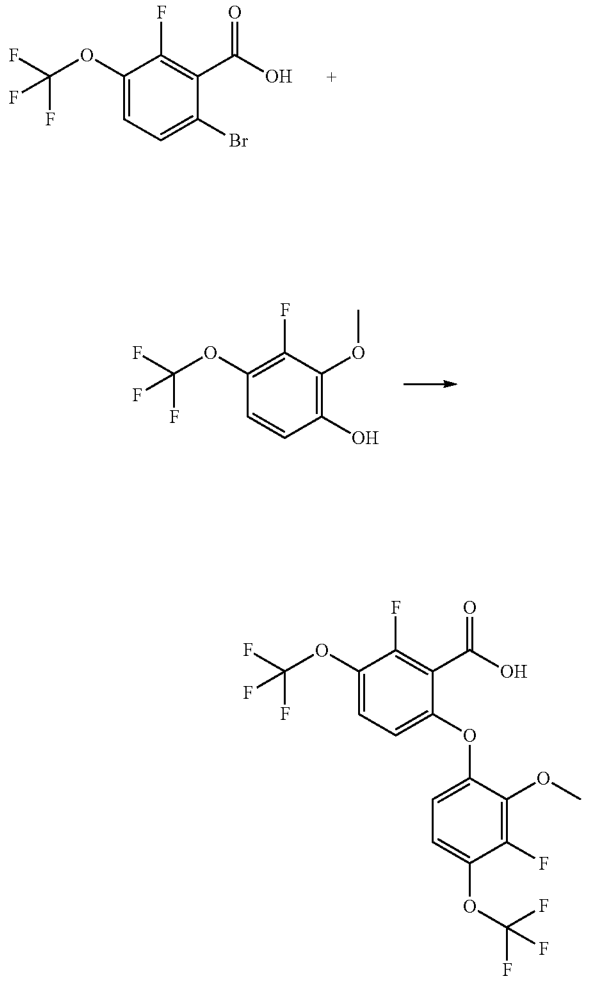

A mixture of 6-bromo-2-fluoro-3-(trifluoromethoxy)benzoic acid (966 mg, 3.19 mmol, see Example 90, Step 1), 3-fluoro-2-methoxy-4-(trifluoromethoxy)phenol (750 mg, 3.32 mmol, see Example 113, Step 1) and $Cs_2CO_3$ (1.2 g, 3.7 mmol) in toluene (15 mL) was treated with copper (I) iodide (230 mg, 1.21 mmol) and the mixture heated at 100° C. with vigorous stirring overnight. The mixture is then acidified with 2 M aqueous HCl, filtered and the layers separated. The aqueous layer was extracted with ethyl acetate, and the combined aqueous layers washed with brine, dried over $MgSO_4$, filtered and concentrated in vacuo to provide crude 2-fluoro-6-[3-fluoro-2-methoxy-4-(trifluoromethoxy)phenoxy]-3-(trifluoromethoxy)benzoic acid (1.5 g, 105%). ESI-MS m z calc. 448.02, no ionization observed; LC/MS retention time (Method F): 0.63 minutes. $^1H$ NMR (400 MHz, $CDCl_3$) δ 9.63 (s, 1H), 7.36 (ddq, J=9.3, 8.2, 1.1 Hz, 1H), 7.08 (ddq, J=9.0, 7.7, 1.3 Hz, 1H), 6.98-6.81 (m, 1H), 6.59 (dd, J=9.2, 1.9 Hz, 1H), 3.96 (d, J=1.5 Hz, 3H) ppm. This material was used without further purification.

Step 2: 4-[[2-Fluoro-6-[3-Fluoro-2-Methoxy-4-(Trifluoromethoxy)Phenoxy]-3-(Trifluoromethoxy)Benzoyl]Amino]Pyridine-2-Carboxamide (322)

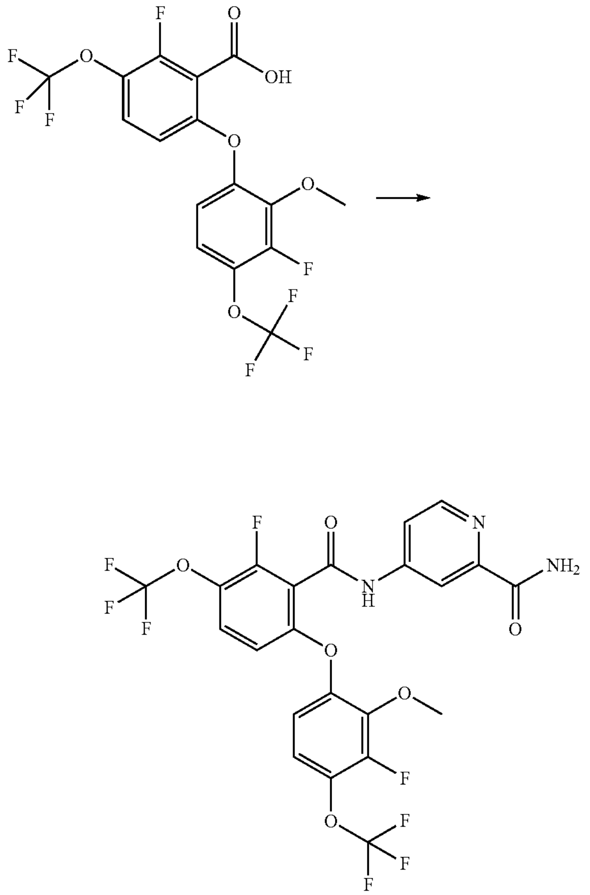

A solution of 2-fluoro-6-[3-fluoro-2-methoxy-4-(trifluoromethoxy)phenoxy]-3-(trifluoromethoxy)benzoic acid (300 mg, 0.669 mmol) and DMF (5 μL, 0.07 mmol) in dichloromethane (5 mL) at 0° C. was treated dropwise with oxalyl chloride (235 μL, 2.69 mmol) (gas evolution) and stirred for 1 hour. The mixture was concentrated in vacuo, and the resulting acid chloride dissolved in dichloromethane (5 mL) and added dropwise to a stirring solution of methyl 4-aminopyridine-2-carboxylate (112 mg, 0.736 mmol), DIPEA (350 μL, 2.01 mmol) and DMAP (82 mg, 0.67 mmol) in dichloromethane (5 mL). The mixture was stirred overnight, concentrated in vacuo, and the residue stirred in a solution of ammonia in methanol (5.0 mL of 7 M, 35 mmol) for 24 hours. The mixture was concentrated in vacuo and purified by reverse phase HPLC (47-95% acetonitrile/0.1% ammonium hydroxide) to provide 4-[[2-fluoro-6-[3-fluoro-2-methoxy-4-(trifluoromethoxy)phenoxy]-3-(trifluoromethoxy)benzoyl]amino]pyridine-2-carboxamide (112 mg, 28% yield). ESI-MS m z calc. 567.07, found 568.1 $(M+1)^+$; 566.1 $(M-1)^-$; LC/MS retention time (Method F): 0.95 minutes. $^1H$ NMR (400 MHz, $CDCl_3$) δ 9.82 (s, 1H), 8.55 (d, J=5.5 Hz, 1H), 8.49 (dd, J=5.7, 2.0 Hz, 1H), 8.19 (d, J=2.2 Hz, 1H), 7.91 (d, J=4.3 Hz, 1H), 7.37 (tq, J=8.2, 1.2 Hz, 1H), 7.13-6.92 (m, 2H), 6.60 (ddd, J=20.3, 9.2, 1.8 Hz, 1H), 5.23 (d, J=4.5 Hz, 1H), 3.89 (d, J=1.8 Hz, 3H) ppm.

Example 128

4-[[2-Fluoro-6-[3-Fluoro-2-Methoxy-4-(Trifluoromethoxy)Phenoxy]-3-Methyl-4-(Trifluoromethyl) Benzoyl]Amino]Pyridine-2-Carboxamide (323)

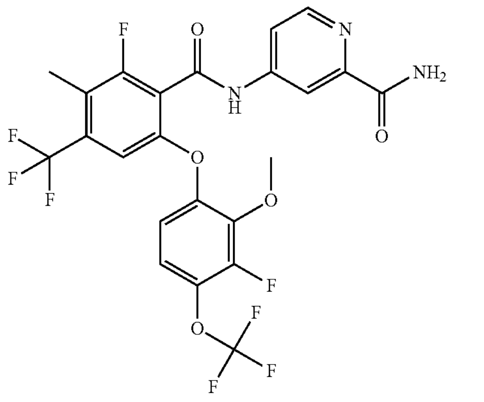 [SMILES: COc1c(Oc2cc(C(F)(F)F)c(C)c(F)c2C(=O)Nc2ccnc(C(N)=O)c2)ccc(OC(F)(F)F)c1F]

Step 1: 2-Fluoro-6-[3-Fluoro-2-Methoxy-4-(Trifluoromethoxy)Phenoxy]-3-Methyl-4-(Trifluoromethyl) Benzoic Acid

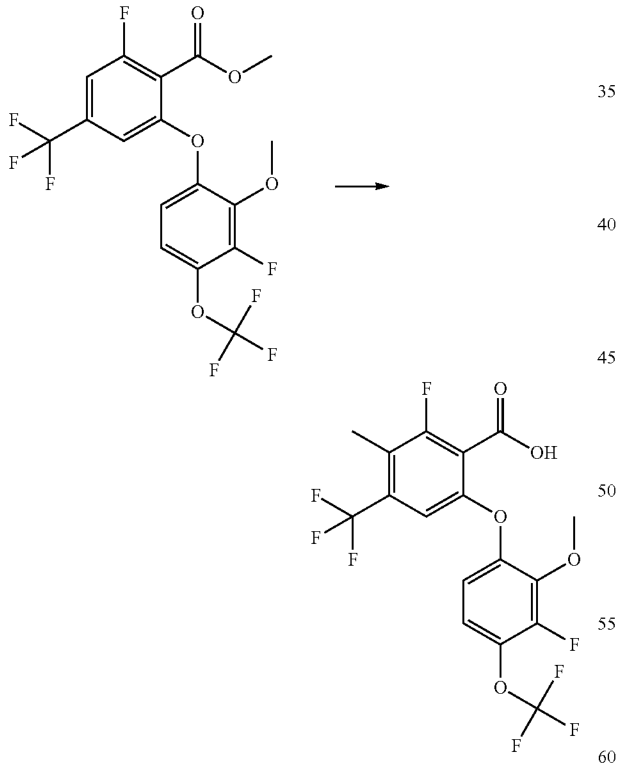

A solution of n-butyllithium (760 μL of 1.6 M in hexanes, 1.22 mmol) was added to a stirring solution of diisopropylamine (121 mg, 1.20 mmol) in THF (5 mL) at −78° C. and the mixture stirred at 0° C. for 20 minutes. The resulting LDA solution was added dropwise to a solution methyl 2-fluoro-6-[3-fluoro-2-methoxy-4-(trifluoromethoxy)phenoxy]-4-(trifluoromethyl)benzoate (450 mg, 1.01 mmol, see Example 123, Step 1) in THF (5 mL) at −78° C. The mixture was stirred at this temperature for 20 minutes then methyl iodide (232 mg, 1.64 mmol) was added. The mixture was stirred at −78° C. for 30 minutes then allowed to warm to room temperature and stirred overnight. The mixture was diluted with water and extracted with ethyl acetate (3×). The combined organic extracts were dried over $MgSO_4$, filtered and concentrated in vacuo to provide methyl 2-fluoro-6-[3-fluoro-2-methoxy-4-(trifluoromethoxy)phenoxy]-3-methyl-4-(trifluoromethyl)benzoate. The residue was taken up in ethanol (5 mL), treated with aqueous LiOH (3 mL of 2 M, 6 mmol) and stirred overnight. The mixture was acidified with 2 M aqueous HCl and extracted with ethyl acetate (2×30 mL). The combined organic extracts were dried over $MgSO_4$, filtered and then concentrated in vacuo to provide 2-fluoro-6-[3-fluoro-2-methoxy-4-(trifluoromethoxy)phenoxy]-3-methyl-4-(trifluoromethyl)benzoic acid (350 mg, 78%). ESI-MS m z calc. 446.04, found 445.1 $(M-1)^-$; LC/MS retention time (Method F): 0.65 minutes.

Step 2: 4-[[2-Fluoro-6-[3-Fluoro-2-Methoxy-4-(Trifluoromethoxy)Phenoxy]-3-Methyl-4-(Trifluoromethyl)Benzoyl]Amino]Pyridine-2-Carboxamide (323)

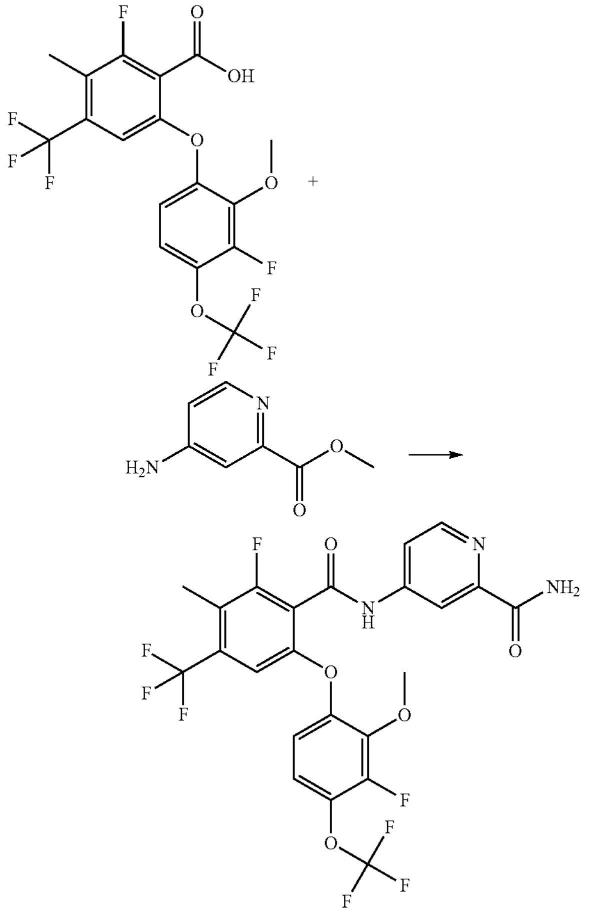

To a solution of 2-fluoro-6-[3-fluoro-2-methoxy-4-(trifluoromethoxy)phenoxy]-3-methyl-4-(trifluoromethyl)benzoic acid (460 mg, 1.03 mmol) and DMF (8 μL, 0.1 mmol)

in dichloromethane (10 mL) at 0° C. was added oxalyl chloride (1.6 mL of 2 M, 3.2 mmol) dropwise. The mixture was stirred for 2 hours and concentrated in vacuo. The residue was dissolved in dichloromethane (10 mL) and added dropwise to a mixture of methyl 4-aminopyridine-2-carboxylate (220 mg, 1.45 mmol) and TEA (9 μL, 0.06 mmol) in dichloromethane (10 mL) at 0° C. The resulting mixture was allowed to warm to room temperature overnight, then concentrated in vacuo. Purification by reverse phase HPLC (47-95% acetonitrile/0.1% ammonium hydroxide) provided methyl 4-[[2-fluoro-6-[3-fluoro-2-methoxy-4-(trifluoromethoxy)phenoxy]-3-methyl-4-(trifluoromethyl)benzoyl]amino]pyridine-2-carboxylate. The material was dissolved in a solution of ammonia in methanol (2 mL of 7 M, 14 mmol) and stirred overnight at room temperature. The mixture was concentrated in vacuo to provide 4-[[2-fluoro-6-[3-fluoro-2-methoxy-4-(trifluoromethoxy)phenoxy]-3-methyl-4-(trifluoromethyl)benzoyl]amino]pyridine-2-carboxamide (58.5 mg, 10%). ESI-MS m z calc. 565.09, found 566.1 $(M+1)^+$; 564.2 $(M-1)^-$; LC/MS retention time (Method F): 0.98 minutes. $^1H$ NMR (400 MHz, $CDCl_3$) δ 9.53 (s, 1H), 8.55 (d, J=5.5 Hz, 1H), 8.43 (dd, J=5.6, 2.1 Hz, 1H), 8.14 (d, J=2.1 Hz, 1H), 7.90 (d, J=4.2 Hz, 1H), 7.07 (ddq, J=8.9, 7.6, 1.2 Hz, 1H), 6.97 (dd, J=9.2, 2.1 Hz, 1H), 6.89 (d, J=1.4 Hz, 1H), 5.23 (d, J=4.3 Hz, 1H), 3.88 (d, J=1.8 Hz, 3H), 2.41 (p, J=1.8 Hz, 3H) ppm.

Example 129

4-[[3-Chloro-2-Fluoro-6-[3-Fluoro-2-Methoxy-4-(Trifluoromethoxy)Phenoxy]-4-Methoxy-Benzoyl]Amino]Pyridine-2-Carboxamide (324)

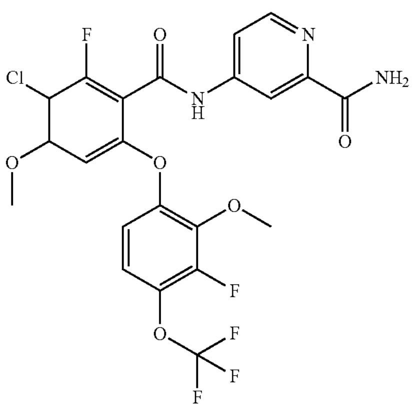 [SMILES: COc1c(OC2=CC(OC)C(Cl)C(F)=C2C(=O)Nc2ccnc(C(N)=O)c2)ccc(OC(F)(F)F)c1F]

Step 1: 3-Chloro-2-Fluoro-6-[3-Fluoro-2-Methoxy-4-(Trifluoromethoxy)Phenoxy]-4-Methoxy-Benzoic Acid

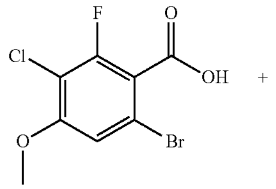

-continued

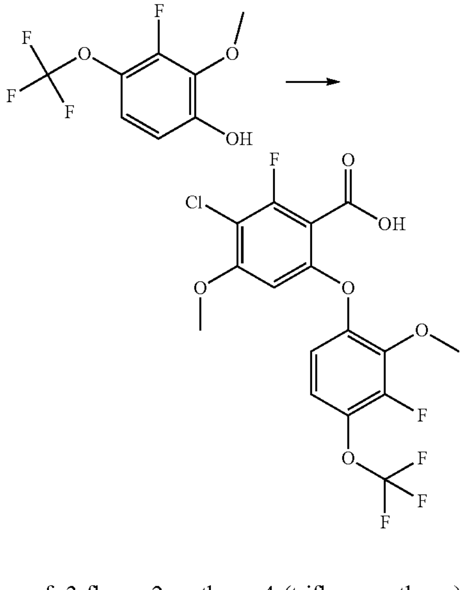

A solution of 3-fluoro-2-methoxy-4-(trifluoromethoxy)phenol (2.001 g, 8.849 mmol, see Example 113, Step 1) in toluene (50 mL) was bubbled with nitrogen for 10 minutes. 6-Bromo-3-chloro-2-fluoro-4-methoxy-benzoic acid (2.5 g, 8.8 mmol, see Example 76, Step 2), copper (I) iodide (338 mg, 1.78 mmol) and $Cs_2CO_3$ (5.749 g, 17.64 mmol) were added and the mixture was bubbled with nitrogen for 10 minutes. The mixture was heated to 100° C. for 21 hours. The cooled mixture was diluted with ethyl acetate (175 mL) and washed with saturated aqueous $NH_4Cl$ (175 mL). The aqueous layer was extracted with additional ethyl acetate (2×100 mL), and the combined organic extracts dried over $MgSO_4$, filtered and concentrated in vacuo. Purification by silica gel chromatography (0-50% ethyl acetate/heptane) provided 3-chloro-2-fluoro-6-[3-fluoro-2-methoxy-4-(trifluoromethoxy)phenoxy]-4-methoxy-benzoic acid (1.789 g, 47%). ESI-MS m z calc. 428.01, found 429.5 $(M+1)^+$; LC/MS retention time (Method F): 0.59 minutes. $^1H$ NMR (500 MHz, DMSO-$d_6$) δ 13.60 (s, 1H), 7.25 (t, J=8.5 Hz, 1H), 6.83 (m, 2H), 3.93 (s, 3H), 3.84 (s, 3H) ppm.

Step 2: Methyl 4-[[3-Chloro-2-Fluoro-6-[3-Fluoro-2-Methoxy-4-(Trifluoromethoxy)Phenoxy]-4-Methoxy-Benzoyl]Amino]Pyridine-2-Carboxylate

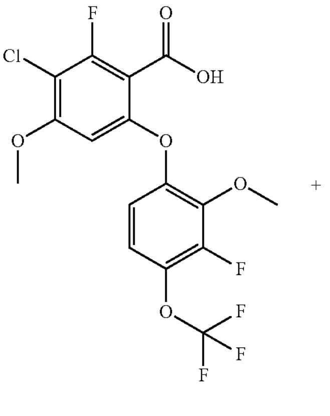

-continued

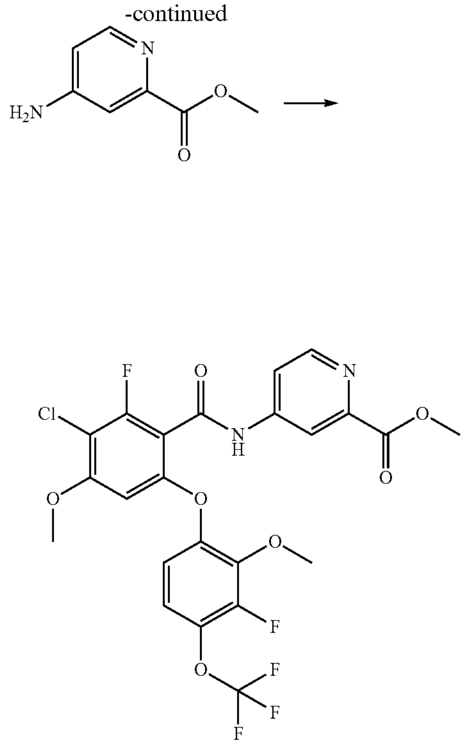

To a solution of 3-chloro-2-fluoro-6-[3-fluoro-2-methoxy-4-(trifluoromethoxy)phenoxy]-4-methoxy-benzoic acid (250 mg, 0.583 mmol) in dichloromethane (5 mL) and DMF (5 μL, 0.07 mmol) at 0° C. was added oxalyl chloride (150 μL, 1.72 mmol). The mixture was warmed to room temperature, stirred for 30 minutes, then concentrated in vacuo. The residue was dissolved in dichloromethane (2.5 mL) and added to a solution of methyl 4-aminopyridine-2-carboxylate (110 mg, 0.723 mmol) and TEA (250 μL, 1.79 mmol) in dichloromethane (2.5 mL) at 0° C. The mixture was warmed to room temperature and stirred for 1 hour. The mixture was diluted with dichloromethane (20 mL) and washed with water (30 mL). The aqueous layer was extracted with additional dichloromethane (2×20 mL), and the combined organic extracts dried over $MgSO_4$, filtered and concentrated in vacuo. Purification by silica gel chromatography (0-80% ethyl acetate/heptane) provided methyl 4-[[3-chloro-2-fluoro-6-[3-fluoro-2-methoxy-4-(trifluoromethoxy)phenoxy]-4-methoxy-benzoyl]amino]pyridine-2-carboxylate (164 mg, 50%). ESI-MS m z calc. 562.06, found 563.4 $(M+1)^+$; 561.6 $(M-1)^-$; LC/MS retention time (Method F): 0.94 minutes. $^1H$ NMR (500 MHz, DMSO-$d_6$) δ 11.28 (s, 1H), 8.59 (d, J=5.4 Hz, 1H), 8.28 (d, J=2.1 Hz, 1H), 7.75 (dd, J=5.5, 2.1 Hz, 1H), 7.29-7.22 (m, 1H), 6.97 (dd, J=9.4, 2.1 Hz, 1H), 6.81 (d, J=1.9 Hz, 1H), 3.87 (s, 6H), 3.85 (d, J=0.8 Hz, 3H) ppm.

Step 3: 4-[[3-Chloro-2-Fluoro-6-[3-Fluoro-2-Methoxy-4-(Trifluoromethoxy)Phenoxy]-4-Methoxy-Benzoyl]Amino]Pyridine-2-Carboxamide (325)

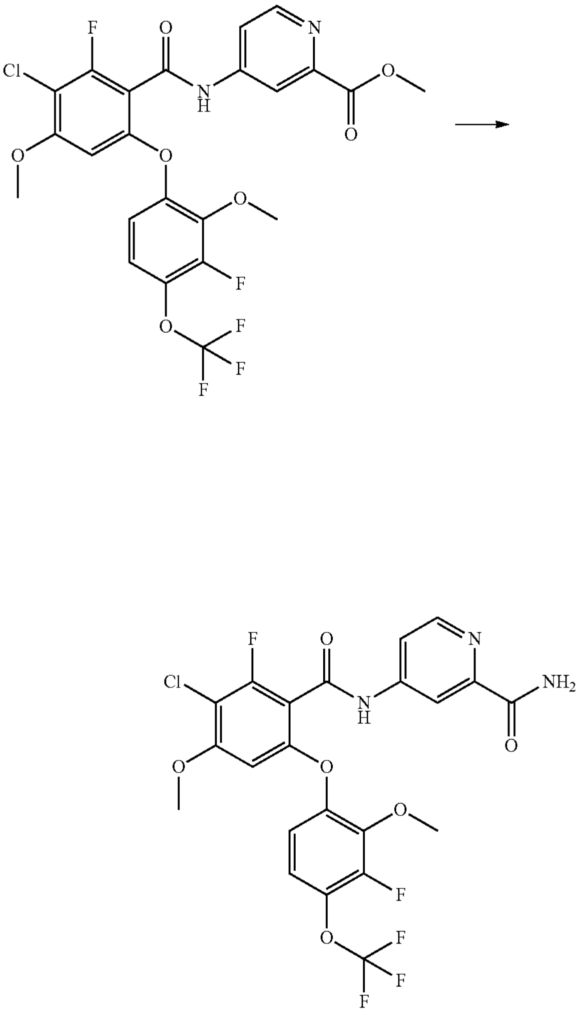

Methyl 4-[[3-chloro-2-fluoro-6-[3-fluoro-2-methoxy-4-(trifluoromethoxy)phenoxy]-4-methoxy-benzoyl]amino]pyridine-2-carboxylate (160 mg, 0.284 mmol) was dissolved in a solution of ammonia in methanol (1.5 mL of 7 M, 10.5 mmol) and stirred at room temperature for 68 hours. The mixture was concentrated in vacuo. The residue was partitioned between dichloromethane (20 mL) and water (20 mL) and the layers separated. The aqueous layer was extracted with additional dichloromethane (2×20 mL), and the combined organic extracts dried over $MgSO_4$, filtered and concentrated in vacuo to provide 4-[[3-chloro-2-fluoro-6-[3-fluoro-2-methoxy-4-(trifluoromethoxy)phenoxy]-4-methoxy-benzoyl]amino]pyridine-2-carboxamide (57.9 mg, 35%). ESI-MS m z calc. 547.06, found 548.4 $(M+1)^+$; 546.4 $(M-1)^-$; LC/MS retention time (Method E): 3.21 minutes. $^1H$ NMR (500 MHz, DMSO-$d_6$) δ 11.23 (s, 1H), 8.51 (d, J=5.4 Hz, 1H), 8.23 (d, J=2.1 Hz, 1H), 8.07 (d, J=2.8 Hz, 1H), 7.75 (dd, J=5.6, 2.2 Hz, 1H), 7.63 (d, J=2.8 Hz, 1H), 7.26 (ddd, J=9.3, 8.1, 1.3 Hz, 1H), 6.97 (dd, J=9.4, 2.1 Hz, 1H), 6.80 (d, J=1.6 Hz, 1H), 3.87 (s, 3H), 3.86 (s, 3H) ppm.

Example 130

4-[[2-Fluoro-6-[3-Fluoro-2-Methoxy-4-(Trifluoromethoxy)Phenoxy]-3-Methoxy-4-(Trifluoromethyl)Benzoyl]Amino]Pyridine-2-Carboxamide (325)

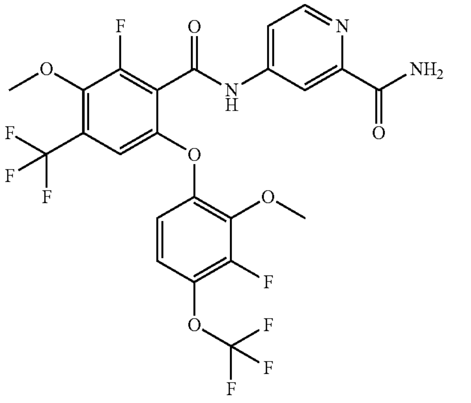 [SMILES: COc1c(Oc2cc(C(F)(F)F)c(OC)c(F)c2C(=O)Nc2ccnc(C(N)=O)c2)ccc(OC(F)(F)F)c1F]

Step 1: 2-Fluoro-6-[3-Fluoro-2-Methoxy-4-(Trifluoromethoxy)Phenoxy]-3-Methoxy-4-(Trifluoromethyl)Benzoic Acid

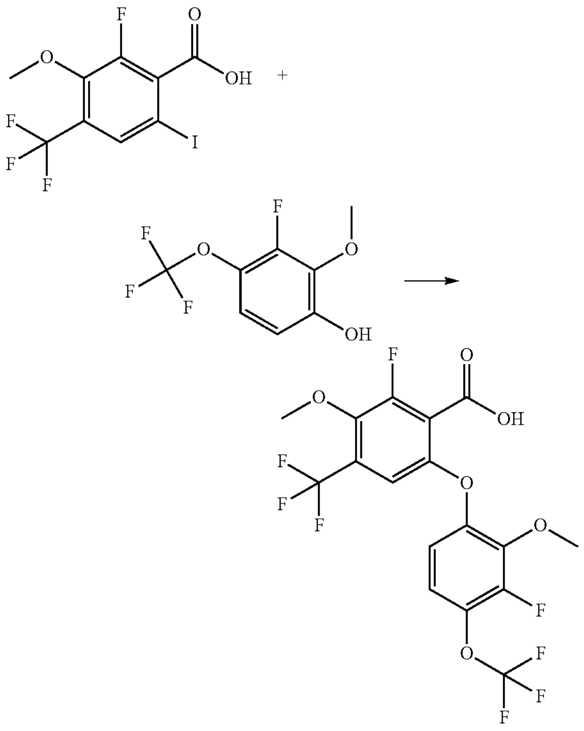

A mixture of 2-fluoro-6-iodo-3-methoxy-4-(trifluoromethyl)benzoic acid (750 mg, 1.65 mmol, see Example 94, Step 4), 3-fluoro-2-methoxy-4-(trifluoromethoxy)phenol (516 mg, 2.28 mmol, see Example 113, Step 1) and $Cs_2CO_3$ (1.086 g, 3.333 mmol) in toluene (15 mL) was bubbled with nitrogen for 10 minutes. Copper (I) iodide (63.4 mg, 0.333 mmol) was added and the mixture heated at 100° C. under nitrogen for 20 hours. The cooled mixture was partitioned between water (100 ml) and ethyl acetate (100 mL) and acidified to pH=3 with 2 M aqueous HCl. The mixture was extracted with ethyl acetate (4×75 mL), and the combined organic extracts washed with water (100 mL), dried over $MgSO_4$, filtered and concentrated in vacuo. Purification using silica gel chromatography (0-30% ethyl acetate/heptane) provided 2-fluoro-6-[3-fluoro-2-methoxy-4-(trifluoromethoxy)phenoxy]-3-methoxy-4-(trifluoromethyl)benzoic acid (240 mg, 27%). ESI-MS m z calc. 462.03, found 461.4 $(M-1)^-$; LC/MS retention time (Method F): 0.63 minutes.

Step 2: 4-[[2-Fluoro-6-[3-Fluoro-2-Methoxy-4-(Trifluoromethoxy)Phenoxy]-3-Methoxy-4-(Trifluoromethyl)Benzoyl]Amino]Pyridine-2-Carboxamide (325)

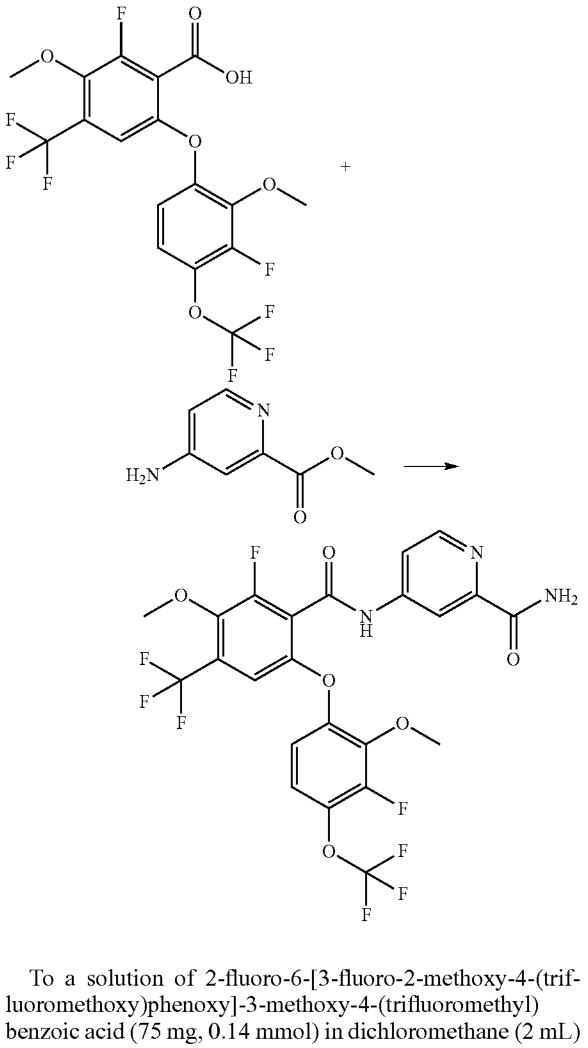

To a solution of 2-fluoro-6-[3-fluoro-2-methoxy-4-(trifluoromethoxy)phenoxy]-3-methoxy-4-(trifluoromethyl) benzoic acid (75 mg, 0.14 mmol) in dichloromethane (2 mL) and DMF (1 µL, 0.01 mmol) at 0° C. was added oxalyl chloride (40 µL, 0.46 mmol). The mixture was warmed to room temperature, stirred for 30 minutes and then concentrated in vacuo. The residue was dissolved in dichloromethane (1 mL) and added to a solution of methyl 4-aminopyridine-2-carboxylate (23.4 mg, 0.154 mmol) and TEA (60 µL, 0.43 mmol) in dichloromethane (1 mL) at 0° C. The mixture was warmed to room temperature and stirred for 20 hours. The mixture was diluted with dichloromethane (20 mL) and washed with water (20 mL). The aqueous layer was extracted with additional dichloromethane (2×20 mL), and the combined organic extracts were dried over $MgSO_4$, filtered and concentrated in vacuo. The residue was dissolved in a solution of ammonia in methanol (1 mL of 7 M, 7 mmol) and stirred for 20 hours. The mixture was concentrated in vacuo and purified by reverse phase HPLC (47-95% acetonitrile/0.1% ammonium hydroxide) to provide 4-[[2-fluoro-6-[3-fluoro-2-methoxy-4-(trifluoromethoxy)phenoxy]-3-methoxy-4-(trifluoromethyl)benzoyl]amino]pyridine-2-carboxamide (17 mg, 21%). ESI-MS m z calc. 581.08, found 582.4 $(M+1)^+$; 580.4 $(M-1)^-$; LC/MS retention time (Method F): 3.44 minutes. $^1H$ NMR (500 MHz, DMSO-$d_6$) δ 11.44 (s, 1H), 8.54 (d, J=5.5 Hz, 1H), 8.26 (d, J=2.2 Hz, 1H), 8.09 (d, J=2.8 Hz, 1H), 7.75 (dd, J=5.4, 2.2 Hz, 1H), 7.65 (d, J=2.8 Hz, 1H), 7.30 (ddd, J=9.6, 8.2, 1.2 Hz, 1H), 7.23 (d, J=1.5 Hz, 1H), 7.01 (dd, J=9.3, 2.2 Hz, 1H), 4.00 (d, J=1.3 Hz, 3H), 3.85 (d, J=0.8 Hz, 3H) ppm.

Example 131

4-[[4-Chloro-2-Fluoro-6-[3-Fluoro-2-Methoxy-4-(Trifluoromethoxy)Phenoxy]-3-Methoxy-Benzoyl]Amino]Pyridine-2-Carboxamide (326)

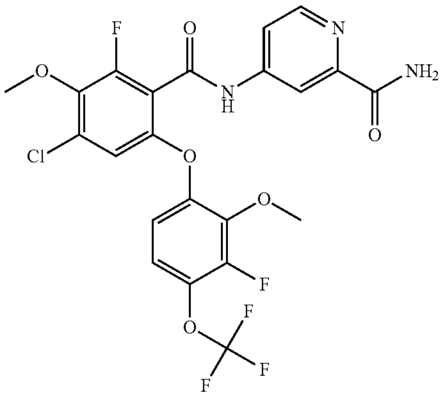 [SMILES: COc1c(Cl)cc(Oc2ccc(OC(F)(F)F)c(F)c2OC)c(C(=O)Nc2ccnc(C(N)=O)c2)c1F]

Step 1: 6-Bromo-4-Chloro-2-Fluoro-3-Methoxy-Benzoic Acid

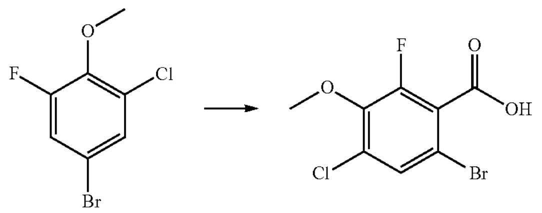

To a solution of 5-bromo-1-chloro-3-fluoro-2-methoxybenzene (2.8 g, 11.7 mmol) in THF (20 mL) was added a solution of LDA (7 mL of 2 M in THF/heptane/ethylbenzene, 14 mmol) dropwise while maintaining the temperature below −65° C. The mixture was stirred at −70° C. for 30 minutes then poured onto solid carbon dioxide (dry ice) and stirred until at room temperature and no more effervescence was observed. The mixture was partitioned between water (20 mL) and ethyl acetate (20 mL) and the layers separated. The aqueous layer was acidified to pH=3 by addition of 1 M aqueous HCl and then extracted with ethyl acetate (3×30 mL). The combined extracts were dried over $MgSO_4$, filtered and concentrated in vacuo to provide 6-bromo-4-chloro-2-fluoro-3-methoxy-benzoic acid (2.6 g, 78%). $^1H$ NMR (500 MHz, DMSO-$d_6$) δ 14.39 (s, 1H), 7.77 (d, J=2.0 Hz, 1H), 3.92 (d, J=1.4 Hz, 3H) ppm

Step 2: 4-Chloro-2-Fluoro-6-[3-Fluoro-2-Methoxy-4-(Trifluoromethoxy)Phenoxy]-3-Methoxy-Benzoic Acid

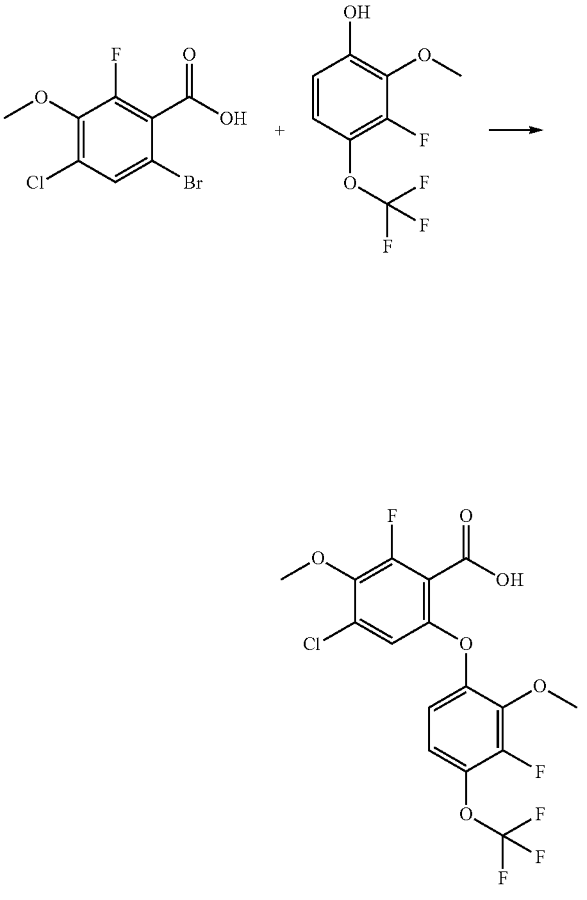

A mixture of 6-bromo-4-chloro-2-fluoro-3-methoxy-benzoic acid (800 mg, 2.82 mmol), 3-fluoro-2-methoxy-4-(trifluoromethoxy)phenol (700 mg, 3.10 mmol, see Example 113, Step 1), copper (I) iodide (110 mg, 0.578 mmol) and $Cs_2CO_3$ (1.84 g, 5.65 mmol) in toluene (25 mL) was heated at 100° C. overnight. The cooled mixture was diluted with water and ethyl acetate (50 mL), then acidified with 2 M aqueous HCl (30 mL). The ethyl acetate layer was washed with water, then dried over $Na_2SO_4$, filtered and concentrated in vacuo to provide 4-chloro-2-fluoro-6-[3-fluoro-2-methoxy-4-(trifluoromethoxy)phenoxy]-3-methoxy-benzoic acid (870 mg, 72%). ESI-MS m z calc. 428.01, found 427.1 $(M-1)^-$; LC/MS retention time (Method F): 0.58 minutes.

Step 3: 4-[[4-Chloro-2-Fluoro-6-[3-Fluoro-2-Methoxy-4-(Trifluoromethoxy)Phenoxy]-3-Methoxy-Benzoyl]Amino]Pyridine-2-Carboxamide (326)

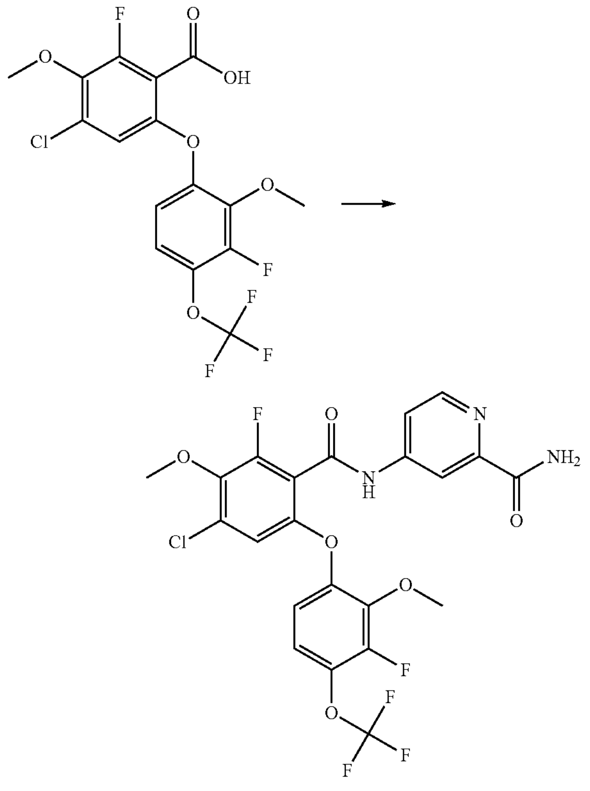

A solution of 4-chloro-2-fluoro-6-[3-fluoro-2-methoxy-4-(trifluoromethoxy)phenoxy]-3-methoxy-benzoic acid (220 mg, 0.513 mmol) in dichloromethane (3 mL) at 0° C. was treated with DMF (40 μL, 0.52 mmol) followed by the dropwise addition of oxalyl chloride (180 μL, 2.06 mmol) (gas evolution). The mixture was stirred for 1 hour, and then concentrated in vacuo. The residue was dissolved in dichloromethane (3 mL) and added dropwise to a stirring solution of methyl 4-aminopyridine-2-carboxylate (91 mg, 0.57 mmol), DIPEA (280 μL, 1.61 mmol) and DMAP (64 mg, 0.52 mmol) in dichloromethane (3 mL). The mixture was stirred overnight then concentrated in vacuo. The residue was treated with excess ammonia (7 M in methanol) and stirred for three days at room temperature. Purification by reverse phase HPLC (47-95% acetonitrile/0.1% ammonium hydroxide) provided 4-[[4-chloro-2-fluoro-6-[3-fluoro-2-methoxy-4-(trifluoromethoxy)phenoxy]-3-methoxy-benzoyl]amino]pyridine-2-carboxamide (26.6 mg, 9%). ESI-MS m z calc. 547.06, found 548.1 $(M+1)^+$; 546.1 $(M-1)^-$; LC/MS retention time (Method F): 0.94 minutes. $^1H$ NMR (400 MHz, $CDCl_3$) δ 9.54 (s, 1H), 8.54 (d, J=5.5 Hz, 1H), 8.43 (dd, J=5.6, 2.1 Hz, 1H), 8.15-8.09 (m, 1H), 7.91 (d, J=4.5 Hz, 1H), 7.06 (ddq, J=8.9, 7.6, 1.2 Hz, 1H), 6.96 (dd, J=9.2, 2.1 Hz, 1H), 6.66 (d, J=2.0 Hz, 1H), 5.47 (d, J=4.4 Hz, 1H), 3.99 (d, J=1.0 Hz, 3H), 3.91 (d, J=1.8 Hz, 3H) ppm.

Example 132

4-[[2,2-Difluoro-6-[3-Fluoro-2-Methoxy-4-(Trifluoromethoxy)Phenoxy]-4-Methyl-1,3-Benzodioxole-5-Carbonyl]Amino]Pyridine-2-Carboxamide (327)

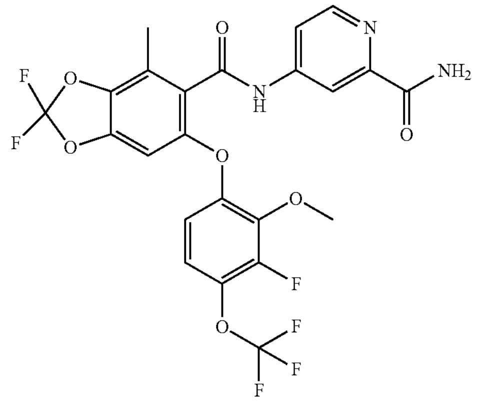 [SMILES: COc1c(Oc2cc3c(c(C)c2C(=O)Nc2ccnc(C(N)=O)c2)OC(F)(F)O3)ccc(OC(F)(F)F)c1F]

Step 1: 2,2-Difluoro-4-Methyl-1,3-Benzodioxole-5-Carboxylic Acid

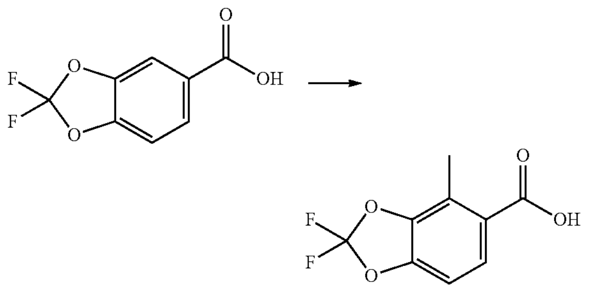

To a solution of 2,2-difluoro-1,3-benzodioxole-5-carboxylic acid (0.10 g, 0.49 mmol) in THF (7.0 mL) cooled to −78° C. was added n-butyllithium (0.5 mL of 2 M, 1 mmol). The mixture was allowed to warm to 4° C. and stirred for 4 hours, and then cooled to −78° C. and methyl iodide (160 mg, 0.07 mL, 1.1 mmol) added. The mixture was allowed to warm to 4° C. and stirred for 4 hours, and then allowed to warm to room temperature and stirred overnight. The mixture was diluted with 1 M aqueous HCl and the volatiles removed under reduced pressure. The resulting aqueous mixture was extracted with ethyl acetate. The organic phase was washed with water and concentrated in vacuo to provide 2,2-difluoro-4-methyl-1,3-benzodioxole-5-carboxylic acid (100 mg, 79%) as a pale yellow solid. ESI-MS m z calc. 216.02, no ionization observed; LC/MS retention time (Method S): 2.64 minutes. $^1H$ NMR (250 MHz, $CDCl_3$) δ 7.96 (d, J=8.7 Hz, 1H), 6.99 (d, J=8.5 Hz, 1H), 2.61 (s, 3H) ppm.

Step 2: 2,2-Difluoro-4-Methyl-6-Nitro-1,3-Benzodioxole-5-Carboxylic Acid

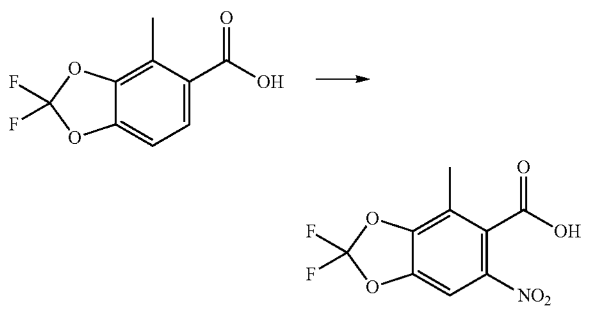

A solution of 2,2-difluoro-4-methyl-1,3-benzodioxole-5-carboxylic acid (0.50 g, 2.1 mmol) in fuming $HNO_3$ (11 mL) was stirred at room temperature overnight. The mixture was diluted with ethyl acetate and water while cooling in ice bath. The layers were separated, and the organic phase was washed with water (2×) and concentrated in vacuo to provide 2,2-difluoro-4-methyl-6-nitro-1,3-benzodioxole-5-carboxylic acid (0.59 g, 98%). ESI-MS m z calc. 261.01, no ionization observed; LC/MS retention time (Method S): 2.48 minutes. H NMR (250 MHz, $CDCl_3$) δ 7.81 (s, 1H), 2.47 (s, 3H) ppm.

Step 3: 6-Amino-2,2-Difluoro-4-Methyl-1,3-Benzodioxole-5-Carboxylic Acid

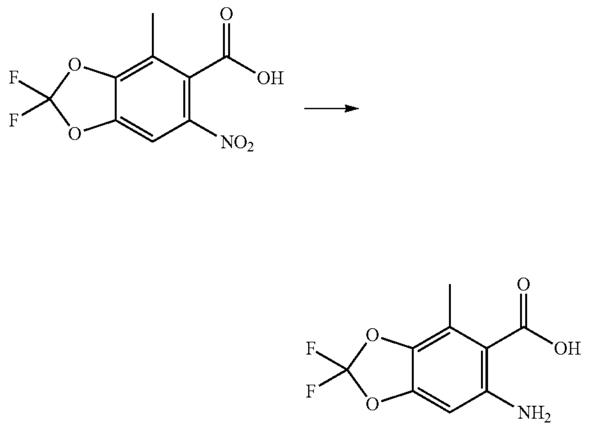

To a solution of 2,2-difluoro-4-methyl-6-nitro-1,3-benzodioxole-5-carboxylic acid (0.70 g, 2.4 mmol) in ethyl acetate (35 mL), water (35 mL) and acetic acid (1.9 g, 1.8 mL, 32 mmol) was added Fe (500 mg, 8.95 mmol). The mixture was stirred at 80° C. for 2 hours. The cooled mixture was basified to pH 7-8 with $NaHCO_3$ and filtered. The layers were separated and the organic phase was washed with brine, dried over $MgSO_4$, filtered and concentrated to provide 6-amino-2,2-difluoro-4-methyl-1,3-benzodioxole-5-carboxylic acid (0.685 g, 98%) as a dark brown solid. ESI-MS m z calc. 231.03, found 232.0 $(M+1)^+$; LC/MS retention time (Method S): 2.5 minutes.

Step 4: 6-Bromo-2,2-Difluoro-4-Methyl-1,3-Benzodioxole-5-Carboxylic Acid

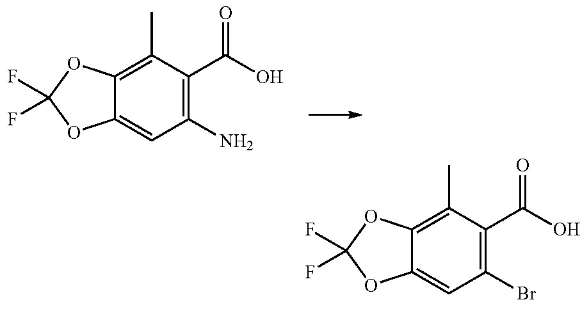

To a solution of 6-amino-2,2-difluoro-4-methyl-1,3-benzodioxole-5-carboxylic acid (100 mg, 0.346 mmol) in acetonitrile (2 mL) at 0° C. was added tert-butyl nitrite (60 mg, 0.07 mL, 0.58 mmol). The mixture was stirred at 4° C. for 15 minutes, then copper (II) bromide (130 mg, 0.582 mmol) added. The mixture was allowed to warm to room temperature and stirred for 3 hours. The mixture was diluted with ethyl acetate/hexanes and water, and then filtered. The layers were separated and the organic phase was washed with brine, dried over $MgSO_4$ and concentrated to provide 6-bromo-2,2-difluoro-4-methyl-1,3-benzodioxole-5-carboxylic acid (95 mg, 65%) as a brown solid. ESI-MS m z calc. 293.93, no ionization observed; LC/MS retention time (Method S): 2.67 minutes.

Step 5: 2,2-Difluoro-6-[3-Fluoro-2-Methoxy-4-(Trifluoromethoxy)Phenoxy]-4-Methyl-1,3-Benzodioxole-5-Carboxylic Acid

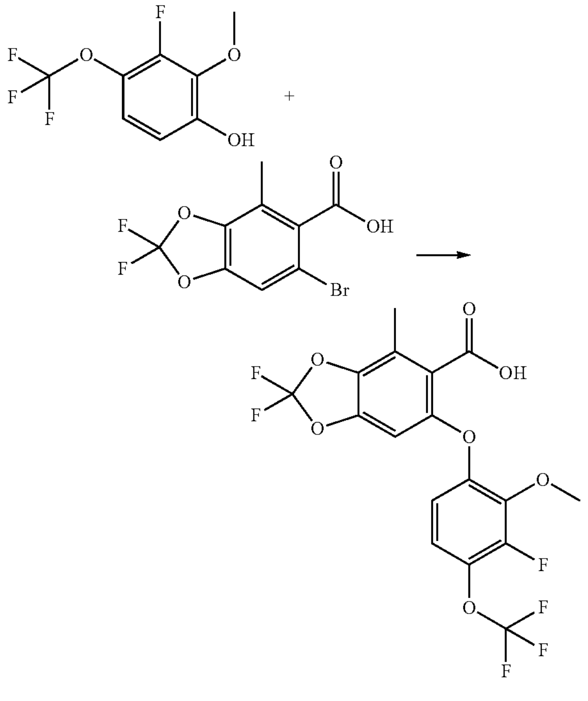

A mixture of 6-bromo-2,2-difluoro-4-methyl-1,3-benzodioxole-5-carboxylic acid (514 mg, 1.74 mmol) in toluene (12 mL) was flushed with nitrogen for 10 minutes. 3-Fluoro-2-methoxy-4-(trifluoromethoxy)phenol (604 mg, 2.67 mmol, see Example 113, Step 1) and $Cs_2CO_3$ (1.24 g, 3.806 mmol) were added to the mixture and flushed with nitrogen. Copper (I) iodide (106 mg, 0.558 mmol) was added to the mixture and flushed with nitrogen for 10 minutes. The mixture was heated at 100° C. with vigorous stirring for 20 hours under nitrogen. The cooled mixture was diluted with ethyl acetate, water and acidified with 1 M aqueous HCl. The layers were separated and the aqueous layer extracted with additional ethyl acetate (3×). The combined organic extracts were filtered, and the layers separated. The organic phase was washed with water and brine, dried over $Na_2SO_4$, filtered through Celite and concentrated. The residue was purified by reverse phase HPLC (1-99% acetonitrile/5 mM HCl) to provide 2,2-difluoro-6-[3-fluoro-2-methoxy-4-(trifluoromethoxy)phenoxy]-4-methyl-1,3-benzodioxole-5-carboxylic acid (204.7 mg, 27%) as an off white solid. ESI-MS m z calc. 440.03, found 441.3 $(M+1)^+$; LC/MS retention time (Method C): 2.8 minutes.

Step 6: 4-[[2,2-Difluoro-6-[3-Fluoro-2-Methoxy-4-(Trifluoromethoxy)Phenoxy]-4-Methyl-1,3-Benzodioxole-5-Carbonyl]Amino]Pyridine-2-Carboxamide (327)

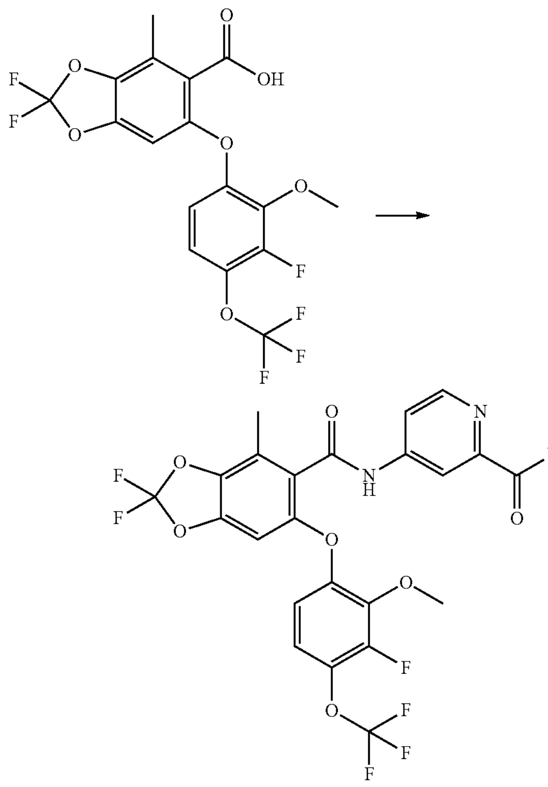

To a solution of 2,2-difluoro-6-[3-fluoro-2-methoxy-4-(trifluoromethoxy)phenoxy]-4-methyl-1,3-benzodioxole-5-carboxylic acid (32.6 mg, 0.0741 mmol) and DMF (15 μL, 0.19 mmol) in dichloromethane (1 mL) at 0° C. was added oxalyl chloride (30 μL, 0.34 mmol) dropwise under nitrogen. The ice bath was removed after 10 minutes and the mixture was stirred at room temperature for 1 hour. The mixture was concentrated in vacuo to afford 2,2-difluoro-6-[3-fluoro-2-methoxy-4-(trifluoromethoxy)phenoxy]-4-methyl-1,3-benzodioxole-5-carbonyl chloride. The acid chloride was dissolved in 2-MeTHF (500 μL) and added slowly to a mixture of 4-aminopyridine-2-carboxamide (13 mg, 0.095 mmol) and DIEA (32 μL, 0.18 mmol) in 2-MeTHF (500 μL) at 0° C. The suspension was stirred at 75° C. for 17 hours. The mixture was concentrated in vacuo and purified by reverse phase HPLC (1-99% acetonitrile/5 mM HCl) to provide 4-[[2,2-difluoro-6-[3-fluoro-2-methoxy-4-(trifluoromethoxy)phenoxy]-4-methyl-1,3-benzodioxole-5-carbonyl]amino]pyridine-2-carboxamide (14.0 mg, 34%) as a white solid. ESI-MS m z calc. 559.08, found 560.2 $(M+1)^+$; LC/MS retention time (Method C): 2.7 minutes. $^1H$ NMR (400 MHz, DMSO-$d_6$) δ 11.17 (s, 1H), 8.51 (d, J=5.5 Hz, 1H), 8.29 (d, J=2.1 Hz, 1H), 8.08 (d, J=2.8 Hz, 1H), 7.77 (dd, J=5.5, 2.2 Hz, 1H), 7.64 (d, J=2.8 Hz, 1H), 7.32-7.22 (m, 2H), 6.93 (dd, J=9.4, 2.1 Hz, 1H), 3.81 (s, 3H), 2.31 (s, 3H) ppm.

Example 133

4-[[2,2,4-Trifluoro-6-[3-Fluoro-2-Methoxy-4-(Trifluoromethoxy)Phenoxy]-1,3-Benzodioxole-5-Carbonyl]Amino]Pyridine-2-Carboxamide (328)

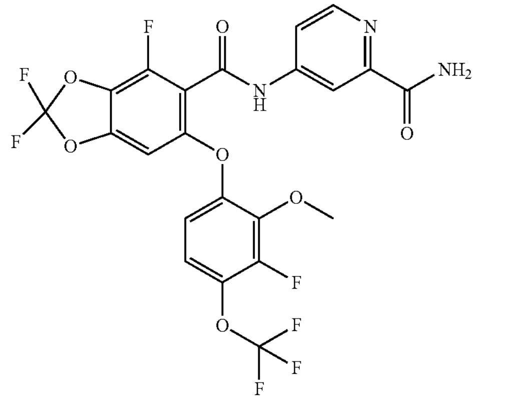 [SMILES: COc1c(Oc2cc3c(c(F)c2C(=O)Nc2ccnc(C(N)=O)c2)OC(F)(F)O3)ccc(OC(F)(F)F)c1F]

Step 1: 2,2,4-Trifluoro-1,3-Benzodioxole-5-Carboxylic Acid

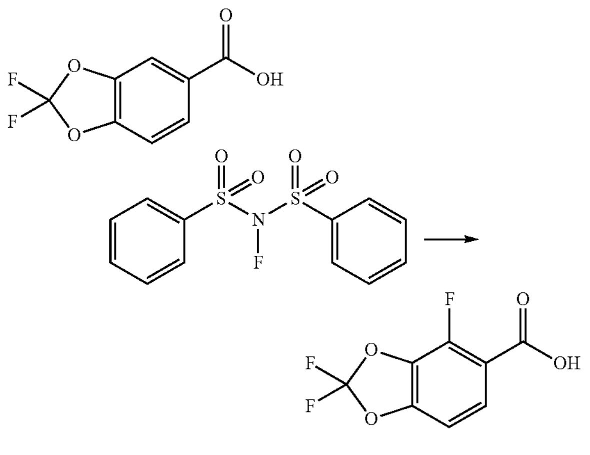

To a solution of 2,2-difluoro-1,3-benzodioxole-5-carboxylic acid (200 mg, 0.990 mmol) in anhydrous THF (5 mL) was added n-butyllithium (1 mL of 2.5 M in hexane, 2.5 mmol) dropwise at −78° C. The mixture was stirred at the same temperature for 10 minutes and then warmed to 0° C. and stirred for 1 hour. The mixture was cooled to −78° C. and treated dropwise with a solution N-(benzenesulfonyl)-N-fluoro-benzenesulfonamide (939 mg, 2.98 mmol) in anhydrous THF (5 mL). The mixture was warmed to room temperature and diluted with water (10 mL). The volatiles were removed in vacuo and 2 N $Na_2CO_3$ solution added to adjust the pH to 10. The aqueous solution was washed with diethyl ether (20 mL), and then acidified with 1 M aqueous HCl to pH 2. The solution was extracted with ethyl acetate (3×25 mL), and the combined organic extracts were washed with brine (25 mL), dried over anhydrous $Na_2SO_4$, filtered and concentrated in vacuo. The residue was purified by silica gel chromatography (0-10% methanol/dichloromethane containing 0.3% acetic acid) to provide 2,2,4-trifluoro-1,3-benzodioxole-5-carboxylic acid (114 mg, 52%) as an off-white solid. ESI-MS m z calc. 220.00, found 220.7 $(M+1)^+$; LC/MS retention time (Method N): 3.96 minutes. $^1$H NMR (250 MHz, dimethyl sulfoxide-$d_6$) δ 7.79 (dd, J=8.4, 6.9 Hz, 1H), 7.39 (d, J=8.7 Hz, 1H) ppm.

Step 2: 2,2,4-Trifluoro-6-Iodo-1,3-Benzodioxole-5-Carboxylic Acid

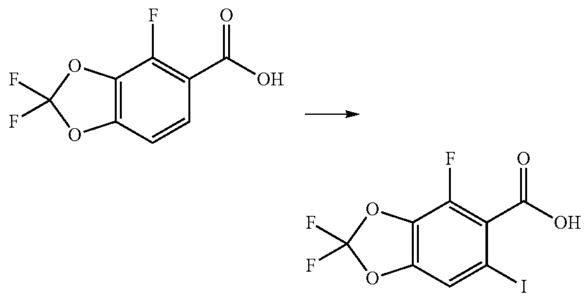

A mixture of 2,2,4-trifluoro-1,3-benzodioxole-5-carboxylic acid (2.588 g, 10.58 mmol), iodobenzene diacetate (7.046 g, 21.88 mmol), iodine (5.412 g, 21.32 mmol) and $Pd(OAc)_2$ (266 mg, 1.19 mmol) in DMF (50 mL) was stirred at 60° C. for 24 hours. The mixture was diluted with water (50 mL) and adjusted to pH=12 with 1 M aqueous NaOH. The aqueous solution was diluted with diethyl ether (50 mL) and the biphasic mixture filtered through Celite to remove the solids. The layers were separated, and the aqueous layer washed with additional diethyl ether (50 mL). The aqueous layer was acidified with 1 M aqueous HCl to pH=2 and extracted with ethyl acetate (3×100 mL). The combined organic extracts were washed with saturated aqueous $Na_2S_2O_3$ (100 mL) and brine (3×100 mL), dried over anhydrous $Na_2SO_4$, filtered and concentrated in vacuo. Purification by silica gel chromatography (0-20% methanol/dichloromethane containing 0.3% acetic acid) was followed by reverse phase HPLC purification (0-100% acetonitrile/water containing 0.1% TFA). The volatiles from the HPLC purification were removed in vacuo, and the remaining aqueous solution extracted with ethyl acetate (4×100 mL). The combined organic extracts were washed with brine (100 mL), dried over anhydrous $Na_2SO_4$, filtered and concentrated in vacuo to provide 2,2,4-trifluoro-6-iodo-1,3-benzodioxole-5-carboxylic acid (2.33 g, 64%) as a white solid. ESI-MS m z calc. 345.90, found 347.0 $(M+1)^+$; LC/MS retention time (Method N): 4.47 minutes. $^1$H NMR (250 MHz, DMSO-$d_6$) δ 7.92 (s, 1H) ppm.

Step 3: 2,2,4-Trifluoro-6-[3-Fluoro-2-Methoxy-4-(Trifluoromethoxy)Phenoxy]-1,3-Benzodioxole-5-Carboxylic Acid

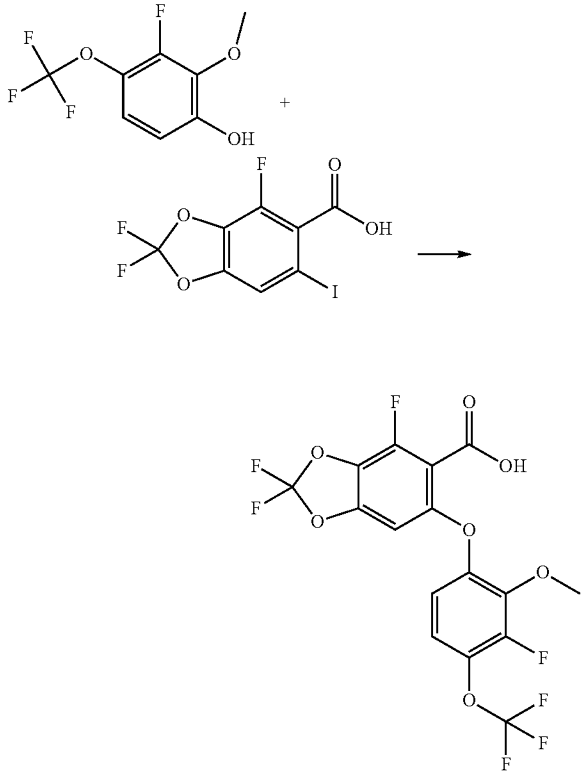

A pressure vessel containing 2,2,4-trifluoro-6-iodo-1,3-benzodioxole-5-carboxylic acid (801 mg, 2.31 mmol) and toluene (17.5 mL) was flushed with nitrogen for 10 minutes. 3-Fluoro-2-methoxy-4-(trifluoromethoxy)phenol (1.024 g, 4.528 mmol, see Example 113, Step 1) and $Cs_2CO_3$ (1.771 g, 5.436 mmol) were added to the mixture and flushed with nitrogen for 10 minutes. Copper (I) iodide (461 mg, 2.42 mmol) was added to the mixture and flushed with nitrogen for 10 min. The mixture was heated at 100° C. with vigorous stirring for 5 hours. The cooled mixture was diluted with ethyl acetate and water, and then acidified with 1 M aqueous HCl. The layers were separated and the aqueous layer was extracted with additional ethyl acetate (3×). The combined organic extracts were washed with water and brine, dried over $Na_2SO_4$, filtered through Celite and concentrated. Purification by reverse phase HPLC (1-99% acetonitrile/5 mM HCl) provided 2,2,4-trifluoro-6-[3-fluoro-2-methoxy-4-(trifluoromethoxy)phenoxy]-1,3-benzodioxole-5-carboxylic acid (321.9 mg, 31%). ESI-MS m z calc. 444.01, found 445.09 $(M+1)^+$; LC/MS retention time (Method C): 2.76 minutes. $^1$H NMR (400 MHz, DMSO-$d_6$) δ 13.99 (s, 1H), 7.42-7.19 (m, 2H), 6.91 (dd, J=9.3, 2.1 Hz, 1H), 3.91 (s, 3H) ppm.

Step 4: 4-[[2,2,4-Trifluoro-6-[3-Fluoro-2-Methoxy-4-(Trifluoromethoxy)Phenoxy]-1,3-Benzodioxole-5-Carbonyl]Amino]Pyridine-2-Carboxamide (328)

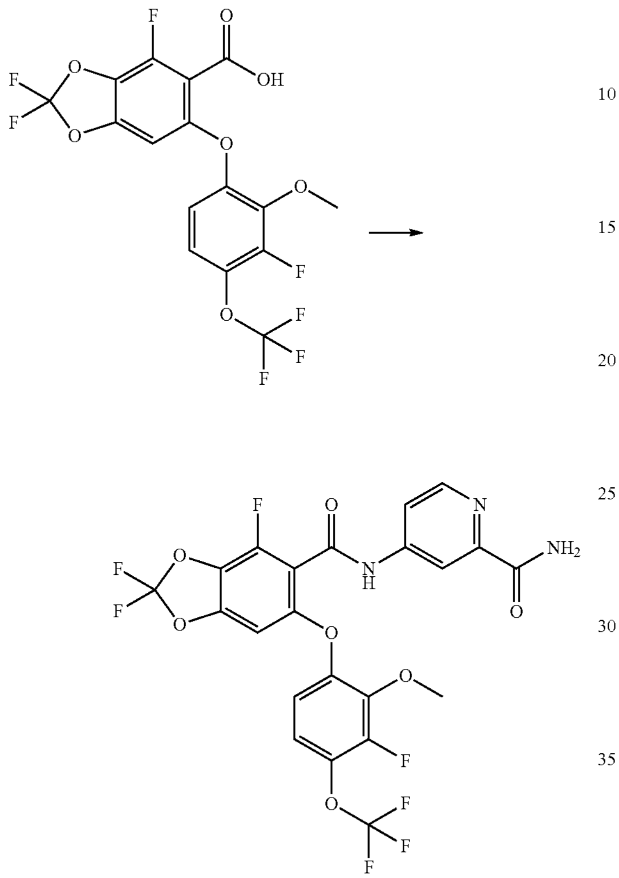

To a solution of 2,2,4-trifluoro-6-[3-fluoro-2-methoxy-4-(trifluoromethoxy)phenoxy]-1,3-benzodioxole-5-carboxylic acid (70 mg, 0.16 mmol) and DMF (15 μL, 0.19 mmol) in dichloromethane (2 mL) at 0° C. was added oxalyl chloride (41 μL, 0.47 mmol) dropwise under nitrogen. The ice bath was removed after 10 minutes and the mixture was stirred at room temperature for 1 hour. The mixture was concentrated in vacuo to afford 2,2,4-trifluoro-6-[3-fluoro-2-methoxy-4-(trifluoromethoxy)phenoxy]-1,3-benzodioxole-5-carbonyl chloride. The acid chloride was suspended in 2-MeTHF (1 mL), cooled to 0° C., and treated with a mixture of 4-aminopyridine-2-carboxamide (34.1 mg, 0.249 mmol) and DIEA (72 μL, 0.41 mmol) in 2-MeTHF (1 mL) cooled to 0° C. The resulting mixture was stirred at 75° C. for 21 hours. The mixture was concentrated in vacuo and purified using reverse phase HPLC (1-99% acetonitrile/5 mM HCl) to provide 4-[[2,2,4-trifluoro-6-[3-fluoro-2-methoxy-4-(trifluoromethoxy)phenoxy]-1,3-benzodioxole-5-carbonyl]amino]pyridine-2-carboxamide (19.5 mg, 21%). ESI-MS m z calc. 563.06, found 564.1 $(M+1)^+$; LC/MS retention time (Method C): 2.79 minutes. $^1H$ NMR (400 MHz, DMSO-$d_6$) δ 11.38 (s, 1H), 8.54 (d, J=5.4 Hz, 1H), 8.27 (d, J=2.1 Hz, 1H), 8.10 (d, J=2.7 Hz, 1H), 7.77 (dd, J=5.5, 2.2 Hz, 1H), 7.66 (d, J=2.8 Hz, 1H), 7.43-7.14 (m, 2H), 7.03 (dd, J=9.3, 2.1 Hz, 1H), 3.84 (s, 3H) ppm.

Example 134

6-[[2-Fluoro-6-[3-Fluoro-2-Methoxy-4-(Trifluoromethoxy)Phenoxy]-3-(Trifluoromethyl)Benzoyl]Amino]Pyrimidine-4-Carboxamide (329)

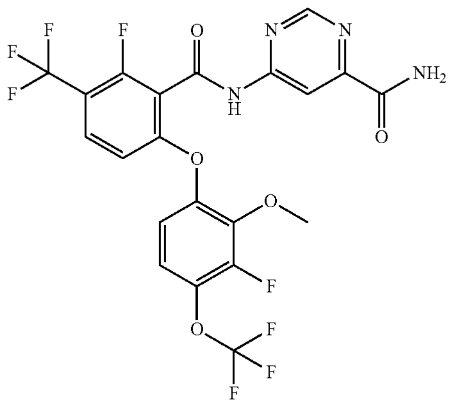 [SMILES: COc1c(Oc2ccc(C(F)(F)F)c(F)c2C(=O)Nc2cc(C(N)=O)ncn2)ccc(OC(F)(F)F)c1F]

Step 1: 2-Fluoro-6-[3-Fluoro-2-Methoxy-4-(Trifluoromethoxy)Phenoxy]-3-(Trifluoromethyl)Benzoic Acid

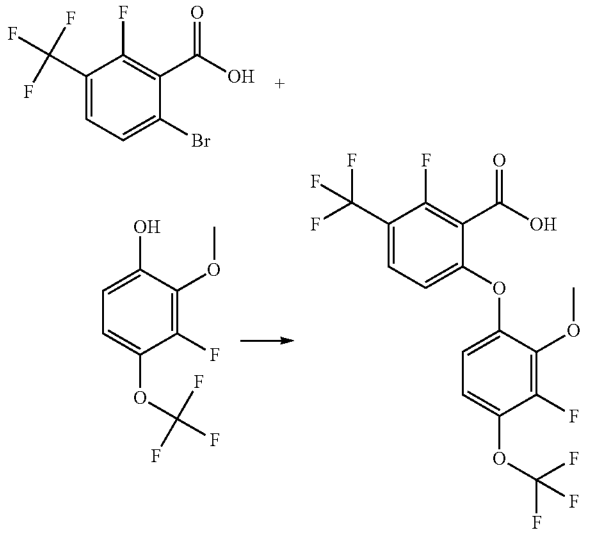

A mixture of 6-bromo-2-fluoro-3-(trifluoromethyl)benzoic acid (35.0 g, 122 mmol), 3-fluoro-2-methoxy-4-(trifluoromethoxy)phenol (27.6 g, 122 mmol, see Example 113, Step 1) and $Cs_2CO_3$ (79.5 g, 244 mmol) in degassed toluene (657 mL, bubbled with nitrogen for 20 minutes) was stirred for 10 minutes. Copper (I) iodide (4.65 g, 24.4 mmol) was added and the mixture heated at 100° C. for 1 hour. The mixture was cooled to room temperature and diluted with MTBE (350 mL). The solution was washed with 4 M aqueous $NH_4Cl$ (4×200 mL), 1 M aqueous HCl (183 mL) and brine (125 mL). The organic layer was dried over $MgSO_4$ and concentrated in vacuo to provide 52.1 g of crude oil. The oil was crystallized from heptane (225 mL) to provide 2-fluoro-6-[3-fluoro-2-methoxy-4-(trifluoromethoxy)phenoxy]-3-(trifluoromethyl)benzoic acid (39.0 g, 73%). $^1$H NMR (400 MHz, DMSO-$d_6$) δ 14.22 (s, 1H), 7.80 (t, J=8.6 Hz, 1H), 7.45-7.33 (m, 1H), 7.19 (dd, J=9.3, 2.2 Hz, 1H), 6.87 (d, J=8.9 Hz, 1H), 3.87 (s, 3H) ppm.

Step 2: Methyl 6-[[2-Fluoro-6-[3-Fluoro-2-Methoxy-4-(Trifluoromethoxy)Phenoxy]-3-(Trifluoromethyl)Benzoyl]Amino]Pyrimidine-4-Carboxylate

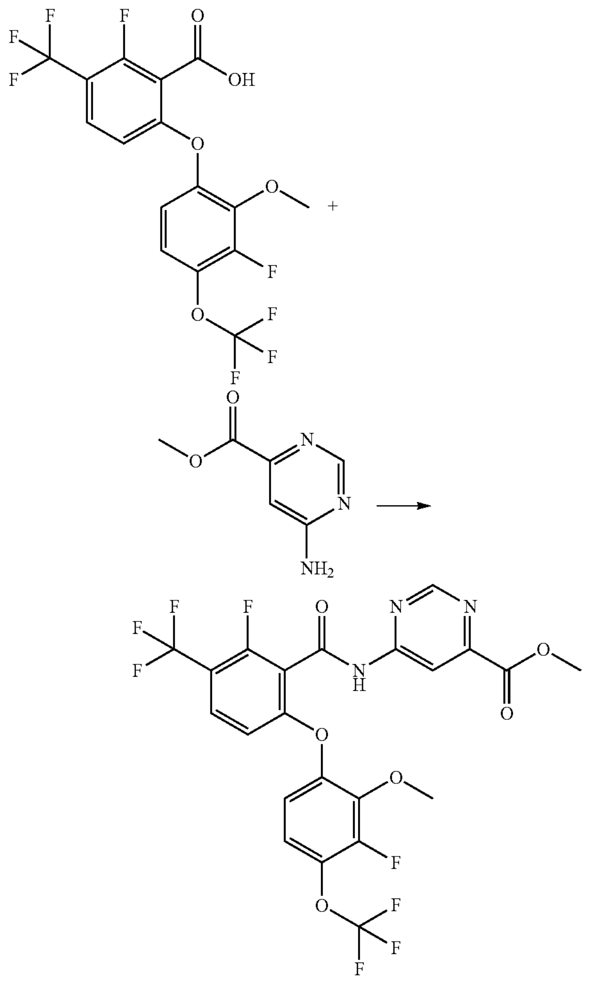

To a solution of 2-fluoro-6-[3-fluoro-2-methoxy-4-(trifluoromethoxy)phenoxy]-3-(trifluoromethyl)benzoic acid (350 mg, 0.802 mmol) and DMF (10 μL, 0.13 mmol) in dichloromethane (9 mL) at 0° C. was added oxalyl chloride (250 μL, 2.87 mmol) dropwise under nitrogen. The ice bath was removed after 1 hour and the mixture was stirred at room temperature for 1 hour. The solution was concentrated in vacuo to afford 2-fluoro-6-[3-fluoro-2-methoxy-4-(trifluoromethoxy)phenoxy]-3-(trifluoromethyl)benzoyl chloride. A portion of the acid chloride (50 mg, 0.11 mmol) was dissolved in NMP (0.3 mL) and added to a mixture of methyl 6-aminopyrimidine-4-carboxylate (25.5 mg, 0.166 mmol) and DIEA (57 mg, 77 μL, 0.44 mmol) in NMP (0.3 mL). The mixture was stirred at room temperature for 16 hours. Purification by reverse phase HPLC (30-99% acetonitrile/5 mM HCl) provided methyl 6-[[2-fluoro-6-[3-fluoro-2-methoxy-4-(trifluoromethoxy)phenoxy]-3-(trifluoromethyl)benzoyl]amino]pyrimidine-4-carboxylate (10 mg, 16%).

ESI-MS m z calc. 567.07, found 568.0 (M+1)$^+$; LC/MS retention time (Method B): 2.0 minutes.

Step 3: 6-[[2-Fluoro-6-[3-Fluoro-2-Methoxy-4-(Trifluoromethoxy)Phenoxy]-3-(Trifluoromethyl)Benzoyl]Amino]Pyrimidine-4-Carboxamide (329)

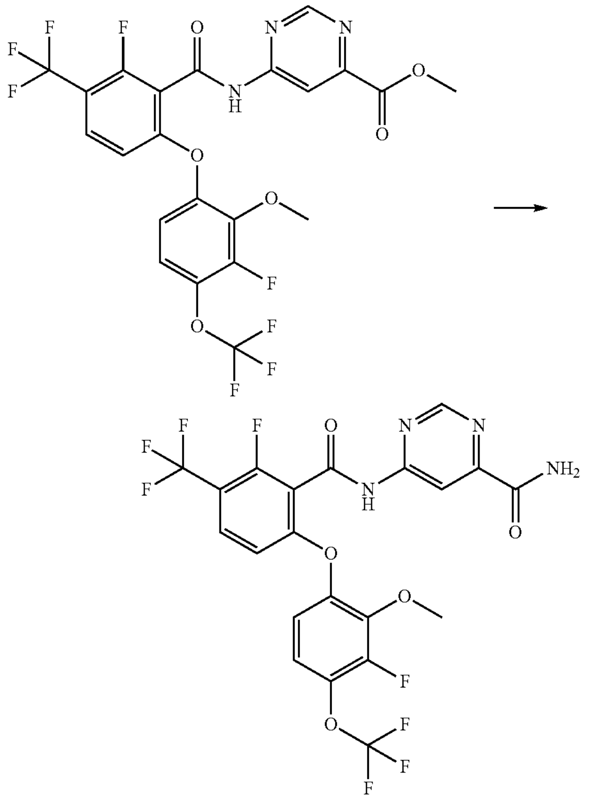

Methyl 6-[[2-fluoro-6-[3-fluoro-2-methoxy-4-(trifluoromethoxy)phenoxy]-3-(trifluoromethyl)benzoyl]amino]pyrimidine-4-carboxylate (10 mg, 0.018 mmol) was dissolved in a solution of ammonia in methanol (500 μL of 7 M, 3.5 mmol) and stirred at room temperature for 16 hours. The mixture was filtered, concentrated and purified by reverse phase HPLC (40-70% acetonitrile/5 mM HCl) to provide 6-[[2-fluoro-6-[3-fluoro-2-methoxy-4-(trifluoromethoxy)phenoxy]-3-(trifluoromethyl)benzoyl]amino]pyrimidine-4-carboxamide (6.8 mg, 70%). ESI-MS m z calc. 552.07, found 553.0 (M+1)$^+$; LC/MS retention time (Method B): 1.85 minutes. $^1$H NMR (400 MHz, DMSO-$d_6$) δ 12.10 (s, 1H), 9.04 (s, 1H), 8.68 (s, 1H), 8.29 (s, 1H), 7.96 (t, 1H), 7.84 (t, J=8.6 Hz, 1H), 7.40 (t, J=8.6 Hz, 1H), 7.22 (dd, J=9.3, 2.1 Hz, 1H), 6.90 (d, J=8.9 Hz, 1H), 3.86 (d, J=1.1 Hz, 3H) ppm.

The compounds set forth in Table 34 were prepared by methods analogous to the preparation of compound 329, Example 134 above), i.e., amide coupling with 2-fluoro-6-[3-fluoro-2-methoxy-4-(trifluoromethoxy)phenoxy]-3-(trifluoromethyl)benzoic acid was followed by conversion of the ester to the corresponding carboxamide via treatment with methanolic ammonia.

TABLE 34

Additional Compounds Prepared by Methods Analogous to Example 134

| Cmpd No. | Compound Name | LC/MS | NMR (shifts in ppm) |
|---|---|---|---|
| 330 | 2-[[2-fluoro-6-[3-fluoro-2-methoxy-4-(trifluoromethoxy)phenoxy]-3-(trifluoromethyl)benzoyl]amino]pyridine-4-carboxamide | ESI-MS m/z calc. 551.07, found 552.0 $(M + 1)^+$; LC/MS retention time (Method C): 2.44 minutes | $^1H$ NMR (400 MHz, DMSO-$d_6$) δ 11.57 (s, 1H), 8.54 (s, 1H), 8.48 (d, J = 5.1 Hz, 1H), 8.26 (s, 1H), 7.81 (t, J = 8.6 Hz, 1H), 7.72 (s, 1H), 7.56 (d, J = 5.2 Hz, 1H), 7.40 (t, J = 8.6 Hz, 1H), 7.21 (dd, J = 9.3, 2.1 Hz, 1H), 6.87 (d, J = 8.9 Hz, 1H), 3.86 (d, J = 3.1 Hz, 3H). |
| 331 | 5-[[2-fluoro-6-[3-fluoro-2-methoxy-4-(trifluoromethoxy)phenoxy]-3-(trifluoromethyl)benzoyl]amino]pyrimidine-2-carboxamide | ESI-MS m/z calc. 552.07, found 553.0 $(M + 1)^+$; LC/MS retention time (Method C): 2.35 minutes | $^1H$ NMR (400 MHz, DMSO-$d_6$) δ 11.70 (s, 1H), 9.20 (s, 2H), 8.17 (s, 1H), 7.89 (t, J = 8.6 Hz, 1H), 7.78 (s, 1H), 7.42 (t, J = 8.6 Hz, 1H), 7.25 (dd, J = 9.5, 2.1 Hz, 1H), 6.95 (d, J = 8.9 Hz, 1H), 3.87 (d, J = 1.2 Hz, 3H). |

Example 135

N-(2-Carbamoyl-4-Pyridyl)-3-Fluoro-5-[3-Fluoro-2-Methoxy-4-(Trifluoromethoxy)Phenoxy]-2-(Trifluoromethyl)Pyridine-4-Carboxamide (332)

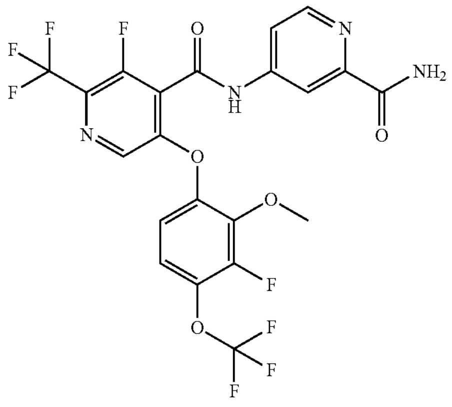 [SMILES: COc1c(Oc2cnc(C(F)(F)F)c(F)c2C(=O)Nc2ccnc(C(N)=O)c2)ccc(OC(F)(F)F)c1F]

Step 1: Ethyl 3-Fluoro-5-[3-Fluoro-2-Methoxy-4-(Trifluoromethoxy)Phenoxy]-2-(Trifluoromethyl)Pyridine-4-Carboxylate

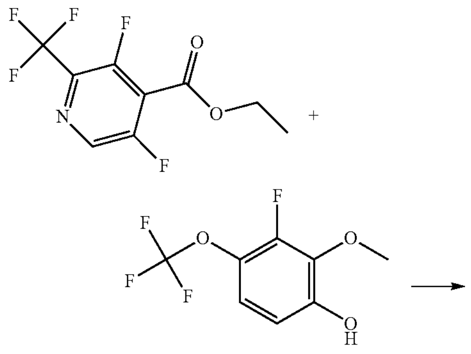

-continued

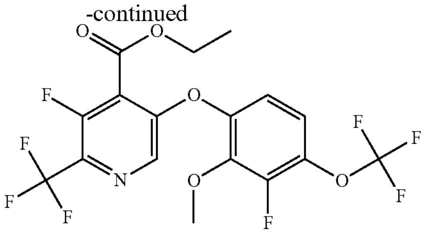

Ethyl 3,5-difluoro-2-(trifluoromethyl)pyridine-4-carboxylate (5.0 g, 20 mmol, see US 2019/0016671, Example 12, Step 1, which is incorporated by reference) was dissolved in anhydrous DMF (30 mL) under a nitrogen atmosphere and then cooled to 3° C. 3-Fluoro-2-methoxy-4-(trifluoromethoxy)phenol (4.52 g, 20.0 mmol, see Example 113, Step 1) was added in one portion followed by $Cs_2CO_3$ (12.84 g, 39.41 mmol). An exotherm increasing the mixture temperature to 9° C. was observed. The mixture was stirred in an ice bath for 1 hour, then allowed to warm to room temperature and stirred for 1.5 hours. The mixture was partitioned between ethyl acetate (150 mL) and water (150 mL) and the layers separated. The organic layer was washed with water (150 mL) and brine (50 mL), dried over $Na_2SO_4$, filtered and concentrated in vacuo. Purification by silica gel chromatography (0-10% ethyl acetate/heptane) provided ethyl 3-fluoro-5-[3-fluoro-2-methoxy-4-(trifluoromethoxy)phenoxy]-2-(trifluoromethyl)pyridine-4-carboxylate (8310 mg, 92%). ESI-MS m z calc. 461.05, no ionization observed; LC/MS retention time (Method F): 1.12 minutes. $^1H$ NMR (400 MHz, $CDCl_3$) δ 7.97 (s, 1H), 7.08 (ddt, J=8.8, 7.6, 1.2 Hz, 1H), 6.98 (dd, J=9.2, 2.2 Hz, 1H), 4.45 (q, J=7.1 Hz, 2H), 3.93 (d, J=1.9 Hz, 3H), 1.39 (t, J=7.1 Hz, 3H) ppm.

Step 2: 3-Fluoro-5-[3-Fluoro-2-Methoxy-4-(Trifluoromethoxy)Phenoxy]-2-(Trifluoromethyl)Pyridine-4-Carboxylic Acid

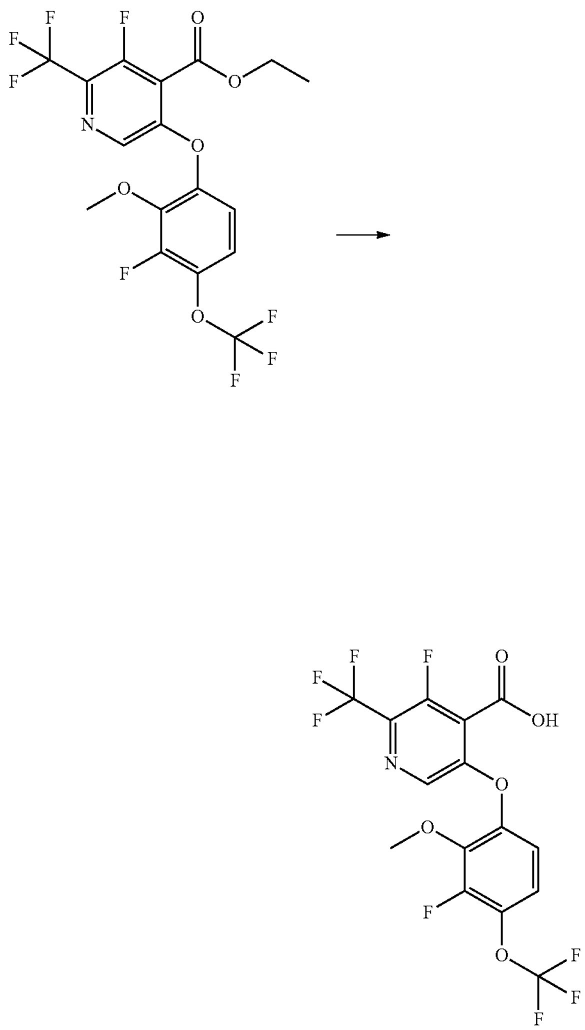

To a solution of ethyl 3-fluoro-5-[3-fluoro-2-methoxy-4-(trifluoromethoxy)phenoxy]-2-(trifluoromethyl)pyridine-4-carboxylate (2.0 g, 4.3 mmol) in THF (6 mL) was added LiOH hydrate (550 mg, 13.1 mmol) and water (2 mL). The resulting mixture was stirred at room temperature for 24 hours. The volatiles were removed in vacuo and the remaining aqueous mixture was acidified with 1 M aqueous HCl. The resulting solid was collected by filtration, washed with water and dried in vacuo. The solid was dissolved in ethyl acetate, dried over $Na_2SO_4$, filtered and concentrated in vacuo to provide 3-fluoro-5-[3-fluoro-2-methoxy-4-(trifluoromethoxy)phenoxy]-2-(trifluoromethyl)pyridine-4-carboxylic acid (1.76 g, 94%) as white solid. ESI-MS m z calc. 433.02, found 434.0 $(M+1)^+$; LC/MS retention time (Method B): 1.78 minutes. $^1H$ NMR (400 MHz, DMSO-$d_6$) δ 8.35 (s, 1H), 7.37 (ddd, J=9.3, 8.0, 1.2 Hz, 1H), 7.21 (dd, J=9.3, 2.2 Hz, 1H), 3.89 (d, J=1.3 Hz, 3H) ppm.

Step 3: N-(2-Carbamoyl-4-Pyridyl)-3-Fluoro-5-[3-Fluoro-2-Methoxy-4-(Trifluoromethoxy)Phenoxy]-2-(Trifluoromethyl)Pyridine-4-Carboxamide (332)

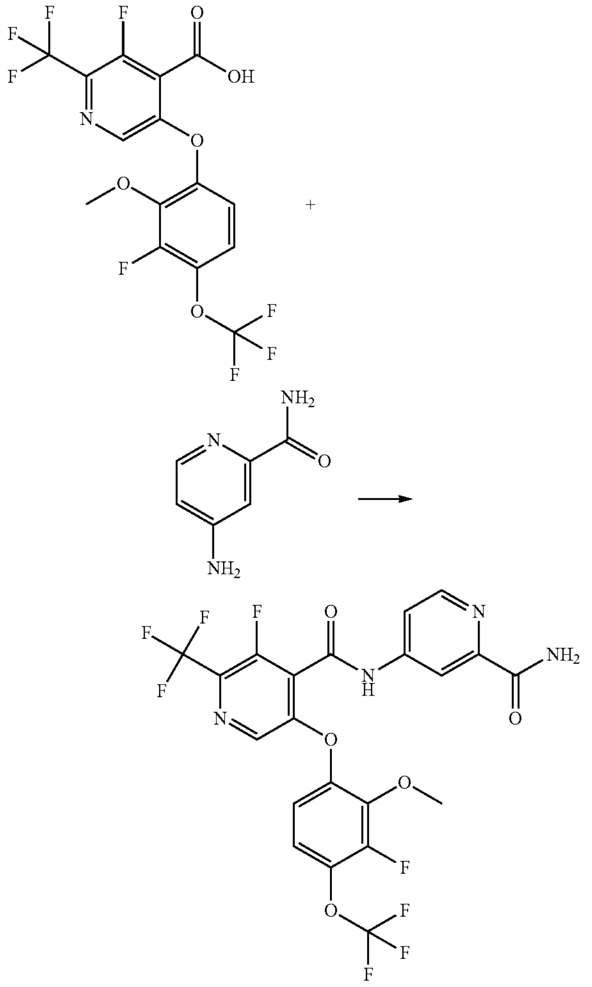

A solution of 3-fluoro-5-[3-fluoro-2-methoxy-4-(trifluoromethoxy)phenoxy]-2-(trifluoromethyl)pyridine-4-carboxylic acid (40 mg, 0.092 mmol) and DMF (2 μL, 0.03 mmol) in dichloromethane (0.5 mL) at 0° C. was treated with oxalyl chloride (48 μL, 0.55 mmol). The mixture was stirred for 30 minutes at room temperature. The mixture was concentrated in vacuo, and the resulting acid chloride was dissolved in NMP (0.5 mL) and slowly added to a mixture of 4-aminopyridine-2-carboxamide (38 mg, 0.28 mmol) and DIEA (72 mg, 97 μL, 0.55 mmol) in NMP (0.4 mL). The mixture was allowed to warm to room temperature and stirred for 16 hours. Purification by reverse phase HPLC (acetonitrile/5 mM HCl gradient) provided N-(2-carbamoyl-4-pyridyl)-3-fluoro-5-[3-fluoro-2-methoxy-4-(trifluoromethoxy)phenoxy]-2-(trifluoromethyl)pyridine-4-carboxamide (14 mg, 27%). ESI-MS m z calc. 552.07, found 553.3 $(M+1)^+$; LC/MS retention time (Method B): 1.19 minutes. $^1H$ NMR (400 MHz, DMSO-$d_6$) δ 11.78 (s, 1H), 8.59 (d, J=5.5 Hz, 1H), 8.46 (s, 1H), 8.30 (s, 1H), 8.17 (s, 1H), 7.82-7.77 (m, 1H), 7.73 (s, 1H), 7.38 (t, J=8.5 Hz, 1H), 7.31 (d, J=9.5 Hz, 1H), 3.88 (d, J=1.4 Hz, 3H) ppm.

Example 136

N-(2-Carbamoyl-4-Pyridyl)-5-[3-Fluoro-2-Methoxy-4-(Trifluoromethoxy)Phenoxy]-3-Methoxy-2-(Trifluoromethyl)Pyridine-4-Carboxamide (333)

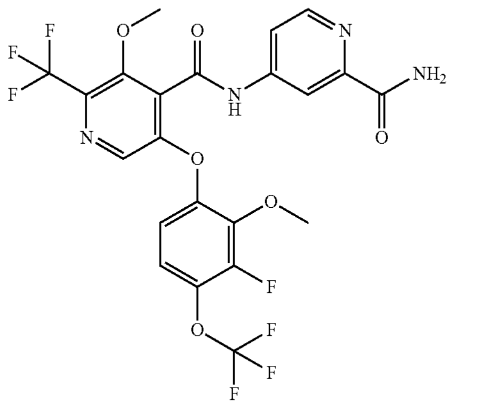 [SMILES: COc1c(Oc2cnc(C(F)(F)F)c(OC)c2C(=O)Nc2ccnc(C(N)=O)c2)ccc(OC(F)(F)F)c1F]

Step 1: 5-[3-Fluoro-2-Methoxy-4-(Trifluoromethoxy)Phenoxy]-3-Methoxy-2-(Trifluoromethyl)Pyridine-4-Carboxylic Acid

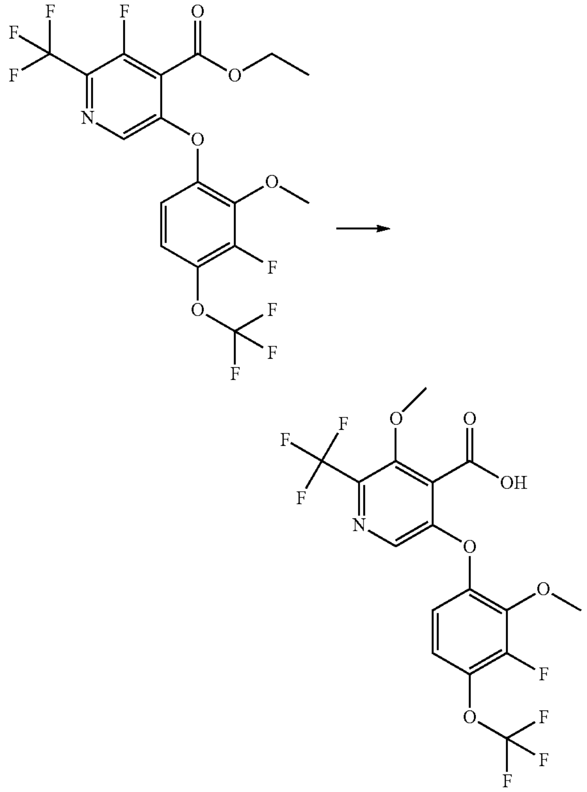 [SMILES: CCOC(=O)c1c(Oc2ccc(OC(F)(F)F)c(F)c2OC)cnc(C(F)(F)F)c1F ; COc1c(Oc2cnc(C(F)(F)F)c(OC)c2C(=O)O)ccc(OC(F)(F)F)c1F]

A solution of ethyl 3-fluoro-5-[3-fluoro-2-methoxy-4-(trifluoromethoxy)phenoxy]-2-(trifluoromethyl)pyridine-4-carboxylate (600 mg, 1.30 mmol, see Example 135, Step 1) in a solution of sodium methoxide (10 mL of 25% w/w in methanol, 44 mmol) was stirred at room temperature for 70 minutes. The mixture was concentrated and acidified with 1 M aqueous HCl. The aqueous mixture was extracted with ethyl acetate (3×), and the combined extracts were washed with brine, dried over $Na_2SO_4$, filtered and concentrated in vacuo. The residue was purified by reverse phase HPLC (30-99% acetonitrile/5 mM HCl) to provide 5-[3-fluoro-2-methoxy-4-(trifluoromethoxy)phenoxy]-3-methoxy-2-(trifluoromethyl)pyridine-4-carboxylic acid (166 mg, 29%) as white solid. ESI-MS m z calc. 445.04, found 446.0 $(M+1)^+$; LC/MS retention time (Method B): 1.79 minutes. $^1H$ NMR (400 MHz, DMSO-$d_6$) δ 14.61 (s, 1H), 8.17 (s, 1H), 7.36 (t, J=8.7 Hz, 1H), 7.15 (dd, J=9.3, 2.1 Hz, 1H), 3.98 (s, 3H), 3.89 (d, J=1.2 Hz, 3H) ppm.

Step 2: N-(2-Carbamoyl-4-Pyridyl)-5-[3-Fluoro-2-Methoxy-4-(Trifluoromethoxy)Phenoxy]-3-Methoxy-2-(Trifluoromethyl)Pyridine-4-Carboxamide

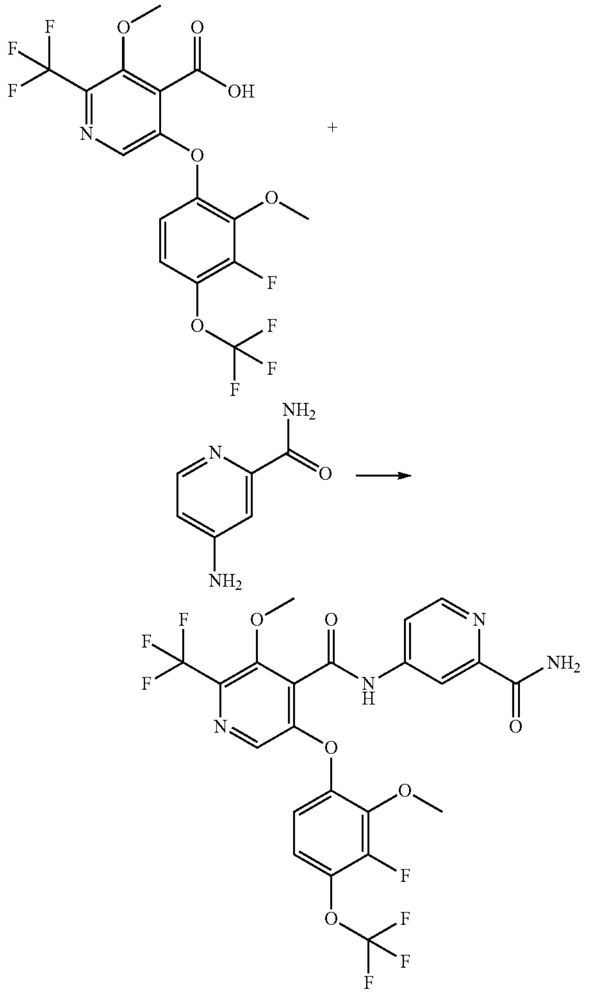

A solution of 5-[3-fluoro-2-methoxy-4-(trifluoromethoxy)phenoxy]-3-methoxy-2-(trifluoromethyl)pyridine-4-carboxylic acid (30 mg, 0.067 mmol) and DMF (one drop) in dichloromethane (375 μL) at 0° C. was slowly treated with oxalyl chloride (12 μL, 0.14 mmol). The resulting mixture was stirred at 0° C. for 5 minutes and then for 20 minutes at room temperature. The mixture was concentrated in vacuo. The resulting acid chloride dissolved in NMP (375 μL) and added slowly to a solution of 4-amino-pyridine-2-carboxamide (27.7 mg, 0.202 mmol) and DIEA (70 μL, 0.40 mmol) in NMP (300 μL) at 0° C. The mixture was allowed to warm to room temperature and stirred for 16 hours. Purification by reverse phase HPLC (acetonitrile/5 mM HCl gradient) provided N-(2-carbamoyl-4-pyridyl)-5-[3-fluoro-2-methoxy-4-(trifluoromethoxy)phenoxy]-3-methoxy-2-(trifluoromethyl)pyridine-4-carboxamide (24.8 mg, 64%). ESI-MS m z calc. 564.09, found 565.1 $(M+1)^+$; LC/MS retention time (Method B): 1.76 minutes. $^1H$ NMR (400 MHz, DMSO-$d_6$) δ 11.56 (s, 1H), 8.57 (d, J=5.5 Hz, 1H), 8.32 (d, J=2.2 Hz, 1H), 8.23 (s, 1H), 8.12 (d, J=2.7 Hz, 1H), 7.79 (dd, J=5.5, 2.2 Hz, 1H), 7.68 (d, J=2.7 Hz, 1H), 7.36 (t, J=8.7 Hz, 1H), 7.21 (dd, J=9.3, 2.1 Hz, 1H), 3.97 (s, 3H), 3.86 (d, J=1.2 Hz, 3H) ppm.

Example 137

N-(2-Carbamoyl-5-Methyl-4-Pyridyl)-5-[3-Fluoro-2-Methoxy-4-(Trifluoromethoxy)Phenoxy]-3-Methoxy-2-(Trifluoromethyl)Pyridine-4-Carboxamide (334)

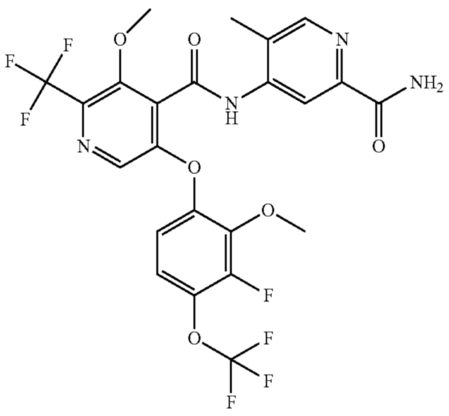 [SMILES: COc1c(Oc2cnc(C(F)(F)F)c(OC)c2C(=O)Nc2cc(C(N)=O)ncc2C)ccc(OC(F)(F)F)c1F]

Step 1: Methyl 4-[[3-Fluoro-5-[3-Fluoro-2-Methoxy-4-(Trifluoromethoxy)Phenoxy]-2-(Trifluoromethyl)Pyridine-4-Carbonyl]Amino]-5-Methyl-Pyridine-2-Carboxylate

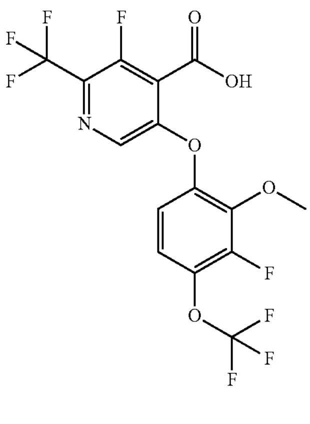

+

-continued

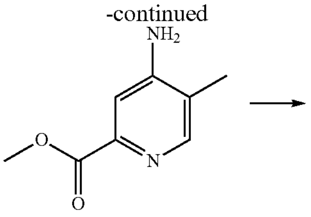

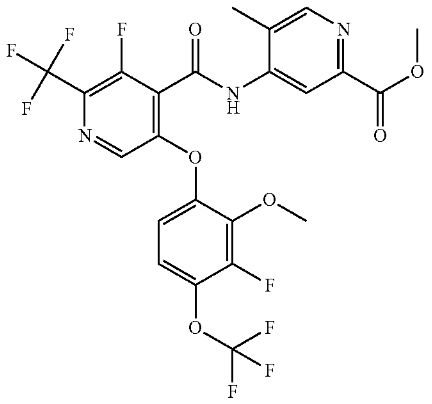

A solution of 3-fluoro-5-[3-fluoro-2-methoxy-4-(trifluoromethoxy)phenoxy]-2-(trifluoromethyl)pyridine-4-carboxylic acid (40 mg, 0.09 mmol, see Example 135, Step 2) and DMF (2 μL, 0.03 mmol) in dichloromethane (0.5 mL) at 0° C. was treated with oxalyl chloride (70 mg, 48 μL, 0.55 mmol). The resulting mixture was stirred for 30 minutes at room temperature, and then concentrated in vacuo. The residue was dissolved in NMP (0.5 mL) and added slowly to a solution of methyl 4-amino-5-methyl-pyridine-2-carboxylate (46 mg, 0.28 mmol, Preparation 1) and DIEA (97 μL, 0.55 mmol) in NMP (0.4 mL) at 0° C. The mixture was allowed to warm to room temperature and stirred for 16 hours. Purification by HPLC (acetonitrile/5 mM HCl gradient) provided methyl 4-[[3-fluoro-5-[3-fluoro-2-methoxy-4-(trifluoromethoxy)phenoxy]-2-(trifluoromethyl)pyridine-4-carbonyl]amino]-5-methyl-pyridine-2-carboxylate (26.8 mg, 49%). ESI-MS m z calc. 581.08, found 582.1 $(M+1)^+$; LC/MS retention time (Method B): 1.26 minutes. $^1H$ NMR (400 MHz, DMSO-$d_6$) δ 10.79 (s, 1H), 8.59 (s, 1H), 8.47 (d, J=13.3 Hz, 2H), 7.39 (t, J=8.7 Hz, 1H), 7.26 (dd, J=9.4, 2.0 Hz, 1H), 3.93-3.85 (m, 6H), 2.32 (s, 3H) ppm.

Step 2: N-(2-Carbamoyl-5-Methyl-4-Pyridyl)-5-[3-Fluoro-2-Methoxy-4-(Trifluoromethoxy)Phenoxy]-3-Methoxy-2-(Trifluoromethyl)Pyridine-4-Carboxamide (334)

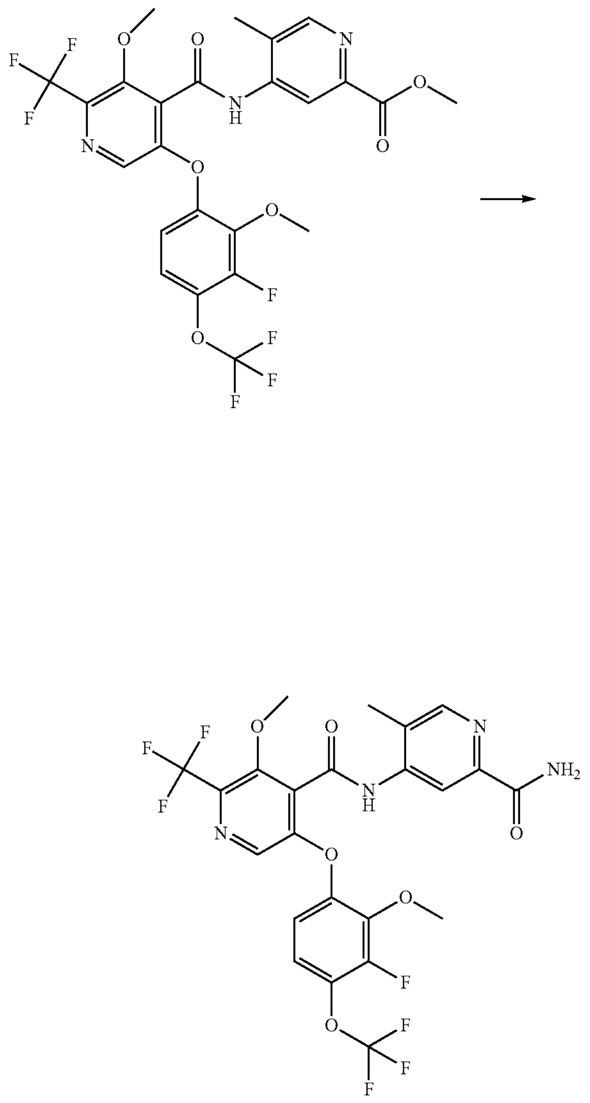

Methyl 4-[[3-fluoro-5-[3-fluoro-2-methoxy-4-(trifluoromethoxy)phenoxy]-2-(trifluoromethyl)pyridine-4-carbonyl]amino]-5-methyl-pyridine-2-carboxylate (21 mg, 0.035 mmol) was dissolved in ammonia in methanol (1.5 mL of 7 M, 11 mmol) and stirred at room temperature for 16 hours. The mixture was concentrated in vacuo and purified by reverse phase HPLC (acetonitrile/5 mM HCl gradient) to provide N-(2-carbamoyl-5-methyl-4-pyridyl)-5-[3-fluoro-2-methoxy-4-(trifluoromethoxy)phenoxy]-3-methoxy-2-(trifluoromethyl)pyridine-4-carboxamide (14 mg, 68%) as a white solid. ESI-MS m z calc. 578.10, found 579.1 $(M+1)^+$; LC/MS retention time (Method C): 2.43 minutes. $^1H$ NMR (400 MHz, DMSO-$d_6$) δ 10.70 (s, 1H), 8.48 (d, J=2.9 Hz, 2H), 8.21 (s, 1H), 8.07 (s, 1H), 7.63 (s, 1H), 7.38 (t, J=8.7 Hz, 1H), 7.20 (dd, J=9.3, 2.1 Hz, 1H), 4.03 (s, 3H), 3.89 (d, J=1.2 Hz, 3H), 2.30 (s, 3H) ppm.

Example 138

5-[[5-[3-Fluoro-2-Methoxy-4-(Trifluoromethoxy)Phenoxy]-3-Methyl-2-(Trifluoromethyl)Pyridine-4-Carbonyl]Amino]Pyrimidine-2-Carboxamide (335)

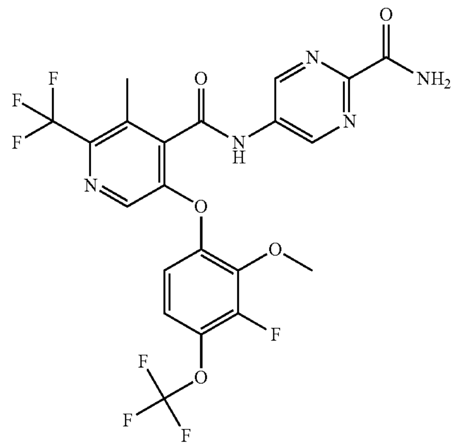 [SMILES: COc1c(Oc2cnc(C(F)(F)F)c(C)c2C(=O)Nc2cnc(C(N)=O)nc2)ccc(OC(F)(F)F)c1F]

Step 1: 5-[3-Fluoro-2-Methoxy-4-(Trifluoromethoxy)Phenoxy]-3-Methyl-2-(Trifluoromethyl)Pyridine-4-Carboxylic Acid

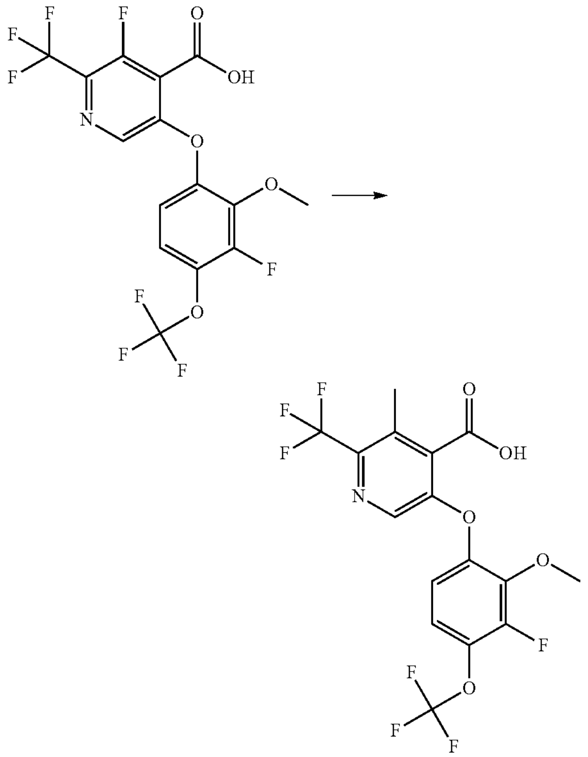

To a solution of 3-fluoro-5-[3-fluoro-2-methoxy-4-(trifluoromethoxy)phenoxy]-2-(trifluoromethyl)pyridine-4-carboxylic acid (900 mg, 2.08 mmol, see Example 135, Step 2) in THF (5 mL) was slowly added a solution of methyl magnesium bromide (9.0 mL of 1 M in diethyl ether, 9 mmol) under nitrogen atmosphere at 0° C. (exotherm observed). The mixture was removed from the ice bath and heated at 55° C. for 2 hours. The mixture was diluted with 1 M aqueous HCl and extracted with ethyl acetate (3×). The combined organic extracts were concentrated in vacuo and purified by reverse phase HPLC (10-99% acetonitrile/5 mM HCl) to provide 5-[3-fluoro-2-methoxy-4-(trifluoromethoxy)phenoxy]-3-methyl-2-(trifluoromethyl)pyridine-4-carboxylic acid (621 mg, 70%). ESI-MS m z calc. 429.05, found 430.4 $(M+1)^+$; LC/MS retention time (Method A): 0.68 minutes. $^1H$ NMR (400 MHz, DMSO-$d_6$) δ 14.46 (br s, 1H), 8.27 (s, 1H), 7.35 (ddd, J=9.4, 8.1, 1.3 Hz, 1H), 7.12 (dd, J=9.3, 2.2 Hz, 1H), 3.88 (d, J=1.1 Hz, 3H), 2.45 (d, J=2.0 Hz, 3H) ppm.

Step 2: Methyl 5-[[5-[3-Fluoro-2-Methoxy-4-(Trifluoromethoxy)Phenoxy]-3-Methyl-2-(Trifluoromethyl)Pyridine-4-Carbonyl]Amino]Pyrimidine-2-Carboxylate

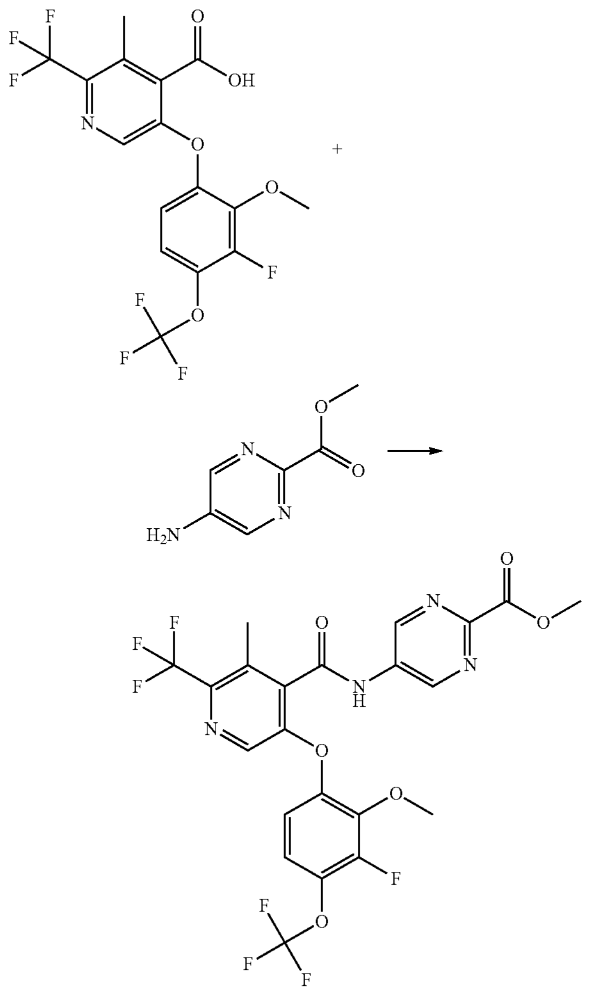

A mixture of 5-[3-fluoro-2-methoxy-4-(trifluoromethoxy)phenoxy]-3-methyl-2-(trifluoromethyl)pyridine-4-carboxylic acid (30 mg, 0.070 mmol) and DMF (1 drop) in dichloromethane (0.5 mL) at 0° C. was treated with oxalyl chloride (37 µL, 0.42 mmol). The resulting mixture was stirred at room temperature for 30 minutes. The mixture was concentrated in vacuo. The resulting acid chloride dissolved in NMP (0.4 mL) and added to a mixture of methyl 5-aminopyrimidine-2-carboxylate (32 mg, 0.21 mmol) and DIEA (73 µL, 0.42 mmol) in NMP (0.3 mL) at 0° C. The mixture was stirred overnight, concentrated in vacuo, and purified by reverse phase HPLC (1-99% acetonitrile/5 mM HCl gradient) to provide methyl 5-[[5-[3-fluoro-2-methoxy-4-(trifluoromethoxy)phenoxy]-3-methyl-2-(trifluoromethyl)pyridine-4-carbonyl]amino]pyrimidine-2-carboxylate (38.8 mg, 98%). ESI-MS m z calc. 564.09, found 565.1 $(M+1)^+$; LC/MS retention time (Method A): 0.47 minutes.

Step 3: 5-[[5-[3-Fluoro-2-Methoxy-4-(Trifluoromethoxy)Phenoxy]-3-Methyl-2-(Trifluoromethyl)Pyridine-4-Carbonyl]Amino]Pyrimidine-2-Carboxamide (335)

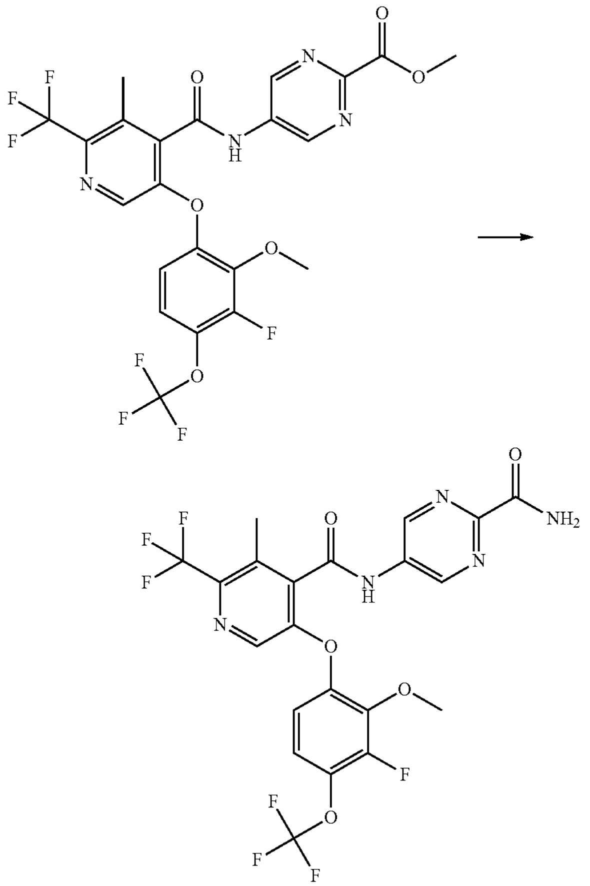

Methyl 5-[[5-[3-fluoro-2-methoxy-4-(trifluoromethoxy)phenoxy]-3-methyl-2-(trifluoromethyl)pyridine-4-carbonyl]amino]pyrimidine-2-carboxylate (15 mg, 0.027 mmol) was dissolved a solution of ammonia in methanol (1 mL of 7 M, 7 mmol) and stirred at room temperature for 16 hours. The mixture was concentrated in vacuo and purified by reverse phase HPLC (10-99% acetonitrile/5 mM HCl) to provide 5-[[5-[3-fluoro-2-methoxy-4-(trifluoromethoxy)phenoxy]-3-methyl-2-(trifluoromethyl)pyridine-4-carbonyl]amino]pyrimidine-2-carboxamide (13.9 mg, 95%). ESI-MS m z calc. 549.09, found 550.1 $(M+1)^+$; LC/MS retention time (Method C): 2.25 minutes. $^1H$ NMR (400 MHz, DMSO-$d_6$)

δ 11.57 (s, 1H), 9.16 (s, 2H), 8.34 (s, 1H), 8.13 (s, 1H), 7.74 (s, 1H), 7.34 (d, J=8.5 Hz, 1H), 7.18 (d, J=9.8 Hz, 1H), 3.86 (d, J=1.2 Hz, 3H), 3.29 (s, 3H) ppm.

Example 139

N-(2-Carbamoyl-5-Methyl-4-Pyridyl)-5-[3-Fluoro-2-Methoxy-4-(Trifluoromethoxy)Phenoxy]-3-Methyl-2-(Trifluoromethyl)Pyridine-4-Carboxamide (336)

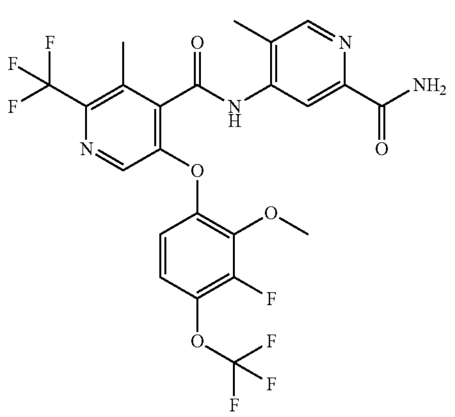 [SMILES: COc1c(Oc2cnc(C(F)(F)F)c(C)c2C(=O)Nc2cc(C(N)=O)ncc2C)ccc(OC(F)(F)F)c1F]

This compound was made in an analogous fashion to the synthesis of compound 335 in Example 138, except employing methyl 4-amino-5-methyl-pyridine-2-carboxylate (Preparation 1) in the amide formation step, followed by conversion of the ester to the corresponding carboxamide via treatment with methanolic ammonia. The yield ofN-(2-carbamoyl-5-methyl-4-pyridyl)-5-[3-fluoro-2-methoxy-4-(trifluoromethoxy)phenoxy]-3-methyl-2-(trifluoromethyl) pyridine-4-carboxamide after purification was 5.393 g (95%). ESI-MS m z calc. 562.11, found 563.1 $(M+1)^+$; 561.2 $(M-1)^-$; LC/MS retention time (Method E): 3.21 minutes. $^1$H NMR (400 MHz, DMSO-$d_6$) δ 10.62 (s, 1H), 8.54-8.45 (m, 2H), 8.31 (s, 1H), 8.07 (d, J=2.9 Hz, 1H), 7.62 (d, J=2.9 Hz, 1H), 7.38 (tq, J=8.1, 1.2 Hz, 1H), 7.18 (dd, J=9.3, 2.2 Hz, 1H), 3.89 (d, J=1.2 Hz, 3H), 2.53 (q, J=1.8 Hz, 3H), 2.29 (s, 3H) ppm.

Example 140

N-(6-Carbamoyl-3-Pyridyl)-5-[3-Fluoro-2-Methoxy-4-(Trifluoromethoxy)Phenoxy]-3-Methyl-2-(Trifluoromethyl)Pyridine-4-Carboxamide (337)

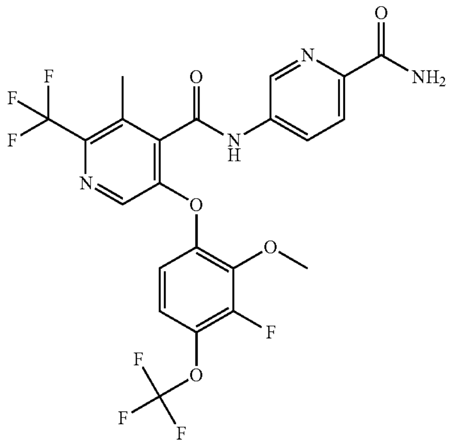 [SMILES: COc1c(Oc2cnc(C(F)(F)F)c(C)c2C(=O)Nc2ccc(C(N)=O)nc2)ccc(OC(F)(F)F)c1F]

This compound was made in an analogous fashion to the synthesis of compound 335 in Example 138, except employing 5-aminopyridine-2-carboxamide in the amide formation step. The yield of N-(6-carbamoyl-3-pyridyl)-5-[3-fluoro-2-methoxy-4-(trifluoromethoxy)phenoxy]-3-methyl-2-(trifluoromethyl)pyridine-4-carboxamide after purification was 23.1 mg (45%). ESI-MS m z calc. 548.09, found 549.1 $(M+1)^+$; LC/MS retention time (Method C): 2.4 minutes. $^1$H NMR (400 MHz, DMSO-$d_6$) δ 11.37 (s, 1H), 8.82 (s, 1H), 8.33 (s, 1H), 8.27 (d, J=8.7 Hz, 1H), 8.09-7.99 (m, 2H), 7.58 (s, 1H), 7.35 (t, J=8.6 Hz, 1H), 7.17 (d, J=9.5 Hz, 1H), 3.86 (d, J=1.2 Hz, 3H), 2.48 (s, 3H) ppm.

Example 141

4-[[6-[2-Ethoxy-4-(Trifluoromethoxy)Phenoxy]-2-Fluoro-3-(Trifluoromethyl)Benzoyl]Amino]Pyridine-2-Carboxamide (346)

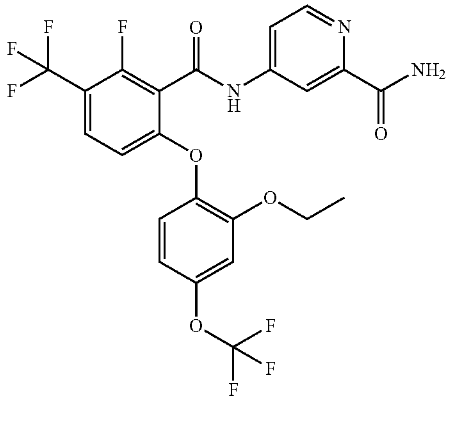 [SMILES: CCOc1cc(OC(F)(F)F)ccc1Oc1ccc(C(F)(F)F)c(F)c1C(=O)Nc1ccnc(C(N)=O)c1]

Step 1: 6-[2-Ethoxy-4-(Trifluoromethoxy)Phenoxy]-2-Fluoro-3-(Trifluoromethyl)Benzoic Acid

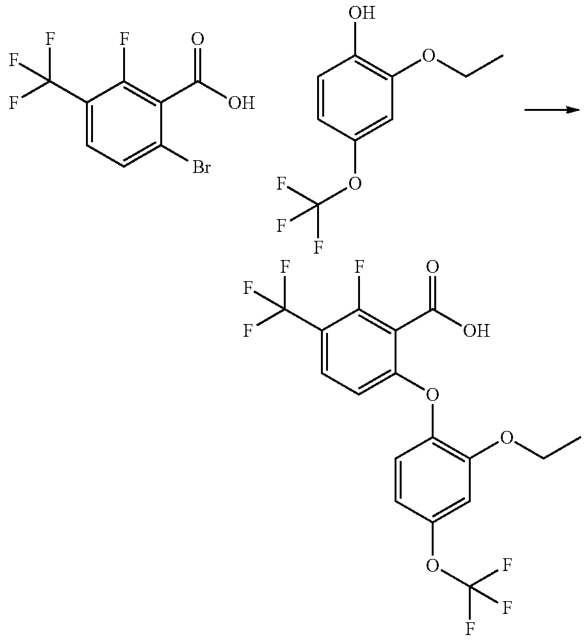

A solution of 2-ethoxy-4-(trifluoromethoxy)phenol (4.45 g, 20.0 mmol, Preparation 10) in toluene (150 mL) was bubbled with nitrogen for 10 minutes. 6-Bromo-2-fluoro-3-(trifluoromethyl)benzoic acid (5.755 g, 20.05 mmol), $Cs_2CO_3$ (13.26 g, 40.70 mmol) and copper (I) iodide (768 mg, 4.03 mmol) were added and the mixture heated at 100° C. under nitrogen for 5 hours. The cooled mixture was washed with saturated aqueous $NH_4Cl$ solution and 0.1 M aqueous HCl. The organic layer was dried over $MgSO_4$, filtered and concentrated in vacuo to provide 6-[2-ethoxy-4-(trifluoromethoxy)phenoxy]-2-fluoro-3-(trifluoromethyl)benzoic acid (8.04 g, 94%). ESI-MS m z calc. 428.05, found 427.6 $(M-1)^-$; LC/MS retention time (Method F): 0.64 minutes. The material was taken to the next step without further purification.

Step 2: 4-[[6-[2-Ethoxy-4-(Trifluoromethoxy)Phenoxy]-2-Fluoro-3-(Trifluoromethyl)Benzoyl]Amino]Pyridine-2-Carboxamide (346)

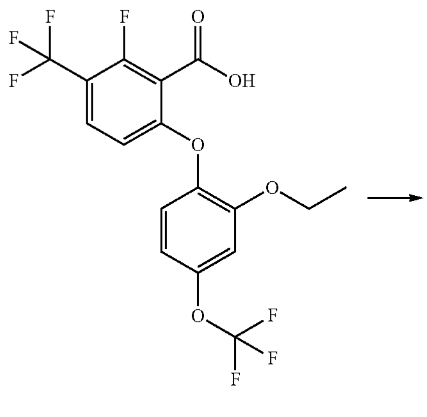

-continued

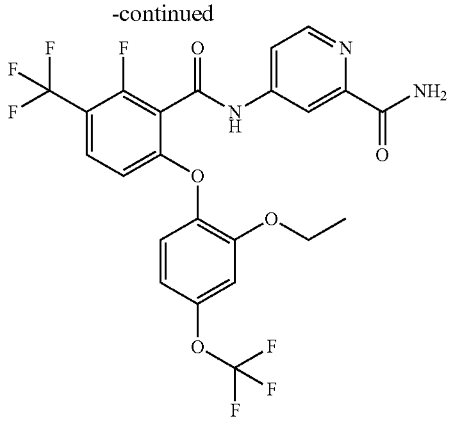

To a solution of 6-[2-ethoxy-4-(trifluoromethoxy)phenoxy]-2-fluoro-3-(trifluoromethyl)benzoic acid (300 mg, 0.701 mmol) and DMF (6 µL, 0.07 mmol) in dichloromethane (10 mL) at 0° C. was added oxalyl chloride (610 µL, 6.99 mmol) dropwise (gas evolution). The mixture was stirred for 1 hour and concentrated in vacuo. The resulting acid chloride was dissolved in dichloromethane (10 mL) and added dropwise to a stirring solution of methyl 4-aminopyridine-2-carboxylate (118 mg, 0.776 mmol), DMAP (86 mg, 0.70 mmol) and DIPEA (365 µL, 2.10 mmol) in dichloromethane (10 mL). The mixture was stirred for 72 hours. The mixture was concentrated in vacuo, and the residue stirred overnight in a solution of ammonia in methanol (5 mL of 7 M, 35 mmol). Purification by reverse phase HPLC (47-95% acetonitrile/0.1% ammonium hydroxide) provided 4-[[6-[2-ethoxy-4-(trifluoromethoxy)phenoxy]-2-fluoro-3-(trifluoromethyl)benzoyl]amino]pyridine-2-carboxamide (55.8 mg, 14%). ESI-MS m z calc. 547.10, found 548.1 $(M+1)^+$; 546.2 $(M-1)^-$; LC/MS retention time (Method F): 0.96 minutes. $^1H$ NMR (400 MHz, $CDCl_3$) δ 9.18 (s, 1H), 8.60-8.52 (m, 1H), 8.45 (dd, J=5.6, 2.2 Hz, 1H), 7.97-7.88 (m, 2H), 7.59 (ddd, J=8.6, 7.8, 0.7 Hz, 1H), 7.30-7.21 (m, 1H), 6.94 (pd, J=2.7, 1.4 Hz, 2H), 6.62 (ddd, J=8.9, 1.4, 0.7 Hz, 1H), 5.48 (d, J=4.0 Hz, 1H), 4.12 (q, J=7.0 Hz, 2H), 1.29 (t, J=7.0 Hz, 3H) ppm.

Example 142

4-[[6-[2-Ethoxy-4-(Trifluoromethoxy)Phenoxy]-2-Fluoro-4-Methoxy-3-(Trifluoromethyl)Benzoyl]Amino]Pyridine-2-Carboxamide (347)

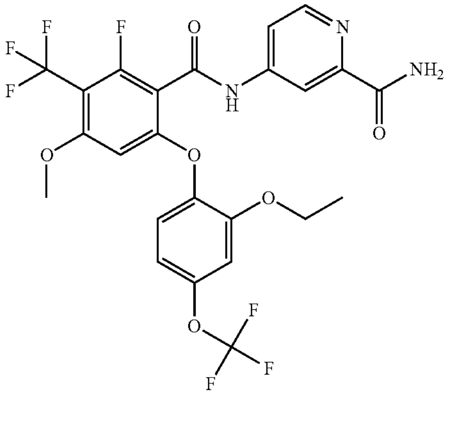 [SMILES: CCOc1cc(OC(F)(F)F)ccc1Oc1cc(OC)c(C(F)(F)F)c(F)c1C(=O)Nc1ccnc(C(N)=O)c1]

A mixture of 4-[[6-bromo-2-fluoro-4-methoxy-3-(trifluoromethyl)benzoyl]amino]pyridine-2-carboxamide (350 mg, 0.803 mmol, see Example 109, Step 2), 2-ethoxy-4-(trifluoromethoxy)phenol (170 mg, 0.765 mmol, Preparation 10) and $Cs_2CO_3$ (280 mg, 0.859 mmol) in toluene (10 mL) was bubbled with nitrogen for 10 minutes, then copper (I) iodide (53 mg, 0.28 mmol) added. The mixture was heated at 100° C. under nitrogen with vigorous stirring for 1 hour. The cooled mixture was acidified with aqueous HCl, filtered and the aqueous layer was extracted with ethyl acetate (3×50 mL). The combined extracts were washed with brine, dried over $MgSO_4$, filtered and concentrated in vacuo. Purification by silica gel chromatography (0-100% ethyl acetate/heptane), followed by reverse phase HPLC purification (47-95% acetonitrile/0.1% ammonium hydroxide) provided 4-[[6-[2-ethoxy-4-(trifluoromethoxy)phenoxy]-2-fluoro-4-methoxy-3-(trifluoromethyl)benzoyl]amino]pyridine-2-carboxamide (52.1 mg, 11%) as a white powder. ESI-MS m z calc. 577.11, found 578.5 $(M+1)^+$; 576.4 $(M-1)^-$; LC/MS retention time (Method E): 3.39 minutes. $^1H$ NMR (500 MHz, DMSO-$d_6$) δ 11.20 (s, 1H), 8.52 (d, J=5.5 Hz, 1H), 8.26 (d, J=2.1 Hz, 1H), 8.08 (d, J=2.8 Hz, 1H), 7.79 (dd, J=5.6, 2.3 Hz, 1H), 7.64 (d, J=2.9 Hz, 1H), 7.31 (d, J=8.8 Hz, 1H), 7.16 (d, J=2.7 Hz, 1H), 6.96 (ddd, J=8.9, 2.8, 1.3 Hz, 1H), 6.45 (s, 1H), 4.05 (q, J=6.9 Hz, 2H), 3.80 (s, 3H), 1.17 (t, J=6.9 Hz, 3H) ppm.

Example 143

4-[[6-(3,4-Difluoro-2-Methyl-Phenoxy)-2-Fluoro-4-Methoxy-3-(Trifluoromethyl)Benzoyl]Amino]Pyridine-2-Carboxamide (348)

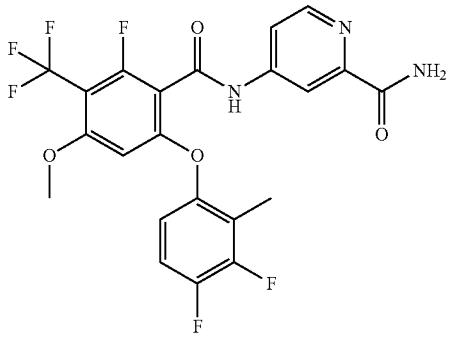 [SMILES: COc1cc(Oc2ccc(F)c(F)c2C)c(C(=O)Nc2ccnc(C(N)=O)c2)c(F)c1C(F)(F)F]

Step 1: 6-(3,4-Difluoro-2-Methyl-Phenoxy)-2-Fluoro-4-Methoxy-3-(Trifluoromethyl)Benzoic Acid

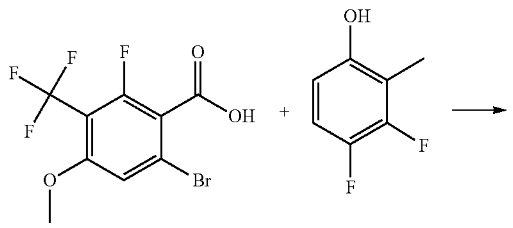

-continued

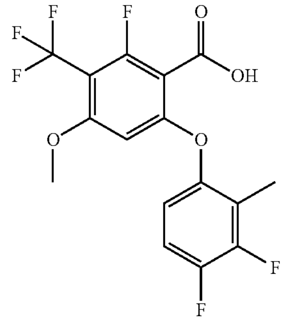

A mixture of 6-bromo-2-fluoro-4-methoxy-3-(trifluoromethyl)benzoic acid (900 mg, 2.84 mmol, see US 2019/0016671, Example 129, Step 3, which is incorporated by reference), 3,4-difluoro-2-methyl-phenol (410 mg, 2.85 mmol, Preparation 11) and $Cs_2CO_3$ (1.110 g, 3.407 mmol) in toluene (5 mL) was bubbled with nitrogen for 10 minutes, then copper (I) iodide (210 mg, 1.10 mmol) added. The mixture was heated at 100° C. with vigorous stirring for 1 hour. The cooled mixture was acidified with 1 M aqueous HCl, filtered and the aqueous layer was extracted into ethyl acetate (3×50 mL). The organic layer was washed with brine, dried over $MgSO_4$, filtered and concentrated in vacuo. Purification by silica gel chromatography (0-70% ethyl acetate/hexanes) provided 6-(3,4-difluoro-2-methyl-phenoxy)-2-fluoro-4-methoxy-3-(trifluoromethyl)benzoic acid (552 mg, 51%). ESI-MS m z calc. 380.05, found 381.2 $(M+1)^+$; LC/MS retention time (Method A): 0.67 minutes. $^1H$ NMR (400 MHz, DMSO-$d_6$) δ 13.72 (s, 1H), 7.35 (q, J=9.5 Hz, 1H), 6.96 (ddd, J=9.2, 4.1, 1.9 Hz, 1H), 6.39 (s, 1H), 3.77 (s, 3H), 2.15 (d, J=2.0 Hz, 3H) ppm.

Step 2: Methyl 4-[[6-(3,4-Difluoro-2-Methyl-Phenoxy)-2-Fluoro-4-Methoxy-3-(Trifluoromethyl)Benzoyl]Amino]Pyridine-2-Carboxylate

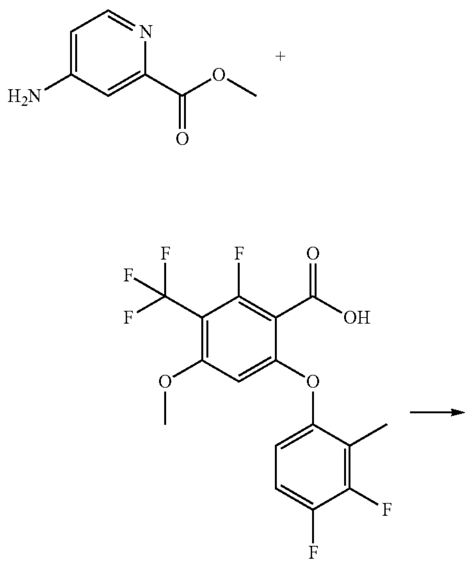

-continued

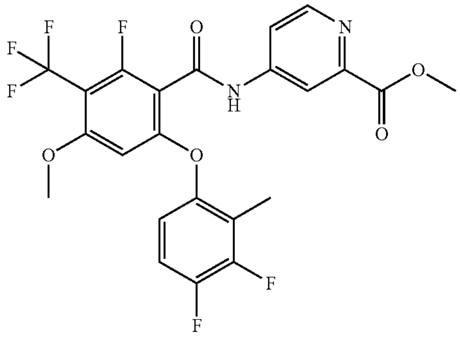

A solution of 6-(3,4-difluoro-2-methyl-phenoxy)-2-fluoro-4-methoxy-3-(trifluoromethyl)benzoic acid (200 mg, 0.526 mmol) in dichloromethane (10 mL) was cooled to 0° C. and oxalyl chloride (150 μL, 1.72 mmol) added followed by DMF (3 μL, 0.04 mmol). The mixture was stirred for 1 hour and concentrated in vacuo. The resulting acid chloride was dissolved in dichloromethane (10 mL) and methyl 4-aminopyridine-2-carboxylate (80 mg, 0.53 mmol) and TEA (150 μL, 1.08 mmol) added. The mixture was stirred at room temperature overnight and concentrated in vacuo. Purification by silica gel chromatography (0-100% ethyl acetate/heptane) provided methyl 4-[[6-(3,4-difluoro-2-methyl-phenoxy)-2-fluoro-4-methoxy-3-(trifluoromethyl) benzoyl]amino]pyridine-2-carboxylate (75 mg, 28%) as a white powder. ESI-MS m z calc. 514.10, found 515.5 $(M+1)^+$; 513.4 $(M-1)^-$; LC/MS retention time (Method F): 0.94 minutes. $^1H$ NMR (500 MHz, DMSO-$d_6$) δ 11.34 (s, 1H), 8.62 (d, J=5.5 Hz, 1H), 8.32 (d, J=2.1 Hz, 1H), 7.79 (dd, J=5.4, 2.2 Hz, 1H), 7.36 (q, J=9.4 Hz, 1H), 7.07-6.99 (m, 1H), 6.44 (s, 1H), 3.89 (s, 3H), 3.81 (s, 3H), 2.13 (d, J=2.0 Hz, 3H) ppm.

Step 3: 4-[[6-(3,4-Difluoro-2-Methyl-Phenoxy)-2-Fluoro-4-Methoxy-3-(Trifluoromethyl)Benzoyl] Amino]Pyridine-2-Carboxamide (348)

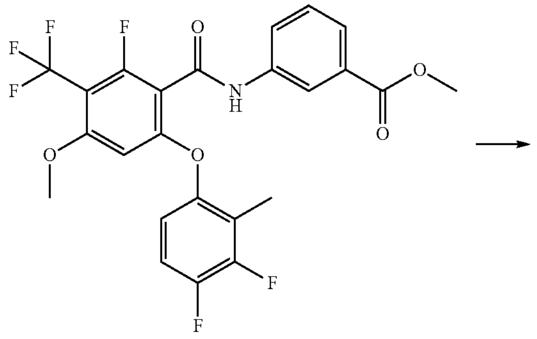

-continued

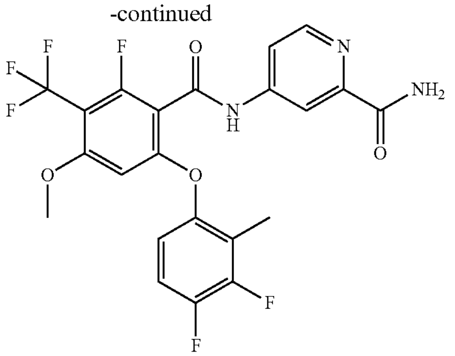

Methyl 4-[[6-(3,4-difluoro-2-methyl-phenoxy)-2-fluoro-4-methoxy-3-(trifluoromethyl)benzoyl]amino]pyridine-2-carboxylate (75 mg, 0.15 mmol) was dissolved in a solution of ammonia in methanol (3 mL of 7 M, 21 mmol) and the mixture stirred at room temperature for 3 hours. The mixture was concentrated in vacuo and purified by reverse phase HPLC (38-53% acetonitrile/0.1% ammonium hydroxide) to provide 4-[[6-(3,4-difluoro-2-methyl-phenoxy)-2-fluoro-4-methoxy-3-(trifluoromethyl)benzoyl]amino]pyridine-2-carboxamide (41.8 mg, 57%) as a white powder. ESI-MS m z calc. 499.10, found 500.5 $(M+1)^+$; 498.4 $(M-1)^-$; LC/MS retention time (Method E): 3.16 minutes. $^1H$ NMR (500 MHz, DMSO-$d_6$) δ 11.28 (s, 1H), 8.54 (d, J=5.5 Hz, 1H), 8.27 (d, J=2.2 Hz, 1H), 8.09 (d, J=2.9 Hz, 1H), 7.79 (dd, J=5.5, 2.2 Hz, 1H), 7.65 (d, J=3.0 Hz, 1H), 7.36 (q, J=9.4 Hz, 1H), 7.04 (ddd, J=9.4, 4.3, 1.9 Hz, 1H), 6.43 (s, 1H), 3.81 (s, 3H), 2.13 (d, J=2.0 Hz, 3H) ppm.

Example 144

4-Benzyl-6-Tert-Butyl-N-(2-Carbamoyl-4-Pyridyl) Pyridine-3-Carboxamide (349)

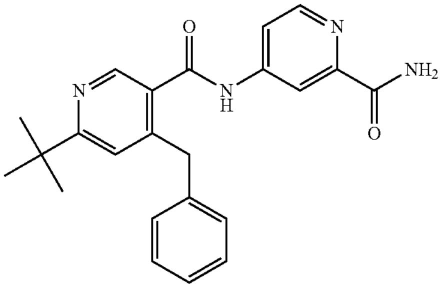 [SMILES: CC(C)(C)c1cc(Cc2ccccc2)c(C(=O)Nc2ccnc(C(N)=O)c2)cn1]

Step 1: 6-Tert-Butyl-4-Chloro-Pyridine-3-Carboxylic Acid

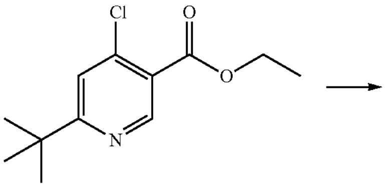

-continued

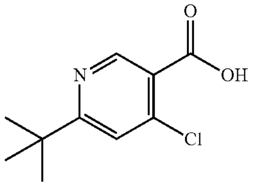

A solution of ethyl 6-tert-butyl-4-chloro-pyridine-3-carboxylate (2.0 g, 8.3 mmol) in methanol (20 mL) was treated with aqueous NaOH (20 mL of 2.5 M, 50 mmol) at room temperature and the mixture heated at 70° C. for 1 hour. The cooled mixture was diluted with 4 M aqueous HCl (15 mL, 60 mmol) and ethyl acetate (50 mL). The layers were separated and the aqueous layer extracted with ethyl acetate (10×30 mL). The combined organic extracts were washed with brine (2×20 mL), dried over anhydrous $Na_2SO_4$, filtered and concentrated in vacuo to provide 6-tert-butyl-4-chloro-pyridine-3-carboxylic acid (1.77 g, 100%). ESI-MS m z calc. 213.06, found 214.1 $(M+1)^+$; LC/MS retention time (Method A): 0.43 minutes.

Step 2: Methyl 4-[(6-Tert-Butyl-4-Chloro-Pyridine-3-Carbonyl)Amino]Pyridine-2-Carboxylate

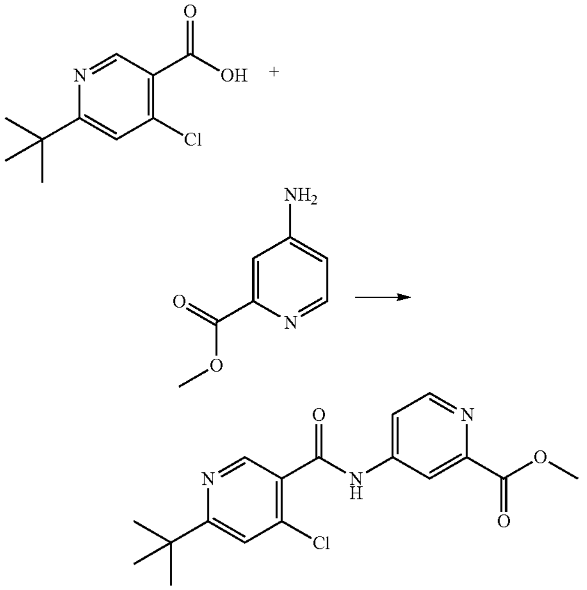

A dichloromethane (15 mL) solution of 6-tert-butyl-4-chloro-pyridine-3-carboxylic acid (1.27 g, 5.94 mmol) at 0° C. under nitrogen was treated with DMF (20 µL, 0.26 mmol) followed by the dropwise addition of oxalyl chloride (1.6 mL, 18.3 mmol). The mixture was warmed to room temperature, stirred for 20 minutes and then concentrated in vacuo. The residue was dissolved in NMP (12.5 mL), cooled to 0° C. under nitrogen, and treated with methyl 4-amino-pyridine-2-carboxylate (1.05 g, 6.90 mmol) and DIEA (6 mL, 34 mmol). The mixture was warmed to room temperature and stirred for 4 hours. The mixture was diluted with saturated aqueous $NH_4Cl$ (20 mL) and extracted with ethyl acetate (30 mL). The organic layer was washed with water (3×10 mL) and brine (2×10 mL), dried over anhydrous $Na_2SO_4$, filtered and concentrate in vacuo to provide methyl 4-[(6-tert-butyl-4-chloro-pyridine-3-carbonyl)amino]pyridine-2-carboxylate (2.12 g, 103%). ESI-MS m z calc. 347.10, found 348.2 $(M+1)^+$; LC/MS retention time (Method B): 1.31 minutes. The compound was used without further purification.

Step 3: 6-Tert-Butyl-N-(2-Carbamoyl-4-Pyridyl)-4-Chloro-Pyridine-3-Carboxamide

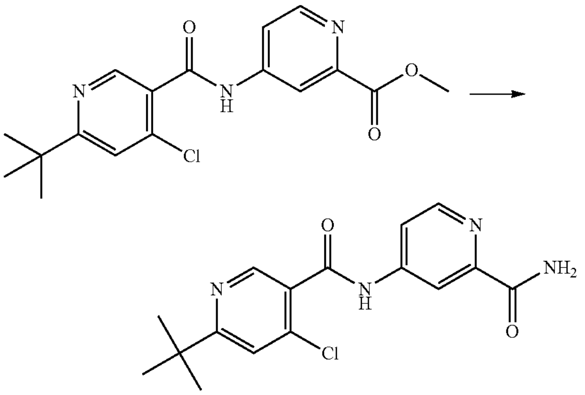

Methyl 4-[(6-tert-butyl-4-chloro-pyridine-3-carbonyl)amino]pyridine-2-carboxylate (1.12 g, 3.22 mmol) was dissolved in a solution of ammonia in methanol (25 mL of 7 M, 175 mmol) at 0° C. and then stirred for 16 hours at room temperature. The resulting solid was collected by filtration and washed with cold methanol (2×5 mL). The solid was collected and dried in vacuo to provide 6-tert-butyl-N-(2-carbamoyl-4-pyridyl)-4-chloro-pyridine-3-carboxamide (0.98 g, 91%). ESI-MS m z calc. 332.10, found 333.2 $(M+1)^+$; LC/MS retention time (Method B): 1.22 minutes. $^1H$ NMR (400 MHz, DMSO-$d_6$) δ 11.20 (s, 1H), 8.78 (s, 1H), 8.55 (d, J=5.5 Hz, 1H), 8.36 (d, J=2.1 Hz, 1H), 8.10 (d, J=2.8 Hz, 1H), 7.86 (dd, J=5.5, 2.2 Hz, 1H), 7.68 (d, J=14.1 Hz, 2H), 1.35 (s, 9H) ppm.

Step 4: 4-Benzyl-6-Tert-Butyl-N-(2-Carbamoyl-4-Pyridyl)Pyridine-3-Carboxamide (349)

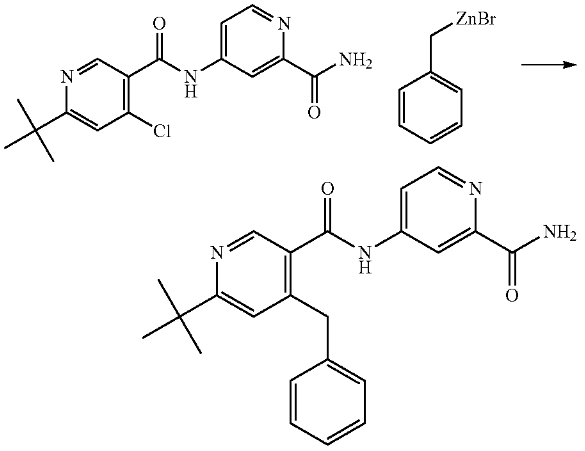

6-tert-Butyl-N-(2-carbamoyl-4-pyridyl)-4-chloro-pyridine-3-carboxamide (20 mg, 0.06 mmol) and Pd(t-$Bu_3P)_2$ (11.3 mg, 0.022 mmol) were treated with a solution benzyl (bromo)zinc (800 μL of 0.5 M in THF, 0.4 mmol) and the mixture stirred at room temperature for 20 minutes. The mixture was filtered and concentrated in vacuo. The residue was purified by reverse phase HPLC (1-99% acetonitrile/5 mM HCl) to provide 4-benzyl-6-tert-butyl-N-(2-carbamoyl-4-pyridyl)pyridine-3-carboxamide (7.9 mg, 34%). ESI-MS m z calc. 388.19, found 389.3 $(M+1)^+$; LC/MS retention time (Method C): 1.64 minutes. $^1H$ NMR (400 MHz, DMSO-$d_6$) δ 11.34 (s, 1H), 8.80 (s, 1H), 8.58 (d, J=5.6 Hz, 1H), 8.41 (s, 1H), 8.29 (s, 1H), 7.88 (d, J=5.7 Hz, 1H), 7.83 (s, 1H), 7.70 (s, 1H), 7.29-7.12 (m, 5H), 4.29 (s, 2H), 1.38 (d, J=1.4 Hz, 9H) ppm.

Example 145

6-Tert-Butyl-N-(2-Carbamoyl-4-Pyridyl)-4-[(3,4-Difluorophenyl)Methyl]Pyridine-3-Carboxamide (350)

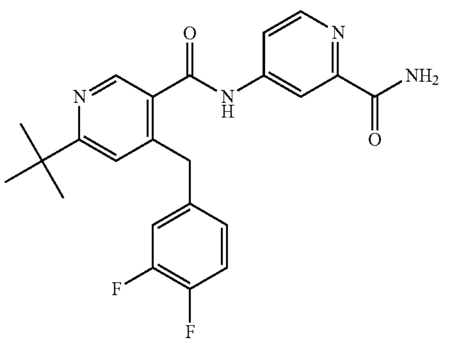 [SMILES: CC(C)(C)c1cc(Cc2ccc(F)c(F)c2)c(C(=O)Nc2ccnc(C(N)=O)c2)cn1]

This compound was made in an analogous fashion to the synthesis of compound 349 in Example 144, except employing bromo-[(3,4-difluorophenyl)methyl]zinc in the final palladium-catalyzed Negishi coupling. The yield of 6-tert-butyl-N-(2-carbamoyl-4-pyridyl)-4-[(3,4-difluorophenyl)methyl]pyridine-3-carboxamide after purification was 3.9 mg (31%). ESI-MS m z calc. 424.17, found 425.3 $(M+1)^+$; LC/MS retention time (Method C): 1.85 minutes. $^1H$ NMR (400 MHz, DMSO-$d_6$) δ 11.30 (s, 1H), 8.80 (s, 1H), 8.58 (d, J=5.7 Hz, 1H), 8.41 (s, 1H), 8.27 (s, 1H), 7.87 (d, J=5.7 Hz, 1H), 7.81 (s, 1H), 7.68 (s, 1H), 7.40-7.23 (m, 2H), 7.13-7.02 (m, 1H), 4.25 (s, 2H), 1.38 (s, 9H) ppm.

Example 146

N-(2-Carbamoyl-4-Pyridyl)-4-(4-Fluoro-2-Methoxy-Phenoxy)-2-Methyl-6-(Trifluoromethyl)Pyridine-3-Carboxamide (351)

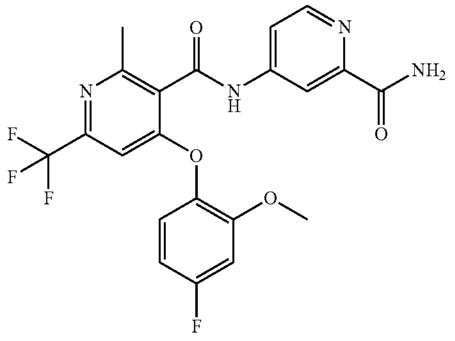 [SMILES: COc1cc(F)ccc1Oc1cc(C(F)(F)F)nc(C)c1C(=O)Nc1ccnc(C(N)=O)c1]

Step 1: Ethyl 2-Methyl-6-(Trifluoromethyl)Pyridine-3-Carboxylate

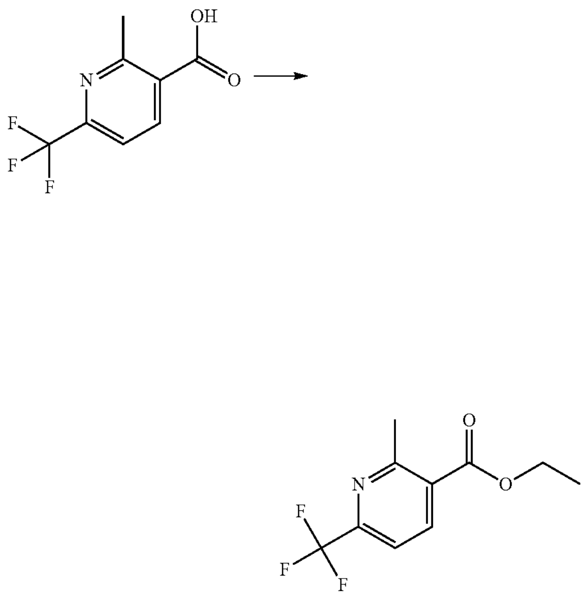

2-Methyl-6-(trifluoromethyl)pyridine-3-carboxylic acid (10.0 g, 48.8 mmol) was dissolved in acetone (100 mL) and cooled in ice-cool bath. Acetyl chloride (11.0 g, 10.0 mL, 141 mmol) was added dropwise and the mixture was heated at 60° C. for 16 hours. The mixture was cooled and solvent was removed in vacuo, and the residue partitioned between saturated aqueous $NaHCO_3$ and ethyl acetate. The organic layer was separated, dried over $Na_2SO_4$, filtered and concentrated in vacuo to provide ethyl 2-methyl-6-(trifluoromethyl)pyridine-3-carboxylate (10.5 g, 92%). $^1H$ NMR (400 MHz, $CDCl_3$) δ 8.32 (d, J=8.0 Hz, 1H), 7.56 (d, J=8.0 Hz, 1H), 4.41 (q, J=7.1 Hz, 2H), 2.87 (s, 3H), 1.41 (t, J=7.2 Hz, 3H) ppm.

Step 2: Ethyl 2-Methyl-1-Oxido-6-(Trifluoromethyl)Pyridin-1-Ium-3-Carboxylate

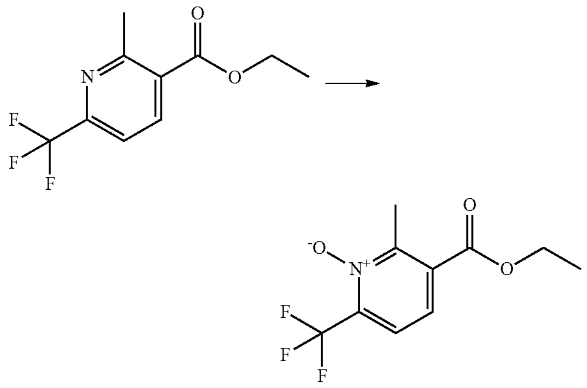

To a stirring solution of ethyl 2-methyl-6-(trifluoromethyl)pyridine-3-carboxylate (8.0 g, 34 mmol) in dichloromethane was added urea-hydrogen peroxide (6.8 g, 72 mmol). The mixture was cooled at 0° C. and treated dropwise with trifluoracetic anhydride (15 g, 10 mL, 72 mmol). The mixture was allowed to warm to room temperature and was treated solid $Na_2S_2O_3$. The mixture was washed with 0.5 M aqueous HCl and the layers separated. The organic layer was dried over $Na_2SO_4$, filtered and concentrated in vacuo to provide ethyl 2-methyl-1-oxido-6-(trifluoromethyl)pyridin-1-ium-3-carboxylate (8.3 g, 97%) as white solid. $^1H$ NMR (400 MHz, DMSO-$d_6$) δ 7.95 (d, J=8.5 Hz, 1H), 7.77 (d, J=8.4 Hz, 1H), 4.38 (q, J=6.9 Hz, 2H), 2.66 (s, 3H), 1.34 (t, J=7.1 Hz, 3H) ppm.

Step 3: Ethyl 4-Chloro-2-Methyl-6-(Trifluoromethyl)Pyridine-3-Carboxylate

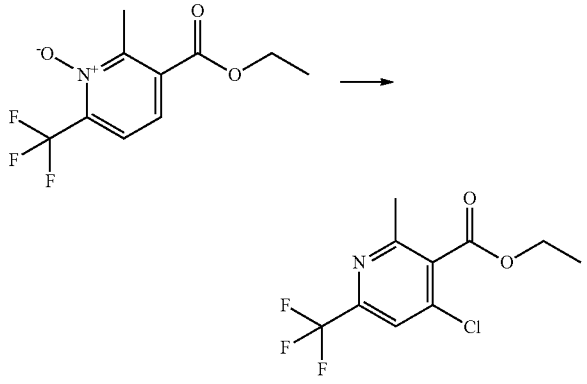

Ethyl 2-methyl-1-oxido-6-(trifluoromethyl)pyridin-1-ium-3-carboxylate (4.5 g, 18 mmol) and $POCl_3$ (36 g, 22 mL, 236 mmol) were heated in a sealed tube at 120° C. for 5 hours. The cooled mixture was poured onto crushed ice and $Na_2CO_3$ added until neutral pH. The mixture was partitioned between water and ethyl acetate. The organic phase was dried over $Na_2SO_4$, filtered and concentrated in vacuo. Silica gel chromatography (0-10% ethyl acetate/hexanes) provided ethyl 4-chloro-2-methyl-6-(trifluoromethyl)pyridine-3-carboxylate (1.6 g, 33%). $^1H$ NMR (400 MHz, $CDCl_3$) δ 7.57 (s, 1H), 4.47 (q, J=7.1 Hz, 2H), 2.62 (s, 3H), 1.41 (t, J=7.2 Hz, 3H) ppm.

Step 4: 4-(4-Fluoro-2-Methoxy-Phenoxy)-2-Methyl-6-(Trifluoromethyl)Pyridine-3-Carboxylic Acid

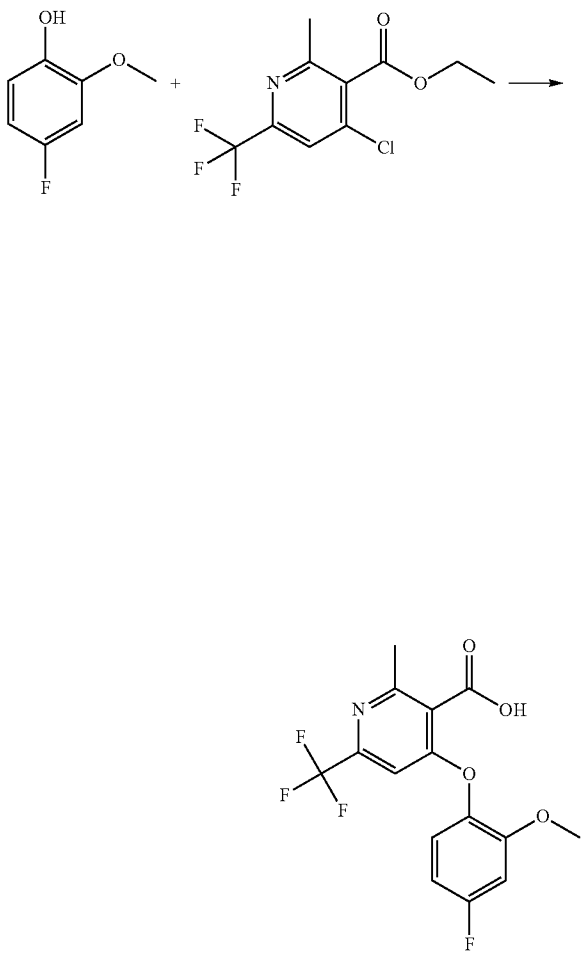

A solution of 4-fluoro-2-methoxy-phenol (470 μL, 4.12 mmol) in acetonitrile (10 mL) was treated with $Cs_2CO_3$ (1.416 g, 4.346 mmol) and ethyl 4-chloro-2-methyl-6-(trifluoromethyl)pyridine-3-carboxylate (1.0 g, 3.7 mmol). The mixture was stirred at room temperature for 2 hours, and then at 50° C. for 4.5 hours. The mixture was diluted with ethyl acetate and washed with 2 M aqueous NaOH. The organic layer dried over $MgSO_4$, filtered and concentrated. The residue was purified by silica gel chromatography (0-10% ethyl acetate/heptane) to provided ethyl 4-(4-fluoro-2-methoxy-phenoxy)-2-methyl-6-(trifluoromethyl)pyridine-3-carboxylate, which was dissolved in dissolved in ethanol (10 mL) and 2 M aqueous NaOH (6 mL, 12 mmol). The mixture was stirred 16 hours, and then additional 2 M aqueous NaOH added (2 mL, 4 mmol) and the mixture stirred for 3 hours. The mixture was acidified with 2 M aqueous HCl (9 mL) and extracted into ethyl acetate. The organic layer was separated, dried over $MgSO_4$, filtered and concentrated to provide 4-(4-fluoro-2-methoxy-phenoxy)-2-methyl-6-(trifluoromethyl)pyridine-3-carboxylic acid (919.6 mg, 71%). ESI-MS m z calc. 345.06, found 346.2 $(M+1)^+$; LC/MS retention time (Method E): 0.48 minutes.

Step 5: N-(2-Carbamoyl-4-Pyridyl)-4-(4-Fluoro-2-Methoxy-Phenoxy)-2-Methyl-6-(Trifluoromethyl)Pyridine-3-Carboxamide (351)

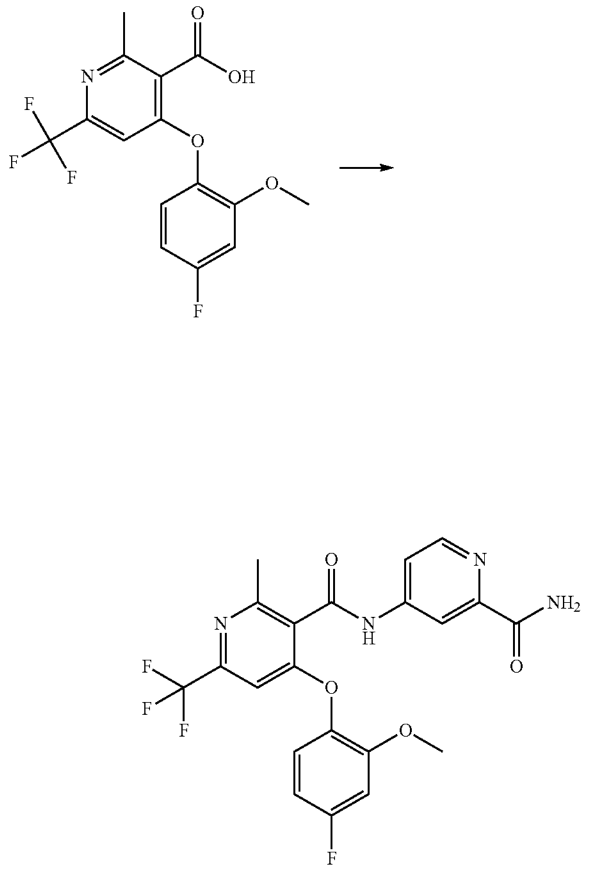

A solution of 4-(4-fluoro-2-methoxy-phenoxy)-2-methyl-6-(trifluoromethyl)pyridine-3-carboxylic acid (77 mg, 0.22 mmol) and DMF (1 drop) in dichloromethane (2 mL) was treated with oxalyl chloride (75 μL, 0.86 mmol). The mixture was stirred at room temperature for 3.5 hours, and then concentrated. The resulting acid chloride was dissolved in dichloromethane (2 mL) and treated with methyl 4-aminopyridine-2-carboxylate (36.3 mg, 0.239 mmol) and TEA (60 μL, 0.43 mmol). The mixture was stirred at room temperature for 3 hours, and then concentrated and treated with a solution of ammonia in methanol (5 mL of 7 M, 35 mmol). The mixture was stirred for 2 hours, and then concentrated and purified by reverse phase HPLC (38-53% acetonitrile/0.1% ammonium hydroxide) to provide N-(2-carbamoyl-4-pyridyl)-4-(4-fluoro-2-methoxy-phenoxy)-2-methyl-6-(trifluoromethyl)pyridine-3-carboxamide (11.6 mg, 11%). ESI-MS m z calc. 464.11, found 465.0 $(M+1)^+$; LC/MS retention time (Method E): 2.81 minutes. $^1H$ NMR (400 MHz, DMSO-$d_6$) δ 11.33 (s, 1H), 8.57 (dd, J=5.5, 0.6 Hz, 1H), 8.35 (dd, J=2.1, 0.6 Hz, 1H), 8.10 (s, 1H), 7.87 (dd, J=5.5, 2.2 Hz, 1H), 7.66 (d, J=2.9 Hz, 1H), 7.33 (dd, J=8.9, 5.8 Hz, 1H), 7.20 (dd, J=10.7, 2.9 Hz, 1H), 6.89 (ddd, J=8.8, 8.1, 2.9 Hz, 1H), 6.80 (s, 1H), 3.78 (s, 3H), 2.58 (s, 3H) ppm.

Example 147

4-[[2-Fluoro-4-Methoxy-6-[2-Methoxy-4-(Trifluoromethoxy)Phenoxy]-3-(Trifluoromethyl)Benzoyl]Amino]Pyridine-2-Carboxamide (352)

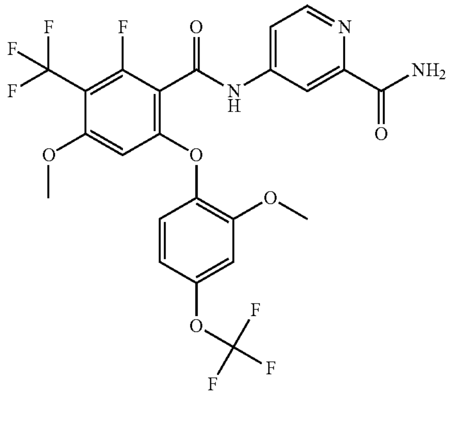 [SMILES: COc1cc(OC(F)(F)F)ccc1Oc1cc(OC)c(C(F)(F)F)c(F)c1C(=O)Nc1ccnc(C(N)=O)c1]

Step 1: 2-Fluoro-4-Methoxy-6-[2-Methoxy-4-(Trifluoromethoxy)Phenoxy]-3-(Trifluoromethyl)Benzoic Acid

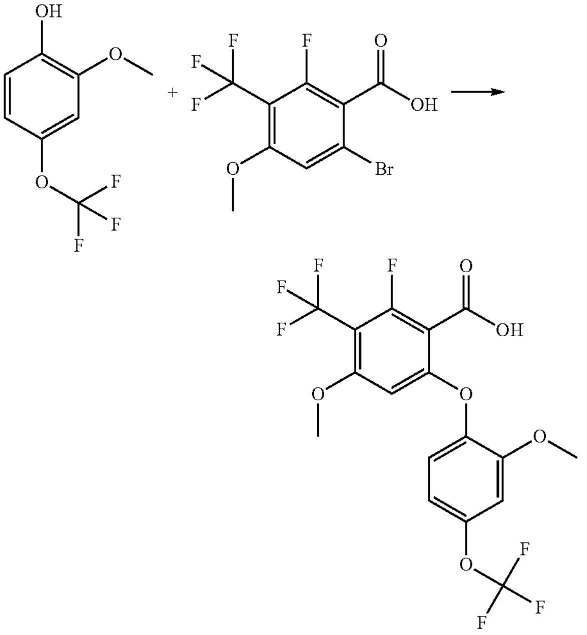

A mixture of 6-bromo-2-fluoro-4-methoxy-3-(trifluoromethyl)benzoic acid (3.0 g, 8.5 mmol, see US 2019/0016671, Example 129, Step 3, which is incorporated by reference), 2-methoxy-4-(trifluoromethoxy)phenol (1.6 g, 7.7 mmol) and $Cs_2CO_3$ (3.0 g, 9.2 mmol) in toluene (30 mL) was bubbled with nitrogen for 10 minutes, then copper (I) iodide (570 mg, 2.99 mmol) was added. The mixture was heated at 100° C. under nitrogen with vigorous stirring for 30 minutes. The cooled mixture was acidified with aqueous HCl, filtered and the mixture extracted with ethyl acetate (3×50 mL). The combined organic extracts were washed with brine, dried over $MgSO_4$, filtered and concentrated. Purification by silica gel chromatography (0-100% ethyl acetate/hexanes) provided 2-fluoro-4-methoxy-6-[2-methoxy-4-(trifluoromethoxy)phenoxy]-3-(trifluoromethyl)benzoic acid (3.31 g, 88%) as a pale yellow powder. ESI-MS m/z calc. 444.04, found 445.5 $(M+1)^+$; 443.6 $(M-1)^-$; LC/MS retention time (Method F): 0.61 minutes. $^1H$ NMR (500 MHz, DMSO-$d_6$) δ 13.63 (s, 1H), 7.28-7.19 (m, 2H), 7.01 (ddd, J=8.8, 2.7, 1.3 Hz, 1H), 6.28 (s, 1H), 3.83 (s, 3H), 3.74 (s, 3H) ppm.

Step 2: Methyl 4-[[2-Fluoro-4-Methoxy-6-[2-Methoxy-4-(Trifluoromethoxy)Phenoxy]-3-(Trifluoromethyl)Benzoyl]Amino]Pyridine-2-Carboxylate

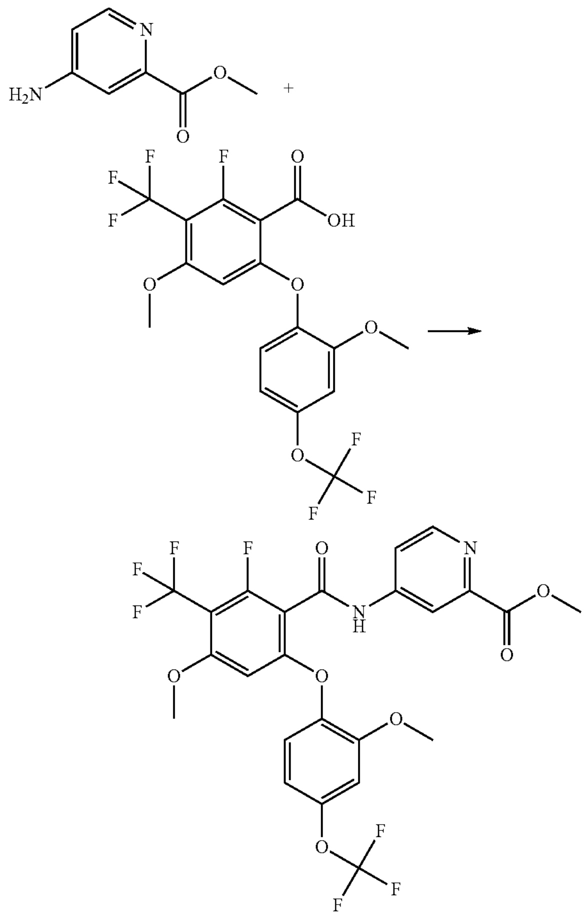

A solution of 2-fluoro-4-methoxy-6-[2-methoxy-4-(trifluoromethoxy)phenoxy]-3-(trifluoromethyl)benzoic acid (200 mg, 0.450 mmol) in dichloromethane (10 mL) was cooled to 0° C. and treated with oxalyl chloride (100 μL, 1.15 mmol) followed by DMF (2 μL, 0.03 mmol). The resulting mixture was stirred for 1 hour and then concentrated in vacuo. The residue was dissolved in dichloromethane (10 mL) and methyl 4-aminopyridine-2-carboxylate (68.5 mg, 0.450 mmol) and TEA (150 μL, 1.08 mmol) added. The mixture was stirred at room temperature overnight then concentrated in vacuo. The residue was purified by silica gel chromatography (0-100% ethyl acetate/heptane) to provide methyl 4-[[2-fluoro-4-methoxy-6-[2-methoxy-4-(trifluoromethoxy)phenoxy]-3-(trifluoromethyl)benzoyl]amino]pyridine-2-carboxylate (140 mg, 54%). ESI-MS m z calc. 578.09, found 579.5 $(M+1)^+$; 577.6 $(M-1)^-$; LC/MS retention time (Method F): 0.97 minutes. $^1H$ NMR (500 MHz, DMSO-$d_6$) δ 11.28 (s, 1H), 8.61 (d, J=5.5 Hz, 1H), 8.33 (d, J=2.0 Hz, 1H), 7.79 (dd, J=5.5, 2.2 Hz, 1H), 7.31 (d, J=8.8 Hz, 1H), 7.19 (d, J=2.8 Hz, 1H), 6.99 (ddd, J=8.8, 2.8, 1.2 Hz, 1H), 6.39 (s, 1H), 3.89 (s, 3H), 3.79 (s, 3H), 3.78 (s, 3H) ppm.

Step 3: 4-[[2-Fluoro-4-Methoxy-6-[2-Methoxy-4-(Trifluoromethoxy)Phenoxy]-3-(Trifluoromethyl)Benzoyl]Amino]Pyridine-2-Carboxamide (352)

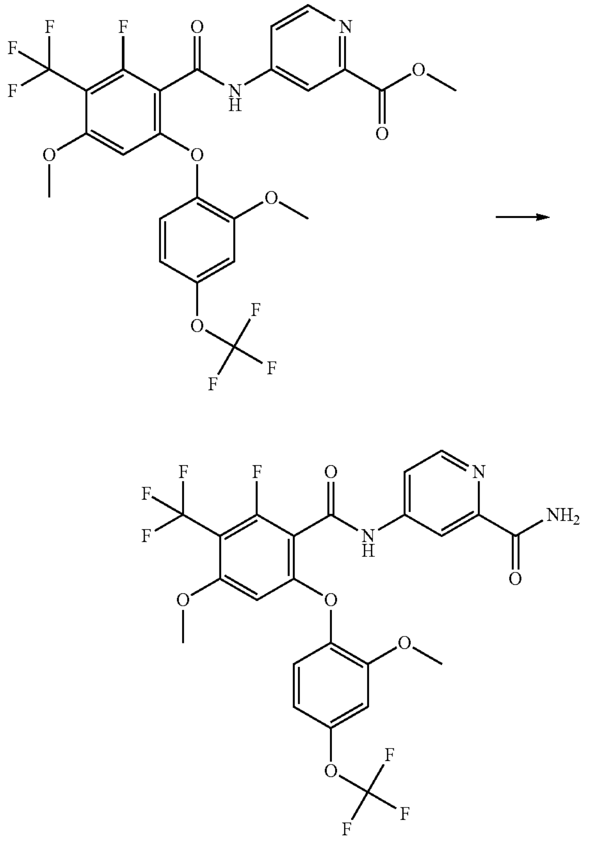 [SMILES: COC(=O)c1cc(NC(=O)c2c(Oc3ccc(OC(F)(F)F)cc3OC)cc(OC)c(C(F)(F)F)c2F)ccn1 ; COc1cc(OC(F)(F)F)ccc1Oc1cc(OC)c(C(F)(F)F)c(F)c1C(=O)Nc1ccnc(C(N)=O)c1]

Methyl 4-[[2-fluoro-4-methoxy-6-[2-methoxy-4-(trifluoromethoxy)phenoxy]-3-(trifluoromethyl)benzoyl]amino]pyridine-2-carboxylate (140 mg, 0.242 mmol) was dissolved in a solution of ammonia in methanol (3 mL of 7 M, 21 mmol) and the resulting mixture stirred at room temperature for 3 hours. The mixture was concentrated in vacuo and the residue purified by silica gel chromatography (0-100% ethyl acetate/heptane) to provide 4-[[2-fluoro-4-methoxy-6-[2-methoxy-4-(trifluoromethoxy)phenoxy]-3-(trifluoromethyl)benzoyl]amino]pyridine-2-carboxamide (80.1 mg, 57%). ESI-MS m z calc. 563.09, found 564.5 $(M+1)^+$; 562.6 $(M-1)^-$; LC/MS retention time (Method E): 3.28 minutes. H NMR (500 MHz, DMSO-$d_6$) δ 11.22 (s, 1H), 8.53 (dd, J=5.4, 0.6 Hz, 1H), 8.27 (d, J=2.1 Hz, 1H), 8.08 (d, J=2.8 Hz, 1H), 7.80 (dd, J=5.5, 2.2 Hz, 1H), 7.64 (d, J=3.0 Hz, 1H), 7.32 (d, J=8.8 Hz, 1H), 7.20 (d, J=2.9 Hz, 1H), 7.00 (ddt, J=8.8, 2.7, 1.2 Hz, 1H), 6.38 (s, 1H), 3.79 (m, 6H) ppm.

Example 148

5-[[2-Fluoro-4-Methoxy-6-[2-Methoxy-4-(Trifluoromethoxy)Phenoxy]-3-(Trifluoromethyl)Benzoyl]Amino]Pyridine-2-Carboxamide (353)

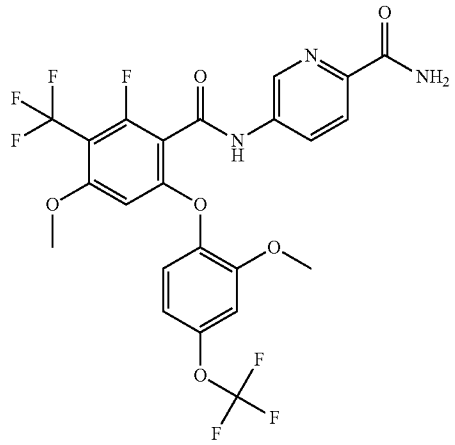 [SMILES: COc1cc(OC(F)(F)F)ccc1Oc1cc(OC)c(C(F)(F)F)c(F)c1C(=O)Nc1ccc(C(N)=O)nc1]

This compound was made in an analogous fashion to Example 147, except employing 5-aminopyridine-2-carboxamide in the amide formation step to provide the final compound. The yield of 5-[[2-fluoro-4-methoxy-6-[2-methoxy-4-(trifluoromethoxy)phenoxy]-3-(trifluoromethyl)benzoyl]amino]pyridine-2-carboxamide after purification was 105.8 mg (41%). ESI-MS m z calc. 563.09, found 564.5 $(M+1)^+$; 562.5 $(M-1)^-$; LC/MS retention time (Method E): 3.25 minutes. $^1H$ NMR (500 MHz, DMSO-$d_6$) δ 11.14 (s, 1H), 8.82 (d, J=2.4 Hz, 1H), 8.23 (dd, J=8.6, 2.5 Hz, 1H), 8.06-7.98 (m, 2H), 7.55 (d, J=2.8 Hz, 1H), 7.32 (d, J=8.8 Hz, 1H), 7.20 (d, J=2.7 Hz, 1H), 7.00 (ddt, J=7.7, 2.7, 1.3 Hz, 1H), 6.39 (s, 1H), 3.79 (s, 6H) ppm.

Example 149

4-[[2-Fluoro-6-[2-Methoxy-4-(Trifluoromethoxy)Phenoxy]-3-(Trifluoromethyl)Benzoyl]Amino]-5-Methyl-1-Oxido-Pyridin-1-Ium-2-Carboxamide (354)

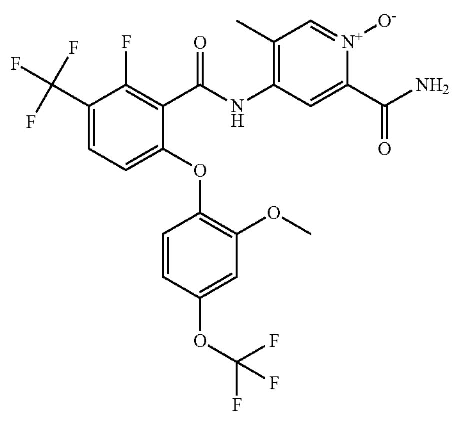 [SMILES: COc1cc(OC(F)(F)F)ccc1Oc1ccc(C(F)(F)F)c(F)c1C(=O)Nc1cc(C(N)=O)[n+]([O-])cc1C]

Step 1: N-(2-Bromo-5-Methyl-4-Pyridyl)-2-Fluoro-6-[2-Methoxy-4-(Trifluoromethoxy)Phenoxy]-3-(Trifluoromethyl)Benzamide

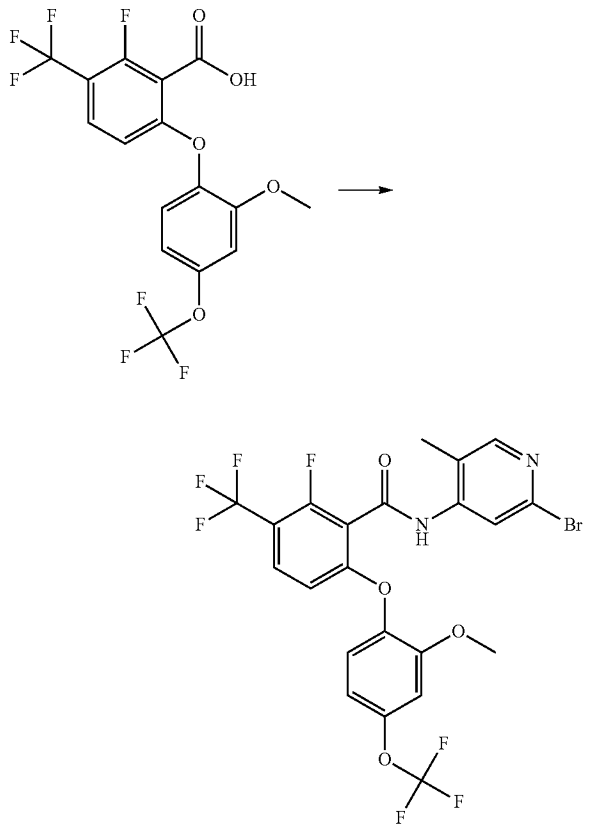

To solution of 2-fluoro-6-[2-methoxy-4-(trifluoromethoxy)phenoxy]-3-(trifluoromethyl)benzoic acid (300 mg, 0.681 mmol, see US 2019/0016671, Example 2, Step 3, which is incorporated by reference) in dichloromethane (5 mL) at 0° C. was added DMF (6 μL, 0.08 mmol) and oxalyl chloride (200 μL, 2.29 mmol) dropwise. The mixture was allowed to warm to room temperature over 3.5 hours, and then concentrated in vacuo. The residue was dissolved in dichloromethane (5 mL) and cooled to 0° C. The solution was treated with 2-bromo-5-methyl-pyridin-4-amine (165 mg, 0.882 mmol) followed by TEA (500 μL, 3.59 mmol). The resulting mixture was allowed to warm to room temperature and stirred for 48 hours. The mixture was diluted with water (10 mL) and extracted with dichloromethane (2×10 mL). The combined organics were dried over $MgSO_4$, filtered and concentrated in vacuo. Silica gel chromatography (0-20% ethyl acetate/petroleum ether) provided N-(2-bromo-5-methyl-4-pyridyl)-2-fluoro-6-[2-methoxy-4-(trifluoromethoxy)phenoxy]-3-(trifluoromethyl)benzamide (217 mg, 55%) as an off-white solid. ESI-MS m z calc. 582.00, found 583.1 $(M+1)^+$; 581.1 $(M-1)^-$; LC/MS retention time (Method F): 1.15 minutes. $^1H$ NMR (500 MHz, $CDCl_3$) δ 8.61 (s, 1H), 8.15 (s, 2H), 7.60-7.57 (m, 1H), 7.23 (d, J=8.7 Hz, 1H), 6.98-6.96 (m, 1H), 6.94 (d, J=2.4 Hz, 1H), 6.53 (d, J=9.0 Hz, 1H), 3.82 (s, 3H), 2.17 (s, 3H) ppm. $^{19}F$ NMR (471 MHz, $CDCl_3$) δ −58.01, −60.82 (d, J=13.0 Hz), −112.20 (q, J=14.3, 13.3 Hz) ppm.

Step 2: Methyl 4-[[2-Fluoro-6-[2-Methoxy-4-(Trifluoromethoxy)Phenoxy]-3-(Trifluoromethyl)Benzoyl]Amino]-5-Methyl-Pyridine-2-Carboxylate

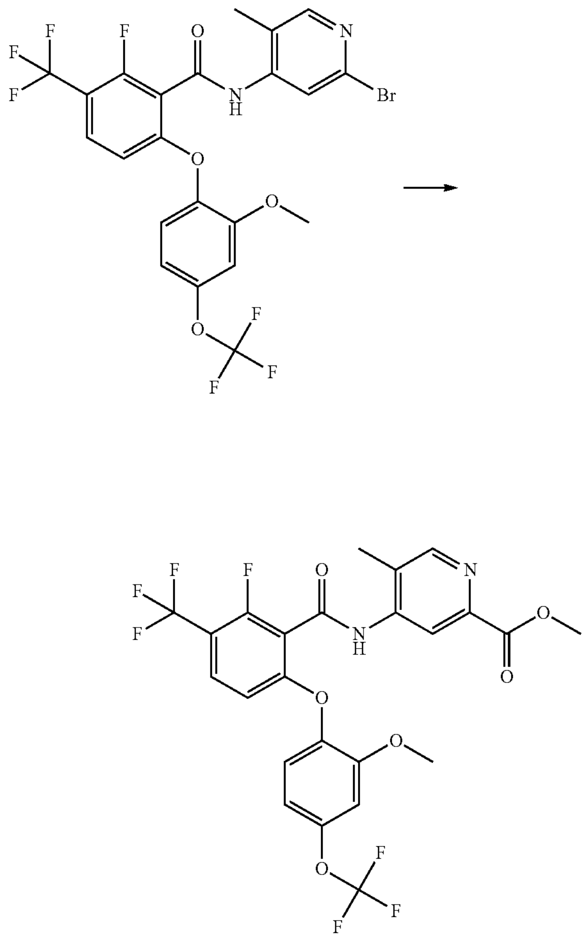

In a pressure tube N-(2-bromo-5-methyl-4-pyridyl)-2-fluoro-6-[2-methoxy-4-(trifluoromethoxy)phenoxy]-3-(trifluoromethyl)benzamide (217 mg, 0.372 mmol) was dissolved in methanol (10 mL) and TEA (110 μL, 0.789 mmol) and Pd(dppf)$Cl_2$-dichloromethane (60 mg, 0.074 mmol) were added. Carbon monoxide was bubbled through the vigorously stirring mixture for 5 minutes. The reaction vessel was sealed and heated to 75° C. for 16 hours. The mixture was cooled to room temperature, filtered through a pad of Celite eluting with methanol and concentrated in vacuo. Silica gel chromatography (0-100% ethyl acetate/petroleum ether) provided methyl 4-[[2-fluoro-6-[2-methoxy-4-(trifluoromethoxy)phenoxy]-3-(trifluoromethyl)benzoyl]amino]-5-methyl-pyridine-2-carboxylate (178.6 mg, 85%). ESI-MS m z calc. 562.10, found 563.2 $(M+1)^+$; 561.2 $(M-1)^-$; LC/MS retention time (Method F): 1.04 minutes. $^1$H NMR (500 MHz, $CDCl_3$) δ 9.06 (s, 1H), 8.54 (s, 1H), 8.20 (s, 1H), 7.59 (d, J=17.0 Hz, 1H), 7.24 (d, J=8.7 Hz, 1H), 6.98-6.96 (m, 1H), 6.94-6.93 (m, 1H), 6.55 (d, J=9.4 Hz, 1H), 4.03 (s, 3H), 3.83 (s, 3H), 2.30 (s, 3H) ppm. $^{19}$F NMR (471 MHz, $CDCl_3$) δ −58.01, −60.82 (d, J=12.9 Hz), −112.16--112.24 (m) ppm.

Step 3: 4-[[2-Fluoro-6-[2-Methoxy-4-(Trifluoromethoxy)Phenoxy]-3-(Trifluoromethyl)Benzoyl]Amino]-5-Methyl-Pyridine-2-Carboxamide

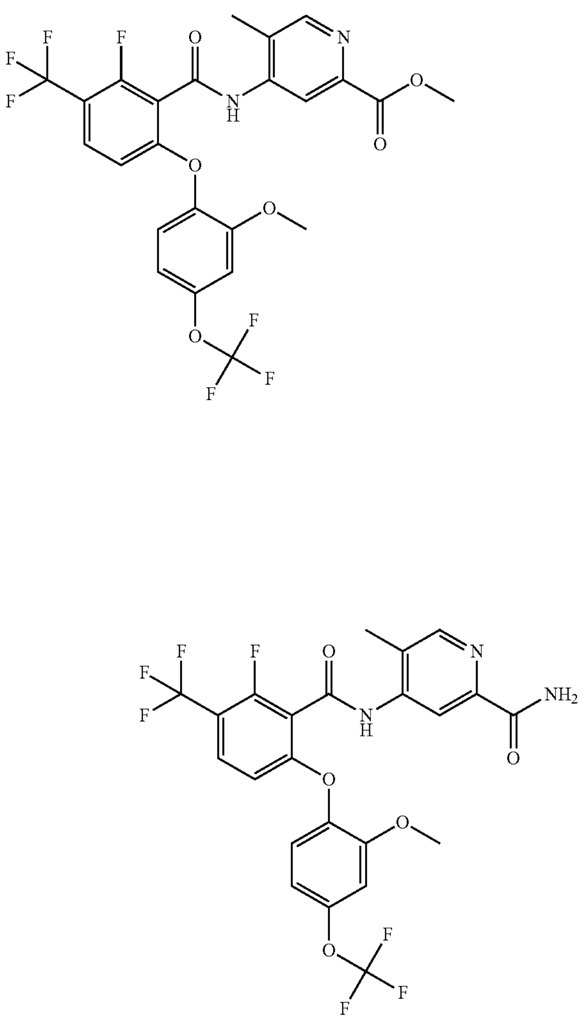

A mixture of methyl 4-[[2-fluoro-6-[2-methoxy-4-(trifluoromethoxy)phenoxy]-3-(trifluoromethyl)benzoyl]amino]-5-methyl-pyridine-2-carboxylate (178 mg, 0.317 mmol) and ammonia (5 mL of 7 M in methanol, 35 mmol) was stirred at room temperature for 16 hours. SPM32 silica metal scavenger (150 mg) was added and the mixture was stirred for 15 minutes. The mixture was filtered and the filtrate was concentrated in vacuo. Silica gel chromatography (0-100% ethyl acetate/petroleum ether) provided 4-[[2-fluoro-6-[2-methoxy-4-(trifluoromethoxy)phenoxy]-3-(trifluoromethyl)benzoyl]amino]-5-methyl-pyridine-2-carboxamide (54.5 mg, 31%) as a white solid. ESI-MS m/z calc. 547.10, found 548.1 $(M+1)^+$; 546.0 $(M-1)^-$; LC/MS retention time (Method E): 3.32 minutes. $^1$H NMR (500 MHz, DMSO-$d_6$) δ 10.58 (s, 1H), 8.49-8.48 (m, 2H), 8.06 (d, J=2.9 Hz, 1H), 7.81 (t, J=8.6 Hz, 1H), 7.61-7.60 (m, 1H), 7.39 (d, J=8.8 Hz, 1H), 7.29 (d, J=2.7 Hz, 1H), 7.09-7.06 (m, 1H), 6.66 (d, J=8.9 Hz, 1H), 3.82 (s, 3H), 2.33 (s, 3H) ppm. 19F NMR (471 MHz, DMSO-$d_6$) δ −56.85, −59.11 (d, J=12.2 Hz), −117.84 (q, J=12.5 Hz) ppm.

Step 4: 4-[[2-Fluoro-6-[2-Methoxy-4-(Trifluoromethoxy)Phenoxy]-3-(Trifluoromethyl)Benzoyl]Amino]-5-Methyl-1-Oxido-Pyridin-1-Ium-2-Carboxamide (354)

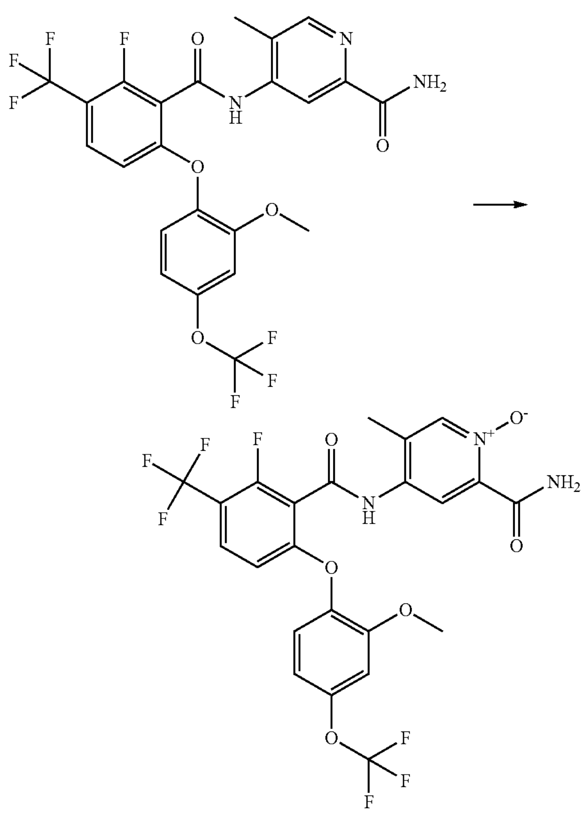

A solution of 4-[[2-fluoro-6-[2-methoxy-4-(trifluoromethoxy)phenoxy]-3-(trifluoromethyl)benzoyl]amino]-5-methyl-pyridine-2-carboxamide (11.6 mg, 0.0209 mmol) in dichloromethane (2.5 mL) at 0° C. was treated with meta-chloroperoxybenzoic acid (20 mg, 0.089 mmol). The mixture was allowed to warm to room temperature and stirred for 3 days. The mixture was partitioned between dichloromethane and water and the layers separated (phase separation cartridge). The organic filtrate was concentrated in vacuo and purified by reverse phase HPLC (38-53% acetonitrile/0.1% ammonium hydroxide) to provide 4-[[2-fluoro-6-[2-methoxy-4-(trifluoromethoxy)phenoxy]-3-(trifluoromethyl)benzoyl]amino]-5-methyl-1-oxido-pyridin-1-ium-2-carboxamide (1.7 mg, 14H). ESI-MS m/z calc. 563.09, found 564.4 $(M+1)^+$; 562.5 (M−1); LC/MS retention time (Method E): 3.1 minutes. $^1H$ NMR (500 MHz, $CDCl_3$) δ 10.75 (s, 1H), 9.05 (s, 1H), 8.20 (s, 1H), 8.15 (s, 1H), 7.56 (t, J=8.3 Hz, 1H), 7.24 (d, J=8.7 Hz, 1H), 6.96 (dt, J=8.7, 1.8 Hz, 1H), 6.92 (d, J=2.3 Hz, 1H), 6.53 (d, J=8.9 Hz, 1H), 6.01 (s, 1H), 3.82 (s, 3H), 2.27 (d, J=0.8 Hz, 3H) ppm.

The compounds set forth in Table 35 were prepared by methods analogous to the preparation of compound 4-[[2-fluoro-6-[2-methoxy-4-(trifluoromethoxy)phenoxy]-3-(trifluoromethyl)benzoyl]amino]-5-methyl-pyridine-2-carboxamide (see Example 149, Step 3). The amide coupling with the appropriate amine was followed by conversion of the ester to the corresponding carboxamide via treatment with methanolic ammonia.

TABLE 35

Additional Compounds Prepared by Methods Analogous to Example 149

| Cmpd No. | Compound Name | LC/MS | NMR (shifts in ppm) |
|---|---|---|---|
| 355 | 6-[[2-fluoro-6-[2-methoxy-4-(trifluoromethoxy)phenoxy]-3-(trifluoromethyl)benzoyl]amino]pyrimidine-4-carboxamide | ESI-MS m/z calc. 534.08, found 534.0 $(M + 1)^+$; LC/MS retention time (Method C): 2.47 minutes | $^1H$ NMR (400 MHz, DMSO-$d_6$) δ 12.01 (s, 1H), 9.04 (s, 1H), 8.69 (s, 1H), 8.29 (s, 1H), 7.96 (s, 1H), 7.80 (m, 1H), 7.36 (d, J = 8.6 Hz, 1H), 7.25 (s, 1H), 7.04 (d, J = 8.0 Hz, 1H), 6.66 (d, J = 8.8 Hz, 1H), 3.78 (s, 3H) |
| 356 | 5-[[2-fluoro-6-[2-methoxy-4-(trifluoromethoxy)phenoxy]-3-(trifluoromethyl)benzoyl]amino]pyridazine-3-carboxamide | ESI-MS m/z calc. 534.08, found 535.0 $(M + 1)^+$; LC/MS retention time (Method E): 2.37 minutes | |
| 357 | 5-[[2-fluoro-6-[2-methoxy-4-(trifluoromethoxy)phenoxy]-3-(trifluoromethyl)benzoyl]amino]pyrimidine-2-carboxamide | ESI-MS m/z calc. 534.08, found 535.0 $(M + 1)^+$; LC/MS retention time: 2.3 minutes (5 min. run) | $^1H$ NMR (400 MHz, DMSO-$d_6$) δ 11.60 (s, 1H), 9.20 (s, 2H), 8.14 (s, 1H), 7.83 (t, J = 8.6 Hz, 1H), 7.74 (s, 1H), 7.38 (d, J = 8.8 Hz, 1H), 7.26 (d, J = 2.7 Hz, 1H), 7.05 (ddd, J = 8.8, 2.7, 1.3 Hz, 1H), 6.70 (d, J = 8.9 Hz, 1H), 3.79 (s, 3H). |

Example 150

N-(6-Carbamoyl-3-Pyridyl)-5-(3,4-Difluoro-2-Methoxy-Phenoxy)-3-Methyl-2-(Trifluoromethyl) Pyridine-4-Carboxamide (358)

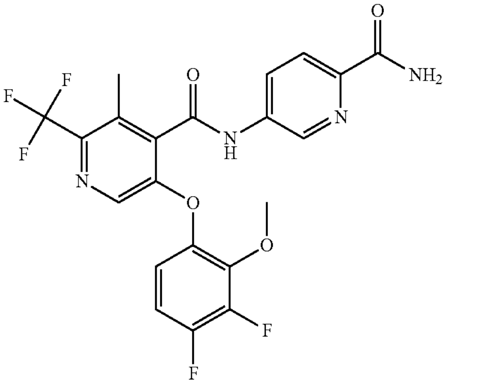 [SMILES: COc1c(Oc2cnc(C(F)(F)F)c(C)c2C(=O)Nc2ccc(C(N)=O)nc2)ccc(F)c1F]

Step 1: N-(6-Carbamoyl-3-Pyridyl)-5-Fluoro-3-Methyl-2-(Trifluoromethyl)Pyridine-4-Carboxamide

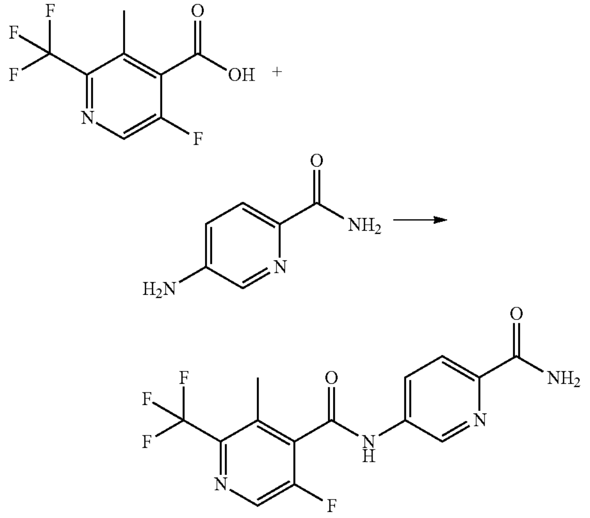

A solution of 5-fluoro-3-methyl-2-(trifluoromethyl)pyridine-4-carboxylic acid (150 mg, 0.672 mmol) in 2-MeTHF (2 mL) and DMF at 0° C. was treated dropwise with oxalyl chloride (120 μL, 1.376 mmol) then allowed to warm to room temperature over 1 hour. The mixture was concentrated in vacuo, then diluted with dichloromethane and evaporated. The residue was dissolved in 2-MeTHF (2 mL) and treated with 5-aminopyridine-2-carboxamide (95 mg, 0.69 mmol). NMP (1 mL) was added to the suspension to fully dissolve the solid. A solution of $K_2CO_3$ (280 mg, 2.03 mmol) in water (2 mL) was then added and the mixture stirred vigorously at room temperature for 18 hours. The layers were separated and the aqueous layer extracted with dichloromethane (2×). The combined extracts were washed with water (2×), dried over $Na_2SO_4$, filtered and concentrated in vacuo. Purification by silica gel chromatography (0-100% ethyl acetate/heptanes) provided N-(6-carbamoyl-3-pyridyl)-5-fluoro-3-methyl-2-(trifluoromethyl)pyridine-4-carboxamide (240 mg, 65%). ESI-MS m z calc. 342.07, found 343.0 $(M+1)^+$; 341.0 $(M-1)^-$; LC/MS retention time: 0.64 minutes (Method F). $^1H$ NMR (500 MHz, DMSO-$d_6$) δ 11.42 (s, 1H), 8.85 (d, J=2.5 Hz, 1H), 8.82 (s, 1H), 8.30 (dd, J=8.5, 2.5 Hz, 1H), 8.09 (d, J=8.5 Hz, 1H), 8.04 (s, 1H), 7.58 (s, 1H), 2.48 (d, J=1.8 Hz, 3H) ppm. $^{19}F$ NMR (471 MHz, DMSO-$d_6$) δ −62.94, −125.34 ppm.

Step 2: N-(6-Carbamoyl-3-Pyridyl)-5-(3,4-Difluoro-2-Methoxy-Phenoxy)-3-Methyl-2-(Trifluoromethyl) Pyridine-4-Carboxamide (358)

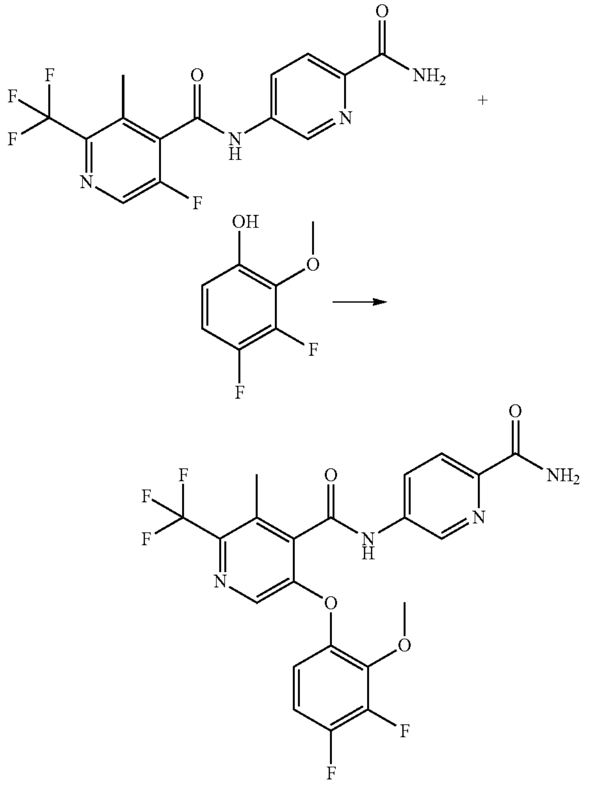

N-(6-carbamoyl-3-pyridyl)-5-fluoro-3-methyl-2-(trifluoromethyl)pyridine-4-carboxamide (240 mg, 0.435 mmol), 3,4-difluoro-2-methoxy-phenol (70 mg, 0.44 mmol) and $K_2CO_3$ (120 mg, 0.868 mmol) were combined in acetonitrile (2 mL). The reaction vial was sealed and heated at 50° C. for 16 hours. The mixture was cooled to room temperature, filtered and purified directly by reverse phase HPLC (38-53% acetonitrile/0.1% ammonium hydroxide) to provide N-(6-carbamoyl-3-pyridyl)-5-(3,4-difluoro-2-methoxy-phenoxy)-3-methyl-2-(trifluoromethyl)pyridine-4-carboxamide (22.0 mg, 10%) as a white solid. ESI-MS m z calc. 482.10, found 483.0 $(M+1)^+$; 481.0 $(M-1)^-$; LC/MS retention time (Method E): 2.86 minutes. $^1H$ NMR (500 MHz, DMSO-$d_6$) δ 11.27 (s, 1H), 8.71 (s, 1H), 8.29-8.19 (m, 1H), 8.13 (s, 1H), 7.98 (d, J=8.5 Hz, 1H), 7.94 (s, 1H), 7.45 (s, 1H), 7.21 (q, J=9.4 Hz, 1H), 7.13-7.03 (m, 1H), 3.86 (d, J=1.0 Hz, 3H), 2.46 (d, J=1.9 Hz, 3H) ppm. $^{19}F$ NMR (471 MHz, DMSO-d6) δ −62.60, −139.00, −152.37 ppm.

Example 151

N-(6-Carbamoyl-3-Pyridyl)-5-(2-Chloro-4-Fluoro-Phenoxy)-3-Methyl-2-(Trifluoromethyl)Pyridine-4-Carboxamide (359)

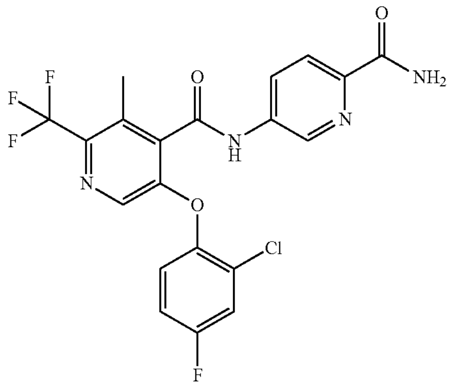 [SMILES: Cc1c(C(F)(F)F)ncc(Oc2ccc(F)cc2Cl)c1C(=O)Nc1ccc(C(N)=O)nc1]

This compound was made in an analogous fashion to the synthesis of compound 358 in Example 150, except employing 2-chloro-4-fluoro-phenol in the final ether formation step. The yield of N-(6-carbamoyl-3-pyridyl)-5-(2-chloro-4-fluoro-phenoxy)-3-methyl-2-(trifluoromethyl)pyridine-4-carboxamide was 17.1 mg (21%). ESI-MS m z calc. 468.06, found 469.1 $(M+1)^+$; 467.1 $(M-1)^-$; LC/MS retention time (Method E): 2.81 minutes. $^1H$ NMR (400 MHz, DMSO-$d_6$) δ 11.33 (s, 1H), 8.82 (s, 1H), 8.27 (dd, J=8.6, 2.5 Hz, 1H), 8.16 (s, 1H), 8.06 (d, J=8.5 Hz, 1H), 8.01 (s, 1H), 7.65 (dd, J=8.4, 3.0 Hz, 1H), 7.56 (s, 1H), 7.44 (dd, J=9.1, 5.1 Hz, 1H), 7.33 (ddd, J=9.1, 8.0, 3.0 Hz, 1H), 2.48 (s, 3H) ppm.

Example 152

4-[[2,4-Difluoro-6-[2-Methoxy-4-(Trifluoromethoxy)Phenoxy]Benzoyl]Amino]Pyridine-2-Carboxamide (360)

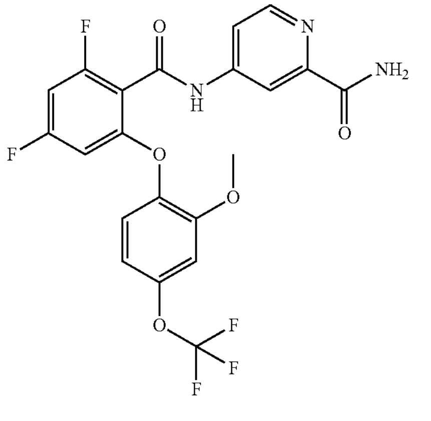 [SMILES: COc1cc(OC(F)(F)F)ccc1Oc1cc(F)cc(F)c1C(=O)Nc1ccnc(C(N)=O)c1]

Step 1: 2,4-Difluoro-6-[2-Methoxy-4-(Trifluoromethoxy)Phenoxy]Benzoic Acid

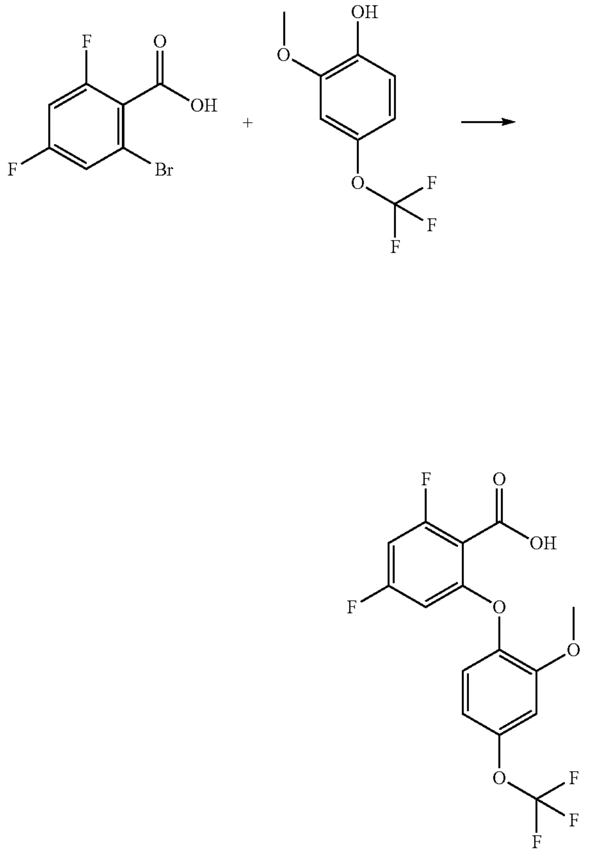

A mixture of 2-bromo-4,6-difluoro-benzoic acid (750 mg, 3.17 mmol), 2-methoxy-4-(trifluoromethoxy)phenol (720 mg, 3.46 mmol) and $Cs_2CO_3$ (1.1 g, 3.4 mmol) in toluene (15 mL) was treated with copper (I) iodide (120 mg, 0.630 mmol) and heated to 100° C. for 3 hours in a sealed vial. The mixture was allowed to cool overnight then diluted with ethyl acetate (5 mL) and 1 M aqueous HCl (~5 mL). The layers were separated and the aqueous layer extracted with additional ethyl acetate (2×5 mL). The combined organic extracts were dried over $Na_2SO_4$, filtered and concentrated in vacuo. Purification silica gel chromatography (0-100% ethyl acetate/heptane) provided 2,4-difluoro-6-[2-methoxy-4-(trifluoromethoxy)phenoxy]benzoic acid (495 mg, 21%). ESI-MS m z calc. 364.04, found 365.0 $(M+1)^+$; 363.0 $(M-1)^-$; LC/MS retention time (Method F): 0.6 minutes. $^1H$ NMR (500 MHz, DMSO-$d_6$) δ 13.30 (s, 1H), 7.24-7.16 (m, 2H), 7.09 (td, J=9.5, 2.4 Hz, 1H), 6.99 (ddd, J=8.7, 2.7, 1.3 Hz, 1H), 6.40 (dt, J=10.2, 1.9 Hz, 1H), 3.80 (s, 3H) ppm. The isolated product contained some residual starting materials but was taken forward with no additional purification.

Step 2: Methyl 4-[[2,4-Difluoro-6-[2-Methoxy-4-(Trifluoromethoxy)Phenoxy]Benzoyl]Amino]Pyridine-2-Carboxylate

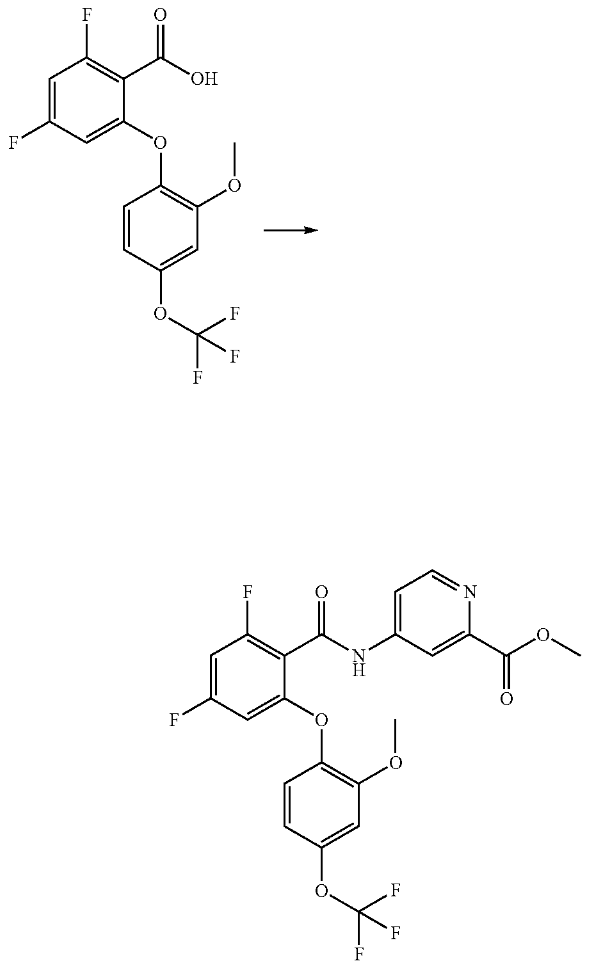

A solution of 2,4-difluoro-6-[2-methoxy-4-(trifluoromethoxy)phenoxy]benzoic acid (495 mg, 1.36 mmol) in dichloromethane (5 mL) and DMF (5 μL) at 0° C. was treated with oxalyl chloride (180 μL, 2.06 mmol) dropwise. The mixture was allowed to warm to room temperature over 2 hours, concentrated in vacuo, then diluted and evaporated twice with dichloromethane. The residue was dissolved in dichloromethane (5 mL) and cooled to 0° C. Methyl 4-aminopyridine-2-carboxylate (200 mg, 1.31 mmol) was added in one portion and then TEA (400 μL, 2.87 mmol) added dropwise. The mixture was allowed to warm to room temperature and stirred overnight. The mixture was diluted with water (3 mL) and the layers separated. The aqueous layer was extracted with additional dichloromethane (2×3 mL) and the combined organics dried over $Na_2SO_4$, filtered and concentrated in vacuo. Purification by silica gel chromatography (10-70% ethyl acetate/heptane) provided methyl 4-[[2,4-difluoro-6-[2-methoxy-4-(trifluoromethoxy) phenoxy]benzoyl]amino]pyridine-2-carboxylate (165 mg, 24%) as an off-white solid. ESI-MS m z calc. 498.09, found 499.0 $(M+1)^+$; 497.0 $(M-1)^-$; LC/MS retention time (Method F): 0.92 minutes. $^1H$ NMR (500 MHz, DMSO-$d_6$) δ 11.31 (s, 1H), 8.61 (d, J=5.5 Hz, 1H), 8.36 (d, J=2.1 Hz, 1H), 7.82 (dd, J=5.5, 2.2 Hz, 1H), 7.29 (d, J=8.8 Hz, 1H), 7.23-7.15 (m, 2H), 6.99 (ddd, J=8.8, 2.7, 1.3 Hz, 1H), 6.54-6.46 (m, 1H), 3.88 (s, 3H), 3.77 (s, 3H) ppm. $^{19}F$ NMR (471 MHz, DMSO-$d_6$) δ −56.89, −104.52-−105.44 (m), −112.16 (d, J=7.9 Hz) ppm.

Step 3: 4-[[2,4-Difluoro-6-[2-Methoxy-4-(Trifluoromethoxy)Phenoxy]Benzoyl]Amino]Pyridine-2-Carboxamide (360)

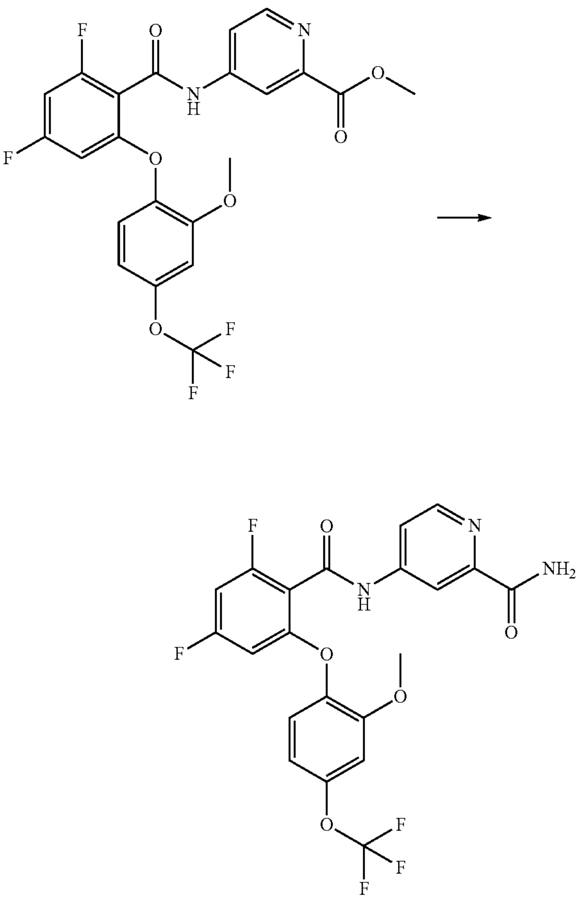

A solution of methyl 5-(2,4-difluoro-6-(2-methoxy-4-(trifluoromethoxy)phenoxy)benzamido) picolinate (165 mg, 0.3311 mmol) in methanol (0.5 mL) was treated with a solution of ammonia in methanol (2 mL of 7 M, 14 mmol) and stirred overnight at room temperature. The mixture was concentrated in vacuo and purified by reverse phase HPLC (47-95% acetonitrile/0.1% ammonium hydroxide) to provide 4-[[2,4-difluoro-6-[2-methoxy-4-(trifluoromethoxy) phenoxy]benzoyl]amino]pyridine-2-carboxamide (146.0 mg, 87%) as a white solid. ESI-MS m z calc. 483.09, found 484.0 $(M+1)^+$; 482.0 (M−1)+; LC/MS retention time (Method E): 3.04 minutes. $^1H$ NMR (500 MHz, DMSO-$d_6$) δ 11.25 (s, 1H), 8.53 (d, J=5.5 Hz, 1H), 8.30 (d, J=2.1 Hz, 1H), 8.08 (d, J=2.8 Hz, 1H), 7.83 (dd, J=5.5, 2.2 Hz, 1H), 7.63 (d, J=2.9 Hz, 1H), 7.30 (d, J=8.8 Hz, 1H), 7.22-7.15 (m, 2H), 7.00 (ddd, J=8.8, 2.7, 1.2 Hz, 1H), 6.48 (dt, J=10.2, 1.8 Hz, 1H), 3.78 (s, 3H) ppm. $^{19}F$ NMR (471 MHz, DMSO-$d_6$) δ −56.89, −112.20, −112.22 ppm.

Example 153

4-[[2-(3,4-Difluoro-2-Methyl-Phenoxy)-5-(Trifluoromethyl)Benzoyl]Amino]Pyridine-2-Carboxamide (361)

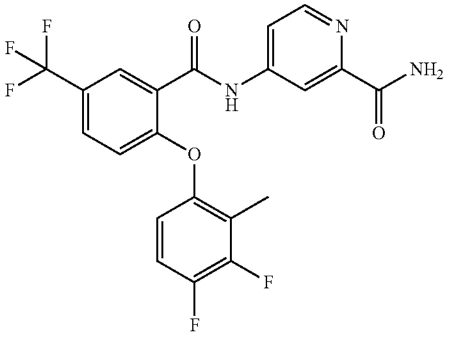 [SMILES: Cc1c(Oc2ccc(C(F)(F)F)cc2C(=O)Nc2ccnc(C(N)=O)c2)ccc(F)c1F]

To a solution of 2-(3,4-difluoro-2-methyl-phenoxy)-5-(trifluoromethyl)benzoic acid (150 mg, 0.452 mmol) in dichloromethane (5 mL) at 0° C. was added a solution of oxalyl chloride (4.0 mL of 2.0 M in dichloromethane, 8.0 mmol) followed by DMF (50 μL). The mixture was allowed to come to room temperature over 1 hour, then concentrated in vacuo. The residue was dissolved in dichloromethane (5 mL) and treated with DIEA (500 μL, 2.87 mmol) then methyl 4-aminopyridine-2-carboxylate (150 mg, 0.988 mmol). The mixture was stirred at room temperature for 20 hours, then purified directly by silica gel chromatography (0-100% ethyl acetate/hexanes) to provide methyl 4-[[2-(3,4-difluoro-2-methyl-phenoxy)-5-(trifluoromethyl)benzoyl]amino]pyridine-2-carboxylate (100.2 mg, 48%). ESI-MS m z calc. 466.10, found 467.142 $(M+1)^+$; LC/MS retention time: 1.41 minutes (Method B).

The solid was dissolved in a solution of ammonia in methanol (3 mL, 7 M, 21 mmol) and stirred for approximately 72 hours. The mixture was concentrated in vacuo to provide 4-[[2-(3,4-difluoro-2-methyl-phenoxy)-5-(trifluoromethyl)benzoyl]amino]pyridine-2-carboxamide (60.5 mg, 29%). ESI-MS m z calc.

451.10, found 452.1 $(M+1)^+$; LC/MS retention time: 2.34 minutes (Method C). $^1$H NMR (400 MHz, DMSO-$d_6$) δ 11.10 (s, 1H), 8.54 (d, J=5.5 Hz, 1H), 8.33 (s, 1H), 8.09 (dd, J=7.0, 2.6 Hz, 2H), 7.86 (dd, J=5.5, 2.1 Hz, 1H), 7.83 (dd, J=8.8, 2.3 Hz, 1H), 7.64 (s, 1H), 7.37 (q, J=9.4 Hz, 1H), 7.09-7.00 (m, 1H), 6.98 (d, J=8.7 Hz, 1H), 2.12 (d, J=2.3 Hz, 3H) ppm.

Example 154

4-[[2-Fluoro-4-Methoxy-6-[2-Methoxy-4-(Trifluoromethoxy)Phenoxy]-3-Methyl-Benzoyl]Amino]Pyridine-2-Carboxamide (362)

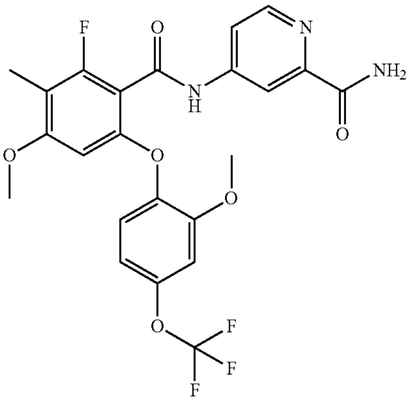 [SMILES: COc1cc(OC(F)(F)F)ccc1Oc1cc(OC)c(C)c(F)c1C(=O)Nc1ccnc(C(N)=O)c1]

Step 1: Methyl 6-Bromo-2,4-Difluoro-3-Methyl-Benzoate

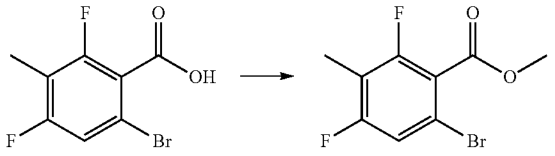

To a mixture of 6-bromo-2,4-difluoro-3-methyl-benzoic acid (1.0 g, 3.0 mmol) in DMF (3.7 mL) was added $Cs_2CO_3$ (1.85 g, 5.68 mmol). The mixture was stirred for 5 minutes at room temperature, then treated with methyl iodide (809 mg, 0.355 mL, 5.70 mmol) and stirred for 1 hour. The mixture was diluted with ethyl acetate (50 mL) and washed with aqueous $NH_4Cl$ solution (20 mL), water (75 mL) and brine. The organic layer was dried over $Na_2SO_4$, filtered and concentrated to provide methyl 6-bromo-2,4-difluoro-3-methyl-benzoate (900 mg, 85%). ESI-MS m z calc. 263.96, found 264.9 $(M+1)^+$; LC/MS retention time (Method N): 5.69 minutes. $^1$H NMR (250 MHz, $CDCl_3$) δ 7.17-7.08 (m, 1H), 3.95 (s, 3H), 2.16 (td, J=2.0, 0.4 Hz, 3H) ppm.

Step 2: Methyl 6-Bromo-2-Fluoro-4-Methoxy-3-Methyl-Benzoate

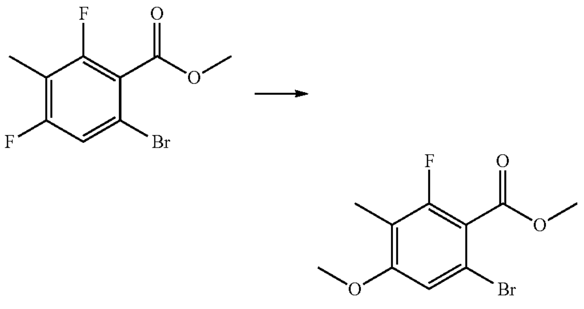

To a solution of methyl 6-bromo-2,4-difluoro-3-methyl-benzoate (10.39 g, 39.20 mmol) in anhydrous methanol (37 mL) was added 18-Crown-6 (20.8 g, 78.7 mmol) followed by solid NaOMe (3.18 g, 58.7 mmol) under nitrogen. The mixture was heated at 62° C. for 21 hours, then cooled in an ice bath and diluted with saturated aqueous $NH_4Cl$ solution (50 mL). The mixture was concentrated in vacuo to remove the methanol, then diluted with ethyl acetate (300 mL) and washed with water (700 mL). The aqueous layer was extracted with additional ethyl acetate (200 mL), and the combined extracts dried over $Na_2SO_4$, filtered and concentrated in vacuo to provide methyl 6-bromo-2-fluoro-4-methoxy-3-methyl-benzoate (10.44 g, 82%) as a yellow oil. $^1H$ NMR (500 MHz, $CDCl_3$) δ 6.84 (d, J=1.6 Hz, 1H), 3.93 (s, 3H), 3.85 (s, 3H), 2.07 (d, J=2.3 Hz, 3H) ppm.

Step 3: 6-Bromo-2-Fluoro-4-Methoxy-3-Methyl-Benzoic Acid

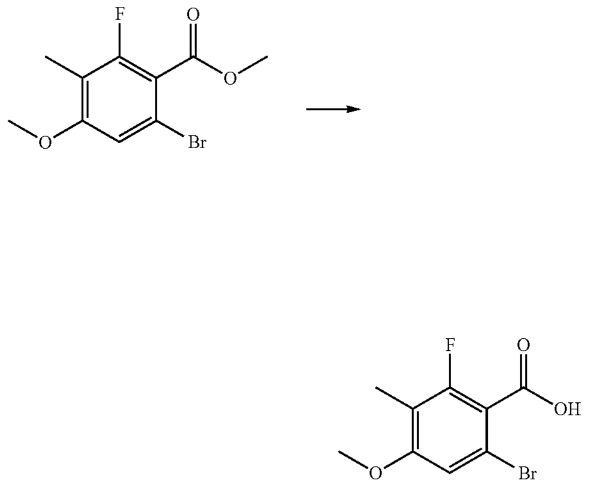

Methyl 6-bromo-2-fluoro-4-methoxy-3-methyl-benzoate (5.0 g, 12.6 mmol) in a 1:1:1 mixture of methanol/water/THF (45 mL) was treated with LiOH hydrate (5.35 g, 128 mmol) and stirred at room temperature for 24 hours. Additional LiOH hydrate (3.23 g, 77.0 mmol) and 1:1:1 methanol/water/THF (45 mL) were added and the mixture stirred for 12 hours. LiOH hydrate (1.0 g, 24 mmol) and 1:1:1 methanol/water/THF (45 mL) were again added and the mixture stirred at room temperature 12 hours. The mixture was diluted with saturated aqueous $NH_4Cl$ (50 mL) and concentrated to remove the volatiles. The remaining aqueous mixture was then diluted with 1 M aqueous NaOH (200 mL) and washed with ethyl acetate, then acidified with 3 M aqueous HCl (until pH=2) and extracted with ethyl acetate (3x300 mL). The combined organic layers were washed with brine, dried over $Na_2SO_4$, filtered and concentrated in vacuo. The resulting solid was dried 42° C. at 16 Torr for 6 hours to provide 6-bromo-2-fluoro-4-methoxy-3-methyl-benzoic acid (3.87 g, 95%) as an off-white solid. ESI-MS m z calc. 261.96, found 262.9 $(M+1)^+$; LC/MS retention time (Method N): 4.43 minutes. $^1H$ NMR (500 MHz, DMSO-$d_6$) δ 13.64 (s, 1H), 7.11 (d, J=1.5 Hz, 1H), 3.86 (s, 3H), 2.02 (d, J=2.1 Hz, 3H) ppm.

Step 4: 2-Fluoro-4-Methoxy-6-[2-Methoxy-4-(Trifluoromethoxy)Phenoxy]-3-Methyl-Benzoic Acid

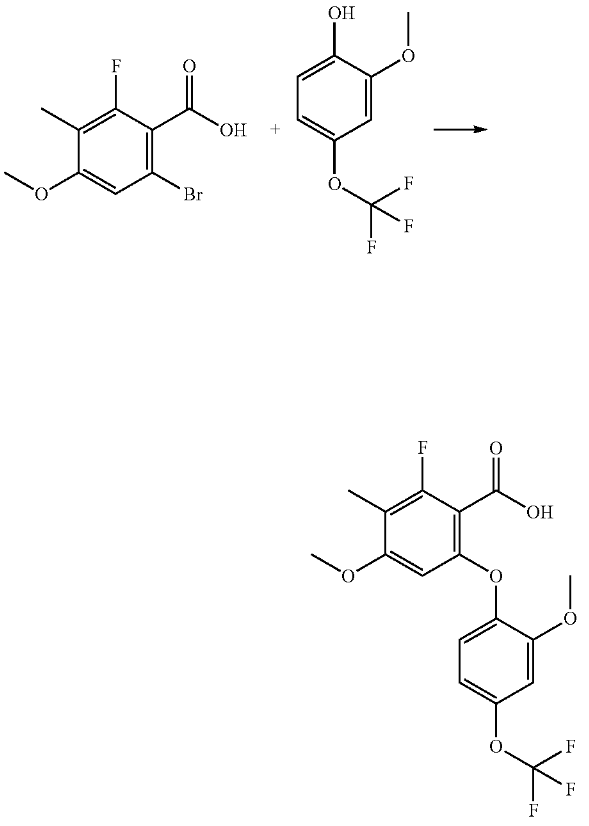

A mixture of 6-bromo-2-fluoro-4-methoxy-3-methyl-benzoic acid (1.31 g, 4.98 mmol), Cs2CO3 (4.87 g, 15.0 mmol), 2-methoxy-4-(trifluoromethoxy)phenol (1.56 g, 7.50 mmol) and pyridine (822 mg, 0.840 mL, 10.4 mmol) in toluene (9 mL) was sparged with nitrogen gas for 10 minutes, and then copper (I) iodide (142.3 mg, 0.7472 mmol) added and the mixture degassed for an additional 3 minutes. The reaction vessel was sealed and heated in a microwave reactor at 130° C. for 1.5 hours under nitrogen. This reaction was performed on the same scale two additional times and the crude reaction mixtures combined. The combined mixture was acidified with 3 M aqueous HCl (until pH=1) and extracted with ethyl acetate (3x200 mL). The combined extracts were washed with brine, dried over $Na_2SO_4$, filtered and concentrated in vacuo. Purification by silica gel chromatography (10-50% ethyl acetate/hexanes, column pre-equilibrated with 0.1% acetic acid in hexanes), followed by additional purification by reverse phase HPLC (45-90% acetonitrile+0.1% TFA/water+0.1% TFA) provided 2-fluoro-4-methoxy-6-[2-methoxy-4-(trifluoromethoxy)phenoxy]-3-methyl-benzoic acid (1.06 g, 18%) as a white solid. ESI-MS m z calc. 390.07, found 391.4 $(M+1)^+$; LC/MS retention time (Method Q): 2.59 minutes. $^1H$ NMR (500 MHz, DMSO-$d_6$) δ 13.12 (s, 1H), 7.16 (d, J=2.5 Hz, 1H), 7.01-6.82 (m, 2H), 6.29 (s, 1H), 3.82 (s, 3H), 3.69 (s, 3H), 2.03 (d, J=2.0 Hz, 3H) ppm.

Step 5: 4-[[2-Fluoro-4-Methoxy-6-[2-Methoxy-4-(Trifluoromethoxy)Phenoxy]-3-Methyl-Benzoyl]Amino]Pyridine-2-Carboxamide (362)

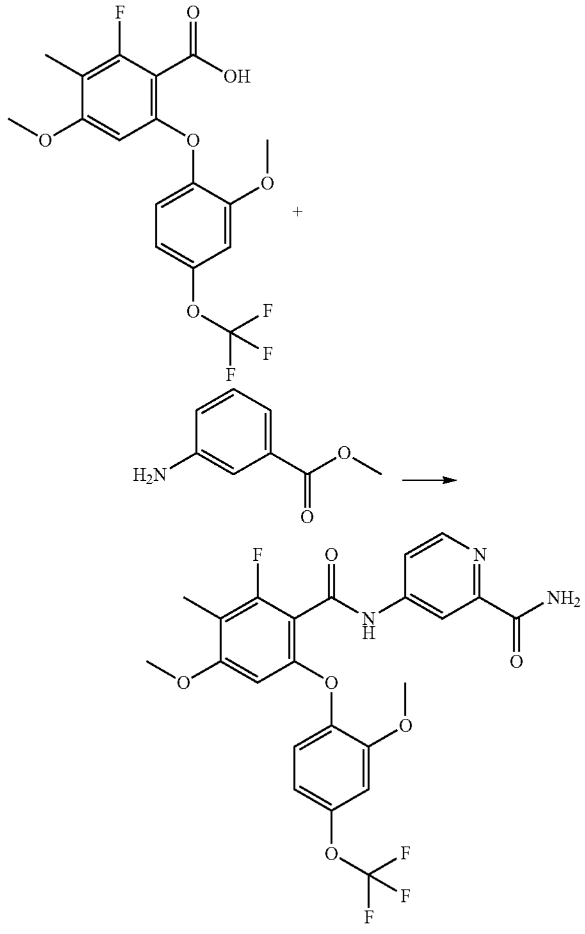

A mixture of 2-fluoro-4-methoxy-6-[2-methoxy-4-(trifluoromethoxy)phenoxy]-3-methyl-benzoic acid (300 mg, 0.769 mmol) and DMF (5 μL) in 2-MeTHF (5 mL) at 0° C. was treated with oxalyl chloride (150 μL, 1.72 mmol) slowly over 5 minutes. The mixture was allowed to warm to room temperature over 1 hour. The mixture was concentrated in vacuo, then diluted and evaporated twice with dichloromethane. The residue was dissolved in 2-MeTHF (5 mL) and methyl 4-aminopyridine-2-carboxylate (120 mg, 0.789 mmol) added. NMP (2 mL) was added to ensure complete dissolution of the solid. A solution of $K_2CO_3$ (350 mg, 2.53 mmol) in water (5 mL) was added and the mixture stirred vigorously for 4 hours. The layers were separated and the aqueous layer extracted with ethyl acetate (2×). The combined organic extracts were dried over $Na_2SO_4$, filtered and concentrated in vacuo. The residue was dissolved in a solution of ammonia in methanol (2 mL of 7 M, 14 mmol) and stirred for 66 hours. The mixture was concentrated in vacuo and purified by reverse phase HPLC (38-53% acetonitrile/0.1% ammonium hydroxide) to provide 4-[[2-fluoro-4-methoxy-6-[2-methoxy-4-(trifluoromethoxy)phenoxy]-3-methyl-benzoyl]amino]pyridine-2-carboxamide (87.9 mg, 22%) as a white solid. ESI-MS m z calc. 509.12, found 510.0 $(M+1)^+$; 508.0 $(M-1)^-$; LC/MS retention time (Method E): 3.14 minutes. $^1H$ NMR (500 MHz, DMSO-$d_6$) δ 11.02 (s, 1H), 8.48 (d, J=5.6 Hz, 1H), 8.25 (d, J=2.0 Hz, 1H), 8.05 (d, J=2.8 Hz, 1H), 7.77 (d, J=5.2 Hz, 1H), 7.60 (d, J=2.9 Hz, 1H), 7.10 (dd, J=5.8, 3.0 Hz, 2H), 6.91 (ddd, J=8.9, 2.8, 1.2 Hz, 1H), 6.34 (s, 1H), 3.74 (s, 3H), 3.72 (s, 3H), 2.06 (d, J=1.8 Hz, 3H) ppm. $^{19}F$ NMR (471 MHz, DMSO-$d_6$) δ −56.94, −118.56 ppm.

Example 155

4-[[2-Chloro-4-Methoxy-6-[2-Methoxy-4-(Trifluoromethoxy)Phenoxy]-3-Methyl-Benzoyl]Amino]Pyridine-2-Carboxamide (363)

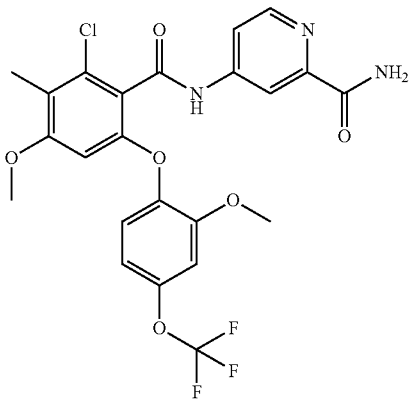 [SMILES: COc1cc(OC(F)(F)F)ccc1Oc1cc(OC)c(C)c(Cl)c1C(=O)Nc1ccnc(C(N)=O)c1]

Step 1: 1-(2-Chloro-4-Methoxy-3-Methyl-Phenyl)Ethanone

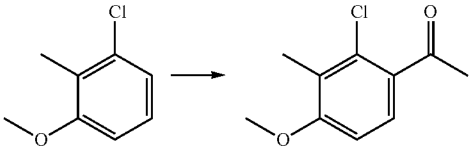

A slurry of 1-chloro-3-methoxy-2-methyl-benzene (15.0 g, 12.9 mL, 95.8 mmol) and aluminum trichloride (26.2 g, 197 mmol) in dichloromethane was cooled to 10° C. and treated dropwise with acetylchloride (15.4 g, 14.0 mL, 196 mmol) over 22 min. The cold bath was removed after 15 minutes and the slurry was stirred for 1 hour at room temperature. The reaction mixture was poured into 1 M aqueous HCl (400 mL) and diluted with dichloromethane (300 mL). The organic layer was separated, washed with water (2×100 mL) and filtered through Celite. The filtrate was dried over $Na_2SO_4$, filtered and concentrated to provide 1-(2-chloro-4-methoxy-3-methyl-phenyl)ethanone (18.24 g, 94%) which was used without additional purification. ESI-MS m z calc. 198.05, found 199.0 $(M+1)^+$; LC/MS retention time (Method N): 4.94 minutes. $^1H$ NMR (250 MHz, $CDCl_3$) δ 7.45 (dd, J=8.6, 0.6 Hz, 1H), 7.08-6.30 (m, 1H), 3.87 (s, 3H), 2.61 (s, 3H), 2.29 (s, 3H) ppm.

Step 2: 2-Chloro-4-Methoxy-3-Methyl-Benzoic Acid

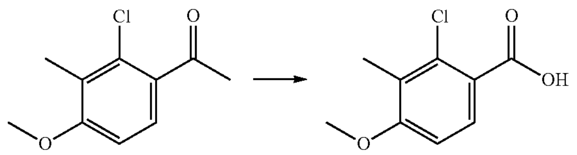

A solution of 1-(2-chloro-4-methoxy-3-methyl-phenyl) ethanone (18.1 g, 91.1 mmol) in dioxane (90.5 mL) was treated with sodium hypochlorite (475 mL of 5% w/v, 319 mmol) at room temperature dropwise over 1 hour. The mixture was vigorously stirred at room temperature for 3 hours after the addition was complete. The mixture was treated with conc. HCl until pH~1-2 and the resulting precipitate collected by filtration. The solid was rinsed thoroughly with deionized water and dried under vacuum to provide 2-chloro-4-methoxy-3-methyl-benzoic acid (17.2 g, 85%). A portion of the crude product (10 g) was partially dissolved in ethyl acetate (500 mL) and extracted with 1 M aqueous NaOH (4×100 mL) at 0° C. The basic aqueous phase was acidified at 0° C. with 3 M aqueous HCl (~160 mL) until pH=1-2. The resulting precipitate was collected by filtration and rinsed with ethyl acetate (70 mL). The solid was dissolved in ethyl acetate (1.4 L) and washed with an aqueous solution of $Na_2S_2O_5$ (10% wt/vol, 3×100 mL) and brine (100 mL). The organic phase was dried over $Na_2SO_4$, filtered and concentrated to provide 2-chloro-4-methoxy-3-methyl-benzoic acid (7.45 g, 75% recovery from 10 g). ESI-MS m z calc. 200.02, found 200.8 $(M+1)^+$; LC/MS retention time (Method N): 4.01 minutes. $^1H$ NMR (250 MHz, DMSO-$d_6$) δ 12.95 (s, 1H), 7.70 (d, J=8.7 Hz, 1H), 7.03 (d, J=8.8 Hz, 1H), 3.87 (s, 3H), 2.24 (s, 3H) ppm.

Step 3: 2-Chloro-6-Iodo-4-Methoxy-3-Methyl-Benzoic Acid

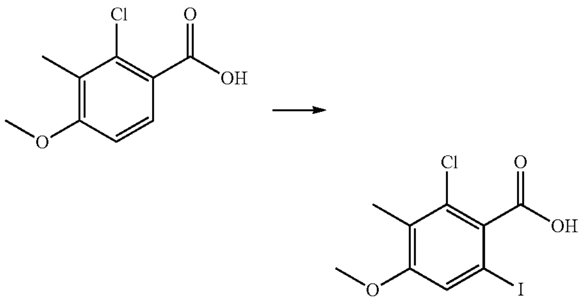

To a vessel charged with 2-chloro-4-methoxy-3-methyl-benzoic acid (6.55 g, 32.7 mmol), N-iodosuccinimide (8.08 g, 35.9 mmol) and $Pd(OAc)_2$ (1.83 g, 8.15 mmol) was added DMF (48 mL) at room temperature and open to air. The vessel was sealed and the mixture heated at 55° C. for 28 hours. The mixture was cooled in an ice bath, acidified with 1 M aqueous HCl (250 mL) and extracted with ethyl acetate (3×150 mL). The combined organic layers were extracted with 1 M aqueous NaOH (3×350 mL) and washed with hexanes (3×150 mL). The aqueous solution was acidified with 3 M aqueous HCl (500 mL) at 0° C. The resulting solid was collected by filtration, then dissolved in ethyl acetate (325 mL) and washed with aqueous $Na_2S_2O_5$ (10% solution, 2×65 mL). The aqueous layer was extracted with additional ethyl acetate (3×50 mL), and the combined organic layers were washed with brine, dried over $Na_2SO_4$, filtered and concentrated in vacuo to provide 2-chloro-6-iodo-4-methoxy-3-methyl-benzoic acid (7.90 g, 66%). ESI-MS m z calc. 325.92, found 327.3 $(M+1)^+$; LC/MS retention time (Method Q): 2.1 minutes. $^1H$ NMR (500 MHz, DMSO-$d_6$) δ 13.52 (s, 1H), 7.35 (s, 1H), 3.83 (s, 3H), 2.15 (s, 3H) ppm.

Step 4: 2-Chloro-4-Methoxy-6-[2-Methoxy-4-(Trifluoromethoxy)Phenoxy]-3-Methyl-Benzoic Acid

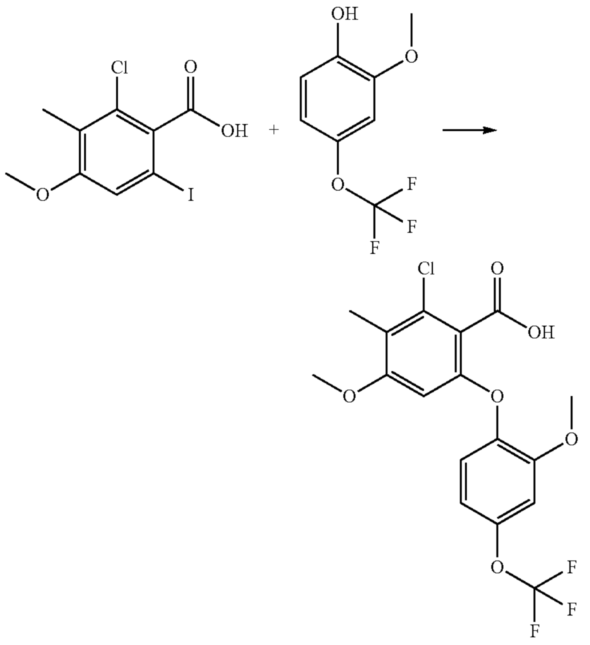

A mixture of $Cs_2CO_3$ (7.74 g, 23.8 mmol), 2-chloro-6-iodo-4-methoxy-3-methyl-benzoic acid (2.56 g, 7.84 mmol), 2-methoxy-4-(trifluoromethoxy)phenol (2.45 g, 11.8 mmol) in DMF (8.5 mL) and pyridine (1.3 g, 1.3 mL, 16.1 mmol) was stirred under an argon atmosphere for 3 minutes at room temperature, then treated with copper (I) iodide (134 mg, 0.704 mmol). The reaction vessel was sealed and the mixture stirred at room temperature for 15 minutes, then heated at 80° C. for 12 hours. The mixture was cooled in an ice bath, acidified with 1 M aqueous HCl until pH=2, and extracted with ethyl acetate (3×150 mL). The combined extracts were washed with 0.1 M aqueous HCl (3×75 mL) and brine, dried over $Na_2SO_4$, filtered and concentrated in vacuo. Purification by reverse phase HPLC (40-100% acetonitrile+0.1% TFA/water+0.1% TFA) provided 2-chloro-4-methoxy-6-[2-methoxy-4-(trifluoromethoxy)phenoxy]-3-methyl-benzoic acid (591 mg, 18%). ESI-MS m z calc. 406.04, found 407.2 $(M+1)^+$; LC/MS retention time (Method Q): 2.68 minutes. $^1H$ NMR (500 MHz, DMSO-$d_6$) δ 13.30 (s, 1H), 7.16 (d, J=2.5 Hz, 1H), 6.93 (d, J=8.8 Hz, 1H), 6.90 (ddd, J=8.8, 2.6, 1.2 Hz, 1H), 6.42 (s, 1H), 3.82 (s, 3H), 3.67 (s, 3H), 2.16 (s, 3H) ppm.

Step 5: Methyl 4-[[2-Chloro-4-Methoxy-6-[2-Methoxy-4-(Trifluoromethoxy)Phenoxy]-3-Methyl-Benzoyl]Amino]Pyridine-2-Carboxylate

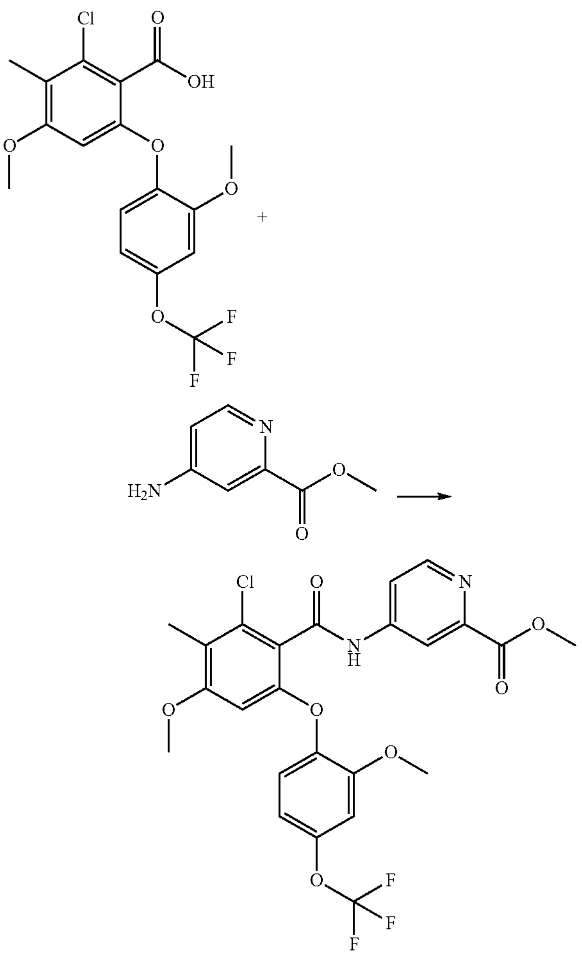

To a solution of 2-chloro-4-methoxy-6-[2-methoxy-4-(trifluoromethoxy)phenoxy]-3-methyl-benzoic acid (150 mg, 0.367 mmol) and DMF (5 μL, 0.07 mmol) in 2-MeTHF (4 mL) at 0° C. was added oxalyl chloride (70 μL, 0.8024 mmol). The mixture was warmed to room temperature, stirred for 30 minutes and then concentrated in vacuo. The residue was dissolved in 2-MeTHF (2 mL) and added to a solution of methyl 4-aminopyridine-2-carboxylate (65 mg, 0.43 mmol) and TEA (230 μL, 1.65 mmol) in 2-MeTHF (2 mL) at 0° C. The mixture was warmed to room temperature and stirred for 3 hours, then heated at 50° C. for 20 hours. The mixture was diluted with water (30 mL) and extracted with ethyl acetate (30 mL). The organic layer was washed with water (4×30 mL), dried over $MgSO_4$, filtered and concentrated in vacuo. Purification by silica gel chromatography (0-60% ethyl acetate/heptane provided methyl 4-[[2-chloro-4-methoxy-6-[2-methoxy-4-(trifluoromethoxy)phenoxy]-3-methyl-benzoyl]amino]pyridine-2-carboxylate (52 mg, 26%). ESI-MS m z calc. 540.09, found 540.9 $(M+1)^+$; 538.9 $(M-1)^-$; LC/MS retention time (Method F): 1.02 minutes. $^1H$ NMR (500 MHz, DMSO-$d_6$) δ 11.11 (s, 1H), 8.57 (d, J=5.4 Hz, 1H), 8.35 (d, J=2.1 Hz, 1H), 7.76 (dd, J=5.4, 2.1 Hz, 1H), 7.13-7.05 (m, 2H), 6.92 (d, J=8.3 Hz, 1H), 6.47 (s, 1H), 3.87 (s, 3H), 3.74 (s, 3H), 3.72 (s, 3H), 2.21 (s, 3H) ppm.

Step 6: 4-[[2-Chloro-4-Methoxy-6-[2-Methoxy-4-(Trifluoromethoxy)Phenoxy]-3-Methyl-Benzoyl]Amino]Pyridine-2-Carboxamide (363)

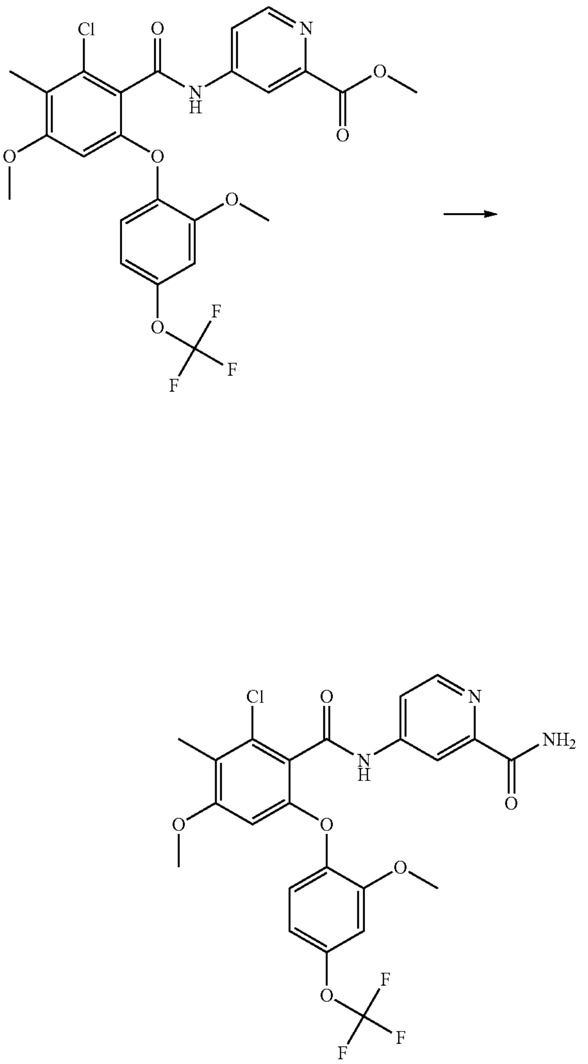

Methyl 4-[[2-chloro-4-methoxy-6-[2-methoxy-4-(trifluoromethoxy)phenoxy]-3-methyl-benzoyl]amino]pyridine-2-carboxylate (52 mg, 0.096 mmol) was dissolved in a solution of ammonia in methanol (1 mL of 7 M, 7 mmol) and stirred for 20 hours. The mixture was concentrated in vacuo and purified by silica gel chromatography (0-80% ethyl acetate/heptane) to provide 4-[[2-chloro-4-methoxy-6-[2-methoxy-4-(trifluoromethoxy)phenoxy]-3-methyl-benzoyl]amino]pyridine-2-carboxamide (19 mg, 37%). ESI-MS m z calc. 525.09, found 525.9 $(M+1)^+$; 523.9 $(M-1)^-$; LC/MS retention time (Method E): 3.49 minutes. $^1H$ NMR (500 MHz, DMSO-$d_6$) δ 11.06 (s, 1H), 8.49 (d, J=5.4 Hz, 1H), 8.28 (d, J=2.5 Hz, 1H), 8.05 (d, J=2.7 Hz, 1H), 7.78 (dd, J=5.6, 2.2 Hz, 1H), 7.61 (d, J=2.8 Hz, 1H), 7.13-7.06 (m, 2H), 6.92 (ddd, J=8.8, 2.7, 1.3 Hz, 1H), 6.46 (s, 1H), 3.75 (s, 3H), 3.71 (s, 3H), 2.21 (s, 3H) ppm.

Example 156

6-Tert-Butyl-N-(2-Carbamoyl-4-Pyridyl)-4-(2-Chloro-4-Fluoro-Phenoxy)-2-Methyl-Pyridine-3-Carboxamide (364)

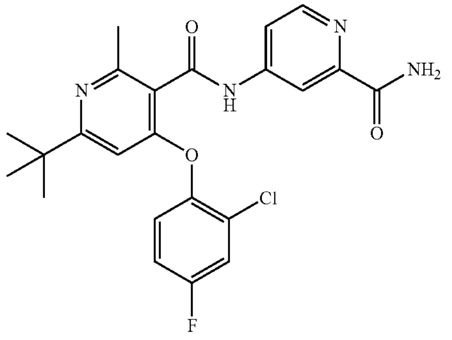 [SMILES: Cc1nc(C(C)(C)C)cc(Oc2ccc(F)cc2Cl)c1C(=O)Nc1ccnc(C(N)=O)c1]

Step 1: Methyl 4-Chloro-2-Methyl-1-Oxido-Pyridin-1-Ium-3-Carboxylate

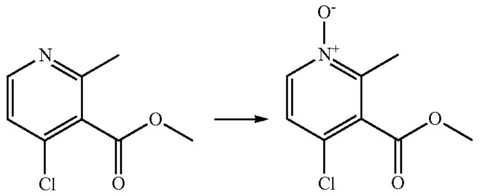

A solution of methyl 4-chloro-2-methyl-pyridine-3-carboxylate (590 mg, 3.18 mmol) in dichloromethane (10 mL) was treated with 3-chlorobenzenecarboperoxoic acid (900 mg, 3.65 mmol) and stirred for 2 hours. The mixture was filtered and concentrated in vacuo to provide methyl 4-chloro-2-methyl-1-oxido-pyridin-1-ium-3-carboxylate (620 mg, 97%). ESI-MS m z calc. 201.02, found 202.1 $(M+1)^+$; LC/MS retention time (Method F): 0.41 minutes. The material was taken to the next step without additional purification.

Step 2: Methyl 6-Tert-Butyl-4-Chloro-2-Methyl-Pyridine-3-Carboxylate

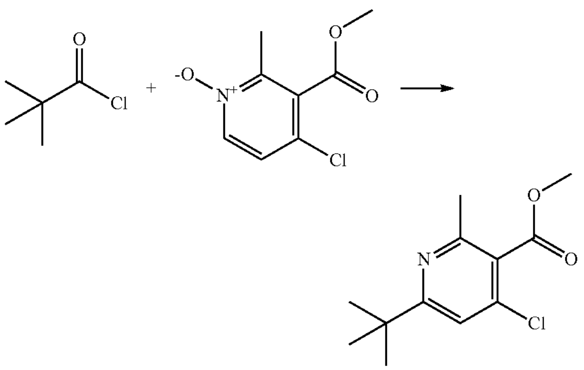

A solution of methyl 4-chloro-2-methyl-1-oxido-pyridin-1-ium-3-carboxylate (600 mg, 2.98 mmol) and $[Ir(ppy)_2(dtbbpy)]PF_6$ (32 mg, 0.035 mmol) in acetonitrile (6 mL) was treated with 2,2-dimethylpropanoyl chloride (400 μL, 3.25 mmol) and stirred for 5 minutes. The reaction vial was then sealed and the mixture stirred under 450 nm LED light for 4 hours. The mixture was concentrated in vacuo and purified by silica gel chromatography (0-50% ethyl acetate/heptane) to provide methyl 6-tert-butyl-4-chloro-2-methyl-pyridine-3-carboxylate (350 mg, 49%). ESI-MS m z calc. 241.09, found 242.2 $(M+1)^+$; LC/MS retention time (Method F): 1.04 minutes. $^1H$ NMR (400 MHz, $CDCl_3$) δ 7.19 (d, J=0.7 Hz, 1H), 3.95 (s, 3H), 2.53 (d, J=0.5 Hz, 3H), 1.32 (s, 9H) ppm.

Step 3: 6-Tert-Butyl-4-(2-Chloro-4-Fluoro-Phenoxy)-2-Methyl-Pyridine-3-Carboxylic Acid

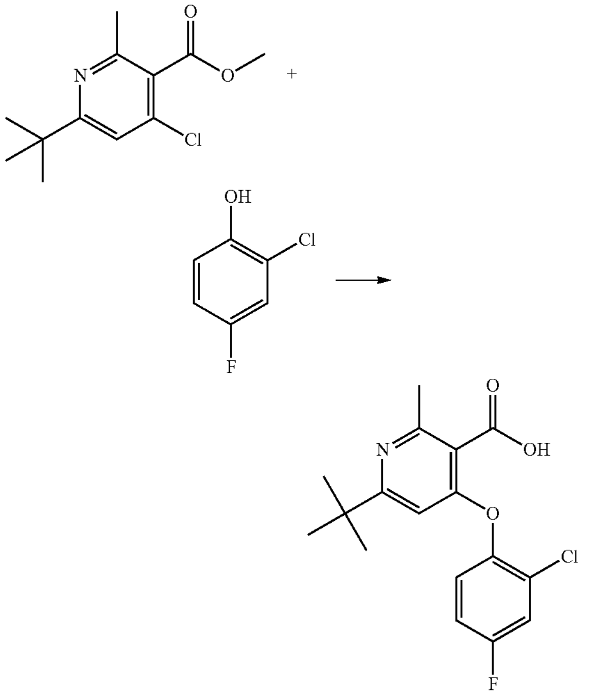

A solution of methyl 6-tert-butyl-4-chloro-2-methyl-pyridine-3-carboxylate (350 mg, 1.45 mmol) in acetonitrile (3 mL) was treated with $Cs_2CO_3$ (600 mg, 1.84 mmol) and 2-chloro-4-fluoro-phenol (170 μL, 1.56 mmol) and stirred at room temperature for 4 hours. Aqueous LiOH (3.5 mL of 2 M, 7 mmol) and ethanol (3 mL) were added and the mixture stirred at room temperature for 3 days. The mixture was diluted with ethyl acetate and washed with 2 M aqueous NaOH. The organic layer was dried over $MgSO_4$, filtered and concentrated to provide crude methyl 6-tert-butyl-4-(2-chloro-4-fluoro-phenoxy)-2-methyl-pyridine-3-carboxylate. Aqueous LiOH (3.5 mL of 2 M, 7 mmol) and ethanol (3 mL) were added and the mixture stirred to afford the hydrolyzed ester. The mixture was acidified with 2 M aqueous HCl (6 mL) and extracted into ethyl acetate. The organic layer was separated, dried over $MgSO_4$ and concentrated to provide 6-tert-butyl-4-(2-chloro-4-fluoro-phenoxy)-2-methyl-pyridine-3-carboxylic acid (350 mg, 72%). ESI-MS m z calc. 337.09, no ionization observed; LC/MS retention time (Method F): 0.59 minutes.

Step 4: Methyl 4-[[6-Tert-Butyl-4-(2-Chloro-4-Fluoro-Phenoxy)-2-Methyl-Pyridine-3-Carbonyl]Amino]Pyridine-2-Carboxylate

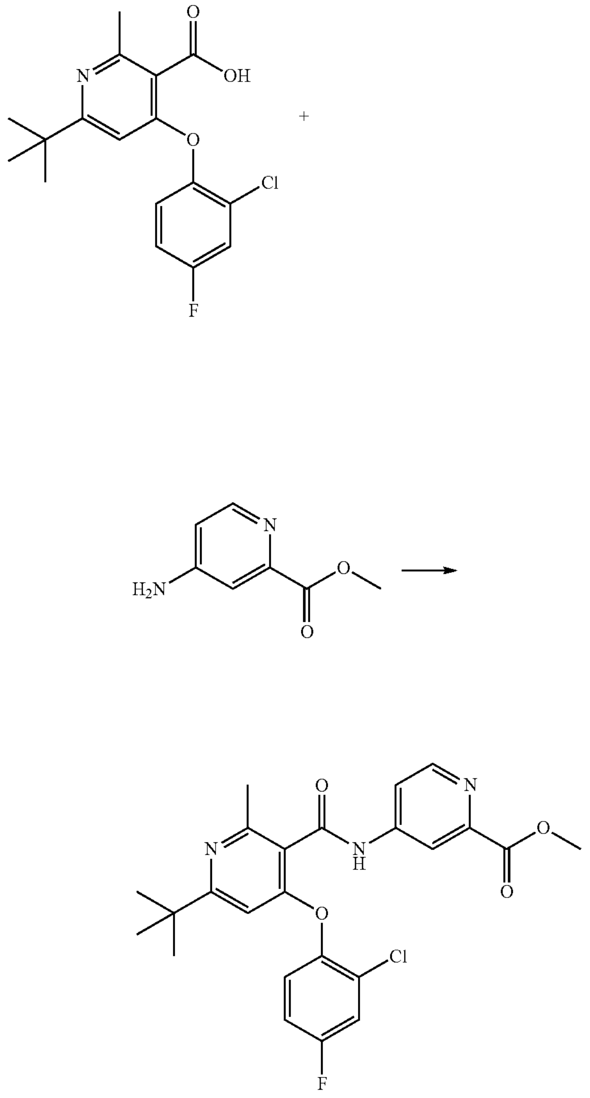

To a solution of 6-tert-butyl-4-(2-chloro-4-fluoro-phenoxy)-2-methyl-pyridine-3-carboxylic acid (50 mg, 0.15 mmol) in dichloromethane (2 mL) cooled to 0° C. was added DMF (2 μL, 0.03 mmol) followed by oxalyl chloride (50 μL, 0.57 mmol). The mixture was allowed to warm to room temperature over 1 hour, then concentrated in vacuo. The residue was dissolved in dichloromethane (2 mL), cooled in an ice bath, and TEA (50 μL, 0.36 mmol) and methyl 4-aminopyridine-2-carboxylate (30 mg, 0.20 mmol) added sequentially. The mixture was stirred for 16 hours. The mixture was filtered (0.45 M filter), diluted with 3:1 acetonitrile/water and purified directly by reverse phase HPLC (47-95% acetonitrile/0.1% ammonium hydroxide) to provide methyl 4-[[6-tert-butyl-4-(2-chloro-4-fluoro-phenoxy)-2-methyl-pyridine-3-carbonyl]amino]pyridine-2-carboxylate (20 mg, 29%). ESI-MS m z calc. 471.14, found 472.4 $(M+1)^+$; 470.3 (M−1)+; LC/MS retention time (Method F): 0.97 minutes.

Step 5: 6-Tert-Butyl-N-(2-Carbamoyl-4-Pyridyl)-4-(2-Chloro-4-Fluoro-Phenoxy)-2-Methyl-Pyridine-3-Carboxamide (364)

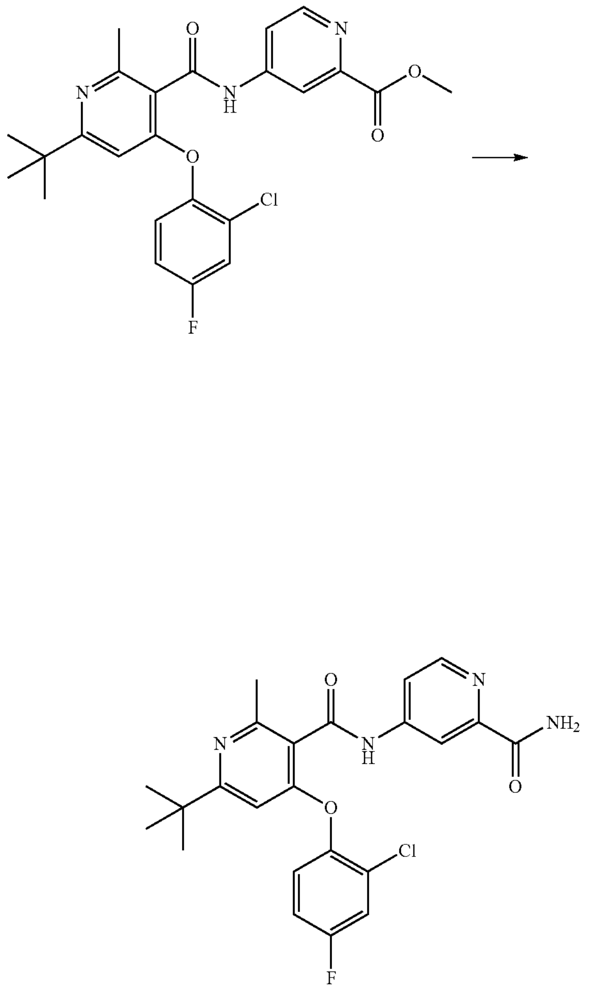

Methyl 4-[[6-tert-butyl-4-(2-chloro-4-fluoro-phenoxy)-2-methyl-pyridine-3-carbonyl]amino]pyridine-2-carboxylate (20 mg, 0.042 mmol) was dissolved in a solution of ammonia in methanol (2 mL of 7 M, 14 mmol) and stirred in a sealed vial at 40° C. for 16 hours. The solvent was removed in vacuo to provide 6-tert-butyl-N-(2-carbamoyl-4-pyridyl)-4-(2-chloro-4-fluoro-phenoxy)-2-methyl-pyridine-3-carboxamide (10.9 mg, 55%). ESI-MS m z calc. 456.14, found 457.2 $(M+1)^+$; 455.2 $(M-1)^-$; LC/MS retention time (Method E): 3.14 minutes. $^1H$ NMR (400 MHz, $CDCl_3$) δ 9.50 (s, 1H), 8.56-8.40 (m, 2H), 8.22-8.10 (m, 1H), 7.76 (d, J=4.7 Hz, 1H), 7.22 (dd, J=7.9, 3.0 Hz, 1H), 7.21-7.16 (m, 1H), 7.04 (ddd, J=9.0, 7.5, 3.0 Hz, 1H), 6.38 (s, 1H), 5.18 (d, J=4.7 Hz, 1H), 2.65 (s, 3H), 1.25 (s, 9H) ppm.

Example 157

4-[[6-(2-Chloro-4-Fluoro-Phenoxy)-2-Fluoro-4-Methoxy-3-(Trifluoromethyl)Benzoyl]Amino]Pyridine-2-Carboxamide (6M5)

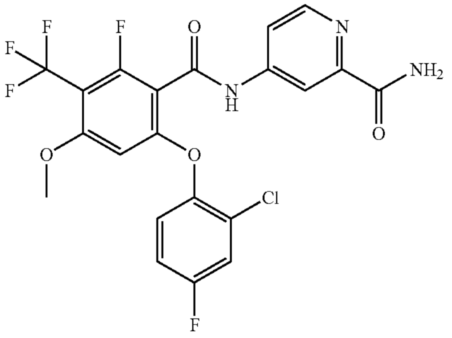 [SMILES: COc1cc(Oc2ccc(F)cc2Cl)c(C(=O)Nc2ccnc(C(N)=O)c2)c(F)c1C(F)(F)F]

Step 1: 6-(2-Chloro-4-Fluoro-Phenoxy)-2-Fluoro-4-Methoxy-3-(Trifluoromethyl)Benzoic Acid

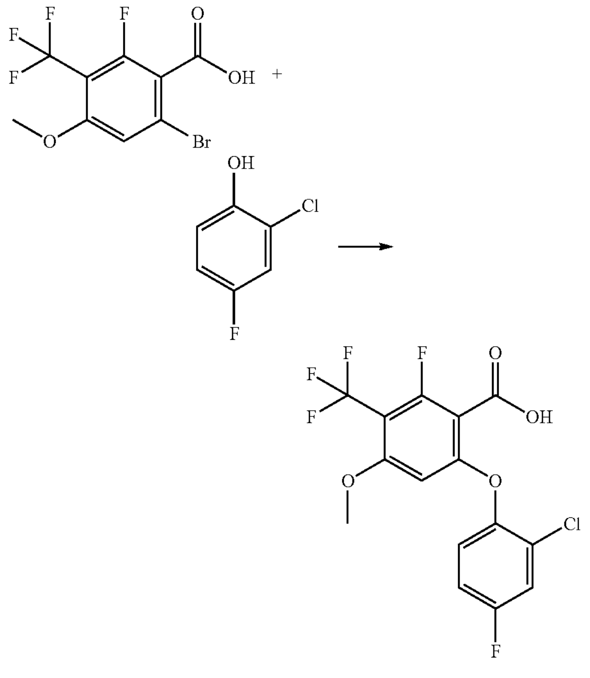

A mixture of 6-bromo-2-fluoro-4-methoxy-3-(trifluoromethyl)benzoic acid (3.0 g, 9.5 mmol, see US 2019/0016671, Example 129, Step 3, which is incorporated by reference), 2-chloro-4-fluoro-phenol (1.57 g, 1.17 mL, 10.7 mmol), $Cs_2CO_3$ (3.37 g, 10.3 mmol) and copper iodide (395 mg, 2.07 mmol) was flushed with nitrogen before adding in toluene (60 mL). The mixture was stirred at 100° C. under nitrogen for 2 hours. The cooled mixture was acidified with 1 M aqueous HCl, then diluted with water and ethyl acetate. The layers were separated and the aqueous layer was extracted with ethyl acetate (2×60 mL). The combined organic layers were washed with brine, dried over $MgSO_4$, filtered, and concentrated in vacuo. Purification by silica gel chromatography (0-60% ethyl acetate/heptane) provided 6-(2-chloro-4-fluoro-phenoxy)-2-fluoro-4-methoxy-3-(trifluoromethyl)benzoic acid (2.94 g, 81%). $^1$H NMR (400 MHz, $CDCl_3$) δ 7.30-7.27 (m, 1H), 7.17 (dd, J=9.0, 5.0 Hz, 1H), 7.07 (ddd, J=9.0, 7.4, 3.0 Hz, 1H), 5.97 (s, 1H), 3.72 (s, 3H) ppm. ESI-MS m z calc. 382.00, LC/MS retention time (Method F): 0.96 minutes.

Step 2: Methyl 4-[[6-(2-Chloro-4-Fluoro-Phenoxy)-2-Fluoro-4-Methoxy-3-(Trifluoromethyl)Benzoyl]Amino]Pyridine-2-Carboxylate

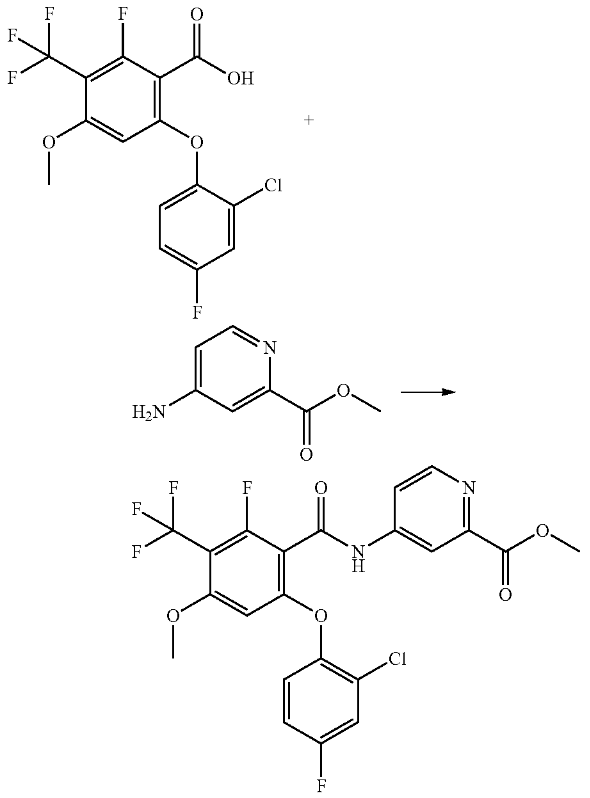

A solution of 6-(2-chloro-4-fluoro-phenoxy)-2-fluoro-4-methoxy-3-(trifluoromethyl)benzoic acid (280 mg, 0.732 mmol) in dichloromethane (14 mL) at 0° C. was treated with oxalyl chloride (210 μL, 2.41 mmol) followed by addition of DMF (5 μL, 0.07 mmol). The resulting mixture was stirred for 1 hour, then treated with additional oxalyl chloride (100 μL) and DMF (2 drops). The mixture was stirred at room temperature for 3 hours then concentrated in vacuo. The residue was dissolved in dichloromethane (14 mL), cooled to 0° C., and then treated with methyl 4-aminopyridine-2-carboxylate (120 mg, 0.789 mmol) and TEA (210 μL, 1.51 mmol). The mixture was allowed to warm to room temperature and stirred overnight. The mixture was concentrated in vacuo and purified by silica gel chromatography (0-100% ethyl acetate/heptane) to provide methyl 4-[[6-(2-chloro-4-fluoro-phenoxy)-2-fluoro-4-methoxy-3-(trifluoromethyl)benzoyl]amino]pyridine-2-carboxylate (215 mg, 57%). ESI-MS m z calc. 516.05, found 517.1 $(M+1)^+$; 515.1 $(M-1)^-$; LC/MS retention time (Method F): 0.9 minutes. $^1$H NMR (400 MHz, $CDCl_3$) δ 8.68 (d, J=5.5 Hz, 1H), 8.24 (s, 1H), 8.16 (d, J=2.2 Hz, 1H), 8.08-8.04 (m, 1H), 7.30 (dd, J=7.8, 2.9 Hz, 1H), 7.23 (d, J=5.0 Hz, 1H), 7.11 (ddd, J=9.0, 7.4, 3.0 Hz, 1H), 5.98 (s, 1H), 4.01 (s, 3H), 3.73 (s, 3H) ppm.

Step 3: 4-[[6-(2-Chloro-4-Fluoro-Phenoxy)-2-Fluoro-4-Methoxy-3-(Trifluoromethyl)Benzoyl]Amino]Pyridine-2-Carboxamide (365)

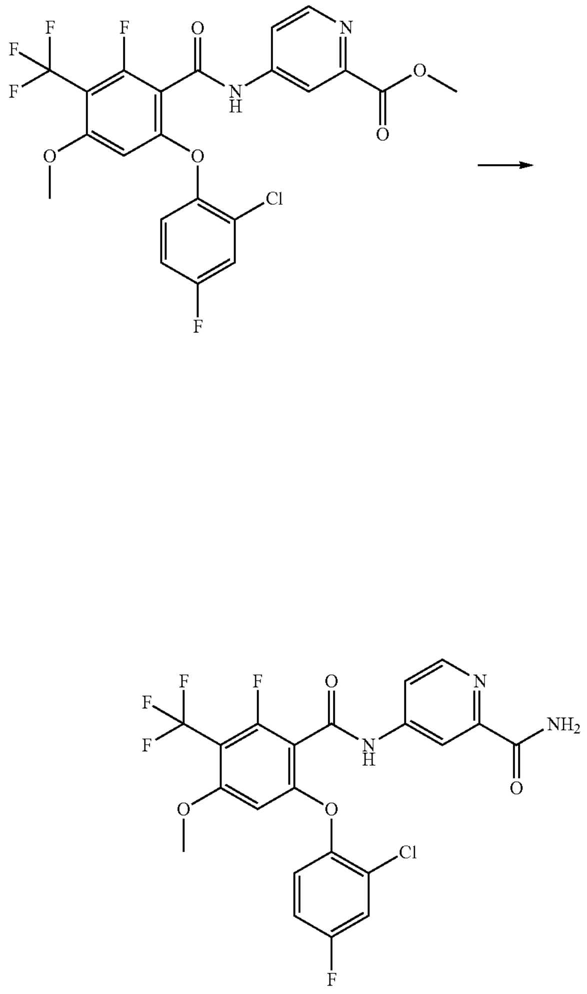

Methyl 4-[[6-(2-chloro-4-fluoro-phenoxy)-2-fluoro-4-methoxy-3-(trifluoromethyl)benzoyl]amino]pyridine-2-carboxylate (215 mg, 0.416 mmol) was dissolved in a solution of ammonia in methanol (5 mL of 7 M, 35 mmol) and stirred overnight. The mixture was concentrated in vacuo and by reverse phase HPLC (47-95% acetonitrile/0.1% ammonium hydroxide) to provide 4-[[6-(2-chloro-4-fluoro-phenoxy)-2-fluoro-4-methoxy-3-(trifluoromethyl)benzoyl]amino]pyridine-2-carboxamide (66.5 mg, 32%). ESI-MS m z calc. 501.05, found 502.1 $(M+1)^+$; 500.1 $(M-1)^-$; LC/MS retention time (Method E): 3.04 minutes. H NMR (400 MHz, DMSO-$d_6$) δ 11.26 (s, 1H), 8.53 (d, J=5.5 Hz, 1H), 8.26 (d, J=2.2 Hz, 1H), 8.08 (s, 1H), 7.79 (dd, J=5.6, 2.2 Hz, 1H), 7.63 (dd, J=8.3, 3.0 Hz, 2H), 7.42 (dd, J=9.1, 5.1 Hz, 1H), 7.32 (ddd, J=9.2, 8.0, 3.1 Hz, 1H), 6.46 (s, 1H), 3.81 (s, 3H) ppm.

Example 158

5-[[6-(2-Chloro-4-Fluoro-Phenoxy)-2-Fluoro-4-Methoxy-3-(Trifluoromethyl)Benzoyl]Amino]Pyrimidine-2-Carboxamide (366)

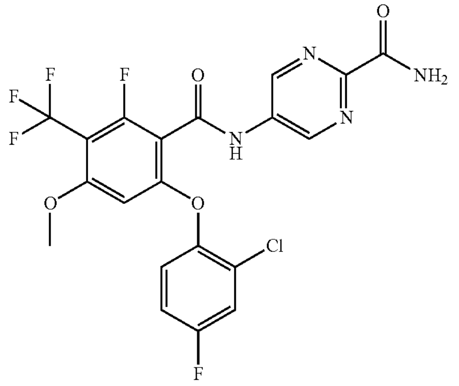 [SMILES: COc1cc(Oc2ccc(F)cc2Cl)c(C(=O)Nc2cnc(C(N)=O)nc2)c(F)c1C(F)(F)F]

This compound was made in an analogous fashion to the synthesis of compound 365 in Example 157, except employing methyl 5-aminopyrimidine-2-carboxylate for the amide formation step to provide methyl 5-[[6-(2-chloro-4-fluoro-phenoxy)-2-fluoro-4-methoxy-3-(trifluoromethyl)benzoyl]amino]pyrimidine-2-carboxylate (30 mg, 10%). $^1$H NMR (400 MHz, $CDCl_3$) δ 9.25 (s, 2H), 8.07 (s, 1H), 7.32 (dd, J=7.7, 2.9 Hz, 1H), 7.24-7.20 (m, 1H), 7.16-7.09 (m, 1H), 6.05 (s, 1H), 4.07 (s, 3H), 3.75 (s, 3H) ppm. ESI-MS m z calc. 517.05, found 518.1 $(M+1)^+$; 516.1 $(M-1)^-$; LC/MS retention time (Method F): 0.86 minutes.

Analogous treatment with methanolic ammonia provided 5-[[6-(2-chloro-4-fluoro-phenoxy)-2-fluoro-4-methoxy-3-(trifluoromethyl)benzoyl]amino]pyrimidine-2-carboxamide (10.4 mg, 38%). ESI-MS m/z calc. 502.05, found 503.1 $(M+1)^+$; 501.1 $(M-1)^-$; LC/MS retention time (Method E): 2.8 minutes. $^1$H NMR (400 MHz, DMSO-$d_6$) δ 11.40 (s, 1H), 9.11 (s, 2H), 8.11 (s, 1H), 7.71 (s, 1H), 7.63 (dd, J=8.3, 3.0 Hz, 1H), 7.40 (dd, J=9.1, 5.1 Hz, 1H), 7.31 (td, J=9.0, 8.6, 3.0 Hz, 1H), 6.51 (s, 1H), 3.82 (s, 3H) ppm.

Example 159

5-[[6-(2-Chloro-4-Fluoro-Phenoxy)-2-Fluoro-4-Methoxy-3-(Trifluoromethyl)Benzoyl]Amino]Pyridine-2-Carboxamide (367)

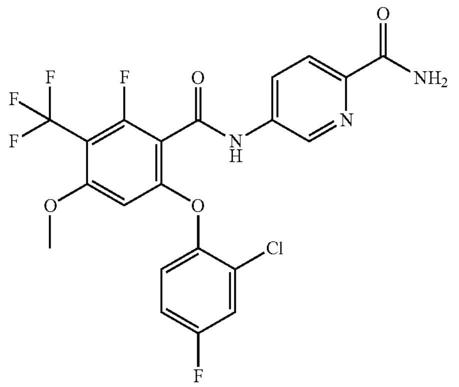 [SMILES: COc1cc(Oc2ccc(F)cc2Cl)c(C(=O)Nc2ccc(C(N)=O)nc2)c(F)c1C(F)(F)F]

This compound was made in an analogous fashion to the synthesis of compound 365 in Example 157, above, except employing 5-aminopyridine-2-carboxamide in the amide coupling step to provide 5-[[6-(2-chloro-4-fluoro-phenoxy)-2-fluoro-4-methoxy-3-(trifluoromethyl)benzoyl]amino]pyridine-2-carboxamide (93.8 mg, 23%). $^1$H NMR (400 MHz, DMSO-$d_6$) δ 11.19 (s, 1H), 8.80 (d, J=2.4 Hz, 1H), 8.23 (dd, J=8.6, 2.5 Hz, 1H), 8.07-7.97 (m, 2H), 7.63 (dd, J=8.4, 3.0 Hz, 1H), 7.55 (s, 1H), 7.41 (dd, J=9.1, 5.2 Hz, 1H), 7.31 (ddd, J=9.1, 8.0, 3.0 Hz, 1H), 6.49 (s, 1H), 3.82 (s, 3H) ppm. ESI-MS m z calc. 501.05, found 502.1 $(M+1)^+$; 500.1 $(M-1)^-$; LC/MS retention time (Method E): 2.97 minutes.

Example 160

4-[[6-[2-Chloro-4-(Trifluoromethoxy)Phenoxy]-2-Fluoro-4-Methoxy-3-(Trifluoromethyl)Benzoyl]Amino]Pyridine-2-Carboxamide (368)

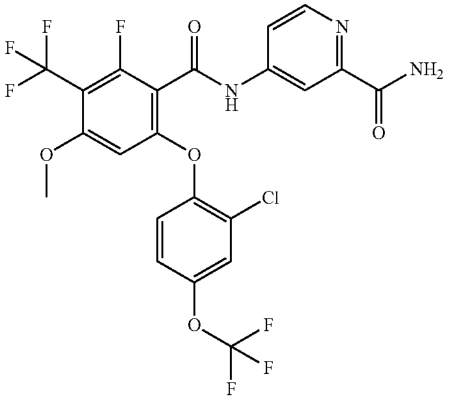 [SMILES: COc1cc(Oc2ccc(OC(F)(F)F)cc2Cl)c(C(=O)Nc2ccnc(C(N)=O)c2)c(F)c1C(F)(F)F]

Step 1: 6-[2-Chloro-4-(Trifluoromethoxy)Phenoxy]-2-Fluoro-4-Methoxy-3-(Trifluoromethyl)Benzoic Acid

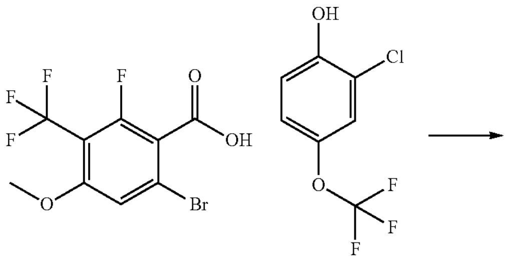

-continued

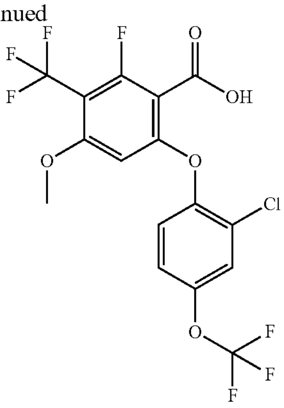

A mixture of 6-bromo-2-fluoro-4-methoxy-3-(trifluoromethyl)benzoic acid (502 mg, 1.58 mmol, see US 2019/0016671, Example 129, Step 3, which is incorporated by reference), 2-chloro-4-(trifluoromethoxy)phenol (400 mg, 1.88 mmol) and $Cs_2CO_3$ (600 mg, 1.84 mmol) in toluene (10 mL) was bubbled with nitrogen for 10 minutes, then treated with copper (I) iodide (72 mg, 0.38 mmol). The mixture was stirred at 100° C. for 3 hours. The cooled mixture was acidified with 1 M aqueous HCl, then diluted with water and ethyl acetate. The layers were separated and the aqueous layer was extracted with additional ethyl acetate (2×30 mL). The combined organic extracts were washed with brine, dried over $MgSO_4$, filtered and concentrated in vacuo. Purification by silica gel chromatography (0-100% ethyl acetate/heptane) provided 6-[2-chloro-4-(trifluoromethoxy)phenoxy]-2-fluoro-4-methoxy-3-(trifluoromethyl)benzoic acid (625 mg, 88%). ESI-MS m z calc. 448.00, no ionization observed; LC/MS retention time (Method F): 0.6 minutes. $^1$H NMR (400 MHz, $CDCl_3$) δ 7.42 (d, J=2.6 Hz, 1H), 7.24-7.18 (m, 1H), 7.18-7.14 (m, 1H), 6.06 (s, 1H), 3.76 (s, 3H) ppm.

Step 2: Methyl 4-[[6-[2-Chloro-4-(Trifluoromethoxy)Phenoxy]-2-Fluoro-4-Methoxy-3-(Trifluoromethyl)Benzoyl]Amino]Pyridine-2-Carboxylate

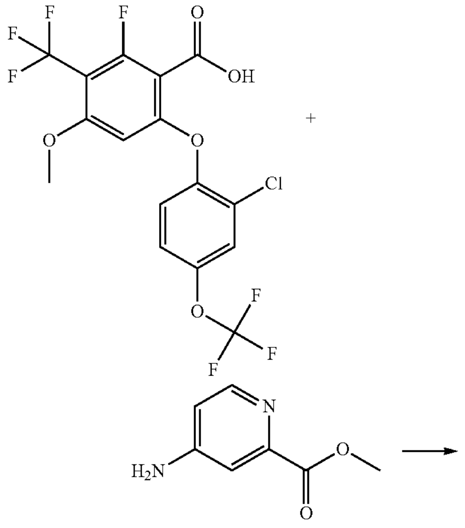

-continued

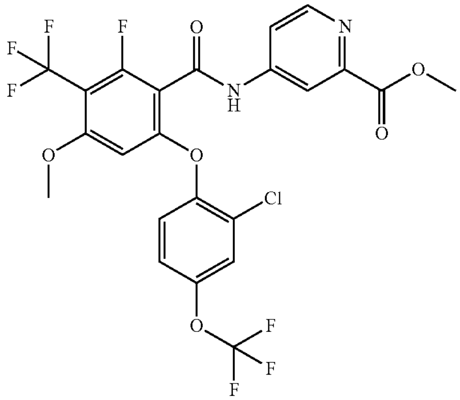

A solution of 6-[2-chloro-4-(trifluoromethoxy)phenoxy]-2-fluoro-4-methoxy-3-(trifluoromethyl)benzoic acid (301 mg, 0.671 mmol) in dichloromethane (6 mL) at 0° C. was treated with oxalyl chloride (193 μL, 2.21 mmol) followed by addition of DMF (5 μL, 0.07 mmol). The resulting mixture was stirred for 15 minutes at 0° C., then allowed to warm to room temperature over 1 hour. The mixture was concentrated in vacuo. The residue was dissolved in dichloromethane (6 mL), cooled in an ice bath, and treated with methyl 4-aminopyridine-2-carboxylate (124 mg, 0.815 mmol) and TEA (217 μL, 1.56 mmol). The mixture was allowed to warm to room temperature and stirred overnight. The mixture was concentrated in vacuo and purified by silica gel chromatography (0-100% ethyl acetate/heptane) to provide methyl 4-[[6-[2-chloro-4-(trifluoromethoxy)phenoxy]-2-fluoro-4-methoxy-3-(trifluoromethyl)benzoyl]amino]pyridine-2-carboxylate (40 mg, 8%). ESI-MS m z calc. 582.045, found 583.0 $(M+1)^+$; 581.1 $(M-1)^-$; LC/MS retention time (Method F): 0.96 minutes. $^1$H NMR (400 MHz, $CDCl_3$) δ 8.65 (d, J=5.5 Hz, 1H), 8.40-8.28 (m, 1H), 8.13 (d, J=2.3 Hz, 1H), 8.01 (dd, J=5.5, 2.2 Hz, 1H), 7.42 (dq, J=1.6, 0.9 Hz, 1H), 7.23 (d, J=1.5 Hz, 2H), 6.04 (d, J=1.5 Hz, 1H), 3.98 (s, 3H), 3.75 (s, 3H) ppm.

Step 3: 4-[[6-[2-Chloro-4-(Trifluoromethoxy)Phenoxy]-2-Fluoro-4-Methoxy-3-(Trifluoromethyl)Benzoyl]Amino]Pyridine-2-Carboxamide (369)

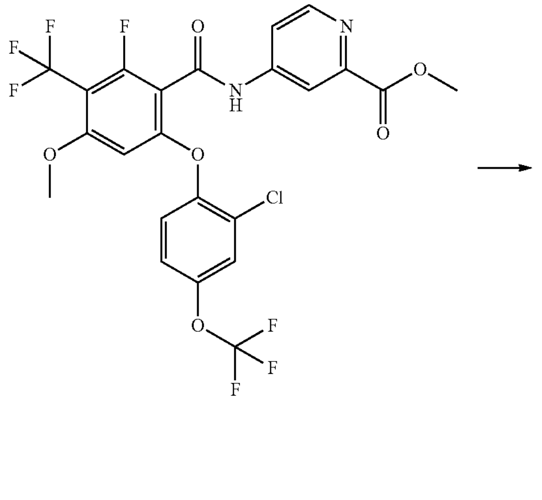

-continued

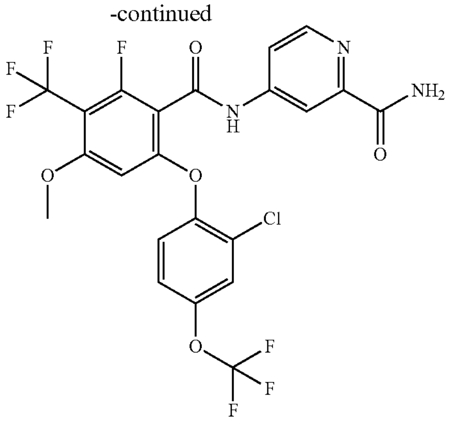

Methyl 4-[[6-[2-chloro-4-(trifluoromethoxy)phenoxy]-2-fluoro-4-methoxy-3-(trifluoromethyl)benzoyl]amino]pyridine-2-carboxylate (38 mg, 0.06520 mmol) was dissolved in a solution of ammonia in methanol (1 mL of 7 M, 7 mmol) and stirred for approximately 72 hours. The mixture was concentrated in vacuo and purified by reverse phase HPLC (47-95% acetonitrile/0.1% ammonium hydroxide) to provide 4-[[6-[2-chloro-4-(trifluoromethoxy)phenoxy]-2-fluoro-4-methoxy-3-(trifluoromethyl)benzoyl]amino]pyridine-2-carboxamide (8.4 mg, 22%). ESI-MS m z calc. 567.04, found 568.0 $(M+1)^+$; LC/MS retention time (Method E): 3.32 minutes. $^1$H NMR (400 MHz, DMSO-$d_6$) δ 8.50 (d, J=5.4 Hz, 1H), 8.21 (d, J=2.1 Hz, 1H), 7.96 (s, 1H), 7.73 (dd, J=5.5, 2.2 Hz, 1H), 7.65 (d, J=1.9 Hz, 1H), 7.46 (s, 1H), 7.39 (d, J=1.5 Hz, 2H), 6.67 (s, 1H), 3.85 (s, 3H) ppm.

Example 161

5-[[6-[2-Chloro-4-(Trifluoromethoxy)Phenoxy]-2-Fluoro-4-Methoxy-3-(Trifluoromethyl)Benzoyl]Amino]Pyrimidine-2-Carboxamide (369)

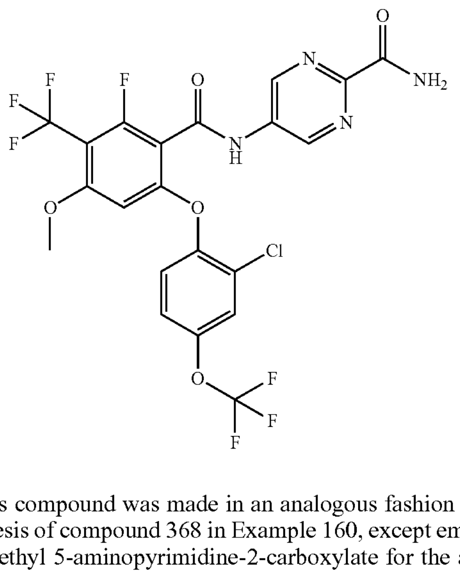

This compound was made in an analogous fashion to the synthesis of compound 368 in Example 160, except employing methyl 5-aminopyrimidine-2-carboxylate for the amide formation step (Step 2). The yield of methyl 5-[[6-[2-chloro-4-(trifluoromethoxy)phenoxy]-2-fluoro-4-methoxy-3-(trifluoromethyl)benzoyl]amino]pyrimidine-2-carboxylate was 70 mg (23%). ESI-MS m z calc. 583.04, found 584.1 $(M+1)^+$; 582.1 $(M-1)^-$; LC/MS retention time (Method F): 0.95 minutes. $^1$H NMR (400 MHz, $CDCl_3$) δ 9.24 (s, 2H), 8.04 (s, 1H), 7.45 (dd, J=2.2, 1.1 Hz, 1H), 7.25 (s, 1H), 6.08 (s, 1H), 4.07 (s, 3H), 3.78 (s, 3H) ppm.

Analogous treatment with methanolic ammonia provided 5-[[6-[2-chloro-4-(trifluoromethoxy)phenoxy]-2-fluoro-4-methoxy-3-(trifluoromethyl)benzoyl]amino]pyrimidine-2-carboxamide (12.2 mg, 17%). $^1$H NMR (400 MHz, DMSO-$d_6$) δ 11.40 (s, 1H), 9.07 (s, 2H), 8.10 (s, 1H), 7.72 (s, 2H), 7.40 (d, J=7.1 Hz, 2H), 6.78 (s, 1H), 3.88 (s, 3H). ESI-MS m z calc. 568.04, found 569.1 $(M+1)^+$; 567.0 $(M-1)^-$; LC/MS retention time (Method E): 3.11 minutes.

Example 162

5-[[6-[2-Chloro-4-(Trifluoromethoxy)Phenoxy]-2-Fluoro-4-Methoxy-3-(Trifluoromethyl)Benzoyl]Amino]Pyridine-2-Carboxamide (370)

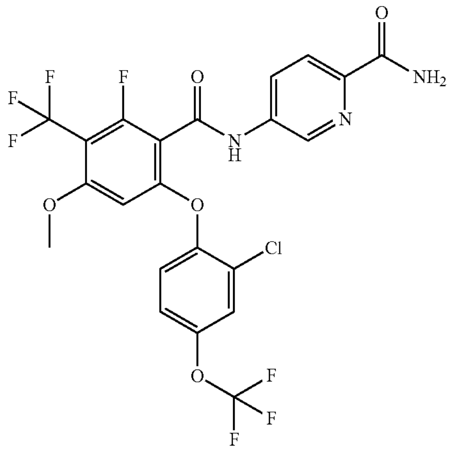 [SMILES: COc1cc(Oc2ccc(OC(F)(F)F)cc2Cl)c(C(=O)Nc2ccc(C(N)=O)nc2)c(F)c1C(F)(F)F]

This compound was made in an analogous fashion to the synthesis of compound 368 in Example 160, except employing 5-aminopyridine-2-carboxamide for the amide formation step (Step 2). The yield of 5-[[6-[2-chloro-4-(trifluoromethoxy)phenoxy]-2-fluoro-4-methoxy-3-(trifluoromethyl)benzoyl]amino]pyridine-2-carboxamide was 49.1 mg (12%). ESI-MS m z calc. 567.04, found 568.0 $(M+1)^+$; 566.1 (M−1)+; LC/MS retention time (Method E): 3.26 minutes. $^1$H NMR (400 MHz, DMSO-$d_6$) δ 11.18 (s, 1H), 8.75 (dd, J=2.5, 0.7 Hz, 1H), 8.17 (dd, J=8.6, 2.5 Hz, 1H), 8.08-7.91 (m, 2H), 7.72 (d, J=2.7 Hz, 1H), 7.54 (s, 1H), 7.44-7.40 (m, 1H), 7.38 (d, J=9.0 Hz, 1H), 6.77 (s, 1H), 3.87 (s, 3H) ppm.

Example 163

4-[[2-(3,4-Difluoro-2-Methoxy-Phenoxy)-4-Fluoro-6-Methyl-Benzoyl]Amino]Pyridine-2-Carboxamide (371)

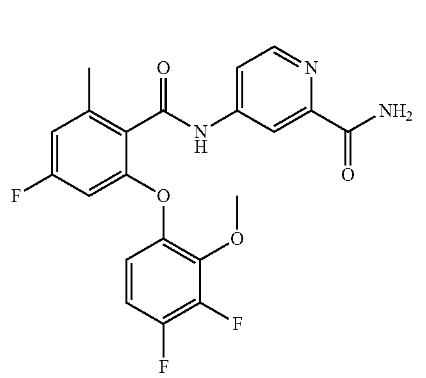 [SMILES: COc1c(Oc2cc(F)cc(C)c2C(=O)Nc2ccnc(C(N)=O)c2)ccc(F)c1F]

Step 1: 2-(3,4-Difluoro-2-Methoxy-Phenoxy)-4-Fluoro-6-Methyl-Benzoic Acid

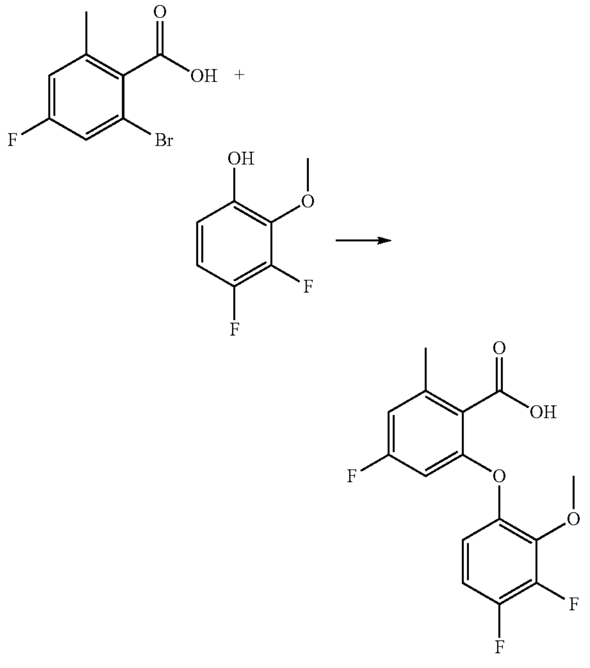

2-Bromo-4-fluoro-6-methyl-benzoic acid (1.5 g, 6.4 mmol) and $Cs_2CO_3$ (2.4 g, 7.4 mmol) were suspended in toluene (15 mL). The mixture was treated with copper (I) iodide (240 mg, 1.26 mmol) and 3,4-difluoro-2-methoxy-phenol (1.0 g, 6.25 mmol) then heated in a sealed reaction vial at 100° C. for 3 hours. The cooled mixture was diluted with ethyl acetate (5 mL) and acidified with 1 M aqueous HCl (~5 mL) to pH=1. The aqueous layer was extracted with additional ethyl acetate (2×5 mL), and the combined extracts dried over $Na_2SO_4$, filtered and concentrated in vacuo. Purification by silica gel chromatography (0-80% ethyl acetate/heptane), followed by a second silica gel chromatography purification (10-60% ethyl acetate/heptane) provided 2-(3,4-difluoro-2-methoxy-phenoxy)-4-fluoro-6-methyl-benzoic acid (547 mg, 27%). $^1$H NMR (500 MHz, DMSO-$d_6$) δ 13.30 (s, 1H), 7.19 (td, J=9.8, 8.5 Hz, 1H), 6.99-6.86 (m, 2H), 6.51 (dd, J=10.2, 2.3 Hz, 1H), 3.90-3.82 (m, 3H), 2.33 (s, 3H) ppm.

Step 2: Methyl 4-[[2-(3,4-Difluoro-2-Methoxy-Phenoxy)-4-Fluoro-6-Methyl-Benzoyl]Amino]Pyridine-2-Carboxylate

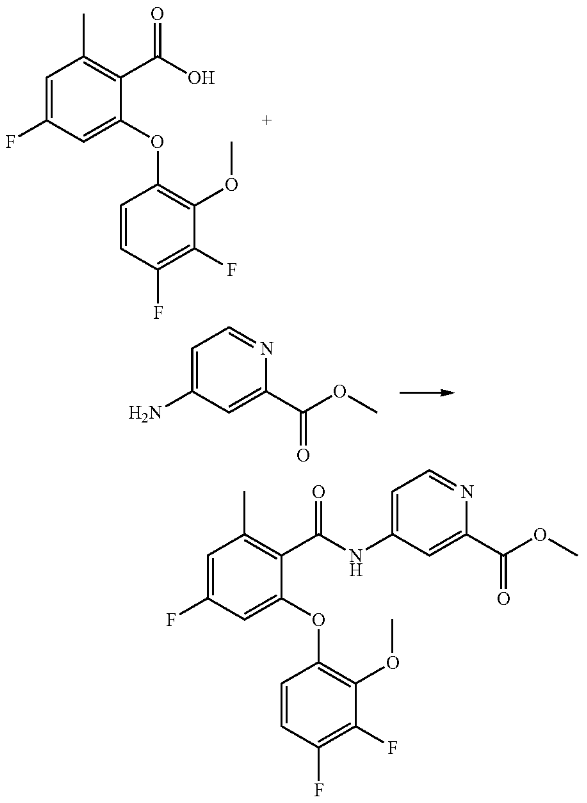

A solution of 2-(3,4-difluoro-2-methoxy-phenoxy)-4-fluoro-6-methyl-benzoic acid (270 mg, 0.865 mmol) and DMF (5 μL) in dichloromethane (5 mL) at 0° C. was treated dropwise with oxalyl chloride (150 μL, 1.72 mmol) and stirred for stirred for 1 hour. The mixture was concentrated in vacuo, then diluted and evaporated twice with dichloromethane. The residue was dissolved in dichloromethane (1 mL) and added to a solution of methyl 4-aminopyridine-2-carboxylate (130 mg, 0.854 mmol) and TEA (500 μL, 3.59 mmol) in dichloromethane (5 mL) at 0° C. The mixture was allowed to warm to room temperature and stirred for 18 hours. The mixture was diluted with water with water (1 mL) and the phases separated. The organic phase was concentrated and purified by silica gel chromatography (0-70% ethyl acetate/heptane) to provide methyl 4-[[2-(3,4-difluoro-2-methoxy-phenoxy)-4-fluoro-6-methyl-benzoyl]amino] pyridine-2-carboxylate (107 mg, 28%) as an orange oil. ESI-MS m z calc. 446.11, found 447.0 $(M+1)^+$; 445.0 $(M-1)^-$; LC/MS retention time (Method F): 0.87 minutes. $^1$H NMR (500 MHz, DMSO-$d_6$) δ 11.17 (s, 1H), 8.60 (d, J=5.4 Hz, 1H), 8.43 (d, J=2.0 Hz, 1H), 7.84 (dd, J=5.4, 2.1 Hz, 1H), 7.22 (td, J=9.9, 8.5 Hz, 1H), 7.05-6.97 (m, 2H), 6.56 (dd, J=10.2, 2.4 Hz, 1H), 3.88 (s, 3H), 3.83 (d, J=1.0 Hz, 3H), 2.35 (s, 3H) ppm. $^{19}$F NMR (471 MHz, DMSO-$d_6$) δ −109.38, −139.86 (d, J=21.7 Hz), −152.46 (d, J=21.1 Hz) ppm.

Step 3: 4-[[2-(3,4-Difluoro-2-Methoxy-Phenoxy)-4-Fluoro-6-Methyl-Benzoyl]Amino]Pyridine-2-Carboxamide (371)

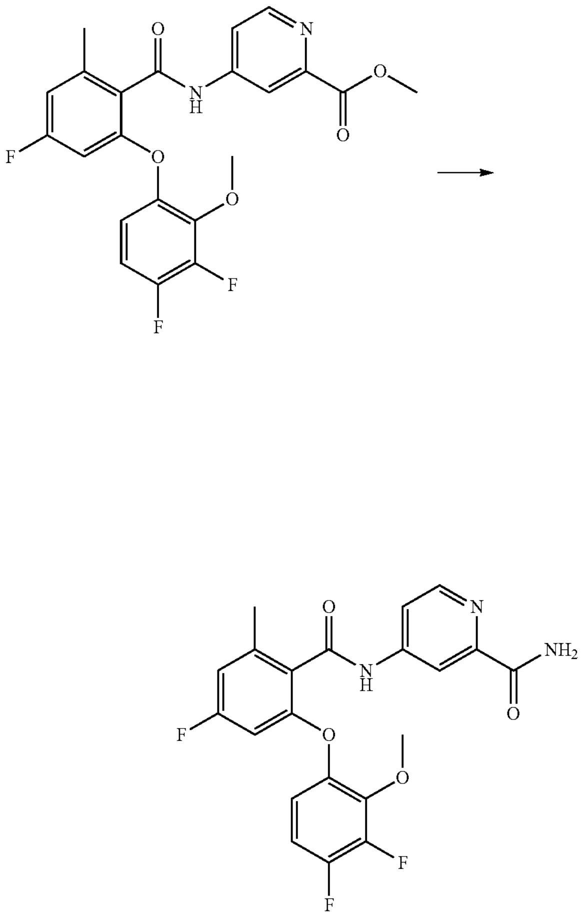

Methyl 4-[[2-(3,4-difluoro-2-methoxy-phenoxy)-4-fluoro-6-methyl-benzoyl]amino]pyridine-2-carboxylate (107 mg, 0.2397 mmol) was dissolved in a solution of ammonia in methanol (1 mL of 7 M, 7 mmol) and stirred for 18 hours. The mixture was concentrated in vacuo and the residue purified by reverse phase HPLC (47-95% acetonitrile/0.1% ammonium hydroxide) to provide 4-[[2-(3,4-difluoro-2-methoxy-phenoxy)-4-fluoro-6-methyl-benzoyl] amino]pyridine-2-carboxamide (24.3 mg, 23%) as a white solid. ESI-MS m z calc. 431.11, found 432.0 $(M+1)^+$; 430.0 $(M-1)^-$; LC/MS retention time (Method E): 2.84 minutes. $^1$H NMR (500 MHz, DMSO-$d_6$) δ 11.11 (s, 1H), 8.51 (d, J=5.5 Hz, 1H), 8.35 (d, J=2.2 Hz, 1H), 8.06 (d, J=2.8 Hz, 1H), 7.83 (dd, J=5.5, 2.2 Hz, 1H), 7.61 (d, J=2.8 Hz, 1H), 7.25-7.16 (m, 1H), 7.04-6.96 (m, 2H), 6.54 (dd, J=10.2, 2.4 Hz, 1H), 3.82 (d, J=0.8 Hz, 3H), 2.35 (s, 3H) ppm. $^{19}$F NMR (471 MHz, DMSO-$d_6$) δ −109.52, −139.90 (d, J=21.7 Hz), −152.49 (d, J=22.2 Hz) ppm.

Example 164

4-[[6-(3,4-Difluoro-2-Methoxy-Phenoxy)-2-Fluoro-4-Methoxy-3-Methyl-Benzoyl]Amino]Pyridine-2-Carboxamide (372)

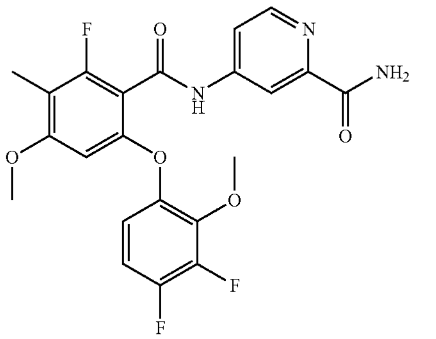 [SMILES: COc1cc(Oc2ccc(F)c(F)c2OC)c(C(=O)Nc2ccnc(C(N)=O)c2)c(F)c1C]

Step 1: 6-(3,4-Difluoro-2-Methoxy-Phenoxy)-2-Fluoro-4-Methoxy-3-Methyl-Benzoic Acid

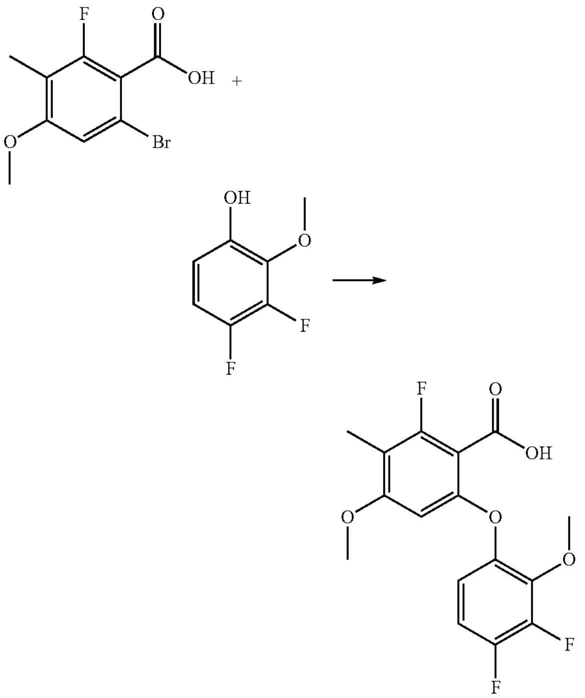

6-Bromo-2-fluoro-4-methoxy-3-methyl-benzoic acid (0.5 g, 2 mmol, see Example 154, Step 3), 3,4-difluoro-2-methoxy-phenol (300 mg, 1.87 mmol) and $Cs_2CO_3$ (1.2 g, 3.683 mmol) were combined in toluene (10 mL) and the mixture bubbled with nitrogen for 5 minutes. The mixture was treated with copper (I) iodide (90 mg, 0.47 mmol) and heated in a sealed vial at 100° C. for 90 minutes. The cooled mixture was then partitioned between ethyl acetate and water, and the aqueous layer acidified to pH=1. The layers were separated and the aqueous layer extracted with additional ethyl acetate (2×). The combined extracts were washed with brine, dried over $Na_2SO_4$, filtered and concentrated in vacuo. Purification by silica gel chromatography (0-100% ethyl acetate/heptane), followed by a second silica gel chromatography purification (0-50% ethyl acetate/heptane) provided 6-(3,4-difluoro-2-methoxy-phenoxy)-2-fluoro-4-methoxy-3-methyl-benzoic acid (279 mg, 43%). $^1H$ NMR (500 MHz, DMSO-$d_6$) δ 13.20 (s, 1H), 7.14 (td, J=9.9, 8.6 Hz, 1H), 6.77 (ddd, J=9.4, 5.0, 2.3 Hz, 1H), 6.37 (d, J=1.4 Hz, 1H), 3.89 (d, J=0.8 Hz, 3H), 3.72 (s, 3H), 2.03 (d, J=2.1 Hz, 3H) ppm.

Step 2: Methyl 4-[[6-(3,4-Difluoro-2-Methoxy-Phenoxy)-2-Fluoro-4-Methoxy-3-Methyl-Benzoyl]Amino]Pyridine-2-Carboxylate

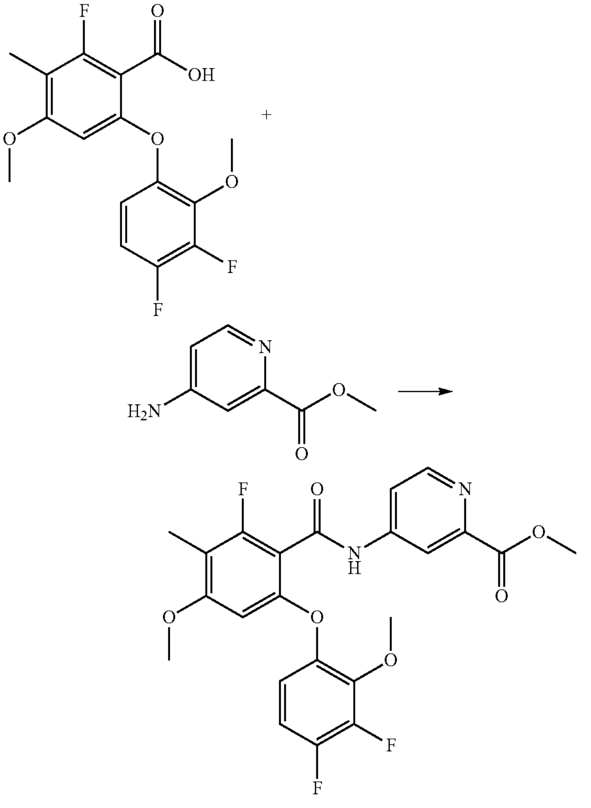

A solution of 6-(3,4-difluoro-2-methoxy-phenoxy)-2-fluoro-4-methoxy-3-methyl-benzoic acid (279 mg, 0.815 mmol) and DMF (5 μL) in dichloromethane (5 mL) at 0° C. was treated dropwise with oxalyl chloride (150 μL, 1.72 mmol) and stirred for 1 hour. The mixture was concentrated in vacuo, then diluted and evaporated twice with dichloromethane. The residue was dissolved in dichloromethane (1 mL) and added to a solution of methyl 4-aminopyridine-2-carboxylate (125 mg, 0.822 mmol) and TEA (500 μL, 3.59 mmol) in dichloromethane (5 mL) at 0° C. The mixture was allowed to warm to room temperature and stirred for 18 hours. The mixture was diluted with water (1 mL) and the layers separated. The organic phase was concentrated and purified by silica gel chromatography (0-100% ethyl acetate/heptane) to provide methyl 4-[[6-(3,4-difluoro-2-methoxy-phenoxy)-2-fluoro-4-methoxy-3-methyl-benzoyl]amino]pyridine-2-carboxylate (135 mg, 35%). ESI-MS m z calc. 476.12, found 477.0 $(M+1)^+$; 475.0 $(M-1)^-$; LC/MS retention time (Method F): 0.89 minutes. $^1$H NMR (500 MHz, DMSO-$d_6$) δ 11.16 (s, 1H), 8.58 (d, J=5.4 Hz, 1H), 8.35 (d, J=2.0 Hz, 1H), 7.79 (dd, J=5.5, 2.1 Hz, 1H), 7.16 (td, J=9.7, 8.5 Hz, 1H), 6.90 (ddd, J=9.3, 5.0, 2.2 Hz, 1H), 6.38 (d, J=1.4 Hz, 1H), 3.87 (s, 3H), 3.84 (d, J=0.9 Hz, 3H), 3.74 (s, 3H), 2.11-2.04 (m, 3H) ppm. $^{19}$F NMR (471 MHz, DMSO-$d_6$) δ −118.38, −141.00 (d, J=21.7 Hz), −152.81 (d, J=21.5 Hz) ppm.

Step 3: 4-[[6-(3,4-Difluoro-2-Methoxy-Phenoxy)-2-Fluoro-4-Methoxy-3-Methyl-Benzoyl]Amino]Pyridine-2-Carboxamide (372)

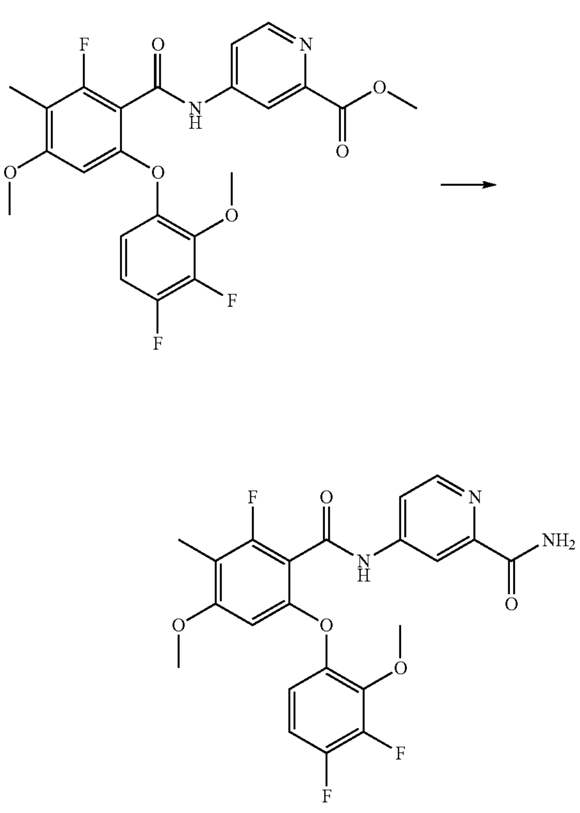

Methyl 4-[[6-(3,4-difluoro-2-methoxy-phenoxy)-2-fluoro-4-methoxy-3-methyl-benzoyl]amino]pyridine-2-carboxylate (134 mg, 0.281 mmol) was dissolved in a solution of ammonia in methanol (1 mL of 7 M, 7 mmol). The mixture was stirred at room temperature overnight. The mixture was concentrated in vacuo and purified by reverse phase HPLC (47-95% acetonitrile/0.1% ammonium hydroxide) to provide 4-[[6-(3,4-difluoro-2-methoxy-phenoxy)-2-fluoro-4-methoxy-3-methyl-benzoyl]amino]pyridine-2-carboxamide (23.2 mg, 18%) as a white solid. ESI-MS m z calc. 461.12, found 461.6 (M+1)$^+$; 460.0 (M−1)$^-$; LC/MS retention time (Method E): 2.99 minutes. $^1$H NMR (500 MHz, DMSO-$d_6$) δ 11.11 (s, 1H), 8.50 (d, J=5.5 Hz, 1H), 8.29 (d, J=2.2 Hz, 1H), 8.06 (d, J=2.9 Hz, 1H), 7.79 (dd, J=5.5, 2.2 Hz, 1H), 7.62 (d, J=2.9 Hz, 1H), 7.16 (td, J=9.7, 8.4 Hz, 1H), 6.91 (ddd, J=9.4, 5.0, 2.2 Hz, 1H), 6.38 (d, J=1.3 Hz, 1H), 3.84 (d, J=0.8 Hz, 3H), 3.74 (s, 3H), 2.07 (d, J=1.8 Hz, 3H) ppm. $^{19}$F NMR (471 MHz, DMSO-$d_6$) δ −118.44, −141.00 (d, J=21.0 Hz), −152.82 (d, J=21.6 Hz) ppm.

Example 165

4-[[4-Chloro-6-(3,4-Difluoro-2-Methoxy-Phenoxy)-2-Fluoro-3-Methyl-Benzoyl]Amino]Pyridine-2-Carboxamide (373)

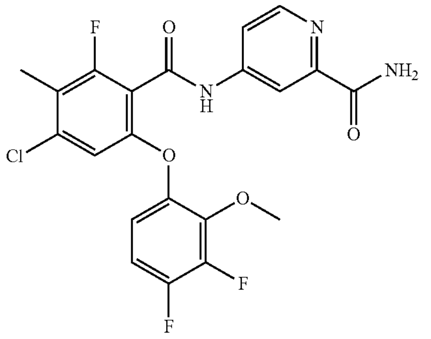 [SMILES: COc1c(Oc2cc(Cl)c(C)c(F)c2C(=O)Nc2ccnc(C(N)=O)c2)ccc(F)c1F]

Step 1: Methyl 4-Chloro-2-(3,4-Difluoro-2-Methoxy-Phenoxy)-6-Fluoro-Benzoate

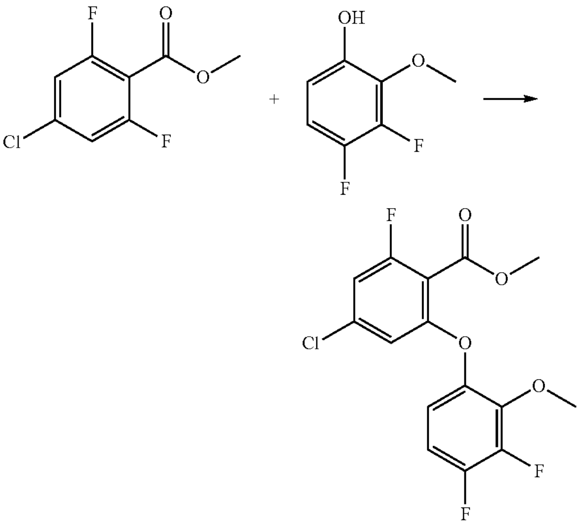

A mixture of $Cs_2CO_3$ (2.40 g, 7.37 mmol), 3,4-difluoro-2-methoxy-phenol (819 mg, 5.12 mmol) and methyl 4-chloro-2,6-difluoro-benzoate (1.00 g, 4.84 mmol) in DMF (17.5 mL) was stirred at room temperature for 21 hours, then heated at 50° C. for 3 hours. The mixture was then diluted with ethyl acetate and washed with water (3×) and brine (2×). The organic layer was dried over $MgSO_4$, filtered and concentrated in vacuo. The residue was purified by silica gel chromatography (0-10% ethyl acetate/petroleum ether) to provide methyl 4-chloro-2-(3,4-difluoro-2-methoxy-phenoxy)-6-fluoro-benzoate (1.23 g, 73%) as a colorless oil. ESI-MS m z calc. 346.02, no ionization observed; LC/MS retention time (Method F): 0.99 minutes. $^1$H NMR (400 MHz, $CDCl_3$) δ 6.97-6.83 (m, 3H), 6.47 (t, J=1.6 Hz, 1H), 3.95 (s, 3H), 3.94 (d, J=1.5 Hz, 3H) ppm.

Step 2: Methyl 4-Chloro-6-(3,4-Difluoro-2-Methoxy-Phenoxy)-2-Fluoro-3-Methyl-Benzoate

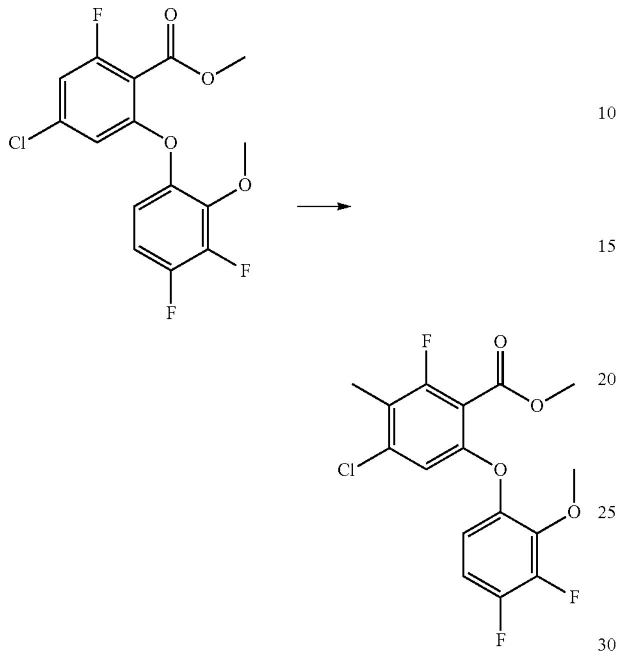

A solution of LDA (1.78 mL of 2 M in THF/heptane/ethylbenzene, 3.56 mmol) was added dropwise to a solution of methyl 4-chloro-2-(3,4-difluoro-2-methoxy-phenoxy)-6-fluoro-benzoate (1.226 g, 3.536 mmol) in THF (12.0 mL) at −78° C. The mixture was stirred at this temperature for 10 minutes then methyl iodide (335 μL, 5.38 mmol) was added. The mixture was stirred at −78° C. for 30 minutes then allowed to warm to room temperature. The mixture was diluted with water and extracted with ethyl acetate (3×20 mL). The combined organic extracts were dried over $MgSO_4$, filtered and concentrated in vacuo. The residue was purified by silica gel chromatography (0-100% ethyl acetate/heptane) to provide methyl 4-chloro-6-(3,4-difluoro-2-methoxy-phenoxy)-2-fluoro-3-methyl-benzoate as a colorless oil which was taken directly to the next step.

Step 3: 4-Chloro-6-(3,4-Difluoro-2-Methoxy-Phenoxy)-2-Fluoro-3-Methyl-Benzoic Acid

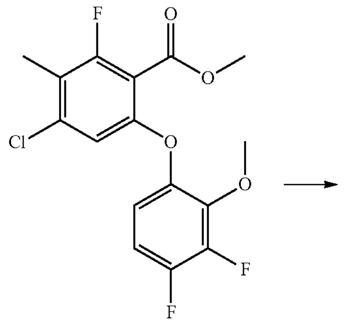

-continued

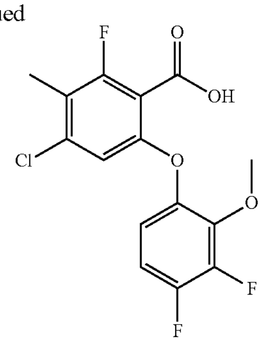

To a slurry of methyl 4-chloro-6-(3,4-difluoro-2-methoxy-phenoxy)-2-fluoro-3-methyl-benzoate in methanol (36 mL) and water (36 mL) was added NaOH (1.40 g, 35.0 mmol) and the mixture stirred at room temperature for approximately 72 hours. The mixture was cooled to room temperature and acidified with 2 M aqueous HCl (22 mL, 44 mmol). The volatiles were removed in vacuo and the aqueous mixture extracted with ethyl acetate (3×). The combined organic extracts were dried over $MgSO_4$, filtered and concentrated in vacuo to impure provide 4-chloro-6-(3,4-difluoro-2-methoxy-phenoxy)-2-fluoro-3-methyl-benzoic acid (1.12 g, 91%). ESI-MS m z calc. 346.02, no ionization observed, LC/MS retention time (Method F): 0.58 minutes. The isolated material was taken directly to the subsequent amide coupling step without additional purification.

Step 4: 4-[[4-Chloro-6-(3,4-Difluoro-2-Methoxy-Phenoxy)-2-Fluoro-3-Methyl-Benzoyl]Amino]Pyridine-2-Carboxamide (373)

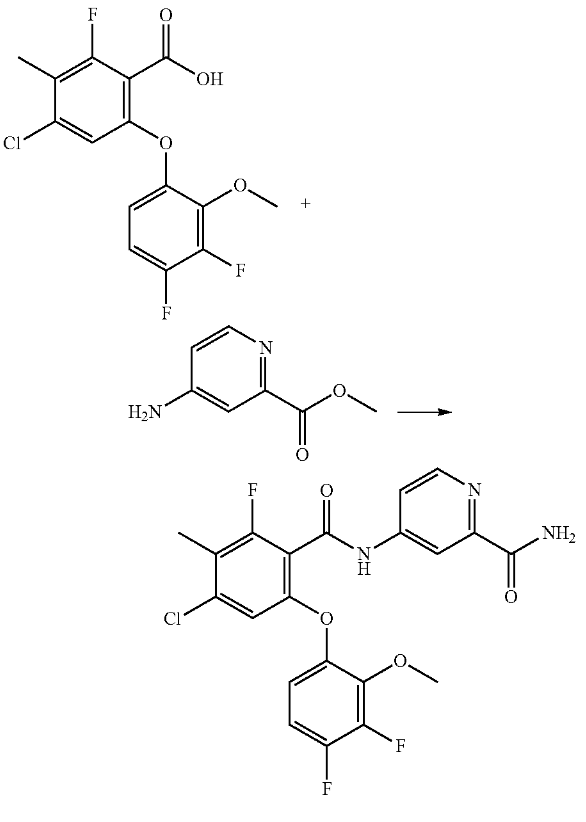

To a solution of 4-chloro-6-(3,4-difluoro-2-methoxy-phenoxy)-2-fluoro-3-methyl-benzoic acid (160 mg, 0.462 mmol) and DMF (4 μL, 0.05 mmol) in dichloromethane (3 mL) at 0° C. was added oxalyl chloride (120 μL, 1.42 mmol) dropwise. The mixture was stirred for 2 hours then concentrated in vacuo. The residue was dissolved in dichloromethane (3 mL) and added dropwise to a mixture of methyl 4-aminopyridine-2-carboxylate (92 mg, 0.61 mmol) and TEA (390 μL, 2.80 mmol) in dichloromethane (3 mL) at 0° C. The resulting mixture was allowed to warm to room temperature and stirred overnight. The mixture was concentrated in vacuo and the resulting residue dissolved in a solution of ammonia in methanol (650 μL of 7 M, 4.6 mmol) and stirred overnight. The mixture was concentrated in vacuo and purified by reverse phase HPLC (acetonitrile/0.1% ammonium hydroxide gradient), followed by additional reverse phase HPLC purification (0-100% acetonitrile/0.05% trifluoroacetic acid) to provide 4-[[4-chloro-6-(3,4-difluoro-2-methoxy-phenoxy)-2-fluoro-3-methyl-benzoyl]amino]pyridine-2-carboxamide (trifluoroacetate salt) (7.9 mg, 3%). ESI-MS m z calc. 465.07, found 466.1 $(M+1)^+$; 464.1 $(M-1)^-$; LC/MS retention time (Method E): 3.24 minutes. $^1H$ NMR (400 MHz, $CDCl_3$) δ 9.62 (s, 1H), 8.58 (d, J=5.7 Hz, 1H), 8.41 (d, J=5.0 Hz, 1H), 8.34 (s, 1H), 8.26 (s, 1H), 7.02-6.89 (m, 2H), 6.88 (s, 1H), 6.58 (d, J=1.6 Hz, 1H), 3.91 (d, J=2.0 Hz, 3H), 2.29 (d, J=2.4 Hz, 3H) ppm.

Example 166

4-[[3-(Cyclopropoxy)-6-(3,4-Difluoro-2-Methoxy-Phenoxy)-2-Fluoro-Benzoyl]Amino]Pyridine-2-Carboxamide (374)

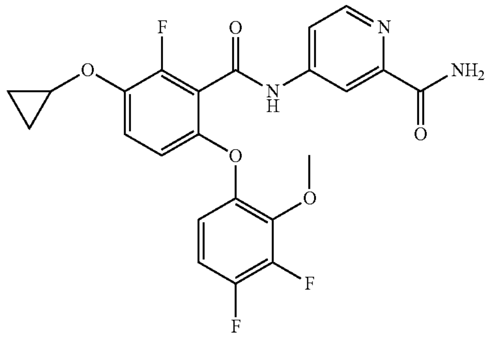 [SMILES: COc1c(Oc2ccc(OC3CC3)c(F)c2C(=O)Nc2ccnc(C(N)=O)c2)ccc(F)c1F]

Step 1: 4-Bromo-1-(Cyclopropoxy)-2-Fluoro-Benzene

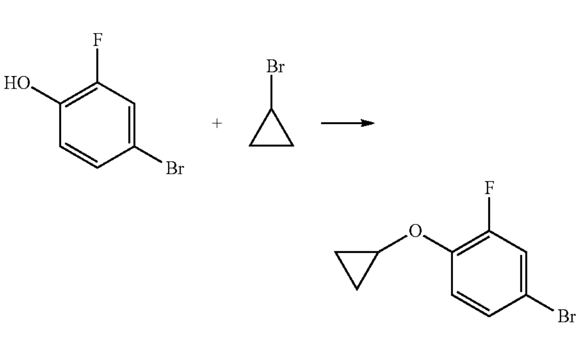

To a stirring solution of 4-bromo-2-fluoro-phenol (400 mg, 0.0021 mol) in NMP (8 mL) at room temperature were added $Cs_2CO_3$ (651 mg, 0.0020 mol) followed by bromocyclopropane (373 mg, 0.0030 mol). The mixture was heated at 150° C. for 16 hours. The cooled mixture was diluted with water and extracted with diethyl ether (2×15 mL). The organic extracts were concentrated in vacuo and purified by silica gel chromatography (100% hexanes) to provide 4-bromo-1-(cyclopropoxy)-2-fluoro-benzene (145 mg, 27%) as a colorless liquid. $^1H$ NMR (400 MHz, $CDCl_3$) δ 7.26-7.13 (m, 3H), 3.8-3.76 (m, 1H), 0.86-0.76 (m, 4H) ppm.

Step 2: 6-Bromo-3-(Cyclopropoxy)-2-Fluoro-Benzoic Acid

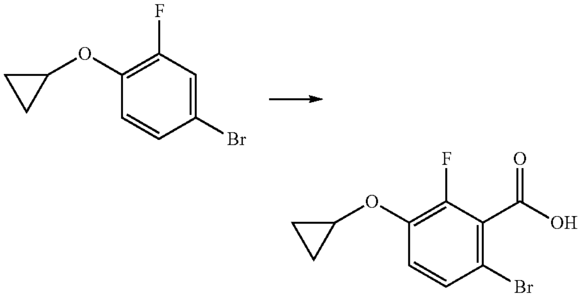

To a stirring solution of 4-bromo-1-(cyclopropoxy)-2-fluoro-benzene (500 mg, 0.0020 mol) in THF (5.0 mL) was added LDA (3.7 mL of 2 M, 0.0074 mol) at −78° C. The mixture was allowed to warm to room temperature and stirred for 1 hour, then cooled to −78° C. and treated with solid carbon dioxide (dry ice, ~3.0 g). The mixture was stirred for 30 minutes at −78° C. then allowed to warm to room temperature and stirred for 30 minutes. The mixture was diluted with water (30 mL) and washed with diethyl ether (20 mL). The aqueous layer was acidified with 1 M aqueous HCl until pH=2 and extracted with ethyl acetate (3×25 mL). The combined extracts were dried over $Na_2SO_4$, filtered and concentrated in vacuo to provide 6-bromo-3-(cyclopropoxy)-2-fluoro-benzoic acid (350 mg, 62%). $^1H$ NMR (400 MHz, DMSO-$d_6$) δ 14.01 (br s, 1H), 7.5-7.39 (m, 2H), 4.02-3.97 (m, 1H), 0.85-0.7 (m, 4H) ppm.

Step 3: 3-(Cyclopropoxy)-6-(3,4-Difluoro-2-Methoxy-Phenoxy)-2-Fluoro-Benzoic Acid

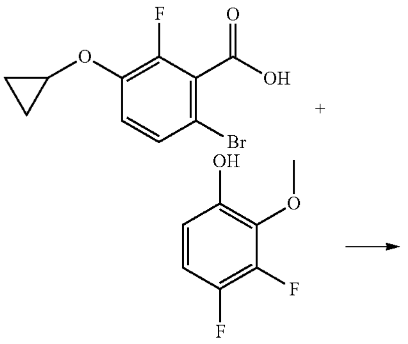

-continued

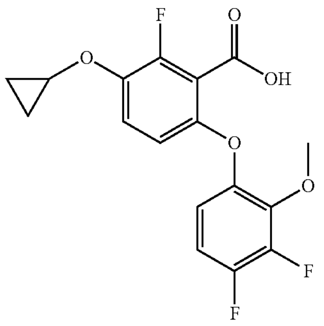

A mixture of 6-bromo-3-(cyclopropoxy)-2-fluoro-benzoic acid (120 mg, 0.4363 mmol), 3,4-difluoro-2-methoxy-phenol (70 mg, 0.44 mmol) and $Cs_2CO_3$ (285 mg, 0.875 mmol) in toluene (2 mL) was bubbled with nitrogen for 5 minutes, then treated with copper (I) iodide (20 mg, 0.11 mmol). The reaction vial was sealed and the mixture heated at 100° C. for 90 minutes. The mixture was cooled to room temperature and partitioned between ethyl acetate and water. The aqueous layer was acidified to pH=1 and the layers separated. The aqueous layer was extracted with additional ethyl acetate (2×). The combined extracts were washed with brine, dried over $Na_2SO_4$, filtered and the concentrated in vacuo. Purification by silica gel chromatography (0-100% ethyl acetate/heptane), followed by additional purification by silica gel chromatography (0-50% ethyl acetate/heptane) provided 3-(cyclopropoxy)-6-(3,4-difluoro-2-methoxy-phenoxy)-2-fluoro-benzoic acid (124 mg, 80%). ESI-MS m z calc. 354.07, ionization not observed; LC/MS retention time (Method F): 0.63 minutes. $^1$H NMR (500 MHz, DMSO-$d_6$) δ 13.24 (br s, 1H), 7.62 (td, J=8.0, 1.7 Hz, 1H), 7.39 (ddd, J=7.9, 6.2, 1.6 Hz, 1H), 7.23 (td, J=8.1, 1.3 Hz, 1H), 6.95 (dd, J=11.3, 8.8 Hz, 1H), 3.97 (tt, J=6.2, 3.0 Hz, 1H), 3.87 (s, 3H), 0.88-0.76 (m, 2H), 0.75-0.66 (m, 2H) ppm.

Step 4: Methyl 4-[[3-(Cyclopropoxy)-6-(3,4-Difluoro-2-Methoxy-Phenoxy)-2-Fluoro-Benzoyl] Amino]Pyridine-2-Carboxylate

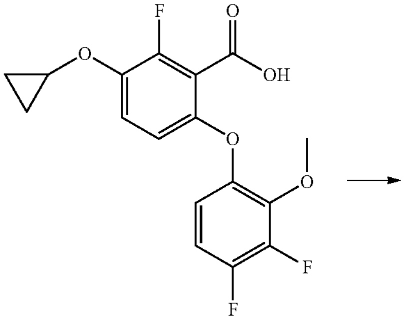

-continued

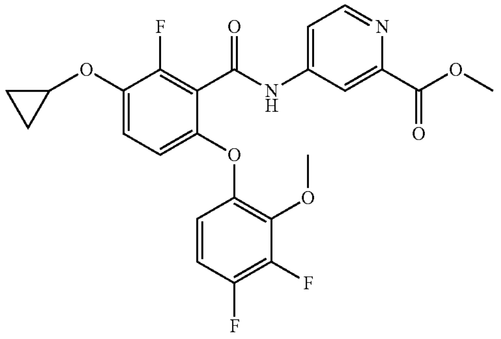

A solution of 3-(cyclopropoxy)-6-(3,4-difluoro-2-methoxy-phenoxy)-2-fluoro-benzoic acid (275 mg, 0.776 mmol) and DMF (5 μL) in dichloromethane (2 mL) at 0° C. was treated dropwise with oxalyl chloride (150 μL, 1.72 mmol) and stirred for 1 hour. The mixture was concentrated in vacuo, then diluted and evaporated twice with dichloromethane. The residue was dissolved in dichloromethane (2 mL) and added to a mixture of methyl 4-aminopyridine-2-carboxylate (120 mg, 0.789 mmol) and TEA (450 μL, 3.23 mmol) in dichloromethane at 0° C. The mixture was allowed to warm to room temperature over 18 hours, and then diluted with water (1 mL) and the phases separated. The organic phase was concentrated and the residue purified by silica gel chromatography (0-100% ethyl acetate/heptane) to provide methyl 4-[[3-(cyclopropoxy)-6-(3,4-difluoro-2-methoxy-phenoxy)-2-fluoro-benzoyl]amino]pyridine-2-carboxylate (124 mg, 33%). ESI-MS m z calc. 488.12, found 489.0 $(M+1)^+$; 487.0 $(M-1)^-$; LC/MS retention time (Method F): 0.89 minutes. $^1$H NMR (500 MHz, DMSO-$d_6$) δ 11.36 (s, 1H), 8.61 (t, J=5.6 Hz, 1H), 8.36 (d, J=2.0 Hz, 1H), 7.83-7.76 (m, 1H), 7.48 (t, J=9.3 Hz, 1H), 7.17 (q, J=9.4 Hz, 1H), 6.93-6.85 (m, 1H), 6.77 (dd, J=9.1, 1.6 Hz, 1H), 4.02-3.96 (m, 1H), 3.87 (s, 3H), 3.82 (d, J=0.8 Hz, 3H), 0.88-0.69 (m, 4H) ppm.

Step 5: 4-[[3-(Cyclopropoxy)-6-(3,4-Difluoro-2-Methoxy-Phenoxy)-2-Fluoro-Benzoyl]Amino]Pyridine-2-Carboxamide (374)

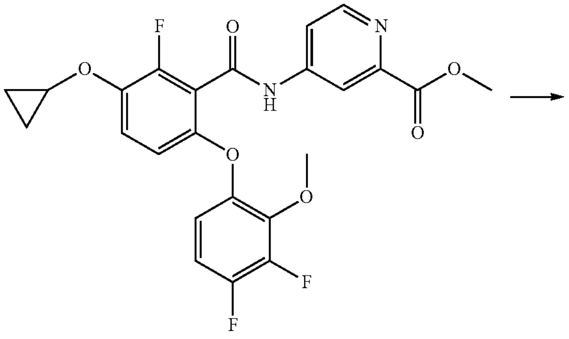

-continued

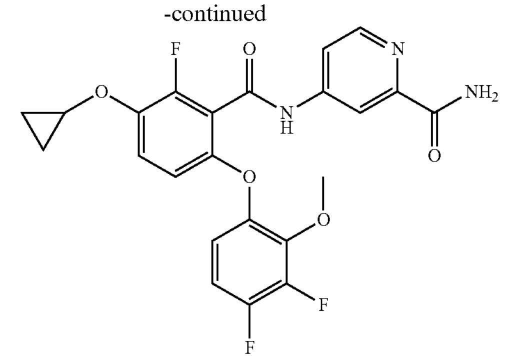

Methyl 4-[[3-(cyclopropoxy)-6-(3,4-difluoro-2-methoxy-phenoxy)-2-fluoro-benzoyl]amino]pyridine-2-carboxylate (124 mg, 0.254 mmol) was dissolved in a solution of ammonia in methanol (1 mL of 7 M, 7 mmol) and stirred overnight. The mixture was concentrated in vacuo and purified by reverse phase HPLC (47-95% acetonitrile/0.1% ammonium hydroxide) to provide 4-[[3-(cyclopropoxy)-6-(3,4-difluoro-2-methoxy-phenoxy)-2-fluoro-benzoyl]amino]pyridine-2-carboxamide (15.2 mg, 13%) as a white solid. ESI-MS m z calc. 473.12, found 474.9 $(M+1)^+$; 472.0 $(M-1)^-$; LC/MS retention time (Method E): 2.97 minutes. $^1H$ NMR (500 MHz, DMSO-$d_6$) δ 11.30 (s, 1H), 8.52 (d, J=5.5 Hz, 1H), 8.30 (d, J=2.2 Hz, 1H), 8.07 (d, J=2.8 Hz, 1H), 7.79 (dd, J=5.5, 2.2 Hz, 1H), 7.63 (d, J=2.9 Hz, 1H), 7.47 (t, J=9.3 Hz, 1H), 7.23-7.13 (m, 1H), 6.90 (ddd, J=9.4, 5.0, 2.2 Hz, 1H), 6.76 (dd, J=9.2, 1.7 Hz, 1H), 3.99 (tt, J=5.9, 2.9 Hz, 1H), 3.83 (d, J=0.8 Hz, 3H), 0.84-0.77 (m, 2H), 0.77-0.68 (m, 2H) ppm. $^{19}F$ NMR (471 MHz, DMSO-$d_6$) δ −135.78, −140.97 (d, J=20.9 Hz), −152.88 (d, J=21.5 Hz) ppm.

Example 167

N-(2-Carbamoyl-4-Pyridyl)-5-(3,4-Difluoro-2-Methoxy-Phenoxy)-3-Methyl-2-(Trifluoromethyl) Pyridine-4-Carboxamide (375)

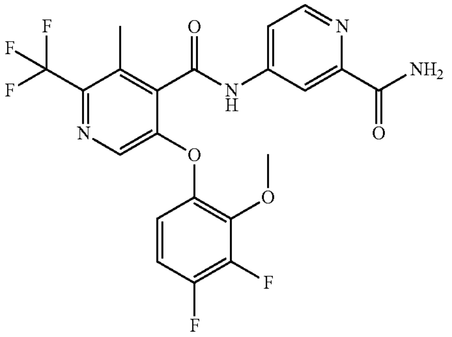 [SMILES: COc1c(Oc2cnc(C(F)(F)F)c(C)c2C(=O)Nc2ccnc(C(N)=O)c2)ccc(F)c1F]

Step 1: 5-Fluoro-3-Methyl-2-(Trifluoromethyl)Pyridine

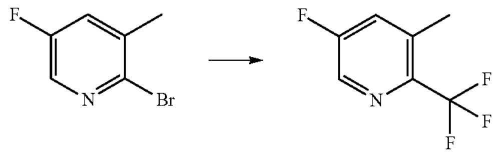

2-Bromo-5-fluoro-3-methyl-pyridine (7.0 g, 37 mmol) was dissolved in dry NMP (100 mL) under a nitrogen atmosphere. Copper(I) iodide (9.1 g, 48 mmol) was added followed by methyl 2,2-difluoro-2-fluorosulfonyl-acetate (17.7 g, 11.7 mL, 92.1 mmol). The mixture was heated at 84° C. overnight with an attached condenser. The mixture was cooled to room temperature and the product was isolated by distillation (8.5 mbar, bath temperature 95° C.) as a light yellow oil. The oil was diluted in diethyl ether and washed with saturated aqueous $NaHCO_3$, dried over $MgSO_4$ and concentrated in vacuo to afford 5-fluoro-3-methyl-2-(trifluoromethyl)pyridine (6.11 g, 93%) as a colorless oil. $^1H$ NMR (400 MHz, $CDCl_3$) δ 8.36 (d, J=2.6 Hz, 1H), 7.38 (dd, J=8.6, 2.7 Hz, 1H), 2.53 (d, J=1.9 Hz, 3H) ppm.

Step 2: 5-Fluoro-3-Methyl-2-(Trifluoromethyl)Pyridine-4-Carboxylic Acid

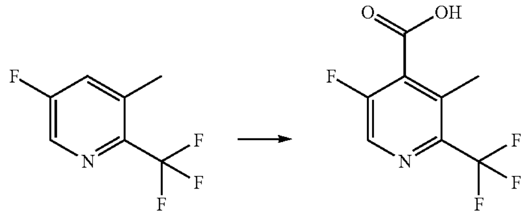

A solution of diisopropylamine (14.5 mL, 104 mmol) in THF (85 mL) was cooled to −20° C. A solution of n-butyllithium (38 mL of 2.5 M in hexanes, 95 mmol) was added at a rate to maintain internal temperature below −15° C. After the addition was complete, the cooling bath was removed and the mixture was allowed to warm to 0° C., and then cooled back to −74° C. A solution of 5-fluoro-3-methyl-2-(trifluoromethyl)pyridine (12.83 g, 71.63 mmol) in THF (40 mL) was added over 30 minutes while maintaining the internal temperature below −70° C. After the addition was complete, the mixture was stirred for 30 minutes at −78° C. then poured into a beaker containing excess solid carbon dioxide (dry ice) in anhydrous THF. The mixture was allowed to warm to room temperature and stirred until no more effervescence was observed. The mixture was basified with 2 M aqueous NaOH and diluted with water and ethyl acetate. The aqueous phase was separated and washed with additional ethyl acetate. The aqueous phase was then acidified with 6 M aqueous HCl (to pH=0) and extracted with ethyl acetate (2×). The combined organic extracts were dried over $MgSO_4$, filtered and concentrated in vacuo to provide 5-fluoro-3-methyl-2-(trifluoromethyl)pyridine-4-carboxylic acid (11.14 g, 70% yield). $^1H$ NMR (400 MHz, DMSO-$d_6$) δ 14.74 (br s, 1H), 8.78 (s, 1H), 2.53-2.48 (m, 3H) ppm.

Step 3: Methyl 4-[[5-Fluoro-3-Methyl-2-(Trifluoromethyl)Pyridine-4-Carbonyl]Amino]Pyridine-2-Carboxylate

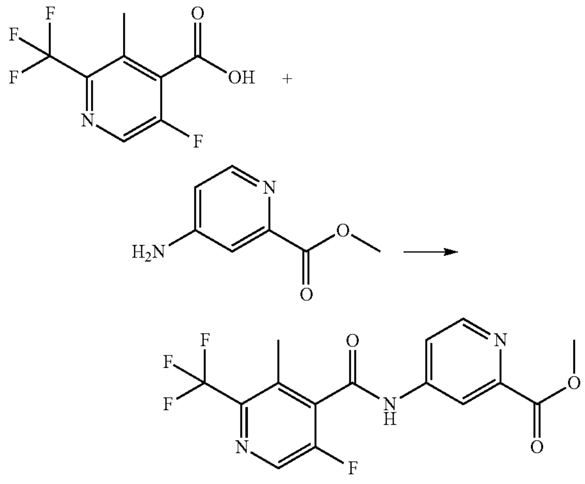

A solution of 5-fluoro-3-methyl-2-(trifluoromethyl)pyridine-4-carboxylic acid (500 mg, 2.24 mmol) and DMF (5 μL) in 2-MeTHF (2 mL) at 0° C. was treated dropwise with oxalyl chloride (350 μL, 4.01 mmol) over 10 minutes, allowing the bubbles to subside between additions. The mixture was stirred at 0° C. for 30 minutes. The mixture was concentrated in vacuo, then diluted and evaporated twice with dichloromethane. The residue was dissolved in 2-MeTHF (2 mL) and added dropwise to a solution of methyl 4-aminopyridine-2-carboxylate (320 mg, 2.10 mmol) and TEA (600 μL, 4.31 mmol) in 2-MeTHF (10 mL) at 0° C. The mixture was allowed to warm to room temperature over 1 hour. The mixture was diluted with water (5 mL) the layers separated. The aqueous layer was extracted with ethyl acetate (2×5 mL), and the combined organics dried over $Na_2SO_4$, filtered and concentrated in vacuo. Purification by silica gel chromatography (0-100% ethyl acetate/heptane) provided methyl 4-[[5-fluoro-3-methyl-2-(trifluoromethyl)pyridine-4-carbonyl]amino]pyridine-2-carboxylate (312 mg, 39%) as an off-white solid. ESI-MS m z calc. 357.07, found 358.0 $(M+1)^+$; 356.0 $(M-1)^-$; LC/MS retention time (Method F): 0.72 minutes. $^1H$ NMR (500 MHz, DMSO-$d_6$) δ 11.56 (s, 1H), 8.82 (s, 1H), 8.66 (s, 1H), 8.37 (s, 1H), 7.81 (s, 1H), 3.89 (s, 3H), 2.47 (d, J=1.9 Hz, 3H) ppm.

Step 4: N-(2-Carbamoyl-4-Pyridyl)-5-Fluoro-3-Methyl-2-(Trifluoromethyl)Pyridine-4-Carboxamide

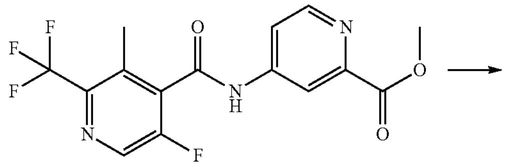

-continued

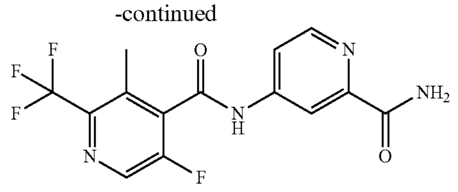

Methyl 4-[[5-fluoro-3-methyl-2-(trifluoromethyl)pyridine-4-carbonyl]amino]pyridine-2-carboxylate (150 mg, 0.420 mmol) was dissolved in methanol (1 mL) and treated with a solution of ammonia in methanol (2 mL of 7 M, 14 mmol). The mixture was stirred for approximately 72 hours, then concentrated in vacuo and purified by reverse phase HPLC (acetonitrile/0.1% ammonium hydroxide gradient) to provide N-(2-carbamoyl-4-pyridyl)-5-fluoro-3-methyl-2-(trifluoromethyl)pyridine-4-carboxamide (43 mg, 30%) as a white solid. ESI-MS m z calc. 342.07, found 343.0 $(M+1)^+$; 341.0 $(M-1)^-$; LC/MS retention time (Method F): 0.67 minutes. $^1H$ NMR (500 MHz, DMSO-$d_6$) δ 11.50 (s, 1H), 8.82 (s, 1H), 8.59 (d, J=5.5 Hz, 1H), 8.32 (d, J=2.2 Hz, 1H), 8.11 (s, 1H), 7.80 (s, 1H), 7.67 (s, 1H), 2.47 (q, J=1.9 Hz, 3H) ppm. $^{19}F$ NMR (471 MHz, DMSO-$d_6$) δ −62.35, −62.95 ppm.

Step 5: N-(2-Carbamoyl-4-Pyridyl)-5-(3,4-Difluoro-2-Methoxy-Phenoxy)-3-Methyl-2-(Trifluoromethyl) Pyridine-4-Carboxamide (375)

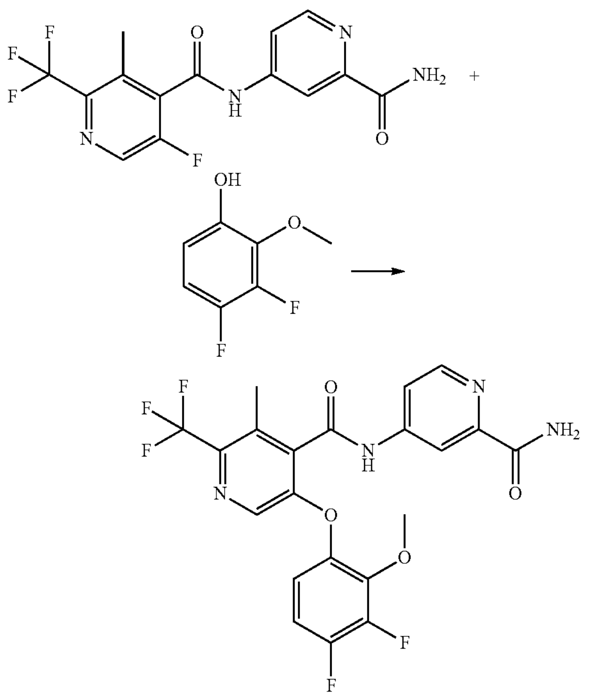

N-(2-carbamoyl-4-pyridyl)-5-fluoro-3-methyl-2-(trifluoromethyl)pyridine-4-carboxamide (45 mg, 0.13 mmol), 3,4-difluoro-2-methoxy-phenol (20 mg, 0.13 mmol) and $Cs_2CO_3$ (100 mg, 0.307 mmol) were combined in acetonitrile (2 mL) and heated to 90° C. overnight. The cooled mixture was diluted with water to dissolve the solids and purified directly by reverse phase HPLC (38-53% acetonitrile/0.1% ammonium hydroxide) to provide N-(2-carbamoyl-4-pyridyl)-5-(3,4-difluoro-2-methoxy-phenoxy)-3-methyl-2-(trifluoromethyl)pyridine-4-carboxamide (17.8 mg, 28%) as a white solid. ESI-MS m z calc. 482.10, found 483.0 $(M+1)^+$; 481.0 $(M-1)^-$; LC/MS retention time (Method E): 2.92 minutes. H NMR (500 MHz, DMSO-$d_6$) δ 11.42 (s, 1H), 8.49 (d, J=5.3 Hz, 1H), 8.27 (s, 1H), 8.14 (s, 1H), 8.06 (d, J=3.0 Hz, 1H), 7.74 (s, 1H), 7.60 (s, 1H), 7.29-7.18 (m, 1H), 7.11 (ddd, J=9.3, 5.0, 2.1 Hz, 1H), 3.85 (d, J=1.1 Hz, 3H), 2.45 (d, J=2.0 Hz, 3H) ppm. $^{19}F$ NMR (471 MHz, DMSO-$d_6$) δ −62.61, −138.96, −152.18 ppm.

Example 168

4-[[6-(3,4-Difluoro-2-Methoxy-Phenoxy)-2-Fluoro-3-Methoxy-4-(Trifluoromethyl)Benzoyl]Amino]-5-Methyl-Pyridine-2-Carboxamide (376)

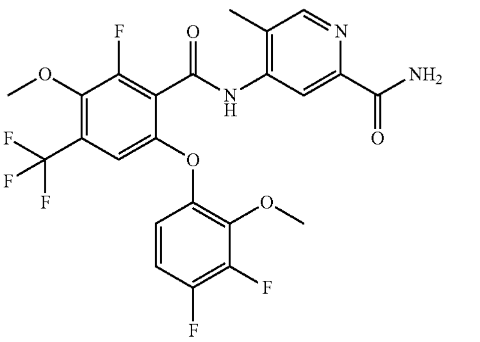 [SMILES: COc1c(Oc2cc(C(F)(F)F)c(OC)c(F)c2C(=O)Nc2cc(C(N)=O)ncc2C)ccc(F)c1F]

Step 1: 6-Bromo-2-Fluoro-3-Methoxy-4-(Trifluoromethyl)Benzoic Acid

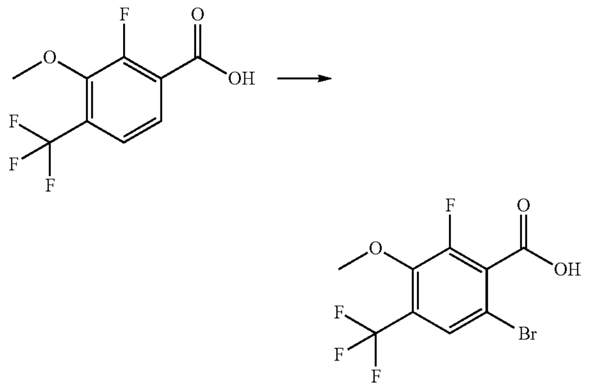

A solution of 2-fluoro-3-methoxy-4-(trifluoromethyl)benzoic acid (10 g, 42 mmol, see Example 94, Step 2) in trifluoroacetic acid (20 mL) and sulfuric acid (5 mL) was treated with N-bromosuccinimide (11.2 g, 62.9 mmol) in one portion and the mixture stirred at room temperature for 2.5 hours. The resulting thick slurry was diluted with dichloromethane (20 mL) and treated with water (20 mL, exotherm observed). The phases were separated and the aqueous layer extracted with additional dichloromethane (4×20 mL). The organic extracts were combined, diluted with heptane (50 mL) and cooled in an ice water bath. The resulting white crystals were collected by filtration to provide 11.94 g of solid. The solid was slurried in ice-cold dichloromethane (50 mL) and filtered to provide 5.15 g of 6-bromo-2-fluoro-3-methoxy-4-(trifluoromethyl)benzoic acid. An additional crop of product (1.9 g) was obtained by slurring and filtering the concentrated mother liquors in ice-cold heptane. The mother liquor was concentrated in vacuo and purified by silica gel chromatography. (0-100% ethyl acetate/heptane) to provide 7 g of product. All the product solids were then combined in ethyl acetate and concentrated in vacuo to provide 6-bromo-2-fluoro-3-methoxy-4-(trifluoromethyl) benzoic acid (12.77 g, 96%). $^1H$ NMR (400 MHz, $CDCl_3$) δ 7.65 (dd, J=1.9, 0.7 Hz, 1H), 5.32 (s, 1H), 4.07 (d, J=2.3 Hz, 3H) ppm. ESI-MS m z calc. 315.94, no ionization detected; LC/MS retention time (Method F): 0.41 minutes.

Step 2: 6-(3,4-Difluoro-2-Methoxy-Phenoxy)-2-Fluoro-3-Methoxy-4-(Trifluoromethyl)Benzoic Acid

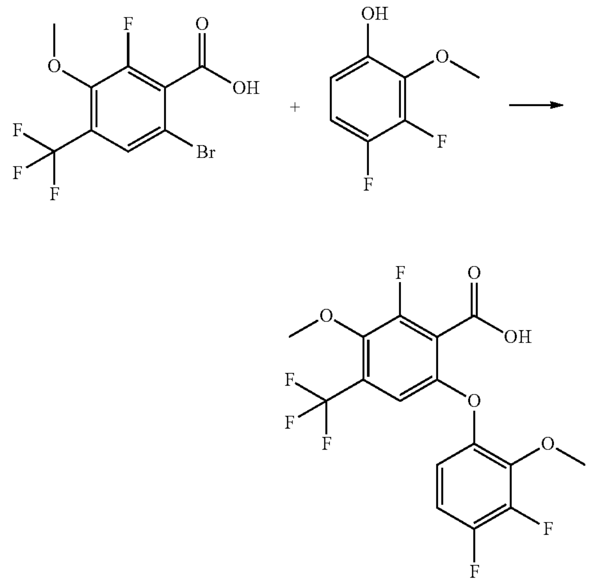

A solution of 6-bromo-2-fluoro-3-methoxy-4-(trifluoromethyl)benzoic acid (2.000 g, 6.309 mmol), 3,4-difluoro-2-methoxy-phenol (1.002 g, 6.258 mmol) and $Cs_2CO_3$ (2.275 g, 6.982 mmol) in toluene (12 mL) was flushed with nitrogen for 10 minutes. Copper (I) iodide (480 mg, 2.52 mmol) was added and the mixture heated at 100° C. under nitrogen for 20 hours. The cooled mixture was partitioned between ethyl acetate (100 mL) and water (100 mL), and the aqueous layer washed with additional ethyl acetate (2×100 mL). The aqueous layer was acidified to pH=3 with 2 M aqueous HCl and extracted with ethyl acetate (3×100 mL). The combined organic layers were dried over $MgSO_4$, filtered and concentrated in vacuo. Purification by silica gel chromatography (0-30% ethyl acetate/heptane gradient, followed by elution with 3:1 ethyl acetate/ethanol) provided 6-(3,4-difluoro-2-methoxy-phenoxy)-2-fluoro-3-methoxy-4-(trifluoromethyl) benzoic acid (333 mg, 13%). ESI-MS m z calc. 396.04, found 395.1 $(M-1)^-$; LC/MS retention time (Method F): 0.6 minutes. $^1H$ NMR (500 MHz, DMSO-$d_6$) δ 7.20 (q, J=9.7 Hz, 1H), 6.98-6.93 (m, 1H), 6.91 (s, 1H), 3.94 (d, J=1.4 Hz, 3H), 3.88 (d, J=0.9 Hz, 3H) ppm.

Step 3: Methyl 4-[[6-(3,4-Difluoro-2-Methoxy-Phenoxy)-2-Fluoro-3-Methoxy-4-(Trifluoromethyl)Benzoyl]Amino]-5-Methyl-Pyridine-2-Carboxylate

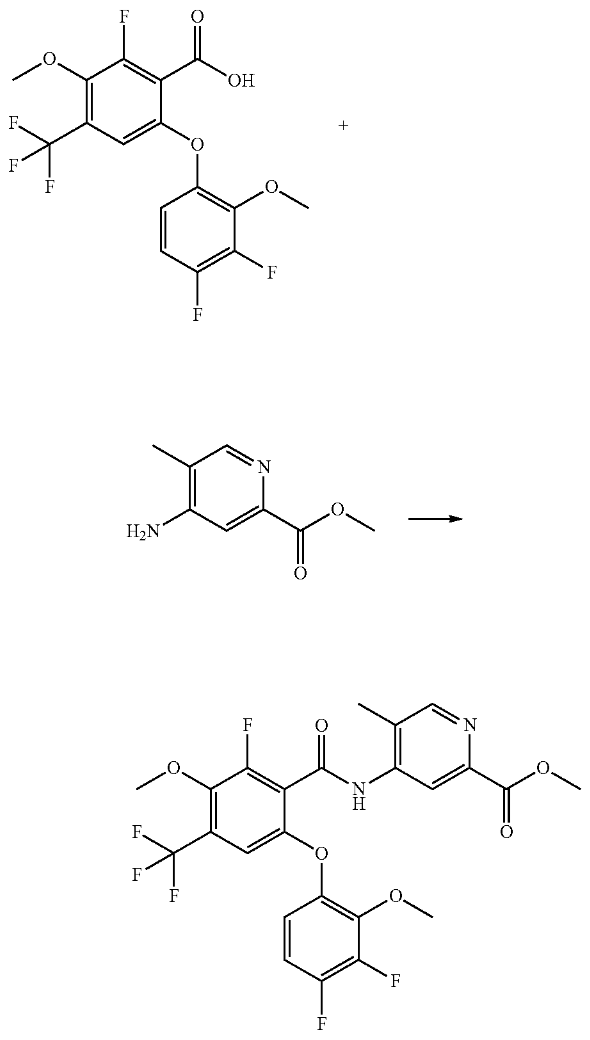

A solution of 6-(3,4-difluoro-2-methoxy-phenoxy)-2-fluoro-3-methoxy-4-(trifluoromethyl)benzoic acid (125 mg, 0.316 mmol) in 2-MeTHF (5 mL) and DMF (3 μL, 0.04 mmol) was treated with oxalyl chloride (55 μL, 0.63 mmol). The mixture warmed to room temperature and stirred for 30 minutes, then concentrated in vacuo. The residue was dissolved in 2-MeTHF (3 mL) and NMP (1 mL), then added to a solution of methyl 4-amino-5-methyl-pyridine-2-carboxylate (57.1 mg, 0.344 mmol, Preparation 1) and TEA (200 μL, 1.44 mmol) in 2-MeTHF (3 mL) at 0° C. The mixture was warmed to room temperature and stirred for 90 minutes. The mixture was diluted with ethyl acetate (30 mL) and washed with water (4×30 mL). The organic layer was dried over $MgSO_4$, filtered and concentrated in vacuo. Purification by silica gel chromatography (0-70% ethyl acetate/heptane) provided methyl 4-[[6-(3,4-difluoro-2-methoxy-phenoxy)-2-fluoro-3-methoxy-4-(trifluoromethyl)benzoyl]amino]-5-methyl-pyridine-2-carboxylate (63 mg, 37%). ESI-MS m z calc. 544.11, found 544.9 $(M+1)^+$; 543.0 $(M-1)^-$; LC/MS retention time (Method F): 0.95 minutes.

Step 4: 4-[[6-(3,4-Difluoro-2-Methoxy-Phenoxy)-2-Fluoro-3-Methoxy-4-(Trifluoromethyl)Benzoyl]Amino]-5-Methyl-Pyridine-2-Carboxamide (376)

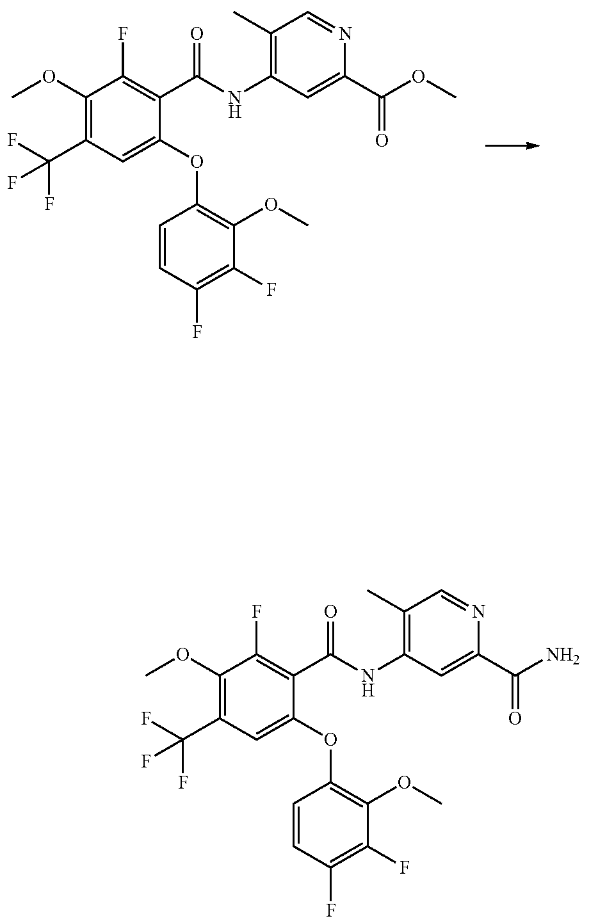

Methyl 4-[[6-(3,4-difluoro-2-methoxy-phenoxy)-2-fluoro-3-methoxy-4-(trifluoromethyl)benzoyl]amino]-5-methyl-pyridine-2-carboxylate (63 mg, 0.12 mmol) was dissolved in a solution of ammonia in methanol (1 mL of 7 M, 7 mmol) and stirred at room temperature for 48 hours. The mixture was concentrated in vacuo and purified by reverse phase HPLC (47-95% acetonitrile/0.1% ammonium hydroxide) to provide 4-[[6-(3,4-difluoro-2-methoxy-phenoxy)-2-fluoro-3-methoxy-4-(trifluoromethyl)benzoyl]amino]-5-methyl-pyridine-2-carboxamide (29 mg, 47%). ESI-MS m z calc. 529.10, found 529.8 $(M+1)^+$; 528.0 $(M-1)^-$; LC/MS retention time (Method E): 3.21 minutes. $^1H$ NMR (500 MHz, DMSO-$d_6$) δ 10.59 (s, 1H), 8.48 (s, 1H), 8.43 (s, 1H), 8.05 (s, 1H), 7.60 (s, 1H), 7.23 (q, J=9.3 Hz, 1H), 7.09-7.01 (m, 1H), 6.96 (s, 1H), 3.99 (d, J=1.3 Hz, 3H), 3.88 (d, J=1.0 Hz, 3H), 2.29 (s, 3H) ppm.

Example 169

5-[[6-(3,4-Difluoro-2-Methoxy-Phenoxy)-2-Fluoro-3-Methoxy-4-(Trifluoromethyl)Benzoyl]Amino] Pyridine-2-Carboxamide (377)

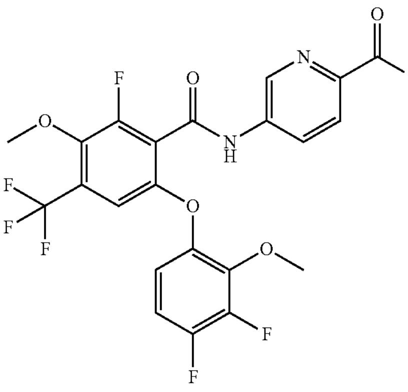

This compound was made in an analogous fashion to the synthesis of compound 376 in Example 168, except employing 5-aminopyridine-2-carboxamide for the amide formation step. The yield of 5-[[6-(3,4-difluoro-2-methoxy-phenoxy)-2-fluoro-3-methoxy-4-(trifluoromethyl)benzoyl] amino]pyridine-2-carboxamide was 45 mg (24%). ESI-MS m z calc. 515.09, found 516.0 $(M+1)^+$; 514.0 (M−1)+; LC/MS retention time (Method E): 3.14 minutes. $^1H$ NMR (500 MHz, DMSO-$d_6$) δ 11.38 (s, 1H), 8.82 (d, J=2.4 Hz, 1H), 8.26 (dd, J=8.6, 2.5 Hz, 1H), 8.06 (d, J=8.5 Hz, 1H), 8.01 (s, 1H), 7.64-7.48 (m, 1H), 7.21 (td, J=9.7, 8.5 Hz, 1H), 7.04 (dt, J=4.5, 2.2 Hz, 1H), 6.98 (d, J=1.5 Hz, 1H), 3.98 (d, J=1.2 Hz, 3H), 3.84 (d, J=1.0 Hz, 3H) ppm.

Example 170

4-[[6-(3,4-Difluoro-2-Methoxy-Phenoxy)-4-Methoxy-2-(Methylamino)-3-(Trifluoromethyl)Benzoyl]Amino]-N-Methyl-Pyridine-2-Carboxamide (378)

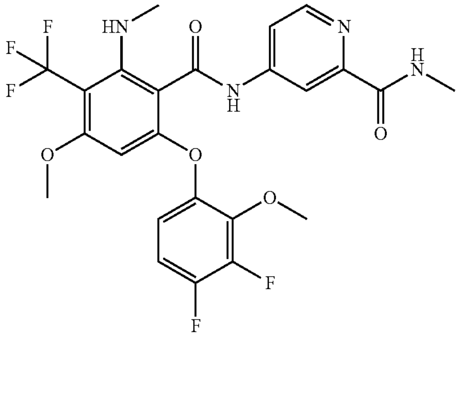

And

Example 171

4-[[6-(3,4-Difluoro-2-Methoxy-Phenoxy)-2-Fluoro-4-Methoxy-3-(Trifluoromethyl)Benzoyl]Amino]-N-Methyl-Pyridine-2-Carboxamide (379)

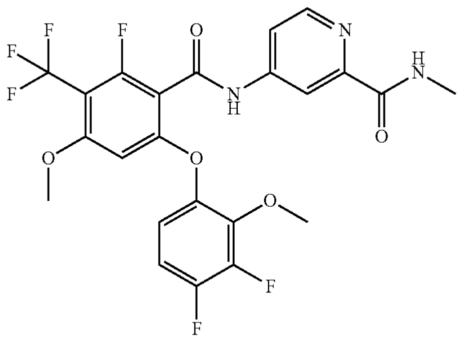

Step 1: 6-(3,4-Difluoro-2-Methoxy-Phenoxy)-2-Fluoro-4-Methoxy-3-(Trifluoromethyl)Benzoic Acid

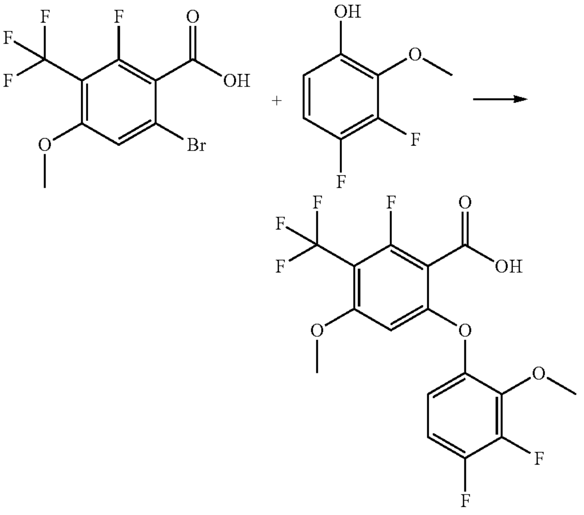

A mixture of 6-bromo-2-fluoro-4-methoxy-3-(trifluoromethyl)benzoic acid (2.15 g, 6.78 mmol, see US 2019/0016671, Example 129, Step 3, which is incorporated by reference), 3,4-difluoro-2-methoxy-phenol (1.0 g, 6.3 mmol) and $Cs_2CO_3$ (2.3 g, 7.1 mmol) in toluene (10 mL) was bubbled with nitrogen for 10 minutes, then copper (I) iodide (456 mg, 2.39 mmol) was added. The mixture was heated at 100° C. under nitrogen with vigorous stirring for 1.5 hours. The cooled mixture was acidified with 1 M aqueous HCl (15 mL), filtered and the aqueous layer extracted with ethyl acetate (3×50 mL). The organic layer was washed with brine, dried over $MgSO_4$, filtered and concentrated in vacuo. Purification by silica gel chromatography (0-100% ethyl acetate/heptane) provided 6-(3,4-difluoro-2-methoxy-phenoxy)-2-fluoro-4-methoxy-3-(trifluoromethyl)benzoic acid (2.105 g, 78%) as an off-white solid.

ESI-MS m z calc. 396.04, found 396.8 $(M+1)^+$; 395.0 $(M-1)^-$; LC/MS retention time (Method F): 0.55 minutes. $^1H$ NMR (500 MHz, DMSO-$d_6$) δ 13.71 (s, 1H), 7.28-7.22 (m, 1H), 7.08 (ddd, J=9.3, 5.1, 2.2 Hz, 1H), 6.41 (s, 1H), 3.89 (d, J=0.9 Hz, 3H), 3.78 (s, 3H) ppm. $^{19}F$ NMR (471 MHz, DMSO-$d_6$) δ −54.63 (d, J=29.9 Hz), −114.37 (q, J=30.3 Hz), −139.34 (d, J=22.0 Hz), −152.12 (d, J=22.0 Hz) ppm.

Step 2: Methyl 4-[[6-(3,4-Difluoro-2-Methoxy-Phenoxy)-2-Fluoro-4-Methoxy-3-(Trifluoromethyl)Benzoyl]Amino]Pyridine-2-Carboxylate

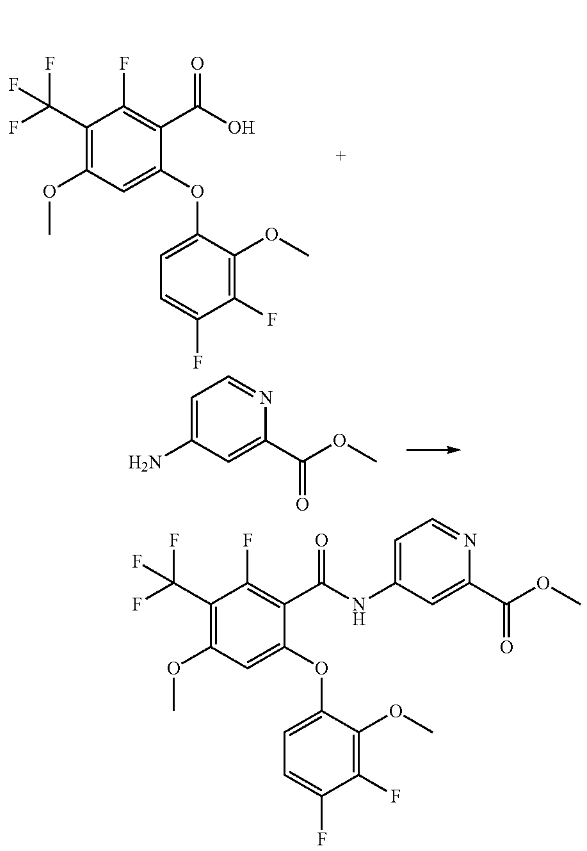

To a solution of 6-(3,4-difluoro-2-methoxy-phenoxy)-2-fluoro-4-methoxy-3-(trifluoromethyl)benzoic acid (500 mg, 1.26 mmol) and DMF (10 μL, 0.13 mmol) in dichloromethane (6 mL) at 0° C. was added oxalyl chloride (250 μL, 2.87 mmol). The mixture was allowed to warm to room temperature over 30 minutes and was then concentrated in vacuo. The residue was dissolved in dichloromethane (3 mL) and added to a solution of methyl 4-aminopyridine-2-carboxylate (240 mg, 1.58 mmol) and TEA (250 μL, 1.79 mmol) in dichloromethane (3 mL) at 0° C. The resulting mixture was stirred and warmed to ambient temperature over 2 hours. The mixture was diluted with aqueous $NH_4Cl$ solution and extracted with dichloromethane (2×5 mL). The combined organic extracts were dried over $MgSO_4$, filtered and concentrated in vacuo. Purification by silica gel chromatography (0-100% ethyl acetate/hexane) provided methyl 4-[[6-(3,4-difluoro-2-methoxy-phenoxy)-2-fluoro-4-methoxy-3-(trifluoromethyl)benzoyl]amino]pyridine-2-carboxylate (200 mg, 30%). ESI-MS m z calc. 530.09, found 531.0 $(M+1)^+$; 529.1 (M−1); LC/MS retention time (Method E): 3.21 minutes.

Step 3: 4-[[6-(3,4-Difluoro-2-Methoxy-Phenoxy)-4-Methoxy-2-(Methylamino)-3-(Trifluoromethyl)Benzoyl]Amino]-N-Methyl-Pyridine-2-Carboxamide (378) and 4-[[6-(3,4-Difluoro-2-Methoxy-Phenoxy)-2-Fluoro-4-Methoxy-3-(Trifluoromethyl)Benzoyl]Amino]-N-Methyl-Pyridine-2-Carboxamide (379)

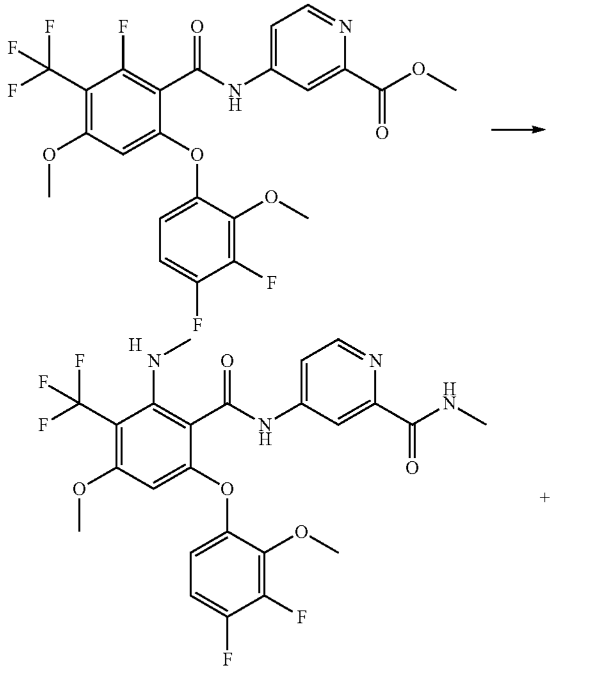

378

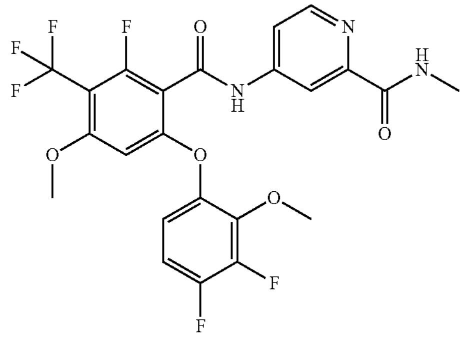 [SMILES: CNC(=O)c1cc(NC(=O)c2c(Oc3ccc(F)c(F)c3OC)cc(OC)c(C(F)(F)F)c2F)ccn1]

379

Methyl 4-[[6-(3,4-difluoro-2-methoxy-phenoxy)-2-fluoro-4-methoxy-3-(trifluoromethyl)benzoyl]amino]pyridine-2-carboxylate (100 mg, 0.189 mmol) was dissolved in a solution of $MeNH_2$ in methanol (20 mL of 2 M, 40 mmol) and stirred for 60 hours at room temperature. The mixture was concentrated in vacuo and the residue purified by reverse phase HPLC (0-100% acetonitrile/0.05% trifluoroacetic acid) to afford the following two compounds:

4-[[6-(3,4-difluoro-2-methoxy-phenoxy)-4-methoxy-2-(methylamino)-3-(trifluoromethyl)benzoyl]amino]-N-methyl-pyridine-2-carboxamide (378) (16.3 mg, 16%). ESI-MS m/z calc. 540.14, found 541.1 $(M+1)^+$; 539.2 $(M-1)^-$; LC/MS retention time (Method E): 3.12 minutes. $^1H$ NMR (500 MHz, DMSO-$d_6$) δ 11.09 (s, 1H), 8.71 (d, J=4.9 Hz, 1H), 8.49 (d, J=5.5 Hz, 1H), 8.30 (d, J=2.5 Hz, 1H), 7.84 (dd, J=5.4, 2.1 Hz, 1H), 7.27-7.12 (m, 1H), 7.06-6.89 (m, 1H), 5.85 (s, 1H), 5.60 (s, 1H), 3.81 (s, 3H), 3.65 (s, 3H), 2.84 (s, 3H), 2.81 (d, J=4.9 Hz, 3H) ppm; and 4-[[6-(3,4-difluoro-2-methoxy-phenoxy)-2-fluoro-4-methoxy-3-(trifluoromethyl)benzoyl]amino]-N-methyl-pyridine-2-carboxamide (379) (2.7 mg, 3%). ESI-MS m/z calc. 529.11, found 530.1 $(M+1)^+$; 528.2 $(M-1)^-$; LC/MS retention time (Method E): 3.18 minutes. $^1H$ NMR (400 MHz, DMSO-$d_6$) δ 11.34 (s, 1H), 8.82-8.73 (m, 1H), 8.55 (d, J=5.5 Hz, 1H), 8.27 (d, J=2.2 Hz, 1H), 7.84 (dd, J=5.8, 2.2 Hz, 1H), 7.25 (q, J=9.3 Hz, 1H), 7.20-7.08 (m, 1H), 6.44 (s, 1H), 3.86 (s, 3H), 3.81 (s, 3H), 2.82 (d, J=4.7 Hz, 3H) ppm.

Example 172

5-[[6-(3,4-Difluoro-2-Methoxy-Phenoxy)-2-Fluoro-4-Methoxy-3-(Trifluoromethyl)Benzoyl]Amino] Pyrimidine-2-Carboxamide (380)

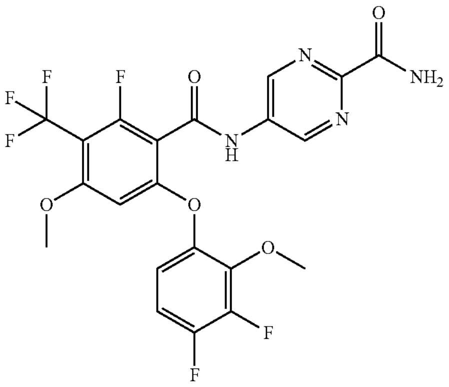 [SMILES: COc1cc(Oc2ccc(F)c(F)c2OC)c(C(=O)Nc2cnc(C(N)=O)nc2)c(F)c1C(F)(F)F]

This compound was made in an analogous fashion to Example 171, except employing methyl 5-aminopyrimidine-2-carboxylate for the amide formation step. The yield of methyl 5-[[6-(3,4-difluoro-2-methoxy-phenoxy)-2-fluoro-4-methoxy-3-(trifluoromethyl)benzoyl]amino]pyrimidine-2-carboxylate was 195 mg (36%). ESI-MS m z calc. 531.09, found 532.0 $(M+1)^+$; 530.0 (M−1)+; LC/MS retention time (Method F): 0.9 minutes. $^1H$ NMR (500 MHz, DMSO-$d_6$) δ 11.51 (s, 1H), 9.20 (s, 2H), 7.24 (q, J=9.3 Hz, 1H), 7.12 (d, J=8.4 Hz, 1H), 6.48 (d, J=20.6 Hz, 1H), 3.89 (s, 3H), 3.86 (d, J=1.3 Hz, 3H), 3.81 (s, 3H) ppm.

Analogous treatment with methanolic ammonia provided 5-[[6-(3,4-difluoro-2-methoxy-phenoxy)-2-fluoro-4-methoxy-3-(trifluoromethyl)benzoyl]amino]pyrimidine-2-carboxamide (38 mg, 19%). ESI-MS m/z calc. 516.09, found 517.1 $(M+1)^+$; 515.1 $(M-1)^-$; LC/MS retention time (Method E): 2.84 minutes. $^1H$ NMR (500 MHz, DMSO-$d_6$) δ 11.41 (s, 1H), 9.15 (s, 2H), 8.11 (s, 1H), 7.71 (s, 1H), 7.29-7.19 (m, 1H), 7.12 (ddd, J=9.4, 5.1, 2.1 Hz, 1H), 6.47 (s, 1H), 3.87 (d, J=1.1 Hz, 3H), 3.81 (s, 3H) ppm.

Example 173

5-[[6-(3,4-Difluoro-2-Methoxy-Phenoxy)-2-Fluoro-4-Methoxy-3-(Trifluoromethyl)Benzoyl]Amino] Pyridine-2-Carboxamide (381)

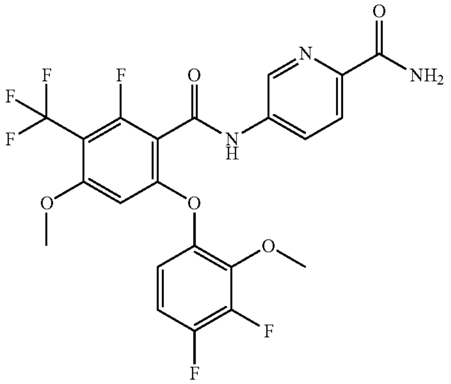 [SMILES: COc1cc(Oc2ccc(F)c(F)c2OC)c(C(=O)Nc2ccc(C(N)=O)nc2)c(F)c1C(F)(F)F]

This compound was made in an analogous fashion to Example 171, except employing 5-aminopyridine-2-carboxamide for the amide formation step. The yield of 5-[[6-(3,4-difluoro-2-methoxy-phenoxy)-2-fluoro-4-methoxy-3-(trifluoromethyl)benzoyl]amino]pyridine-2-carboxamide after purification by silica gel chromatography (0-40% ethyl acetate/hexane) was 47 mg (10%). ESI-MS m z calc. 515.09, found 516.0 $(M+1)^+$; 514.1 (M−1)+; LC/MS retention time (Method E): 3.03 minutes. $^1H$ NMR (500 MHz, DMSO-$d_6$) δ 11.24 (s, 1H), 8.82 (s, 1H), 8.27 (dd, J=8.6, 2.5 Hz, 1H), 8.04 (d, J=8.4 Hz, 2H), 7.58 (s, 1H), 7.25 (q, J=9.4 Hz, 1H), 7.16-7.08 (m, 1H), 6.45 (s, 1H), 3.87 (d, J=1.1 Hz, 3H), 3.81 (s, 3H) ppm.

Example 174

4-(6-(2-Chloro-4-Fluorophenoxy)-2-Fluoro-3-Methoxy-4-(Trifluoromethyl)Benzamido)-5-Methylpicolinamide (382)

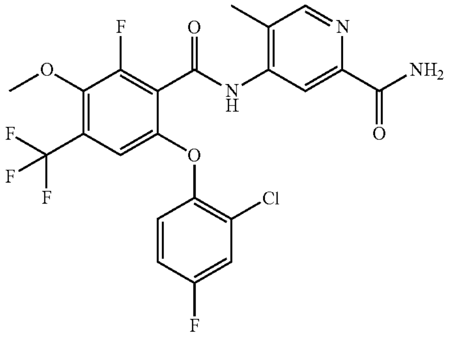 [SMILES: COc1c(C(F)(F)F)cc(Oc2ccc(F)cc2Cl)c(C(=O)Nc2cc(C(N)=O)ncc2C)c1F]

Step 1: 6-(2-Chloro-4-Fluoro-Phenoxy)-2-Fluoro-3-Methoxy-4-(Trifluoromethyl)Benzoic Acid

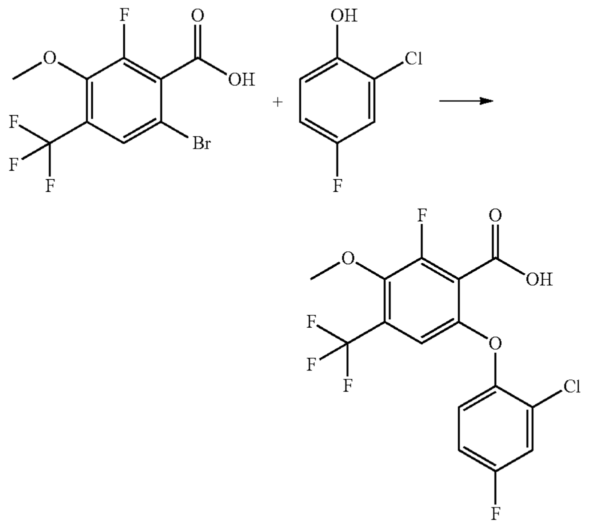

A mixture of 6-bromo-2-fluoro-3-methoxy-4-(trifluoromethyl)benzoic acid (220 mg, 0.694 mmol), 2-chloro-4-fluoro-phenol (80 μL, 0.74 mmol) and $Cs_2CO_3$ (340 mg, 1.044 mmol) in toluene (1 mL) was bubbled with nitrogen for 10 minutes, then copper (I) iodide (50 mg, 0.2625 mmol) was added. The mixture was heated at 125° C. with vigorous stirring for 4 hours under nitrogen. The mixture was cooled to room temperature and acidified with 1 M aqueous HCl (15 mL), filtered and extracted with ethyl acetate (3×50 mL). The combined extracts were washed with brine (10 mL), dried over $MgSO_4$, filtered and concentrated in vacuo. The residue was purified by silica gel chromatography (0-100% ethyl acetate/heptane) to provide 6-(2-chloro-4-fluoro-phenoxy)-2-fluoro-3-methoxy-4-(trifluoromethyl)benzoic acid (120 mg, 43%). ESI-MS m z calc. 382.00, found 380.8 $(M-1)^-$; LC/MS retention time (Method F): 0.74 minutes.

Step 2: 4-(6-(2-Chloro-4-Fluorophenoxy)-2-Fluoro-3-Methoxy-4-(Trifluoromethyl)Benzamido)-5-Methylpicolinamide (382)

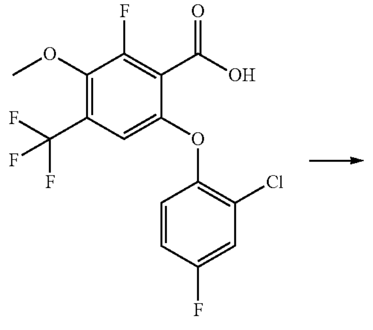

-continued

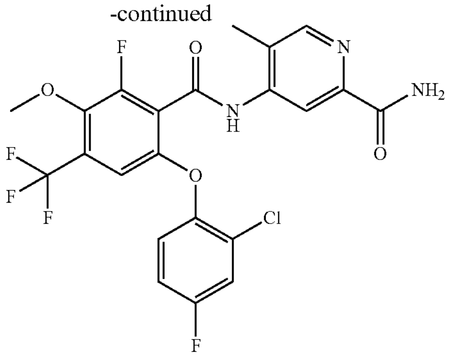

Using 6-(2-chloro-4-fluoro-phenoxy)-2-fluoro-3-methoxy-4-(trifluoromethyl)benzoic acid above, this compound was made in an analogous fashion to steps 3 and 4 of Example 168. ESI-MS m z calc. 515.07, found 515.8 $(M+1)^+$; 513.9 $(M-1)^-$; LC/MS retention time (Method E): 3.8 minutes.

Example 201

4-[(Z)-[(Tert-Butylamino)-Phenylsulfanyl-Methylene]Amino]Pyridine-2-Carboxamide

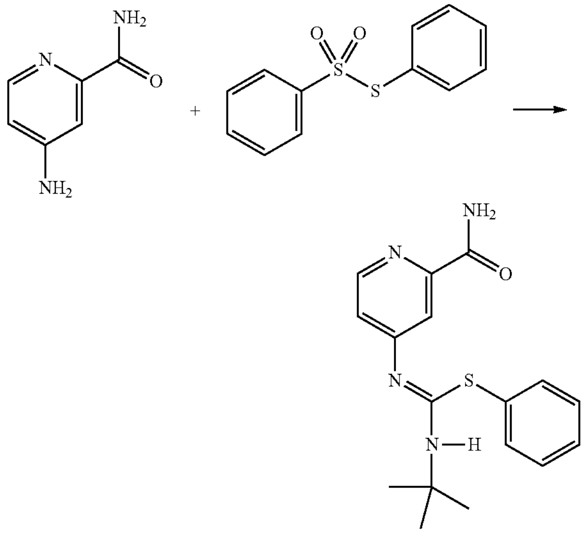

A flask equipped with a reflux condenser was charged with 4-aminopyridine-2-carboxamide (1.12 g, 8.17 mmol), benzenesulfonylsulfanylbenzene (1.85 g, 7.39 mmol), 2-isocyano-2-methyl-propane (3.0 mL, 27 mmol), copper (I) iodide (60 mg, 0.32 mmol) and molecular sieves (2.2 g) in 2-methyltetrahydrofuran (10 mL), and the mixture was heated at 75° C. for 24 hours. The reaction mixture was filtered through Celite and the cake was rinsed with ethyl acetate. The filtrate was concentrated and dried under vacuum. The residue was purified by silica gel chromatography (ethyl acetate/hexanes gradient) to obtain 4-[(Z)-[(tert-butylamino)-phenylsulfanyl-methylene]amino]pyridine-2-carboxamide (1.25 g, 51%). ESI-MS m/z calc. 328.14, found 329.2 $(M+1)^+$; retention time (Method B): 1.07 minutes. $^1H$ NMR (400 MHz, DMSO-d6) δ 8.17 (dd, J=5.3, 0.6 Hz, 1H), 7.94 (d, J=3.0 Hz, 1H), 7.49 (s, 1H), 7.28

(dd, J=2.2, 0.6 Hz, 1H), 7.25-7.17 (m, 5H), 6.74 (dd, J=5.3, 2.2 Hz, 1H), 6.66 (s, 1H), 1.35 (s, 9H) ppm.

Example 202

4-[[4-(Cyclohexen-1-Yl)-2-Fluoro-6-[2-(Trideuteriomethoxy)-4-(Trifluoromethoxy)Phenoxy]Benzoyl]Amino]Pyridine-2-Carboxamide (1001)

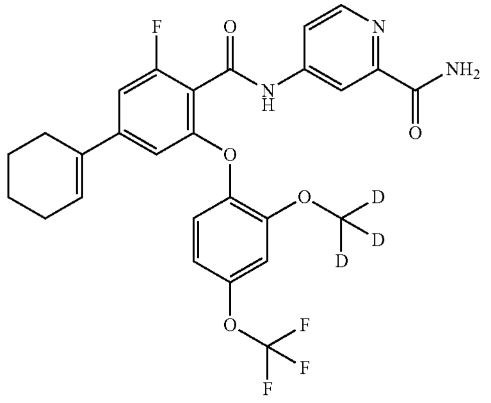 [SMILES: [2H]C([2H])([2H])Oc1cc(OC(F)(F)F)ccc1Oc1cc(C2=CCCCC2)cc(F)c1C(=O)Nc1ccnc(C(N)=O)c1]

Step 1: 1-Bromo-2-(Trideuteriomethoxy)-4-(Trifluoromethoxy)Benzene

2-Bromo-5-(trifluoromethoxy)phenol (57.5 g, 224 mmol) in DMF (400 mL) was treated with $K_2CO_3$ (62 g, 450 mmol), stirred for 15 minutes, and cooled in an ice bath, and iodomethane-d3 (Aldrich, >99.5% D, 15.3 mL, 246 mmol) was added dropwise. The pale yellow suspension was removed from the ice bath and stirred at RT for 16 hours. The suspension was partitioned between water (2 L) and MTBE (500 mL) and separated. The organic phase was washed with 0.5 M NaOH (500 mL) and brine (2×300 mL) and the aqueous phases were back extracted once with MTBE (250 mL). The combined organic phases were dried, filtered and evaporated to give 1-bromo-2-(trideuteriomethoxy)-4-(trifluoromethoxy)benzene (62.4 g, 97%) as a pale yellow liquid. LC/MS retention time (Method B): 1.84 minutes. $^1$H NMR (400 MHz, DMSO-d6) δ 7.71 (d, J=8.7 Hz, 1H), 7.14 (d, J=2.6 Hz, 1H), 6.92 (ddq, J=8.7, 2.5, 1.3 Hz, 1H) ppm.

Step 2: 2-(Trideuteriomethoxy)-4-(Trifluoromethoxy)Phenol

A 1000-mL 3-neck round-bottom flask was fitted with a mechanical stirrer, a heating mantle, a water cooled reflux condenser, temperature probe/controller and a nitrogen inlet/outlet was charged under a nitrogen atmosphere with tetrabutylammonium hydroxide (355 mL of 55% w/w, 730 mmol) and 1-bromo-2-(trideuteriomethoxy)-4-(trifluoromethoxy)benzene (50.0 g, 182 mmol). With stirring, the solution was degassed with nitrogen for 15 minutes. 1,10-Phenanthroline-4,7-diol (3.871 g, 18.24 mmol) was then added as a solid in one portion followed by copper (I) oxide (1.305 g, 9.120 mmol) added as a solid in one portion. After these additions, the gas dispersion tube was removed and the vessel was fitted with a septum. The resulting mixture was then heated to a pot temperature of 100° C. for 15 hours. After cooling to RT, the reaction mixture was poured into ice cold hydrochloric acid (912 mL of 1 M, 912 mmol). The mixture was diluted with ethyl acetate (500 mL) and mixed for several minutes. The phases were separated and the aqueous phase was extracted with ethyl acetate (2×200 mL). The combined organic phases were washed with brine (2×250 mL), dried over $Na_2SO_4$ (200 g), filtered and concentrated. The residue was purified by silica gel chromatography (ethyl acetate/hexanes gradient) to provide 2-(trideuteriomethoxy)-4-(trifluoromethoxy)phenol (33 g, 86%) as a clear pale yellow oil. LC/MS retention time (Method B): 1.38 minutes. $^1$H NMR (400 MHz, DMSO-d6) δ 9.31 (s, 1H), 6.91 (dd, J=2.8, 0.9 Hz, 1H), 6.82 (d, J=8.6 Hz, 1H), 6.79-6.70 (m, 1H) ppm.

Step 3: Methyl 4-Bromo-2-Fluoro-6-[2-(Trideuteriomethoxy)-4-(Trifluoromethoxy)Phenoxy]Benzoate

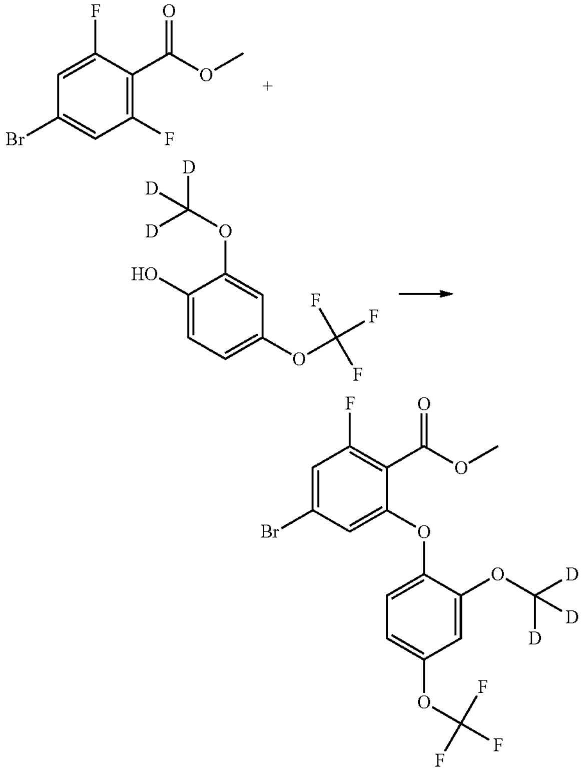

A mixture of $Cs_2CO_3$ (7.89 g, 24.2 mmol), 2-(trideuteriomethoxy)-4-(trifluoromethoxy)phenol (3.54 g, 16.8 mmol) and methyl 4-bromo-2,6-difluoro-benzoate (4.00 g, 15.9 mmol) in DMF (70 mL) was stirred at RT for 20 hours. The reaction was diluted with ethyl acetate and washed with water (3×) and brine. The organic layer was dried over anhydrous $MgSO_4$, filtered and concentrated under reduced pressure. Silica gel chromatography (ethyl acetate/hexanes gradient) provided methyl 4-bromo-2-fluoro-6-[2-(trideuteriomethoxy)-4-(trifluoromethoxy)phenoxy]benzoate (6.09 g, 86%). ESI-MS m/z calc. 440.99, found 443.1 $(M+1)^+$; Retention time (Method A): 0.82 minutes. $^1$H NMR (400 MHz, DMSO-d6) δ 7.47 (dd, J=9.0, 1.7 Hz, 1H), 7.26 (d, J=8.8 Hz, 1H), 7.24 (d, J=2.8 Hz, 1H), 7.00 (ddd, J=8.8, 2.7, 1.3 Hz, 1H), 6.73 (t, J=1.5 Hz, 1H), 3.83 (s, 3H) ppm.

Step 4: 4-Bromo-2-Fluoro-6-[2-(Trideuteriomethoxy)-4-(Trifluoromethoxy)Phenoxy]Benzoic Acid

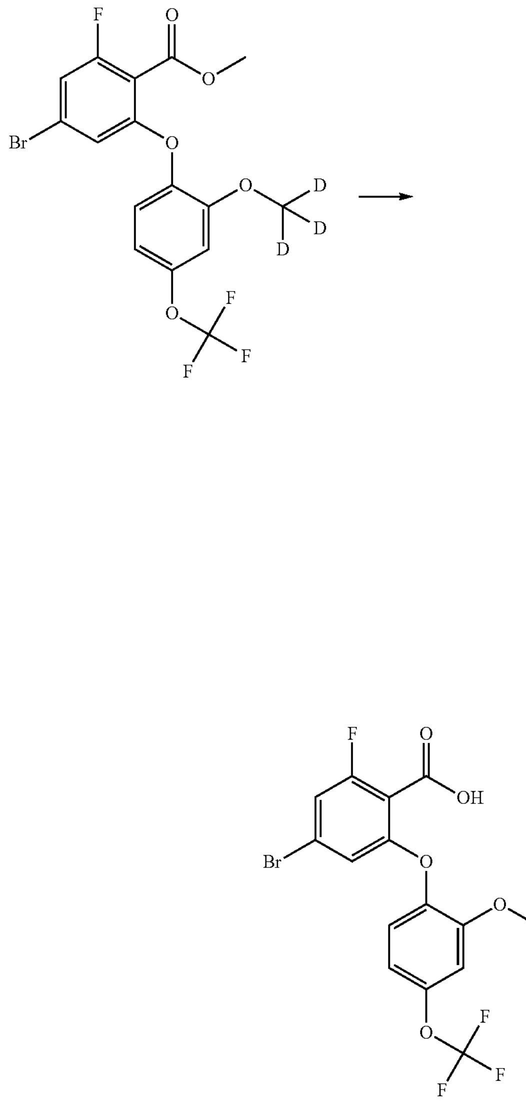

Methyl 4-bromo-2-fluoro-6-[2-(trideuteriomethoxy)-4-(trifluoromethoxy)phenoxy]benzoate (6.09 g, 13.8 mmol) was dissolved in methanol (60 mL) and treated with NaOH (40 mL of 1 M, 40 mmol). The reaction was heated to 40° C. and stirred for 2 hours. Additional NaOH (23 mL of 6 M, 138 mmol) was added and the reaction stirred at 45° C. for 1 hour. The reaction mixture was acidified with aqueous HCl (210 mL of 1 M, 210 mmol) and extracted with ethyl acetate (3×). The combined organic layers were dried over anhydrous $MgSO_4$, filtered and concentrated in vacuo to provide 4-bromo-2-fluoro-6-[2-(trideuteriomethoxy)-4-(trifluoromethoxy)phenoxy]benzoic acid (5.81 g, 99%) as a glassy oil. ESI-MS m/z calc. 426.98, found 429.0 $(M+1)^+$; Retention time (Method A): 0.72 minutes. H NMR (400 MHz, DMSO-d6) δ 13.78 (s, 1H), 7.42 (dd, J=8.9, 1.6 Hz, 1H), 7.25-7.20 (m, 2H), 7.00 (ddd, J=8.8, 2.7, 1.3 Hz, 1H), 6.67 (t, J=1.4 Hz, 1H) ppm.

Step 5: 4-[[4-Bromo-2-Fluoro-6-[2-(Trideuteriomethoxy)-4-(Trifluoromethoxy)Phenoxy]Benzoyl]Amino]Pyridine-2-Carboxamide

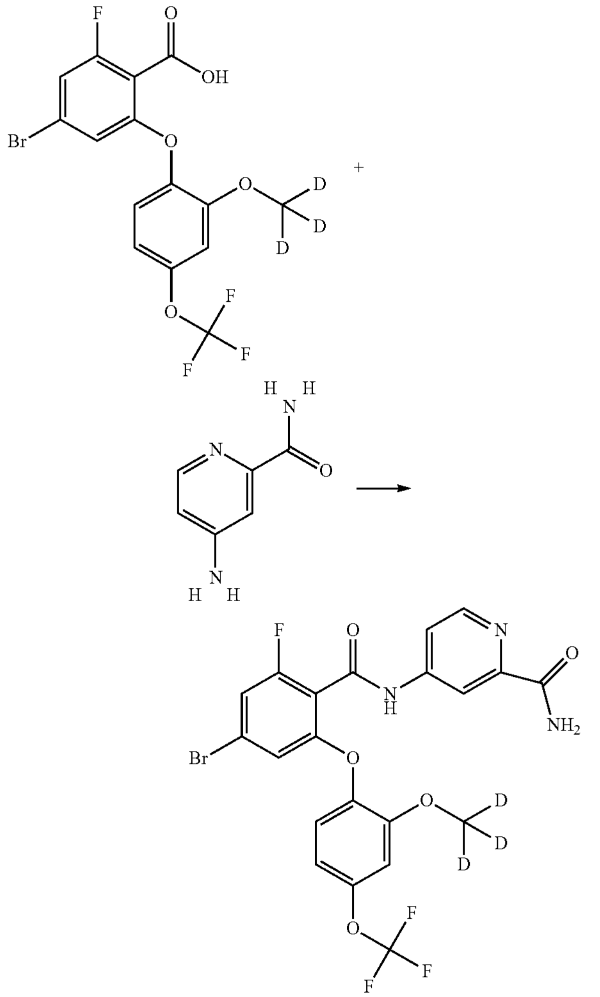

To a solution of 4-bromo-2-fluoro-6-[2-(trideuteriomethoxy)-4-(trifluoromethoxy)phenoxy]benzoic acid (4.0 g, 9.3 mmol), DMF (210 μL, 2.71 mmol) in dichloromethane (48 mL) at 0° C. under nitrogen was added oxalyl chloride (7 mL, 80 mmol). The reaction was stirred at 0° C. for 10 minutes and then at RT for 1 hour. The mixture was concentrated under reduced pressure and the residue was dissolved in NMP (5 mL). This solution was added dropwise to a suspension of 4-aminopyridine-2-carboxamide (1.28 g, 9.33 mmol) in DMF (1.5 mL), DIEA (10 mL, 57 mmol) and NMP (10 mL) under nitrogen atmosphere at 0° C. The reaction mixture was allowed to warm to RT and stirred for 16 hours. The mixture was partitioned between water and ethyl acetate. The phases were separated and the aqueous layer was extracted with ethyl acetate. The combined organic layers were washed with water (2×) and brine. The organic layer was dried over $Na_2SO_4$, filtered and concentrated. The crude product was purified by silica chromatography (ethyl acetate/hexanes gradient) to provide 4-[[4-bromo-2-fluoro-6-[2-(trideuteriomethoxy)-4-(trifluoromethoxy)phenoxy]benzoyl]amino]pyridine-2-carboxamide (1.26 g, 25%). ESI-MS m/z calc. 546.02, found 549.0 $(M+1)^+$; Retention time (Method B): 1.94 minutes. $^1H$ NMR (400 MHz, DMSO-d6) δ 11.30 (s, 1H), 8.54 (d, J=5.4 Hz, 1H), 8.29 (d, J=2.1 Hz, 1H), 8.16-7.99 (m, 1H), 7.82 (dd, J=5.6, 2.2 Hz, 1H), 7.65 (d, J=2.8 Hz, 1H), 7.52 (dd, J=8.6, 1.5 Hz, 1H), 7.30 (d, J=8.8 Hz, 1H), 7.20 (d, J=2.7 Hz, 1H), 7.10-6.91 (m, 1H), 6.75 (s, 1H) ppm.

Step 6: 4-[[4-(Cyclohexen-1-Yl)-2-Fluoro-6-[2-(Trideuteriomethoxy)-4-(Trifluoromethoxy)Phenoxy]Benzoyl]Amino]Pyridine-2-Carboxamide (1001)

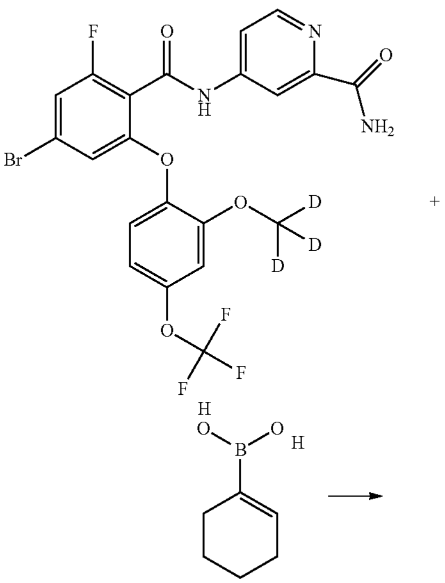

-continued

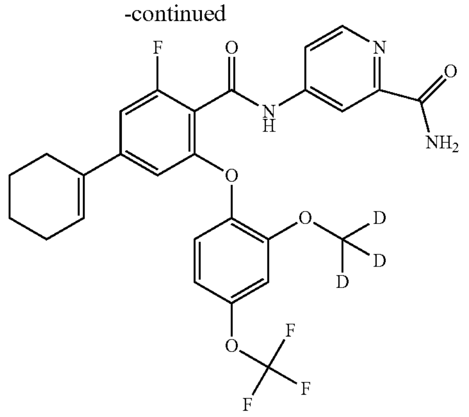

A solution of 4-[[4-bromo-2-fluoro-6-[2-(trideuteriomethoxy)-4-(trifluoromethoxy)phenoxy]benzoyl]amino]pyridine-2-carboxamide (25 mg, 0.046 mmol), cyclohexen-1-ylboronic acid (14 mg, 0.11 mmol), $K_2CO_3$ (13 mg, 0.094 mmol) and Pd(dppf)$Cl_2$.DCM (8 mg, 0.01 mmol) in dioxane (500 μL) and water (50 μL) was heated at 100° C. for 16 hours. The reaction mixture was filtered and purified by HPLC (10-99% $CH_3CN$/5 mM HCl) to provide 4-[[4-(cyclohexen-1-yl)-2-fluoro-6-[2-(trideuteriomethoxy)-4-(trifluoromethoxy)phenoxy]benzoyl]amino]pyridine-2-carboxamide (18 mg, 72%). ESI-MS m/z calc. 548.18, found 549.01 $(M+1)^+$; Retention time (Method B): 2.07 minutes. $^1H$ NMR (400 MHz, DMSO-d6) δ 11.24 (s, 1H), 8.52 (d, J=5.5 Hz, 1H), 8.29 (d, J=2.2 Hz, 1H), 8.11 (s, 1H), 7.86-7.77 (m, 1H), 7.65 (s, 1H), 7.20 (d, J=8.8 Hz, 1H), 7.15 (dd, J=6.8, 4.0 Hz, 2H), 6.97 (d, J=9.3 Hz, 1H), 6.57 (s, 1H), 6.18 (s, 1H), 2.23 (s, 2H), 2.14 (s, 2H), 1.66 (d, J=6.2 Hz, 2H), 1.56 (d, J=7.1 Hz, 2H) ppm.

The compounds set forth in Table 102 were prepared by methods analogous to the preparation of compound 1001:

TABLE 102

Additional Compounds Prepared by Methods Analogous to Example 202

| Cmpd No. | Compound Name | LC/MS | NMR (shifts in ppm) |
|---|---|---|---|
| 1002 | 4-[[4-(3,4-dihydro-2H-pyran-5-yl)-2-fluoro-6-[2-(trideuteriomethoxy)-4-(trifluoromethoxy)phenoxy]benzoyl]amino]pyridine-2-carboxamide | ESI-MS m/z calc. 550.16, found 551.1 (M + 1)+; Retention time (Method B): 1.19 minutes. | |
| 1003 | 4-[[4-(4,4-difluorocyclohexen-1-yl)-2-fluoro-6-[2-(trideuteriomethoxy)-4-(trifluoromethoxy)phenoxy]benzoyl]amino]pyridine-2-carboxamide | ESI-MS m/z calc. 584.16, found 585.01 (M + 1)+; Retention time (Method B): 1.94 minutes. | $^1H$ NMR (400 MHz, DMSO-d6) δ 11.26 (s, 1H), 8.52 (d, J = 5.5 Hz, 1H), 8.30 (d, J = 2.0 Hz, 1H), 8.11 (s, 1H), 7.85-7.77 (m, 1H), 7.66 (s, 1H), 7.23 (dd, J = 11.6, 9.6 Hz, 2H), 7.16 (d, J = 2.6 Hz, 1H), 7.01-6.90 (m, 1H), 6.65 (s, 1H), 6.04 (s, 1H), 2.72 (t, J = 15.0 Hz, 2H), ~2.5 (2H, obscured by DMSO peak), 2.14 (tt, J = 14.0, 6.6 Hz, 2H). |
| 1004 | 4-[[4-(2,5-dihydrofuran-3-yl)-2-fluoro-6-[2-(trideuteriomethoxy)-4-(trifluoromethoxy)phenoxy]benzoyl]amino]pyridine-2-carboxamide | ESI-MS m/z calc. 536.14, found 537.3 (M + 1)+; Retention time (Method B): 1.58 minutes. | |

TABLE 102-continued

| Additional Compounds Prepared by Methods Analogous to Example 202 | | | |
|---|---|---|---|
| Cmpd No. | Compound Name | LC/MS | NMR (shifts in ppm) |
| 1005 | 4-[[4-(3,6-dihydro-2H-pyran-4-yl)-2-fluoro-6-[2-(trideuteriomethoxy)-4-(trifluoromethoxy)phenoxy]benzoyl]amino]pyridine-2-carboxamide | ESI-MS m/z calc. 550.16, found 551.3 (M + 1)+; Retention time (Method B): 1.6 minutes. | |
| 1006 | 4-[[4-(2-carbamoylphenyl)-2-fluoro-6-[2-(trideuteriomethoxy)-4-(trifluoromethoxy)phenoxy]benzoyl]amino]pyridine-2-carboxamide | ESI-MS m/z calc. 587.15, found 588.3 (M + 1)+; Retention time (Method B): 1.74 minutes. | $^1$H NMR (400 MHz, DMSO-d6) δ 11.43 (s, 1H), 8.54 (d, J = 5.5 Hz, 1H), 8.34 (d, J = 2.1 Hz, 1H), 8.12 (s, 1H), 7.86 (dd, J = 5.6, 2.2 Hz, 1H), 7.78 (s, 1H), 7.67 (s, 1H), 7.53-7.39 (m, 3H), 7.32 (d, J = 8.3 Hz, 2H), 7.27 (d, J = 8.8 Hz, 1H), 7.18-7.10 (m, 2H), 6.99 (d, J = 8.8 Hz, 1H), 6.60 (s, 1H). |
| 1007 | 4-[[2-fluoro-4-(4-methoxyphenyl)-6-[2-(trideuteriomethoxy)-4-(trifluoromethoxy)phenoxy]benzoyl]amino]pyridine-2-carboxamide | ESI-MS m/z calc. 574.16, found 575.2 (M + 1)+; Retention time (Method B): 1.82 minutes. | $^1$H NMR (400 MHz, DMSO-d6) δ 11.28 (s, 1H), 8.53 (d, J = 5.5 Hz, 1H), 8.31 (s, 1H), 8.11 (s, 1H), 7.85-7.77 (m, 1H), 7.66 (s, 1H), 7.55 (t, J = 8.0 Hz, 3H), 7.46-7.37 (m, 1H), 7.27 (d, J = 8.8 Hz, 1H), 7.17 (d, J = 2.8 Hz, 1H), 7.04-6.95 (m, 2H), 6.80 (s, 1H), 3.78 (d, J = 1.8 Hz, 3H). |
| 1008 | 4-[[4-(2,3-dihydrofuran-4-yl)-2-fluoro-6-[2-(trideuteriomethoxy)-4-(trifluoromethoxy)phenoxy]benzoyl]amino]pyridine-2-carboxamide | ESI-MS m/z calc. 536.14, found 537.3 (M + 1)+; Retention time (Method B): 1.64 minutes. | |
| 1009 | 4-[[2-fluoro-4-(4-methoxycyclohexen-1-yl)-6-[2-(trideuteriomethoxy)-4-(trifluoromethoxy)phenoxy]benzoyl]amino]pyridine-2-carboxamide | ESI-MS m/z calc. 578.19, found 579.3 (M + 1)+; Retention time (Method B): 1.76 minutes. | $^1$H NMR (400 MHz, DMSO-d6) δ 11.27 (s, 1H), 8.53 (d, J = 5.5 Hz, 1H), 8.31 (s, 1H), 8.13 (s, 1H), 7.87-7.79 (m, 1H), 7.69 (s, 1H), 7.27-7.13 (m, 3H), 7.01-6.91 (m, 1H), 6.58 (s, 1H), 6.07 (s, 1H), 3.25 (s, 3H), ~2.5 (2H, obscured by DMSO), 2.44 (d, 1H), 2.33 (t, J = 15.1 Hz, 1H), 2.09 (d, J = 18.6 Hz, 1H), 1.90 (d, J = 12.1 Hz, 1H), 1.65 (dq, J = 13.9, 7.4 Hz, 1H). |
| 1010 | 4-[[4-(cyclopenten-1-yl)-2-fluoro-6-[2-(trideuteriomethoxy)-4-(trifluoromethoxy)phenoxy]benzoyl]amino]pyridine-2-carboxamide | ESI-MS m/z calc. 534.16, found 534.96 (M + 1)+; Retention time (Method B): 2.01 minutes. | |
| 1011 | 4-[[4-(3-cyanophenyl)-2-fluoro-6-[2-(trideuteriomethoxy)-4-(trifluoromethoxy)phenoxy]benzoyl]amino]pyridine-2-carboxamide | ESI-MS m/z calc. 569.14, found 570.2 (M + 1)+; Retention time (Method B): 1.97 minutes. | $^1$H NMR (400 MHz, DMSO-d6) δ 11.34 (s, 1H), 8.54 (d, J = 5.5 Hz, 1H), 8.31 (d, J = 2.1 Hz, 1H), 8.18 (t, J = 1.8 Hz, 1H), 8.11 (d, J = 2.8 Hz, 1H), 7.97 (dt, J = 8.1, 1.6 Hz, 1H), 7.89 (dt, J = 7.7, 1.4 Hz, 1H), 7.83 (dd, J = 5.5, 2.2 Hz, 1H), 7.72-7.63 (m, 2H), 7.62 (dd, J = 10.2, 1.5 Hz, 1H), 7.25 (d, J = 8.8 Hz, 1H), 7.15 (d, J = 2.8 Hz, 1H), 7.04 (d, J = 1.5 Hz, 1H), 6.96 (ddd, J = 8.9, 2.9, 1.4 Hz, 1H). |
| 1012 | 4-[[4-(4-cyanophenyl)-2-fluoro-6-[2-(trideuteriomethoxy)-4-(trifluoromethoxy)phenoxy]benzoyl]amino]pyridine-2-carboxamide | ESI-MS m/z calc. 569.14, found 570.2 (M + 1)+; Retention time (Method B): 1.98 minutes. | $^1$H NMR (400 MHz, DMSO-d6) δ 11.37 (s, 1H), 8.54 (d, J = 5.5 Hz, 1H), 8.31 (d, J = 2.2 Hz, 1H), 8.13 (d, J = 3.0 Hz, 1H), 7.94 (d, J = 8.2 Hz, 2H), 7.83 (d, J = 8.3 Hz, 3H), 7.66 (d, J = 2.9 Hz, 1H), 7.59 (d, J = 10.1 Hz, 1H), 7.27 (d, J = 8.8 Hz, 1H), 7.16 (d, J = 2.8 Hz, 1H), 6.97 (d, J = 10.5 Hz, 2H). |

Example 203

4-[[2-Fluoro-6-[2-Methoxy-4-(Trifluoromethoxy) Phenoxy]-4-[4-(Trifluoromethyl)Cyclohexen-1-Yl] Benzoyl]Amino]Pyridine-2-Carboxamide (1013)

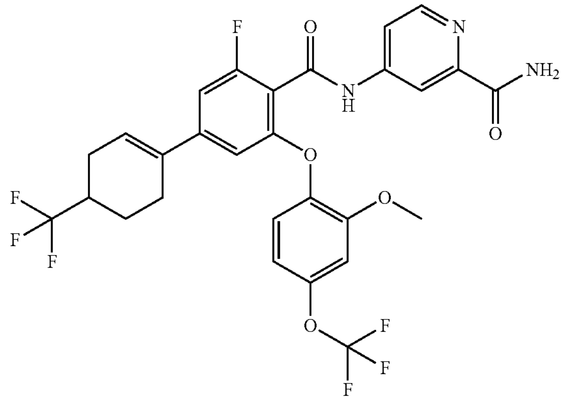 [SMILES: COc1cc(OC(F)(F)F)ccc1Oc1cc(C2=CCC(C(F)(F)F)CC2)cc(F)c1C(=O)Nc1ccnc(C(N)=O)c1]

Step 1: Methyl 4-Bromo-2-Fluoro-6-[2-Methoxy-4-(Trifluoromethoxy)Phenoxy]Benzoate

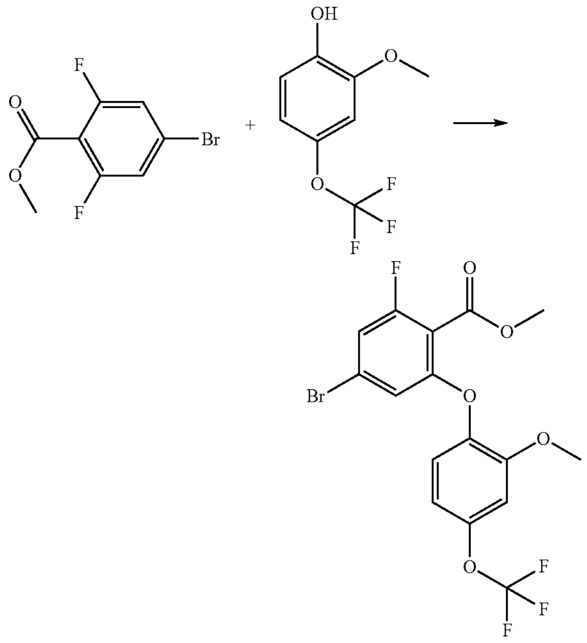

Methyl 4-bromo-2,6-difluoro-benzoate (6.1 g, 24 mmol), 2-methoxy-4-(trifluoromethoxy)phenol (5.2 g, 25 mmol) and $Cs_2CO_3$ (6.3 g, 19 mmol) in DMF (74 mL) were stirred at 80° C. for 1 hour in a sealed vial. The reaction mixture was cooled to RT, diluted with ethyl acetate (150 mL) and washed with brine (3×). The organic layer was dried over $Na_2SO_4$, filtered and concentrated in vacuo. Silica gel chromatography (ethyl acetate/hexanes gradient) provided methyl 4-bromo-2-fluoro-6-[2-methoxy-4-(trifluoromethoxy)phenoxy]benzoate (9.23 g, 87%) as a clear oil. $^1H$ NMR (400 MHz, DMSO-d6) δ 7.47 (dd, J=9.0, 1.6 Hz, 1H), 7.29-7.21 (m, 2H), 7.04-6.96 (m, 1H), 6.73 (d, J=2.1 Hz, 1H), 3.83 (s, 3H), 3.80 (s, 3H) ppm.

Step 2: 4-Bromo-2-Fluoro-6-[2-Methoxy-4-(Trifluoromethoxy)Phenoxy]Benzoic Acid

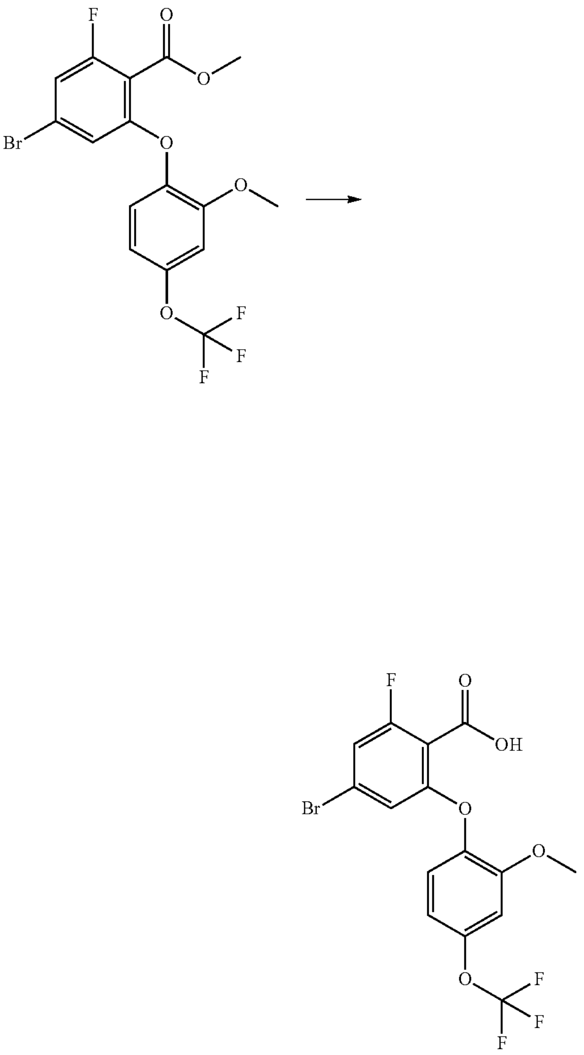

To a slurry of methyl 4-bromo-2-fluoro-6-[2-methoxy-4-(trifluoromethoxy)phenoxy]benzoate (6.0 g, 13.7 mmol) in methanol (60 mL) and water (60 mL) was added NaOH (5.5 g, 138 mmol). The reaction mixture was stirred at RT for 5 hours. The solvent was evaporated and the residue was taken up in water, cooled in an ice bath and acidified by slow addition of 6 M HCl (pH~ 2). The resulting solid was filtered and washed with water. The solid was then dissolved in dichloromethane/ethyl acetate, dried over $MgSO_4$, filtered and concentrated. The above filtrate was extracted by ethyl acetate, dried over $MgSO_4$ and combined with above concentrate. The solution was concentrated in vacuo and dried under high vacuum to provide 4-bromo-2-fluoro-6-[2-methoxy-4-(trifluoromethoxy)phenoxy]benzoic acid (5.6 g, 96%) as clear oil. ESI-MS m/z calc. 423.96, found 427.0 $(M+1)^+$; Retention time (Method B): 1.82 minutes.

Step 3: 4-[[4-Bromo-2-Fluoro-6-[2-Methoxy-4-(Trifluoromethoxy)Phenoxy]Benzoyl]Amino]Pyridine-2-Carboxamide

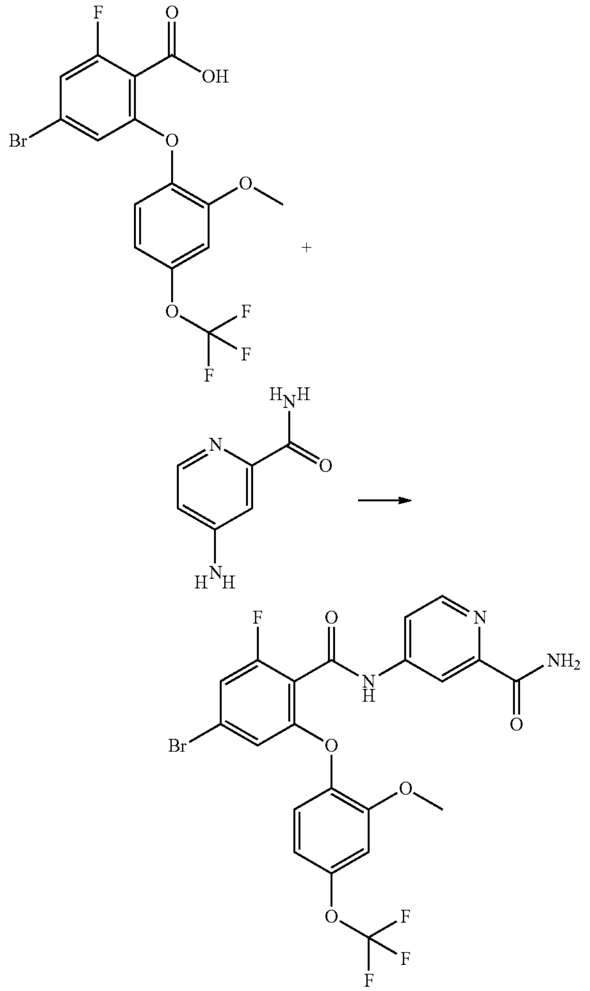

To a solution of 4-bromo-2-fluoro-6-[2-methoxy-4-(trifluoromethoxy)phenoxy]benzoic acid (2.0 g, 4.7 mmol) and DMF (100 μL, 1.29 mmol) in dichloromethane (24 mL) at 0° C. under nitrogen was added oxalyl chloride (3.3 mL, 38 mmol). The reaction was stirred at 0° C. for 10 minutes and allowed to warm to RT and stirred for 1 hour. The mixture was concentrated under reduced pressure and the residue was dissolved in NMP (5 mL). This solution was added dropwise to a suspension of 4-aminopyridine-2-carboxamide (700 mg, 5.10 mmol) in DMF (720 μL), DIEA (5 mL, 29 mmol) and NMP (10 mL) under nitrogen atmosphere at 0° C. The resulting reaction mixture was slowly warmed to room temperature and stirred for 18 hours. The reaction mixture was partitioned between water and ethyl acetate. The phases were separated and the aqueous layer was extracted with ethyl acetate. The combined organic layers were washed with water (2×) and brine, dried over $Na_2SO_4$, filtered and concentrated. Silica gel chromatography (ethyl acetate/hexanes gradient) provided 4-[[4-bromo-2-fluoro-6-[2-methoxy-4-(trifluoromethoxy)phenoxy]benzoyl]amino]pyridine-2-carboxamide (710 mg, 28%) as a white solid. ESI-MS m/z calc. 543.01, found 546.1 $(M+1)^+$; Retention time (Method B): 1.72 minutes. $^1H$ NMR (400 MHz, DMSO-d6) δ 11.30 (s, 1H), 8.54 (d, J=5.5 Hz, 1H), 8.29 (d, J=2.1 Hz, 1H), 8.10 (d, J=2.8 Hz, 1H), 7.82 (dd, J=5.5, 2.2 Hz, 1H), 7.65 (d, J=2.8 Hz, 1H), 7.52 (dd, J=8.6, 1.6 Hz, 1H), 7.30 (d, J=8.8 Hz, 1H), 7.20 (d, J=2.7 Hz, 1H), 7.05-6.97 (m, 1H), 6.75 (d, J=1.6 Hz, 1H), 3.78 (s, 3H) ppm.

Step 4: 4-[[2-Fluoro-6-[2-Methoxy-4-(Trifluoromethoxy)Phenoxy]-4-[4-(Trifluoromethyl)Cyclohexen-1-Yl]Benzoyl]Amino]Pyridine-2-Carboxamide (1013)

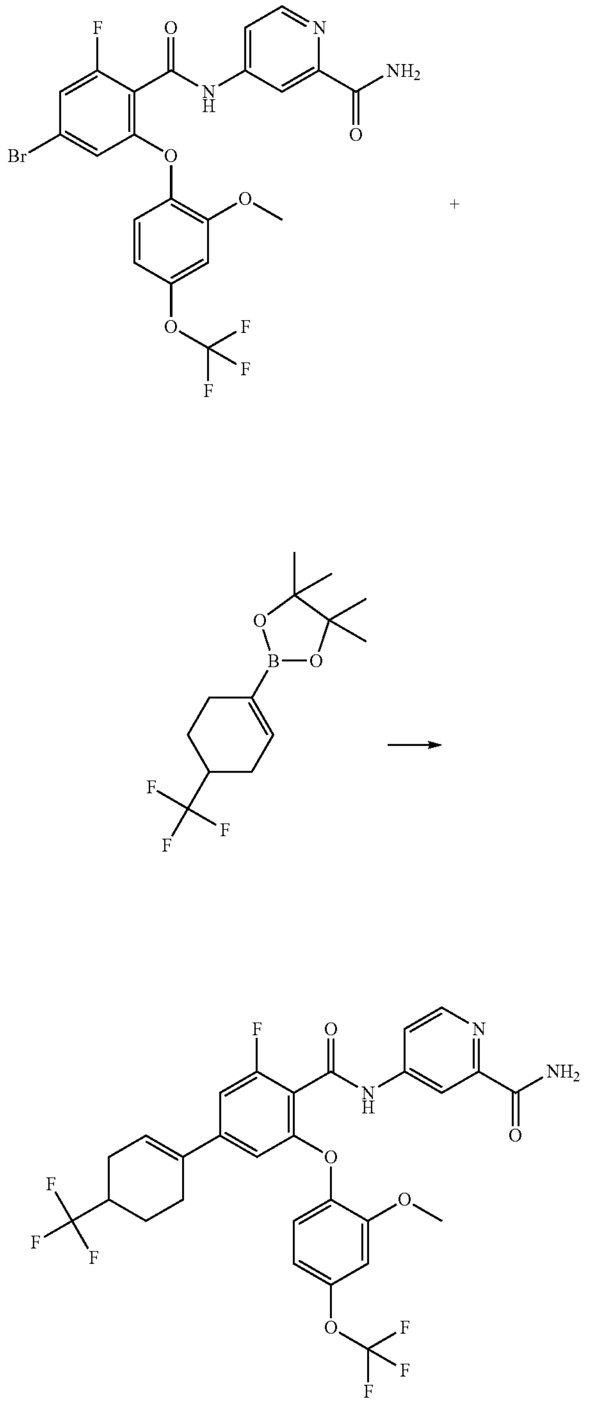

A vial charged with 4-[[4-bromo-2-fluoro-6-[2-methoxy-4-(trifluoromethoxy)phenoxy]benzoyl]amino]pyridine-2-carboxamide (25 mg, 0.046 mmol), 4,4,5,5-tetramethyl-2-[4-(trifluoromethyl)cyclohexen-1-yl]-1,3,2-dioxaborolane (25 mg, 0.092 mmol), $K_2CO_3$ (13 mg, 0.092 mmol), and $Pd(dppf)Cl_2$.DCM (8 mg, 0.009 mmol) in dioxane (500 μL) and water (50 μL) was flushed with nitrogen and heated at 100° C. for 16 hours. The reaction mixture was filtered and purified by HPLC (1-99% $CH_3CN$/5 mM HCl) to provide 4-[[2-fluoro-6-[2-methoxy-4-(trifluoromethoxy)phenoxy]-4-[4-(trifluoromethyl)cyclohexen-1-yl]benzoyl]amino]pyridine-2-carboxamide (21.3 mg, 76%). ESI-MS m/z calc. 613.15, found 614.3 $(M+1)^+$; Retention time (Method B): 2.01 minutes. $^1H$ NMR (400 MHz, DMSO-d6) δ 11.22 (s, 1H), 8.52 (d, J=5.5 Hz, 1H), 8.29 (d, J=2.2 Hz, 11), 8.09 (d, 1=2.9 Hz, 1-), 7.81 (dd, =5.5, 2.2 Hz, H1), 7.64 (d, J=2.9 Hz, 1H), 7.24-7.14 (m, 3H), 6.97 (dd, J=9.2, 2.3 Hz, 1H), 6.61 (s, 1H), 6.17 (s, 1H), 3.77 (s, 3H), 2.40 (d, J=7.3 Hz, 3H), 2.28-2.09 (m, 2H), 2.03 (d, B=12.4 Hz, 1H), 1.55 (td, =12.4, 6.0 Hz, 1H) ppm.

The compounds set forth in Table 103 were prepared by methods analogous to the preparation of compound 1013.

TABLE 103

Additional Compounds Prepared by Methods Analogous to Example 203.

| Cmpd No. | Compound Name | LC/MS | NMR (shifts in ppm) |
|---|---|---|---|
| 1014 | 4-[[4-(2-bicyclo[2.2.1]hept-2-enyl)-2-fluoro-6-[2-methoxy-4-(trifluoromethoxy)phenoxy]benzoyl]amino]pyridine-2-carboxamide | ESI-MS m/z calc. 603.16, found 604.3 (M + 1)+; Retention time (Method B): 1.69 minutes. | $^1H$ NMR (400 MHz, DMSO-d6) δ 11.24 (s, 1H), 8.52 (d, J = 5.5 Hz, 1H), 8.30 (d, J = 2.2 Hz, 1H), 8.10 (d, J = 2.9 Hz, 1H), 7.82 (dd, J = 5.5, 2.2 Hz, 1H), 7.65 (d, J = 2.9 Hz, 1H), 7.25-7.13 (m, 3H), 7.01-6.94 (m, 1H), 6.60 (s, 1H), 6.04 (d, J = 4.2 Hz, 1H), 3.90 (s, 4H), 3.77 (s, 3H), 2.42 (d, J = 7.4 Hz, 2H), 2.37-2.31 (m, 2H), 1.77 (t, J = 6.5 Hz, 2H). |
| 1015 | 4-[[4-(1,4-dioxaspiro[4.5]dec-7-en-8-yl)-2-fluoro-6-[2-methoxy-4-(trifluoromethoxy)phenoxy]benzoyl]amino]pyridine-2-carboxamide | ESI-MS m/z calc. 557.16, found 558.2 (M + 1)+; Retention time (Method B): 2.01 minutes. | $^1H$ NMR (400 MHz, DMSO-d6) δ 11.25 (s, 1H), 8.52 (d, J = 5.5 Hz, 1H), 8.30 (d, J = 2.1 Hz, 1H), 8.11 (s, 1H), 7.82 (dd, J = 5.8, 2.1 Hz, 1H), 7.66 (s, 1H), 7.27-7.13 (m, 3H), 6.97 (d, J = 8.7 Hz, 1H), 6.60 (s, 1H), 6.05 (s, 1H), 3.89 (s, 4H), 3.76 (s, 3H), 2.43 (s, 2H), 2.34 (s, 2H), 1.77 (t, J = 6.4 Hz, 2H). |
| 1016 | 4-[[4-(4-tert-butylcyclohexen-1-yl)-2-fluoro-6-[2-methoxy-4-(trifluoromethoxy)phenoxy]benzoyl]amino]pyridine-2-carboxamide | ESI-MS m/z calc. 601.22, found 602.3 (M + 1)+; Retention time (Method B): 2.34 minutes. | $^1H$ NMR (400 MHz, DMSO-d6) δ 11.23 (s, 1H), 8.52 (d, J = 5.5 Hz, 1H), 8.30 (s, 1H), 8.17-8.07 (m, 1H), 7.86-7.79 (m, 1H), 7.70-7.57 (m, 1H), 7.21 (d, J = 8.8 Hz, 1H), 7.19-7.11 (m, 2H), 6.98 (d, J = 8.8 Hz, 1H), 6.57 (s, 1H), 6.19 (s, 1H), 3.76 (s, 3H), 2.40-2.12 (m, 3H), 1.99-1.80 (m, 2H), 1.32-1.09 (m, 2H), 0.86 (s, 9H). |

Example 204

4-[[2-Fluoro-4-(4-Methoxycyclohexyl)-6-[2-(Trideuteriomethoxy)-4-(Trifluoromethoxy)Phenoxy]Benzoyl]Amino]Pyridine-2-Carboxamide (1017)

1017-a

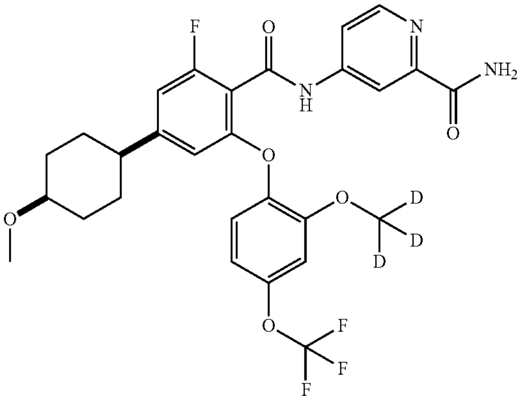

1017-b

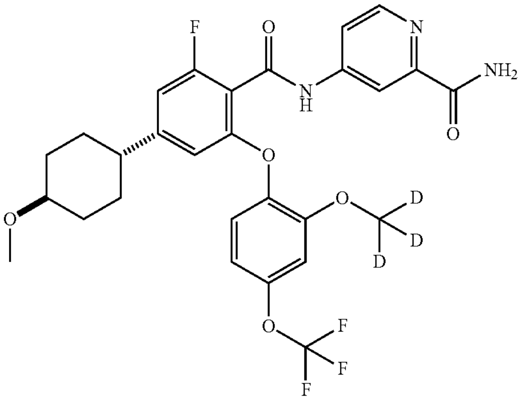

4-[[2-fluoro-4-(4-methoxycyclohexen-1-yl)-6-[2-(trideuteriomethoxy)-4-(trifluoromethoxy)phenoxy]benzoyl]amino]pyridine-2-carboxamide (1009, Table 102) (9 mg, 0.016 mmol) was dissolved in ethyl acetate (250 μL) and methanol (250 μL) and treated with 10% Pd/C palladium (1 mg, 0.009 mmol). The mixture was degassed with a flow of nitrogen for 2 minutes, then flushed with hydrogen (balloon). The reaction mixture was stirred at RT for 16 hours, then filtered and purified by HPLC (1-99% $CH_3CN$/5 mM HCl) to provide the two separated diastereomers assigned as diastereomer 1 and diastereomer 2, respectively based on HPLC elution order. It is appreciated that both diastereomers of 4-[[2-fluoro-4-(4-methoxycyclohexyl)-6-[2-(trideuteriomethoxy)-4-(trifluoromethoxy)phenoxy]benzoyl]amino] pyridine-2-carboxamide (17) were isolated and that those diastereomers have the structure of compounds 1017-a and 1017-b (above). However, the relative stereochemistry of diastereomers 1 and 2 was not determined.

Diastereomer 1: 4-[[2-fluoro-4-(4-methoxycyclohexyl)-6-[2-(trideuteriomethoxy)-4-(trifluoromethoxy)phenoxy] benzoyl]amino]pyridine-2-carboxamide (1017) (1.3 mg, 14%). ESI-MS m/z calc. 580.20, found 581.4 $(M+1)^+$; Retention time (Method B): 1.74 minutes.

Diastereomer 2: 4-[[2-fluoro-4-(4-methoxycyclohexyl)-6-[2-(trideuteriomethoxy)-4-(trifluoromethoxy)phenoxy] benzoyl]amino]pyridine-2-carboxamide (1017) (5.0 mg, 55%). ESI-MS m/z calc. 580.20, found 581.3 $(M+1)^+$; Retention time (Method B): 1.82 minutes. 1H NMR (400 MHz, DMSO-$d_6$) δ 11.25 (s, 1H), 8.52 (d, J=5.5 Hz, 1H), 8.32 (d, J=2.1 Hz, 1H), 8.11 (s, 1H), 7.82 (dd, J=5.7, 2.1 Hz, 1H), 7.67 (s, 1H), 7.23 (d, J=8.8 Hz, 1H), 7.19 (d, J=2.7 Hz, 1H), 7.03-6.97 (m, 1H), 6.95 (d, J=10.1 Hz, 1H), 6.40 (s, 1H), 3.42-3.39 (m, 1H), 3.20 (s, 3H), 2.61-2.56 (m, 1H), 2.03-1.80 (m, 2H), 1.68-1.30 (m, 6H).

The compounds set forth in Table 104 were prepared by methods analogous to the preparation of compound 1017

TABLE 104

Additional Compounds Prepared by Methods Analogous to Example 204

| Cmpd No. | Compound Name | LC/MS | NMR (shifts in ppm) |
|---|---|---|---|
| 1018 | 4-[[2-fluoro-4-tetrahydrofuran-3-yl-6-[2-(trideuteriomethoxy)-4-(trifluoromethoxy)phenoxy]benzoyl]amino]pyridine-2-carboxamide | ESI-MS m/z calc. 538.16, found 539.2 (M + 1)+; Retention time (Method B): 1.53 minutes. | $^1$H NMR (400 MHz, DMSO-d6) δ 11.23 (s, 1H), 8.52 (d, J = 5.5 Hz, 1H), 8.30 (d, J = 2.1 Hz, 1H), 8.10 (d, J = 2.9 Hz, 1H), 7.81 (dd, J = 5.6, 2.2 Hz, 1H), 7.65 (d, J = 2.8 Hz, 1H), 7.22 (d, J = 8.7 Hz, 1H), 7.17 (d, J = 2.8 Hz, 1H), 7.07 (d, J = 10.1 Hz, 1H), 7.02-6.95 (m, 1H), 6.52 (s, 1H), 3.93 (t, J = 7.7 Hz, 1H), 3.86 (dd, J = 8.3, 4.8 Hz, 1H), 3.73 (q, J = 7.7 Hz, 1H), 3.50 (dd, J = 8.3, 6.8 Hz, 1H), 3.44-3.37 (m, 1H), 2.32-2.19 (m, 1H), 1.90-1.75 (m, 1H). |
| 1019 | 4-[[2-fluoro-4-tetrahydropyran-4-yl-6-[2-(trideuteriomethoxy)-4-(trifluoromethoxy)phenoxy]benzoyl]amino]pyridine-2-carboxamide | ESI-MS m/z calc. 552.17, found 553.2 (M + 1)+; Retention time (Method B): 1.58 minutes. | $^1$H NMR (400 MHz, DMSO-d6) δ 11.24 (s, 1H), 8.52 (d, J = 5.5 Hz, 1H), 8.31 (d, J = 2.1 Hz, 1H), 8.10 (d, J = 2.7 Hz, 1H), 7.82 (dd, J = 5.6, 2.2 Hz, 1H), 7.66 (d, J = 2.8 Hz, 1H), 7.23 (d, J = 8.8 Hz, 1H), 7.18 (d, J = 2.7 Hz, 1H), 7.06 (d, J = 10.2 Hz, 1H), 7.02-6.92 (m, 1H), 6.49 (s, 1H), 3.98-3.82 (m, 2H), 3.39 (m, 2H, partially obscured by H2O peak), 2.78 (dq, J = 10.4, 5.7 Hz, 1H), 1.69-1.49 (m, 4H). |

TABLE 104-continued

| Additional Compounds Prepared by Methods Analogous to Example 204 | | | |
|---|---|---|---|
| Cmpd No. | Compound Name | LC/MS | NMR (shifts in ppm) |
| 1020 | 4-[[2-fluoro-6-[2-methoxy-4-(trifluoromethoxy)phenoxy]-4-norboman-2-yl-benzoyl]amino]pyridine-2-carboxamide | ESI-MS m/z calc. 559.17, found 560.3 (M + 1)+; Retention time (Method B): 2.03 minutes. | $^1$H NMR (400 MHz, DMSO-d6) δ 11.20 (s, 1H), 8.52 (d, J = 5.5 Hz, 1H), 8.31 (d, J = 2.1 Hz, 1H), 8.09 (d, J = 2.9 Hz, 1H), 7.83 (dd, J = 5.7, 2.2 Hz, 1H), 7.64 (s, 1H), 7.23 (d, J = 8.8 Hz, 1H), 7.18 (d, J = 2.7 Hz, 1H), 6.98 (t, J = 9.6 Hz, 2H), 6.37 (s, 1H), 3.76 (s, 3H), 3.18 (d, J = 11.9 Hz, 1H), 2.29 (s, 1H), 2.24 (s, 1H), 1.86 (t, J = 12.4 Hz, 1H), 1.49 (t, J = 10.3 Hz, 2H), 1.35 (d, J = 9.3 Hz, 1H), 1.29-1.12 (m, 2H), 1.10-0.99 (m, 2H). |

Example 205

4-[[2-Fluoro-4-(4-Methylpent-1-Ynyl)-6-[2-(Trideuteriomethoxy)-4-(Trifluoromethoxy)Phenoxy]Benzoyl]Amino]Pyridine-2-Carboxamide (1021)

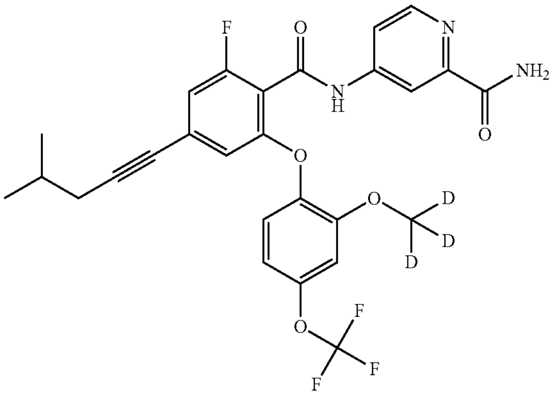 [SMILES: [2H]C([2H])([2H])Oc1cc(OC(F)(F)F)ccc1Oc1cc(C#CCC(C)C)cc(F)c1C(=O)Nc1ccnc(C(N)=O)c1]

In a 4-mL vial was combined 4-[[4-bromo-2-fluoro-6-[2-methoxy-4-(trifluoromethoxy)phenoxy]benzoyl]amino]pyridine-2-carboxamide (30 mg, 0.055 mmol) and TEA (100 μL, 0.7175 mmol). The mixture was bubbled with nitrogen for 15 minutes. To this suspension, was added copper (I) iodide (2 mg, 0.01 mmol) followed by $Pd(Ph_3)_4$ (7 mg, 0.006 mmol). The resulting mixture was stirred for 5 minutes under nitrogen. 4-Methylpent-1-yne (50 μL, 0.42 mmol) was then added and the reaction mixture stirred at 92° C. for 1 hour. The mixture was cooled to RT, filtered and purified by HPLC (1-99% $CH_3CN$/5 mM HCl) to provide 4-[[2-fluoro-4-(4-methylpent-1-ynyl)-6-[2-(trideuteriomethoxy)-4-(trifluoromethoxy)phenoxy]benzoyl]amino]pyridine-2-carboxamide (23 mg, 77%). ESI-MS m/z calc. 548.18, found 549.3 $(M+1)^+$; Retention time (Method B): 2.04 minutes. $^1$H NMR (400 MHz, DMSO-d6) δ 11.28 (s, 1H), 8.53 (d, J=5.5 Hz, 1H), 8.30 (d, J=2.1 Hz, 1H), 8.09 (d, J=2.8 Hz, 1H), 7.82 (dd, J=5.5, 2.2 Hz, 1H), 7.65 (d, J=2.8 Hz, 1H), 7.28 (d, J=8.9 Hz, 1H), 7.22-7.13 (m, 2H), 7.01 (ddd, J=8.8, 2.7, 1.2 Hz, 1H), 6.48 (d, J=1.3 Hz, 1H), 2.31 (d, J=6.5 Hz, 2H), 1.82 (dp, J=13.2, 6.6 Hz, 1H), 0.96 (d, J=6.6 Hz, 6H) ppm.

The compounds set forth in Table 105 were prepared by methods analogous to the preparation of compound 1021.

TABLE 105

| Additional Compounds Prepared by Methods Analogous to Example 205. | | | |
|---|---|---|---|
| Cmpd No. | Compound Name | LC/MS | NMR (shifts in ppm) |
| 1022 | 4-[[4-(3,3-dimethylbut-1-ynyl)-2-fluoro-6-[2-(trideuteriomethoxy)-4-(trifluoromethoxy)phenoxy]benzoyl]amino]pyridine-2-carboxamide | ESI-MS m/z calc. 548.17621, found 549.3 (M + 1)+; Retention time (Method B): 2.03 minutes. | $^1$H NMR (400 MHz, DMSO-d6) δ 11.27 (s, 1H), 8.53 (d, J = 5.5 Hz, 1H), 8.30 (d, J = 2.1 Hz, 1H), 8.09 (d, J = 2.9 Hz, 1H), 7.82 (dd, J = 5.5, 2.2 Hz, 1H), 7.65 (d, J = 2.8 Hz, 1H), 7.28 (d, J = 8.8 Hz, 1H), 7.22-7.10 (m, 2H), 7.00 (ddt, J = 8.8, 2.4, 1.3 Hz, 1H), 6.46 (d, J = 1.3 Hz, 1H), 1.25 (s, 9H). |
| 1023 | 4-[[4-(2-cyclopropylethynyl)-2-fluoro-6-[2-(trideuteriomethoxy)-4-(trifluoromethoxy)phenoxy]benzoyl]amino]pyridine-2-carboxamide | ESI-MS m/z calc. 532.14491, found 533.2 (M + 1)+; Retention time (Method B): 1.85 minutes. | $^1$H NMR (400 MHz, DMSO-d6) δ 11.31 (s, 1H), 8.53 (d, J = 5.4 Hz, 1H), 8.31 (s, 1H), 8.12 (s, 1H), 7.86-7.78 (m, 1H), 7.67 (s, 1H), 7.28 (d, J = 8.7 Hz, 1H), 7.19 (s, 1H), 7.14 (d, J = 9.5 Hz, 1H), 7.00 (d, J = 8.9 Hz, 1H), 6.46 (s, 1H), 1.60-1.48 (m, 1H), 0.94-0.83 (m, 2H), 0.78-0.71 (m, 2H). |

TABLE 105-continued

Additional Compounds Prepared by Methods Analogous to Example 205.

| Cmpd No. | Compound Name | LC/MS | NMR (shifts in ppm) |
|---|---|---|---|
| 1024 | 4-[[4-(2-cyclobutylethynyl)-2-fluoro-6-[2-(trideuteriomethoxy)-4-(trifluoromethoxy)phenoxy]benzoyl]amino]pyridine-2-carboxamide | ESI-MS m/z calc. 546.16056, found 547.3 (M + 1)+; Retention time (Method B): 2.0 minutes. | $^1$H NMR (400 MHz, DMSO-d6) δ 11.32 (s, 1H), 8.53 (d, J = 5.4 Hz, 1H), 8.31 (s, 1H), 8.11 (s, 1H), 7.82 (d, J = 5.4 Hz, 1H), 7.67 (s, 1H), 7.29 (d, J = 8.7 Hz, 1H), 7.23-7.12 (m, 2H), 7.01 (d, J = 8.8 Hz, 1H), 6.48 (s, 1H), 3.31-3.19 (m, 1H), 2.31-2.20 (m, 2H), 2.17-2.04 (m, 2H), 2.00-1.74 (m, 2H). |

Example 206

4-[[6-[2-Methoxy-4-(Trifluoromethoxy)Phenoxy]-2-Methylsulfanyl-3-(Trifluoromethyl)Benzoyl]Amino] Pyridine-2-Carboxamide (1025)

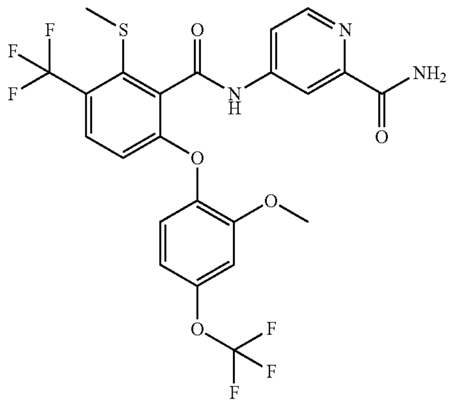 [SMILES: COc1cc(OC(F)(F)F)ccc1Oc1ccc(C(F)(F)F)c(SC)c1C(=O)Nc1ccnc(C(N)=O)c1]

Step 1: 1-Bromo-2-Methoxy-4-(Trifluoromethoxy)Benzene

A 500-mL 3-neck round-bottom flask was fitted with a mechanical stirrer, a cooling bath, an addition funnel, temperature probe and a nitrogen inlet/outlet. The vessel was charged under a nitrogen atmosphere with 2-bromo-5-(trifluoromethoxy)phenol (80 g, 311 mmol) and DMF (800 mL) then treated with $K_2CO_3$ (56.05 g, 405.6 mmol). The mixture was stirred at RT for 15 minutes and then cooled in an ice bath. Methyl iodide (19.4 mL, 311 mmol) was added dropwise over 5 minutes. The cooling bath was removed and the resulting suspension was allowed to slowly warm to room temperature and continued to stir for 10 hours. The reaction mixture was then poured into crushed ice/water (1000 mL) and stirred for 5 minutes. The mixture was diluted with methyl tert-butyl ether (1000 mL) and transferred to a separatory funnel and allowed to stand for 10 minutes. The organic phase was separated and the aqueous was extracted with methyl tert-butyl ether (2×500 mL). The combined organic phases were washed with brine, dried over $Na_2SO_4$, filtered and concentrated. Silica gel chromatography (starting with hexane, then 9:1 hexane:dichloromethane and finally 8:1:1 hexane:dichloromethane:ethyl acetate) provided 1-bromo-2-methoxy-4-(trifluoromethoxy) benzene (82 g, 97%) as a pale yellow oil. $^1$H NMR (400 MHz, DMSO-d6) δ 7.71 (d, J=8.7 Hz, 1H), 7.25-7.06 (m, 1H), 6.93 (ddq, J=8.7, 2.5, 1.2 Hz, 1H), 3.89 (s, 3H) ppm.

Step 2: 2-Methoxy-4-(Trifluoromethoxy)Phenol

A 1000-mL 3-neck round-bottom flask was fitted with a mechanical stirrer, a heating mantle, a water cooled reflux condenser, a temperature probe/controller and a nitrogen inlet/outlet. The vessel was charged under a nitrogen atmosphere with tetrabutylammonium hydroxide (287 mL of 40% w/v, 443 mmol) in water and 1-bromo-2-methoxy-4-(trifluoromethoxy)benzene (30.0 g, 111 mmol). The solution was degassed with nitrogen for 15 minutes with stirring. The vessel was then charged with 1,10-phenanthroline-4,7-diol (2.349 g, 11.07 mmol) added as a solid in one portion followed by copper (I) oxide (792 mg, 5.54 mmol) added as a solid in one portion. After these additions the gas dispersion tube was removed and the vessel was fitted with a septum. The mixture was then heated to a pot temperature of 100° C. for 15 hours. After cooling to RT the reaction mixture was poured into ice cold hydrochloric acid (554 mL of 1 M HCl, 554 mmol). The mixture was diluted with ethyl acetate (500 mL) and mixed for several minutes. The biphasic mixture was transferred to a separatory funnel and allowed to stand for 5 minutes. The phases were separated and the aqueous was extracted with ethyl acetate (2×200 mL). The combined organic phases were washed with brine (2×250 mL), dried over $Na_2SO_4$, filtered and concentrated. Silica gel chromatography (ethyl acetate/hexanes gradient) provided 2-methoxy-4-(trifluoromethoxy)phenol (18 g, 78%) as a pale yellow oil. LC/MS retention time (Method B): 1.34 minutes. $^1$H NMR (400 MHz, DMSO-d6) δ 9.35 (s, 1H), 6.92 (dd, J=2.7, 0.8 Hz, 1H), 6.82 (d, J=8.6 Hz, 1H), 6.79-6.70 (m, 1H), 3.79 (s, 3H) ppm.

Step 3: 2-Fluoro-6-[2-Methoxy-4-(Trifluoromethoxy)Phenoxy]-3-(Trifluoromethyl)Benzoic Acid A pressure flask was charged with 6-bromo-2-fluoro-3-(trifluoromethyl)benzoic acid (5.0 g, 17.42 mmol), 2-methoxy-4-(trifluoromethoxy)phenol (4.35 g, 20.90 mmol), $Cs_2CO_3$ (11.35 g, 34.84 mmol) and toluene (50 mL). The mixture was degassed with nitrogen. After approximately 2 minutes, copper (I) iodide (663 mg, 3.48 mmol) was added and the reaction was stirred at 100° C. for 1 hour. The reaction was diluted with 300 mL ethyl acetate and 200 mL of water and the phases were separated. The aqueous layer was acidified to pH-3 and extracted with ethyl acetate. The combined organic phases were dried over $Na_2SO_4$, filtered and concentrated. The residue was purified by silica gel chromatography (ethyl acetate/hexanes gradient, followed by 1:9 methanol/dichloromethane) to afford 2-fluoro-6-[2-methoxy-4-(trifluoromethoxy)phenoxy]-3-(trifluoromethyl)benzoic acid (5.45 g, 76%) as a pale green solid. ESI-MS m/z calc. 414.03, found 415.0 $(M+1)^+$; retention time (Method B): 1.94 minutes. $^1H$ NMR (400 MHz, DMSO-d6) δ 7.53 (t, J=8.4 Hz, 1H), 7.27-7.11 (m, 2H), 6.99 (ddd, J=8.8, 2.7, 1.3 Hz, 1H), 6.49 (d, J=8.8 Hz, 1H), 3.80 (s, 3H) ppm.

Step 4: 4-[[2-Fluoro-6-[2-Methoxy-4-(Trifluoromethoxy)Phenoxy]-3-(Trifluoromethyl)Benzoyl]Amino]Pyridine-2-Carboxamide A microwave vial charged with 4-[(Z)-[(tert-butylamino)-phenylsulfanyl-methylene]amino]pyridine-2-carboxamide (75 mg, 0.29 mmol, prepared as described in Example 201), tris[(Z)-1-methyl-3-oxo-but-1-enoxy]iron (2 mg, 0.006 mmol) and 2-fluoro-6-[2-methoxy-4-(trifluoromethoxy)phenoxy]-3-(trifluoromethyl)benzoic acid (94 mg, 0.29 mmol) in isopropanol (2 mL) was heated at 83° C. for 16 hours. The reaction mixture was cooled to room temperature and the solvent evaporated. The crude material was taken up in dichloromethane and washed with 1N HCl. The organic layer was dried over $MgSO_4$, filtered and concentrated. The residue was purified by silica gel chromatography (ethyl acetate/hexanes gradient) to afford 4-[[2-fluoro-6-[2-methoxy-4-(trifluoromethoxy)phenoxy]-3-(trifluoromethyl)benzoyl]amino]pyridine-2-carboxamide (80 mg, 64%). ESI-MS m/z calc. 533.08, found 534.1 $(M+1)^+$; Retention time (Method B): 1.77 minutes. $^1H$ NMR (400 MHz, DMSO-d6) δ 11.45 (s, 1H), 8.56 (d, J=5.5 Hz, 1H), 8.32 (d, J=2.2 Hz, 1H), 8.12 (d, J=2.7 Hz, 1H), 7.86-7.77 (m, 2H), 7.72-7.64 (m, 1H), 7.38 (d, J=8.8 Hz, 1H), 7.27 (d, J=2.8 Hz, 1H), 7.08-7.01 (m, 1H), 6.68 (d, J=8.9 Hz, 1H), 3.79 (s, 3H) ppm.

Step 5: 4-[[6-[2-Methoxy-4-(Trifluoromethoxy)Phenoxy]-2-Methylsulfanyl-3-(Trifluoromethyl)Benzoyl]Amino]Pyridine-2-Carboxamide (1025)

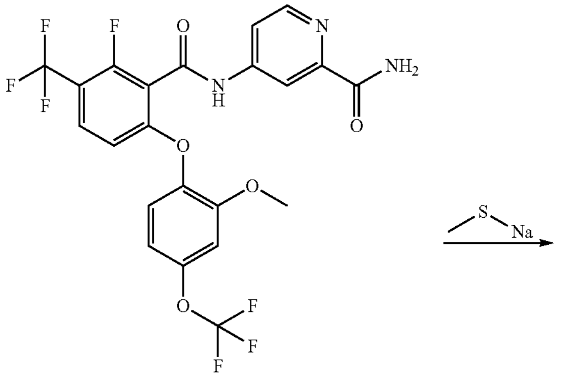

-continued

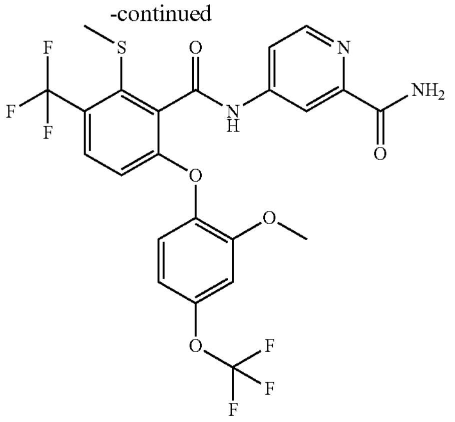

A solution of 4-[[2-fluoro-6-[2-methoxy-4-(trifluoromethoxy)phenoxy]-3-(trifluoromethyl)benzoyl]amino]pyridine-2-carboxamide (100 mg, 0.187 mmol) and sodium methylthiol (13 mg, 0.19 mmol) in THF (2 mL) was heated at 60° C. for 24 hours. The mixture was cooled RT and partitioned between ethyl acetate and water. The layers were separated and the organic layer was washed with water (3×) and brine, dried over $Na_2SO_4$, filtered and concentrated. Silica gel chromatography (methanol/dichloromethane gradient) provided 4-[[6-[2-methoxy-4-(trifluoromethoxy)phenoxy]-2-methylsulfanyl-3-(trifluoromethyl)benzoyl]amino]pyridine-2-carboxamide (27 mg, 23%) as a white solid. ESI-MS m/z calc. 561.08, found 562.44 $(M+1)^+$; Retention time (Method B): 1.85 minutes. $^1H$ NMR (400 MHz, DMSO-d6) δ 11.21 (s, 1H), 8.54 (d, J=5.5 Hz, 1H), 8.37 (d, J=2.1 Hz, 1H), 8.09 (d, J=2.9 Hz, 1H), 7.90-7.78 (m, 2H), 7.65 (d, J=2.9 Hz, 1H), 7.36-7.20 (m, 2H), 7.04 (ddd, J=8.8, 2.8, 1.3 Hz, 1H), 6.85 (d, J=8.9 Hz, 1H), 3.80 (s, 3H), 2.45 (s, 3H) ppm.

Example 207

4-[[6-[2-Methoxy-4-(Trifluoromethoxy)Phenoxy]-2-(Oxetan-3-Yloxy)-3-(Trifluoromethyl)Benzoyl]Amino]Pyridine-2-Carboxamide (1026)

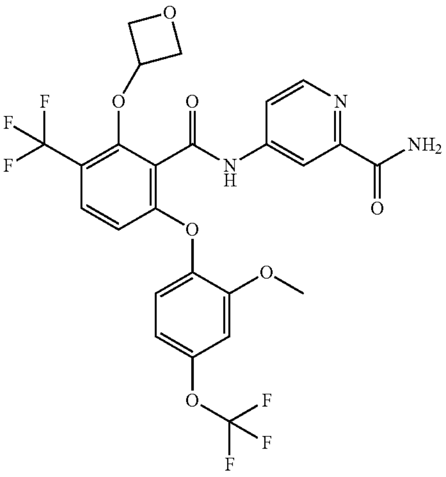 [SMILES: COc1cc(OC(F)(F)F)ccc1Oc1ccc(C(F)(F)F)c(OC2COC2)c1C(=O)Nc1ccnc(C(N)=O)c1]

Oxetan-3-ol (21 mg, 0.28 mmol) and finely-ground potassium carbonate (31 mg, 0.22 mmol) were added to a solution of 4-[[2-fluoro-6-[2-methoxy-4-(trifluoromethoxy)phenoxy]-3-(trifluoromethyl)benzoyl]amino]pyridine-2-carboxamide (30 mg, 0.056 mmol) in DMSO (0.5 mL) and the mixture stirred at 140° C. for 30 minutes in a sealed vial. The reaction mixture was filtered and purified by HPLC (1-99% $CH_3CN$/5 mM HCl) to provide 4-[[6-[2-methoxy-4-(trifluoromethoxy)phenoxy]-2-(oxetan-3-yloxy)-3-(trifluoromethyl)benzoyl]amino]pyridine-2-carboxamide (1.5 mg, 5%). ESI-MS m/z calc. 587.11, found 588.1 $(M+1)^+$; Retention time (Method B): 1.75 minutes.

The compounds set forth in Table 106 were prepared by methods analogous to the preparation of compound 1026.

TABLE 106

Additional Compounds Prepared by Methods Analogous to Example 207.

| Cmpd No. | Compound Name | LC/MS | NMR (shifts in ppm) |
|---|---|---|---|
| 1027 | 4-[[2-[2-(dimethylamino)ethoxy]-6-[2-methoxy-4-(trifluoromethoxy)phenoxy]-3-(trifluoromethyl)benzoyl]amino]pyridine-2-carboxamide | ESI-MS m/z calc. 602.16, found 603.2 (M + 1)+; Retention time (Method B): 1.37 minutes. | $^1$H NMR (400 MHz, DMSO-d6) δ 11.69 (s, 1H), 10.46 (s, 1H), 8.57 (s, 1H), 8.44 (s, 1H), 8.21 (s, 1H), 7.94 (s, 1H), 7.81-7.66 (m, 2H), 7.43 (d, J = 8.7 Hz, 1H), 7.25 (d, J = 2.7 Hz, 1H), 7.05 (d, J = 8.7 Hz, 1H), 6.60 (d, J = 8.9 Hz, 1H), 4.46 (s, 2H), 3.78 (s, 3H, partially obscured by water peak), 3.44 (d, J = 5.5 Hz, 2H), 2.77 (d, J = 4.6 Hz, 6H). |
| 1028 | 4-[[2-(2-cyclopropylethoxy)-6-[2-methoxy-4-(trifluoromethoxy)phenoxy]-3-(trifluoromethyl)benzoyl]amino]pyridine-2-carboxamide | ESI-MS m/z calc. 599.15, found 600.3 (M + 1)+; Retention time (Method B): 2.05 minutes. | $^1$H NMR (400 MHz, DMSO-d6) δ 11.38 (s, 1H), 8.60 (d, J = 5.4 Hz, 1H), 8.42 (d, J = 2.4 Hz, 1H), 8.17 (s, 1H), 7.94-7.88 (m, 1H), 7.80-7.67 (m, 2H), 7.36 (d, J = 8.9 Hz, 1H), 7.29 (s, 1H), 7.08 (d, J = 8.8 Hz, 1H), 6.58 (d, J = 9.0 Hz, 1H), 4.18 (t, J = 6.5 Hz, 2H), 3.84 (d, J = 2.4 Hz, 3H), 1.57 (d, J = 6.8 Hz, 2H), 0.83-0.67 (m, 1H), 0.30 (d, J = 7.7 Hz, 2H), 0.00 (d, J = 4.9 Hz, 2H). |

Example 208

4-[[2-[2-Methoxy-4-(Trifluoromethoxy)Phenoxy]-4-[4-(Trifluoromethyl)Cyclohexen-1-Yl]Benzoyl]Amino]Pyridine-2-Carboxamide (1029)

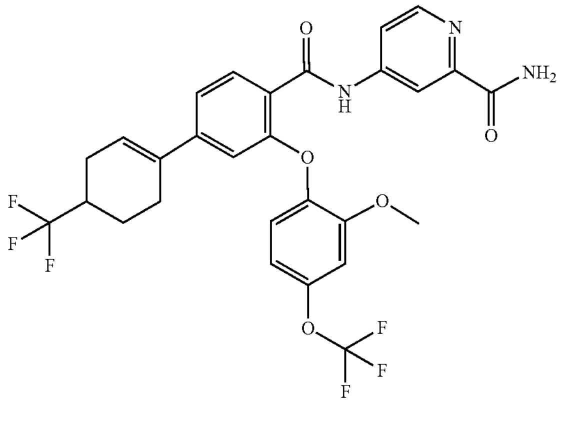 [SMILES: COc1cc(OC(F)(F)F)ccc1Oc1cc(C2=CCC(C(F)(F)F)CC2)ccc1C(=O)Nc1ccnc(C(N)=O)c1]

Step 1: 4-Bromo-2-[2-Methoxy-4-(Trifluoromethoxy)Phenoxy]Benzaldehyde

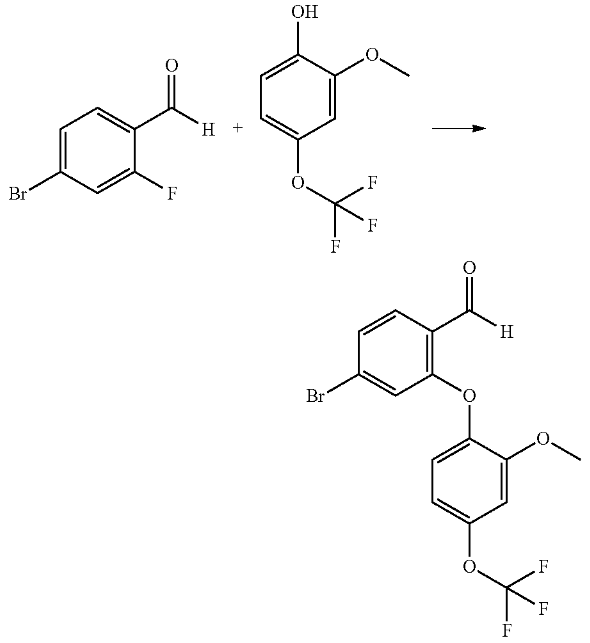

To a stirring solution of 4-bromo-2-fluoro-benzaldehyde (3.70 g, 18.2 mmol) in DMF (35 mL) was added $Cs_2CO_3$ (7.50 g, 23.0 mmol) and 2-methoxy-4-(trifluoromethoxy) phenol (4.17 g, 20.0 mmol). The reaction mixture was stirred at RT for 16 hours, and then partitioned between ethyl acetate and water. The organic layer was washed with water, 50% saturated aqueous $NaHCO_3$ and brine, then dried over $MgSO_4$, filtered and concentrated in vacuo. Silica gel chromatography (ethyl acetate/hexanes gradient) provided 4-bromo-2-[2-methoxy-4-(trifluoromethoxy)phenoxy]benzaldehyde (6.77 g, 95%). ESI-MS m/z calc. 389.97, found 392.9 $(M+1)^+$; Retention time (Method A): 0.8 minutes. $^1H$ NMR (400 MHz, DMSO-d6) δ 10.43 (s, 1H), 7.75 (d, J=8.3 Hz, 1H), 7.48-7.43 (m, 1H), 7.40 (d, J=8.8 Hz, 1H), 7.28 (d, J=2.7 Hz, 1H), 7.05 (ddd, J=8.8, 2.8, 1.3 Hz, 1H), 6.88 (d, J=1.7 Hz, 1H), 3.80 (s, 3H) ppm.

Step 2: 4-Bromo-2-[2-Methoxy-4-(Trifluoromethoxy)Phenoxy]Benzoic Acid

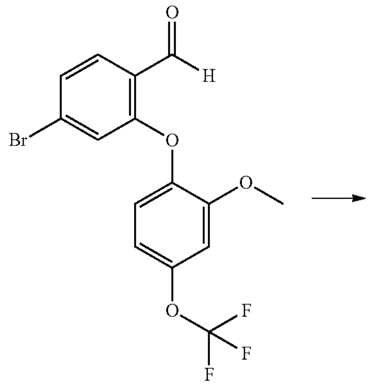

-continued

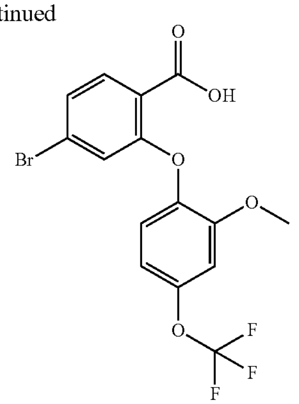

A mixture of 4-bromo-2-[2-methoxy-4-(trifluoromethoxy)phenoxy]benzaldehyde (6.74 g, 17.2 mmol) and sodium dihydrogenphosphate (3.10 g, 25.8 mmol) in tert-butyl alcohol (60 mL), water (35 mL), and acetonitrile (35 mL) at 0° C. was treated with 2-methylbut-2-ene (8.0 mL, 75 mmol) followed by the portion-wise addition of sodium chlorite (2.92 g, 25.8 mmol) over 10 minutes. The mixture was allowed to warm to RT and stirred for 16 hours. Additional sodium dihydrogenphosphate (3.10 g, 25.8 mmol) and sodium chlorite (2.92 g, 25.8 mmol) were added and the reaction mixture stirred for 30 minutes. The reaction mixture was acidified to pH~1-2 using aqueous HCl (175 mL of 1 M, 175 mmol) and partitioned with ethyl acetate. The organic layer was washed with an aqueous sodium sulfite solution to remove the faint yellow color. The two layers were separated and the combined aqueous layers extracted with ethyl acetate (3×25 mL). The combined organics were washed with brine, dried over $Na_2SO_4$, filtered and concentrated. The resulting solid was triturated with hexanes (100 mL) and filtered to provide 4-bromo-2-[2-methoxy-4-(trifluoromethoxy)phenoxy]benzoic acid (6.70 g, 96%) as a white solid. ESI-MS m/z calc. 405.97, found 407.9 $(M+1)^+$; Retention time (Method A): 0.72 minutes. $^1H$ NMR (400 MHz, DMSO-d6) δ 13.03 (s, 1H), 7.75 (d, J=8.4 Hz, 1H), 7.39 (dd, J=8.3, 1.8 Hz, 1H), 7.21 (d, J=2.7 Hz, 1H), 7.09 (d, J=8.8 Hz, 1H), 6.99-6.94 (m, 1H), 6.88 (d, J=1.8 Hz, 1H), 3.80 (s, 3H) ppm.

Step 3: 4-[[4-Bromo-2-[2-Methoxy-4-(Trifluoromethoxy)Phenoxy]Benzoyl]Amino]Pyridine-2-Carboxamide

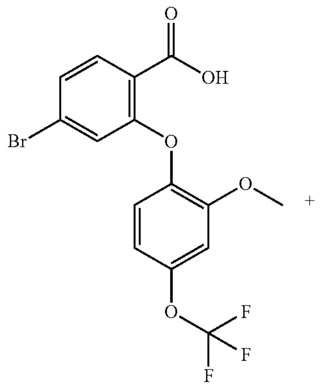

-continued

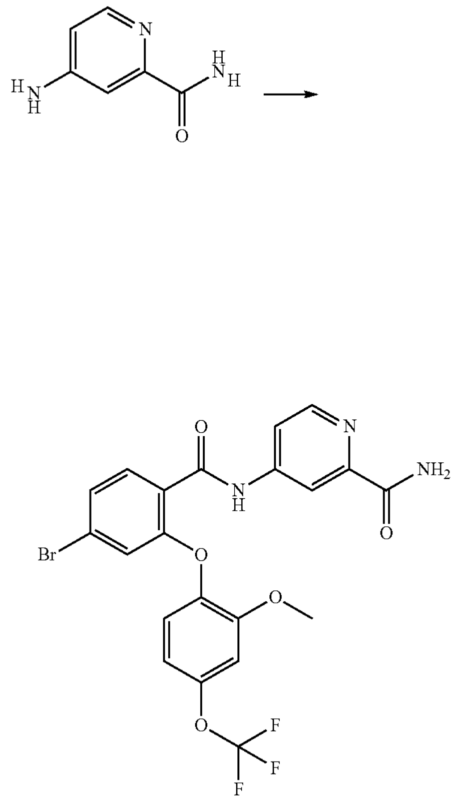

A solution of 4-bromo-2-[2-methoxy-4-(trifluoromethoxy)phenoxy]benzoic acid (2.01 g, 4.94 mmol) and DMF (20 μL, 0.26 mmol) in anhydrous dichloromethane (16 mL) under nitrogen at 0° C. was treated dropwise with oxalyl chloride (700 μL, 8.02 mmol). The solution was stirred for 15 minutes and then at 35° C. for 15 minutes (until no further gas evolution was observed). The reaction mixture was concentrated in vacuo and dried under high vacuum for 10 minutes. The resulting solid was dissolved in dichloromethane (5 mL) and the solution was added dropwise to a solution of 4-aminopyridine-2-carboxamide (0.812 g, 5.92 mmol) and DIEA (2.2 mL, 13 mmol) in NMP (20 mL) at 0° C. The reaction mixture was removed from the ice bath and stirred at RT for 2 hours. The dichloromethane was removed from the reaction mixture under reduced pressure and the reaction mixture diluted with ethyl acetate and washed with water (2×), 50% aqueous saturated $NaHCO_3$ and brine. The organic phase was dried over $Na_2SO_4$, filtered and concentrated in vacuo. The resulting solid was triturated with cold dichloromethane (25 mL) and filtered. The solid was rinsed with minimal cold dichloromethane and air dried to provide 4-[[4-bromo-2-[2-methoxy-4-(trifluoromethoxy)phenoxy]benzoyl]amino]pyridine-2-carboxamide (1.21 g, 47%). ESI-MS m/z calc. 525.02, found 527.0 $(M+1)^+$; Retention time (Method A): 0.71 minutes. $^1H$ NMR (400 MHz, DMSO-d6) δ 10.88 (s, 1H), 8.51 (d, J=5.5 Hz, 1H), 8.30 (d, J=2.1 Hz, 1H), 8.08 (d, J=2.9 Hz, 1H), 7.85 (dd, J=5.5, 2.1 Hz, 1H), 7.64 (d, J=8.1 Hz, 2H), 7.45 (dd, J=8.2, 1.7 Hz, 1H), 7.31 (d, J=8.8 Hz, 1H), 7.19 (d, J=2.6 Hz, 1H), 7.05-6.97 (m, 1H), 6.93 (d, J=1.7 Hz, 1H), 3.77 (s, 3H) ppm.

Step 4: 4-[[2-[2-Methoxy-4-(Trifluoromethoxy)Phenoxy]-4-[4-(Trifluoromethyl)Cyclohexen-1-Yl]Benzoyl]Amino]Pyridine-2-Carboxamide (1029)

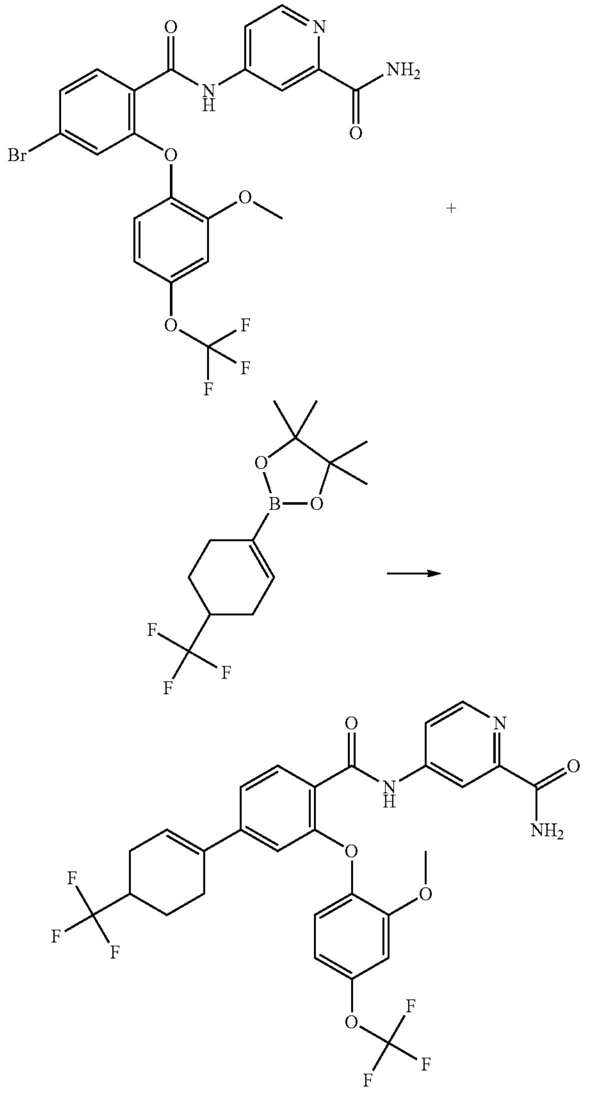

A vial charged with 4-[[4-bromo-2-[2-methoxy-4-(trifluoromethoxy)phenoxy]benzoyl]amino]pyridine-2-carboxamide (30 mg, 0.057 mmol), 4,4,5,5-tetramethyl-2-[4-(trifluoromethyl)cyclohexen-1-yl]-1,3,2-dioxaborolane (31 mg, 0.11 mmol), $K_2CO_3$ (8 mg, 0.06 mmol) and Pd(dppf) $Cl_2$.DCM (5 mg, 0.006 mmol) in dioxane (500 μL) and water (50 μL) was flushed with nitrogen and heated at 100° C. for 16 hours. The reaction mixture was filtered and purified by HPLC (1-99% $CH_3CN$/5 mM HCl) to provide 4-[[2-[2-methoxy-4-(trifluoromethoxy)phenoxy]-4-[4-(trifluoromethyl)cyclohexen-1-yl]benzoyl]amino]pyridine-2-carboxamide (33 mg, 97%). ESI-MS m/z calc. 595.15, found 596.2 $(M+1)^+$; Retention time (Method B): 2.07 minutes. $^1H$ NMR (400 MHz, DMSO-d6) δ 10.77 (s, 1H), 8.49 (d, J=5.5 Hz, 1H), 8.29 (d, J=2.1 Hz, 1H), 8.07 (s, 1H), 7.84 (dd, J=5.5, 2.2 Hz, 1H), 7.67 (d, J=8.1 Hz, 1H), 7.62 (s, 1H), 7.54 (s, 1H), 7.32 (d, J=8.3 Hz, 1H), 7.19-7.12 (m, 2H), 6.96 (d, J=8.8 Hz, 1H), 6.85 (s, 1H), 3.76 (s, 3H), 2.11-1.86 (m, 4H), 1.65-1.47 (m, 1H), 1.39-1.24 (m, 2H) ppm.

The compounds set forth in Table 107 were prepared by methods analogous to the preparation of compound 1029

TABLE 107

| Additional Compounds Prepared by Methods Analogous to Example 208. | | | |
|---|---|---|---|
| Cmpd No. | Compound Name | LC/MS | NMR (shifts in ppm) |
| 1030 | 4-[[4-(2,5-dihydrofuran-3-yl)-2-[2-methoxy-4-(trifluoromethoxy)phenoxy]benzoyl]amino]pyridine-2-carboxamide | ESI-MS m/z calc. 515.13, found 516.2 (M + 1)+; Retention time (Method B): 1.59 minutes. | $^1$H NMR (400 MHz, DMSO-d6) δ 10.84 (s, 1H), 8.49 (d, J = 5.4 Hz, 1H), 8.27 (d, J = 2.4 Hz, 1H), 8.09 (s, 1H), 7.83 (dd, J = 5.6, 2.5 Hz, 1H), 7.70 (d, J = 8.0 Hz, 1H), 7.64 (s, 1H), 7.31 (d, J = 8.0 Hz, 1H), 7.14-7.06 (m, 2H), 6.99-6.89 (m, 2H), 6.59 (s, 1H), 4.84 (br s, 2H), 4.72 (d, J = 5.5 Hz, 2H), 3.75 (s, 3H). |
| 1031 | 4-[[4-(4-methoxycyclohexen-1-yl)-2-[2-methoxy-4-(trifluoromethoxy)phenoxy]benzoyl]amino]pyridine-2-carboxamide | ESI-MS m/z calc. 557.18, found 558.2 (M + 1)+; Retention time (Method B): 1.81 minutes. | $^1$H NMR (400 MHz, DMSO-d6) δ 10.78 (s, 1H), 8.50 (d, J = 5.5 Hz, 1H), 8.30 (d, J = 2.2 Hz, 1H), 8.10 (s, 1H), 7.85 (dd, J = 5.4, 2.2 Hz, 1H), 7.65 (t, J = 6.2 Hz, 2H), 7.31 (d, J = 8.1 Hz, 1H), 7.19-7.12 (m, 2H), 6.96 (d, J = 9.3 Hz, 1H), 6.83 (s, 1H), 6.06 (s, 1H), 3.76 (s, 3H), 3.26 (s, 3H), 2.50 (m, 3H), 2.37 (s, 1H), 2.12 (t, J = 11.8 Hz, 1H), 1.93 (d, J = 11.8 Hz, 1H), 1.68 (dt, J = 13.4, 6.9 Hz, 1H). |

Example 209

4-[[4-(4-Methoxycyclohexyl)-2-[2-Methoxy-4-(Trifluoromethoxy)Phenoxy]Benzoyl]Amino]Pyridine-2-Carboxamide (1032)

1032-a

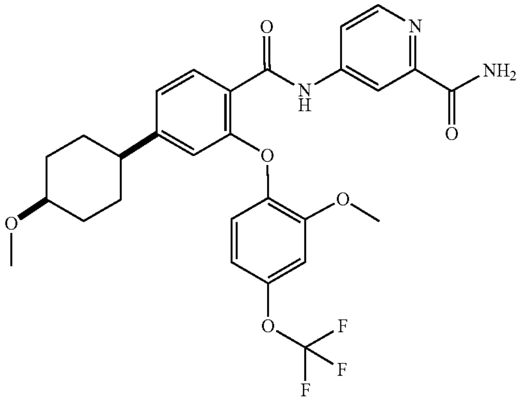

1032-b

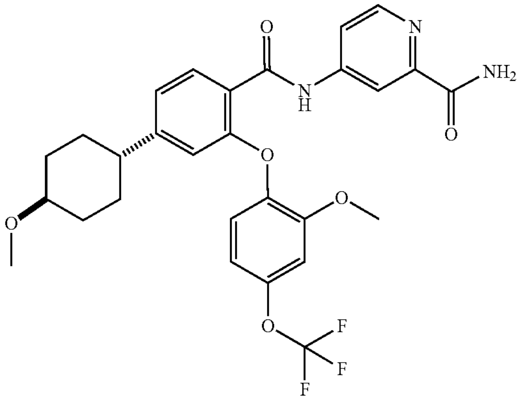

4-[[4-(4-Methoxycyclohexen-1-yl)-2-[2-methoxy-4-(trifluoromethoxy)phenoxy]benzoyl]amino]pyridine-2-carboxamide (16 mg, 0.029 mmol) was dissolved in ethyl acetate (250 μL)/methanol (250 μL). The mixture was flushed with nitrogen then treated with 10% Pd/C (2 mg, 0.01879 mmol). The resulting mixture was degassed with a flow of nitrogen for 2 minutes, then purged with hydrogen. The reaction was stirred at room temperature for 16 hours. The mixture was filtered and purified by phase HPLC (1-99% $CH_3CN$/5 mM HCl) to provide the two separated diastereomers, assigned as diastereomer 1 and diastereomer 2, respectively based on HPLC elution order. It is appreciated that both diastereomers of 4-[[4-(4-methoxycyclohexyl)-2-[2-methoxy-4-(trifluoromethoxy)phenoxy]benzoyl]amino]pyridine-2-carboxamide (1032) were isolated and that those diastereomers have the structure of compounds 1032-a and 1032-b (above). However, the relative stereochemistry of diastereomers 1 and 2 was not determined.

Diastereomer 1: 4-[[4-(4-methoxycyclohexyl)-2-[2-methoxy-4-(trifluoromethoxy)phenoxy]benzoyl]amino]pyridine-2-carboxamide (32) (2.4 mg, 15%). ESI-MS m/z calc. 559.19, found 560.2 $(M+1)^+$; Retention time (Method B): 1.79 minutes. 1H NMR (400 MHz, DMSO-$d_6$) δ 10.92 (s, 1H), 8.52 (d, J=5.7 Hz, 1H), 8.36 (s, 1H), 8.21 (s, 1H), 7.89 (dd, J=5.7, 2.2 Hz, 1H), 7.75 (s, 1H), 7.61 (d, J=7.9 Hz, 1H), 7.26-7.15 (m, 2H), 7.11 (d, 1H), 6.99 (d, 1H), 6.62 (s, 1H), 3.75 (s, 3H), 3.49-3.38 (m, 1H), 3.21 (s, 3H), 2.58 (m, 1H, obscured by solvent peak), 2.00-1.81 (m, 2H), 1.68-1.34 (m, 6H).

Diastereomer 2: 4-[[4-(4-methoxycyclohexyl)-2-[2-methoxy-4-(trifluoromethoxy)phenoxy]benzoyl]amino]pyridine-2-carboxamide (32) (6.6 mg, 41%). ESI-MS m/z calc. 559.19, found 560.3 $(M+1)^+$; Retention time (Method B): 1.89 minutes. 1H NMR (400 MHz, DMSO-$d_6$) δ 10.78 (s, 1H), 8.48 (d, J=5.5 Hz, 1H), 8.29 (d, J=2.1 Hz, 1H), 8.08 (d, J=2.8 Hz, 1H), 7.84 (dd, J=5.5, 2.2 Hz, 1H), 7.72-7.50 (m, 2H), 7.26-7.08 (m, 3H), 6.97 (dd, J=8.8, 1.7 Hz, 1H), 6.69 (d, J=1.4 Hz, 1H), 3.75 (s, 3H), 3.23 (s, 3H), 3.20-3.07 (m, 1H), 2.48 (m, 1H, obscured by solvent peak), 2.15-1.96 (m, 2H), 1.85-1.65 (m, 2H), 1.54-1.31 (m, 2H), 1.31-1.09 (m, 2H).

The compounds set forth in Table 108 were prepared by methods analogous to the preparation of compound 1032

TABLE 108

| Additional Compounds Prepared by Methods Analogous to Example 209 | | | |
|---|---|---|---|
| Cmpd No. | Compound Name | LC/MS | NMR (shifts in ppm) |
| 1033 | 4-[[2-[2-methoxy-4-(trifluoromethoxy)phenoxy]-4-tetrahydrofuran-3-yl-benzoyl]amino]pyridine-2-carboxamide | ESI-MS m/z calc. 517.15, found 518.2 (M + 1)+; Retention time (Method B): 0.83 minutes. | $^1$H NMR (400 MHz, DMSO-d6) δ 10.86 (s, 1H), 8.51 (d, J = 5.5 Hz, 1H), 8.32 (d, J = 2.1 Hz, 1H), 8.15 (s, 1H), 7.87 (dd, J = 5.6, 2.1 Hz, 1H), 7.69 (s, 1H), 7.64 (d, J = 7.9 Hz, 1H), 7.21-7.12 (m, 3H), 7.01-6.93 (m, 1H), 6.74 (s, 1H), 3.96 (t, J = 7.8 Hz, 1H), 3.87 (td, J = 8.2, 4.8 Hz, 1H), 3.75 (s, 4H), 3.53 (m, 1H), 3.44-3.29 (m, 1H), 2.28 (ddt, J = 12.6, 7.8, 3.9 Hz, 1H), 1.83 (dq, J = 12.2, 7.7 Hz, 1H). |

Example 210

5-[[5-Fluoro-7-[2-Methoxy-4-(Trifluoromethoxy)Phenoxy]-2,3-Dihydro-1,4-Benzodioxine-6-Carbonyl]Amino]Pyridine-2-Carboxamide (1034)

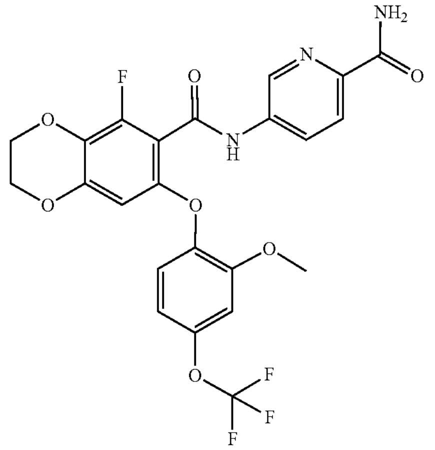 [SMILES: COc1cc(OC(F)(F)F)ccc1Oc1cc2c(c(F)c1C(=O)Nc1ccc(C(N)=O)nc1)OCCO2]

Step 1: 7-Bromo-5-Fluoro-2,3-Dihydro-1,4-Benzodioxine

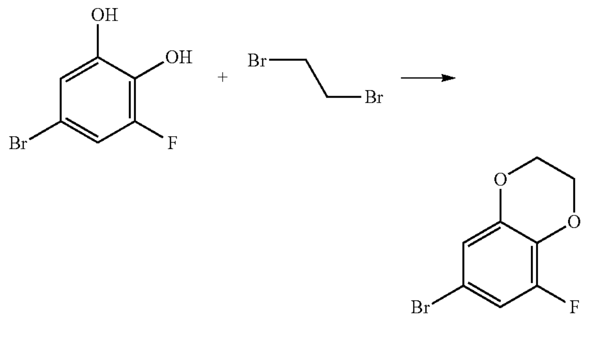

To a mixture of 5-bromo-3-fluoro-benzene-1,2-diol (50 mg, 0.24 mmol) and $K_2CO_3$ (100 mg, 0.724 mmol) in DMF (0.75 mL) was added 1,2-dibromoethane (228 mg, 0.105 mL, 1.21 mmol). The reaction mixture was heated at 80° C. for 4 hours, then cooled to RT and stirred overnight. The reaction mixture was partitioned between water and ethyl acetate. Layers were separated and the aqueous phase was extracted with ethyl acetate (2×). The combined organic layers were concentrated under reduced pressure. Purification of the resulting residue via silica gel chromatography (ethyl acetate/hexanes gradient) provided 7-bromo-5-fluoro-2,3-dihydro-1,4-benzodioxine (36 mg, 63%) as a white solid. Retention time (Method V): 2.91 minutes. $^1$H NMR (250 MHz, $CDCl_3$) δ 6.92-6.78 (m, 2H), 4.29 (s, 4H) ppm.

Step 2: 7-Bromo-5-Fluoro-2,3-Dihydro-1,4-Benzodioxine-6-Carboxylic Acid

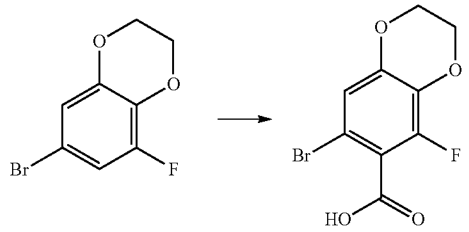 [SMILES: Fc1cc(Br)cc2c1OCCO2 ; O=C(O)c1c(Br)cc2c(c1F)OCCO2]

Lithium diisopropylamide (5.6 mL of 2 M, 11.2 mmol) was added to a solution of 7-bromo-5-fluoro-2,3-dihydro-1,4-benzodioxine (2.25 g, 9.27 mmol) in anhydrous THF (90 mL) at −78° C. and stirred at this temperature for 2 hours. The reaction mixture was transferred via cannula to dry ice and the slurry was allowed to come to RT over 48 hours. The solvent was evaporated in vacuo. The resulting solid was dissolved in 200 mL of 1 M NaOH solution and extracted once with 200 mL of ether. The aqueous layer was acidified to pH=1 using concentrated HCl and extracted with ethyl acetate (2×200 mL). The combined organic layers were washed with water (100 mL), brine (100 mL), dried over $Na_2SO_4$, filtered, and concentrated in vacuo to provide 7-bromo-5-fluoro-2,3-dihydro-1,4-benzodioxine-6-carboxylic acid (2.3 g, 86%) as a white solid. ESI-MS m/z calc. 275.94, found 276.9 $(M+1)^+$; Retention time (Method W): 1.5 minutes. $^1$H NMR (500 MHz, DMSO-d6) δ 7.10 (d, J=2.0 Hz, 1H), 4.35 (s, 4H) ppm.

Step 3: 5-Fluoro-7-[2-Methoxy-4-(Trifluoromethoxy)Phenoxy]-2,3-Dihydro-1,4-Benzodioxine-6-Carboxylic Acid

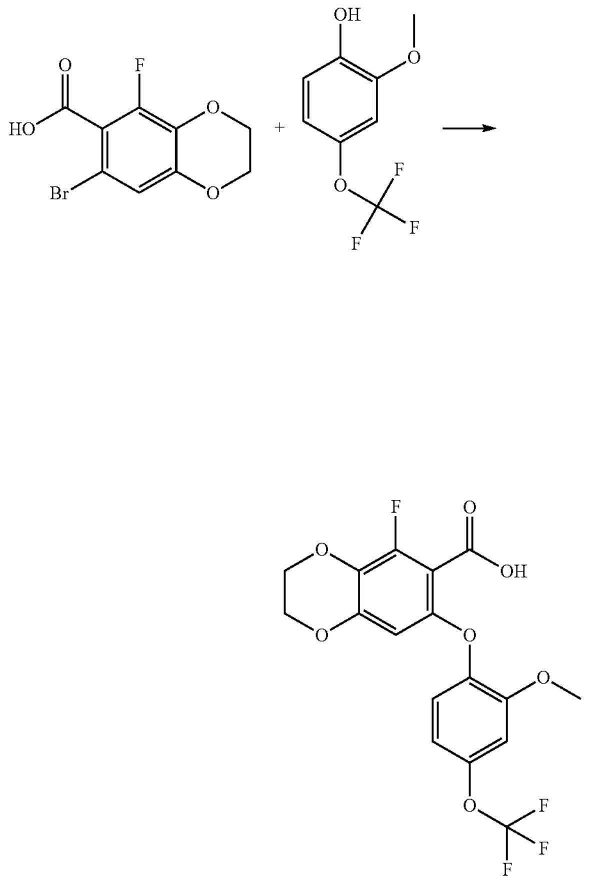

To a pressure flask was added 7-bromo-5-fluoro-2,3-dihydro-1,4-benzodioxine-6-carboxylic acid (1.03 g, 3.72 mmol), 2-methoxy-4-(trifluoromethoxy)phenol (811 mg, 3.91 mmol), $Cs_2CO_3$ (1.27 g, 3.90 mmol) and toluene (10 mL). The reaction mixture was bubbled with nitrogen for 10 minutes, then copper (I) iodide (164 mg, 0.861 mmol) added. The flask was flushed with nitrogen, capped, and heated at 100° C. with vigorous stirring for 6 hours. Additional 2-methoxy-4-(trifluoromethoxy)phenol (811 mg, 3.90 mmol), $Cs_2CO_3$ (1.27 g, 3.90 mmol), copper (I) iodide (164 mg, 0.861 mmol) and toluene (6 mL) were added and the reaction was stirred at 100° C. for 3 hours. The mixture was allowed to cool, and then diluted with ethyl acetate and water, and the aqueous layer acidified with 1 M HCl. The two layers were separated. The aqueous layer was extracted with ethyl acetate (3×). The combined organic layers were washed with water and brine, dried over $Na_2SO_4$, filtered through a plug of Celite and concentrated. Purification by silica gel chromatography (ethyl acetate/hexanes gradient) provided 5-fluoro-7-[2-methoxy-4-(trifluoromethoxy)phenoxy]-2,3-dihydro-1,4-benzodioxine-6-carboxylic acid (455 mg, 30%). ESI-MS m/z calc. 404.05, found 405.11 $(M+1)^+$; Retention time (Method C): 2.24 minutes. $^1H$ NMR (400 MHz, DMSO-d6) δ 13.29 (s, 1H), 7.15 (d, J=2.7 Hz, 1H), 7.04-6.87 (m, 2H), 6.14 (s, 1H), 4.30 (s, 4H), 3.81 (s, 3H) ppm.

Step 4: 5-Fluoro-7-[2-Methoxy-4-(Trifluoromethoxy)Phenoxy]-2,3-Dihydro-1,4-Benzodioxine-6-Carbonyl Chloride

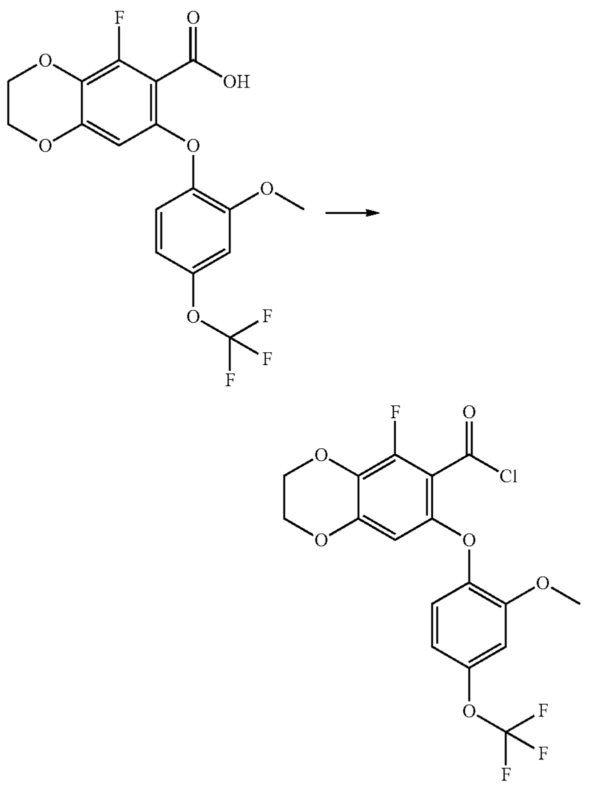 [SMILES: COc1cc(OC(F)(F)F)ccc1Oc1cc2c(c(F)c1C(=O)O)OCCO2 ; COc1cc(OC(F)(F)F)ccc1Oc1cc2c(c(F)c1C(=O)Cl)OCCO2]

To a solution of 5-fluoro-7-[2-methoxy-4-(trifluoromethoxy)phenoxy]-2,3-dihydro-1,4-benzodioxine-6-carboxylic acid (103 mg, 0.25 mmol) and DMF (15 μL, 0.19 mmol) in dichloromethane (1 mL) at 0° C. was added oxalyl chloride (35 μL, 0.40 mmol) dropwise under nitrogen atmosphere. The ice bath was removed after 10 minutes and the reaction was stirred at RT for 1 hour. The solvent was evaporated under reduced pressure to afford 5-fluoro-7-[2-methoxy-4-(trifluoromethoxy)phenoxy]-2,3-dihydro-1,4-benzodioxine-6-carbonyl chloride (108 mg, 100%). The intermediate was used in the next step without further purification.

Step 5: 5-[[5-Fluoro-7-[2-Methoxy-4-(Trifluoromethoxy)Phenoxy]-2,3-Dihydro-1,4-Benzodioxine-6-Carbonyl]Amino]Pyridine-2-Carboxamide (1034)

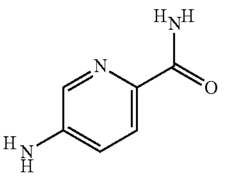

-continued

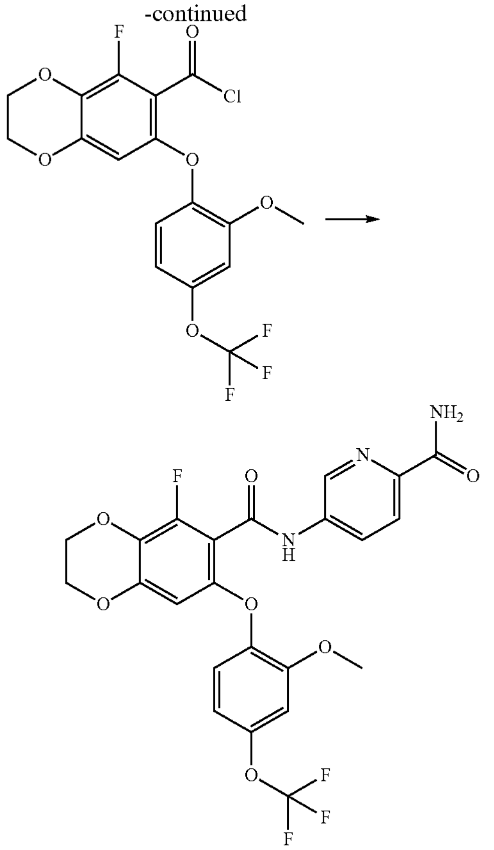

To 5-aminopyridine-2-carboxamide (65 mg, 0.47 mmol) in NMP (500 μL) and DIEA (153 mg, 206 μL, 1.18 mmol) at 0° C. was slowly added a solution of 5-fluoro-7-[2-methoxy-4-(trifluoromethoxy)phenoxy]-2,3-dihydro-1,4-benzodioxine-6-carbonyl chloride (100 mg, 0.237 mmol) in NMP (1 mL). The mixture was stirred at RT for 1 hour. The reaction mixture was filtered and purified by HPLC (1-99% $CH_3CN$/5 mM HCl) to provide 5-[[5-fluoro-7-[2-methoxy-4-(trifluoromethoxy)phenoxy]-2,3-dihydro-1,4-benzodioxine-6-carbonyl]amino]pyridine-2-carboxamide (40 mg, 33%). ESI-MS m/z calc. 523.10, found 524.2 $(M+1)^+$; Retention time (Method C): 2.18 minutes. $^1H$ NMR (400 MHz, DMSO-d6) δ 11.05 (s, 1H), 8.82 (d, J=2.4 Hz, 1H), 8.21 (dd, J=8.6, 2.4 Hz, 1H), 8.12-7.90 (m, 2H), 7.54 (s, 1H), 7.23-7.03 (m, 2H), 6.93 (d, J=9.3 Hz, 1H), 6.21 (s, 1H), 4.33 (s, 4H), 3.74 (s, 3H) ppm.

The compounds set forth in Table 109 were prepared by methods analogous to the preparation of compound 1034.

TABLE 109

Additional Compounds Prepared by Methods Analogous to Example 210 (compound 1034)

| Cmpd No. | Compound Name | LC/MS | NMR (shifts in ppm) |
|---|---|---|---|
| 1035 | 4-[[5-fluoro-7-[2-methoxy-4-(trifluoromethoxy)phenoxy]-2,3-dihydro-1,4-benzodioxine-6-carbonyl]amino]pyridine-2-carboxamide | ESI-MS m/z calc. 523.10, found 524.17 (M + 1)+; Retention time (Method C): 2.17 minutes. | $^1H$ NMR (400 MHz, DMSO-d6) δ 11.16 (s, 1H), 8.50 (d, J = 5.5 Hz, 1H), 8.27 (d, J = 2.2 Hz, 1H), 8.10 (s, 1H), 7.96-7.75 (m, 1H), 7.65 (d, J = 2.9 Hz, 1H), 7.19-7.04 (m, 2H), 6.93 (d, J = 8.9 Hz, 1H), 6.19 (d, J = 1.8 Hz, 1H), 4.33 (s, 4H), 3.74 (s, 3H). |

Example 211

4-[[6-[2-(Trideuteriomethoxy)-4-(Trifluoromethoxy)Phenoxy]-2,3-Dihydro-1,4-Benzodioxine-7-Carbonyl]Amino]Pyridine-2-Carboxamide (1036)

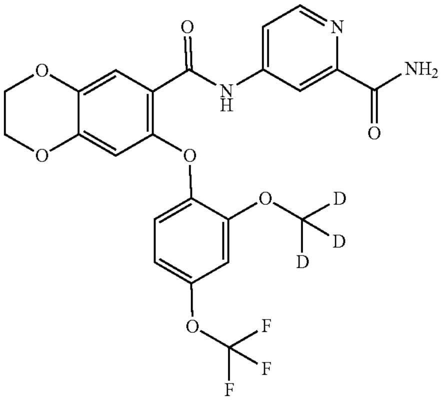 [SMILES: [2H]C([2H])([2H])Oc1cc(OC(F)(F)F)ccc1Oc1cc2c(cc1C(=O)Nc1ccnc(C(N)=O)c1)OCCO2]

Step 1: 6-[2-(Trideuteriomethoxy)-4-(Trifluoromethoxy)Phenoxy]-2,3-Dihydro-1,4-Benzodioxine-7-Carboxylic Acid

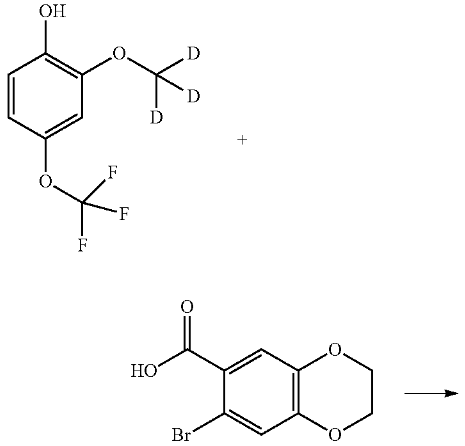

-continued

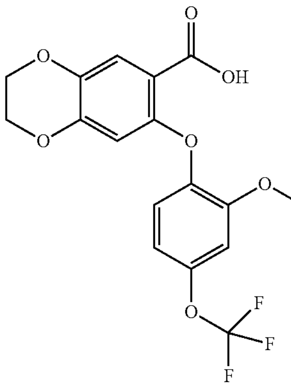

To a pressure flask was added 6-bromo-2,3-dihydro-1,4-benzodioxine-7-carboxylic acid (2.0 g, 7.7 mmol), 2-(trideuteriomethoxy)-4-(trifluoromethoxy)phenol Example 202, Step 2) (1.70 g, 8.04 mmol), $Cs_2CO_3$ (2.62 g, 8.04 mmol) and toluene (15 mL). The reaction mixture was bubbled with nitrogen for 10 minutes, then copper (I) iodide (345 mg, 1.81 mmol) added. The flask was flushed with nitrogen, capped, and heated at 100° C. with vigorous stirring for 22 hours. The mixture was allowed to cool to RT and then partitioned between ethyl acetate and water. The organic layer was washed with water (×2), brine, dried over $Na_2SO_4$, filtered through a plug of Celite and concentrated. Purification via silica gel chromatography (ethyl acetate/hexanes gradient) provided 6-[2-(trideuteriomethoxy)-4-(trifluoromethoxy)phenoxy]-2,3-dihydro-1,4-benzodioxine-7-carboxylic acid (449 mg, 15%). ESI-MS m/z calc. 389.08, found 390.2 $(M+1)^+$; Retention time (Method C): 2.29 minutes. $^1H$ NMR (400 MHz, DMSO-d6) δ 12.59 (s, 1H), 7.34 (s, 1H), 7.12 (d, J=2.8 Hz, 1H), 6.90-6.82 (m, 1H), 6.76 (d, J=8.8 Hz, 1H), 6.36 (s, 1H), 4.33-4.22 (m, 4H) ppm.

Step 2: 6-[2-(Trideuteriomethoxy)-4-(Trifluoromethoxy)Phenoxy]-2,3-Dihydro-1,4-Benzodioxine-7-Carbonyl Chloride

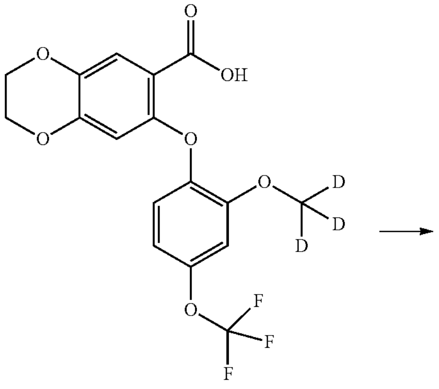

-continued

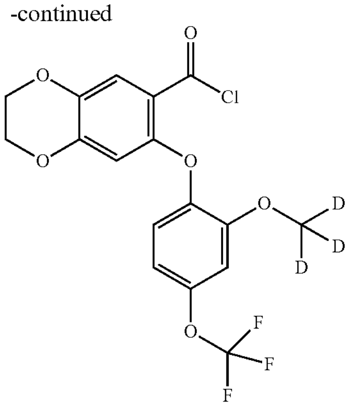

To a solution of 6-[2-(trideuteriomethoxy)-4-(trifluoromethoxy)phenoxy]-2,3-dihydro-1,4-benzodioxine-7-carboxylic acid (440 mg, 1.13 mmol) and DMF (15 μL, 0.19 mmol) in dichloromethane (3.5 mL) at 0° C. was added oxalyl chloride (150 μL, 1.72 mmol) dropwise under nitrogen atmosphere. The ice bath was removed after 10 minutes and the reaction was stirred at RT for 1 hour. The solvent was evaporated under reduced pressure to afford 6-[2-(trideuteriomethoxy)-4-(trifluoromethoxy)phenoxy]-2,3-dihydro-1,4-benzodioxine-7-carbonyl chloride. The intermediate was used in the next step without further purification.

Step 3: 4-[[6-[2-(Trideuteriomethoxy)-4-(Trifluoromethoxy)Phenoxy]-2,3-Dihydro-1,4-Benzodioxine-7-Carbonyl]Amino]Pyridine-2-Carboxamide (1036)

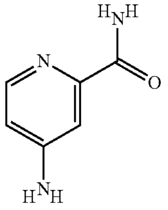

+

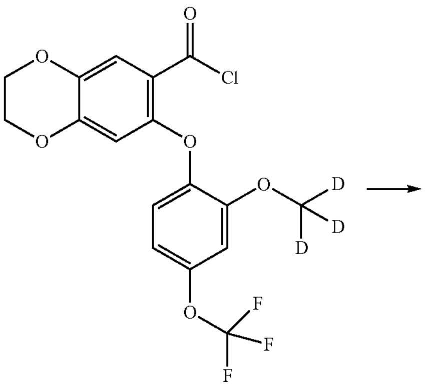

-continued

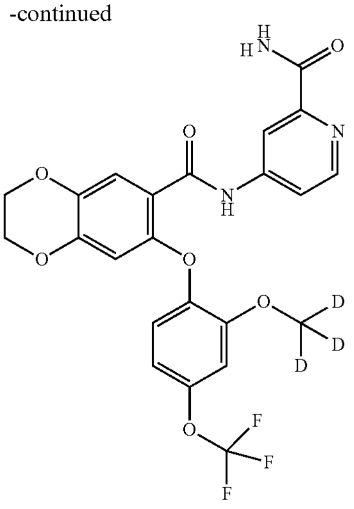

To a solution of 4-aminopyridine-2-carboxamide (20 mg, 0.15 mmol) and DIEA (47 mg, 64 μL, 0.37 mmol) in NMP (500 μL) at 0° C. was slowly added a solution of 6-[2-(trideuteriomethoxy)-4-(trifluoromethoxy)phenoxy]-2,3-dihydro-1,4-benzodioxine-7-carbonyl chloride (50 mg, 0.12 mmol) in NMP (200 μL). The reaction was allowed to warm to RT and stirred for 1 hour. The crude product was filtered and purified by HPLC (1-99% $CH_3CN$/5 mM HCl) to provide 4-[[6-[2-(trideuteriomethoxy)-4-(trifluoromethoxy)phenoxy]-2,3-dihydro-1,4-benzodioxine-7-carbonyl]amino]pyridine-2-carboxamide (11.7 mg, 19%). ESI-MS m/z calc. 508.13, found 508.95 $(M+1)^+$; Retention time (Method B): 1.72 minutes. $^1H$ NMR (400 MHz, DMSO-d6) δ 10.63 (s, 1H), 8.48 (d, J=5.5 Hz, 1H), 8.26 (d, J=2.6 Hz, 1H), 8.10 (s, 1H), 7.83 (dd, J=5.6, 2.5 Hz, 1H), 7.64 (s, 1H), 7.25 (d, J=2.2 Hz, 1H), 7.14-7.03 (m, 2H), 6.93 (d, J=8.8 Hz, 1H), 6.41 (d, J=2.1 Hz, 1H), 4.28 (d, J=8.0 Hz, 4H) ppm.

The compounds set forth in Table 110 were prepared by methods analogous to the preparation of compound 1036

TABLE 110

Additional Compounds Prepared by Methods Analogous to Example 211

| Cmpd No. | Compound Name | LC/MS | NMR (shifts in ppm) |
|---|---|---|---|
| 1037 | 5-[[6-[2-(trideuteriomethoxy)-4-(trifluoromethoxy)phenoxy]-2,3-dihydro-1,4-benzodioxine-7-carbonyl]amino]pyridine-2-carboxamide | ESI-MS m/z calc. 508.13, found 509.1 (M + 1)+; Retention time (Method C): 2.51 minutes. | $^1H$ NMR (400 MHz, DMSO-$d_6$) δ 10.53 (s, 1H), 8.83 (d, J = 2.6 Hz, 1H), 8.25-8.12 (m, 1H), 7.99 (d, J = 11.0 Hz, 2H), 7.53 (s, 1H), 7.25 (t, J = 2.0 Hz, 1H), 7.11 (d, J = 2.6 Hz, 1H), 7.06 (d, J = 8.8 Hz, 1H), 6.93 (d, J = 8.9 Hz, 1H), 6.42 (d, J = 2.0 Hz, 1H), 4.28 (d, J = 6.8 Hz, 4H). |

Example 212

4-[[4-(3-Fluorocyclobut-2-En-1-Yl)Oxy-2-[2-Methoxy-4-(Trifluoromethoxy)Phenoxy]-6-Methyl-Benzoyl]Amino]Pyridine-2-Carboxamide (1038)

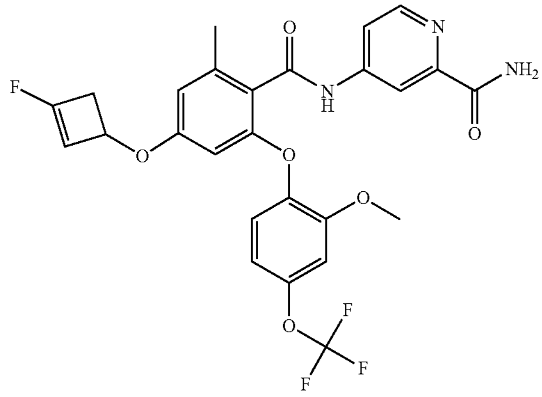 [SMILES: COc1cc(OC(F)(F)F)ccc1Oc1cc(OC2C=C(F)C2)cc(C)c1C(=O)Nc1ccnc(C(N)=O)c1]

Step 1: 2,6-Dichloro-4-(3,3-Difluorocyclobutoxy) Benzonitrile

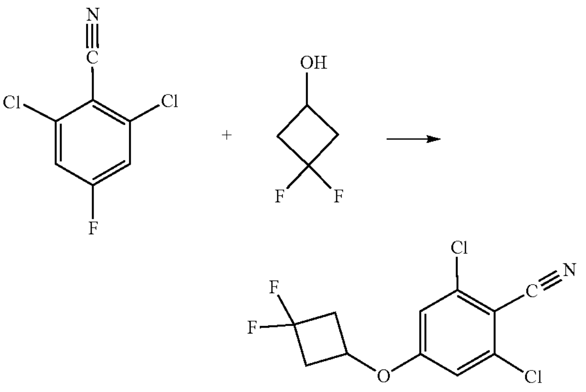

2,6-Dichloro-4-fluoro-benzonitrile (940 mg, 4.95 mmol), 3,3-difluorocyclobutanol (625 mg, 5.78 mmol) and NaH (283 mg of 60% w/w, 7.08 mmol) were combined in THF (8 mL) and heated at 60° C. under nitrogen for 2 hours. The mixture was allowed to cool, diluted with ethyl acetate and washed with 2 M NaOH. The organic layer was separated, dried over $MgSO_4$ and concentrated to provide 2,6-dichloro-4-(3,3-difluorocyclobutoxy)benzonitrile (1.485 g, 108%). $^1$H NMR (500 MHz, Chloroform-d) δ 6.88 (s, 2H), 4.79-4.62 (m, 1H), 3.25-3.10 (m, 2H), 2.91-2.71 (m, 2H) ppm. The crude material was taken on to the next step.

Step 2: 2-Chloro-4-(3,3-Difluorocyclobutoxy)-6-[2-Methoxy-4-(Trifluoromethoxy)Phenoxy]Benzonitrile

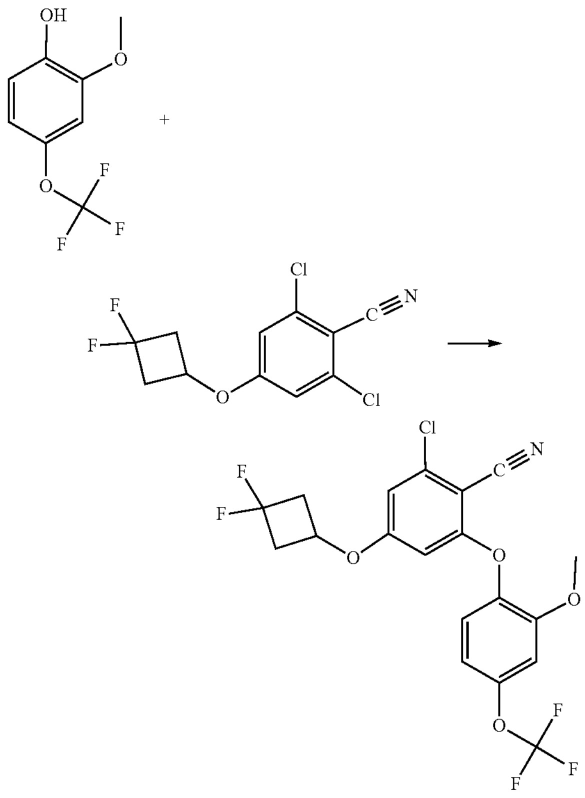

2-Methoxy-4-(trifluoromethoxy)phenol (1.288 g, 6.188 mmol), 2,6-dichloro-4-(3,3-difluorocyclobutoxy)benzonitrile (1.485 g, 5.340 mmol) and $Cs_2CO_3$ (2.162 g, 6.636 mmol) were combined in DMF (8 mL) and heated at 95° C. for 16 hours. The reaction was allowed to cool then was partitioned between ethyl acetate and brine. The organic layer was separated, dried over $MgSO_4$ and concentrated. Silica gel chromatography (0-20% ethyl acetate/heptane) provided 2-chloro-4-(3,3-difluorocyclobutoxy)-6-[2-methoxy-4-(trifluoromethoxy)phenoxy]benzonitrile (1.794 g, 75%). $^1$H NMR (500 MHz, DMSO-d6) δ 8.70 (dd, J=8.6, 1.9 Hz, 1H), 8.50-8.40 (m, 2H), 8.13 (d, J=2.2 Hz, 1H), 7.54 (d, J=2.3 Hz, 1H), 6.21-6.08 (m, 1H), 5.36 (s, 3H), 4.58 (dddd, J=15.4, 13.9, 8.0, 4.4 Hz, 2H), 4.32-4.14 (m, 2H) ppm.

Step 3: 4-(3,3-Difluorocyclobutoxy)-2-[2-Methoxy-4-(Trifluoromethoxy)Phenoxy]-6-Methyl-Benzonitrile

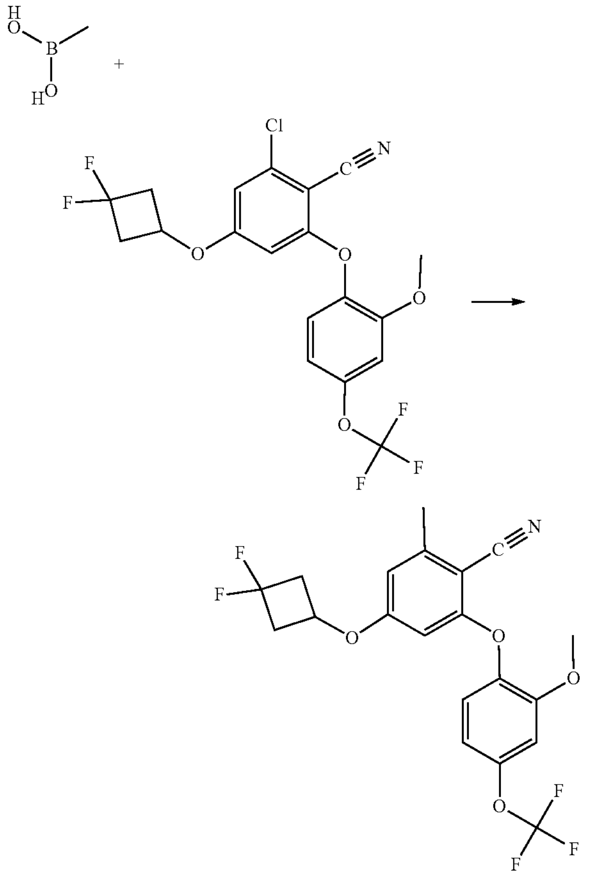

Methylboronic acid (651 mg, 10.9 mmol), $Cs_2CO_3$ (2.16 g, 6.63 mmol) and 2-chloro-4-(3,3-difluorocyclobutoxy)-6-[2-methoxy-4-(trifluoromethoxy)phenoxy]benzonitrile (971 mg, 2.16 mmol) were degassed in dioxane (15 mL) then treated with Pd(dppf)$Cl_2$ (79 mg, 0.11 mmol). The mixture was heated at 100° C. under nitrogen for 17 hours, and then at 110° C. for 4 hours. The mixture was allowed to cool then diluted with ethyl acetate and washed with saturated aqueous $NaHCO_3$. The organic layer was separated, dried over $MgSO_4$ and concentrated. Silica gel chromatography (0-10% ethyl acetate/heptane) provided 4-(3,3-difluorocyclobutoxy)-2-[2-methoxy-4-(trifluoromethoxy)phenoxy]-6-methyl-benzonitrile (275 mg, 30%). ESI-MS m/z calc. 429.10, found 430.6 $(M+1)^+$; Retention time (Method F): 1.05 minutes. $^1$H NMR (500 MHz, Chloroform-d) δ 7.11 (d, J=8.5 Hz, 1H), 6.93-6.88 (m, 2H), 6.39-6.33 (m, 1H), 5.90 (d, J=2.2 Hz, 1H), 4.56 (dtq, J=8.7, 5.1, 1.9 Hz, 1H), 3.82 (s, 3H), 3.01 (ddt, J=15.3, 12.1, 6.8 Hz, 2H), 2.79-2.61 (m, 2H), 2.54 (s, 3H) ppm.

Step 4: 4-(3-Fluorocyclobut-2-En-1-Yl)Oxy-2-[2-Methoxy-4-(Trifluoromethoxy)Phenoxy]-6-Methyl-Benzamide

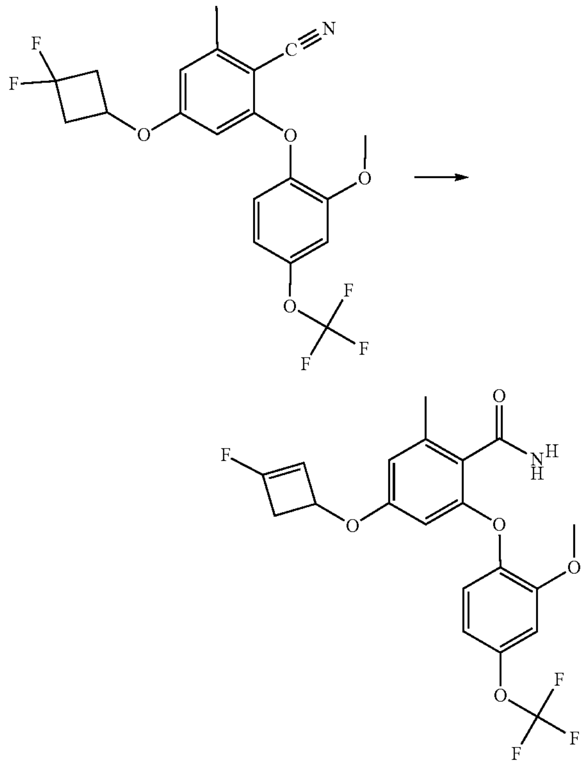

4-(3,3-Difluorocyclobutoxy)-2-[2-methoxy-4-(trifluoromethoxy)phenoxy]-6-methyl-benzonitrile (275 mg, 0.641 mmol) in ethanol (3 mL) and NaOH (3 mL of 2 M, 6 mmol) were heated at 150° C. in the microwave for 1 hour. The mixture was diluted with ethyl acetate and washed with saturated aqueous $NaHCO_3$. The organic layer was separated, dried over $MgSO_4$ and concentrated to provide 4-(3-fluorocyclobut-2-en-1-yl)oxy-2-[2-methoxy-4-(trifluoromethoxy)phenoxy]-6-methyl-benzamide (254 mg, 93%). ESI-MS m/z calc. 427.10, found 428.6 $(M+1)^+$; Retention time (Method F): 0.92 minutes.

Step 5: 4-[[4-(3-Fluorocyclobut-2-En-1-Yl)Oxy-2-[2-Methoxy-4-(Trifluoromethoxy)Phenoxy]-6-Methyl-Benzoyl]Amino]Pyridine-2-Carboxamide (1038)

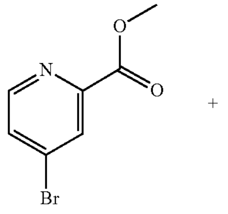

-continued

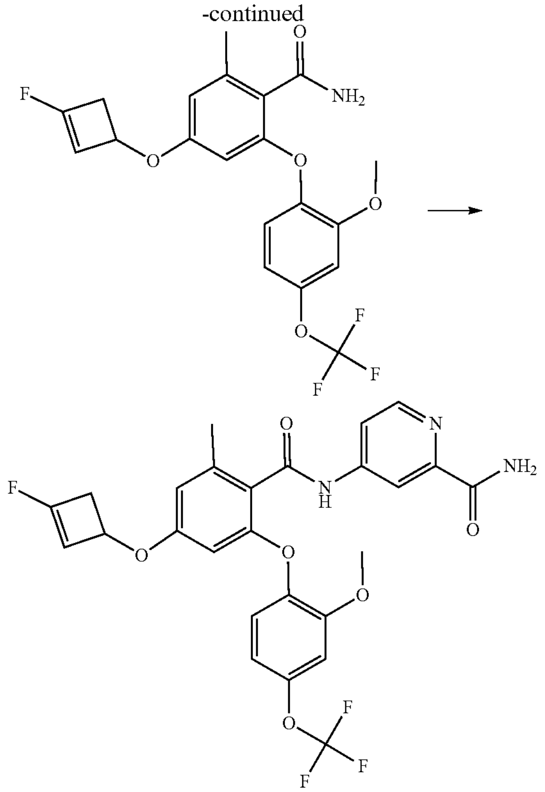

Methyl 4-bromopyridine-2-carboxylate (159 mg, 0.737 mmol), Xantphos (74 mg, 0.13 mmol), cesium carbonate (467 mg, 1.43 mmol), $Pd(OAc)_2$ (14 mg, 0.062 mmol) and 4-(3-fluorocyclobut-2-en-1-yl)oxy-2-[2-methoxy-4-(trifluoromethoxy)phenoxy]-6-methyl-benzamide (258 mg, 0.604 mmol) were combined in dioxane (8 mL). The mixture was degassed then heated at 100° C. under nitrogen for 1 hour. The mixture was allowed to cool then diluted with ethyl acetate and washed with saturated aqueous $NaHCO_3$. The organic layer was dried over $MgSO_4$, filtered and concentrated. Silica gel chromatography (0-80% ethyl acetate/heptane gradient) provided the intermediate 4-(4-((3-fluorocyclobut-2-en-1-yl)oxy)-2-(2-methoxy-4-(trifluoromethoxy)phenoxy)-6-methylbenzamido)picolinamide. The intermediate was dissolved in a solution of ammonia in methanol (4.5 mL of 7 M, 31.5 mmol) and stirred at room temperature for 14 hours. The reaction mixture was concentrated and purified by HPLC ($CH_3CN$/water with ammonia modifier gradient) to provide 4-[[4-(3-fluorocyclobut-2-en-1-yl)oxy-2-[2-methoxy-4-(trifluoromethoxy)phenoxy]-6-methyl-benzoyl]amino]pyridine-2-carboxamide (8.3 mg, 2%). ESI-MS m/z calc. 547.14, found 548.6 $(M+1)^+$; Retention time (Method E): 3.43 minutes. $^1H$ NMR (400 MHz, DMSO-d6) δ 11.02 (s, 1H), 8.50 (d, J=5.5 Hz, 1H), 8.34 (d, J=2.4 Hz, 1H), 8.07 (d, J=2.9 Hz, 1H), 7.83 (dd, J=5.5, 2.2 Hz, 1H), 7.62 (d, J=2.9 Hz, 1H), 7.24-7.12 (m, 3H), 6.98 (ddd, J=8.8, 2.7, 1.2 Hz, 1H), 6.92 (dd, J=2.3, 0.7 Hz, 1H), 6.26 (d, J=2.3 Hz, 1H), 6.01 (dd, J=27.0, 12.1 Hz, 1H), 4.71-4.65 (m, 1H), 4.59 (dd, J=41.1, 3.0 Hz, 1H), 3.76 (s, 3H), 2.34 (s, 3H) ppm.

Example 213

4-[[3-Methyl-2-[2-(Trideuteriomethoxy)-4-(Trifluoromethoxy)Phenoxy]-5-(Trifluoromethyl)Benzoyl]Amino]Pyridine-2-Carboxamide (1039)

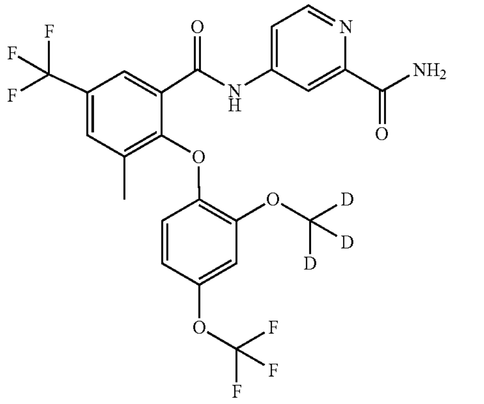 [SMILES: [2H]C([2H])([2H])Oc1cc(OC(F)(F)F)ccc1Oc1c(C)cc(C(F)(F)F)cc1C(=O)Nc1ccnc(C(N)=O)c1]

Step 1: 3-Bromo-2-Fluoro-5-(Trifluoromethyl)Benzoic Acid

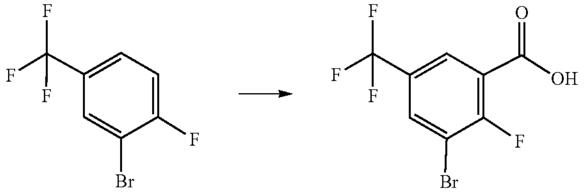 [SMILES: Fc1ccc(C(F)(F)F)cc1Br ; O=C(O)c1cc(C(F)(F)F)cc(Br)c1F]

n-BuLi (45 mL of 2.5 M, 112.50 mmol) in hexane was added to a solution of diisopropylamine (11.6 g, 16.0 mL, 114 mmol) in tetrahydrofuran (100 mL) at −30° C. The mixture was stirred at −30° C. for 45 minutes, then cooled to −78° C. and a solution of 2-bromo-1-fluoro-4-(trifluoromethyl)benzene (25.0 g, 103 mmol) in tetrahydrofuran (25 mL) was slowly added. The reaction mixture was stirred at −78° C. for 3 hours. Solid $CO_2$ (40-50 g) were added portionwise. The cold bath was removed and the reaction allowed to warm to RT. The solvents were evaporated and the residue was diluted with 1 M NaOH (100 mL) and water (50 mL). The aqueous layer was washed with dichloromethane (2×) then acidified with 3 M HCl until pH<2 was reached. The aqueous layer was extracted with dichloromethane (3×) and the combined organics dried over $Na_2SO_4$, filtered and concentrated to provide 18.1 g of beige solid. The solid was triturated in heptane (125 mL) to provide 3-bromo-2-fluoro-5-(trifluoromethyl)benzoic acid (8.9 g) as a beige solid. The filtrate was evaporated and the residue was triturated with minimal heptane to provide additional 3-bromo-2-fluoro-5-(trifluoromethyl)benzoic acid (3.03 g). Both crops of solid were combined in dichloromethane (300 mL). The organic layer was washed with 1 M HCl, dried over $Na_2SO_4$, filtered and concentrated to provide 3-bromo-2-fluoro-5-(trifluoromethyl)benzoic acid (9.86 g, 29%) as a light brown solid. $^{1}H$ NMR (300 MHz, DMSO-d6) δ 8.39 (dd, J=5.6, 2.2 Hz, 1H), 8.10 (dd, J=5.9, 2.2 Hz, 1H) ppm. $^{19}F$ NMR (282 MHz, DMSO-d6) δ −60.90 (s, 3F), −98.40-98.51 (m, 1F) ppm.

Step 2: 3-Bromo-2-[2-(Trideuteriomethoxy)-4-(Trifluoromethoxy)Phenoxy]-5-(Trifluoromethyl)Benzoic Acid

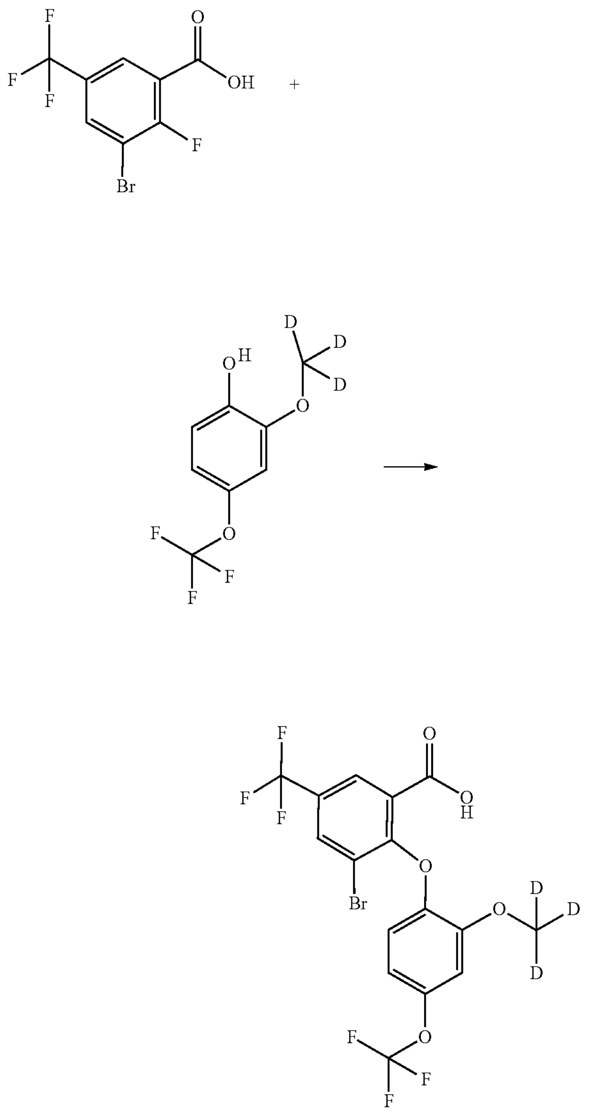

$Cs_2CO_3$ (2.55 g, 7.83 mmol) was added to a solution of 2-(trideuteriomethoxy)-4-(trifluoromethoxy)phenol (prepared in Example 202, Step 2, 674 mg, 3.19 mmol) in NMP (10 mL). The mixture was stirred for 10 minutes then treated with 3-bromo-2-fluoro-5-(trifluoromethyl)benzoic acid (900 mg, 2.76 mmol) and heated at 120° C. for 18 hours. The reaction was cooled to RT and diluted with 1 M HCl. The aqueous layer was extracted with ethyl acetate (3×). The combined organic layers were washed with water and brine, dried over $Na_2SO_4$, filtered and concentrated in vacuo to provide 3-bromo-2-[2-(trideuteriomethoxy)-4-(trifluoromethoxy)phenoxy]-5-(trifluoromethyl)benzoic acid (2.32 g, 56%). ESI-MS m/z calc. 476.97, found 475.9 (M−1)+; Retention time (Method E): 2.2 minutes.

Step 3: 3-Methyl-2-[2-(Trideuteriomethoxy)-4-(Trifluoromethoxy)Phenoxy]-5-(Trifluoromethyl)Benzoic Acid

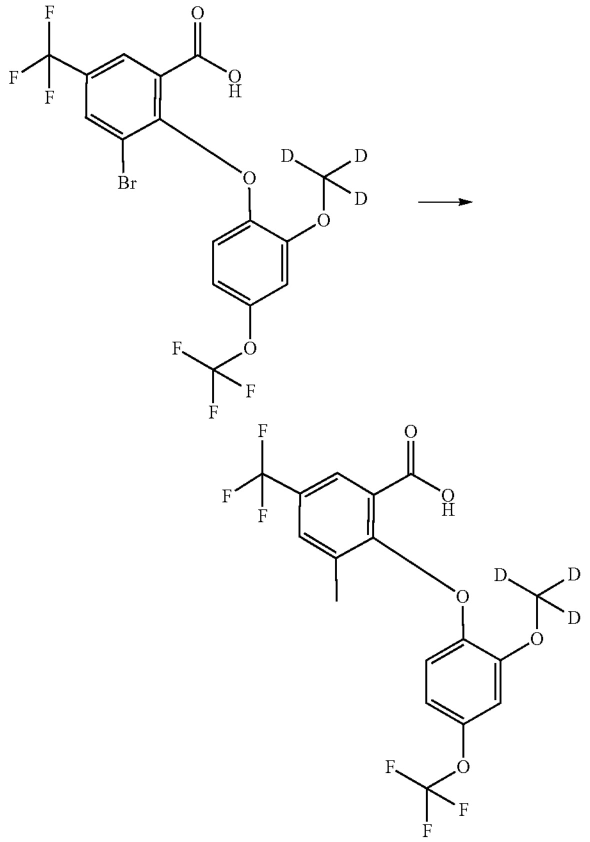

A mixture of 3-bromo-2-[2-(trideuteriomethoxy)-4-(trifluoromethoxy)phenoxy]-5-(trifluoromethyl)benzoic acid (4.00 g, 8.37 mmol), $Cs_2CO_3$ (6.95 g, 21.3 mmol) and trimethyl boroxine (2.2 g, 2.4 mL, 17 mmol) in dioxane (35 mL) and water (6 mL) was degassed with nitrogen for 5 minutes. Pd(dppf)$Cl_2$.DCM (334 mg, 0.409 mmol) was added and the reaction mixture was purged with nitrogen (3×). The reaction mixture was stirred at 100° C. for 17 hours, then cooled to RT and partitioned between 1 M HCl and dichloromethane. The organic layer was separated and the aqueous layer extracted with additional dichloromethane (2×). The combined organic layers were dried over $Na_2SO_4$, filtered and concentrated in vacuo. Silica gel chromatography (0-5% methanol/dichloromethane gradient) provided 2.81 g of an off-white solid. The solid was triturated in 5:1 heptane/dichloromethane (20 mL) to provide 3-methyl-2-[2-(trideuteriomethoxy)-4-(trifluoromethoxy)phenoxy]-5-(trifluoromethyl)benzoic acid (2.51 g, 72%). ESI-MS m/z calc. 413.08, found 412.2 $(M-1)^-$; Retention time (Method M): 3.33 minutes. $^1H$ NMR (300 MHz, DMSO-d6) δ 13.30 (br s., 1H), 7.95 (s, 2H), 7.12 (d, J=2.6 Hz, 1H), 6.75 (dd, J=8.8, 1.5 Hz, 1H), 6.40 (d, J=8.8 Hz, 1H), 2.12 (s, 3H) ppm. $^{19}F$ NMR (282 MHz, DMSO-d6) δ −57.13 (s, 3F), −60.95 (s, 3F) ppm.

Step 4: 4-[[3-Methyl-2-[2-(Trideuteriomethoxy)-4-(Trifluoromethoxy)Phenoxy]-5-(Trifluoromethyl) Benzoyl]Amino]Pyridine-2-Carboxamide (1039)

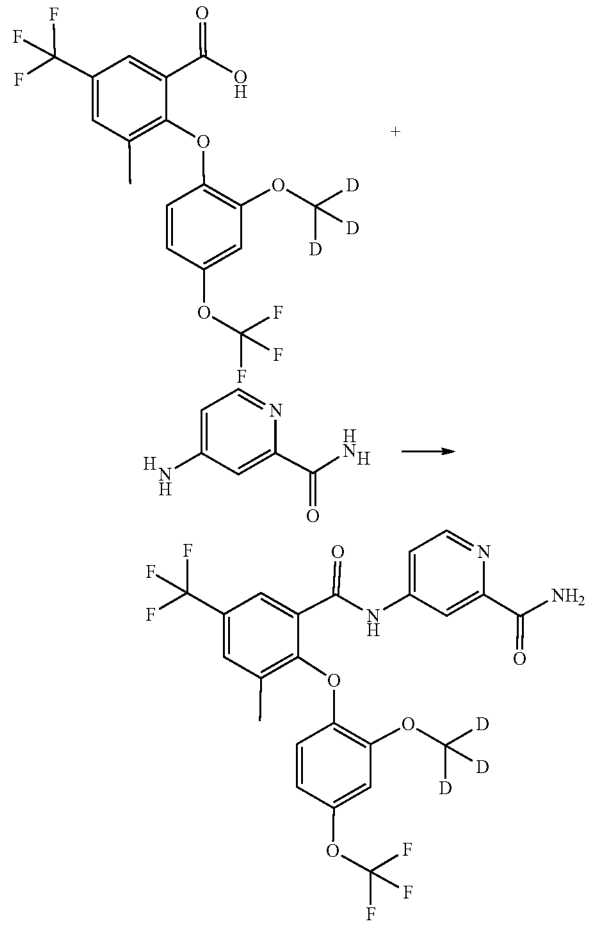

To a solution of 3-methyl-2-[2-(trideuteriomethoxy)-4-(trifluoromethoxy)phenoxy]-5-(trifluoromethyl)benzoic acid (100 mg, 0.242 mmol) and DMF (1 μL, 0.01 mmol) in dichloromethane (1 mL) was slowly added oxalyl chloride (175 μL, 2.01 mmol). The reaction mixture was allowed to stir at RT for 1 hour and then concentrated in vacuo. The resulting residue was taken up in dichloromethane (1 mL) and added dropwise to a stirring solution of 4-aminopyridine-2-carboxamide (40 mg, 0.29 mmol) and DIEA (250 μL, 1.44 mmol) in dichloromethane (1 mL). The reaction was stirred for 16 hours then purified by HPLC (10-75% $CH_3CN$/5 mM HCl) to provide 4-[[3-methyl-2-[2-(trideuteriomethoxy)-4-(trifluoromethoxy)phenoxy]-5-(trifluoromethyl)benzoyl]amino]pyridine-2-carboxamide (32 mg, 25%). ESI-MS m/z calc. 532.13, found 533.2 $(M+1)^+$; Retention time (Method B): 1.86 minutes. $^1H$ NMR (400 MHz, DMSO-$d_6$) δ 11.00 (s, 1H), 8.45 (d, J=5.5 Hz, 1H), 8.15 (d, J=2.2 Hz, 1H), 8.07 (d, J=2.8 Hz, 1H), 8.03-7.92 (m, 1H), 7.87 (d, J=2.4 Hz, 1H), 7.74-7.52 (m, 2H), 6.97 (d, J=2.8 Hz, 1H), 6.83-6.68 (m, 1H), 6.59 (d, J=8.9 Hz, 1H), 2.24 (s, 3H) ppm.

Example 214

4-[[2-Hydroxy-6-[2-Methoxy-4-(Trifluoromethoxy) Phenoxy]-3-(Trifluoromethyl)Benzoyl]Amino]Pyridine-2-Carboxamide (383)

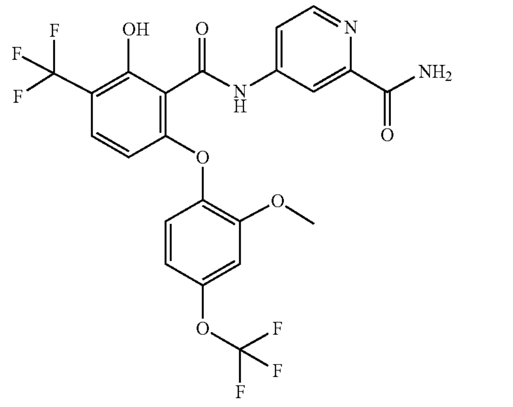 [SMILES: COc1cc(OC(F)(F)F)ccc1Oc1ccc(C(F)(F)F)c(O)c1C(=O)Nc1ccnc(C(N)=O)c1]

Step 1: 2-Fluoro-6-[2-Methoxy-4-(Trifluoromethoxy)Phenoxy]-3-(Trifluoromethyl)Benzoyl Chloride

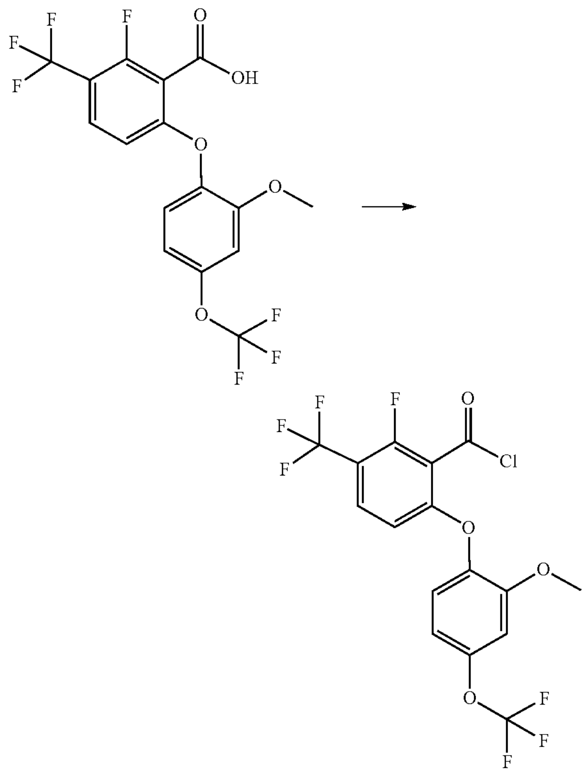

Thionyl chloride (13.2 mL, 181 mmol) was added to a solution of 2-fluoro-6-[2-methoxy-4-(trifluoromethoxy)phenoxy]-3-(trifluoromethyl)benzoic acid (50.0 g, 121 mmol, See Example 5, Step 2) in toluene (375 mL) under nitrogen. The mixture was heated at 70° C. for 14 hours. The reaction was cooled to 0° C. then washed with ice water (2×375 mL) and brine. The organic layer was dried over $MgSO_4$, filtered and concentrated to provide 2-fluoro-6-[2-methoxy-4-(trifluoromethoxy)phenoxy]-3-(trifluoromethyl)benzoyl chloride.

Step 2: Methyl 4-[[2-Fluoro-6-[2-Methoxy-4-(Trifluoromethoxy)Phenoxy]-3-(Trifluoromethyl)Benzoyl]Amino]Pyridine-2-Carboxylate

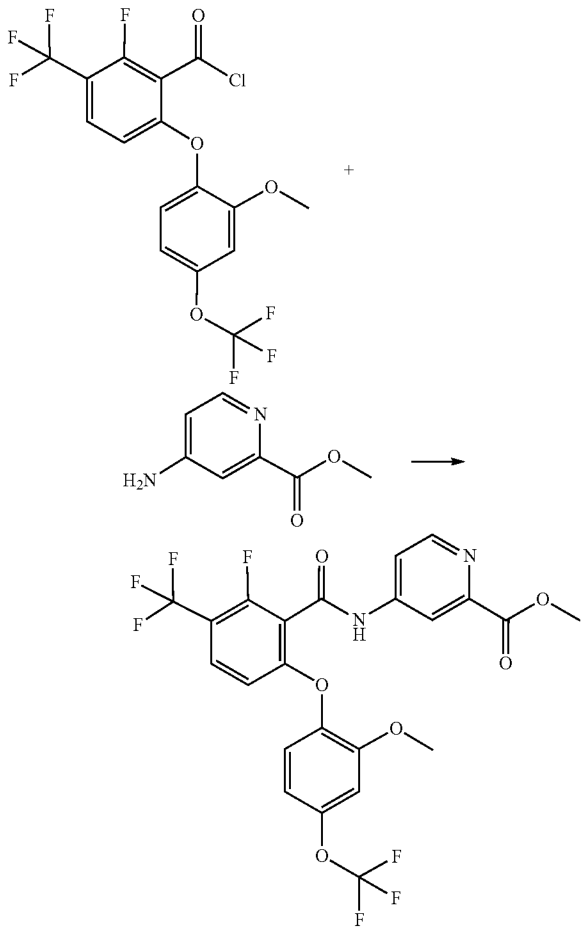

A solution of 2-fluoro-6-[2-methoxy-4-(trifluoromethoxy)phenoxy]-3-(trifluoromethyl)benzoyl chloride (6.35 g, 14.7 mmol) in dichloromethane (16 mL) was added to a suspension of methyl 4-aminopyridine-2-carboxylate (2.69 g, 17.7 mmol) in 2-MeTHF (63.5 mL) and DIEA (6.4 mL, 37 mmol) at 19.2° C. over 4 minutes (reaction exotherm raised the solution temperature to 27.8° C.). The mixture was stirred for 23 hours, then washed sequentially with 2:1 water/brine (100 mL), a solution of 2:1 brine/1 M aqueous HCl (2×100 mL), a solution of 1:1 brine/saturated sodium bicarbonate (100 mL) and brine. The organic phase was dried over $MgSO_4$, filtered and concentrated. Purification by silica gel chromatography (10-70% ethyl acetate/hexanes) provided methyl 4-[[2-fluoro-6-[2-methoxy-4-(trifluoromethoxy)phenoxy]-3-(trifluoromethyl)benzoyl]amino] pyridine-2-carboxylate (6.6 g, 81%). ESI-MS m/z calc. 548.08, found 549.2 $(M+1)^+$; LC/MS retention time (Method B): 1.86 minutes. $^1H$ NMR (400 MHz, DMSO-$d_6$)

δ 11.51 (s, 1H), 8.64 (d, J=5.5 Hz, 1H), 8.39 (d, J=2.1 Hz, 1H), 7.91-7.75 (m, 2H), 7.37 (d, J=8.8 Hz, 1H), 7.26 (d, J=2.7 Hz, 1H), 7.10-6.99 (m, 1H), 6.69 (d, J=8.9 Hz, 1H), 3.89 (s, 3H), 3.79 (s, 3H) ppm.

Step 3: Methyl 4-[[2-Hydroxy-6-[2-Methoxy-4-(Trifluoromethoxy)Phenoxy]-3-(Trifluoromethyl)Benzoyl]Amino]Pyridine-2-Carboxylate

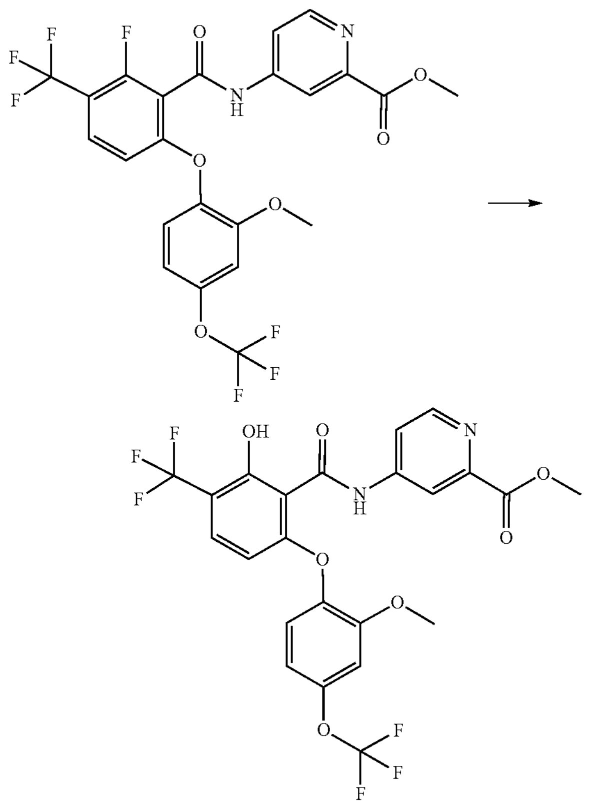

A mixture of methyl 4-[[2-fluoro-6-[2-methoxy-4-(trifluoromethoxy)phenoxy]-3-(trifluoromethyl)benzoyl]amino]pyridine-2-carboxylate (50 mg, 0.091 mmol), hydroxylamine hydrochloride (32 mg, 0.46 mmol) and $K_2CO_3$ (63 mg, 0.46 mmol) in DMF (500 μL) was stirred at room temperature for 24 hours and then at 75° C. for 18 hours. In a separate reaction vessel, a mixture of methyl 4-[[2-fluoro-6-[2-methoxy-4-(trifluoromethoxy)phenoxy]-3-(trifluoromethyl)benzoyl]amino]pyridine-2-carboxylate (50 mg, 0.091 mmol), N-methylhydroxylamine hydrochloride (38 mg, 0.46 mmol) and $K_2CO_3$ (63 mg, 0.46 mmol) in DMF (500 μL) was stirred at room temperature for 24 hours and then at 75° C. for 18 hours. Both reactions resulted in predominant formation of methyl 4-[[2-hydroxy-6-[2-methoxy-4-(trifluoromethoxy)phenoxy]-3-(trifluoromethyl)benzoyl]amino]pyridine-2-carboxylate. The two reaction mixtures were combined, partitioned between ethyl acetate and 1 M aqueous citric acid and the layers separated. The organic layer was concentrated and purified by silica gel chromatography (0-100% ethyl acetate/hexanes) to provide methyl 4-[[2-hydroxy-6-[2-methoxy-4-(trifluoromethoxy)phenoxy]-3-(trifluoromethyl)benzoyl]amino]pyridine-2-carboxylate (22 mg, 22%). ESI-MS m/z calc. 546.09, found 547.0 $(M+1)^+$; LC/MS retention time (Method E): 2.92 minutes. $^1H$ NMR (400 MHz, DMSO-$d_6$) δ 11.17 (s, 1H), 10.87 (s, 1H), 8.59 (d, J=5.5 Hz, 1H), 8.44 (d, J=2.1 Hz, 1H), 7.83 (dd, J=5.6, 2.1 Hz, 1H), 7.56 (d, J=8.9 Hz, 1H), 7.28 (d, J=9.0 Hz, 1H), 7.20 (d, J=2.7 Hz, 1H), 7.01 (ddd, J=8.8, 2.9, 1.4 Hz, 1H), 6.22 (d, J=8.8 Hz, 1H), 3.88 (s, 3H), 3.77 (s, 3H) ppm.

Step 4: 4-[[2-Hydroxy-6-[2-Methoxy-4-(Trifluoromethoxy)Phenoxy]-3-(Trifluoromethyl)Benzoyl]Amino]Pyridine-2-Carboxamide

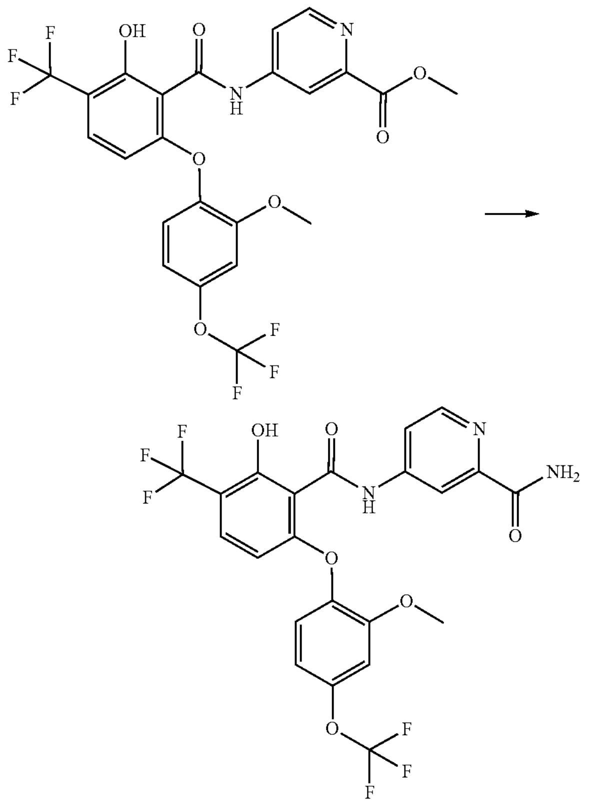

Methyl 4-[[2-hydroxy-6-[2-methoxy-4-(trifluoromethoxy)phenoxy]-3-(trifluoromethyl)benzoyl]amino]pyridine-2-carboxylate (9 mg, 0.02 mmol) was dissolved in acetonitrile and treated with aqueous 28% $NH_4OH$ (~1 mL). The solution was left standing for approximately 48 hours and was then concentrated and purified by reverse phase HPLC (acetonitrile/5 mM HCl gradient) to provide 4-[[2-hydroxy-6-[2-methoxy-4-(trifluoromethoxy)phenoxy]-3-(trifluoromethyl)benzoyl]amino]pyridine-2-carboxamide (6 mg, 70%). ESI-MS m z calc. 531.09, found 532.0 $(M+1)^+$; LC/MS retention time (Method C): 2.84 minutes. $^1H$ NMR (400 MHz, DMSO-$d_6$) δ 11.20-10.99 (m, 1H), 10.90 (s, 1H), 8.51 (d, J=5.5 Hz, 1H), 8.37 (d, J=2.1 Hz, 1H), 8.08 (d, J=2.9 Hz, 1H), 7.84 (dd, J=5.5, 2.1 Hz, 1H), 7.63 (d, J=2.9 Hz, 1H), 7.55 (d, J=8.9 Hz, 1H), 7.30 (d, J=8.9 Hz, 1H), 7.21 (d, J=2.7 Hz, 1H), 7.12-6.92 (m, 1H), 6.22 (d, J=8.8 Hz, 1H), 3.78 (s, 3H) ppm.

Example 215

Additional Compounds of the Invention

The compounds set forth in Table 111 were prepared by the general method set forth in Scheme 2. Alkylation of 5-bromo-3-fluorobenzene-1,2-diol with 3-bromo-2-methyl-prop-1-ene, followed by ring closure afforded a pair of isomeric substituted dihydrobenzodioxines. After separation of the isomers, carbonylation, Ullmann coupling, and amide formation afforded compounds 1040 and 1041. As an alternative to the method shown in Scheme 2, the isomeric dihydrobenzodioxines can be separated after the carbonylation step.

Scheme 2. Synthesis of Compounds 1040 and 1041

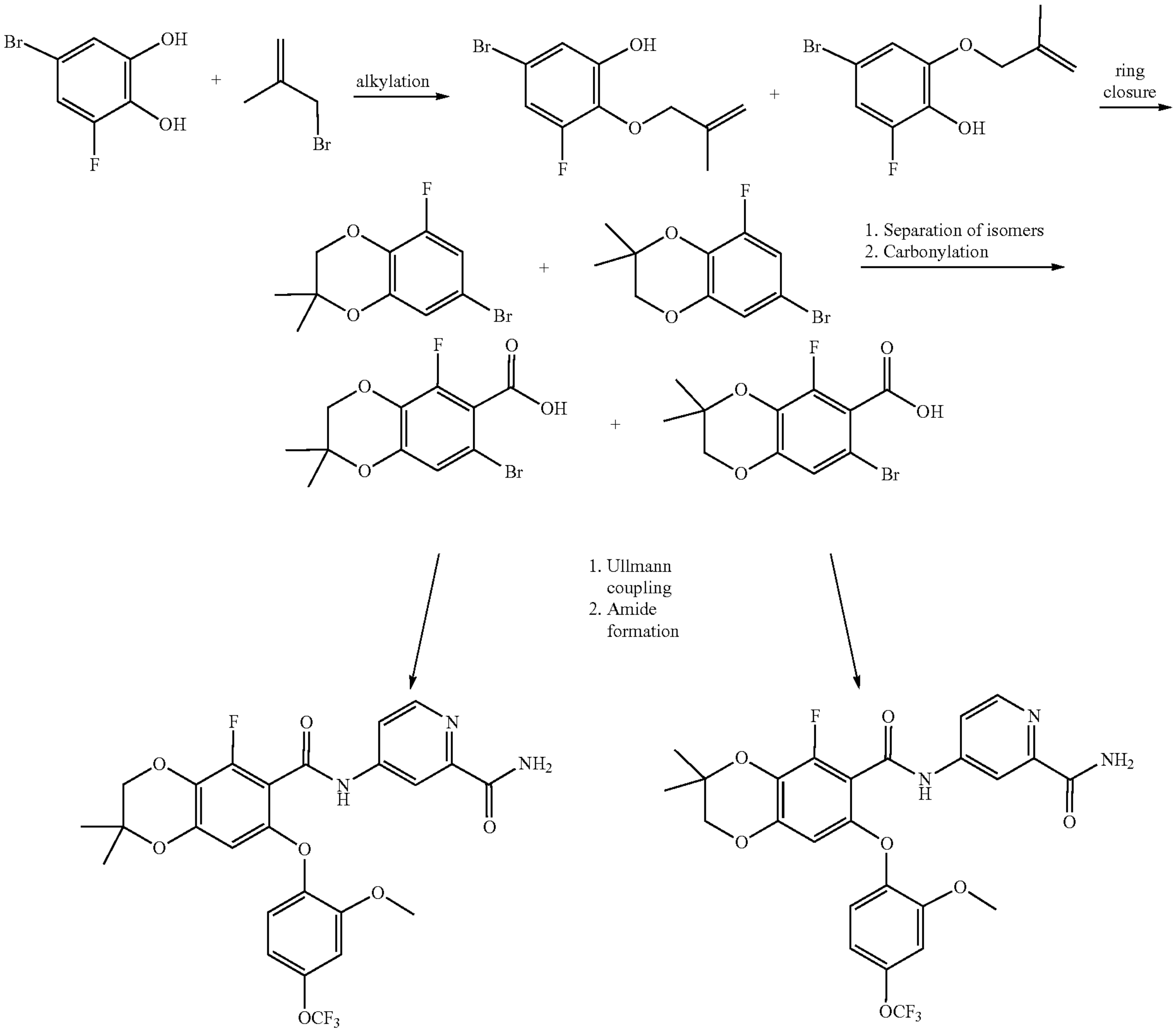

1040

1041

TABLE 111

| Additional Compounds Prepared By the Methods of Scheme 2 | | | |
|---|---|---|---|
| Cmpd No. | Compound Name | LC/MS | NMR (shifts in ppm) |
| 1040 | 4-(5-fluoro-7-(3-fluoro-2-methoxy-4-(trifluoromethoxy)phenoxy)-2,2-dimethyl-2,3-dihydrobenzo[b][1,4]dioxine-6-carboxamido)picolinamide | ESI-MS m/z found 570.2 (M + 1); Retention time: 2.56 minutes. | $^1$H NMR (400 MHz, DMSO-$d_6$) δ 11.23 (s, 1H), 8.50 (d, J = 5.5 Hz, 1H), 8.27 (d, J = 2.1 Hz, 1H), 8.08 (d, J = 2.8 Hz, 1H), 7.77 (dd, J = 5.5, 2.2 Hz, 1H), 7.64 (d, J = 2.7 Hz, 1H), 7.27 (t, J = 8.7 Hz, 1H), 6.90 (dd, J = 9.3, 2.1 Hz, 1H), 6.44 (d, J = 1.8 Hz, 1H), 4.06 (s, 2H), 3.83 (s, 3H), 1.33 (s, 6H). |
| 1041 | 4-(5-fluoro-7-(3-fluoro-2-methoxy-4-(trifluoromethoxy)phe- | ESI-MS m/z found 570.2 (M + 1); | $^1$H NMR (400 MHz, DMSO-$d_6$) δ 11.22 (s, 1H), 8.49 (d, J = 5.5 Hz, 1H), 8.26 (d, J = 2.2 Hz, 1H), 8.07 (d, J = 2.9 Hz, 1H), 7.76 |

TABLE 111-continued

| Additional Compounds Prepared By the Methods of Scheme 2 | | | |
|---|---|---|---|
| Cmpd No. | Compound Name | LC/MS | NMR (shifts in ppm) |
| | noxy)-3,3-dimethyl-2,3-dihydrobenzo[b][1,4]dioxine-6-carboxamido)picolinamide | Retention time: 2.48 minutes. | (dd, J = 5.5, 2.2 Hz, 1H), 7.63 (d, J = 2.8 Hz, 1H), 7.35-7.18 (m, 1H), 6.89 (dd, J = 9.4, 2.1 Hz, 1H), 6.59 (d, J = 1.8 Hz, 1H), 4.07 (s, 2H), 3.83 (s, 3H), 1.35 (s, 6H). |

Example 216

E-VIPR Assay for Detecting and Measuring $Na_V$ Inhibition Properties

Sodium ion channels are voltage-dependent proteins that can be activated by inducing membrane voltage changes by applying electric fields. The electrical stimulation instrument and methods of use, referred to as E-VIPR, are described in International Publication No. WO 2002/008748 A3 and C.-J. Huang et al. Characterization of voltage-gated sodium channel blockers by electrical stimulation and fluorescence detection of membrane potential, 24 Nature Biotech. 439-46 (2006), both of which are incorporated by reference in their entirety. The instrument comprises a microtiter plate handler, an optical system for exciting the coumarin dye while simultaneously recording the coumarin and oxonol emissions, a waveform generator, a current- or voltage-controlled amplifier, and parallel electrode pairs that are inserted into assay plate wells. Under integrated computer control, this instrument passes user-programmed electrical stimulus protocols to cells within the wells of the microtiter plate.

16-20 hours prior to running the assay on E-VIPR, HEK cells expressing a truncated form of human $Na_V$ 1.8 with full channel activity were seeded into microtiter 384-well plates, pre-coated with matrigel, at a density of 25,000 cells per well. 2.5-5% KIR2.1 Bacmam virus was added to the final cell suspension before seeding into cell plates. HEK cells were grown in Dulbecco's Modified Eagle's Medium (DMEM) supplemented with 10% FBS (Fetal Bovine Serum, qualified; Sigma #F4135), 1% NEAA (Non-Essential Amino Acids, Gibco #11140), 1% HEPES (Gibco #15630), 1% Pen-Strep (Penicillin-Streptomycin; Gibco #15140) and 5 μg/ml Blasticidin (Gibco #R210-01). Cells were expanded in vented cap cell culture flasks, with 90-95% humidity and 5% $CO_2$.

Reagents and Stock Solutions:

100 mg/mL Pluronic F-127 (Sigma #P2443), in dry DMSO

Compound Plates: Corning 384-well Polypropylene Round Bottom #3656

Cell Plates: 384-well tissue culture treated plates (Greiner #781091-1B)

2.5-5% KIR 2.1 Bacmam virus (produced in-house), prepared as described in Section 3.3 of J. A. Fornwald et al., *Gene Expression in Mammalian Cells Using BacMam, a Modified Baculovirus System,* 1350 Methods in Molecular Biology 95-116 (2016), the entire contents of which are incorporated by reference. The concentration used can be dependent on viral titer of each batch.

5 mM $DiSBAC_6(3)$, a voltage sensitive oxonol acceptor (CAS number 169211-44-3; 5-[3-(1,3-dihexylhexahydro-4,6-dioxo-2-thioxo-5-pyrimidinyl)-2-propen-1-ylidene]-1,3-dihexyldihydro-2-thioxo-4,6(1H,5H)-pyrimidinedione), in dry DMSO. The preparation of $DiSBAC_6(3)$ is analogous to that of $DiSBAC_4(3)$ as described in *Voltage Sensing by Fluorescence Resonance Energy Transfer in Single Cells*, Gonzalez, J. E. and Tsien, R. Y. (1995) *Biophys. J* 69, 1272-1280.

5 mM CC2-DMPE, a commercially available membrane-bound coumarin phospholipid FRET donor (ThermoFisher Scientific catalog number K1017, CAS number 393782-57-5; tetradecanoic acid, 1,1'-[(1R)-1-[8-(6-chloro-7-hydroxy-2-oxo-2H-1-benzopyran-3-yl)-3-hydroxy-3-oxido-8-oxo-2,4-dioxa-7-aza-3-phosphaoct-1-yl]-1,2-ethanediyl]ester) was prepared in dry DMSO. See also, *Improved indicators of cell membrane potential that use fluorescence resonance energy transfer*, Gonzalez, J. E. and Tsien, R. Y. (1997) Chem. Biol. 4, 269-277.

Voltage Assay Background Suppression Compound (VABSC-1) is prepared in $H_2O$ (89-363 mM, range used to maintain solubility)

Human Serum (HS, Millipore #S1P1-01KL, or Sigma SLBR5469V and SLBR5470V as a 50%/50% mixture, for 25% assay final concentration)

Bath1 Buffer:

Sodium Chloride 160 mM (9.35 g/L), Potassium Chloride, 4.5 mM (0.335 g/L), Glucose 10 mM (1.8 g/L), Magnesium Chloride (Anhydrous) 1 mM (0.095 g/L), Calcium Chloride 2 mM (0.222 g/L), HEPES 10 mM (2.38 g/L) in water.

Na/TMA Cl Bath1 Buffer:

Sodium Chloride 96 mM (5.61 g/L), Potassium Chloride 4.5 mM (0.335 g/L), Tetramethylammonium (TMA)-Cl 64 mM (7.01 g/L), Glucose 10 mM (1.8 g/L), Magnesium Chloride (Anhydrous) 1 mM (0.095 g/L), Calcium Chloride 2 mM (0.222 g/L) HEPES 10 mM (2.38 g/L) in water.

Hexyl Dye Solution (2× Concentration):

Bath1 Buffer containing 0.5% β-cyclodextrin (made fresh prior to each use, Sigma #$C_{4767}$), 8 μM CC2-DMPE and 2 μM $DiSBAC_6(3)$. The solution was made by adding 10% Pluronic F127 stock equal to combined volumes of CC2-DMPE and $DiSBAC_6(3)$. The order of preparation was first mix Pluronic and CC2-DMPE, then add $DiSBAC_6(3)$, then while vortexing add Bath1/β-Cyclodextrin.

Compound Loading Buffer (2× concentration): Na/TMA Cl Bath1 Buffer containing HS (omitted in experiments run in the absence of human serum (HS)) 50%, VABSC-1 1 mM, BSA 0.2 mg/ml (in Bath-1), KCl 9 mM, DMSO 0.75%.

Assay Protocol (7 Key Steps):

1) To reach the final concentration in each well, 400 nL of each compound was pre-spotted (in neat DMSO) into polypropylene compound plates at 250× desired final concentration from an intermediate stock concentration of 0.075 mM, in an 11 point dose response, 3-fold dilution, resulting in a top dose of 300 nM final concentration in the cell plate. Vehicle control (neat DMSO), and positive control (an established $Na_V$1.8 inhibitor, 25 μM final in assay in DMSO) were added manually to the outermost columns of each plate respectively. The compound plate was backfilled with 45 μL per well of Compound Loading Buffer resulting in a 250 fold dilution of compound following a 1:1 transfer of compound into the cell plate (see Step 6). Final DMSO concentration for all wells in the assay was 0.625% (0.75% DMSO was supplemented to the Compound Loading Buffer for a final DMSO concentration of 0.625%). This assay dilution protocol was adjusted to enable a higher dose range to be tested in the presence of HS or if the final assay volume was altered.

2) Hexyl Dye Solution was prepared.
3) Cell plates were prepared. On the day of the assay, the media was aspirated, and the cells were washed three times with 80 μL of Bath-1 buffer, maintaining 25 μL residual volume in each well.
4) 25 μL per well of Hexyl Dye Solution was dispensed into the cell plates. The cells were incubated for 20 minutes at room temperature or ambient conditions in darkness.
5) 45 μL per well of Compound Loading Buffer was dispensed into compound plates.
6) The cell plates were washed three times with 80 μL per well of Bath-1 Buffer, leaving 25 L of residual volume. Then 25 μL per well from compound plate was transferred to each cell plate. The mixture was incubated for 30 minutes at room temperature/ambient conditions.
7) The cell plate containing compound was read on E-VIPR using the current-controlled amplifier to deliver stimulation wave pulses using a symmetrical biphasic waveform. The user-programmed electrical stimulus protocols were 1.25-4 Amps and 4-6 millisecond pulse width (dependent on electrode composition) were delivered at 10 Hz for 10 seconds. A pre-stimulus recording was performed for each well for 0.5 seconds to obtain the un-stimulated intensities baseline. The stimulatory waveform was followed by 0.5 seconds of post-stimulation recording to examine the relaxation to the resting state. All E-VIPR responses were measured at 200 Hz acquisition rate.

Data Analysis:

Data were analyzed and reported as normalized ratios of emission intensities measured in the 460 nm and 580 nm channels. The response as a function of time was reported as the ratios obtained using the following formula:

$$R(t) = \frac{(intensity_{460\ nm})}{(intensity_{580\ nm})}$$

The data were further reduced by calculating the initial (Ri) and final ($R_f$) ratios. These were the average ratio values during part or all of the pre-stimulation period and during sample points during the stimulation period. The fluorescence ratio ($R_f$/Ri) was then calculated and reported as a function of time.

Control responses were obtained by performing assays in the presence of the positive control, and in the absence of pharmacological agents (DMSO vehicle negative control). Responses to the negative (N) and positive (P) controls were calculated as above. The compound antagonist % activity A was then defined as:

$$A = \frac{X - N}{P - N} \times 100$$

where X is the ratio response of the test compound. Using this analysis protocol, dose response curves were plotted and $IC_{50}$ values were generated for various compounds of the present invention as reported below in Table 112.

TABLE 112

$IC_{50}$ Values of Compounds of the Invention in E-VIPR Assay

| Cmpd # | $IC_{50}$ (μM) |
|---|---|
| 1 | 0.39 |
| 2 | 0.45 |
| 3 | 1.4 |
| 4 | 0.65 |
| 5 | 1.2 |
| 6 | 1.7 |
| 7 | 0.66 |
| 8 | 0.51 |
| 9 | 1.3 |
| 10 | 0.65 |
| 11 | 1.4 |
| 12 | 2.1 |
| 13 | >3 |
| 14 | >3 |
| 15 | >3 |
| 16 | >3 |
| 17 | >3 |
| 18 | 0.019 |
| 19 | 0.057 |
| 20 | 0.048 |
| 21 | 1 |
| 22 | 0.54 |
| 23 | 0.15 |
| 24 | 0.2 |
| 25 | 0.16 |
| 26 | 1.3 |
| 27 | 0.17 |
| 28 | 0.024 |
| 29 | 0.045 |
| 30 | 0.043 |
| 31 | 0.009 |
| 32 | 0.2 |
| 33 | 0.017 |
| 34 | 0.12 |
| 35 | 0.51 |
| 36 | 0.18 |
| 37 | 0.026 |
| 38 | 0.043 |
| 39 | >3 |
| 40 | >3 |
| 41 | 0.01 |
| 42 | 0.008 |
| 43 | 0.013 |
| 44 | 0.022 |
| 45 | >3 |
| 46 | >3 |
| 47 | 1.4 |
| 48 | 0.05 |
| 49 | 0.042 |
| 50 | 0.033 |
| 51 | 0.2 |
| 52 | 0.17 |
| 53 | 0.11 |
| 54 | 0.51 |
| 55 | 0.42 |
| 56 | 0.048 |
| 57 | 0.35 |
| 58 | 0.15 |
| 59 | 0.1 |
| 60 | 0.52 |
| 61 | 0.49 |
| 62 | 0.44 |
| 63 | 1.8 |
| 64 | 0.063 |
| 65 | 0.036 |
| 66 | 0.016 |
| 67 | 0.11 |
| 68 | 0.29 |
| 69 | >3 |
| 70 | >3 |

TABLE 112-continued

| $IC_{50}$ Values of Compounds of the Invention in E-VIPR Assay | |
|---|---|
| Cmpd # | $IC_{50}$ (μM) |
| 71 | |
| 72 | 0.56 |
| 73 | 1.5 |
| 74 | 1.2 |
| 75 | 1.75 |
| 76 | |
| 77 | >3 |
| 78 | >3 |
| 79 | >3 |
| 80 | >3 |
| 81 | >3 |
| 82 | >3 |
| 83 | 0.16 |
| 84 | 0.625 |
| 85 | 0.18 |
| 86 | 1 |
| 87 | 1.5 |
| 88 | 0.039 |
| 89 | 0.036 |
| 90 | 0.21 |
| 91 | 0.44 |
| 92 | 0.063 |
| 93 | 0.013 |
| 94 | 0.039 |
| 95 | 0.14 |
| 96 | 0.013 |
| 97 | 0.014 |
| 98 | 0.023 |
| 99 | 0.38 |
| 100 | 0.63 |
| 101 | 0.525 |
| 102 | 0.036 |
| 103 | 0.013 |
| 104 | 0.38 |
| 105 | 0.073 |
| 106 | 1.4 |
| 107 | 2.379 |
| 108 | >3 |
| 109 | >3 |
| 110 | >3 |
| 111 | >3 |
| 112 | >3 |
| 113 | >3 |
| 114 | 0.51 |
| 115 | >3 |
| 116 | 0.025 |
| 117 | 0.002 |
| 118 | 0.695 |
| 119 | 0.008 |
| 120 | 0.02 |
| 121 | 0.016 |
| 122 | 0.025 |
| 123 | 0.053 |
| 124 | 0.016 |
| 125 | 0.14 |
| 126 | 0.18 |
| 127 | 0.15 |
| 128 | 0.083 |
| 129 | 0.02 |
| 130 | 0.04 |
| 131 | 0.155 |
| 132 | >3 |
| 133 | 0.009 |
| 134 | 0.12 |
| 135 | 0.47 |
| 136 | 0.14 |
| 137 | 0.054 |
| 138 | 0.02 |
| 139 | 0.033 |
| 140 | 0.068 |
| 141 | 0.22 |
| 142 | 1.7 |
| 143 | >3 |
| 144 | 0.765 |
| 145 | >3 |
| 146 | 0.017 |

TABLE 112-continued

| $IC_{50}$ Values of Compounds of the Invention in E-VIPR Assay | |
|---|---|
| Cmpd # | $IC_{50}$ (μM) |
| 147 | 0.003 |
| 148 | 0.009 |
| 149 | 0.019 |
| 150 | 0.002 |
| 151 | 0.004 |
| 152 | 0.012 |
| 153 | 0.007 |
| 154 | 0.988 |
| 155 | 0.505 |
| 156 | 0.73 |
| 157 | 0.408 |
| 158 (first diastereomer) | 0.96 |
| 158 (second diastereomer) | 0.395 |
| 159 | >3 |
| 160 | >3 |
| 161 | >3 |
| 162 | |
| 163 | >3 |
| 164 | >3 |
| 165 | >3 |
| 166 | >3 |
| 167 | >3 |
| 168 (second diastereomer) | 0.01 |
| 168 (first diastereomer) | 0.018 |
| 169 (first diastereomer) | 0.011 |
| 169 (second diastereomer) | 0.021 |
| 170 | 0.23 |
| 171 | 0.009 |
| 172 | 0.05 |
| 173 | 1.3 |
| 174 | >3 |
| 175 | >3 |
| 176 | 0.49 |
| 177 | 0.02 |
| 178 | 0.027 |
| 179 | 2 |
| 180 | 0.51 |
| 181 | 0.012 |
| 182 | 0.29 |
| 183 | 0.014 |
| 184 | 0.14 |
| 185 | 0.011 |
| 186 | 0.11 |
| 187 | 0.49 |
| 188 | 0.024 |
| 189 | 0.17 |
| 190 | 1.5 |
| 191 | 0.002 |
| 192 | 0.004 |
| 193 | 0.006 |
| 194 | 0.002 |
| 195 | 0.005 |
| 196 | 0.009 |
| 197 | 0.12 |
| 198 | 0.015 |
| 199 | 0.021 |
| 200 | 0.085 |
| 201 | 0.53 |
| 202 | 0.006 |
| 203 | 0.14 |
| 204 | 0.17 |
| 205 | 1.1 |
| 206 | 0.36 |
| 207 | 0.37 |
| 208 | >3 |
| 209 | 0.008 |
| 210 | 0.28 |
| 211 | >3 |
| 212 | >3 |
| 213 | >3 |

TABLE 112-continued

IC$_{50}$ Values of Compounds of the Invention in E-VIPR Assay

| Cmpd # | IC$_{50}$ (μM) |
|---|---|
| 214 | >3 |
| 215 | 0.57 |
| 216 | 0.34 |
| 217 | 0.16 |
| 218 | 0.735 |
| 219 | 1.5 |
| 220 | 0.53 |
| 221 | 0.43 |
| 222 | 0.12 |
| 223 | 0.13 |
| 224 | 0.006 |
| 225 | 1.5 |
| 226 | 0.14 |
| 227 | 0.61 |
| 228 | >3 |
| 229 | >3 |
| 230 | >3 |
| 231 | >3 |
| 232 | 1.5 |
| 233 | 1.4 |
| 234 | >3 |
| 235 | 1.4 |
| 236 | 0.17 |
| 237 | 0.093 |
| 238 | 0.695 |
| 239 | 0.072 |
| 240 | 0.57 |
| 241 | 0.19 |
| 242 | 0.013 |
| 243 | 1.85 |
| 244 | 0.017 |
| 245 | 0.333 |
| 246 | 0.14 |
| 247 | 0.19 |
| 248 | 0.027 |
| 249 | 2.933 |
| 250 | >3 |
| 251 | >3 |
| 252 | >3 |
| 253 | >3 |
| 254 | >3 |
| 255 | >3 |
| 256 | >3 |
| 257 | 0.008 |
| 258 | >3 |
| 259 | 0.059 |
| 260 | 0.066 |
| 261 | 0.008 |
| 262 | 0.05 |
| 263 | 0.02 |
| 264 | 0.052 |
| 265 | 0.035 |
| 266 | 0.0028 |
| 267 | 0.084 |
| 268 | 0.028 |
| 269 | 0.037 |
| 270 | 0.033 |
| 271 | 0.024 |
| 272 | 0.089 |
| 273 | 0.059 |
| 274 | 0.0393 |
| 275 | 0.17 |
| 276 | 0.44 |
| 277 | 0.17 |
| 278 | 0.0036 |
| 279 | 0.019 |
| 280 | 0.004 |
| 281 | 0.13 |
| 282 | 0.057 |
| 283 | 0.0042 |
| 284 | 0.004 |
| 285 | 0.026 |
| 286 | 0.014 |
| 287 | 0.59 |
| 288 | 0.0203 |
| 289 | 0.039 |

TABLE 112-continued

IC$_{50}$ Values of Compounds of the Invention in E-VIPR Assay

| Cmpd # | IC$_{50}$ (μM) |
|---|---|
| 290 | 0.0099 |
| 291 | 0.0128 |
| 292 | 0.0545 |
| 293 | 0.0039 |
| 294 | 0.0068 |
| 295 | 0.0065 |
| 296 | 0.0246 |
| 297 | 0.074 |
| 298 | 0.0098 |
| 299 | 0.0064 |
| 300 | 1.4 |
| 301 | 0.022 |
| 302 | 0.28 |
| 303 | 0.019 |
| 304 | 0.054 |
| 305 | 0.0023 |
| 306 | 0.019 |
| 307 | 0.0059 |
| 308 | 0.036 |
| 309 | 0.0014 |
| 310 | 0.0025 |
| 311 | 0.013 |
| 312 | 0.0079 |
| 313 | 0.1213 |
| 314 | 0.0065 |
| 315 | 0.12 |
| 316 | 0.024 |
| 317 | 0.52 |
| 318 | 0.0151 |
| 319 | 0.0052 |
| 320 | 0.0004 |
| 321 | 0.011 |
| 322 | 0.0061 |
| 323 | 0.0008 |
| 324 | 0.0017 |
| 325 | 0.0016 |
| 326 | 0.0013 |
| 327 | 0.0083 |
| 329 | 0.0127 |
| 330 | 0.029 |
| 331 | 0.0046 |
| 332 | 0.0027 |
| 333 | 0.0049 |
| 334 | 0.007 |
| 335 | 0.0155 |
| 336 | 0.0056 |
| 337 | 0.0205 |
| 338 | 0.047 |
| 339 | 0.027 |
| 340 | >3 |
| 341 | 0.33 |
| 343 | 0.0048 |
| 344 | 0.0047 |
| 345 | 0.0025 |
| 346 | 0.0058 |
| 347 | 0.0031 |
| 348 | 0.02 |
| 349 | >3 |
| 350 | >3 |
| 351 | 0.41 |
| 352 | 0.0018 |
| 353 | 0.0174 |
| 354 | 0.03 |
| 355 | 0.15 |
| 356 | 0.0033 |
| 357 | 0.015 |
| 358* | 0.075 |
| 359 | |
| 360* | 0.014 |
| 361* | 0.044 |
| 362* | 0.002 |
| 363* | 0.003 |
| 364* | 0.046 |
| 365 | 0.05 |
| 366* | 0.013 |
| 367 | 0.33 |

TABLE 112-continued $IC_{50}$ Values of Compounds of the Invention in E-VIPR Assay

| Cmpd # | $IC_{50}$ (μM) |
|---|---|
| 368 | 0.005 |
| 369 | 0.009 |
| 370 | 0.043 |
| 372 | 0.012 |
| 373 | 0.006 |
| 374 | 0.034 |
| 375 | 0.029 |
| 376 | 0.009 |
| 377 | 0.021 |
| 378 | 1.4 |
| 379 | 0.022 |
| 380 | 0.026 |
| 381 | 0.016 |
| 382* | 0.005 |
| 383 | >3 |
| 1001 | 0.019 |
| 1002 | 0.03 |
| 1003 | 0.026 |
| 1004 | 0.029 |
| 1005 | 0.12 |
| 1006 | >3 |
| 1007 | 0.17 |
| 1008 | 0.021 |
| 1009 | 0.17 |
| 1010 | 0.013 |
| 1011 | 0.47 |
| 1012 | 0.19 |
| 1013 | 0.013 |
| 1014 | 0.033 |
| 1015 | 0.36 |
| 1016 | 0.06 |
| 1017 (first diastereomer) | 0.252 |
| 1017 (second diastereomer) | 0.017 |
| 1018 | 0.13 |
| 1019 | 0.079 |
| 1020 | 0.009 |
| 1021 | 0.041 |
| 1022 | 0.19 |
| 1023 | 0.1 |
| 1024 | 0.15 |
| 1025 | 0.002 |
| 1026 | |
| 1027 | >3 |
| 1028 | 0.59 |
| 1029 | 0.695 |
| 1030 | 0.33 |
| 1031 | 2.05 |
| 1032 (first diastereomer) | 0.524 |
| 1032 (second diastereomer) | 1.55 |
| 1033 | 0.84 |
| 1034 | 0.16 |
| 1035 | 0.017 |
| 1036 | 1.75 |
| 1037 | >3 |
| 1038 | 0.17 |
| 1039 | >3 |
| 1040 | 0.006 |
| 1041 | 0.038 |

*The indicated compounds were analyzed in an E-VIPR assay conducted in the absence of human serum.
All other compounds were analyzed in an E-VIPR assay conducted in the presence of human serum.

Many modifications and variations of the embodiments described herein may be made without departing from the scope, as is apparent to those skilled in the art. The specific embodiments described herein are offered by way of example only.

What is claimed is:

1. A compound of formula (I) or (II)

I

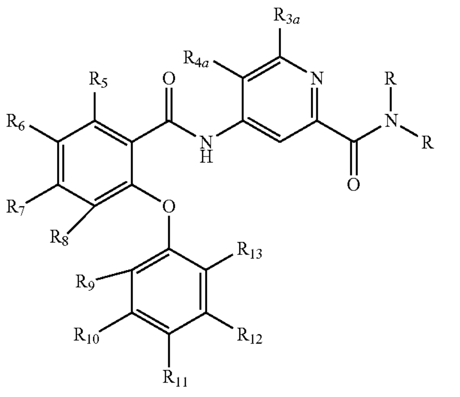

II

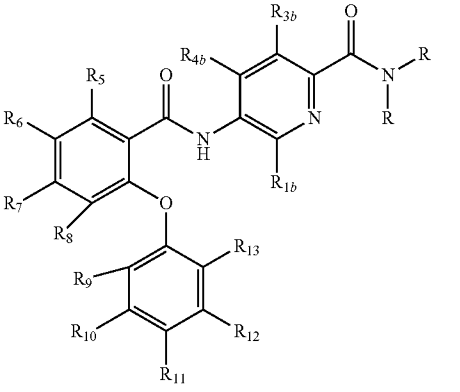

or a pharmaceutically acceptable salt thereof, wherein:

each R is independently H or $C_1$-$C_6$ alkyl;

$R_{3a}$ is H, halo, $C_1$-$C_6$ alkyl, $C_1$-$C_6$ haloalkyl, $C_1$-$C_6$ alkoxy, or $C_1$-$C_6$ haloalkoxy;

$R_{4a}$ is H, halo, $C_1$-$C_6$ alkyl, $C_1$-$C_6$ haloalkyl, $C_1$-$C_6$ alkoxy, or $C_1$-$C_6$ haloalkoxy;

$R_{1b}$ is H, halo, $C_1$-$C_6$ alkyl, $C_1$-$C_6$ haloalkyl, $C_1$-$C_6$ alkoxy, or $C_1$-$C_6$ haloalkoxy;

$R_{3b}$ is H, halo, $C_1$-$C_6$ alkyl, $C_1$-$C_6$ haloalkyl, $C_1$-$C_6$ alkoxy, or $C_1$-$C_6$ haloalkoxy;

$R_{4b}$ is H, halo, $C_1$-$C_6$ alkyl, $C_1$-$C_6$ haloalkyl, $C_1$-$C_6$ alkoxy, or $C_1$-$C_6$ haloalkoxy;

$R_5$, $R_6$, $R_7$, and $R_8$ are defined as follows:

(i) $R_5$, $R_6$, and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is $C_1$-$C_6$ alkyl;

(ii) $R_5$ is W—$(CH_2)_n$—$R_z$, $C_1$-$C_6$ alkylsulfanyl, —O—$(CH_2)_p$—$R_w$, or —O—$(CH_2)_p$—N($C_1$-$C_6$ alkyl$)_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H;

(iii) $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$, —C≡C—$R_x$, or 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H; or (iv) $R_5$ is H, halo, $C_1$-$C_6$ alkyl, $C_1$-$C_6$ haloalkyl, $C_1$-$C_6$ alkoxy, or $C_1$-$C_6$ haloalkoxy; $R_6$ and $R_7$, together with the carbon atoms to which they are attached, form a ring of formula

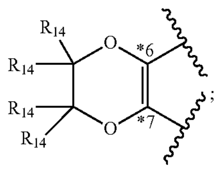;

and $R_8$ is H;

$R_9$ is H, halo, $C_1$-$C_6$ alkyl, $C_1$-$C_6$ haloalkyl, $C_1$-$C_6$ alkoxy, or $C_1$-$C_6$ haloalkoxy;

$R_{10}$ is H, halo, $C_1$-$C_6$ alkyl, $C_1$-$C_6$ haloalkyl, $C_1$-$C_6$ alkoxy, or $C_1$-$C_6$ haloalkoxy;

$R_{11}$ is H, halo, $C_1$-$C_6$ alkyl, $C_1$-$C_6$ haloalkyl, $C_1$-$C_6$ alkoxy, or $C_1$-$C_6$ haloalkoxy;

$R_{12}$ is H, halo, $C_1$-$C_6$ alkyl, $C_1$-$C_6$ haloalkyl, $C_1$-$C_6$ alkoxy, or $C_1$-$C_6$ haloalkoxy;

$R_{13}$ is H, halo, $C_1$-$C_6$ alkyl, $C_1$-$C_6$ haloalkyl, $C_1$-$C_6$ alkoxy, or $C_1$-$C_6$ haloalkoxy;

each $R_{14}$ is independently H, halo, $C_1$-$C_4$ alkyl, or $C_1$-$C_4$ haloalkyl;

each W is independently O or a single bond;

$R_x$ is $C_1$-$C_6$ alkyl or 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl;

$R_z$ is 3-6 membered heterocyclyl, 7-8 membered cycloalkyl, or 4-8 membered cycloalkenyl, wherein said 3-6 membered heterocyclyl, 7-8 membered cycloalkyl, or 4-8 membered cycloalkenyl may be unsubstituted or may be substituted with 1-3 substituents selected from a group consisting of halo, $C_1$-$C_6$ alkyl, $C_1$-$C_6$ haloalkyl, and $C_1$-$C_6$ alkoxy, or wherein 2 substituents together with the atom to which they are attached form a 5-6 membered heterocyclyl ring;

n is 0 or 1; and p is 2 or 3.

2. The compound of claim 1, wherein the compound has formula (I)

I

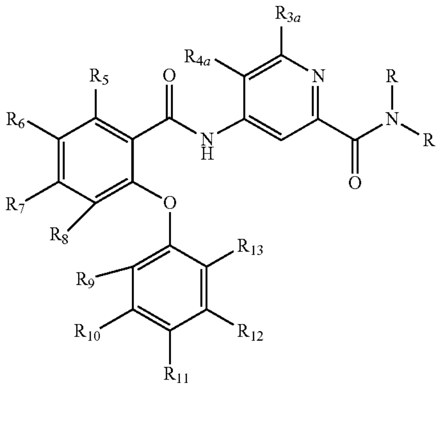

or a pharmaceutically acceptable salt thereof, wherein R, $R_{3a}$, $R_{4a}$, $R_5$, $R_6$, $R_7$, $R_8$, $R_9$, $R_{10}$, $R_{11}$, $R_{12}$, and $R_{13}$ are as defined in claim 1.

3. The compound of claim 2, or a pharmaceutically acceptable salt thereof, wherein $R_{3a}$ and $R_{4a}$ are each H.

4. The compound of claim 1, wherein the compound has formula (II)

II

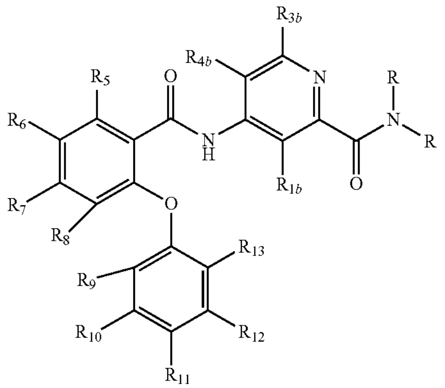

or a pharmaceutically acceptable salt thereof, wherein R, $R_{1b}$, $R_{3b}$, $R_{4b}$, $R_5$, $R_6$, $R_7$, $R_8$, $R_9$, $R_{10}$, $R_{11}$, $R_{12}$, and $R_{13}$ are as defined in claim 1.

5. The compound of claim 4, or a pharmaceutically acceptable salt thereof, wherein $R_{1b}$, $R_{3b}$, and $R_{4b}$ are each H.

6. The compound of claim 1, or a pharmaceutically acceptable salt thereof, wherein each R is H.

7. The compound of claim 1, or a pharmaceutically acceptable salt thereof, wherein $R_5$, $R_6$, and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is $C_1$-$C_6$ alkyl.

8. The compound of claim 1, or a pharmaceutically acceptable salt thereof, wherein $R_5$ is W—$(CH_2)_n$—$R_z$, $C_1$-$C_6$ alkylsulfanyl, —O—$(CH_2)_p$—$R_w$, or —O—$(CH_2)_p$—N($C_1$-$C_6$ alkyl$)_2$; $R_6$ and $R_7$ are each independently H, halo, $C_1$-$C_6$ alkyl, $C_1$-$C_6$ haloalkyl, $C_1$-$C_6$ alkoxy, or $C_1$-$C_6$ haloalkoxy; and $R_8$ is H.

9. The compound of claim 1, or a pharmaceutically acceptable salt thereof, wherein $R_5$ and $R_6$ are each independently H, halo, $C_1$-$C_6$ alkyl, $C_1$-$C_6$ haloalkyl, $C_1$-$C_6$ alkoxy, or $C_1$-$C_6$ haloalkoxy; $R_7$ is W—$(CH_2)_n$—$R_z$, —C≡C—$R_x$, or 3-6 membered cycloalkyl or phenyl, wherein said 3-6 membered cycloalkyl or phenyl is substituted with 1-3 substituents selected from a group consisting of $C_1$-$C_6$ alkoxy, CN, and —C(O)$NH_2$; and $R_8$ is H.

10. The compound of claim 1, or a pharmaceutically acceptable salt thereof, wherein $R_5$ is H, F, or $CH_3$; $R_6$ is H; $R_7$ is

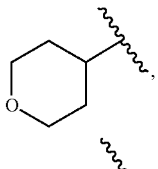, 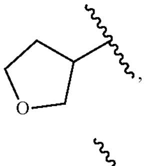, 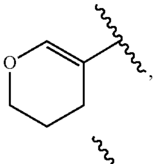,

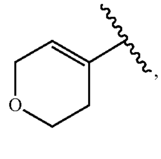, 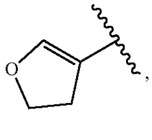, 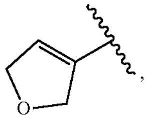,

-continued

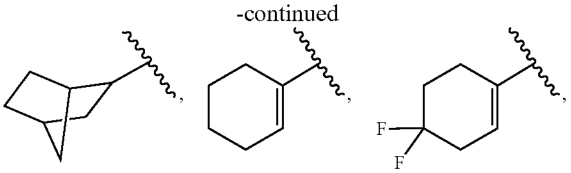

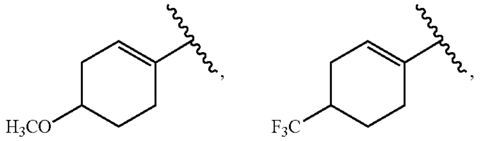

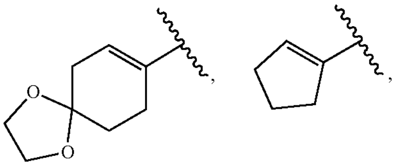

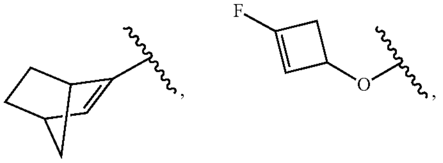

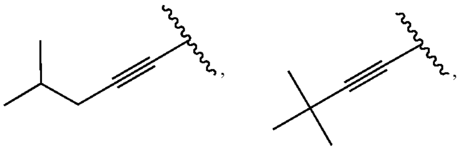

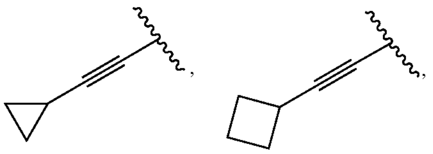

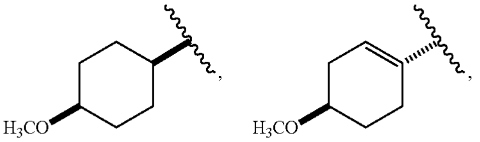

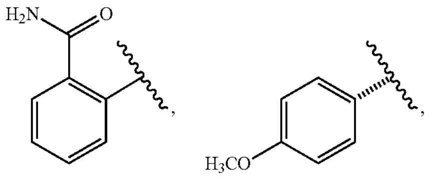

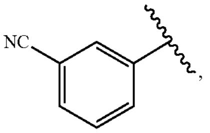

or

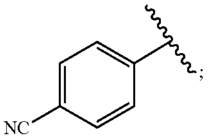

and $R_8$ is H.

11. The compound of claim 1, or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ haloalkoxy; $R_6$ and $R_7$, together with the carbon atoms to which they are attached, form a ring of formula

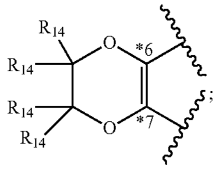

and $R_8$ is H.

12. The compound of claim 1, or a pharmaceutically acceptable salt thereof, wherein $R_9$ is $C_1$-$C_6$ alkoxy.

13. The compound of claim 1, or a pharmaceutically acceptable salt thereof, wherein $R_{10}$ is H.

14. The compound of claim 1, or a pharmaceutically acceptable salt thereof, wherein $R_{10}$ is F.

15. The compound of claim 1, or a pharmaceutically acceptable salt thereof, wherein $R_{11}$ is $C_1$-$C_6$ haloalkoxy.

16. The compound of claim 1, or a pharmaceutically acceptable salt thereof, wherein $R_{12}$ is H.

17. The compound of claim 1, or a pharmaceutically acceptable salt thereof, wherein $R_{13}$ is H.

18. A compound selected from:

1

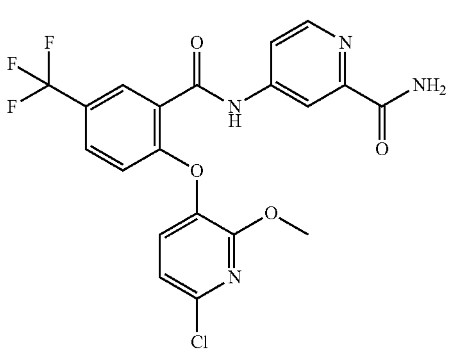

2

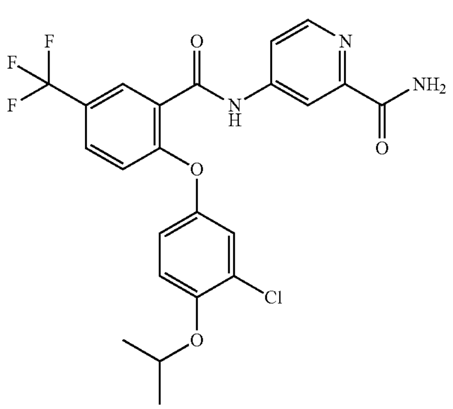

3
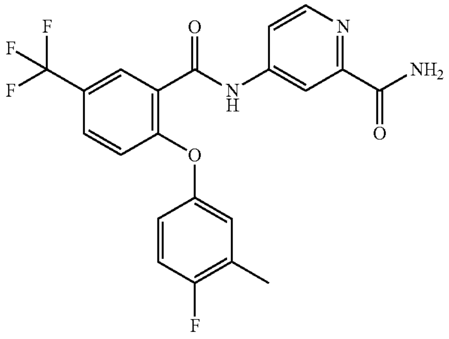
4
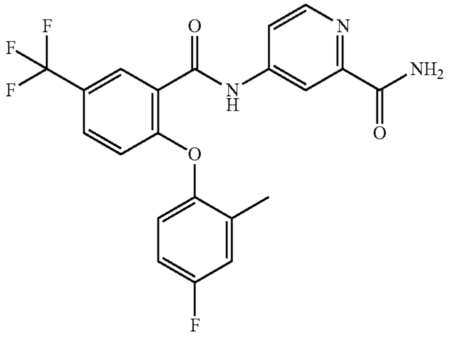
5
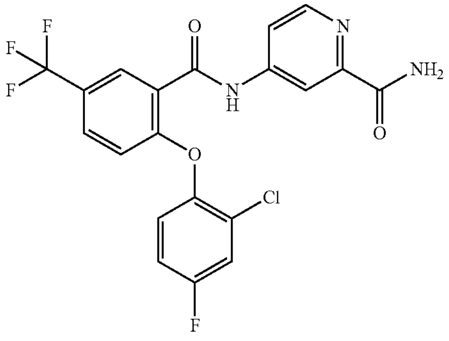
6
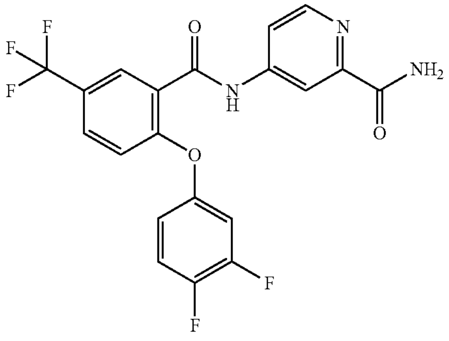
7
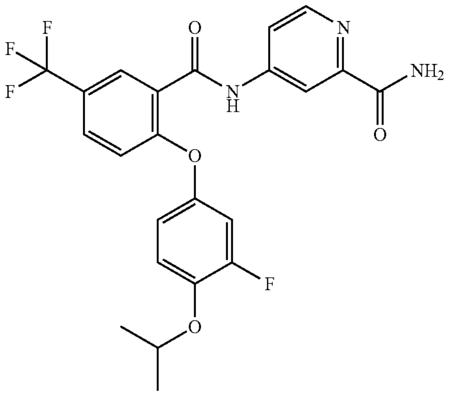
8
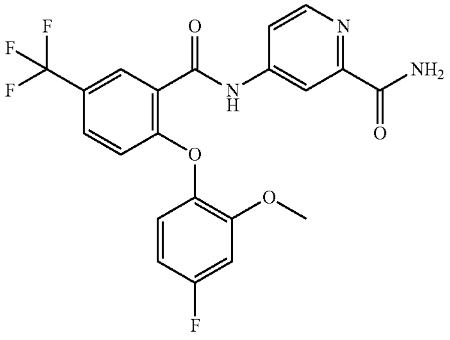
9
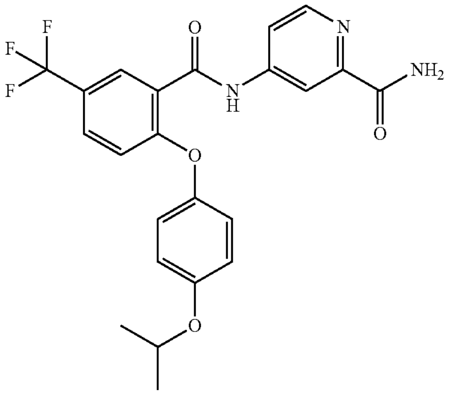
10
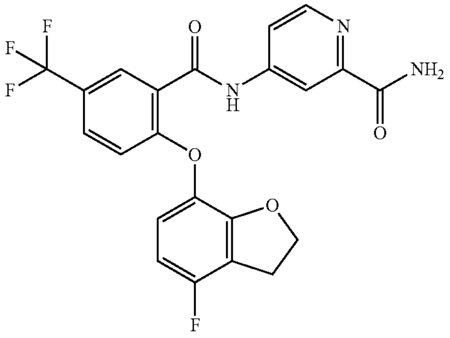

11
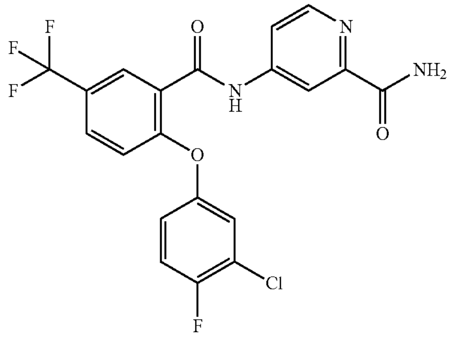
12
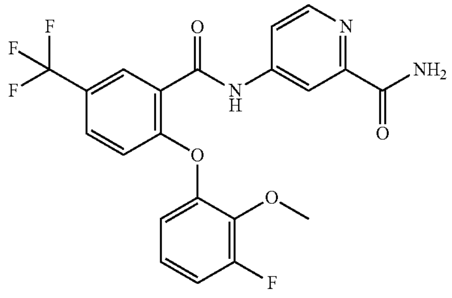
18
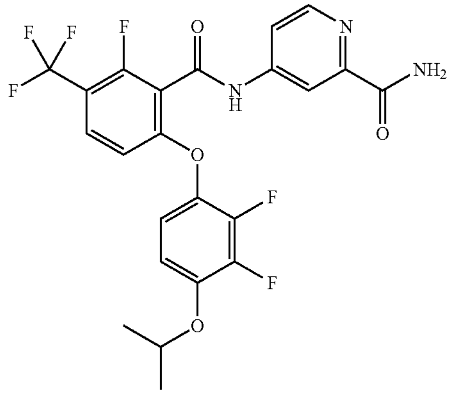
19
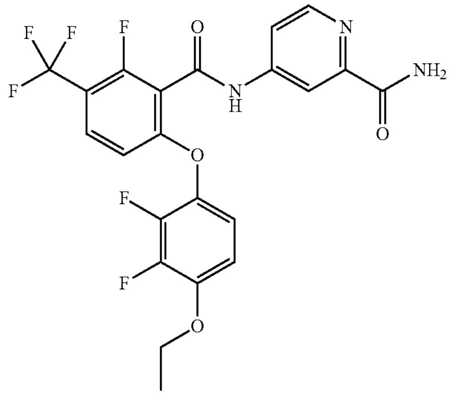
20
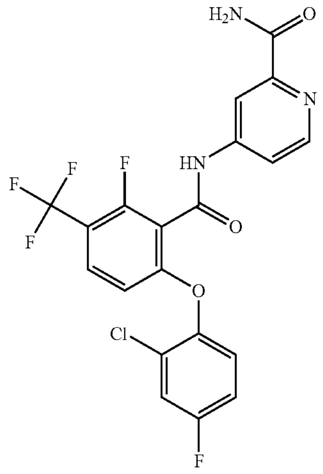
21
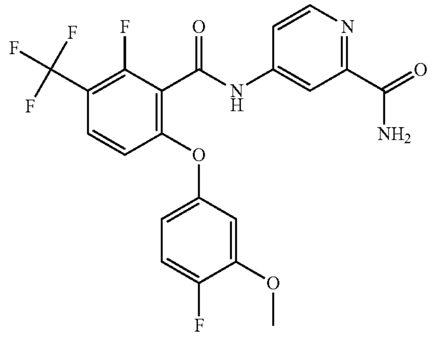
22
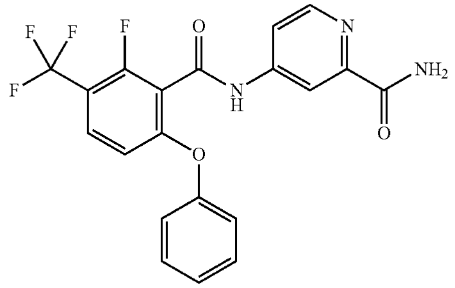
23
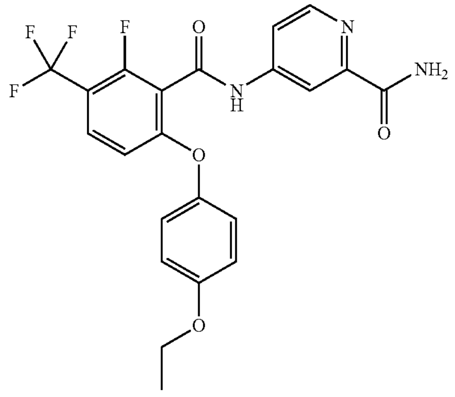

-continued
24
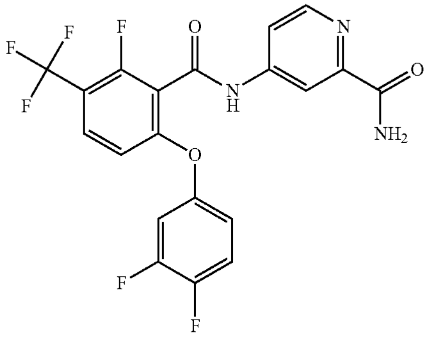
25
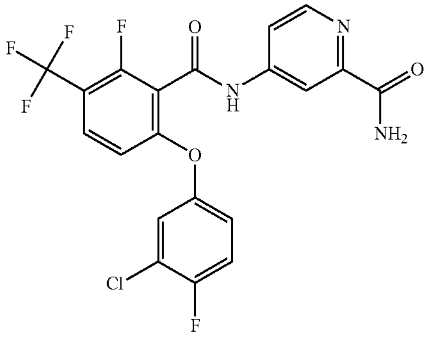
26
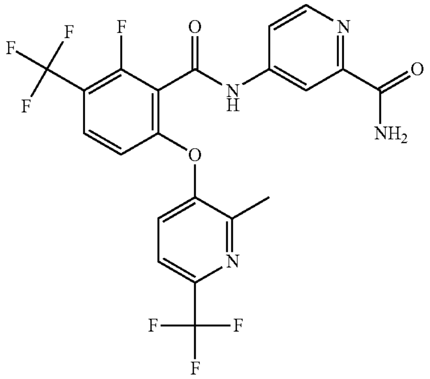
27
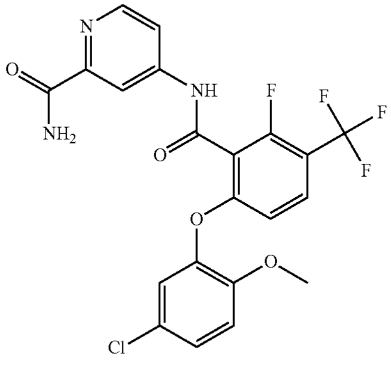
-continued
28
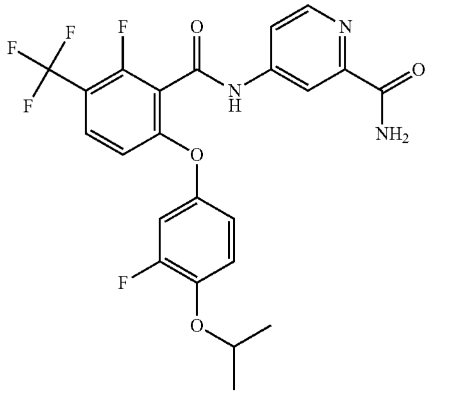
29
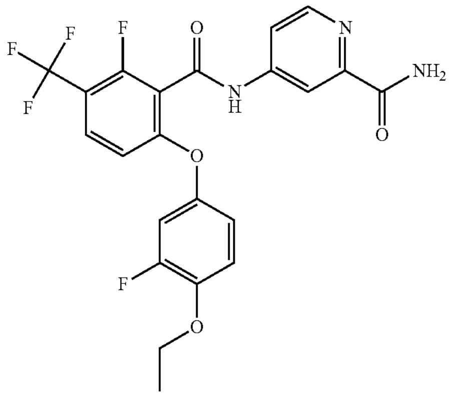
30
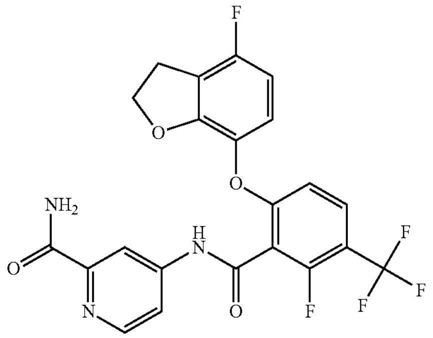
31
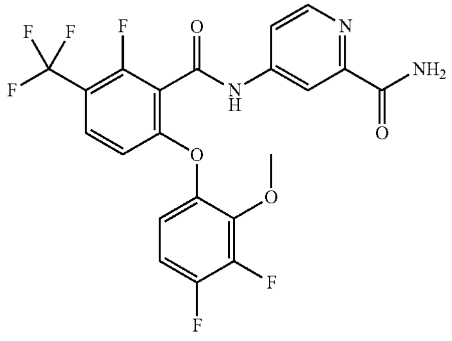

-continued
32
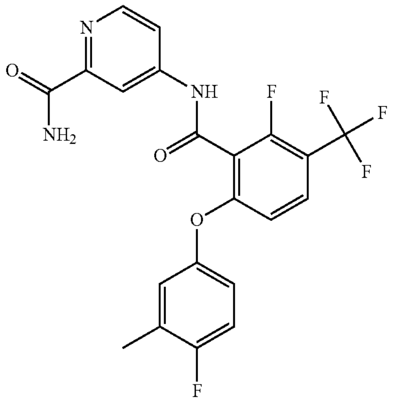
33
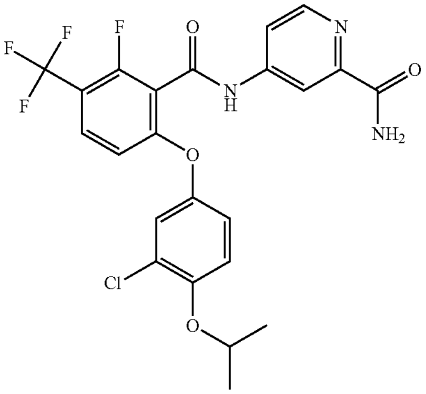
34
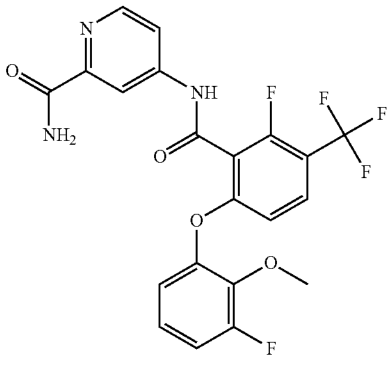
-continued
35
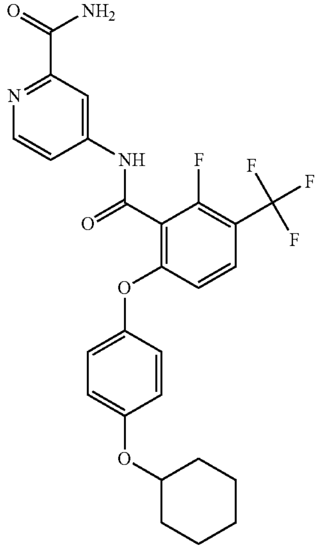
36
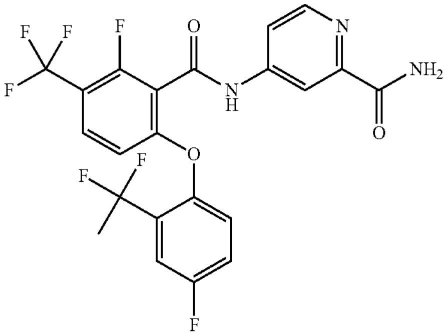
37
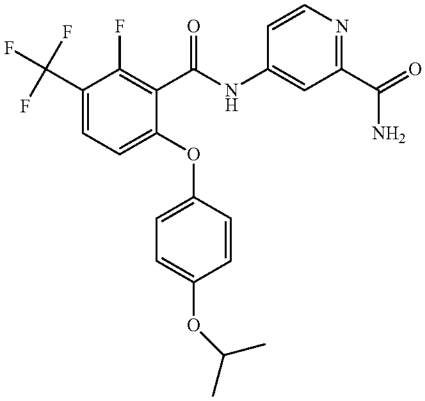
38
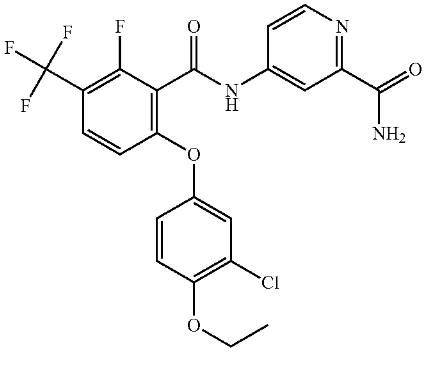

-continued
39
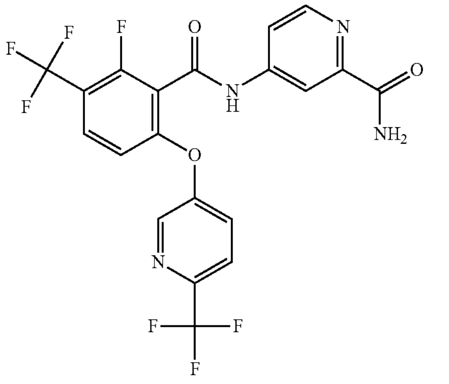
40
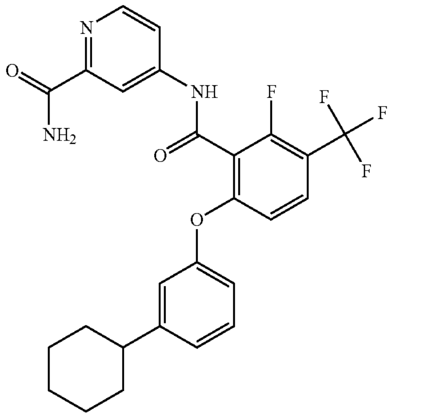
41
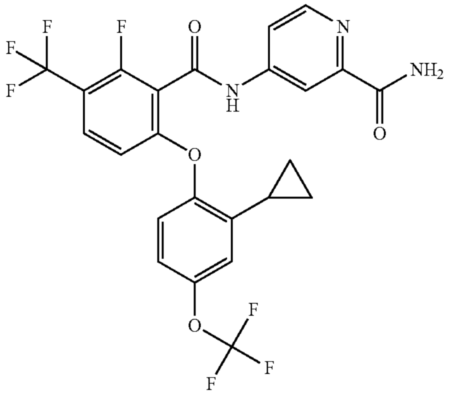
42
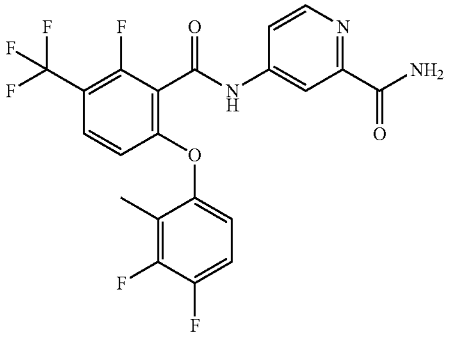
-continued
43
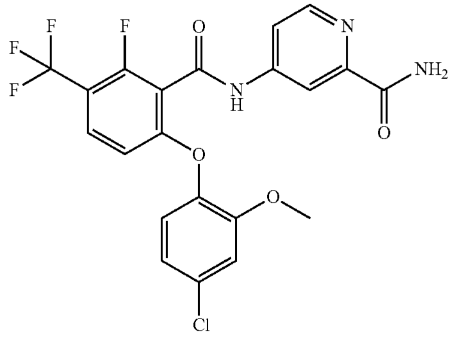
44
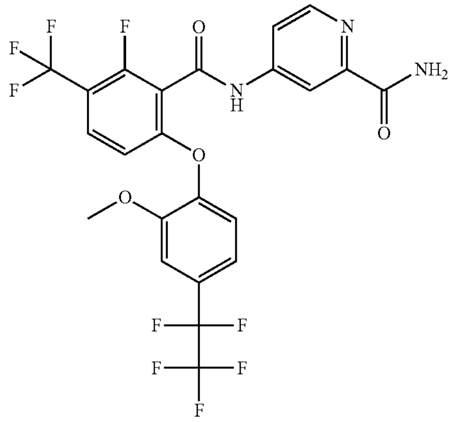
45
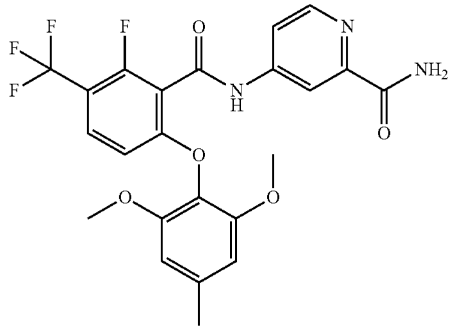
46
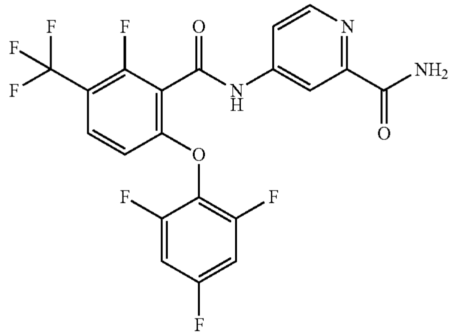

47
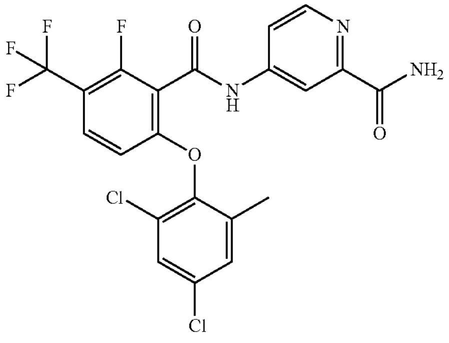
48
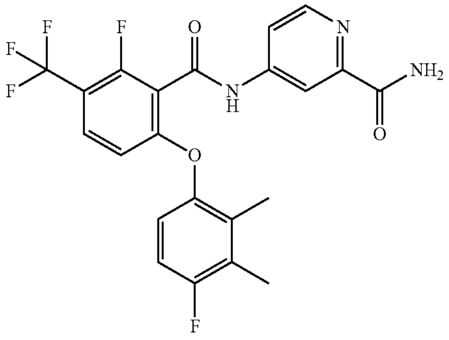
49
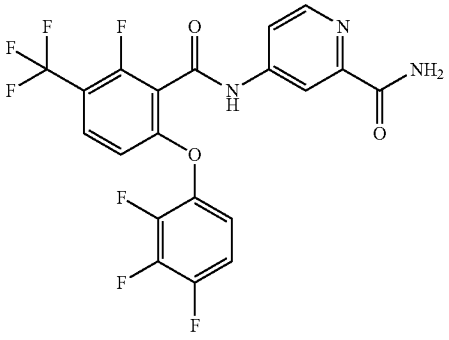
50
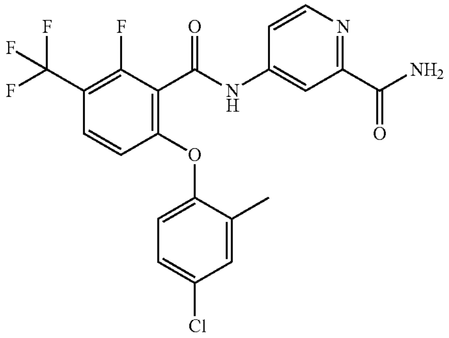
51
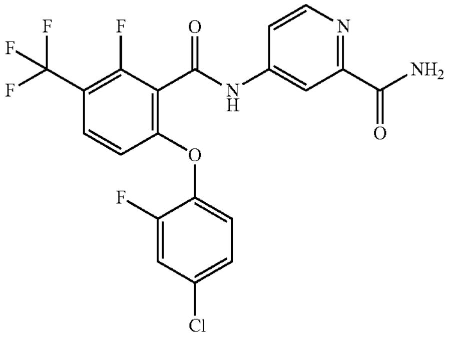
52
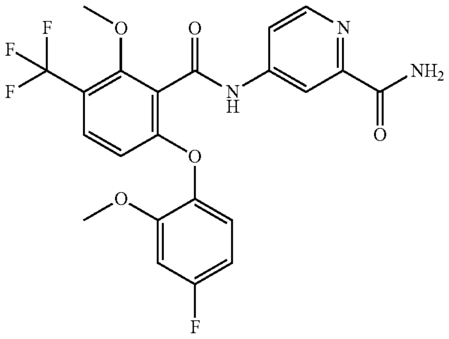
53
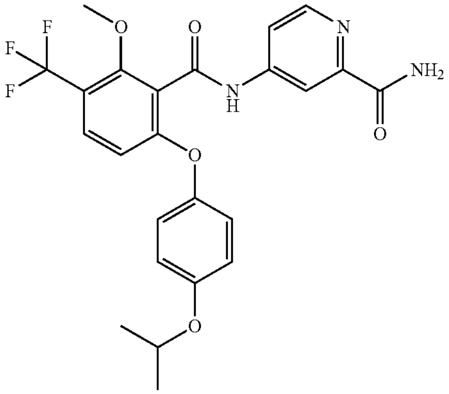
54
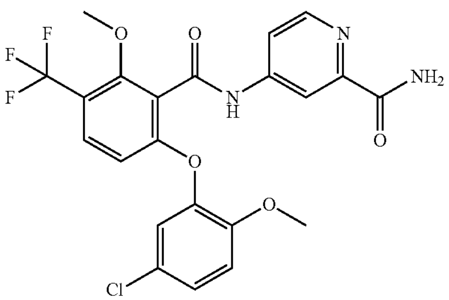

-continued
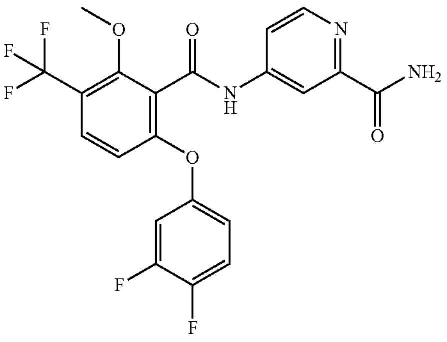
55
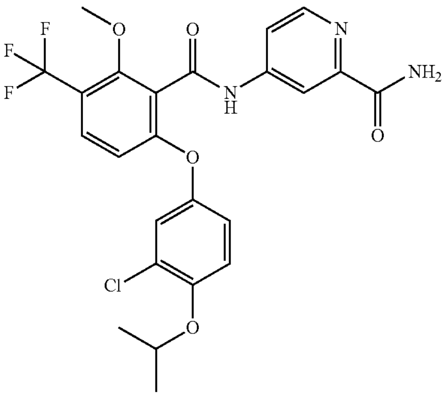
56
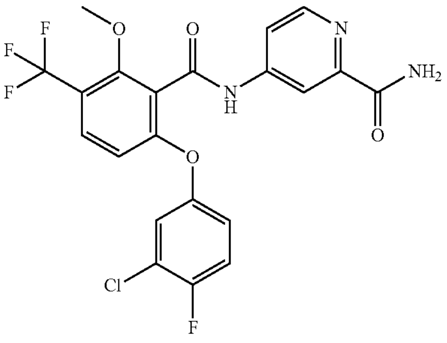
57
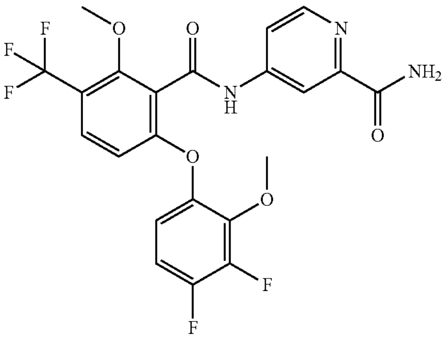
58
-continued
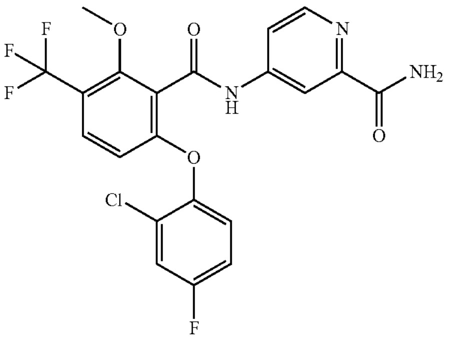
59
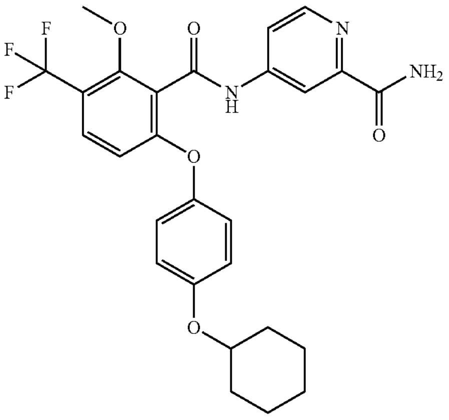
60
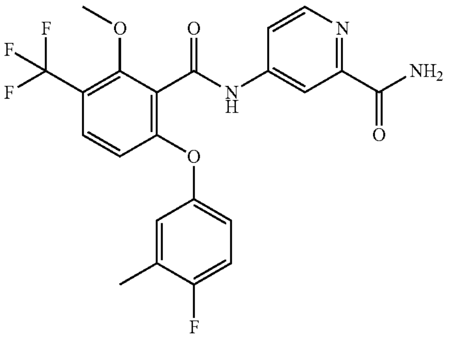
61
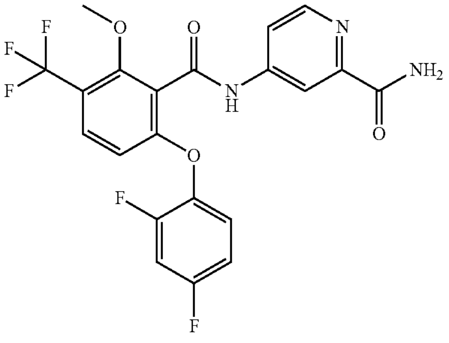
62

-continued
63
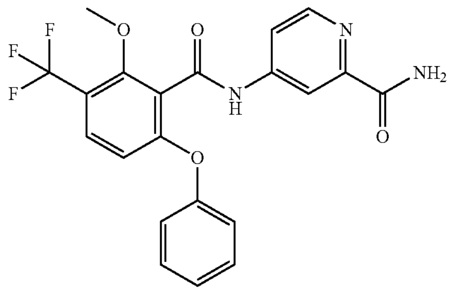
64
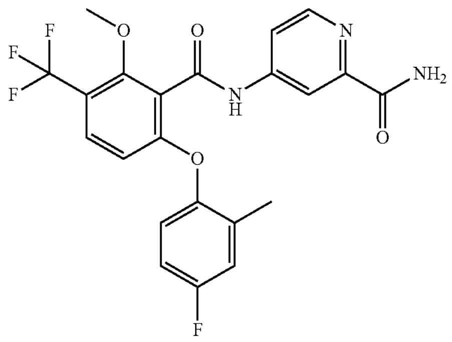
65
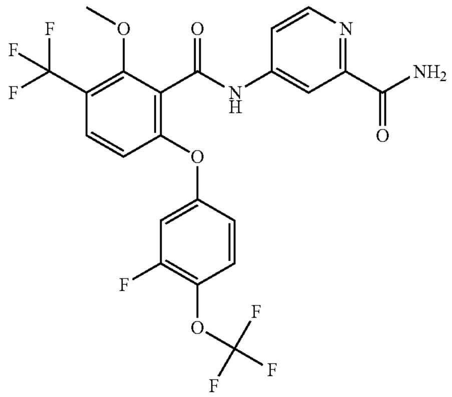
66
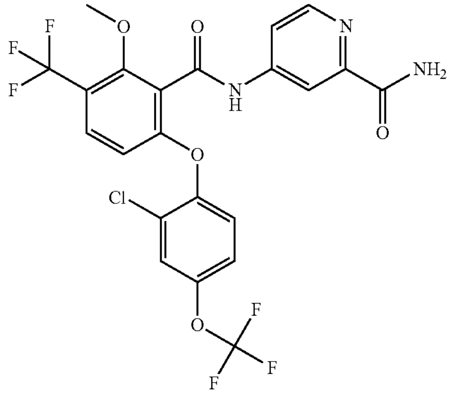
-continued
67
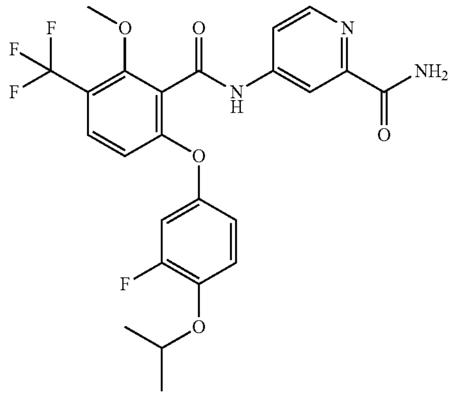
68
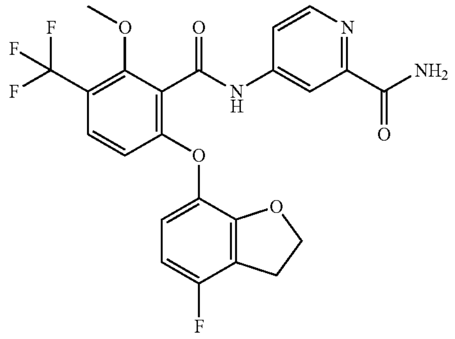
69
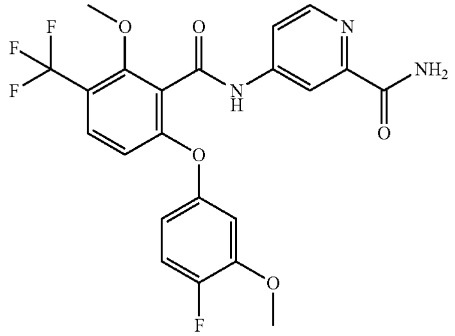
70
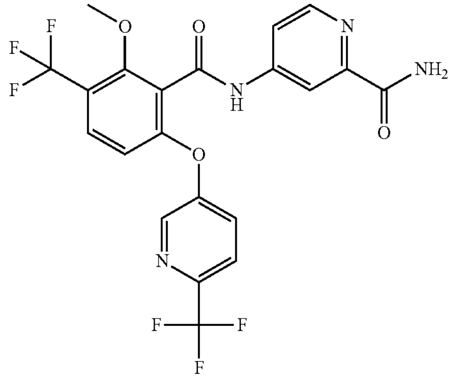

-continued
71
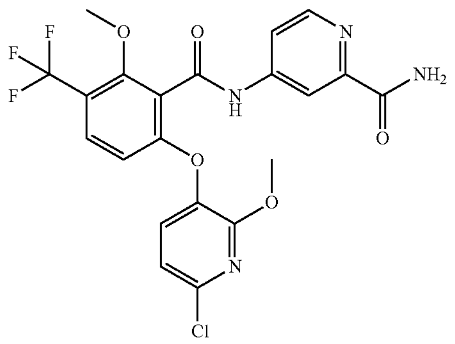
72
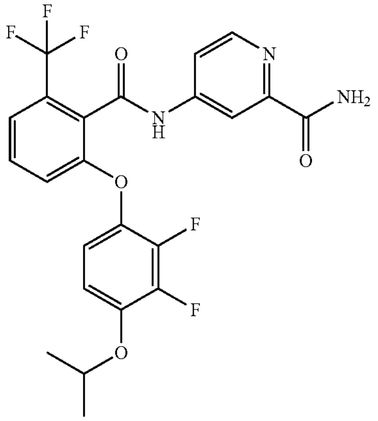
73
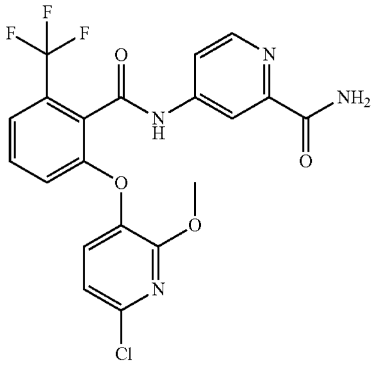
74
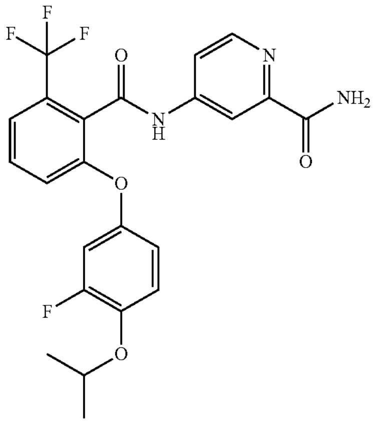
-continued
75
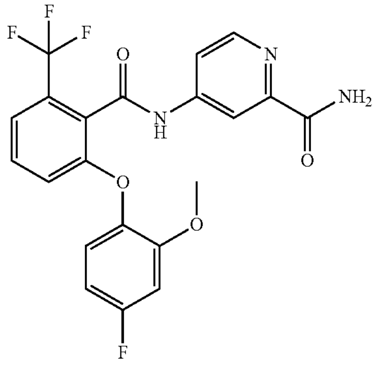
76
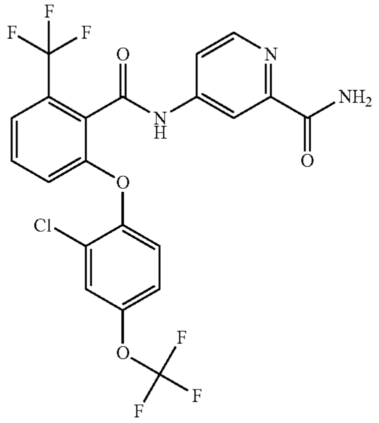
77
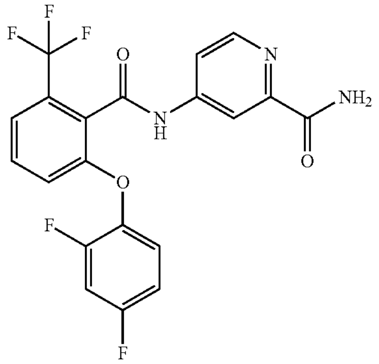
78
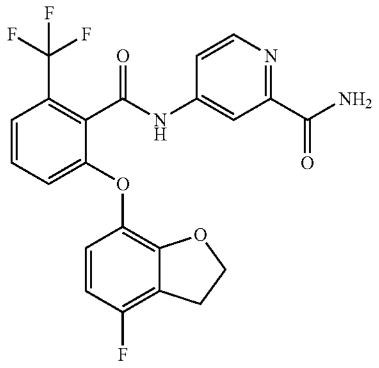

-continued
79
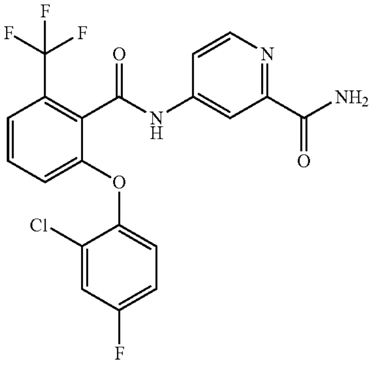
80
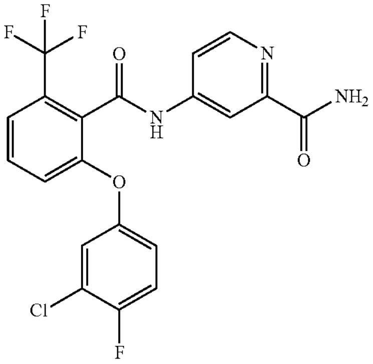
83
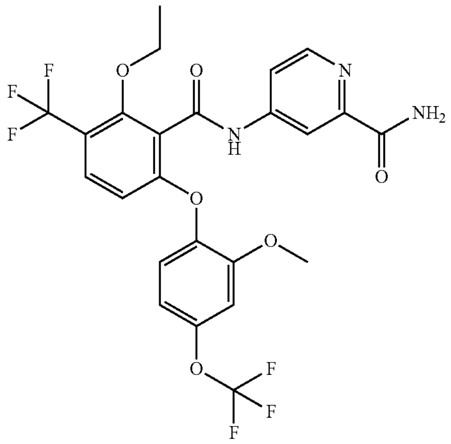
84
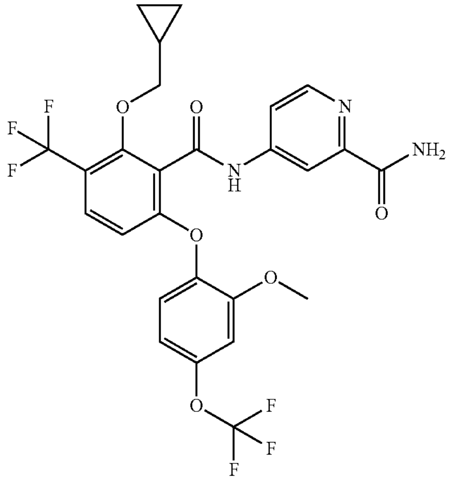
-continued
85
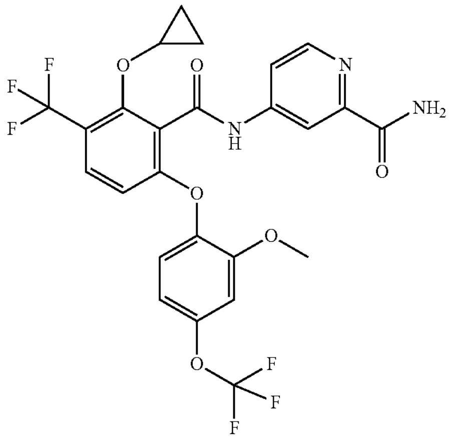
86
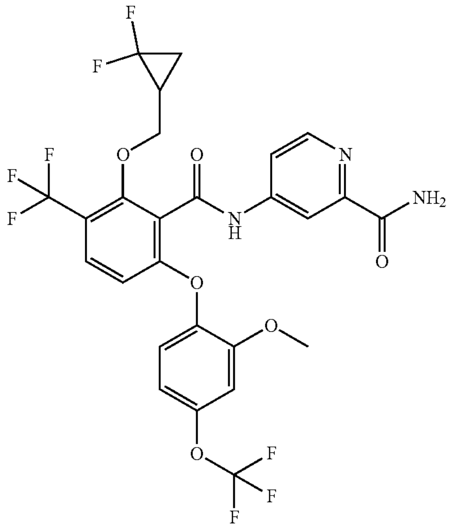
87
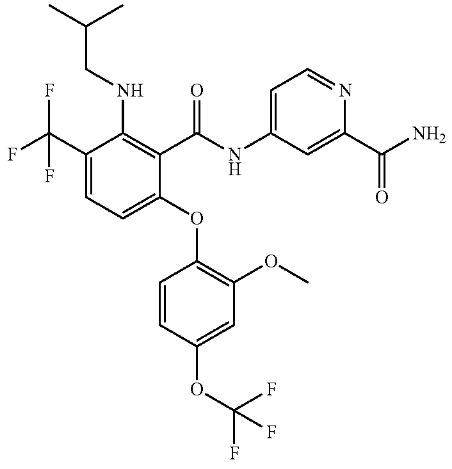

-continued
88
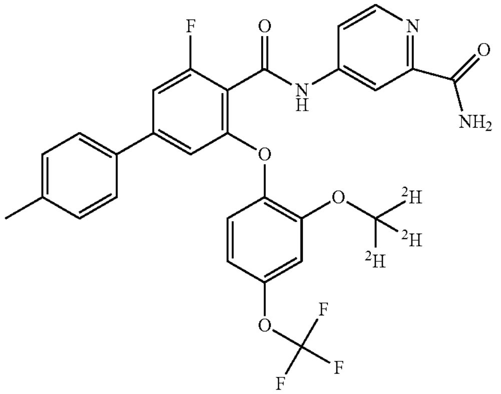
89
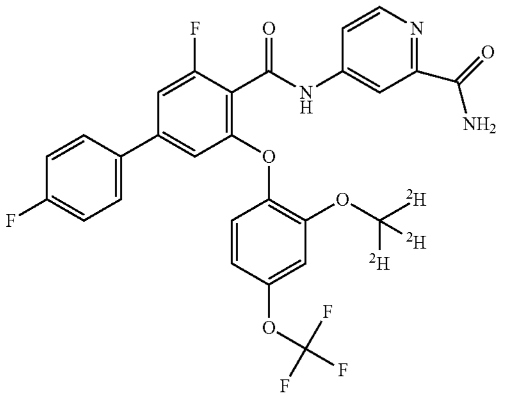
90
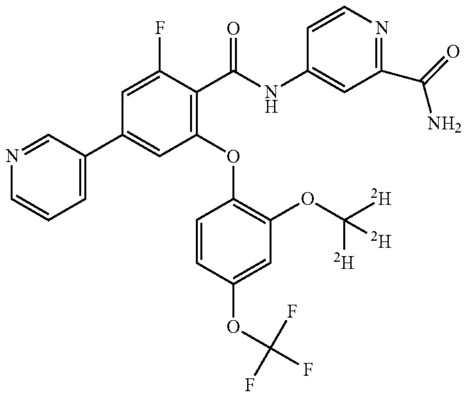
91
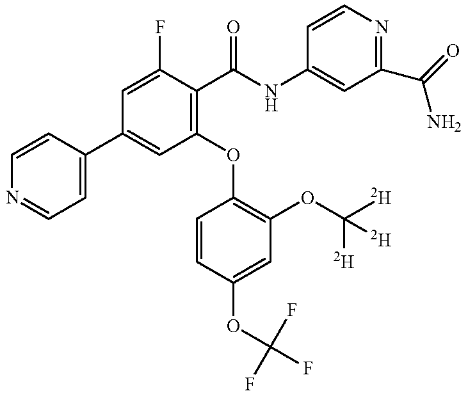
-continued
92
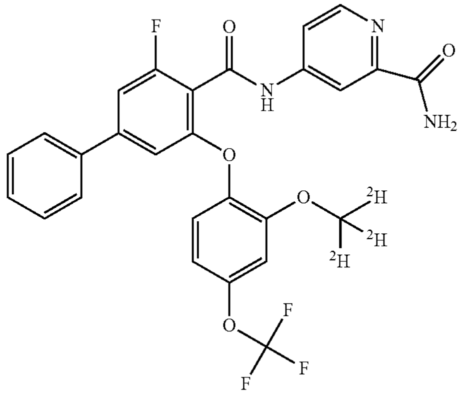
93
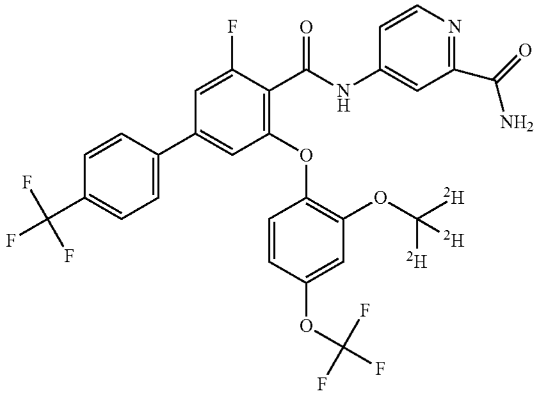
94
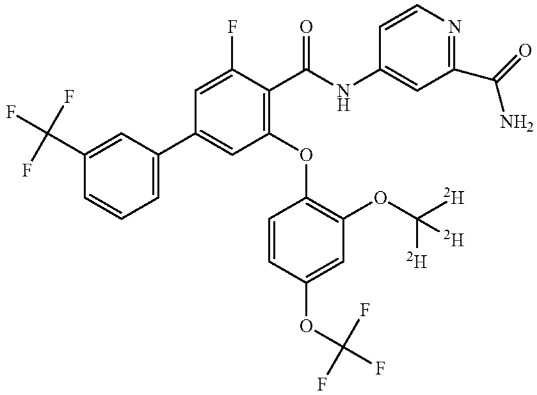
95
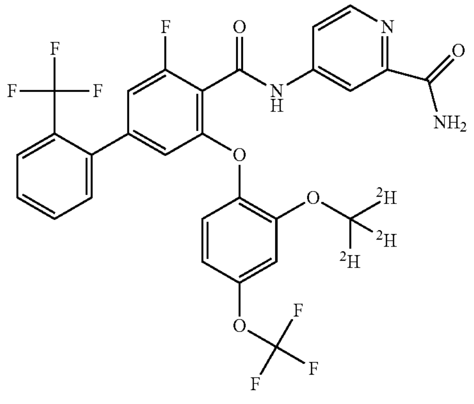

96
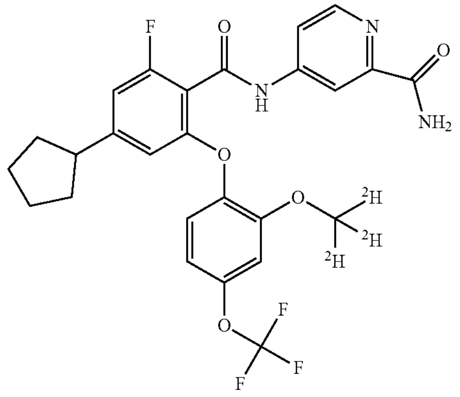
97
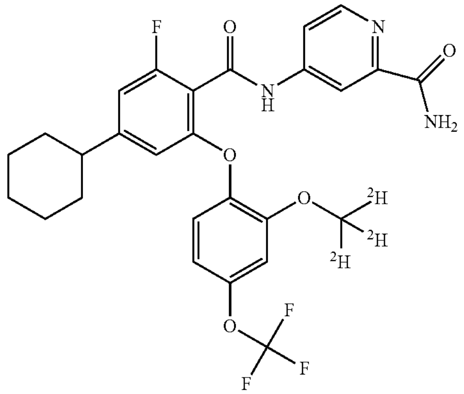
98
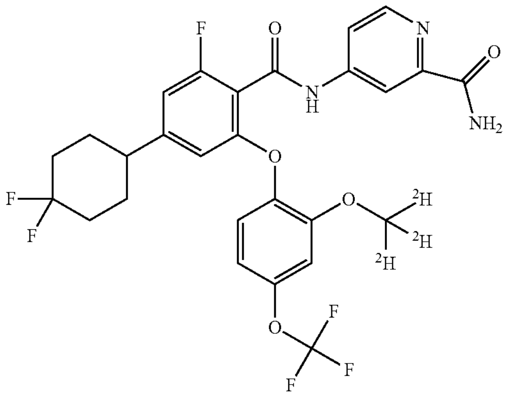
99
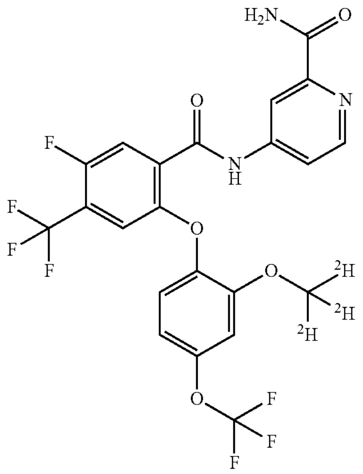
100
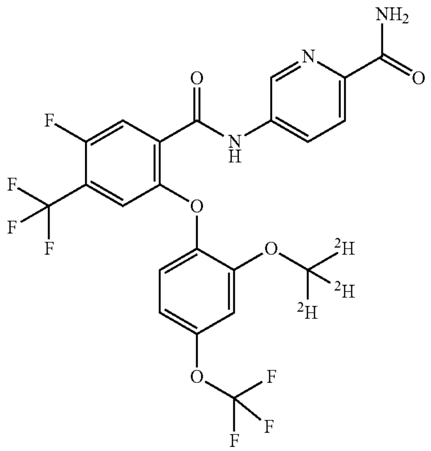
101
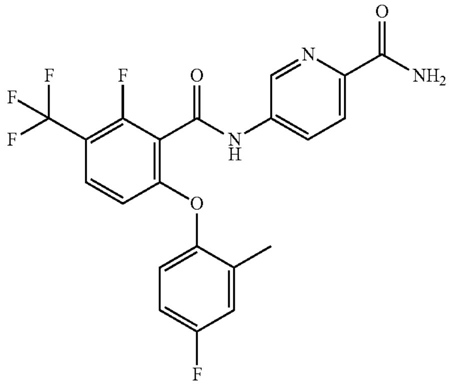

-continued
102
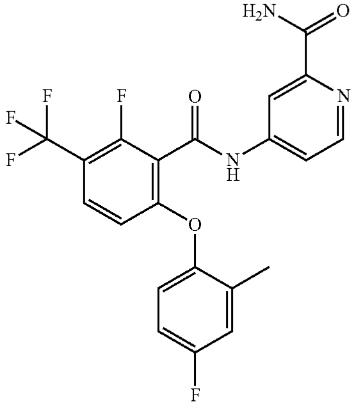
103
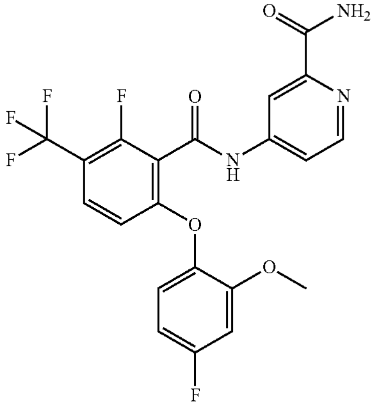
104
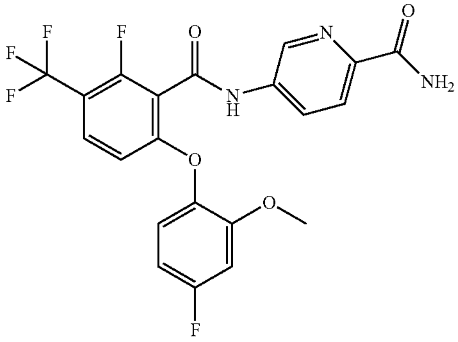
105
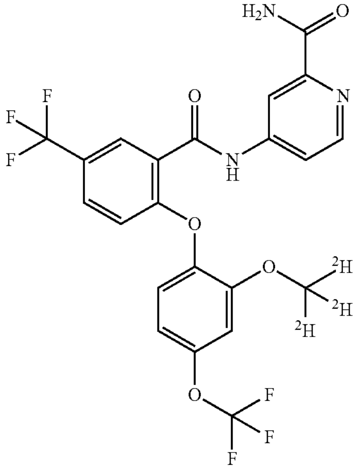
-continued
106
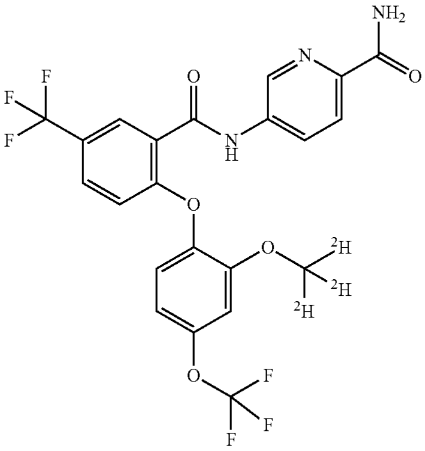
107
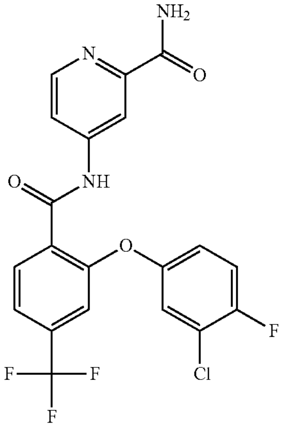
114
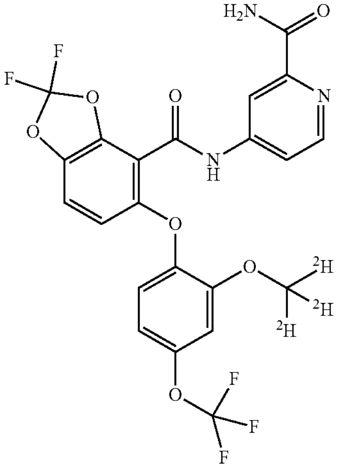

-continued
115
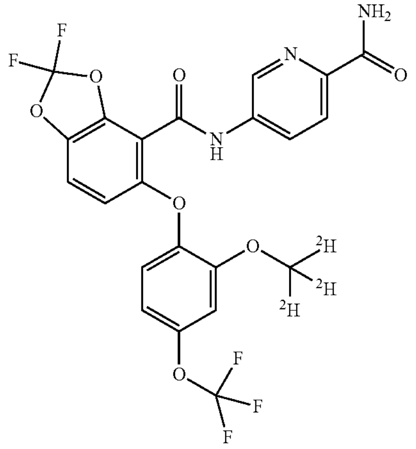
116
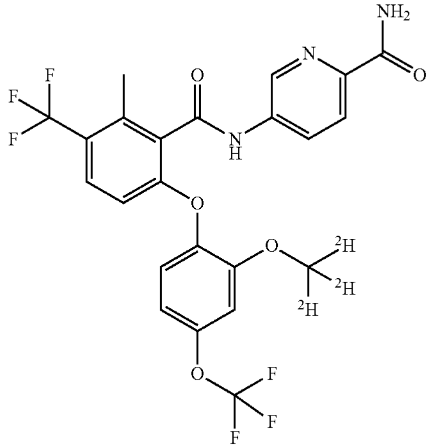
117
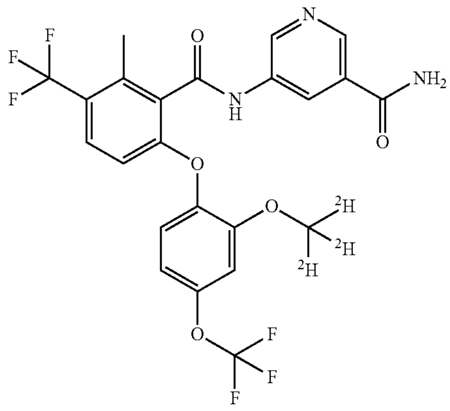
-continued
118
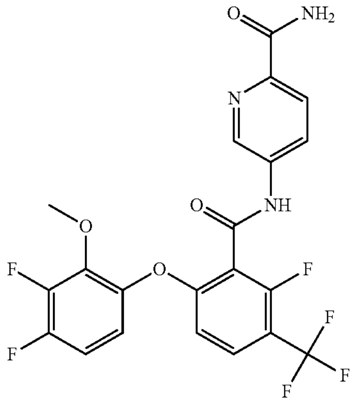
119
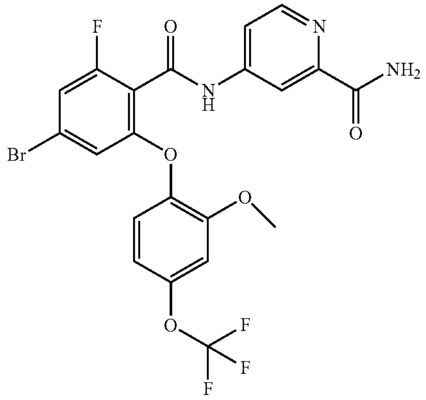
120
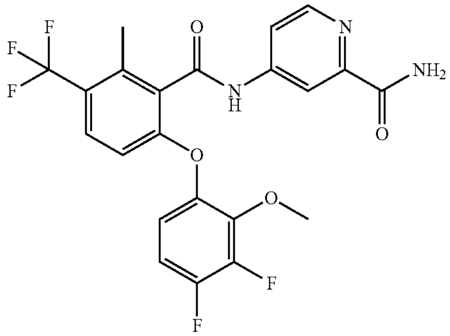
121
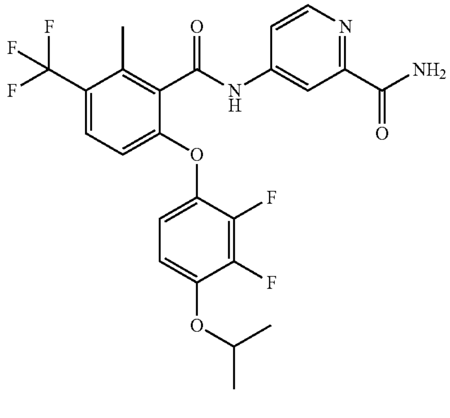

122
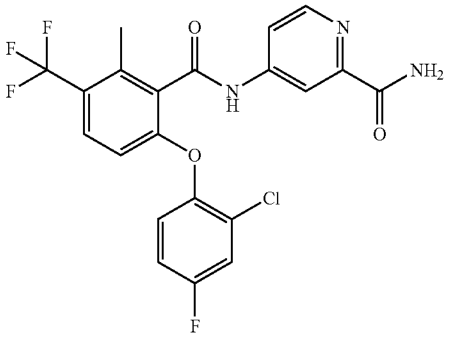
123
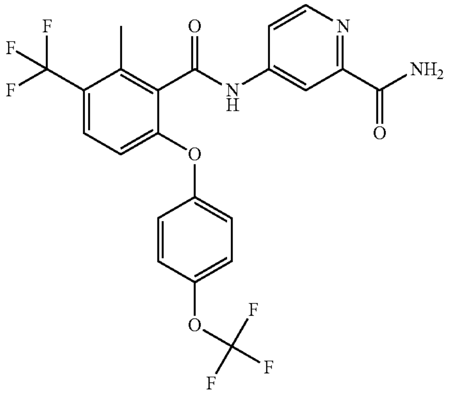
124
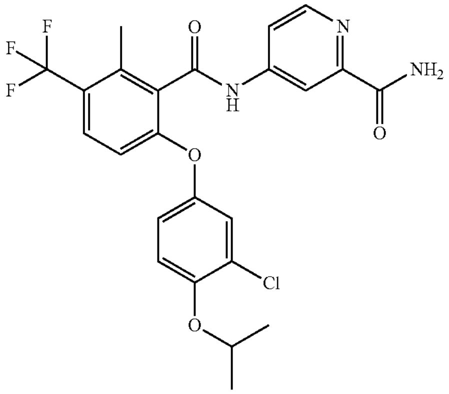
125
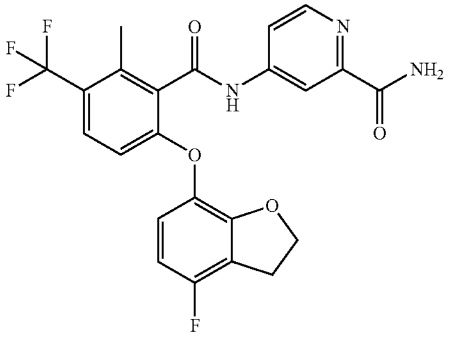
-continued
126
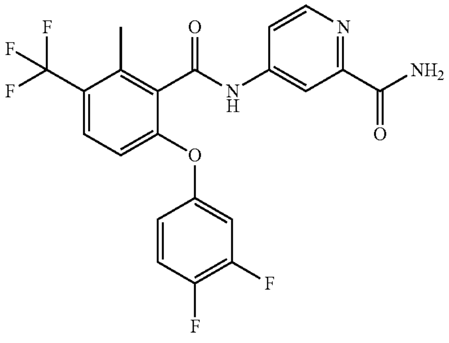
127
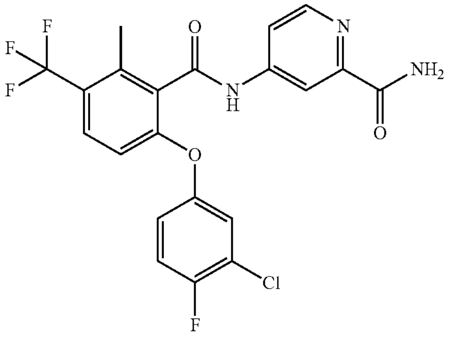
128
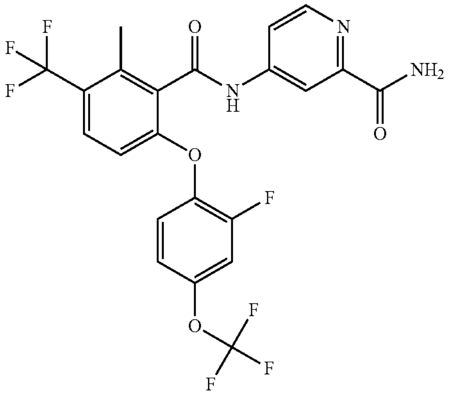
129
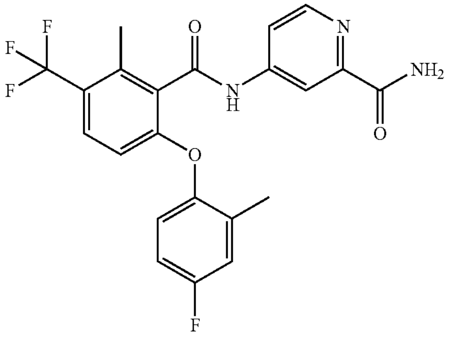

-continued
130
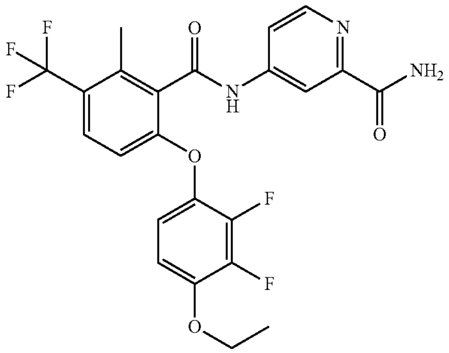
131
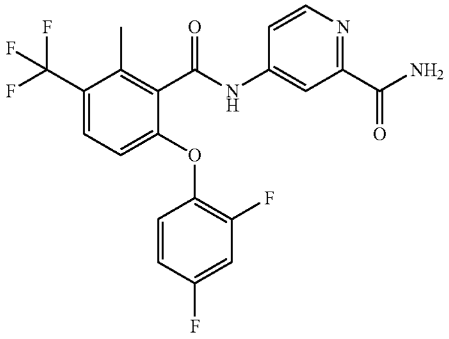
132
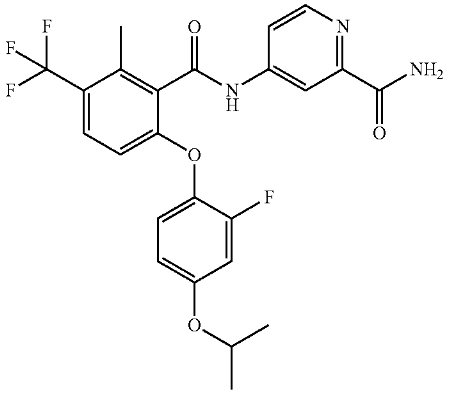
133
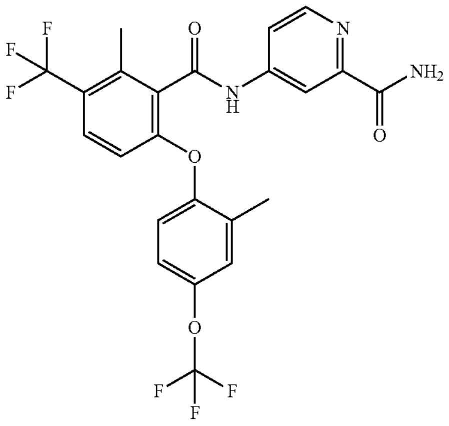
-continued
134
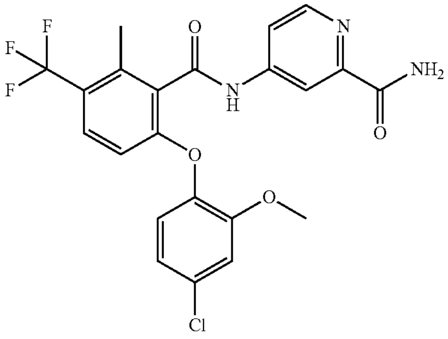
135
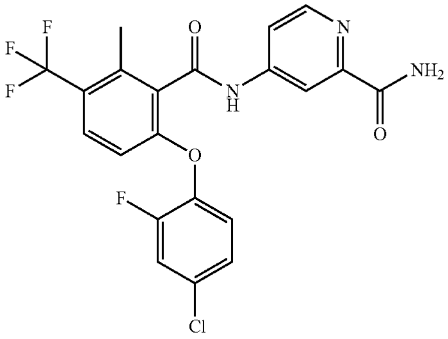
136
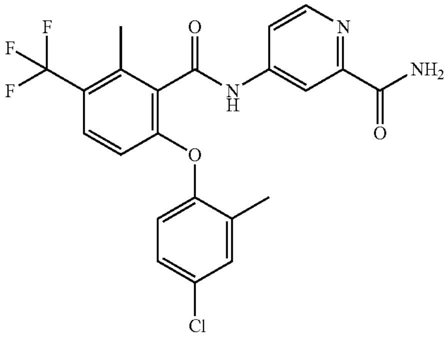
137
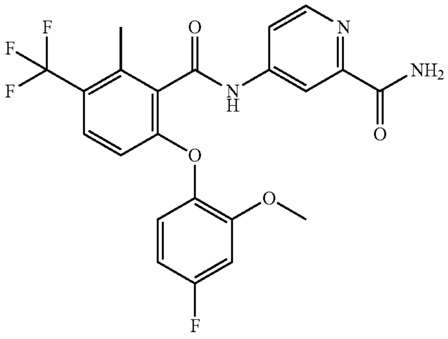

-continued
138
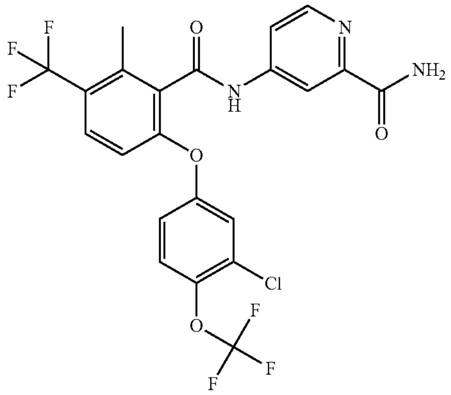
139
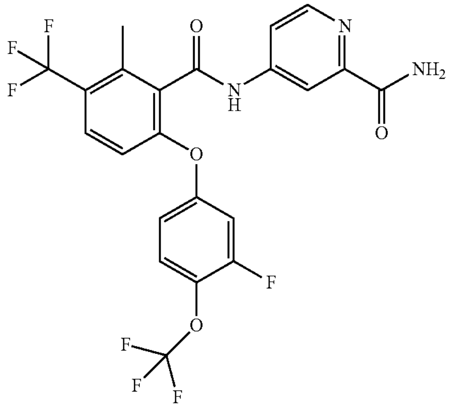
140
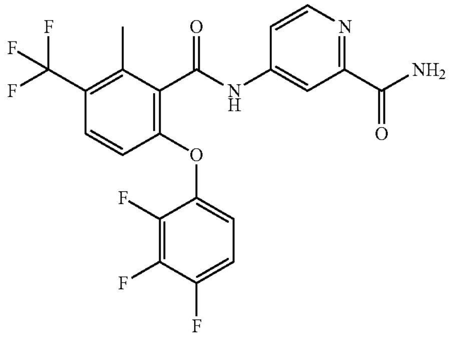
141
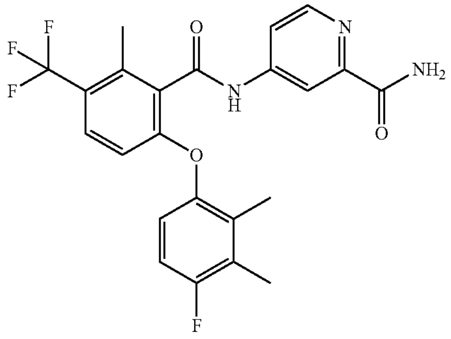
-continued
142
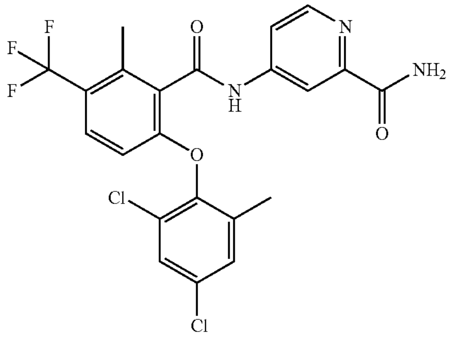
143
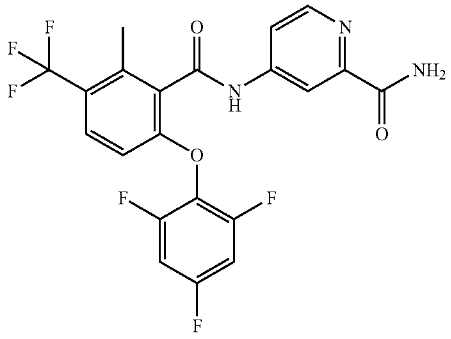
144
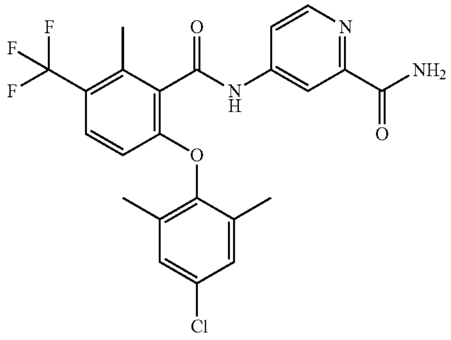
145
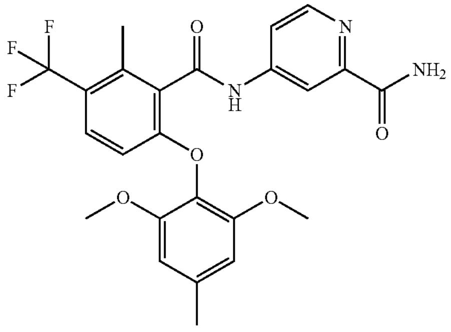

-continued
146
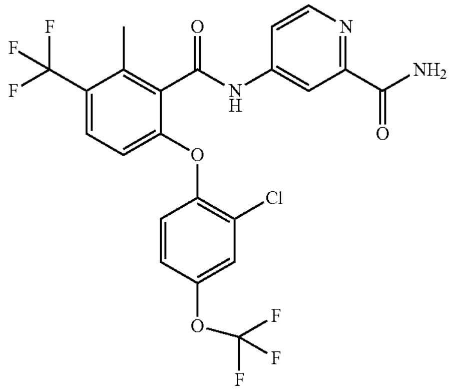
147
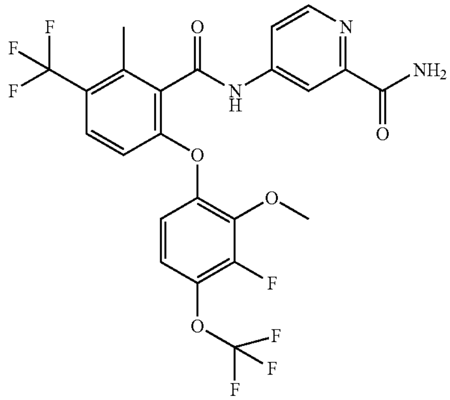
148
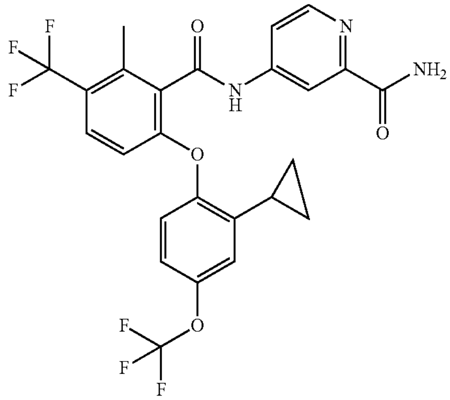
149
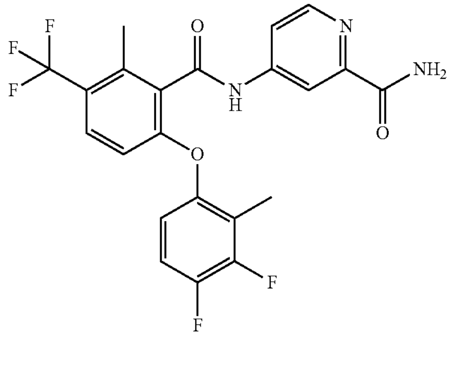
-continued
150
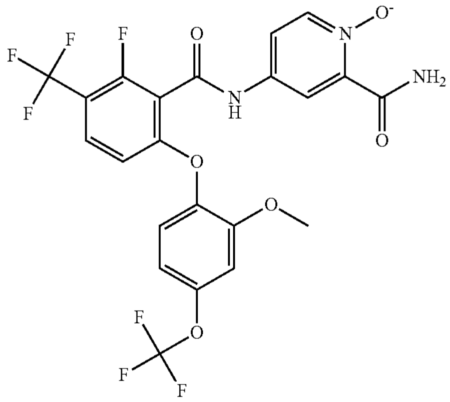
151
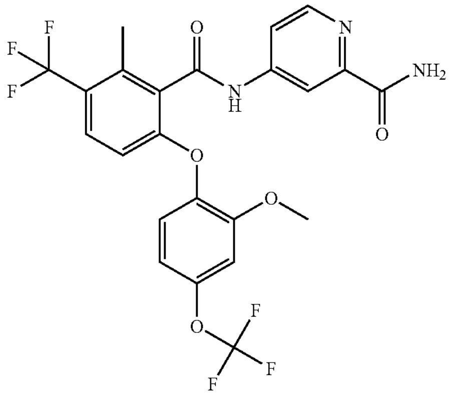
152
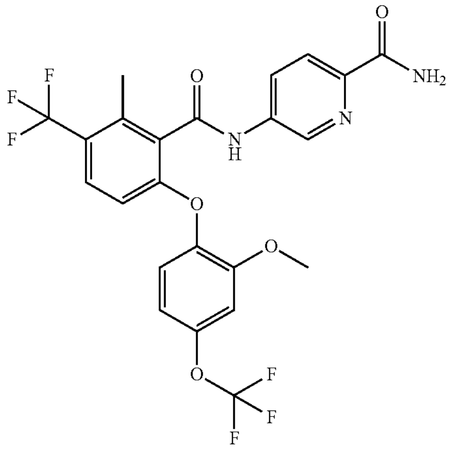
153
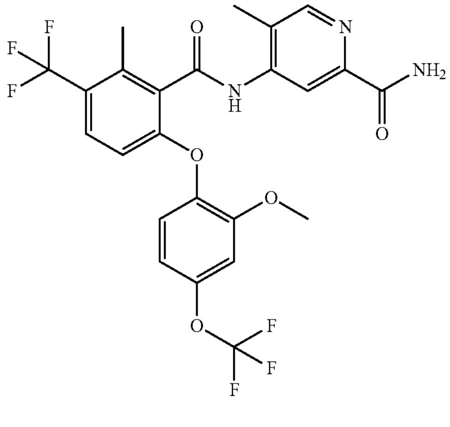

-continued
154
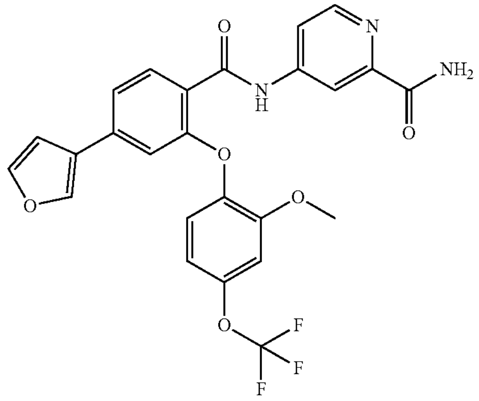
155
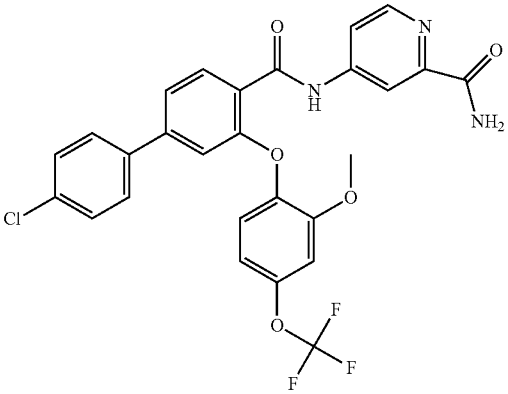
156
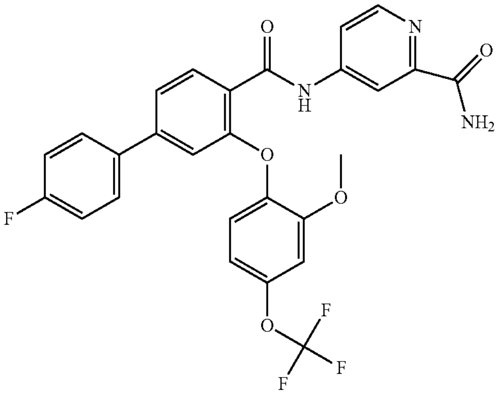
157
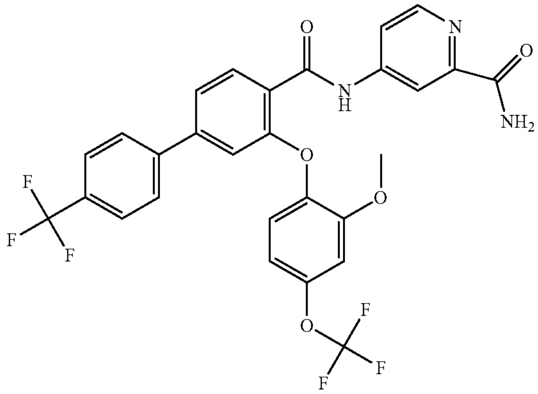
-continued
158-a
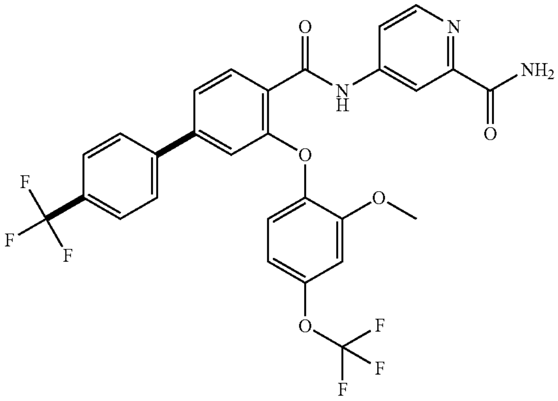
158-b
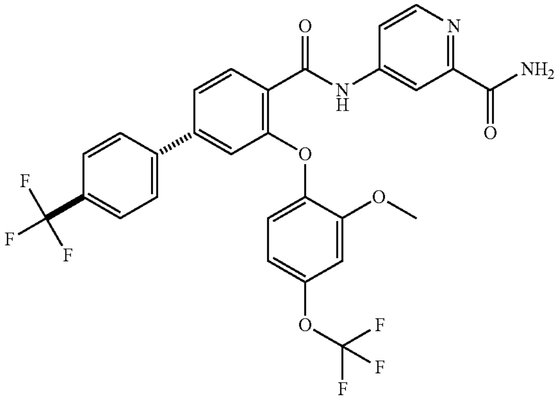
159
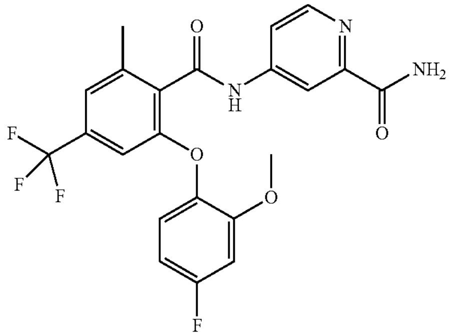
160
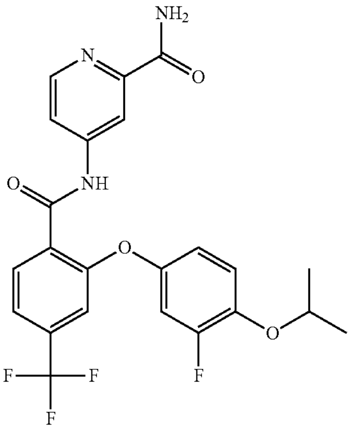

-continued
161
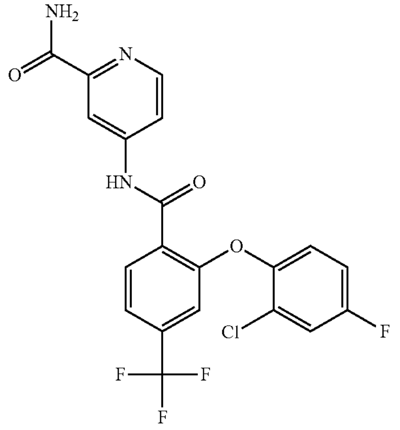
162
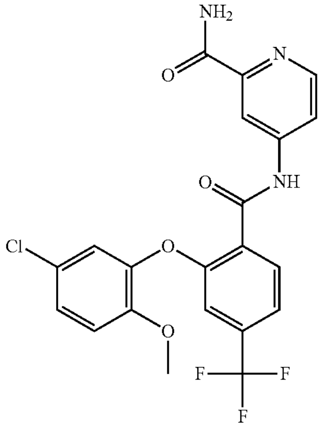
163
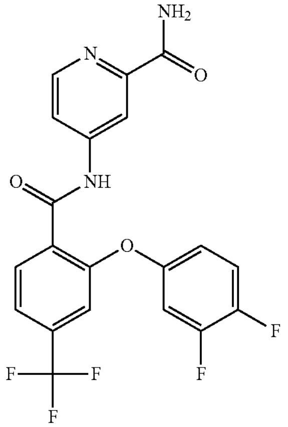
164
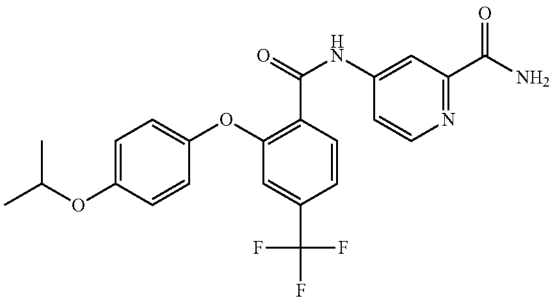
-continued
165
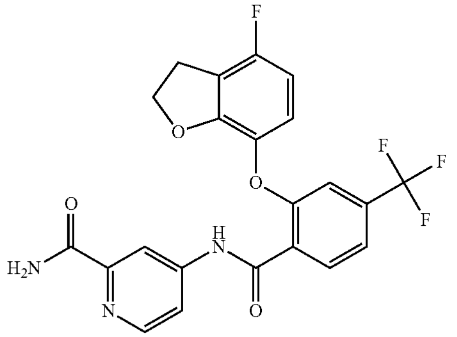
166
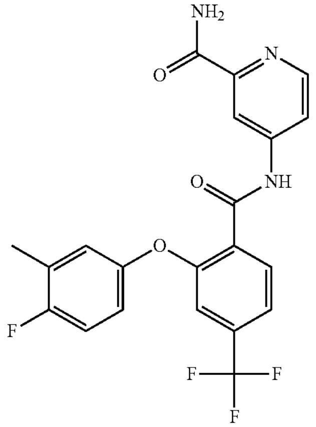
167
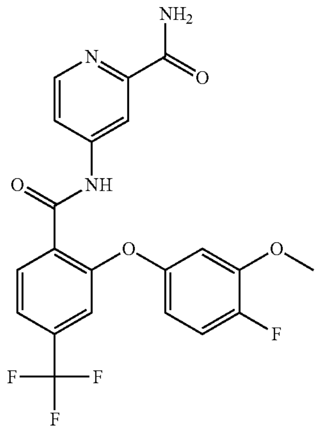
168-a
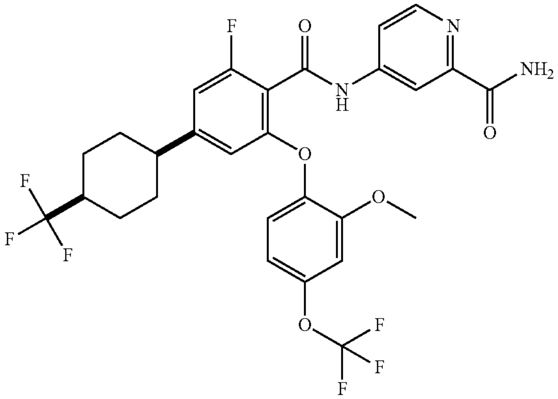

-continued
168-b
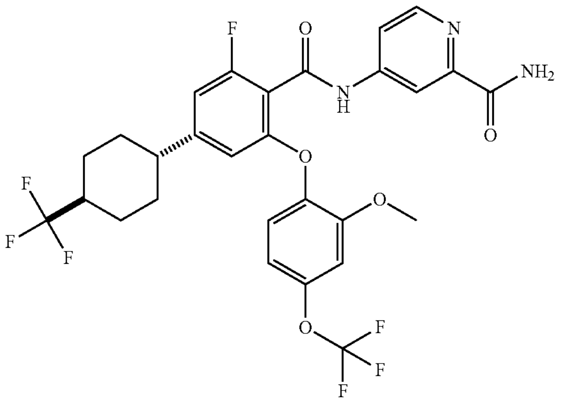
169-a
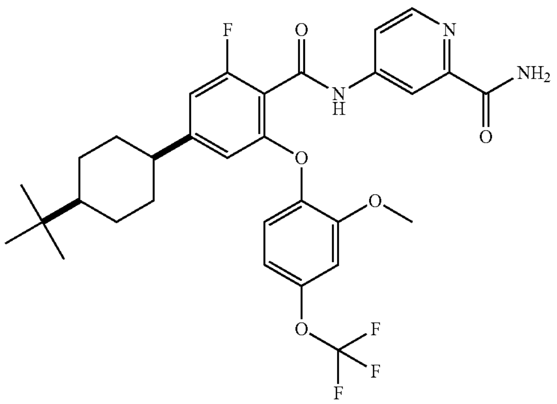
169-b
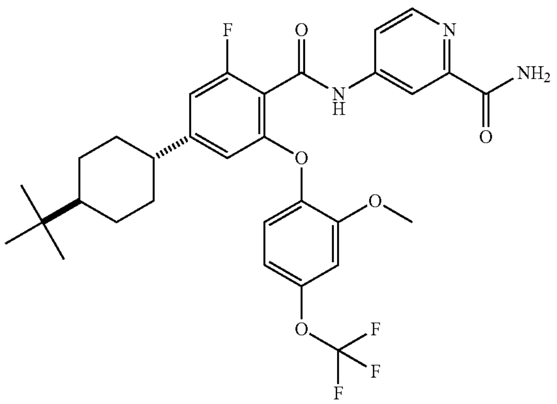
-continued
170
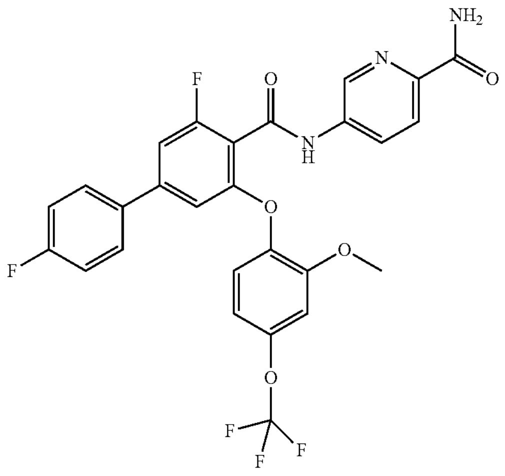
171
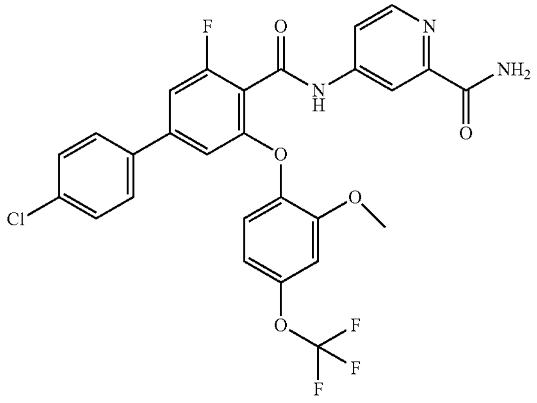
172
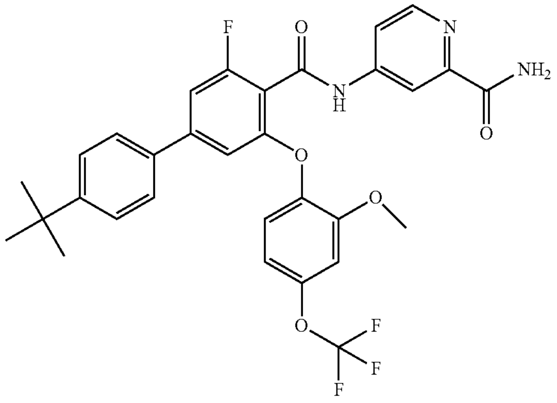

-continued
173
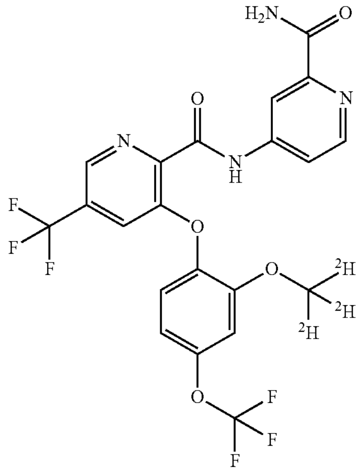
177
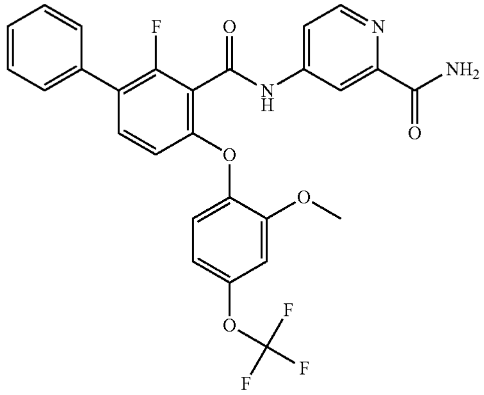
174
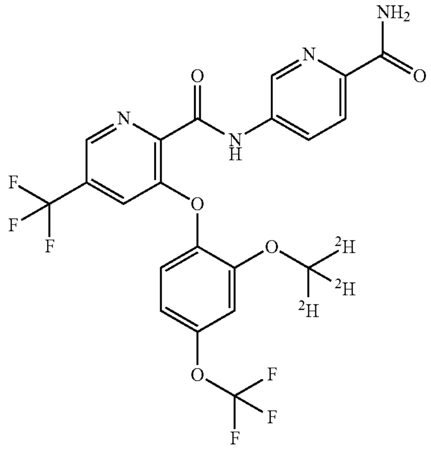
178
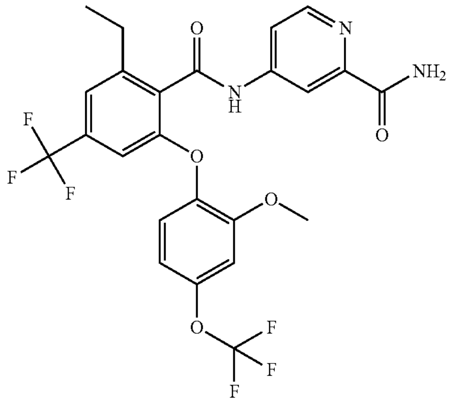
175
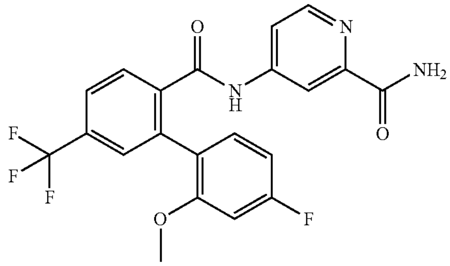
179
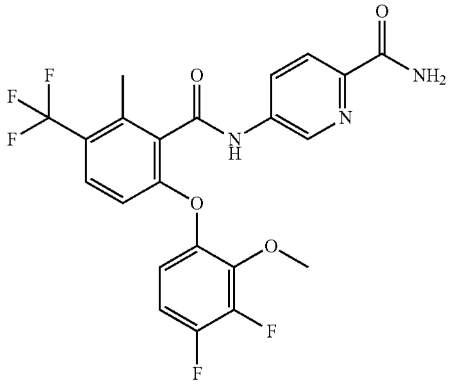
176
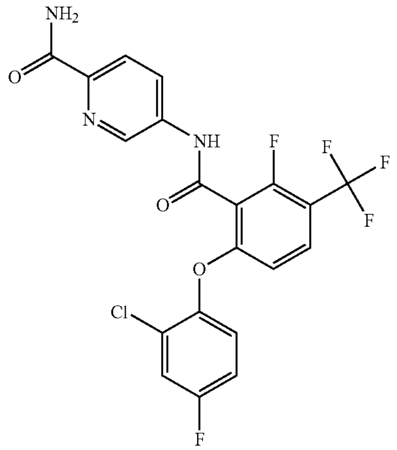
180
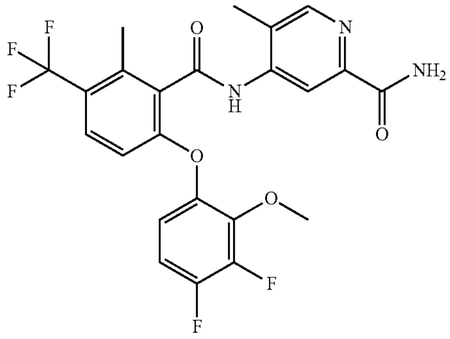

181
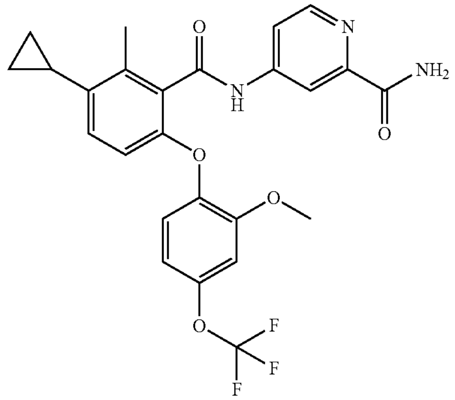
182
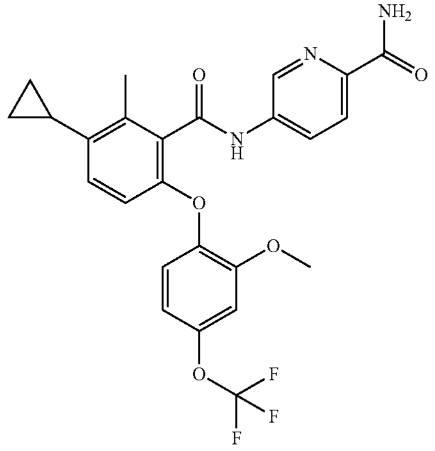
183
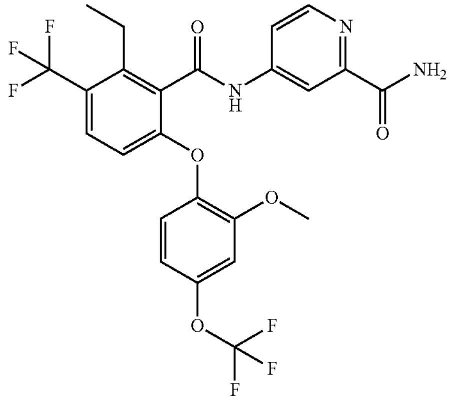
184
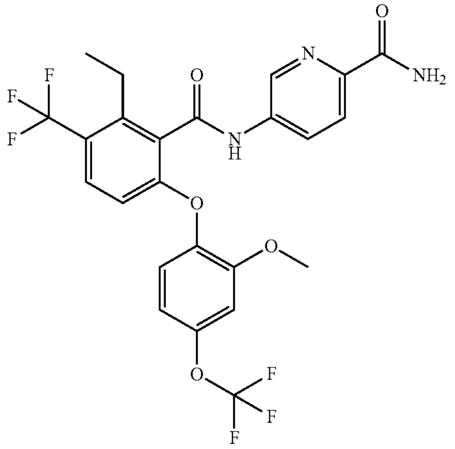
185
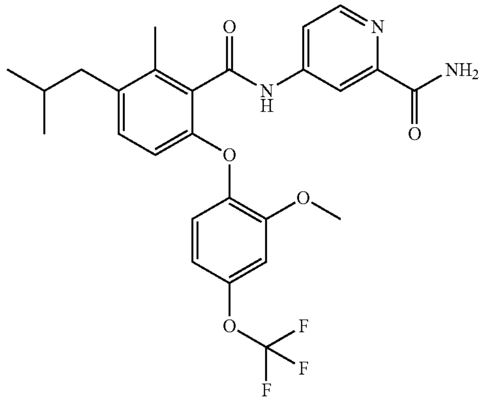
186
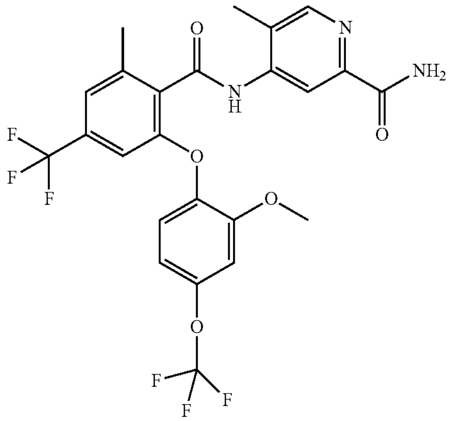

-continued
187
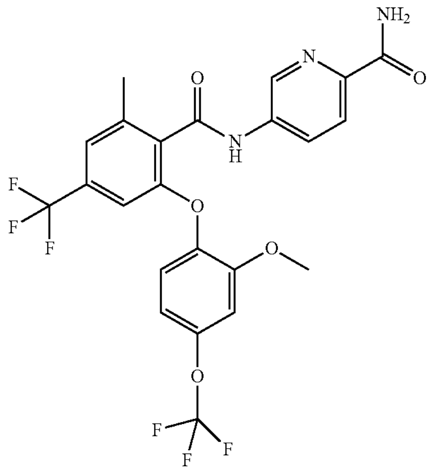
188
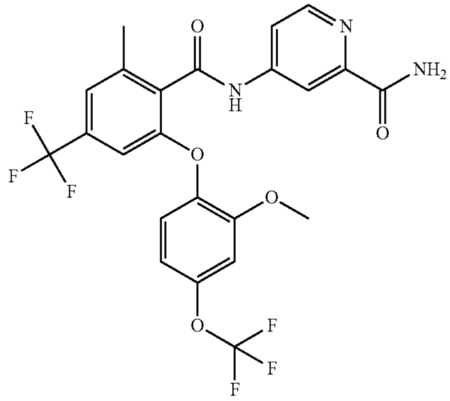
189
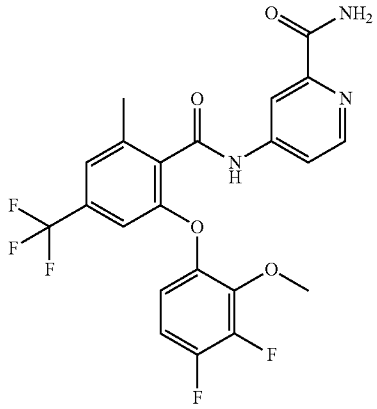
-continued
190
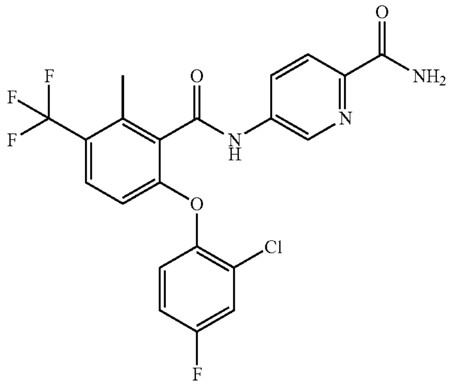
191
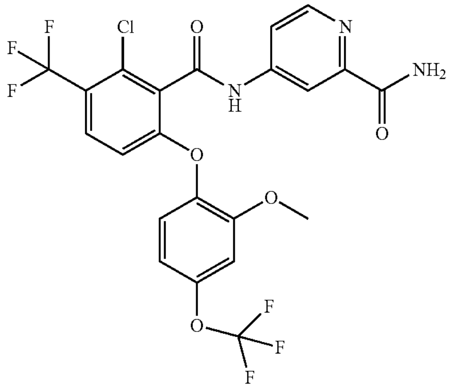
192
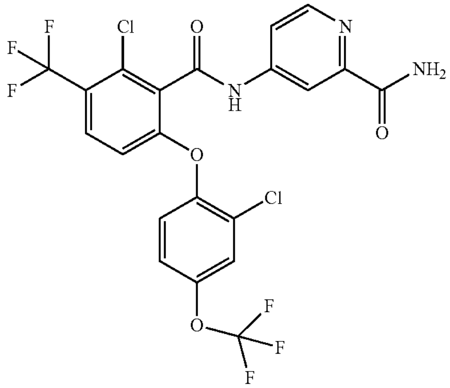
193
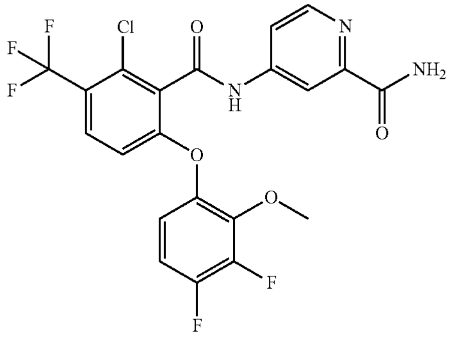

-continued
194
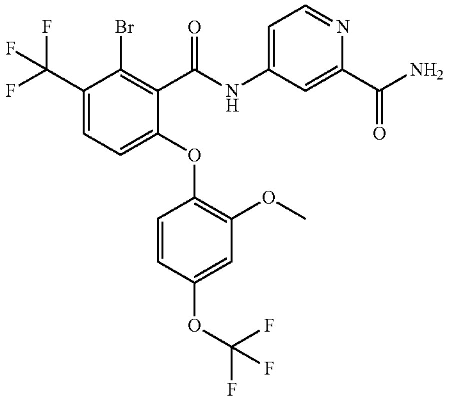
195
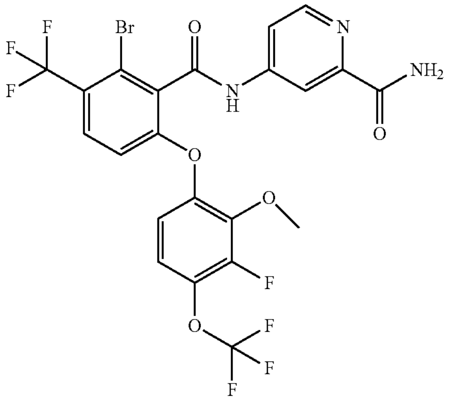
196
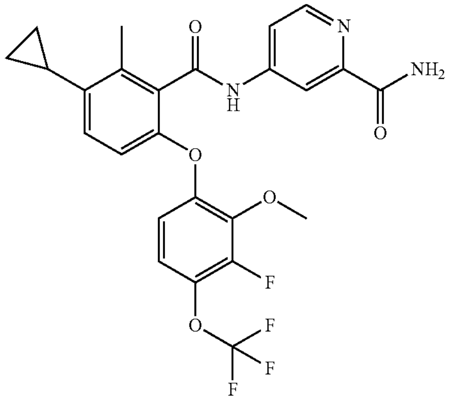
-continued
197
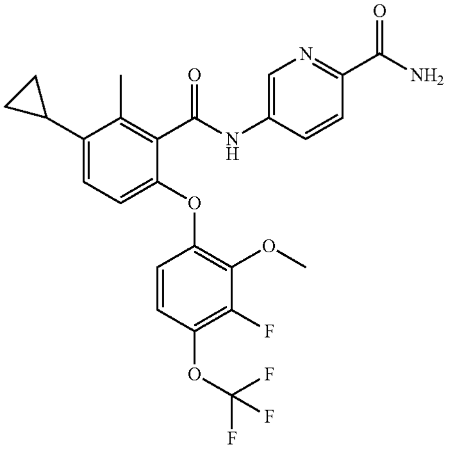
198
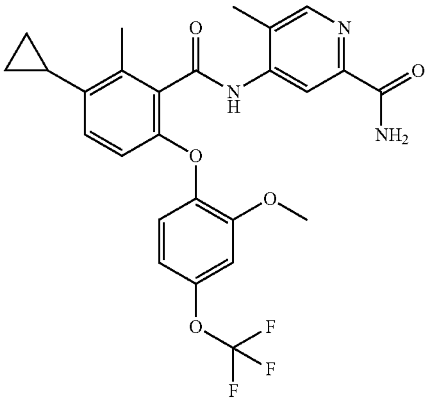
199
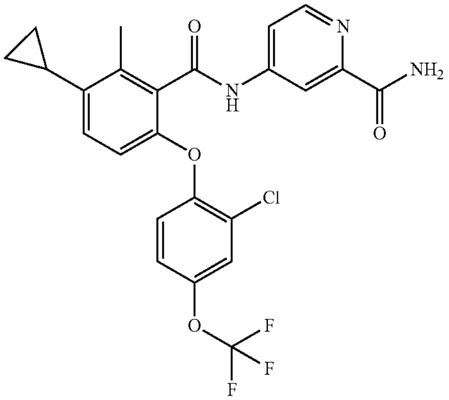
200
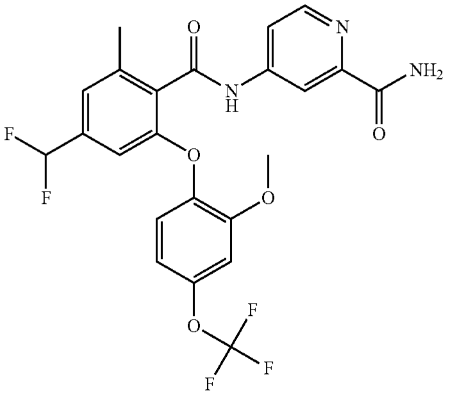

201
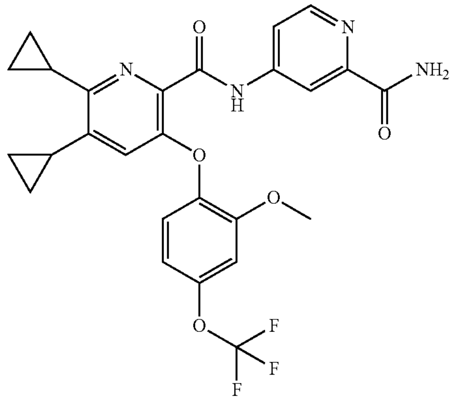
202
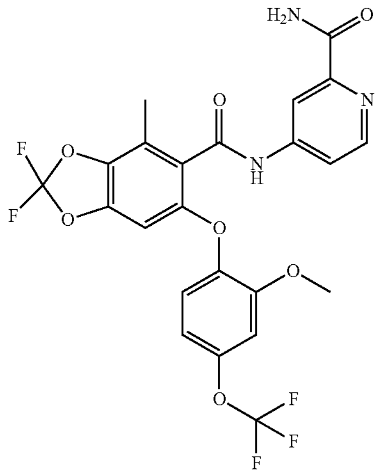
203
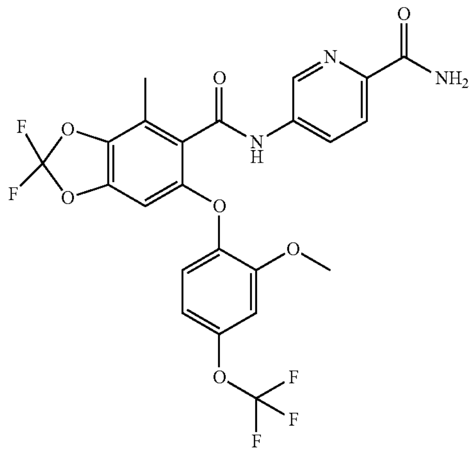
204
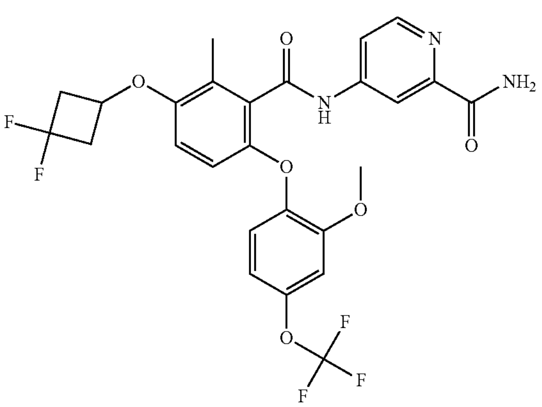
205
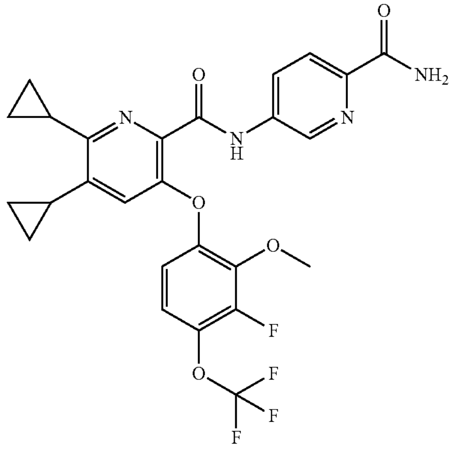
206
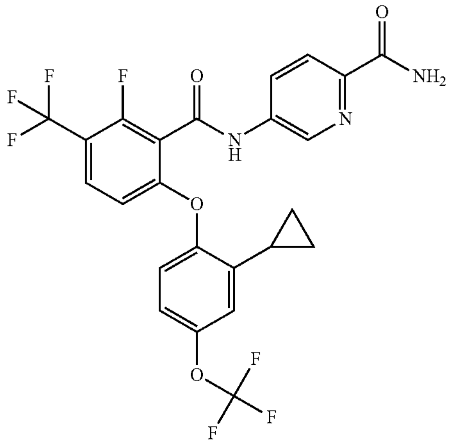

-continued
207
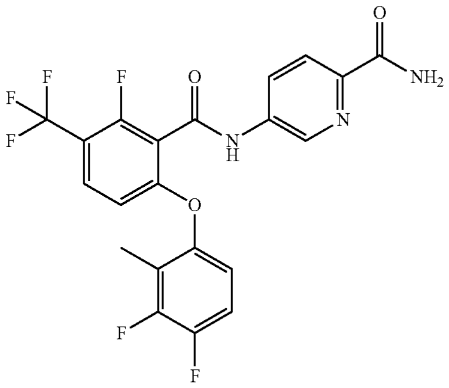
208
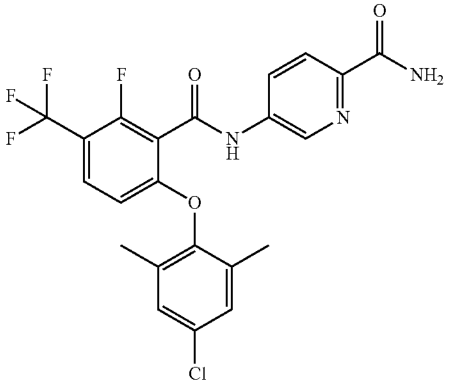
209
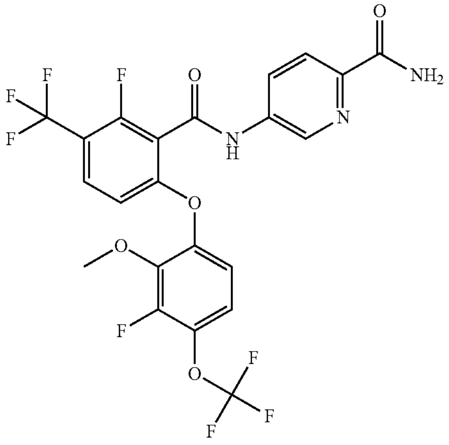
-continued
210
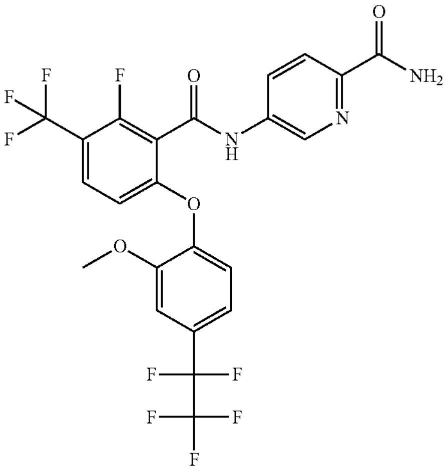
211
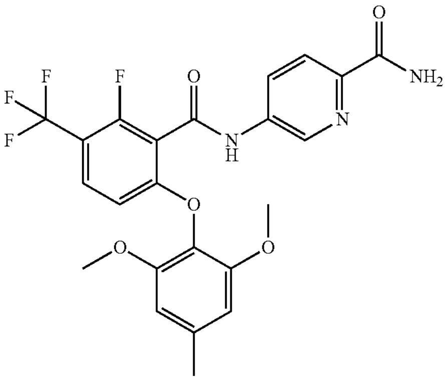
212
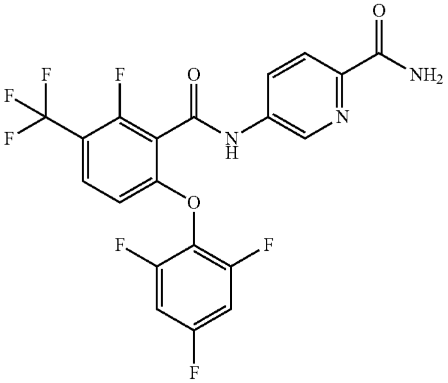
213
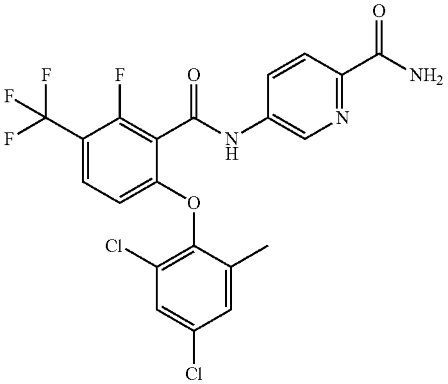

-continued
214
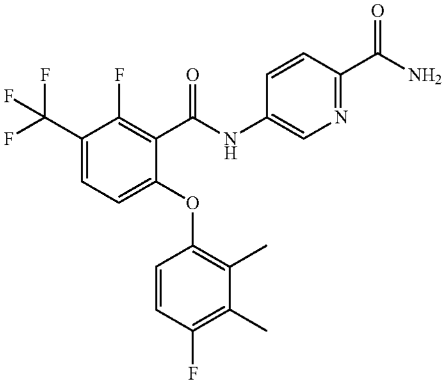
215
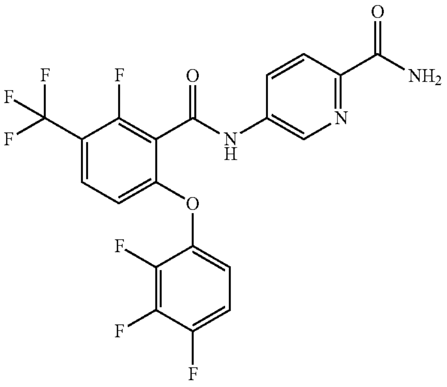
216
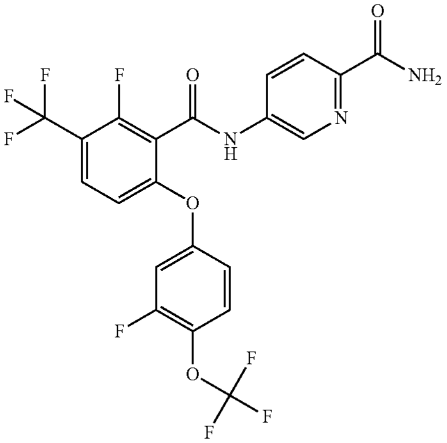
-continued
217
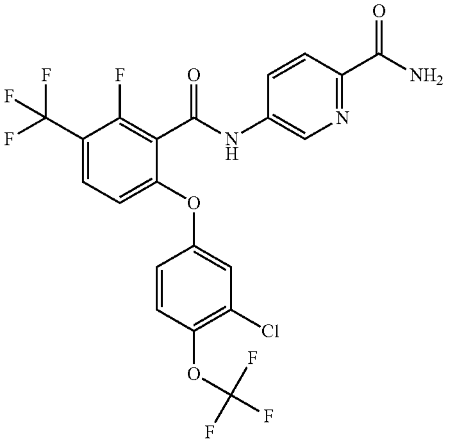
218
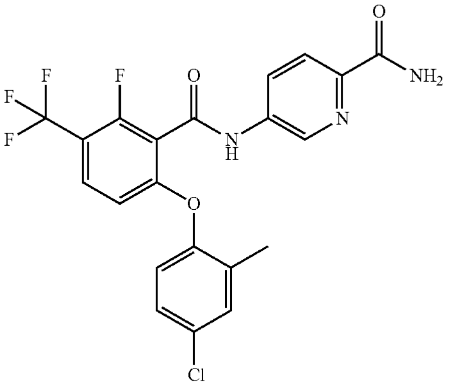
219
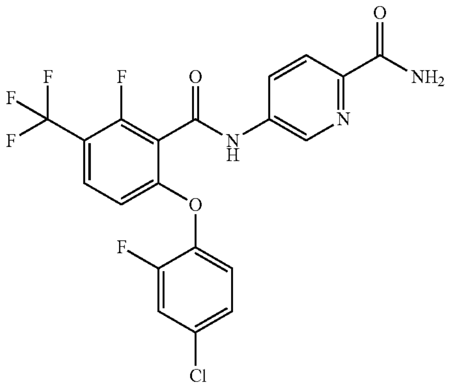

-continued
220
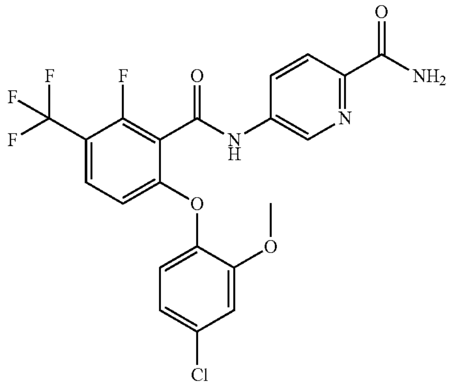
221
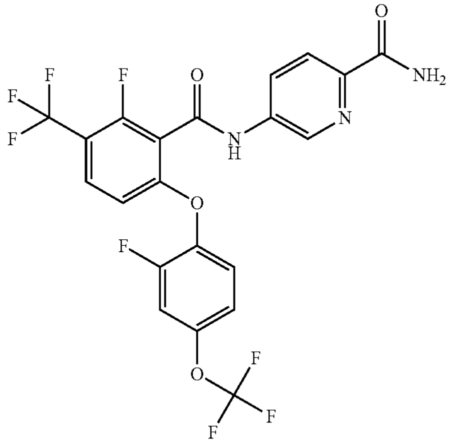
222
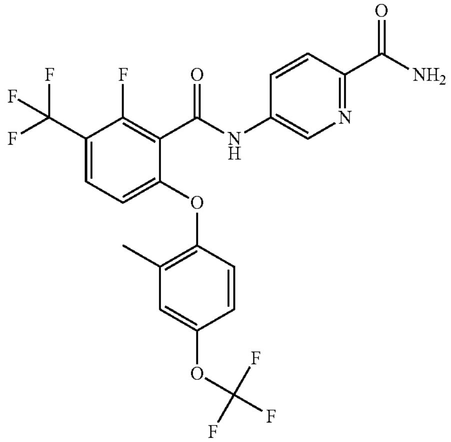
-continued
223
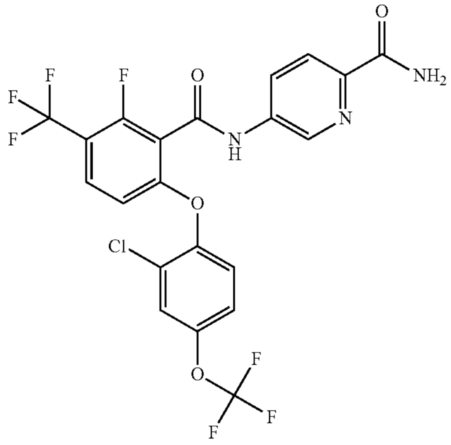
224
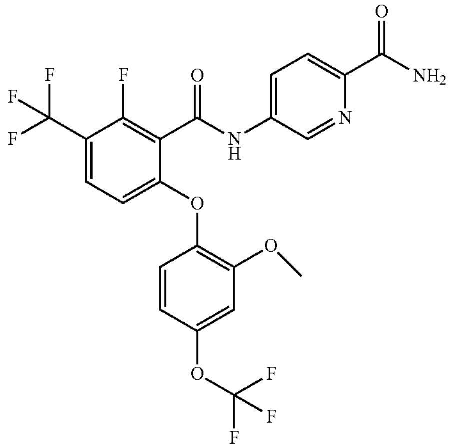
225
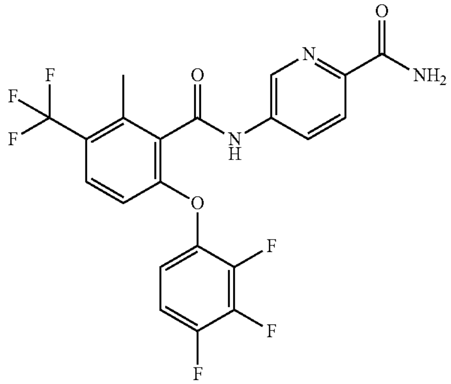

226
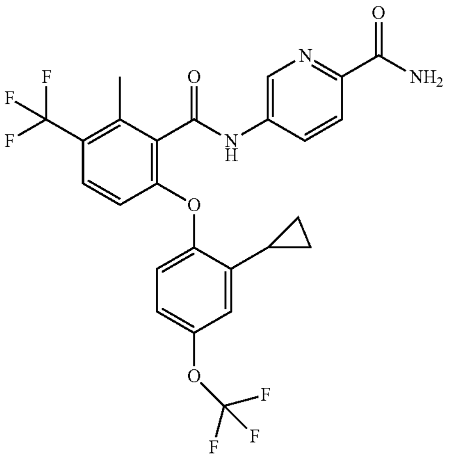
227
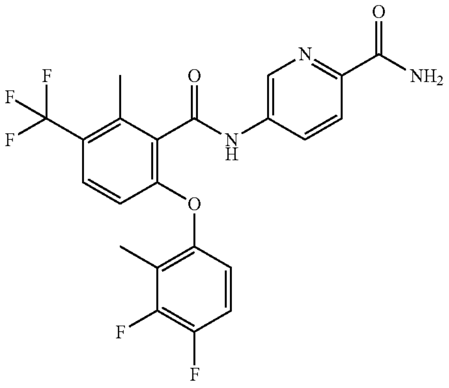
228
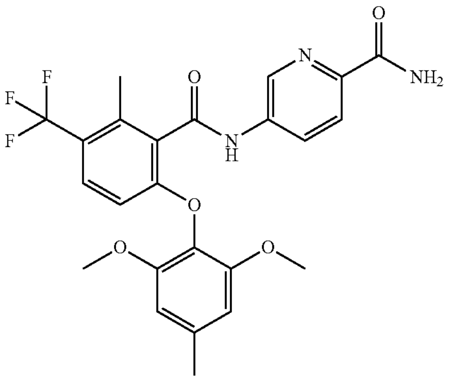
229
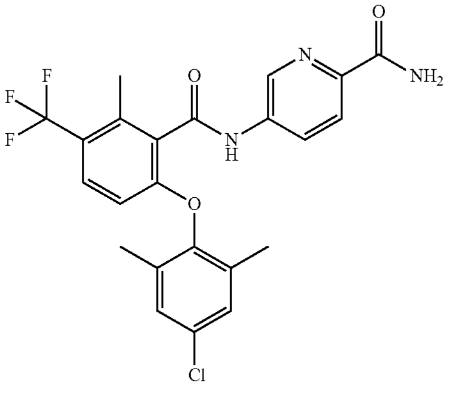
230
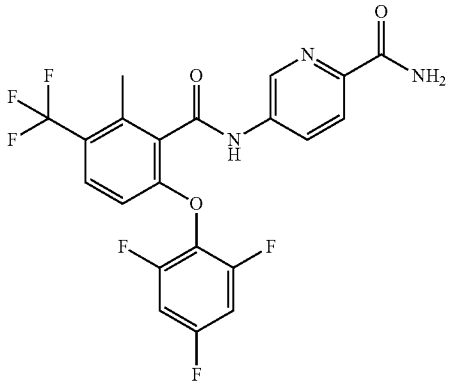
231
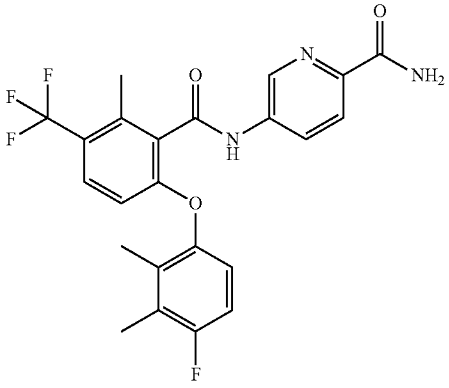
232
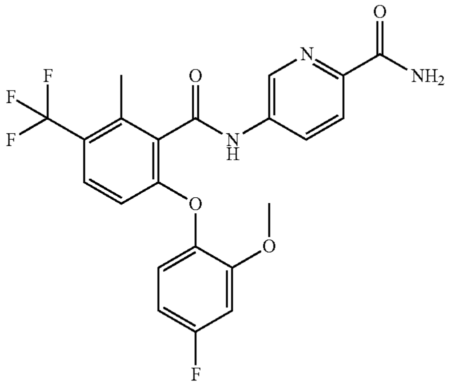
233
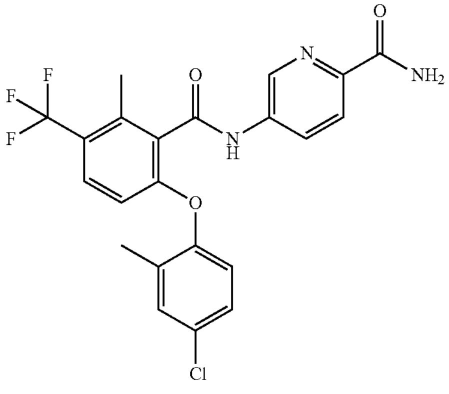

-continued
234
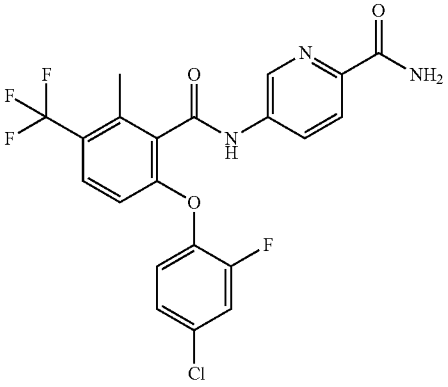
235
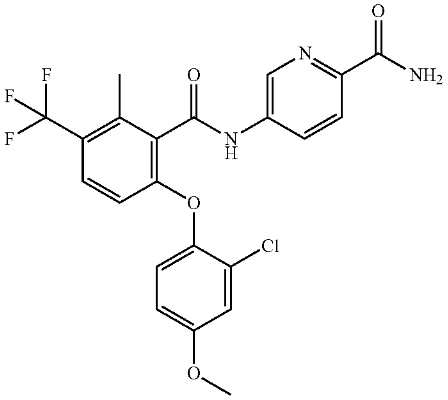
236
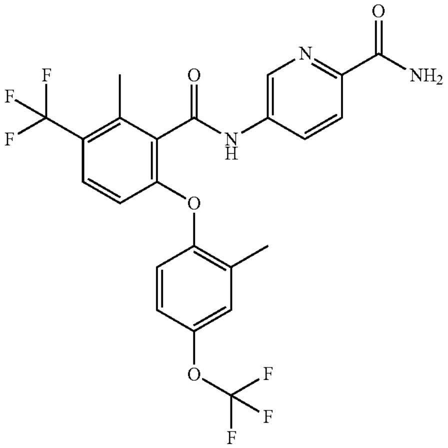
237
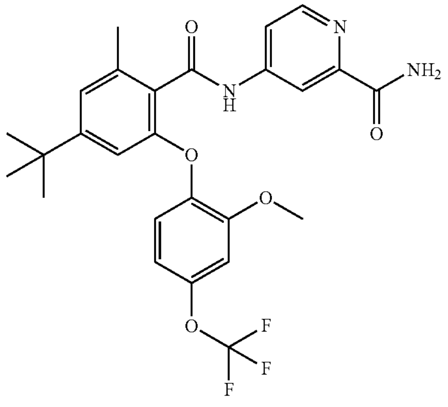
-continued
238
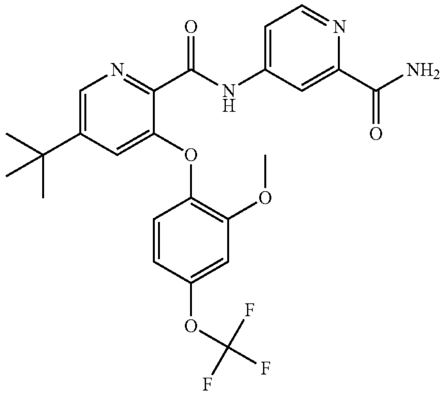
239
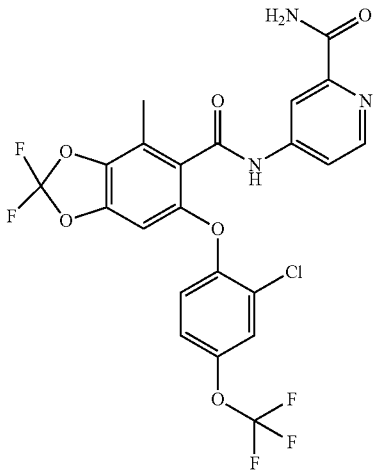
240
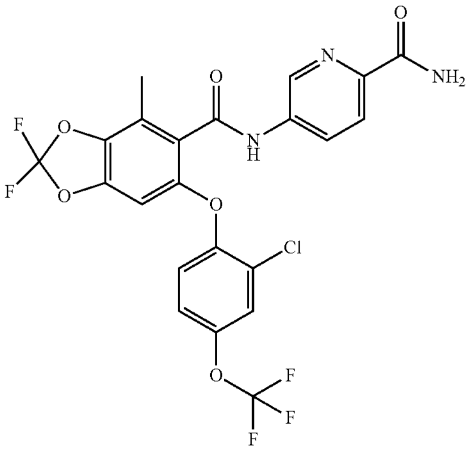

-continued
241
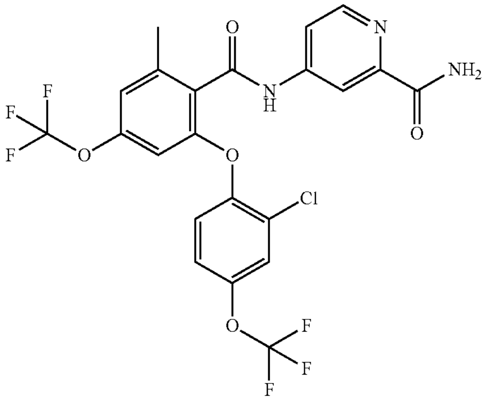
242
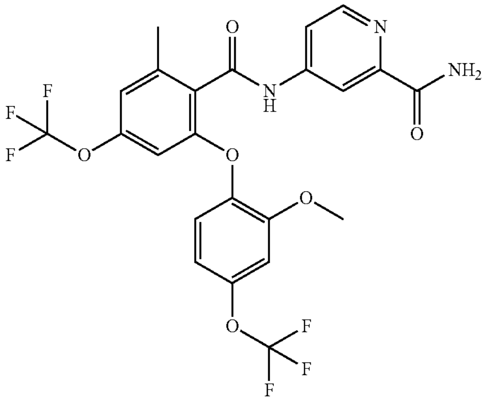
243
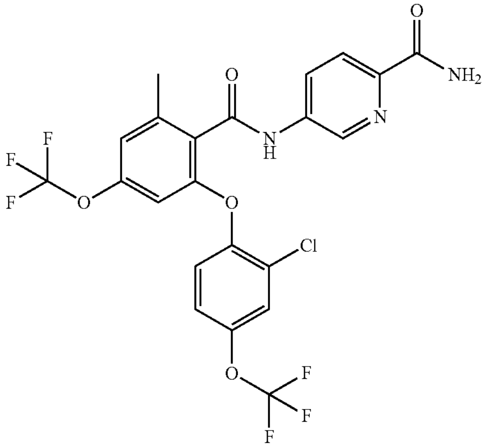
244
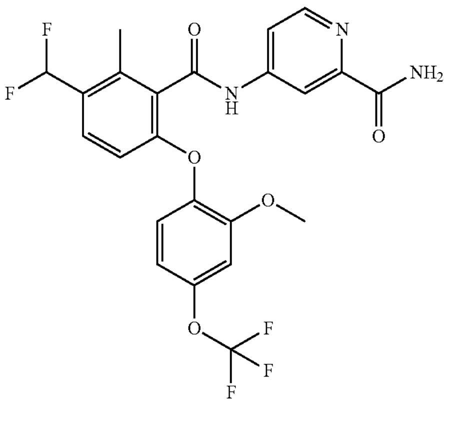
-continued
245
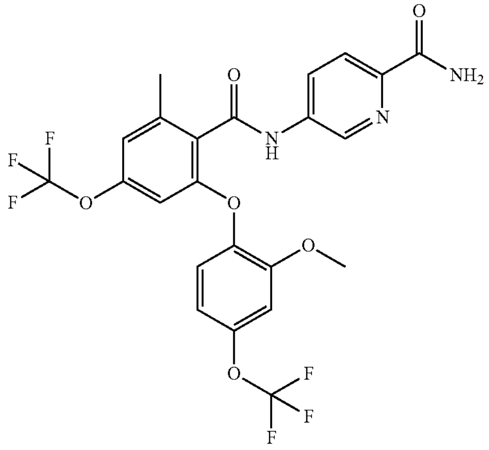
246
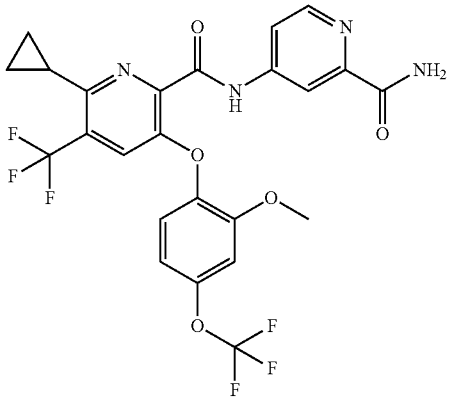
247
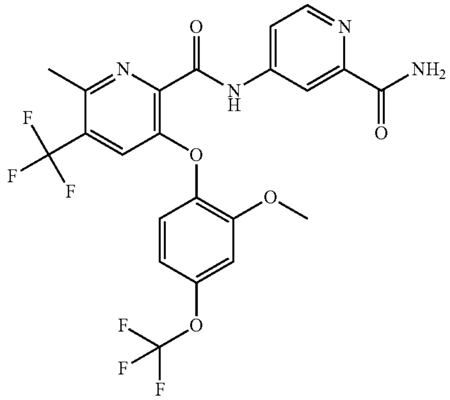
248
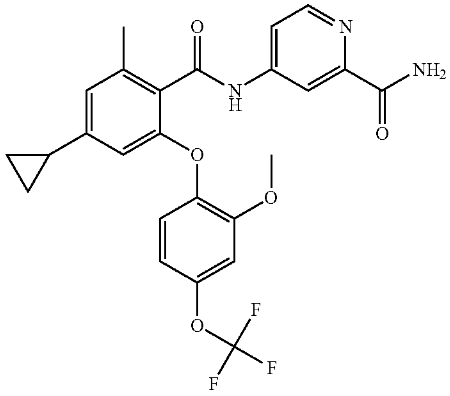

-continued
249
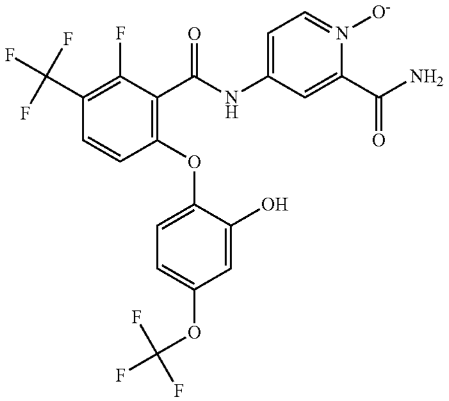
255
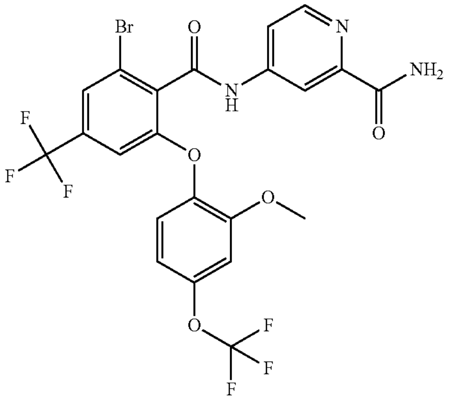
256
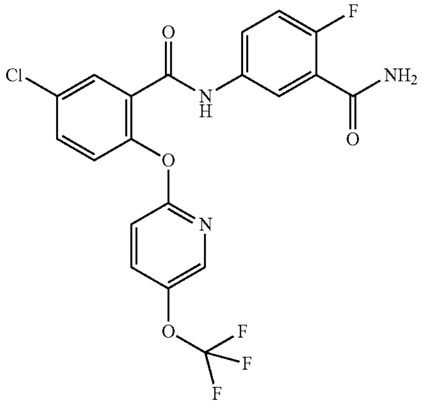
253
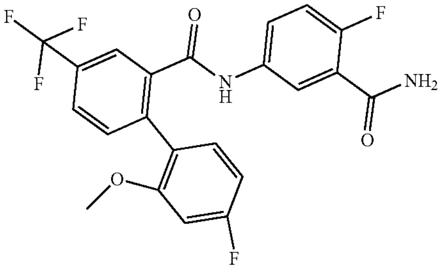
-continued
254
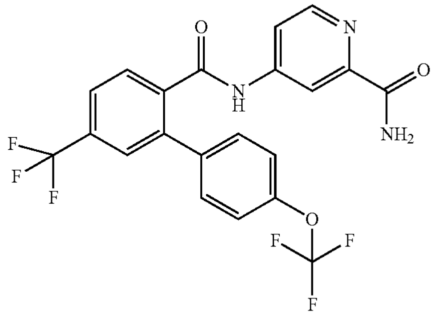
82
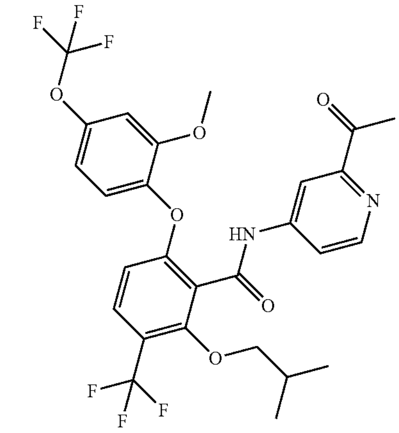
250
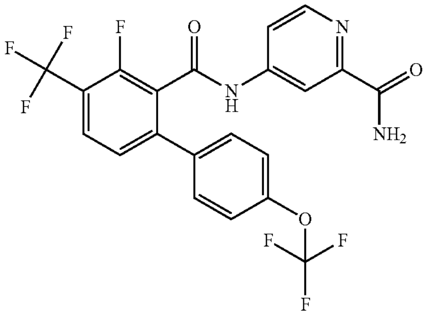
252
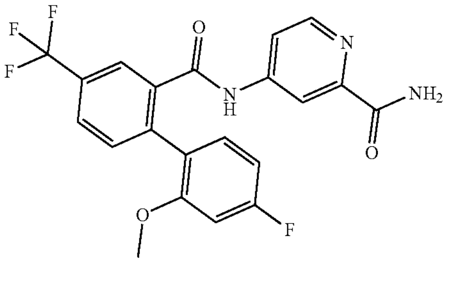

-continued
81
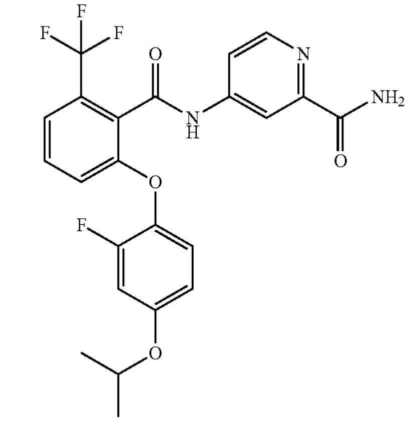
258
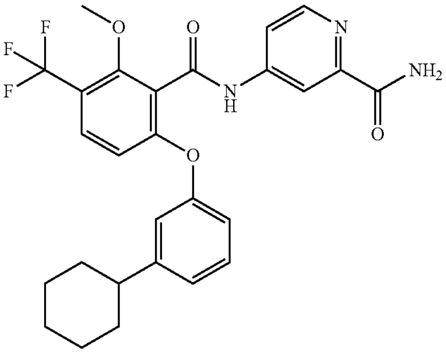
108
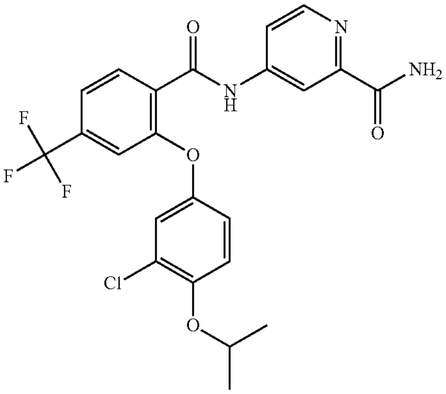
110
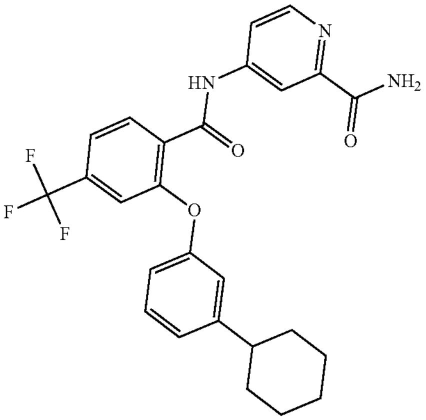
-continued
111
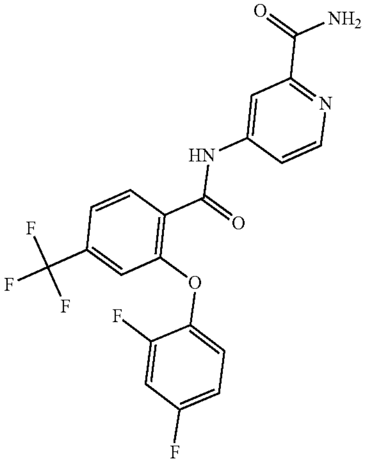
251
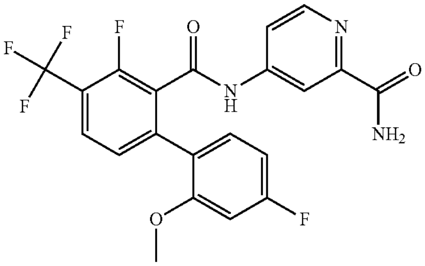
112
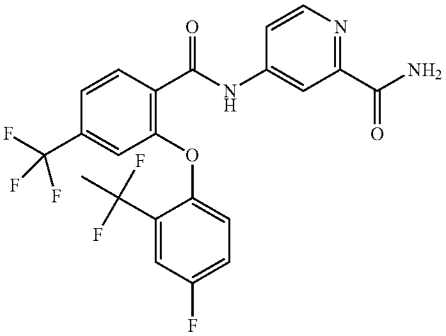
13
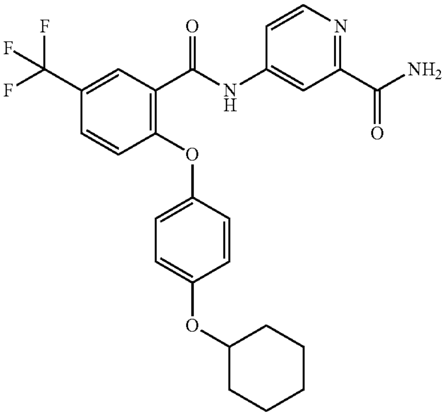

-continued
14
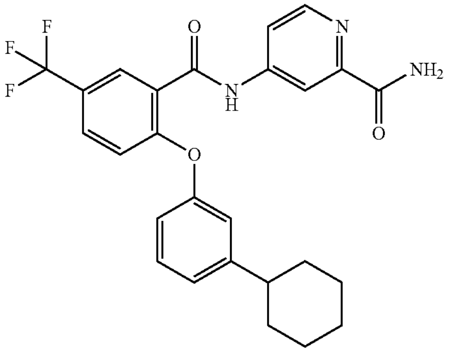
15
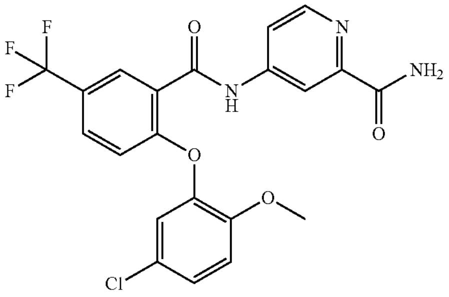
16
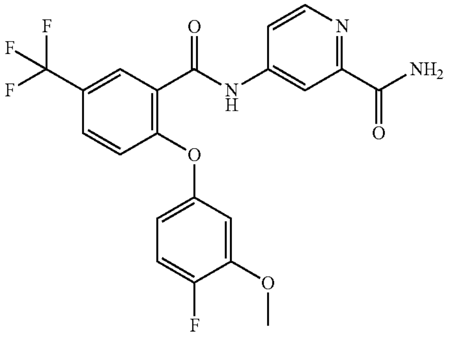
17
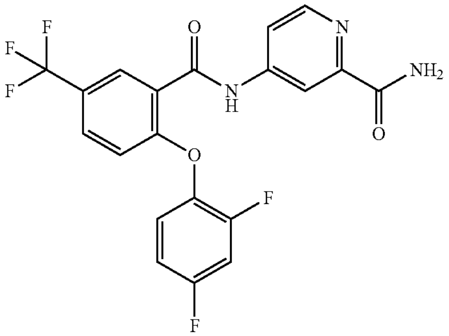
-continued
113
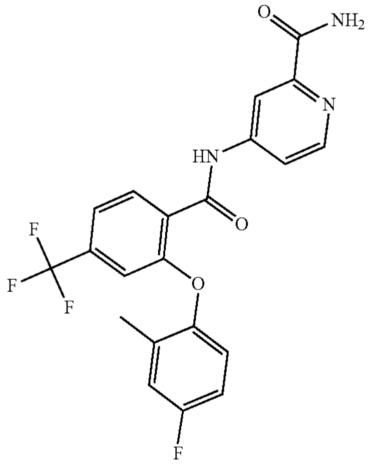
and
257
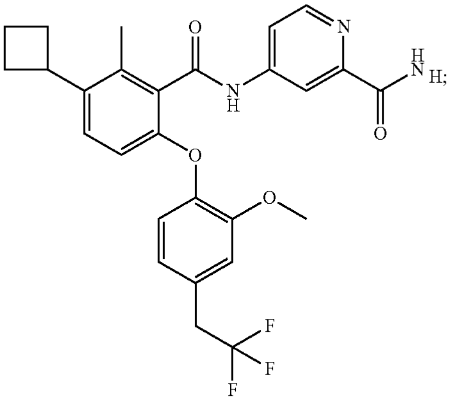
or a pharmaceutically acceptable salt thereof.
19. A compound selected from:
259
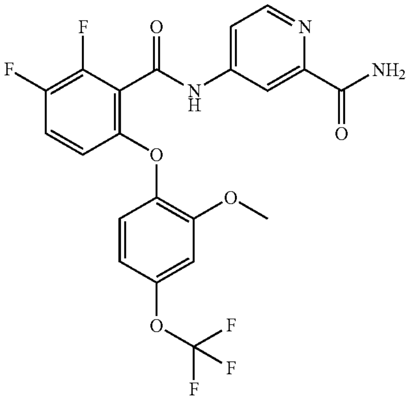

-continued
260
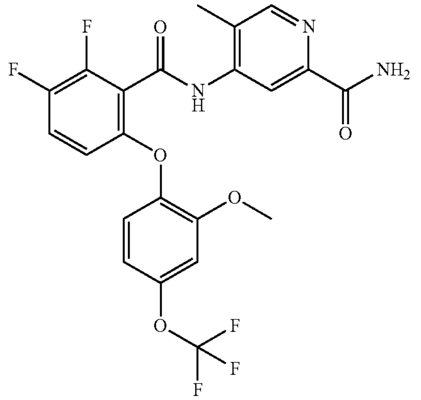
261
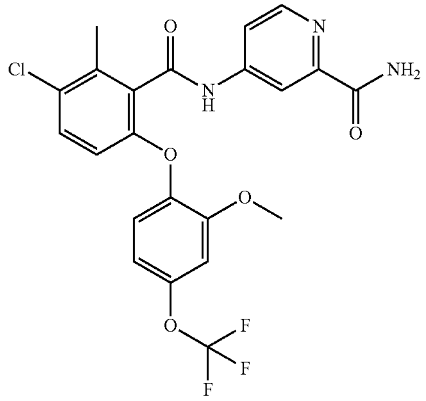
262
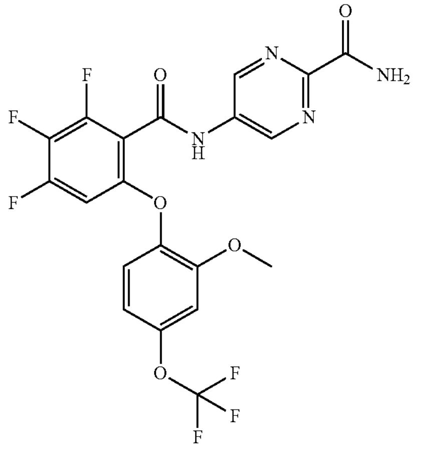
263
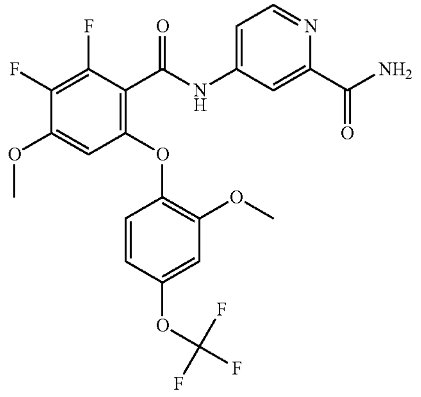
-continued
264
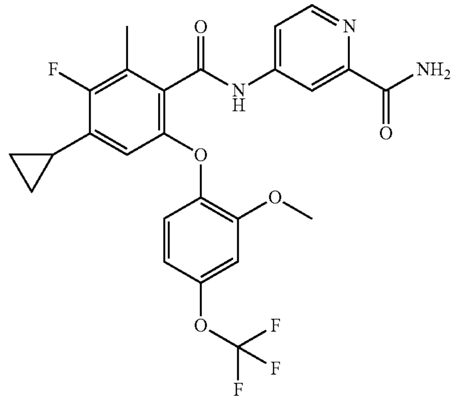
265
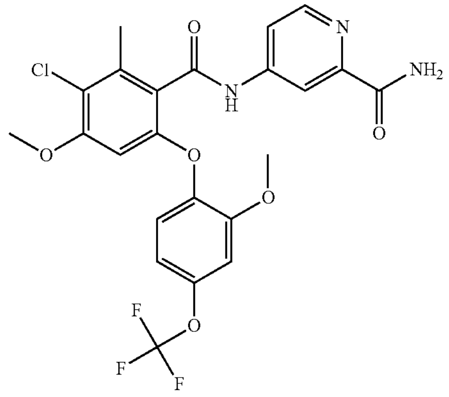
266
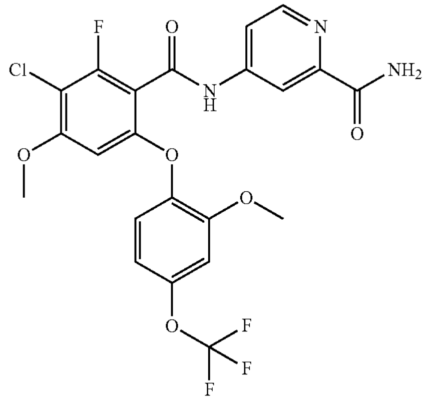
267
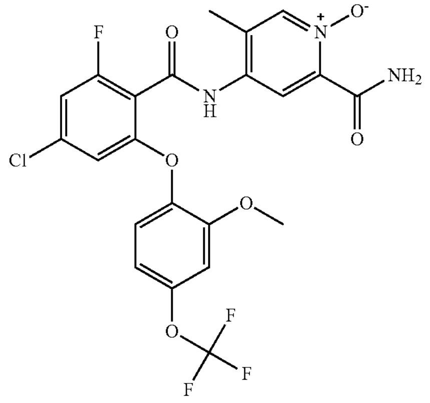

-continued
268
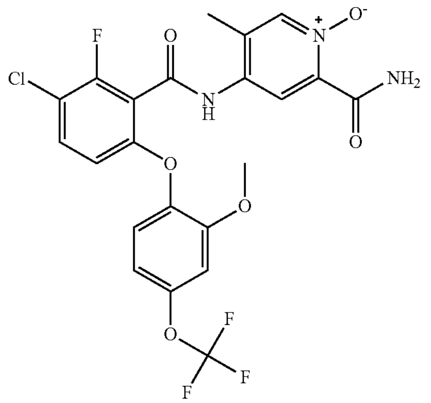
269
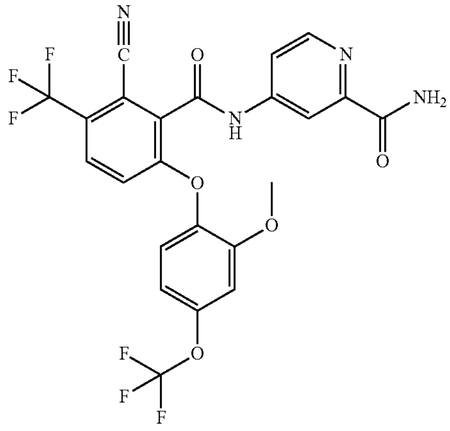
270
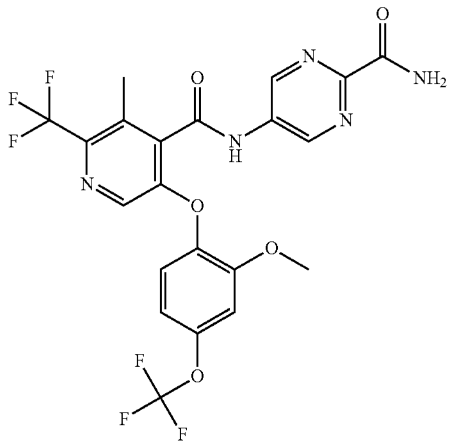
-continued
271
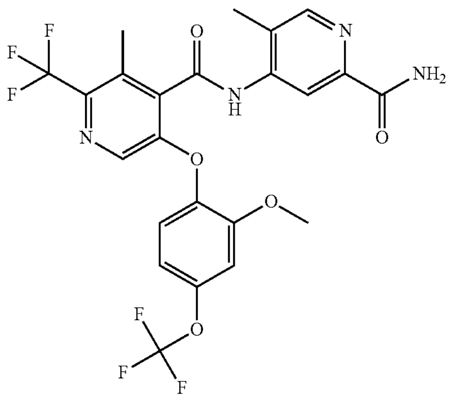
272
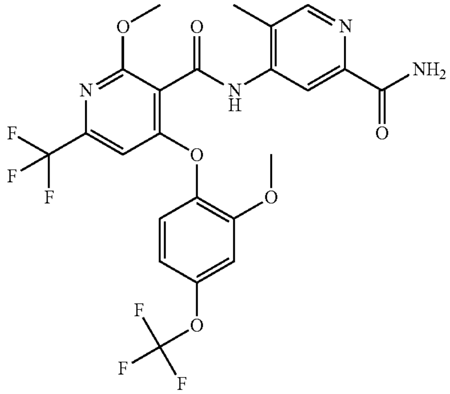
273
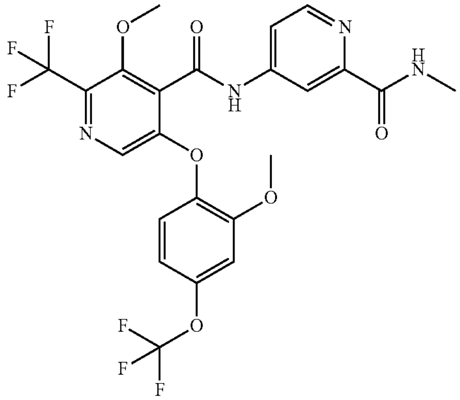
274
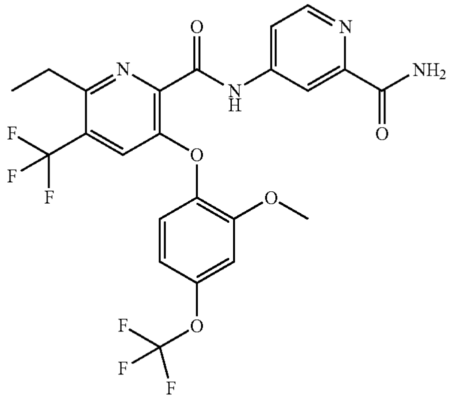

-continued
275
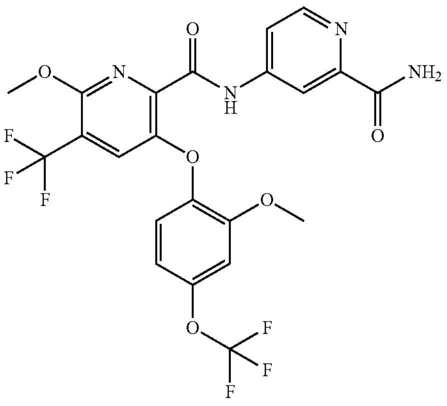
276
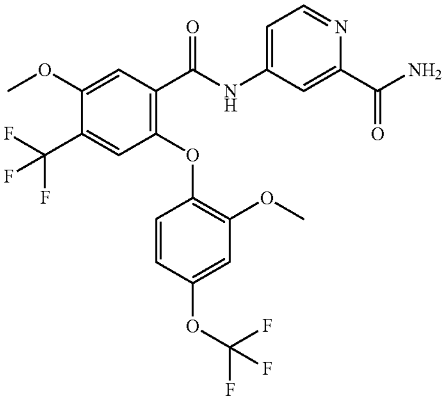
277
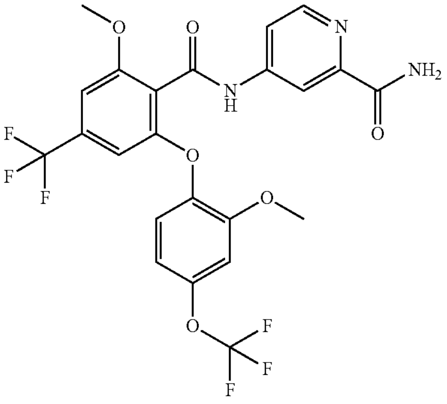
278
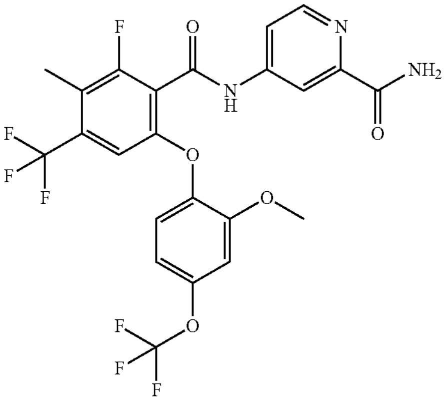
-continued
279
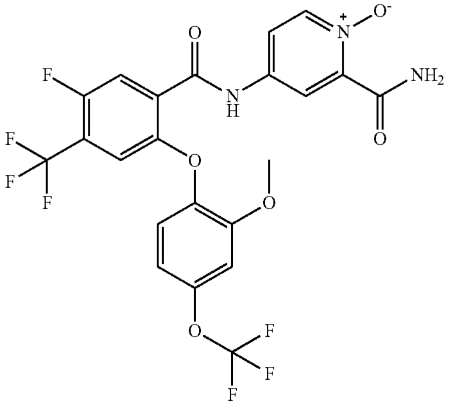
280
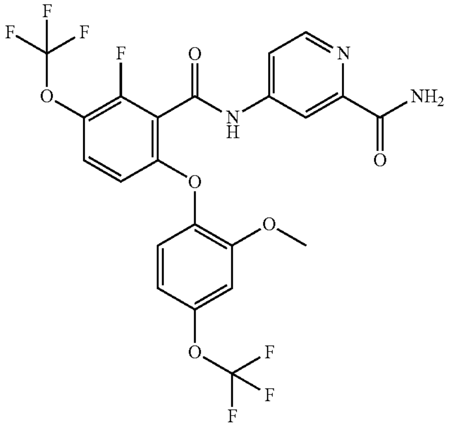
281
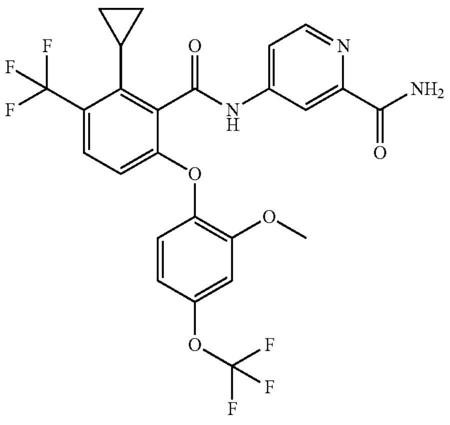

282
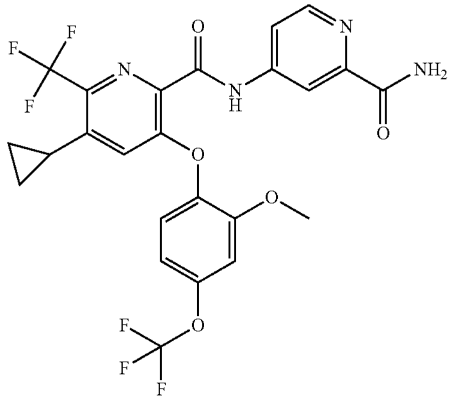
283
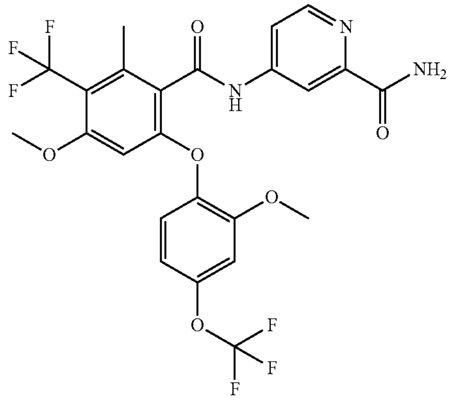
284
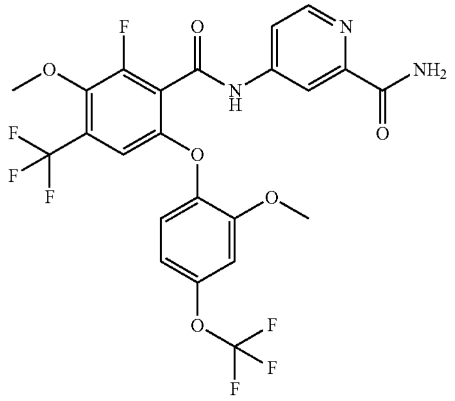
285
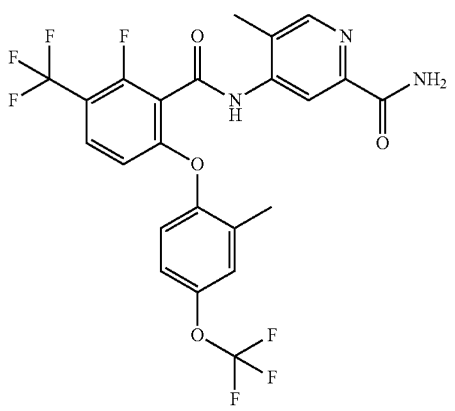
286
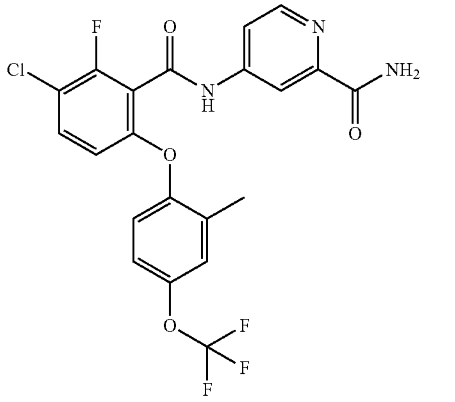
287
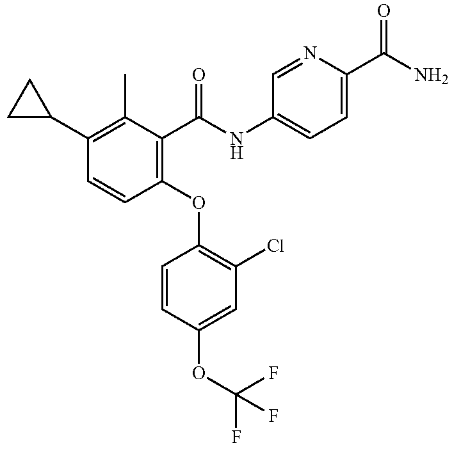
288
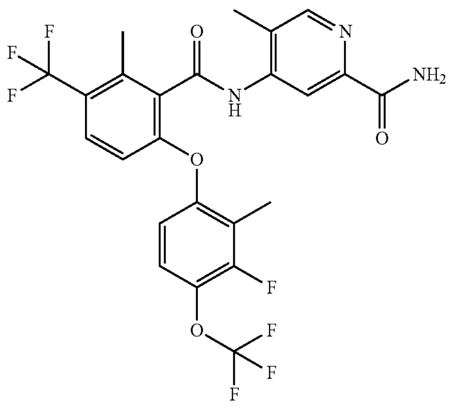

-continued
289
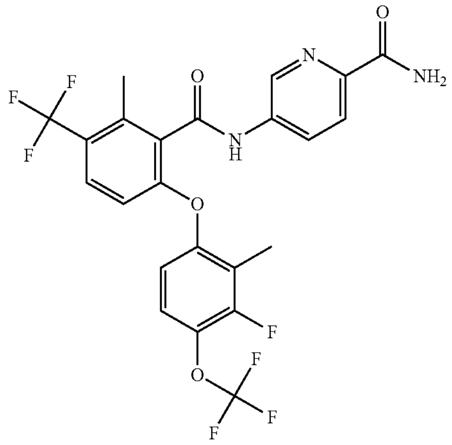
290
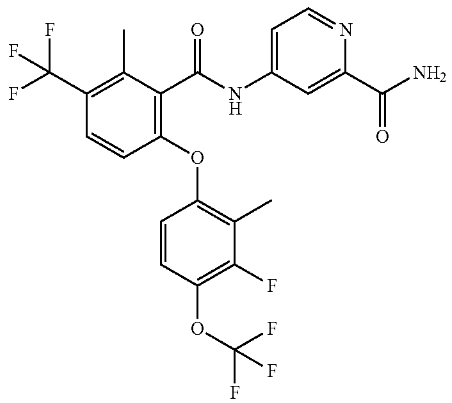
291
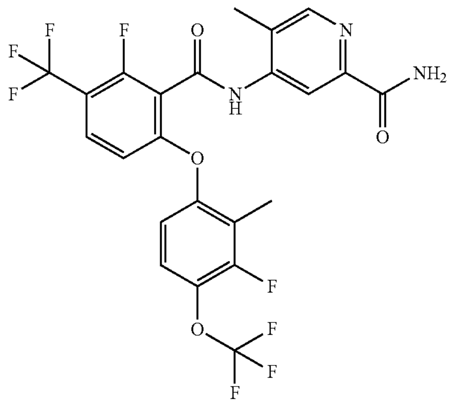
-continued
292
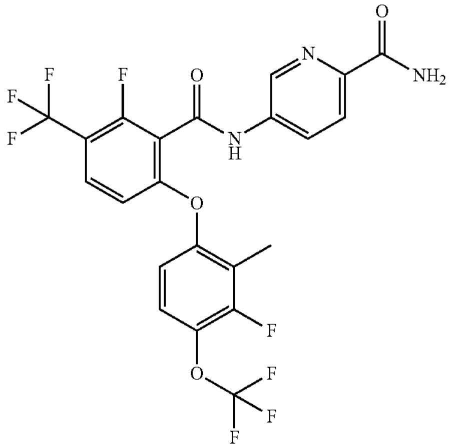
293
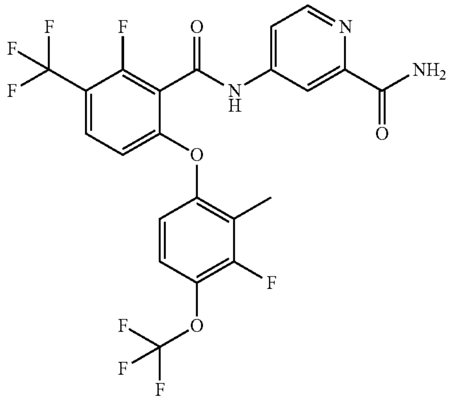
294
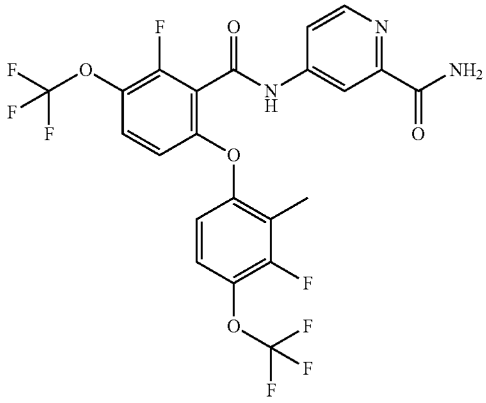
295
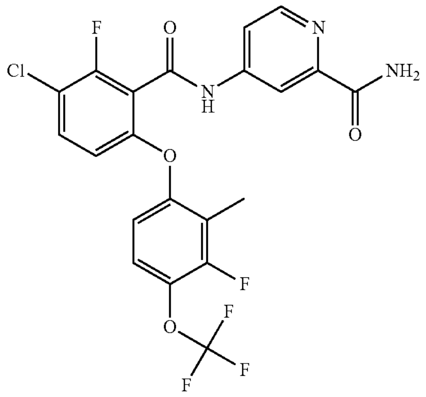

-continued
296
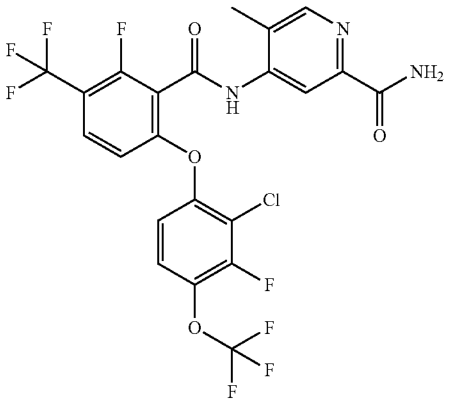
297
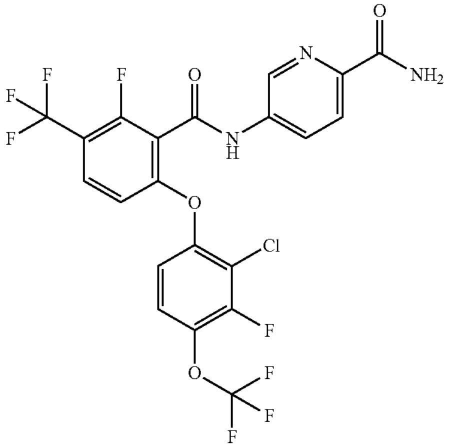
298
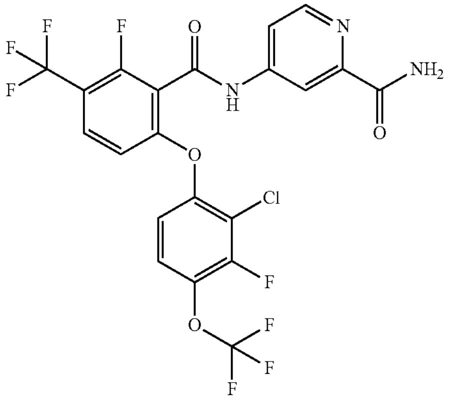
299
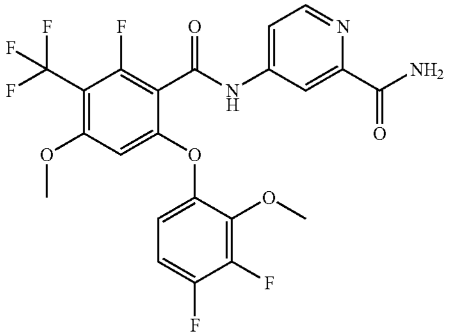
-continued
300
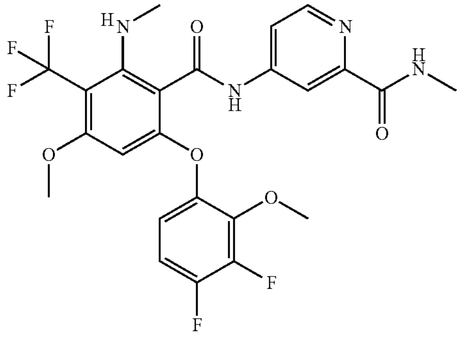
301
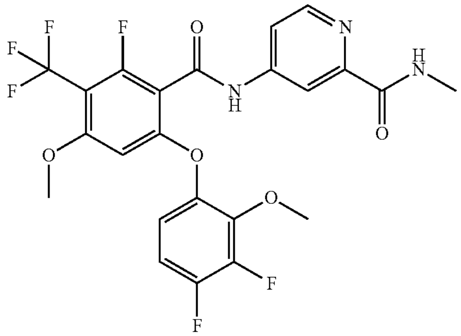
302
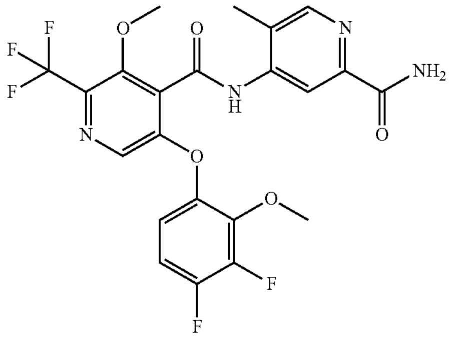
303
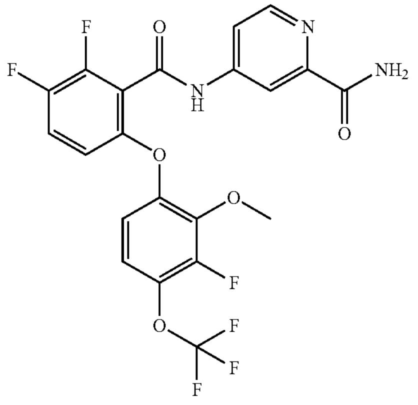

-continued
304
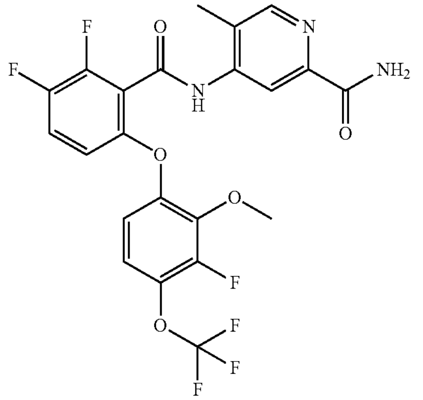
305
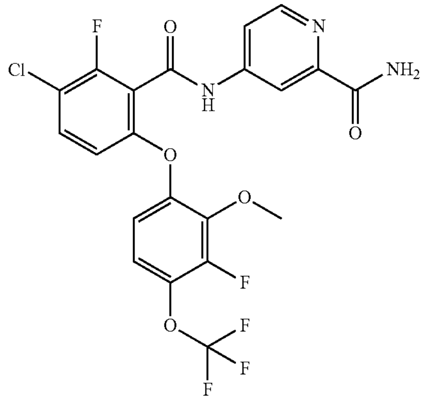
306
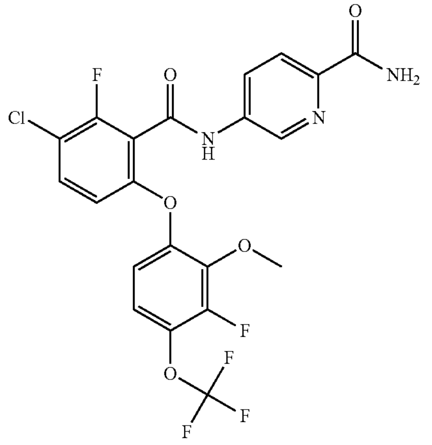
307
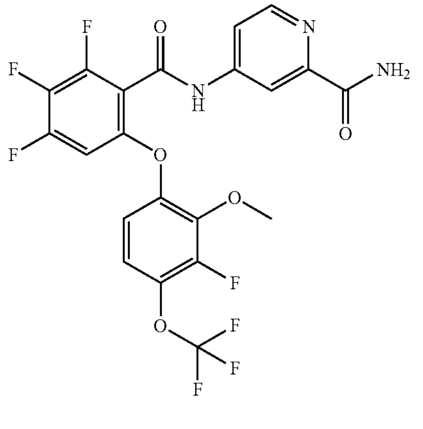
-continued
308
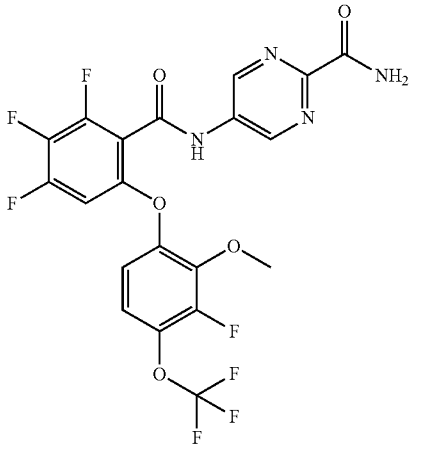
309
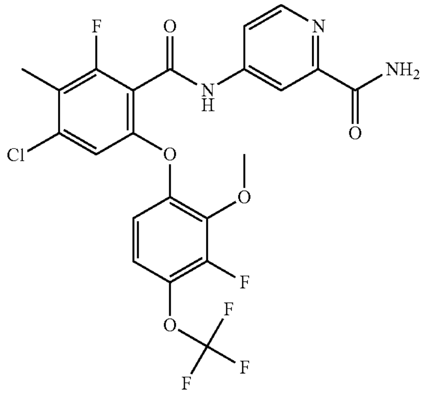
310
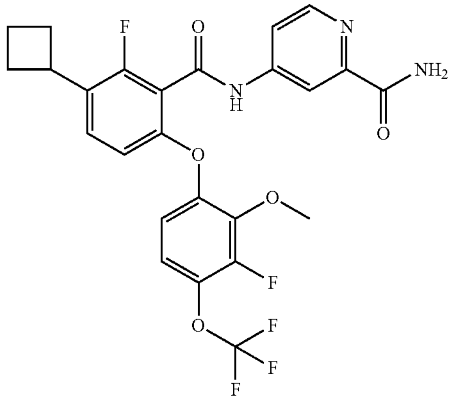
311
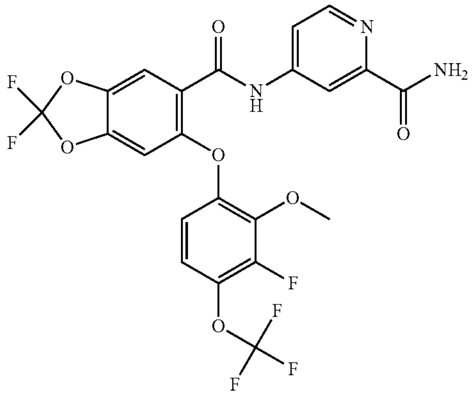

-continued
312
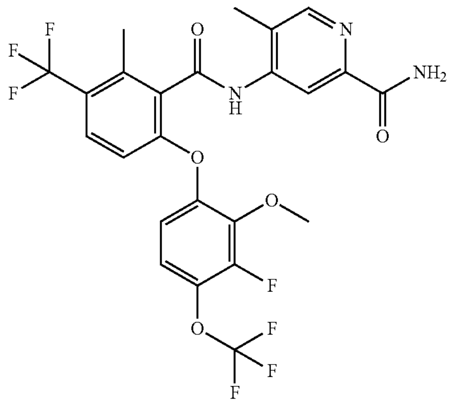
313
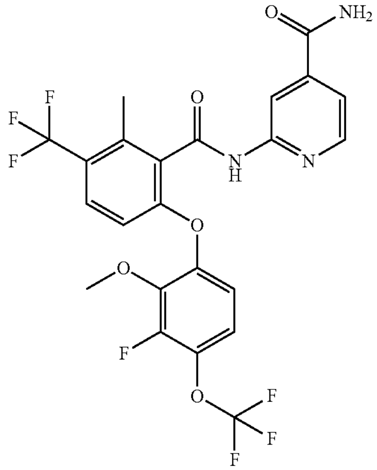
314
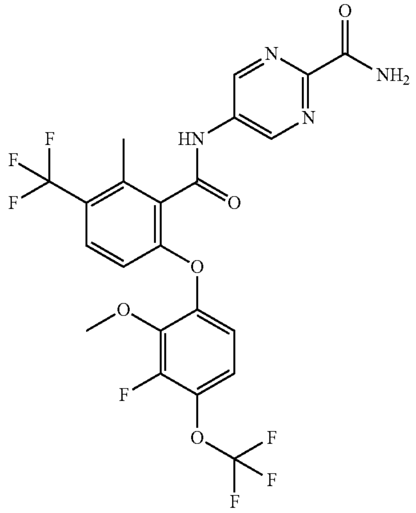
-continued
315
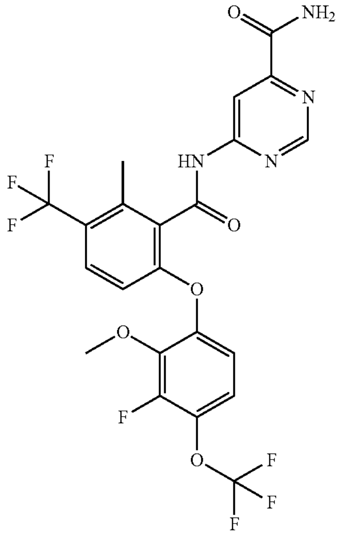
316
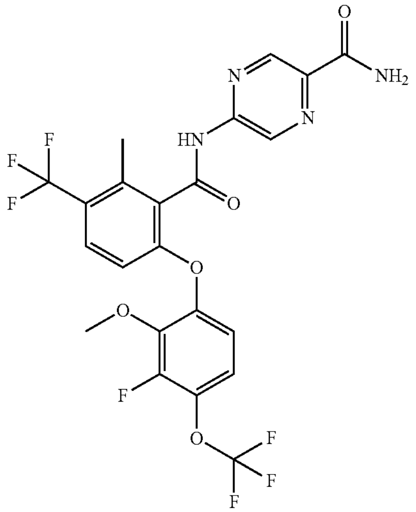
317
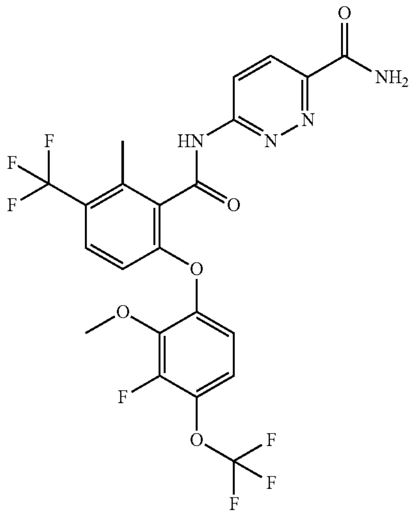

-continued
318
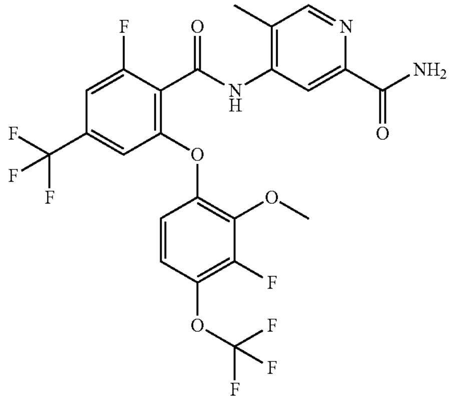
319
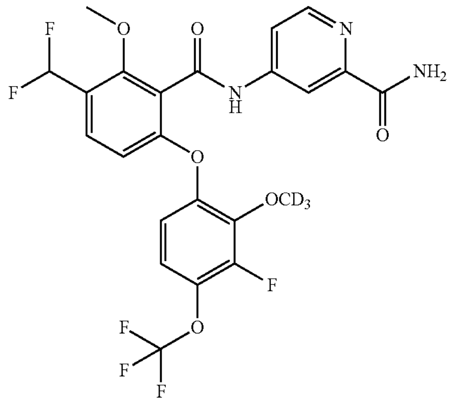
320
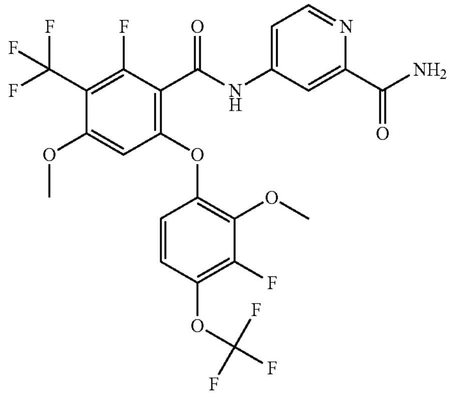
321
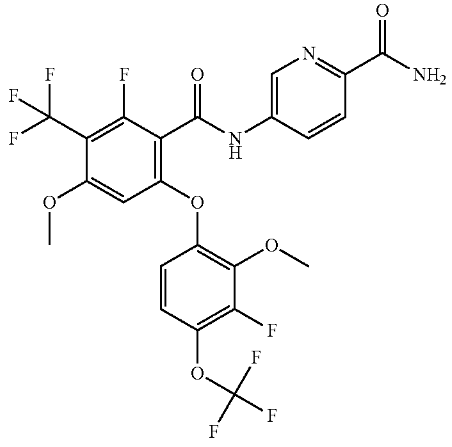
-continued
322
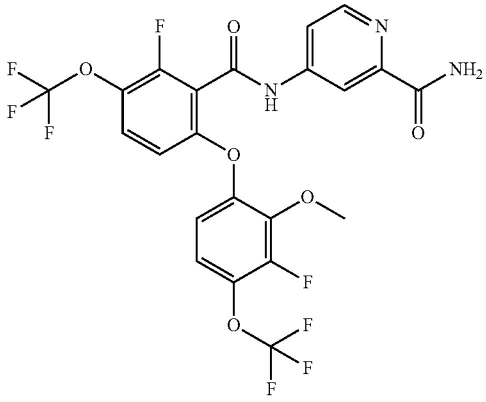
323
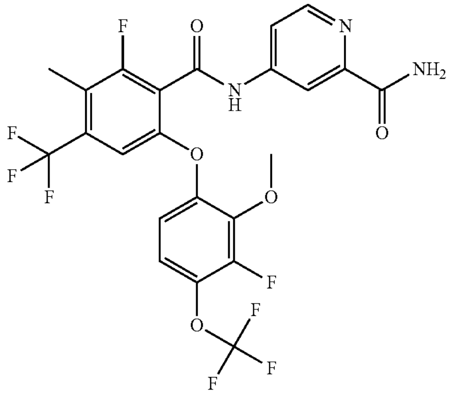
324
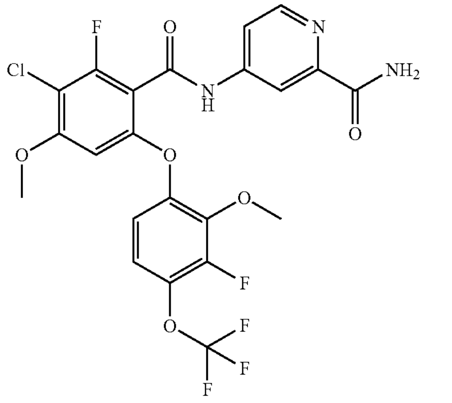
325
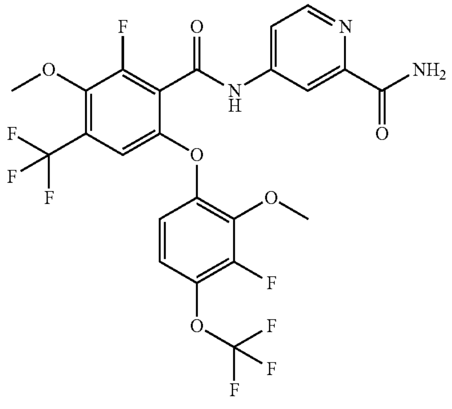

-continued
326
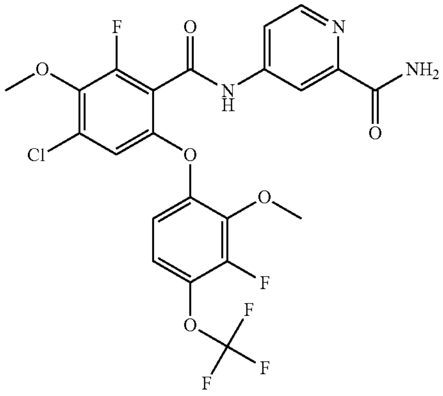
327
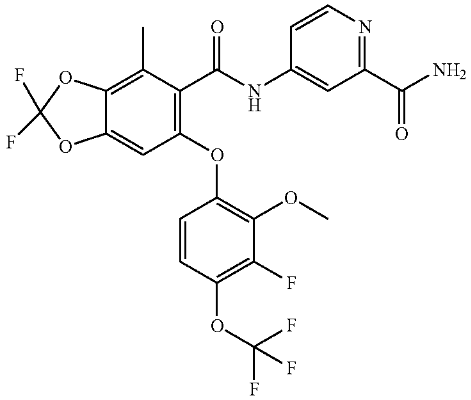
328
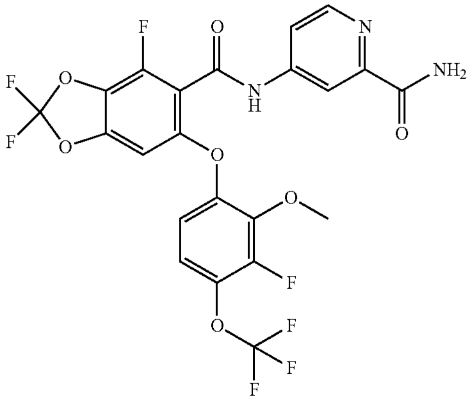
329
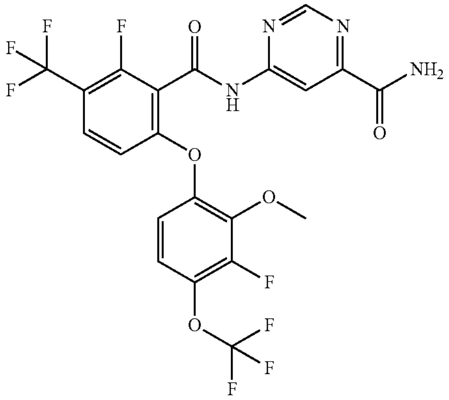
-continued
330
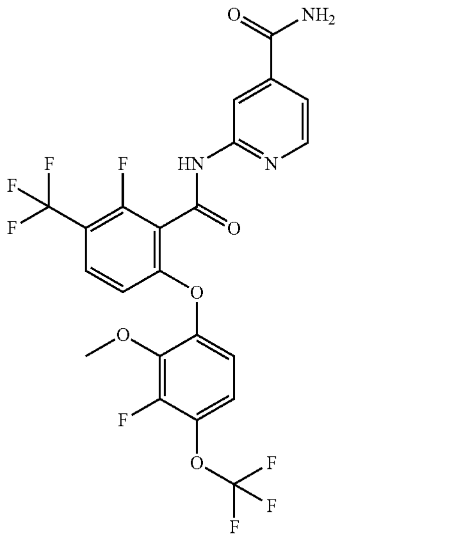
331
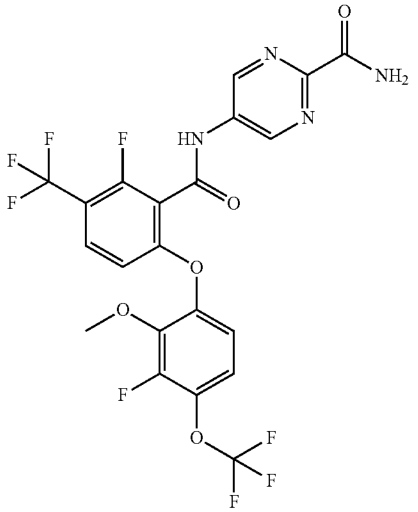
332
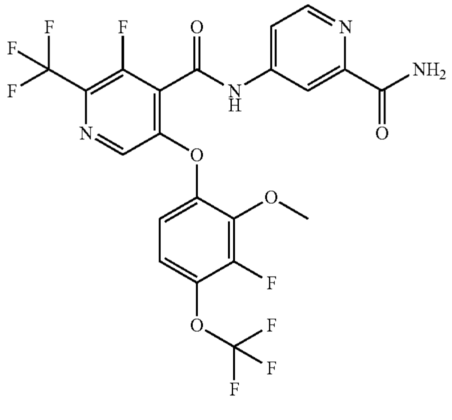

-continued
333
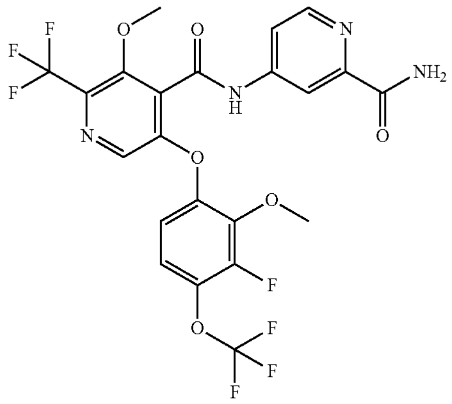
334
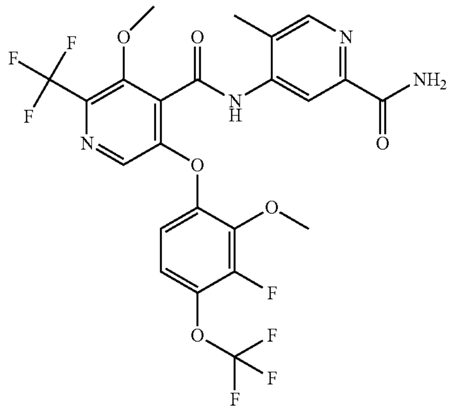
335
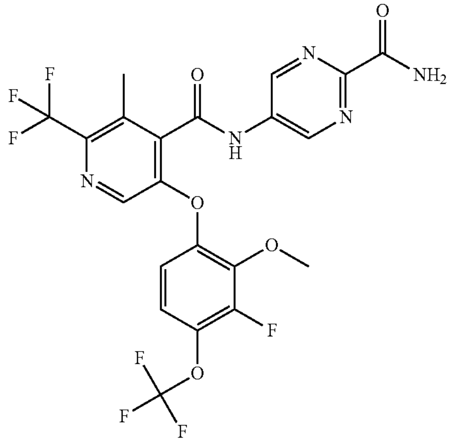
-continued
336
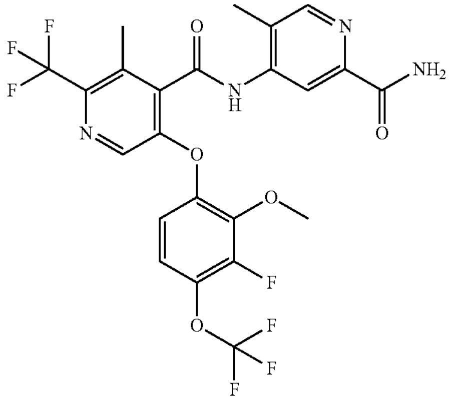
337
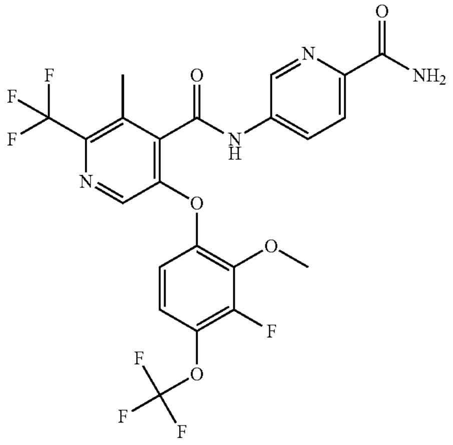
338
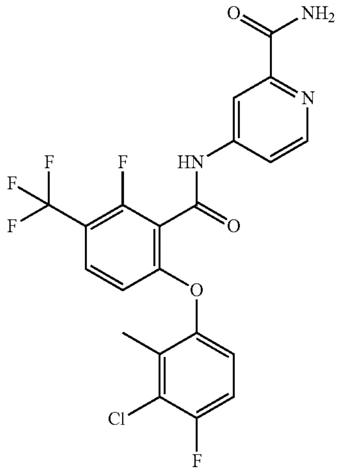

-continued
339
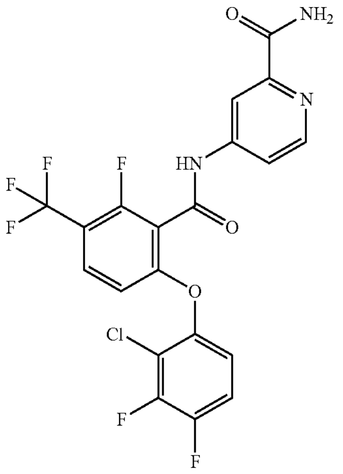
340
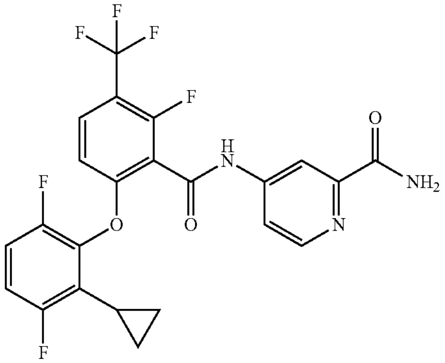
341
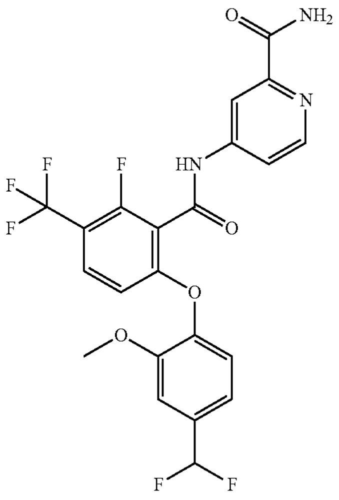
-continued
342
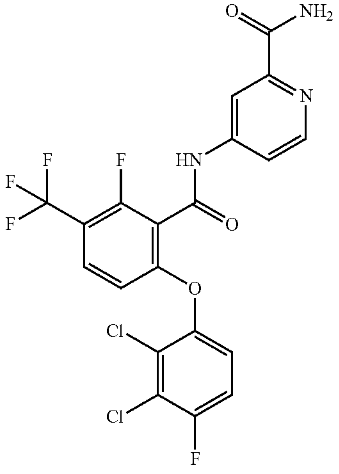
343
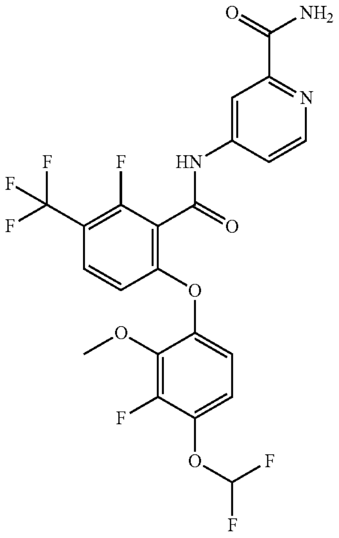
344
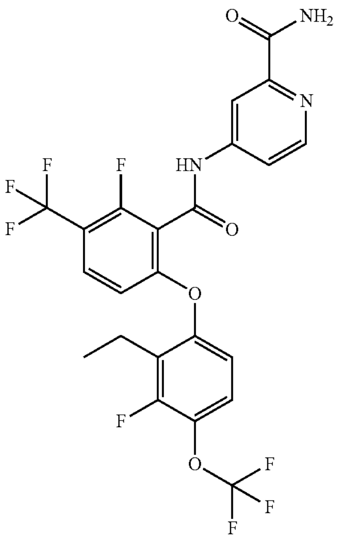

-continued
345
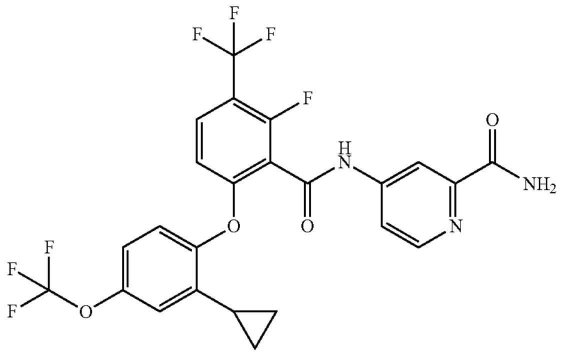
346
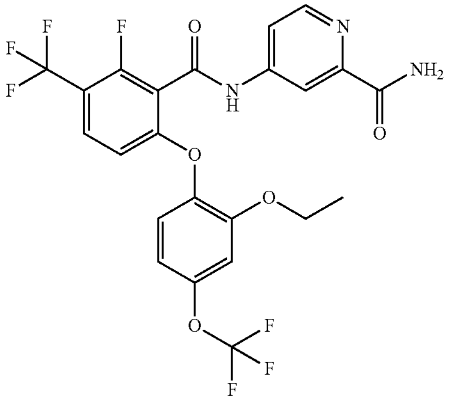
347
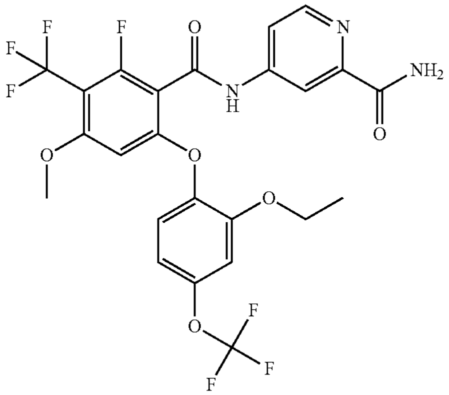
348
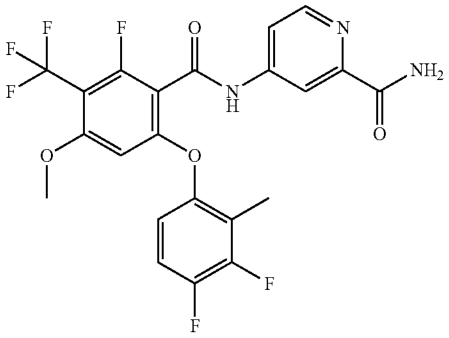
-continued
349
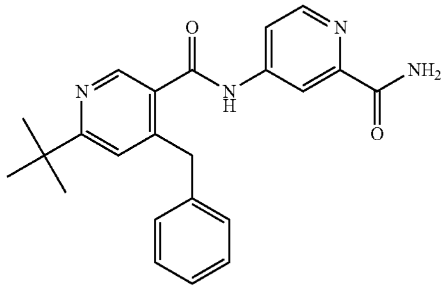
350
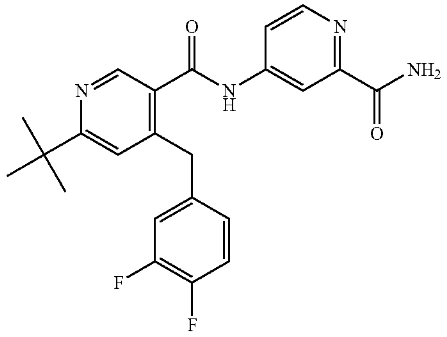
351
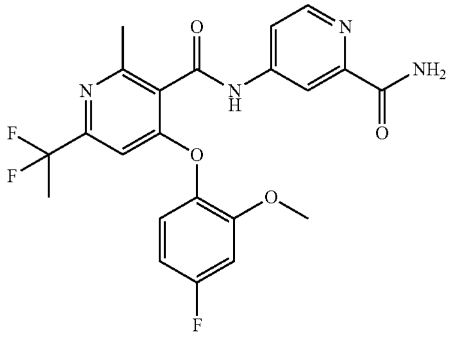
352
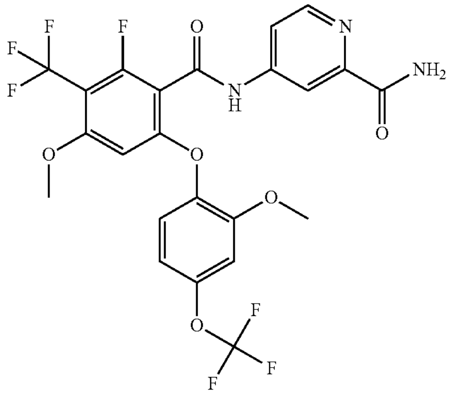

-continued
353
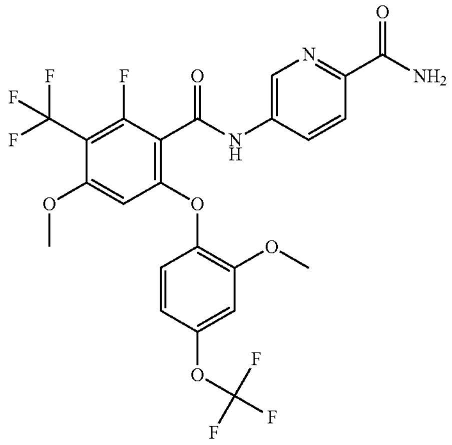
354
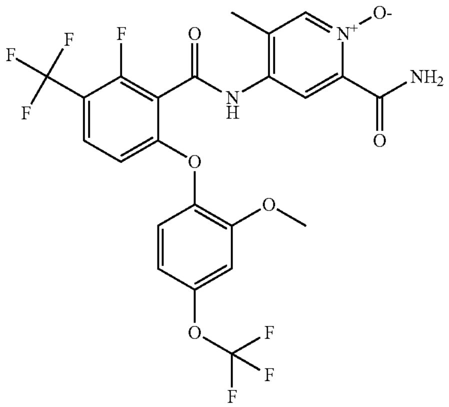
355
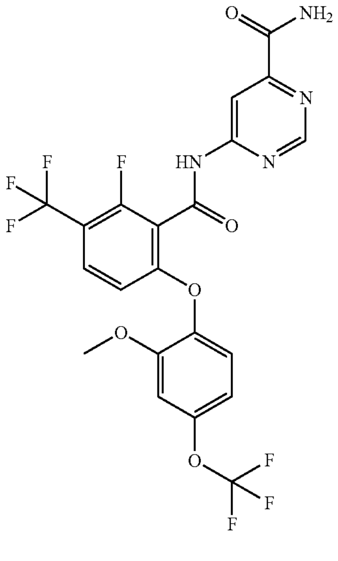
-continued
356
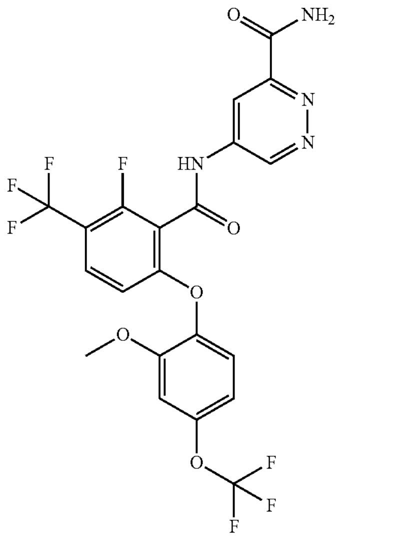
357
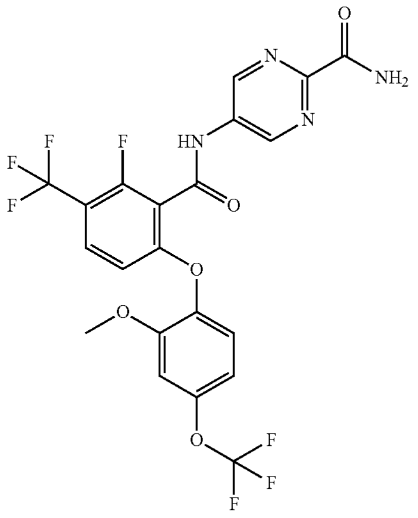
358
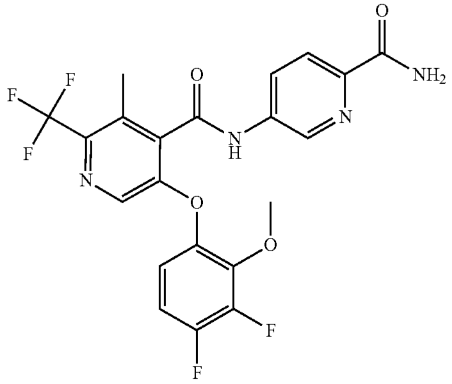

-continued
359
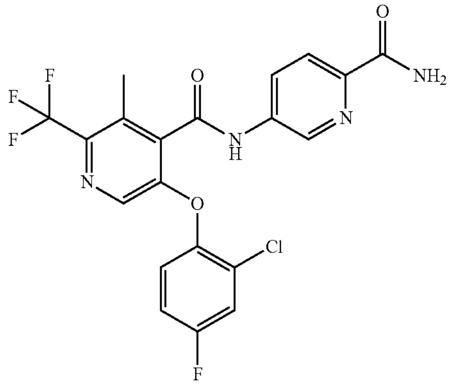
360
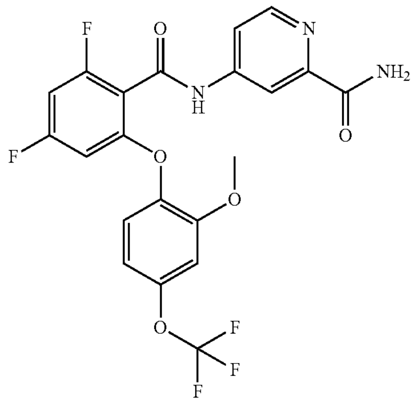
361
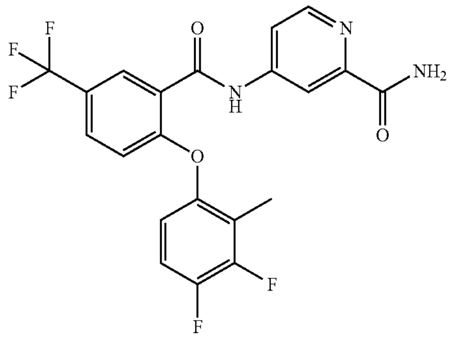
362
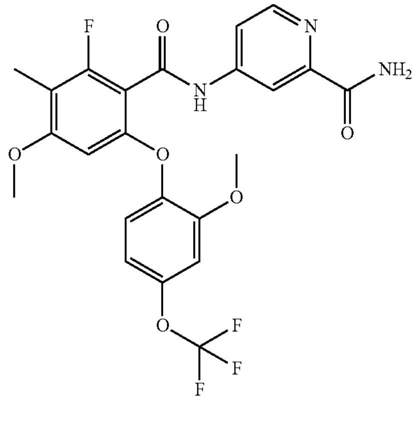
-continued
363
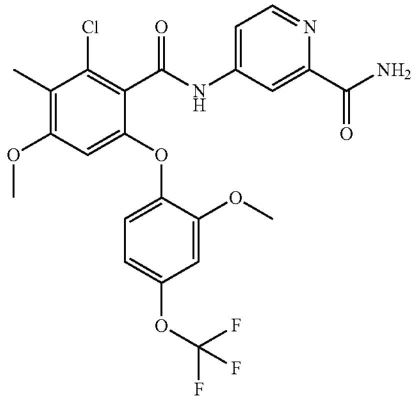
364
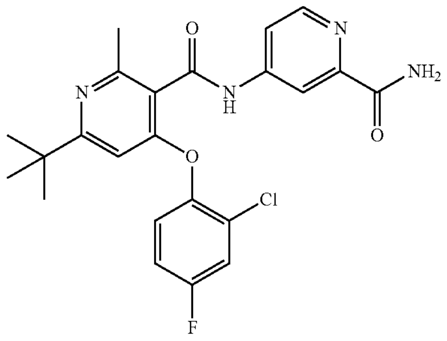
365
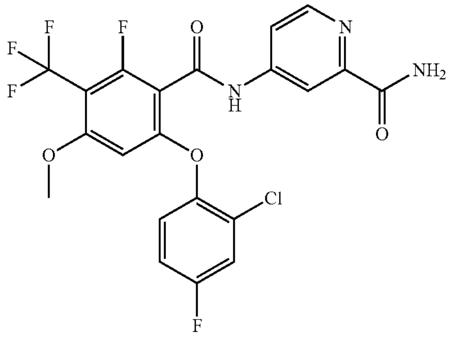
366
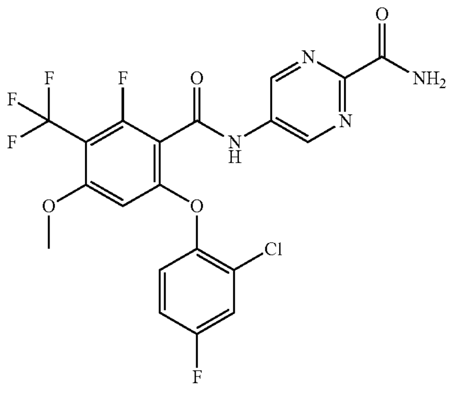

367
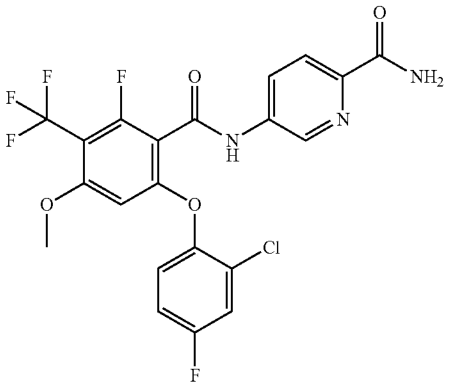
368
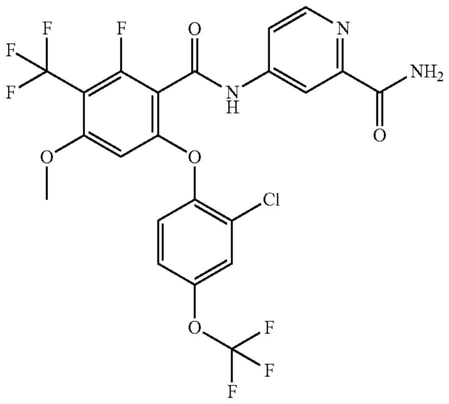
369
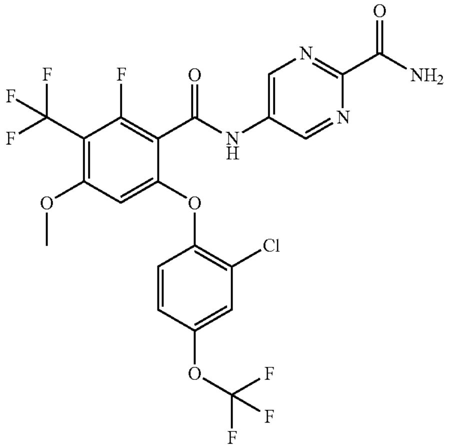
370
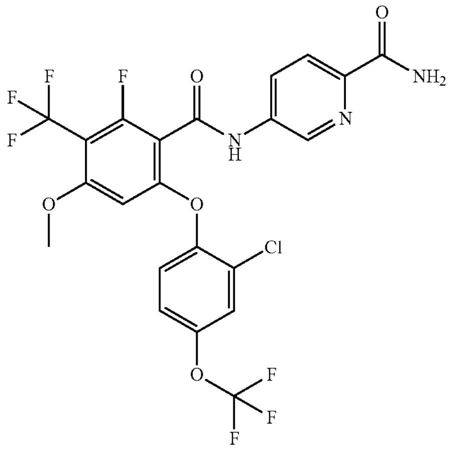
371
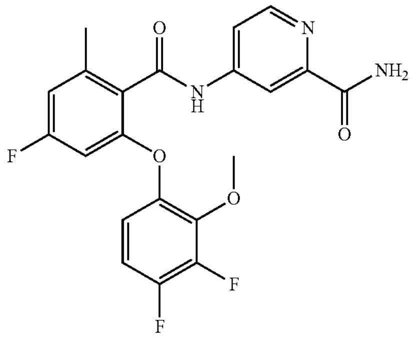
372
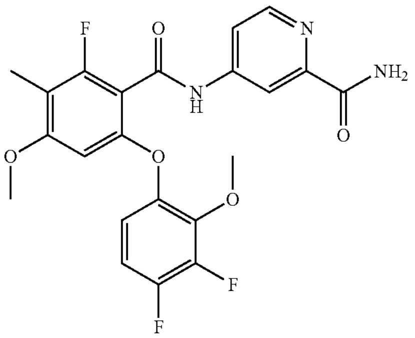
373
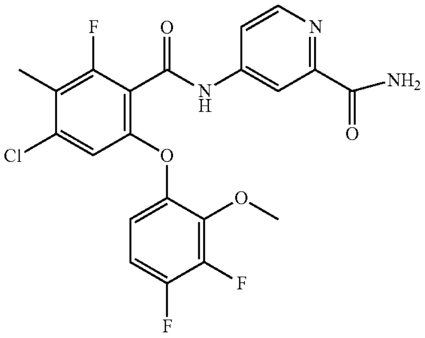

-continued
374
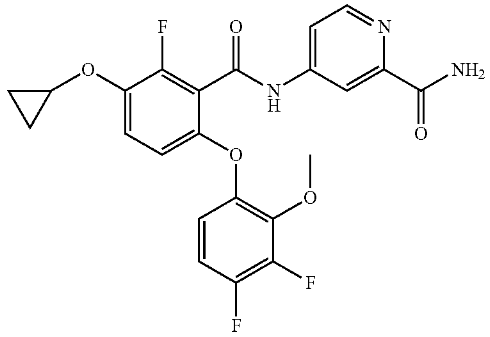
375
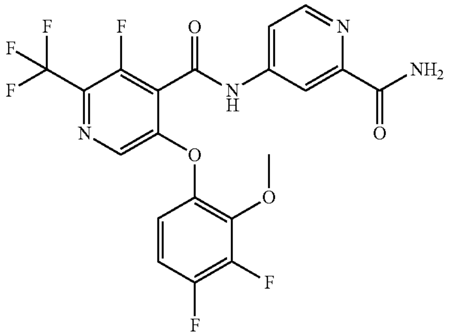
376
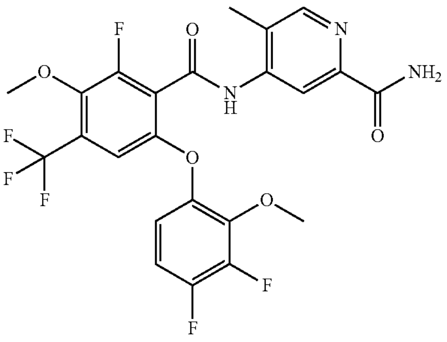
377
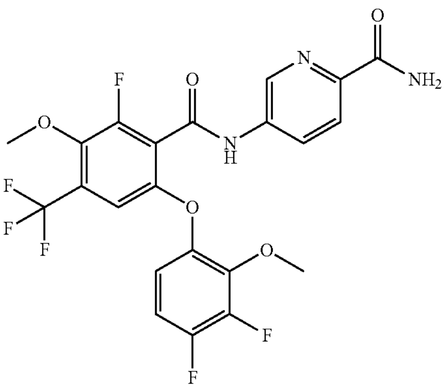
-continued
378
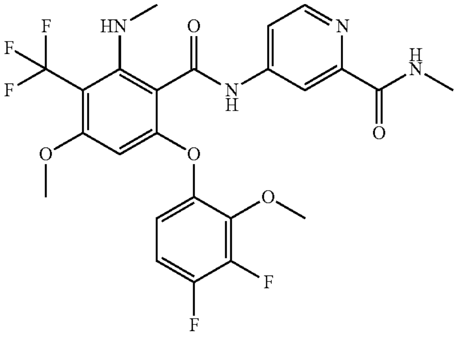
379
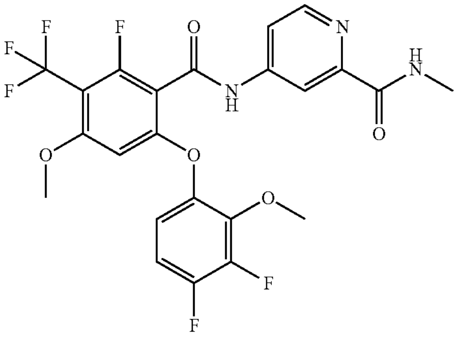
380
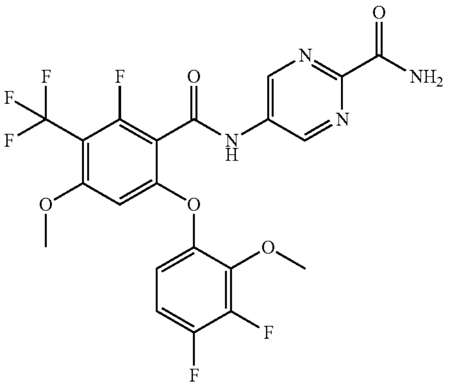
381
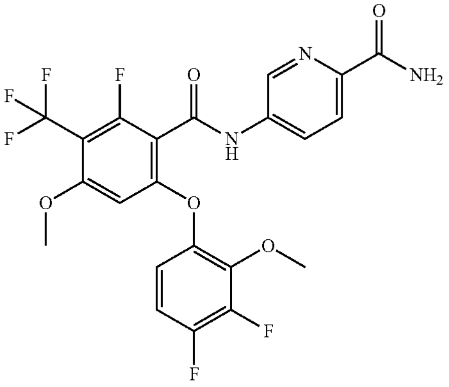

-continued
382
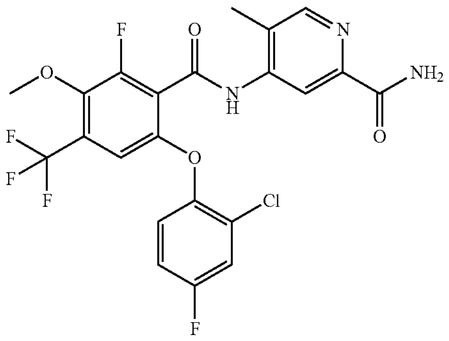
383
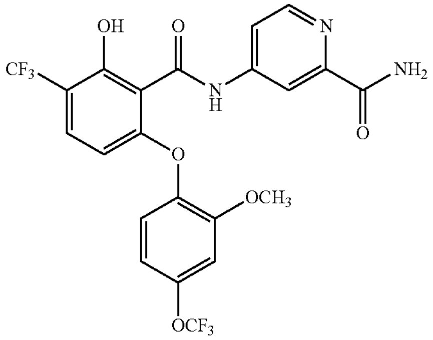
and
109
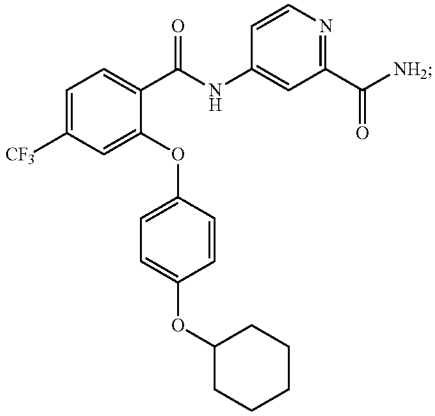
;
or a pharmaceutically acceptable salt thereof.
20. The compound of claim 1, wherein the compound is selected from:
1001
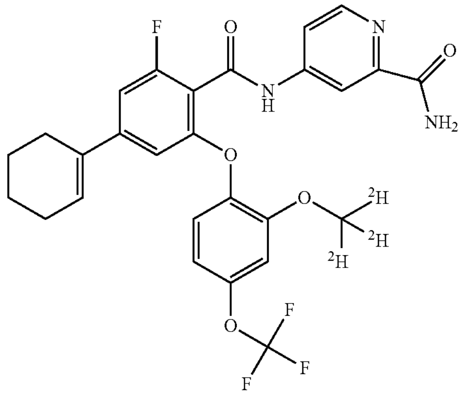
1002
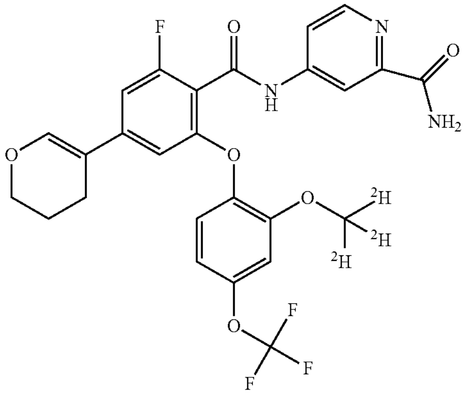
1003
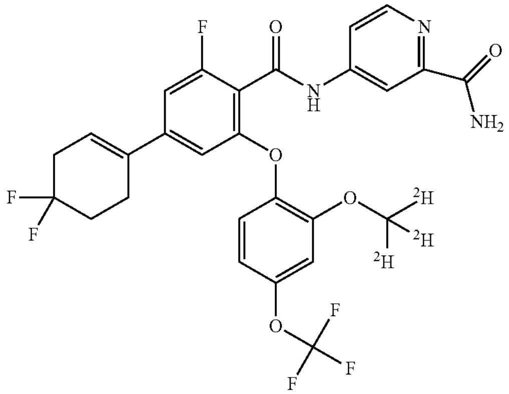
1004
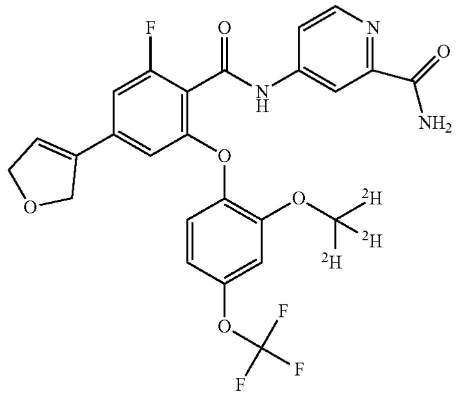

-continued
1005
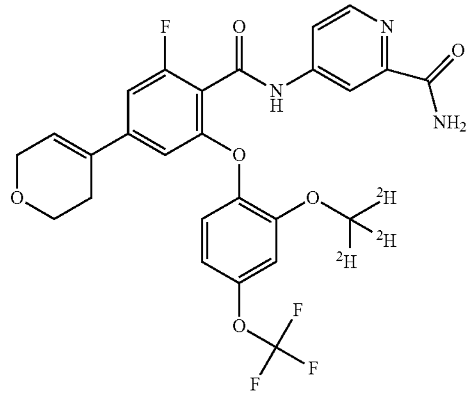
1006
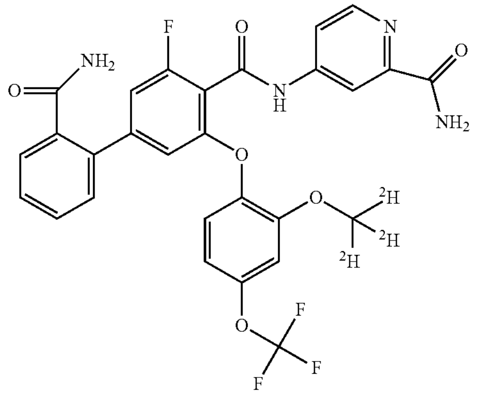
1007
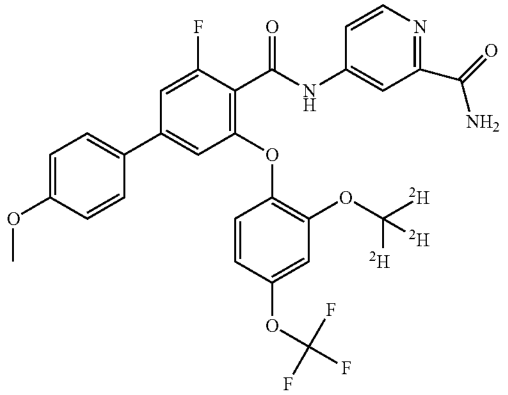
1008
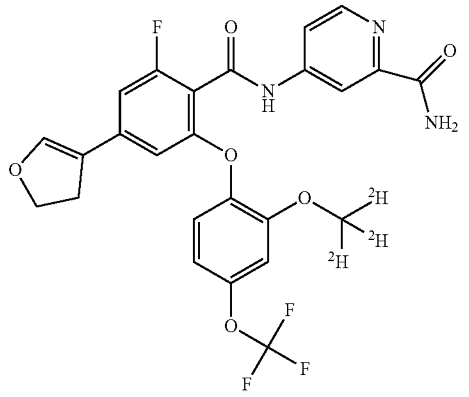
-continued
1009
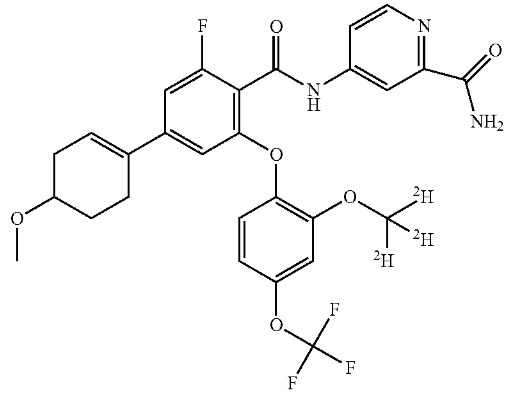
1010
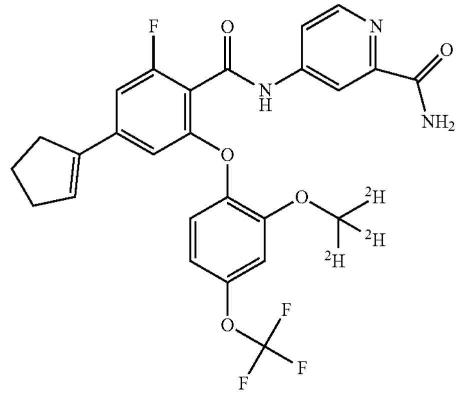
1011
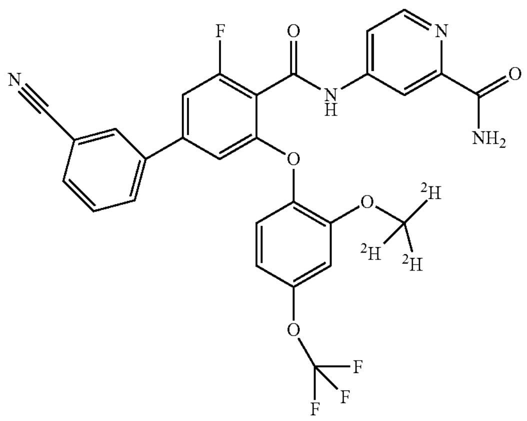

-continued
1012
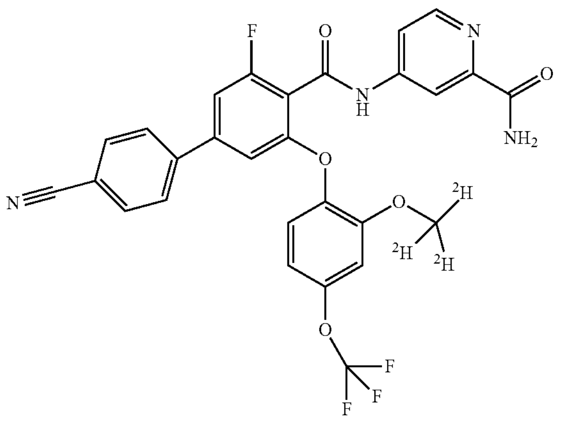
1013
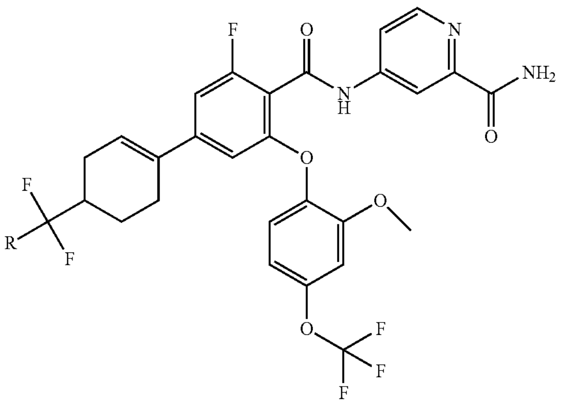
1014
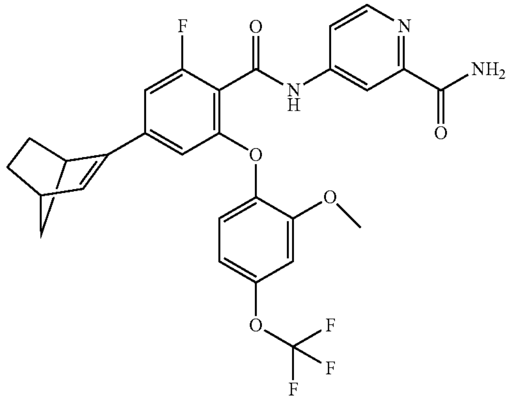
-continued
1015
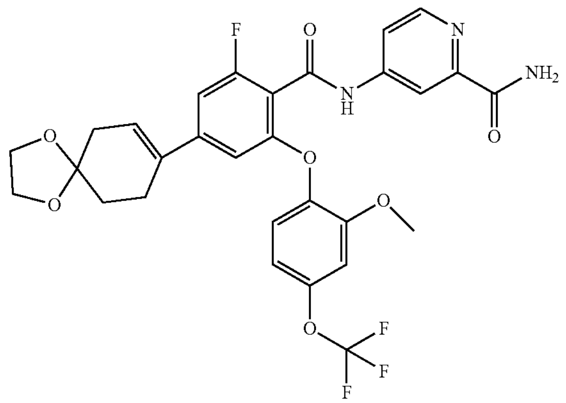
1016
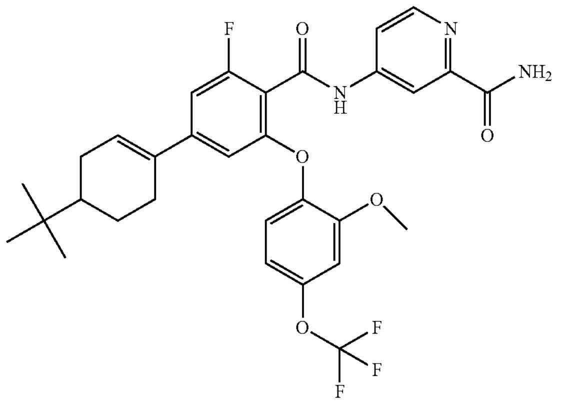
1017-a
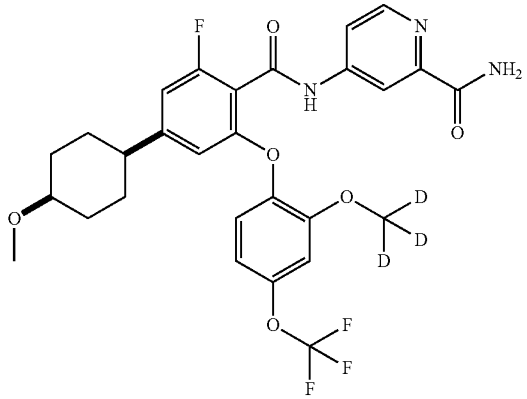

-continued
1017-b
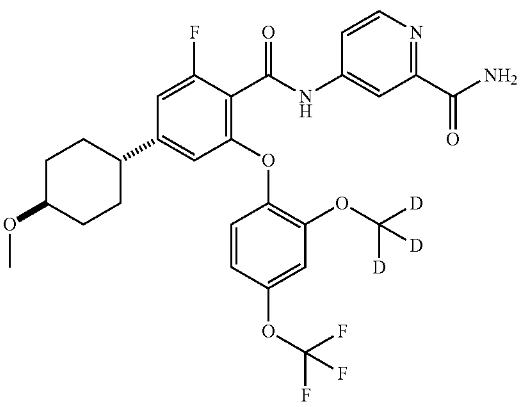
1018
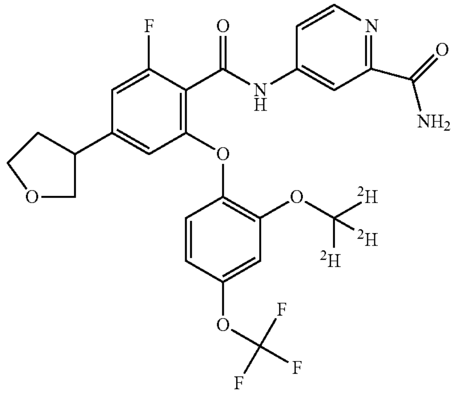
1019
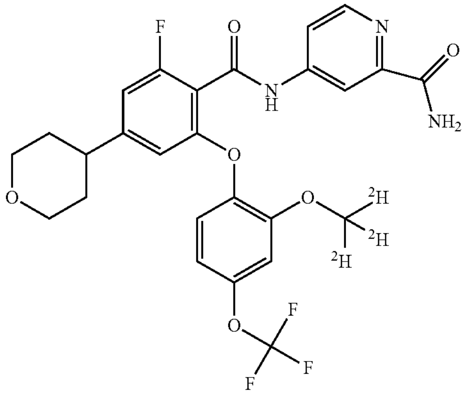
120
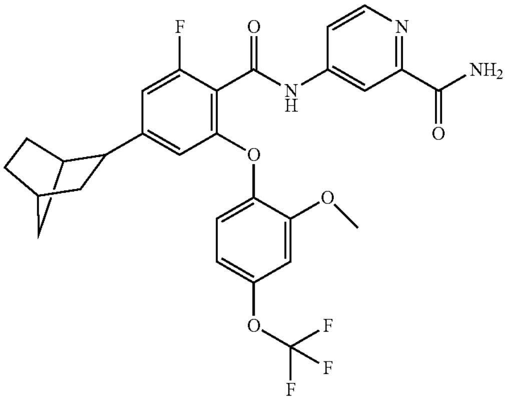
-continued
1021
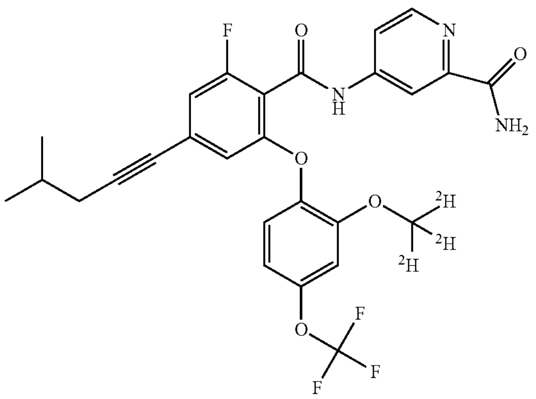
1022
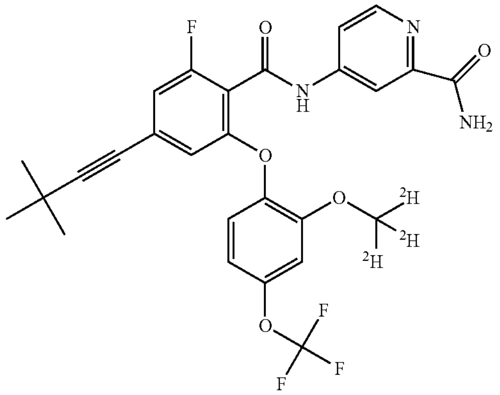
1023
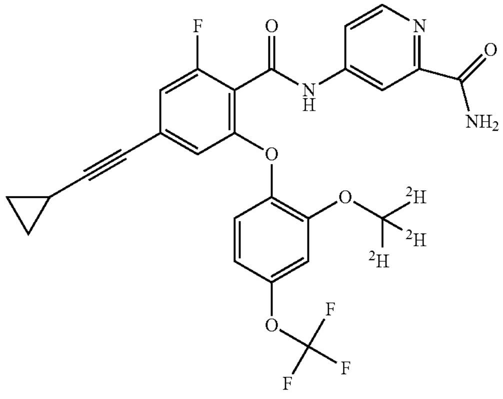
1024
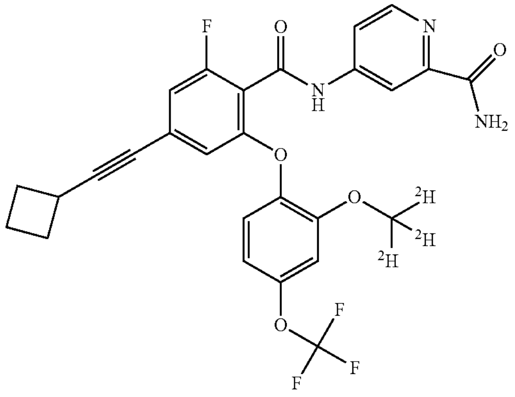

-continued
1025
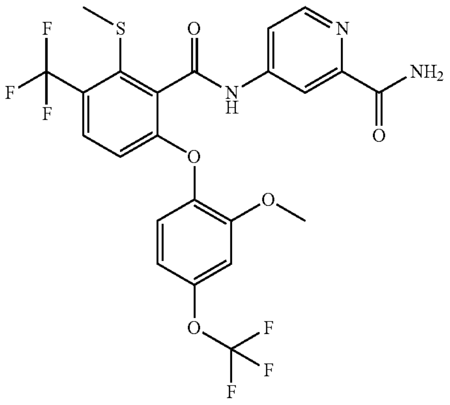
1026
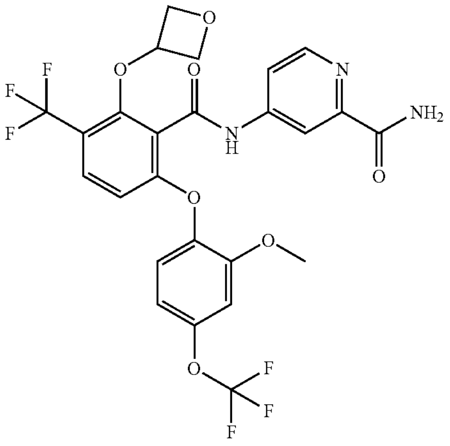
1027
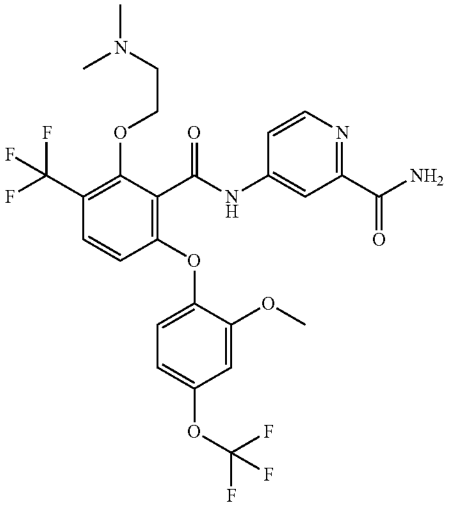
-continued
1028
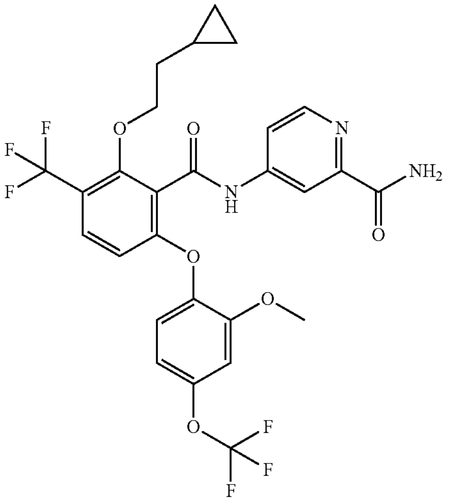
1029
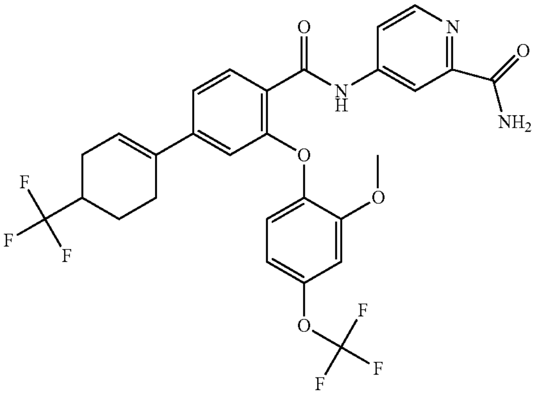
1030
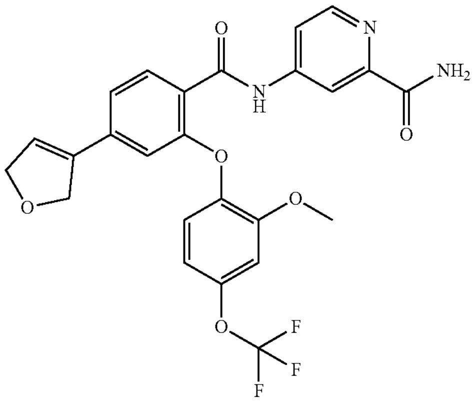

-continued
1031
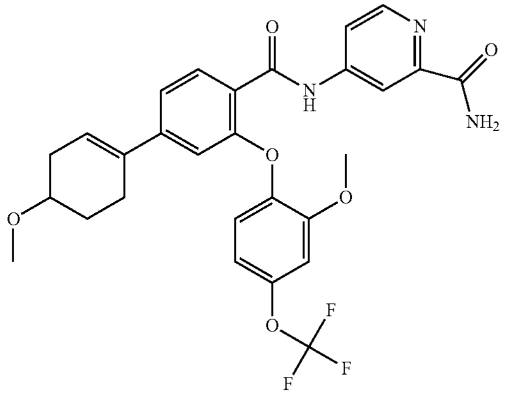
1032-a
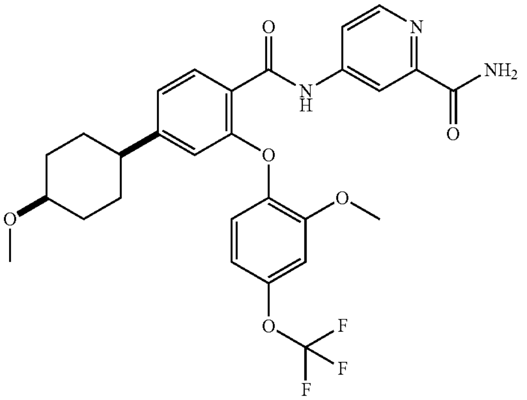
1032-b
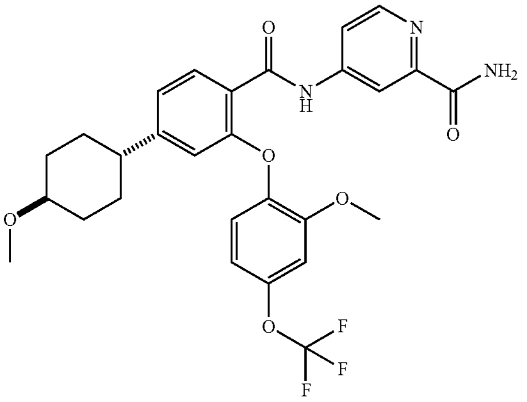
1033
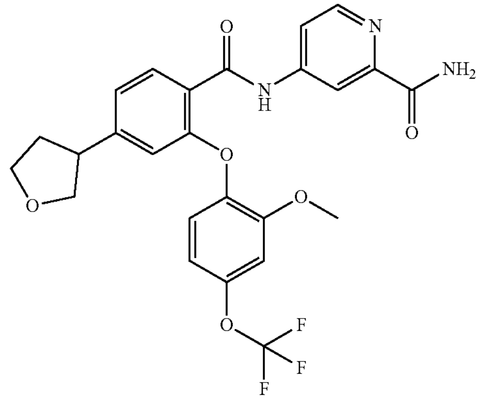
-continued
1034
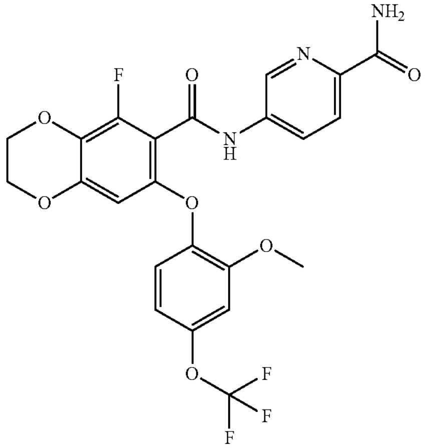
1035
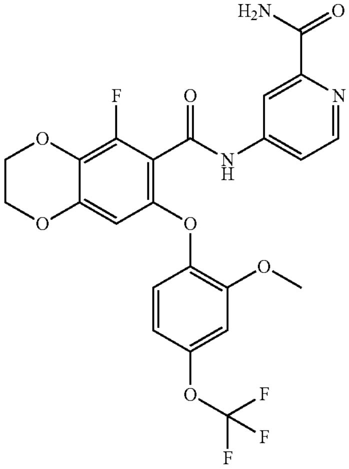
1036
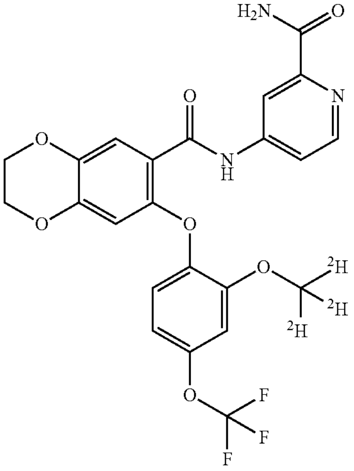

-continued

1037

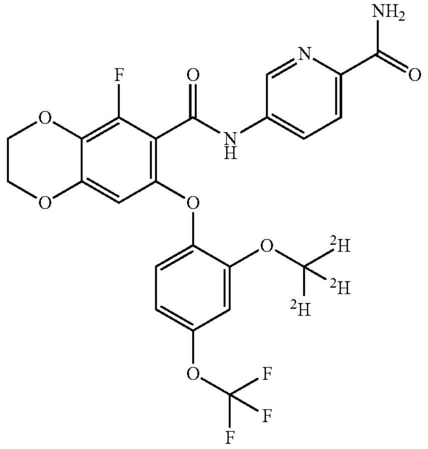

1038

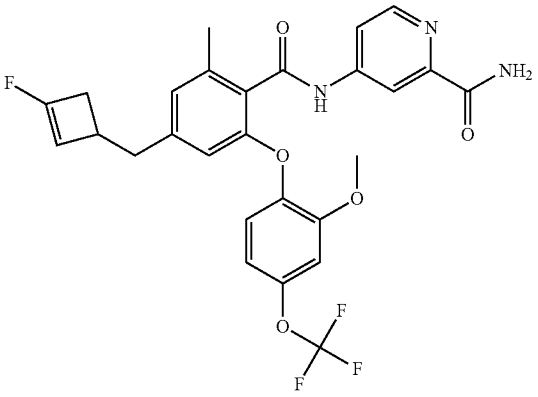

and

1039

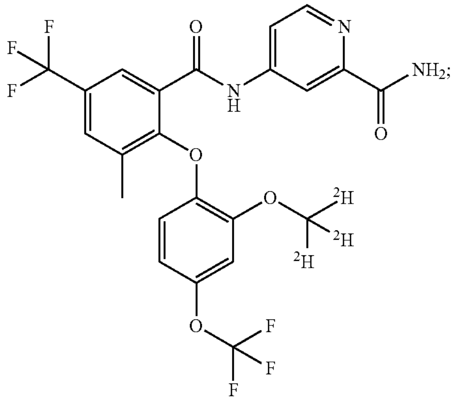

;

or a pharmaceutically acceptable salt thereof.

21. The compound of claim 1, wherein the compound is selected from:

1040

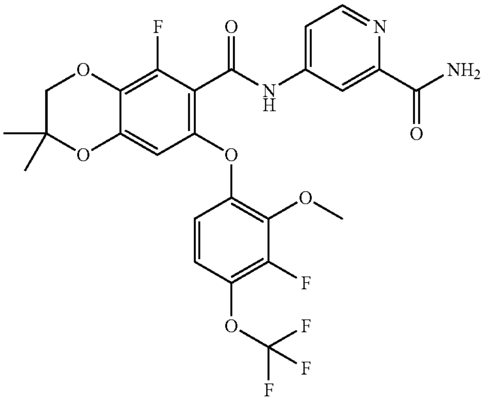

and

1041

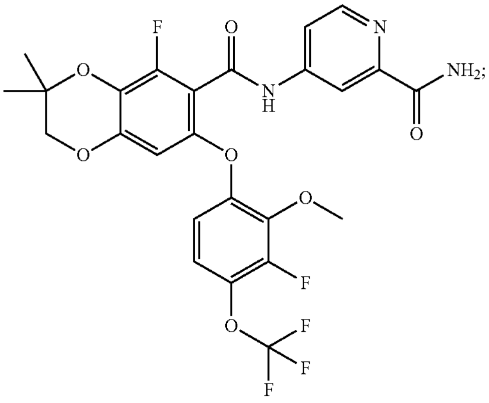

;

or a pharmaceutically acceptable salt thereof.

22. A pharmaceutical composition comprising the compound of claim 1, or a pharmaceutically acceptable salt thereof, and one or more pharmaceutically acceptable carriers or vehicles.

23. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 1, or a pharmaceutically acceptable salt thereof.

* * * * *